(12) United States Patent
Forsell

(10) Patent No.: US 11,564,709 B2
(45) Date of Patent: Jan. 31, 2023

(54) CONVERTIBLE SURGICAL ACCESS PORT

(76) Inventor: Peter Forsell, Bouveret (CH)

( * ) Notice: Subject to any disclaimer, the term of this patent is extended or adjusted under 35 U.S.C. 154(b) by 423 days.

(21) Appl. No.: 14/233,089

(22) PCT Filed: Jul. 13, 2012

(86) PCT No.: PCT/SE2012/000112
§ 371 (c)(1),
(2), (4) Date: Jan. 15, 2014

(87) PCT Pub. No.: WO2013/012368
PCT Pub. Date: Jan. 24, 2013

(65) Prior Publication Data
US 2014/0163326 A1 Jun. 12, 2014

Related U.S. Application Data

(60) Provisional application No. 61/670,701, filed on Jul. 12, 2012.

(30) Foreign Application Priority Data

Jul. 15, 2011 (SE) ...................................... 150701-9

(51) Int. Cl.
A61B 17/34 (2006.01)
A61B 90/40 (2016.01)
(Continued)

(52) U.S. Cl.
CPC .......... *A61B 17/3423* (2013.01); *A61B 90/40* (2016.02); *B25J 21/02* (2013.01);
(Continued)

(58) Field of Classification Search
CPC .......... A61B 2017/00557; A61B 2017/00561; A61B 2017/00597; A61B 2017/00592;
(Continued)

(56) References Cited

U.S. PATENT DOCUMENTS 2,473,033 A 6/1949 Letac
3,850,172 A 11/1974 Cazalis
(Continued)

FOREIGN PATENT DOCUMENTS

EP 0950376 A1 10/1999
JP 2003199755 A 7/2003

OTHER PUBLICATIONS

International Search Report for PCT/SE2012/000112, dated Nov. 23, 2012.
(Continued)

*Primary Examiner* — Eduardo C Robert
*Assistant Examiner* — Tara Rose E Carter

(57) ABSTRACT

A interconnectable port is provided. The interconnectable port is adapted to be at least partially placed in an incision in a patient's body. The interconnectable port comprises a first and second port adapted be interconnected to form the interconnectable port, wherein the second port is disconnectable from the first port, wherein the first port is connected to a first portion of a flexible wall, and the second port is connected to a second portion of the flexible wall, and wherein the flexible wall is adapted to form a chamber.

30 Claims, 511 Drawing Sheets

(51) Int. Cl.
  *B25J 21/02* (2006.01)
  *A61B 46/20* (2016.01)
  *A61B 42/00* (2016.01)
  *A61B 46/27* (2016.01)

(52) U.S. Cl.
  CPC ............... *A61B 42/00* (2016.02); *A61B 46/27* (2016.02); *A61B 2017/3466* (2013.01); *A61B 2017/3492* (2013.01); *A61B 2046/201* (2016.02); *A61B 2046/205* (2016.02)

(58) Field of Classification Search
  CPC ...... A61B 17/3431; A61B 2017/00265; A61B 2017/3443; A61B 1/32; A61B 17/3423; A61B 2046/201
  USPC ............................ 600/201–210; 606/192, 195
  See application file for complete search history.

(56) References Cited

U.S. PATENT DOCUMENTS

| | | | |
|---|---|---|---|
| 4,275,719 A | 6/1981 | Mayer | |
| 4,367,728 A | 1/1983 | Mutke | |
| 5,480,410 A | 1/1996 | Cuschieri | |
| 5,640,977 A * | 6/1997 | Leahy | A61B 17/3423 128/850 |
| 5,728,041 A | 3/1998 | Fowler | |
| 5,813,409 A | 9/1998 | Leahy et al. | |
| 5,853,395 A | 12/1998 | Crook | |
| 5,906,577 A * | 5/1999 | Beane | A61B 42/10 600/206 |
| 6,033,426 A * | 3/2000 | Kaji | A61B 42/10 600/207 |
| 6,095,966 A * | 8/2000 | Chornenky | A61N 5/1001 600/3 |
| 6,440,063 B1 | 8/2002 | Beane et al. | |
| 7,008,377 B2 | 3/2006 | Beane | |
| 7,153,261 B2 * | 12/2006 | Wenchell | A61B 17/3423 600/208 |
| 7,717,847 B2 * | 5/2010 | Smith | A61B 17/3423 600/208 |
| 7,850,667 B2 | 12/2010 | Gresham | |
| 7,998,068 B2 * | 8/2011 | Bonadio | A61B 17/3423 600/208 |
| 2002/0045796 A1 | 4/2002 | O'Connor et al. | |
| 2004/0171998 A1 | 9/2004 | Marasco | |
| 2004/0260254 A1 | 12/2004 | Neilson | |
| 2005/0155611 A1 * | 7/2005 | Vaugh | A61B 17/3423 128/887 |
| 2006/0129165 A1 * | 6/2006 | Edoga | A61B 17/34 606/108 |
| 2006/0135978 A1 | 6/2006 | Franer | |
| 2007/0118175 A1 * | 5/2007 | Butler | A61B 90/40 606/213 |
| 2008/0041399 A1 | 2/2008 | Kriek | |
| 2009/0036918 A1 | 2/2009 | Burgess | |
| 2009/0216069 A1 | 8/2009 | Woodstock | |
| 2010/0113882 A1 * | 5/2010 | Widenhouse | A61B 17/3423 600/208 |
| 2010/0139669 A1 | 6/2010 | Piferi | |
| 2010/0174244 A1 | 7/2010 | Dankelman | |
| 2010/0249516 A1 | 9/2010 | Shelton | |
| 2010/0249526 A1 * | 9/2010 | Shelton, IV | A61B 17/3423 600/208 |
| 2010/0312066 A1 * | 12/2010 | Cropper | A61B 17/3423 600/207 |
| 2011/0015560 A1 | 1/2011 | Marasco | |
| 2012/0283518 A1 * | 11/2012 | Hart | A61B 17/3462 600/207 |

OTHER PUBLICATIONS

Written Opinion of the International Searching Authority for PCT/SE2012/000112, dated Nov. 23, 2012.

* cited by examiner

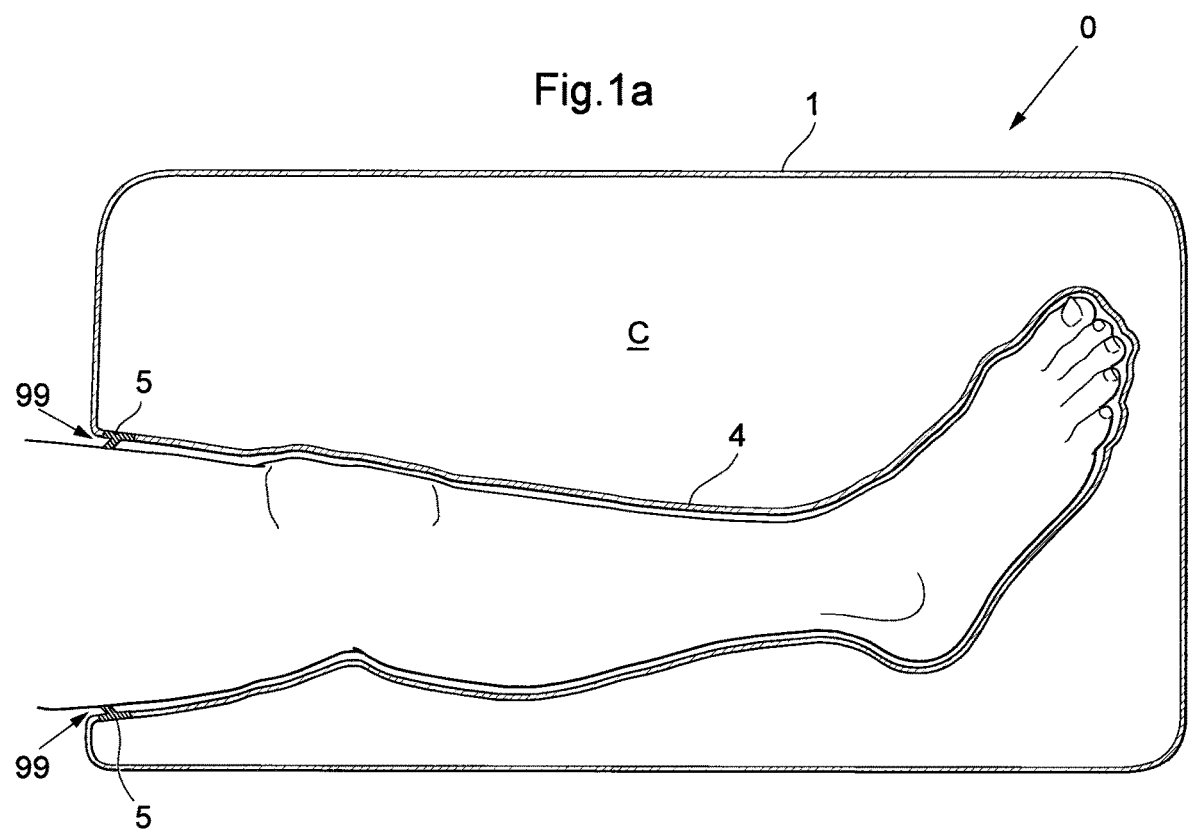
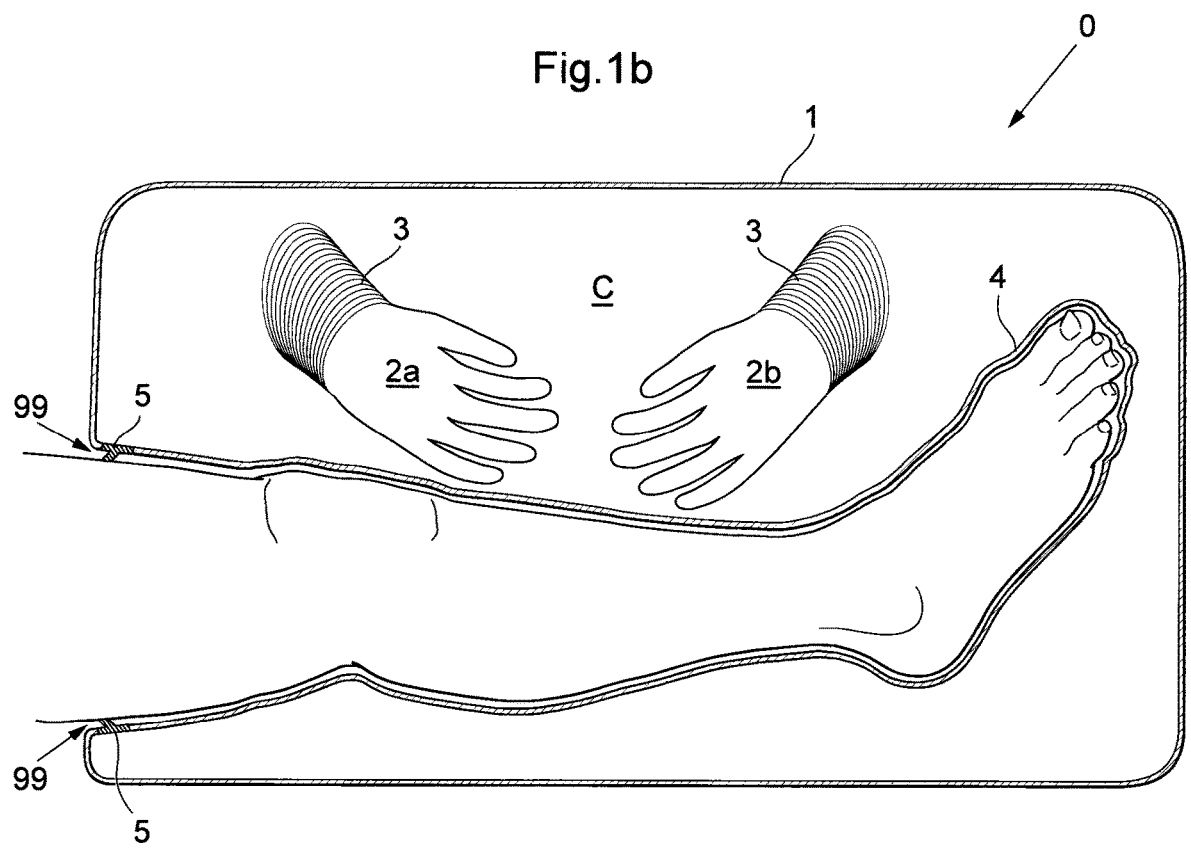

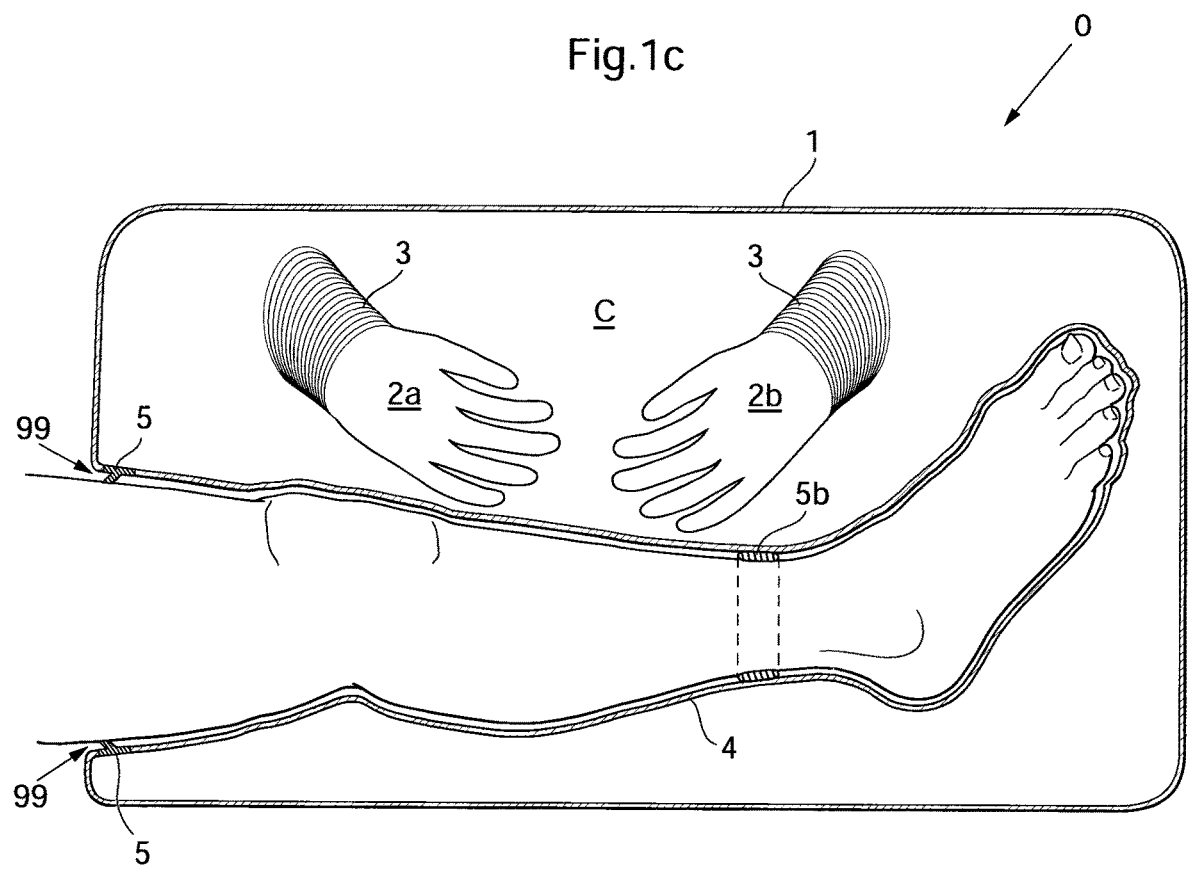

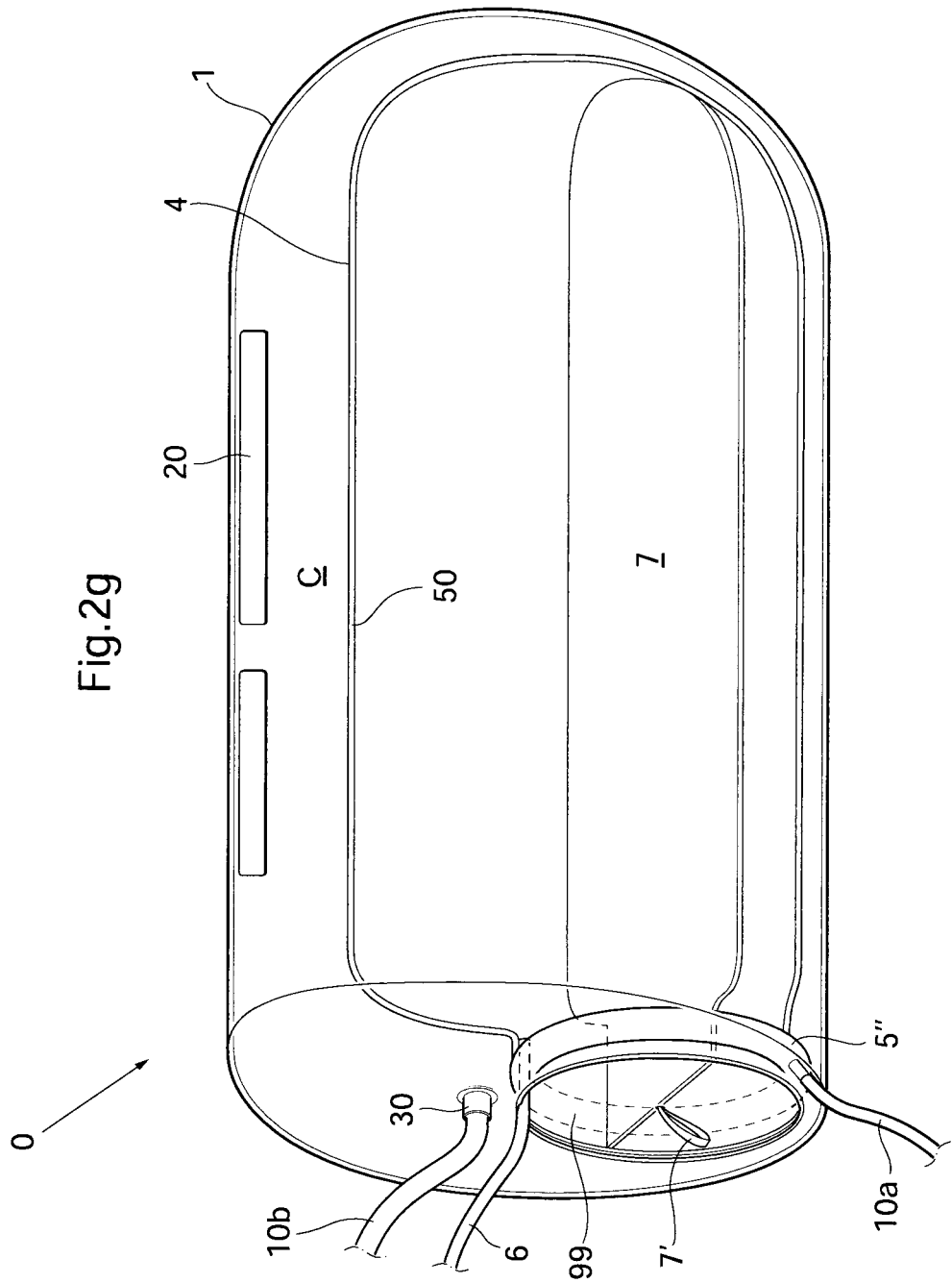

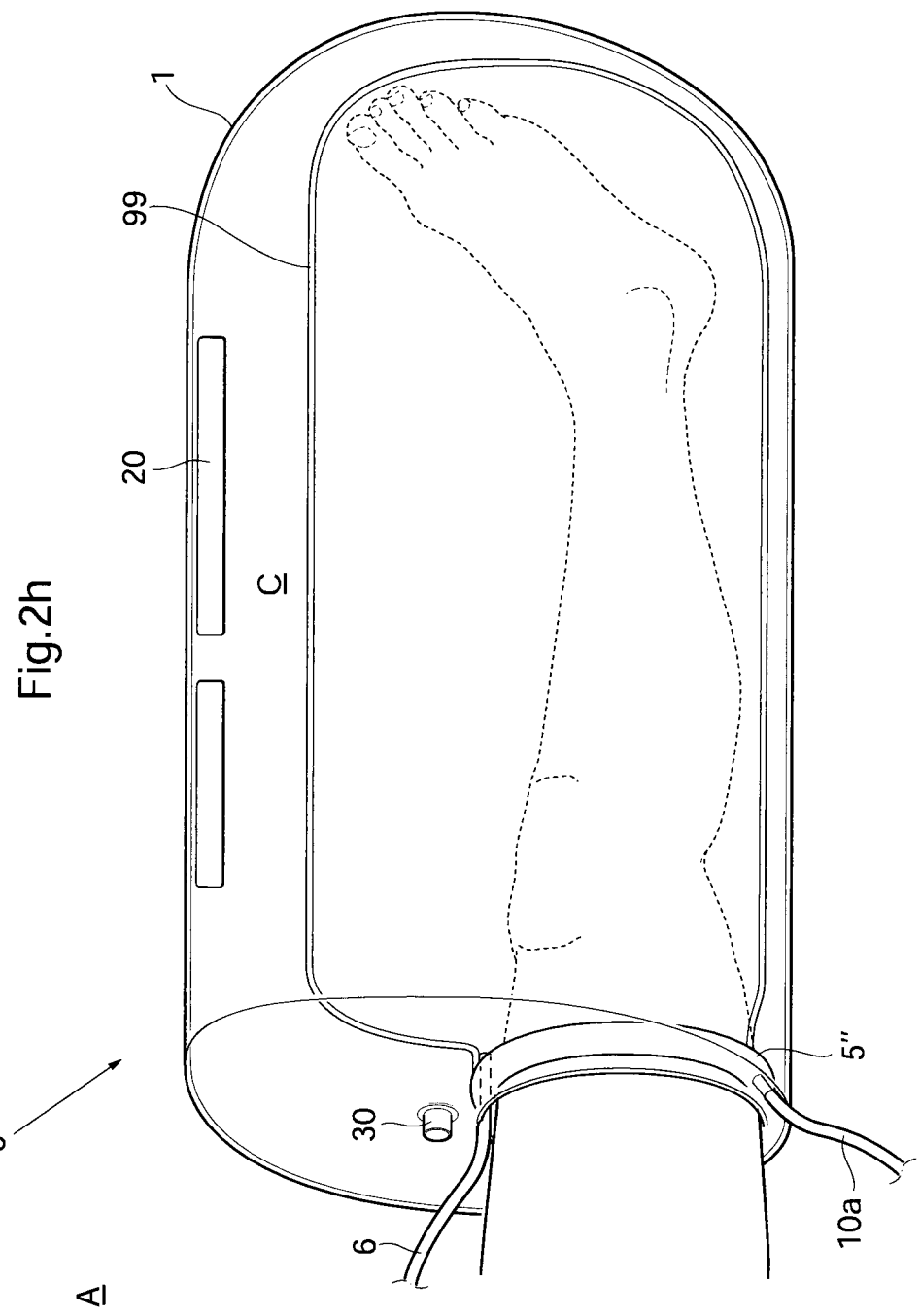

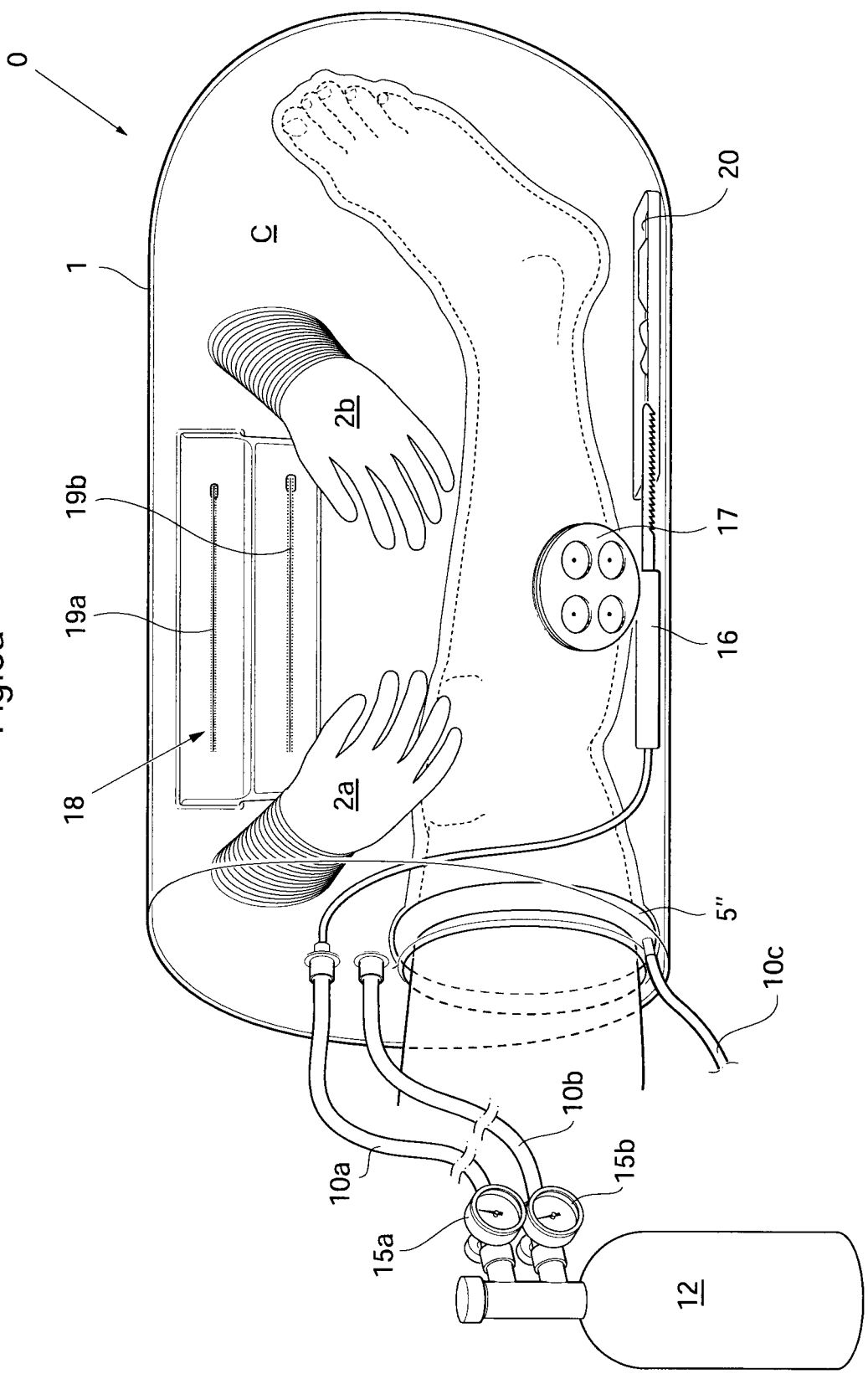

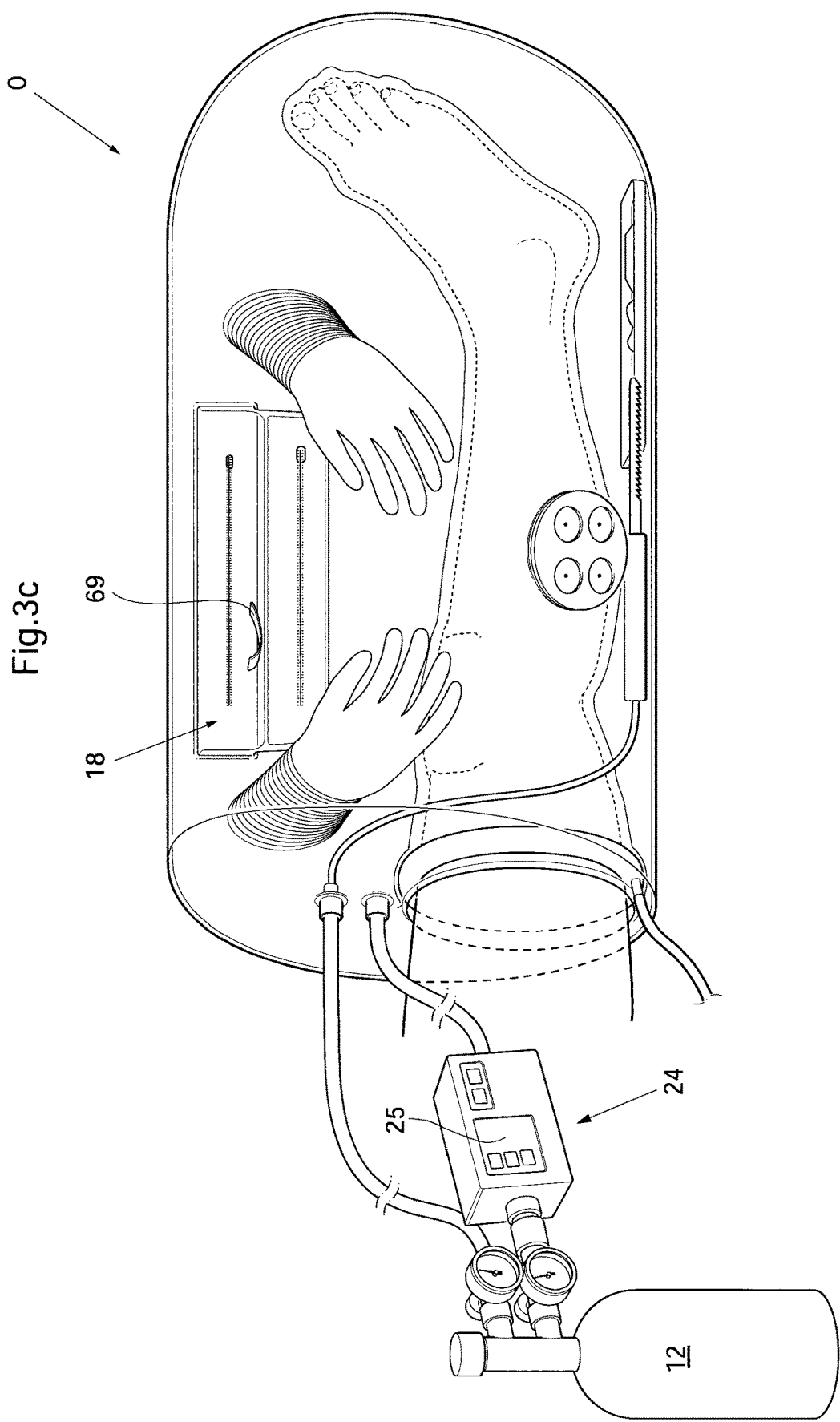

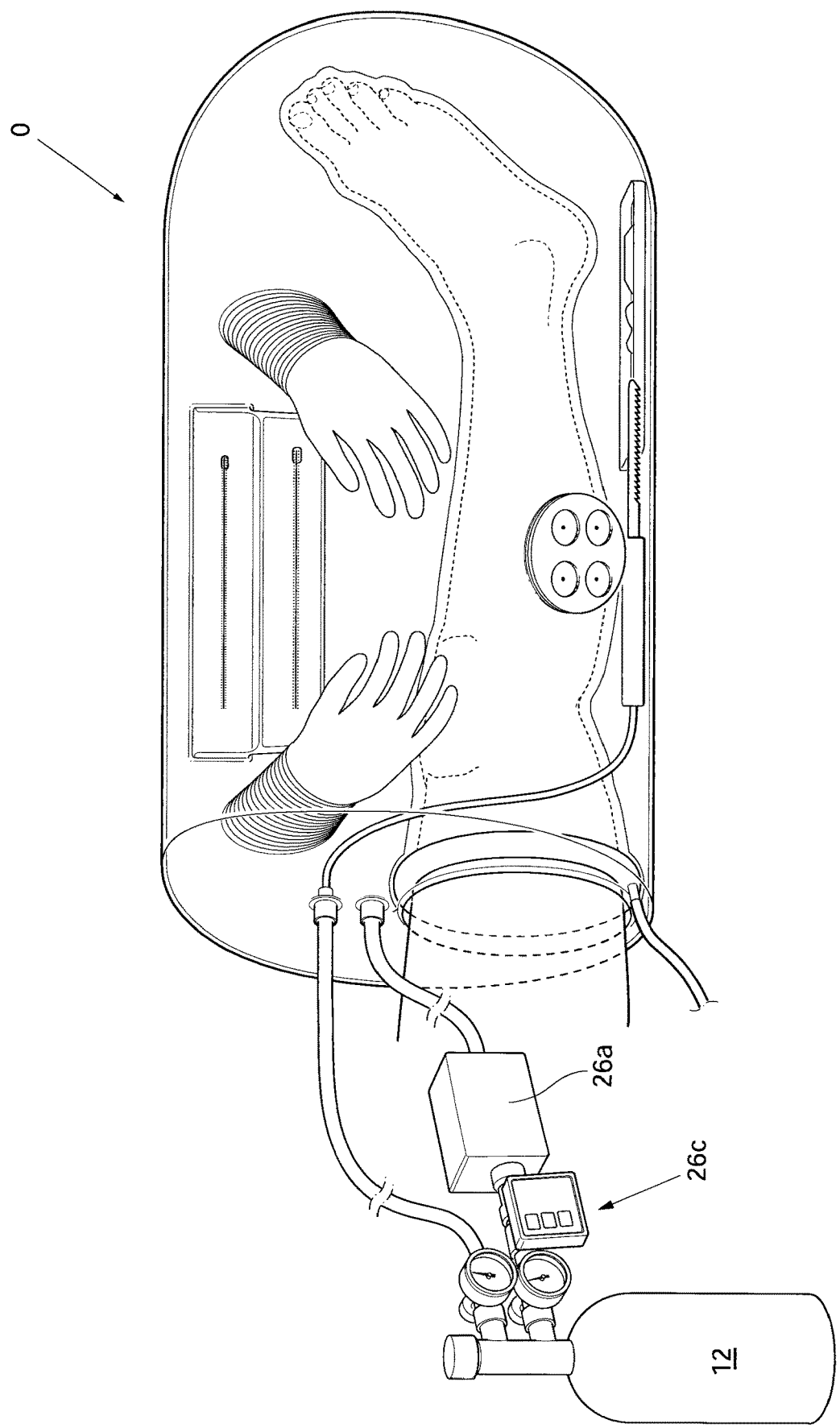

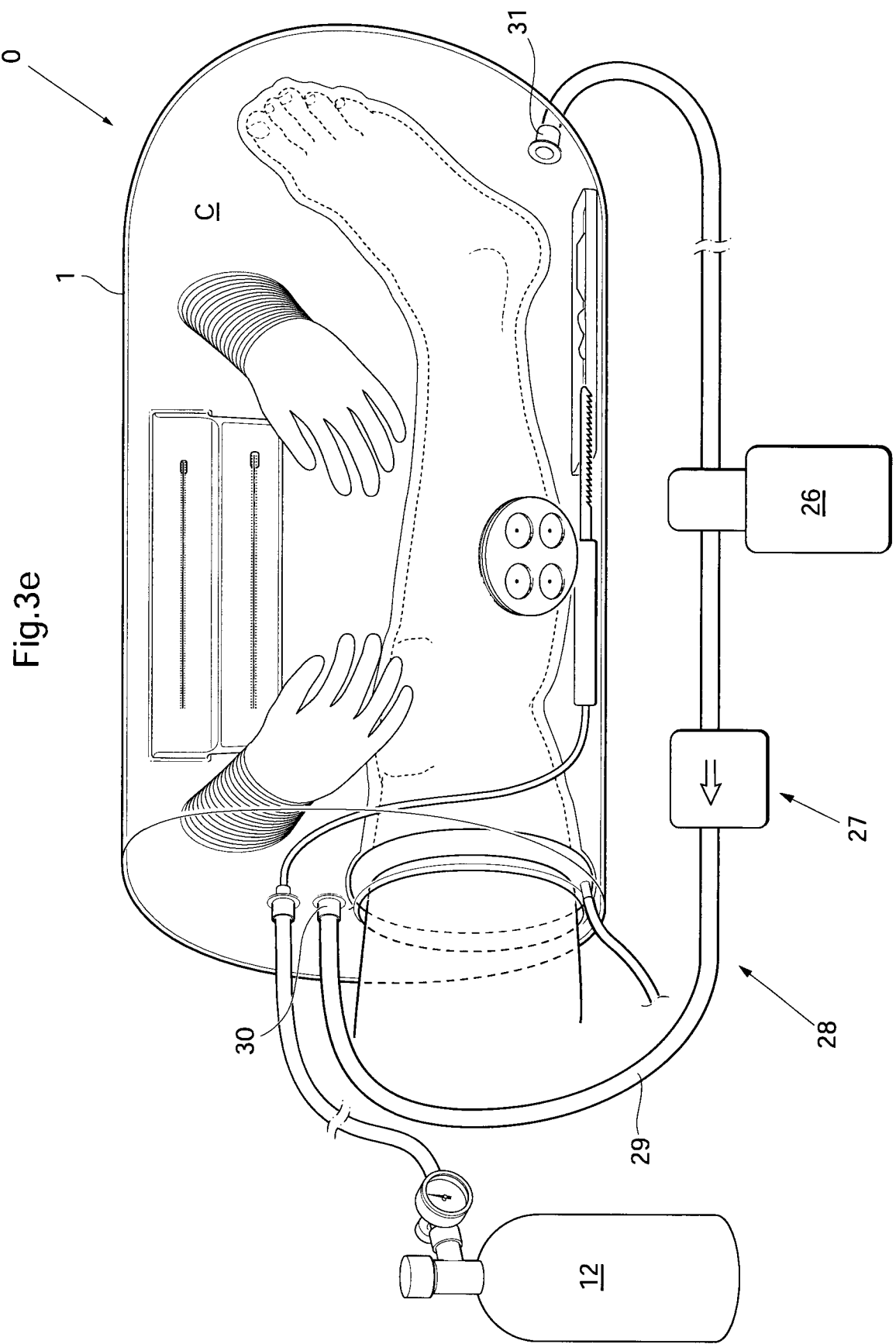

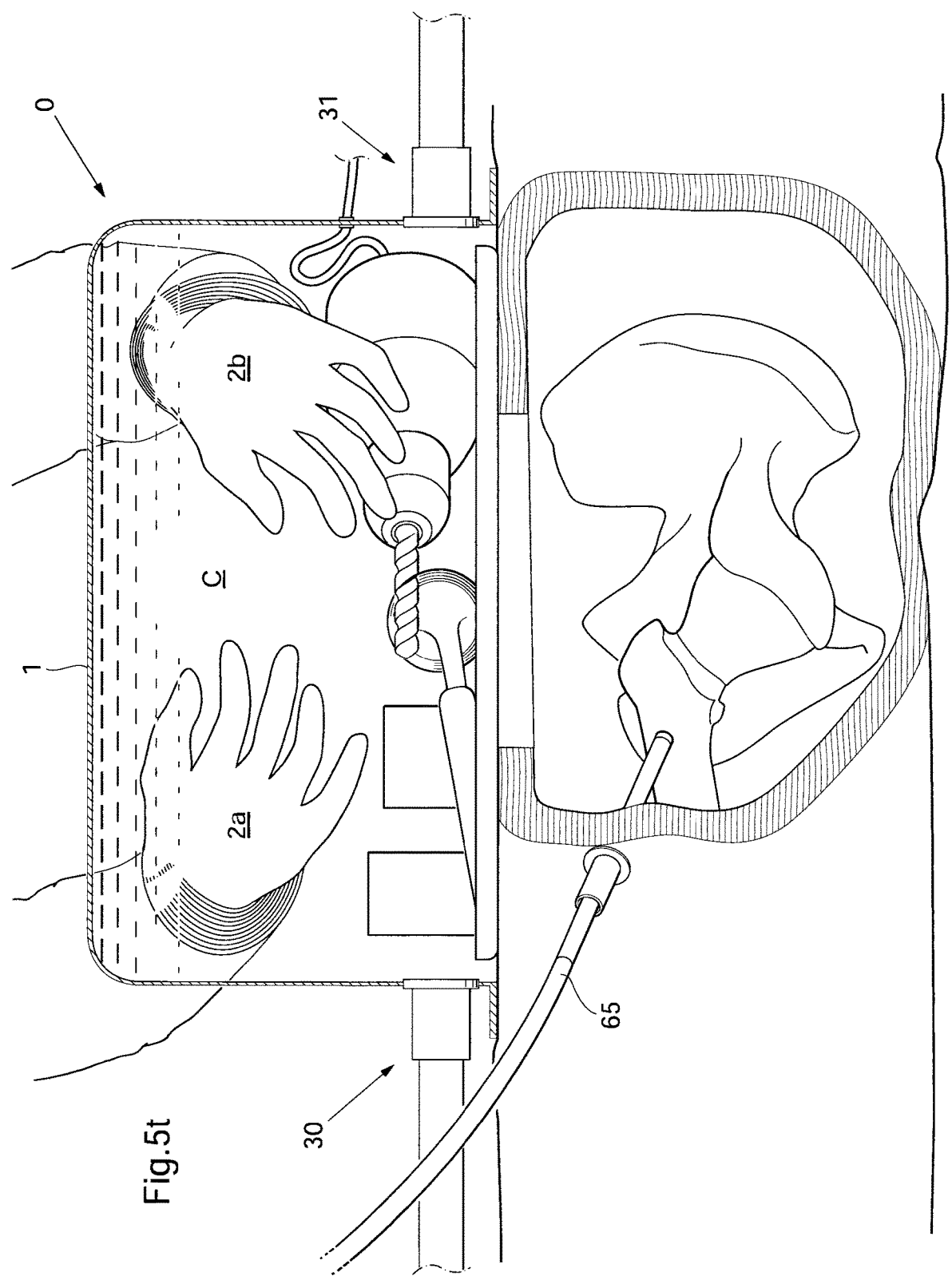

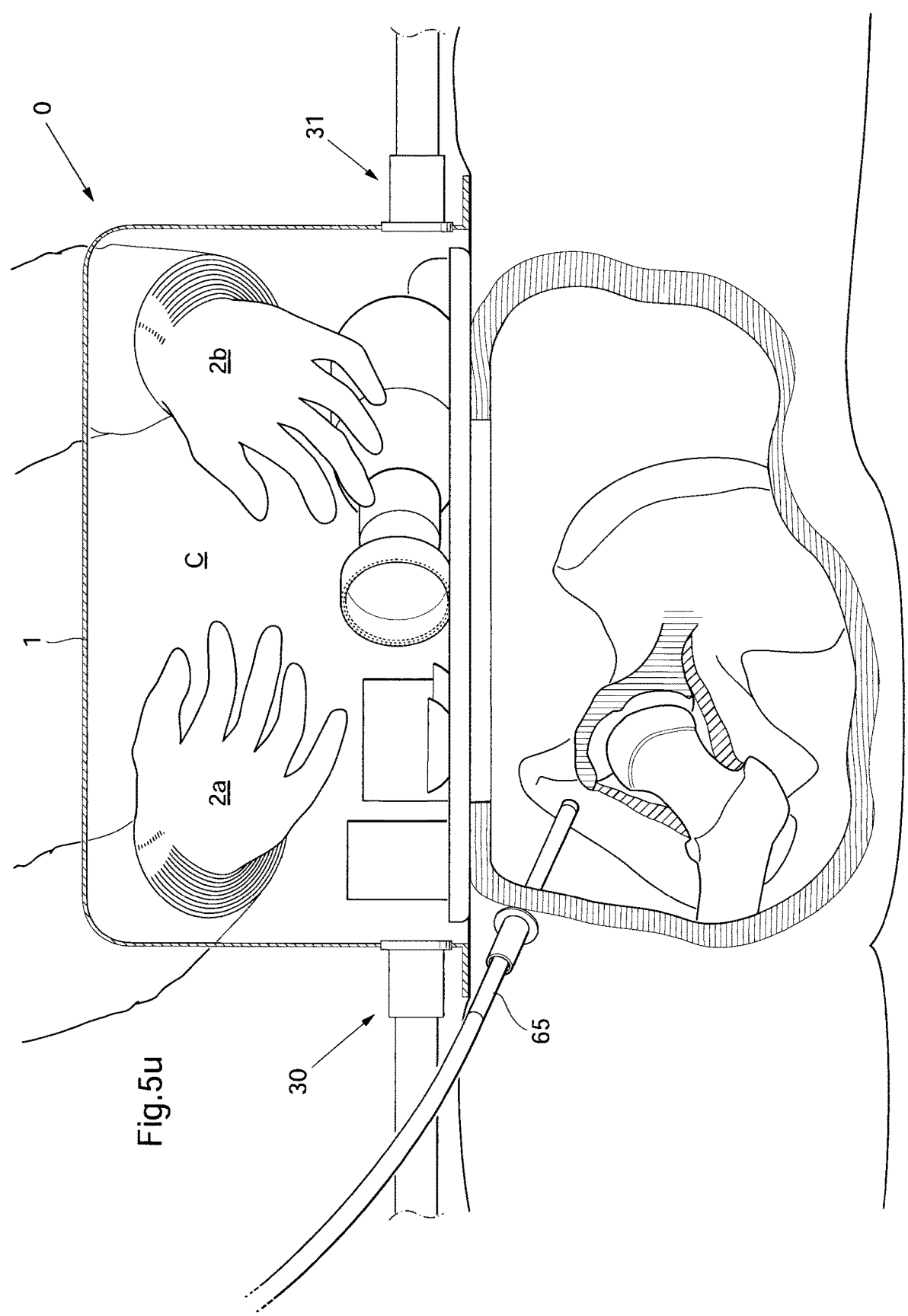

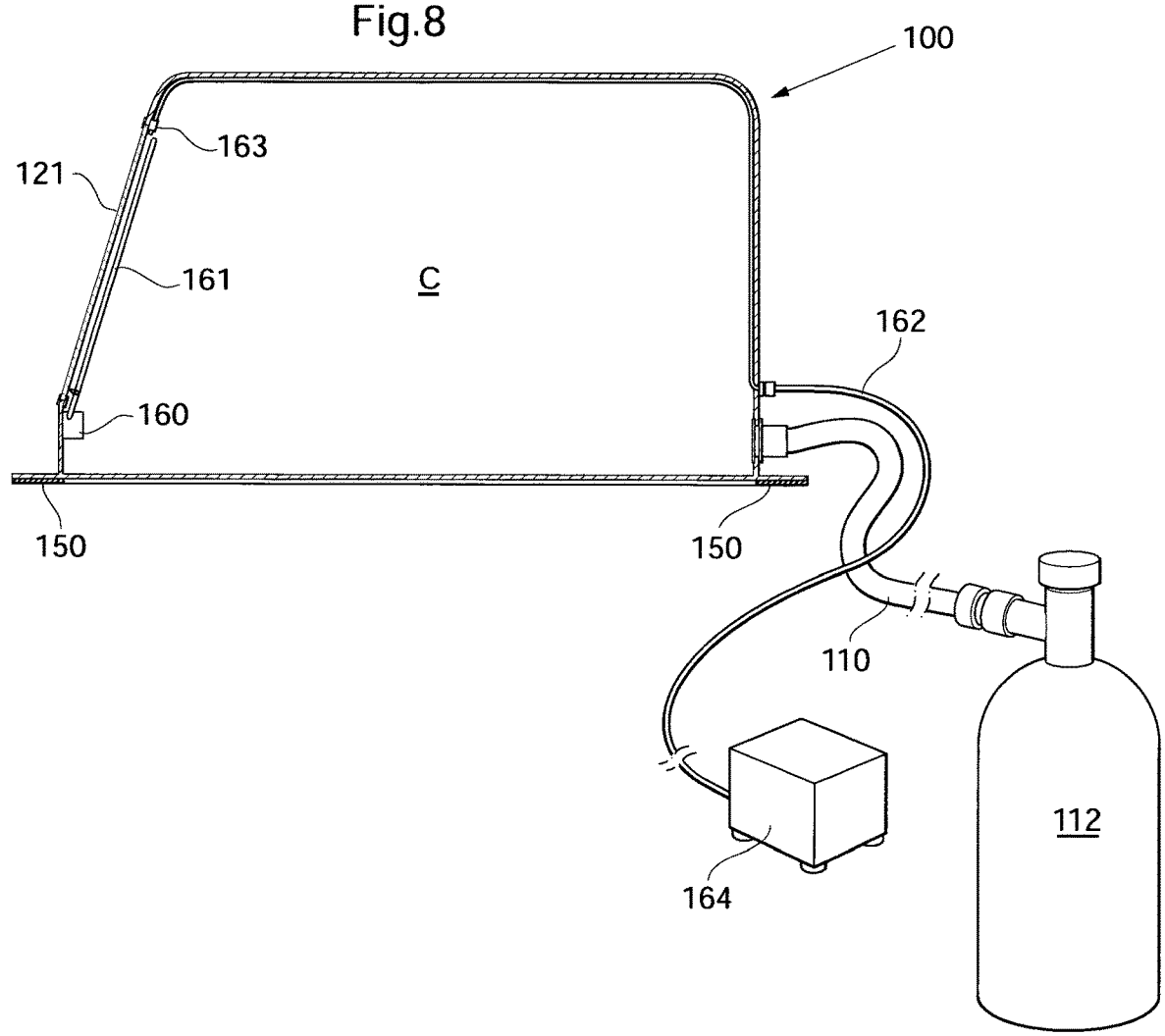
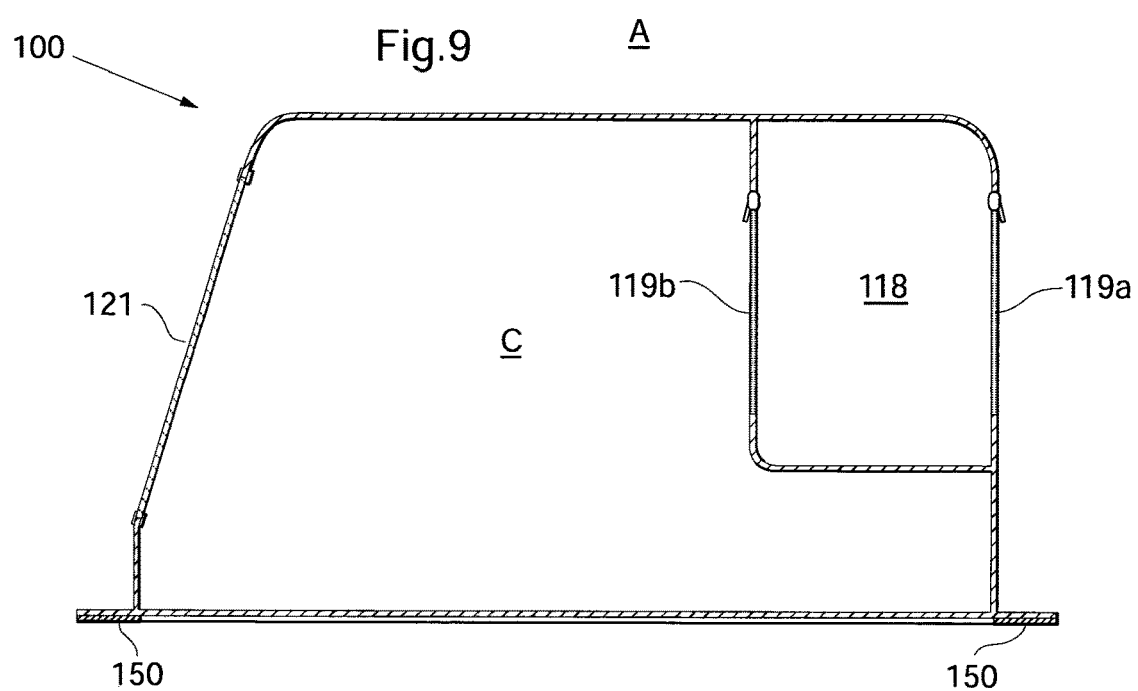

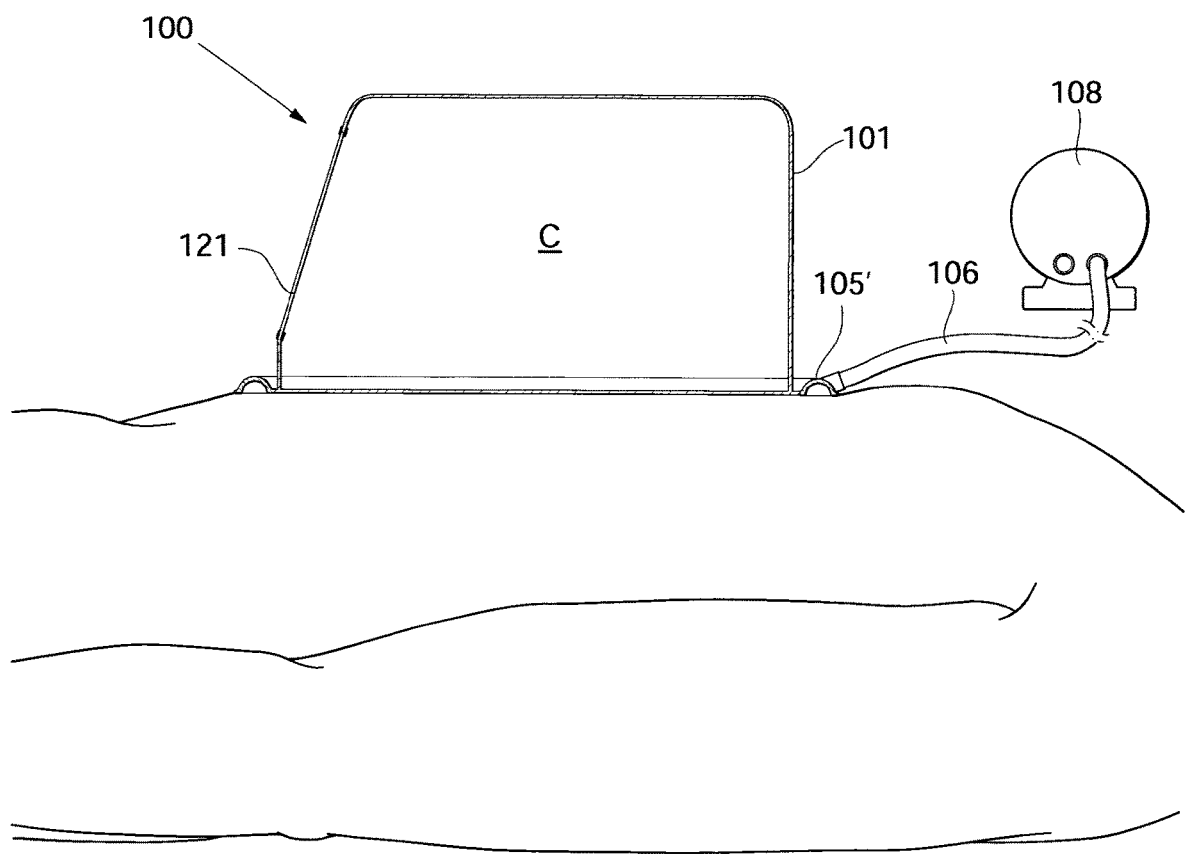

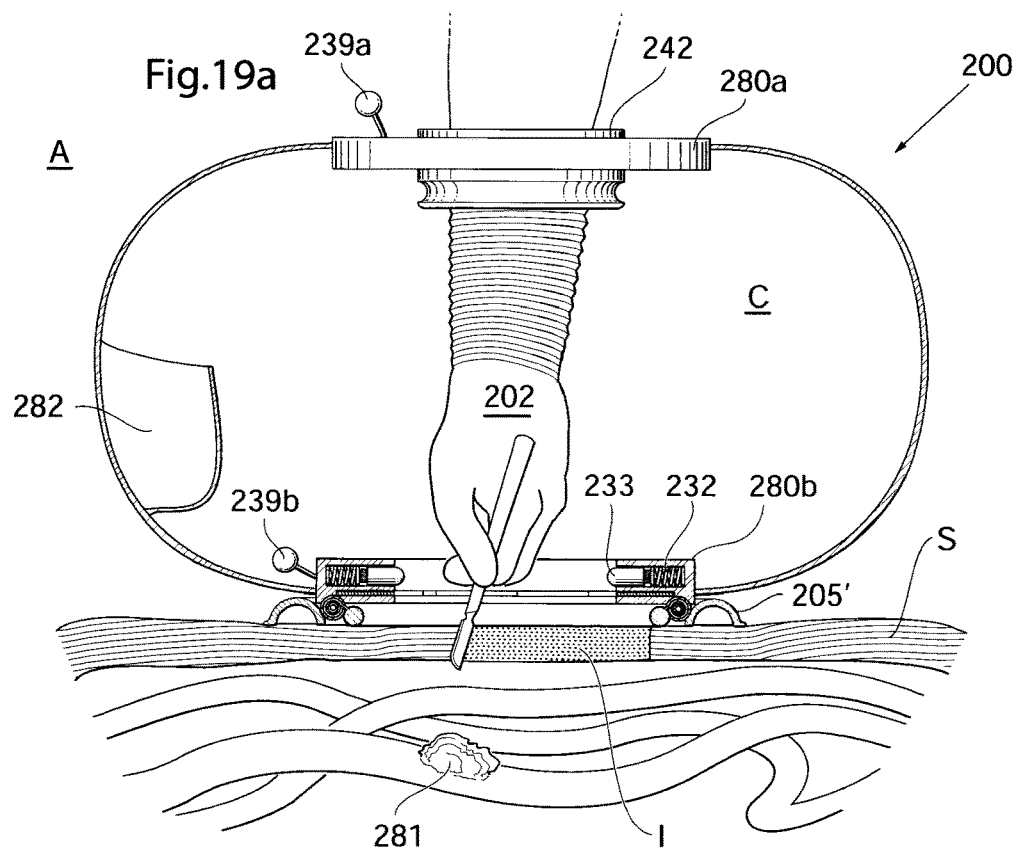
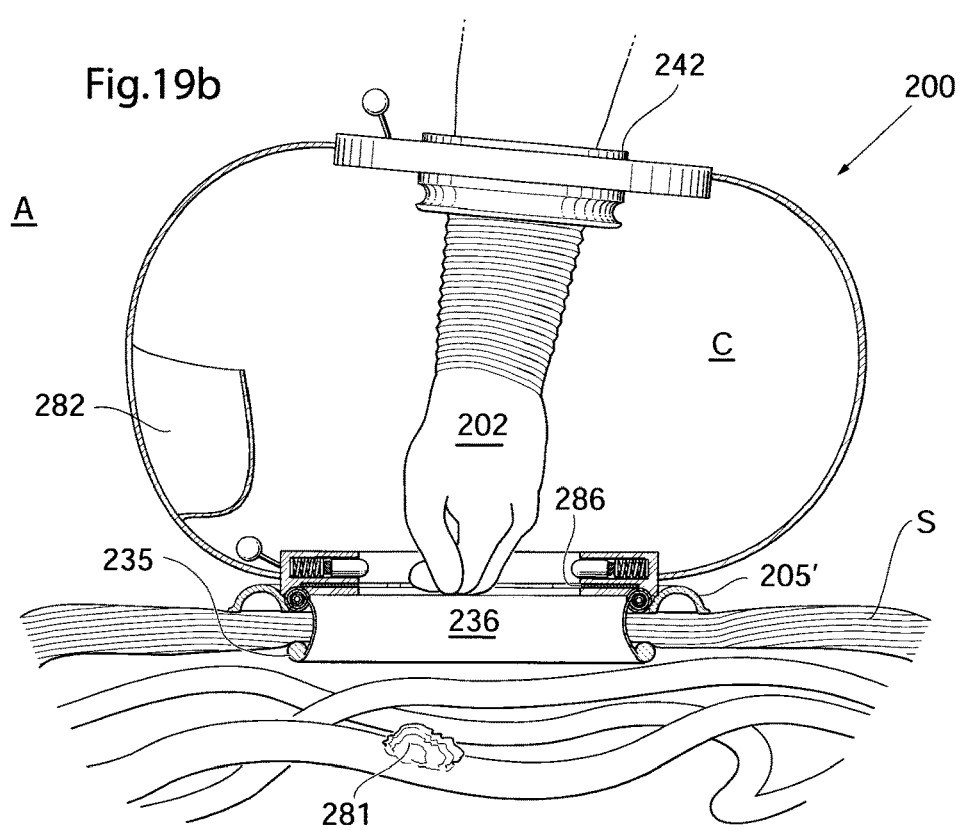

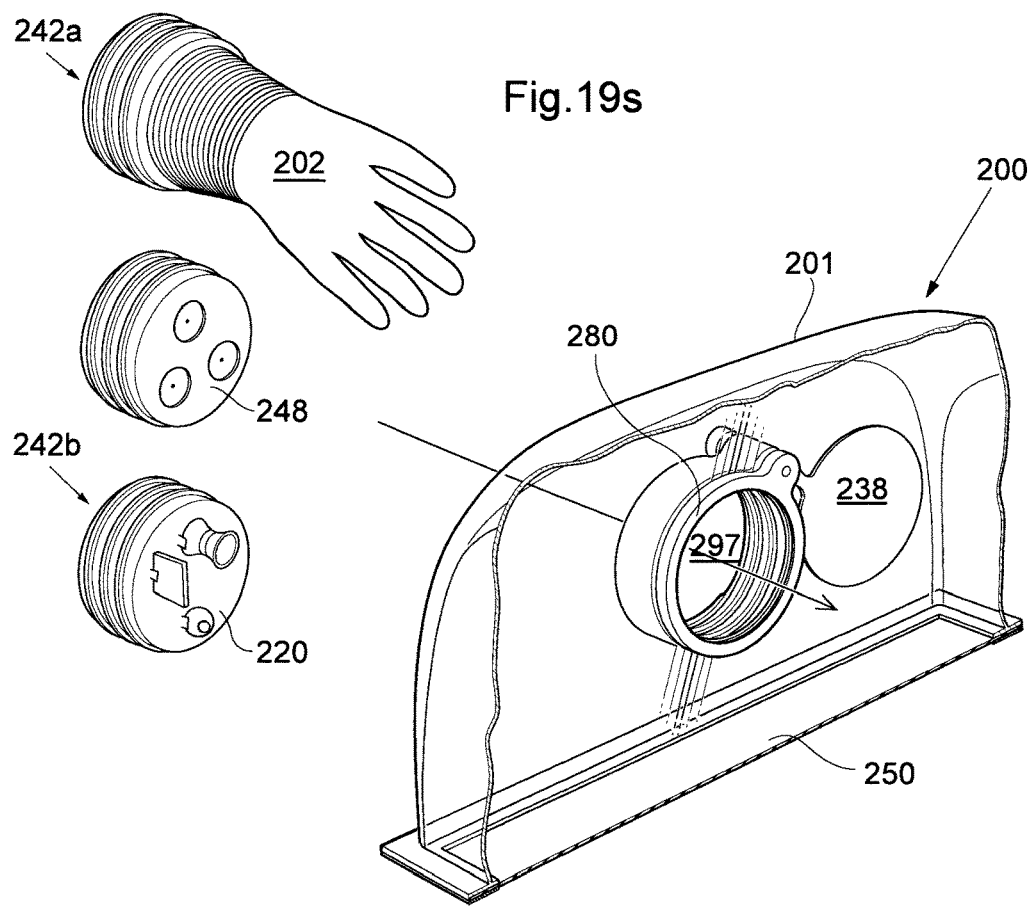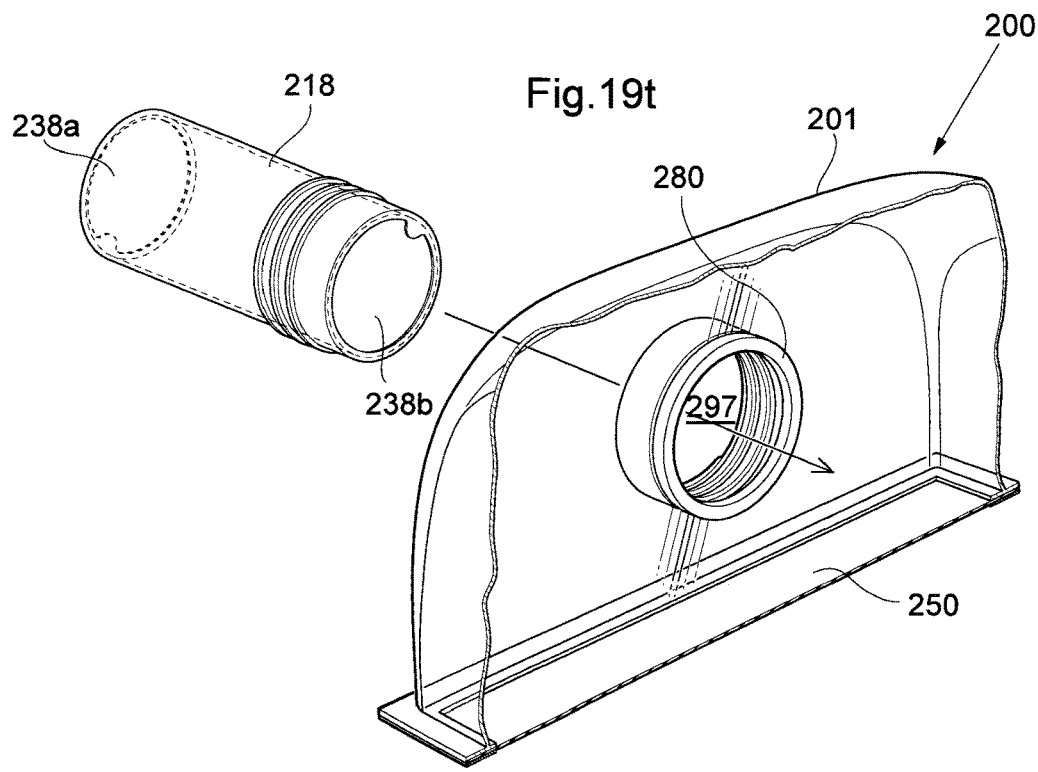

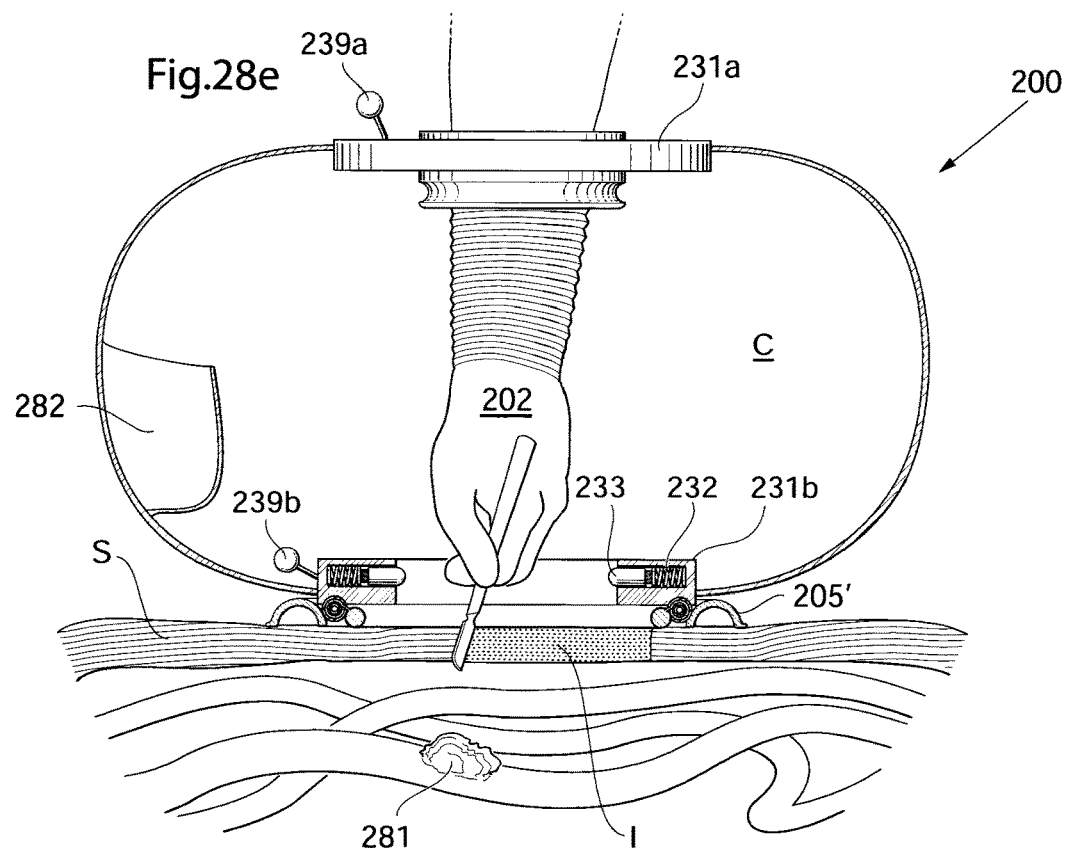
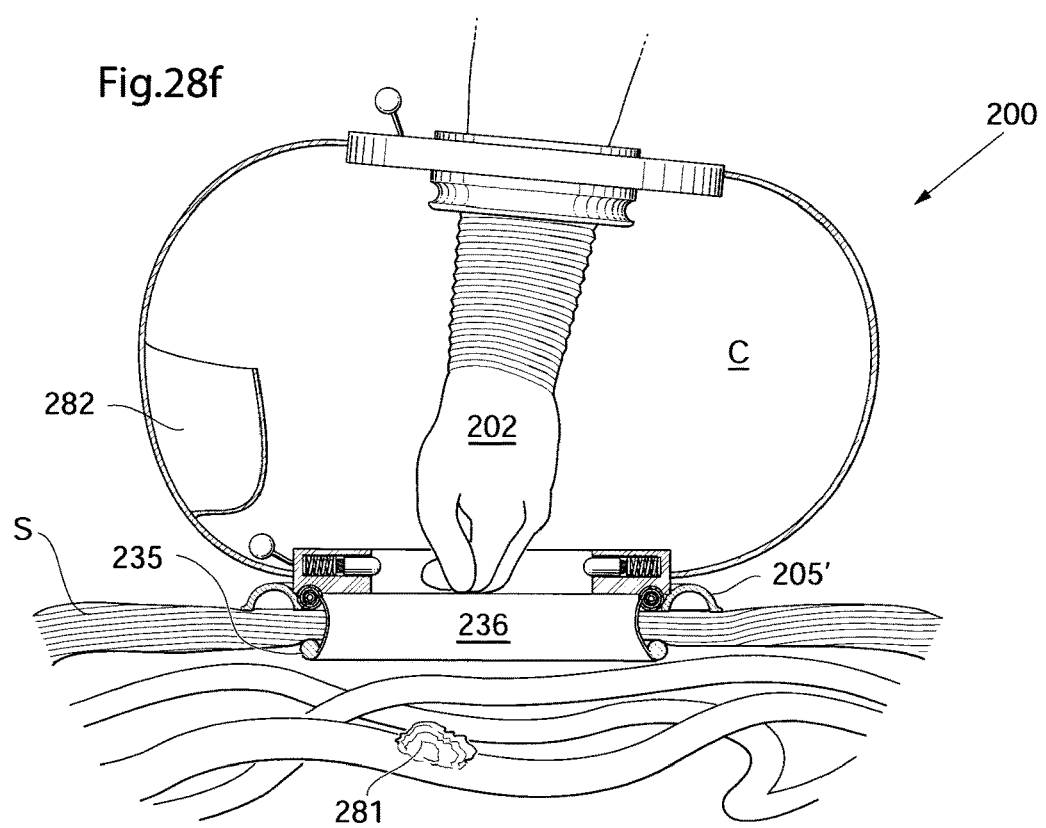

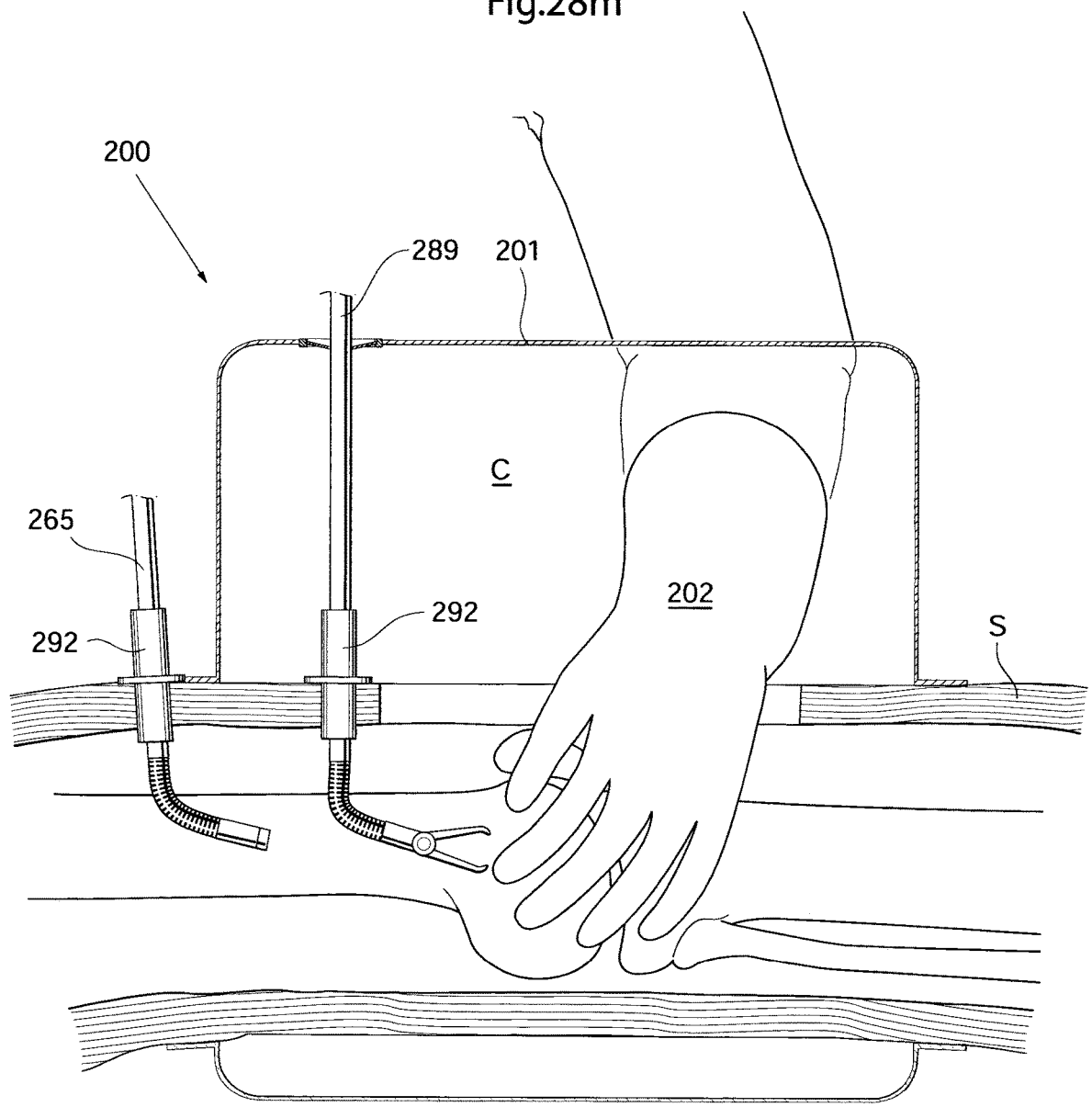

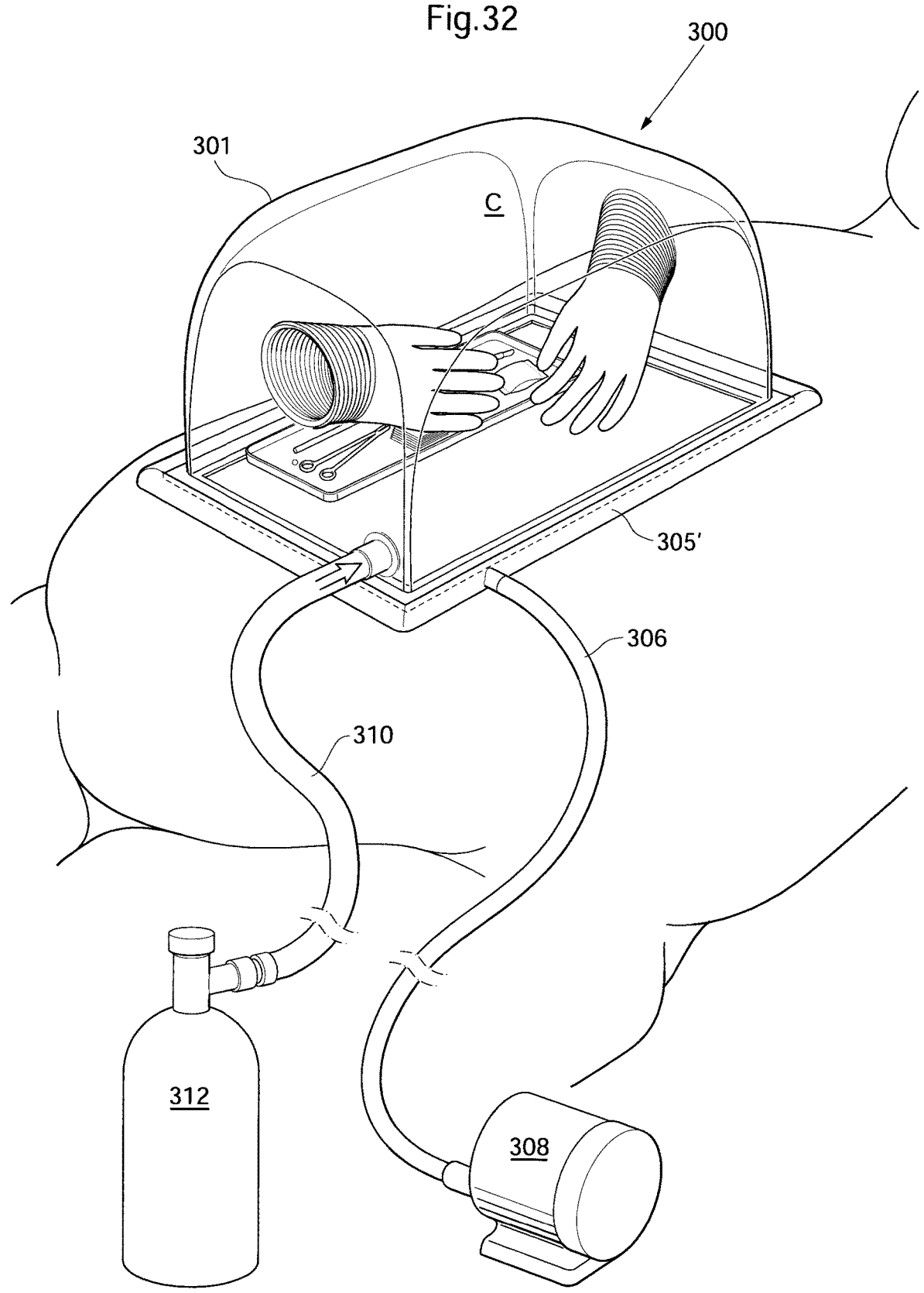

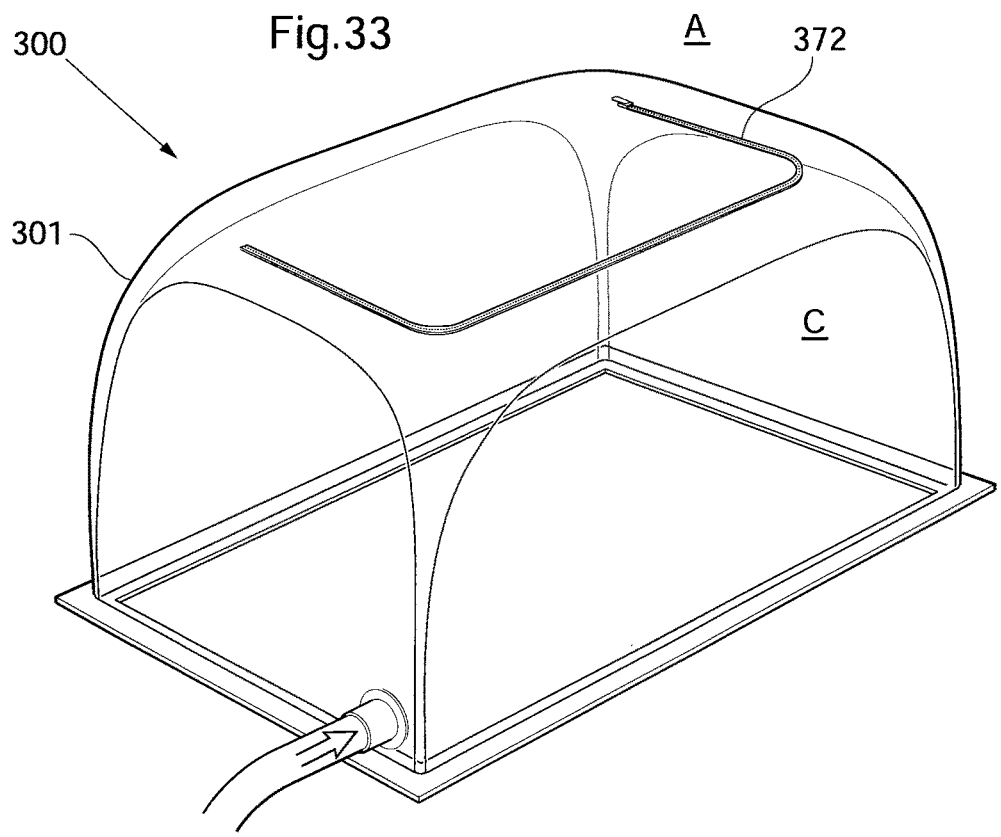
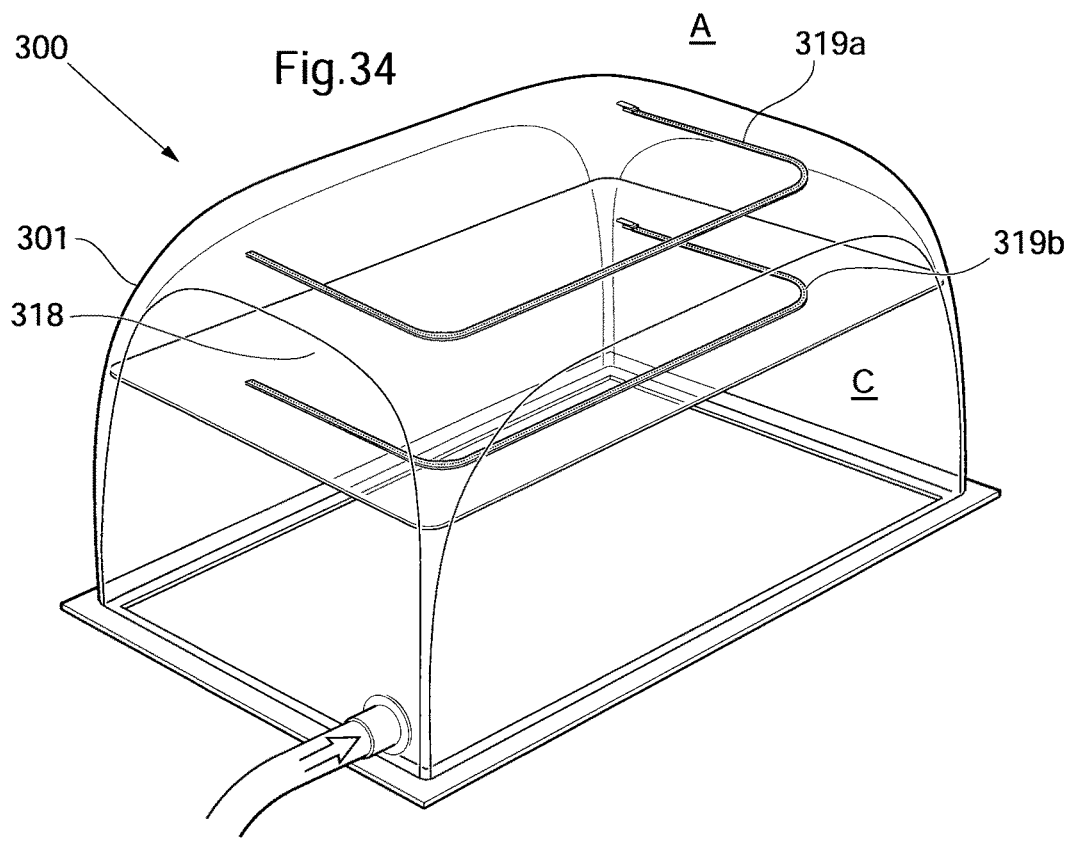

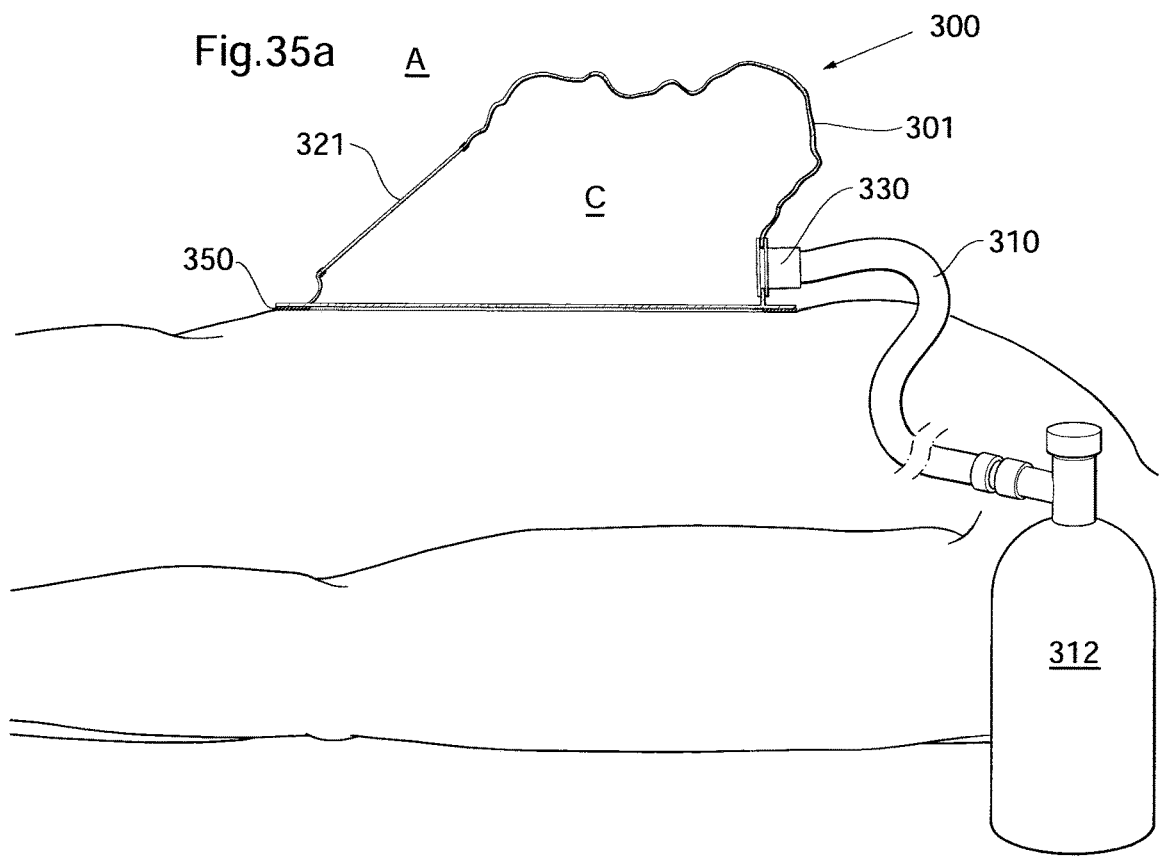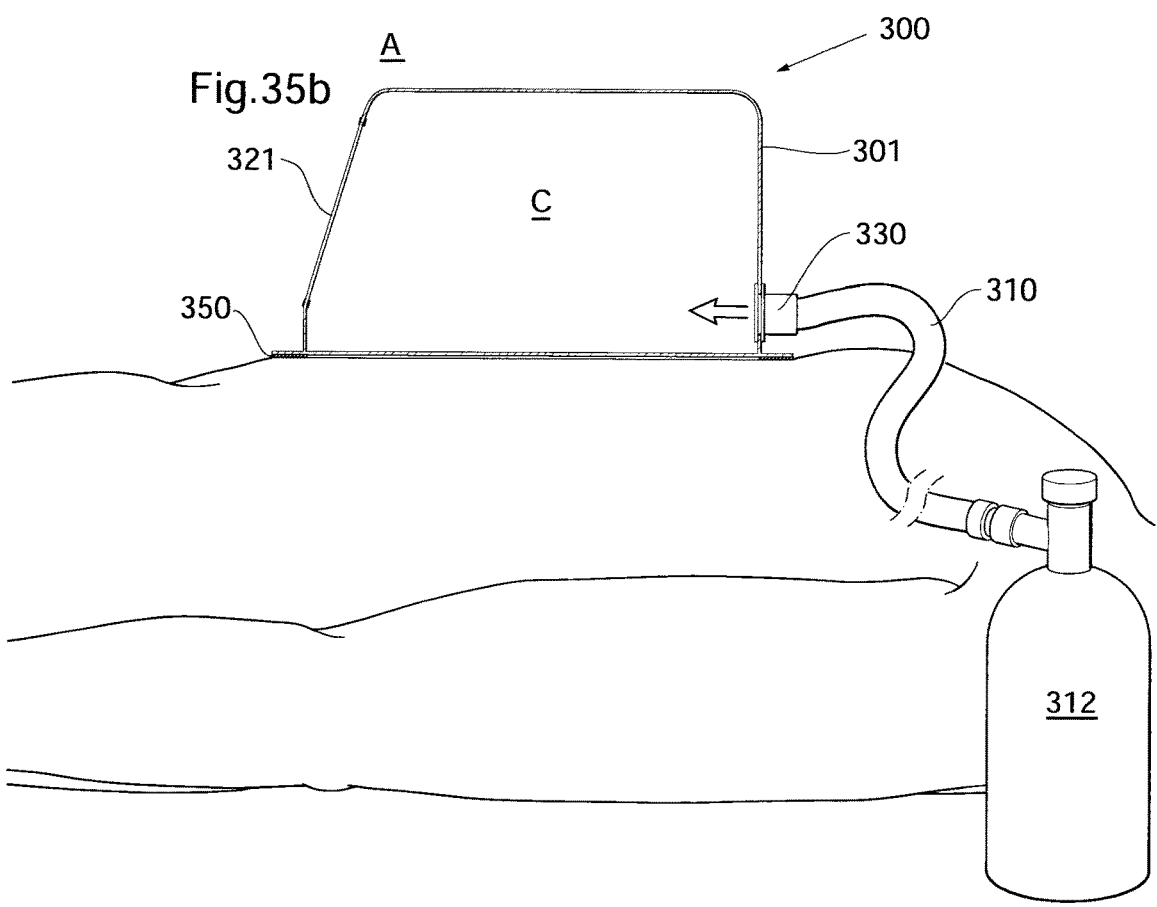

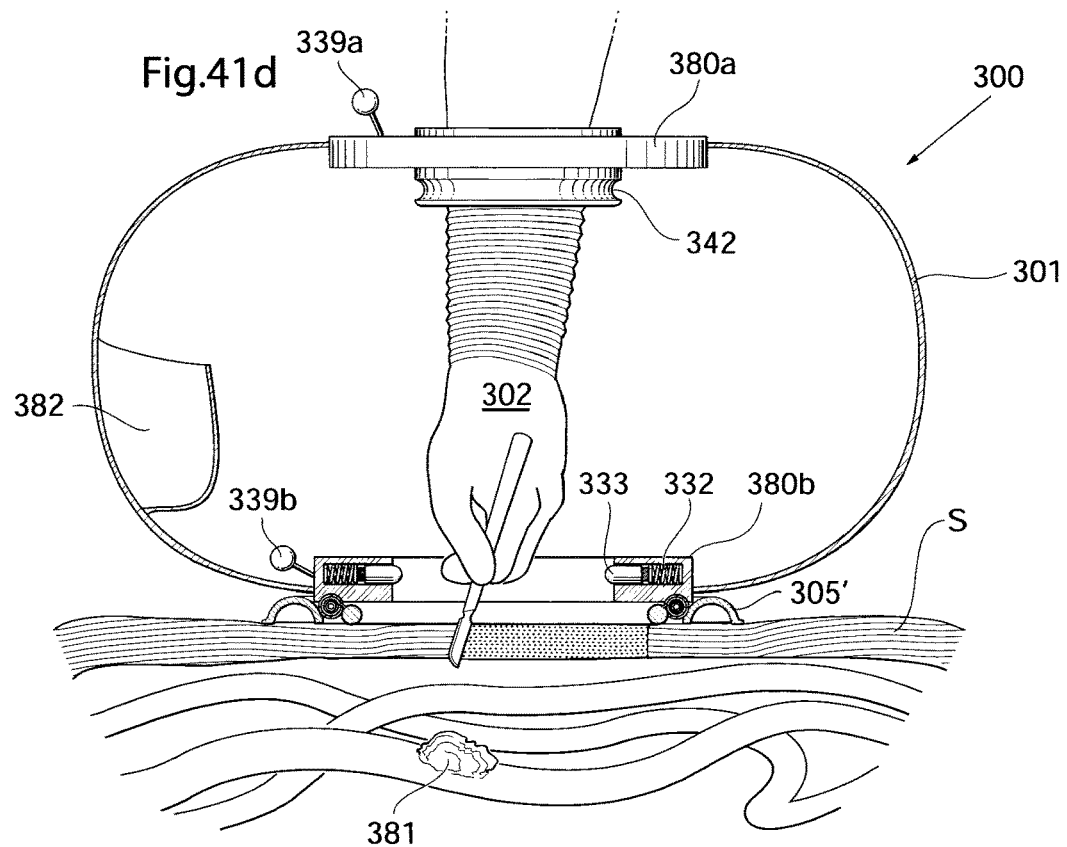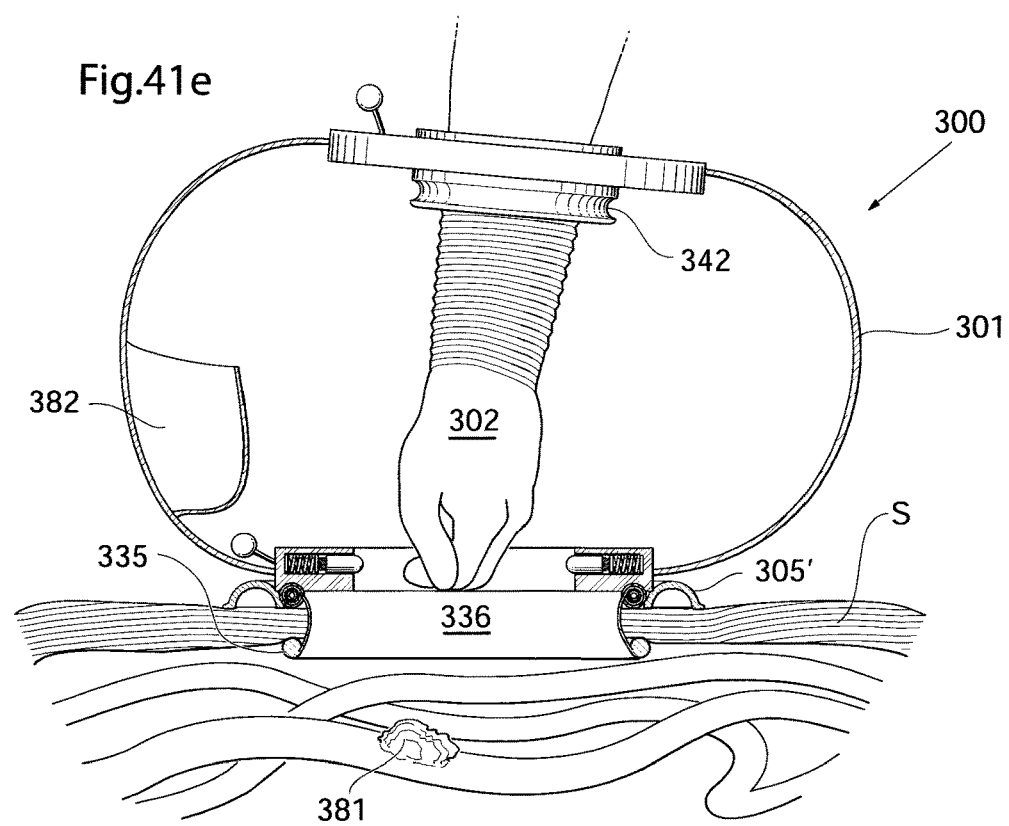

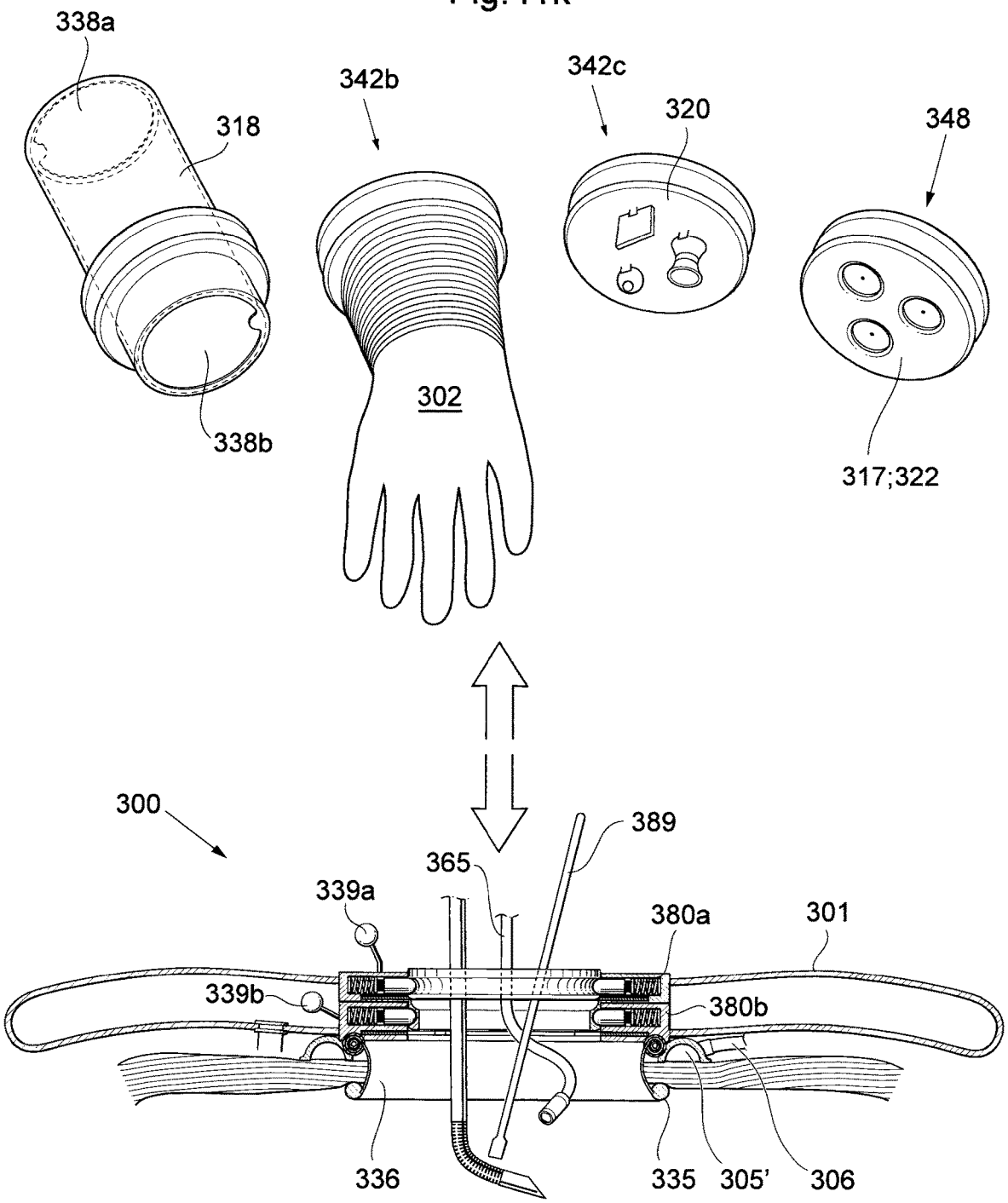

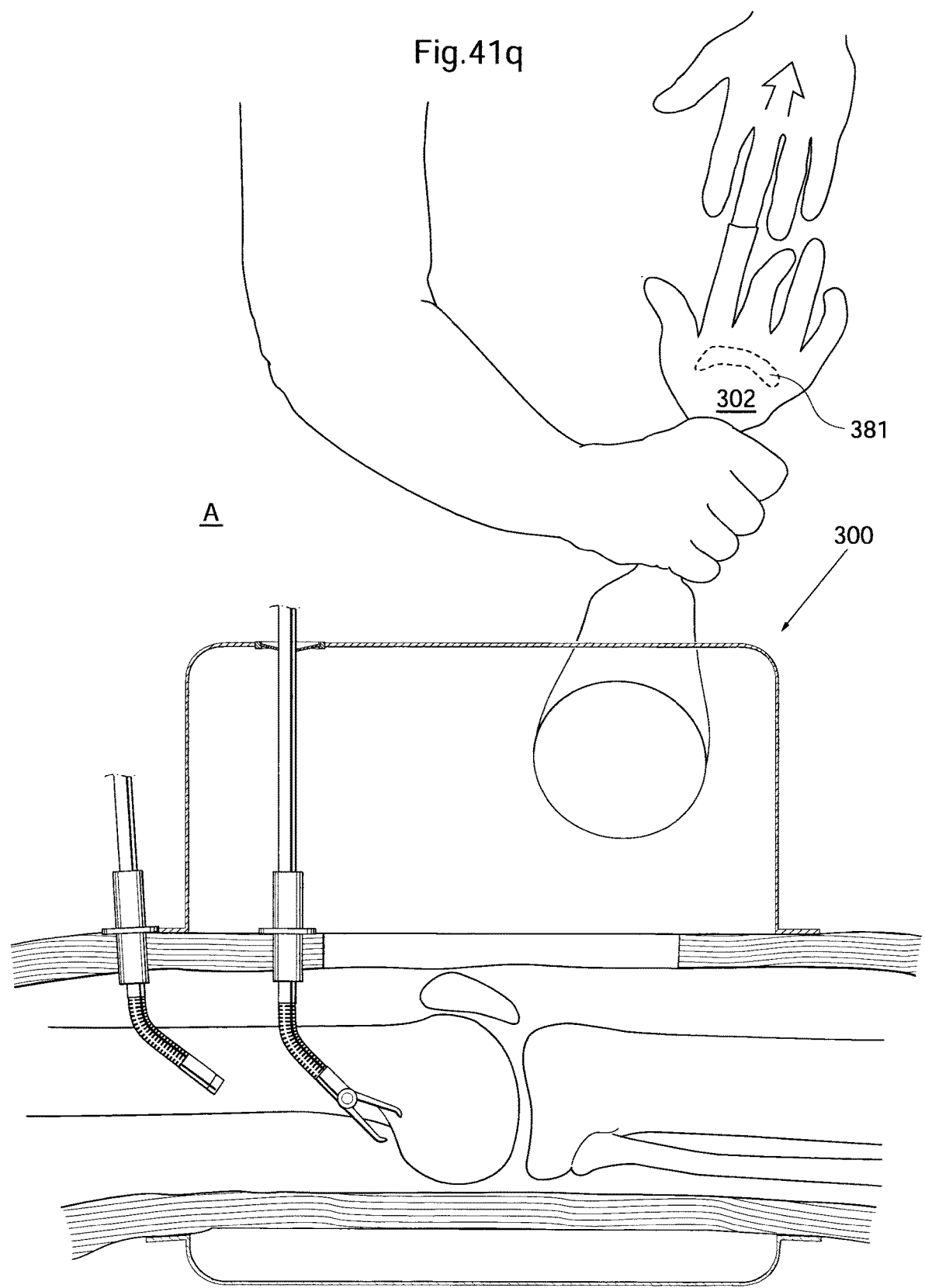

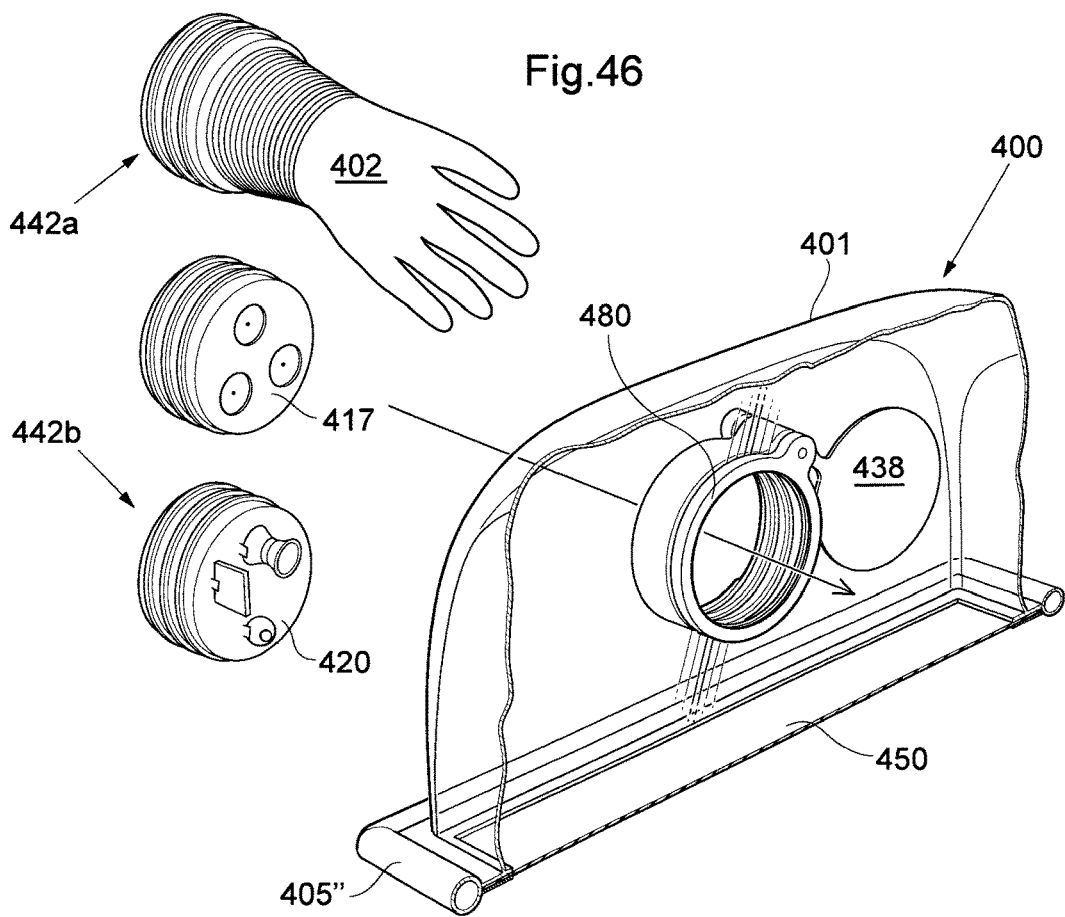
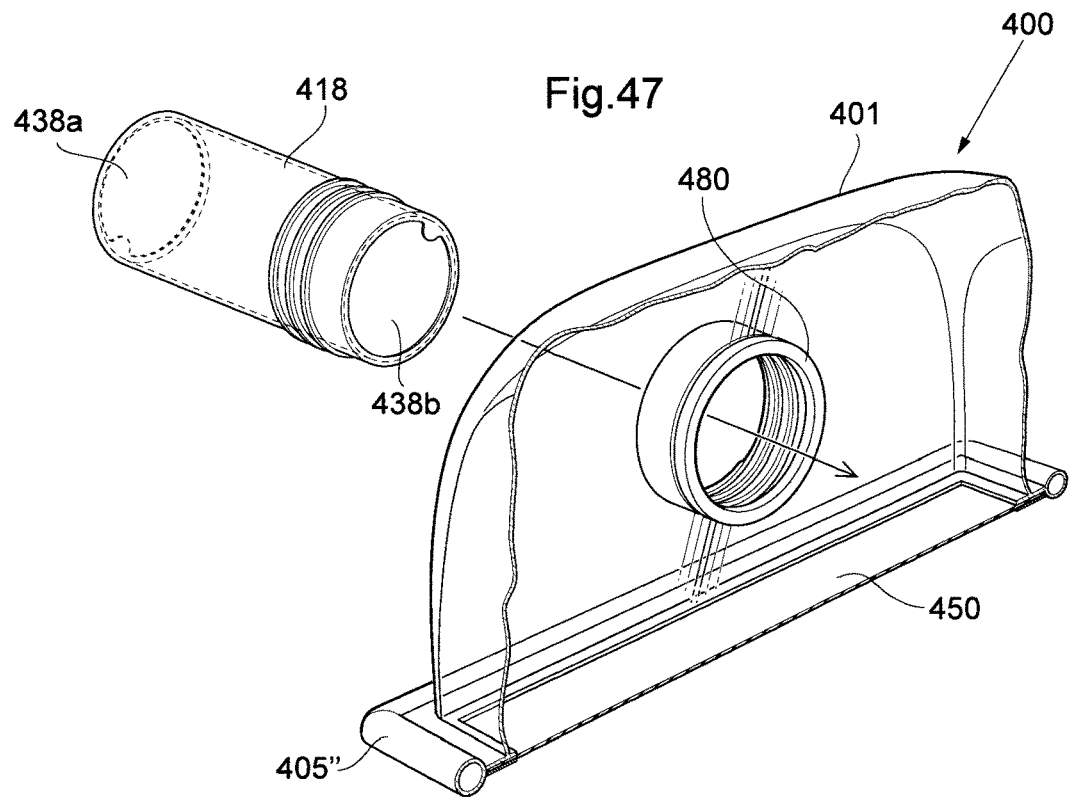

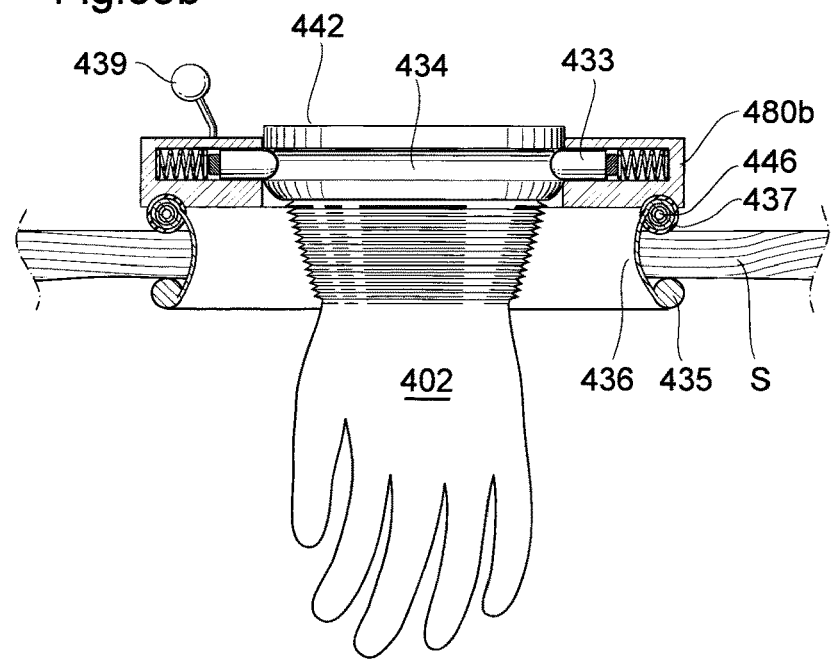
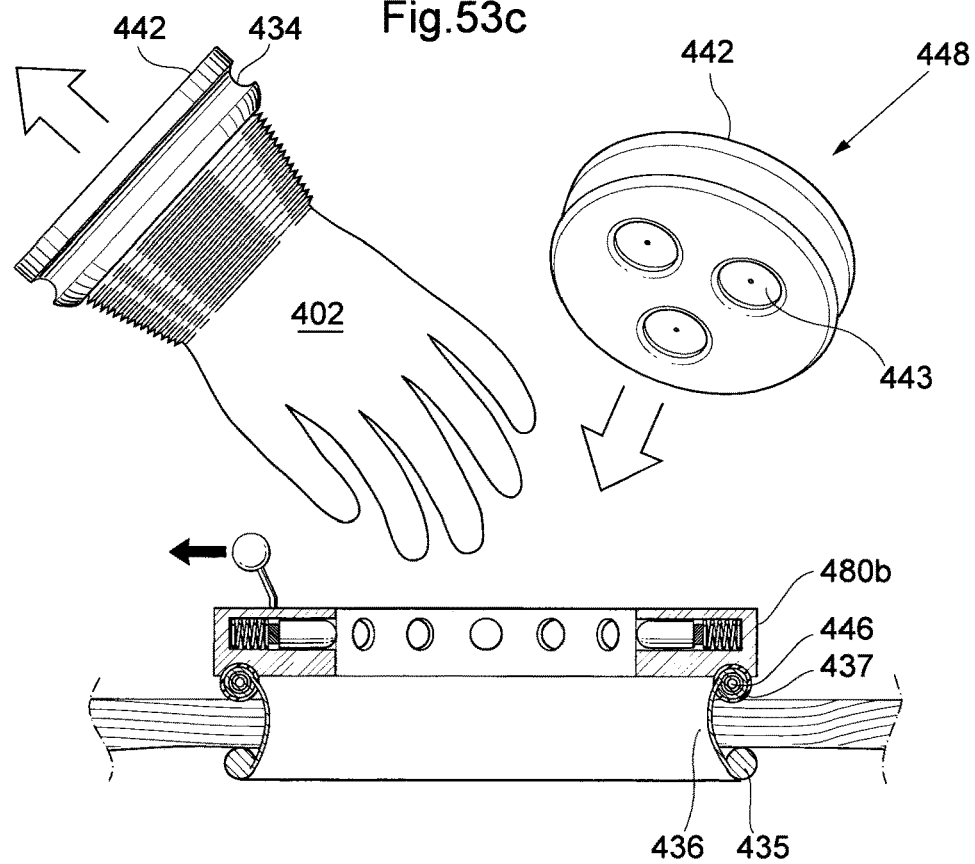

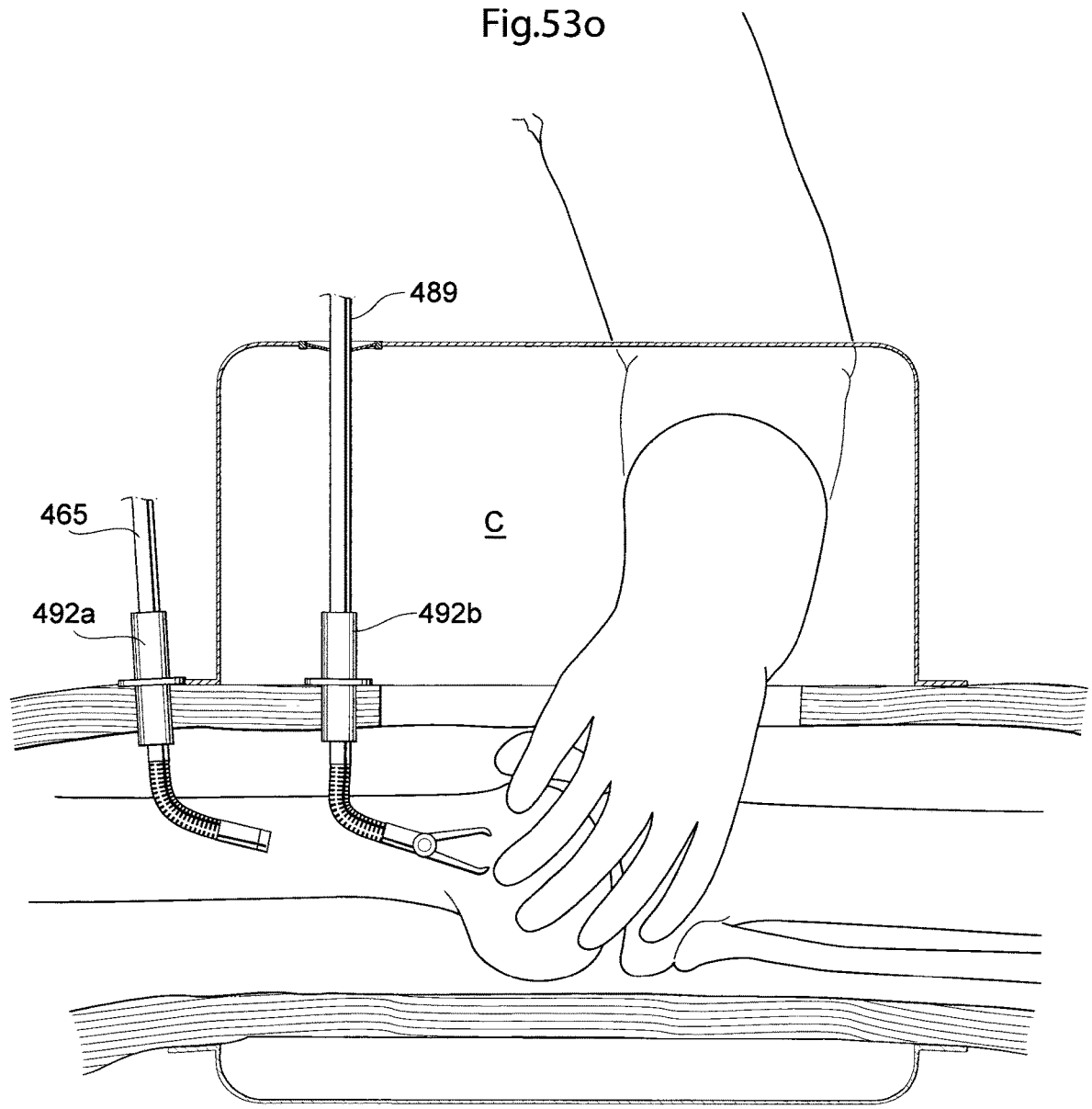

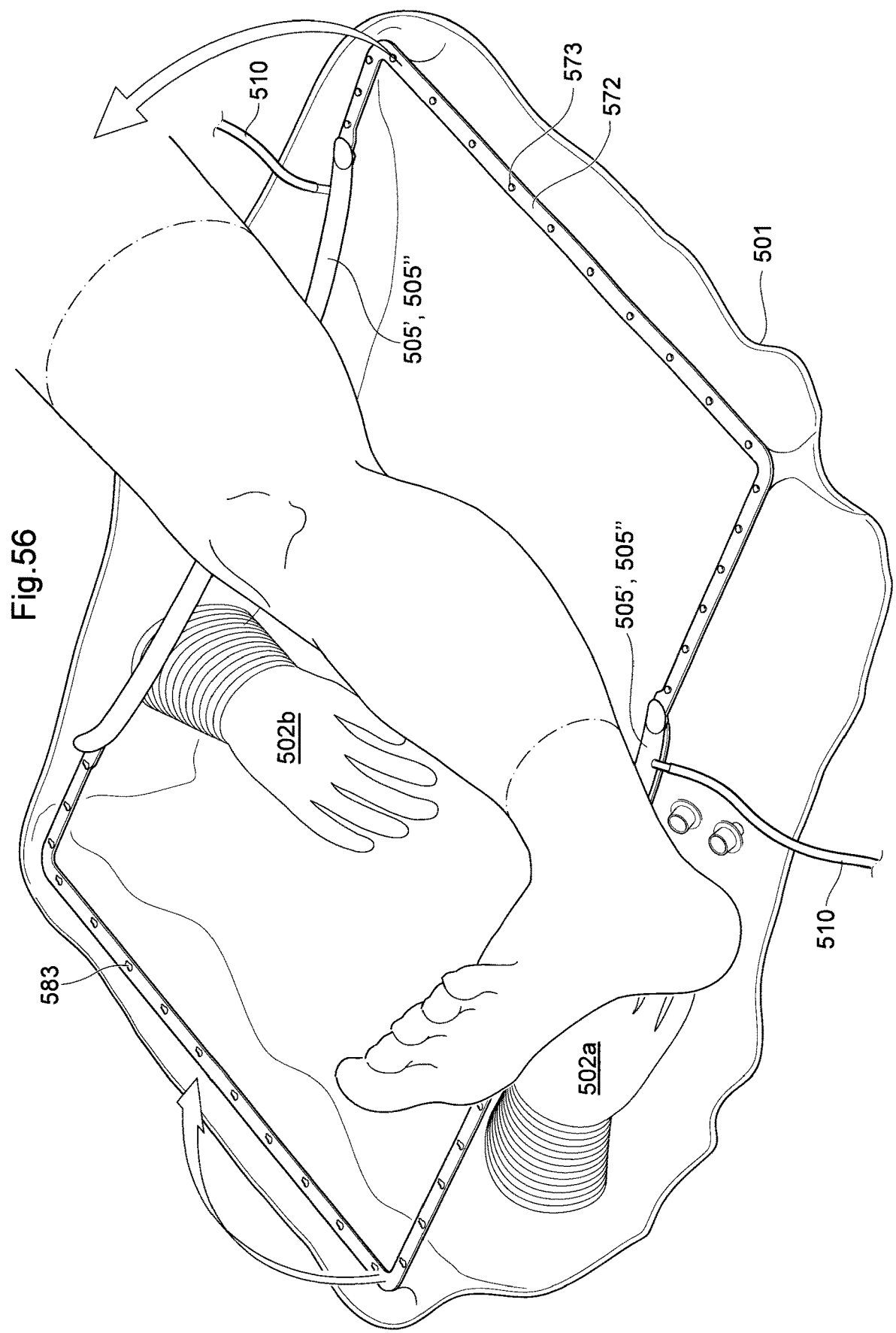

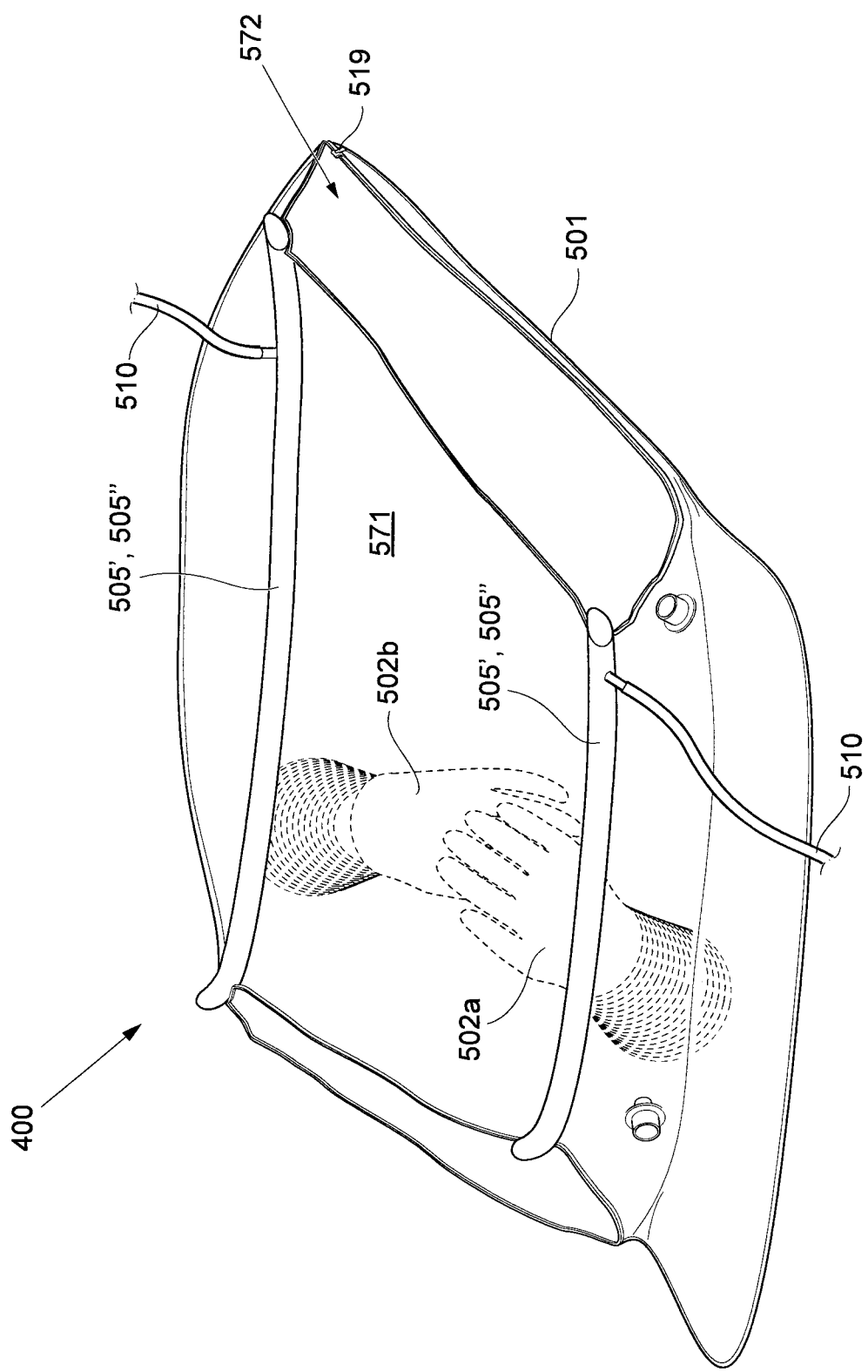

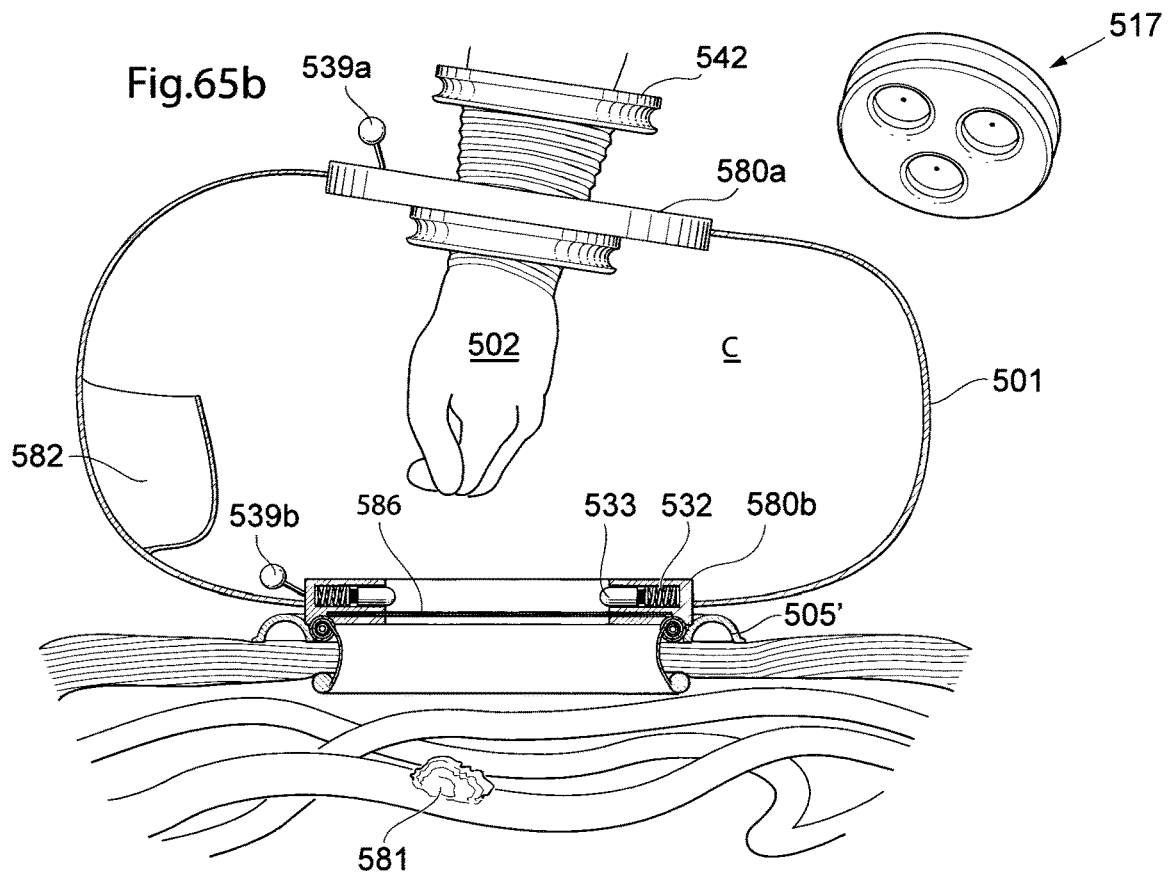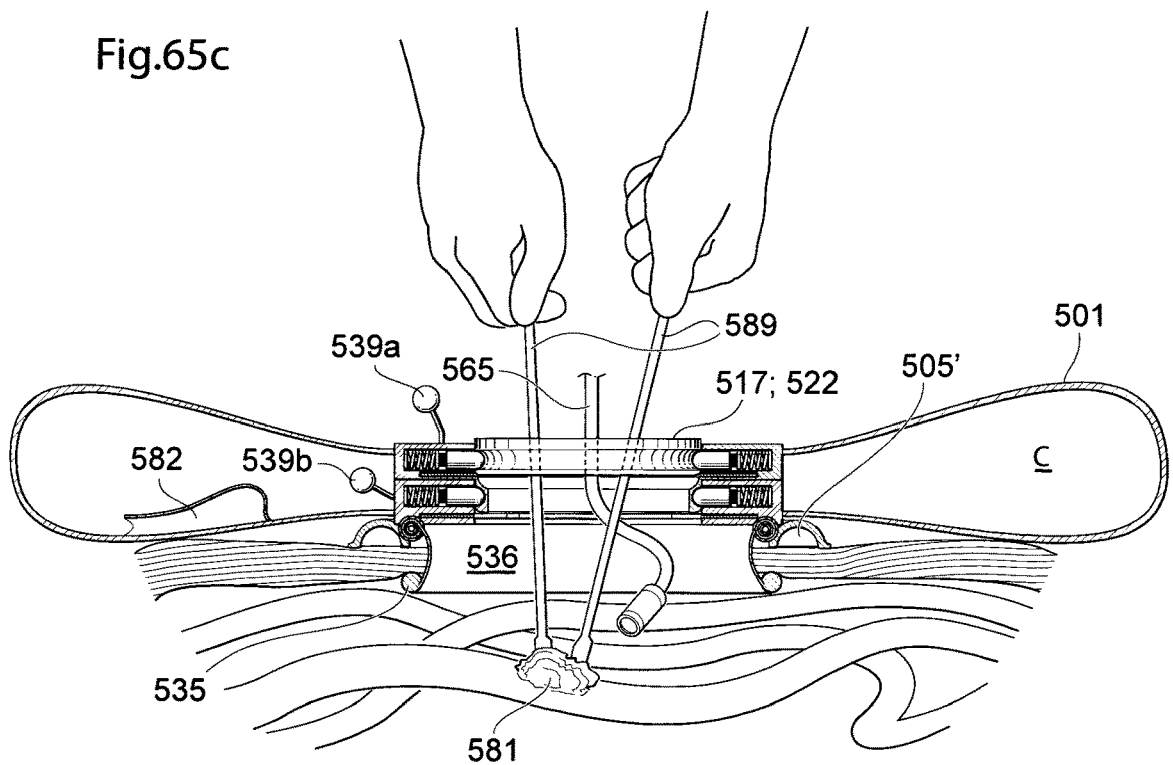

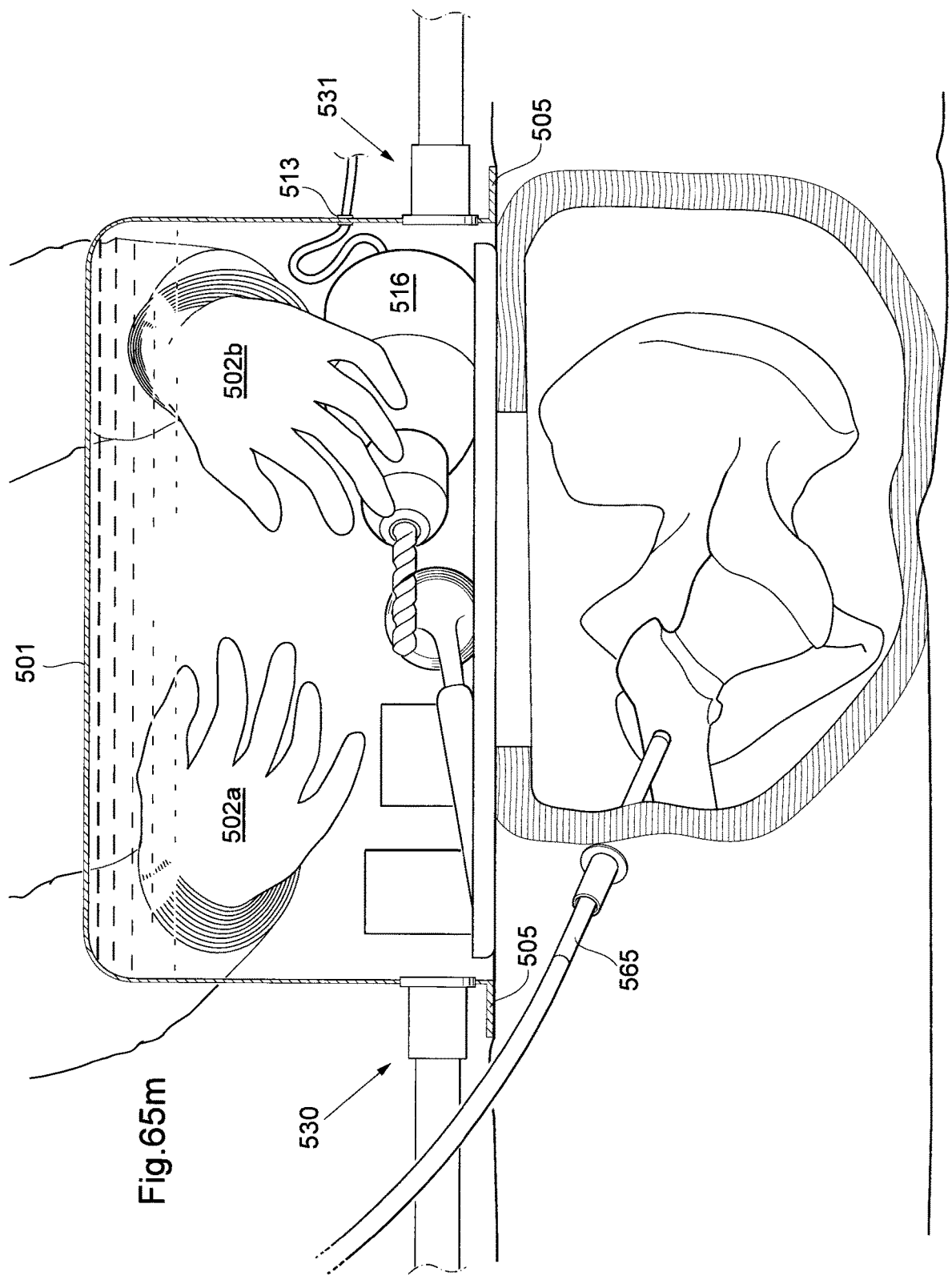

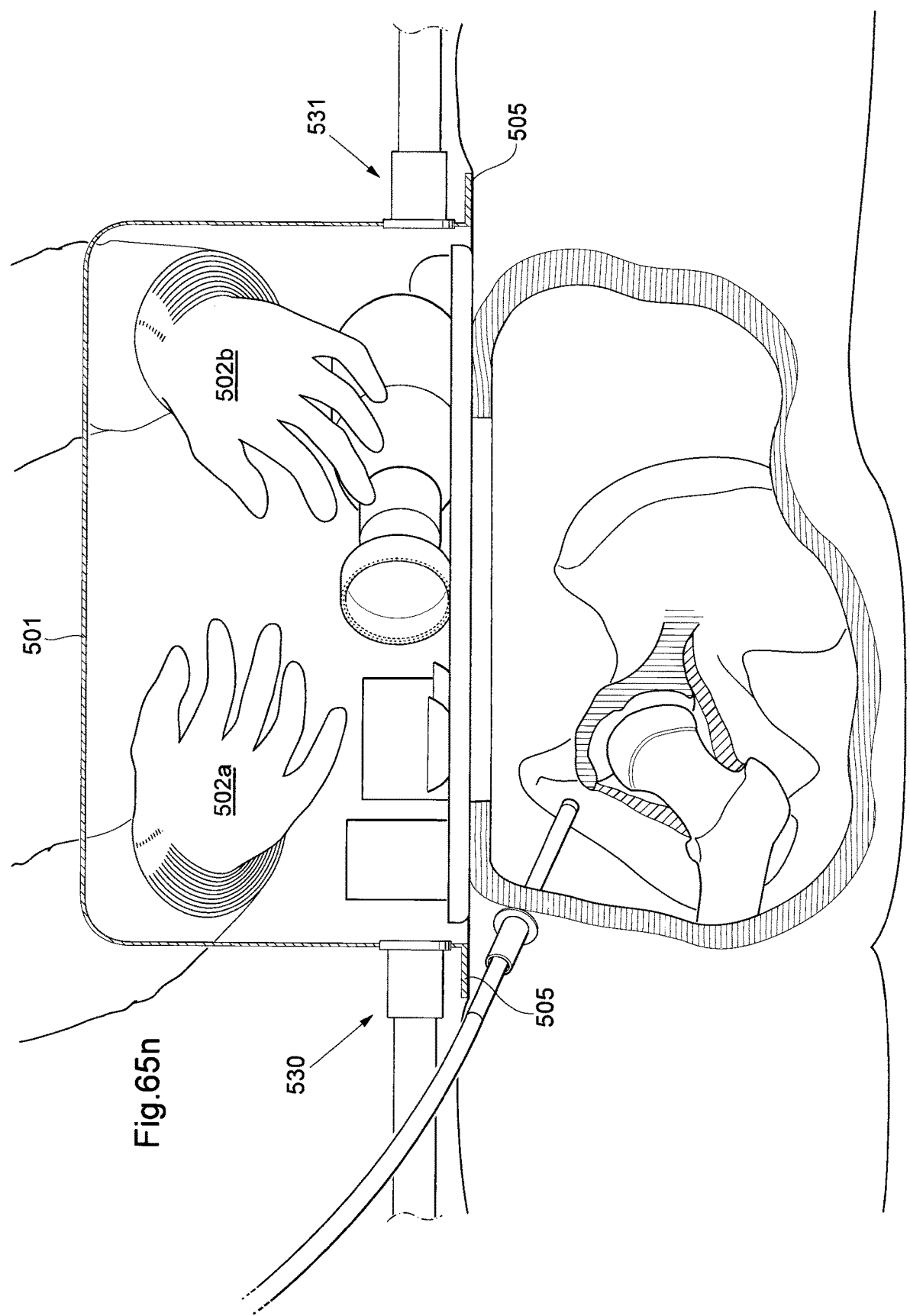

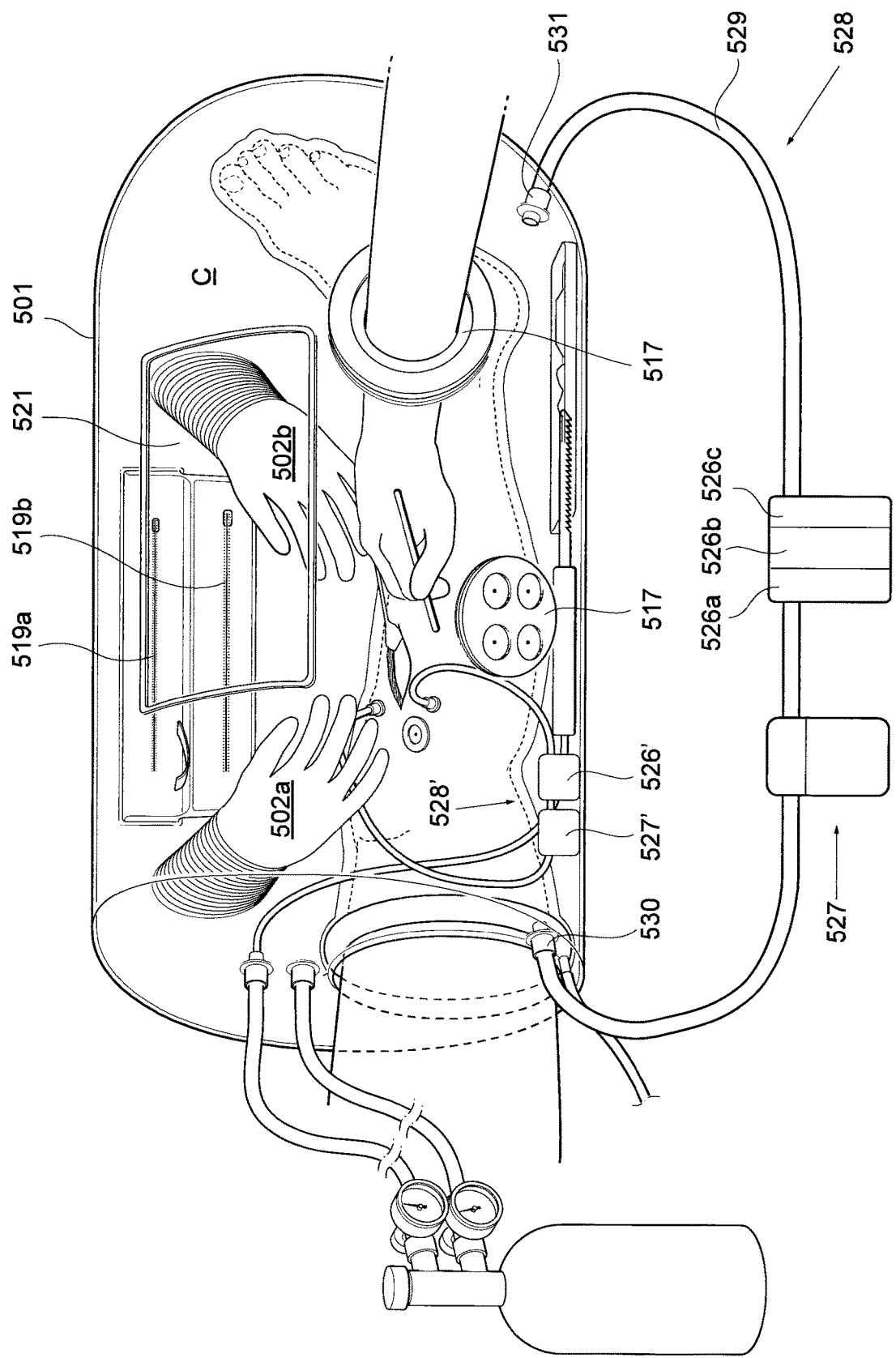

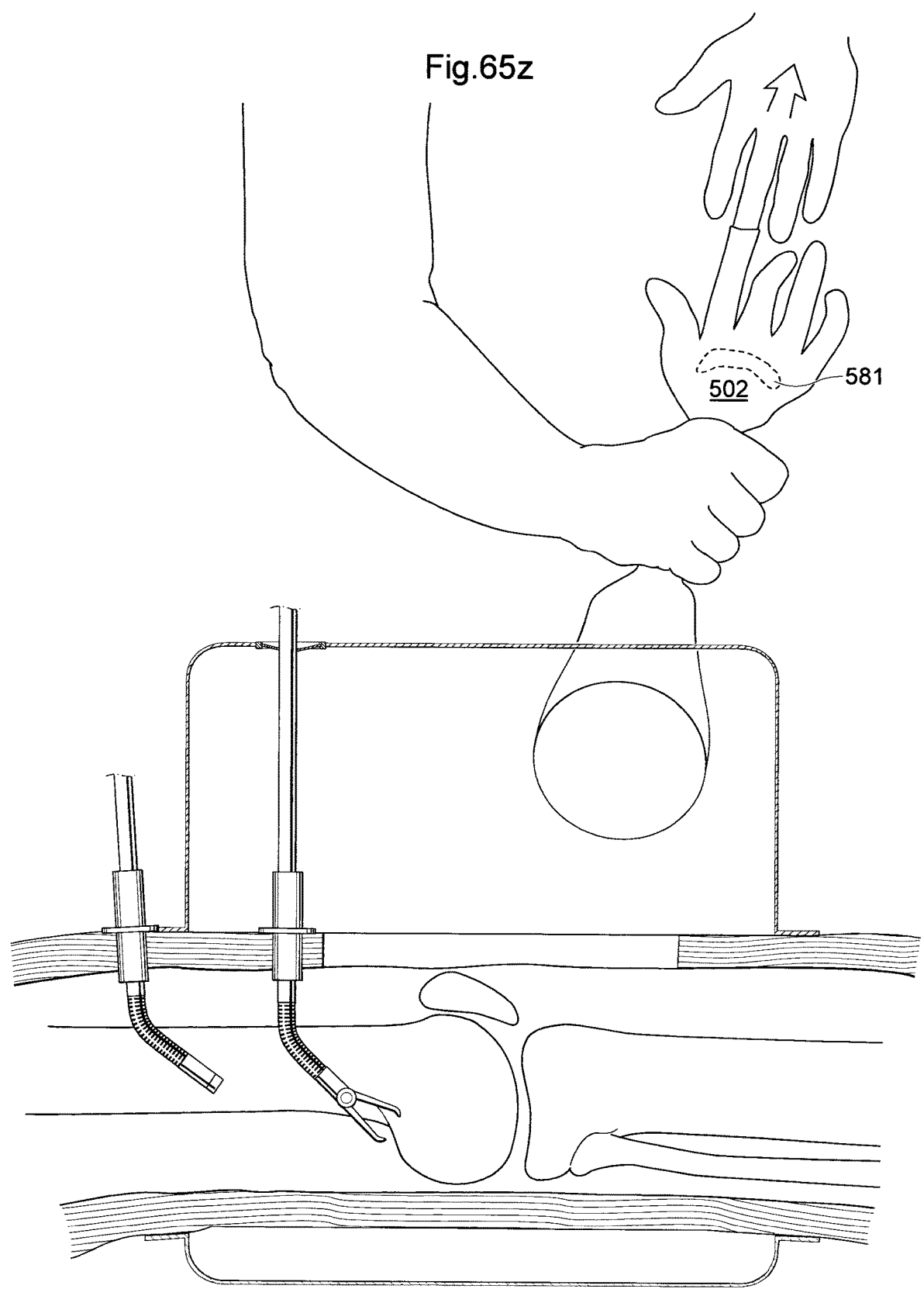

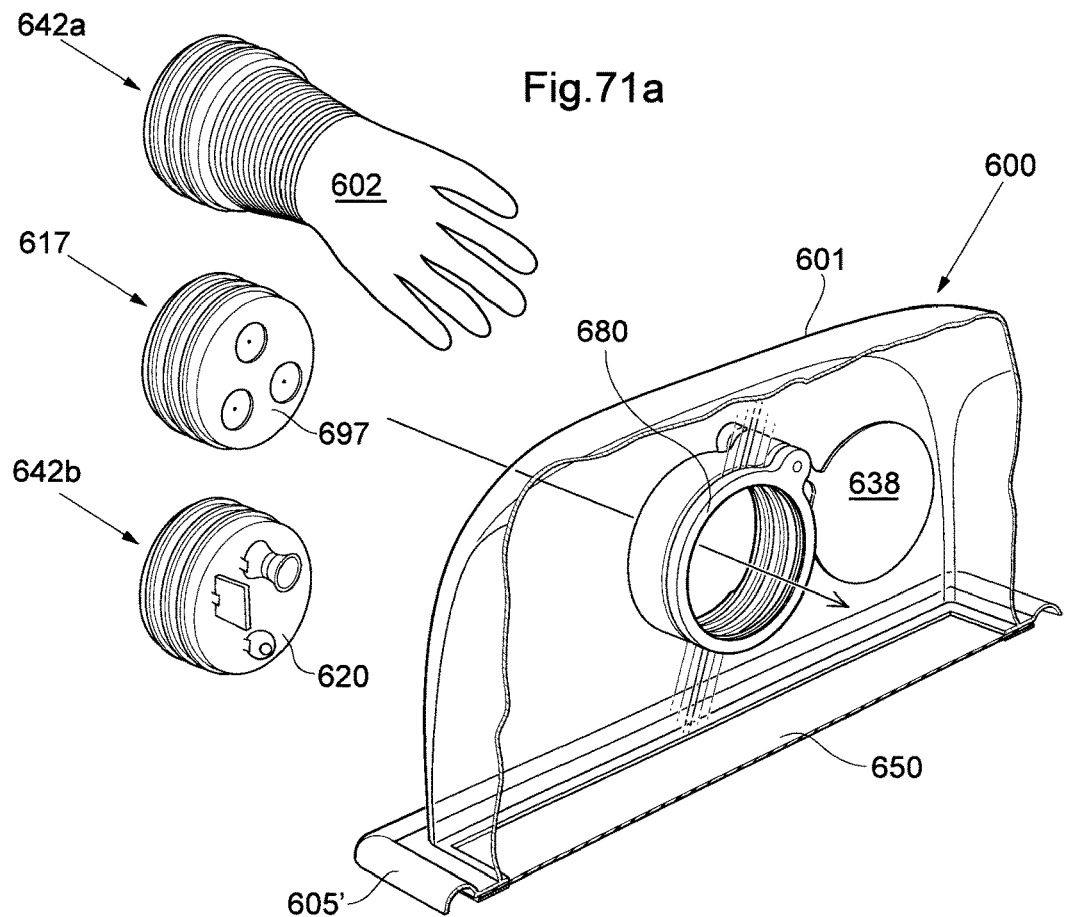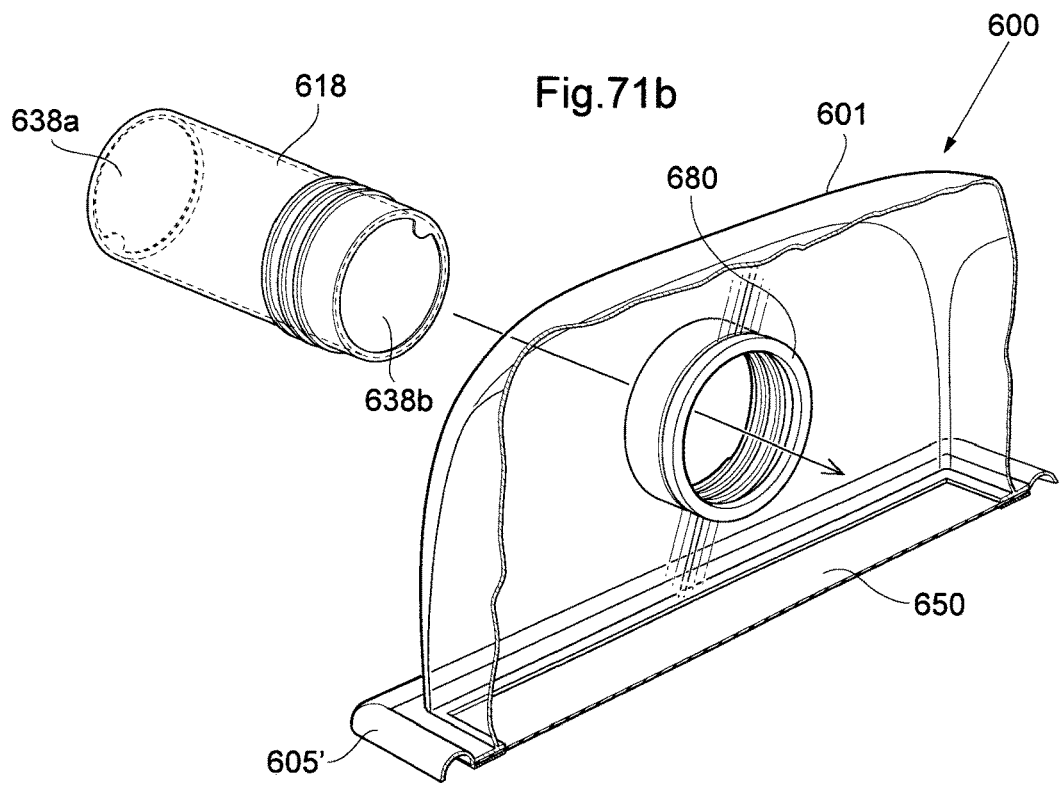

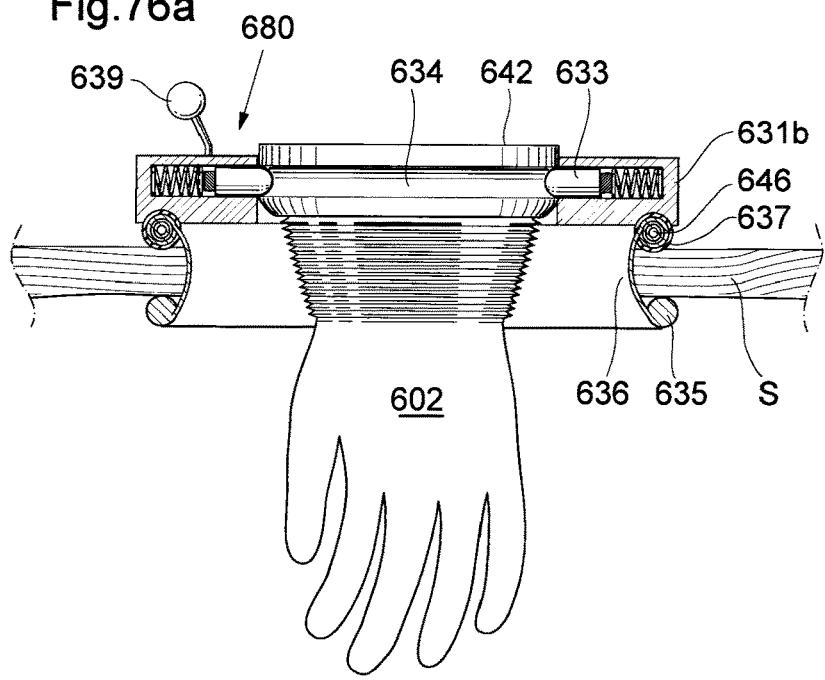
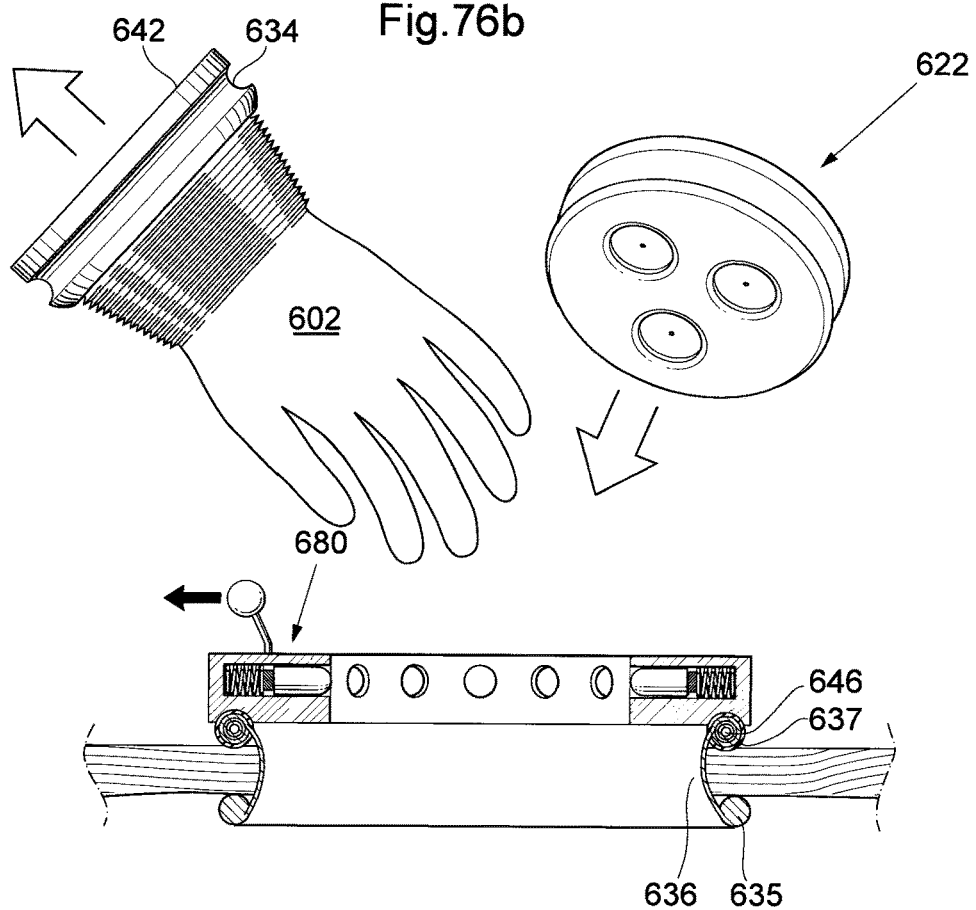

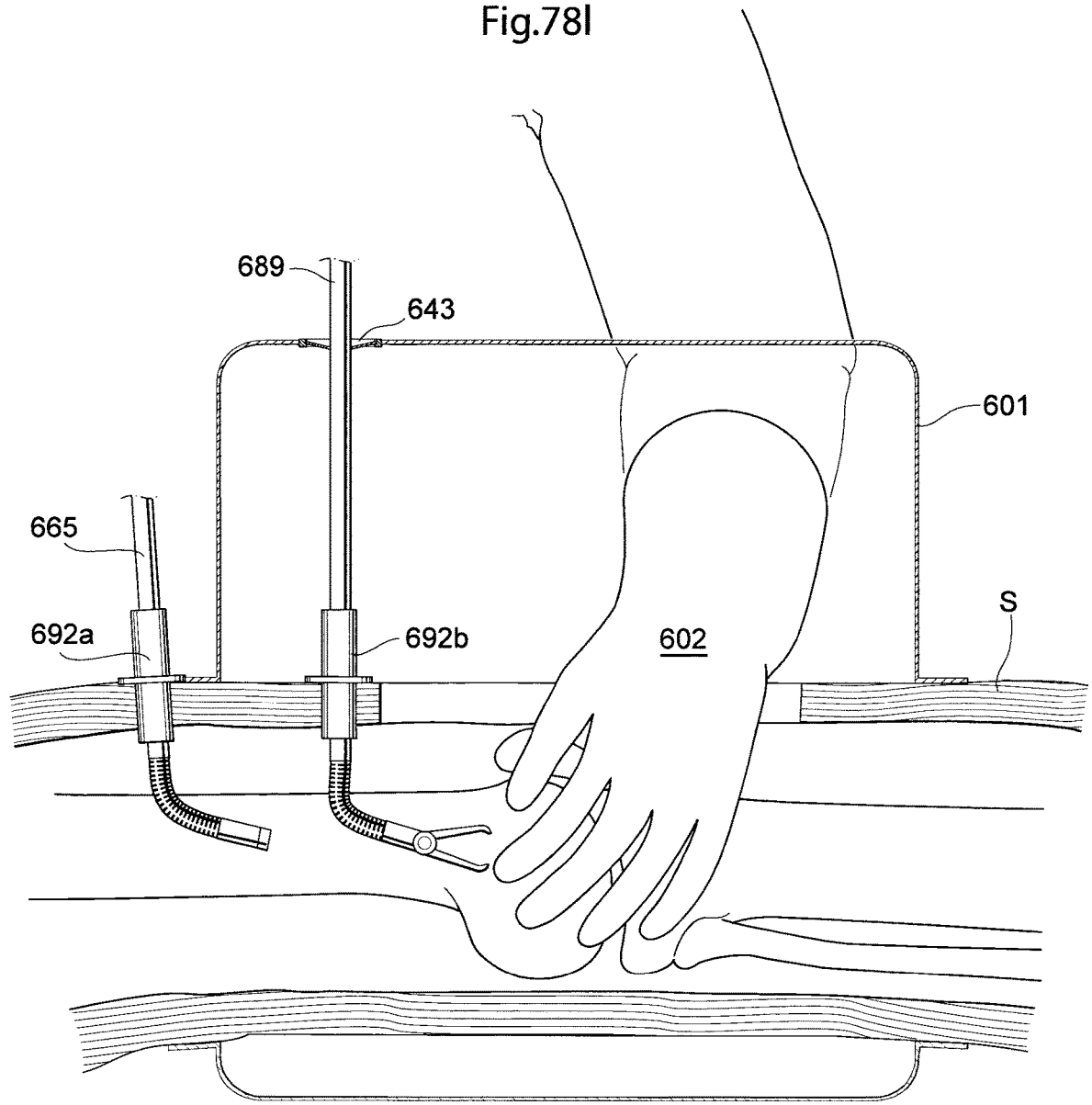

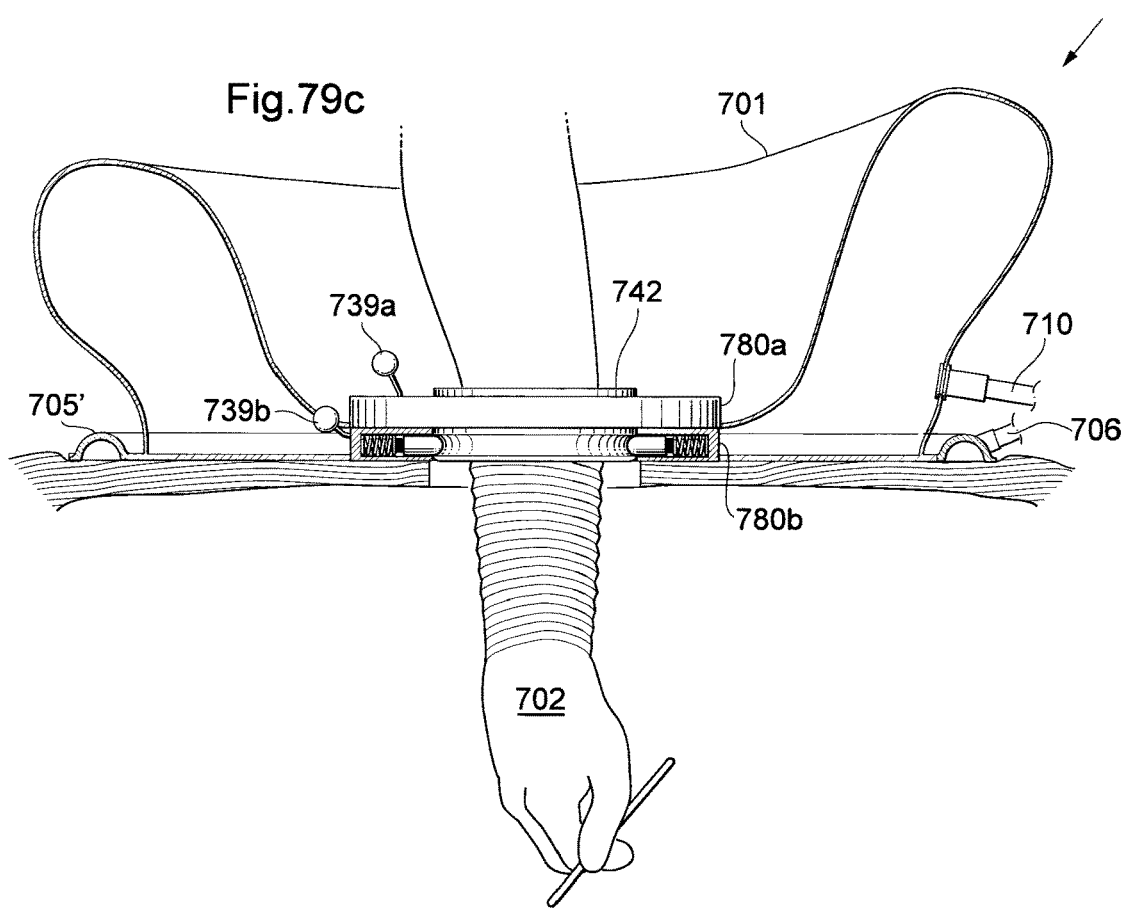
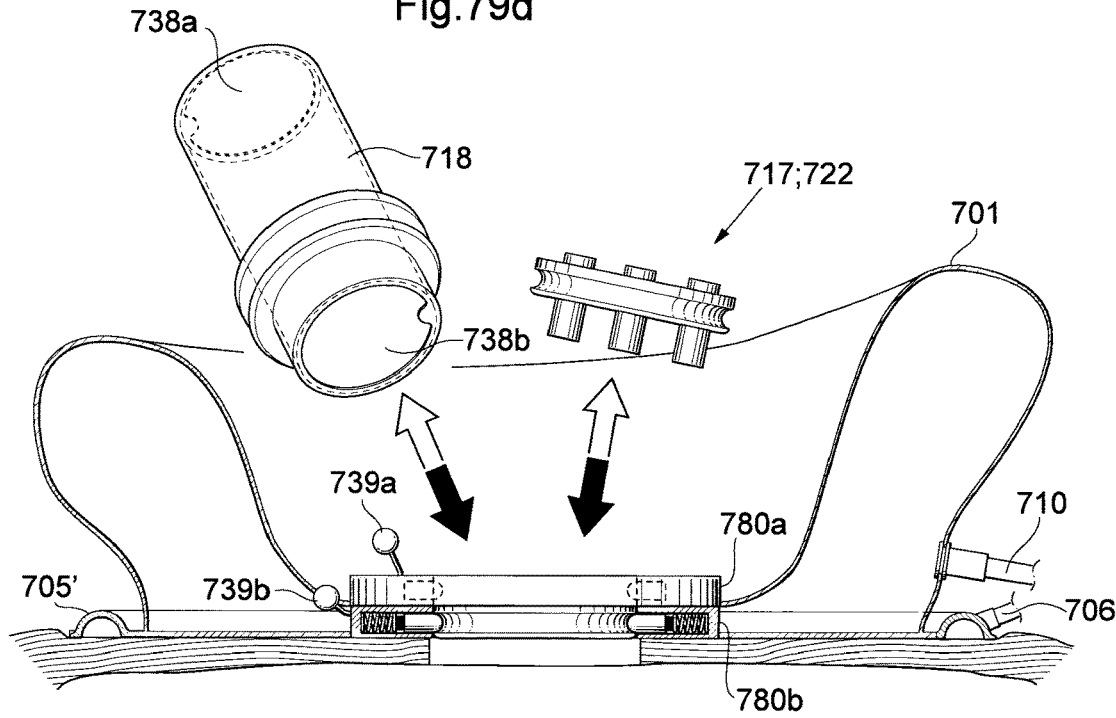

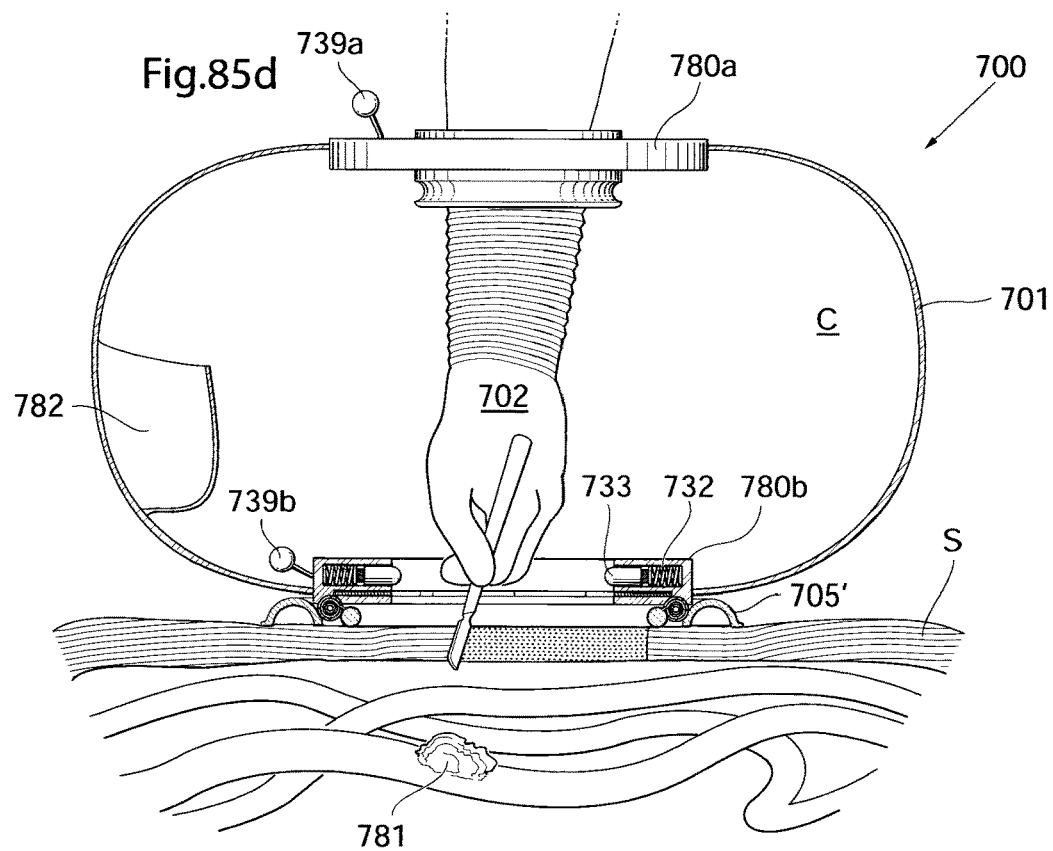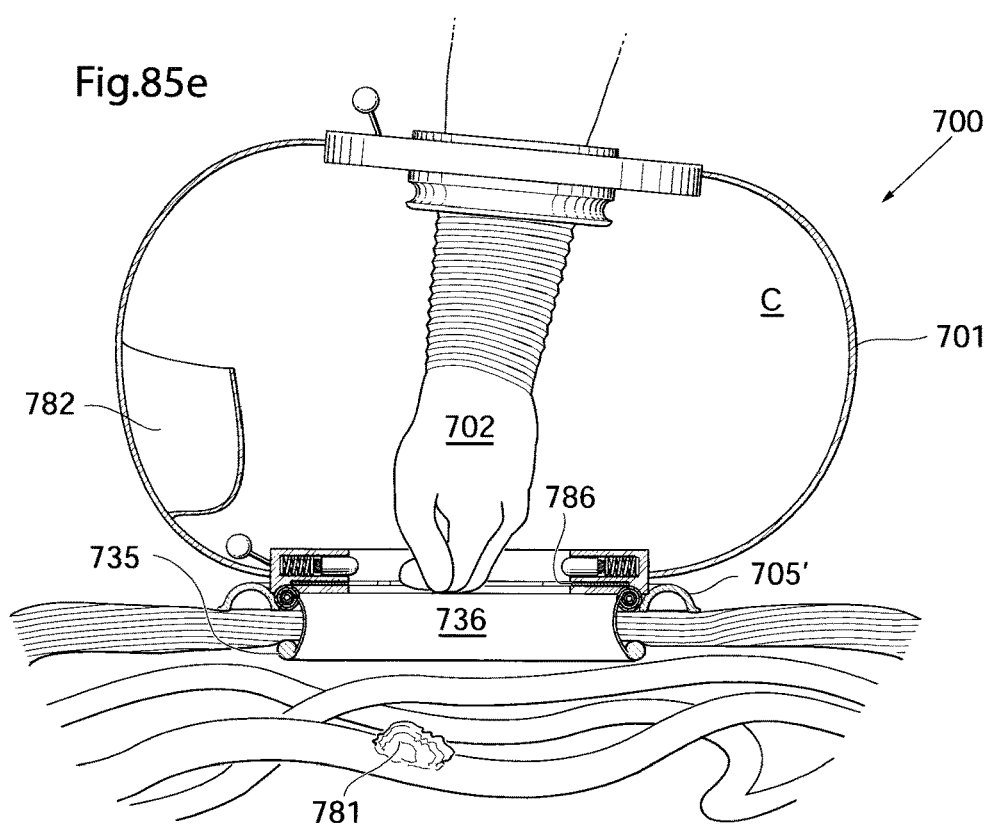

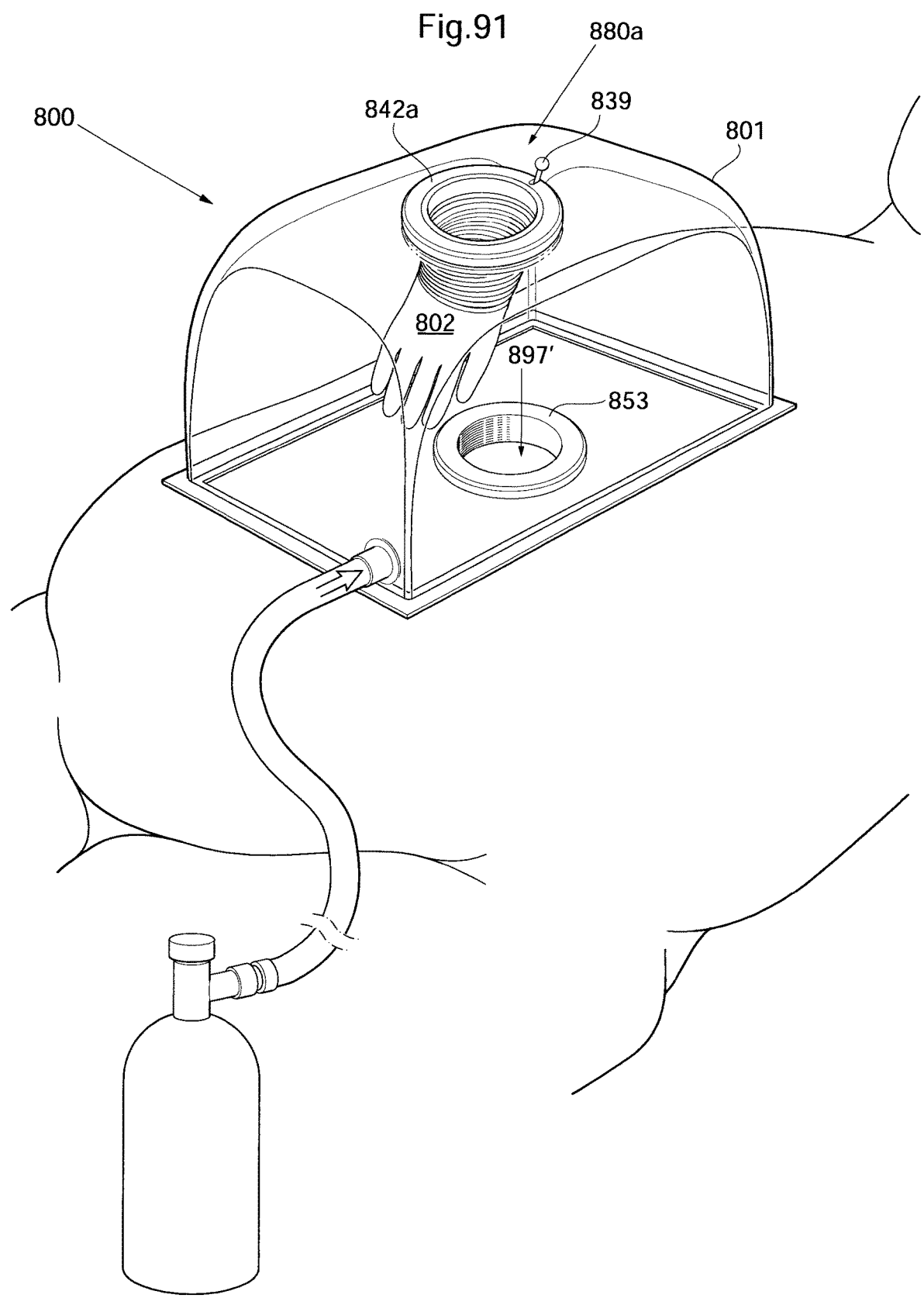

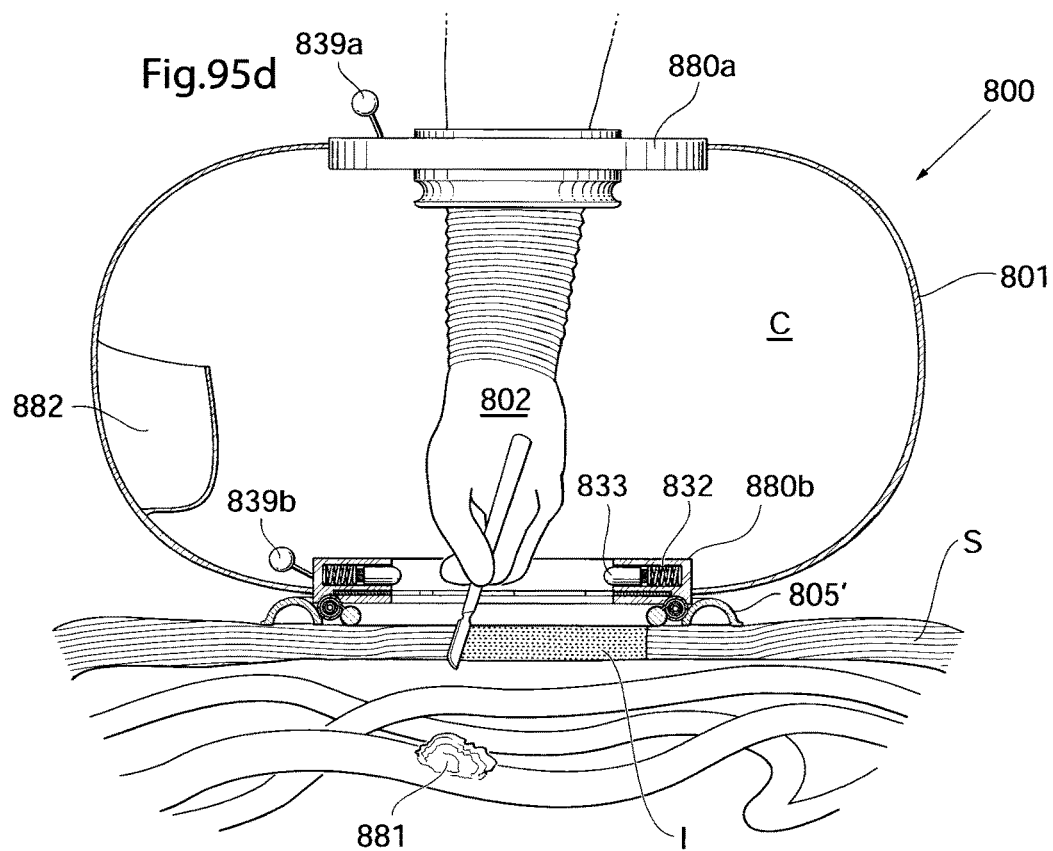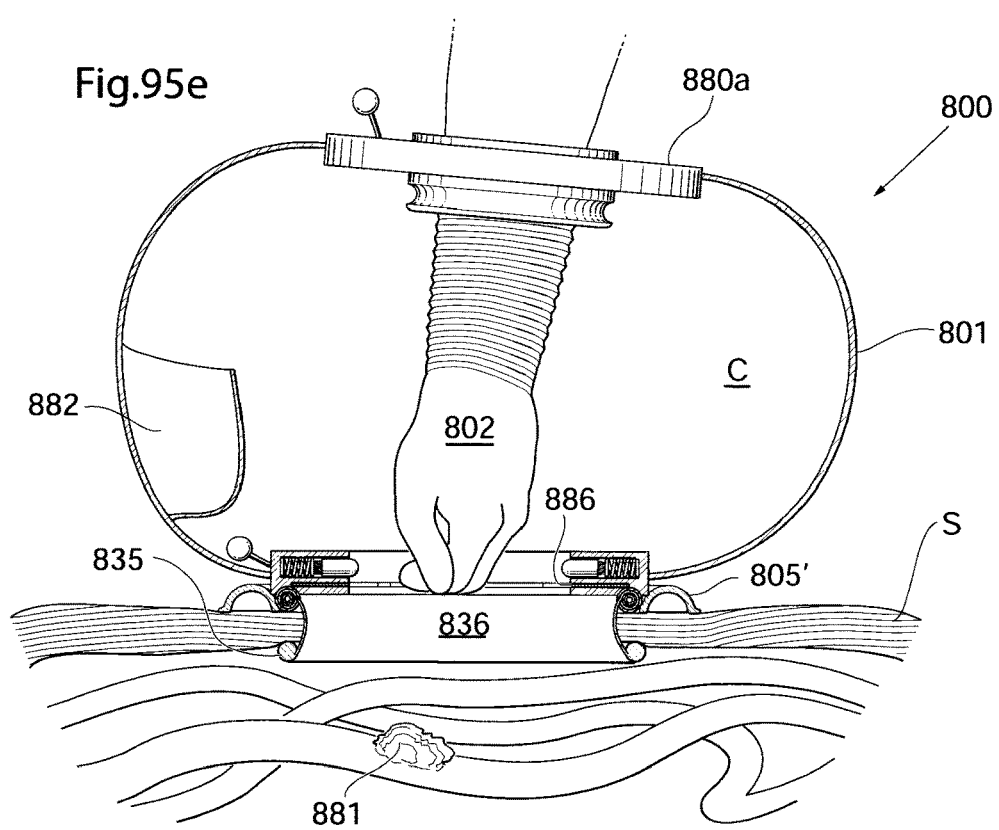

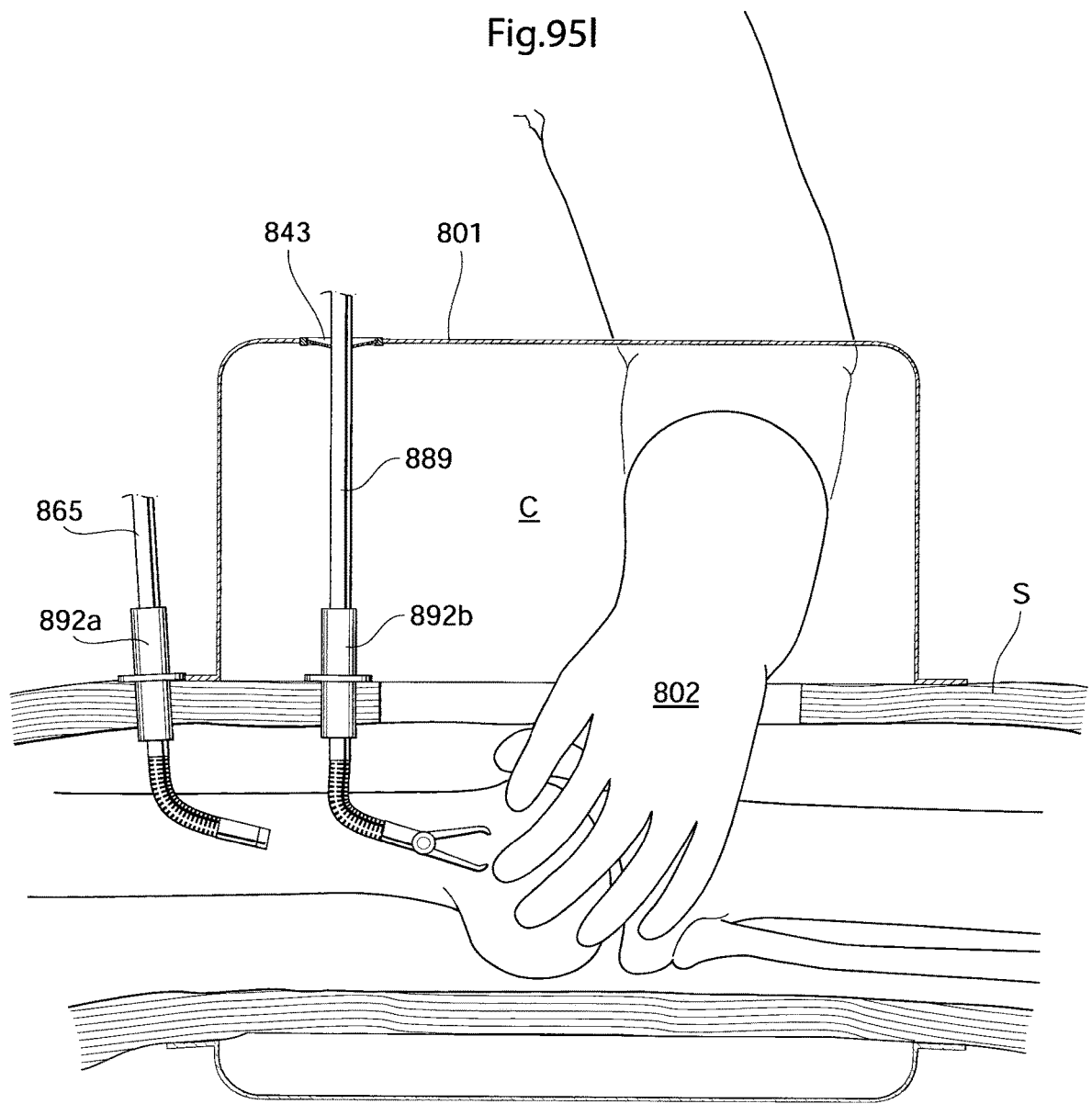

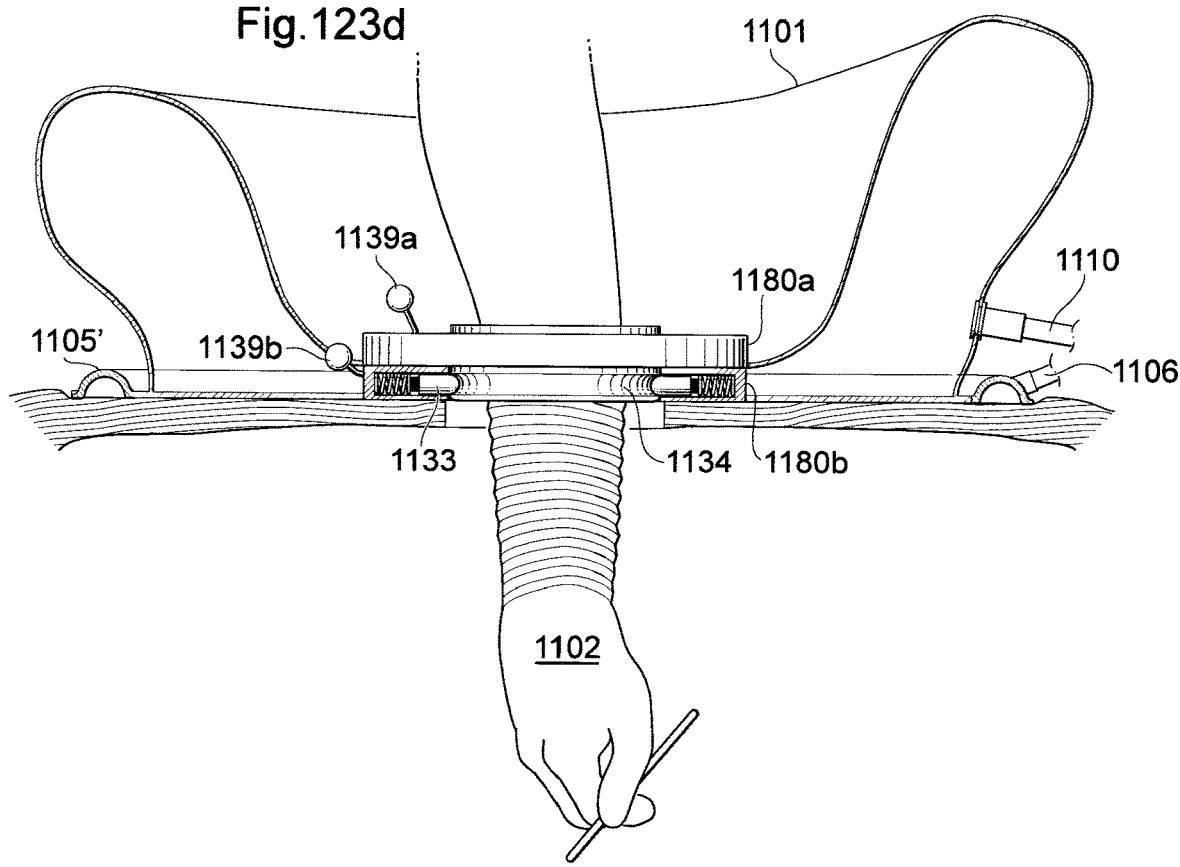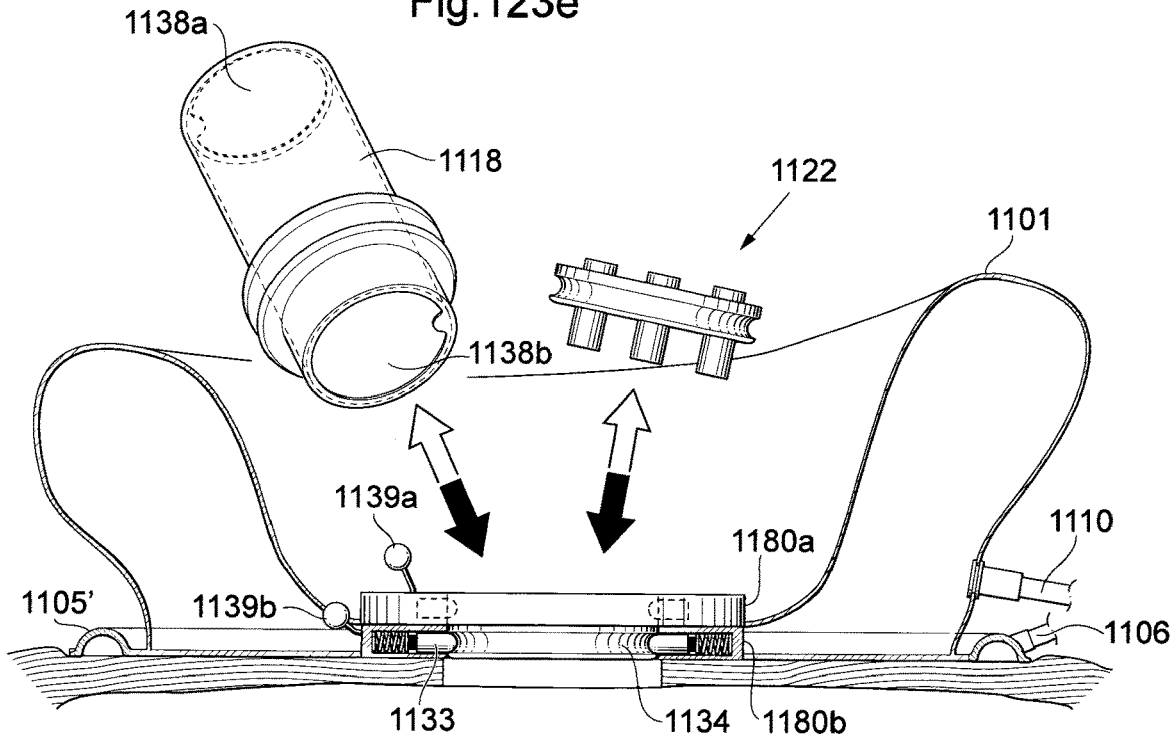

Fig.123'a
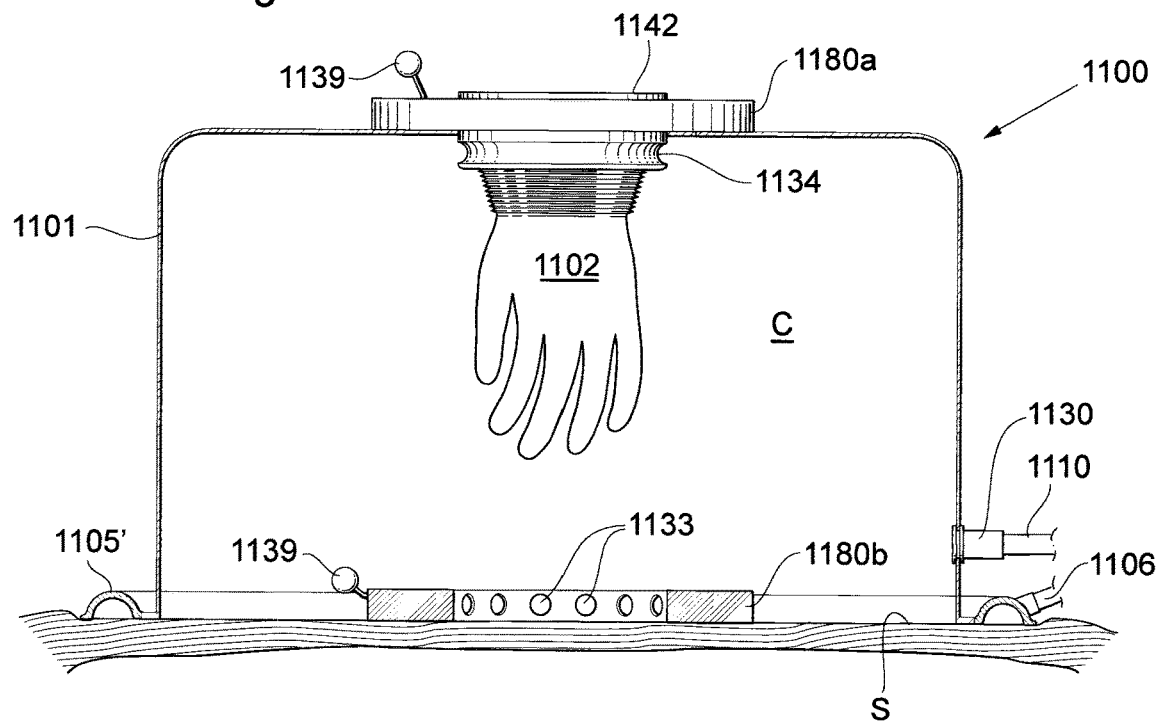
Fig.123'b
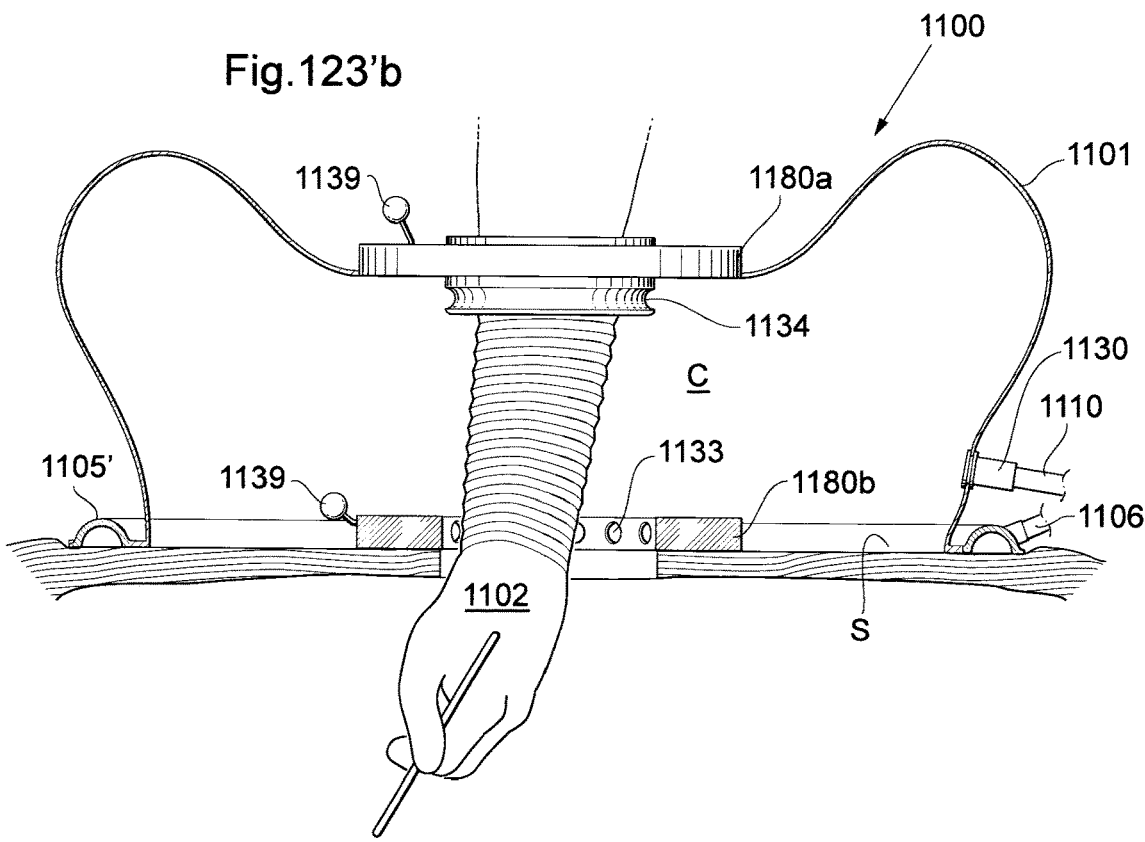

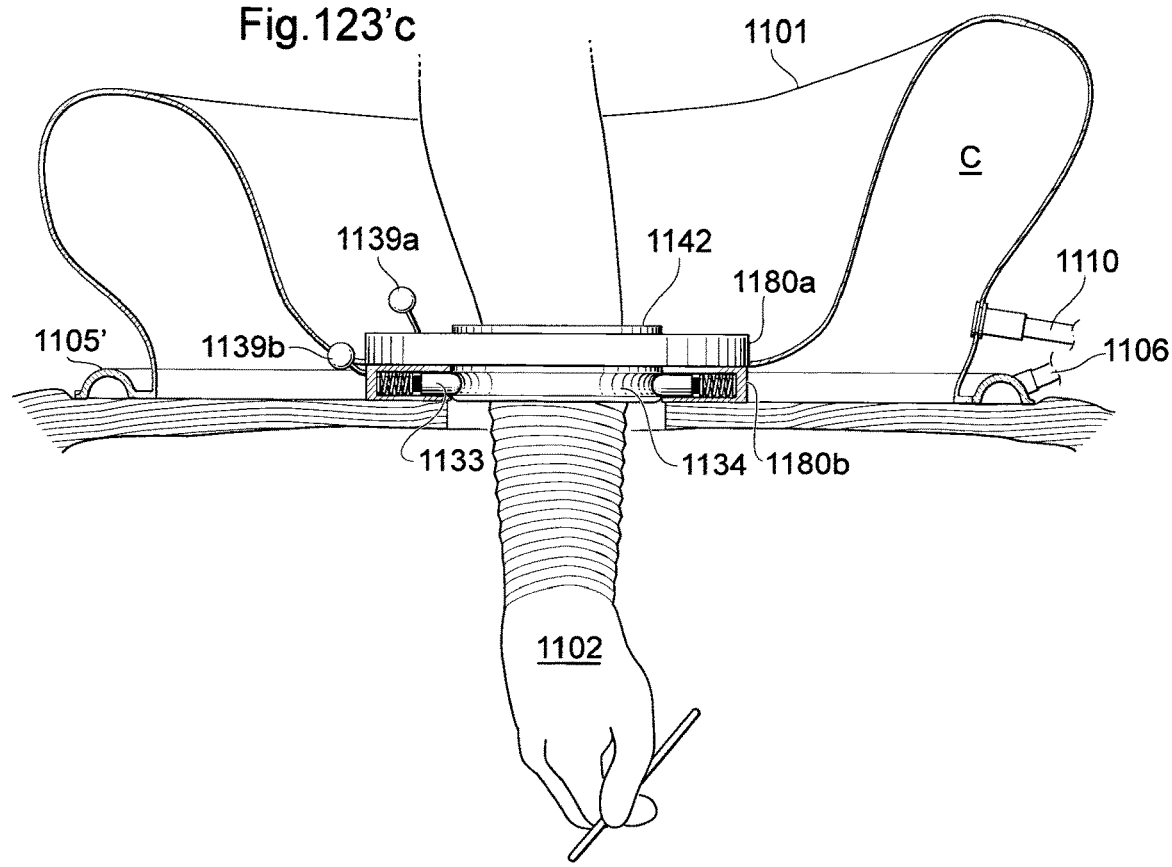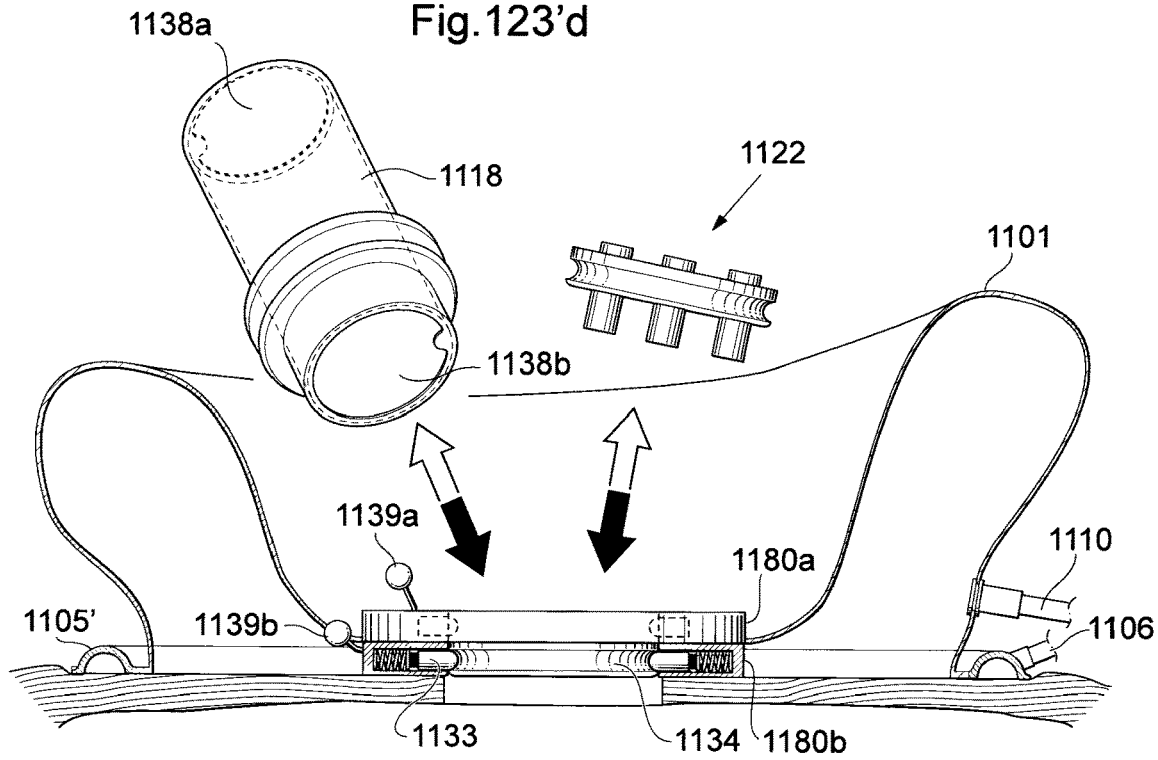

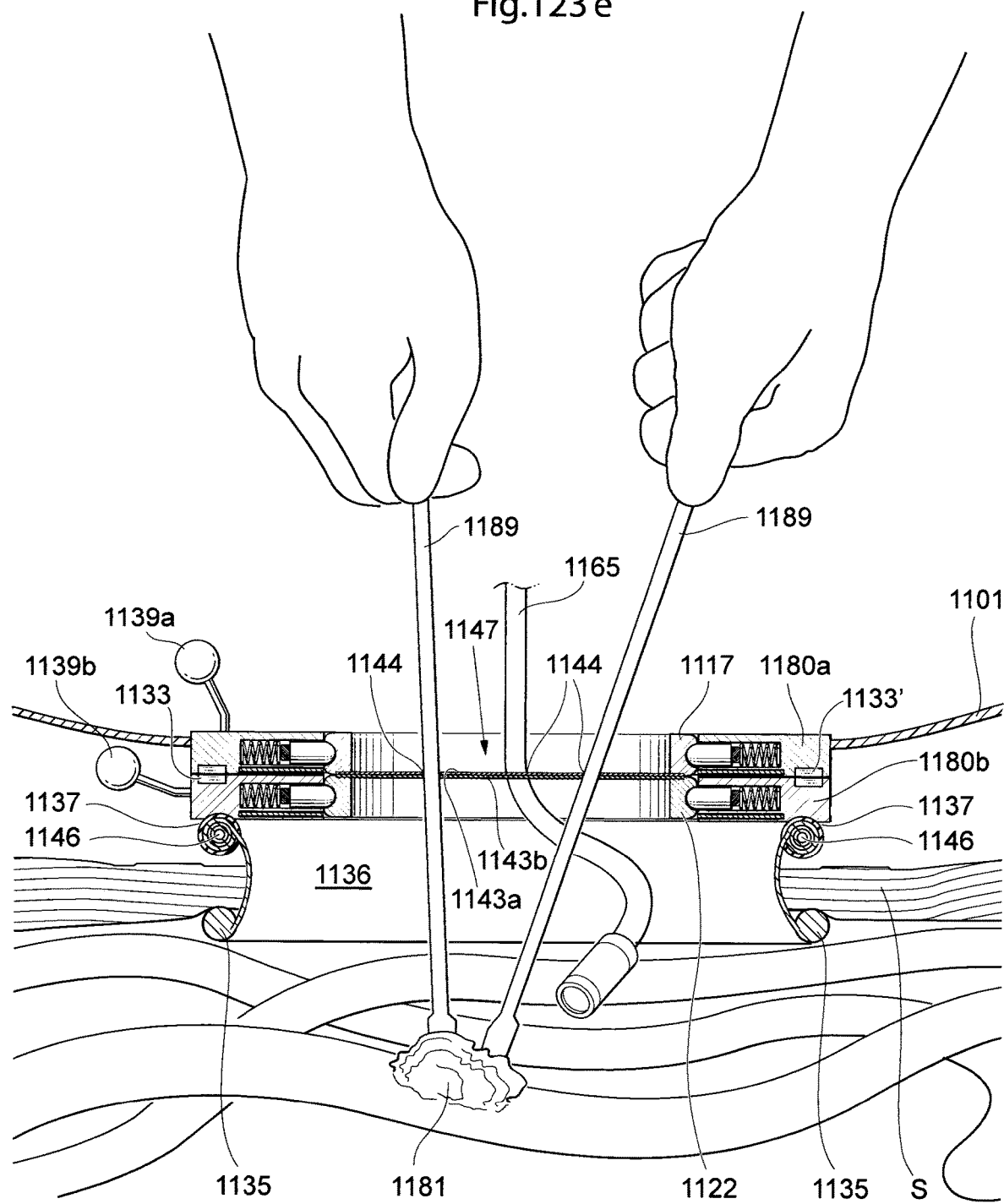
Fig.123'e

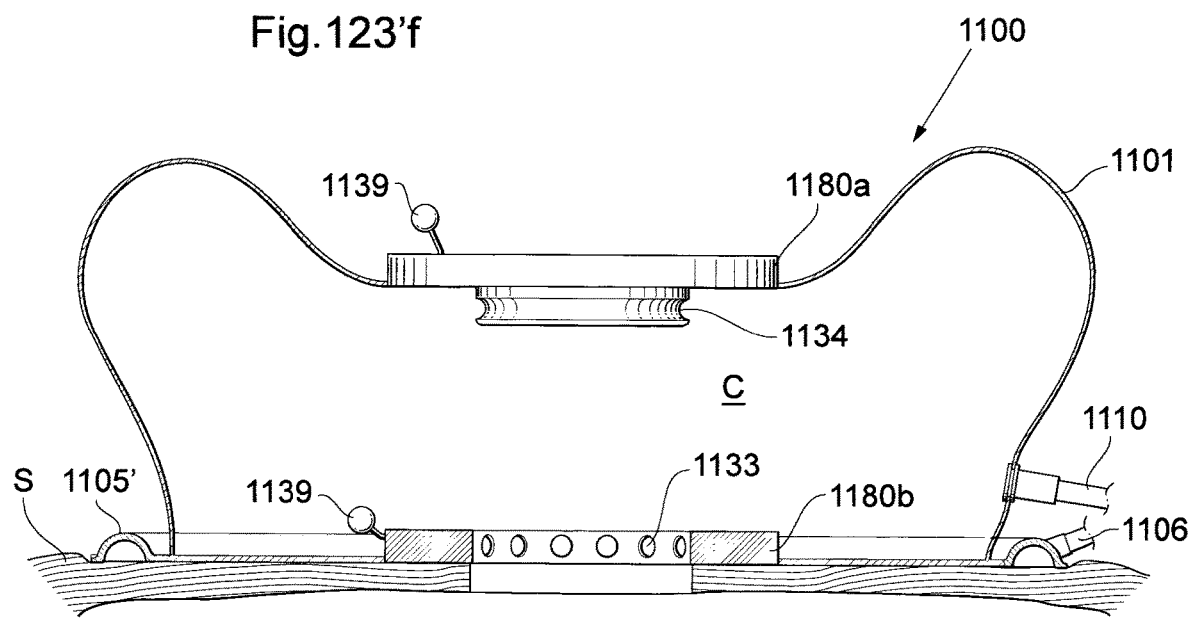

Fig.123'g
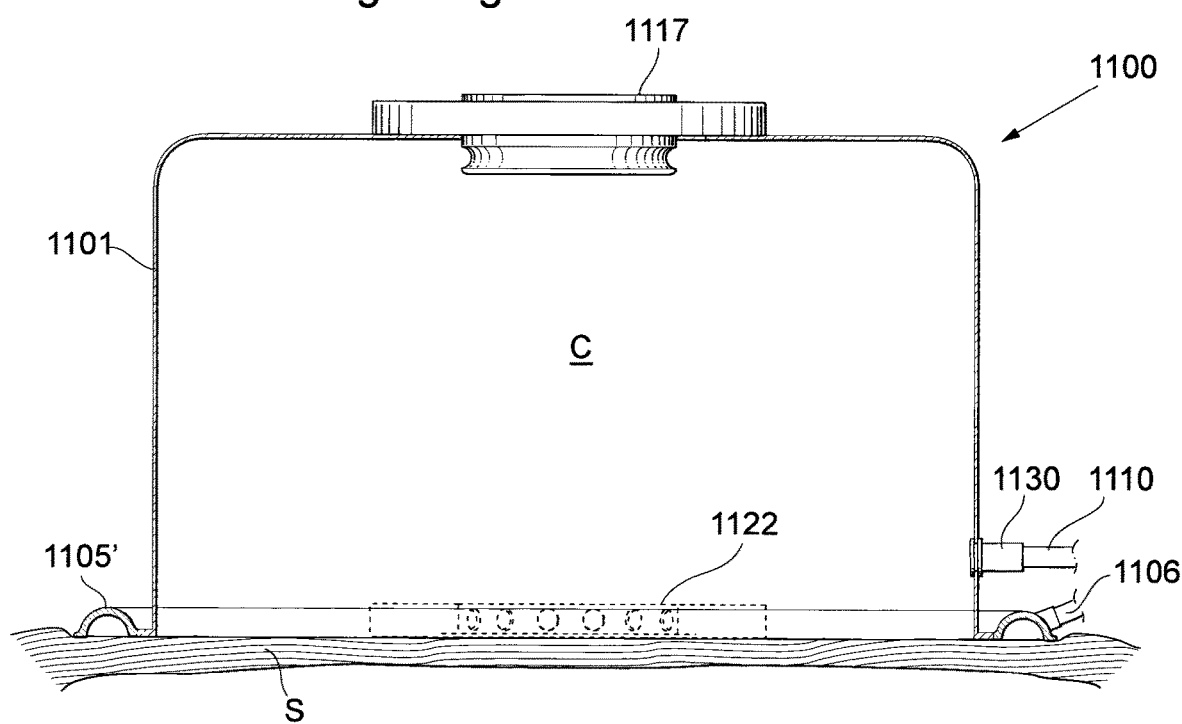
Fig.123'h
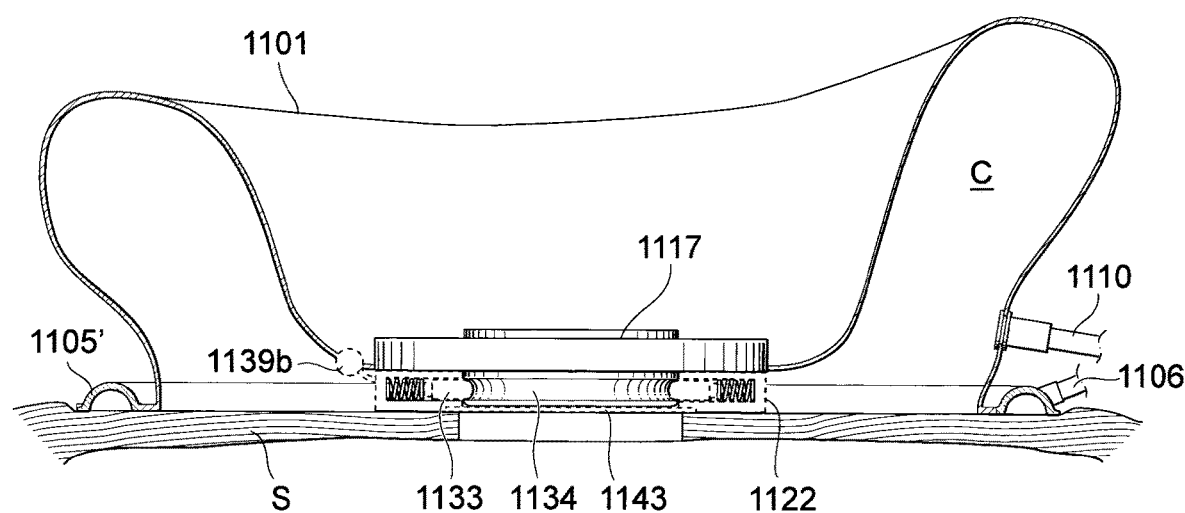

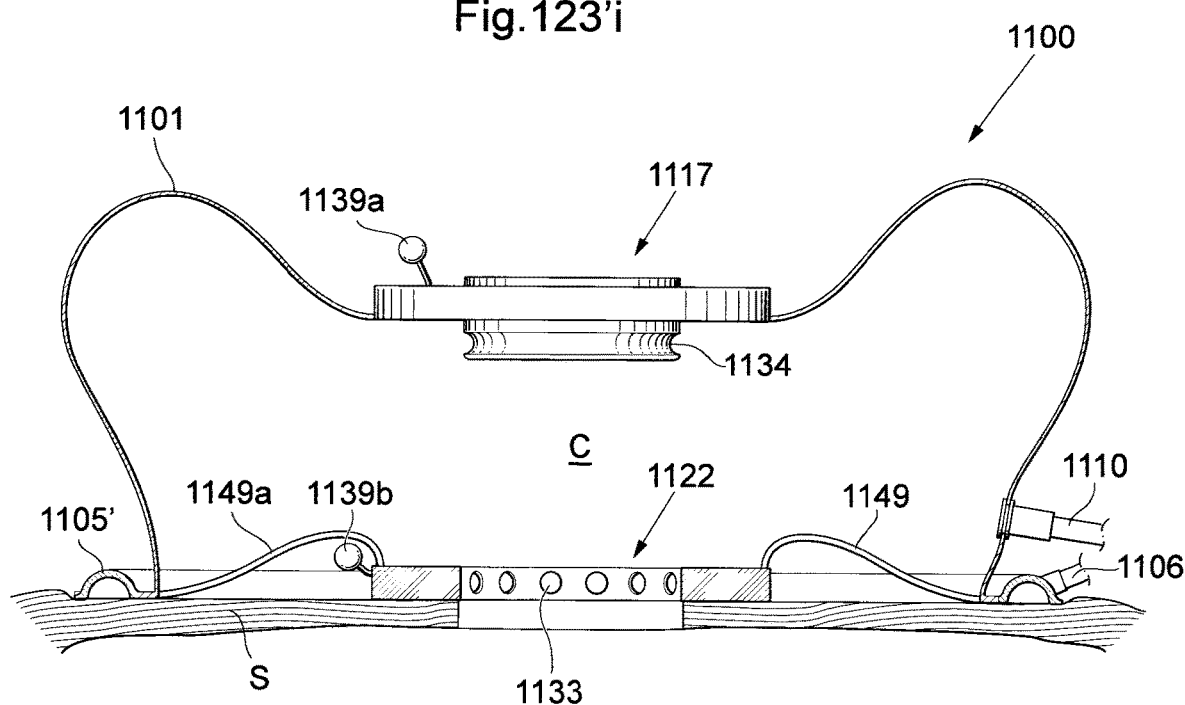
Fig.123'i

Fig.123'j
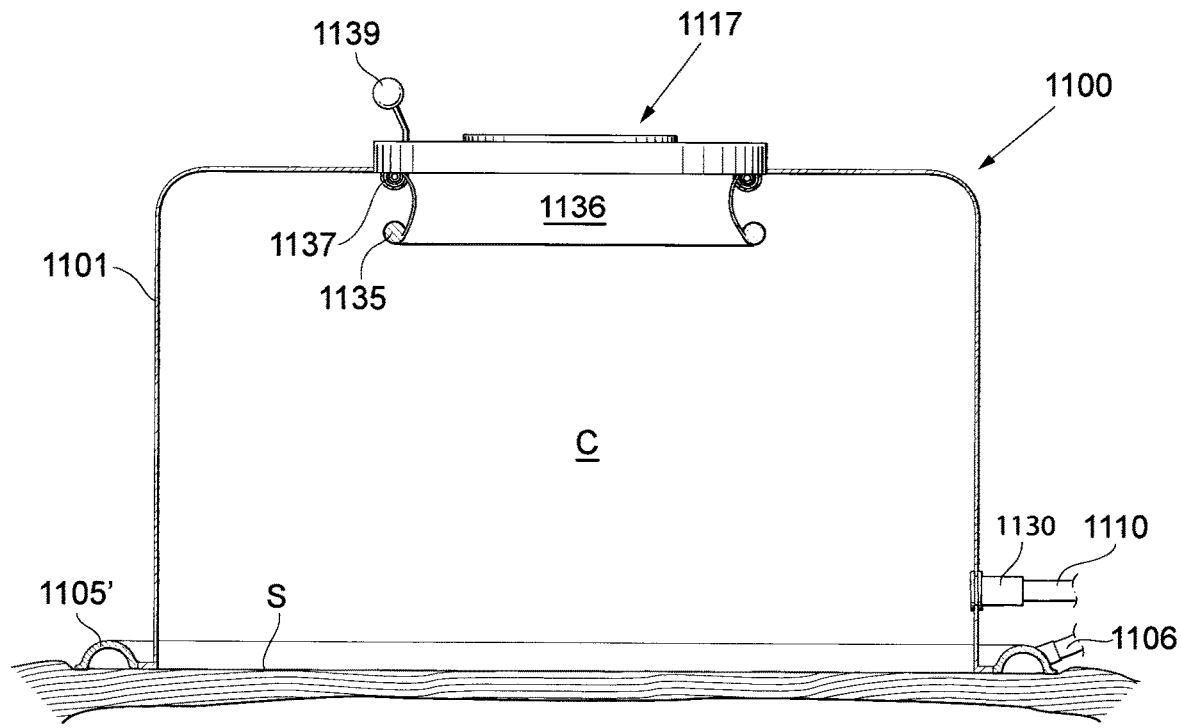
Fig.123'k
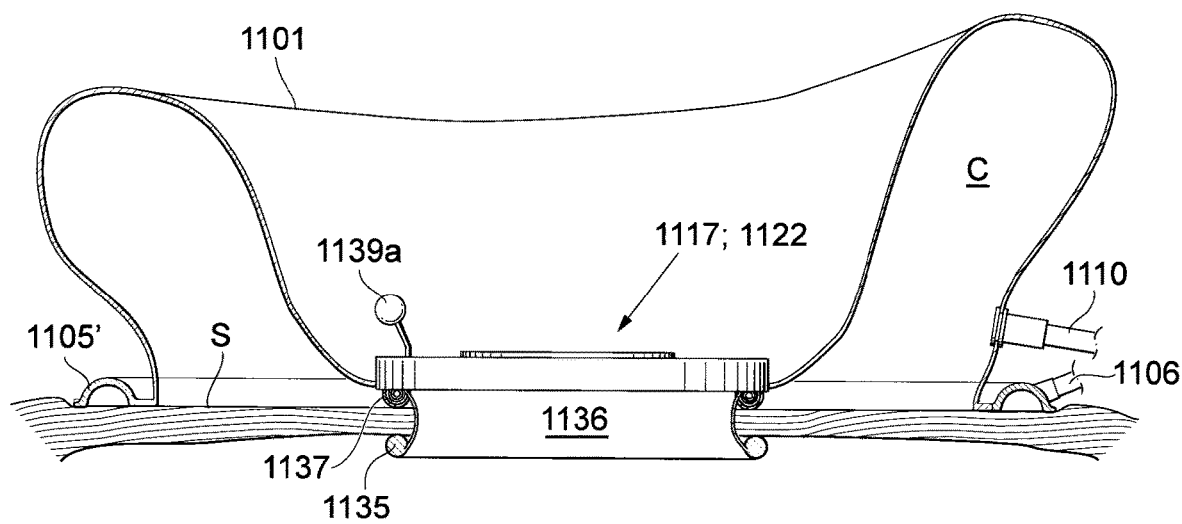

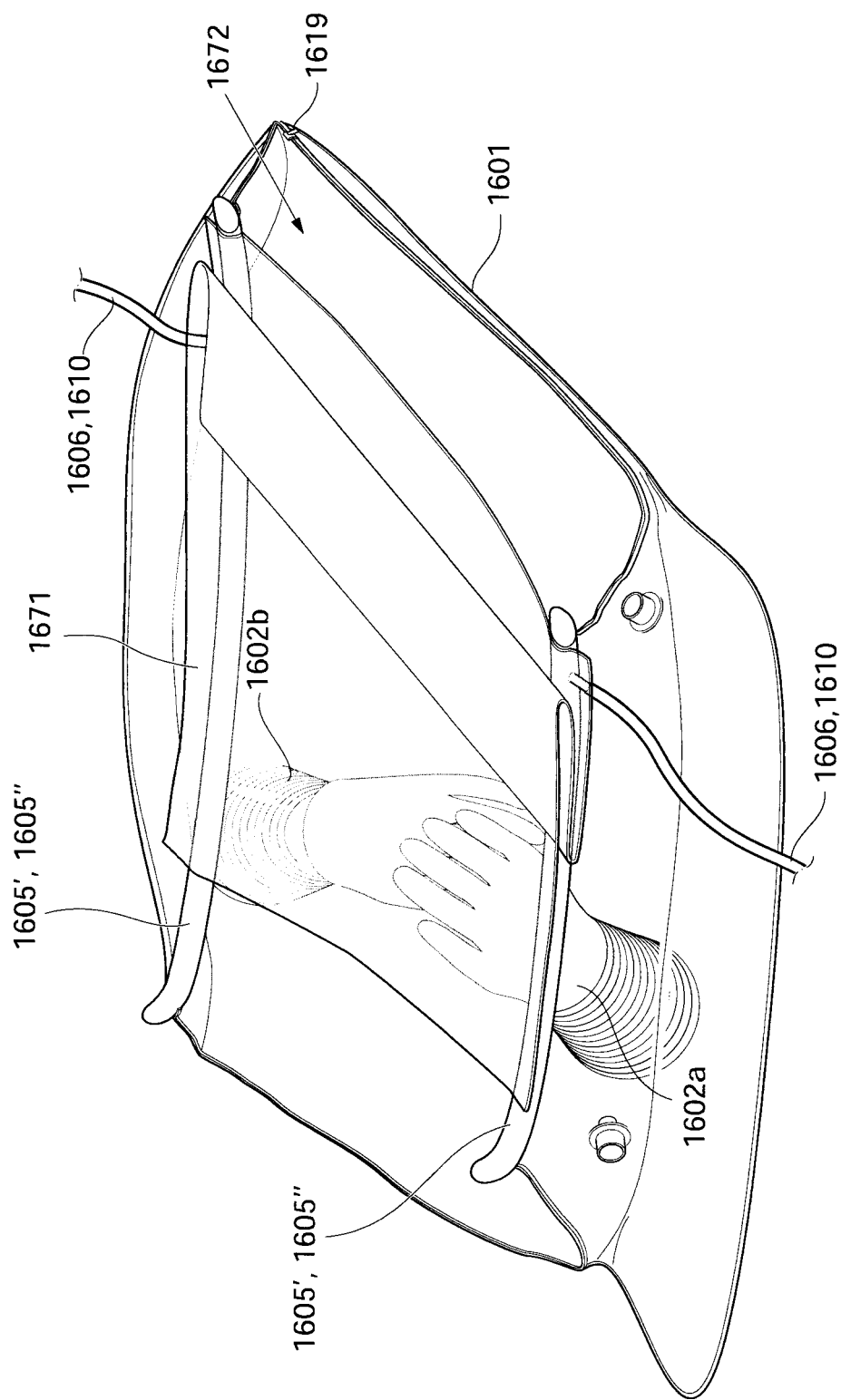

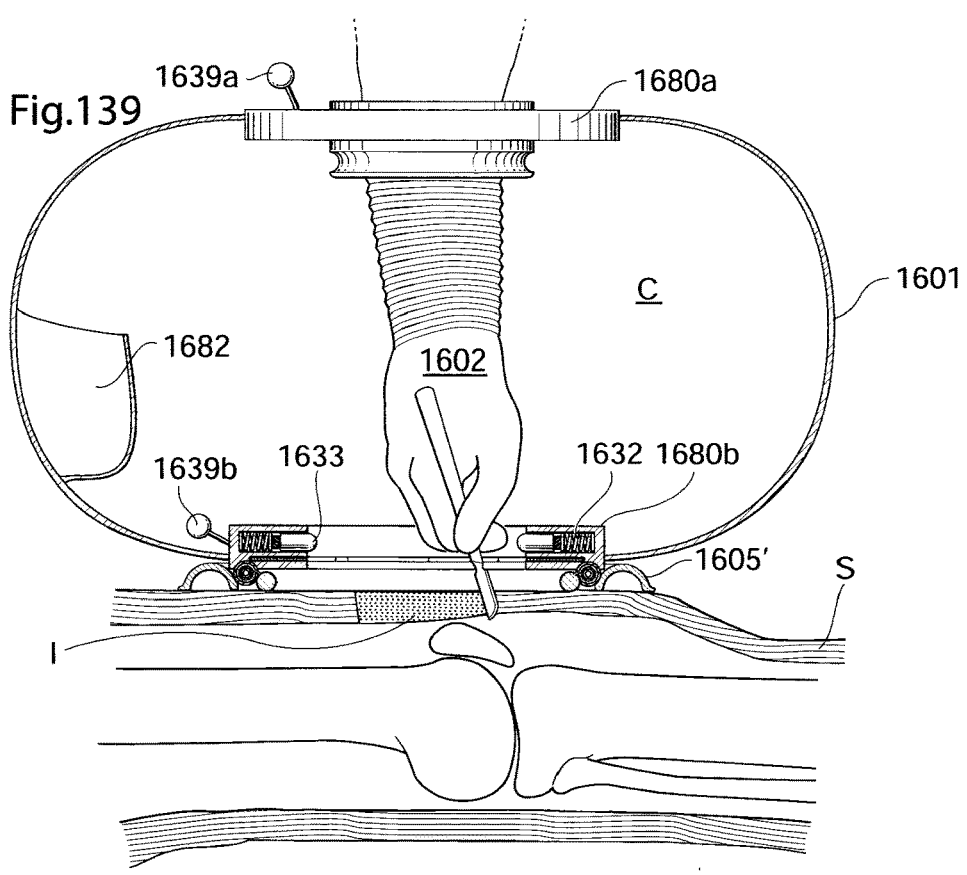
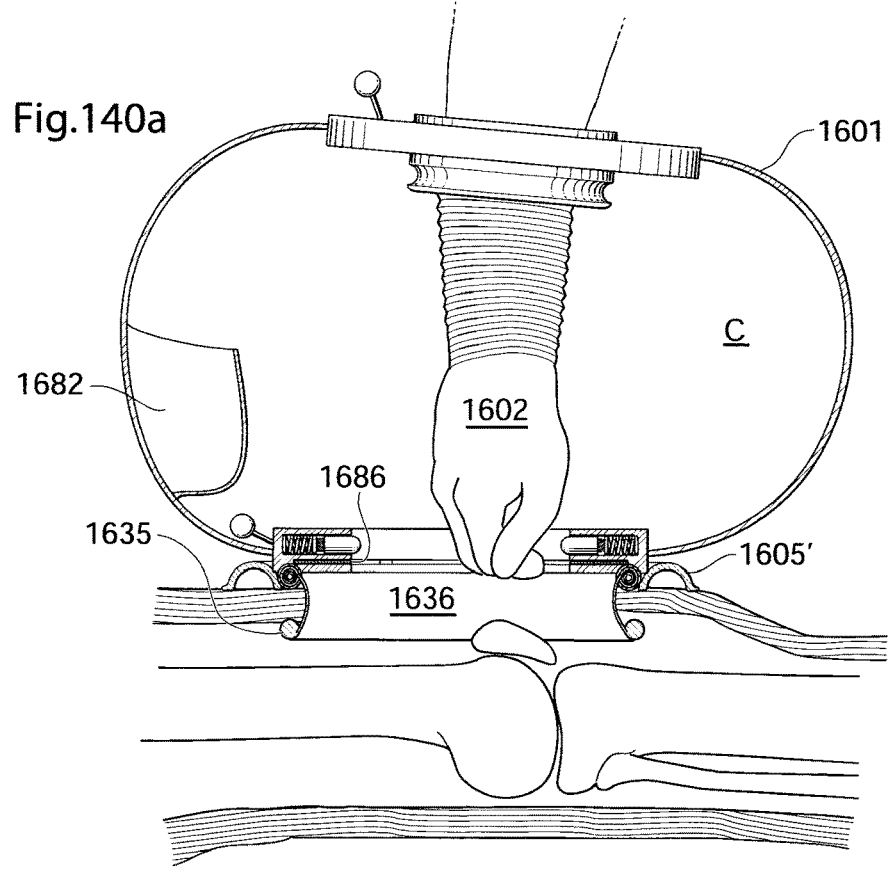

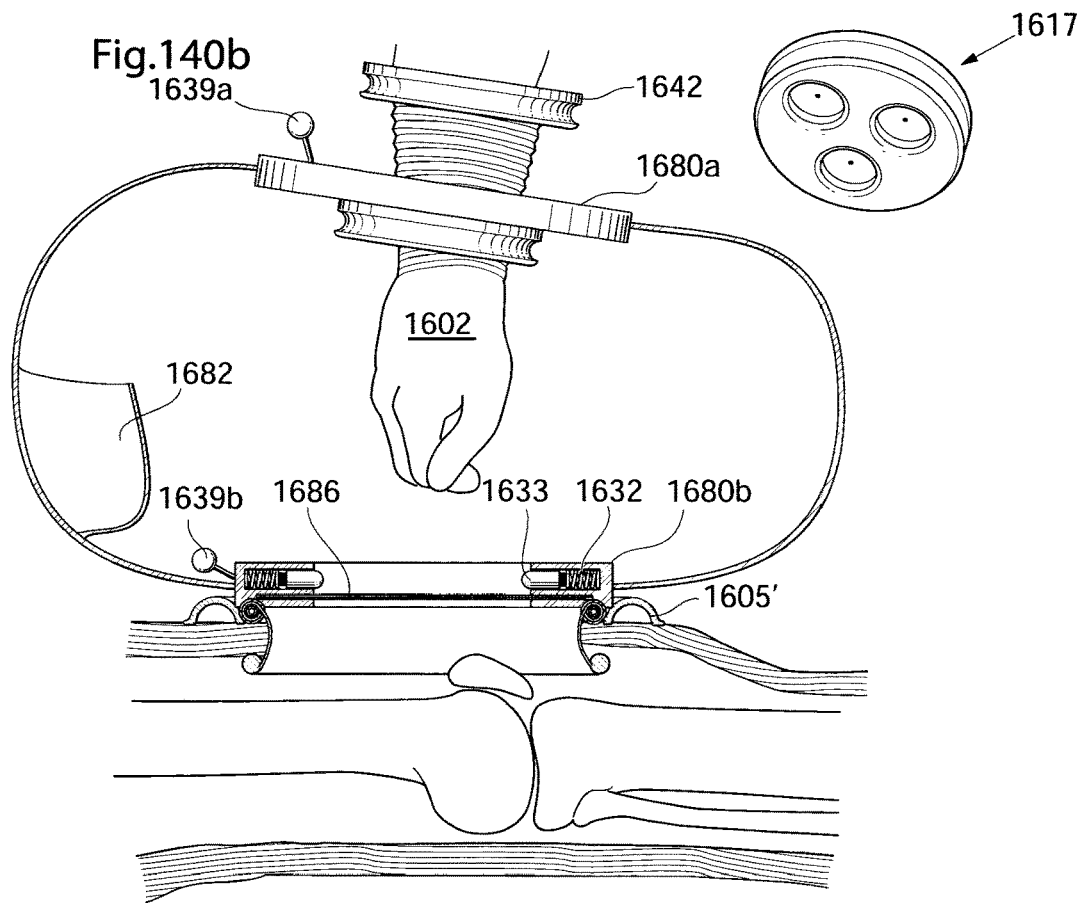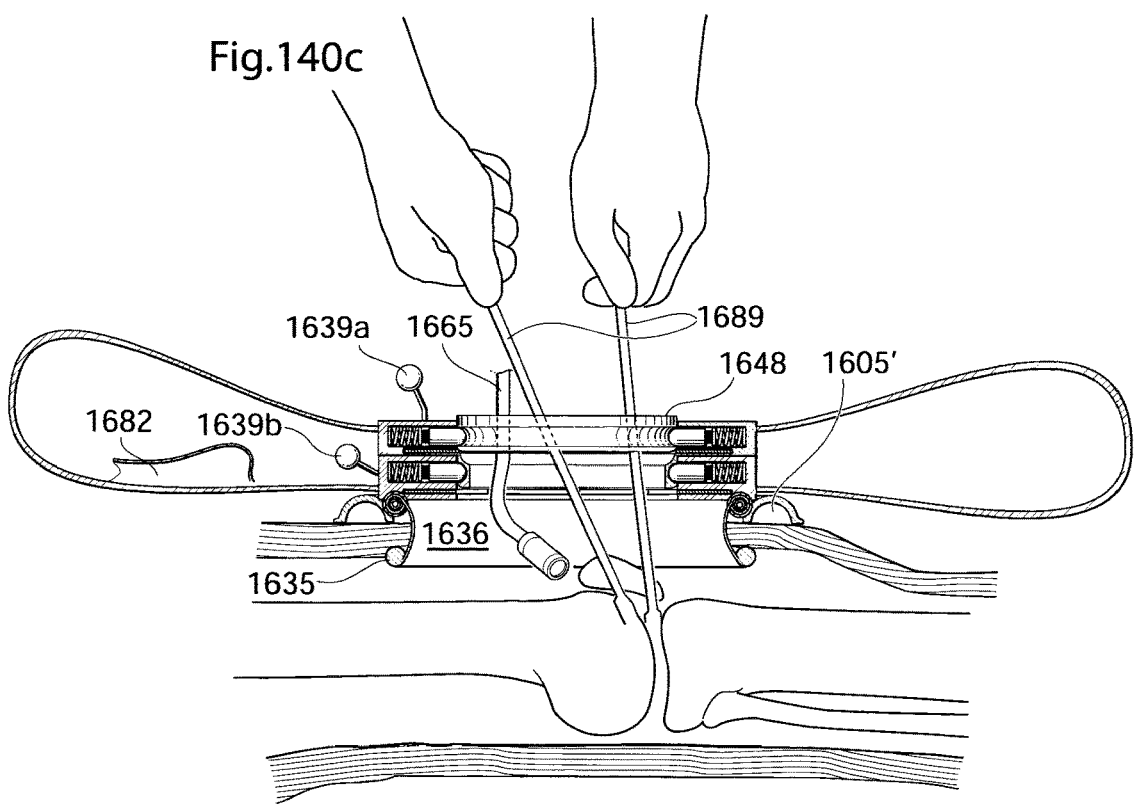

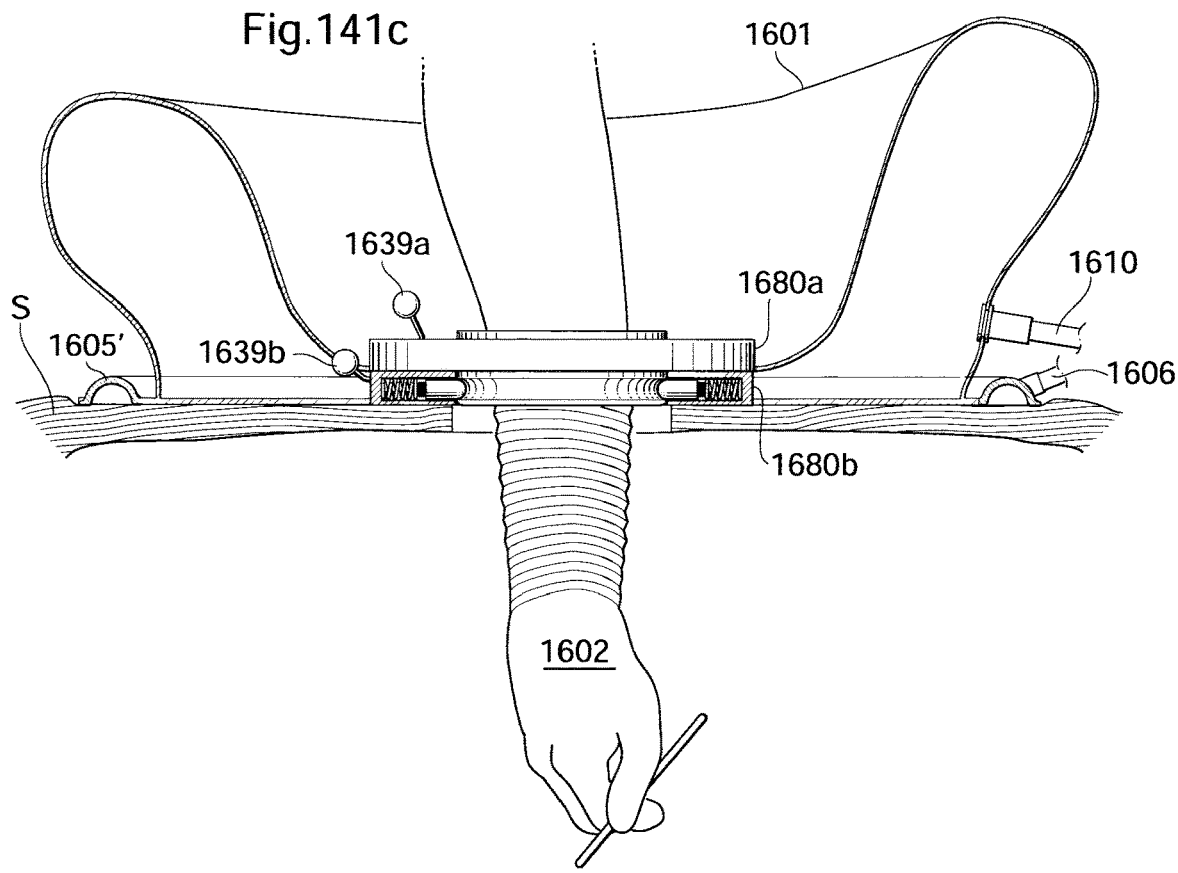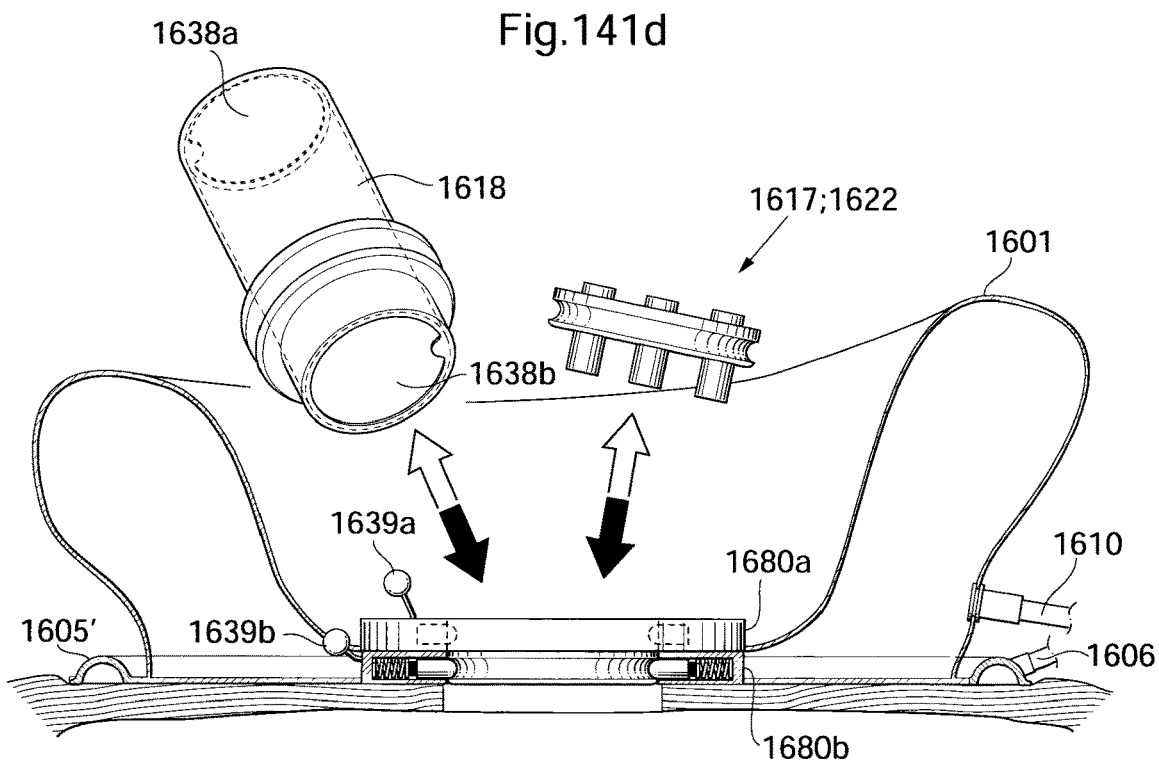

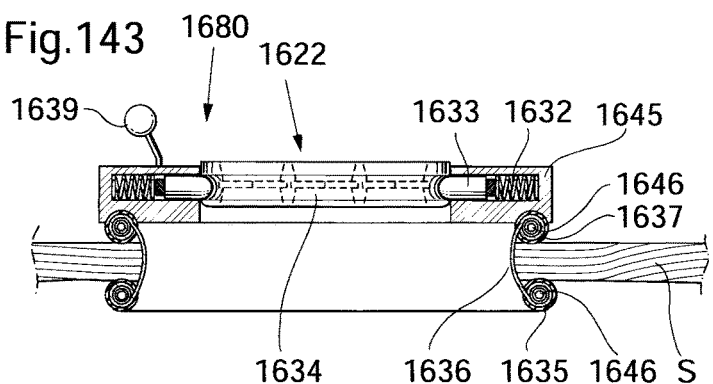
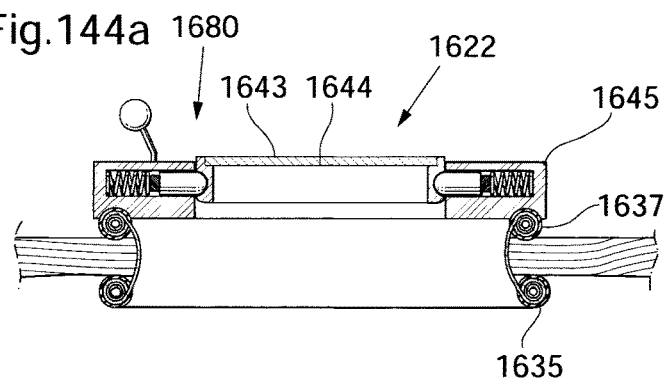
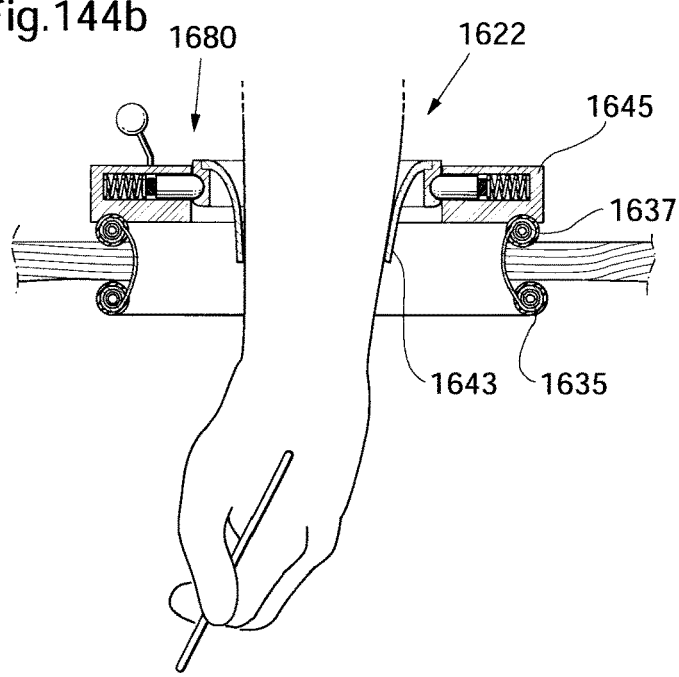

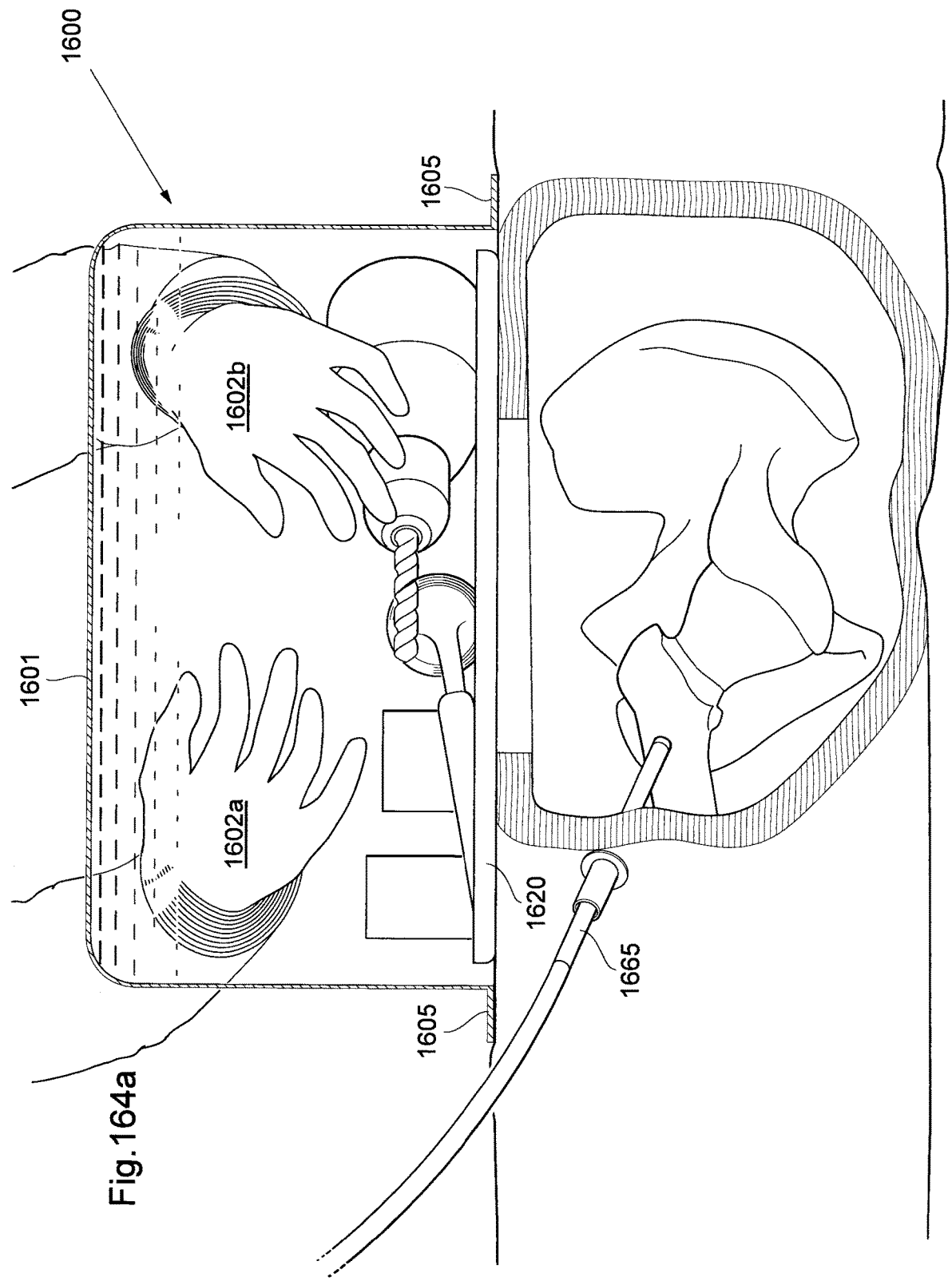

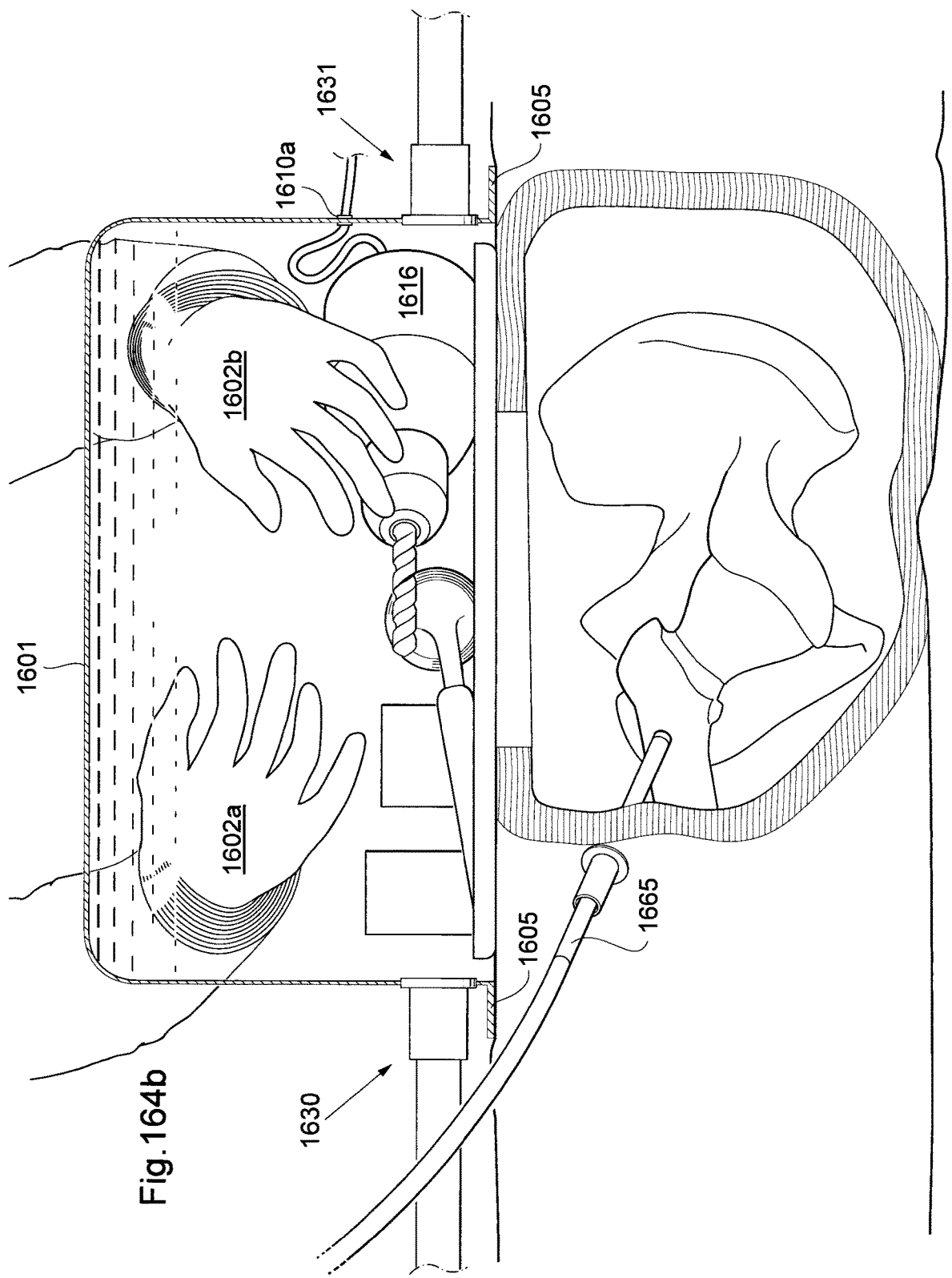

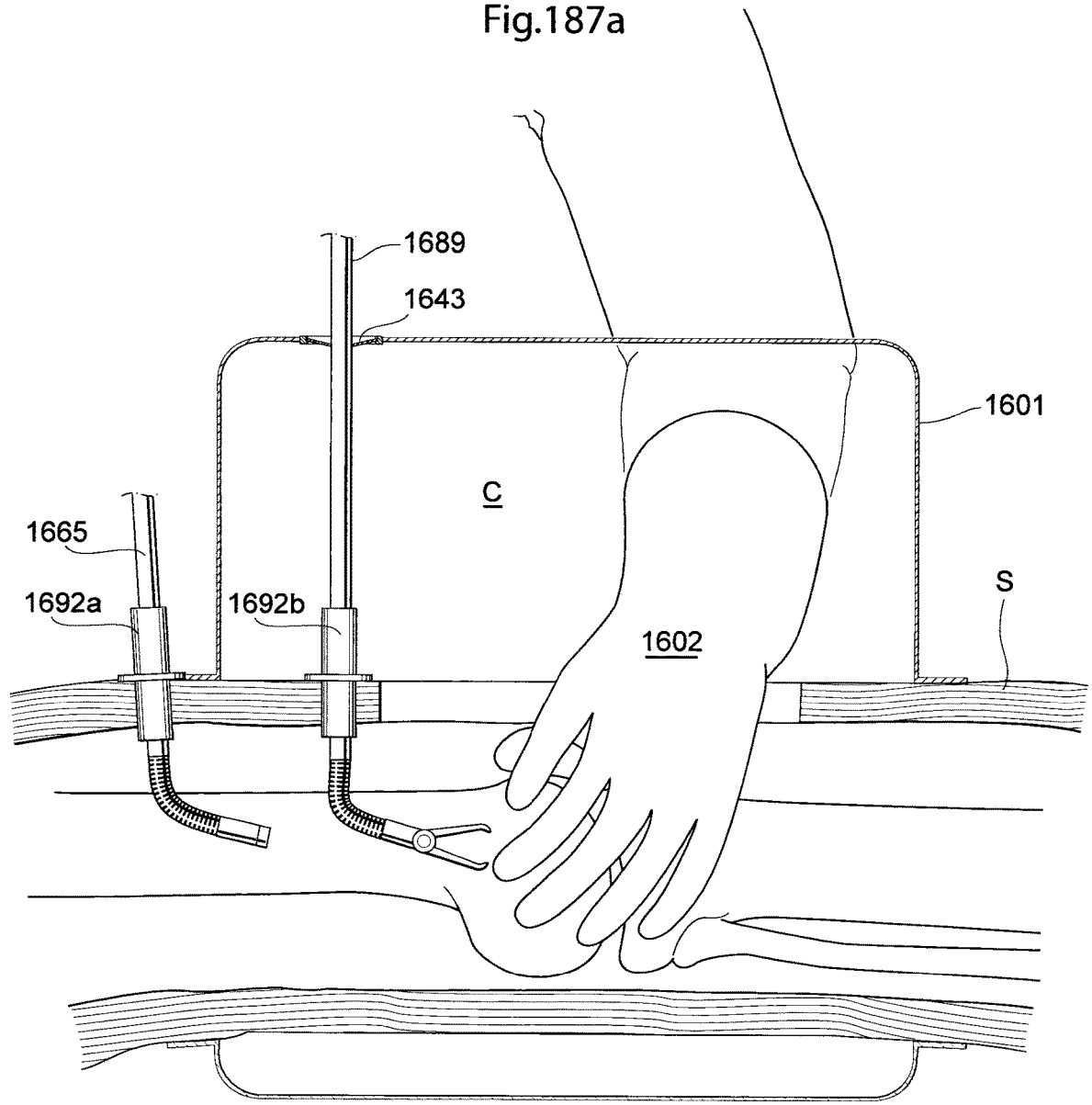

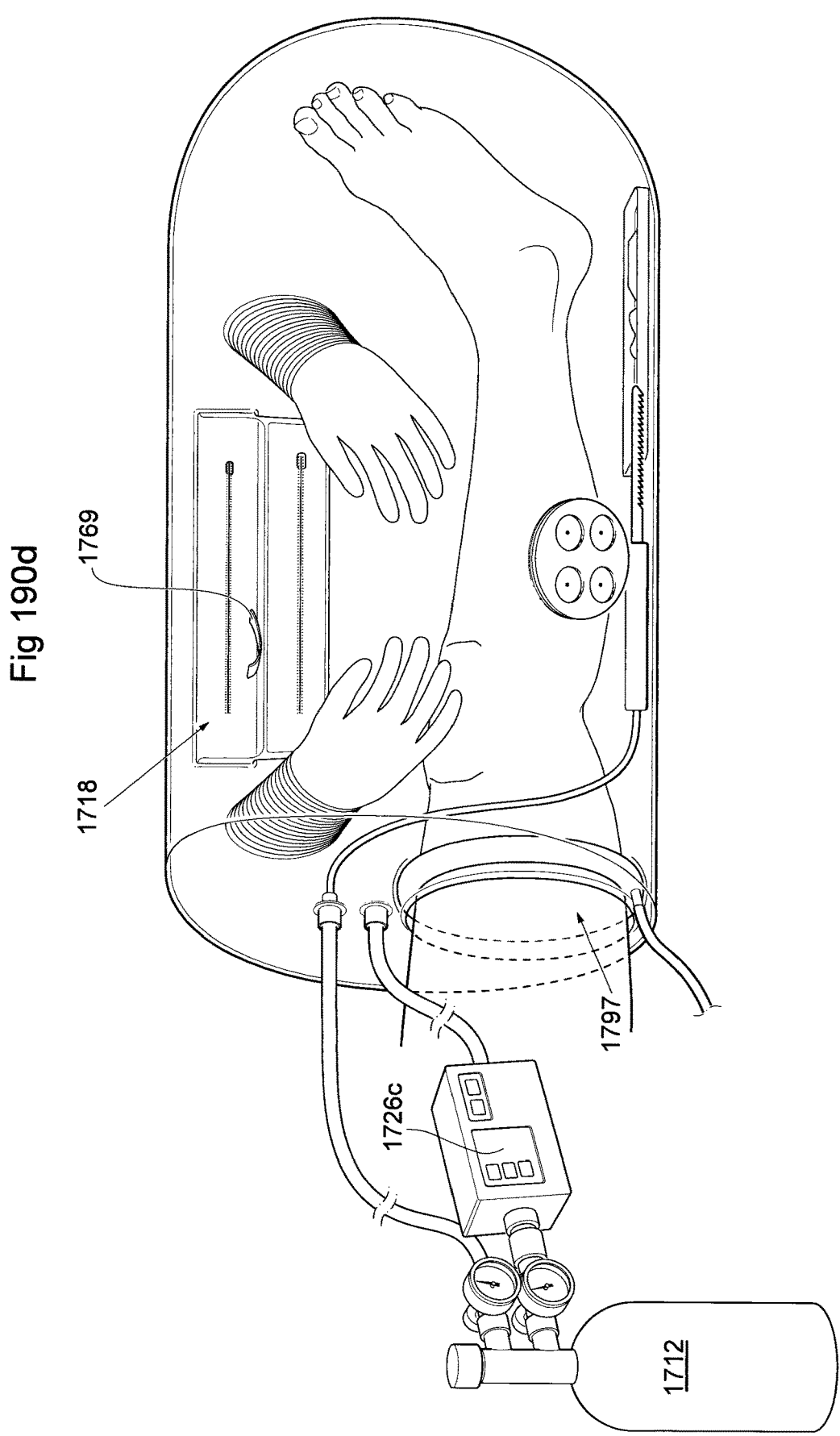

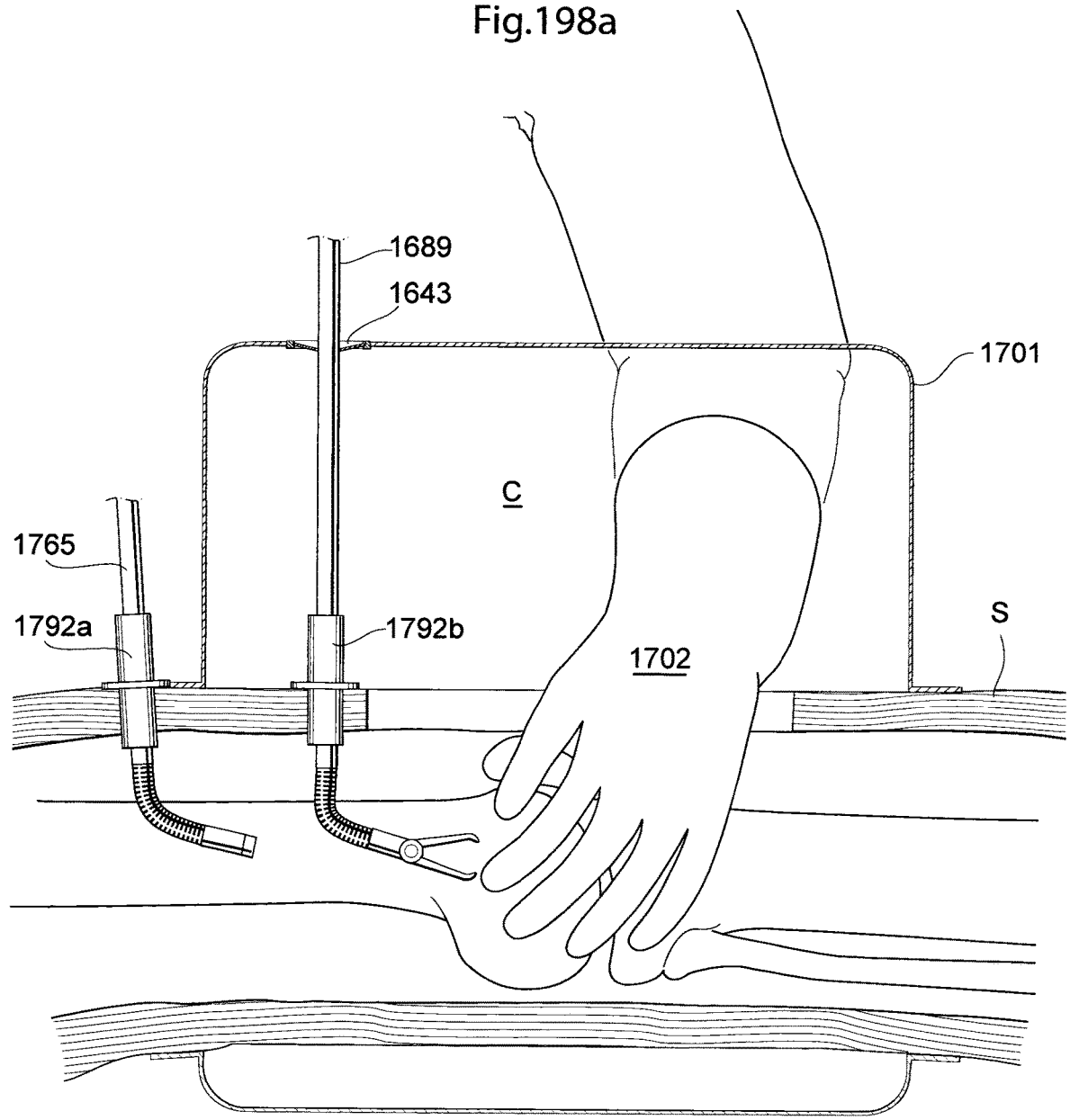

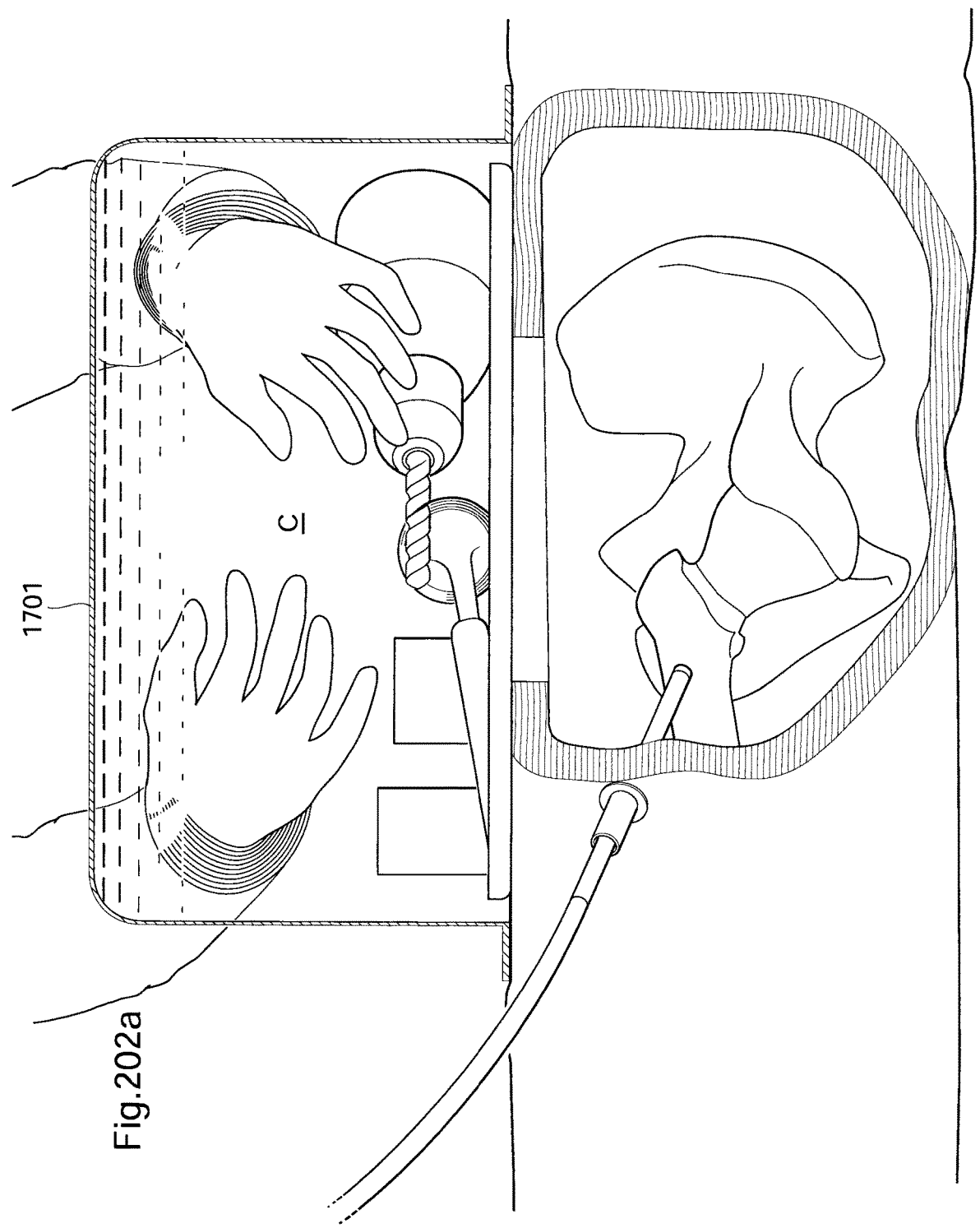

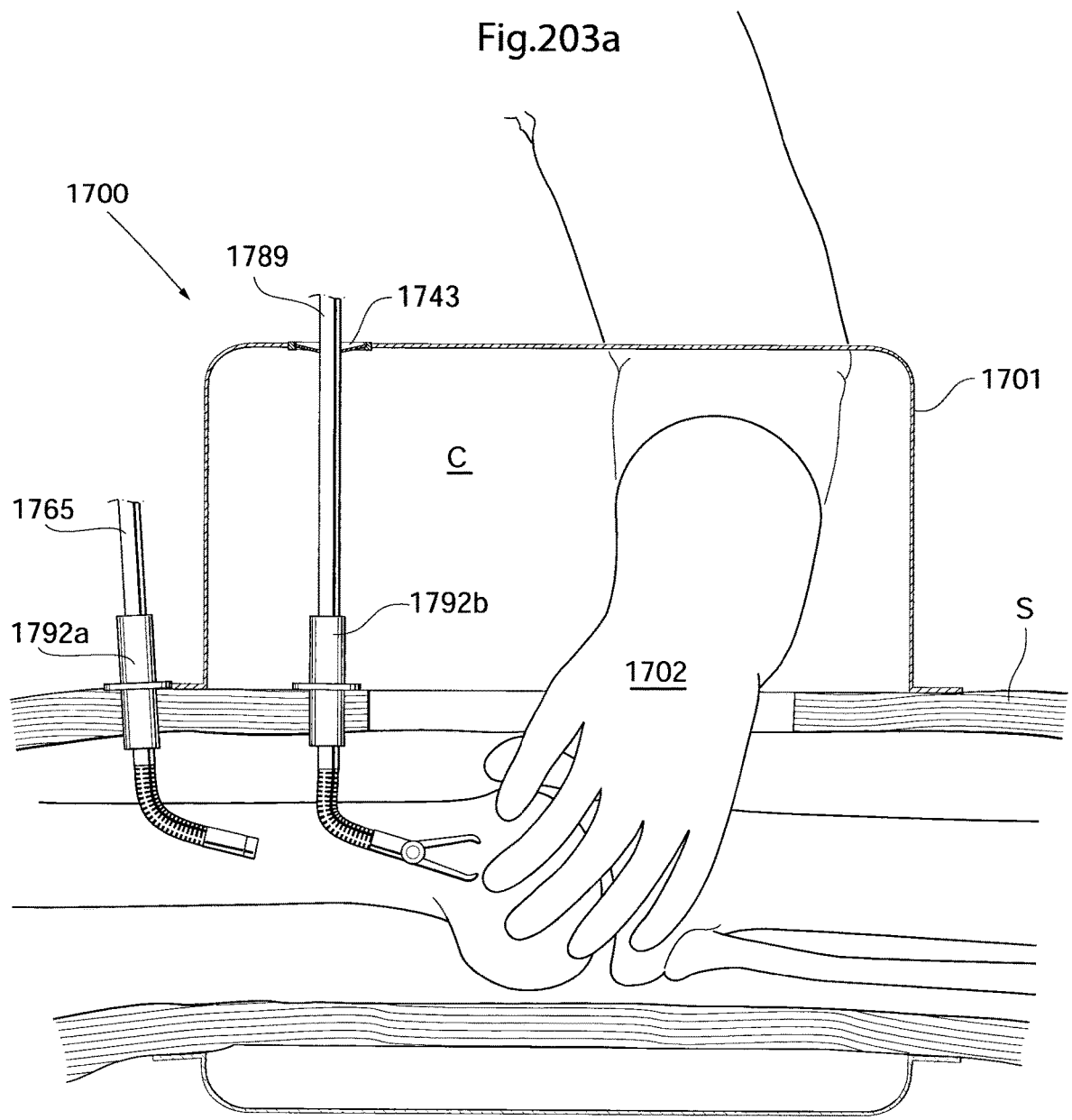

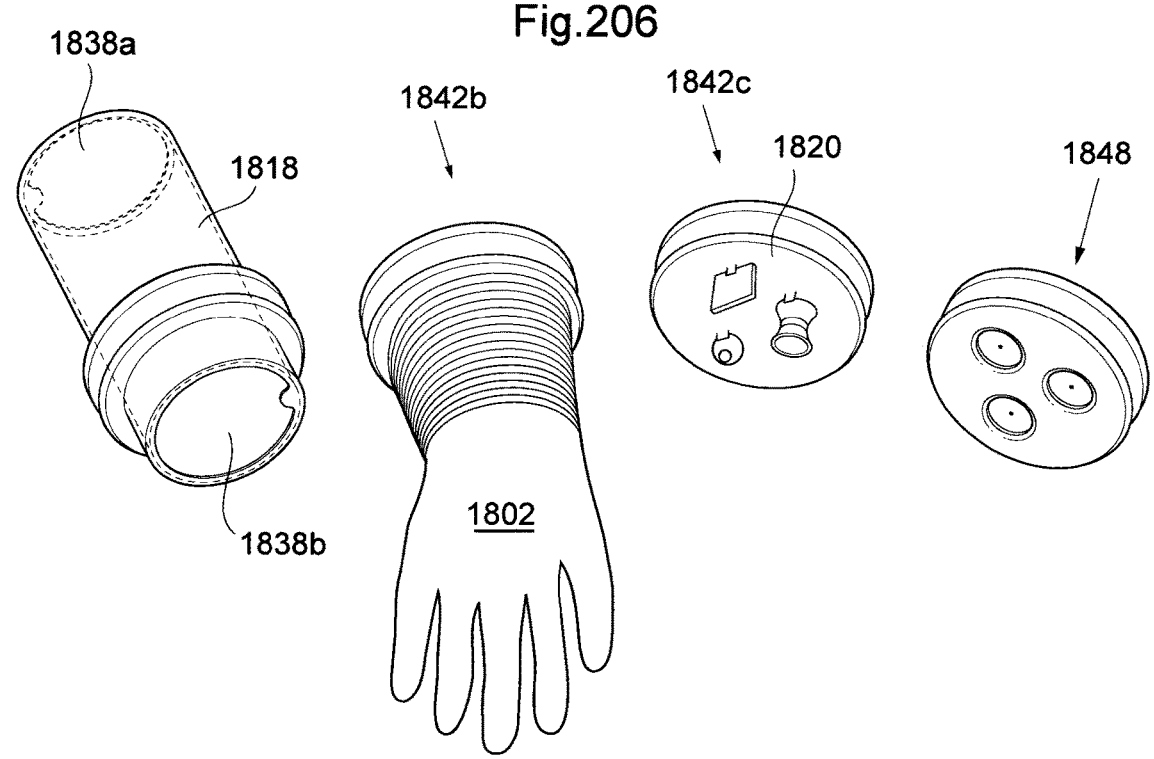
Fig. 206
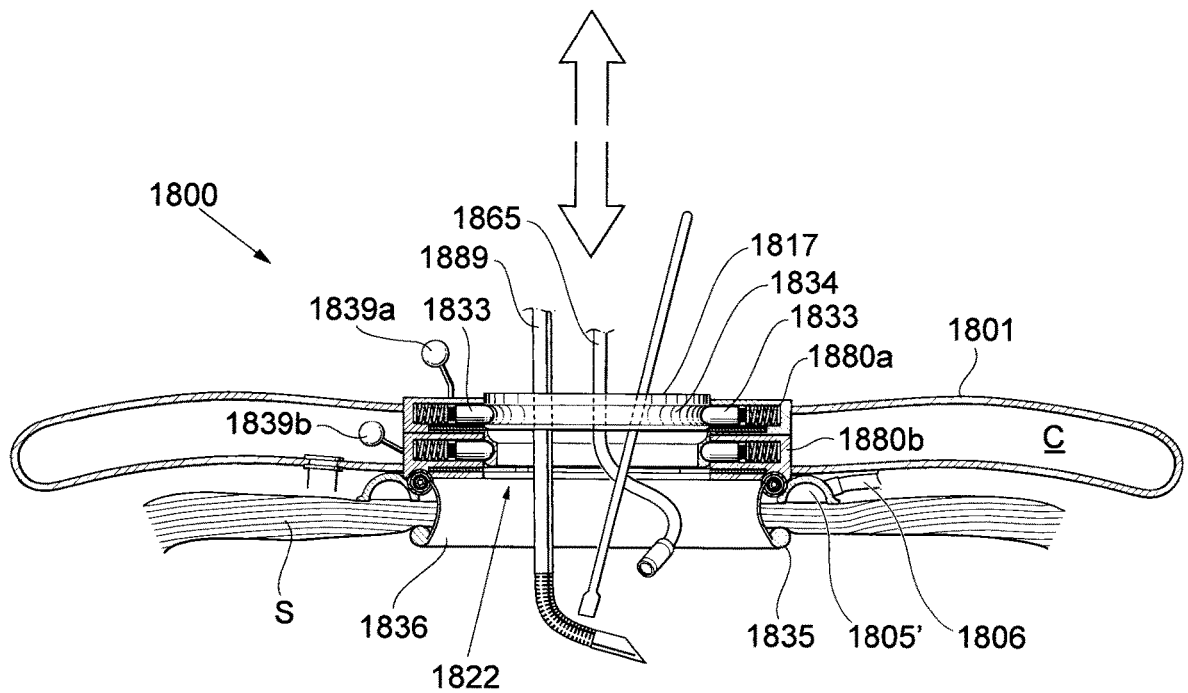

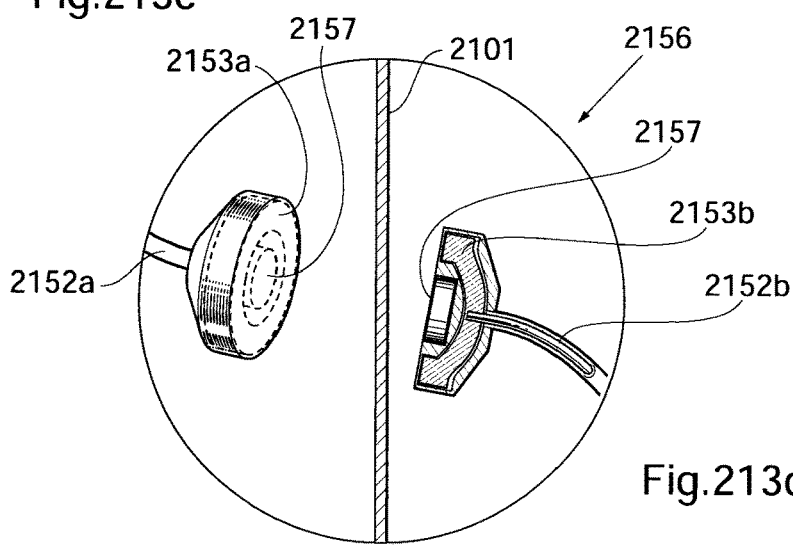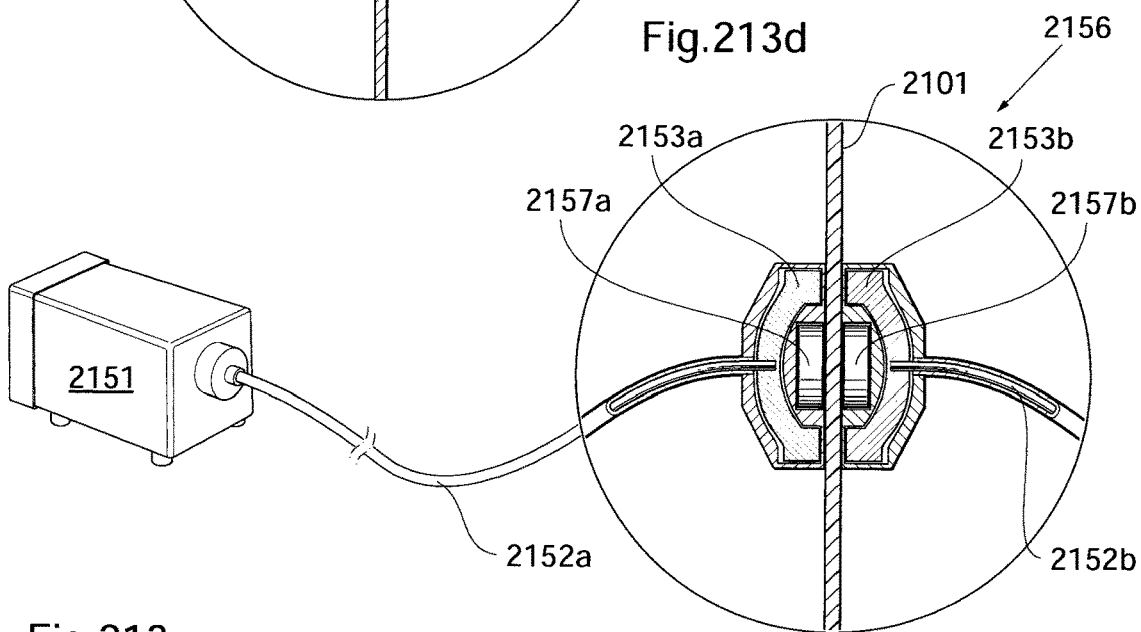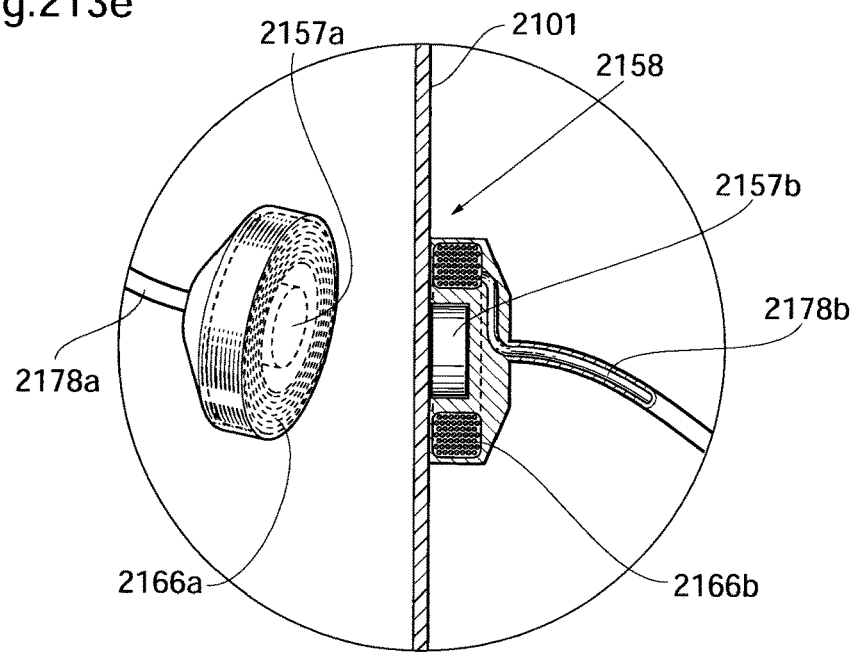

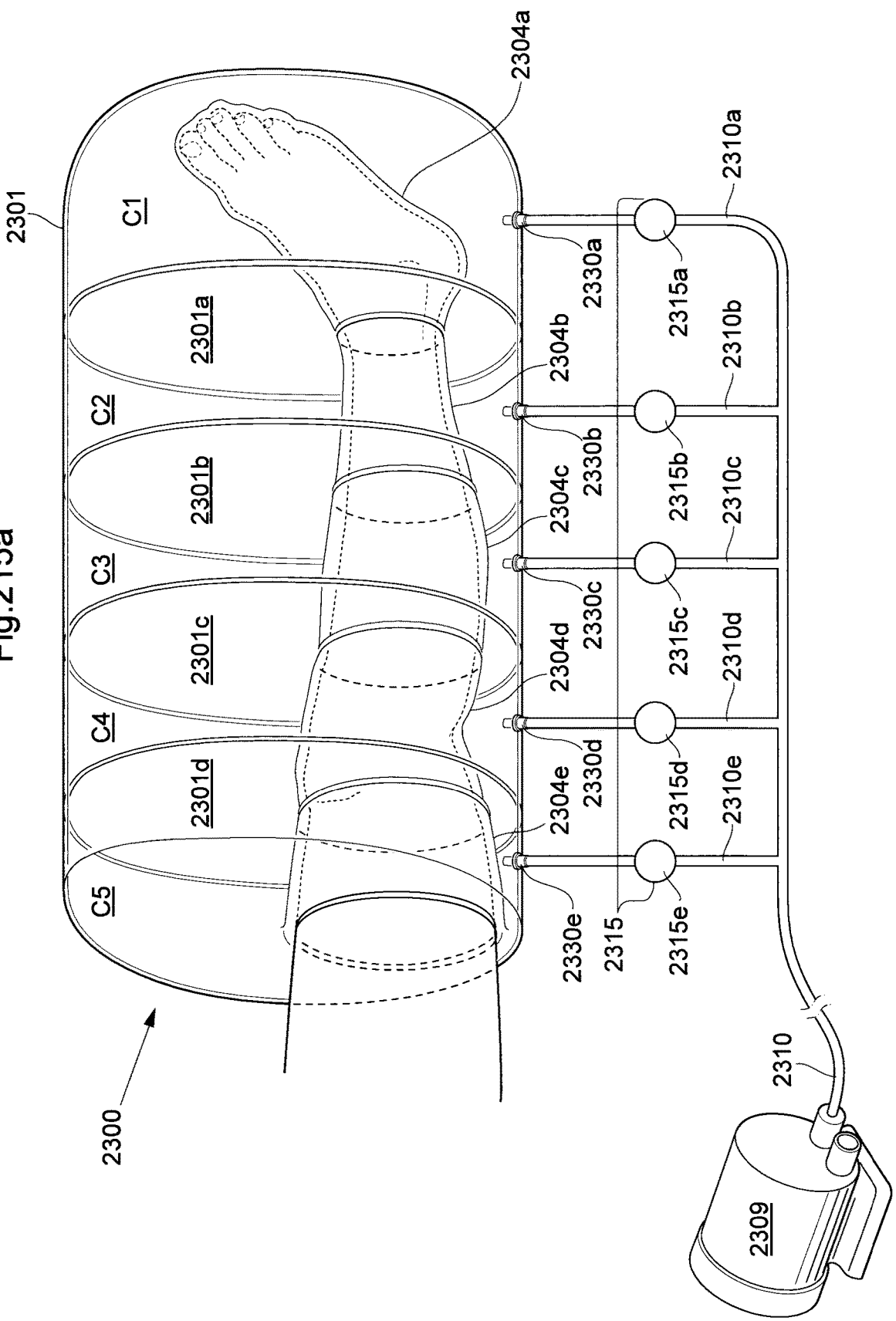

Fig.218b
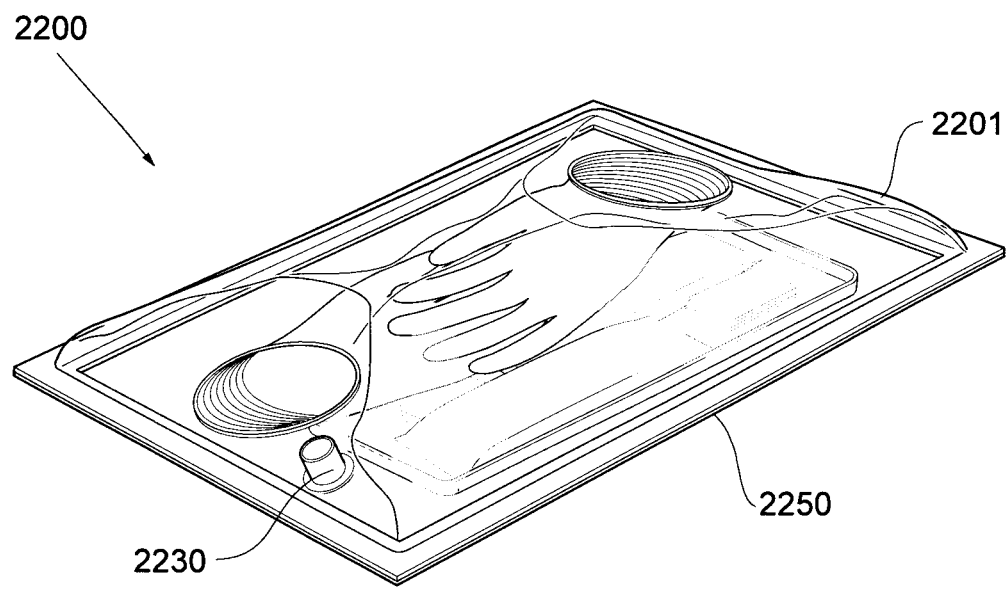
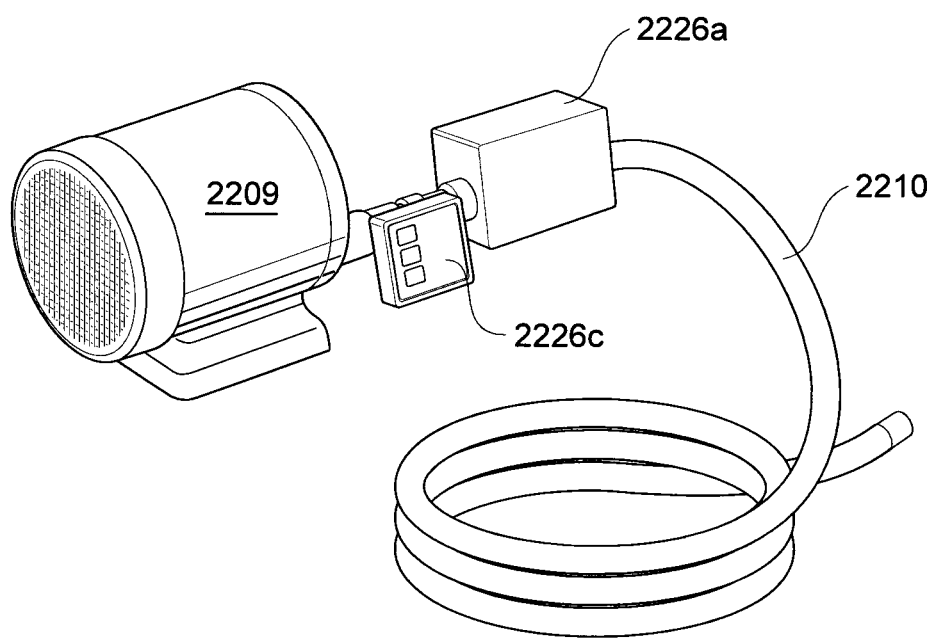

Fig.220a
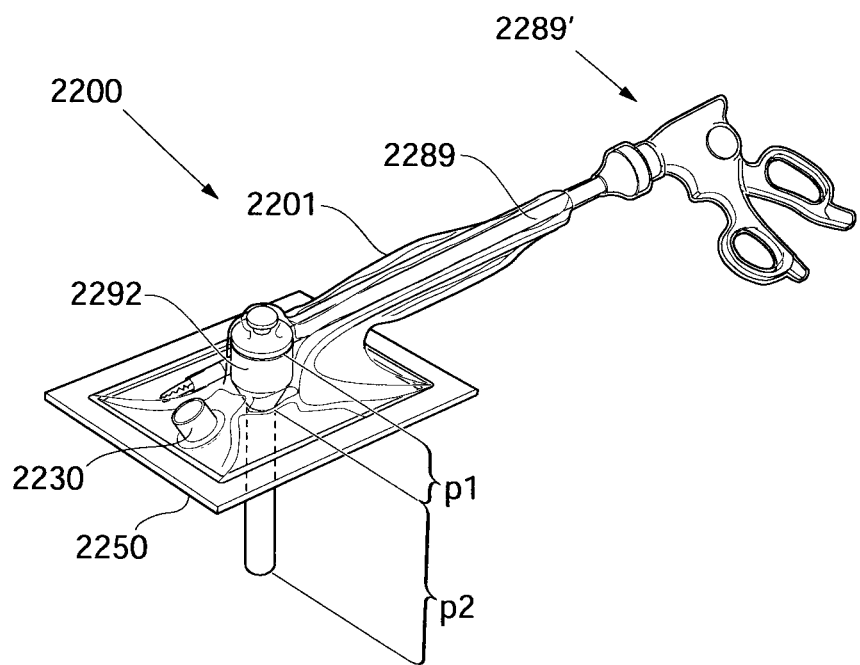
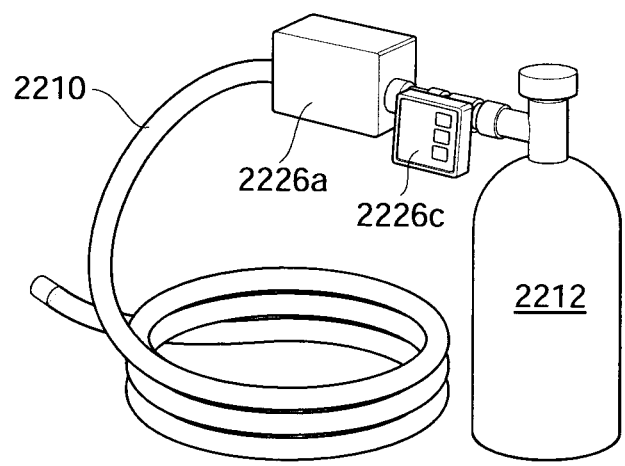

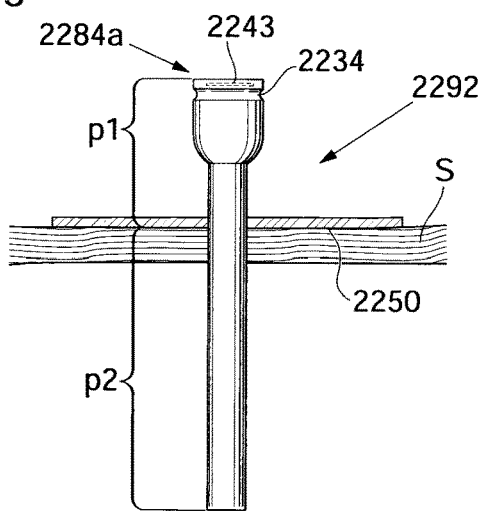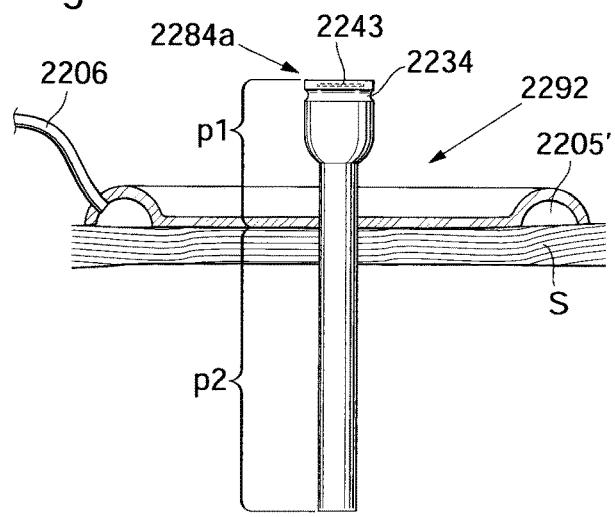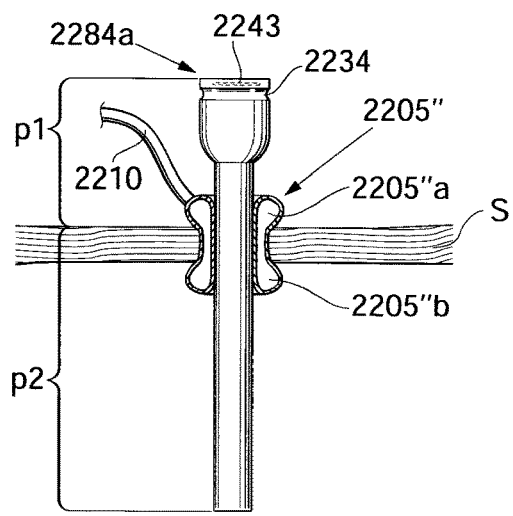

Fig.220l
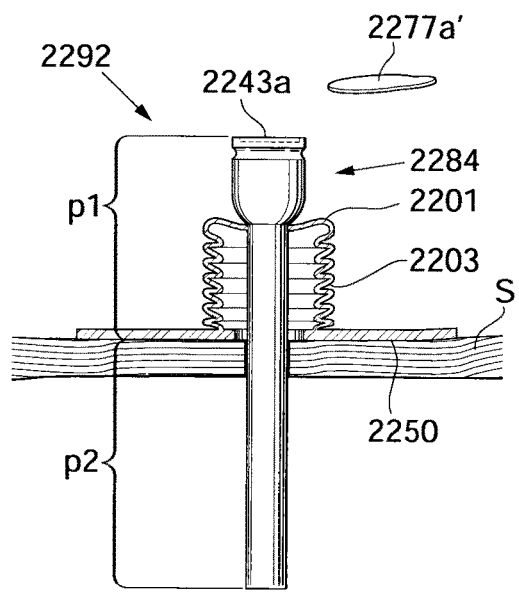
Fig.220m
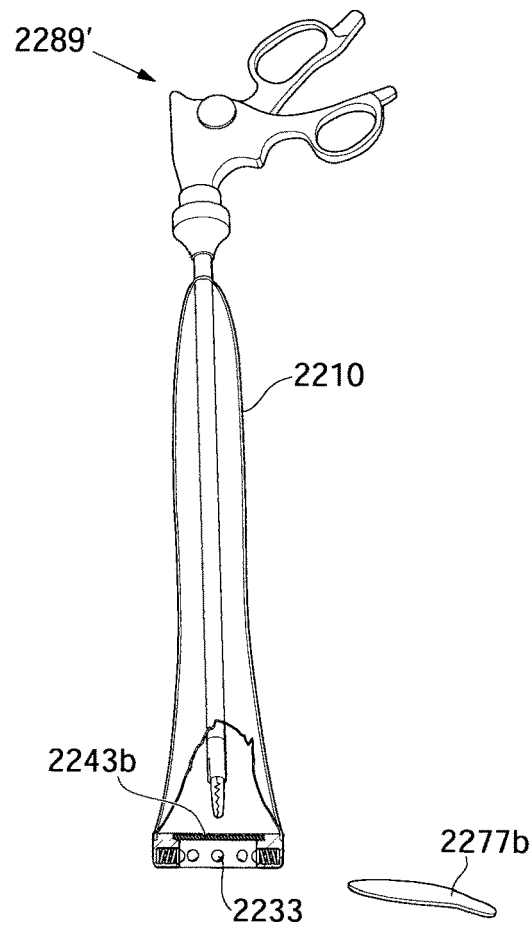
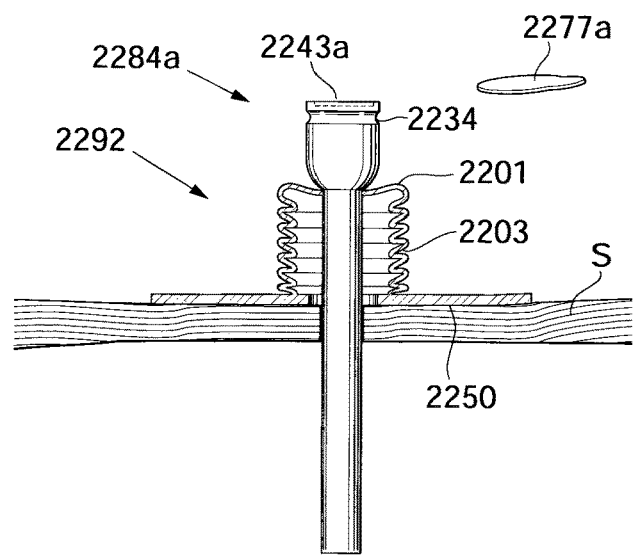

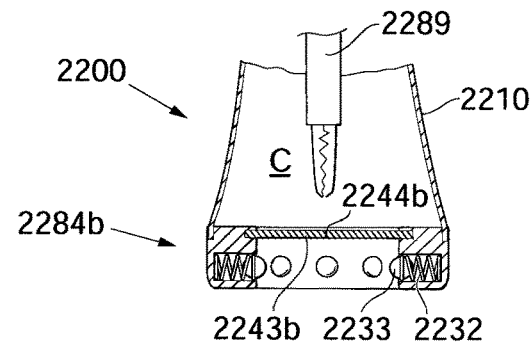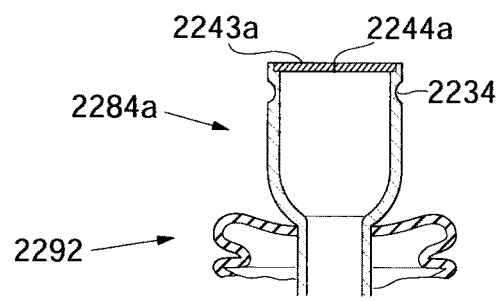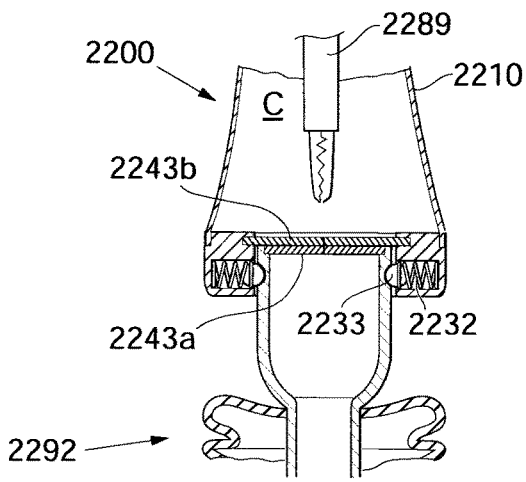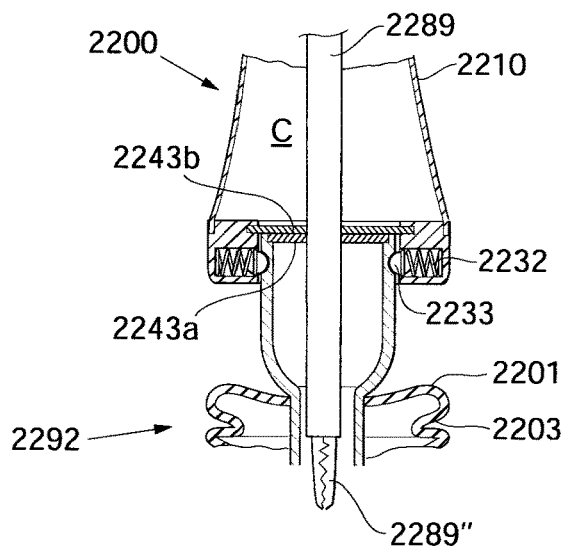

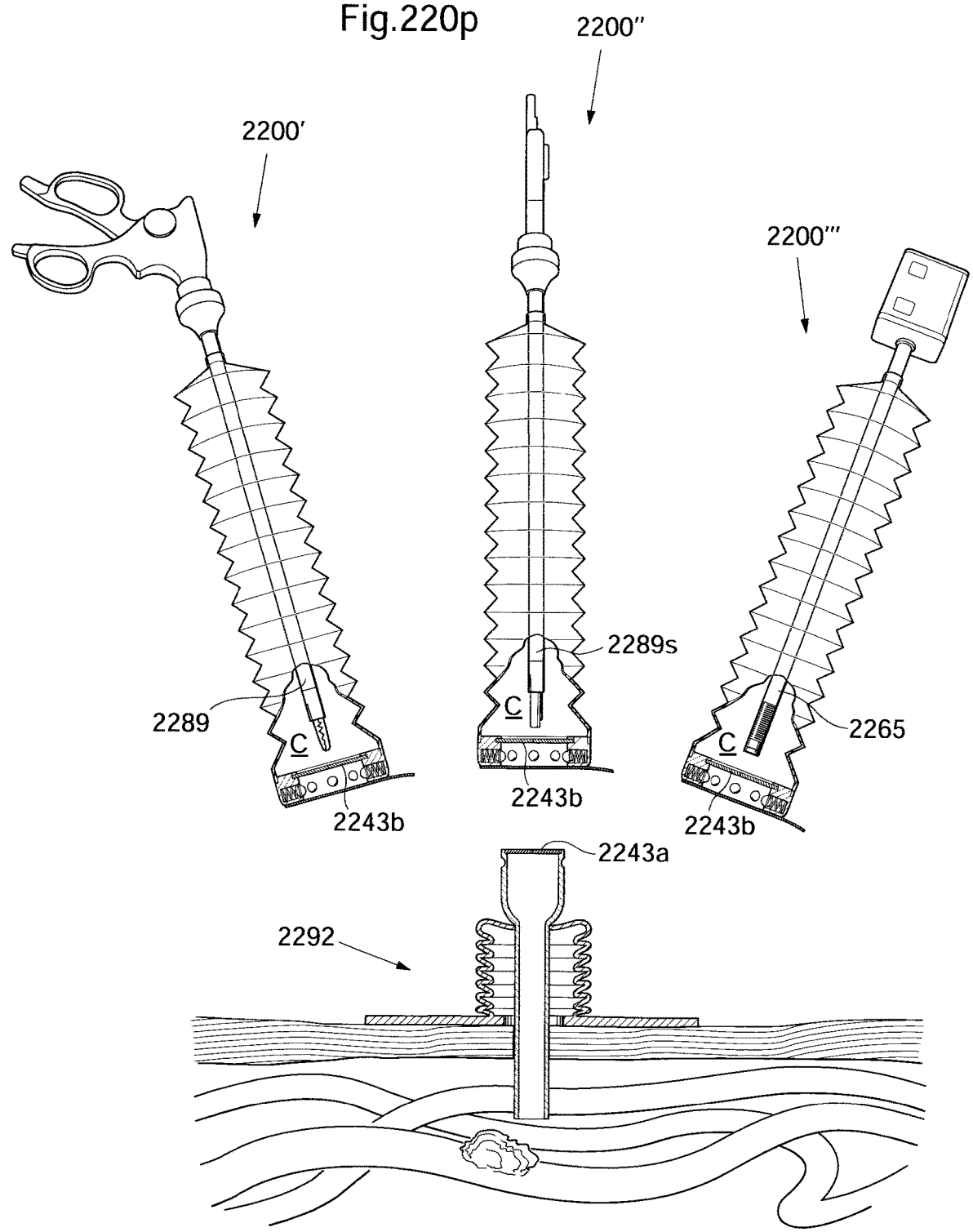

Fig.220q"
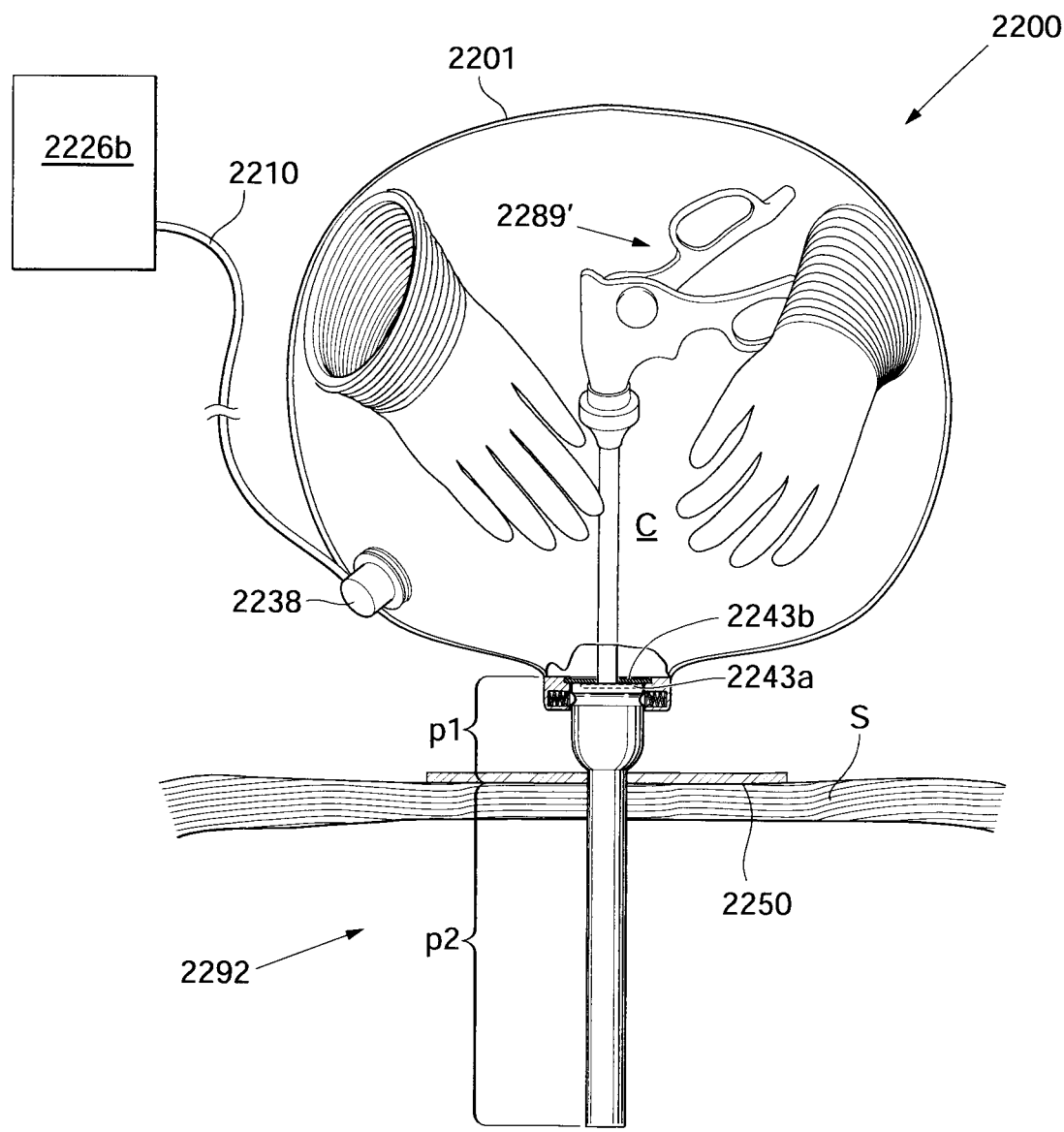

Fig.220q'''
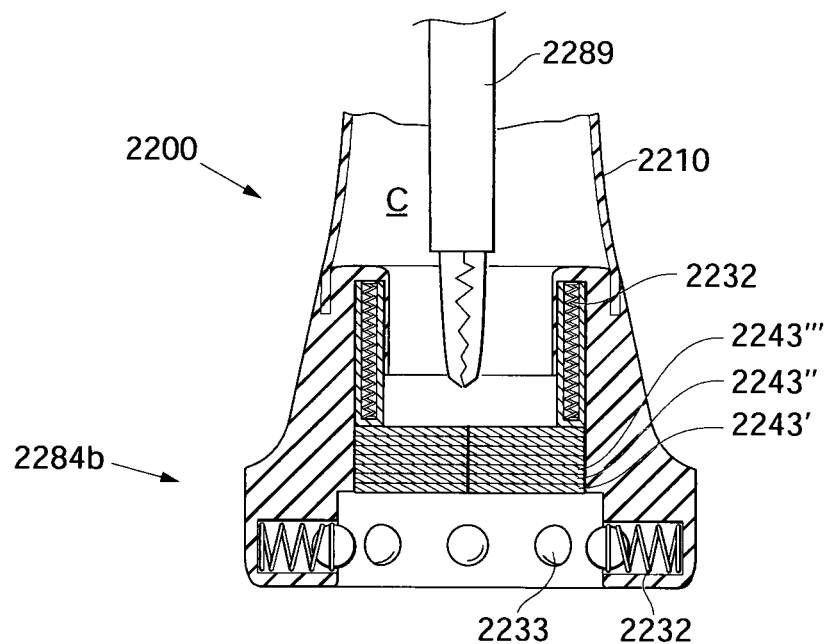
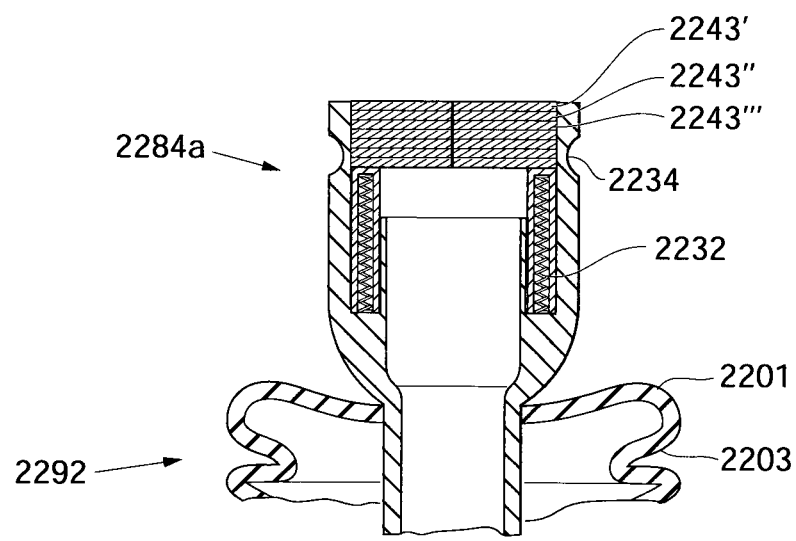

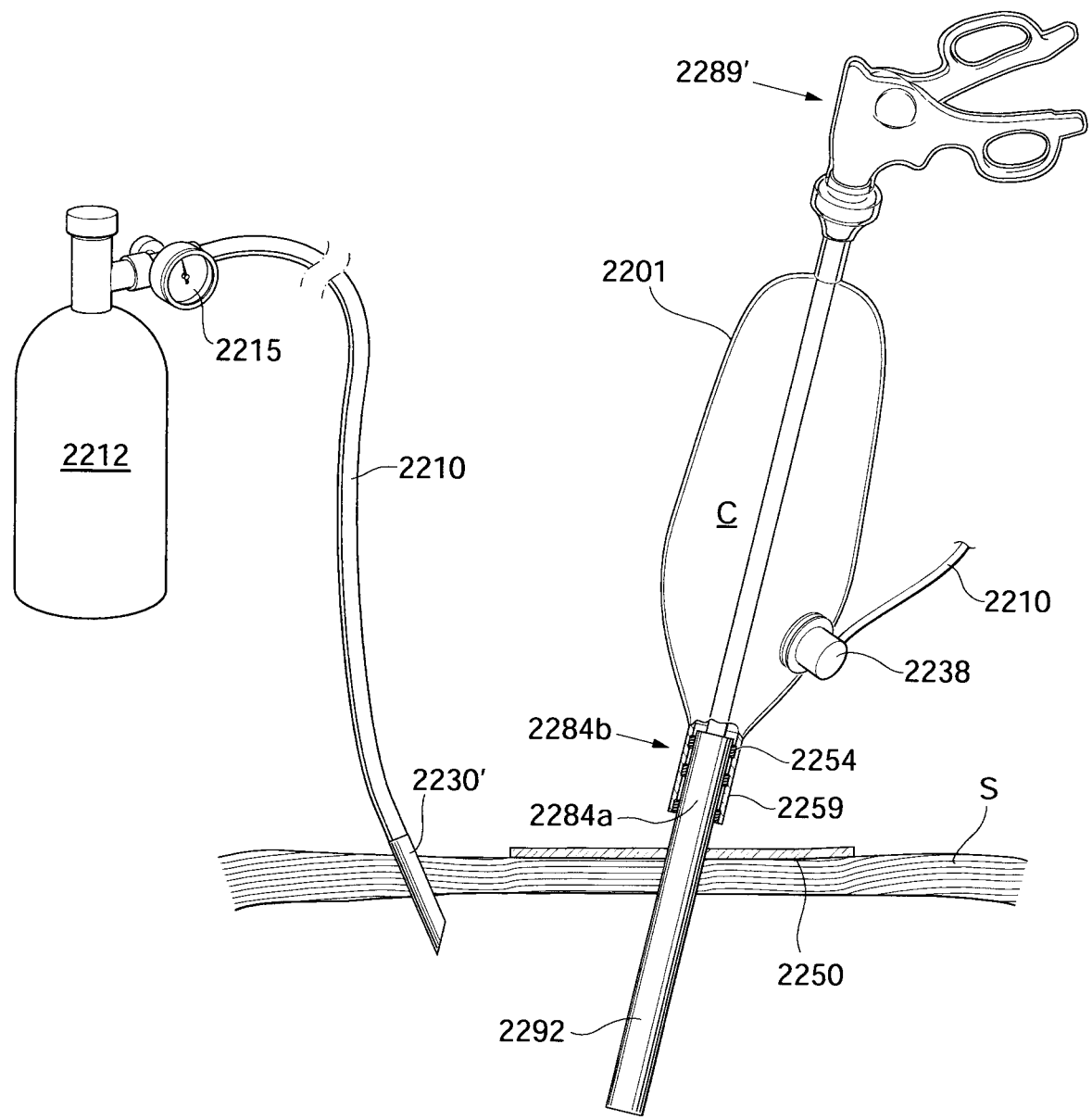
Fig.220q''''

Fig.237
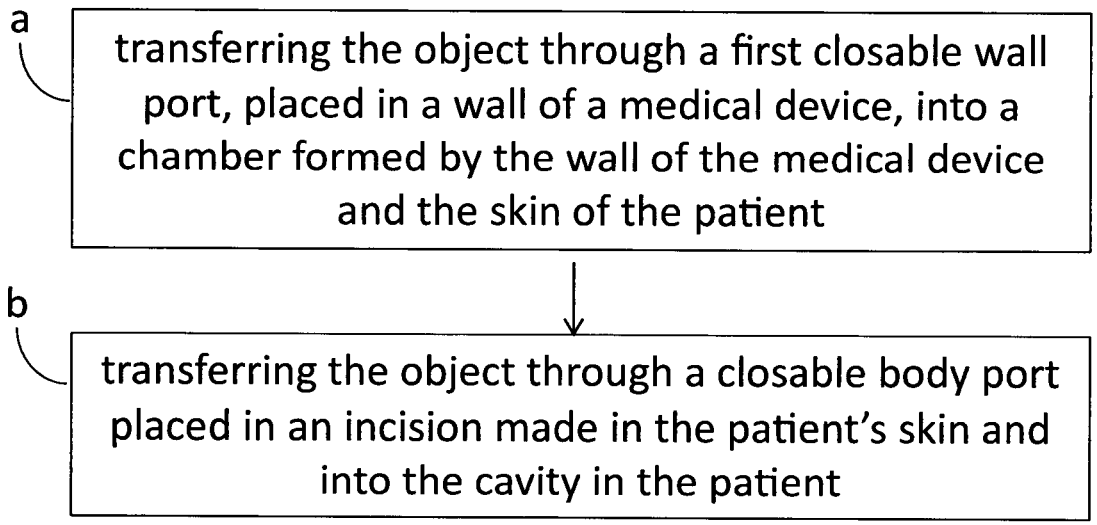
18(4)
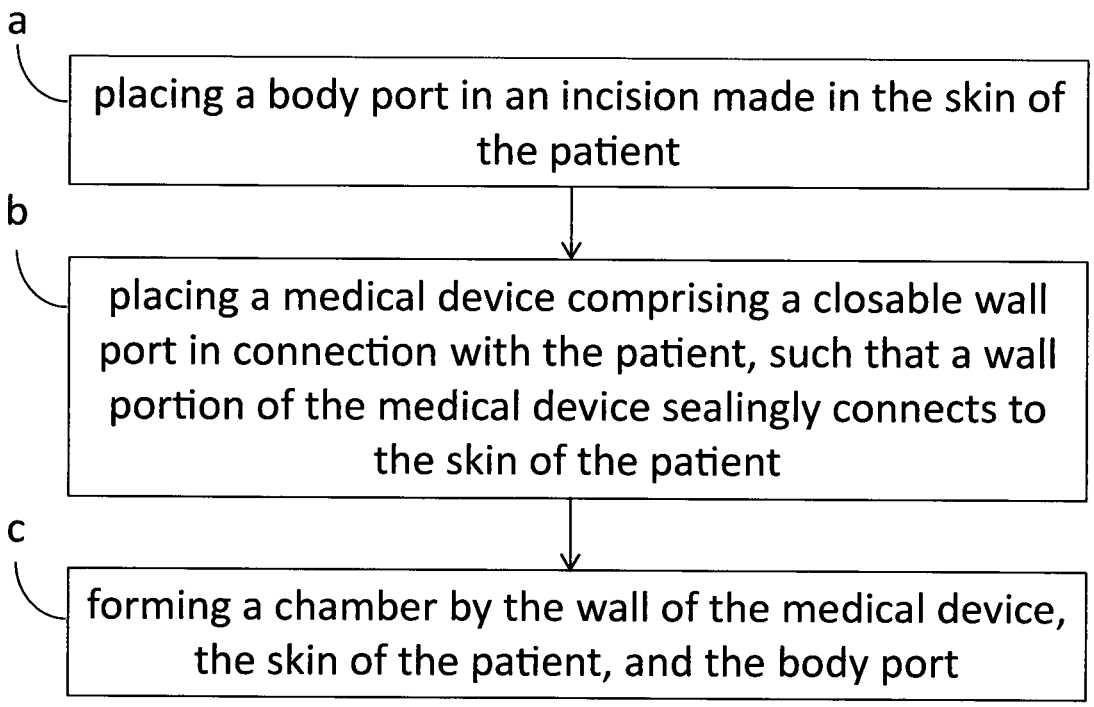

Fig.249a a — applying a wall on the skin of the patient to form a chamber in which a sealed environment can be maintained b — making an incision in the skin of the patient c — placing a fluid inlet through the incision d — supplying a fluid into the patient, thereby creating a cavity within the body of the patient e — making one or more additional incision(s) in the wall and skin of the patient f — inserting a trocar the additional incision(s)

g — Inserting a camera and/or a surgical instrument h — performing at least one step of endoscopic surgery i — making a second incision in the wall and skin

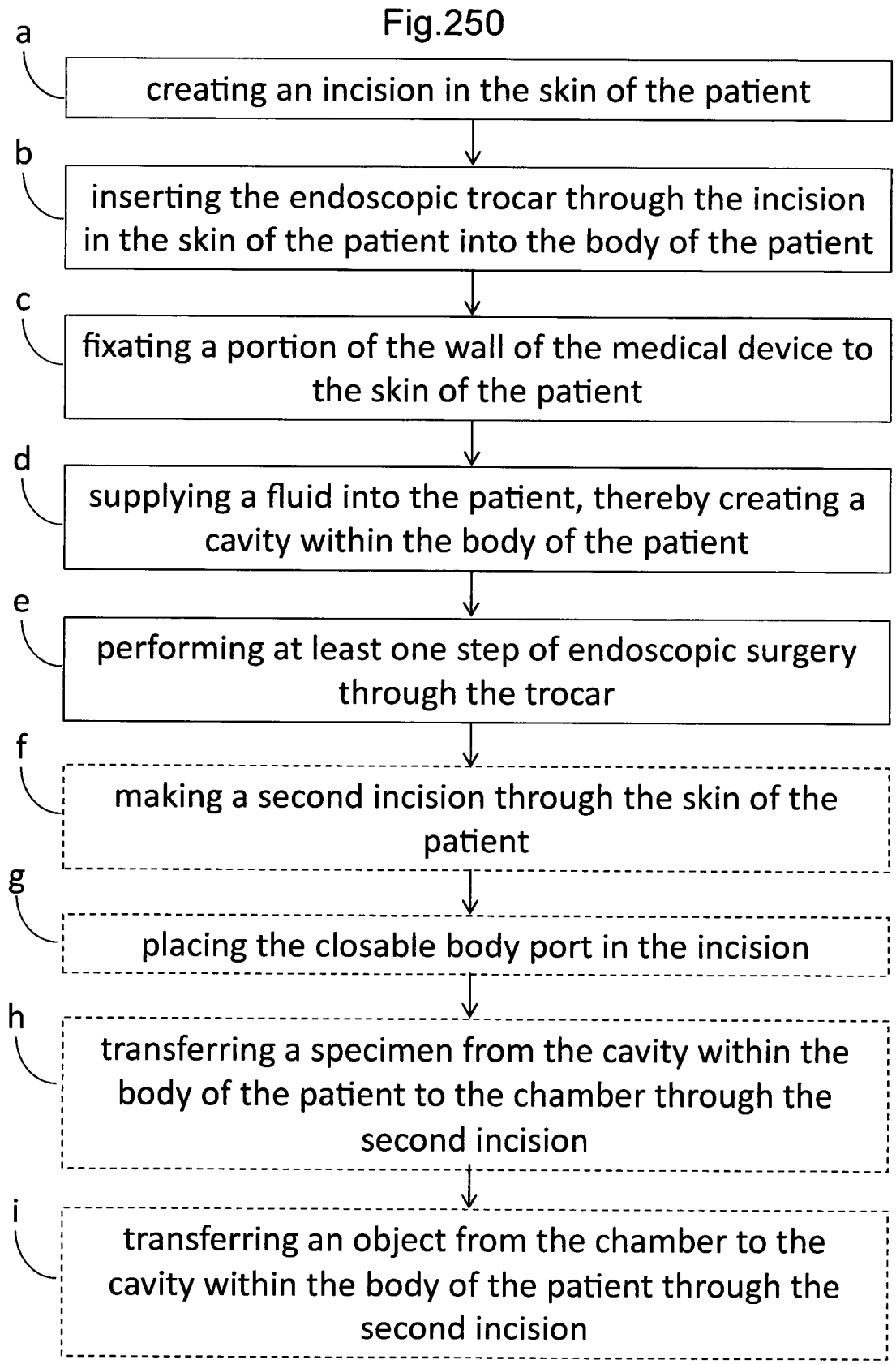

Fig. 259 a. forming a chamber using the wall b. placing at the chamber on the patient's body c. sealing between the wall and the skin or tissue of the patient d. sealing from at least one of: the anal orifice, the urethra orifice and at least part of the perineum region e. holding the medical device in place by encircling at least one leg of the patient f. holding the medical device in place by encircling the whole body left to right a second holding member g. sealing from the medial cranial part of the leg h. exclude from the chamber at least one of; the anal orifice, the urethra orifice and at least part of the perineum region

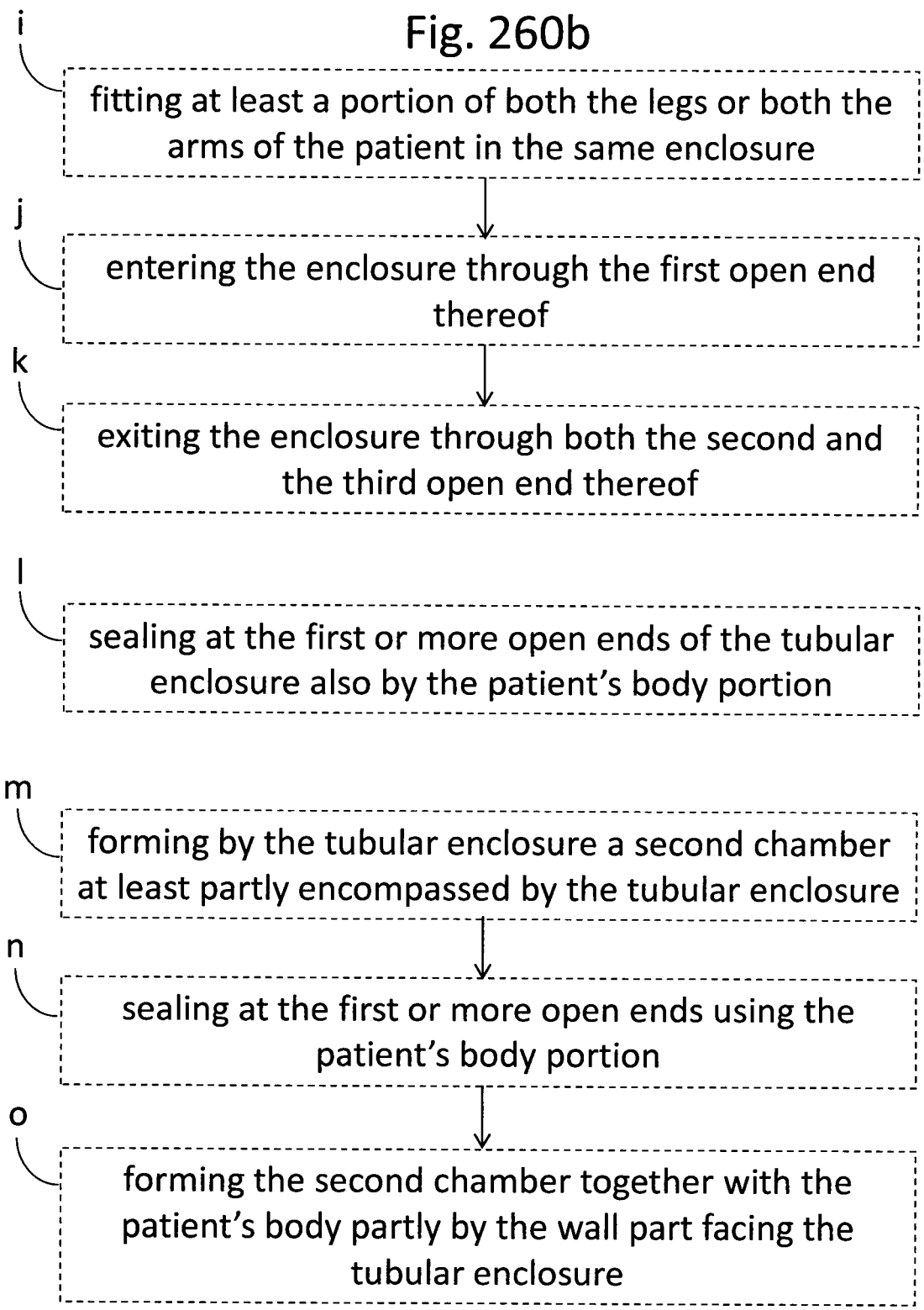

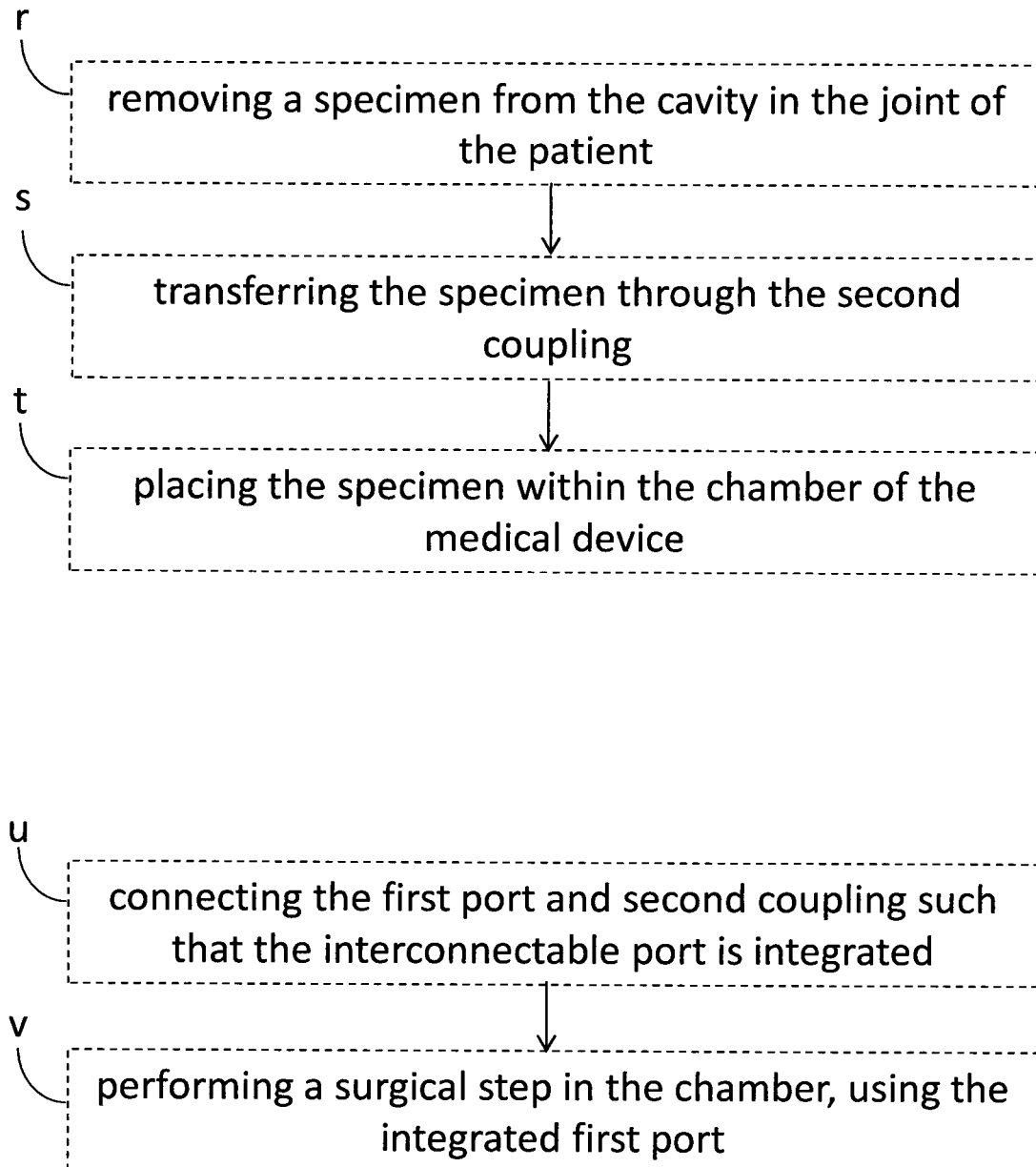

CONVERTIBLE SURGICAL ACCESS PORT

This application is the U.S. national phase of International Application No. PCT/SE2012/000112, filed 13 Jul. 2012, which designated the U.S. and claims the benefit from U.S. Provisional Application No. 61/670,701, filed 12 Jul. 2012, and claims priority to SE Application No. 1150701-9, filed 15 Jul. 2011, the entire contents of each of which are hereby incorporated by reference.

TECHNICAL FIELD

The present invention relates to the field of endoscopic and/or open surgery.

BACKGROUND ART

Surgical procedures have to some extent been performed as long as the human being have existed, however the techniques that started looking like the surgery being used today started its development during the 16:th century. Minimally invasive surgery is a concept in which the surgeon aims to minimize the scarring and post-operative hospital stay by performing the procedure through a small incision in the skin. The first minimally invasive procedure was performed in the beginning of the 20:th century and has developed into the most preferred technique in the industrialized world for procedures that allow a laparoscopic approach. Laparoscopic surgery is usually performed through 1-4 trocars placed in small incisions in the skin. For creating a cavity in the body of the patient for enabling the surgeon to view inside of the body $CO_2$ gas is usually inserted through one of the trocars inflating the body. The use of $CO_2$ gas requires that the trocars seal properly against the skin of the patient, since to large leaking would reduce the inflation of the cavity, thus not creating a large enough cavity for the surgeon to see. The optical vision is usually provided by means of a fiber optic endoscope possible to move from the outside to get the required views. Even if laparoscopic techniques are widely used today complications do occur, which in some instances leads to conversion into open surgery. The reasons for having to convert a laparoscopic procedure to open surgery could for example be accidental invasion of the adjacent tissue, the size of for example a tumor being removed exceeding the expected size or due to inflammatory disease. Normal conversion rates for laparoscopic procedures range between 5-36%. Since the conversions are done without proper preparation and usually as response to a problem, patients that have undergone converted surgery require longer postoperative hospital stay than scheduled open surgical patients. Complications with converted patients are also a lot higher than with scheduled open surgical patients, as much as 70% higher. In for example laparoscopic Cholecystectomy, 10% is converted to open surgery, due to bleedings, abscess and inflammations and of the converted patients the complications leading to the death of the patient is as much as twice as high. A general drawback with all minimally invasive procedure is that there is a size limitation of the objects possible to transfer between the inside of the patient body and the outside thereof. Usually the removing of larger specimens from the body is performed by means of making a larger incision at the end of the surgery while releasing the $CO_2$ gas which has occupied the cavity in which the laparoscopic surgery is performed. Examples of surgical procedure where relatively large specimens are removed from the body are: appendectomy, cholecystectomy, nephrectomy, hysterectomy, oophorectomy, adrenalectomy, splenectomy, colon resection and liver resection.

Arthroscopy is a surgical discipline similar to laparoscopic surgery but focuses on the joints of the patient, which in arthroscopic surgery can be operated without being fully opened. Usually, a plurality of smaller incisions are made so as to enable a surgeon to insert at least one optical instrument (arthroscope) for optical inspection of the joint, and at least one manipulating instrument for performing a manipulating operation within the joint. A clear liquid is circled in the joint to expand the joint and enable vision within the joint. The advantage of arthroscopy over traditional open surgery is that it reduces recovery time and increases the rate of surgical success, since the procedure imposes less trauma to the tissue. Arthroscopy is especially useful for professional athletes since they require fast healing time.

Since normal arthroscopy is performed with a plurality of small incisions it has the same drawbacks as laparoscopic surgery in that it imposes a limitation on the size of objects that can be transferred into the joint, for example can most arthroplastic surgery normally not be performed using arthroscopy since typically all implants have a size far exceeding that of the typical incisions made in the normal arthroscopic procedures. Arthroplastic procedures are therefore confined to the use of open surgery in which incisions, and thus the opening into the area of the joints needs to be of considerable size creating a large surface exposed to the environment of the operating room. The risk of the patient getting an infectious disease following orthopedic surgery is considerably larger than in abdominal surgery, which has been a focus area of leading orthopedic surgeons the last decades. Generally, the effect of bacterial infection if connection with orthopedic surgery includes: prolong rehabilitation, morbidity and mortality. Disease-carrying bacteria, viruses, and parasites that get into the body can destroy healthy tissue, multiply and spread through the blood. Even if the infection occurs superficially in the skin and other soft tissue, the infection can lead to infection of bones (osteomyelitis) and joints (septic arthritis). Orthopedic infections can, if not promptly treated become chronic and lead to paralysis or morbidity of infected extremities.

The increased awareness of the high risk of infections in connection with orthopedic surgery has increased precaution during and after orthopedic surgery. Important factors for maintaining a low incidence of infection is typically: operating theatre design, meticulous surgical technique and aseptic discipline within all involved areas of the operation. Specific precautions during orthopedic surgery includes: use of especially sterilized operating rooms, for example requiring special air filters in the air conditioning systems, limiting of the amount of staff present in the operating room, imposing special requirements on clothing to be worn in the operating rooms, including the use of full body protective suits. Complex instruments and parts of machinery are generally very difficult to sterilize. The most commonly occurring solution to this problem is that the robots are fully covered with disposable sheets, a process being both time-consuming and costly.

The operating environments of the industrialized world are generally both very clean and all measures are taken to reduce the risk that infectious disease should affect the post-operative care. However, environments where surgery is performed around the globe is far from always at the operating theatres of the industrialized world, which in some cases make the proper sterilization of the operating environment or the tools to be used in that environment difficult to perform. In any instance, surgery is still needed in remote places and transportable sterile environments and pre-sterilized instruments is therefore of importance.

SUMMARY

A medical device in form of an interconnectable port adapted to be at least partially placed in an incision in a patient's body is provided. The interconnectable port comprises a first and second port adapted to be interconnected to form the interconnectable port, wherein the second port is disconnectable from the first port. The first port is connected to a first portion of a flexible wall, and the second port is connected to a second portion of the flexible wall, and wherein the flexible wall is adapted to form a chamber in which a step of a surgical procedure me be conducted.

According to one embodiment, the interconnectable port enables choosing between performing an endoscopic procedure through the port, in a cavity in the body of the patient, and performing at least one step of the surgical procedure inside the chamber of the medical device using endoscopic instruments or a hand inserted into the chamber. As an example, a laparoscopic procedure may be performed until an object should be inserted into the body of the patient, or specimen should be removed from the body of the patient, at what time the interconnected port is disconnected such that the object or specimen can be transferred from the chamber of the medical device to a cavity in the patient, or in the opposite direction.

According to one embodiment of the interconnectable port, the first port forms a closable wall port when disconnected from the second port, such that the chamber can remain sealed.

According to one embodiment of the interconnectable port the second port forms a closable body port by itself when the first port has been disconnected from the second port, such that the chamber and cavity of the patient remains separated even as the interconnectable port is separated. The chamber may have a first volume when the first and second ports are interconnected and a second volume when the second port is disconnected from the first port, and the second could be larger than the first volume. According to one embodiment, the first volume is smaller than 100 000 mm3. According to one embodiment, the second volume is larger than 500 000 mm3.

According to one embodiment, the medical device comprises a first and second coupling, and the first port is connected to the first coupling, and the second port is connected to the second coupling. at least one of the first and second coupling may comprise a protruding member, and at least one of the first and second coupling may comprise a recess, which may be a groove, and the protruding member may be adapted to engage the recess for locking the first coupling to the second coupling.

According to one embodiment, the interconnectable port is adapted to, in a first state, when the first and second ports are interconnected, enable a surgeon to operate through the interconnected interconnectable port, and in a second state, when the second port is disconnected from the first part enable the surgeon to perform steps of the procedure within the chamber formed by the flexible wall between the first and second ports of the interconnectable port. The interconnectable port may be adapted to, in the second state, enable the surgeon to remove a specimen from the body of the patient through the second port and into the chamber, and to perform one of: placing the specimen within the chamber, and removing the specimen from the chamber through the second port.

According to one embodiment, the first and second ports are adapted to be reconnected after having been disconnected, such that the surgeon can continue operating through the interconnected port after the specimen has been removed.

The interconnectable port may further comprise an inset detachably fixated to at least one of the first and second coupling, such that the inset could be detached and replaced by a different inset. The inset may comprise at least one of: a surgical glove and a device or instrument mount.

According to one embodiment, at least one of the first and second ports comprises an elastic or flexible membrane adapted to, in a non-compressed state, provide sealing, and in a compressed state enable a hand or an object to be inserted through the membrane.

According to one embodiment of the interconnectable port the first port may comprise a first elastic or flexible membrane and the second port may comprise a second elastic or flexible membrane, and the first and second membranes may be adapted to be placed tightly together such that they act as a single elastic or flexible membrane adapted to, in a non-compressed state, provide sealing, and in a compressed state enable a hand or an object to be inserted through the membrane. The first and second membranes may comprise a plurality of self sealing holes enabling insertion of instruments through the membranes.

According to one embodiment, the interconnectable port further comprises at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

The interconnectable port according to any one of the preceding embodiments, may further comprises at least one of: a filtering unit for filtering the fluid, a sterilization unit for directly or indirectly sterilizing the fluid and a fluid tempering unit adapted change the temperature of the fluid, A surgical method to be performed on the body of a patient using an interconnectable port is further provided. The interconnectable port comprises a first and second port, the method comprising: creating an incision in the skin of the patient, placing the interconnectable port in the incision, disconnecting the first port from the second port, such that a chamber is formed by a wall connected to the first and second port, and performing a step of the surgical procedure within the chamber. The step of performing a step of the surgical procedure within the chamber may comprises removing a specimen from the cavity in the body of the patient, transferring the specimen through the second port, and placing the specimen within the chamber of the medical device. The surgical method may further comprise: reconnecting the first and second ports such that the interconnectable port is formed, and performing a surgical step in a cavity of the patient, through the interconnectable port.

A medical device for performing a surgical procedure on a patient is provided. The medical device comprises a wall adapted to be at least partially applied on the patient's body to form a chamber in which a sealed environment can be maintained, the chamber being adapted to encompass part of the surgical procedure to be performed, wherein a portion of the wall directly or indirectly forms an elongated tubular enclosure having a single open end, the elongated tubular enclosure extending in the chamber and being adapted to fit a portion of an extremity of the patient inserted into the elongated tubular enclosure through the open end thereof, such that the surgical procedure can be performed on the portion of the patient's extremity, and a fluid evacuation system adapted to evacuate fluid from the interior of the elongated tubular enclosure, when the portion of the patient's extremity is placed in the enclosure.

By evacuating the fluid from the elongated tubular enclosure, the wall of the inside of the elongated tubular enclosure can fit snuggly against the extremity of the patient for example reducing the risk that bacteria or viruses caught in the skin of the patient, is transported to the incision site in the chamber of the medical device.

According to one embodiment, the elongated tubular enclosure comprises an adhesive surface adapted to contact the skin of the patient when the fluid has been evacuated from the interior of the elongated tubular enclosure.

According to one embodiment, a first portion of the elongated tubular enclosure may comprise an adhesive surface, and the medical device may further comprise a separating layer adapted to cover the first portion, and the separating layer may be adapted to be removed from the first portion, when the adhesive surface is placed onto the skin of the patient.

According to one embodiment, the medical device comprises at least one sealing device adapted to seal between the skin of the extremity of the patient and at least one of: the wall of the medical device and the elongated tubular enclosure. The sealing device may be adapted to exert an adjustable sealing force.

According to one embodiment, the sealing device comprises a hydraulically, pneumatically, or electrically powered pressure sealing member.

According to one embodiment, the sealing device comprises a vacuum sealing member attached to at least one of, the wall and enclosure and adapted to provide a pressure less than atmospheric pressure to create a vacuum seal between the skin of the patient's extremity and at least one of the wall and elongated tubular enclosure.

According to one embodiment, the medical device further comprises at least one of: a pressure creating member connected to the at least one of the hydraulically, pneumatically and electrically powered sealing member, and a vacuum creating member connected to the vacuum sealing member.

According to one embodiment, the body multi port is fixated in the elongated tubular enclosure.

A method embodiment of forming a sterile environment using a medical device is further provided, the medical device comprises a wall adapted to form a chamber, in which a sealed environment can be maintained, wherein a portion of the wall directly or indirectly forms an elongated tubular enclosure extending in the chamber, having a single open end. The method comprises fitting the medical device on an extremity of a patient, such that the extremity of the patient is placed inside the elongated tubular enclosure, and evacuating a fluid from the elongated tubular enclosure such that the tubular enclosure fits snuggly against the skin of the extremity.

According to one embodiment, the method further comprises inflating the wall of the medical device such that an inflated chamber is formed.

According to one embodiment, the method further comprises inflating the elongated tubular enclosure prior to fitting the medical device on the extremity of the patient, and/or removing a separating layer from the elongated tubular enclosure prior to fitting the medical device on the extremity of the patient.

A medical device for performing a surgical procedure on a patient when performing an incision in the patient's body for communication with a body cavity is further provided. The medical device comprises: a wall adapted to be applied exteriorly on the patient's body to form a chamber, in which a sealed environment can be maintained for encompassing part of the surgical procedure to be performed, a sealing device adapted to seal between the medical device and the patient's body, to allow the chamber to be in fluid connection with a cavity in the patient's body, sealed from the ambient environment, The medical device further comprises at least one of: at least one first port detachably fixed to the wall for enabling access to and manipulation within the chamber, and at least one first inset detachably fixed to the wall and forming part of the chamber, and at least one of: at least one second port adapted to be detachably fixed to the wall, the second port having a design different from the first port, and at least one second inset adapted to be detachably fixed to the wall, the second inset having a design different from the first inset, wherein the first port is exchangeable by at least one of: the second port, the first inset and the second inset, and the first inset is exchangeable by at least one of the first port, the second port and the second inset.

The exchangeable ports enable the shift from for example an endoscopic to an open procedure, or from manual manipulation within a cavity in the patient or chamber of the medical device to manipulation using endoscopic instruments in a cavity of the patient or in the chamber of the medical device.

According to one embodiment, the medical device comprises a valve member adapted to remain closed until at least one of at least a part of an inset, and at least a part of a port, is placed in the first hole in the wall.

According to one embodiment, the wall of the medical device comprises an outer wall and at least one partition wall dividing the chamber into at least a first compartment and a second compartment. The first port or first inset is fixed to the outer wall of the first compartment and the second port or second inset is fixed to the partition wall, whereby the first port, and the first compartment and the second port function as an airlock sluice, such that the environment in the second compartment remains closed, also when the first port is detached from the outer wall of the first chamber.

According to one embodiment of the medical device, the medical device further comprises an adhesive surface adapted to provide at least one of: fixation of the wall to the skin of the patient and sealing between the wall and the skin of patient.

According to one embodiment, the wall comprises a free top wall portion and a bottom wall portion adapted to contact the patient's skin surface to surface. The chamber is defined by the top and bottom wall portions, and the bottom wall portion is adapted to be attached to the patient's body prior to the start of the surgical procedure, such that an incision in the patient can be performed inside the chamber through the bottom wall portion and the skin of the patient.

According to one embodiment, the medical device further comprises a retractor adapted to be placed in an incision cut in the skin of the patient within the chamber and adapted to be continuously open for enabling passage between the chamber and the inside of the patient's body.

A method of performing a surgical procedure on a patient using a medical device is further provided. The medical device comprises a wall adapted to be applied exteriorly on the patient's body to form a chamber, in which a sealed environment can be maintained for encompassing part of the surgical procedure to be performed, a sealing device adapted to seal between the medical device and the patient's body, to allow the chamber to be in fluid connection with a cavity in the patient's body, sealed from the ambient environment, at least one of: at least one first port detachably fixed to the wall for enabling access to and manipulation within the chamber, and at least one first inset detachably fixed to the wall and forming part of the chamber, and at least one of: at least one second port adapted to be detachably fixed to the wall, the second port having a design different from the first port, and at least one second inset adapted to be detachably fixed to the wall, the second inset having a design different from the first inset. The method comprises the steps of: applying a wall on the patient's body to form a chamber together with the patient's body, such that the sealed environment can be maintained, applying a sealing device against the skin of the patient, such that sealing is created between the wall of the medical device and the skin of the patient, and at least one of: exchanging the first port to at least one of: the second port, the first inset and the second inset, and exchanging the first inset to at least one of: the first port, the second port and the second inset, such that different operational steps in different operational sites using different instruments (or hands) can be performed.

A medical device for performing a surgical procedure on a patient is provided. The medical device comprises a wall adapted to be at least partially applied on the patient's body to form a first chamber adapted to hold a first pressure exceeding atmospheric pressure, in which a sealed environment can be maintained for encompassing part of the surgical procedure to be performed. A portion of the wall is adapted to contact the skin of the patient to create a substantially airtight seal between the wall portion and the skin of the patient, to enable an incision to be performed through the skin of the patient in sealed environment such that a fluid connection between a cavity within the patient and the first chamber can be created. The wall is adapted to maintain the seal between the wall portion and the patient's skin substantially airtight after such an incision has been performed. The medical device is adapted to hold a pressure in the first chamber, allowing fluid connection with the cavity, exceeding atmospheric pressure, when such an incision has been performed during the surgical procedure, wherein the wall comprises: a first wall part, designed to allow the first pressure to be maintained in the first chamber, and a second wall part, designed to allow a second pressure to be maintained in a second chamber adapted to create a sealing between the medical device and the patient's body, and the first and second pressures are different. By the provided medical device, a first positive or negative pressure could be provided for sealing between the skin and/or tissue of the patient, and a second positive pressure could be provided in the chamber of the medical device and/or in a cavity in the patient's body.

According to one embodiment of the medical device, the wall comprises a top portion and a bottom portion, which is adapted to contact and press against the patient's skin, surface to surface, to seal between the bottom wall portion and the skin of the patient. The first wall part is adapted to allow a pressure in the first chamber exceeding atmospheric pressure. The bottom wall portion may be adapted to be cut through when the incision in the skin of the patient is made in the sealed environment, such that the incision is performed inside of the sealed environment, reducing the risk that bacteria can enter the incision site.

According to one embodiment, the bottom wall portion comprises an adhesive surface for at least one of: fixating the wall to the patient's skin, and sealing between the bottom wall portion and the patient.

According to one embodiment, the bottom wall portion comprises a vacuum sealing member, at least one of attached to and integrated in the wall and adapted to provide a pressure less than atmospheric pressure between the vacuum sealing member and the patient's skin to create a vacuum sealing between the skin and the wall.

According to one embodiment, the volume of the chamber is larger than 100 000 mm3 or larger than 500 000 mm3.

A method of performing a surgical procedure in a sealed environment is further provided. The method comprises applying a first wall part on the patient's body to form a first chamber, together with the patient's body, such that a sealed environment can be maintained. Applying a second wall part on the patient's body to form a second chamber together with the patient's body, for providing a sealing between the ambient environment and the first chamber, inflating the first chamber with a fluid for creating a first pressure in the first chamber, inflating the second chamber with a fluid for creating a second pressure in the second chamber, the second chamber being different from the first pressure, and creating an incision in the patient's body in the sealed environment of the first chamber.

A medical device for performing a surgical procedure on a patient is further provided. The medical device comprises a wall adapted to be applied at least partially on the patient's body to form a chamber, by itself or together with the body of the patient, in which a sealed environment can be maintained for encompassing part of the surgical procedure to be performed. The medical device further comprises a sealing device adapted to seal between a portion of the wall and the patient's body, when the wall is applied on the patient's body. The sealing device comprises a pressurized sealing member adapted to exert a pneumatic, hydraulic or mechanic pressure against the body of the patient such that the chamber is at least substantially sealed from the ambient environment, allowing a pressure inside the chamber higher than atmospheric pressure during the surgical procedure, thus the wall sealing device being adapted to seal the chamber, after the medical device has been applied at least partially on the patient's body, when at least one of; an incision has been performed in the wall of the chamber contacting the patient's body and an incision has been performed in the skin of the patient forming part of the chamber for creating a fluid connection between the chamber and a cavity in the patient inside the incision, and wherein the sealing device is adapted to remain unaffected by the incision and thus sealing with unaffected force, wherein the sealing device has a closed geometrical configuration. The medical device further comprises a holding member adapted to hold the medical device in a direction substantially opposite to the direction of the pressure applied from the sealing device onto the skin of the patient, thus holding the closed geometrical configuration sealingly in contact with the skin of the patient. The medical device further comprises at least one of a pressure adjustment device adapted to adjust the pressure exerted by the sealing device, and a monitoring unit for monitoring at least one of: the pressure exerted by the sealing device, the blood flow passing the sealing device, and the direct or indirect leakage of fluid from the chamber. By monitoring the pressure exerted by the sealing device, or the effects of the body of the patient, the exerted force can be adapted such that sufficient sealing is provided while doing minimal damage to the body of the patient.

According to one embodiment, the sealing device has a closed geometrical configuration adapted to be applied on a surface of the skin without encircling any limb of the patient and/or a closed geometrical configuration adapted to encircle a limb of the patient.

The medical device may further comprise at least one of at least one glove integrated in the wall such that a surgeon is able to use the glove from outside the chamber to make manual manipulations inside the chamber while maintaining sealed environment in the chamber, at least one inset, and at least one inset comprising an integrated glove such that a surgeon is able to use the glove from outside the chamber to make manual manipulations inside the chamber while maintaining sealed environment in the chamber.

According to one embodiment, the wall comprises a bottom portion adapted to contact and press against the patient's skin, to seal between the bottom wall portion and the skin of the patient. The wall of the medical device is adapted to allow a pressure in the chamber exceeding atmospheric pressure. The bottom wall portion may be adapted to be cut through when an incision in the skin of the patient is to be performed in sealed environment.

According to one embodiment, the bottom wall portion comprises an adhesive surface for at least one of: fixating the wall to the patient's skin and sealing between the bottom wall portion and the patient.

According to one embodiment, the volume of the chamber is larger than 100 000 mm3 or larger than 500 000 mm3.

The medical device may comprises a second sealing device which may be adapted to be at least one of sealingly connected to at least one of the wall and the closable body port, an integrated part of at least one of; the wall and the closable body port, and adapted to seal against at least one of the skin and tissue of the patient.

A method embodiment of performing a surgical procedure on a patient using a medical device is further provided. The method comprises: applying a wall on the skin of the patient to form a chamber, in which a sealed environment can be maintained for encompassing part of the surgical procedure to be performed, applying a pressure sealing device adapted to seal between a portion of the wall and the patient's body, applying a holding member adapted to hold the medical device in a direction substantially opposite to the direction of the pressure applied from the sealing device onto the skin of the patient, injecting a fluid into the chamber, such that the pressure inside the chamber exceeds atmospheric pressure, creating an incision in the skin of the patient in the sealed environment of the chamber, and at least one of: adjusting the pressure exerted by the sealing device, and monitoring at least one of: the pressure exerted by the sealing device, the blood flow passing the sealing device, and the direct or indirect leakage of fluid from the chamber.

A medical device for performing a surgical procedure on a patient is provided, the medical device comprises a wall adapted to be at least partially applied on the patient's body and further adapted to form a chamber alone or together with the patient's body, in which a sealed environment can be maintained for encompassing part of the surgical procedure to be performed, wherein a portion of the wall is adapted to be in contact with the patient's skin, and at least one wall inset or wall port attached to the wall and adapted to enable manipulation within the chamber, wherein the wall inset or wall port is displaceable between: a first position, in which the inset or wall port is fixated relative to the skin or tissue of the patient, and a second position, more remote from the patient's skin than the first position, in which the inset or wall port is moveable relative to the skin or tissue of the patient. Having the port or inset more remote from the patient's skin enables manipulation using hands or instruments within the chamber of the medical device, whereas the location close to the skin facilitates manipulation in a cavity in the body of the patient using endoscopic instruments or a hand.

According to one embodiment, the wall inset or wall port comprises a first coupling adapted to fixate the inset or wall port directly or indirectly to the skin or tissue of the patient.

According to one embodiment, the wall comprises a first and second coupling, the first coupling is adapted to be positioned at a first position, and wherein the second coupling is adapted to connect to the first coupling for locking the wall inset or wall port in the first position.

The medical device may further comprise a body inset or body port adapted to be mounted in another wall portion or the skin or tissue of the patient. The first coupling may be adapted to be positioned in connection with the body port or body inset, and the wall port and the body port may be adapted to form an integrated port when the first and second coupling are connected in the first position. The body port may comprise a second coupling adapted to connect to the first coupling.

According to one embodiment, the chamber may assume a first volume when the wall inset or wall port is in the first position, and assumes a second volume larger than the first volume, when the inset or wall port is in the second position.

According to one embodiment, at least one of the wall inset or at least part of the wall port may be detachably fixed to the wall across a hole formed in the wall. The wall port may comprise a valve for closing the hole in the wall port to close the chamber.

According to one embodiment, the portion of the wall adapted to be applied on the patient's body when the surgical procedure is to be performed further comprises a vacuum sealing member adapted to hold a pressure less than atmospheric pressure between the wall portion and the patient's skin to seal between the wall portion and the patient's skin. The vacuum sealing member may be adapted to create a substantially airtight seal between the wall portion and the skin of the patient, to enable an incision to be performed through the skin of the patient in sealed environment such that a fluid connection between a cavity within the patient and the chamber can be created.

According to one embodiment, the portion of the wall adapted to be applied on the patient's body when the surgical procedure is to be performed further comprises a pressure sealing member adapted to hold a pressure above atmospheric pressure between the wall portion and the patient's skin to seal between the wall portion and the patient's skin.

A surgical method for performing a laparoscopic procedure in a sealed environment is further provided. The surgical method comprises placing a medical device comprising a wall in connection with the patient, such that a portion of the wall of the medical device sealingly connects to the skin of the patient, such that a chamber is formed by the wall of the medical device and the skin of the patient. The wall further comprises a wall inset or wall port, moving the wall inset or wall port from a first position, in which the wall inset or wall port is fixated relative to the skin or tissue of the patient to a second position, more remote from the patient's skin than the first position, in which the wall inset or wall port is moveable relative to the skin or tissue of the patient.

According to one embodiment, the surgical method further comprises the step of making an incision in the skin of the patient's body creating a fluid connection between the chamber and a cavity in the patient's body.

According to one embodiment, the surgical method further comprises the step of placing a portion of the wall inset or wall port in the incision made in the skin of the patient and/or sealing the wall portion to the skin of the patient by applying a negative pressure to a sealing device and/or inflating a cavity in the patient using a laparoscopic fluid, such that a cavity enabling visual inspection within the body of the patient is formed.

According to one embodiment, the surgical method further comprises the step of exchanging the wall inset or wall port to an additional inset or port for performing an operational step in the chamber of the medical device or in the cavity in the patient.

A medical device for performing an endoscopic surgical procedure on a patient is provided. The medical device comprising a wall adapted to at least partially be applied on the patient's body to form a chamber, by itself or together with the patient's body, in which a sealed environment can be maintained for encompassing part of the surgical procedure to be performed. A wall portion of the medical device is adapted to contact the patient's skin when the surgical procedure is performed, and a vacuum sealing member is adapted to hold a pressure in a second chamber between the skin and the wall, or in a second chamber and between the skin and the wall, contacting the skin of the patient, the pressure being: different than the pressure in the chamber, and less than atmospheric pressure, for providing sealing between the wall portion and the patient's skin. The vacuum sealing member thus enables the maintaining of a pressure exceeding atmospheric pressure in the chamber and being below atmospheric pressure in the vacuum sealing member.

According to one embodiment, the vacuum sealing member is adapted to create a substantially airtight seal between the wall portion and the skin of the patient, to enable an incision to be performed through the skin of the patient in the sealed environment for creating a fluid connection between a cavity within the patient and the chamber.

The medical device may comprise a plurality of vacuum sealing members positioned consecutively for enhancing the sealing effect provided by the vacuum sealing and/or for changing the sealing position, such that the skin of the patient is less affected by the vacuum sealing member.

The multiple vacuum sealing members may comprise multiple vacuum sealing grooves adapted to be placed consecutively.

According to one embodiment, the medical device further comprises at least one of at least one glove integrated in the wall such that a surgeon is able to use the glove from outside the chamber to make manual manipulations inside the chamber while maintaining sealed environment in the chamber, at least one inset, and at least one inset comprising a glove such that a surgeon is able to use the glove from outside the chamber to make manual manipulations inside the chamber while maintaining sealed environment in the chamber.

The medical device may further comprise an adhesive surface adapted to provide at least one of: fixation of at least one of the wall and enclosure to the skin of the patient, and sealing between the skin of the patient and at least one of the wall and enclosure.

According to one embodiment, the medical device further comprises at least one wall port placed in the wall enabling passage between the chamber and the outside of the chamber. The wall port may be detachably fixated to the wall such that the wall port can be exchanged by another wall port or inset.

According to one embodiment, the chamber is in fluid connection with the cavity in the patient's body through an incision in the patient's body, when the medical device is applied on the patient's body for performing a surgical procedure, and the medical device further comprises: at least one inlet provided in at least one of: the wall of the medical device, and the skin of the patient for supplying a fluid to at least one of, the chamber, and the cavity in the patient's body, and at least one outlet provided in at least one of: the wall of the medical device, and the skin of the patient for discharging the fluid from at least one of: the chamber, and the body cavity. The medical device may further comprises a pump adapted to circulate the fluid from the outlet member to the inlet member.

According to one embodiment, the medical device further comprises a body port adapted to be placed inside the chamber in an incision to be performed in the skin of the patient to enable passage between the chamber and the inside of the patient's body.

According to one embodiment, the medical device comprises a second sealing device adapted to be at least one of sealingly connected to at least one of; the wall and the closable body port, and an integrated part of at least one of; the wall and the closable body port, the second sealing device is further adapted to seal against at least one of the skin and tissue of the patient.

The closeable body port in any of the embodiments may comprise a closeable body multi-port adapted to be placed from inside the chamber in an incision to be performed in the skin of the patient, the body multiport may be adapted to be connected to at least one of the wall port, and a wall multiport, when the medical device is applied on the patient's body for performing a surgical procedure, and the closable wall port in any of the embodiments may comprises a closeable wall multiport adapted to be connected to at least one of; the body port, and a body multiport placed in an incision in the patient's body, when the medical device is applied on the patient's body for performing a surgical procedure.

A method of performing a surgical procedure on a patient using a medical device is further provided. The method comprising applying a wall on the skin of the patient to form a chamber, in which a sealed environment can be maintained for encompassing part of the surgical procedure to be performed, applying a vacuum sealing member adapted to hold a pressure in a second chamber between the skin and the wall, evacuating fluid from the vacuum sealing member such that a negative pressure is created in the second chamber between the skin and the wall, the pressure being different than the pressure in the chamber, and less than atmospheric pressure, such that a vacuum seal is provided, creating an incision in the skin of the patient, in the sealed environment of the chamber. The method may further comprise the step of injecting a fluid into the chamber, such that a pressure in the chamber exceeding atmospheric pressure is created.

A medical device for performing a surgical procedure on a patient is provided. The medical device comprises a wall adapted to be at least partially applied on the patient's body to form a chamber, in which a sealed environment can be maintained for encompassing part of the surgical procedure to be performed, a closeable wall port placed in a portion of the wall, a closeable body port placed in a second portion of the wall and adapted to be placed in an incision in the patient's body, and a sealing device adapted to be at least one of; sealingly connected to at least one of the wall and the closable body port, and an integrated part of at least one of; the wall and the closable body port, the sealing device is further adapted to seal against at least one of: the skin and tissue of the patient. The wall, wall port and body port are adapted to together form an airlock sluice between a cavity in the body of the patient and the ambient environment, when the surgical procedure is performed. By forming an airlock sluice, objects or specimens from the body of the patient may be transferred between the cavity in the body of the patient and the ambient environment, or in the opposite direction, whilst keeping the cavity in the patient's body sealed at all times.

According to one embodiment, the wall and body ports are positioned relative to each other such that an elongated object is longitudinally displaceable through the wall and body ports.

According to one embodiment, the wall port is displaceable between a first position and a second position, wherein the second position is situated more remote from the body port.

According to one embodiment, the wall port is adapted to be at least one of: connected to the body port, abutting the body port, locked to the body port, and formed into an integrated port together with the body port.

According to one embodiment, at least one of; the closable wall port and closable body port comprises a penetratable self sealing gel, such that an object or hand can be inserted through the wall port while maintaining the sealed environment.

According to one embodiment, the medical device further comprises at least one of an additional body port, additional body inset, additional wall port and additional wall inset, and at least one of the wall port and body port is exchangeable by the additional port or additional inset.

According to one embodiment, the wall portion adapted to be applied on the patient's body, when the surgical procedure is to be performed, further comprises at least one of a vacuum sealing member adapted to hold a pressure less than atmospheric pressure between the wall portion and the patient's skin to seal between the wall portion and the patient's skin, and a pressure sealing member adapted to hold a pressure above atmospheric pressure between the wall and the patient's skin to seal between the wall and the patient's skin.

According to one embodiment, the vacuum sealing member or pressure sealing member is adapted to create a substantially airtight seal between the wall portion and the skin of the patient, to enable an incision to be performed through the skin of the patient in sealed environment such that a fluid connection between a cavity within the patient and the chamber can be created.

According to one embodiment, at least one of a closeable body multi-port may be adapted to be placed from inside the chamber in an incision to be performed in the skin of the patient, and the body multiport is adapted to be connected to at least one of; the wall port, and a wall multiport, when the medical device is applied on the patient's body for performing a surgical procedure, and the closable wall port comprises a closable wall multiport, wherein the wall multiport is adapted to be connected to at least one of; the body port, and a body multiport placed in an incision in the patient's body, when the medical device is applied on the patient's body for performing a surgical procedure.

According to one embodiment, the closeable body port is adapted to be placed in an incision performed in the skin of the patient to enable passage between the chamber and a cavity in the patient's body.

According to one embodiment, the body port is adapted to be fitted in the patient's skin after the incision has been made, before the medical device is applied on the patient's body. The closeable wall port and/or the closeable body port may be connected by a portion of the wall, such that the closeable wall and body ports can be moved in relation to each other whilst being connected by means of the wall portion.

A surgical method for performing a laparoscopic procedure in a sealed environment is further provided, the surgical method comprises making an incision in the patients skin, providing a medical device comprising a wall connected both to a closable wall port and a closable body port, such that a chamber is formed by the wall and the closable wall port and the closable body port, placing the closeable body port in the incision made in the skin of the patient, such that a fluid connection is created between the chamber and a cavity in the patient, providing a sealing device being at least one of connected to at least one of: the body port or the wall, and integrated in at least one of the body port or the wall, to sealingly connect between, at least one of; the body port placed in the incision and the wall, and at least one of body tissue and skin of the patient.

A surgical method for performing a laparoscopic procedure in a sealed environment is further provided. The surgical method comprises making an incision in the patients skin, providing a medical device comprising a wall, a closable wall port and a closable body port in connection with the patient, placing the body port in the incision, forming a chamber by the wall, the closable wall and body port, allowing communication with a cavity in the patient's body sealing the medical device to the skin or tissue of the patient, to form a sealed environment, including the chamber and the body cavity, moving the closable wall port, adapted to connect to the body port, connecting to the body port, and forming an integrated port.

The surgical method may further comprise the steps of inflating the cavity in the patient using a laparoscopic fluid, such that a cavity enabling visual inspection within the body of the patient is formed and/or exchanging the closeable body port to an additional port or inset for performing an operational step in the cavity in the body of the patient and/or exchanging the closeable wall port to an additional port or inset for performing an operational step in the chamber of the medical device.

A method of transferring an object from the ambient environment to a cavity in a patient during a surgical procedure using a medical device according to any of the embodiments is further provided. The method comprises transferring the object through the closable wall port, placed in the wall of the medical device, into a chamber formed by the wall of the medical device and the closable wall and body port and transferring the object through the closable body port placed in the incision made in the patient's skin and into the cavity in the patient.

A method of forming an airlock sluice between the ambient environment and a cavity in a patient is further provided. The method comprises providing a medical device comprising a wall connected to both a wall port and a body port, making an incision in the patients skin connected to a body cavity, placing the body port in the incision, forming a chamber with the wall of the medical device, the closable body port, and the closable wall port, allowing communication with the cavity, and thus forming a an airlock sluice.

A medical device for performing a surgical procedure on a patient is provided. The medical device comprising a wall adapted to be at least partially applied on the patient's body to form a first chamber in which a sealed environment can be maintained for encompassing part of the surgical procedure to be performed, wherein a portion of the wall is adapted to be in contact with the skin of the patient when the surgical procedure is performed a body port positioned in an incision in the skin of the patient adapted to be placed between the first chamber and a body cavity, and an airlock sluice positioned in the wall of the medical device, the airlock sluice comprises: a first valve, a second valve, and a second chamber located between the valves, wherein the airlock sluice is adapted to form part of the sealed environment, wherein the medical device is adapted to allow reversible passage of objects from the body cavity of the patient, through the body port into the first chamber, further through the second valve, into the second chamber of the sluice and further through the first valve out to the ambient environment, and vice versa, whereby the risk of contamination is reduced.

According to one embodiment, the medical device is adapted to hold a pressure within the first chamber exceeding atmospheric pressure, such that a cavity in the patient may be expanded for providing a cavity for improved visibility, and/or a pressure above atmospheric pressure may be provided in the chamber thus reducing the risk that particles enters the chamber.

According to one embodiment, the second chamber has a volume larger than one of: 100 000 mm3, 200 000 mm3, 300 000 mm3, 400 000 mm3, and 500 000 mm3.

According to one embodiment, the wall is at least partially collapsible and adapted to be inflated by a fluid.

The medical device may further comprise a wall inset and/or a body inset. The wall and/or body inset may comprise at least one glove integrated in the body inset such that a surgeon is able to use the glove from outside the chamber via a wall port or wall inset to make manual manipulations inside the body cavity while maintaining sealed environment in at least one of the first chamber and the body cavity.

According to one embodiment, the medical device further comprises at least one of: a vacuum sealing member adapted to hold a pressure less than atmospheric pressure between the wall and the skin of the patient to seal between the wall and the skin of the patient, and a pressure sealing member adapted to press against the skin of the patient to create a pressurized sealing between the skin of the patient and the wall, wherein the pressure sealing member is adapted to be hydraulically, pneumatically or mechanically forced against the patient's skin.

According to one embodiment, the medical device further comprises at least one wall port provided in the wall enabling passage of an object between the first chamber and the environment outside of the first chamber. The wall port comprises at least one of an elastic membrane and a flexible membrane, and the membrane is adapted to, in a non-compressed state, seal between the first chamber and the environment outside of the first chamber, and in a compressed state enable a hand or an object to be inserted through the membrane.

The medical device may further comprise a coupling adapted to detachably attach the body port to the patient's skin to enable exchange and removal of the body port.

A method of transferring an object from the ambient environment to a cavity in a patient, and vice versa, is further provided, using a medical device. The method comprises transferring the object through a body port, placed in the skin of the patient, to a first chamber enclosed by a wall of the medical device, transferring the object through a second valve to an airlock sluice, and transferring the object through a first valve to the ambient environment, such that the risk of contamination is reduced.

A medical device for performing a surgical procedure on a patient is provided. The medical device comprises: a wall adapted to be at least partially applied on the patient's body to form a chamber, in which a sealed environment can be maintained for encompassing part of the surgical procedure to be performed, wherein a portion of the wall is adapted to contact the skin of the patient to create a substantially airtight seal between the wall portion and the skin of the patient before an incision has been performed through the skin of the patient such that a fluid connection between a cavity within the patient and the chamber is created, at least one wall port or wall inset positioned in a portion of the wall, and a sealing device connected to the wall having a first sealing member adapted to be positioned in the cavity inside the patient's body wall around the incision, a second sealing member adapted to be positioned at the outside of the patient's skin around the incision, and a sealing connecting member adapted to connect the first and second sealing members, wherein the sealing device is adapted to seal between at least one of: the second sealing member and directly or indirectly the outside of the patient's skin, and the first sealing member and tissue inside the cavity by exerting pressure from the inside of the cavity in the direction of the skin of the patient, wherein the sealing device, the wall, and the wall port or wall inset are connected such that they enclose a chamber in fluid connection with the body cavity. By using the medical device in a surgical procedure, the first incision in the skin of the patient may be performed in the sealed chamber of the medical device, thus the risk of infections is reduced.

According to one embodiment, the wall of the medical device is at least partially collapsible and adapted to be inflated by a fluid, the chamber may be adapted to hold a fluid having a pressure exceeding atmospheric pressure.

According to one embodiment, the wall inset comprises at least one glove integrated in the wall such that a surgeon is able to use the glove from outside the chamber to make manual manipulations inside the chamber while maintaining sealed environment in the chamber.

The medical device may further comprise at least one of: a vacuum sealing member adapted to hold a pressure less than atmospheric pressure between the wall and the skin of the patient to seal between the wall and the skin of the patient, and a pressure sealing member adapted to press against the skin of the patient to create a pressurized sealing between the skin of the patient and the wall, wherein the pressure sealing member is adapted to be hydraulically, pneumatically or mechanically forced against the patient's skin.

The medical device may further comprise an adhesive surface adapted to provide at least one of: fixation of the wall to the skin of the patient and sealing between the wall and the skin of patient.

The medical device may further comprise a body multi-port adapted to be placed inside the chamber in an incision in the skin of the patient. The body multi-port comprises at least two ports adapted to enable passage of an object between the chamber and the inside of the patient's body via the incision.

According to one embodiment, the sealing connecting member is spring-loaded or elastic to seal between at least one of the second sealing member and the skin of the patient, and the first sealing member and tissue of the patient.

The medical device may further comprise a closable body port connected to at least one of the sealing device and the wall, and adapted to be positioned in the incision in the skin of the patient inside the chamber to enable passage of an object between the chamber and the inside of the patient's body, when positioned.

According to one embodiment, the medical device further comprises a coupling adapted to detachably attach the body port to the sealing device and/or the wall and/or the patient's skin to enable exchange and removal of the body port.

A method of performing a surgical procedure on a patient using a medical device is further provided. The method comprises applying a wall on the skin of the patient to form a chamber, in which a sealed environment can be maintained for encompassing part of the surgical procedure to be performed, creating an incision through the wall of the medical device and the skin of the patient, such that a fluid connection between a cavity within the patient and the chamber is created, placing a first sealing member in the cavity inside the patient's body wall around the incision, placing a second sealing member on the outside of the patient's skin around the incision, and placing a sealing connecting member connecting the first and second sealing members, such that at least one of: the second sealing member seals directly or indirectly against the skin of the patient, and the first sealing member seals directly or indirectly against the tissue of the patient.

A medical device for performing a surgical procedure is provided. The medical device comprises a wall adapted to at least partially enclose a chamber for encompassing part of the surgical procedure, a wall port placed in the wall, a sealing device connected to the wall and adapted to seal against the patient's body, such that the chamber is formed by the wall and the patient's body. The wall port is adapted to be detachably connected to a body port at least partially placed in an incision cut in a patient's body during a surgical procedure.

By the wall port being detachably connected to a body port, the wall port may be connected to a body port such that for example endoscopic operations within a cavity in the body of the patient can be performed through the wall port when connected to the body port. The wall port may further be disconnected from the body port to enable further movement of the wall port in relation to the body port, and enable manipulation to be performed within the chamber of the medical device by means of endoscopic instruments through the wall port or by means of a hand inserted through the wall port. The connectable/disconnectable wall/body port thus enables a combination of endoscopic, open and/or hand assisted endoscopic surgery to be performed.

According to one embodiment, the medical device is adapted to have a first volume when the wall port is connected to a body port, and a second volume when the wall port is disconnected therefrom. According to one embodiment, the second volume is larger than the first volume. The first volume may be smaller than 100 000 mm3, and the second volume may be larger than 500 000 mm3.

According to one embodiment, the wall is adapted to hold a pressure in the chamber exceeding atmospheric pressure.

According to one embodiment, the medical device further comprises a coupling placed in wall, the coupling being adapted to receive and fixate an inset. The medical device may further comprise a detachable inset adapted to be fixated to the coupling.

According to one embodiment, the medical device may further comprise the body port.

At least one of the wall and body port in any of the embodiments may comprise a protruding member and/or a recess. The protruding member is adapted to engage the recess for locking the wall port to the body port. The recess may be a groove in at least one of the wall port and body port.

According to one embodiment, the wall port is adapted to be fixated to a first coupling and the body port is adapted to be fixated to a second coupling. The first and second couplings are adapted to be connected for connecting the wall port and body port.

The first or second coupling may comprises a magnet or magnetic material adapted to engage a magnet or magnetic material of the first or second coupling for locking the first coupling to the second coupling.

According to one embodiment, at least one of the first and second coupling comprises a protruding member, and at least one of the first and second coupling comprises a recess, the protruding member is adapted to engage the recess for locking the first coupling to the second coupling.

According to one embodiment, the recess is a groove in at least one of the coupling and the second coupling.

The medical according to any of the embodiments may further comprises at least one of: a vacuum seal adapted to hold a pressure less than atmospheric pressure between the patient's skin and the vacuum seal to seal the chamber by sealing towards the patient's skin, and a pressure seal adapted to hold a pressure above atmospheric pressure between the pressure seal and the patient's skin to seal the chamber by sealing towards the patient's skin.

The wall port in any of the embodiments may be adapted to, in a first state, when the wall port is connected to a body port, enable a surgeon to operate inside a cavity of the patient through the wall port, and in a second state, when the wall port is disconnected from the body port, enable the surgeon to perform steps of the procedure within the chamber formed by the wall.

A method of performing a surgical procedure on a patient using a medical device is further provided, the method comprises applying a wall (01) on the body of a patient such that a sealed chamber is formed by the wall and the body of the patient, and connecting a wall port attached to the wall of the medical device, to a body port placed in an incision in the body of the patient, such that an interconnected port is formed, and performing a step of the surgical procedure through the interconnected port.

A medical device for performing a surgical procedure on a patient is provided. The medical device comprises a first wall portion adapted to at least partially enclose a first chamber for encompassing part of the surgical procedure, and a second wall portion adapted to at least partially enclose a second chamber for providing sealing between the wall and the patient. The first wall portion is adapted to allow a first pressure above atmospheric pressure to be maintained in the first chamber, the second wall portion is adapted to allow a second pressure to be maintained in the second chamber for creating a sealing between the medical device and the patient's body, wherein the second pressure is one of: above atmospheric pressure and below atmospheric pressure, for providing sealing between the medical device and the patient, and the first and second pressures are different.

The medical device enables a first under or over pressure to be provided in the second chamber engaging the skin of the patient, such that a pressure or vacuum sealing may be provided between the wall of the medical device and the skin of the patient, at the same time as an overpressure is provided in the first chamber of the medical device such that an expanded cavity may be maintained in the body of the patient and/or an overpressure hindering particles from entering the chamber may be maintained.

According to one embodiment, the second chamber is adapted to hold a pressure above atmospheric pressure for exerting a pressure force on the skin and/or tissue of the patient for creating the sealing between the medical device and the patient's body.

The second pressure may be higher than the first pressure, such that the first pressure of the sealing member can withstand the force exerted by the pressure in the chamber on the sealing device.

According to one embodiment, the second chamber is adapted to hold a negative pressure for exerting a suction force on the skin and/or tissue of the patient for creating the sealing between the medical device and the patient. The first chamber may be adapted to be in fluid connection with a cavity of the patient via an incision in the skin of the patient, the chamber and the cavity in the patient forms a joint volume having the same pressure and partially being enclosed by the medical device.

According to one embodiment, the medical device is adapted to enclose the second chamber together with the skin and/or tissue of the patient, the second chamber may be adapted to be in fluid connection with a vacuum creating device capable of producing a negative pressure for creating a negative pressure in the second chamber.

According to one embodiment, the first chamber is adapted to hold a positive pressure between 5 mmHg and 120 mmHg, and wherein the second chamber is adapted to hold a negative pressure between 5 mmHg and 120 mmHg.

The second chamber may be adapted to encircle an extremity of the patient and create a sealing along the encircled portion of the extremity of the patient. The second wall portion may be adapted to hold the second pressure exceeding the first pressure such that the second chamber exerts a pressure force on the extremity of the patient for creating a sealing between the medical device and the skin of the patient.

The medical device may further comprise a monitoring unit for monitoring at least one of: the blood pressure of the patient, the pressure in the first chamber, and the pressure in the second chamber and a pressure creating member adapted to create the pressure in the second chamber. The pressure creating member may be adapted to receive feedback from the monitoring unit and create the pressure in the second chamber based on the received feedback.

The monitoring unit may be adapted monitor the blood pressure of the patient and provide feedback to the pressure creating member.

A system is further provided, the system comprised the medical device according to any one of embodiments above, a pressure creating member adapted to create a pressure exceeding 5 mmHg in the first chamber of the medical device, and a vacuum creating device adapted to create a negative pressure of 5 mmHg in the second chamber of the medical device for creating a sealing between the medical device and the skin and/or tissue of the patient.

A second system is further provided comprising: the medical device according to any one of embodiments, a first pressure creating member adapted to create a pressure exceeding 5 mmHg in the first chamber of the medical device, and a second pressure creating member adapted to create a second pressure exceeding 5 mmHg in the second chamber of the medical device for creating a sealing between the medical device and the skin of the patient.

The second pressure may be higher than the first pressure, such that the first pressure of the sealing member can withstand the force exerted by the pressure in the chamber on the sealing device.

A method of creating a chamber in a medical device and sealing between the medical device and the skin of a patient is further provided. The method comprising applying a first wall portion of the medical device against the skin of a patient such that a first chamber is formed by the wall itself or by the wall and the skin of the patient, inflating the first chamber to a pressure exceeding atmospheric pressure, applying a second wall portion of the medical device against the skin of a patient such that a second chamber is formed by the wall itself or by the wall and the skin of the patient, and at least one of: inflating the second chamber to a pressure exceeding atmospheric pressure, such that the second wall portion is pressed against the skin of the patient and thereby provides sealing, wherein the pressure in the second chamber is different from the pressure in the first chamber, and evacuating fluid from the second chamber such that a pressure below atmospheric pressure is created in the second chamber, such that a vacuum sealing is created between the second wall portion and the skin of the patient.

The step of inflating the first chamber may comprise inflating the first chamber to a pressure between 5 mmHg and 120 mmHg, and the step of evacuating fluid from the second chamber may comprises evacuating fluid such that a negative pressure between 5 mmHg and 120 mmHg is created in the second chamber.

According to one embodiment, the step of inflating the first chamber may comprise inflating the first chamber to a pressure between 5 mmHg and 120 mmHg, and the step of inflating the second chamber may comprise inflating the second chamber to a pressure between 5 mmHg and 120 mmHg.

The method may further comprise the step of monitoring the pressure in as least one of the first chamber and the second chamber.

The method may further comprise the step of monitoring a physiological parameter of the patient, and inflate or evacuate at least one of the first and second chambers on the basis of the monitored physiological parameter. The physiological parameter may be the blood pressure or blood flow of the patient.

The method may further comprise the step of creating an incision in the skin of the patient inside of the first chamber, such that a fluid connection is created between the first chamber and a cavity in the body of the patient.

A medical device for performing a surgical procedure on a patient provided. The medical device comprises a wall adapted to be at least partially applied on the patient's body to form a chamber together with the patient's body, in which a sealed environment can be maintained for encompassing part of the surgical procedure to be performed. The medical device may further comprise a closeable wall port placed in a portion of the wall and being adapted to be connected to a port placed in an incision in the patient's body, when the medical device is applied on the patient's body for performing the surgical procedure. The medical device further comprises a sealing device connected to the wall and adapted to seal against the skin of the patient, the closable wall port may be adapted to form at least a part of an airlock sluice together with a closable port placed in the skin, the airlock sluice between a cavity in the patient's body and the ambient environment, when the medical device is applied on the patient's body for performing the surgical procedure.

The airlock sluice formed by the medical device enables that transfer of objects and/or specimens from the cavity in the body of the patient to the ambient environment, whilst keeping the cavity in the body of the patient sealed.

According to one embodiment, the closeable wall port is adapted to be positioned relative to an openable port (which may be any of the bodyports disclosed herein) placed in an incision in the patient's body, such that an elongated object is longitudinally displaceable through the ports, when the medical device is applied on the patient's body for performing the surgical procedure.

According to one embodiment, the closeable wall port is displaceable between a first position, in which the closeable wall port is situated relatively close to at least one of, the skin of the patient and a skin port (which may be any of the bodyports disclosed herein) placed in a skin opening, and a second position, in which the closeable wall port is situated more remote from the skin of the patient, when the medical device is applied on the patient's body for performing the surgical procedure.

The closeable wall port may be adapted to be at least one of; connected to a port connecting to a cavity in the patient's body, and locked to a port connecting to a cavity in the patient's body.

According to one embodiment, the closeable wall port comprises a penetratable self sealing gel, such that an object or hand can be inserted through the closeable wall port while maintaining the sealed environment in the chamber.

The medical device may further comprise at least one of; an additional port, an inset, and a coupling, and the closeable wall port is adapted to be replaced by at least one of; the additional port, the inset and the coupling, when the medical device is applied on the patient's body for performing the surgical procedure.

According to one embodiment, the wall is adapted to hold a fluid within the chamber having a pressure exceeding atmospheric pressure.

The sealing device may comprise a vacuum sealing member adapted to hold a pressure less than atmospheric pressure between the wall and the patient's skin to seal between the wall and the patient's skin.

The medical device may further comprise at least one of: an airlock placed separately from the wall port, and an airlock integrated in the wall port. The airlock in both cases allowing passage of objects between the chamber and the ambient environment without any substantial leakage of fluid from the chamber.

The vacuum seal may be adapted to create a substantially airtight seal between the wall and the skin of the patient, to enable an incision to be performed through the skin of the patient in sealed environment such that a fluid connection between a cavity in the body of the patient and the chamber can be created without any substantial fluid leakage outside of the connected chamber and cavity, when the medical device is applied on the patient's body for performing the surgical procedure.

According to one embodiment, the chamber may be in fluid connection with the cavity in the patient's body through an incision in the patient's body, when the medical device is applied on the patient's body for performing a surgical procedure. The medical device may further comprises at least one of: at least one inlet provided in at least one of: the wall of the medical device, and the skin of the patient for supplying a fluid to at least one of the chamber. The medical device may further comprise at least one outlet provided in at least one of: the wall of the medical device, and the skin of the patient for discharging the fluid from at least one of: the chamber, and the body cavity.

The medical device may further comprise a pump adapted to circulate the fluid from the outlet member to the inlet member.

According to one embodiment, the medical device further comprises a coupling adapted to detachably; abut, be attached to, or placed in a defined position, locked or disconnected to at least one of; the closeable wall port, to a detach performing port (which may be any of the bodyports disclosed herein), placed in an incision in the patient's body connecting to the body cavity, and the wall, adapted to be at least partially applied on the patient's body, to a detach performing port, when the medical device is applied on the patient's body for performing the surgical procedure.

The closeable wall port in any of the embodiments herein may be positioned in the wall portion and adapted to allow handling of an instrument for at least one of cutting through the patient's skin via the closeable wall port and cutting through the patient's skin with the instrument fully placed inside the chamber, when the wall is applied on the patient's body for performing the surgical procedure.

The wall portion may in any of the embodiments be adapted to allow itself to be cut through to reach and make an incision in the patient's skin, for allowing a surgical procedure when the wall is applied on the patient's body.

A medical device system for performing a surgical procedure is further provided. The medical device system comprising the medical device according to any one of embodiments, and the closeable body port adapted to be placed in an incision in the patient's body connecting the chamber created by the medical device to a cavity in the patient's body, when the medical device is applied on the patient's body for performing the surgical procedure.

According to one embodiment, the closeable wall port and the closeable body ports are connected by a portion of the wall, and the closeable wall port and closable body port can be moved in relation to each other whilst being connected by means of the wall portion.

A surgical method for performing a laparoscopic procedure in a sealed environment is further provided. The surgical method comprises placing a medical device comprising a wall and a closable wall port in connection with the patient, such that a wall portion of the medical device sealingly connects to the skin of the patient, such that a chamber is formed by the wall of the medical device and the skin of the patient, making an incision in the patient's body, inside the chamber, and placing a closeable body port in the incision made in the skin of the patient, inside of the chamber, such that a fluid connection is created between the chamber and a cavity in the patient.

A surgical method for performing a laparoscopic procedure in a sealed environment is further provided. The surgical method comprising: placing a medical device comprising a wall and a closable wall port in connection with the patient, such that a wall portion of the medical device sealingly connects to the skin of the patient, such that a chamber is formed by the wall of the medical device and the skin of the patient, sealing the wall portion, to the skin of the patient by applying a negative pressure, making an incision in the skin of the patient's body creating a contact between the chamber and a cavity in the patient's body, and moving the closable wall port, adapted to connect directly or indirectly to the incision in the skin of the patient, towards the incision in the skin of the patient's body.

The surgical methods may further comprise inflating the cavity in the patient using a laparoscopic fluid, such that a cavity enabling visual inspection within the body of the patient is formed.

The surgical methods may further comprise exchanging the closeable body port to at least one of an additional port, an inset and a coupling for performing an operational step in the cavity in the body of the patient.

The surgical methods may further comprise exchanging the closeable wall port to at least one of an additional port, an inset and a coupling for performing an operational step in the chamber of the medical device.

A method of transferring an object from the ambient environment to a cavity in a patient during a surgical procedure is further provided, the method comprising: transferring the object through a first closable wall port, placed in a wall of a medical device, into a chamber formed by the wall of the medical device and the skin of the patient, and transferring the object through a closable body port placed in an incision made in the patient's skin and into the cavity in the patient.

A method of forming an airlock sluice between the ambient environment and a cavity in a patient is further provided, The method comprises two in time interchangeable steps: placing a body port in an incision made in the skin of the patient, and placing a medical device comprising a closable wall port in connection with the patient, such that a wall portion of the medical device sealingly connects to the skin of the patient, and forming a chamber by the wall of the medical device, the skin of the patient, and the body port.

A medical device for performing a surgical procedure on a patient is provided. The medical device comprises a wall adapted to form a chamber in which a sealed environment can be maintained for encompassing part of the surgical procedure to be performed. The medical device further comprising a closeable wall port placed in a portion of the wall, a closeable body port adapted to be placed in a portion of the wall and further placed an incision in the body of the patient, and a sealing device connected to the wall and adapted to seal against the skin and/or body of the patient. The wall port and body port together forms an airlock sluice between a cavity in the body of the patient and the ambient environment and at least one of the closable wall port, closable body port and the closable wall port and closable body port together are adapted to form an airlock sluice between a cavity in the body of the patient and the ambient environment, when the medical device is applied on the patient's body for performing the surgical procedure.

The airlock sluice formed by the medical device enables that transfer of objects and/or specimens from the cavity in the body of the patient to the ambient environment, whilst keeping the cavity in the body of the patient sealed.

According to one embodiment, the sealing device comprises a pressure sealing member adapted to seal between the wall of the medical device and the skin of the patient by pressing against the skin or tissue of the patient.

According to one embodiment, the sealing device may further comprise a vacuum sealing member adapted to seal against the skin or tissue of the patient by means of a pressure below atmospheric pressure.

The closeable wall and body ports may be positioned relative to each other such that an elongated object is longitudinally displaceable through the closeable wall and body ports.

According to one embodiment, the closeable wall port is displaceable between a first position, in which the closeable wall port is situated relatively close to the closeable body port, and a second position, in which the closeable wall port is situated more remote from the closeable body port.

According to one embodiment, the closeable wall port is adapted to be at least one of; attached, mounted together in a predefined position and locked to the closeable body port.

The medical device may comprise an additional port or additional inset, wherein at least one of the closeable wall port and closeable body port is exchangeable by the additional port or inset.

According to one embodiment, the closeable body port may comprise a closeable body multi-port adapted to be placed from inside the chamber in an incision to be performed in the skin of the patient, wherein the closeable body multi-port comprises at least two closeable body ports adapted to enable passage of an object between the chamber and the inside of the patient's body, wherein the closable body multiport is adapted to be connected to at least one of; a wall port and a wall multiport together placed in an incision in the patient's body connecting to a body cavity, when the medical device is applied on the patient's body for performing a surgical procedure, and the closeable wall port comprises a wall multiport, comprising at least two closable wall ports, wherein the wall multiport is adapted to be connected to at least one of; a closable body port and a closable body multiport placed in an incision in the patient's body connecting to a body cavity, when the medical device is applied on the patient's body for performing a surgical procedure.

The medical device may further comprise at least one of: at least one inlet provided in at least one of: the wall of the medical device, and the skin of the patient for supplying a fluid to at least one of the chamber, and the cavity in the patient's body. The medical device may further comprise at least one outlet provided in at least one of: the wall of the medical device, and the skin of the patient for discharging the fluid from at least one of: the chamber, and the body cavity. The medical device may further comprising a pump adapted to circulate the fluid from the outlet to the inlet.

According to one embodiment, the closeable body port is adapted to be placed inside the chamber in an incision to be performed in the skin of the patient to enable passage between the chamber and the inside of the patient's body.

The medical device may further comprise a coupling adapted to detachably attach the closeable body port to at least one of the patient's skin and the closeable wall port to enable exchange and removal of the closeable body port.

According to one embodiment, the closeable wall port may be adapted to and positioned in the wall portion such that it allows handling of an instrument for at least one of; cutting through the patient's skin via the closeable wall port and cutting through the patient's skin with the instrument fully placed inside the chamber, when the wall is applied on the patient's body.

According to one embodiment, the wall portion is adapted to allow itself to be cut through to reach and make an incision in the patient's skin, for allowing a surgical procedure when the wall is applied on the patient's body.

The closable body port may be adapted to be at least one of; fitted in the patient's skin after an incision has been made in the skin, and fitted to the closable wall port after the closable body has been fitted in the patient's skin after an incision has been made in the skin, when the medical device is applied on the patient's body.

According to one embodiment, the closeable wall port and the closeable body port are connected by a portion of the wall, and wherein the closeable wall and body ports can be moved in relation to each other whilst being connected by means of the wall portion.

A method of forming an airlock sluice for use when performing a surgical procedure on a patient is provided, the method comprising applying a wall on the patient's body to form a chamber together with the patient's body, in which a sealed environment can be maintained for encompassing part of the surgical procedure to be performed, the wall comprising a closeable wall port and a closeable body port. The method further comprises placing the closeable body port in an incision in the body of the patient, such that an airlock sluice is formed between the closeable wall port and the body port, and placing a sealing device connected to the wall against the skin and/or body of the patient, for sealing between the wall of the medical device and the skin of the patient.

A medical device for performing hip joint surgery on a patient is provided. The medical device comprising: a wall adapted to least partly be placed on the patient's body for forming a chamber alone or together with the patient's body, such that a sealed surgical environment is created in the chamber. The chamber is adapted to encompass an incision of the hip joint surgery in the skin of the patient and at least one step of the hip joint surgery to be performed, while maintaining the sealed surgical environment. The medical device further comprises a sealing device connected to the wall and adapted to seal between the wall and the skin or tissue of the patient, wherein the sealing device forms a special loop at least partly encircling at least a portion of one or more of the following; the leg, the pelvic region, the abdominal region, the inguinal region, the gluteal region, the thoraxial region and the region of the lower back, such that the sealing device seals between the incision site of the hip joint surgery and at least one of: the anal orifice, the urethra orifice, and the perineum region. By creating a sealed environment, the risk of infections can be substantially reduced. The risk of infections is particularly large when performing prosthesis surgery inside the joints of patients, which is why the maintaining of a controlled environment is important.

According to one embodiment, the sealing device is positioned such that both of the urethra and the anus are excluded from the enclosed chamber forming the sealed surgical environment.

According to one embodiment, the medical device further comprises a second sealing device connected to the wall and adapted to encircle the leg of the patient for sealing between the ambient environment and the chamber.

The medical device may further comprise a holding member adapted to encircle a portion of the patient's body, by itself or together with the medical device, for holding the medical device in the desired position.

A portion of the wall may be adapted to directly or indirectly form an elongated tubular enclosure having at least one open end. The enclosure is adapted to fit at least a portion of a leg of the patient, and the medical device is arranged such that a portion of the leg extends into the enclosure through the first open end thereof, when the surgical procedure is performed on the leg of the patient.

The wall of the medical device may be adapted to form the chamber without involving the patient's body. The wall portion forming the chamber may also form the tubular enclosure, and the tubular enclosure may also form a second chamber together with the patient's body. The second chamber may be adapted to be sealed at the first or more open ends by the patient's body.

According to one embodiment, the chamber is adapted to be in communication with an operating field during the surgical procedure, when the skin of the patient has been cut in a position inside of the chamber. The wall enclosing the chamber may comprise a wall port or wall inset mounted in a wall portion for allowing at least one of objects being moved into the chamber or operating field and/or manual manipulation being performed in the chamber or operating field.

The medical device may further comprise a body port or body inset, and the wall port or wall inset may be adapted to be connected to the body port or body inset for forming one of: an integrated port allowing the transfer of objects from the ambient environment to the operating field, and an integrated inset allowing manual manipulation to be performed in the operating field from the ambient environment. The body port and wall port may be adapted to be disconnected from each other such that the wall port can allow objects to be transferred into the chamber from the ambient environment, or the wall inset can allow manual manipulation to be performed in the chamber from the ambient environment, and the body port can allow objects to be transferred from the chamber into the operating field or the body inset can allow manual manipulation to be performed in the operating field in a cavity in the patient's body.

According to one embodiment, the chamber may be adapted to be in communication with an operating field during the surgical procedure. The part of the wall forming both the chamber and the tubular enclosure, at a portion thereof, is adapted to be opened and wherein the opening together with the hip joint surgery incision of the patient is adapted to be positioned inside of the chamber allowing such communication with the operating field. A portion of the wall port encompassing only the chamber has a wall port or wall inset mounted therein for allowing, from outside the chamber at least one of; objects to be moved into at least one of the following; the chamber, and the operating field, and manual manipulation to be performed in at least one of; the chamber and the operating field.

According to one embodiment, the port or inset includes a first and second part, wherein the second part comprises the wall port or wall inset and the first part comprises a first wall port or first wall inset mounted in the opening in the portion of the part of the wall forming both the chamber and the tubular enclosure and adapted to be opened to create the communication between the chamber and the operating field to allow; objects to be moved further from the chamber into the operating field and/or manual manipulation to be performed from the chamber further into the operating field, and wherein the passage between the chamber and the operating field includes the first wall port or wall inset, and wherein the second chamber is located in between the tubular enclosure and the skin of the patient, and wherein the second chamber has a size equal to or larger than zero.

The body port and wall port may be adapted to be locked together in at least one fixed position.

The medical device may comprise at least one of: a second exchangeable wall port, and a second exchangeable wall inset, different from the wall port and wall inset, adapted to replace at least one of the wall port or wall inset.

According to one embodiment, the medical device may comprise at least one of: a second exchangeable body port, and a second exchangeable body inset different from the body port and body inset, and adapted to replace at least one of the body port and body inset.

The medical device may further comprise a second exchangeable integrated port different from the integrated port, and adapted to replace the integrated port during the surgical procedure.

The wall of the medical device may be at least partially collapsible and/or the chamber may be adapted to be inflated by a fluid.

According to one embodiment, the inset comprises at least one glove integrated in the wall such that a surgeon is able to use the glove from outside the chamber to make manual manipulations inside the chamber while maintaining the sterile environment in the chamber.

According to one embodiment, the medical device further comprises a device or instrument mount adapted to retain instruments within the chamber.

According to one embodiment, the sealing device may comprise a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

The sealing device may comprise a pressure sealing member attached to at least one of the wall and enclosure and adapted to press against the patient's skin to create a pressurized sealing between the skin of the patient's extremity and at least one of the wall and enclosure. The pressure sealing member may be adapted to be hydraulically, pneumatically or mechanically forced against the patient's skin.

The medical device may further comprise an adhesive adapted to provide at least one of: fixation of at least one of the wall and enclosure to the skin of the patient, and sealing between the skin of the patient and at least one of the wall and enclosure.

According to one embodiment, the medical device further comprises an air evacuation system adapted to evacuate air from the second chamber, when the portion of the patient's extremity is placed in the enclosure. The air evacuation system may be adapted to evacuate air from the vacuum sealing member.

The medical device may further comprise a slit for placing the chamber around at least a portion of the extremity of the patient radially in relation to the length axis of the extremity, and the slit may be adapted to be at least partially closed by closing elements mounted to the wall of the medical device. The medical device may comprise a first and a second portion located on a first and second side of the slit when the chamber is placed around at least a portion of the extremity, and wherein the first and second portions are adapted to be interconnected by means of at least one of: an adhesive and a mechanical connecting member.

At least one inset or port may be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

A method of performing a portion of a hip joint surgery on a patient using a medical device is further provided. The method comprises applying a wall on the skin of the patient to form a chamber, in which a sealed environment can be maintained for encompassing part of the surgical procedure to be performed, applying a sealing device between the wall and the skin of the patient such that the sealing device forms a special loop at least partly encircling at least a portion of one or more of the following; the leg, the pelvic region, the abdominal region, the inguinal region, the gluteal region, the thoraxial region and the region of the lower back, such that the first sealing device seals between an incision site of the hip joint surgery and at least one of: the anal orifice, the urethra orifice, and the perineum region. The method further comprises creating an incision at the incision site in the sealed environment within the chamber of the medical device.

A medical device for performing hip joint surgery on a patient is provided. The medical device comprises a wall adapted to form a chamber together with or without the patient's body and at least partly to be placed on the patient's body. The chamber is adapted to encompass the hip joint surgery incision in the skin of the patient and at least a part of the hip joint surgery to be performed while maintaining a sealed environment for the surgical procedure.

The medical device further comprises a first sealing device connected to the wall and adapted to seal between the wall and the skin or tissue of the patient to seal the hip surgery incision and at least a part of the hip joint surgery operational field from at least one of: the anal orifice, the urethra orifice and at least part of the perineum region, while still maintaining the chamber sealed, the sealing device comprising at least one of: a first part of the sealing device, and a first holding member adapted to hold the medical device in place by encircling at least one leg of the patient or the prolongation thereof to be involved in the sealing of the chamber. The medical device further comprises at least one of a second part of the sealing device, and a second holding member adapted to hold the medical device in place by encircling the whole body left to right on the level above the legs selected from at least one of; the level of the pelvic, abdominal or thorax region of the patient to further be involved in the sealing of the chamber. The medical device further comprises at least one of a third part of the sealing device adapted to seal from the medial cranial part of the leg where it is meeting the inguinal region or its prolongation, further in a cranial direction lateral of the patient's ventro-dorsal midsagittal plane, on the side where the hip surgery is performed, and wherein the third part of the sealing device at least partly extends in cranial direction until meeting the second sealing device, and wherein the wall is interconnecting to the first, second and third part of the sealing device to seal the chamber and/or a third holding member adapted to seal the chamber and exclude from the chamber at least one of the anal orifice, the urethra orifice and at least part of the perineum region.

By creating a sealed environment, the risk of infections can be substantially reduced. The risk of infections is particularly large when performing prosthesis surgery inside the joints of patients, which is why the maintaining of a controlled environment is important.

According to one embodiment, the sealing device is positioned such that both of the urethra and the anus are excluded from the enclosed chamber forming the sealed environment.

The medical device may further comprise a second sealing device comprising a first sealing member adapted to be positioned at the inside of the patient's skin around an incision to be performed in the skin and a second sealing member adapted to be positioned at outside of the patient's skin around the incision, and a connecting member sealingly interconnecting the first and second sealing members. The second sealing device is adapted to seal between at least one of: the second sealing member and the skin of the patient, and the first sealing member and tissue of the patient.

According to one embodiment, at least one of the first and second holding members are adapted to encircle a portion of the patient's body, by itself or together with the sealing device, for holding the medical device in the desired position.

At least a portion of the wall may directly or indirectly form an elongated tubular enclosure having at least one open end. The enclosure may be adapted to fit at least a portion of the leg of the patient, and the medical device may be arranged such that the portion of the leg extends into the enclosure through the first open end thereof, when the surgical procedure is to be performed on the portion of the patient's body.

According to one embodiment, the chamber is formed by the wall without involving the patient's body, and the part of the wall forming the chamber is adapted to also form the tubular enclosure. The wall comprises two wall sides of which one is facing the inside of the chamber and the other is facing the tubular enclosure, when performing the surgical procedure. The tubular enclosure may form a second chamber at least partly encompassed by the tubular enclosure and adapted to be sealed at the first or more open ends by the patient's body portion. The wall part facing the tubular enclosure may be adapted to form the second chamber together with the patient's body.

According to one embodiment, the chamber is adapted to be in communication with an operating field during the surgical procedure, when the skin of the patient has been cut in a position inside of the chamber. The wall encompassing the chamber has a wall port or wall inset mounted in a wall portion of the chamber for allowing; objects to be moved into the chamber or operating field and/or manual manipulation to be performed in the chamber or operating field.

According to one embodiment, the medical device further comprises a port having a first and second part. The second part may comprise the wall port or wall inset and the first part may comprise a body port or body inset adapted to be mounted in the cut skin of the patient to allow objects to be moved further from the chamber into the operating field and/or manual manipulation to be performed from the chamber further into the operating field.

Two parts of the port or inset may be adapted to be mounted together, touching each other for forming an integrated port or inset and thereby allowing objects to be moved into the operating field and/or manual manipulation to be performed in the operating field directly from outside the chamber. The two parts of the port or inset are adapted to be separable from each other and be placed in to one or more positions and thereby be adapted to use the second part of the port or inset to allow objects to be moved into the chamber and/or manual manipulation to be performed in the chamber and to use the first part of the port or inset to allow objects to be moved from the chamber passing the cut skin into the operating field and/or manual manipulation to be performed from the chamber through the cut skin further into the operating field in the patient's body.

According to one embodiment, the chamber is adapted to be in communication with an operating field during the surgical procedure, and wherein the part of the wall forming both the chamber and the tubular enclosure, at a portion thereof, is adapted to be opened and wherein the opening together with the hip joint surgery incision of the patient is adapted to be positioned inside of the chamber allowing such communication with the operating field, wherein a portion of the wall part encompassing only the chamber has a wall port or wall inset mounted therein for allowing, from outside the chamber, at least one of; a) objects to be moved into at least one of; the chamber and the operating field, and manual manipulation to be performed in at least one of; the chamber and the operating field.

According to one embodiment, the medical device comprises a port or inset including a first and second part. The second part comprises the wall port or wall inset and the first part comprises a first wall port or first wall inset mounted in the opening in the portion of the part of the wall forming both the chamber and the tubular enclosure and adapted to be opened to create the communication between the chamber and the operating field to allow; objects to be moved further from the chamber into the operating field and/or manual manipulation to be performed from the chamber further into the operating field, and wherein the passage between the chamber and the operating field includes the first wall port or inset, and wherein the second chamber is located in between the tubular enclosure and the skin of the patient, and wherein the second chamber has a size equal to or larger than zero.

According to one embodiment, the two parts of the port or inset are adapted to be mounted together, touching each other for forming an integrated port and inset and thereby allowing; objects to be moved into the operating field and/or manual manipulation to be performed in the operating field directly from outside the chamber using the integrated port or inset, and wherein the two parts of the port or inset are adapted to be separated from each into one or more positions in which they are not touching each other and thereby; to use the wall port or inset of the second part to allow; objects to be moved into the chamber and/or manual manipulation to be performed in the chamber and further to use the first wall port or first wall inset of the first part to allow; objects to be moved from the chamber passing the cut skin into the operating field and/or manual manipulation to be performed from the chamber through the cut skin further into the operating field.

The two parts of the port or inset may be adapted to be locked together in at least one fixed position.

The chamber encompassing the surgical procedure may be adapted to reduce infection risk of the surgical procedure. Both of the two parts of the port may be adapted to comprise a fluid sealing valve when the two parts are separated.

According to one embodiment, the second part comprises a fluid sealing valve, when the two parts are separated.

The sealing device in any of the embodiments above may comprises a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

The sealing device in any of the embodiments above may comprises a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

The medical device may further comprise an adhesive surface adapted to provide at least one of: fixation of at least one of the wall and enclosure to the skin of the patient, and sealing between the skin of the patient and at least one of the wall and enclosure.

According to one embodiment, the medical device further comprises an air evacuation system adapted to evacuate air from the second chamber, when the portion of the patient's extremity is placed in the enclosure. The air evacuation system may further be adapted to evacuate air from the vacuum sealing member.

According to one embodiment, the medical device comprises a slit for placing the chamber around at least a portion of the extremity of the patient radially in relation to the length axis of the extremity. The slit may be adapted to be at least partially closed by closing elements mounted on the wall of the medical device.

The medical device may comprise a first and a second portion located on a first and second side of the slit when the chamber is placed around at least a portion of the extremity. The first and second portions are adapted to be interconnected by means of at least one of: an adhesive surface and a mechanical connecting member.

According to one embodiment, at least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

A method of performing hip joint surgery on a patient using a medical device is provided. The method comprising forming a chamber using the wall together with or without the patient's body, placing, at least partly on the patient's body, the chamber encompassing at least part of one step of the hip joint surgery procedure to be performed and maintaining by the chamber a sealed environment for the surgical procedure, sealing with the first sealing device connected to the wall between the wall and the skin or tissue of the patient, the step of sealing including: sealing at least a part of the hip joint surgery operational field from at least one of: the anal orifice, the urethra orifice and at least part of the perineum region, while still maintaining the chamber sealed, holding the medical device in place by encircling at least one leg of the patient or the prolongation thereof to be involved in the sealing of the chamber, using at least one of a first part of the sealing device and a first holding member, holding the medical device in place by encircling the whole body left to right on the level above the legs selected from at least one of; the level of the pelvic, abdominal or thorax region of the patient to further be involved in the sealing of the chamber, using at least one of; a second part of the sealing device and a second holding member, sealing from the medial cranial part of the leg where it is meeting the inguinal region or its prolongation, further in a cranial direction lateral of the patient's ventro-dorsal mid-sagittal plane on the side where the hip surgery is performed, using a third part of the sealing device at least partly extending in cranial direction until meeting the second part of the sealing device, using at least one of; a third part of the sealing device and a third holding member, the wall interconnecting the first, second and third part of the sealing device to seal the chamber, thus sealing the chamber and exclude from the chamber at least one of; the anal orifice, the urethra orifice and at least part of the perineum region.

The method may further comprise positioning the sealing device such that both of the urethra and the anus is excluded from the enclosed chamber forming the sealed environment.

The medical device may further comprise a second sealing device comprising a first and second sealing member. The method may include the steps of: positioning the first sealing member at the inside of the patient's skin around an incision to be performed in the skin, positioning the second sealing member at the outside of the patient's skin around the incision, interconnecting sealingly the first and second sealing members, using a connecting member, sealing with the sealing device between at least one of: (a) the second sealing member and the skin of the patient, and (b) the first sealing member and tissue of the patient.

The method may further comprise encircling a portion of the patient's body by at least one of the first and second holding member, by itself or together with the sealing device, and holding the medical device in the desired position.

A medical device for performing knee joint surgery on a patient is provided. The medical device comprises a wall adapted to form a chamber at least partially encapsulating the knee joint of the patient, the chamber being adapted to encompass at least a part of the knee joint surgery to be performed while maintaining a sealed environment for the surgical procedure, and a closeable wall port or inset placed in a portion of the wall. The closeable wall port or inset is adapted to be at least one of: abutting, attaching, and placed in a fixed position in relation to a body port placed in an incision in the knee region of the patient's body, such that an arthroscopic step of the knee joint surgery can be performed.

By creating a sealed environment, the risk of infections can be substantially reduced. The risk of infections is particularly large when performing prosthesis surgery inside the joints of patients, which is why the maintaining of a controlled environment is important.

The medical device may further comprise a sealing device connected to the wall and adapted to seal against the patient's body, such that the sealed chamber is formed by the wall and the patient's body.

According to one embodiment, the medical device may further comprise a closable body port connected to a first portion of the wall. The closable body port may be connected to a second portion of the wall. The closable wall port and the closable body port are adapted be detachably connected to form an interconnected port.

According to one embodiment, the wall port and the body port are adapted to be positioned relative to each other such that: an object is displaceable from outside of the chamber, through the wall port, into the chamber, through the body port into the patient, when the knee joint surgery is performed.

According to one embodiment, the wall port or wall inset is displaceable between: a first position relatively close to the skin of the patient, and a second position more remote from the skin of the patient than the first position. The wall port may be adapted to be locked to the body port.

According to one embodiment, the medical device may further comprise a vacuum sealing member adapted to hold a pressure less than atmospheric pressure between the first wall portion and the patient's skin to seal between the first wall portion and the patient's skin.

According to one embodiment, the vacuum sealing member is adapted to create a substantially airtight seal between the wall portion and the skin of the patient, to enable an incision to be performed through the skin of the patient in sealed environment such that a fluid connection between a cavity in the patient and the chamber can be created.

A method of performing a portion of knee joint surgery on a patient using a medical device is provided. The method comprises applying a wall on the skin of the patient to form a chamber in which a sealed environment can be maintained for encompassing part of the knee joint surgery to be performed. The wall comprises a closeable wall port connecting the closeable wall port to a body port, such that the closeable wall port is at least one of: abutting the body port and attached to the body port, such that an arthroscopic step of the knee joint surgery can be performed.

The method may further comprise the steps of displacing an object from outside of the chamber through the wall port and into the chamber, displacing the object through the body port into a cavity in the patient the patient, when the knee joint surgery is performed.

According to one embodiment, the method further comprises displacing the wall port from a first position relatively close to the skin of the patient to a second position more remote from the skin of the patient than the first position.

A medical device for performing a surgical procedure on a patient is provided. The medical device comprises a wall adapted to be at least partially applied on the patient's body to form a chamber together with the patient's body, in which a sealed environment can be maintained for encompassing part of the surgical procedure to be performed, at least one of; a closeable wall port and inset placed in a portion of the wall and being adapted to be detachably connected to a closeable body port placed in an incision in the patient's body connecting to a body cavity, when the medical device is applied on the patient's body for performing the surgical procedure, at least one of; a closeable body port and an inset adapted to be placed in an incision in the patient's body and further adapted to be detachably connected to the closeable wall port, when the medical device is applied on the patient's body for performing the surgical procedure, a sealing device connected to the wall and adapted to seal against the skin of the patient, when the medical device is applied on the patient's body. At least one of; the closable wall port, the closable body port and the closable wall port and the closable body port together, are adapted to form an airlock sluice between a cavity in the body of the patient and the ambient environment, when the medical device is applied on the patient's body for performing the surgical procedure.

By providing a medical device forming an airlock sluice, objects or specimens, from the body of the patient, can be transferred between a cavity in the patient of the body and the ambient environment.

According to one embodiment, the closeable wall port and closeable body port are adapted to be positioned relative to each other such that an elongated object is longitudinally displaceable through the closeable wall port and closeable and body port.

According to one embodiment, at least one of the closeable wall port and the inset is displaceable between a first position, in which the closeable wall port or inset is situated relatively close to at least one of the closeable body port and the inset, and a second position, in which at least one of the closeable wall port and the inset is situated more remote from the closeable body port or the inset.

The closeable wall port or inset may be adapted to be at least one of; connected to the closeable body port and locked to the closeable body port, when the medical device is applied on the patient's body for performing a surgical procedure.

According to one embodiment, at least one of the closable body port and the closeable wall port comprises a penetratable self sealing gel, such that an object or hand can be inserted through the closeable wall port while maintaining the sealed environment.

According to one embodiment, the medical device comprises a sealing device adapted to be positioned in the portion of the wall adapted to be applied on the patient's body when the surgical procedure is to be performed. The sealing device comprises a vacuum sealing member adapted to hold a pressure less than atmospheric pressure between the first wall portion and the patient's skin to seal between the first wall portion and the patient's skin.

The airlock sluice may be at least one of: placed separate from the wall port, partly using the wall port in the airlock sluice and fully integrated in the wall port for allowing passage of objects between the chamber and the outside of the chamber.

According to one embodiment, the vacuum sealing member is adapted to create a substantially airtight seal between the wall portion and the skin of the patient, to enable an incision to be performed through the skin of the patient in sealed environment such that a fluid connection between a cavity within the patient and the chamber can be created.

According to one embodiment, the closeable body port comprises a closeable body multi-port adapted to be placed from inside the chamber in an incision to be performed in the skin of the patient. The closeable body multi-port may comprise at least two closeable body ports adapted to enable passage of an object between the chamber and the inside of the patient's body. The body multiport may be adapted to be connected to at least one of; a closable wall port and a closable wall multiport together placed in an incision in the patient's body connecting to a body cavity, when the medical device is applied on the patient's body for performing a surgical procedure, and the closable wall port comprises a wall multiport, comprising at least two closable wall ports, wherein the wall multiport is adapted to be connected to at least one of; a closable body port and a closable body multiport placed in an incision in the patient's body connecting to a body cavity, when the medical device is applied on the patient's body for performing a surgical procedure.

According to one embodiment, the medical device further comprises a sealing device having a first sealing member adapted to be positioned at the inside of the patient's skin around an incision to be performed in the skin and a second sealing member adapted to be positioned at outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

The closeable body port may be adapted to be placed inside the chamber in an incision to be performed in the skin of the patient to enable passage between the chamber and a cavity in the patient's body.

The medical device may further comprise a coupling adapted to detachably attach the closable body port to at least one of; the patient's skin and the closable wall port or inset to enable exchange and removal of the closable body port or inset.

According to one embodiment, the closeable wall port may be positioned in the wall portion and adapted such that it allows handling of an instrument for at least one of cutting through the patient's skin via the closeable wall port and cutting through the patient's skin with the instrument fully placed inside the chamber, when the wall is applied on the patient's body.

The wall portion may be adapted to allow itself to be cut through to reach and make an incision in the patient's skin for allowing a surgical procedure, when the wall is applied on the patient's body.

The closable body port may be adapted to be at least one of; fitted in the patient's skin after an incision has been made in the skin, and fitted to the closable wall port after the closable body has been fitted in the patient's skin after an incision has been made in the skin, when the medical device is applied on the patient's body.

According to one embodiment, the closeable wall port or inset and the closeable body port or inset may be connected by a portion of the wall, such that the closeable wall port or inset and closeable body port or inset can be moved in relation to each other whilst being connected by means of the wall portion.

The medical device according to anyone of the embodiments may further comprise a coupling adapted to be at least one of; an integrated part of at least one of the body port or the body inset, an integrated part of at least one of the wall port or the wall inset, a body coupling adapted to be placed in close relation to the skin of the patient, and further adapted to be connected to the wall port or inset, and a wall coupling adapted to be placed in close relation to the wall of the medical device. The coupling may further be adapted to be connected to the body port or inset.

A method of forming an airlock sluice for use when performing a surgical procedure on a patient is further provided. The method comprises applying a wall on the patient's body to form a chamber together with the patient's body, in which a sealed environment can be maintained for encompassing part of the surgical procedure to be performed, applying a sealing device against the skin of the patient, such that sealing is created between the wall of the medical device and the skin of the patient, connecting at least one of; a closeable wall port and an inset placed in a portion of the wall to a closeable body port placed in an incision in the patient's body.

A medical device for performing a surgical procedure on a patient is provided. The medical device comprises a wall adapted to at least partially be applied on the patient's body to form a chamber by itself or together with the patient's body, in which a sealed environment can be maintained for encompassing part of the surgical procedure to be performed, wherein a portion of the wall is adapted to contact the patient's skin when the surgical procedure is performed, a vacuum sealing device comprising a vacuum sealing member adapted to hold a pressure less than atmospheric pressure between the wall portion and the patient's skin to seal between the wall portion and the patient's skin, and a vacuum adjustment device adapted to adjust the pressure in the vacuum sealing member.

According to one embodiment, the vacuum adjustment device may be adapted to adjust the pressure in the vacuum sealing member as a response to at least one of: a physiological parameter of the patient, and a parameter of the medical device. The parameter of the medical device is one of: the pressure in the chamber, the pressure in the vacuum sealing member, and the physiological parameter of the patient may be one of: the blood pressure of the patient, the blood flow of the patient, and a temperature of the body of the patient.

The medical device may further comprise a monitoring unit connected to the adjustment device. The monitoring unit is adapted to monitor at least one of: the pressure in the chamber, the pressure in the vacuum sealing member, the blood pressure of the patient, the blood flow of the patient, and a temperature of the patient.

According to one embodiment, the adjustment device may be adapted to adjust the pressure in the vacuum sealing member such that the blood flow of the patient remains substantially unaffected.

According to one embodiment, the medical device comprises a first monitoring unit adapted to monitor the blood flow or blood pressure of the patient and a second monitoring unit, adapted to monitor the pressure in the vacuum sealing member. The adjustment device may be adapted to adjust the pressure in the vacuum sealing member in response to input from both the first and second monitoring unit, for mediating between keeping the chamber sealed and keeping the blood flow of the patient substantially unaffected.

In one embodiment, the adjustment device may be adapted to adjust the pressure in the vacuum sealing member for keeping the pressure between at least one of: −135 mmHg and 0 mmHg, −115 mmHg and 0 mmHg, −100 mmHg and 0 mmHg, −50 mmHg and 0 mmHg, −30 mmHg and 0 mmHg, −20 mmHg and 0 mmHg, −10 mmHg and 0 mmHg, and −5 mmHg and 0 mmHg, and thus keeping the blood flow of the patient substantially unaffected.

The vacuum sealing device may be adapted to create a substantially airtight seal between the wall portion and the skin of the patient, to enable an incision to be performed through the skin of the patient in the sealed environment such that a fluid connection between a cavity within the patient and the chamber is formed.

According to one embodiment, the wall is adapted to hold a pressure within the chamber exceeding atmospheric pressure, and the vacuum sealing device is adapted to seal between the wall of the medical device and the skin of the patient such that the pressure in the chamber, exceeding atmospheric pressure, can be maintained.

According to one embodiment, the medical device may further comprise a first monitoring unit adapted to monitor the pressure in the vacuum sealing, and a chamber pressure monitoring unit adapted to monitor the pressure inside the chamber. The adjustment device may be adapted to adjust the pressure in the vacuum sealing member such that at least one of the pressure in the chamber, exceeding atmospheric pressure, can be maintained, and the pressure difference between atmospheric pressure and the pressure in the vacuum sealing exceeds the pressure difference between atmospheric pressure and the pressure in the chamber.

The pressure in the chamber may be between 5 mmHg and 75 mmHg above atmospheric pressure, and the pressure in the vacuum sealing may be between 6 mmHg and 76 mmHg below atmospheric pressure.

According to one embodiment, the medical device may further comprise at least one closeable wall port placed in the wall enabling passage between the chamber and the outside of the chamber. The closeable wall port may be detachably fixated to the wall such that the wall port can be exchanged to another wall port or wall inset. The closable body port may further be adapted to be placed inside the chamber in an incision to be performed in the skin of the patient to enable passage between the chamber and the inside of the patient's body.

According to one embodiment, a part of the wall of the medical device forms an elongated tubular enclosure extending within the chamber of the medical device, contacting the skin of the patient and being adapted to separate the skin of the patient from the sealed environment of the chamber of the medical device, when implanted.

The medical device may further comprise an adhesive adapted to provide at least one of fixation of the wall to the skin of the patient, and sealing between the skin of the patient and the wall.

The vacuum sealing device in any of the embodiments, may further comprise a vacuum pump, and the vacuum adjusting device may be connected to the vacuum pump and thereby adjusts the pressure in the vacuum sealing member.

According to one embodiment, the vacuum adjustment device may be adapted to control the vacuum pump as a response to an input from the monitoring unit.

A method of providing a sealed environment using a medical device is further provided, such that a surgical procedure can be performed in the sealed environment. The method comprises: applying a wall on the skin of the patient to form a chamber, in which a sealed environment can be maintained for encompassing part of the surgical procedure to be performed, applying a vacuum sealing member contacting the skin of the patient, the vacuum sealing member being connected to the wall of the medical device and adapted to seal the chamber from the ambient environment, adjusting the pressure in the vacuum sealing member such that sealing between the skin of the patient and the wall of the medical device is created.

According to one embodiment, the step of adjusting the pressure in the vacuum sealing member further comprises adjusting the pressure in the vacuum sealing member as a response to at least one of: a monitored parameter of the medical device, and a monitored physiological parameter of the patient.

The step of adjusting the pressure in the vacuum sealing member as a response to a monitored parameter of the medical device may comprise adjusting the pressure in the vacuum sealing member as a response to: the pressure in the chamber and the pressure in the vacuum sealing member.

According to one embodiment, the step of adjusting the pressure in the vacuum sealing member as a response to a monitored physiological parameter of the patient may comprise adjusting the pressure in the vacuum sealing member as a response to: the blood pressure of the patient, the blood flow of the patient, and a temperature of the body of the patient.

A medical device for performing arthroscopic surgery on a joint of a patient is provided. The medical device comprises a wall adapted to form a chamber for encapsulating at least a part of the joint of the patient for allowing the arthroscopic surgery to be performed. The chamber is adapted to encompass part of the surgery to be performed while maintaining a sealed environment. The medical device comprises a fluid inlet placed in the wall and adapted for supplying a fluid to the chamber, and a fluid outlet adapted to be placed in an incision performed in the joint region of the patient for evacuating the fluid from the joint region.

The wall may be adapted to hold a liquid at least partially filling the chamber; the liquid may be at least one of; an isotonic solution and an antibiotic liquid.

The medical device may be adapted for use in knee joint procedures, and thus comprise at least one of a first opening arranged such that the leg of a patient can enter the medical device and a second opening arranged such that the leg of a patient can exit the medical device.

According to one embodiment, the medical device comprises a fluid system for withdrawing fluid from the fluid outlet and supplying fluid to the fluid inlet. The fluid system may further comprise a fluid pump for circling fluid from the fluid outlet to the fluid inlet. The fluid system may comprise at least one of: a filtering unit for filtering the fluid, a sterilization unit for directly or indirectly sterilizing the fluid, a fluid tempering unit adapted change the temperature of the fluid.

A part of the wall may form an elongated tubular enclosure extending in the chamber of the medical device, contacting the skin of the patient and being adapted to separate the skin of the patient from the sealed environment of the chamber of the medical device. The fluid outlet may be placed through the wall of the elongated tubular enclosure.

According to one embodiment, medical device comprises a sealing device for sealing between the medical device and the patient, the sealing device may comprise a vacuum sealing member adapted to hold a pressure being less than atmospheric pressure thus creating the vacuum sealing between the skin of the patient and the medical device and/or a pressure sealing member adapted to hold a pressure exceeding atmospheric pressure and thereby mechanically press against the skin of the patient to provide a sealing between the skin of the patient and the medical device.

The medical device may further comprise an energy transferring coupling adapted to transfer energy from outside the chamber into the sealed environment, such that a tool can be energized. The medical device may be adapted to hold a pre-placed energy consuming tool within the sealed environment before the medical device is placed in connection with the patient.

A method of performing an arthroscopic surgical procedure on a patient using a medical device is further provided. The method comprising: applying a wall on the skin of the patient to form a chamber, in which a sealed environment can be maintained for encompassing part of the surgical procedure to be performed, creating an incision in the skin of the patient, in the sealed environment, such that a fluid connection is created between the chamber and a cavity in the body of the patient, positioning a fluid outlet in the incision created in the skin of the patient, supplying fluid to the chamber through a first fluid inlet placed in the wall, and discharging fluid from the incision site through the fluid outlet placed in the incision.

A medical device for performing arthroscopic surgery on a joint of a patient is provided. The medical device comprises a wall adapted to form a chamber adapted to encapsulate the joint of the patient, the chamber being adapted to encompass part of the surgical procedure to be performed while maintaining a sealed environment, a first fluid inlet placed in the wall and adapted for supplying fluid to the chamber, a first fluid outlet placed in the wall and adapted for discharging fluid from the chamber, a second fluid inlet adapted to be placed in an incision in the skin of the patient, in the area of the joint, for supplying fluid to the joint, and a second fluid outlet adapted to be placed in an incision in the skin of the patient, in the area of the joint, for discharging fluid from the joint.

By providing a first and second fluid system, a higher flow can be achieved in the incision in the body of the patient, for more efficiently transporting blood and other bodily matter from the incision site. The first fluid system may have a slower fluid flow e.g. for filtering, sterilizing and tempering the fluid in the chamber of the medical device.

The first fluid system may be adapted to at least one of: supply fluid to the first fluid inlet and evacuate fluid from at least one of the first and second fluid outlet, and circulate a fluid from at least one of the first or second fluid outlet to the first fluid inlet.

The first fluid system may be adapted to at least one of: supply fluid to the second fluid inlet, and evacuate fluid from at least one of the first and second fluid outlet and circulate a fluid from at least one of the first or second fluid outlet to the second fluid inlet.

According to one embodiment, the first fluid system is adapted to supply fluid to the first fluid inlet and evacuate fluid from the first fluid outlet and/or to circulate a fluid from the first fluid outlet to the first fluid inlet.

According to one embodiment, the medical device further comprises a second fluid system adapted to supply fluid to the second fluid inlet and evacuate fluid from the second fluid outlet, and circulate a fluid from the second fluid outlet to the second fluid inlet.

The fluid may be a liquid fluid, such as an isotonic solution and an antibiotic liquid.

The first and second fluid systems may comprise a fluid pump for circulating the fluid from the first or second fluid outlet to the first or second fluid inlet.

The medical device may be adapted for use in knee joint procedures, and may thus comprise a first opening arranged such that the leg of a patient can enter the medical device and a second opening arranged such that the leg of a patient can exit the medical device.

According to one embodiment, a part of the wall may form an elongated tubular enclosure extending within the chamber of the medical device, contacting the skin of the patient and being adapted to separate the skin of the patient from the sterile environment of the chamber of the medical device.

At least one of the first fluid inlet and the first fluid outlet may be positioned through the wall of the elongated tubular enclosure.

The medical device may further comprise a sealing device for sealing between the medical device and the patient. The sealing device may comprise a vacuum sealing member adapted to hold a pressure being less than atmospheric pressure thus creating a vacuum sealing between the skin of the patient and the medical device and/or a pressure sealing member adapted to hold a pressure exceeding atmospheric pressure and thereby mechanically press against the skin of the patient to provide a sealing between the skin of the patient and the medical device.

According to one embodiment, the medical device may further comprise an energy transferring coupling adapted to transfer energy from outside the chamber into the sealed environment, such that a tool can be energized.

According to one embodiment, the medical device may be adapted to hold a pre-placed energy consuming tool within the sealed environment before the medical device is placed in connection with the patient.

The medical device may further comprise a body port or body inset adapted to be placed in an incision in the skin of the patient, wherein the body port or inset comprises at least one of: a body multi port comprising at least two ports adapted to enable passage of at least one of; one or more tools, one or more devices and one or more parts of the human body, from outside of the patient's body to inside of the patient's body or the opposite direction, a body port comprising one port adapted to enable passage of at least one of; one or more tools, one or more devices and one or more parts of the human body, from outside of the patient's body to inside of the patient's body or the opposite direction, and a body inset comprising at least one of: a glove and a device or instrument mount.

According to one embodiment, the medical device may further comprise at least one wall port enabling passage of at least one of: surgical tools, surgical devices and one or more parts of the human body, between the sealed environment and the environment outside of the sealed environment or in the opposite direction. The at least one port may comprise an elastic membrane adapted to, in a non-expanded state, seal between the sealed environment and the environment outside of the sealed environment, and in an expanded state enable a hand to be inserted through the elastic membrane.

A method of performing an arthroscopic surgical procedure on a patient using a medical device is further provided. the method comprising: applying a wall on the skin of the patient to form a chamber, in which a sealed environment can be maintained for encompassing part of the surgical procedure to be performed, supplying fluid to the chamber through a first fluid inlet placed in the wall, discharging fluid from the chamber through a fluid outlet placed in the wall, supplying fluid to a cavity in the body of the patient through a second fluid inlet placed in an incision in the skin of the patient, and discharging fluid from the cavity in the body of the patient through a second fluid outlet placed in an incision in the skin of the patient.

A medical device for performing a surgical procedure is further provided. The medical device comprising: a wall adapted to be applied at least partially on the patient's body to form a chamber by itself or together with the body of the patient, in which a sealed environment can be maintained for encompassing part of the surgical procedure to be performed, a pressure sealing device adapted to seal between a wall portion and the patient's body, when the wall is applied on the patient's body, wherein the pressure sealing device comprises a pneumatically, hydraulically or mechanically powered pressure sealing member adapted to press the wall portion against the body of the patient such that the chamber is substantially sealed from the ambient environment allowing a pressure inside the chamber to be higher than the atmospheric pressure during the surgical procedure, and at least one of: a pressure adjustment device adapted to adjust the pressure in the sealing member, and a monitoring unit for monitoring at least one of: a parameter of the medical device, and a physiological parameter of the patient. By monitoring and adjusting the pressure in the sealing member the pressure can be maintained high enough for the sealing member to provide sealing, while being as low as possible not to injure or make marks in the skin of the patient.

The pressure adjustment device may be adapted to adjust the pressure in the sealing member as a response to input from the monitoring unit.

The parameter of the medical device may be one of: the pressure in the sealing member, the pressure in the chamber, and the direct or indirect leakage of fluid from the chamber. The physiological parameter of the patient may be at least one of: the blood flow passing the sealing device, the blood pressure of the patient, and a temperature of the body of the patient.

The adjusting device may be adapted to adjust the pressure in the sealing device based on input from the monitoring unit, such that the sealing does not substantially hinder the flow of blood passed the sealing member.

According to one embodiment, the medical device may comprise a first and second monitoring unit. The first monitoring unit may be adapted to monitor at least one of: the blood pressure of the patient, the blood flow passing the sealing and a temperature of the body of the patient, and wherein the second monitoring unit may be adapted to monitor at least one of: the pressure in the sealing, the pressure in the chamber, and the direct or indirect leakage of fluid from the chamber.

According to one embodiment, the pressure adjustment device is adapted to adjust the pressure in the sealing member based on input from the first and second monitoring unit.

The pressure adjustment device may be adapted to adjust the pressure in the sealing member such that the pressure in the sealing member is between one of: 10 mmHg-160 mmHg, 20 mmHg-140 mmHg, 30 mmHg-120 mmHg, 30 mmHg-100 mmHg, 40 mmHg-100 mmHg, 40 mmHg-80 mmHg, and 50 mmHg-70 mmHg.

The pressure adjustment device may comprise at least one of: a fluid pump for pumping a gaseous fluid to the sealing member, a fluid pump for pumping a liquid fluid to the sealing, a spring loaded device involved in causing the pressure, and a prefilled reservoir involved in causing the pressure.

The medical device according to any of the embodiments herein may comprise a closable body port adapted to be placed in the patient's skin between a cavity in the patient's body and the chamber, when a surgical procedure is performed. The closable body port may comprise at least one of; an elastic membrane and a flexible membrane. The membrane may be adapted to, in a non-compressed state, seal between the chamber and the environment outside the chamber, and in a compressed state enable a hand or an object to be inserted through the membrane. In other embodiments, the closable body port may comprise an adaptation to be connected to a wall port, placed in the wall and/or an adaptation to be detachable and exchanged by a different second port or a body inset.

The medical device may comprise an adhesive adapted to provide fixation of at least one of the wall and enclosure to the skin of the patient and/or sealing between the skin of the patient and at least one of the wall and enclosure.

According to one embodiment, the medical device further comprises at least one wall port adapted to enable passage between the chamber and the outside of the chamber or at least one wall inset positioned in the wall. The wall port or wall inset may be detachably fixated to the wall such that the wall port or wall inset can be exchanged to another wall port or wall inset.

According to one embodiment, a part of the wall forms an elongated tubular enclosure extending within the chamber of the medical device, contacting the skin of the patient and being adapted to separate the skin of the patient from the sealed environment of the chamber of the medical device.

The monitoring unit may in any of the embodiments be adapted to encircle an extremity of the patient and measure the blood pressure of the patient periodically or monitor the blood pressure of the patient by exerting a pressure on the encircled extremity exceeding the systolic arterial pressure, such that the blood flow is momentarily stopped.

The monitoring unit may be adapted to measure the blood pressure of the patient with an interval of one of: 1-5 minutes, 5-10 minutes, 10-20 minutes, and 20-30 minutes.

A method of providing a sealed environment using a medical device, such that a surgical procedure can be performed in the sealed environment, is further provided. The method comprises applying a wall on the skin of the patient to form a chamber, in which a sealed environment can be maintained for encompassing part of the surgical procedure to be performed. The method further comprises, applying a pressure sealing member contacting the skin of the patient, the pressure sealing member being connected to the wall of the medical device and adapted to seal the chamber from the ambient environment, The method further comprises adjusting the pressure in the pressure sealing member such that sealing between the skin of the patient and the wall of the medical device is created.

The step of adjusting the pressure in the pressure sealing member may further comprise adjusting the pressure in the pressure sealing member as a response to at least one of: a monitored parameter of the medical device, and a monitored physiological parameter of the patient.

The step of adjusting the pressure in the pressure sealing member as a response to a monitored parameter of the medical device may comprise adjusting the pressure in the pressure sealing member as a response to: the pressure in the chamber and the pressure in the pressure sealing member.

The step of adjusting the pressure in the pressure sealing member as a response to a monitored physiological parameter of the patient may further comprise adjusting the pressure in the pressure sealing member as a response to: the blood pressure of the patient, the blood flow of the patient, and a temperature of the body of the patient.

A medical device for performing a surgical procedure on a patient is provided. The medical device comprises a wall adapted to be applied at least partially on the patient's body to form a chamber by itself or together with the body of the patient, in which a sealed environment can be maintained for encompassing part of the surgical procedure to be performed. The medical device further comprises at least one wall port or wall inset placed in the wall, at least one of: an energy transferring member for transferring energy from outside of the chamber to inside of the chamber, and an information transferring member for transferring information from outside of the chamber to inside of the chamber, whilst maintaining the sealed environment.

By providing the medical device, a device or instrument consuming energy may be operated within the chamber of the medical device.

The energy transferring member may be adapted to transfer at least one of; pneumatic, hydraulic and kinetic energy.

According to one embodiment, the energy transferring member comprises a valve such that the energy transferring member can be opened for enabling transfer of at least one of; kinetic, pneumatic and hydraulic energy through the wall of the medical device.

The medical device may comprise a tool placed inside of the chamber of the medical device and connected to the energy transferring member. The tool may be adapted to be operated by at least one of the pneumatic, hydraulic and kinetic energy.

The energy transferring member may comprise a magnetic coupling comprising a first part comprising a magnetic material adapted to be positioned on the outside of the wall of the medical device, and second part comprising magnetic material positioned on the inside of the wall of the medical device. The first part is adapted to receive kinetic energy and transfer the kinetic energy to the second part by magnetic coupling between the first and second part, such that kinetic energy can be transferred from the outside of the chamber to the inside of the chamber while maintaining the sealed environment in the chamber. The energy transferring member may be adapted to transfer rotational kinetic energy by the first part transferring rotational kinetic energy to the second part by the magnetic coupling between the first and second part.

According to one embodiment, the energy transferring member comprises a sleeve fixed to the wall of the medical device. The sleeve may be adapted to receive a rotating shaft and the sleeve may have a first portion adapted to be positioned on the outside of the chamber, and a second portion adapted to be positioned on the inside of the chamber, such that rotational kinetic energy can be transferred from the first portion of the sleeve to the second portion of the sleeve by the rotating shaft.

According to one embodiment, the energy transferring member may be adapted to transfer electric energy via at least one of; a wireless link, and a cable connection. In an alternative embodiment, the energy transferring member may comprise an inductive coupling for transferring electric energy by a magnetic field between a first conductor positioned on the outside of the chamber, and a second conductor positioned on the inside of the chamber.

In any of the embodiments, the medical device may comprise a tool placed inside of the chamber of the medical device and connected to the energy transferring member, wherein the tool is adapted to be operated by electric energy.

According to one embodiment, the information transferring member is adapted to transfer data from the inside of the chamber to the outside of the chamber, through the wall of the medical device.

According to one embodiment, the information transferring member comprises at least one of: an optical information transferring member, a capacitive information transferring member, an inductive information transferring member, and a radio based information transferring member. The optical information transferring member may be a infra red information transferring member.

The medical device may comprise a camera placed inside the chamber. The camera may be connected to the information transferring member for transferring data from the camera to the outside of the chamber.

According to one embodiment, the medical device comprises a data communication unit adapted to communicate with an implant implanted in the patient. The data communication unit may be connected to the information transferring member such that data from the implant can be transferred to the outside of the chamber.

The medical device may further comprise a sensing probe positioned inside the chamber and connected to the information transferring member. The sensing probe may be adapted to sense at least one of: the blood pressure of the patient, the blood flow of the patient, a temperature of the patient, saturation of the blood of the patient, at least one ischemia marker of the patient and/or the skin tone of the patient.

The chamber of the medical device may be adapted to hold a pressure exceeding atmospheric pressure. The pressure may exceed atmospheric pressure by more than one of: 10 mmHg, 20 mmHg, 40 mmHg, 60 mmHg, 80 mmHg, 100 mmHg, and 140 mmHg.

According to one embodiment, the medical device may comprise a sealing device adapted to seal directly or indirectly between the wall of the medical device and at least one of the skin of the patient, and tissue of the patient.

The medical device in any of the embodiments may comprise a sealing device comprising at least one of a vacuum sealing member, and a pressure sealing member.

A method of performing a surgical procedure on a patient using a medical device is further provided. The method comprises applying a wall on the skin of the patient to form a chamber, in which a sealed environment can be maintained for encompassing part of the surgical procedure to be performed, creating an incision through the skin of the patient in the sealed chamber, such that a fluid connection between a cavity within the patient and the chamber is created, transferring at least one of: energy and information through the wall of the medical device whilst maintaining the sealed environment.

The step of transferring energy through the wall of the medical device may comprise at least one of: pneumatic, hydraulic and kinetic energy through the wall of the medical device.

The step of transferring energy through the wall of the medical device may comprise supplying energy to an energy consuming tool inside the chamber of the medical device, and operating the energy consuming tool inside the chamber of the medical device.

The step of transferring information through the wall of the medical device may comprise transferring data, for example image data, through the wall of the medical device.

A medical device for performing arthroscopic surgery on a joint of a patient is provided. The medical device comprises a wall adapted to form a chamber adapted to encapsulate at least a part of the joint of the patient, allowing an arthroscopic surgery to be performed when the medical device is applied on the patient, the wall forming a sealed surgical environment. The wall is adapted to contain a liquid filling the chamber for creating a liquid operating environment, and the medical device is adapted to receive the liquid through at least one liquid inlet placed in at least one of the wall of the medical device and the skin of the patient for supplying the liquid to at least one of: the chamber and the joint in the patient's body.

By providing a liquid environment, an arthroscopic procedure or a combination of an arthroscopic and open surgical procedure can be performed in a liquid sealed environment.

The medical device may be adapted to discharge the liquid through at least one liquid outlet placed in at least one of: the wall of the medical device and the skin of the patient for discharging the liquid from at least one of: the chamber and the joint in the patient's body.

According to one embodiment, the medical device further comprises a liquid inlet for receiving liquid to the chamber and/or a liquid outlet for evacuating liquid from the chamber. The liquid outlet is adapted to be placed in an incision performed in the patient for evacuating the liquid from the joint within the patient.

The liquid system may be adapted to circulate the liquid from the liquid outlet to the liquid inlet.

The medical device may further comprise at least one inlet and at least one outlet selected from the following: a first liquid inlet placed in the wall and adapted for supplying liquid to the chamber, a first liquid outlet placed in the wall and adapted for evacuating liquid from the chamber, a second liquid inlet adapted to be placed in an incision in the skin of the patient, in the area of the joint, for supplying liquid to the joint, and a second liquid outlet adapted to be placed in an incision in the skin of the patient, in the area of the joint, for evacuating liquid from the joint.

According to one embodiment, the medical device may further comprise a first liquid system adapted to at least one of: supply liquid to the first liquid inlet and evacuate liquid from at least one of: the first liquid outlet, and the second liquid outlet, and circulate a liquid from the first or second liquid outlet to the first liquid inlet.

According to one embodiment, a first liquid system may be adapted to supply liquid to the second liquid inlet and evacuate liquid from at least one of: the first liquid outlet, and the second liquid outlet, and circulate a liquid from at least one of the first or second liquid outlet to the second liquid inlet.

The first liquid system may be adapted to supply liquid to the first liquid inlet and evacuate liquid from the first liquid outlet, and/or circulate liquid from the first liquid outlet to the first liquid inlet. The medical device may further comprise a second liquid system adapted to circulating a liquid from the second liquid outlet to the second liquid inlet.

The liquid may be is at least one of; an isotonic solution and an antibiotic liquid.

The system may comprise a pump for pumping the liquid from the liquid outlet to the liquid inlet. The system may further comprise a filtering unit for filtering the liquid supplied to the chamber a sterilization unit for directly or indirectly sterilizing the liquid supplied to the chamber, a liquid tempering unit adapted change the temperature of the liquid supplied to the chamber.

According to one embodiment, the medical device may comprise a sealing device adapted to seal between the wall of the medical device and the patient's skin for containing the liquid within the chamber. The sealing device may comprise a pressure sealing member adapted to seal against the skin of the patient by exerting a pressure on the skin of the patient and/or a vacuum sealing member adapted to hold a pressure being less than atmospheric pressure thus creating a vacuum seal between the skin of the patient and the medical device.

The medical device may further be adapted for use in knee joint procedures. The medical device may further comprise a first opening arranged such that the leg of a patient can enter the medical device and a second opening arranged such that the leg of a patient can exit the medical device, such that the chamber is positioned between the first and second opening.

A part of the wall of the medical device may form an elongated tubular enclosure extending within the chamber of the medical device, contacting the skin of the patient and being adapted to separate the skin of the patient from the sealed environment of the chamber, such that the chamber is formed between the wall of the medical device and the elongated tubular enclosure.

At least one of the first liquid inlet and the first liquid outlet may be positioned through the wall of the elongated tubular enclosure.

The medical device may comprise a first port positioned in the wall of the medical device, and a second port positioned in the wall of the elongated tubular enclosure. The first and second ports may be adapted to be connected for forming an integrated port.

The medical device may further comprise a wall inset, comprising a glove for enabling manual manipulation within the liquid environment of the chamber.

The medical device may further comprise a liquid lock for allowing passage of objects between the sealed environment and the environment outside of the sealed environment and vice versa, when the medical device is positioned in connection with the patient, for hindering liquid leakage through the liquid lock.

A method of performing a surgical procedure on a patient using a medical device is further provided. The method comprises applying a wall of the medical device on the skin of the patient to form a chamber, in which a sealed liquid operating environment can be maintained for encompassing part of the surgical procedure to be performed, filling the chamber with a liquid through a liquid inlet for creating the liquid operating environment, and creating an incision in the skin of the patient, in the liquid operating environment, such that a fluid connection between a cavity within the patient and the chamber is created.

The step of filling the chamber with a liquid through a liquid inlet may comprise filling the chamber with a liquid through a liquid inlet placed in at least one of: the wall of the medical device, and the body of the patient.

The method may further comprise discharging the liquid through a liquid outlet. The step of discharging the liquid through a liquid outlet may comprise discharging the liquid through a liquid outlet placed in at least one of: the wall of the medical device, and the body of the patient.

A medical device for performing a surgical procedure on a patient on an extremity having a reduced amount of blood is provided. The medical device comprises a wall enclosing a compartmentalized chamber in which a sealed environment can be maintained for encompassing part of the surgical procedure to be performed. The compartmentalized chamber comprises a first inflatable compartment placed around a first distal portion of the extremity, the first inflatable compartment comprising a first fluid inlet a second inflatable compartment placed around a second, more proximal portion of the extremity, the second inflatable compartment comprising a second fluid inlet, and a control system adapted to inflate the first and second compartment consecutively, such that blood pushed from the distal to the proximal portions of the extremity.

By reducing the amount of blood in the extremity of the patient, a surgical procedure can be performed on the extremity of the patient in a sealed environment with less bleeding and/or blood loss.

The medical device may further comprise a monitoring unit connected to the control system. The monitoring unit may be adapted to monitor at least one of: the blood pressure of the patient, the blood flow of the patient, a temperature of the patient, saturation of the blood of the patient, at least one ischemia marker of the patient, and the skin tone of the patient.

The control system may be adapted to inflate at least one of the first and second inflatable compartments on the basis of input from the monitoring unit.

The control system may be adapted to inflate at least one of the first and second inflatable compartments to a pressure exceeding the systolic blood pressure by at least one of: 0 mmHg 10 mmHg, 20 mmHg, 40 mmHg, 60 mmHg, 80 mmHg, 100 mmHg and 140 mmHg.

According to one embodiment, the wall comprise at least one detachable wall inset or integrated wall inset comprising a glove enabling manual manipulation within the chamber.

According to one embodiment, the wall is adapted to be at least partially applied on the patient's body to form a chamber together with the patient's body, in which the sealed environment can be maintained for encompassing part of the surgical procedure to be performed. The medical device may further comprise a sealing device connected to the wall and adapted to seal against the skin of the patient, when the medical device is applied on the patient's body, a closeable wall port placed in a portion of the wall, a closeable body port adapted to be placed in an incision in the patient's body forming a fluid connection between the chamber and a cavity in the patient's body. The closable wall port may be adapted to be connected to the closeable body port, when the medical device is applied on the patient's body for performing the surgical procedure, and the closable wall port and closable body port are adapted to form an airlock sluice between the cavity in the body of the patient and the ambient environment, when the medical device is applied on the patient's body for performing the surgical procedure.

According to one embodiment, the closeable wall port is displaceable between a first position, in which the closeable wall port is situated relatively close to the closeable body port, and a second position, in which the closeable wall port is situated more remote from the closeable body port.

According to one embodiment, the closeable wall port is adapted to be at least one of; connected to the previously mentioned body port, abutting the previously mentioned body port, and locked to the previously mentioned body port, when the medical device is applied on the body of the patient.

According to one embodiment, the medical device further comprises an additional port, wherein at least one of the closeable wall port and the closeable body port is exchangeable by the additional port.

According to one embodiment, the closeable body port may comprise a closeable body multi-port adapted to be placed from inside the chamber in an incision to be performed in the skin of the patient, and wherein the body multiport is adapted to be connected to at least one of; the wall port, and a wall multiport, when the medical device is applied on the patient's body for performing a surgical procedure, and the closable wall port comprises a closeable wall multiport, wherein the wall multiport is adapted to be connected to at least one of; the body port, and a body multiport placed in an incision in the patient's body, when the medical device is applied on the patient's body for performing a surgical procedure.

A surgical method of performing a step of a surgical procedure on an extremity of the patient having a reduced amount of blood using a medical device is further provided. The medical device comprises an inflatable wall enclosing a compartmentalized chamber in which a sealed environment can be maintained for encompassing part of the surgical procedure to be performed. The surgical method comprises inflating a first compartment of the compartmentalized chamber around a first distal portion of the extremity of the patient, for reducing the amount of blood in the first distal portion of the extremity, inflating a second compartment of the compartmentalized chamber around a second more proximal portion of the extremity of the patient, for reducing the amount of blood in the second more proximal portion of the extremity, and creating an incision in sealed environment inside the chamber enclosed by the wall of the medical device.

The method may further comprise the step of releasing the pressure in the first portion of the compression apparatus and maintaining the pressure in the second portion of the compression apparatus.

According to one embodiment, the step of inflating the first and second chambers may comprise inflating the first and second chambers with a liquid.

A medical device for performing a combination of open surgery and endoscopic surgery is provided. The medical device comprises a wall adapted to be inflated by a fluid for forming a chamber in which a sealed environment can be maintained for encompassing part of the surgical procedure to be performed. The medical device further comprises at least one endoscopic trocar enclosed within the chamber and being adapted to be placed through the wall of the medical device and through an incision performed in the body of the patient, for passing from the chamber to a cavity within the patient, when the surgical procedure is performed.

By enclosing the trocar in the chamber of the medical device the trocar can be kept sterile prior to insertion of the trocar into the cavity of the patient.

The medical device may further comprise at least one endoscopic instrument enclosed within the chamber and adapted to be used through the trocar. The endoscopic instrument may be at least one of: an endoscopic grasper, an endoscopic claw grasper, an endoscopic stone grasper, an endoscopic needle holder, an endoscopic hook, a camera, scissors, a knife, an ultrasound dissector, a suction instrument, an endoscopic dissector, and an endoscopic diathermy instrument.

According to one embodiment, the wall of the medical device may comprise an adhesive surface adapted to contact the skin of the patient for fixating the medical device to the skin of the patient.

The medical device may further comprise a pressure source adapted to supply a fluid having a pressure above atmospheric pressure to the sealed chamber of the medical device and/or be enclosed in the chamber.

The medical device may further comprise a sealing device adapted to seal between the wall of the medical device and the patient's skin. The sealing device may comprises a pressure sealing member adapted to seal against the skin of the patient by exerting a pressure on the skin of the patient or a vacuum sealing member adapted to hold a pressure being less than atmospheric pressure thus creating a vacuum seal between the skin of the patient and the medical device.

The medical device may further comprise a camera enclosed within the chamber of the medical device. The camera may be adapted to be inserted through the trocar for enabling visual inspection within a cavity of the patient.

According to one embodiment, the medical device is adapted for surgery on extremities of the patient, and thus the medical device may comprise at least one of a first opening arranged such that the leg of a patient can enter the medical device and a second opening arranged such that the leg of a patient can exit the medical device, such that the chamber is positioned between the first and second opening, and an elongated tubular enclosure extending within the chamber of the medical device formed by a part of the wall, contacting the skin of the patient and being adapted to separate the skin of the patient from the sterile environment of the chamber of the medical device.

The medical device may further comprise at least one of: an energy transferring member, and an information transferring member. The energy transferring member may be adapted to transfer at least one of: hydraulic energy, pneumatic energy, kinetic energy, and electric energy.

The medical device may further comprise an energy consuming tool placed inside of the chamber of the medical device, wherein the energy consuming tool is adapted to be connected to the energy transferring member.

The medical device may further comprises an information transferring member comprises at least one of: an optical information transferring member, a capacitive information transferring member, an inductive information transferring member, a radio based information transferring member.

The medical device may comprises at least one endoscopic instrument enclosed within the chamber performing a surgical procedure through the at least one trocar and allowing handling of the instrument from outside the chamber contacting the instrument indirect through the wall. The medical device may comprise at least one of; at least one flexible portion of the wall, such that a handling portion of the instrument can be manually handled through holding the handling portion on the outside of the flexible portion of the wall of the medical device, and at least one glove in the wall allowing the handling of the at least one instrument inside the chamber.

According to one embodiment, the medical device further comprises at least one of the following; at least one closable wall port or wall inset placed in the wall, and at least one closable body port or body inset placed in an incision in the body of the patient.

The medical device may further comprises at least one closable wall port or wall inset placed in the wall, and the at least one closable body port or body inset may be placed in the incision in the skin of the patient are adapted to be detachable interconnected to form an interconnected port or inset, when the surgical procedure is performed. The interconnected port may be a multiport adapted to enable transfer of at least one of a camera, and a surgical instrument. The interconnected inset may comprise a glove.

One of: the wall port, the body port, the wall inset, and the body inset may be adapted to be at least one of detached and replaced by a different type of port or inset, and an integrated part of an fluid sluice for allowing at least one of; a medical device, replacement tissue, or a part or tissue to be used inside the cavity to be introduced into the cavity from the outside environment of the chamber, and a part of the body or foreign part from inside the body to be to be taken out from the cavity.

According to one embodiment, the at least one trocar comprise a multiport adapted to have at least one of a camera and at least one surgical instrument introduced in separate trocar compartments into the cavity, when the surgical procedure is performed using endoscopic instruments, wherein the at least one trocar is an integrated part of an fluid sluice for allowing at least one of; a medical device, replacement tissue, or a part or tissue to be used inside the cavity to be introduced into the cavity from the outside environment of the chamber, and a part of the body or foreign part from inside the body to be to be taken out from the cavity.

A method of performing a combination of open and endoscopic surgery using a medical device is further provided. The medical device comprises a wall adapted to be inflated by a fluid for forming a chamber in which a sealed environment can be maintained for encompassing part of the surgical procedure to be performed. The method comprises fixating a portion of the wall of the medical device to the skin of the patient, making an incision in the skin of the patient inside or outside the chamber, placing a fluid inlet through the incision, supplying a fluid into the patient, thereby creating a cavity within the body of the patient, making one or more additional incision(s) in the wall of the medical device continuing through the skin of the patient, inserting a trocar in each of the one or more additional incision(s) made in the wall of the medical device, inserting at least one of; a camera and a surgical instrument, through one of the one or more trocar(s), performing at least one step of endoscopic surgery through the trocar(s), making a second incision in the wall of the medical device continuing through the skin of the patient, and at least one of: placing a closable body port, transferring a specimen from the cavity within the body of the patient to the chamber through the second incision, transferring an object from the chamber to the cavity within the body of the patient through the second incision.

The method may further comprise the step of suturing the incisions made in the skin of the patient from within the chamber of the medical device.

A medical device for performing a combination of open surgery and endoscopic surgery is provided. The medical device comprises a wall adapted to be inflated by a fluid for forming a chamber in which a sealed environment can be maintained for encompassing part of the surgical procedure to be performed. The medical device further comprises at least one endoscopic trocar positioned through the wall of the medical device and sealingly attached to the wall, such that a first portion of the trocar is positioned inside of the chamber, and a second portion of the trocar is positioned outside of the chamber of the medical device.

By having a trocar placed through the wall of the medical device, an endoscopic procedure can be performed in a cavity of the patient from within the chamber of the medical device.

According to one embodiment, the medical device further comprises a removable covering sheet, covering the second portion of the trocar, such that the second portion can be kept sterile prior to the insertion of the trocar.

According to one of the embodiments, the medical device further comprises at least one endoscopic instrument enclosed within the chamber and adapted to be used through the trocar. The endoscopic instrument may be an endoscopic grasper, an endoscopic claw grasper, an endoscopic stone grasper, an endoscopic needle holder, an endoscopic hook, a camera, scissors, a knife, an ultrasound dissector, a suction instrument, an endoscopic dissector, and an endoscopic diathermy instrument.

The medical device may comprise an adhesive surface adapted to contact the skin of the patient for fixating the medical device to the skin of the patient.

The medical device may further comprise at least one of a fluid inlet for supplying a fluid into the medical device and an adaptation for directly or indirectly receiving fluid from a fluid inlet placed in the patient's skin, for inflating at least one of; the chamber and a cavity in the patient's body, for performing the surgical procedure.

According to one embodiment may comprise a wall inset, comprising a glove enabling manual manipulation within the chamber of the medical device.

The medical device may further comprise a pressure source adapted to at least one of; supply a fluid having a pressure above atmospheric pressure to the sealed chamber of the medical device, and be enclosed in the chamber.

The medical device may further comprise a sealing device adapted to seal between the wall of the medical device and the patient's skin. The sealing device may comprise at least one of: a pressure sealing member adapted to seal against the skin of the patient by exerting a pressure on the skin of the patient, and a vacuum sealing member adapted to hold a pressure being less than atmospheric pressure thus creating a vacuum seal between the skin of the patient and the medical device.

The medical device may further comprise a camera enclosed within the chamber of the medical device. The camera may be adapted to be inserted through the trocar for enabling visual inspection within a cavity of the patient.

The medical device may be adapted for surgery on extremities of the patient. The medical device may comprise at least one of; a first opening arranged such that the leg of a patient can enter the medical device and a second opening arranged such that the leg of a patient can exit the medical device, such that the chamber is positioned between the first and second opening, and an elongated tubular enclosure extending within the chamber of the medical device formed by a part of the wall, contacting the skin of the patient and being adapted to separate the skin of the patient from the sterile environment of the chamber of the medical device.

The medical device may further comprise an energy transferring member and/or an information transferring member. The energy transferring member may be adapted to transfer hydraulic energy and/or pneumatic energy and/or kinetic energy and/or electric energy. The medical device may further comprise an energy consuming tool placed inside of the chamber of the medical device, wherein the energy consuming tool is adapted to be connected to the energy transferring member.

The medical device may further comprises an information transferring member comprises at least one of: an optical information transferring member, a capacitive information transferring member, an inductive information transferring member, a radio based information transferring member.

The medical device may be adapted to having the at least one endoscopic instrument enclosed within the chamber performing a surgical procedure through the at least one trocar and allowing handling of the instrument from outside the chamber contacting the instrument indirect through the wall. The medical device may comprise at least one of the following; at least one flexible portion of the wall, such that a handling portion of the instrument can be manually handled through holding the handling portion on the outside of the flexible portion of the wall of the medical device, and at least one glove in the wall allowing the handling of the at least one instrument inside the chamber.

The medical device may further comprise at least one of the following; at least one closable wall port or wall inset placed in the wall, and at least one closable body port or body inset placed in an incision in the body of the patient.

According to one embodiment, the medical device may further comprise at least one closable wall port or wall inset placed in the wall and at least one closable body port or body inset placed in the incision in the skin of the patient. The at least one closable wall port or wall inset may be adapted to be detachably interconnected to form an interconnected port or inset, when the surgical procedure is performed.

The interconnected port may be a multiport adapted to enable transfer of at least one of; a camera, and a surgical instrument. The interconnected inset may comprise a glove for enabling manipulation.

At least one of the wall port, the body port, the wall inset, and the body inset may be adapted to be detached and replaced by a different type of port or inset or be an integrated part of an fluid sluice for allowing at least one of a medical device, replacement tissue, or a part or tissue to be used inside the cavity to be introduced into the cavity from the outside environment of the chamber, and a part of the body or foreign part from inside the body to be to be taken out from the cavity.

The at least one trocar may comprise a multiport adapted to have at least one of; a camera and at least one surgical instrument to be introduced in separate trocar compartments into the cavity, when the surgical procedure is performed using endoscopic instruments, wherein the at least one trocar is an integrated part of an fluid sluice for allowing at least one of a medical device, replacement tissue, or a part or tissue to be used inside the cavity to be introduced into the cavity from the outside environment of the chamber, and a part of the body or foreign part from inside the body to be to be taken out from the cavity.

A method of performing endoscopic surgery using a medical device is further provided. The medical device comprises a wall adapted to be inflated by a fluid for forming a chamber in which a sealed environment can be maintained for encompassing part of the surgical procedure to be performed, and at least one endoscopic trocar positioned through the wall of the medical device, such that a first portion of the trocar is positioned inside of the chamber, and a second portion of the trocar is positioned outside of the chamber, the method comprising: creating an incision in the skin of the patient, inserting the endoscopic trocar through the incision in the skin of the patient into the body of the patient, fixating a portion of the wall of the medical device to the skin of the patient, supplying a fluid into the patient, thereby creating a cavity within the body of the patient, performing at least one step of endoscopic surgery through the trocar.

According to one embodiment of the method, the medical device comprises a closable body port integrated in the wall adapted to be placed in an incision in the skin, when the surgical procedure is performed. The method further comprises making a second incision through the skin of the patient, and at least one of: placing the closable body port in the incision, transferring a specimen from the cavity within the body of the patient to the chamber through the second incision, and transferring an object from the chamber to the cavity within the body of the patient through the second incision.

The method may further comprise the step of suturing the incisions made in the skin of the patient from within the chamber of the medical device.

A medical device for use in an endoscopic surgical procedure is provided. The medical device comprises a wall forming a chamber, wherein a portion of the wall is adapted to be fixated to the skin of the patient. The medical device further comprises an endoscopic instrument enclosed within the chamber, and a trocar, wherein the trocar is at least one of: enclosed within the chamber, and positioned sealingly through the wall of the medical device. By having a trocar extending from a chamber of the medical device to a cavity in the patient body, and endoscopic procedure can be performed in the body of the patient, from within the chamber of the medical device. The surgical instrument may comprise a handle portion operably encapsulated by the wall such that the handle portion can be manipulated from outside the chamber.

The wall may be flexible or elastic.

The medical device may comprise a wall inset, comprising a glove for enabling manual manipulation within the chamber of the medical device.

The portion of the wall adapted to be fixated to the skin of the patient may comprise at least one of: a vacuum sealing member adapted to seal between the wall of the medical device and the skin of the patient, and an adhesive surface adapted to adhere to the skin of the patient.

The trocar may comprise a pressure sealing member adapted to provide sealing by pressing on the surface of the skin of the patient.

According to one embodiment, wall may be adapted to hold a pressure exceeding atmospheric pressure.

The medical device may further comprise an evacuation valve for evacuating a fluid from the chamber. The evacuation valve may be connected to a filtering unit for filtering the evacuated fluid. The medical device may further comprise a control system for controlling the opening of the evacuation valve. The control system may be adapted to control the evacuation valve on the basis of at least one of: the pressure in the chamber, manual detection of the visibility in the chamber, the visibility in the chamber, detection of smoke in the chamber, the temperature in the chamber, and a time related variable.

The endoscopic instrument could for example be an endoscopic grasper an endoscopic claw grasper, an endoscopic stone grasper, an endoscopic needle holder, an endoscopic hook, a camera, scissors, a knife, an ultrasound dissector, a suction instrument, an endoscopic dissector, and an endoscopic diathermy instrument.

A method of performing an endoscopic surgical procedure on a patient using a medical device is further provided. The medical device comprises a wall enclosing a chamber in which a sealed environment can be maintained, in which an endoscopic instrument is enclosed. The method comprising: creating an incision in the skin of the patient, placing a second portion of a trocar through the incision into a cavity of the patient's body, wherein the first portion of the trocar is positioned inside the chamber of the medical device, such that a fluid connection is created between the chamber of the medical device and a cavity in the body of the patient, placing the endoscopic instrument through the trocar into the cavity of the patient, using the endoscopic instrument in a step of the endoscopic surgical procedure by manipulating a handle portion of the endoscopic instrument from the outside of the wall of the medical device.

The method may further comprise opening an evacuation valve in the wall of the medical device for evacuating a fluid from the chamber of the medical device.

A trocar for performing an endoscopic procedure in a cavity in a patient's body is provided. The trocar comprises a first seal within the trocar adapted to seal between the cavity in the body of the patient and the ambient environment, when the trocar is placed through the skin of the patient during the surgical procedure, and a second seal sealingly connected around the trocar and adapted to engage the surface of the skin of the patient for further sealing against the skin of the patient.

The seal for example enables the trocar to be inserted into the body of the patient in a sealed environment.

The second seal may comprise an adhesive portion adapted to be placed in contact with the skin of the patient for sealing against the skin of the patient.

The second seal may comprise a vacuum sealing member adapted to hold a pressure less than atmospheric pressure such that a vacuum seal is created between the skin of the patient and the vacuum sealing member, or a pressure sealing member adapted to provide sealing by pressing against the surface of the skin of the patient. The pressure sealing member may be adapted to press against the skin or tissue of the patient from within the cavity of the patient, in a direction substantially parallel to the elongation of the trocar.

According to one embodiment, the trocar further comprises a pressure sealing device comprising an inflatable pressure sealing member adapted to be inflated by a fluid.

According to one embodiment, the inflatable pressure sealing member is shaped such that when inflated, a first sealing chamber is formed on the outside skin of the patient and a second sealing chamber is formed inside the cavity of the patient, such that fluid in the first sealing chamber indirectly presses on the skin of the patient and the fluid in the second sealing chamber indirectly presses on the skin and or tissue of the patient from within the cavity of the patient.

According to one embodiment, the trocar comprises a trocar connecting portion adapted to engage a device connecting portion of a medical device. The medical device comprises a wall enclosing a chamber connected to the device connection portion, the chamber containing an endoscopic instrument, such that the endoscopic instrument can be inserted into the cavity of the patient through the trocar when the trocar and the medical device is connected.

The connecting portion may comprise a recess or protruding member adapted to engage a corresponding recess or protruding member of the connecting portion of the medical device.

The first seal may comprise a first self sealing membrane.

According to one embodiment, the first self sealing membrane may be positioned at the first connecting portion of the trocar, such that the self sealing membrane is abutting a second self sealing membrane of the medical device when the medical device and the trocar are connected, such that an integrated self sealing membrane is formed enabling insertion of the endoscopic instrument, contained in the medical device, into the trocar through the integrated self sealing membrane.

A medical device for use in an endoscopic surgical procedure is further provided. The medical device comprises a flexible wall enclosing a chamber. The medical device further comprises a device connecting portion positioned in the flexible wall and adapted to connect to a trocar connecting portion of a trocar, such that a fluid connection is created between the chamber enclosed by the wall, and a cavity within the patient.

The medical device may further comprise a surgical instrument enclosed within the chamber and adapted to operate within the cavity of the patient through the trocar.

The surgical instrument may comprise a handle portion. The handle portion may be operably encapsulated by the wall such that the handle portion can be manipulated from outside the chamber.

According to one embodiment, the medical device comprises a penetrable second self sealing membrane adapted to seal between the chamber and the ambient environment.

The second self sealing membrane may be positioned at the device connecting portion of the medical device, such that the self sealing membrane is abutting a first self sealing membrane of the trocar when the medical device and the trocar are connected, such that an integrated self sealing membrane is formed enabling insertion of the endoscopic instrument, contained in the medical device, into the trocar through the integrated self sealing membrane.

The second connecting portion may comprise a sleeve adapted to connect to the first connecting portion of the trocar by one of: engaging the trocar on the outside thereof, and engaging the trocar on the inside thereof. The sleeve may comprise a sealing member for sealing between the sleeve and the trocar.

The device connecting portion of the medical device may comprise a recess or protruding member adapted to engage a corresponding recess or protruding member of the trocar connecting portion.

The flexible wall of the medical device may be is elastic.

The wall of the medical device may be adapted to hold a pressure exceeding atmospheric pressure in the chamber.

The medical device may comprise an evacuation valve for evacuating a fluid from the chamber. The evacuation valve may be connected to a filtering unit for filtering the evacuated fluid.

The medical device may further comprise a control system for controlling the opening of the evacuation valve, wherein the control system is adapted to control the evacuation valve on the basis of at least one of: the pressure in the chamber, manual visibility in the chamber, the visibility in the chamber, detection of smoke in the chamber, the temperature in the chamber, and a time related variable.

A medical device system for performing endoscopic surgery on a patient is further provided. The medical device system comprises a medical device comprising a flexible wall enclosing a chamber. The medical device further comprises a device connecting portion positioned in the flexible wall, and a trocar adapted to be positioned though the skin of the patient for establishing a fluid connection with a cavity within the patient, wherein the trocar comprises a trocar connecting portion. The device connecting portion of the medical device may be adapted to be connected to the trocar connecting portion of the trocar for establishing a fluid connection between the chamber of the medical device and the cavity in the patient.

According to one embodiment, the device connecting portion of the medical device comprises a sleeve adapted to connect to the trocar connecting portion of the trocar by one of: engaging the trocar on the outside thereof, and engaging the trocar on the inside thereof. At least one of the sleeve and the trocar may comprise a sealing member for sealing between the sleeve and the trocar.

The device connecting portion may comprise a recess or protruding member. The trocar connecting portion of the trocar may comprises a recess or protruding member, the protruding member may be adapted to engage the recess for connecting the connecting portion of the medical device to the connecting portion of the trocar.

According to one embodiment, the device connecting portion comprises a penetrable second self sealing membrane. The connecting portion of the trocar comprises a penetrable first self sealing membrane, and the self sealing membrane of the medical device is abutting the self sealing membrane of the trocar when the medical device and the trocar are connected, such that an integrated self sealing membrane is formed enabling insertion of an endoscopic instrument from the chamber of the medical device to the cavity in the patient's body through the integrated self sealing membrane.

The medical device may further comprise a surgical instrument enclosed within the chamber and adapted to operate within the cavity of the patient through the trocar. The surgical instrument may comprise a handle portion, and the handle portion may be operably encapsulated by the wall, such that the handle portion can be manipulated from outside the chamber.

An endoscopic surgical method of performing an endoscopic procedure in a cavity in a patient's body is further provided. The method comprises: placing a trocar through the skin of a patient, the trocar having a first sealing device within the trocar adapted to seal between the cavity in the body of the patient and the ambient environment and placing a second sealing device against the surface of the skin, the second sealing being sealingly connected to the trocar and adapted to engage the surface of the skin of the patient for further sealing against the skin of the patient, and performing an endoscopic procedure in the cavity of the patient through the trocar.

A medical device for a surgical procedure is provided. The medical device comprises a wall adapted to: form a chamber together with or without the patient's body, and at least partly to be placed on the patient's skin, the chamber being adapted to encompass a surgical incision in the skin of the patient in fluid connection with a cavity in the patient's body, while maintaining a sealed environment for the surgical procedure. The medical device further comprises a sealing device connected to the wall and adapted to seal between the wall and the skin or tissue of the patient to seal the chamber, and at least one evacuation valve for evacuating a fluid from the chamber, when performing a laparoscopic, open or both laparoscopic and open surgical procedure, at least one of; a fluid inlet adapted to injecting a fluid directly into the chamber, and an adaptation to indirect receive fluid from an inlet placed in the patient's skin, for inflating at least one of; the chamber and the cavity in the patient's body.

A medical device for performing an endoscopic surgical procedure is further provided. The medical device comprises a wall forming a chamber. A portion of the wall is adapted to be fixated to the skin (S) of the patient, the medical device further comprises at least three of the following: an endoscopic instrument enclosed within the chamber, a trocar enclosed within the chamber or positioned sealingly through the wall of the medical device, an evacuation valve for evacuating a fluid from the chamber, and a closable wall port or inset, and a closable body port or inset, for performing an endoscopic, open or both endoscopic and open surgical procedure.

According to one embodiment, the evacuation valve is connected to a filter for filtering the evacuated fluid.

According to one embodiment, the medical device further comprises a control system for controlling the opening of the evacuation valve. The control system is adapted to control the evacuation valve on the basis of at least one of: the pressure in the chamber, manually detected visibility in the chamber, the visibility in the chamber, detection of smoke in the chamber, the temperature in the chamber, and a time related variable.

The wall of the medical device may be adapted to hold a pressure exceeding atmospheric pressure.

The medical device may further comprise a sealing device comprises at least one of: a pressure sealing member adapted to seal against the skin of the patient by exerting a pressure on the skin of the patient, and a vacuum sealing member adapted to hold a pressure being less than atmospheric pressure thus creating a vacuum seal between the skin of the patient and the medical device.

According to one embodiment, the wall of the medical device comprises a transparent layer enabling viewing into the chamber of the medical device.

The wall of the medical device may further comprise an adhesive surface adapted to provide at least one of: fixation of the wall to the skin of the patient and sealing between the wall and the skin of patient.

According to one embodiment, the wall of the medical device comprises a closeable wall port adapted to enable transfer of objects from the chamber of the medical device to the ambient environment and vice versa.

A method of performing a surgical procedure on a patient using a medical device is further provided. The method comprising applying a wall on the skin of the patient to form a chamber, in which a sealed environment can be maintained for encompassing part of the surgical procedure to be performed, applying a sealing device against the skin of the patient for sealing between the wall and the skin of the patient, inflating at least one of a cavity of the patient and the chamber of the medical device with a fluid, creating an incision (I) in the skin of the patient, in the sealed environment, such that a fluid connection between the cavity in the patient and the chamber is created, performing a step of the surgical procedure in the cavity of the patient, and opening an evacuation valve in the wall of the medical device for evacuating a fluid from the chamber.

A medical device for performing knee joint surgery on a patient is provided. The medical device comprising a wall adapted to form a chamber adapted to encapsulate an area in connection with the knee joint of the patient. The chamber being adapted to encompass part of the knee joint surgery to be performed while maintaining a sterile environment. The medical device further comprising a closeable wall port placed in a portion of the wall, wherein the closeable wall port comprises a connecting member for connecting the closeable wall port to a body port placed in an incision in the knee region of the patient, such that the chamber can encompass part of the surgical procedure when the wall and body ports are disconnected and the arthroscopic instruments may be moved whilst performing the knee joint procedure when the body port and wall ports are connected, enabling a combination of an open surgical procedure and an arthroscopic procedure to be performed.

A medical device for assisting in performing a surgical procedure is further provided. The medical device comprises a flexible wall, and an interconnectable port comprising; a first port, a second coupling adapted be interconnected with the first port to form the interconnectable port, wherein the second coupling is disconnectable from the first port. The first port is connected to a first portion of the flexible wall, the second coupling is connected to a second portion of the flexible wall, the flexible wall is adapted to form a chamber together with the first port and the second coupling, the second coupling having a closable opening, the chamber is adapted to allow communication through the coupling into a cavity inside the patient's body, when a surgical procedure is performed, the first port in a first position is adapted to connect to the second coupling in close relation to the patients skin, wherein the chamber having a first smaller volume, and the first port in a second position is adapted to be disconnected from the second coupling, being separated from the coupling in a more remote position in relation to the patients skin, wherein the chamber having a second larger volume, and the medical device further comprising a sealing device, adapted to be placed in connection with at least one of; the flexible wall and the second coupling, to seal between the medical device and the skin or tissue of the patient, to seal the combined volume of the chamber and the body cavity to the outer environment, when the second coupling is open.

According to one embodiment, the first port forms a closable wall port when disconnected from the second coupling.

According to one embodiment, the second coupling forms a closable body port by itself when the first port has been disconnected from the second coupling.

According to one embodiment, the chamber has a first volume when the first port and the second coupling are interconnected and a second volume when the second coupling is disconnected from the first port.

According to one embodiment, the second volume is larger than the first volume. The first volume may be smaller than 100 000 mm3, and the second volume may be larger than 500 000 mm3.

The flexible wall may comprise a pleated portion such that the flexible wall can be expanded.

According to one embodiment, the medical device further comprises a first coupling, and the first port may be connected to the second coupling, and the second coupling may be connected to the first coupling.

According to one embodiment, at least one of the first and second couplings comprises protruding members, and at least one of the first and second couplings comprises a recess, and wherein, the protruding member is adapted to engage the recess for locking the first coupling to the second coupling.

According to one embodiment, the recess is a groove in at least one of the first and second coupling.

According to one embodiment, the chamber formed by the flexible wall is adapted to hold a pressure exceeding atmospheric pressure.

The interconnectable port may be adapted to: in a first state, when the first port and second coupling are interconnected, enable a surgeon to operate through the interconnected interconnectable port, and in a second state, when the second coupling is disconnected from the first port enable the surgeon to perform steps of the procedure within the chamber formed by the flexible wall between the first port and second coupling of the interconnectable port.

The interconnectable port may be adapted to, in the second state, enable the surgeon to remove a specimen from the body of the patient through the second coupling and into the chamber, and to perform one of: placing the specimen within the chamber, and removing the specimen from the chamber through the first port.

According to one embodiment, the chamber further comprises a pouch for holding the specimen within the chamber. The pouch may be possible to close for creating a pouch-chamber within the chamber for isolating the removed specimen within the chamber.

According to one embodiment, the medical device comprises a second port adapted to also be placed in the second coupling, wherein at least one of the first port, the second port and a first coupling are adapted to be reconnected after having been disconnected, such that the surgeon can continue operating through the interconnected port after the specimen has been removed.

According to one embodiment, the medical device further comprises an inset detachably fixated to at least one of the first and second coupling, such that the inset could be detached and replaced by a different inset. The insets may be a surgical glove or a device or instrument mount.

According to one embodiment, the medical device comprises a second port adapted to be placed in the second coupling. The first and second port may comprise an elastic or flexible membrane adapted to, in a non-compressed state, provide sealing, and in a compressed state enable a hand or an object to be inserted through the membrane.

The first port may comprise an first elastic or flexible membrane and the second port may comprise a second elastic or flexible membrane. The first and second membranes may be adapted to be placed tightly together such that they act as a single elastic or flexible membrane adapted to, in a non-compressed state, provide sealing, and in a compressed state enable a hand or an object to be inserted through the membrane. The first and second membranes may comprise a plurality of self sealing holes enabling insertion of instruments through the membranes.

According to one embodiment, at least one of said first port and second port comprises a penetrable self sealing gel, such that an object or hand can be inserted through the interconnectable port while maintaining a seal.

According to one embodiment, the first port comprises a first penetrable self sealing gel and the second port comprises a second penetrable self sealing gel. The first and second penetrable self sealing gels may be adapted to be placed tightly together such that they act as a single penetrable self sealing gel adapted to, in a non-compressed state, provide sealing, and in a compressed state enable a hand or an object to be inserted through the self sealing gel while maintaining the seal.

The wall of the medical device may further comprise a fluid inlet for inflating the chamber with a fluid.

According to one embodiment, the medical device further comprises a fluid outlet provided in the wall for discharging the fluid from the chamber.

The medical device may further comprise a pump adapted to circulate the fluid from the outlet member to the inlet member.

The first port and second coupling may comprise a non-penetrable valve such that the chamber is sealed from at least one of the ambient environment and a cavity in the patient.

The medical device may comprises at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

The second coupling of the medical device may further be adapted to allow passage of a hand into the body cavity. The second coupling may form an opening, when the first port has been disconnected from the second coupling.

According to one embodiment, the second coupling comprises a detachable second inset.

The medical device may further comprise a first port comprises a detachable third inset.

According to one embodiment, the second coupling forms an opening, when the first port has been disconnected from the second coupling. The second inset may be adapted to close between the body cavity and the chamber.

According to one embodiment, the third port comprising a detachable third inset.

The second coupling may comprise a body port being a detachable part of the second coupling.

The first port may be a multiport comprising two or more individual ports, and the coupling may be adapted to connect to the multiport to together form an integrated multiport placed in close relation to the skin.

The body port may be a multiport comprising two or more individual ports, and the body port may be adapted to connect to the first port being a multiport, to together form an integrated multiport placed in close relation to the skin.

A surgical method to be performed on the body of a patient using an interconnectable port is further provided. The medical device comprising a first port and a second coupling. The method comprising: creating an incision in the skin of the patient, connecting to a body cavity, placing the interconnectable port in the incision, disconnecting the first port from the second coupling, such that a chamber is formed by a wall connected to the first port and second coupling, and performing a step of the surgical procedure within at least one of the body cavity and the chamber.

The method may further comprise the steps of: placing a sealing device in connection with at least one of; the flexible wall and the second coupling, to seal between the medical device and the skin or tissue of the patient, and sealing the combined volume of the chamber and the body cavity to the outer environment, when the second coupling is open.

The step of performing a step of the surgical procedure within the chamber may comprise: removing a specimen from the cavity in the body of the patient, transferring the specimen through the second coupling, and placing the specimen within the chamber of the medical device.

The method may further comprise the steps of: reconnecting the first port and second coupling such that the interconnectable port is formed, and performing a surgical step in a cavity of the patient, through the interconnectable port.

A medical device for assisting in performing a surgical procedure is provided. The medical device comprises a first flexible wall, and an interconnectable port, comprising; a first port, and a second coupling adapted be interconnected with the first port to form the interconnectable port, wherein the second coupling is disconnectable from the first port. The first port may be connected to a first portion of the first flexible wall, the second coupling may be connected to a second portion of the first flexible wall, the first flexible wall is adapted to form a chamber together with the first port and the second coupling, the second coupling having a closable opening. The chamber is adapted to allow communication through the second coupling into a cavity inside the patient's body, when an incision has been performed in the patient's skin and a surgical procedure is performed, the first port in a first position is adapted to connect to the second coupling in close relation to the patients skin, wherein the chamber having a first smaller volume, and the first port in a second position is adapted to be disconnected from the second coupling, being separated from the coupling in a more remote position in relation to the patients skin, wherein the chamber has a second larger volume. The medical device further comprises a sealing device comprising a flexible connecting member, a first sealing member, adapted to be positioned at the inside of the patient's skin around an incision to be performed in the skin and being sealingly connected to the flexible connecting member, and a second sealing member sealingly connected to at least one of; the first flexible wall, the flexible connecting member, and the second coupling or being an integrated part of the second coupling, adapted to be positioned at the outside of the patient's skin around the incision.

The flexible connecting member is sealingly interconnecting the first and second sealing members, whereby the first and second sealing members are adapted to be larger than the incision to seal between at least one of: the second sealing member and the skin or tissue of the patient, and the first sealing member and tissue of the patient, and the flexible connecting member is adapted to be placed sealingly in connection with at least one of the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.

According to one embodiment, the first port forms a closable wall port when disconnected from the second coupling.

According to one embodiment, the second coupling forms a closable body port by itself when the first port has been disconnected from the second coupling.

According to one embodiment, the chamber has a first volume when the first port and second coupling are interconnected and a second volume when the second coupling is disconnected from the first port.

According to one embodiment, the second volume is larger than the first volume. The first volume may be smaller than 100 000 mm3, and the second volume may be larger than 500 000 mm3.

The flexible wall may comprise a pleated portion such that the flexible wall can be expanded.

The medical device may further comprise a first coupling, and the first port may be connected to the first coupling, and the first coupling may be adapted to be connected to the second coupling.

At least one of the first and second coupling may comprise a protruding member, and at least one of the first and second coupling may comprise a recess, and the protruding member may be adapted to engage the recess for locking the first coupling to the second coupling.

According to one embodiment, the recess could be a groove in at least one of the first and second coupling.

The interconnectable port may be adapted to: in a first state, when the first port and second coupling are interconnected, enable a surgeon to operate through the interconnected interconnectable port, and in a second state, when the second coupling is disconnected from the first port enable the surgeon to perform steps of the procedure within the chamber formed by the flexible wall between the first port and second coupling of the interconnectable port.

The interconnectable port may be adapted to, in the second state, enable the surgeon to remove a specimen from the body of the patient through the second coupling and into the chamber, and to perform one of: placing the specimen within the chamber, and removing the specimen from the chamber through the first port.

According to one embodiment, the chamber further comprises a pouch for holding the specimen within the chamber.

The pouch may be closed for creating a pouch-chamber within the chamber for isolating the removed specimen within the chamber.

According to one embodiment, the medical device further comprises a second port adapted to also be placed in the second coupling. At least one of the first port, the second port and a first coupling may be adapted to be reconnected after having been disconnected, such that the surgeon can continue operating through the interconnected port after the specimen has been removed.

According to one embodiment, the medical device further comprises an inset detachably fixated to at least one of the first and second coupling, such that the inset could be detached and replaced by a different inset.

According to one embodiment, the inset may comprise at least one of: a surgical glove and a device or instrument mount.

The medical device may further comprise a second port adapted to be placed in the first coupling. At least one of the first and second ports may comprise an elastic or flexible membrane adapted to, in a non-compressed state, provide sealing, and in a compressed state enable a hand or an object to be inserted through the membrane.

The first port may comprise a first elastic or flexible membrane and the second port may comprise a second elastic or flexible membrane. The first and second membranes may be adapted to be placed tightly together such that they act as a single elastic or flexible membrane adapted to, in a non-compressed state, provide sealing, and in a compressed state enable a hand or an object to be inserted through the membrane.

According to one embodiment, the first and second membranes may comprise a plurality of self sealing holes enabling insertion of instruments through the membranes.

According to one embodiment, at least one of said first port and second port may comprise a penetrable self sealing gel, such that an object or hand can be inserted through the interconnectable port while maintaining a seal.

The first port may comprise a first penetrable self sealing gel and the second port may comprise a second penetrable self sealing gel, and the first and second penetrable self sealing gels may be adapted to be placed tightly together such that they act as a single penetrable self sealing gel adapted to, in a non-compressed state, provide sealing, and in a compressed state enable a hand or an object to be inserted through the self sealing gel while maintaining the seal.

According to one embodiment, the wall may comprise a fluid inlet for inflating the chamber with a fluid, and/or a fluid outlet provided in the wall for discharging the fluid from the chamber.

The medical device may further comprise a pump adapted to circulate the fluid from the outlet member to the inlet member.

According to one embodiment, at least one of the first port and second couplings may comprise a non-penetrable valve such that the chamber is sealed from at least one of the ambient environment and a cavity in the patient.

The medical device may further comprise a vacuum seal adapted to hold a pressure less than atmospheric pressure between the interconnectable port and the patient's skin to seal between the interconnectable port and the patient's skin, and/or a pressure seal adapted to hold a pressure above atmospheric pressure between the interconnectable port and the patient's skin to seal between the interconnectable port and the patient's skin.

According to one embodiment, the second coupling is adapted to allow passage of a hand into the body cavity, and the second coupling may form an opening, when the first port has been disconnected from the second coupling.

According to one embodiment, the second coupling may comprise a detachable second inset, and the first port may comprise a detachable third inset.

According to one embodiment, the second inset may be adapted to close between the body cavity and the chamber.

According to one embodiment, the medical device may comprise a third port comprising a detachable third inset.

The second coupling may comprise a body port being a detachable part of the second coupling.

The first port may be a multiport comprising two or more individual ports, wherein the coupling being adapted to connect to the multiport to together form an integrated multiport placed in close relation to the skin.

The body port may be a multiport comprising two or more individual ports, and the body port may be adapted to connect to the first port being a multiport, to together form an integrated multiport placed in close relation to the skin.

A surgical method to be performed on the body of a patient is further provide. The method comprising: creating an incision in the skin of the patient, connecting to a body cavity, placing the sealing device with its flexible connecting member through the incision, positioning the first sealing member, at the inside of the patient's skin around the incision being sealingly connected to the flexible connecting member, positioning the second sealing member at the outside of the patient's skin around the incision, placing the interconnectable port in the incision, disconnecting the first port from the second port, such that a chamber is formed by a wall connected to the first and second port, sealing by the second sealing member towards the skin or tissue of the patient, sealing by the first sealing member towards tissue of the patient, and performing a step of the surgical procedure within at least one of; the chamber and the body cavity.

According to one embodiment, the step of performing a step of the surgical procedure within the chamber comprises: removing a specimen from the cavity in the body of the patient, transferring the specimen through the first port, and placing the specimen within the chamber of the medical device.

The surgical method may further comprise: reconnecting the first port and second coupling such that the interconnectable port is formed, performing a surgical step in a cavity of the patient, through the interconnectable port.

A medical device for assisting in performing a surgical procedure is provided. The medical device comprises a first flexible wall, and an interconnectable port comprising; a first port, and a second coupling adapted be interconnected with the first port to form the interconnectable port, wherein the second coupling is disconnectable from the first port. The first port is connected to a first portion of the first flexible wall, the second coupling is connected to a second portion of the first flexible wall, the first flexible wall is adapted to form a chamber together with the first port and the second coupling, the second coupling having a closable opening. The chamber is adapted to allow communication through the second coupling into a cavity inside the patient's body, when an incision has been performed in the patient's skin and a surgical procedure is performed, the first port in a first position is adapted to connect to the second coupling in close relation to the patient's skin. The chamber has a first smaller volume, and the first port in a second position is adapted to be disconnected from the second coupling, being separated from the second coupling in a more remote position in relation to the patients skin, wherein the chamber having a second larger volume. The medical device further comprises a retracting system, comprising a flexible connecting member, a inside retracting member, adapted to be positioned at the inside of the patient's skin around an incision to be performed in the skin and being connected to the flexible connecting member, and an outside retracting member connected to at least one of; the first flexible wall, the flexible connecting member, and the second coupling or being an integrated part of the second coupling, adapted to be positioned at the outside of the patient's skin around the incision. The flexible connecting member is interconnecting the inside and outside retracting members, whereby the inside and outside retracting members are adapted to be larger than the incision allowing the flexible connecting member to retract the skin and tissue in the incision opening substantially parallel to the skin. The flexible connecting member is adapted to be placed in connection with at least one of; the first flexible wall and the second coupling or is an integrated part of the first flexible wall, adapted to be placed through the incision into the body cavity. The flexible connecting member is adapted to together with the inside and outside retracting members retracting substantially parallel to the skin, the skin and tissue in close relation to the incision, to enlarge the incision passage from the chamber into the body cavity, during the surgical procedure.

According to one embodiment, the first port forms a closable wall port when disconnected from the second coupling.

According to one embodiment, the second coupling forms a closable body port by itself when the first port has been disconnected from the second coupling.

According to one embodiment, the chamber has a first volume when the first port and second coupling are interconnected and a second volume when the second coupling is disconnected from the first port.

According to one embodiment, the second volume is larger than the first volume.

The first volume may be smaller than 100 000 mm3, and the second volume may be larger than 500 000 mm3.

The medical device may comprise a first coupling. The first port may be connected to the second coupling, and the second coupling may be adapted to be connected to the first coupling.

The first and/or second coupling may comprise a protruding member, and at least one of the first and second coupling may comprise a recess, and, the protruding member may be adapted to engage the recess for locking the first coupling to the second coupling. The recess may be a groove in at least one of the first and second coupling.

According to one embodiment, the chamber formed by the flexible wall is adapted to hold a pressure exceeding atmospheric pressure.

According to one embodiment, the interconnectable port may be adapted to: in a first state, when the first port and second coupling are interconnected, enable a surgeon to operate through the interconnected interconnectable port, and in a second state, when the second coupling is disconnected from the first port enable the surgeon to perform steps of the procedure within the chamber formed by the flexible wall between the first port and second coupling of the interconnectable port.

The interconnectable port may be adapted to, in the second state, enable the surgeon to remove a specimen from the body of the patient through the second coupling and into the chamber, and to perform one of: placing the specimen within the chamber, and removing the specimen from the chamber through the first port.

The medical device may further comprise a second port adapted to also be placed in the second coupling. At least one of the first port, the second port and a first coupling may be adapted to be reconnected after having been disconnected, such that the surgeon can continue operating through the interconnected port after the specimen has been removed.

The medical device may further comprise an inset detachably fixated to at least one of the first and second coupling, such that the inset could be detached and replaced by a different inset. The inset may comprise at least one of: a surgical glove and a device or instrument mount.

According to one embodiment, the medical device comprises a second port adapted to be placed in the second coupling. At least one of the first and second ports may comprise an elastic or flexible membrane adapted to, in a non-compressed state, provide sealing, and in a compressed state enable a hand or an object to be inserted through the membrane.

The medical device may further comprise a first elastic or flexible membrane and the second port may comprise a second elastic or flexible membrane. The first and second membranes may be adapted to be placed tightly together such that they act as a single elastic or flexible membrane adapted to, in a non-compressed state, provide sealing, and in a compressed state enable a hand or an object to be inserted through the membrane.

The first and second membranes may comprise a plurality of self sealing holes enabling insertion of instruments through the membranes.

At least one of the first port and second coupling may comprise a non-penetrable valve such that the chamber is sealed from at least one of the ambient environment and a cavity in the patient.

The medical device may further comprise at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

The port may further comprise a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: the port and the skin of the patient, and the first sealing member and tissue of the patient.

The coupling may in any of the embodiments be adapted to allow passage of a hand into the body cavity.

According to one embodiment, the coupling forms an opening, when the first port has been disconnected from the coupling.

According to one embodiment, the inside retracting member is sealingly connected to the flexible connecting member and the outside retracting member is sealingly connected to at least one of the first flexible wall, the flexible connecting member, and the second coupling or being an integrated part of the second coupling, wherein the flexible connecting member is sealingly direct or indirect interconnecting the inside and outside retracting members, adapted to be placed sealingly in connection with at least one of; the first flexible wall and the second coupling or being an integrated part of the first flexible wall.

The second coupling may comprise a body port being a detachable part of the second coupling. The first port may be a multiport comprising two or more individual ports. The coupling may be adapted to connect to the multiport to together form an integrated multiport placed in close relation to the skin.

The body port may be a multiport comprising two or more individual ports. The body port may be adapted to connect to the first port being a multiport, to together form an integrated multiport placed in close relation to the skin.

The second coupling may comprise a detachable second inset, the first port may comprise a detachable third inset.

The second inset may be adapted to close between the body cavity and the chamber.

According to one embodiment, the medical device further comprises a third port comprising a detachable third inset.

A surgical method to be performed on the body of a patient using a medical device is further provided. The medical device comprises a retracting system and an interconnectable port having a first port and a second coupling. The retracting system includes a flexible connecting member and a inside and outside retracting member. The method comprises: creating an incision in the skin of the patient, connecting to a body cavity, placing the retracting system with its flexible connecting member through the incision, positioning the inside retracting member, at the inside of the patient's skin around the incision being sealingly connected to the flexible connecting member, positioning the outside retracting member at the outside of the patient's skin around the incision, placing the interconnectable port in the incision, disconnecting the first port from the second port, such that a chamber is formed by a wall connected to the first and second port, retracting the incision and enlarging the opening by the flexible connecting member placed onto the inside and outside retracting members, retracting substantially parallel to the skin, the skin and tissue in close relation to the incision, to enlarge the incision passage from the chamber into the body cavity, during the surgical procedure, and performing a step of the surgical procedure within at least one of; the chamber and the body cavity.

The step of performing a step of the surgical procedure within the chamber may comprise: removing a specimen from the cavity in the body of the patient, transferring the specimen through the second port, and placing the specimen within the chamber of the medical device.

The surgical method may further comprise: reconnecting the first port and second coupling such that the interconnectable port is formed and performing a surgical step in a cavity of the patient, through the interconnectable port.

A medical device for assisting in performing a surgical procedure is provided. The medical device comprised a flexible wall, a first a first inset, and an interconnectable port. The interconnectable port comprises a first port, a second coupling adapted be interconnected with at least one of the first port to form the interconnectable port, and the first inset, wherein the second coupling is disconnectable from the first port or first inset. The first port is connected to a first portion of the flexible wall, the first inset is connected to a third portion of the flexible wall, the second coupling is connected to a second portion of the flexible wall, the flexible wall is adapted to form a chamber together with the first port, first inset and the second coupling, the second coupling having a closable opening, the chamber is adapted to allow communication through the coupling into a cavity inside the patient's body, after an incision has been made in the skin of the patient, when a surgical procedure is performed. At least one of; the first port and first inset in a first position is adapted to connect to the second coupling in close relation to the patients skin, wherein the chamber having a first smaller volume. At least one of; the first port and first inset in a second position is adapted to be disconnected from the second coupling, being separated from the coupling in a more remote position in relation to the patients skin, wherein the chamber having a second larger volume.

According to one embodiment, the first port forms a closable wall port when disconnected from the second coupling.

According to one embodiment, the second coupling forms a closable body port by itself when the first port has been disconnected from the second coupling.

The first volume may be smaller than 100 000 mm3, and the second volume may be larger than 500 000 mm3.

The medical device may further comprise a first coupling, the first port may be connected to the second coupling, and the second coupling may be adapted to be connected to the first coupling.

The first or second coupling may comprise a protruding member, and at least one of the first and second coupling may comprise a recess, the protruding member is adapted to engage the recess for locking the first coupling to the second coupling. The recess may be a groove in at least one of the first and second coupling.

The chamber may be adapted to hold a pressure exceeding atmospheric pressure.

According to one embodiment, the interconnectable port is adapted to: in a first state, when the first port and second coupling are interconnected, enable a surgeon to operate through the interconnected interconnectable port, and in a second state, when the second coupling is disconnected from the first port enable the surgeon to perform steps of the procedure within the chamber formed by the flexible wall between the first port and second coupling of the interconnectable port.

The interconnectable port may be adapted to, in the second state, enable the surgeon to remove a specimen from the body of the patient through the second coupling and into the chamber, and to perform one of: placing the specimen within the chamber, and removing the specimen from the chamber through the first port.

The chamber of the medical device may further comprise a pouch for holding the specimen within the chamber.

According to one embodiment, the pouch may be closed for creating a pouch-chamber within the chamber for isolating the removed specimen within the chamber.

The medical device may further comprise a second port adapted to also be placed in the second coupling. At least one of the first port, the second port and a first coupling may be adapted to be reconnected after having been disconnected, such that the surgeon can continue operating through the interconnected port after the specimen has been removed.

The inset may be detachably fixated to at least one of the first and second coupling, such that the inset could be detached and replaced by a different inset.

According to one embodiment, the medical device further comprises a sealing device comprising: a flexible connecting member, a first sealing member, adapted to be positioned at the inside of the patient's skin around an incision to be performed in the skin and being sealingly connected to the flexible connecting member, and a second sealing member sealingly connected to at least one of the first flexible wall, the flexible connecting member, and the second coupling or being an integrated part of the second coupling, adapted to be positioned at the outside of the patient's skin around the incision. The flexible connecting member may sealingly interconnecting the first and second sealing members, the first and second sealing members may be larger than the incision to seal between at least one of: the second sealing member and the skin or tissue of the patient, and the first sealing member and tissue of the patient. The flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.

The medical device may further comprise a second port adapted to be placed in the second coupling. At least one of the first and second port may comprise an elastic or flexible membrane adapted to, in a non-compressed state, provide sealing, and in a compressed state enable a hand or an object to be inserted through the membrane.

According to one embodiment, the first port may comprise a first elastic or flexible membrane, and the second port may comprise a second elastic or flexible membrane. The first and second membranes may be adapted to be placed tightly together such that they act as According to one embodiment, a single elastic or flexible membrane adapted to, in a non-compressed state, provide sealing, and in a compressed state enable a hand or an object to be inserted through the membrane.

The first and second membranes may comprise a plurality of self sealing holes enabling insertion of instruments through the membranes.

At least one of said first and second ports may comprise a penetrable self sealing gel, such that an object or hand can be inserted through the interconnectable port while maintaining a seal.

The first port may comprise a first penetrable self sealing gel, and the second port may comprise a second penetrable self sealing gel. The first and second penetrable self sealing gels may be adapted to be placed tightly together such that they act as a single penetrable self sealing gel adapted to, in a non-compressed state, provide sealing, and in a compressed state enable a hand or an object to be inserted through the self sealing gel while maintaining the seal.

At least one of the first port and second coupling may comprise a non-penetrable valve such that the chamber is sealed from at least one of the ambient environment and a cavity in the patient.

According to one embodiment, the medical device further comprises at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

According to one embodiment, the port further comprises a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the port and the skin of the patient, and (b) the first sealing member and tissue of the patient.

The second coupling may be adapted to allow passage of a hand into the body cavity.

The second coupling may form an opening, when the first port has been disconnected from the second coupling.

According to one embodiment, the medical device further comprises a retracting system, comprising a flexible connecting member, an inside retracting member (35), adapted to be positioned at the inside of the patient's skin around an incision to be performed in the skin and being connected to the flexible connecting member, and an outside retracting member connected to at least one of; the first flexible wall, the flexible connecting member, and the second coupling or being an integrated part of the second coupling, adapted to be positioned at the outside of the patient's skin around the incision.

The flexible connecting member may be interconnecting the inside and outside retracting members, whereby the inside and outside retracting members is adapted to be larger than the incision allowing the flexible connecting member to retract the skin and tissue in the incision opening substantially parallel to the skin, and the flexible connecting member may be adapted to be placed in connection with at least one of the first flexible wall and the second coupling or being an integrated part of the first flexible wall, adapted to be placed through the incision into the body cavity, adapted to together with inside and outside retracting members retracting substantially parallel to the skin, the skin and tissue in close relation to the incision, to enlarge the incision passage from the chamber into the body cavity, during the surgical procedure.

The inside retracting member may be sealingly connected to the flexible connecting member. The outside retracting member may be sealingly connected to at least one of; the first flexible wall, the flexible connecting member, and the second coupling or being an integrated part of the second coupling. The flexible connecting member may be sealingly directly or indirectly interconnecting the inside and outside retracting members and adapted to be placed sealingly in connection with at least one of the first flexible wall and the second coupling or being an integrated part of the first flexible wall.

The coupling may be adapted to allow passage of a hand into the body cavity.

The coupling may form an opening, when the first port has been disconnected from the coupling.

According to one embodiment, the medical device further comprises a sealing device, comprising a flexible connecting member, a first sealing member, adapted to be positioned at the inside of the patient's skin around an incision to be performed in the skin and being sealingly connected to the flexible connecting member, and a second sealing member sealingly connected to at least one of the first flexible wall, the flexible connecting member, and the second coupling or being an integrated part of the second coupling, adapted to be positioned at the outside of the patient's skin around the incision. The flexible connecting member may be sealingly interconnecting the first and second sealing members, whereby the first and second sealing member is adapted to be larger than the incision to seal between at least one of: the second sealing member and the skin or tissue of the patient, and the first sealing member and tissue of the patient. The flexible connecting member is adapted to be placed sealingly in connection with at least one of; the first flexible wall and the coupling or be an integrated part of the first flexible wall and adapted to be placed through the incision into the body cavity, to together with first and second sealing members being involved in sealing the combined volume of the chamber and the body cavity to the outer environment, when the second coupling is open, during the surgical procedure.

The second coupling may comprise a body port being a detachable part of the second coupling.

According to one embodiment, the first port is a multiport comprising two or more individual ports, the coupling is adapted to connect to the multiport to together form an integrated multiport placed in close relation to the skin.

The body port may be a multiport comprising two or more individual ports, the body port being adapted to connect to the first port being a multiport, to together form an integrated multiport placed in close relation to the skin.

According to one embodiment, the second coupling may comprise a detachable second inset, and the first port may comprise a detachable third inset. The second inset may be adapted to close between the body cavity and the chamber.

According to one embodiment, the medical device comprises a third port comprising a detachable third inset.

According to one embodiment, the medical device comprises a sealing device, adapted to be placed in connection with at least one of the flexible wall and the second coupling, to seal between the medical device and the skin or tissue of the patient, to seal the combined volume of the chamber and the body cavity to the outer environment, when the second coupling is open.

A surgical method to be performed on the body of a patient using a medical device is further provided. The medical device comprising a flexible wall, a first inset and an interconnectable port, comprising a first port being a multiport, and a second coupling. The method comprises: creating an incision in the skin of the patient, connecting to a body cavity, placing the coupling in the incision, such that a chamber is formed by the flexible wall connected to the first port, first inset and second coupling. The method further comprises connecting the first port to the second coupling, performing the surgical procedure through two or more trocars included in the first port being a multiport, introducing a camera through one trocar, detaching the first port from the second coupling, connecting the first inset to the second coupling, and performing a hand assisted step of the surgical procedure within at least one of the body cavity and the chamber, introducing a glove being part of the first inset.

The medical device may further comprise a sealing device, and the method optionally comprises placing a sealing device in connection with at least one of; the flexible wall and the second coupling, to seal between the medical device and the skin or tissue of the patient, and sealing the combined volume of the chamber and the body cavity to the outer environment, when the second coupling is open.

The step of performing a step of the surgical procedure within the chamber may further comprise: removing a specimen from the cavity in the body of the patient, transferring the specimen through the second coupling, and placing the specimen within the chamber of the medical device.

The surgical method may further comprise: disconnecting the first port or and second coupling such that the interconnectable port is separated and performing a surgical step in the chamber, using the first port or first inset.

A medical device for use in performing joint surgery on a patient. The medical device comprises: a wall adapted to least partly be placed on the patient's body for forming a chamber alone or together with the patient's body, such that a sealed surgical environment is created in the chamber, wherein the chamber is adapted to encompass at least part of one step of the joint surgery procedure to be performed, while maintaining the sealed surgical environment. The medical device further comprises a first inset, and an interconnectable port. The interconnectable port comprises a first port, a second coupling adapted be interconnected with at least one of; the first port to form the interconnectable port, and the first inset, wherein the second coupling is disconnectable from the first port or first inset. The first port is connected to a first portion of the wall, the first inset is connected to a third portion of the wall, the second coupling is connected to a second portion of the wall, the wall is adapted to form a chamber together with the first port, first inset and the second coupling, the second coupling has a closable opening, the chamber is adapted to allow communication through the coupling into the hip joint inside the patient's body, after an incision has been made in the skin of the patient, when a surgical procedure is performed. At least one of the first port and first inset in a first position is adapted to connect to the second coupling in close relation to the patients skin, wherein the chamber having a first smaller volume. At least one of; the first port and first inset in a second position is adapted to be disconnected from the second coupling, being separated from the coupling in a more remote position in relation to the patients skin, wherein the chamber having a second larger volume.

According to one embodiment of the medical device, the first port forms a closable wall port when disconnected from the second coupling.

According to one embodiment, the second coupling forms a closable body port by itself when the first port has been disconnected from the second coupling.

According to one embodiment, the first port comprises a multiport, comprising two or more individual ports.

The first volume may be is smaller than 100 000 mm3, the second volume may be larger than 500 000 mm3.

The medical device may further comprise a first coupling, and the first port may be connected to the second coupling, and the second coupling is adapted to be connected to the first coupling.

According to one embodiment the first and/or second coupling comprises a protruding member, and at least one of the first and second coupling may comprise a recess. The protruding member may be adapted to engage the recess for locking the first coupling to the second coupling. The recess may be a groove in at least one of the first and second coupling.

According to one embodiment, the chamber formed by the flexible wall is adapted to hold a pressure exceeding atmospheric pressure.

The interconnectable port may be adapted to: in a first state, when the first port and second coupling are interconnected, enable a surgeon to operate through the interconnected interconnectable port, and in a second state, when the second coupling is disconnected from the first port enable the surgeon to perform steps of the procedure within the chamber formed by the flexible wall between the first port and second coupling of the interconnectable port.

According to one embodiment, the interconnectable port is adapted to, in the second state, enable the surgeon to remove a specimen from the body of the patient through the second coupling and into the chamber, and to perform one of: placing the specimen within the chamber, and removing the specimen from the chamber through the first port.

The chamber may further comprise a pouch for holding the specimen within the chamber. The pouch can be closed for creating a pouch-chamber within the chamber for isolating the removed specimen within the chamber.

According to one embodiment, the medical device comprises a second port adapted to also be placed in the second coupling, wherein at least one of the first port, the second port and a first coupling are adapted to be reconnected after having been disconnected, such that the surgeon can continue operating through the interconnected port after the specimen has been removed.

According to one embodiment the inset inset is detachably fixated to at least one of the first and second coupling, such that the inset could be detached and replaced by a different inset.

The medical device may further comprise a sealing device, comprising a flexible connecting member, a first sealing member, adapted to be positioned at the inside of the patient's skin around an incision to be performed in the skin and being sealingly connected to the flexible connecting member, and a second sealing member sealingly connected to at least one of the first flexible wall, the flexible connecting member, and the second coupling or being an integrated part of the second coupling, adapted to be positioned at the outside of the patient's skin around the incision. The flexible connecting member may be sealingly interconnecting the first and second sealing members, whereby the first and second sealing members is adapted to be larger than the incision to seal between at least one of: the second sealing member and the skin or tissue of the patient, and the first sealing member and tissue of the patient. The flexible connecting member may be adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.

According to one embodiment, the medical device comprises a second port adapted to be placed in the second coupling. At least one of the first and second ports may comprise an elastic or flexible membrane adapted to, in a non-compressed state, provide sealing, and in a compressed state enable a hand or an object to be inserted through the membrane.

According to one embodiment, the first port comprises a first elastic or flexible membrane, and the second port comprises a second elastic or flexible membrane. The first and second membranes are adapted to be placed tightly together such that they act as a single elastic or flexible membrane adapted to, in a non-compressed state, provide sealing, and in a compressed state enable a hand or an object to be inserted through the membrane.

The first and second membranes may further comprise a plurality of self sealing holes enabling insertion of instruments through the membranes.

At least one of said first port and second port may comprise a penetrable self sealing gel, such that an object or hand can be inserted through the interconnectable port while maintaining a seal.

According to one embodiment, the first port comprises a first penetrable self sealing gel, and the second port comprises a second penetrable self sealing gel. The first and second penetrable self sealing gels may be adapted to be placed tightly together such that they act as a single penetrable self sealing gel adapted to, in a non-compressed state, provide sealing, and in a compressed state enable a hand or an object to be inserted through the self sealing gel while maintaining the seal.

At least one of the first port and second coupling may comprise a non-penetrable valve such that the chamber is sealed from at least one of the ambient environment and a cavity in the patient.

According to one embodiment, the medical device further comprises at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

According to one embodiment, the port further comprises a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the port and the skin of the patient, and (b) the first sealing member and tissue of the patient.

The second coupling may be adapted to allow passage of a hand into the body cavity, and the second coupling may form an opening, when the first port has been disconnected from the second coupling.

The medical device may further comprise a retracting system, comprising a flexible connecting member, an inside retracting member, adapted to be positioned at the inside of the patient's skin around an incision to be performed in the skin and being connected to the flexible connecting member, and an outside retracting member connected to at least one of the first flexible wall, the flexible connecting member, and the second coupling or being an integrated part of the second coupling, adapted to be positioned at the outside of the patient's skin around the incision. The flexible connecting member is interconnecting the inside and outside retracting members, whereby the inside and outside retracting members is adapted to be larger than the incision allowing the flexible connecting member to retract the skin and tissue in the incision opening substantially parallel to the skin. The flexible connecting member may be adapted to be placed in connection with at least one of; the first flexible wall and the second coupling or being an integrated part of the first flexible wall, adapted to be placed through the incision into the body cavity, adapted to together with inside and outside retracting members retracting substantially parallel to the skin, the skin and tissue in close relation to the incision, to enlarge the incision passage from the chamber into the body cavity, during the surgical procedure.

The inside retracting member may be sealingly connected to the flexible connecting member, and the outside retracting member may be sealingly connected to at least one of the first flexible wall, the flexible connecting member, and the second coupling or being an integrated part of the second coupling. The flexible connecting member may be sealingly directly or indirectly interconnecting the inside and outside retracting members, adapted to be placed sealingly in connection with at least one of the first flexible wall and the second coupling or being an integrated part of the first flexible wall.

According to one embodiment, the coupling is adapted to allow passage of a hand into the body cavity. The coupling may be adapted to form an opening, when the first port has been disconnected from the coupling.

The medical device may further comprise a second sealing device, comprising a flexible connecting member, a first sealing member, adapted to be positioned at the inside of the patient's skin around an incision to be performed in the skin and being sealingly connected to the flexible connecting member, and a second sealing member sealingly connected to at least one of the first flexible wall, the flexible connecting member, and the second coupling or being an integrated part of the second coupling, adapted to be positioned at the outside of the patient's skin around the incision, wherein the flexible connecting member is sealingly interconnecting the first and second sealing members. The first and second sealing members are adapted to be larger than the incision to seal between at least one of: the second sealing member and the skin or tissue of the patient, and the first sealing member and tissue of the patient. The flexible connecting member may be adapted to be placed sealingly in connection with at least one of; the first flexible wall and the coupling, or be an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.

The second coupling may comprise a body port being a detachable part of the second coupling. The first port may be a multiport comprising two or more individual ports. The coupling may be adapted to connect to the multiport to together form an integrated multiport placed in close relation to the skin.

According to one embodiment, the body port is a multiport comprising two or more individual ports, and the body port may be adapted to connect to the first port being a multiport, to together form an integrated multiport placed in close relation to the skin.

According to one embodiment, the second coupling comprises a detachable second inset and/or a detachable third inset. The second inset may be adapted to close between the body cavity and the chamber. The medical device may comprise a third port comprising a detachable third inset.

According to one embodiment, the medical device further comprises a second sealing device, adapted to be placed in connection with at least one of the flexible wall and the second coupling, to seal between the medical device and the skin or tissue of the patient, to seal the combined volume of the chamber and the body cavity to the outer environment, when the second coupling is open.

According to one embodiment, the medical device comprises a special sealing device connected to the wall and adapted to seal between the wall and the skin or tissue of the patient. The special sealing device forms a special loop at least partly encircling at least a portion of one or more of the following; the leg, the pelvic region, the abdominal region, the inguinal region, the gluteal region, the thoraxial region and the region of the lower back, such that the sealing device seals between the incision site of the hip joint surgery and at least one of: the anal orifice, the urethra orifice, the perineum region.

The special sealing device may be connected to the wall and adapted to seal between the wall and the skin or tissue of the patient to seal at least a part of the hip joint surgery operational field from at least one of: the anal orifice, the urethra orifice and at least part of the perineum region, while still maintaining the chamber sealed, the first sealing device comprising at least one of: a first part of the sealing device, and a first holding member adapted to hold the medical device in place by encircling at least one leg of the patient or the prolongation thereof to be involved in the sealing of the chamber.

The first sealing device further comprises at least one of; a second part of the sealing device, and a second holding member adapted to hold the medical device in place by encircling the whole body left to right on the level above the legs selected from at least one of; the level of the pelvic, abdominal or thorax region of the patient to further be involved in the sealing of the chamber. The first sealing device may further comprise at least one of; a third part of the sealing device adapted to seal from the medial cranial part of the leg where it is meeting the inguinal region or its prolongation, further in a cranial direction lateral of the patient's ventro-dorsal mid-sagittal plane, on the side where the hip surgery is performed, and wherein the third part of the sealing device at least partly extends in cranial direction until meeting the second part of the sealing device, and wherein the wall is interconnecting to the first, second and third part of the sealing device to seal the chamber, and a third holding member adapted to seal the chamber and exclude from the chamber at least one of; the anal orifice, the urethra orifice and at least part of the perineum region.

According to one embodiment, the sealing device is positioned such that both of the urethra and the anus are excluded from the enclosed chamber forming the sealed surgical environment.

The medical device may further comprise a holding member adapted to encircle a portion of the patient's body, by itself or together with the medical device, for holding the medical device in the desired position.

According to one embodiment, at least a portion of the wall is adapted to directly or indirectly form an elongated tubular enclosure having at least one open end. The enclosure is adapted to fit at least a portion of a leg of the patient, and the medical device is arranged such that a portion of the leg extends into the enclosure through the first open end thereof, when the surgical procedure is performed on the leg of the patient.

According to one embodiment, the wall may be adapted to form the chamber without involving the patient's body, the wall portion forming the chamber may also form the tubular enclosure, and the tubular enclosure may form a second chamber together with the patient's body. The second chamber may be adapted to be sealed at the first or more open ends by the patient's body.

According to one embodiment, the medical device further comprises at least one of: one further exchangeable port, and one further exchangeable inset.

According to one embodiment, the inset may comprise at least one glove integrated in the wall such that a surgeon is able to use the glove from outside the chamber to make manual manipulations inside the chamber while maintaining the sterile environment in the chamber.

The medical device may further comprise a sealing device comprising a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

According to one embodiment, the sealing device may comprise a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

According to one embodiment, the medical device further comprises at least one of an airlock sluice and a liquid lock sluice, comprising a first valve and second valve. The first valve is mounted in at least one of the skin or tissue of the patient and the portion of the wall adapted to directly or indirectly form an elongated tubular enclosure, and wherein the second valve is mounted in the wall.

According to one embodiment, the wall may be adapted to contain a liquid filling the chamber for creating a liquid operating environment, and the medical device may be adapted to receive the liquid through at least one liquid inlet placed in at least one of the wall of the medical device and the skin of the patient for supplying the liquid to at least one of: the chamber and the joint in the patient's body. The medical device may further comprise at least one inlet and outlet selected from the following: a first liquid inlet placed in the wall and adapted for supplying liquid to the chamber, a first liquid outlet placed in the wall and adapted for evacuating liquid from the chamber, a second liquid inlet adapted to be placed in an incision in the skin of the patient, in the area of the joint, for supplying liquid to the joint, and a second liquid outlet adapted to be placed in an incision in the skin of the patient, in the area of the joint, for evacuating liquid from the joint.

The liquid may be an isotonic solution or an antibiotic liquid.

The medical device may further comprise a pump for pumping the liquid from the liquid outlet to the liquid inlet.

The medical device may further comprise at least one inlet and at least one outlet selected from the following: a first fluid inlet placed in the wall and adapted for supplying gas to the chamber, a first fluid outlet placed in the wall and adapted for evacuating gas from the chamber, a second fluid inlet adapted to be placed in an incision in the skin of the patient, in the area of the joint, for supplying gas to the joint, and a second fluid outlet adapted to be placed in an incision in the skin of the patient, in the area of the joint, for evacuating gas from the joint.

According to one embodiment, the medical device further comprises a second fluid system is adapted to at least one of: supply fluid to the second fluid inlet and evacuate fluid from the second fluid outlet, and circulate a fluid from the second fluid outlet to the second fluid inlet. At least one of the first and second fluid systems may be adapted to circulate a liquid fluid.

The medical device may further comprise an energy transferring coupling adapted to transfer energy from outside the chamber into the sealed environment, such that a tool can be energized.

According to one embodiment, the medical device comprises one or more further insets. The insets may comprise one glove integrated in the wall in both the first inset and at least one further inset, such that a surgeon is able to use the gloves from outside the chamber to make manual manipulations inside at least one of the chamber and joint cavity, while maintaining the sterile environment in the chamber.

According to one embodiment, the medical device further comprises a fluid sluice adapted to allow introduction of at least one of at least one surgical instrument and at least one artificial joint surface for performing at least a joint surface replacement, when using said gloves when performing the surgical procedure.

The first port may comprise at least one trocar for allowing introduction of at least one arthroscopic surgical instrument into at least one of; the chamber and joint cavity, wherein the at least first port is adapted to allow a arthroscopic surgical procedure to be combined with manual manipulations inside at least one of the chamber and joint cavity, while maintaining the sterile environment in the chamber.

The medical device may further comprise at least one of one or more further ports and the first port comprising a multiport, comprising two or more trocars adapted to allow the introduction of at least one of; a surgical instrument, two or more surgical instruments, and a camera, to allow a arthroscopic surgical procedure to be combined with manual manipulations inside at least one of the chamber and joint cavity, while maintaining the sterile environment in the chamber.

According to one embodiment the wall is adapted to form the chamber without or together with the patient's body. At least a portion of the wall is adapted to directly or indirectly form an elongated tubular enclosure having a first or more open end, the enclosure being adapted to fit at least a portion of the body of the patient. The medical device is arranged such that the portion of the body is going into the enclosure through the first open end thereof, when the surgical procedure is to be performed on the portion of the patient's body.

The elongated tubular enclosure may comprise a first and at least a second open end. The medical device is arranged such that the portion of the body goes into the enclosure through the first open end thereof, and will exit the enclosure through at least the second open end thereof, when the surgical procedure is to be performed on the portion of the patient's body.

The elongated tubular enclosure may further comprise a third open end. The enclosure is adapted to fit at least a portion of both the legs or both the arms of the patient in the same enclosure. The medical device is arranged such that the portion of the body that goes into the enclosure through the first open end thereof will exit the enclosure through both the second and the third open end thereof, preferable the two legs or arms exiting through the second and third opening, when the surgical procedure is performed on at least a part of the portion of the patient's body.

According to one embodiment, the chamber is adapted to be formed together by the wall and the patient's body, the tubular enclosure is adapted to encompass the chamber, and wherein the chamber is adapted to be sealed at the first or more open ends by the patient's body portion.

The chamber may be formed by the wall without involving the patient's body, part of the wall forming the chamber is adapted to also form the tubular enclosure, the wall having two sides whereof one facing the inside of the chamber and the other side of the wall is facing the tubular enclosure, when performing the surgical procedure, wherein the tubular enclosure form a second chamber, the second chamber at least partly encompassed by the tubular enclosure and adapted to be sealed at the first or more open ends by the patient's body portion, and wherein the wall part facing the tubular enclosure is adapted to form the second chamber together with the patient's body.

According to one embodiment, the chamber is adapted to be in communication with an operating field during the surgical procedure, when the skin of the patient has been cut in a position inside of the chamber, wherein the wall encompassing the chamber has a wall port being at least one of the first port and a comprised additional port, and wall inset being at least one of; the first inset and a comprised additional inset, mounted in a wall portion of the chamber for allowing; objects including instruments to be moved into the chamber or operating field and/or manual manipulation to be performed in the chamber or operating field. The wall encompassing the chamber has mounted in a wall portion of the chamber, a wall port being at least one of; the first port and a comprised additional port, and wall inset being at least one of; the first inset and a comprised additional inset, wherein the wall port or wall inset are including two parts, a first and second part, wherein the second part comprising the wall port or wall inset and the first part comprising at least one of the second coupling and a body port or body inset comprised in the second coupling, According to one embodiment the medical device comprises a port or inset including a first and second part, wherein the second part comprises the wall port or wall inset and the first part comprises at least one of the second coupling and a body port or body inset comprised in the second coupling. The body port or body inset being mounted in the cut skin of the patient to allow objects including instruments to be moved further from the chamber into the operating field and/or manual manipulation to be performed from the chamber further into the operating field.

The two parts of the port or inset may be adapted to be mounted together, touching each other forming an integrated port or inset and thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each other to one or more positions not touching each other and thereby; to use the second part of the port or inset to allow objects including instruments to be moved into the chamber and/or manual manipulation to be performed in the chamber and further to use the first part of the port or inset to allow objects including instruments to be moved from the chamber passing the cut skin into the operating field and/or manual manipulation to be performed from the chamber through the cut skin further into the (body) operating field.

According to one embodiment, the chamber may be adapted to be in communication with an operating field during the surgical procedure, when the part of the wall forming both the chamber and the tubular enclosure, at a portion thereof, is adapted to be opened, having an opening, and together with the cut skin of the patient positioned inside of the chamber allowing such communication with the operating field, wherein a portion of the wall part encompassing only the chamber has a wall port or wall inset mounted therein, wherein the wall encompassing the chamber has mounted in a wall portion of the chamber a wall port being at least one of; the first port and a comprised additional port, and wall inset being at least one of; the first inset and a comprised additional inset, for allowing, from outside the chamber; objects including instruments to be moved into the chamber or operating field and/or manual manipulation to be performed in the chamber or operating field.

According to one embodiment, the wall port or wall inset includes a first and second part, the second part comprises the wall port or wall inset and the first part comprising at least one of the second coupling, a body port or body inset comprised in the second coupling, and a first wall port or first wall inset mounted in the opening in the portion of the part of the wall forming both the chamber and the tubular enclosure adapted to be opened to create the communication between the chamber and the operating field to allow; objects including instruments to be moved further from the chamber into the operating field and/or manual manipulation to be performed from the chamber further into the operating field, wherein the passage between the chamber and the operating field includes the first wall port or inset, the second chamber located in between the tubular enclosure and the skin of the patient and the skin of the patient, wherein the second chamber having a size equal to or larger than zero.

According to one embodiment, the two parts of the port or inset are adapted to be mounted together touching each other forming an integrated port and inset thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each into one or more positions when they are not touching each other and thereby; to use the wall port or inset of the second part to allow; objects including instruments to be moved into the chamber and/or manual manipulation to be performed in the chamber and further to use the first wall port or first wall inset of the first part to allow; objects including instruments to be moved from the chamber passing the cut skin into the operating field and/or manual manipulation to be performed from the chamber through the cut skin further into the operating field.

The two parts of the port or inset is adapted to be locked together in at least one fixed position.

The medical device is adapted to allow the surgical procedure with its operating field to be performed on the patient on at least one of; a extremity, the prolongation of the extremity, abdomen, chest, and any joint including the hip and knee joints and the joints of the upper extremity.

According to one embodiment, the chamber encompassing the surgical procedure may be adapted to reduce infection risk of the surgical procedure most important for joint surgery.

The two parts of the port may be adapted to comprise a fluid sealed valve when the two parts is separated.

According to one embodiment, only the second part of the two parts of the port is adapted to comprise a fluid sealed valve, when the two parts being separated.

At least one of a third exchangeable wall port and wall inset different from the wall port and wall inset, may be adapted to replace at least one of the wall port or wall inset.

According to one embodiment, the medical device further comprises at least one of a third exchangeable body port and body inset different from the body port and body inset, and adapted to replace at least one of the body port or body inset.

The medical device may further comprise a second exchangeable integrated port different from the integrated port, and adapted to replace the integrated port during the surgical procedure.

The medical device may further comprise at least one sealing device for sealing the enclosure adapted to seal between the skin of the body portion of the patient and at least one of the wall and enclosure. The sealing device may comprise a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

According to one embodiment, the sealing device comprises a pressure sealing member attached to at least one of the wall and enclosure and adapted to press against the patient's skin to create a pressurized sealing between the skin of the patient's extremity and at least one of the wall and enclosure. The pressure sealing member may be adapted to be hydraulically, pneumatically or mechanically forced against the patient's skin.

The medical device may further comprise an adhesive adapted to provide at least one of: (a) fixation of at least one of the wall and enclosure to the skin of the patient, and sealing between the skin of the patient and at least one of the wall and enclosure.

The medical device may further comprise an air evacuation system adapted to evacuate air from the second chamber, when the portion of the patient's extremity is placed in the enclosure. The air evacuation system may be adapted to evacuate air from the vacuum sealing member.

The medical device may further comprise a multi-port being the first port or an additional port, which comprises at least two ports integrated in the multi port, and adapted to enable passage of an object to the inside of the patient's body via the cut incision in the skin, when performing the surgical procedure.

The wall port of the medical device may comprise a multi-port, which comprises at least two ports integrated in the multi port, and adapted to enable passage of an object into the chamber and further into the inside of the patient's body via the cut incision in the skin, when performing the surgical procedure.

The couplings in any of the embodiments may comprise a body port, the body port may comprise a multi-port, which comprises at least two ports integrated in the multi port, and adapted to enable passage of an object from the chamber and further into the inside of the patient's body via the cut incision in the skin, when performing the surgical procedure.

According to one embodiment, the first wall port comprises a multi-port, which comprises at least two ports integrated in the multi port, and adapted to enable passage of an object from the chamber and further into the inside of the patient's body via the cut incision in the skin, when performing the surgical procedure.

The medical device may further comprise at least one further wall port provided in the wall enabling passage of an object between the chamber and the environment outside of the chamber. The wall port may comprise at least one of an elastic membrane and a flexible membrane, and wherein the membrane is adapted to, in a non-pushed state, seal between the chamber and the environment outside of the chamber, and in a pushed state enable a hand or an object to be inserted through the membrane.

According to one embodiment, the medical device further comprises a further sealing device having a first sealing member adapted to be positioned at the inside of the patient's skin around an incision cut in the patient's skin made from the chamber, a second sealing member adapted to be positioned at the outside of the patient's skin around the incision in the chamber, and at least one of a flexible, spring-loaded and elastic connecting member sealingly interconnecting the first and second sealing members, whereby the at least one of the flexible, spring-loaded and elastic connecting member seals between at least one of the second sealing member and the skin of the patient, and the first sealing member and tissue of the patient.

An object may in any one of the embodiments be at least one of: a tool, a camera, a medical device or a part of a human body.

The medical device may further comprise at least one of an airlock sluice (18) and a liquid lock sluice (18), comprising a first valve (38a) and second valve (38b) and a sluice chamber placed in between the first and second valve, for allowing passage of objects from the chamber through the first valve and further through the second valve out to the environment outside of the chamber, and vice versa. The first valve may be mounted in at least one of the skin or tissue of the patient and the portion of the wall adapted to directly or indirectly form the elongated tubular enclosure, and the second valve may be mounted in the wall.

The chamber and operating field may comprise a circulating liquid fluid during the surgical procedure.

The medical device may comprise an additional sealing subdevice comprising a wall and a sealing device adapted to be placed between the chamber and the skin of the patient and be formed to close the anus or opening of urethra being in contact with the chamber to avoid connection between the anus or opening of the urethra and the chamber, when the surgical procedure is intended to be performed in relation thereto.

According to one embodiment, the elongated tubular enclosure is formed by placing the wall forming the chamber around at least a portion of the extremity of the patient.

The medical device may further comprise a slit for placing the chamber around at least a portion of the extremity of the patient radially in relation to the length axis of the extremity. The slit may be adapted to be at least partially closed by closing elements mounted on the wall of the medical device.

According to one embodiment, the closing elements are elastic or adjustable for fixating the medical device to the extremity of the patient.

The medical device may comprise a first and a second portion located on a first and second side of the slit when the chamber is placed around at least a portion of the extremity. The first and second portions may be adapted to be interconnected by means of at least one of: an adhesive and a mechanical connecting member.

At least one inset or port attached to the wall may be adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

According to one embodiment, the wall forming the chamber may comprise a first and second interconnecting member, and the first interconnecting member may be placed at the first position, and the second interconnecting member may be positioned in the second position. The second interconnecting member may be adapted to connect to the first interconnecting member for locking the inset or wall port in the first position.

According to one embodiment, a port or inset placed in the wall is defined as the wall port or wall inset, and the medical device may further comprise a body port or body inset adapted to be mounted in another wall portion or the skin or tissue of the patient, wherein the first interconnecting member is adapted to be positioned in connection with a body port or body inset, and wherein the wall port and the body port is adapted to form a integrated port when the first and second interconnecting members are connected in the first position.

The wall port and/or the body port may comprise at least one of an elastic membrane and a flexible membrane. The membrane may be adapted to, in a non-pushed state, provide a seal, and in a pushed state, enable a hand or an object to be inserted through the membrane.

According to one embodiment, at least one of said first and second parts comprises a penetratable self sealing gel, such that an object or hand can be inserted through the port while maintaining a seal.

According to one embodiment, the first part comprises a first penetratable self sealing gel and the second part comprises a second penetratable self sealing gel, and wherein the first and second penetratable self sealing gels are adapted to be placed tightly together such that they act as a single penetratable self sealing gel adapted to, in a non-pushed state, provide sealing, and in a pushed state enable a hand or an object to be inserted through the self sealing gel while maintaining the seal.

The first and second parts may be adapted be interconnected to form a integrated port, wherein the second part is adapted to be disconnected from the first part by a surgeon during a surgical procedure. The first part may be connected to a first portion of the wall, and the second part may be connected to a second portion of the wall, and the wall may be a flexible wall.

The chamber may have a first volume when the first and second parts are interconnected and a second volume when the second part is disconnected from the first part. The integrated port may be adapted to: in a first state, when the first and second parts are interconnected, enable a surgeon to operate through the surgical port, and in a second state, when the second part is disconnected from the first part enable the surgeon to perform steps of the procedure within the chamber formed by the flexible wall between the first and second parts of the port.

According to one embodiment, the integrated port may be adapted to, in the second state, enable the surgeon to remove a specimen from the body of the patient through the first part and into the chamber, and to perform one of: placing the specimen within the chamber, and removing the specimen from the chamber through the second part.

According to one embodiment, the chamber further comprises a pouch for holding the specimen within the chamber; the pouch may be closed for creating a pouch-chamber within the chamber for isolating the removed specimen within the chamber.

The first and second parts may be adapted to be reconnected after being disconnected such that the surgeon can continue operating through the interconnected port after the specimen has been removed.

A surgical method using the medical device in any of the embodiments above is further provided. The medical device comprises a wall, a first inset and an interconnectable port, comprising a first port, and a second coupling. The method comprises: creating an incision in the skin of the patient, connecting to a joint cavity, placing the coupling in the incision, such that a chamber is formed by the wall connected to the first port, first inset and second coupling, introducing a camera through at least one of; the first port being a single or multiport including two or more individual ports, an additional port being included in the device, and a trocar introduced into the joint from outside the chamber, performing an arthroscopic surgical procedure through one or more trocars included in the first port being a single or multiport including two or more individual ports or an additional port being included in the device, performing the arthroscopic surgical procedure with the first port being at least one of connected to the second coupling and detached from the second coupling, using at least one glove being part of the first inset or one or more additional insets to introduce one or more hands for assisting the surgical procedure, and performing a hand assisted step of the surgical procedure within at least one of the joint cavity and the chamber, introducing the at least one glove, introducing at least one of; one or more surgical instruments and at least one medical implant through at least one of the trocars and an fluid lock as being part of the medical device, for performing at least one of a hand assisted or arthroscopic surgical procedure such as at least one joint surface replacement or other joint surgical procedure.

The medical device may further comprise a sealing device, and the surgical method may further comprise the steps of: placing a sealing device in connection with at least one of the wall and the second coupling, to seal between the medical device and the skin or tissue of the patient, and sealing the combined volume of the chamber and the joint cavity to the outer environment, when the second coupling is open.

According to one embodiment, performing a step of the surgical procedure within the chamber comprises: removing a specimen from the cavity in the joint of the patient, transferring the specimen through the second coupling, and placing the specimen within the chamber of the medical device.

According to one embodiment, the method further comprises: connecting the first port and second coupling such that the interconnectable port is integrated. Performing a surgical step in the chamber, using the integrated first port.

A medical device for performing a surgical procedure on a patient is provided. The medical device comprises a wall adapted to be at least partially applied on the patient's body and further adapted to form a chamber without or together with the patient's body, in which a sealed environment can be maintained for encompassing part of the surgical procedure to be performed on the patient, wherein at least a portion of the wall is adapted to directly or indirectly form an elongated tubular enclosure having a first or more open end, the enclosure being adapted to fit at least a portion of the body of the patient, and wherein the medical device is arranged such that the portion of the body is going into the enclosure through the first open end thereof, when the surgical procedure is to be performed on the portion of the patient's body.

According to one embodiment, the elongated tubular enclosure of the medical device comprised the first and at least a second open end, wherein the medical device is arranged such that the portion of the body goes into the enclosure through the first open end thereof, and will exit the enclosure through at least the second open end thereof, when the surgical procedure is to be performed on the portion of the patient's body.

According to one embodiment, the elongated tubular enclosure further comprises a third open end, the enclosure being adapted to fit at least a portion of both the legs or both the arms of the patient in the same enclosure, and wherein the medical device is arranged such that the portion of the body that goes into the enclosure through the first open end thereof will exit the enclosure through both the second and the third open end thereof, preferable the two legs or arms exiting through the second and third opening, when the surgical procedure is performed on at least a part of the portion of the patient's body.

According to one embodiment, the chamber is adapted to be formed together by the wall and the patient's body, the tubular enclosure is adapted to encompass the chamber, and wherein the chamber is adapted to be sealed at the first or more open ends by the patient's body portion.

According to one embodiment, the chamber is formed by the wall without involving the patient's body, part of the wall forming the chamber is adapted to also form the tubular enclosure, the wall having two sides whereof one facing the inside of the chamber and the other side of the wall is facing the tubular enclosure, when performing the surgical procedure, wherein the tubular enclosure form a second chamber, the second chamber at least partly encompassed by the tubular enclosure and adapted to be sealed at the first or more open ends by the patient's body portion, and wherein the wall part facing the tubular enclosure is adapted to form the second chamber together with the patient's body.

According to one embodiment, the chamber is adapted to be in communication with an operating field during the surgical procedure. The skin of the patient has been cut in a position inside of the chamber, wherein the wall encompassing the chamber has a wall port or wall inset mounted in a wall portion of the chamber for allowing; objects including instruments to be moved into the chamber or operating field and/or manual manipulation to be performed in the chamber or operating field.

According to one embodiment, medical device comprises a port or inset including two parts, a first and second part, wherein the second part comprising the wall port or wall inset and the first part comprises a body port or body inset adapted to be mounted in the cut skin of the patient to allow objects including instruments to be moved further from the chamber into the operating field and/or manual manipulation to be performed from the chamber further into the operating field.

According to one embodiment, the two parts of the port or inset are adapted to be mounted together, touching each other forming an integrated port or inset and thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each other to one or more positions not touching each other and thereby; to use the second part of the port or inset to allow objects including instruments to be moved into the chamber and/or manual manipulation to be performed in the chamber and further to use the first part of the port or inset to allow objects including instruments to be moved from the chamber passing the cut skin into the operating field and/or manual manipulation to be performed from the chamber through the cut skin further into the (body) operating field.

According to one embodiment, the chamber is adapted to be in communication with an operating field during the surgical procedure, when the part of the wall forming both the chamber and the tubular enclosure, at a portion thereof, is adapted to be opened, having an opening, and together with the cut skin of the patient positioned inside of the chamber allowing such communication with the operating field, wherein a portion of the wall part encompassing only the chamber has a wall port or wall inset mounted therein for allowing, from outside the chamber; objects including instruments to be moved into the chamber or operating field and/or manual manipulation to be performed in the chamber or operating field.

The medical device may further comprise a port or inset including a first and second part, wherein the second part comprises the wall port or wall inset and the first part comprising a first wall port or first wall inset mounted in the opening in the portion of the part of the wall forming both the chamber and the tubular enclosure adapted to be opened to create the communication between the chamber and the operating field to allow; objects including instruments to be moved further from the chamber into the operating field and/or manual manipulation to be performed from the chamber further into the operating field, wherein the passage between the chamber and the operating field includes the first wall port or inset, the second chamber located in between the tubular enclosure and the skin of the patient and the skin of the patient, wherein the second chamber having a size equal to or larger than zero.

The two parts of the port or inset may be adapted to be mounted together touching each other forming an integrated port and inset thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each into one or more positions when they are not touching each other and thereby; to use the wall port or inset of the second part to allow; objects including instruments to be moved into the chamber and/or manual manipulation to be performed in the chamber and further to use the first wall port or first wall inset of the first part to allow; objects including instruments to be moved from the chamber passing the cut skin into the operating field and/or manual manipulation to be performed from the chamber through the cut skin further into the operating field.

According to one embodiment, the two parts of the port or inset may be adapted to be locked together in at least one fixed position.

The medical device may be adapted to allow the surgical procedure with its operating field to be performed on the patient on at least one of an extremity, the prolongation of the extremity, abdomen, chest, and any joint including the hip and knee joints and the joints of the upper extremity.

The chamber encompassing the surgical procedure may be adapted to reduce infection risk of the surgical procedure most important for joint surgery.

According to one embodiment, the two parts of the port may be adapted to comprise a fluid sealing valve when the two parts are separated.

In one embodiment, only the second part of the two parts of the port is adapted to comprise a fluid sealing valve, when the two parts are separated.

According to one embodiment, the medical device comprises at least one of a third exchangeable wall port and wall inset different from the wall port and wall inset, adapted to replace at least one of the wall port or wall inset.

According to one embodiment, the medical device comprises at least one of a third exchangeable body port and body inset different from the body port and body inset, and adapted to replace at least one of the body port or body inset.

According to one embodiment, the medical device comprises a second exchangeable integrated port different from the integrated port, and adapted to replace the integrated port during the surgical procedure.

The inset may comprise at least one glove integrated in the wall such that a surgeon is able to use the glove from outside the chamber to make manual manipulations inside the chamber while maintaining the sterile environment in the chamber.

The medical device may further comprise a device or instrument mount (20) adapted to retain instruments (89) or devices within the chamber.

According to one embodiment, the medical device comprises at least one sealing device adapted to seal between the skin of the body portion of the patient and at least one of the wall and enclosure.

The sealing device may comprise a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure and/or a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

According to one embodiment, the medical device comprises an adhesive surface adapted to provide at least one of: (a) fixation of at least one of the wall and enclosure to the skin of the patient, and (b) sealing between the skin of the patient and at least one of the wall and enclosure.

The medical device may further comprise an air evacuation system adapted to evacuate air from the second chamber, when the portion of the patient's extremity is placed in the enclosure. The air evacuation system may be adapted to evacuate air from the vacuum sealing member.

The medical device may further comprise a multi-port, which comprises at least two ports integrated in the multi port, and adapted to enable passage of an object to the inside of the patient's body via the cut incision in the skin, when performing the surgical procedure.

The wall port may comprise a multi-port, which comprises at least two ports integrated in the multi port, and adapted to enable passage of an object into the chamber and further into the inside of the patient's body via the cut incision in the skin, when performing the surgical procedure.

The body port and/or wall port may comprise a multi-port comprising at least two ports integrated in the multi port, and adapted to enable passage of an object from the chamber and further into the inside of the patient's body via the cut incision in the skin, when performing the surgical procedure.

The medical device may further comprise at least one further wall port provided in the wall enabling passage of an object between the chamber and the environment outside of the chamber, wherein the wall port comprises at least one of an elastic membrane and a flexible membrane, and wherein the membrane is adapted to, in a non-pushed state, seal between the chamber and the environment outside of the chamber, and in an pushed state enable a hand or an object to be inserted through the membrane.

An object may comprise at least one of: a tool, a camera, a medical device or a part of a human body.

The medical device may further comprise at least one of an airlock sluice and a liquid lock sluice, comprising a first valve and second valve and a sluice chamber placed in between the first and second valve, for allowing passage of objects from the chamber through the first valve and further through the second valve out to the environment outside of the chamber, and vice versa.

The medical device may further comprise at least one of an airlock sluice and a liquid lock sluice, comprising a first valve and second valve, wherein the first valve is mounted in at least one of the skin or tissue of the patient and the portion of the wall adapted to directly or indirectly form the elongated tubular enclosure, and wherein the second valve is mounted in the wall.

The chamber and operating field may comprise a circulating liquid fluid during the surgical procedure.

The medical device may further comprise an additional sealing subdevice comprising a wall and a sealing device adapted to be placed between the chamber and the skin of the patient and to be formed to close the anus or opening of urethra being in contact with the chamber to avoid connection between the anus or opening of the urethra and the chamber, when the surgical procedure is intended to be performed in relation thereto.

According to one embodiment, the elongated tubular enclosure is formed by placing the wall forming the chamber around at least a portion of the extremity of the patient. The elongated tubular enclosure may comprise a slit for placing the chamber around at least a portion of the extremity of the patient radially in relation to the length axis of the extremity. The slit may be adapted to be at least partially closed by closing elements mounted on the wall of the medical device. The closing elements are elastic or adjustable for fixating the medical device to the extremity of the patient.

The medical device may comprise a first and a second portion located on a first and second side of the slit when the chamber is placed around at least a portion of the extremity, and wherein the first and second portions are adapted to be interconnected by means of at least one of: an adhesive and a mechanical connecting member.

At least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

According to one embodiment, the medical device may comprise a first and second interconnecting member, and wherein the first interconnecting member is placed at the first position, and wherein the second interconnecting member is positioned in the second position, and wherein the second interconnecting member is adapted to connect to the first interconnecting member for locking the inset or wall port in the first position.

The port or inset may be placed in the wall is defined as the wall port or wall inset, the medical device further comprising a body port or body inset adapted to be mounted in another wall portion or the skin or tissue of the patient, wherein the first interconnecting member is adapted to be positioned in connection with a body port or body inset, and wherein the wall port and the body port is adapted to form a integrated port when the first and second interconnecting members are connected in the first position.

The wall port and the body port may comprise at least one of an elastic membrane and a flexible membrane, and the membrane may be adapted to, in a non-pushed state, provide a seal, and in a pushed state, enable a hand or an object to be inserted through the membrane.

At least one of said first and second part may comprise a penetratable self sealing gel, such that an object or hand can be inserted through the port while maintaining a seal.

According to one embodiment of the medical device, the first part comprises a first penetratable self sealing gel and the second part comprises a second penetratable self sealing gel, and wherein the first and second penetratable self sealing gels are adapted to be placed tightly together such that they act as a single penetratable self sealing gel adapted to, in a non-pushed state, provide sealing, and in a pushed state enable a hand or an object to be inserted through the self sealing gel while maintaining the seal.

The first and second part may be adapted to be interconnected to form a surgical port, wherein the second part is adapted to be disconnected from the first part by a surgeon during a surgical procedure, wherein the first part is connected to a first portion of the wall, and the second part is connected to a second portion of the wall, and wherein the wall is a flexible wall.

The chamber may have a first volume when the first and second parts are interconnected and a second volume when the second part is disconnected from the first part.

The medical device may be adapted to in a first state, when the first and second parts are interconnected, enable a surgeon to operate through the surgical port, and in a second state, when the second part is disconnected from the first part enable the surgeon to perform steps of the procedure within the chamber formed by the flexible wall between the first and second parts of the port.

The medical device may be adapted to, in the second state, enable the surgeon to remove a specimen from the body of the patient through the first part and into the chamber, and to perform one of: placing the specimen within the chamber, and removing the specimen from the chamber through the second part.

The first and second parts may be adapted to be reconnected after being disconnected such that the surgeon can continue operating through the interconnected port after the specimen has been removed.

A method for performing a surgical procedure on a patient is provided. The medical device comprises a wall, a first inset and an interconnectable port. The interconnectable port comprising a first port and a second coupling. The method comprises: applying a wall at least partially on the patient's body forming a chamber without or together with the patient's body, maintaining a sealed environment for encompassing part of the surgical procedure to be performed on the patient, forming by at least a portion of the wall directly or indirectly an elongated tubular enclosure having a first or more open end, the enclosure being adapted to fit at least a portion of the body of the patient, and introducing the portion of the body into the enclosure through the first open end thereof, placing the coupling in an newly made incision, such that the chamber is formed by the wall connected to the first port, first inset and second coupling, introducing a camera through at least one of; the first port being a single or multiport including two or more individual ports, an additional port being included in the device, and a trocar introduced into the joint from outside the chamber. The method further comprises performing at least one of an arthroscopic surgical procedure through one or more trocars included in the first port being a single or multiport including two or more individual ports or an additional port being included in the device, the first port being at least one of; connected to the second coupling and detached from the second coupling, and a hand assisted step of the surgical procedure within at least one of the joint cavity and the chamber, introducing the at least one glove being part of the first inset or one or more additional insets to introduce one or more hands for assisting the surgical procedure, and introducing at least one of one or more surgical instruments and at least one medical implant through at least one of; the trocars and a fluid lock as being part of the medical device, performing at least one of: a hand assisted or arthroscopic surgical procedure such as at least one of; a joint surface replacement and other joint surgical procedure.

According to one embodiment, the elongated tubular enclosure further comprises a second open end. The step of exiting the medical device may comprise exiting such that the portion of the body is exiting through the second open end thereof.

According to one embodiment, the elongated tubular enclosure further comprising a third open end, allowing fitting at least a portion of both the legs or both the arms of the patient in the same enclosure. The medical device is arranged such that the portion of the body is; entering the enclosure through the first open end thereof, and exiting the enclosure through both the second and the third open end thereof.

According to one embodiment, the chamber is adapted to be formed by the wall and the patient's body and the tubular enclosure is adapted to encompass the chamber. The method includes sealing at the first or more open ends of the tubular enclosure also by the patient's body portion.

According to one embodiment, the chamber is formed by the wall without involving the patient's body, and the method comprises forming the chamber by part of the wall also forming the tubular enclosure, the wall comprises two wall sides of which one is facing the inside of the chamber and the other is facing the tubular enclosure, forming by the tubular enclosure a second chamber at least partly encompassed by the tubular enclosure and sealing at the first or more open ends using the patient's body portion, and forming the second chamber together with the patient's body partly by the wall part facing the tubular enclosure.

According to one embodiment, the method may further comprise cutting the skin of the patient in a position inside of the chamber, communicating from the chamber with an operating field during the surgical procedure. The wall encompassing the chamber has a wall port or wall inset mounted in a wall portion of the chamber for allowing at least one of; moving objects into the chamber or operating field and manipulating manually in the chamber or operating field.

The medical device may comprise a port having a first and second part, and the second part may comprise the wall port or wall inset and the first part comprises a body port or body inset. The method may comprise the steps of mounting a body port in the cut skin of the patient allowing at least one of; moving objects from the chamber into the operating field and manipulating manually from the chamber into the operating field.

The method may further comprise mounting the two parts of the port or inset together, touching each other, forming an integrated port or inset and thereby allowing moving objects into the operating field, manipulating manually in the operating field directly from outside the chamber, separating the two parts of the port or inset from each other and placing the port or inset in one or more positions inside the chamber.

A part of the wall may form both the chamber and the tubular enclosure, at a portion thereof. The medical device may comprise opening by cutting the skin of the patient inside of the chamber allowing communication with the operating field, allowing, from outside the chamber, at least one of; moving objects into the chamber or operating field and manually manipulating in the chamber or operating field.

The medical device comprises a port or inset including a first and second part. The second part may comprise the wall port or wall inset and the first part comprises a first wall port or first wall inset mounted in the opening in the portion of the part of the wall forming both the chamber and the tubular enclosure for performing the method steps of; communicating between the chamber and the operating field, wherein the second chamber is located in between the tubular enclosure and the skin of the patient, and wherein the second chamber has a size equal to or larger than zero.

According to one embodiment, the method comprises mounting the two parts of the port or inset touching each other, forming an integrated port and inset, dismounting the two parts of the port or inset.

The method may further comprise locking together in at least one fixed position the two parts of the port or inset.

According to one embodiment, the step of performing the surgical procedure on the patient comprises performing the surgical procedure on at least one of a extremity, the prolongation of the extremity, abdomen, chest, and any joint including the hip and knee joints and the joints of the upper extremity.

Any of the methods herein may comprise reducing the infection risk of the surgical procedure by using the chamber encompassing the surgical procedure.

The method may further comprise using a fluid sealing valve included in both of the two parts of the port when the two parts is separated.

The method may further comprise using fluid sealing valve included in the second part, when the two parts are separated.

The method may further comprise introducing at least one of a third exchangeable wall port and wall inset different from the wall port and wall inset, and replacing at least one of the wall port or wall inset.

The method may further comprise introducing at least one of a third exchangeable body port and body inset different from the body port and body inset, and replacing at least one of the body port or body inset.

The method may further comprise introducing a second exchangeable integrated port different from the integrated port, and replacing the integrated port during the surgical procedure.

The inset may comprise at least one glove integrated in the wall such that a surgeon is able to use the glove from outside the chamber, and manipulate manually inside the chamber while maintaining the sealed environment in the chamber.

According to one embodiment, the medical device further comprises a device or instrument mount for retaining an instrument within the chamber.

According to one embodiment, the method further comprises the steps of introducing at least one sealing device and sealing between the skin of the body portion of the patient and at least one of the wall and enclosure.

According to one embodiment, the medical device is arranged such that the portion of the extremity may be inserted into the enclosure through the first open end thereof and exit the enclosure through a second open end thereof.

The method may further comprise: forming the chamber by the part of the wall is also forming the tubular enclosure, the wall having two sides whereof one facing the inside of the chamber and the other side of the wall is facing the tubular enclosure, forming a second chamber using at least partly the tubular enclosure, the second chamber at least partly encompassed by the tubular enclosure, sealing at the first or more open ends by the patient's body portion, and forming the second chamber together with the patient's body using the wall part facing the tubular enclosure.

According to one embodiment, the medical device further comprising a sealing device, and the method further comprises the steps of: placing a sealing device in connection with at least one of; the wall and the second coupling, to seal between the medical device and the skin or tissue of the patient, sealing the combined volume of the chamber and the joint cavity to the outer environment, when the second coupling is open.

The surgical method may further comprise the steps of: removing a specimen (81) from the cavity in the joint of the patient, transferring the specimen through the second coupling, and placing the specimen within the chamber of the medical device.

The surgical method may further comprise: connecting the first port and second coupling such that the interconnectable port is integrated, performing a surgical step in the chamber, using the integrated first port.

The wall of the medical device in any of the embodiments herein may be collapsible and/or flexible and/or elastic and/or may comprise a pleated portion such that the flexible wall can be expanded. The pleated portion may further allow movement of a wall port, coupling and/or inset in the wall in relation to a body port, a position on the patient's body or another wall port, coupling and/or inset in the wall.

The wall of the medical device in any of the embodiments herein may be adapted to hold a pressure exceeding atmospheric pressure, such as the pressure used to expand a cavity in the body of the patient during laparoscopic surgery.

In any of the embodiments herein, the chamber may comprises a pouch for holding the specimen and/or object within the chamber, the pouch may be closeable for creating a pouch-chamber within the chamber for isolating the removed specimen and/or object within the chamber. Isolating a removed specimen and/or object may be important as the removed specimen for example may contain bacteria which should be kept from the incision site, the specimen may be a piece of bone or cartilage which needs to be secured in the pouch that that it does not risk falling back into the body of the patient.

The wall and body ports in any of the embodiments herein may comprise a penetrable self sealing gel, such that an object or hand can be inserted through the ports while maintaining a seal. Two ports, such as a wall and body port may each comprise a penetrable self sealing gel such that the self sealing gels could be placed tightly together such that they act as a single penetrable self sealing gel adapted to, in a non-compressed state, provide sealing, and in a compressed state enable a hand or an object to be inserted through the self sealing gel while maintaining the seal. Two ports, each comprising a self sealing gel, may be provided in the medical devices of any of the embodiments herein.

The medical device according to any of the embodiments herein may comprise at least one fluid inlet for inflating the chamber with a fluid. The fluid inlet may be positioned in the wall of the medical device or may be positioned in the body of the patient, such that the fluid enters the chamber through an incision in the skin of the patient forming a fluid connection between a cavity in the patient and the chamber of the medical device. The medical device according to any of the embodiments herein may further comprise a fluid outlet for discharging the fluid from the chamber. The fluid outlet may be provided in the wall of the medical device or in the skin of the patient, or in a cavity of the patient's body from within the chamber of the medical device. The outlet may for example be provided at the incision site such that fluid evacuated simultaneously cleans the incision site from for example blood and bone particles. The medical device in any of the embodiments may further comprise a pump adapted to circulate the fluid from the outlet member to the inlet member.

The fluid supplied to the chamber and/or cavity of the patient in any of the embodiments herein may be a liquid fluid such as an isotonic liquid or an antibiotic liquid, such that for example arthroscopic procedures are enabled. The fluid may alternatively be a gaseous fluid such as $CO_2$ gas or purified and/or humidified air, such that for example a laparoscopic procedure is enabled. The medical devices and surgical methods may further be adapted to enable a combination of gaseous fluids and liquid fluids, such that surgical procedures having combinations of arthroscopic and laparoscopic steps may be performed.

The fluid inlet and/or the fluid outlet and/or the pump, or any part of a fluid handling system of the medical device may be connected to one or more of a filtering unit, a sterilization unit, a fluid tempering unit and a fluid humidifying unit.

Any of the wall and body ports herein may comprise a non-penetrable valve such that the chamber is sealed from at least one of the ambient environment and a cavity in the patient.

The medical device according to any of the embodiments herein may further comprise a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: the port and the skin of the patient, and the first sealing member and tissue of the patient. The sealing device may be adapted to fixate the wall of the medical device or at least one of a body port, a body coupling in the skin of the patient.

The medical device according to any of the embodiments herein may further comprise a monitoring unit for monitoring a physiological parameter of the patient and/or a physical parameter of the medical device. By monitoring the physiological parameter of the patient and/or a physical parameter of the medical device a pressure creating member or pressure reducing member may adjust the pressure in a pressure or vacuum sealing member on the basis of input from the monitoring unit. The pressure or vacuum in the sealing device could thus be adapted to provide adequate sealing against the skin of the patient while exerting as low force as possible on the skin and/or tissue of the patient, thus reducing the risk that the skin and/or tissue of the patient is injured.

The medical device in any of the embodiments may further comprise at least one glove integrated in the wall such that a surgeon is able to use the glove from outside the chamber to make manual manipulations inside the chamber while maintaining sterile environment in the chamber. The glove may be comprises in an inset connected to or integrated in the wall and/or may be connected to a coupling for fixation to/in the wall of the medical device.

In any of the embodiments herein, the medical device may further comprise a device/instrument mount adapted to retain instruments within the chamber.

The wall and/or body port in any of the embodiments herein may comprise a multi-port adapted to be placed inside the chamber in an incision in the skin of the patient.

The wall and body ports in any of the embodiments herein may comprise a penetrable an elastic and/or flexible membrane adapted to, in a non-compressed state, seal between the chamber and the ambient environment, and in a compressed state enable a hand or object to be inserted through the membrane.

In any of the embodiments a part of a first inset and/or at least a part of the first port may be detachably fixed to the wall by means of a coupling in the wall. The inset and/or port may be adapted to close the coupling to close the chamber.

The coupling in any of the medical device herein may further comprise a valve member adapted to close the coupling when at least a part of the first inset or first port is removed.

The medical device according to any of the embodiments may further be adapted to enable the change of ports or insets, or parts thereof, with all removed parts removed to the ambient environment outside of the chamber.

The medical device in any of the embodiments may comprise an airlock sluice and/or liquid lock sluice provided in the wall for allowing passage of objects between the chamber and the ambient environment while maintaining the sealed environment in the chamber.

Any of the wall and body ports may be selected from a group consisting of: laparoscopic ports, hand access ports and multi-ports.

An inset in any of the embodiments herein may comprise an indentation, a surgical glove, a bellow, an elastic membrane or a holding device.

The medical device may in any of the embodiments further comprise at least one non-collapsible transparent window provided in the wall for enabling viewing into the chamber.

The object in any of the embodiments herein may comprise a tool, a medical device or a human body part.

According to one embodiment, the medical device further comprises a sealing device connected to the wall and adapted to seal against the patient's body, such that the chamber is formed by the wall and the patient's body, According to yet another embodiment, the medical device further comprises the body port, and the wall port is connected to a first portion of the wall, and the body port is connected to a second portion of the wall, and wherein the wall port and body port are adapted be interconnected to form an interconnected port.

According to one embodiment, the wall port and body port are positioned relative to each other such that an object is displaceable from outside of the chamber, through the wall port, into the chamber, and through the body port into the patient when the surgical procedure is performed.

According to one embodiment, the wall port is displaceable between a first position, in which the wall port is situated relatively close to the tissue or skin of the patient, and a second position, in which the wall port is situated more remote from the skin of the patient than in the first position.

According to one embodiment, the wall port is adapted to be locked to the body port.

According to one embodiment, at least one of the wall port and body port comprises a penetrable self sealing gel, such that an object or hand can be inserted through the wall port while maintaining the sterile environment.

According to one embodiment, the chamber is adapted to hold a fluid having a pressure exceeding atmospheric pressure.

According to one embodiment, the medical device further comprises a vacuum sealing member adapted to hold a pressure less than atmospheric pressure between the first wall portion and the patient's skin to seal between the first wall portion and the patient's skin. The vacuum sealing member may be adapted to create a substantially airtight seal between the wall portion and the skin of the patient, to enable an incision to be performed through the skin of the patient in sterile environment such that a fluid connection between a cavity within the patient and the chamber can be created.

According to one embodiment, the medical device further comprises at least one of: an airlock placed separate from the wall port and an airlock integrated in the wall port for allowing passage of objects between the chamber and the outside of the chamber.

According to one embodiment, at least one of the wall and body port is selected from a group consisting of laparoscopic ports, surgical glove integrated ports, and holding devices integrated ports.

According to one embodiment, at least one of the wall port and the body port comprises a multi-port comprising at least two ports.

According to one embodiment, at least one of the wall port and body port comprises an elastic or flexible membrane adapted to, in a non-compressed state, seal between the chamber and the environment outside the chamber, and in a compressed state enable a hand or an object to be inserted through the membrane.

According to one embodiment, the medical device further comprising a sealing device having a first sealing member adapted to be positioned at the inside of the patient's skin around an incision to be performed in the skin and a second sealing member adapted to be positioned at outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

According to one embodiment, the medical device further comprises a fluid tempering device adapted to temper a fluid within the chamber to a temperature different from the temperature of the environment outside of the chamber.

According to one embodiment, the medical device further comprises a sterilization device for directly or indirectly sterilizing a fluid contained in the chamber.

In any of the embodiments herein, the medical device may further comprise at least one inlet provided in the wall for supplying a fluid into the chamber, and at least one outlet provided in the wall for discharging the fluid from the chamber. The medical device may further comprises a pump adapted to circulate the fluid from the outlet to the inlet.

Any of the body ports described in relation to the medical device may be body multi ports comprising at least two ports adapted to enable passage of at least one of; one or more tools, one or more devices and one or more parts of the human body, from outside of the patient's body to inside of the patient's body or the opposite direction. A body port may further comprise one port adapted to enable passage of at least one of; one or more tools, one or more devices and one or more parts of the human body, from outside of the patient's body to inside of the patient's body or the opposite direction.

The endoscopic instruments described herein may for example be endoscopic graspers, endoscopic claw graspers, an endoscopic stone graspers, an endoscopic needle holders, an endoscopic hooks, a cameras, scissors, knives, an ultrasound dissectors, suction instruments, endoscopic dissectors or endoscopic diathermy instruments.

The medical device may in any of the embodiments have a wall comprising a transparent layer enabling viewing into the chamber of the medical device.

A medical device for performing a surgical procedure on a patient is provided. The medical device comprises a wall adapted to be at least partially applied on the patient's body to form a chamber, in which a sterile environment can be maintained. The chamber is adapted to encompass part of the surgical procedure to be performed. A portion of the wall, directly or indirectly forms an elongated tubular enclosure having a single open end. The enclosure extends in the chamber and is adapted to fit a portion of an extremity of the patient inserted into the enclosure through the open end, such that the surgical procedure can be performed on the portion of the patient's extremity. By the design, a separate environment isolated from the ambient environment can be maintained which makes it possible to have a specially adapted fluid within the chamber and/or maintaining a sterile environment in proximity of the surgical procedure, even if the ambient environment is far from sterile.

According to one embodiment, the wall is at least partially collapsible, and the collapsible wall could be adapted to be inflated by a fluid. By the wall being at least partially collapsible, it may be packaged in a smaller package and may be flexible to adapt to the surroundings or enable the surgeon to move portions of the wall during the procedure.

According to one embodiment, the medical device further comprises a non-collapsible transparent window provided in the wall to enable viewing into the sterile environment. And the transparent window may be equipped with cleaning means, for cleaning the non-collapsible transparent window during the procedure such that visibility to inside the chamber is maintained.

According to one embodiment, the medical device further comprises at least one glove integrated in the wall such that a surgeon is able to use the glove from outside the chamber to make manual manipulations inside the chamber while maintaining sterile environment in the chamber.

According to one embodiment, the medical device further comprises an instrument holder adapted to retain instruments within the chamber.

According to one embodiment, the medical device further comprises at least one sealing device adapted to seal between the skin of the extremity of the patient and at least one of the wall and enclosure.

According to one embodiment, the sealing device comprises a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

According to one embodiment, the sealing device comprises a pressure sealing member attached to at least one of the wall and enclosure and adapted to press against the patient's skin to create a pressure sealing between the skin of the patient's extremity and at least one of the wall and enclosure, and wherein the pressure sealing member is adapted to be hydraulically, pneumatically or mechanically forced against the patient's skin.

According to one embodiment, the medical device further comprises an adhesive adapted to provide fixation of at least one of the wall and enclosure to the skin of the patient and/or sealing between the skin of the patient and at least one of the wall and enclosure.

According to one embodiment, the medical device further comprises an air evacuation system adapted to evacuate air from the interior of the enclosure, when the portion of the patient's extremity is placed in the enclosure.

According to another embodiment, the medical device further comprises an air evacuation system adapted to evacuate air from the vacuum sealing member.

According to yet another embodiment, the medical device further comprises a body multi-port adapted to be placed inside the chamber in an incision in the skin of the patient and comprising at least two body ports adapted to enable passage of an object between the chamber and the inside of the patient's body via the incision.

According to one embodiment, the medical device further comprises at least one wall port provided in the wall enabling passage of an object between the chamber and the environment outside of the chamber. The wall port comprises at least one of an elastic membrane and a flexible membrane, the membrane is adapted to, in a non-compressed state, seal between the chamber and the environment outside of the chamber, and in a compressed state enable a hand or object to be inserted through the membrane.

According to one embodiment, the medical device further comprises a sealing device having a first sealing member adapted to be positioned at the inside of the patient's skin around an incision cut in the patient's skin made from the chamber, and a second sealing member adapted to be positioned at the outside of the patient's skin around the incision in the chamber, and at least one of a flexible and spring-loaded and elastic connecting member sealingly interconnecting the first and second sealing members. The at least one of the flexible and spring-loaded and elastic connecting member seals between at least one of the second sealing member and the skin of the patient, and the first sealing member and tissue of the patient.

According to one embodiment, the medical device further comprises a fluid tempering device adapted to temper a fluid to be used within the chamber to a temperature different from the temperature outside of the chamber.

According to one embodiment, the medical device further comprises a sterilization device for directly or indirectly sterilizing a fluid contained in the chamber.

According to one embodiment, the medical device further comprises at least one inlet provided in the wall for supplying a fluid into the chamber, at least one outlet provided in the wall for discharging the fluid from the chamber, and a pump adapted to circulate the fluid from the outlet to the inlet.

The object, according to any of the embodiments herein, could for example comprise a tool, a medical device or a part of a human body.

According to yet another embodiment, the medical device further comprises an airlock sluice having a first valve and second valve for allowing passage of objects from the chamber through the first valve and further through the second valve out to the environment outside of the chamber, and vice versa.

A medical device for performing a surgical procedure on a patient is further provided. The medical device comprises a wall adapted to be applied exteriorly on the patient's body to form a chamber, in which a sterile environment can be maintained for encompassing part of the surgical procedure to be performed. The medical device further comprising at least one of a first port detachably fixed to the wall for enabling access to and manipulation within the chamber and a first inset detachably fixed to the wall and forming part of the chamber. The medical device further comprising a second port adapted to be detachably fixed to the wall, the second port having a design different from the first port, and at least one second inset adapted to be detachably fixed to the wall, the second inset having a design different from the first inset, wherein the first port is exchangeable by at least one of: the second port, the first inset and the second inset, and the first inset is exchangeable by at least one of: the first port, the second port and the second inset. By the exchangeability, different processes with different tools can take place within the chamber, whilst keeping the chamber closed and sterile.

According to one embodiment, the first inset or at least part of the first port is detachably fixed to the wall across a first hole formed in the wall. The first port comprises a valve member for closing the first hole in the wall to close the chamber. By this construction, the chamber can remain closed when the exchanging of the insets or ports takes place.

According to one embodiment, the wall is collapsible and adapted to be inflated by a fluid, and the chamber is adapted to hold a fluid having a pressure exceeding atmospheric pressure.

According to another embodiment, the wall comprises an outer wall and at least one partition wall dividing the chamber into at least a first compartment and a second compartment. The first port or first inset is fixed to the outer wall of the first compartment and the second port or second inset is fixed to the partition wall. The first port or first inset, and the first compartment and the second port or second inset function as an airlock or a sluice, such that the environment in the second compartment remains closed, when the first port or first inset is detached from the outer wall of the first chamber.

According to another embodiment, the medical device further comprises at least one coupling for attaching and detaching any one of the ports or insets. The coupling could comprise a valve member.

According to another embodiment, the medical device further comprises an adhesive adapted to provide at least one of: (a) fixation of the wall to the skin of the patient and (b) sealing between the wall and the skin of patient.

According to yet another embodiment, the medical device further comprises an airlock provided in the wall to allow passage of an object between the chamber and the environment while maintaining sterile conditions in the chamber.

The first or second ports in any of the embodiments herein are selected from a group consisting of: laparoscopic ports, hand access ports and multi-ports.

According to yet another embodiment, the inset is adapted to form part of the wall forming the chamber such that the sterile environment can be maintained in the chamber. The inset could be selected from a group consisting of: indentations, surgical gloves, bellows, elastic membranes and holding devices.

According to one embodiment, the wall comprises a free top wall portion and a bottom wall portion adapted to contact the patient's skin surface to surface. The chamber is defined by the top and bottom wall portions, and the bottom wall portion is adapted to be attached to the patient's body prior to the start of the surgical procedure, such that an incision in the patient can be performed inside the chamber through the bottom wall portion and the skin of the patient.

According to another embodiment, the medical device further comprises a body multi-port adapted to be placed inside the chamber in an incision in the skin of the patient, the body multi-port comprises at least two ports adapted to enable passage of an object between the chamber and the inside of the patient's body via the incision.

According to yet another embodiment, each port comprises at least one of an elastic membrane and a flexible membrane, and the membrane is adapted to, in a non-compressed state, seal between the chamber and the environment outside the chamber, and in a compressed state enable a hand or an object to be inserted through the membrane.

According to another embodiment, the medical device further comprises a sealing device having a first sealing member adapted to be positioned at the inside of the patient's skin around an incision cut in the patient's skin within the chamber, a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

The medical device could further comprises a fluid tempering device adapted to temper a fluid within the chamber to a temperature different from the temperature outside of the chamber and/or a sterilization device for directly or indirectly sterilizing a fluid contained in the chamber.

According to yet another embodiment, the medical device further comprises at least one inlet provided in the wall for supplying a fluid into the chamber, at least one outlet provided in the wall for discharging the fluid from the chamber, and a pump adapted to circulate the fluid from the outlet to the inlet.

The medical device could further comprise a coupling mounted on the wall or sealing device and adapted to detachably attach any one of the ports or insets to the wall or sealing device to enable exchange of and removal of the port or inset.

According to another embodiment, the medical device further comprises a body port adapted to be placed in an incision cut in the skin of the patient within the chamber to enable passage between the chamber and the inside of the patient's body.

According to another embodiment, the medical device further comprises an elastic hole device adapted to be placed in an incision cut in the skin of the patient within the chamber and adapted to be continuously open for enabling passage between the chamber and the inside of the patient's body. The elastic hole device could be deformable for altering the shape of the open hole.

According to another embodiment, the medical device could further comprise an airlock sluice having a first valve and second valve for allowing passage of an object from the chamber through the first valve and further through the second valve out to the environment outside of the chamber, and vice versa.

The object according to any of the embodiments herein could for example comprise a tool, a medical device or a human body part.

A medical device for performing a surgical procedure on a patient is provided. The medical device comprises a wall adapted to be at least partially applied on the patient's body to form a chamber, in which a sterile environment can be maintained for encompassing part of the surgical procedure to be performed, and at least one non-collapsible transparent window provided in the wall for enabling viewing into the chamber. The non-collapsible transparent window enables visual inspection of the chamber irrespectively of the degree of inflation provided to the medical device.

According to one embodiment, the wall of the medical device is at least partially collapsible and inflatable.

The medical device could comprise a cleaning device for cleaning the transparent window from the inside of the chamber since the transparency otherwise might be obstructed by liquids from within the chamber getting stuck on the window.

The cleaning device could for example comprise a fluid conduit for supplying a cleaning fluid to assist in the cleaning of the transparent window, and/or a window contacting member adapted to mechanically remove objects from the window.

The collapsible wall could be adapted to be inflated by a fluid, and the transparent window could be positioned in the collapsible wall such that the window enables accurate viewing into the chamber where the surgical procedure is to be performed, when the wall is inflated. The chamber may be adapted to hold a fluid having a pressure exceeding atmospheric pressure.

The medical device could further comprise an airlock provided in the wall to allow passage of an object between the chamber and the outside of the chamber while maintaining sterile environment in the chamber.

According to one embodiment, the collapsible wall in any of the embodiments herein could comprise a bottom wall portion adapted to contact the skin of the patient, when the wall is applied on the patient's body, and wherein the bottom wall portion comprises at least one of: an adhesive for affixing the wall to the skin of the patient and a sealing member for sealing between the wall and the skin of the patient.

The medical device could comprise a body multi-port adapted to be placed from inside the chamber in an incision in the skin of the patient, wherein the body multi-port comprises at least two body ports adapted to enable passage of an object between the chamber and the inside of the patient's body.

The object according to any of the embodiments herein could comprise at least one of a tool, a medical device and a part of the patient's body.

According to one embodiment, the medical device could further comprise at least one wall port placed in the wall enabling passage between the chamber and the outside of the chamber. The wall port comprises at least one of an elastic membrane and a flexible membrane and the membrane could be adapted to, in a non-compressed state, seal between the chamber and the environment outside the chamber, and in an compressed state enable a hand or an object to be inserted through the membrane.

According to one embodiment, the medical device could further comprise a sealing device having a first sealing member adapted to be positioned at the inside of the patient's skin around an incision cut in the patient's skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

In one of the embodiments herein, the medical device could further comprise a fluid tempering device adapted to temper a fluid within the chamber to a temperature different from the temperature of the environment outside of the chamber and/or a sterilization device for directly or indirectly sterilizing a fluid contained in the chamber.

According to yet another embodiments, the medical device could comprise at least one inlet provided in the wall for supplying a fluid into the chamber, and at least one outlet provided in the outer wall for discharging the fluid from the chamber. The medical device could according to one embodiment further comprise a pump adapted to circulate the fluid from the outlet to the inlet.

The medical device in any of the embodiments herein could further comprise a body port adapted to be placed inside the chamber in an incision in the skin of the patient to enable passage between the chamber and the inside of the patient's body. A coupling could be provided for detachably attach the body port to the patient's skin to enable exchange and removal of the body port.

According to one embodiment, the medical device could comprise an airlock sluice having a first valve and second valve for allowing passage of objects from the chamber through the first valve and further through the second valve out to the environment outside of the chamber, and vice versa.

A medical device for performing a surgical procedure on a patient is provided. The medical device comprises a wall adapted to be at least partially applied on the patient's body to form a chamber adapted to hold a pressure exceeding atmospheric pressure for maintaining a sterile environment in which part of the surgical procedure can be performed. A portion of the wall is adapted to contact the skin of the patient to create a substantially airtight seal between the wall portion and the skin of the patient, to enable an incision to be performed through the skin of the patient in sterile environment such that a fluid connection between a cavity within the patient and the chamber can be created. The wall is adapted to maintain the seal between the wall portion and the patient's skin substantially airtight after such an incision has been performed, and the medical device is adapted to hold a pressure in the chamber, which is in fluid connection with the cavity, exceeding atmospheric pressure, when such an incision has been performed during the surgical procedure. By creating the sterile chamber prior to making the incision in the skin of the patient, the incision can be made in a sterile environment and the risk that bacteria enters the body of the patient in connection with the creation of the incision is thereby dramatically reduced.

According to one embodiment, the medical device wall comprises a top portion and a bottom portion, which is adapted to contact and press against the patient's skin, surface to surface, to seal between the bottom wall portion and the skin of the patient, and wherein the wall is adapted to allow a pressure in the chamber exceeding atmospheric pressure.

The wall of the medical device could comprise a top portion and a bottom portion, which is adapted to contact the patient's skin, surface to surface, to seal between the bottom wall portion and the skin of the patient. The bottom wall portion could be adapted to be cut through when the incision in the skin of the patient is to be performed in the sterile environment. The bottom wall portion could comprise an adhesive for fixating the wall to the patient's skin and/or sealing between the bottom wall portion and the patient.

According to one embodiment, the medical device could further comprise at least one glove integrated in the wall such that a surgeon is able to use the glove from outside the chamber to make manual manipulations inside the chamber while maintaining sterile environment in the chamber.

According to one embodiment, the medical device could comprise an airlock provided in the wall for allowing passage of an object between the chamber and the environment outside of the chamber while maintaining sterile environment in the chamber.

According to one embodiment, the medical device could further comprise a vacuum sealing member attached to the wall and adapted to provide a pressure less than atmospheric pressure between the vacuum sealing member and the patient's skin to create a vacuum sealing between the skin and the wall.

The wall of the medical device could be at least partially collapsible and adapted to be inflated by a fluid, and comprise at least one non-collapsible transparent window provided in the wall for enabling viewing into the chamber.

The chamber of the medical device could have a volume larger than 100 000 mm3 or larger than 500 000 mm3.

According to one embodiment, the medical device comprises a body multi-port adapted to be placed from inside the chamber in the incision in the skin of the patient, wherein the body multi-port comprises at least two body ports adapted to enable passage of an object between the chamber and the inside of the patient's body.

The medical device could according to one embodiment comprise at least one wall port placed in the wall for enabling passage between the chamber and the outside of the chamber. The wall port comprises at least one of an elastic membrane and a flexible membrane, and the membrane is adapted to, in a non-compressed state, seal between the chamber and the environment outside the chamber, and in an compressed state enable a hand or an object to be inserted through the membrane.

According to one embodiment, the medical device further comprises a sealing device having a first sealing member adapted to be positioned at the inside of the patient's skin around the incision and a second sealing member adapted to be positioned at outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

The medical device may further comprising a fluid tempering device adapted to temper a fluid within the chamber to a temperature different from the temperature of the environment outside of the chamber and/or a sterilization device for directly or indirectly sterilizing a fluid contained in the chamber.

The medical device could further comprise an inlet provided in the wall for supplying a fluid into the chamber, and at least one outlet provided in the outer wall for discharging the fluid from the chamber. The medical device could further comprise a pump adapted to circulate the fluid from the outlet to the inlet.

According to yet another embodiment, the medical device could comprise a body port adapted to be placed inside the chamber in the incision in the skin of the patient to enable passage between the chamber and the inside of the patient's body. The medical device could further comprise a coupling adapted to detachably attach the body port to the patient's skin to enable exchange and removal of the body port.

According to yet another embodiment, the medical device could further comprise an airlock sluice having a first valve and second valve for allowing passage of objects from the chamber through the first valve and further through the second valve out to the environment outside of the chamber, and vice versa.

A medical device for performing a surgical procedure on a patient. The medical device comprises a wall adapted to be applied at least partially on the patient's body to form a chamber by itself or together with the body of the patient in which a sterile environment can be maintained for encompassing part of the surgical procedure to be performed. The medical device further comprises a wall sealing device adapted to seal between a portion of the wall and the patient's body, when the wall is applied on the patient's body. The sealing device comprises a pressure sealing member adapted to pneumatically, hydraulically or mechanically press the wall portion against the body of the patient such that the chamber is at least substantially sealed from the ambient atmosphere allowing a pressure inside the chamber higher than ambient atmospheric pressure during the surgical procedure, thus the wall sealing device being adapted to seal the chamber, after the medical device has been applied at least partially on the patient's body, when at least one of an incision has been performed in the wall of the chamber contacting the patient's body and an incision has been performed in the skin of the patient forming part of the chamber.

According to one embodiment the medical device further comprises at least one glove integrated in the wall such that a surgeon is able to use the glove from outside the chamber to make manual manipulations inside the chamber while maintaining sterile environment in the chamber.

According to one embodiment, the medical device further comprises an airlock sluice having a first valve and second valve for allowing passage of an object from the chamber through the first valve and further through the second valve out to the environment outside of the chamber, and vice versa.

According to one embodiment, the wall comprises a top portion and a bottom portion, which is adapted to contact and press against the patient's skin, surface to surface, to seal between the bottom wall portion and the skin of the patient, and wherein the wall is adapted to allow a pressure in the chamber exceeding atmospheric pressure. The bottom wall portion could be adapted to be cut through when an incision in the skin of the patient is to be performed in sterile environment.

The medical device could according to one embodiment have a bottom wall portion comprising an adhesive for fixating the wall to the patient's skin, or sealing between the bottom wall portion and the patient.

According to one embodiment, the medical device could comprise at least one wall port placed in the wall enabling passage between the chamber and the outside of the chamber. The wall port could be detachably fixated to the wall such that the wall port can be exchanged by another wall port.

The wall of the medical device could have a wall which is at least partially collapsible and adapted to be inflated by a fluid. The medical device could comprise a non-collapsible transparent window provided in the wall for enabling viewing into the chamber. The volume of the chamber of the medical device is in some embodiments herein larger than 100 000 mm3 or larger than 500 000 mm3 to enable manipulation within the chamber.

According to one embodiment, the medical device could further comprise a body multi-port adapted to be placed from inside the chamber in an incision to be performed in the skin of the patient. The body multi-port could comprise at least two body ports adapted to enable passage of an object between the chamber and the inside of the patient's body.

According to one embodiment the medical device could further comprise at least one wall port placed in the wall enabling passage between the chamber and the outside of the chamber. The wall port could comprise at least one of an elastic membrane and a flexible membrane, and could be adapted to, in a non-compressed state, seal between the chamber and the environment outside the chamber, and in a compressed state enable a hand or an object to be inserted through the membrane.

According to one embodiment, the medical device could further comprise a body sealing device having a first sealing member adapted to be positioned at the inside of the patient's skin around an incision to be performed in the skin of the patient, and a second sealing member adapted to be positioned at the outside of the patient's skin around the incision. The medical device further comprises a spring-loaded or elastic connecting member sealingly interconnecting the first and second sealing members. The spring-loaded or elastic connecting member seals between the second sealing member and the skin of the patient or the first sealing member and tissue of the patient.

The medical device could further comprise a fluid tempering device adapted to temper a fluid within the chamber to a temperature different from the temperature of the environment outside of the chamber and/or a sterilization device for directly or indirectly sterilizing a fluid contained in the chamber.

According to one embodiment, the medical device further comprises at least one inlet provided in the wall for supplying a fluid into the chamber, and at least one outlet provided in the wall for discharging the fluid from the chamber. For this purpose, the medical device could further comprise a pump adapted to circulate the fluid from the outlet to the inlet.

According to one embodiment, the medical device further comprises a body port adapted to be placed inside the chamber in an incision to be performed in the skin of the patient to enable passage between the chamber and the inside of the patient's body.

According to one embodiment, the medical device further comprises a coupling adapted to detachably attach the body port to the patient's skin to enable exchange and removal of the body port.

The medical device could comprise an airlock sluice having a first valve and second valve for allowing passage of an object from the chamber through the first valve and further through the second valve out to the environment outside of the chamber, and vice versa.

The object in any of the embodiments herein could for example comprise a tool, a medical device or a human body part.

The medical device could further comprise a pressure device adapted to hold a pressure within the chamber exceeding atmospheric pressure.

A medical device for performing a surgical procedure on a patient is provided. The medical comprises a wall adapted to be at least partially applied on the patient's body to form a chamber, in which a sterile environment can be maintained for encompassing part of the surgical procedure to be performed. A portion of the wall, directly or indirectly forms an elongated tubular enclosure having a first and a second open end. The enclosure is adapted to fit a portion of an extremity of the patient, and the medical device is arranged such that the portion of the extremity may be inserted into the enclosure through the first open end thereof and exit the enclosure through the second open end thereof, and wherein the surgical procedure is to be performed on the portion of the patient's extremity. By the provided medical device, a chamber can be created for a part of an extremity of a patient and thereby provide a sterile environment in which a surgical procedure on the extremity can be performed.

According to one embodiment, the wall of the medical device could be at least partially collapsible and be adapted to be inflated by a fluid. The fluid could according to one embodiment be a liquid According to yet another embodiment, the chamber in the medical device could be adapted to be formed together by the wall and the patient's body, and the tubular enclosure could be adapted to encompass the chamber. The chamber could be adapted to be sealed at the first and second open end by the patient's body portion.

According to another embodiment, the chamber of the medical device could be adapted to be in communication with an operating field during the surgical procedure, when the skin of the patient has been cut in a position inside of the chamber. The wall encompassing the chamber has a wall port or wall inset mounted in a wall portion of the chamber for allowing; objects including instruments to be moved into the chamber or operating field and/or manual manipulation to be performed in the chamber or operating field.

According to another embodiment, the medical device could comprise a port or inset including two parts, a first and second part, wherein the second part comprising the wall port or wall inset and the first part comprising a body port or body inset adapted to be mounted in the cut skin of the patient to allow objects including instruments to be moved further from the chamber into the operating field and/or manual manipulation to be performed from the chamber further into the operating field.

The two parts of the port or inset could be adapted to be mounted together, touching each other forming an integrated port or inset and thereby allowing from outside the chamber; objects including instruments to be moved into the operating field and/or manual manipulation to be performed in the operating field directly from outside the chamber using the integrated port or inset. The two parts of the port or inset could further be adapted to be separated from each other to one or more positions not touching each other and thereby; to use the second part of the port or inset to allow objects including instruments to be moved into the chamber and/or manual manipulation to be performed in the chamber and further to use the first part of the port or inset to allow objects including instruments to be moved from the chamber passing the cut skin into the operating field and/or manual manipulation to be performed from the chamber through the cut skin further into the operating field.

According to another embodiment, the two parts of the port or inset of the medical device could be adapted to be locked together in at least one fixed position.

According to yet another embodiment, the medical device could be adapted to allow the surgical procedure with its operating field to be performed on the patient on at least one of; a extremity, the prolongation of the extremity, abdomen, chest, and any joint including the hip and knee joints and the joints of the upper extremity.

The chamber encompassing the surgical procedure is adapted to reduce infection risk of the surgical procedure most important for joint surgery.

In some embodiments, a non-collapsible transparent window could be provided in the wall of the medical device for enabling viewing into the sterile environment.

According to yet another embodiment, the medical device could comprise at least one glove integrated in the wall such that a surgeon is able to use the glove from outside the chamber to make manual manipulations inside the chamber while maintaining the sterile environment in the chamber.

The medical device could further comprise an instrument holder adapted to retain instruments within the chamber.

According to yet another embodiment, the medical device could comprise at least one sealing device adapted to seal between the skin of the extremity of the patient and at least one of the wall and enclosure.

According to yet another embodiment, the sealing device could comprise a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

In one embodiment, the sealing device comprises a pressure sealing member attached to at least one of the wall and enclosure and adapted to press against the patient's skin to create a pressure sealing between the skin of the patient's extremity and at least one of the wall and enclosure. The pressure sealing member could be adapted to be hydraulically, pneumatically or mechanically forced against the patient's skin.

According to another embodiment, the medical device further comprises an adhesive adapted to provide at least one of: (a) fixation of at least one of the wall and enclosure to the skin of the patient, and (b) sealing between the skin of the patient and at least one of the wall and enclosure.

In yet other embodiments, the medical device further comprises an air evacuation system adapted to evacuate air from the interior of the enclosure, when the portion of the patient's extremity is placed in the enclosure. An air evacuation system could also be provided for evacuating air from the vacuum sealing member.

According to one embodiment, the medical device further comprises a body multi-port adapted to be placed inside the chamber in an incision in the skin of the patient. The body multi-port comprises at least two body ports adapted to enable passage of an object between the chamber and the inside of the patient's body via the incision.

In yet other embodiments, the medical device further comprises at least one wall port provided in the wall enabling passage of an object between the chamber and the environment outside of the chamber. The wall port could comprise at least one of an elastic membrane and a flexible membrane, and wherein the membrane is adapted to, in a non-compressed state, seal between the chamber and the environment outside of the chamber, and in a compressed state enable a hand or an object to be inserted through the membrane.

According to one embodiment, the medical device could further comprise a sealing device having a first sealing member adapted to be positioned at the inside of the patient's skin around an incision cut in the patient's skin made from the chamber, a second sealing member adapted to be positioned at the outside of the patient's skin around the incision in the chamber, and at least one of a flexible, spring-loaded and elastic connecting member sealingly interconnecting the first and second sealing members. At least one of the flexible, spring-loaded and elastic connecting member seals between at least one of the second sealing member and the skin of the patient, and the first sealing member and tissue of the patient.

According to one embodiment, the medical device further comprises a fluid tempering device adapted to temper a fluid to be used within the chamber to a temperature different from the temperature outside of the chamber.

In yet another embodiment, the medical device further comprises a sterilization device for directly or indirectly sterilizing a fluid contained in the chamber.

In yet another embodiment, the medical device further comprises at least one inlet provided in the wall for supplying a fluid into the chamber, at least one outlet provided in the wall for discharging the fluid from the chamber, and a pump adapted to circulate the fluid from the outlet to the inlet.

In the embodiments provided herein, the object could comprise at least one of: a tool, a medical device or a part of a human body.

According to one embodiment, the medical device could further comprise an airlock sluice having a first valve and second valve for allowing passage of objects from the chamber through the first valve and further through the second valve out to the environment outside of the chamber, and vice versa.

In yet other embodiments, the elongated tubular enclosure is formed by placing the wall forming the chamber around at least a portion of the extremity of the patient. The elongated tubular enclosure could comprise a slit for placing the chamber around at least a portion of the extremity of the patient radially in relation to the length axis of the extremity. The slit could be adapted to be at least partially closed by closing elements mounted on the wall of the medical device. The closing elements could be elastic or adjustable for fixating the medical device to the extremity of the patient.

According to one embodiment, the medical device could further comprise a first and second portion located on a first and second side of the slit when the chamber is placed around at least a portion of the extremity. The first and second portions could be adapted to be interconnected by means of at least one of: an adhesive and a mechanical connecting member.

According to yet another embodiment, the medical device could comprise a wall adapted to be applied exteriorly on the patient's body to form a chamber, in which a sterile environment can be maintained for encompassing part of the surgical procedure to be performed.

A medical device for performing a surgical procedure on a patient is provided. The medical device comprises a wall adapted to at least partially be applied on the patient's body to form a chamber by itself or together with the patient's body, in which a sterile environment can be maintained for encompassing part of the surgical procedure to be performed. A portion of the wall is adapted to contact the patient's skin when the surgical procedure is to be performed, and a vacuum sealing member adapted to hold a pressure less than atmospheric pressure between the wall portion and the patient's skin to seal between the wall portion and the patient's skin.

According to one embodiment, the vacuum sealing member is adapted to create a substantially airtight seal between the wall portion and the skin of the patient, to enable an incision to be performed through the skin of the patient in sterile environment such that a fluid connection between a cavity within the patient and the chamber is formed.

According to another embodiment, the medical device further comprises an airlock provided in the wall for allowing passage of an object between the chamber and the environment outside of the chamber when the vacuum sealing member is sealing between the skin of the patient and the wall portion.

According to one embodiment, the wall is at least partially collapsible and could be adapted to be inflated by a fluid, such as a liquid or a gaseous fluid. The medical device could be adapted to hold a pressure within the chamber exceeding atmospheric pressure.

According to one embodiment, the medical device comprises at least one glove integrated in the wall such that a surgeon is able to use the glove from outside the chamber to make manual manipulations inside the chamber while maintaining sterile environment in the chamber.

According to one embodiment, the medical device further comprises an adhesive adapted to provide at least one of: (a) fixation of at least one of the wall and enclosure to the skin of the patient, and (b) sealing between the skin of the patient and at least one of the wall and enclosure.

According to yet another embodiment, the medical device further comprises at least one wall port placed in the wall enabling passage between the chamber and the outside of the chamber. The wall port could be detachably fixated to the wall such that the wall port can be exchanged by another wall port.

According to another embodiment, the medical device could comprise at least one non-collapsible transparent window provided in the wall for enabling viewing into the chamber. The non-collapsible transparent window could be positioned in the collapsible wall such that the window enables accurate viewing into the chamber where the surgical procedure is to be performed, when the wall is inflated.

According to one embodiment, the medical device further comprises a body multi-port adapted to be placed from inside the chamber in an incision to be performed in the skin of the patient. The body multi-port could comprise at least two body ports adapted to enable passage of an object between the chamber and the inside of the patient's body.

According to yet another embodiment, the medical device could comprise at least one wall port placed in the wall enabling passage between the chamber and the outside of the chamber. The wall port could comprise at least one of an elastic membrane and a flexible membrane, and the membrane could be adapted to, in a non-compressed state, seal between the chamber and the environment outside the chamber, and in a compressed state enable a hand or an object to be inserted through the membrane.

According to another embodiment, the medical device further comprises a sealing device having a first sealing member adapted to be positioned at the inside of the patient's skin around an incision to be performed in the skin and a second sealing member adapted to be positioned at outside of the patient's skin around the incision, and a spring-loaded or elastic connecting member sealingly interconnecting the first and second sealing members. The spring-loaded or elastic connecting member seals between at least one of: (a) the second sealing member and the skin of the patient, and (b) the first sealing member and tissue of the patient.

The medical device could further comprise a fluid tempering device adapted to temper a fluid within the chamber to a temperature different from the temperature of the environment outside of the chamber and/or a sterilization device for directly or indirectly sterilizing a fluid contained in the chamber.

According to one embodiment, the medical device could further comprise at least one inlet provided in the wall for supplying a fluid into the chamber, and at least one outlet provided in the wall for discharging the fluid from the chamber. The medical device could further comprise a pump adapted to circulate the fluid from the outlet to the inlet.

According to one embodiment, the medical device further comprises a body port adapted to be placed inside the chamber in an incision to be performed in the skin of the patient to enable passage between the chamber and the inside of the patient's body.

According to one embodiment, the medical device further comprises a coupling adapted to detachably attach the body port to the patient's skin to enable exchange and removal of the body port.

According to one embodiment, the medical device further comprises an airlock sluice having a first valve and second valve for allowing passage of an object from the chamber through the first valve and further through the second valve out to the environment outside of the chamber, and vice versa.

A medical device for performing a surgical procedure on a patient is provided. The medical device comprises a wall, adapted to be at least partially applied on the patient's body and further adapted to form a chamber alone or together with the patient's body, in which a sterile environment can be maintained for encompassing part of the surgical procedure to be performed. A portion of the wall is adapted to be in contact with the patient's skin, and at least one inset or port attached to the wall and adapted to enable manipulation within the chamber. The inset or port is displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

According to one embodiment, the wall forming the chamber comprises a first and second interconnecting member, and the first interconnecting member is placed at the first position, and the second interconnecting member is placed in the second position. The second interconnecting member is adapted to connect to the first interconnecting member for locking the inset or wall port in the first position.

According to another embodiment, the port or inset placed in the wall is defined as the wall port or wall inset, and the medical device further comprises a body port or body inset adapted to be mounted in another wall portion or the skin or tissue of the patient. The first interconnecting member is adapted to be positioned in connection with a body port or body inset, and the wall port and the body port is adapted to form a integrated port when the first and second interconnecting members are connected in the first position.

In another embodiment, the wall port and body port could comprise at least one of an elastic membrane and a flexible membrane, and the membrane could be adapted to, in a non-expanded state, provide a seal, and in an expanded state, enable a hand or an object to be inserted through the membrane.

In one embodiment, the wall is at least partially flexible to enable the wall to flex when the wall inset or wall port is moved between the first and second positions.

The chamber could assumes a first volume, when the inset or wall port is in the first position, and a second volume larger than the first volume, when the inset or wall port is in the second position.

According to one embodiment, the chamber of the medical device could have a circular, tubular or kidney shaped cross-section.

At least one of the wall inset and body inset, could comprise at least one glove integrated in the wall such that a surgeon is able to use the glove from outside the chamber to make manual manipulations inside the chamber while maintaining sterile environment in the chamber.

According to one embodiment, at least one of; the wall inset or at least part of the wall port could be detachably fixed to the wall across a hole formed in the wall. The wall port could comprise a valve member for closing the hole in the wall port to close the chamber.

In one of the embodiments, the wall is collapsible and the chamber adapted to be inflated by a fluid. The chamber could further be adapted to hold a fluid having a pressure exceeding atmospheric pressure.

According to another embodiment, the medical device further comprises at least one coupling for attaching and detaching any one of the ports or insets.

The medical device could further comprise an airlock or liquid lock provided in the wall for allowing passage of an object between the chamber and the environment outside of the chamber or vice versa.

In yet another embodiment, a portion of the wall could be adapted to be applied on the patient's body when the surgical procedure is to be performed and further comprise a vacuum sealing member adapted to hold a pressure less than atmospheric pressure between the wall portion and the patient's skin to seal between the wall portion and the patient's skin.

The vacuum sealing member could be adapted to create a substantially airtight seal between the wall portion and the skin of the patient, to enable an incision to be performed through the skin of the patient in sterile environment such that a fluid connection between a cavity within the patient and the chamber can be created.

In yet another embodiment, a portion of the wall could be adapted to be applied on the patient's body when the surgical procedure is to be performed. The medical device could further comprise a pressure sealing member adapted to hold a pressure above atmospheric pressure between the wall portion and the patient's skin to seal between the wall portion and the patient's skin.

In yet another embodiment, the medical device could further comprise a body multi-port adapted to be placed from inside the chamber in an incision to be performed in the skin of the patient, wherein the body multi-port comprises at least two body ports adapted to enable passage of an object between the chamber and the inside of the patient's body.

A wall port of the medical device could enable passage of an object between the chamber and the outside of the chamber, and the wall port could comprise at least one of an elastic membrane and a flexible membrane, and the membrane could be adapted to, in a non-expanded state, seal between the chamber and the environment outside the chamber, and in an expanded state enable a hand or an object to be inserted through the membrane.

In yet another embodiment, the medical device further comprises a further sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

In yet another embodiment, the medical device further comprises a fluid tempering device adapted to temper a fluid within the chamber to a temperature different from the temperature of the environment outside of the chamber and/or a sterilization device for directly or indirectly sterilizing a fluid contained in the chamber.

The medical device could further comprise at least one inlet provided in the wall for supplying a fluid into the chamber, and at least one outlet provided in the wall for discharging the fluid from the chamber. The medical device could also comprise a pump adapted to circulate the fluid from the outlet to the inlet.

According to one embodiment, the medical device comprises a body port adapted to be placed inside the chamber in an incision to be performed in the skin of the patient to enable passage of an object between the chamber and the inside of the patient's body.

In yet another embodiment, the medical device further comprises at least one of an airlock sluice and a liquid lock sluice, comprising a first valve and second valve and a sluice chamber placed in between the first and second valve, for allowing passage of objects from the chamber through the first valve and further through the second valve out to the environment outside of the chamber, and vice versa.

The medical device could further comprise a coupling adapted to detachably attach the body port to the patient's skin to enable exchange and removal of the body port.

In yet another embodiment, the medical device could be adapted to contact the skin of the patient to create a substantially airtight seal between the wall portion and the skin of the patient, to enable an incision to be performed through the skin of the patient in sterile environment such that a fluid connection between a cavity within the patient and the chamber can be created, when the surgical procedure is performed.

The medical device could according to one embodiment, be adapted to enable the incision to be performed through the portion of the wall adapted to contact the skin of the patient and the skin of the patient in sterile environment such that a fluid connection between a cavity within the patient and the chamber can be created, when the surgical procedure is performed.

The medical device could further comprise a filtering unit to filter the circulating the fluid especially from blood and operating matters.

In one embodiment, at least one of; the wall port or the body port, comprises a multi-port comprising at least two body ports adapted to enable passage of an object to the inside of the patient's body, during the surgical procedure.

According to one embodiment, the medical device comprises at least one of an airlock sluice and a liquid lock sluice, comprising a first valve and second valve. The first valve is mounted in at least one of the skin or tissue of the patient and the portion of the wall adapted to directly or indirectly form the elongated tubular enclosure, and wherein the second valve is mounted in the wall.

A medical device for performing a surgical procedure on a patient is provided. The medical device comprises a wall adapted to be at least partially applied on the patient's body to form a chamber together with the patient's body, in which a sterile environment can be maintained for encompassing part of the surgical procedure to be performed. The medical device further comprises a wall port placed in a portion of the wall, a body port adapted to be placed in an incision in the patient's body, and a sealing device connected to the wall and adapted to seal against the skin of the patient. The wall and body ports are positioned relative to each other such that an object is displaceable from outside of the chamber, through the wall port, into the chamber, through the body port, and further through an incision in the skin of the patient into the patient, when the surgical procedure is performed. By having a construction with two ports and a chamber in between, objects can be transferred from outside of the chamber to inside of the chamber and further into the body of the patient.

According to one embodiment, the wall and body ports are positioned relative to each other such that an elongated object is longitudinally displaceable through the wall and body ports.

According to one embodiment, the wall port is displaceable between a first position, in which the wall port is situated relatively close to the body port, and a second position, in which the wall port is situated more remote from the body port.

According to one embodiment, the wall port is adapted to be locked to the body port.

According to another embodiment, the wall port comprises a penetrable self sealing gel, such that an object or hand can be inserted through the wall port while maintaining the sterile environment.

According to yet another embodiment, the medical device further comprises an additional port, and the at least one of the wall port and body port is exchangeable by the additional port.

According to another embodiment, wherein the chamber is adapted to hold a fluid having a pressure exceeding atmospheric pressure.

According to another embodiment, a portion of the wall comprises a vacuum sealing member adapted to hold a pressure less than atmospheric pressure between the first wall portion and the patient's skin to seal between the first wall portion and the patient's skin. The vacuum sealing member could be adapted to create a substantially airtight seal between the wall portion and the skin of the patient, to enable an incision to be performed through the skin of the patient in sterile environment such that a fluid connection between a cavity within the patient and the chamber can be created.

The medical device could further comprise at least one of: an airlock placed separate from the wall port and an airlock integrated in the wall port for allowing passage of objects between the chamber and the outside of the chamber.

The wall and/or body ports could be selected from a group consisting of: laparoscopic ports, surgical glove integrated ports, and holding devices integrated ports.

The body port in any of the embodiments herein could comprise a body multi-port adapted to be placed from inside the chamber in an incision to be performed in the skin of the patient. The body multi-port comprises at least two body ports adapted to enable passage of an object between the chamber and the inside of the patient's body.

According to one embodiment, the wall port comprises at least one of an elastic membrane and a flexible membrane. The membrane could be adapted to, in a non-compressed state, seal between the chamber and the environment outside the chamber, and in a compressed state enable a hand or an object to be inserted through the membrane.

In some embodiments, the medical device further comprises a sealing device having a first sealing member adapted to be positioned at the inside of the patient's skin around an incision to be performed in the skin and a second sealing member adapted to be positioned at outside of the patient's skin around the incision, and a spring-loaded or elastic connecting member sealingly interconnecting the first and second sealing members. The spring-loaded or elastic connecting member seals between the second sealing member and the skin of the patient, and/or the first sealing member and tissue of the patient.

The medical device could further comprise a fluid tempering device adapted to temper a fluid within the chamber to a temperature different from the temperature of the environment outside of the chamber and/or a sterilization device for directly or indirectly sterilizing a fluid contained in the chamber.

According to one embodiment, the medical device further comprises at least one inlet provided in the wall for supplying a fluid into the chamber, and at least one outlet provided in the wall for discharging the fluid from the chamber. The medical device could further comprise a pump adapted to circulate the fluid from the outlet to the inlet.

According to one embodiment, the body port could be adapted to be placed inside the chamber in an incision to be performed in the skin of the patient to enable passage between the chamber and the inside of the patient's body.

In one embodiment, the medical device further comprises a coupling adapted to detachably attach the body port to the patient's skin to enable exchange and removal of the body port.

The wall port could be able to be positioned in the wall portion such that it allows cutting through the patient's skin via the wall port to create the incision in the patient's skin, when the wall is applied on the patient's body.

According to one embodiment, the wall portion allows cutting through the wall portion and the patient's skin to create the incision in the patient's skin, when the wall is applied on the patient's body.

The body port of the medical device could be adapted to be fitted in the patient's skin after the incision has been made, when the medical device is applied on the patient's body.

A medical device for performing a surgical procedure on a patient is provided. The medical device comprises a wall adapted to be at least partially applied on the patient's body to form a first chamber, in which a sterile environment can be maintained for encompassing part of the surgical procedure to be performed. A portion of the wall is adapted to be in contact with the skin of the patient when the surgical procedure is performed. The medical device further comprises an airlock sluice having a first and second valve and a second chamber located between the valves and able to form part of the sterile environment. The airlock sluice is adapted to allow reversible passage of objects from the chamber through the first valve into the second chamber of the sluice and further through the second valve out to the environment outside of the sterile environment, and vice versa, whereby the risk of contamination is reduced. The first valve is adapted to be opened for an object to pass through whilst the second valve remains closed by itself, thus without any object passing through the second valve.

According to another embodiment, the medical device is adapted to hold a pressure within the chamber exceeding atmospheric pressure.

According to yet another embodiment, the airlock sluice has a volume larger than 100 000 mm3 or larger than 500 000 mm3.

According to another embodiment, the wall is at least partially collapsible and adapted to be inflated by a fluid.

At least one non-collapsible transparent window could furthermore be provided in the wall for enabling viewing into the chamber. At least one glove integrated in the wall could be provided, such that a surgeon is able to use the glove from outside the chamber to make manual manipulations inside the chamber while maintaining sterile environment in the chamber.

The medical device could further comprise an instrument holder for retaining instruments within the chamber.

According to one embodiment, at least one non-collapsible transparent window could be provided in the collapsible wall and positioned in the wall such that the window enables accurate viewing into the chamber where the surgical procedure is to be performed, when the wall is inflated.

According to yet another embodiment, the medical device further comprises a vacuum sealing member adapted to hold a pressure less than atmospheric pressure between the wall and the patient's skin to seal between the wall and the patient's skin.

According to yet another embodiment, the medical device further comprises a pressure sealing member adapted to press against the patient's skin to create a pressure sealing between the skin of the patient and the wall. The pressure sealing member is adapted to be hydraulically, pneumatically or mechanically forced against the patient's skin.

In yet another embodiment, the medical device further comprises an adhesive adapted to provide at least one of: fixation of the wall to the skin of the patient and sealing between the skin of the patient and the wall.

In yet another embodiment, the medical device further comprises a body multi-port adapted to be placed inside the chamber in an incision in the skin of the patient. The body multi-port comprises at least two body ports adapted to enable passage of an object between the chamber and the inside of the patient's body via the incision.

According to one embodiment, the medical device comprises at least one wall port provided in the wall enabling passage of an object between the chamber and the environment outside of the chamber. The wall port comprises at least one of an elastic membrane and a flexible membrane, and the membrane is adapted to, in a non-compressed state, seal between the chamber and the environment outside of the chamber, and in a compressed state enable a hand or an object to be inserted through the membrane.

In another embodiment, the medical device further comprises a sealing device having a first sealing member adapted to be positioned at the inside of the patient's skin around an incision cut in the patient's skin within the chamber, a second sealing member adapted to be positioned at the outside of the patient's skin around the incision, and a spring-loaded or elastic connecting member sealingly interconnecting the first and second sealing members. The spring-loaded or elastic connecting member seals between at least one of: (a) the second sealing member and the skin of the patient, and (b) the first sealing member and tissue of the patient.

The medical device could further comprise a fluid tempering device adapted to temper a fluid within the chamber to a temperature different from the temperature outside of the chamber.

In yet another embodiment, the medical device further comprises a sterilization device for directly or indirectly sterilizing a fluid contained in the chamber.

In other embodiments, the medical device further comprising at least one inlet provided in the wall for supplying a fluid into the chamber, at least one outlet provided in the wall for discharging the fluid from the chamber, and a pump adapted to circulate the fluid from the outlet to the inlet.

The medical device could further comprise a body port adapted to be placed inside the chamber in an incision to be performed in the skin of the patient to enable passage of an object between the chamber and the inside of the patient's body.

The medical device could further comprise a coupling adapted to detachably attach the body port to the patient's skin to enable exchange and removal of the body port.

An object herein, could comprise a tool, a surgical device or a human body part.

A medical device for performing a surgical procedure on a patient is provided. The medicals device comprises a wall adapted to be at least partially applied on the patient's body to form a chamber, in which a sterile environment can be maintained for encompassing part of the surgical procedure to be performed. A portion of the wall is adapted to contact the skin of the patient to create a substantially airtight seal between the wall portion and the skin of the patient, when an incision has been performed substantially perpendicularly through the skin of the patient such that a fluid connection between a cavity within the patient and the chamber can be created, when the surgical procedure is performed. The medical device further comprises a wall port or inset positioned in a portion of the wall and a sealing device having a first sealing member adapted to be positioned in the cavity inside the patient's body wall around the incision. The medical device also comprises a second sealing member adapted to be positioned at the outside of the patient's skin around the incision and a sealing connecting member interconnecting the first and second sealing members. The sealing device is adapted to seal between at least one of: (a) the second sealing member and directly or indirectly the outside of the patient's skin, and (b) the first sealing member and tissue inside the cavity by exerting pressure from the inside of the cavity in the direction of the skin of the patient, when the surgical procedure is performed.

According to one embodiment, the wall is at least partially collapsible and adapted to be inflated by a fluid. The chamber created by the wall could be adapted to hold a fluid having a pressure exceeding atmospheric pressure.

According to another embodiment, the medical device further comprises at least one non-collapsible transparent window provided in the wall for enabling viewing into the chamber, which could be positioned in the wall such that the window enables accurate viewing into the chamber where the surgical procedure is to be performed, when the wall is inflated.

The medical device could further comprise at least one glove integrated in the wall such that a surgeon is able to use the glove from outside the chamber to make manual manipulations inside the chamber while maintaining sterile environment in the chamber.

According to one embodiment, the medical device further comprises an instrument holder for retaining instruments within the chamber.

According to another embodiment, the medical device further comprises a vacuum sealing member adapted to hold a pressure less than atmospheric pressure between the wall and the patient's skin to seal between the wall and the patient's skin.

According to another embodiment, the sealing device of the medical device is adapted to press against the skin of the patient.

According to another embodiment, the medical device further comprises an adhesive adapted to provide at least one of: (a) fixation of the wall to the skin of the patient and (b) sealing between the wall and the skin of patient.

In yet another embodiment, the medical device further comprises a body multi-port adapted to be placed inside the chamber in an incision in the skin of the patient. The body multi-port comprises at least two ports adapted to enable passage of an object between the chamber and the inside of the patient's body via the incision.

According to another embodiment, the medical device further comprising at least one wall port provided in the wall enabling passage of an object between the chamber and the environment outside of the chamber. The wall port comprises at least one of an elastic membrane and a flexible membrane, and the membrane is adapted to, in a non-compressed state, seal between the chamber and the environment outside of the chamber, and in a compressed state enable a hand or an object to be inserted through the membrane.

According to another embodiment, the sealing connecting member is spring-loaded or elastic to seal between at least one of the second sealing member and the skin of the patient, and the first sealing member and tissue of the patient.

The medical device could further comprise fluid tempering device adapted to temper a fluid within the chamber to a temperature different from the temperature outside of the chamber and/or a sterilization device for directly or indirectly sterilizing a fluid contained in the chamber.

In another embodiment, the medical device comprising at least one inlet provided in the wall for supplying a fluid into the chamber, at least one outlet provided in the wall for discharging the fluid from the chamber, and a pump adapted to circulate the fluid from the outlet to the inlet.

The medical device could further comprise a body port adapted to be placed inside the chamber in an incision to be performed in the skin of the patient to enable passage of an object between the chamber and the inside of the patient's body.

According to yet another embodiment, the medical device could further comprise a coupling adapted to detachably attach the body port to the patient's skin to enable exchange and removal of the body port.

An object could herein comprise a tool, a medical device or a human body part.

In one embodiment, the medical device further comprises an airlock sluice having a first valve and second valve for allowing passage of objects from the chamber through the first valve and further through the second valve out to the environment outside of the chamber, and vice versa.

The medical device could further comprise a further sealing device adapted to seal between the wall of the medical device and the skin of the patient prior to the incision, such that the incision can be performed in the sterile environment. The further sealing device could comprise an adhesive layer and the incision could be performed through the adhesive layer.

A surgical port adapted to be at least partially placed in an incision cut in a patient's body is provided. The surgical port comprises a first and second part adapted be interconnected to form the surgical port. The second part is adapted to be disconnected from the first part and the first part is connected to a first portion of a flexible wall. The second part is connected to a second portion of the flexible wall, and the flexible wall is adapted to form a chamber.

The chamber could have a first volume when the first and second parts are interconnected and a second volume when the second part is disconnected from the first part. The second volume could be larger than the first volume, the second volume could be larger than 500 000 mm3.

According to one embodiment of the surgical port, the chamber formed by the flexible wall could be adapted to hold a pressure exceeding atmospheric pressure.

The first part in any of the embodiments herein could comprise a sealing member for sealing between the ambient environment and the chamber whilst allowing a hand or an object to pass from the ambient environment to the chamber, and the second part could comprise a sealing member for sealing between the chamber and a cavity of the patient's body whilst allowing a hand or an object to pass from the chamber to the cavity of the patients body.

According to another embodiment, the first and second sealing members could be adapted to seal against a pressure in the chamber exceeding atmospheric pressure.

In yet another embodiment, at least one of the first and second parts of the port could comprise an elastic or flexible membrane adapted to, in a non-compressed state, provide sealing, and in a compressed state enable a hand or an object to be inserted through the membrane.

According to one embodiment, the first part of the surgical port comprises a first elastic or flexible membrane and the second part comprises a second elastic or flexible membrane, and the first and second membranes could be adapted to be placed tightly together such that they act as a single elastic or flexible membrane adapted to, in a non-compressed state, provide sealing, and in a compressed state enable a hand or an object to be inserted through the membrane.

According to one embodiment, at least one of said first and second part could comprise a penetrable self sealing gel, such that an object or hand can be inserted through the port while maintaining a seal.

According to one embodiment, the first part could comprise a first penetrable self sealing gel and the second part could comprises a second penetrable self sealing gel, and the first and second penetrable self sealing gels could be adapted to be placed tightly together such that they act as a single penetrable self sealing gel adapted to, in a non-compressed state, provide sealing, and in a compressed state enable a hand or an object to be inserted through the self sealing gel while maintaining the seal.

According to one embodiment, the port could be adapted to receive and fixate an inset or the surgical port could further comprise a detachable inset adapted to be fixated to the surgical port.

In one embodiment the inset comprises at least one of: a surgical glove and an instrument mount. According to yet another embodiment, the surgical port could further comprise at least one coupling for attaching and detaching the inset.

According to another embodiment, the wall could comprise a fluid inlet for inflating the chamber with a fluid and/or a fluid outlet provided in the wall for discharging the fluid from the chamber and a pump adapted to circulate the fluid from the outlet to the inlet.

According to one embodiment, at least one of the first and second part comprises a non-penetrable valve for closing the port such that the chamber is sealed from at least one of the ambient environment and a cavity in the patient.

According to one embodiment, the surgical port further comprises a vacuum sealing member adapted to hold a pressure less than atmospheric pressure between the port and the patient's skin to seal between the port and the patient's skin.

According to another embodiment, the surgical port further comprises a pressure sealing member adapted to hold a pressure above atmospheric pressure between the port and the patient's skin to seal between the port and the patient's skin.

In yet another embodiment, the port further comprises a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the port and the skin of the patient, and (b) the first sealing member and tissue of the patient.

In yet another embodiment, the chamber of the surgical port has a circular cross-section when the second part is disconnected from the first part.

The surgical port could according another embodiment comprise a first part comprising a body multi-port comprising at least two body ports adapted to enable passage of an object to the inside of the patient's body.

The surgical port could furthermore comprise a sterilization device for directly or indirectly sterilizing a fluid contained in the chamber and/or a fluid tempering device adapted to temper a fluid within the chamber to a temperature different from the temperature of the environment outside of the chamber.

According to another embodiment, the surgical port could be adapted to, in a first state, when the first and second parts are interconnected, enable a surgeon to operate through the surgical port, and in a second state, when the second part is disconnected from the first part enable the surgeon to perform steps of the procedure within the chamber formed by the flexible wall between the first and second parts of the port.

The surgical port could according to one embodiment be adapted to, in the second state, enable the surgeon to remove a specimen from the body of the patient through the first part and into the chamber, and to perform one of: placing the specimen within the chamber, and removing the specimen from the chamber through the second part.

According to one embodiment, the chamber of the surgical port could further comprises a pouch for holding the specimen within the chamber, and the pouch could be adapted to be closed for creating a pouch-chamber within the chamber for isolating the removed specimen within the chamber.

According to yet another embodiment, the first and second parts are adapted to be reconnected after being disconnected such that the surgeon can continue operating through the interconnected port after the specimen has been removed.

In yet another embodiment, at least one of the first and second part could be adapted to enable an inset to be detachably fixated to the part, such that the inset could be detached and replaced by a different inset.

A medical device for performing a surgical procedure on a patient is provided. The medical device comprising a wall adapted to be at least partially applied on the patient's body and further adapted to form a chamber without or together with the patient's body, in which a sterile environment can be maintained for encompassing part of the surgical procedure to be performed on the patient. At least a portion of the wall is adapted to directly or indirectly form an elongated tubular enclosure having a first or more open end, the enclosure being adapted to fit at least a portion of the body of the patient. The medical device is arranged such that the portion of the body is going into the enclosure through the first open end thereof, when the surgical procedure is to be performed on the portion of the patient's body.

According to one embodiment, the elongated tubular enclosure further comprises a second open end, and the medical device is arranged such that the portion of the body goes into the enclosure through the first open end thereof, and exits the enclosure through the second open end thereof, when the surgical procedure is to be performed on the portion of the patient's body.

According to one embodiment of the medical device, the elongated tubular enclosure further comprising a third open end, and the enclosure is adapted to fit at least a portion of both the legs or both the arms of the patient in the same enclosure. The medical device is arranged such that the portion of the body that goes into the enclosure through the first open end thereof will exit the enclosure through both the second and the third open end thereof, when the surgical procedure is performed on at least a part of the portion of the patient's body.

According to another embodiment, the chamber of the medical device is adapted to be formed by the wall and the patient's body and the tubular enclosure is adapted to encompass the chamber. The chamber is furthermore adapted to be sealed at the first or more open ends by the patient's body portion.

According to another embodiment, the chamber of the medical device is formed by the wall without involving the patient's body, and the part of the wall forming the chamber is adapted to also form the tubular enclosure. The wall comprises two wall sides of which one is facing the inside of the chamber and the other is facing the tubular enclosure, when performing the surgical procedure. The tubular enclosure forms a second chamber at least partly encompassed by the tubular enclosure and adapted to be sealed at the first or more open ends by the patient's body portion, the wall part facing the tubular enclosure is adapted to form the second chamber together with the patient's body.

According to another embodiment, the chamber of the medical device is adapted to be in communication with an operating field during the surgical procedure, when the skin of the patient has been cut in a position inside of the chamber. The wall that encompasses the chamber has a wall port or wall inset mounted in a wall portion of the chamber for allowing; objects including instruments to be moved into the chamber or operating field and/or manual manipulation to be performed in the chamber or operating field.

In one embodiment, the medical device further comprises a port having a first and second part. The second part comprises the wall port or wall inset and the first part comprises a body port or body inset adapted to be mounted in the cut skin of the patient to allow objects to be moved further from the chamber into the operating field and/or manual manipulation to be performed from the chamber further into the operating field.

In yet another embodiment, the two parts of the port or inset are adapted to be mounted together, touching each other for forming an integrated port or inset and thereby allowing objects to be moved into the operating field and/or manual manipulation to be performed in the operating field directly from outside the chamber. The two parts of the port or inset are adapted to be separable from each other and be placed in to one or more positions and thereby be adapted to use the second part of the port or inset to allow objects to be moved into the chamber and/or manual manipulation to be performed in the chamber and to use the first part of the port or inset to allow objects to be moved from the chamber passing the cut skin into the operating field and/or manual manipulation to be performed from the chamber through the cut skin further into the operating field in the patient's body.

In yet another embodiment, the chamber is adapted to be in communication with an operating field during the surgical procedure. The part of the wall forming both the chamber and the tubular enclosure, at a portion thereof, is adapted to be opened and together with the cut skin of the patient be positioned inside of the chamber allowing such communication with the operating field. A portion of the wall part encompassing only the chamber has a wall port or wall inset mounted therein for allowing, from outside the chamber; objects to be moved into the chamber or operating field and/or manual manipulation to be performed in the chamber or operating field.

In another embodiment, the medical device comprises a port or inset including a first and second part. The second part comprises the wall port or wall inset and the first part comprises a first wall port or first wall inset mounted in the opening in the portion of the part of the wall forming both the chamber and the tubular enclosure and adapted to be opened to create the communication between the chamber and the operating field to allow; objects to be moved further from the chamber into the operating field and/or manual manipulation to be performed from the chamber further into the operating field. The passage between the chamber and the operating field includes the first wall port or inset, and the second chamber is located in between the tubular enclosure and the skin of the patient, and the second chamber has a size equal to or larger than zero.

According to another embodiment the two parts of the port or inset are adapted to be mounted together, touching each other for forming an integrated port and inset and thereby allowing; objects including instruments to be moved into the operating field and/or manual manipulation to be performed in the operating field directly from outside the chamber using the integrated port or inset, and wherein the two parts of the port or inset are adapted to be separated from each into one or more positions in which they are not touching each other and thereby; to use the wall port or inset of the second part to allow; objects to be moved into the chamber and/or manual manipulation to be performed in the chamber and further to use the first wall port or first wall inset of the first part to allow; objects to be moved from the chamber passing the cut skin into the operating field and/or manual manipulation to be performed from the chamber through the cut skin further into the operating field.

In another embodiment of the medical device, the two parts of the port or inset are adapted to be locked together in at least one fixed position.

In yet another embodiment, the medical device is adapted to allow the surgical procedure with its operating field to be performed on the patient on at least one of a extremity, the prolongation of the extremity, abdomen, chest, and any joint including the hip and knee joints and the joints of the upper extremity.

The chamber encompassing the surgical procedure could in any of the embodiments herein be adapted to reduce infection risk of the surgical procedure.

According to another embodiment, the two parts of the port are adapted to comprise a fluid sealed valve when the two parts being separated.

In yet another embodiment, the second part is adapted to comprise a fluid sealing valve, when the two parts are separated.

According to one embodiment, the medical device comprises at least one of a third exchangeable wall port and wall inset different from the wall port and wall inset, adapted to replace at least one of the wall port or wall inset.

According to yet another embodiment, the medical device comprises at least one of a third exchangeable body port and body inset different from the body port and body inset, and adapted to replace at least one of the body port or body inset.

The medical device could further comprise a second exchangeable integrated port different from the integrated port, and adapted to replace the integrated port during the surgical procedure.

In yet other embodiments, the wall is at least partially collapsible and may be adapted to be inflated by a fluid.

According to another embodiment, the medical device further comprises a non-collapsible transparent window provided in the wall to enable viewing into the sterile environment.

In yet other embodiments, the inset comprises at least one glove integrated in the wall such that a surgeon is able to use the glove from outside the chamber to make manual manipulations inside the chamber while maintaining the sterile environment in the chamber.

In another embodiment, the medical device, further comprising an instrument holder adapted to retain instruments within the chamber.

The medical device could further comprise at least one sealing device adapted to seal between the skin of the body portion of the patient and at least one of the wall and enclosure.

According to another embodiment, the sealing device comprises a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

The sealing device in any of the embodiments herein could further comprise a pressure sealing member attached to at least one of the wall and enclosure and adapted to press against the patient's skin to create a pressure sealing between the skin of the patient's extremity and at least one of the wall and enclosure, and wherein the pressure sealing member is adapted to be hydraulically, pneumatically or mechanically forced against the patient's skin.

In one embodiment, the medical device comprises an adhesive adapted to provide at least one of: (a) fixation of at least one of the wall and enclosure to the skin of the patient, and (b) sealing between the skin of the patient and at least one of the wall and enclosure.

The medical device could further comprise an air evacuation system adapted to evacuate air from the second chamber, when the portion of the patient's extremity is placed in the enclosure.

In yet another embodiment, the medical device further comprises an air evacuation system adapted to evacuate air from the vacuum sealing member.

In some embodiments disclosed herein, the medical device could further comprise a multi-port, which may be placed in the wall port or body port, and comprising at least two ports integrated in the multi port, and being adapted to enable passage of an object to the inside of the patient's body via the cut incision in the skin, when performing the surgical procedure.

According to one embodiment, the medical device could further comprise at least one further wall port provided in the wall enabling passage of an object between the chamber and the environment outside of the chamber, wherein the wall port comprises at least one of an elastic membrane and a flexible membrane. The membrane is adapted to, in a non-compressed state, seal between the chamber and the environment outside of the chamber, and in a compressed state enable a hand or an object to be inserted through the membrane.

In yet another embodiment, the medical device further comprises a further sealing device having a first sealing member adapted to be positioned at the inside of the patient's skin around an incision cut in the patient's skin made from the chamber, a second sealing member adapted to be positioned at the outside of the patient's skin around the incision in the chamber, and at least one of a flexible, spring-loaded and elastic connecting member sealingly interconnecting the first and second sealing members, whereby the at least one of the flexible, spring-loaded and elastic connecting member seals between at least one of the second sealing member and the skin of the patient, and the first sealing member and tissue of the patient.

The medical device could further comprise a fluid tempering device adapted to temper a fluid to be used within the chamber to a temperature different from the temperature outside of the chamber and/or a sterilization device for directly or indirectly sterilizing a fluid contained in the chamber and/or a cleaning device adapted to clean the circulating fluid, to improve visibility.

According to yet another embodiment, the medical device further comprises at least one inlet provided in the wall for supplying a fluid into the chamber, at least one outlet provided in the wall for discharging the fluid from the chamber, and a pump adapted to circulate the fluid from the outlet to the inlet.

The object in any of the embodiments herein could comprise: a surgical instrument, a tool, a camera, a medical device or a part of a human body.

According to one embodiment, the medical device further comprises at least one of an airlock sluice and a liquid lock sluice, comprising a first valve and second valve and a sluice chamber placed in between the first and second valve, for allowing passage of objects from the chamber through the first valve and further through the second valve out to the environment outside of the chamber, and vice versa.

In yet another embodiment, the medical device further comprises at least one of an airlock sluice and a liquid lock sluice, comprising a first valve and second valve. The first valve is mounted in at least one of the skin or tissue of the patient and the portion of the wall adapted to directly or indirectly form the elongated tubular enclosure, and wherein the second valve is mounted in the wall.

According to one embodiment, the chamber and operating field of the medical device could comprise a circulating liquid fluid during the surgical procedure.

According to one embodiment, the medical device comprises an additional sealing subdevice comprising a wall and a sealing device adapted to be placed between the chamber and the skin of the patient and to be formed to close the anus or opening of urethra being in contact with the chamber to avoid connection between the anus or opening of the urethra and the chamber, when the surgical procedure is intended to be performed in relation thereto.

According to another embodiment, the elongated tubular enclosure is formed by placing the wall forming the chamber around at least a portion of the extremity of the patient.

In other embodiments of the medical device, the elongated tubular enclosure could comprise a slit for placing the chamber around at least a portion of the extremity of the patient radially in relation to the length axis of the extremity. The slit could be adapted to be at least partially closed by closing elements mounted on the wall of the medical device, and the closing elements could be elastic or adjustable for fixating the medical device to the extremity of the patient.

According to yet another embodiment, the medical device comprises a first and a second portion located on a first and second side of the slit when the chamber is placed around at least a portion of the extremity, and the first and second portions are adapted to be interconnected by means of at least one of: an adhesive and a mechanical connecting member.

According to yet another embodiment, at least one inset or port attached to the wall could be adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

In yet another embodiment, the wall forming the chamber could comprise a first and second interconnecting member, and wherein the first interconnecting member could be placed at the first position, and the second interconnecting member could be positioned in the second position. The second interconnecting member could be adapted to connect to the first interconnecting member for locking the inset or wall port in the first position.

A port or inset placed in the wall is defined as the wall port or wall inset, and the medical device could further comprise a body port or body inset adapted to be mounted in another wall portion or the skin or tissue of the patient. The first interconnecting member could be adapted to be positioned in connection with a body port or body inset, and wherein the wall port and the body port is adapted to form a integrated port when the first and second interconnecting members are connected in the first position. A wall port and body port could in any of the embodiments herein comprise at least one of an elastic membrane and a flexible membrane, and wherein the membrane could be adapted to, in a non-compressed state, provide a seal, and in a compressed state, enable a hand or an object to be inserted through the membrane. The membrane could in some embodiments comprise a penetrable self sealing gel, such that an object or hand can be inserted through the port while maintaining a seal.

According to one embodiment, the first part could comprise a first penetrable self sealing gel and the second part a second penetrable self sealing gel. The first and second penetrable self sealing gels could be adapted to be placed tightly together such that they act as a single penetrable self sealing gel adapted to, in a non-compressed state, provide sealing, and in a compressed state enable a hand or an object to be inserted through the self sealing gel while maintaining the seal.

In one embodiment, the first and second part could be adapted be interconnected to form a surgical port, and the second part could be adapted to be disconnected from the first part by a surgeon during a surgical procedure. The first part could be connected to a first portion of the wall, and the second part could be connected to a second portion of the wall, and wherein the wall is a flexible wall.

The chamber of the medical device could have a first volume when the first and second parts are interconnected and a second volume when the second part is disconnected from the first part.

In yet another embodiment, the surgical port could be adapted to: in a first state, when the first and second parts are interconnected, enable a surgeon to operate through the surgical port, and in a second state, when the second part is disconnected from the first part enable the surgeon to perform steps of the procedure within the chamber formed by the flexible wall between the first and second parts of the port.

According to one embodiment, the surgical port is adapted to, in the second state, enable the surgeon to remove a specimen from the body of the patient through the first part and into the chamber, and to perform one of: placing the specimen within the chamber, and removing the specimen from the chamber through the second part.

According to one embodiment, the chamber further comprises a pouch for holding the specimen within the chamber, and the pouch can be closed for creating a pouch-chamber within the chamber for isolating the removed specimen within the chamber.

The first and second parts could, in any of the embodiments herein, be adapted to be reconnected after being disconnected such that the surgeon can continue operating through the interconnected port after the specimen has been removed.

A medical device is further provided. The medical device comprising a surgical port placed in a wall of the medical device and a sealing device connected to the wall and adapted to seal against the patient's body, such that a chamber is formed by the wall and the patient's body. The surgical port is adapted to be detachably connected to a body port adapted to be at least partially placed in an incision cut in a patient's body.

According to one embodiment, the chamber of the medical device has a first volume when the surgical port is connected to the body port, and a second volume when the surgical port is disconnected from the body port. The second volume could be larger than the first volume, and could be larger than 500 000 mm3 to enable part of the surgical procedure to be performed within the chamber.

The chamber formed by the wall could be adapted to hold a pressure exceeding atmospheric pressure.

According to one embodiment, the surgical port comprises an elastic or flexible membrane adapted to, in a non-compressed state, provide sealing, and in a compressed state enable a hand or an object to be inserted through the membrane.

According to another embodiment, the surgical port comprises a first elastic or flexible membrane, and the body port comprises a second elastic or flexible membrane, and the first and second membranes could be adapted to be placed tightly together such that they act as a single elastic or flexible membrane adapted to, in a non-compressed state, provide sealing, and in a compressed state enable a hand or an object to be inserted through the membrane.

According to one embodiment, at least one of the wall port and body port comprises a penetrable self sealing gel, such that an object or hand can be inserted through the port while maintaining a seal. The wall port may comprise a first penetrable self sealing gel and the body port comprise a second penetrable self sealing gel, and the first and second penetrable self sealing gels could be adapted to be placed tightly together such that they act as a single penetrable self sealing gel adapted to, in a non-compressed state, provide sealing, and in a compressed state enable a hand or an object to be inserted through the self sealing gel while maintaining the seal.

According to one embodiment, the surgical port is adapted to receive and fixate an inset, or the surgical port comprises a detachable inset adapted to be fixated to the surgical port. The inset could comprise at least one of: a surgical glove and an instrument mount.

In yet another embodiment, the medical device further comprises at least one coupling for attaching and detaching the inset.

According to yet another embodiment, the wall comprises a fluid inlet for inflating the chamber with a fluid, and an outlet provided in the wall for discharging the fluid from the chamber. It is furthermore conceivable that the medical device comprises a pump adapted to circulate the fluid from the outlet to the inlet.

The wall port and body port could comprise a non-penetrable valve for closing the port such that the chamber is sealed from at least one of the ambient environment and a cavity in the patient.

According to one embodiment, the medical device could further comprise a vacuum sealing member adapted to hold a pressure less than atmospheric pressure between the port and the patient's skin to seal between the port and the patient's skin.

The medical device could further comprise a pressure sealing member adapted to hold a pressure above atmospheric pressure between the port and the patient's skin to seal between the port and the patient's skin.

In yet another embodiment, the surgical port could further comprise a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the port and the skin of the patient, and (b) the first sealing member and tissue of the patient.

According to another embodiment, the chamber could have a circular cross-section when the second part is disconnected from the first part. The body port could according to one embodiment comprise a body multi-port comprising at least two body ports adapted to enable passage of an object to the inside of the patient's body.

According to one embodiment, the medical device further comprises a sterilization device for directly or indirectly sterilizing a fluid contained in the chamber and/or a fluid tempering device adapted to temper a fluid within the chamber to a temperature different from the temperature of the environment outside of the chamber.

The surgical port could according to one embodiment be adapted to, in a first state, when the first and second parts are interconnected, enable a surgeon to operate through the surgical port, and in a second state, when the second part is disconnected from the first part enable the surgeon to perform steps of the procedure within the chamber formed by the flexible wall between the first and second parts of the port.

The body port could be adapted to, in the second state, enable the surgeon to remove a specimen from the body of the patient through the body port and into the chamber, and to perform one of: placing the specimen within the chamber, and removing the specimen from the chamber through the second part.

According to one embodiment, the chamber could further comprise a pouch for holding the specimen within the chamber, and the pouch can be configured to be closed for creating a pouch-chamber within the chamber for isolating the removed specimen within the chamber.

According to one embodiment, a medical device for performing a surgical procedure on a patient is provided. The medical device comprising a wall adapted to be at least partially applied on the patient's body to form a chamber, in which a sterile environment can be maintained for encompassing part of the surgical procedure to be performed. The wall comprises at least one hole adapted to enable passage of at least a portion of an extremity of the patient into the chamber, and at least one sealing device adapted to seal between the skin of the extremity of the patient and the wall at the hole.

The wall may in some embodiments comprise a second hole adapted to enable passage of at least a portion of the extremity of the patient out from the chamber, and at least one additional sealing device adapted to seal between the skin of the extremity of the patient and the wall at the second hole.

According to one embodiment, the wall is at least partially collapsible, and the collapsible wall could be adapted to be inflated by a fluid.

According to another embodiment, the medical device further comprises a non-collapsible transparent window provided in the wall to enable viewing into the chamber.

According to one embodiment, the medical device further comprises at least one glove integrated in the wall such that a surgeon is able to use the glove from outside the chamber to make manual manipulations inside the chamber while maintaining sterile environment in the chamber.

The medical device could further comprise an instrument holder adapted to retain instruments within the chamber while maintaining sterile environment in the chamber.

According to one embodiment, the sealing device of the medical device comprises a vacuum sealing member attached to the wall and adapted to provide a pressure less than atmospheric pressure between the vacuum sealing member and the patient's skin to create a vacuum sealing between the skin of the patient's extremity and the wall. According to another embodiment, the sealing device comprises a pressure sealing member attached to the wall and adapted to press against the patient's skin to create a pressure sealing between the skin of the patient's extremity and the wall.

According to yet another embodiment, the medical device further comprises an adhesive adapted to provide at least one of: (a) fixation of the wall to the skin of the patient and (b) sealing between the skin of the patient and the wall.

The medical device may further comprise an air evacuation system adapted to evacuate air from the chamber, when the portion of the patient's extremity is placed in the chamber. The air evacuation system may further comprise an air evacuation system adapted to evacuate air from the vacuum sealing member.

According to yet another embodiment, the medical device further comprises a body multi-port adapted to be placed inside the chamber in an incision to be performed in the skin of the patient. The body multi-port could comprise at least two body ports adapted to enable passage of an object between the chamber and the inside of the patient's body via the incision.

According to another embodiment, the medical device further comprises at least one wall port provided in the wall enabling passage of an object between the chamber and the environment outside of the chamber. The wall port comprises at least one of an elastic membrane and a flexible membrane, and the membrane is adapted to, in a non-compressed state, seal between the chamber and the environment outside of the chamber, and in a compressed state enables a hand or an object to be inserted through the membrane.

According to another embodiment, the sealing device of the medical device comprises a first sealing member adapted to be positioned at the inside of the patient's skin around an incision to be cut in the patient's skin within the chamber, a second sealing member is adapted to be positioned at the outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

The medical device may further comprise a fluid tempering device adapted to temper a fluid within the chamber to a temperature different from the temperature outside of the chamber, and/or a sterilization device for directly or indirectly sterilizing a fluid contained in the chamber.

An inlet may be provided in the wall for supplying a fluid into the chamber, and an outlet provided in the wall for discharging the fluid from the chamber, and a pump adapted to circulate the fluid from the outlet to the inlet.

A body port could be adapted to be placed inside the chamber in an incision to be performed in the skin of the patient to enable passage of an object between the chamber and the inside of the patient's body.

The medical device may further comprise a coupling adapted to detachably attach the body port to the patient's skin to enable exchange and removal of the body port.

An "object" may herein comprise a tool, a surgical device or a part of a human body.

According to one embodiment, the medical device further comprises an airlock sluice having a first valve and second valve for allowing passage of objects from the chamber through the first valve and further through the second valve out to the environment outside of the chamber, and vice versa.

According to another embodiment, a medical device for performing a surgical procedure on a patient is provided. The medical device comprises a first wall part adapted to at least partially enclose a first chamber for encompassing part of the surgical procedure, and a second wall part adapted to at least partially enclose a second chamber. The first wall part is designed to allow a first pressure to be maintained in the first chamber, the second wall part is designed to allow a second pressure to be maintained in the second chamber for creating a sealing between the medical device and the patient's body, and the first and second pressures are different.

According to one embodiment, the second chamber is adapted to hold a pressure for exerting a pressure force on the skin and/or tissue of the patient for creating the sealing between the medical device and the patient's body.

According to another embodiment, the second pressure is adapted to be higher than the first pressure.

According to yet another embodiment, the second chamber is adapted to hold a negative pressure for exerting a suction force on the skin and/or tissue of the patient for creating the sealing between the medical device and the patient.

According to yet another embodiment, the first chamber is adapted to be in fluid connection with a cavity of the patient via an incision in the skin of the patient, and wherein the chamber and the cavity in the patient forms a joint volume partially enclosed by the medical device.

The medical device may be adapted to enclose the second chamber together with the skin and/or tissue of the patient.

The second chamber of the medical device is further adapted to be in fluid connection with a vacuum device capable of producing a negative pressure for creating a negative pressure in the second chamber.

According to yet another embodiment, the first chamber of the medical device is adapted to hold a pressure between 5 mmHg and 120 mmHg, and the second chamber is adapted to hold a pressure between minus 120 mmHg and minus 5 mmHg.

The second chamber may be adapted to encircle an extremity of the patient and to create a sealing along the encircled portion of the extremity of the patient.

The second wall part of the medical device, may be adapted to hold the second pressure exceeding the first pressure such that the second chamber exerts a pressure force on the extremity of the patient for creating a sealing between the medical device and the skin of the patient.

A system is further provided. The system comprises the medical device according to any one of the preceding embodiments, a pressure creating device adapted to create a pressure exceeding 5 mmHg in the first chamber of the medical device, and a vacuum device capable of producing a pressure below minus 5 mmHg in the second chamber of the medical device for creating a sealing between the medical device and the skin and/or tissue of the patient.

A further system is also provided. The system comprising the medical device according to any one of the preceding embodiments, a first pressure creating device adapted to create a pressure exceeding 5 mmHg in the first chamber of the medical device, and a second pressure creating device adapted to create a second pressure exceeding 5 mmHg in the second chamber of the medical device for creating a sealing between the medical device and the skin of the patient. The system second pressure could be higher than the first pressure.

Another feature that could be included in the various embodiments disclosed herein is that a portion of the wall directly or indirectly forms an elongated tubular enclosure having an open end. The enclosure extends in the chamber and is adapted to fit a portion of an extremity of the patient inserted into the enclosure through the open end thereof. In other embodiments the medical device could comprise a sealing member encircling the extremity of the patient and adapted to seal between the skin of the patient and the wall.

Another feature that could be included in the various embodiments disclosed herein is that the enclosure could be collapsible or deformable, for facilitating the insertion of the extremity into the enclosure, whereas the wall enclosing the chamber could be rigid. However, in other embodiments it is equally conceivable that the wall enclosing the chamber is partially or entirely collapsible.

Another feature that could be included in the various embodiments disclosed herein is that the medical device could further comprise two gloves integrated in the wall enabling manual manipulation within the sterile environment. The gloves could be connected to the wall by means of pleated sections connecting the gloves to the wall and enabling free movement of the gloves within the sterile environment.

Another feature that could be included in the various embodiments disclosed herein is that where the wall is at least partially collapsible, the wall could be inflatable by a gaseous fluid for defining the chamber.

Another feature that could be included in the various embodiments disclosed herein is that the sealing member could comprise a vacuum sealing member adapted to seal between an extremity of the patient and the partially collapsible wall, by the vacuum sealing member being adapted to hold a pressure less than 1 bar for creating a vacuum sealing between the skin of the patient and the wall. The vacuum is created by a vacuum pump connected to the vacuum sealing member by means of a vacuum conduit. The vacuum sealing member could for example be made from a semi-rigid polymer material.

Another feature that could be included in the various embodiments disclosed herein is an air evacuation system, for evacuating air from the enclosure after the portion of an extremity has been placed in the enclosure, thereby tightening the wall around the extremity of the patient. The air evacuation system could comprise a conduit in fluid connection with the enclosure thereby enabling the evacuation of the air from therein.

Another feature that could be included in the various embodiments disclosed herein is a pneumatic pressure sealing member attached to at least one of the wall and enclosure and adapted to press against the patient's skin to create a pressure sealing between the skin of the patient's extremity and at least one of the wall and enclosure, using a pneumatic pressure pressing against the skin of the extremity. The pneumatic pressure could be created by a pneumatic pump being connected to the pneumatic pressure sealing member by means of a fluid conduit adapted to transport a pressurized gas from the pneumatic pump to a cavity within the pressure sealing member. The pressure sealing member could be inflatable such that the size and/or shape of the cavity can be changed for allowing the pneumatic pressure sealing member to press against the skin of the extremity and thereby seal between the extremity and the pneumatic pressure sealing member. The pneumatic pressure sealing member can for example be made from an elastic material such as an elastic polymer.

Another feature that could be included in the various embodiments disclosed herein is that an adhesive could be adapted to provide at least one of: fixation of at least one of the wall and enclosure to the skin of the patient and sealing between the skin of the patient and at least one of the wall and enclosure. The adhesive could for example encircle an extremity of a patient and thereby create a seal. The adhesive could for example be a pressure sensitive adhesive such as 3M's pressure sensitive adhesive Scotch-Grip 4268-NF.

Another feature that could be included in the various embodiments disclosed herein is that the wall has a cylindrical or tube shaped structure. Where the wall is at least partially collapsible, it could be inflatable by means of a pneumatic conduit, which could be connected to a tank containing pressurized gas.

Another feature that could be included in the various embodiments disclosed herein is a pneumatic system for transferring pneumatic force into the chamber. The pneumatic system could be connected to a pneumatic tool, which in the example shown is an orthopedic saw, adapted to be operated within the sterile environment. The pressure provided to the sterile environment and the pneumatic system could be controlled and monitored by a control/monitoring system connected to the pneumatic conduits, respectively. The wall could be sealed to the extremity of the patient by means of a pneumatic pressure sealing member which could encircle the extremity.

Another feature that could be included in the various embodiments disclosed herein is the medical device could incorporate a pneumatic pressure sealing member.

Another feature that could be included in the various embodiments disclosed herein is an air-lock system comprising two zipper-closed consecutive openings, where the outer zipper could be opened for placing and/or removing objects in the airlock between the zippers from the outside of the chamber, and the inner zipper could be opened from the inside of the chamber for placing and/or removing objects from the airlock. For example the airlock system could be used to remove a specimen from the sterile environment while keeping the environment sterile, or the airlock could be used to insert a medical instrument or an implant into the sterile environment.

Another feature that could be included in the various embodiments disclosed herein is a multi-port comprising laparoscopic ports, through which laparoscopic trocars or endoscopic instruments could be inserted.

Another feature that could be included in the various embodiments disclosed herein is an instrument mount for retaining instruments within the sterile environment.

Another feature that could be included in the various embodiments disclosed herein is a non-collapsible transparent window for enabling viewing into the chamber and the sterile environment. Where the wall is at least partially collapsible, the non-collapsible transparent window could ensure that the surgeon has adequate visual control over the procedure since the partially collapsible wall, even if preferably made from a transparent material, could provide limited visibility, e.g. if the medical device is not fully inflated, or in seams or bends of the material.

Another feature that could be included in the various embodiments disclosed herein is a self sealing access port, which for example could be a port comprising a material of gel type. A self sealing access port could enable the insertion of trocars and/or instruments as well as a person's hand, enabling manual manipulation within the chamber.

Another feature that could be included in the various embodiments disclosed herein is an endoscopic body port in direct connection with the extremity of the patient, within the chamber. The endoscopic port could for example enable an arthroscopic procedure with trocars to be performed within the sterile environment and either by the instruments being manipulated from the inside of the sterile environment or by the instruments reaching from wall ports in the wall, or the self sealing port in the wall and to the port within the sterile environment.

Another feature that could be included in the various embodiments disclosed herein is a system for tempering the fluid entering the chamber. The tempering part of the system could be provided to heat or cool the gaseous fluid inflating the collapsible wall. In cases when the surrounding environment is cold, the tempering part of the system could be used to raise the temperature of the sterile environment to provide beneficial operating circumstances both for the patient and for the surgeon. In cases when the surrounding environment is hot, the tempering part of the system could be used to lower the temperature of the sterile environment both to provide beneficial operating circumstances, for the patient and for the surgeon, and for providing a temperature inhibiting bacterial and viral infections. The tempering unit could comprise a temperature regulating device for setting the required temperature.

Another feature that could be included in the various embodiments disclosed herein is a sterilizing unit adapted to sterilize the gaseous fluid entering the chamber. The gaseous fluid entering the chamber could originate from a pressurized tank and could be pre-sterilized. In other embodiments, it is conceivable that the gaseous fluid is the surrounding air which is pressurized. In the embodiments where the surrounding air is used to inflate the collapsible wall and constitute the operating environment this air needs to be properly sterilized.

Another feature that could be included in the various embodiments disclosed herein is a system for circulating a fluid through the chamber of the medical device. The system could comprise a fluid conduit connected at an inlet placed in the wall for supplying fluid to the chamber, and an outlet for draining the fluid from the chamber. The fluid is circled by means of a pumping unit and is circled via a sterilizing/filtering unit adapted to remove impurities and sterilize the fluid.

Another feature that could be included in the various embodiments disclosed herein is a filtering unit adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Another feature that could be included in the various embodiments disclosed herein is that the medical device could be adapted to be placed in relation to an extremity of the patient e.g. a leg or an arm. The medical device could for example be used for performing an amputation both in a hospital environment and in environments where the risk of infections are considerably higher, such as in third world countries or in zones of catastrophe. The medical device could enable surgical procedures to be performed in a fully enclosed environment without any risk of infection disease even in very remote locations and without the access to water or electricity.

Another feature that could be included in the various embodiments disclosed herein is a self sealing port. The self sealing port could comprise a self sealing membrane fixated to a rigid part of the self sealing port. The self sealing membrane could have a small self sealing hole centrally in the membrane. The self sealing membrane could for example be made from a gel-type material being elastic enough to enable a deformation large enough for a person's hand to pass through the small self sealing hole, while still contracting enough to create an airtight seal between the sterile environment and the outside environment. The self sealing port could be fixable to a retractor comprising one intra body ring adapted to be positioned on the inside of the patients skin, and one ring adapted to be placed on the outside of the patients skin. Between the intra body ring and the ring adapted to be placed on the outside of the patients skin, a retractor membrane is positioned which is adapted to exert a pressure of the cut surfaces of the incision for retracting the skin and thereby keeping the wound open. The retractor membrane is preferably made from a resilient of elastic polymer material. The ring adapted to be placed on the outside of the patients skin could comprise an integrated roll up system which could be a spring loaded roll up system adapted to create a suitable pressure on retractor membrane for keeping the wound open.

Another feature that could be included in the various embodiments disclosed herein is a self sealing port connected to a retractor membrane made from a material elastic enough such that one end of the retractor membrane could be fixedly fixated to the rigid part of the port.

Another feature that could be included in the various embodiments disclosed herein is the wall separating the chamber from the outside environment is adapted to be fixated to the skin of the patient by means of an adhesive or by means of a difference in pressure between the outside of the chamber and the inside thereof.

Another feature that could be included in the various embodiments disclosed herein is that the medical device could further comprise an upper and a lower coupling for fixating ring shaped objects, which for example could be insets or ports, where insets for example could be surgical gloves, or holding devices and ports could be endoscopic ports or hand access ports. The coupling could comprise a releasing lever for releasing the object from the coupling. The lever could be connected to latching members which are spring loaded from the rear in order to secure the groove of the object. The inset fixated to the lower coupling could for example be a surgical glove, enabling manual manipulation within the body of the patient.

Another feature that could be included in the various embodiments disclosed herein is a valve member adapted to close the opening in the upper coupling when the upper coupling is not in use.

Another feature that could be included in the various embodiments disclosed herein is that the coupling could be adapted to enable the changing of objects in the coupling from for example a surgical gloves, to a multi-port comprising three endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care.

Another feature that could be included in the various embodiments disclosed herein is that the medical device could be adapted to be applied on the patient prior to the start of the surgical procedure. The medical device could for example be adapted to be fixated to the abdominal area of a patient by means of an adhesive. By fixating the medical device to the patient prior to the start of the surgical procedure a incision in the patient could be performed inside the chamber of the medical device. The medical device could for example be connected to a source of pressurized fluid, which could be lead into the chamber through a fluid conduit.

Another feature that could be included in the various embodiments disclosed herein is that the chamber of the medical device could be adapted to hold a gaseous fluid having a pressure exceeding 1 bar such that a laparoscopic procedure could be performed partially within the chamber and partially within the patient.

Another feature that could be included in the various embodiments disclosed herein is that the medical device could comprise one laparoscopic port detachably fixated to the wall. The laparoscopic port could be adapted to be attached by means of a coupling and thereby detachable. The medical device could further comprise a valve member for closing the hole in the wall while exchanging the laparoscopic port to another inset or port, such that the inset or port can be exchanged while maintaining the sterile environment within the chamber. The detachable insets or ports could be adapted to be fixated to the wall by means of couplings and thereby possible to quickly exchange.

Another feature that could be included in the various embodiments disclosed herein is surgical gloves, which could be integrated in the wall. The surgical gloves could enable manual manipulation within the chamber of the medical device while keeping the chamber hermetically closed.

Another feature that could be included in the various embodiments disclosed herein is that the medical device is an inflatable medical device which could be positioned prior to the start of a normal laparoscopic procedure but remains deflated until the very end of the procedure when the medical device is inflated, for example when a specimen is to be removed.

Another feature that could be included in the various embodiments disclosed herein is a cleaning device for cleaning a transparent window from the inside of the chamber. The cleaning device could comprise an arrangement for supplying a fluid adapted to assist in the cleaning of the transparent window via a fluid conduit to a nozzle placed in proximity to the transparent window. The fluid could for example be an isotonic solution, such as saline solution, or an antiseptic solution such as Chlorhexidine.

Another feature that could be included in the various embodiments disclosed herein is that the medical device could comprise a window contacting member for wiping the window clean after the fluid has been sprayed thereon for mechanically removing objects from the window.

Another feature that could be included in the various embodiments disclosed herein is that the medical device could be adapted to be applied on the abdominal region of the patient. The medical device could be adapted to be fixated to the patient by means of a vacuum affecting the patient along a vacuum groove, which could be connected to a vacuum pump by means of a vacuum conduit.

Another feature that could be included in the various embodiments disclosed herein is a detachable port, which could be positioned in the wall according to any of the embodiments disclosed herein. The port could be attached using a coupling enabling a quick exchange of the port. The port could for example be a self sealing port which could comprise a self sealing membrane fixated to a rigid part of the self sealing port. The self sealing membrane could have a small self sealing hole centrally placed in the membrane. The self sealing membrane could for example be made from a gel-type material being elastic enough to enable a deformation large enough for a person's hand to pass through the small self sealing hole, while still contracting enough to create an airtight seal between the sterile environment and the outside environment.

Another feature that could be included in the various embodiments disclosed herein is that the medical device could include a filtering unit adapted to remove impurities and optionally sterilize the fluid. The filtering unit could be adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Another feature that could be included in the various embodiments disclosed herein is a coupling enabling the changing of objects in the coupling for example from a surgical glove to an endoscopic port unit comprising endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the laparoscopic ports and surgical gloves could additionally be exchanged for holding devices, for example holding instruments or implants.

Another feature that could be included in the various embodiments disclosed herein is that the medical device could be adapted to be applied on the patient prior to the start of the surgical procedure, such that an incision in the patient could be performed in the sterile environment.

Another feature that could be included in the various embodiments disclosed herein is that where the wall of the medical device is at least partially collapsible, it could be adapted to be inflated by a pressurized fluid entering the medical device through a fluid conduit Another feature that could be included in the various embodiments disclosed herein is that the medical device is adapted to placed in contact with the skin of the patient prior to the beginning of the operation and the entire portion of the wall contacting the skin of the patient comprises an adhesive, such that an incision in the patient runs through the wall and further through the skin of the patient. This reduces the risk that infectious objects can be transferred from the skin of the patient to the incision in the patient if the skin of the patient is not adequately disinfected.

Another feature that could be included in the various embodiments disclosed herein is that the coupling could be integrated in the wall. The coupling could enable the changing of objects from for examples ports to insets in form of surgical gloves or holding members. The coupling could additionally comprise a valve member for closing the hole in the coupling when objects should be exchanged such that the sterile environment in the chamber remains sterile.

Another feature that could be included in the various embodiments disclosed herein is that the medical device could comprise a holding device, which could for example be adapted to hold surgical instruments and/or implants or parts of implants.

Another feature that could be included in the various embodiments disclosed herein is that the medical device comprises a coupling integrated in the wall. For example could an airlock for transferring objects between the chamber and the outside thereof be fixated to the coupling. The airlock could comprise a first valve member separating the airlock from the sterile environment, and e second valve separating the airlock from the outside environment. The airlock space could be provided between the first and second valve and could for example be used for passing a medical instrument or device into the chamber, or for passing a specimen or sample out of the chamber.

Another feature that could be included in the various embodiments disclosed herein is that the upper coupling could be used for manual manipulation and preparation within the medical device, such that could be needed for preparing or changing an instrument or preparing an implant for implantation. The manual manipulation could be performed by means of a glove fixated to the wall by the coupling.

Another feature that could be included in the various embodiments disclosed herein is that a surgical glove could be fixated to the upper coupling. In other embodiments, the surgical glove could be exchanged by for example a surgical port or a holding device, as further disclosed with reference to other embodiments herein.

Another feature that could be included in the various embodiments disclosed herein is that a coupling of the medical device could comprise a releasing lever for releasing the object. The lever could be connected to latching members which could be spring loaded from the rear in order to secure the groove of the object.

Another feature that could be included in the various embodiments disclosed herein is that the medical device could be adapted to enable the changing of objects in the coupling from a surgical glove to a multi-port comprising endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care.

Another feature that could be included in the various embodiments disclosed herein is that the chamber could be adapted to, after an incision has been created in the skin of the patient, be in fluid connection with a cavity within the patient's body via the incision in the skin of the patient.

Another feature that could be included in the various embodiments disclosed herein is that the medical device could be adapted to hold a pressure within the chamber exceeding 1 bar. The medical device could be enable to hold a pressure in the chamber exceeding 1 bar by means of an adhesive fixating the medical device to the skin of the patient. The medical device could be adapted to be positioned in connection with the skin of the patient, for creating a substantially airtight seal between the wall of the medical device and the skin of the patient prior to the incision in the skin of the patient which creates the fluid connection between the cavity within the patient and the chamber.

Another feature that could be included in the various embodiments disclosed herein is that the medical device is adapted to enable manual manipulation within the chamber by the wall forming the chamber to have a volume larger than 500 000 mm3.

Another feature that could be included in the various embodiments disclosed herein is that the medical device could comprise a vacuum sealing member adapted to hold a pressure less than atmospheric pressure between the wall and the patient's skin to seal between the wall and the patient's skin. The vacuum sealing member could be fixated to the patient by means of a vacuum affecting the patient along a vacuum groove. The vacuum groove could in turn be connected to a vacuum pump by means of a vacuum conduit. This construction enables maintaining of the pressure within the chamber and in the sterile environment above 1 bar by means of for example a pressurized fluid in a pressurized fluid tank delivered to the chamber through the fluid conduit.

Another feature that could be included in the various embodiments disclosed herein is that the medical device could further comprise an opening between the chamber and the outer environment for allowing passage of objects between the chamber and the outer environment.

Another feature that could be included in the various embodiments disclosed herein is that the medical device could additionally comprises a pressure sealing adapted to be inflated for pressing against the skin of the patient and thereby sealing between the sterile environment within the medical device and the outside environment. The pressure sealing could for example be inflated though a fluid conduit connected to a pressure source, in this embodiment a pressurized tank. The wall of medical device could for example be fixated to the patient by means of an adhesive adapted to withstand the force created by the inflated pressure sealing.

Another feature that could be included in the various embodiments disclosed herein is that the fixation of the wall could be assisted or replaced by a band pressing the wall of the medical device against the skin of the patient. The band could be required if the pressure needed to seal between the skin if the patient and the wall needs to be particularly large, which for example could depend on the positioning of the medical device.

Another feature that could be included in the various embodiments disclosed herein is that the medical device could comprise a detachable port arrangement, which could be positioned in the chamber of the medical device. The port arrangement includes an intra body ring adapted to be placed at the inside of the patients skin around an incision, and an outer ring adapted to be placed on the outside of the patients skin around the incision. Between the intra body ring and outer ring an annular retractor membrane is positioned adapted to exert a pressure on the skin or human tissue at the incision to seal between the rings and the skin or human tissue and additionally for retracting the skin and thereby keep the incision open. The retractor membrane may be made from a resilient or elastic polymer material. The outer ring may comprise an integrated roll up system, which may be spring loaded and adapted to create a suitable pressure on the retractor membrane to keep the incision open.

The port arrangement may also include a coupling having a rigid annular seating attached to the outer ring, spring loaded latching members arranged in radial bores in the seating and a hand lever connected to the latching members to enable retraction thereof against the action of springs. The port arrangement may further include a self sealing body port held by the coupling. The body port may comprise a disc-shaped self sealing membrane fixated to a rigid ring having an outer circumferential groove that receives the latching members of the coupling. The self sealing membrane has a small self sealing hole centrally in the membrane. For example, the self sealing membrane may be made from a gel-type material being elastic enough to enable a deformation large enough for a person's hand to pass through the small self sealing hole while still contracting enough to create an airtight seal between the chamber and the outside environment.

The coupling enables quick exchange of the body port. Thus, the surgeon may release the body port from the port arrangement by simply pulling the hand lever so that the latching members disengage from the groove of the body port, whereby the body port can be removed.

Another feature that could be included in the various embodiments disclosed herein is that the medical device could comprise an upper and a lower coupling for fixating ring shaped objects which for example could be insets or ports, where insets for example could be surgical gloves or holding devices and ports could be endoscopic ports or hand access ports, such as self sealing ports. The coupling could comprise a releasing lever for releasing the object.

Another feature that could be included in the various embodiments disclosed herein is that the medical device could comprise a valve member adapted to close the opening in the upper coupling when the upper coupling is not in use. The upper coupling is for example used for manual manipulation and preparation within the medical device, such that could be needed for preparing or changing an instrument or preparing an implant for implantation. The lower coupling could for example be used for laparoscopic manipulation within the body of the patient, or manual manipulation for e.g. removing a specimen or positioning an implant.

Another feature that could be included in the various embodiments disclosed herein is that an inset, for example a surgical glove, could be fixated to the lower coupling.

Another feature that could be included in the various embodiments disclosed herein is that the medical device could have a coupling integrated in the wall. The coupling enables the changing of objects from for examples ports to insets in form of surgical gloves or holding members. The coupling could comprise a valve member for closing the hole in the coupling when objects should be exchanged such that the sterile environment remains sterile. The holding device could for example be adapted to hold surgical instruments and/or implants or parts of implants. The wall of the medical device is according to this embodiment adapted to be fixated to the skin of the patent by the vacuum sealing.

Another feature that could be included in the various embodiments disclosed herein is that at least a portion of the wall of the medical device could be partially collapsible, and the collapsible wall portion could be adapted to be inflated by a gaseous fluid for defining the chamber. The collapsible wall portion could be inflated by a pressurized fluid entering the chamber through a fluid conduit. The inflation of the wall, in which a window is integrated, positions the window in a position suitable for viewing the procedure being performed on the patient. The inflation of the collapsible wall portion could continue until the pressure in the chamber exceeds 1 bar, which is required in some applications.

Another feature that could be included in the various embodiments disclosed herein is that the medical device could be used in surgical procedures where transitions between open and laparoscopic surgery is needed. A portion of the wall of the medical device could be displaceable between a first position and a second position, where the medical device has an upper coupling and a lower coupling separated from each other, when the wall is in the second position for enabling a larger freedom of motion for the surgeon within the chamber of the medical device, whereas the upper coupling is locked to the lower coupling, when the wall is in the first position, which could enable the use of a laparoscopic trocar or hand access for further reach within the body of the patient. The medical device could further be used in embodiments where manual manipulation in a sterile environment is required, e.g. for preparing a medical device for use in the surgical procedure. Other applications could for example be that the surgeon wishes to remove a specimen from the body of the patient after a laparoscopic procedure has been concluded. The laparoscopic procedure could in these instances be performed with the wall of the medical device being in the first position, being close to the skin of the patient, whereafter the wall could be displaced into the second position for enabling the specimen to be removed from the body of the patient and placed in the chamber of the medical device without contacting the outside environment, and without the release of the pressure that usually fills the abdomen in laparoscopic procedures. The lower coupling could comprise a lever for releasing and/or locking the upper coupling to the lower coupling.

Another feature that could be included in the various embodiments disclosed herein is that an object comprising an airlock could be coupled to the wall of the medical device, for example by means of a coupling. The airlock can be adapted for transferring objects between the outer environment and the chamber of the medical device. The airlock could comprise an inner wall and an outer wall on each side of the airlock enabling the enclosing of an object within the airlock. Another example of an object to which the surgical glove can be exchanged is a port such as a laparoscopic port for performing a laparoscopic procedure.

Another feature that could be included in the various embodiments disclosed herein is that the upper and/or lower coupling could comprises a valve member for closing the opening in the coupling when the objects should be exchanged. The valve member could for example be a flap valve.

Another feature that could be included in the various embodiments disclosed herein is that the wall of the medical device could be placed in contact with the skin of the patient prior to the beginning of the operation and the entire portion of the wall contacting the skin of the patient could comprise an adhesive, such that an incision in the patient runs through the wall and further through the skin of the patient. This reduces the risk that infectious objects can be transferred from the skin of the patient to the incision in the patient if the skin of the patient is not adequately disinfected. The body of the patient could be inflated to allow better visibility within the body from for example a fluid conduit connected to a pressure tank. However, it is equally conceivable that the body of the patient is inflated from within trough another incision in the body of the patient.

Another feature that could be included in the various embodiments disclosed herein is an object coupled to the medical device could be exchanged by a plurality of different objects while the wall of the medical device is locked in the first position, i.e. with the upper coupling locked to the lower coupling. For example, an integrated surgical glove could be exchanged by an airlock comprising a first valve member separating the airlock from the sterile environment, and a second valve separating the airlock from the environment outside the chamber. The airlock space provided between the first and second valves could for example be used for passing a medical instrument or device into the sterile environment, or for passing a specimen or sample out of the sterile environment, or exchanged by a holding member which for example could be adapted to hold surgical instruments and/or parts of an implant, or exchanged for an endoscopic port unit comprising endoscopic ports. The medical device could according to this embodiment be adapted to be fixated to the skin of the patient by a large portion of the wall of the medical device being adhesive, and by means of the vacuum sealing.

Another feature that could be included in the various embodiments disclosed herein is that the medical device could comprise a retainer placed in the skin of the patient for retaining an opening enabling the passing from the chamber of the medical device to a cavity in the body of the patient. The opening enables a pressure being larger than the pressure of the external environment to be present in the in both the cavity of the patient and in the chamber of the medical device, which enables a semi-laparoscopic procedure to be performed both using traditional trocars and by means of hand access through the use of the medical device. The retainer could be a retainer disclosed herein, or could be a different retainer including traditional retainers using hooks. For manual manipulation within the medical device and/or the body of the patient a surgical glove is attached to the wall of the medical device, for example by means of an upper coupling comprising a releasing lever, both further described throughout the application.

Another feature that could be included in the various embodiments disclosed herein is that the chamber of the medical device could have a volume being larger than 500 cm3 for enabling the manipulation of objects within the chamber and/or placing objects of considerable size within the chamber.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way.

BRIEF DESCRIPTION OF DRAWINGS

The invention is now described, by way of example, with reference to the accompanying drawing, in which:

FIGS. 1a-1c shows the medical device when applied to a leg of a patient,

FIG. 2g shows an embodiment of the medical device comprising an elongated tubular enclosure, when inflated, FIG. 2h shows an embodiment of the medical device comprising an elongated tubular enclosure, when a leg of the patient has been inserted into the elongated tubular enclosure.

FIG. 3a shows an embodiment of a medical device, in perspective,

FIGS. 3b-3e shows embodiments of a medical device, in perspective,

FIGS. 5j-5o shows the medical device when used,

FIGS. 5s-5u shows embodiments of the medical device, in section,

FIG. 8 shows the medical device according to yet another embodiment, in a sectional side view, FIG. 9 shows the medical device according to yet another embodiment, in a sectional side view, FIG. 10 shows the medical device when applied to the abdomen of a patient, in a sectional side view, FIGS. 19a-19g shows an embodiment of the medical device being fixated to the patient and used, FIGS. 19k-19n shows an embodiment of the medical device being fixated to the patient and used, FIGS. 19s-19t shows a coupling in the wall of the medical device, FIGS. 28e-28k shows an embodiment of the medical device being fixated to the patient and used, FIGS. 28m-28p shows an embodiment of the medical device being fixated to the patient and used, FIG. 32 shows an embodiment of the medical device having a vacuum fixation, FIG. 33 shows an embodiment of the medical device comprising an opening, FIG. 34 shows an embodiment of the medical device having an airlock, FIG. 35a shows the medical device when applied to the abdomen of a patient, in a deflated state, FIG. 35b shows the medical device when applied to the abdomen of a patient, in an inflated state, FIGS. 41d-41j shows an embodiment of the medical device being fixated to the patient and used, FIG. 41k-41l shows an embodiment of a medical device, in section, FIGS. 41n-41q shows an embodiment of the medical device in section, being fixated to the patient and used, FIG. 46 shows a portion of the medical device having a coupling, FIG. 47 shows a portion of the medical device having a coupling, FIG. 53b shows a coupling, in section, FIG. 53c shows the coupling in section, when objects are being exchanged, FIGS. 53o-53r shows an embodiment of the medical device in section, being fixated to the patient and used, FIGS. 54-59 shows embodiments of the medical device, in perspective, FIG. 71a shows a portion of the medical device including a coupling, FIG. 71b shows a portion of the medical device including a coupling, FIG. 76a shows a coupling in section, FIG. 76b shows a coupling in section, when objects are being exchanged, FIGS. 78l-78o shows an embodiment of the medical device in section, being fixated to the patient and used, FIGS. 79a, 79b, 79c and 79d shows yet another embodiment of the medical device, FIGS. 85d-85g and 85i shows an embodiment of the medical device in section, being fixated to the patient and used, FIGS. 85k-85l shows embodiments of the medical device, in section, FIG. 91 shows an embodiment of the medical device comprising a retainer, FIGS. 95d-95j shows an embodiment of the medical device in section, being fixated to the patient and used, FIGS. 95l-95o shows an embodiment of the medical device in section, being fixated to the patient and used, FIG. 105k-105l shows another embodiment of the medical device, in section.

FIG. 114l shows another embodiment of the medical device, in section.

FIGS. 129-134 shows embodiments of a medical device, in perspective, FIGS. 139-140f shows an embodiment of the medical device in section, being fixated to the patient and used, FIGS. 141a-141d shows another embodiment of the medical device, in section, FIGS. 143-145b shows embodiments of body ports fixated to the tissue of the patient, FIGS. 164a-164c shows an embodiments of the medical device, in section.

FIGS. 187a-187d shows an embodiment of the medical device in section, being fixated to the patient and used, FIGS. 190a-190f shows embodiments of a medical device, in perspective, FIGS. 198a-198d shows the medical device when used, in section, FIGS. 202a-202c shows embodiments of the medical device, in section, FIGS. 203a-203d shows embodiments of the medical device, when being used, in section, FIGS. 218a-218e shows an embodiment of the medical device when deflated, FIGS. 222-260*d* are flow charts describing methods adapted to be performed using the medical devices according to the different embodiments presented herein.

DETAILED DESCRIPTION

Figure 1D:
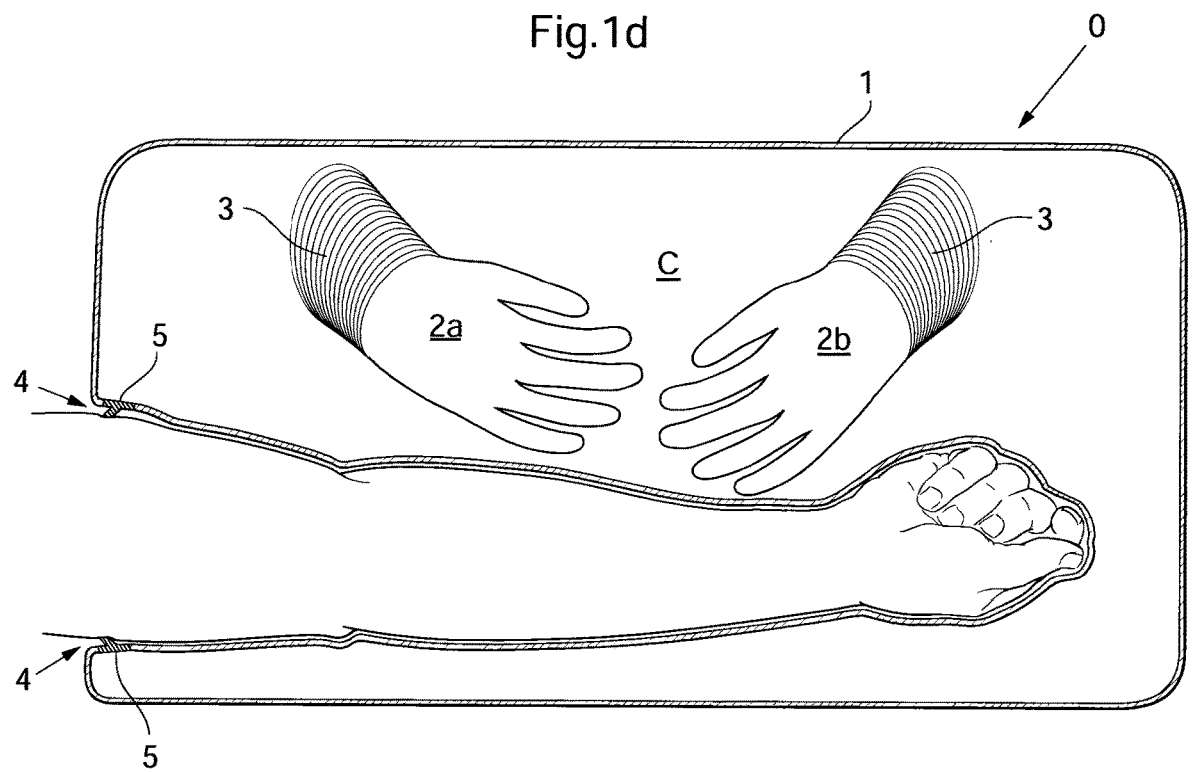
FIG. 1d shows the medical device when applied to an arm of a patient.

The medical device provided herein could in its different embodiments be used as a complement to endoscopic surgery, such as laparoscopic, gastroscopic and arthroscopic surgery, to allow hand access or insertion or removal of objects or instruments from the surgical area inflated. The medical device could further be used in preparation for a possible conversion from endoscopic to open surgery, for reducing complications associated with such conversion. In some embodiments the medical device could be used with a circulating liquid in for example arthroscopic surgery. In some embodiments the medical device could be used as a means for creating a completely sterile and closed surgical environment to be used in open surgery, endoscopic surgery or a mix thereof. The medical device could thus be used as a miniature operating theater in conditions where a proper operating thereafter is not available. The medical device could in instances in which it is used as a miniature operating theater be adapted for a specific surgical procedure, in which case the objects and/or instruments needed in that particular surgery could be pre-placed within the medical facilitating shipping and handling and keeping the objects and/or instruments sterile at all time. Embodiments disclosed herein enable surgical procedures to be performed in a more sealed environment which reduces the risk of bacterial and viral infections. Creating the proper environment for surgical procedures is expensive, time consuming and an environmental burden as most of the sterile products etc. used during a surgical procedures are deposable. The operating theaters are generally equipped with special air filtering ventilation systems reducing the number of particles in the operating environment. Even if the operating theaters are properly sterilized, the air is properly filtered and the medical staff uses proper protective clothing the size of the area which needs to be sterilized in combination with the passing of medical staff in and out of the operating theater risks of errors significant. A normal surgical procedure involves as much as ten different staff members, performing the surgery, assisting in the surgery, being tutored or being involved in the anesthesia. Several of these members of the medical staff needs to move from the controlled environment of the operating theater to less controlled environments outside of the theater as they may be involved in parallel surgical procedures or need to prepare or coordinate subsequent procedures. By sealing the operating field closer to the body of the patient, the area which needs to have the highest level of sterility can be made smaller, which also reduces the number staff that needs to be in direct contact with the most sensitive areas of the surgery and eliminates the need for any medical staff to pass from the most sensitive areas of the surgery to the outside of the operating theater.

In surgical procedures requiring the removal of a material from within the human body, this procedure is preferably done with minimally invasive surgery. Minimally invasive surgery is advantageous since the risk of infections is less with smaller incisions, the time for recovery is shorter and the scars remaining after the procedure are smaller. When for example removing a section of the intestinal system it is sometimes unclear how much of the intestine that needs to be removed and where the intestine in need of removal is located. This could in most cases be determined through optical inspection using a fiber optic camera, well known in the art of laparoscopy and arthroscopy, placed in a trocar inserted through a small incision in the body of the patient. For enabling optical inspection the cavity within the body needs to be created, which is typically done by means of pressurized $CO_2$ gas being introduced through the trocar. Returning to the removal a section of the intestinal system this removal is confined by the size of the laparoscopic trocars, typically not being larger than 418 mm. The medical device provided herein could provide a possibility to combine any of traditional laparoscopic surgery and/or single incision laparoscopic surgery and/or natural orifice transluminal endoscopic surgery and/or hand-assisted laparoscopic surgery and/or open surgery. In surgical procedures where a portion of the intestinal system temporarily is placed outside of the body of the patient, these parts of the intestinal system needs to be kept humid at all time to reduce the forming of scar tissue after the surgical procedure is concluded. By keeping the intestinal portion in the chamber of the medical device disclosed herein, the intestines can be kept in a controlled, sealed, tempered and humid environment which reduces the risk that complicating scar tissue is formed or the risk that the patient gets post operative problems with infections etc.

In hand assisted surgery the surgeon can insert a hand through a small incision in the abdomen. Hand assisted surgery has the benefit of providing sensory perception and the possibility to guide the surgical instruments whilst maintaining the possibility of visually observing the entire procedure on a TV screen overhead. Furthermore, it enables the removal of large organs intact, for example making it possible to evaluate cancer. Hand assisted surgery could also be beneficial to surgeons who are still learning laparoscopic techniques. The medical device may preserve the main idea of Minimal Access Surgery (MAS) and enhance the safety and efficiency of MAS by allowing the completion of the operation with a hand inside the body of the patient. The medical device makes it possible to maintain the intra-abdominal pressure to facilitate the better view and magnification of an endoscopic camera.

The medical device could be used to enable a surgical procedure requiring the removal of a specimen (such as appendectomy or cholecystectomy), to be commenced as a minimally invasive procedure (such as Laparoscopic, SILS, NOTES etc.) and ended as open surgery when the specimen is to be removed. In traditional minimally invasive procedures, the switching from laparoscopic to open surgery means that the positive pressure provided in the area of the procedure (crating the cavity which is needed to obtain visibility) disappears causing the cavity to collapse making it impossible to continue with further laparoscopic surgery. By the use of a medical device, a chamber is created exteriorly to the patient's body in which an equal pressure could be maintained, which enables the cavity in the patient's body to remain inflated during the open phase of the procedure. By retaining the visual conditions throughout the procedure, the procedural steps can be visually followed both from outside and from within the patient's body. The removal of the specimen does not necessarily mean that the procedure is concluded since e.g. additional suturing may very well be required which could be performed using laparoscopic techniques. Using the medical device allows the finding of for example the intestinal section to be removed using an endoscopic camera and the manipulation of the intestinal section to position the section in a position advantageous for the removal of said section through an incision in the skin. Since the chamber of the medical device is part of the environment in which the surgical procedure is performed, an incision in the skin in side of chamber does not puncture the pressurized cavity within the body created by the pressurized $CO_2$ gas and thus enables the surgeon to maintain visual inspection by means of a camera while removing the bodily matter, in this example being the section of intestine.

The medical device provided herein could be adapted for and used with benefit in for example appendectomy, cholecystectomy, nephrectomy, hysterectomy, oophorectomy, adrenalectomy, gastric bypass, Nissen fundoplication, hernia repair, splenectomy, colon resection, liver resection, cryoablation or for creating a cecostomy, colostomy, duodenostomy, Ileostomy, appendicostomy, esophagostomy, gastrostomy, urostomy, nephrostomy, ureterostomy, vesicostomy. In arthroscopy, the medical device could be used for the removal of separated bone or cartilage tissue or the insertion of fixation elements such as screws, nails, plates, prosthetic joints or elements for lubrication.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, it should further be noted that features in the different embodiments having the same last two digits are similar i.e. 74, 474 and 774. A feature in one embodiment could thus be exchanged for a feature from another embodiment having the same last two digits unless clearly contradictory. The descriptions of the similar features having the same last two digits should thus be seen as complementing each other in describing the fundamental idea of the feature and thereby showing the features versatility.

Endoscopy is to be understood as any form of key-hole surgery or minimally invasive surgery using endoscopic instruments. Endoscopy for example includes laparoscopy including Single Incision Laparoscopic Surgery (SILS), arthroscopy, Natural Orifices Translumenal Endoscopic Surgery (NOTES) for example including gastroscopy and proctoscopy and hand-assisted endoscopic surgery.

Inset is to be understood as an indentation in the wall, or a part which could be inserted into the wall of the medical device for making up part of the wall. An insert may for example be a circular object which may be locked to a coupling or opening in the wall of the medical device, or integrated in the wall of the medical device. An inset could for example comprise an integrated glove, or a device or instrument mount for holding for example an implant. The inset, when positioned in the wall of the medical device, keeps the environment in the chamber, enclosed by the wall, sealed, and thus is not possible to pass i.e. objects cannot be transferred through the inset.

Vacuum, when used for providing sealing properties is to be understood as negative pressure i.e. pressure below atmospheric pressure and thus providing a suction to the area on which it is applied, it is not be understood as an absolute vacuum.

A medical implant may for example be an arthroplastic prosthesis, a heart assisting device, and energized implant, control logic, a filling esthetical implant, implantable medicament dispenser, a powering unit, a vascular implant, an urological implant, an abdominal implant, a drug-releasing implant or a gynecological implant An instrument, surgical instrument or endoscopic instrument may for example be a scalpel, at trocar, tweezers, a suturing instrument, scissors, a camera, a clamping instrument, a dissecting instrument, a gripping instrument, a bonding instrument, such as a suturing or stapling instrument, or a severing instrument, such as a scalpel or an electromagnetic or ultrasonic diathermy, it may be a laparoscopic grasper, a laparoscopic claw grasper, a laparoscopic stone grasper, a laparoscopic needle holder, a laparoscopic hook, a laparoscopic dissector, or a laparoscopic diathermy instrument.

Physiological parameter could for example be the blood pressure of the patient, the blood flow of the patient, the saturation of the blood of the patient, or an ischemia marker such as lactate, the temperature at the skin of the patient, the skin tone etc.

The reference numerals in the appended figures refer to the following elements, in the listing below examples are recited, however, they are only to be seen as examples of how the elements may be implemented and not to be understood as limiting the scope of the term:

A=Ambient environment, the environment outside o the surgical environment enclosed or partially enclosed by the chamber of the medical device or within the body of the patient.

C=Chamber
S=Skin
I=Incision
L=Leg
O=Object
T=Tumor
0=Medical device
1=Wall, e.g. a layer of the medical device enclosing a chamber. The wall can be a rigid wall or an flexible, elastic and/or inflatable wall. The wall could be transparent, translucent and/or gas tight and may be made from a transparent polymer material, such as polyvinyl chloride (PVC) with a plasticizer additive. The wall may be a rigid transparent material for example glass or a transparent polymer material such as an acrylic glass, a polycarbonate, polyethylene terephthalate, an acrylic fiber material or a copolymer containing polyacrylonitrile.

2=Glove, e.g. denotes an indentation in the wall of the medical device enabling manual manipulation by medical staff from the outside of the ambient environment or from a second chamber.

3=Pleated section, e.g. denotes a flexible wall portion comprising a plurality of creases enabling the extension of the material of the wall. The pleated portion may additionally be elastic.

4=Enclosure

5=Sealing device, e.g. denotes any sealing or fixating element or combination of elements together performing a sealing or fixating function.

5'=Vacuum sealing member, e.g. denotes an element involved in providing sealing by means of maintaining a pressure below atmospheric pressure.

5"=Pressure sealing member, e.g. denotes an element involved in providing sealing by means of pressing against the an element, which could involve maintaining a fluid pressure above atmospheric pressure.

5'''=Adhesive sealing member, e.g. denotes an element involved in providing sealing by means adhesion.

6=Vacuum conduit, e.g. a flexible polymer conduit designed such that it does not collapse when transferring a pressure being lower than the pressure outside the conduit. The conduit may be re-enforced by for example by annular metallic ring-shaped elements, such that the conduit maintains its flexibility.

7=Separating layer, e.g. a layer having a non-stick surface such that it can be removed from an adhesive surface. The non-stick surface could for example comprise a PTFE coated surface.

8=Vacuum pump, e.g. a pump adapted to create a pressure below atmospheric pressure such that air from a chamber can be evacuated, could for example be in the form of a piston or membrane pump.

9=Fluid pump, e.g. any pump capable of moving a liquid or gaseous fluid, could for example be in the form of a piston or membrane pump.

10=Fluid conduit, e.g. any conduit capable of transferring a liquid or gaseous fluid, could for example be a flexible polymer tubing.

11=Chamber, e.g. any enclosed space.

12=Tank.

13=Pneumatic system, e.g. a system for handling pneumatic fluid which could have a pressure different from the atmospheric pressure. The pneumatic system may be a system for powering pneumatic tools or inflating a chamber. The pneumatic system may for example comprise pneumatic/fluid conduits, valves, gauges, pressure sensors, sterilizing/filtering/tempering/humidifying units, pumps and/or tools consuming pneumatic energy.

15=Control/monitoring system, e.g. a gauge o valve for monitoring or controlling a fluid flow or pressure.

16=Tool e.g. a powered tool for surgical use, such as an orthopedic drill, saw, reamer, stapler etc.

17=Wall port, e.g. any closable/openable port placed in a wall such that an object may be transferred from one side of the wall to the other side of the wall through the port. The wall port may for example comprise a self sealing silicon or gel membrane or an iris or flap valve.

18=Airlock sluice, e.g. any element enabling transfer of an object between a first and second area via a sluice chamber such that some form of closing is provided between the first and second area at all times while the object is transferred.

19=Zipper e.g. a classic zipper, a sealed classic zipper or a Ziploc® type zipper.

20=Instrument and/or device mount, e.g. denotes any mount or holding device capable of holding objects which could be necessary in or around a surgical procedure.

21=Window, e.g. any transparent sheet material.

22=Body port, e.g. any closable/openable port placed in the body such that an object may be transferred from outside the body to a cavity within the body through the port. The body port may for example comprise a self sealing silicon or gel membrane or an iris or flap valve.

23=Elastic element, e.g. a flat elastic sheet material for example made from a polymer material or glass or carbon fiber.

24=Guide slot, e.g. a slot in the wall of the medical device made from the same sheet material as the wall and adapted to guide the elastic element.

25=Lifting member, e.g. a polymer wire adapted to connect the bottom portion of the wall of the medical device and the top portion of the wall of the medical device for lifting the bottom portion.

26=Sterilizing/filtering/tempering/humidifying unit, e.g. a combined unit adapted to enable sterilization, filtering, tempering and humidification of a passing gaseous or liquid fluid passing the unit.

26a=Sterilizing unit, e.g. using a sterilizing method which may comprises the use of heat, such as electrical or chemical heat and/or irradiation, such as UV-light and/or though the addition of a chemical sterilizing agent.

26b=Filtering unit, e.g. unit comprising a mechanical filter, such as a filter textile, and/or a chemical filter such as activated carbon, or by a combination of a mechanical and chemical filters.

26c=Tempering unit, e.g. a unit comprising a heating element, such as an electrical or chemical heating element, or a cooling element, such as a refrigerator element or a chemical cooling elements such as liquid hydrogen or dry ice.

26d=Humidification unit, e.g. a unit adapted to increase the humidity of a passing gaseous fluid by for example introducing water particles or mixing the fluid with vaporized water.

27=Circulating pump, e.g. any pump capable of moving a liquid or gaseous fluid, could for example be in the form of a piston or membrane pump.

28=System for fluid circulation, e.g. a system for handling a circulating fluid. The system for fluid circulation may for example comprise fluid conduits, valves, gauges, pressure sensors, sterilizing/filtering/tempering/humidifying units and fluid pumps.

29=Fluid conduit, e.g. any conduit capable of transferring a liquid or gaseous fluid, could for example be a flexible polymer tubing.

30=Inlet, 30'=Inlet in body

31=Outlet, 31'=Outlet in body

32=Spring, e.g. an elastic member adapted to provide an elastic action when force is applied, such as a metal or polymer helical spring.

33=Protruding member 33' Magnet

34=Recess/Groove

35=Intra body ring, or inner retractor member, e.g. a ring adapted to be positioned inside the body of a patient, for example subcutaneously.

36=Connecting member, e.g. a flexible and/or elastic sheet material adapted for sealing and/or connecting and/or retracting.

37=Outer ring, or outer retractor member e.g. a ring adapted to be positioned outside the body of a patient, for example in connection with the skin.

38=Valve member, e.g. adapted to close an opening or hole, may for example comprise a flap valve.

39=Lever

42=Inset, e.g. denotes any exchangeable portion or any indentation or projection.

42'=Wall inset, e.g. an inset provided in a wall portion.

42"=Body inset, e.g. an inset adapted to be provided in the body of a patient.

43=Self sealing membrane, e.g. denotes a membrane adapted to have flexible or elastic properties such that the membrane can allow transfer of an object therethrough and after which the membrane closes by itself by means of its flexible and/or elastic properties.

44=Self sealing hole, e.g. a hole in a membrane adapted to seal by itself when no external force affects the membrane.

45=Seating

46=Roll up system, e.g. a manually operated, sprig loaded or powered system for rolling a sheet material.

47=Interconnected port, e.g. denotes a closeable/openable port created by the connection of at least two ports, such as for example a body port and a wall port. first and 48=Multiport, e.g. a closeable port or port unit comprising a plurality of closeable ports or port units 48'=Wall multiport, e.g. a multiport adapted for positioning in a wall portion.

48"=Body multiport, e.g. a multiport adapted for positioning in the body of a patient.

49=Support, e.g. denoted any structural element adapted to absorb or transfer force.

50=Adhesive surface, e.g. a surface of a sheet material comprising an adhering substance or composition such that the surface adheres to other objects. The substance or composition may for example be a pressure sensitive adhesive such as 3M's pressure sensitive adhesive Scotch-Grip 4268-NF.

51=Motor, e.g. an electric, pneumatic, hydraulic or combustion motor adapted to create or transfer mechanical work.

52=Kinetic energy transferring member, e.g. any element adapted to transfer kinetic energy of some form.

53=Kinetic energy coupling, e.g. any coupling capable of transferring kinetic energy from a first kinetic energy transferring member to a second kinetic energy transferring member.

54=O-ring

55=Information transferring member, e.g. any element adapted to transfer information of some form, for example data.

56=Fluid coupling, any coupling capable of handling the transfer of a gaseous or liquid fluid.

57=Magnet

58=Electric energy coupling, e.g. any element adapted to transfer electric energy, the electric energy coupling may be a standard electric coupling or a coupling for transferring wireless energy.

59=Sleeve

60=Tool holder, e.g. a chuck for gripping a drilling or milling tool.

61=Window contacting member, e.g. a member comprising a soft polymer element for wiping a window.

62=Fluid conduit (for window cleaning)

63=Nozzle (for window cleaning)

64=Fluid arrangement (for window cleaning)

65=Camera, e.g. an endoscopic camera, such as a camera used in laparoscopic or arthroscopic procedures. The camera may be a camera based on fiber optic technology.

66=Coil

67=Pressure creating member

68=Bellows, e.g. a chamber having a wall with a pleated structure.

69=Objects, e.g. medical device such as implants or medical instruments, such as instruments used in a surgical procedure.

70=Incision retractor

71=Inner wall

72=Connection

73=Sensing probe

74=Diode

75=Detector

76=Cuff

77=Covering sheet, e.g. a removable sheet material with the purpose of covering a portion of a medical device.

78=Lead

79=Retractor member, e.g. an element adapted to retract the skin around an incision made in the skin of a patient.

80=Coupling, e.g. a mechanical element adapted to fixate an object, such as an inset or port, or to couple to an additional coupling.

81=Specimen, e.g. bodily matter which is to be removed from the body of the patient, a specimen could for example be a tumor, a portion of the intestinal system, or an organ such as the appendix or gallbladder of the patient.

82=Pouch

83=Key-hole recess, e.g. a recess capable of holding a protrusion when the protrusion is in a first portion and releasing the protrusion when the protrusion is in a second position.

84=Connecting portion

85=Bushing

86=Iris valve

89=Instrument, e.g. a surgical and/or endoscopic instrument which may be a gripping instrument, a bonding instrument, such as a suturing or stapling instrument, or a severing instrument, such as a scalpel or an electromagnetic or ultrasonic diathermy, it may be a laparoscopic grasper, a laparoscopic claw grasper, a laparoscopic stone grasper, a laparoscopic needle holder, a laparoscopic hook, a laparoscopic dissector, or a laparoscopic diathermy instrument.

89s=Stapling instrument, e.g. a bonding instrument adapted to bond tissue or skin of the patient by means of staplers.

92=Trocar, e.g. a hollow element adapted to be inserted into the body of a patient for enabling insertion of an instrument into a cavity in the patient.

93=Adjustment device

94=Sealing sub device

96=Holding member, e.g. a structural element capable of holding.

97=Hole

98=Monitoring unit, e.g. a unit adapted to receive input parameters to be monitored and provide some form of output based on the received input.

99=Open end, e.g. a hole or opening of an indentation capable of receiving something inserted therethrough.

FIGS. 1a-5u shows an embodiment of the medical device being adapted for surgical procedures on an extremity of a patient, such as a leg or an arm of the patient. The medical device could for example be used for performing foot surgery, ankle surgery, knee surgery or fracture surgery involving femur, tibia or fibula. Surgery on the patients arm for example includes hand surgery, elbow surgery shoulder surgery and fraction surgery on for example the scapula, clavicula, humerus, radius or ulna.

FIG. 1a shows an embodiment of a medical device 0 for performing surgical procedures. The medical device 0 comprises an at least partially collapsible wall 1 enclosing a chamber C in which a sealed environment can be maintained for performing the surgical procedure. The at least partially collapsible wall 1 comprises a wall portion forming at least one elongated tubular enclosure 4 having an open end 99. The enclosure 4 extends in the chamber C and is adapted to fit a portion of an extremity of a patient inserted into the enclosure through the open end thereof. In the embodiment shown in FIG. 1a the extremity is a leg of the patient.

The medical device 0 comprises a sealing device 5 encircling the leg of the patient and being adapted to seal between the skin of the patient and the at least partially collapsible wall 1. The sealing device shown in FIG. 1a comprises an elastic sealing member, for example comprising an elastic polymer material, exerting a pressure on the skin of the patient and thereby providing the seal. According to the embodiment shown in FIG. 1a only the portion of the wall 1 comprising the elongated enclosure 4 is collapsible or deformable, for allowing the insertion of the extremity into the elongated tubular enclosure 4, whereas the rest of the wall 1 enclosing the chamber C is rigid, however, in other embodiments it is equally conceivable that the entire wall 1 enclosing the sealed environment is collapsible.

FIG. 1b shows the medical device 0 in an embodiment similar to that of FIG. 1a with the difference that the embodiment of FIG. 1b further comprises two gloves 2a, 2b integrated in the wall 1 enabling manual manipulation within the sealed environment. The gloves 2a, 2b are connected to the wall 1 by means of pleated sections 3 connecting the gloves 2a, 2b to the wall 1 and enabling free movement of the gloves 2a, 2b within the sealed environment.

FIG. 1c shows the medical device 0 according to an embodiment similar to the embodiment shown in FIG. 1a, with the difference that the medical device 0 comprises a second sealing device 5b is fixated to the wall 1 making up the elongated tubular enclosure 4 encircling the extremity in a more distal location such that the foot of the patient can be isolated, which is advantageous as the foot in very difficult to disinfect. The second sealing device 5b comprises an elastic sealing member exerting pressure of the distal portion of the leg of the patient.

FIG. 1d shows an embodiment of the medical device 0 similar to that of FIG. 1b, the difference being that the embodiment in FIG. 1d is adapted to receive an extremity in the form of an arm.

Figure 2A:
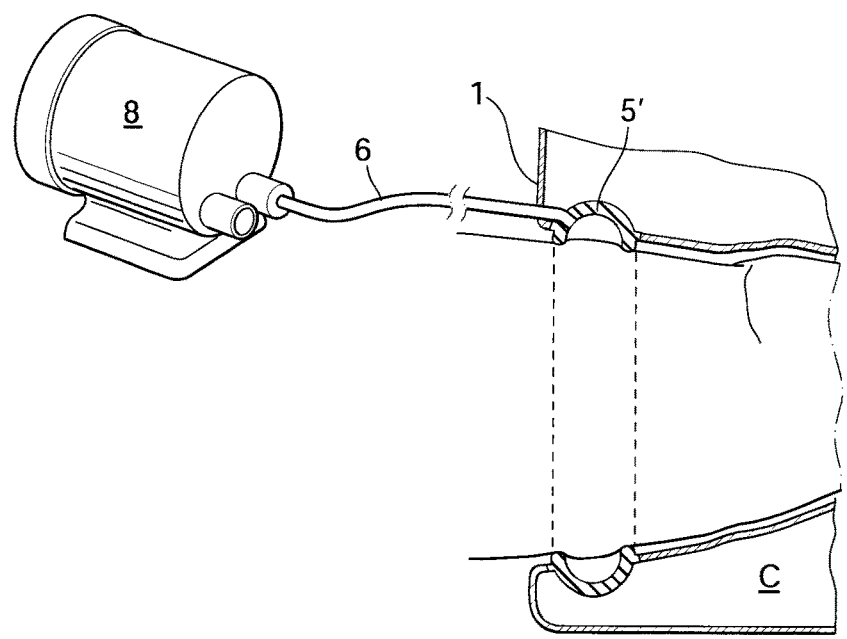
FIG. 2a shows a vacuum seal in detail.

FIG. 2a shows a sealing device in detail, in an embodiment in which the sealing device comprises a vacuum sealing member 5' adapted to seal between an extremity of the patient and the partially collapsible wall 1 by the vacuum sealing member 5' being adapted to hold a pressure less than 1 bar (an underpressure) for creating a vacuum seal between the skin of the patient and the medical device. The vacuum is created by a vacuum pump 8 connected to the vacuum sealing member 5' by means of a vacuum conduit 6. The vacuum sealing member 5' could for example be made from a semi-rigid polymer material.

Figure 2B:
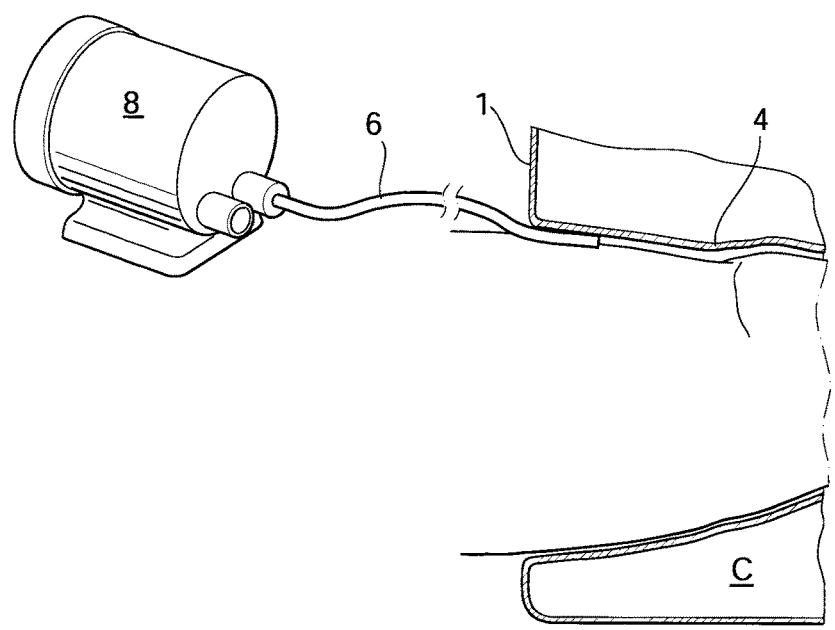
FIG. 2b shows an air evacuation pump, in detail.

FIG. 2b shows an embodiment of the medical device in which the medical device comprises an air evacuation system for evacuating air in the elongated enclosure 4 after the portion of an extremity has been placed in the elongated enclosure 4, thereby tightening the wall 1 of the enclosure 4 around the extremity of the patient. The air evacuation system comprises a vacuum conduit 6 in fluid connection with the elongated enclosure 4 and thereby enabling the evacuation of the air or fluid from the enclosure 4.

Figure 2C:
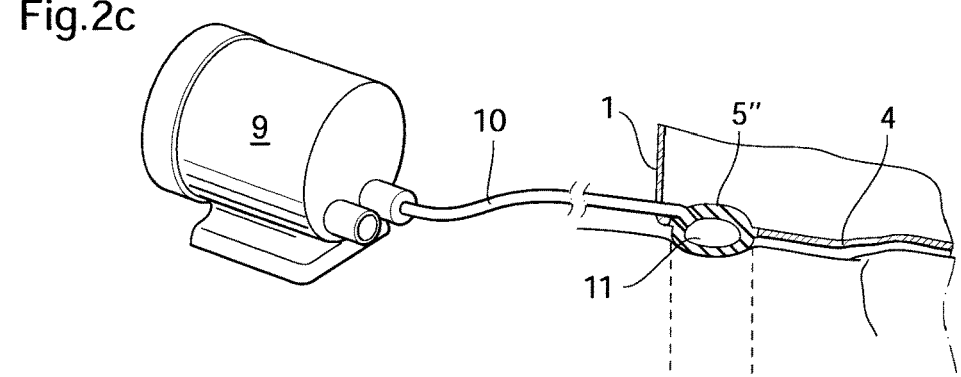
FIG. 2c shows a pressure sealing in detail.

FIG. 2c shows a sealing device in detail in an embodiment in which the sealing device comprises a pneumatic pressure sealing member 5" adapted to seal between an extremity of the patient and the partially collapsible wall 1 using a pneumatic pressure pressing against the skin of the extremity. The pneumatic pressure is created by a fluid pump 9 being connected to the pneumatic pressure sealing member 5" by means of a fluid conduit 10 adapted to transport a pressurized gas from the fluid pump 9 to a chamber 11 within the pressure sealing member 5", the pressure sealing member 5" being inflatable such that the size and/or shape of the cavity 11 can be changed for allowing the pneumatic pressure sealing member 5" to press against the skin of the extremity and thereby sealing between the extremity and the pneumatic pressure sealing member 5". The pneumatic pressure sealing member 5" may for example be made from an elastic material such as an elastic polymer.

Figure 2D:
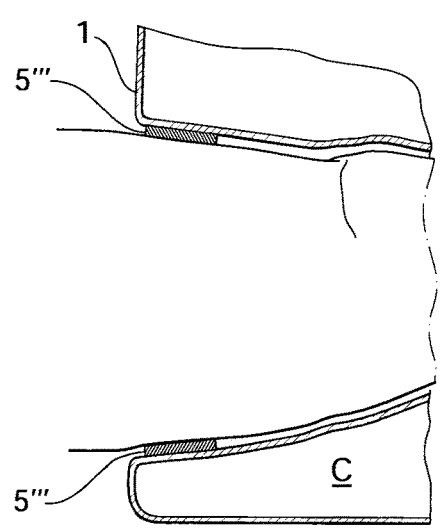
FIG. 2d shows an adhesive sealing.

FIG. 2d shows a sealing device in detail in an embodiment in which the sealing device comprises an adhesive sealing member 5''' adapted to seal between an extremity of the patient and the partially collapsible wall 1 by means of an adhesive contacting the skin of the patient and the elongated enclosure 4 of the medical device. In the embodiment shown in FIG. 2d the adhesive sealing member 5''' encircles the extremity (in this case the leg) of the patient thereby creating a seal. The adhesive may for example be a pressure sensitive adhesive such as 3M's pressure sensitive adhesive Scotch-Grip 4268-NF.

The medical device in FIGS. 2e-2i comprises an elongated tubular enclosure 4 extending in the chamber C of the medical device. The elongated tubular enclosure 4 has an adhesive surface facing the skin of the patient and being adapted to snuggly adhere to the skin of the patient for reducing the risk that bacteria from the skin of the patient contaminates the environment of the chamber C.

Figure 2E:
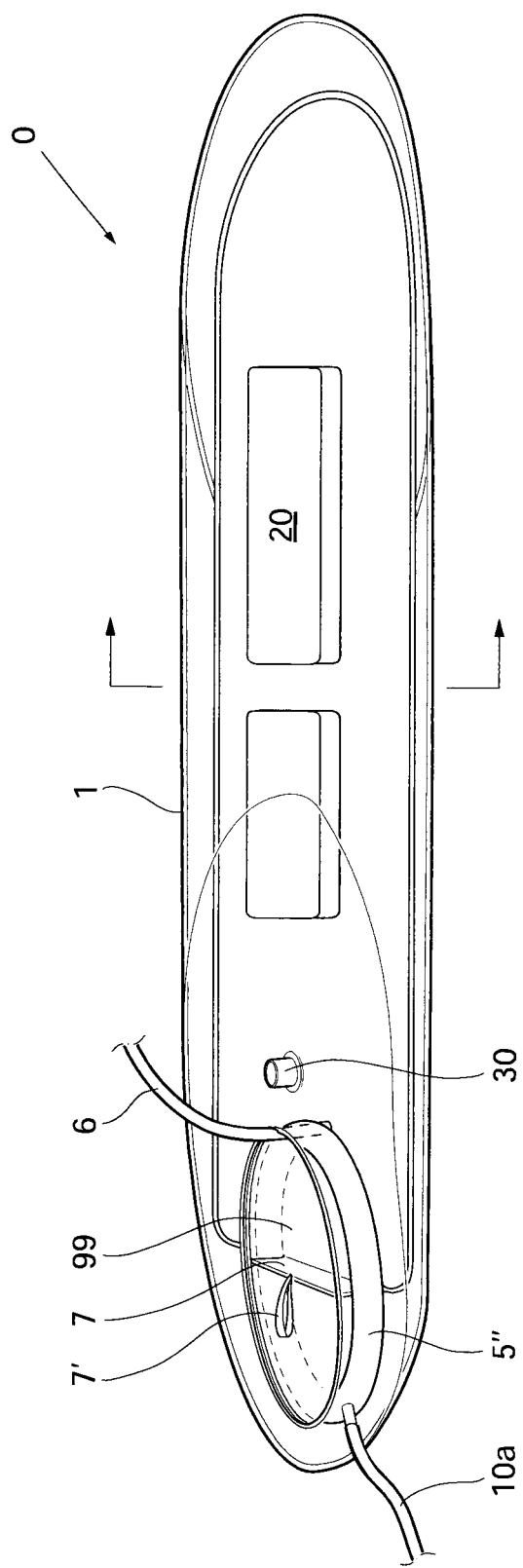
FIG. 2e shows an embodiment of the medical device comprising an elongated tubular enclosure.

FIG. 2e shows an embodiment of the medical device 0 when deflated for packaging and shipping. The medical device 0 comprises a flexible wall 1 made from a transparent polymer material, such as polyvinyl chloride (PVC) with a plasticizer additive. The wall 1 is adapted to form a chamber C for containing a sealed environment in which steps of a surgical procedure can be performed. The medical device 0 comprises a fluid inlet 30 positioned in the wall 1 for supplying a fluid to the chamber and thus inflating the chamber. The fluid inlet 30 is adapted to be connected to a fluid providing member, such as a fluid pump (such as the fluid pump 9 in FIG. 2c, or a pressurized tank, such as the pressurized tank 12 in FIG. 3a). The fluid supplied may be a gaseous fluid, such as $CO_2$ gas, or a liquid fluid, such as saline solution or an antibiotic liquid. The wall 1 of the medical device 0 forms an elongated tubular enclosure 4 having a single open end 99 adapted for insertion of an extremity of the patient. The enclosure 4 extends in the chamber and is adapted to fit a portion the extremity inserted into the elongated tubular enclosure 4 through the open end 99, such that the surgical procedure can be performed on the portion of the patient's extremity partly within the chamber. The medical device 0 further comprises a fluid evacuation system adapted to evacuate fluid from the interior of the elongated tubular enclosure 4, when the portion of the patient's extremity is placed in the elongated tubular enclosure 4. The fluid evacuation system comprises a vacuum conduit 6 adapted to be connected to a vacuum creating member, such as a vacuum pump (for example disclosed as 8 in FIG. 2b).

The medical device 0 according to the embodiment shown in FIG. 2e further comprises a sealing device comprising a pressurized sealing member 5" adapted to provide an adaptive sealing force. A fluid conduit 10a is connected to the pneumatically powered sealing member 5" for providing the pneumatic pressure. The other end of the fluid conduit 10a is connected to a pressure creating member, such as a pneumatic pump or a pressurized tank. In alternative embodiments, the sealing device may be hydraulically or electrically powered.

The inside of the elongated tubular enclosure 4 is an adhesive surface adapted to adhere to the skin of the patient, such that the incision in the skin of the patient is performed through the wall 1 of the elongated tubular enclosure 4. The adhesive layer of the elongated tubular enclosure 4 adhering snuggly against the skin of the patient, the risk that bacteria from the skin of the patient will enter the area of the incision is greatly reduced. The adhesive surface may for example comprises a pressure sensitive adhesive such as 3M's pressure sensitive adhesive Scotch-Grip 4268-NF. When the medical device 0 is packaged, the medical device 0 further comprises a separating layer 7, adapted to separate an adhesive surface of a first portion of the elongated tubular enclosure (shown as 4a in FIG. 2f), from a second portion of the elongated tubular enclosure (shown as 4b in FIG. 2f), such that the elongated tubular enclosure can easily be expanded or inflated after having been packaged as a flat package (which is shown in FIG. 2e). The separating layer 7 comprises a non-stick surface which is easy to remove from the adhesive surface. The non-stick surface could for example be a PTFE covered surface. The separating layer 7 further comprises a gripping portion 7' such that the separating portion 7 can easily be removed after the elongated tubular enclosure 4 has been expanded or inflated.

The medical device 0 further comprises an instrument mount 20 placed within the chamber adapted for retaining instruments within the chamber.

Figure 2F:
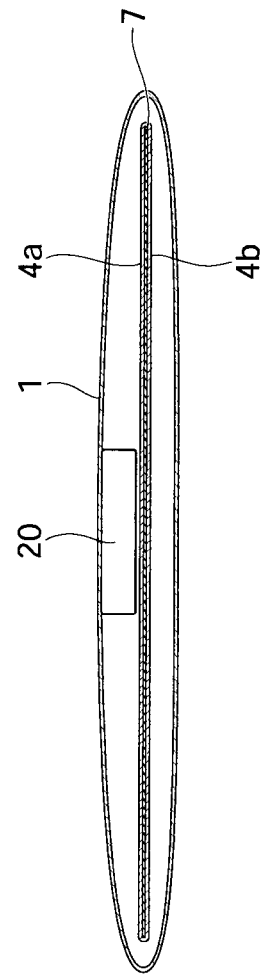
FIG. 2f shows an embodiment of the medical device comprising an elongated tubular enclosure, in cross-sectional view.

FIG. 2f shows the medical device according to the embodiment shown in FIG. 2e in a sectional view from the left, in which the separating layer 7, the first 4a and second 4b portion of the wall of the elongated tubular enclosure 4, and the wall 1 of the medical device creating the chamber can be seen in section.

FIG. 2g shows the medical device 0 when the wall 1 of the medical device 0 has been inflated by the injection of a fluid through the fluid inlet 30 positioned in the wall 1 and connected to a fluid conduit 10b, such that a chamber C is formed. The fluid entering the chamber C could require filtering, and thus the fluid conduit 10b may pass a filtering unit. The filtering unit being adapted to remove particles by a mechanical filter, such as a filter textile, or by means of a chemical filter such as activated carbon, or by a combination of a mechanical and chemical filter. Furthermore, a sterilization device may be provided on the fluid conduit 10b for sterilizing the fluid entering the chamber C. The sterilization device could for example be a sterilization device sterilizing the fluid by means of heat, a chemical sterilization device, or a sterilization device sterilizing by means of radiation, such as UV-radiation. A fluid tempering device may also be provided on the fluid conduit 10b for changing the temperature of the fluid passing fluid tempering device. The fluid sterilization device, tempering device and tempering unit is further shown in e.g. FIG. 210.

In FIG. 2g, the elongated tubular enclosure 4 has been inflated through the vacuum conduit 6, which now has provided a pressurized fluid into the elongated tubular enclosure 4. The inflation of the elongated tubular enclosure 4 facilitates the insertion of the extremity of the patient into the elongated tubular enclosure 4 even when the inner surface of the elongated tubular enclosure 4 is an adhesive surface 50. During the inflation, the open end 99 may be covered by a covering member (not shown) such that a pressure buildup is possible within the elongated tubular enclosure. The elongated tubular enclosure 4 is made from a transparent polymer material rigid enough to retain its shape even when the covering member is removed and the pressure within the elongated tubular enclosure 4 is released. After the inflation and thus separation of the first and second portions of the wall 1 of the elongated tubular enclosure 4, which were connected when the medical device 0 was packaged, the separating layer 7 is removed by pulling the separating layer 7 out of the elongated tubular enclosure 4 by means of the gripping portion 7'. The instrument mount 20 is further shown in FIG. 2g as being placed in the top portion of the chamber C, however, the position of the mount 20 may be adapted for the particular instruments to be retained by the mount 20.

The medical device 0 according to the embodiment shown in FIG. 2g comprises a pressure seal 5" supplied with a pressurized fluid via a fluid conduit 10a. However, in alternative embodiments it is equally conceivable that the pressure sealing member 5" is replaced by a vacuum sealing member, a mechanically pressing sealing member, such as an elastic sealing member, or an adhesive sealing member (examples of which are given in relation to other embodiments herein).

The fluid conduits 10a, 10b are for example connected to a pressure creating member such as a pneumatic pump or a pressurized tank (disclosed throughout the disclosure).

The medical device 0 may additionally comprise a monitoring unit adapted to monitor a physiological parameter of the patient and adapted to control a pressure creating member inflating the sealing member 5" or the inflatable wall 1 such that the inflation of the sealing member, or the inflation of the chamber C can be adjusted such that the blood flow of the extremity of the patient is not hindered by the pressure in the sealing member 5" or by the pressure in the chamber C. The monitoring unit is further described under reference to FIGS. 209a-209g.

The medical device 0 may further comprise a glove integrated in the wall 1 such that a surgeon is able to use the glove from outside the chamber C to make manual manipulations inside the chamber C while maintaining the sealed environment in the chamber C. An example of an integrated glove is shown in FIGS. 2b and 2i.

FIG. 2h shows the medical device 0 when the extremity of the patient has been inserted into the elongated tubular enclosure 4 and the sealing member 5" has been inflated, such that a substantially airtight seal is created between the ambient environment A and the elongated tubular enclosure 4. The vacuum conduit 6 is integrated in the sealing member 5" such that the vacuum conduit 6 is in fluid connection with the elongated tubular enclosure 4 whilst the sealing member 5" provides sealing between the elongated tubular enclosure 4 and the ambient environment A.

Figure 2I:
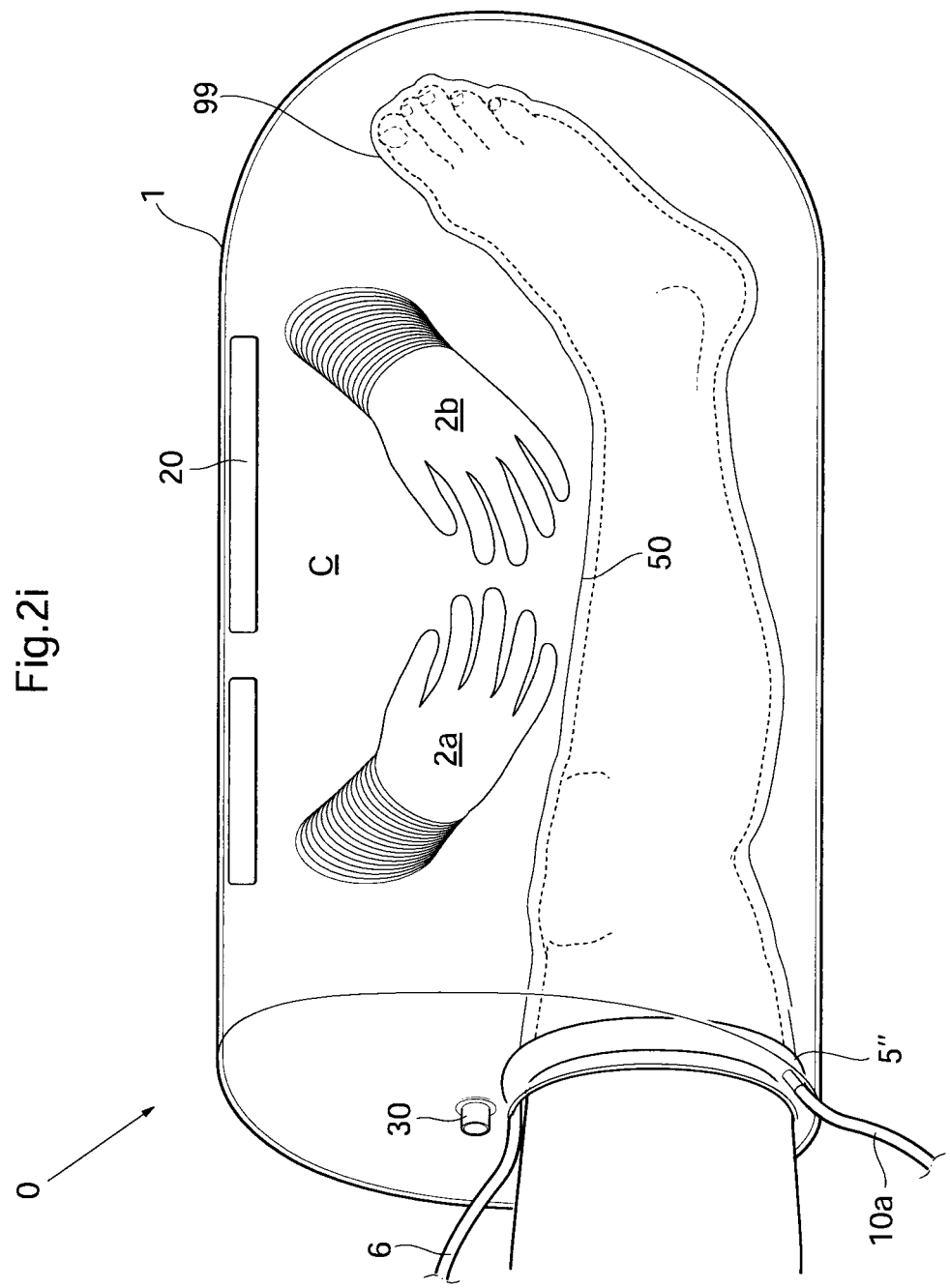
FIG. 2i shows an embodiment of the medical device when the elongated tubular enclosure fits snuggly around the leg of the patient.

FIG. 2i shows the medical device 0 when the inflated fluid in the elongated tubular enclosure 4 has been evacuated by the vacuum conduit 6, such that the wall 1 of the elongated tubular enclosure 4 snuggly encloses the extremity and the adhesive surface 50 of the inside of the elongated tubular enclosure 4 adheres to the skin of the extremity of the patient, such that an adhering layer 50 on the patients skin is formed. The adhering layer is cut through in the beginning of a surgical procedure inside the chamber C of the medical device 0. By the adhering layer 50 covering all of the skin which otherwise would be exposed to the environment of the chamber C, the risk that bacteria from the skin of the patient should contaminate the environment of the chamber C is substantially reduced. FIG. 2i further shows gloves 2a, 2b integrated in the wall 1 of the medical device 0 and enabling manual manipulation within the chamber C of the medical device 0.

After an incision has been performed in the wall 1 of the elongated tubular enclosure 4 and the skin of the patient, a port may be placed in the wall 1 of the elongated tubular enclosure 4 and in the skin of the patient for creating a fluid connection between the chamber C and a cavity in the patient. The port may be fixated to the wall 1 of the elongated tubular enclosure 4 by being integrated in the wall, or the port may be fixated in the skin of the patient, such as for example disclosed under reference to FIGS. 4a-4c. The port disclosed in FIGS. 4a-4c comprises a sealing device having a first sealing member adapted to be positioned at the inside of the patient's skin around an incision cut in wall of the elongated tubular enclosure 4 and the patient's skin, made from within the chamber C, a second sealing member adapted to be positioned at the outside of the patient's skin inside the chamber, around the incision in the skin of the patient and the elongated tubular enclosure 4. The sealing further comprising an elastic connecting member sealingly interconnecting the first and second sealing members, such that the elastic connecting member seals between the second sealing member and the elongated tubular enclosure 4 and/or the first sealing member and the tissue of the patient.

The medical device 0 may further comprise a wall port provided in the wall 1 of the medical device 0 for enabling transfer between the chamber C of the medical device 0 and the ambient environment A (such a wall port for example disclosed as 17 in FIGS. 3a-3e). The wall port may comprises an elastic membrane adapted to, in a non-compressed state, seal between the chamber C and the ambient environment A, and in a compressed state enable a hand or object to be inserted through the membrane.

In alternative embodiments, the medical device 0 may further comprise an outlet member provided in the wall for discharging the fluid from the chamber C, and a pump adapted to circulate the fluid from the outlet member to the inlet member 30 (such as for example disclosed in FIG. 3e).

FIG. 3a shows an embodiment of the medical device 0 in which the medical device 0 comprises a partially collapsible wall 1 having a cylindrical or tube shaped structure. The partially collapsible wall 1 is inflatable by means of a fluid conduit 10b, here connected to a tank 12 containing pressurized gas. The tank 12 is further connected to a fluid conduit 10a for transferring pneumatic force into the chamber C enclosed by the partially collapsible wall 1. Shown in the embodiment herein, the fluid conduit 10a is connected to a pneumatic tool 16, which in the example shown is an orthopedic saw, adapted to be operated within the chamber C. The pressure provided to the chamber C and the fluid conduit 10a is controlled and monitored by two control/monitoring systems 15a, 15b connected to the fluid conduits 10a, 10b, respectively. In the embodiment shown, the partially collapsible wall 1 is sealed from the extremity of the patient by means of a pneumatic pressure sealing member 5" (further disclosed with reference to FIG. 2c) encircling the extremity. In FIG. 3a the medical device 0 is shown incorporating the pneumatic pressure sealing member 5" receiving a fluid pressure by means of a fluid conduit 10c, however it is equally conceivable that the pneumatic pressure sealing member 5" is assisted or replaced by any of the other sealing members disclosed herein. The medical device 0 shown in FIG. 3a further comprises an airlock sluice 18 comprising two zipper-closed consecutive openings, where the outer zipper 19a could be opened for placing and/or removing objects 69, such as implants, in the airlock sluice 18 between the zippers 19a, 19b from the outside of the chamber C and the inner zipper 19b could be opened from the inside of the chamber C for placing and/or removing objects 69 from the airlock sluice 18. For example the airlock sluice 18 could be used to remove a specimen from the chamber C while keeping the environment closed, or the airlock sluice 18 could be used to insert a medical device 0 or an implant into the chamber C. The medical device 0 disclosed with reference to FIG. 3a further incorporates a wall port 17 (which are to be regarded as optional) through which laparoscopic trocars or endoscopic instruments could be inserted. The medical device 0 according to the embodiment disclosed with reference to FIG. 3a further includes an instrument mount 20 for retaining instruments within the chamber C.

Figure 3B:
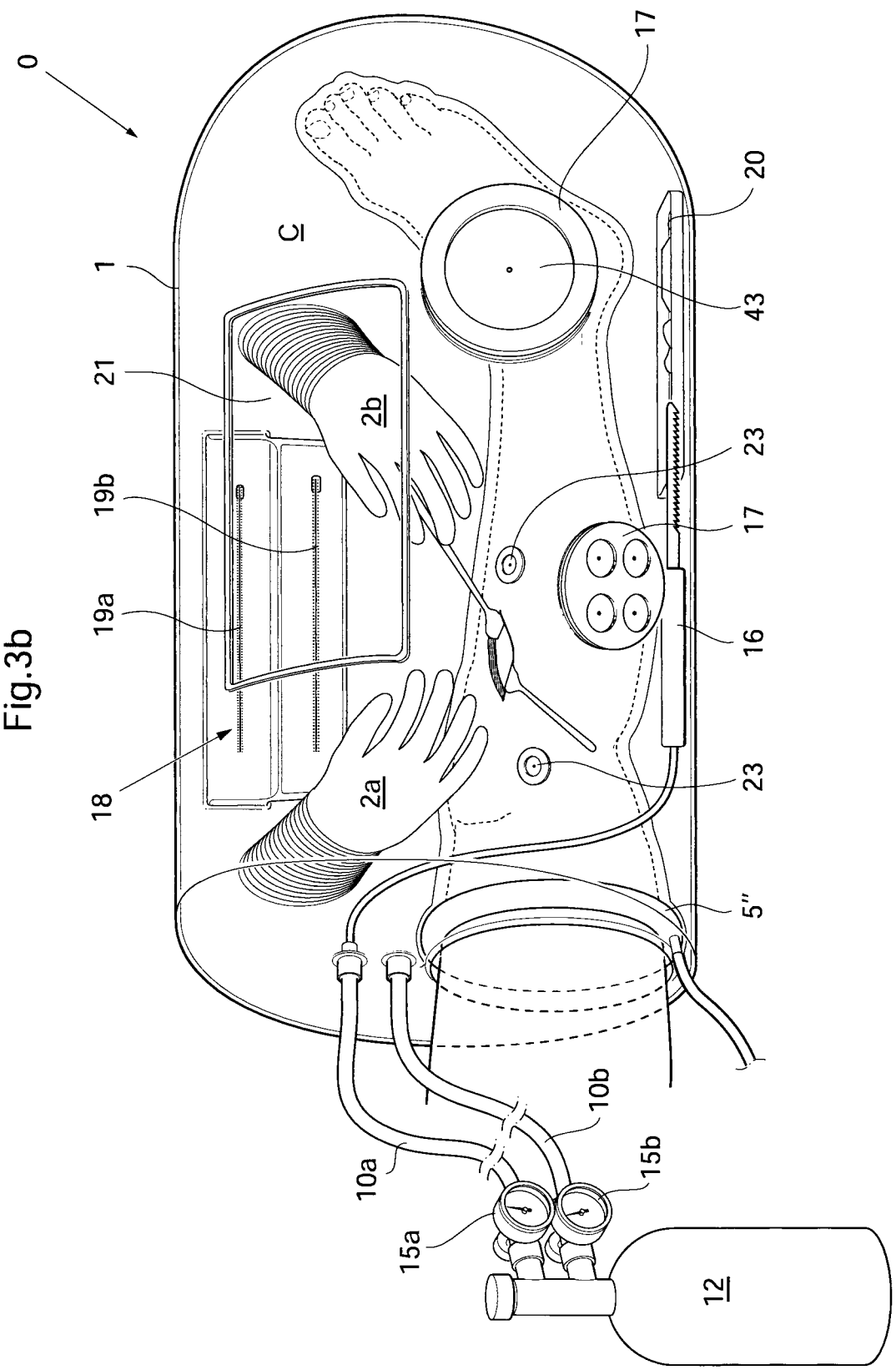
Figure 3B:
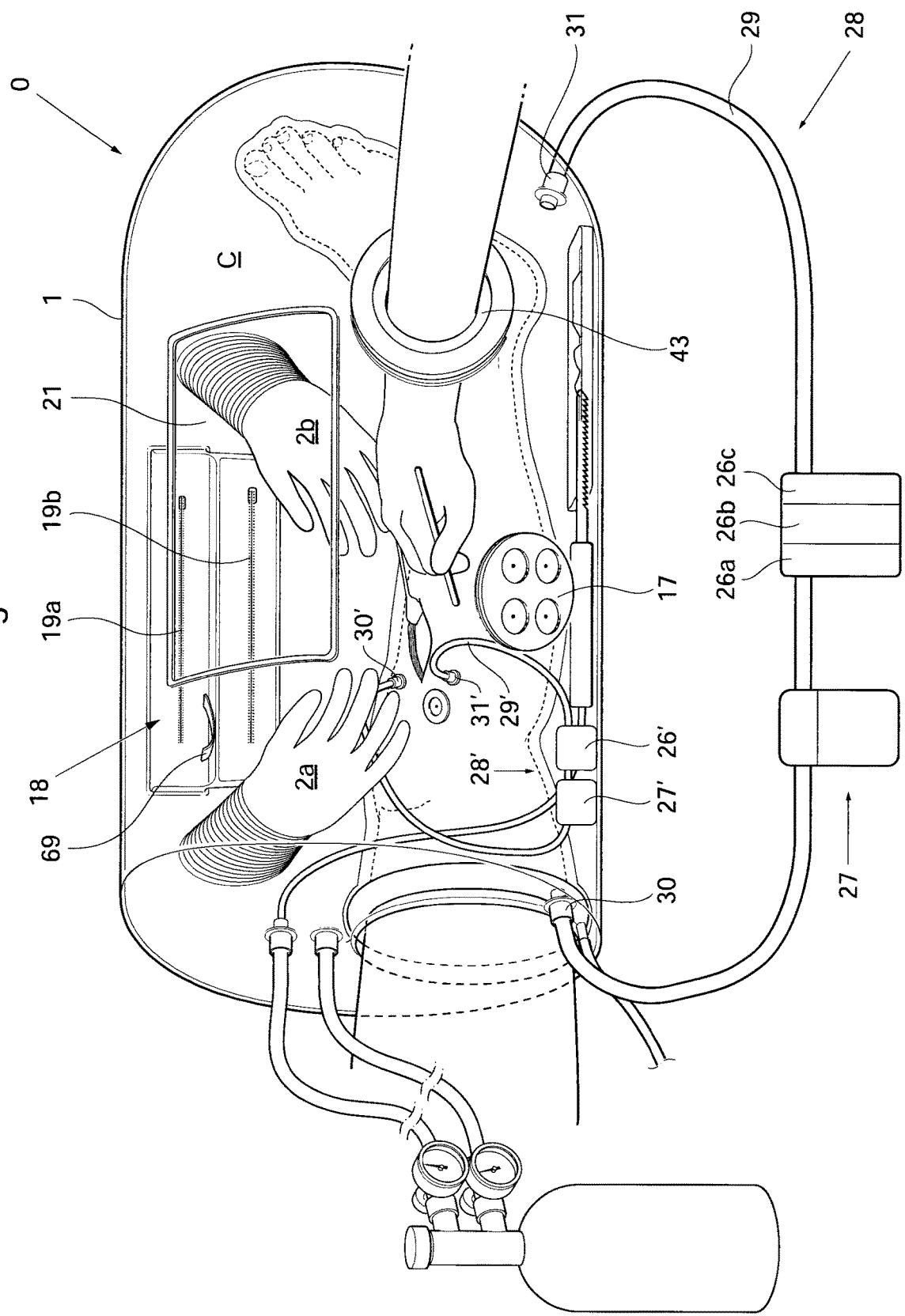

FIG. 3b shows the medical device 0 similar to the embodiment shown in FIG. 3a, however the partially collapsible wall 1 of the medical device 0 according to FIG. 3b comprises a non-collapsible transparent window 21 for enabling viewing into the chamber C. The non-collapsible transparent window 21 will ensure that the surgeon has adequate visual control over the procedure since the partially collapsible wall 1, even if preferably made from a transparent material could provide limited visibility, e.g. if the medical device 0 is not fully inflated, or in seams or bends of the material. The medical device 0 shown in FIG. 3b further comprises a wall port 17 comprising a self sealing membrane 43, which for example could comprise a material of gel type, such as the GelPort available from Applied medical inc. Rancho Santa Margarita, Calif. The wall port 18 with the self sealing membrane 17 enables the insertion of trocars and/or instruments as well as a persons (preferably the surgeons) hand, enabling manual manipulation within the chamber C. The medical device 0 as shown in FIG. 3b further comprises two body ports 23 which incorporate endoscopic ports in direct connection with the extremity of the patient, within the chamber C. The body ports 23 could for example enable an arthroscopic procedure with trocars to be performed within the chamber C and either by the instruments being manipulated from the inside of the chamber C or by the instruments reaching from the ports 17 in the collapsible wall 1 and to the body port 23 within the chamber C.

FIG. 3b' shows the embodiment of the medical device 0 according to FIG. 3b when the arm of the surgeon is inserted through the self sealing membrane 43 of the wall port 17 in the partially collapsible wall 1 for enabling manual manipulation therein. Manual manipulation through the wall port 17 could for example be used as a last resort should complications occur during the procedure, or if additional hands are required for a specific step of the operation. FIG. 3b' further shows an internal system 28' for fluid circulation, and an external system 28 for fluid circulation. Both systems comprises fluid conduits 29; 29', in the external system 28 connected at an inlet 30 placed in the partially collapsible wall 1 for supplying fluid to the chamber C, and an outlet 31 for draining the fluid from the chamber C, and in the internal system 28' connected to an inlet 30' in the patient's body and an outlet 31' in the patient's body for circulating fluid in a body cavity. The fluid is circulated by means pumping units 27; 27' and is circulated via a sterilizing/filtering/tempering unit 26', in the external system disclosed as containing a sterilizing 26a, filtering 26b, and tempering 26c unit adapted to remove impurities, sterilize and temper the fluid. In embodiments where the fluid is a gaseous fluid, the filtering unit is adapted to remove particles that could be suspended in the gas. The filtering unit 26a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 26a could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIG. 3c shows the embodiment of the medical device 0 also shown in FIG. 3a with the addition of a unit 26c for tempering the fluid entering the chamber C. The tempering part of the system could be provided to heat or cool the gaseous fluid inflating the medical device 0. In cases when the surrounding environment is cold the tempering part of the system 24 could be used to raise the temperature of the chamber to provide beneficial operating circumstances both for the patient and for the surgeon. In cases when the surrounding environment is hot, the tempering part of the system 24 could be used to lower the temperature of the sealed environment both to provide beneficial operating circumstances, both for the patient and for the surgeon, and for providing a temperature inhibiting bacterial and viral infections. The tempering unit 24 may comprise a temperature regulator for setting the required temperature. FIG. 3c further shows an object in the airlock sluice 18 being a knee joint prosthesis or a portion of a knee joint prosthesis to be implanted. The prosthesis is being inserted into the chamber C through the air lock sluice 18 further disclosed under reference to FIG. 3a.

FIG. 3d shows the medical device 0 according to FIG. 3c but further comprising a sterilizing unit 26a adapted to sterilize the gaseous fluid entering the medical device 0. In the embodiment disclosed herein, the gaseous fluid entering the medical device 0 originates from a pressurized tank 12 and could be pre-sterilized, however, in other embodiments, it is conceivable that the gaseous fluid is the surrounding air which is pressurized (such as further disclosed with reference to FIG. 3e). In the embodiments where the surrounding air is used to inflate the medical device 0 and constitute the operating environment this air needs to be properly sterilized.

FIG. 3e shows an embodiment of the medical device 0 in which the medical device 0 comprises a system 28 for circulating a fluid through the chamber C of the medical device 0. The system comprises a fluid conduit 29 connected at an inlet 30 placed in the partially collapsible wall 1 for supplying fluid to the chamber C, and an outlet 31 for draining the fluid from the chamber C. The fluid is circulated by means of a pumping unit 27 and is circulated via a sterilizing/filtering/tempering unit 26 adapted to remove impurities, sterilize and temper the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIGS. 1a-3e show different embodiments of a medical device directed to an extremity of the patient e.g. a leg or an arm. The medical device could for example be used for performing an amputation both in a hospital environment and in environments where the risk of infections are considerably higher, such as in third world countries or in zones of catastrophe. The medical device disclosed enables surgical procedures to be performed in a fully enclosed environment without any risk of infection disease even in very remote locations and without the access to water or electricity.

Figure 4A:
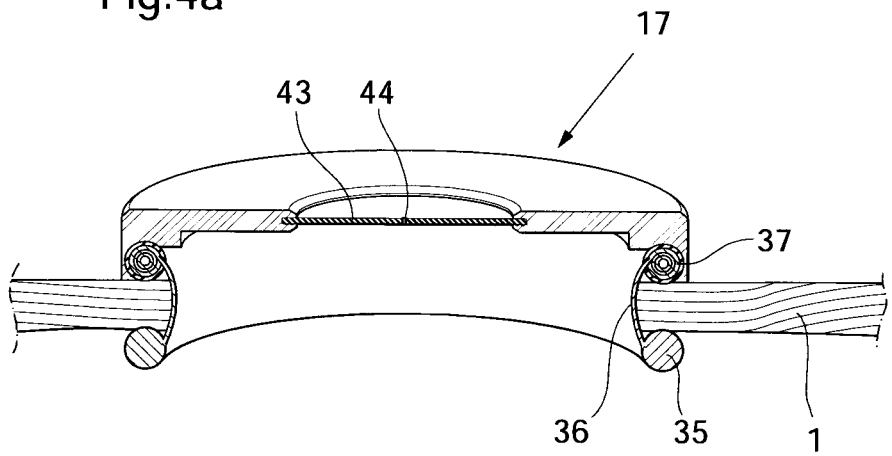
FIGS. 4a-4c shows embodiments of a self sealing port.

FIG. 4a shows a wall port 17 in a close-up, in section, where the wall port 17 comprises a self sealing membrane 43 fixated to a rigid part 45 of the wall port. The self sealing membrane 43 having a small self sealing hole 44 centrally in the membrane 43. The self sealing membrane 43 is for example made from a gel-type material being elastic enough to enable a deformation large enough for a person's hand to pass through the small self sealing hole 44 while still contracting enough to create an airtight seal between the sealed environment and the outside environment. Wall port 17 is fixated to a hole in the wall 1 of the medical device by means of a first intra chamber ring 35 adapted to be positioned on the inside of the wall 1, and a second outer ring 37 adapted to be placed on the outside of the wall 1. Between the intra chamber ring 35 and the outer ring 37 adapted to be placed on the outside of the wall 1 an elastic connecting member 36 is positioned. The connecting member 36 is preferably made from a resilient or elastic polymer material. The outer ring 37 adapted to be placed on the outside of the wall 1 comprises an integrated roll up system which could be a spring loaded roll up system adapted to create a suitable pressure on connecting member 36.

Figure 4B:
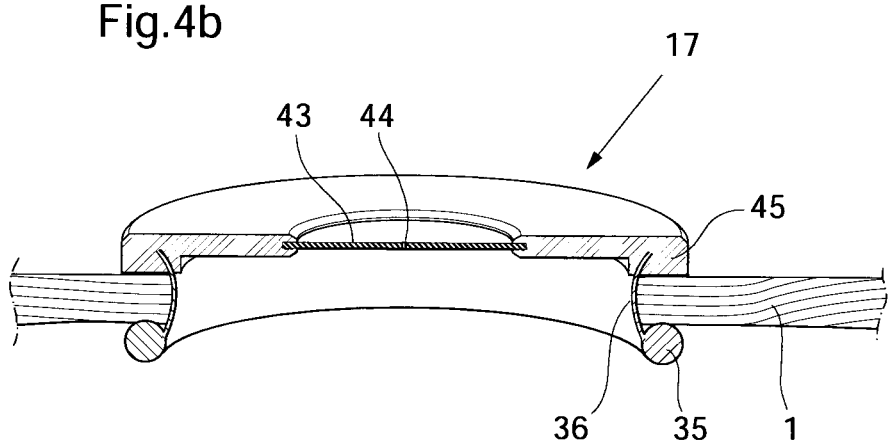

FIG. 4b shows an alternative embodiment of the wall port 17, the difference being that the connecting member 36 is made from a material elastic enough such that one end of the retractor membrane 36 could be fixedly fixated to a rigid part 45 of the wall port 17.

Figure 4C:
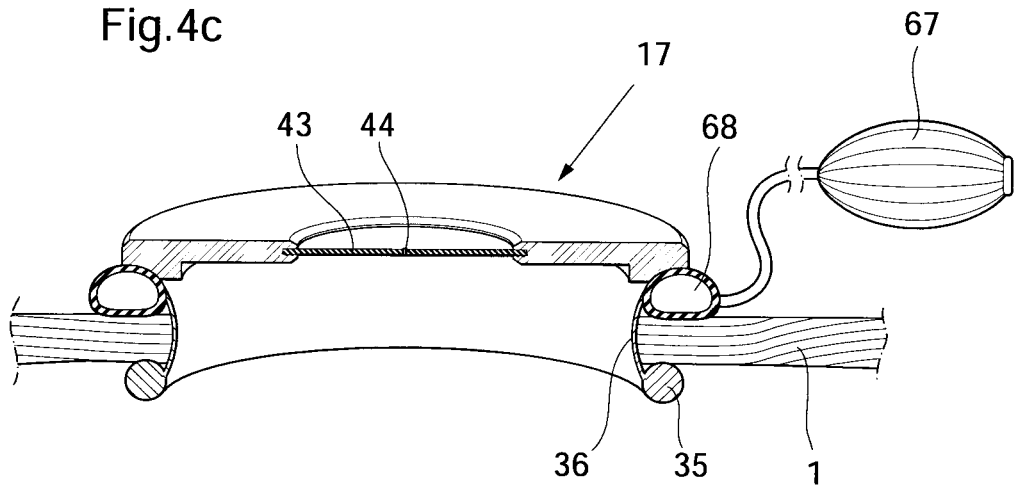

FIG. 4c shows an alternative embodiment of the wall port 17, with the difference that the connecting member 36 is connected to an inflatable bellows 68 which in turn is connected to a pressure creating member 67 for inflating the bellows 68 and tighten the connecting member 36 in a direction substantially perpendicular to the wall 1 of the medical device.

Figure 5A:
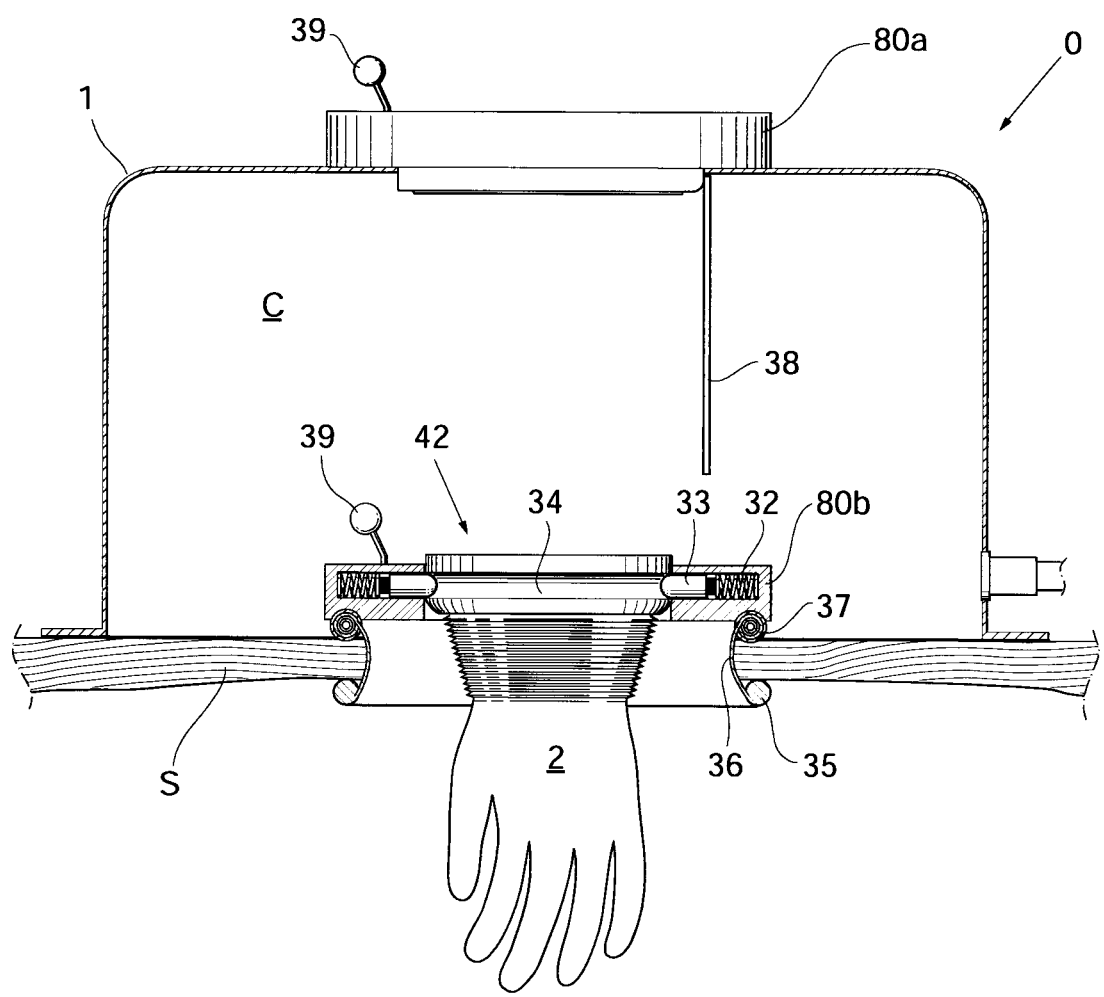
FIG. 5a shows an embodiment of the medical device, in section.

FIG. 5a shows an embodiment of the medical device 0 in which the medical device 0 comprises a wall 1 separating the environment of the chamber C in the medical device 0 from the ambient environment A. The wall 1 is adapted to be fixated to the skin S of the patient, by means of an adhesive or by means of a difference in pressure between the inside of the chamber C and the ambient environment A. The medical device 0 further comprises an upper 80*a* and a lower 80*b* coupling for fixating ring shaped objects which for example could be insets 42 or ports, such as the ports 17; 23 disclosed in FIGS. 1-3 and the insets for example could be a surgical glove 2 as disclosed in various embodiments herein, or holding devices. The ports may further be hand access ports, such as the port disclosed with reference to FIGS. 4*a* and 4*b*. The couplings 80*a*; 80*b* comprises a releasing lever 39 for releasing the inset 42 or port. The lever 39 is connected to protruding members 33 which are spring 32 loaded from the rear in order to secure the recess 34 of the object. In the embodiment disclosed in FIG. 5*a*, the inset 42 fixated to the lower coupling 80*b* is a surgical glove 2 enabling manual manipulation within the body of the patient. The medical device 0 shown in FIG. 5*a* further comprises a valve member 38 adapted to close the opening in the upper coupling 80*a*, when the upper coupling 80*a* is not in use.

Figure 5B:
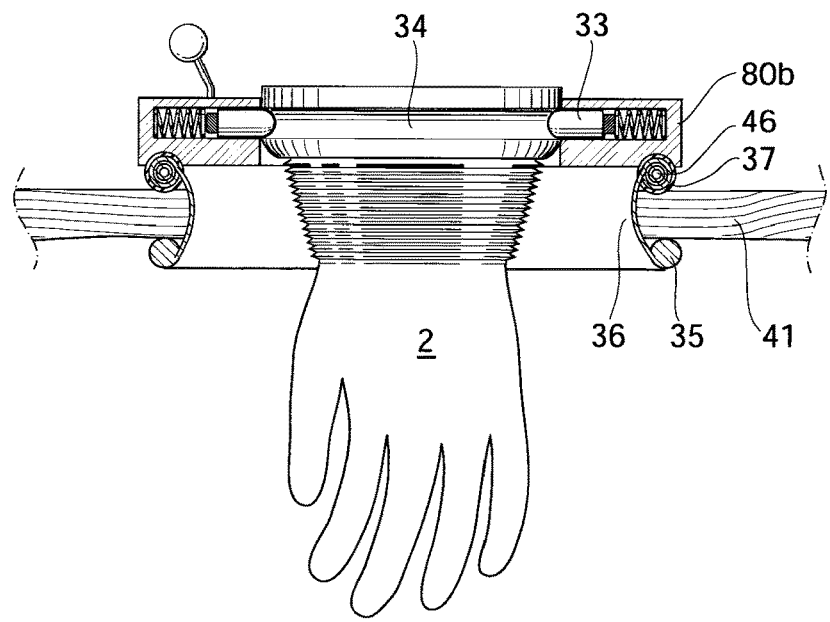
FIG. 5b shows a coupling, in section.

FIG. 5*b* shows the lower coupling 80*b* in further detail when an inset 42 in the form of a surgical glove 2 is fixated to the lower coupling 80*b*. A retractor system comprising an intra body ring 35 and an outer ring 37 adapted to be placed on the outside of the patients skin S further comprises a connecting member 36 in the form of a retractor membrane positioned such that it exerts a pressure on the cut surfaces of the incision for retracting the skin S and thereby keeping the incision open. The retractor membrane 36 could be rolled into a roll up system 46 inside of the outer ring 37 for tightening the retractor membrane 36 such that the incision is kept open.

Figure 5C:
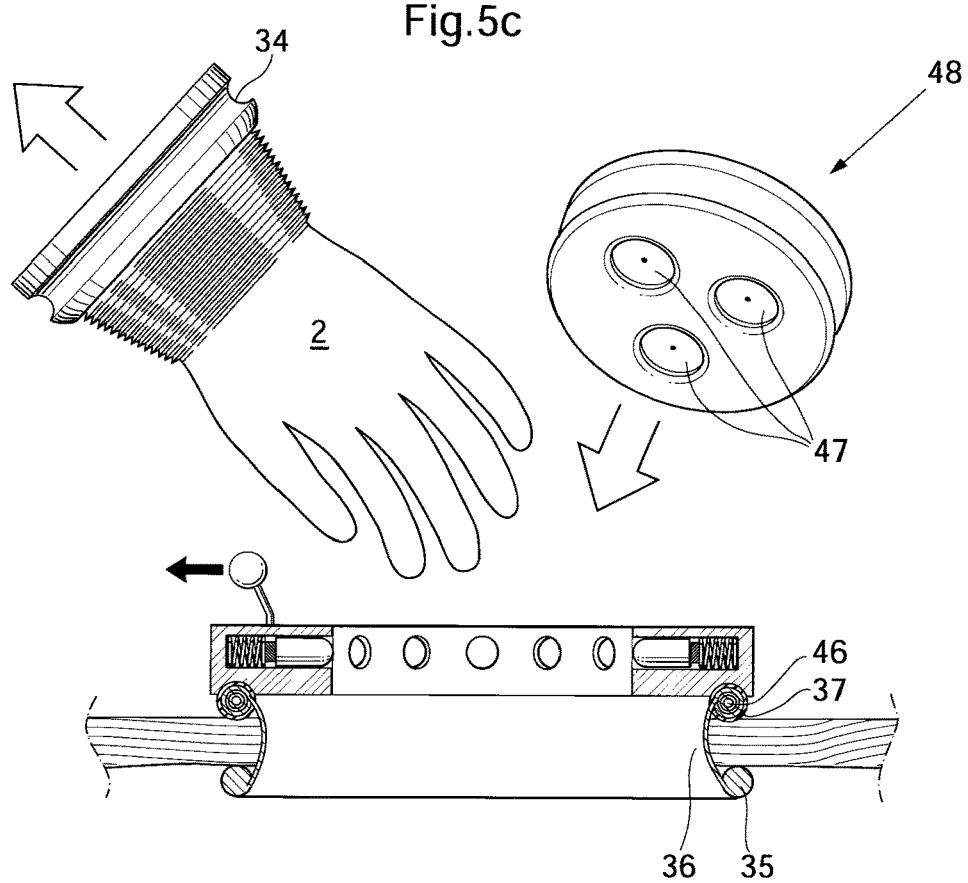
FIG. 5c shows the exchange of objects in a coupling.

FIG. 5*c* shows the changing of objects in the lower coupling 80*b* from an inset 42 comprising a surgical glove 2 to a multi-port 48 comprising three endoscopic ports. To be able to quickly switch from a purely endoscopic system to a hand access or manual manipulation system could be of major importance if complications arise during the procedure and could remove the need for a traditional conversion from endoscopic to open surgery, a conversion which inevitably causes problems increasing the risk of complications and/or postoperative care.

Figure 5D:
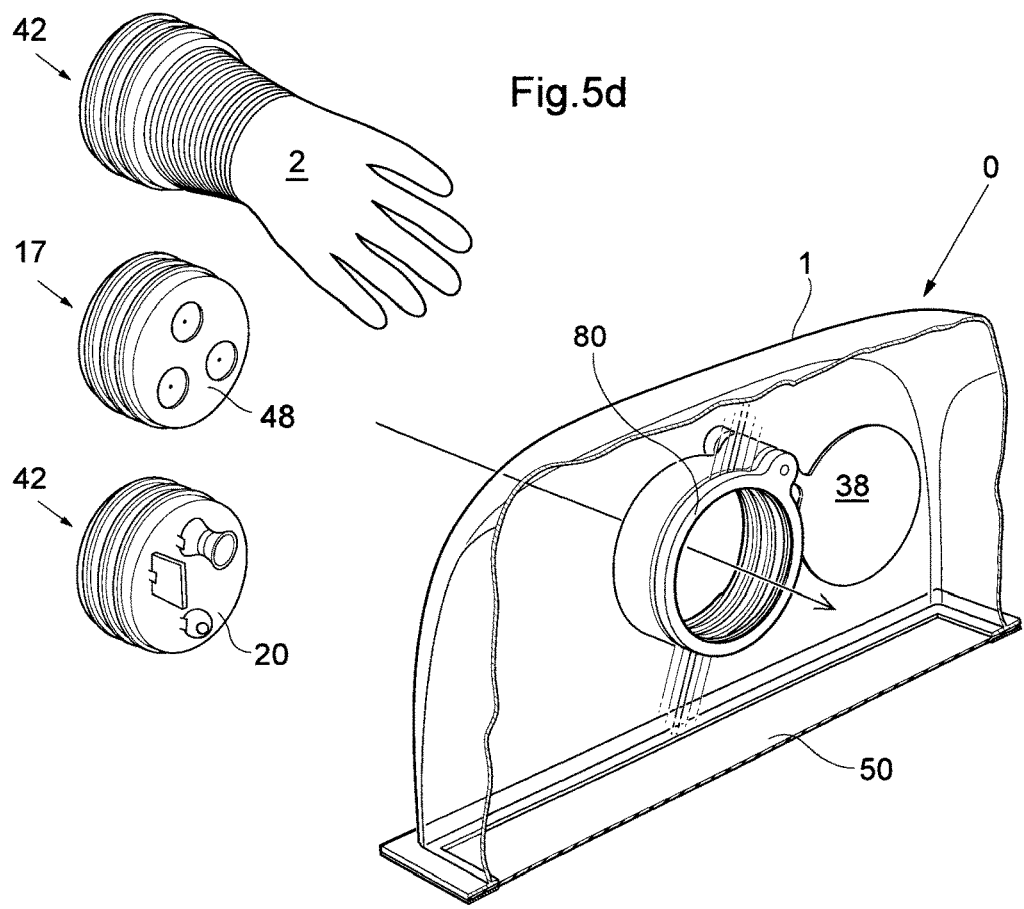
FIGS. 5d-5e shows a coupling in the wall of the medical device.

FIG. 5*d* shows a section of the medical device 0 showing a coupling 80 integrated in the wall 1. The coupling 80 enables the changing of objects from for examples ports, such as the wall port 17 disclosed in other embodiments herein, to insets 42 in form of a surgical glove 2 or an instrument/device mount 20. The coupling 80 comprises a valve member 38 for closing the hole in the coupling 80 when objects should be exchanged such that the environment in the medical device 0 can remain sterile. The instrument or device mount 20 could for example be adapted to hold surgical instruments and/or implants or parts of implants. The medical device 0 is according to this embodiment adapted to be fixated to the skin of the patent by a large portion of the wall of the medical device comprising an adhesive surface 50.

Figure 5E:
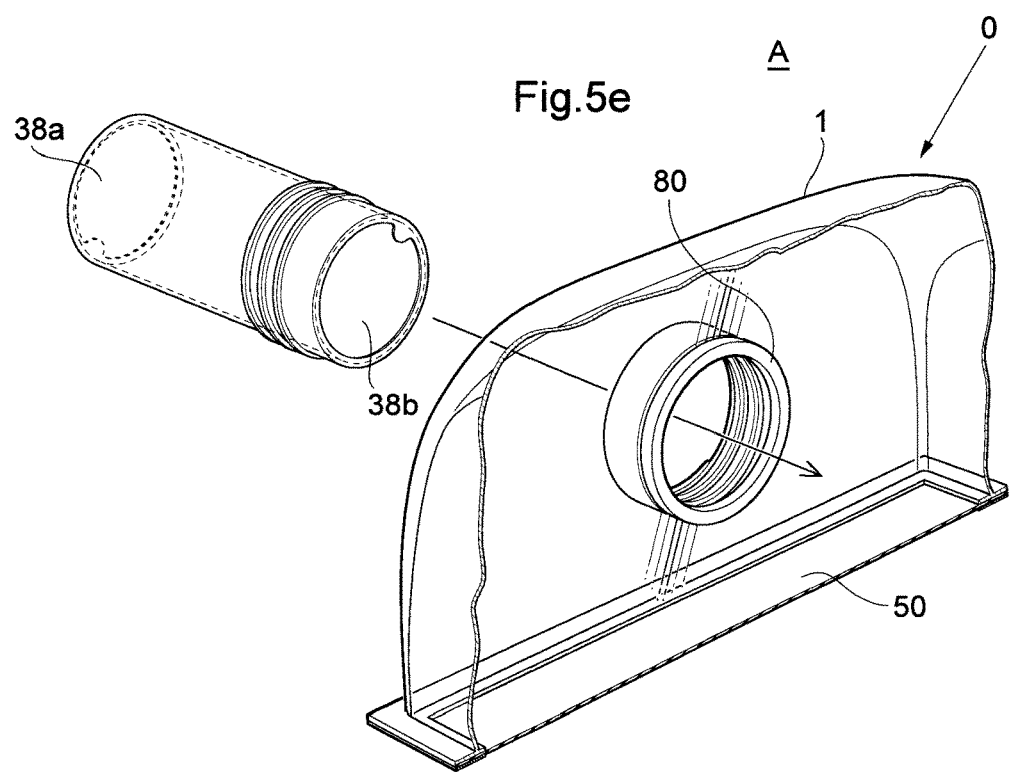

FIG. 5*e* shows the medical device 0 according to the same embodiment as in FIG. 5*d*, but when the ports of insets in the coupling 80 have been replaced by an airlock sluice 18 comprising a first 38*a* and second 38*b* valve member enclosing a sluice chamber placed between the first 38*a* and second 38*b* valve members. The airlock sluice 18 can be used to enable transfer of objects from the ambient environment A to the chamber and vice versa.

Figure 5F:
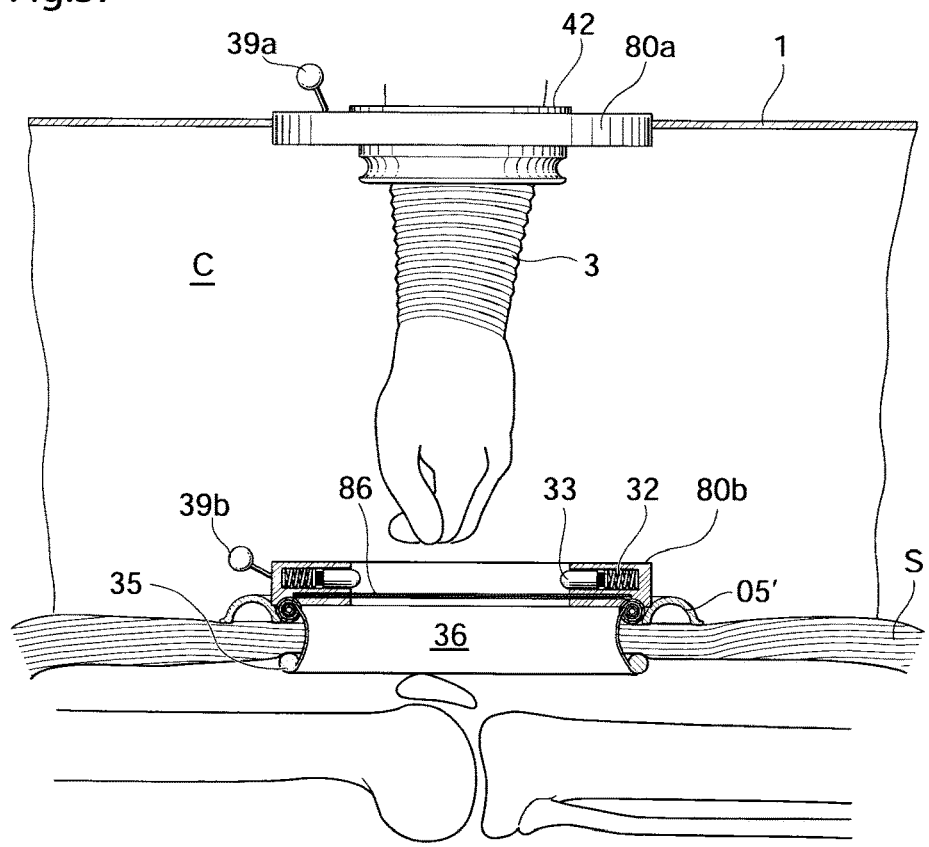
FIGS. 5f-5g shows the medical device when used.

FIG. 5*f* illustrates how an incision in the patient's skin S has been created by the surgeon by means of an inset 42 comprising a glove 2 latched to a first coupling 80*a*. The second coupling 80*b* is fixated and sealed by means of a sealing device comprising a vacuum sealing member 5'. The medical device shown in FIG. 5*f* further comprises a second sealing member that is provided partially within the patient's body 35; 36 which cannot be mounted until the incision in the patient's skin has been concluded. The two different sealing members 5'; 35; 36 disclosed could in some embodiments be replaced by only one of the sealing members, or by a different sealing member, such as the adhesive or pressure sealing members disclosed in other portions herein. The first coupling 80*a* comprises an iris valve 86 which may be opened to enable the surgeon to access the inside of the patient's body, or closed to separate the patient's body from the chamber C enclosed by the wall 1 of the medical device.

Figure 5G:
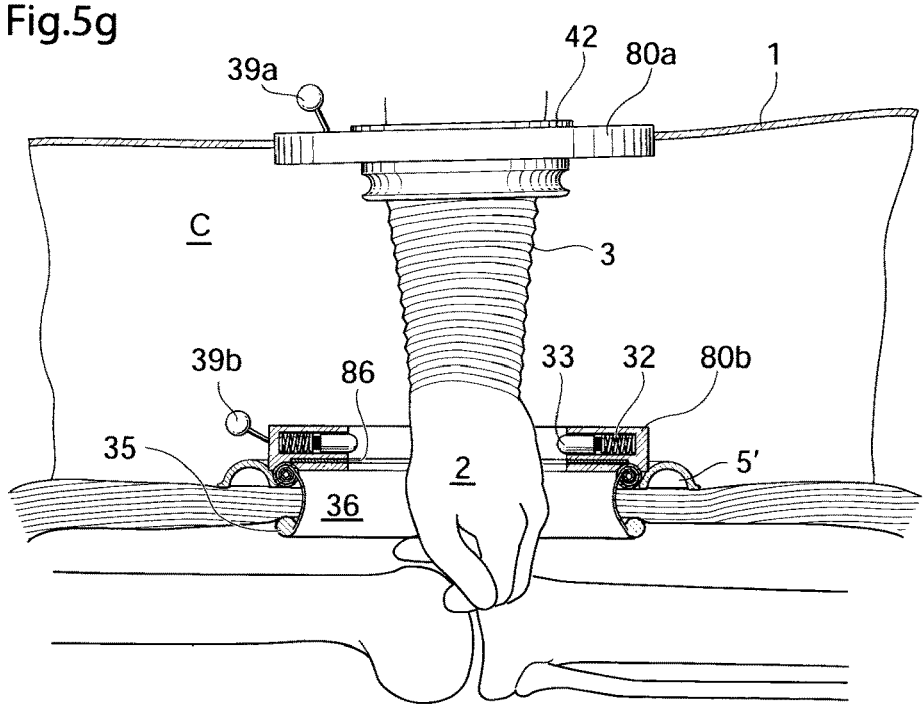

FIG. 5*g* shows the medical device when the second sealing device 35, 36, 37 have been placed in the incision cut in the patient's skin. The wall 1 enclosing the chamber C is elastic or flexible which enables the surgeon to move the first coupling 80*a* in relation to the second coupling 80*b* for getting better access to different angles within the patient's body, for example for removing a specimen or placing a prosthetic part in the knee joint. The embodiment of FIG. 5*f* further comprises an iris valve 86 placed in the first coupling 80*a* for closing the coupling 80*a* such that the chamber is sealed from at least one of the ambient environment and a cavity in the patient. The closing of the iris valve 86 enables activity within the chamber C without maintaining a pressure in the chamber C, at the same time as a pressure and/or sealed environment can be maintained within the body of the patient.

Figure 5H:
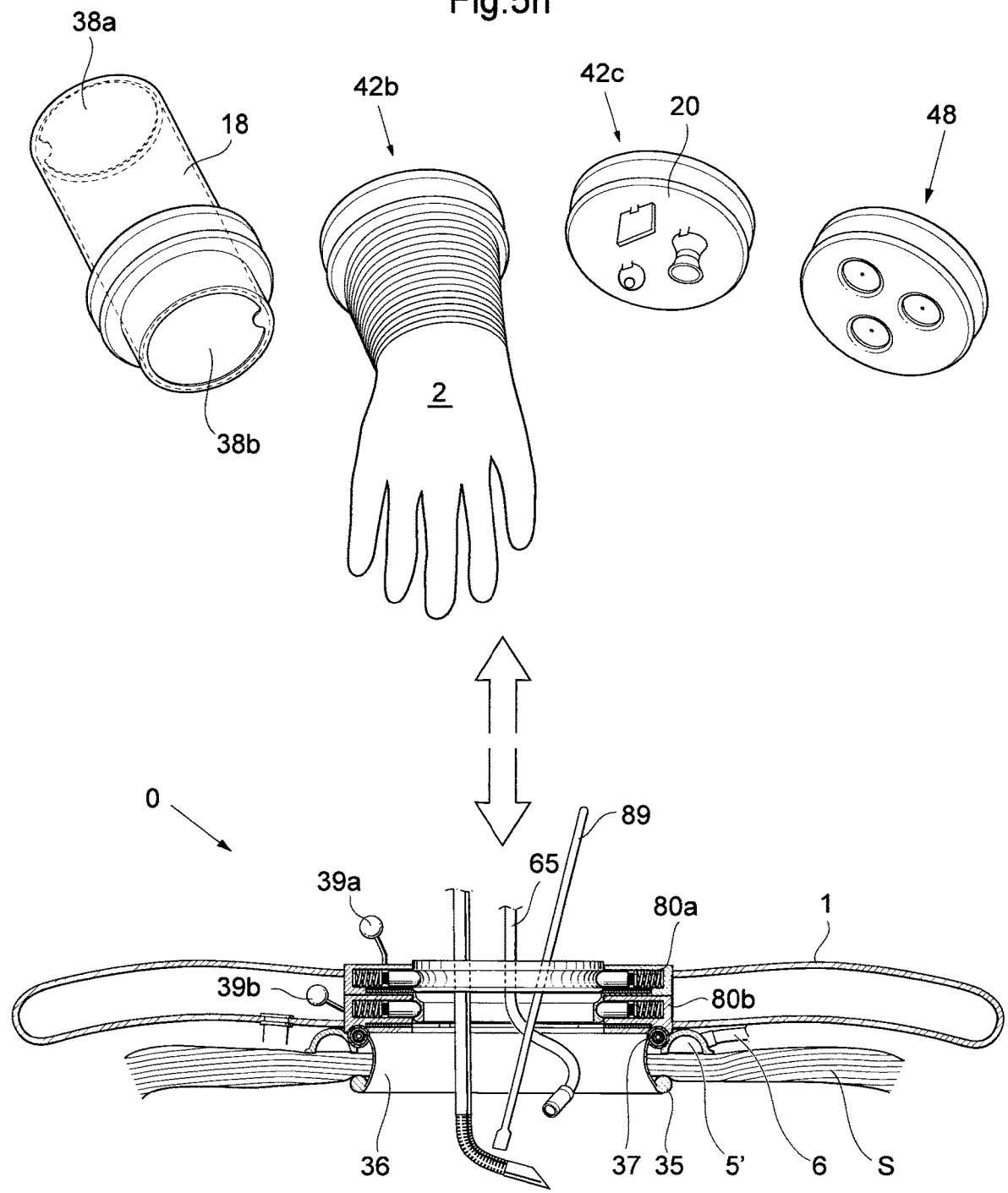
FIGS. 5h-5i shows embodiments of the medical device, in section.

FIG. 5*h* shows the medical device 0 adapted to be at least partially placed in an incision cut in a patient's body. The medical device comprises a first and second coupling 80*a*; 80*b* adapted be interconnected. The first coupling 80*a* is adapted to be disconnected from the second coupling 80*b*, and the first coupling 80*a* is connected to a first portion of a flexible wall 1, and the second coupling 80*b* is connected to a second portion of the flexible wall 1. The flexible wall 1 forms a chamber in which a sealed environment can be maintained, the chamber C is heavily enlarged when the first coupling 80*a* is disengaged from the second coupling 80*b*, thus creating operating space within the chamber enclosed by the wall 1. The first 80*a* and second 80*b* coupling comprise a latching system for locking an inset 42*b*; 42*c*, airlock sluice 18 or a port (such as the multiport 48 disclosed). The inset 42 may for example be an inset 42*b* comprising a glove 2 for manual manipulation within the body of the patient, or within the enclosed chamber, or an inset comprising an instrument or device mount 20 for holding instruments or medical devices within the chamber. Alternatively the insets 42*b*; 42*c* can be replaced by an airlock sluice 18 with a first 38*a* and second 38*b* valve member or a port, such as the multiport 48, comprising a plurality of ports enabling the insertion of a surgical instrument 89, or a camera 88 into the chamber or a cavity in the body of the patient.

In the embodiment shown in FIG. 5*h* the medical device is fixated to the body of the patient by means of a vacuum fixating member 5' connected to a vacuum conduit 6, which in turn is connected to a vacuum source. Furthermore, the medical device in FIG. 5*h* comprises a second sealing device having a first sealing member in the form of an intra body ring 35 adapted to be positioned at the inside of the patient's skin S around an incision to be performed in the skin S and a second sealing member in the form of an outer ring 37 adapted to be positioned at the outside of the patient's skin S around the incision, and a spring-loaded or elastic connecting member 36 sealingly interconnecting the intra body ring 35 and outer ring 37. The spring-loaded or elastic connecting member 36 seals between at least one of the second coupling 80b and the skin of the patient, and the intra body ring 35 and tissue of the patient. As shown in FIG. 5h the surgeon can use the multiport 48 placed in the first coupling 80a to insert laparoscopic instruments into the body of the patient.

Figure 5I:
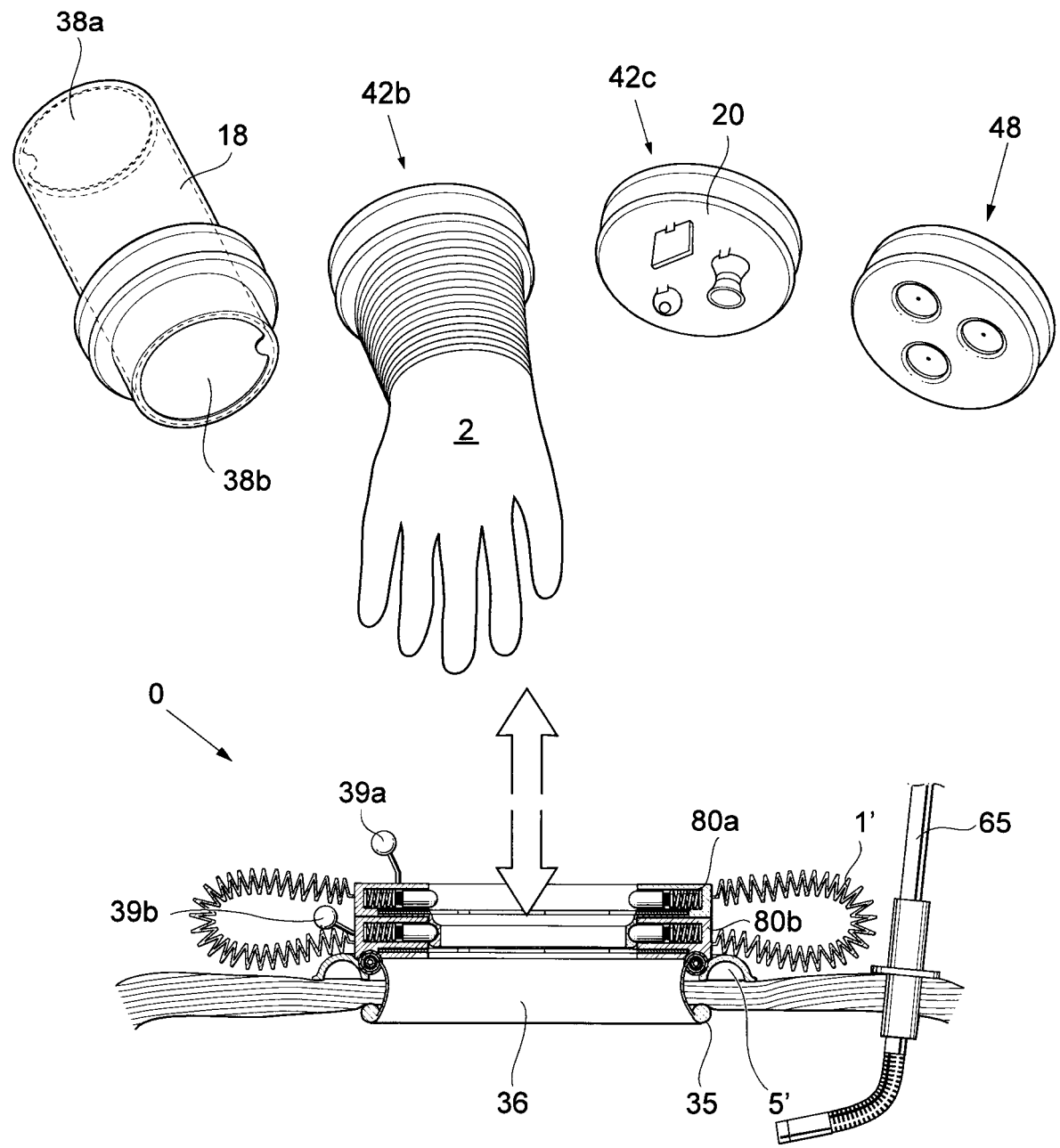

FIG. 5i shows the port in an embodiment very similar to the embodiment shown in FIG. 5h but with the difference that the wall 1' has a bellows structure and thus taking up less space when in its deflated state. The bellows structure enables the wall 1' to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. FIG. 5i also shows a camera 65 placed in the skin of the patient to enable visual inspection of a cavity within the patient's body, the camera being placed outside of the ports and sealed environment.

Figure 5J:
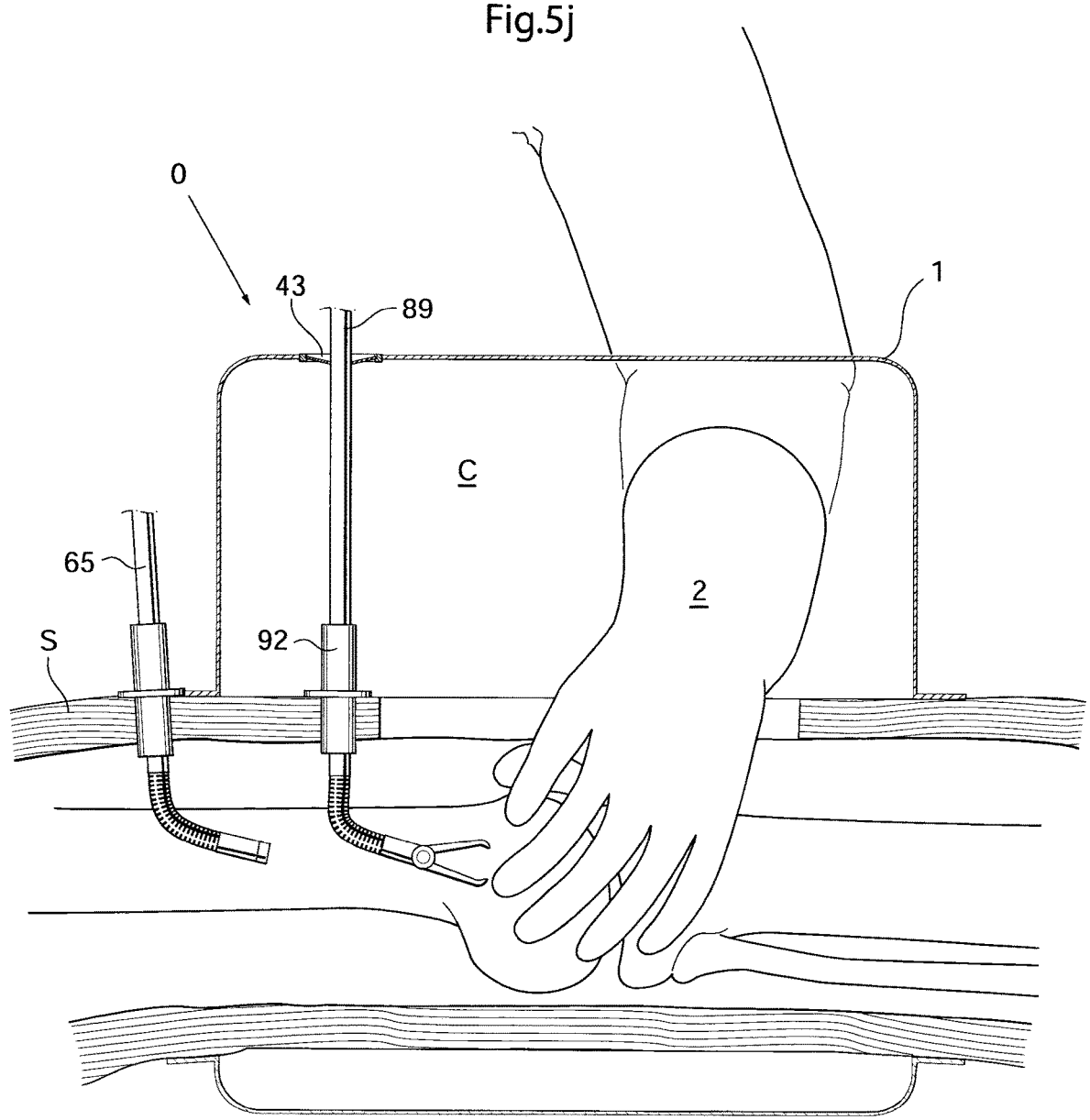

FIG. 5j shows an embodiment of the medical device 0, in which the medical device 0 comprises a glove 2 integrated in the wall 1 and a camera 65 placed in the skin S outside of the medical device 0. The medical device 0 further comprises a trocar 92 placed trough an incision in the skin S of the patient and into an area of the knee of the patient. A surgical instrument 89 travels through a self sealing membrane 43 in the wall 1 of the medical device and further through the trocar 92 placed in the incision in the skin S of the patient and into a cavity in the patient's body. FIG. 5j furthermore schematically illustrates how the surgeon manipulates the knee in the chamber C using the glove 2.

Figure 5K:
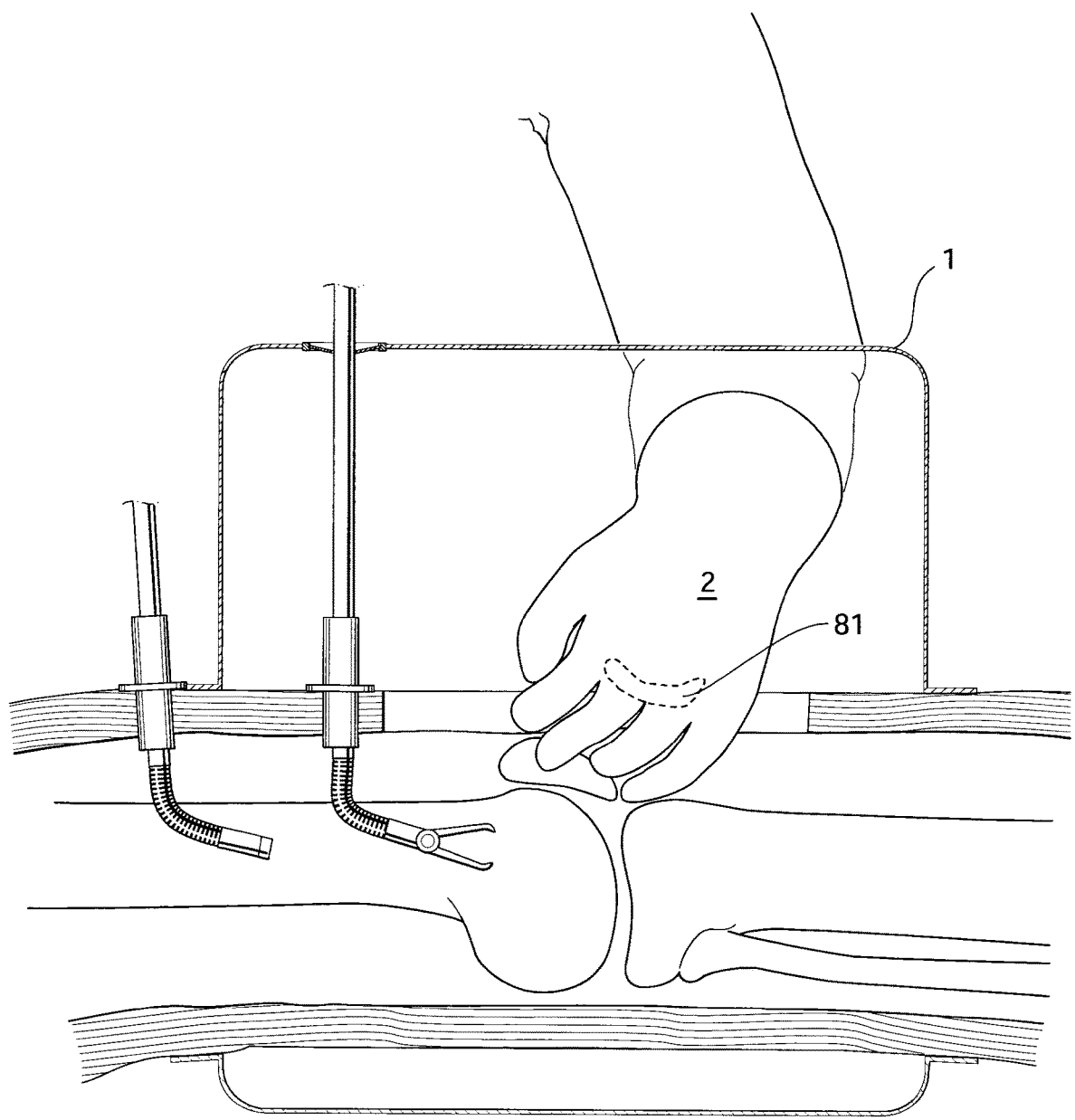
Figure 5I:
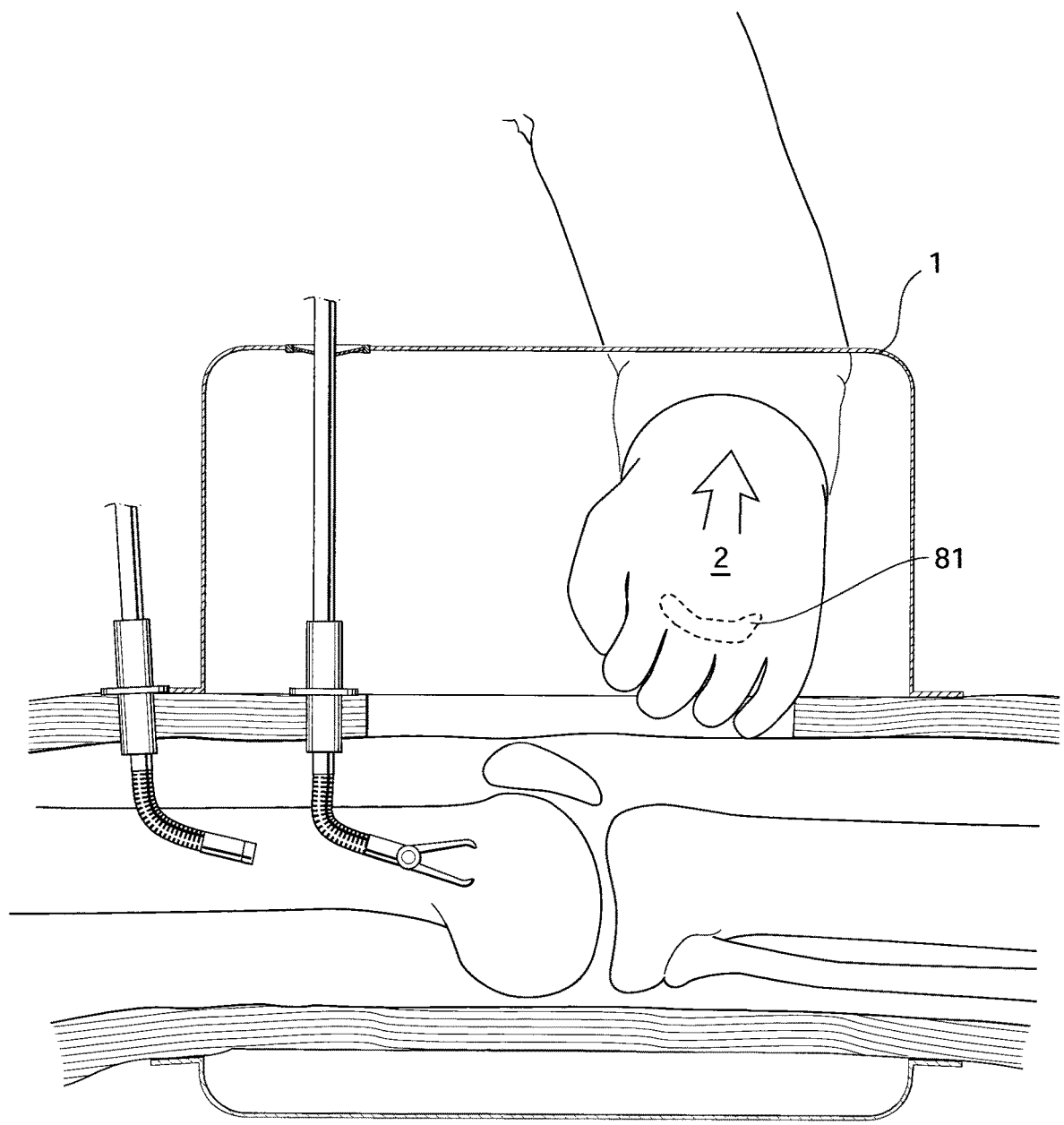

FIGS. 5k, 5l shows the medical device when the surgeon removes a specimen 81 from the knee of the patient using the glove 2 integrated in the wall 1 of the medical device.

Figure 5M:
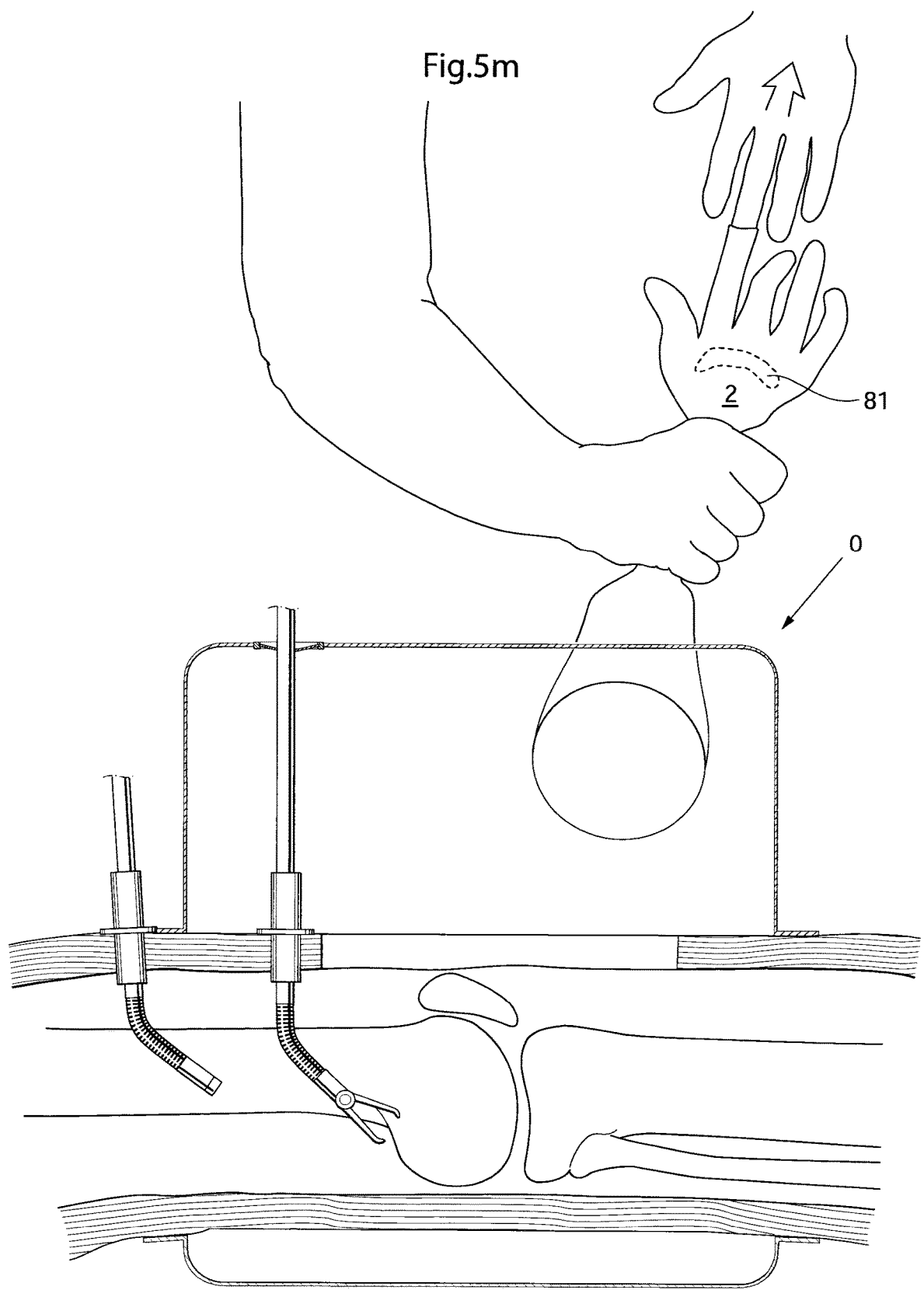

FIG. 5m shows the medical device 0, when the surgeon has turned the integrated glove 2 inside-out such that the specimen 81 can be contained within the integrated glove. By isolating the specimen 81 inside of the glove 2, the specimen 81 is removed both from the rest of the body of the patient and from the ambient environment, and thereby does not risk to infect any other portion of the patient's body or medical staff with any infectious disease.

Figure 5N:
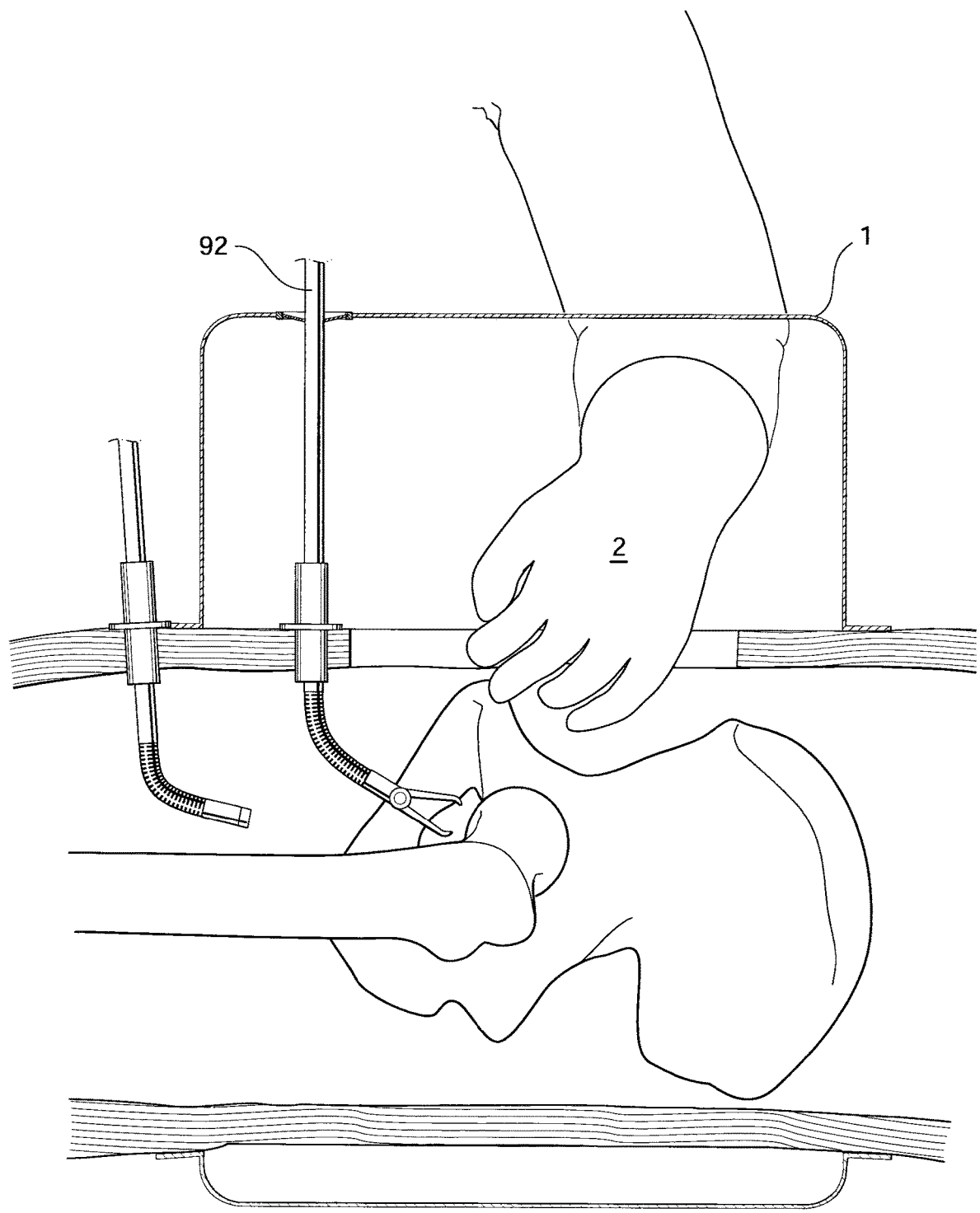

FIG. 5n shows and embodiment similar to the embodiment disclosed with reference to FIG. 5j, the difference being that the medical device is adapted for performing procedures on the hip joint of the patient.

Figure 5O:
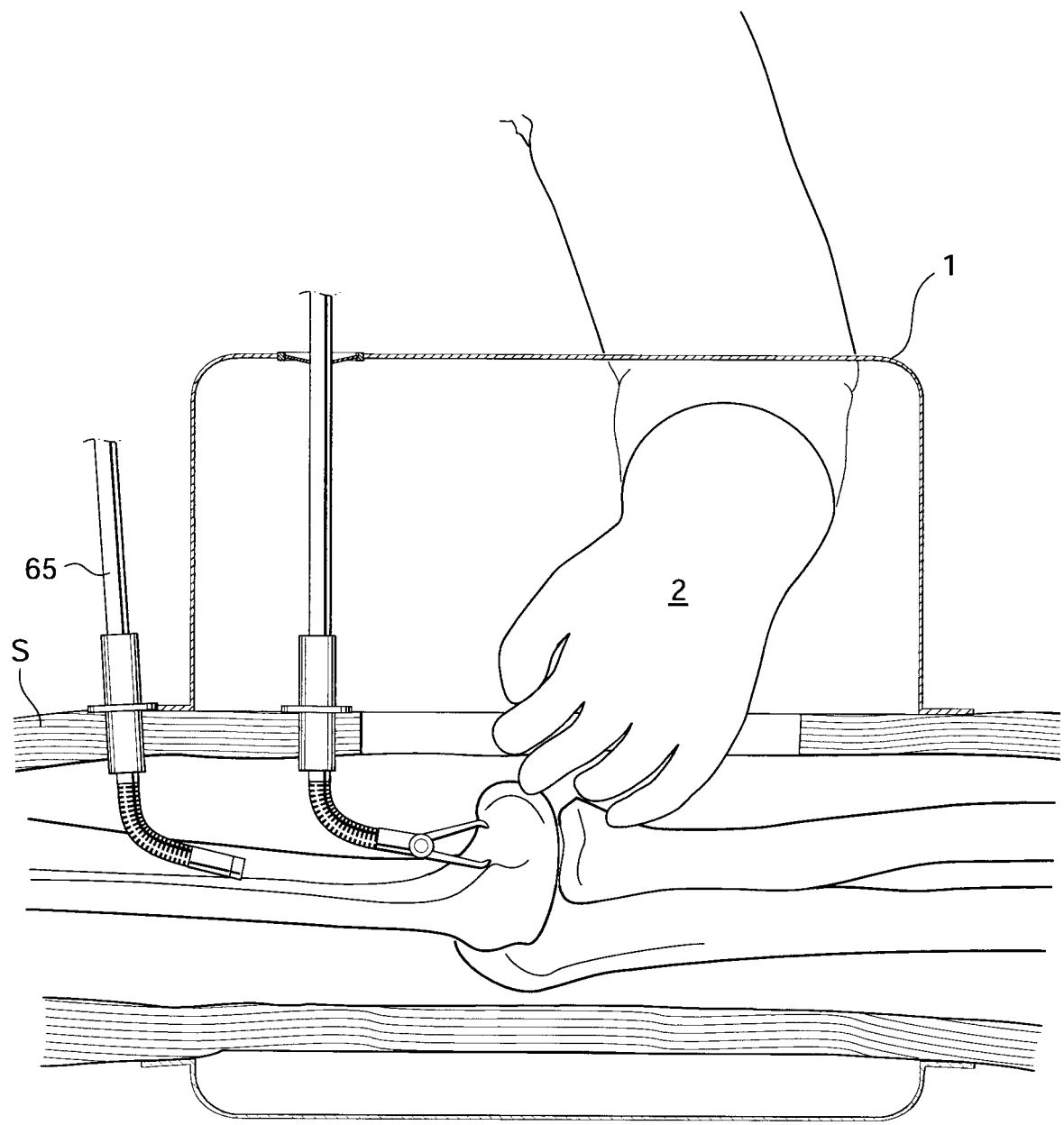

FIG. 5o shows an embodiment of the medical device, in which the medical device comprises a glove 2 integrated in the wall 1 and a camera 65 placed in the skin S outside of the medical device. The medical device further comprises a trocar placed through the skin S of the patient inside the chamber C of the medical device and into an area of the knee of the patient. FIG. 5o schematically illustrates how the surgeon manipulates the knee in the sealed environment using the glove.

Figure 5P:
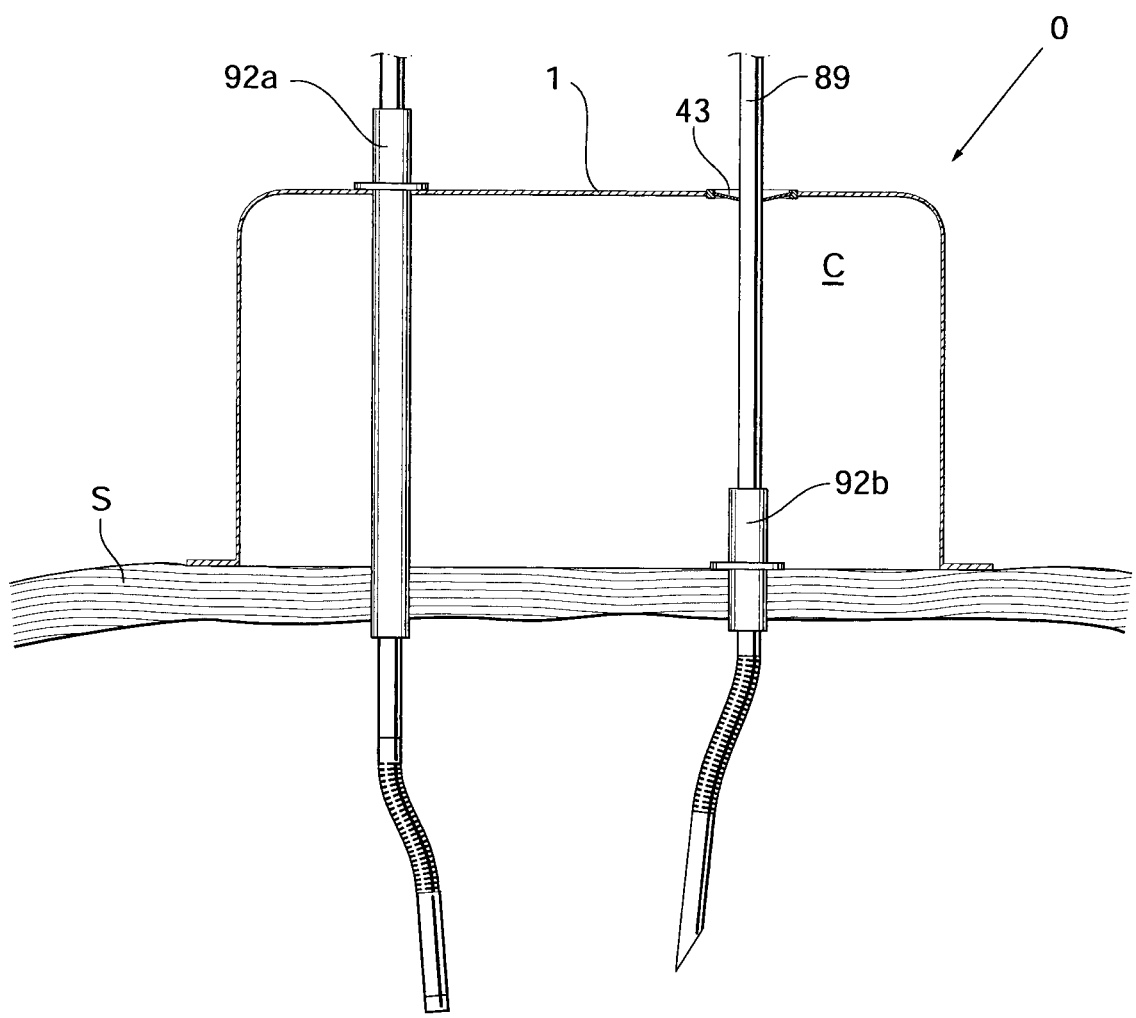
FIG. 5p shows an embodiment of the medical device, in section.

FIG. 5p shows the medical device 0 according to an embodiment in which the medical device 0 comprises a wall 1 placed on the patient's skin S and thereby enclosing a chamber C for creating a sealed environment. The medical device 0 further comprises two trocars 92a; 92b, one 92a traveling through both the wall 1 of the medical device 0 and the skin S of the patient and thus enabling laparoscopic tools to be inserted into the patient through both the wall 1 of the medical device 0 and the skin of the patient through one single trocar. The other trocar 92b being placed inside the chamber C and enabling a laparoscopic tool to be inserted through the skin S of the patient. The endoscopic instrument is in this embodiment inserted into the chamber C enclosed by the wall 1 through a membrane 43 in the wall sealing against the tool 92b.

Figure 5Q:
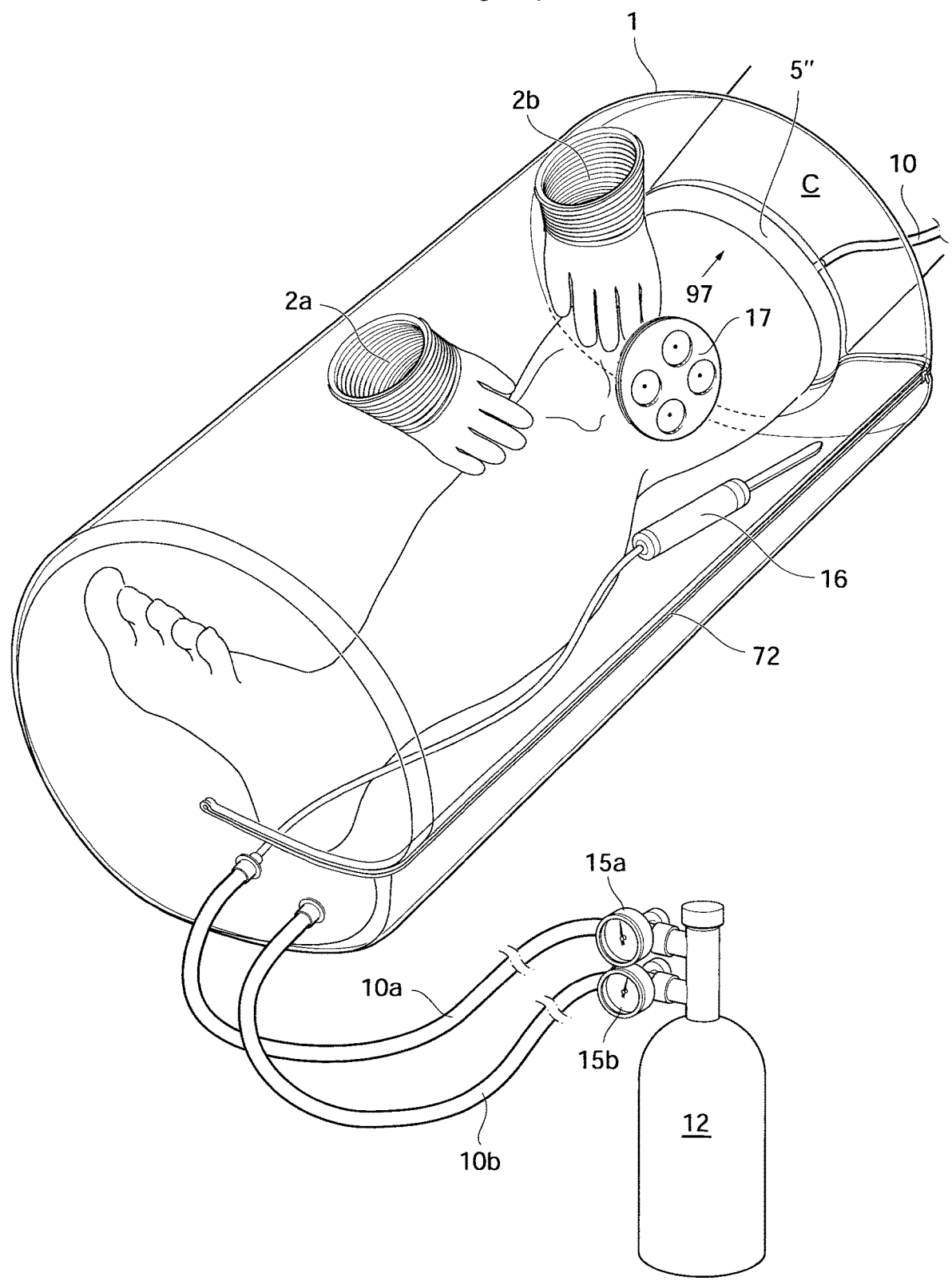
FIGS. 5q-5r shows embodiments of a medical device, in perspective.

FIG. 5q shows the medical device in an embodiment similar to, an possible to combine with the features of, the embodiments shown in FIGS. 3a-3e. The difference being that the wall 1 of the medical device 0 does not form an elongated tubular enclosure extending in the chamber C, but instead the wall 1 comprises a hole 97 through which an extremity of the patient is inserted. The hole 97 is surrounded by a sealing device adapted to seal against the skin of the patient by a pressurized sealing member 5" pressing against the skin by means of a hydraulic or pneumatic force being distributed by means of a conduit 10. The wall 1 is placed around the patient's extremity (in this case leg) by being possible to open by means of a connection 72 in the wall comprising a sealing and a closing device, for example as shown in FIG. 5q designed as a zipper.

Figure 5R:
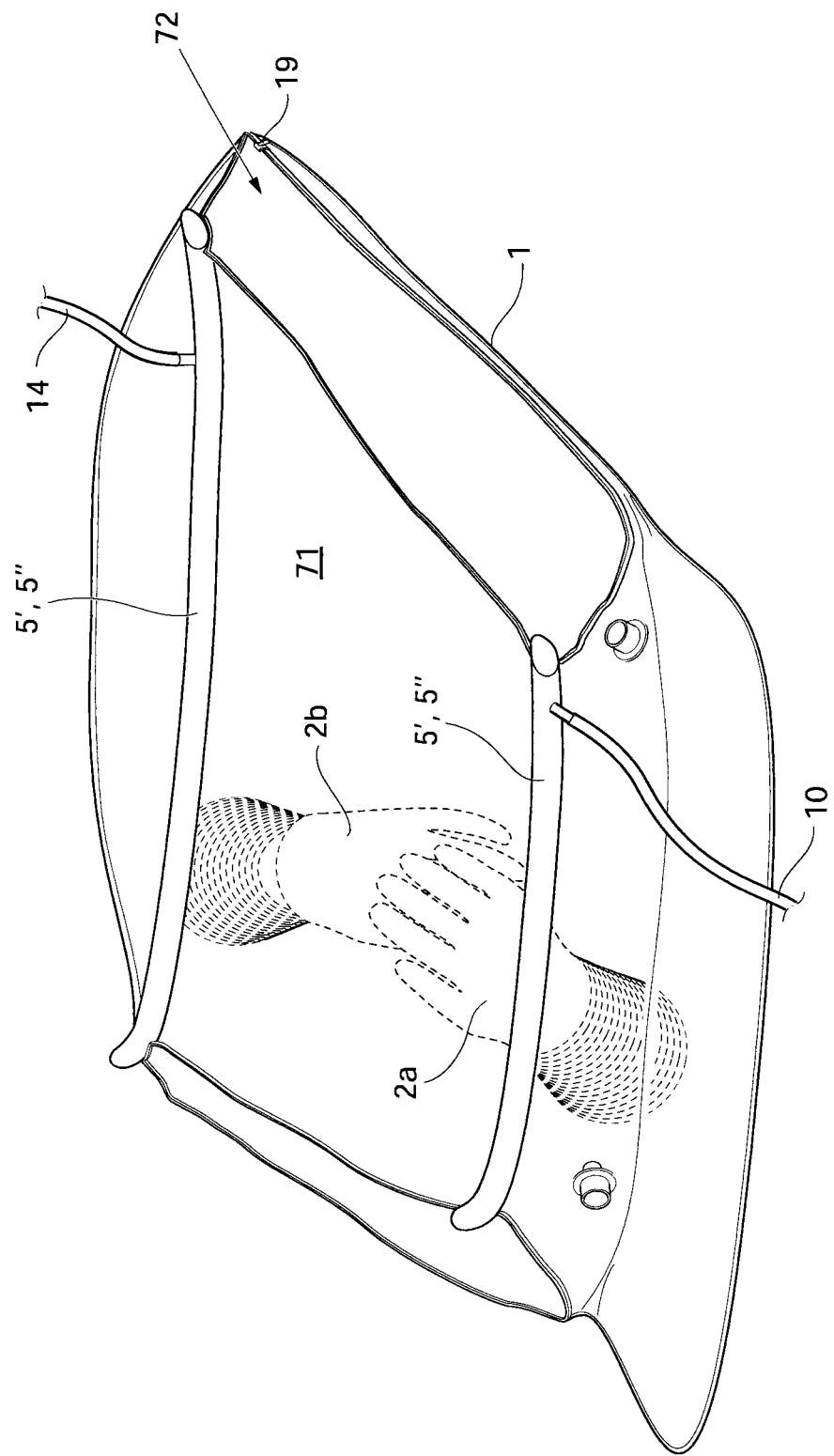

FIG. 5r shows the medical device according to an embodiment similar to the embodiment shown in FIG. 5q when in its open state. The difference between the embodiment shown in FIG. 5q and the embodiment shown in FIG. 5r is that the medical device shown in FIG. 5r comprises an inner wall, closing or layer 71 which is part of the wall 1 and adapted to separate the chamber of the medical device from the skin of the patient when the medical device is assembled. The medical device comprises a vacuum 5' or pressure 5" sealing member adapted to encircle the extremity of the patient when the medical device is assembled. The connection 72 between different portions of the wall 1 is in 5r, as well as in 5q designed as a zipper 19 adapted for connecting the portions of the wall 1 to each other for creating the chamber.

Figure 5S:
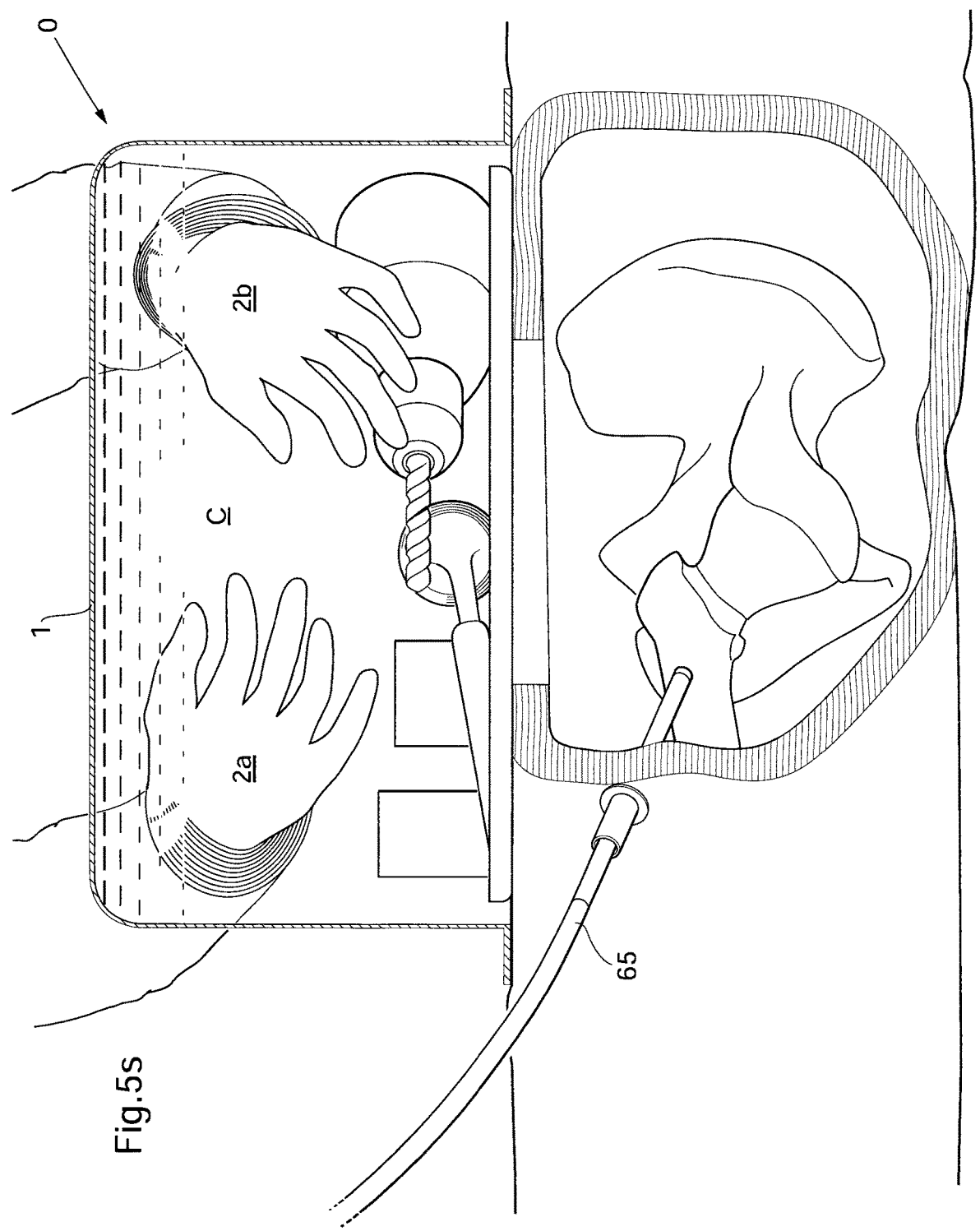

FIG. 5s shows the medical device 0 in an embodiment similar to other embodiments shown herein, the difference being the medical device 0 is adapted to contain a liquid such that a liquid operating environment is created in which an arthroscopic procedure with liquid can be performed. The embodiment shown in FIG. 5s is shown with in an embodiment where the medical device 0 is adapted for an arthroscopic hip joint procedure and prosthetic parts and tools are pre-placed inside of the chamber C within the wall 1 and thus within the liquid inside of the chamber C.

FIG. 5t shows the medical device 0 according to an embodiment similar to the embodiment shown in FIG. 5s, the difference being that a system is provided for circulating the fluid inside of the chamber C. The liquid system comprises an inlet 30 for injecting the liquid into the chamber C, and an outlet 31 for enabling liquid within the chamber C to circle.

FIG. 5u shows the medical device 0 according to an embodiment similar to the shown in FIG. 5t, the difference being that the chamber C is not adapted to hold a liquid, but rather a gaseous fluid such as $CO_2$ gas.

FIGS. 6-16 shows embodiments of the medical device in which the medical device comprises a system for exchanging the ports or insets in the medical device.

Figure 6:
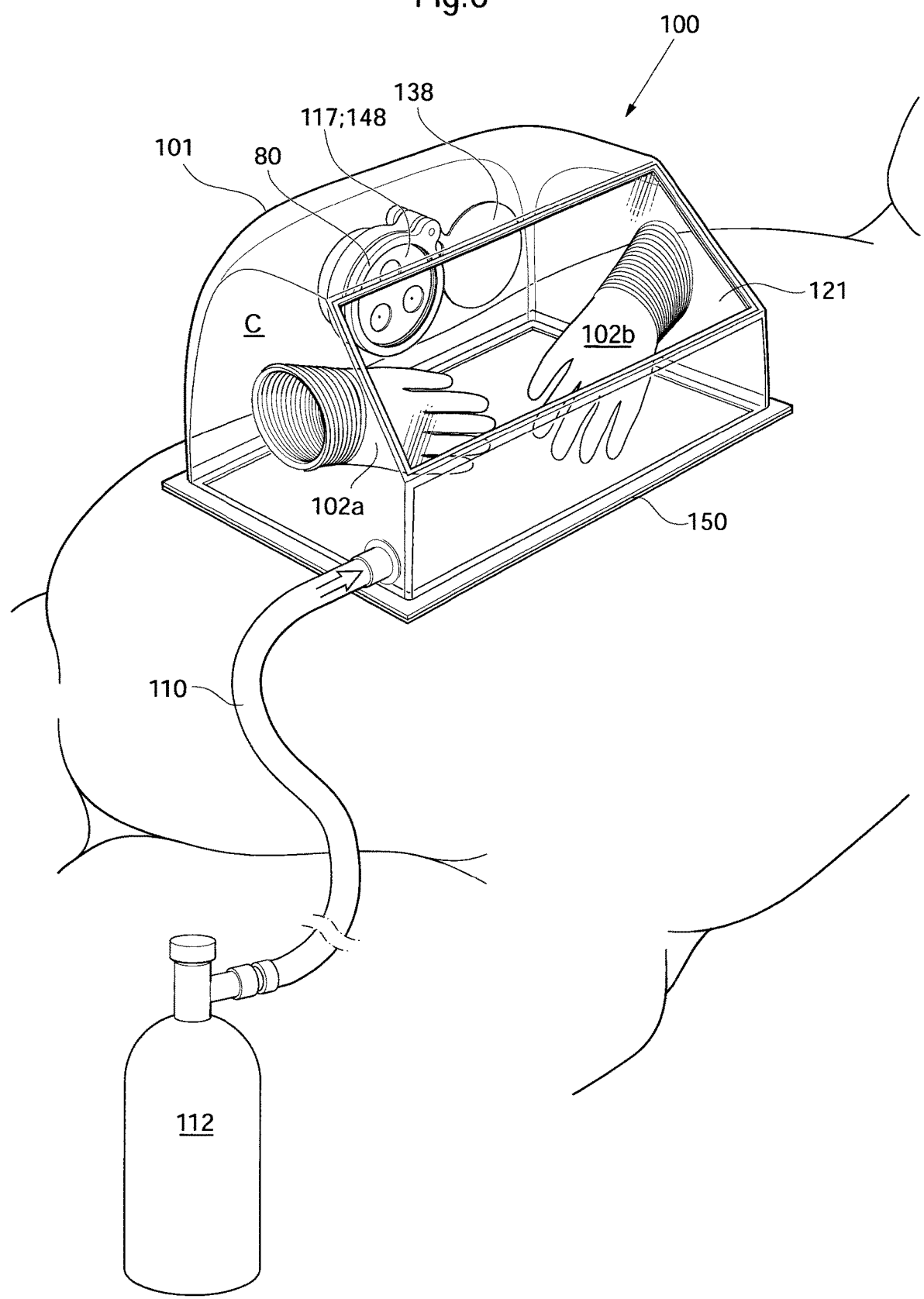
FIG. 6 shows the medical device when applied to the abdomen of a patient.

FIG. 6 shows a medical device 100 for performing surgical procedures on a patient. The medical device 100 is adapted to be attached to the patient prior to the start of the surgical procedure. In the embodiment shown in FIG. 6 the medical device comprises a partially inflatable wall 101 which is adapted to be fixated to the abdominal area of a patient by means of an adhesive surface 150. By fixating the medical device to the patient prior to the start of the surgical procedure the first incision in the patient could be performed inside the chamber created by the medical device. The medical device 100 is according to the embodiment disclosed herein connected to a source of pressurized fluid 12 which is lead into the medical device through a fluid conduit 110. The medical device according to the embodiment disclosed herein is adapted to hold a gaseous fluid having a pressure exceeding 1 bar such that a laparoscopic procedure could be performed partially within the medical device and partially within the patient.

The medical device as shown in FIG. 6 comprises a wall port 117, in the form of a multiport, detachably fixated to the wall 1. The wall port 117 is attached by means of a coupling 80 and thereby detachable. The medical device 100 further comprises a valve member 138 for closing the hole in the wall 101 while exchanging the wall port 117 to another inset or wall port, such that the inset or wall port can be exchanged while maintaining the sealed environment within the medical device 100. The detachable insets or wall ports could be adapted to be fixated to the wall 101 by means of couplings and thereby possible to quickly exchange (as disclosed above with reference to FIGS. 5a-5c). The medical device as shown in FIG. 6 further comprises insets in the form of surgical gloves 102a, 102b integrated in the wall 101 enabling manual manipulation within the chamber C of the medical device 100 while keeping the chamber C hermetically closed. A pressurized fluid tank 12 provides a pressurized fluid to the sealed environment through a fluid conduit 110, however, in alternative embodiments it is conceivable that the pressurized fluid is provided into the body of the patient through a different incision and thus enters the sealed environment from the inside of the patient, this particularly useful when performing laparoscopic or partially laparoscopic procedures as those require the abdomen to be inflated. According to the embodiment shown in FIG. 6 the wall 101 is partially collapsible. The medical device thus comprises a non-collapsible transparent window 121 for enabling viewing into the sealed environment. The non-collapsible transparent window 121 will ensure that the surgeon has adequate visual control over the procedure since the partially collapsible wall 101, even if preferably made from a transparent material could provide limited visibility, e.g. if the medical device is not fully inflated, or in seams or bends of the material. The non-collapsible transparent window 121 could for example be made from a transparent polymer, such as polycarbonate, or made from tempered glass.

Figure 7A:
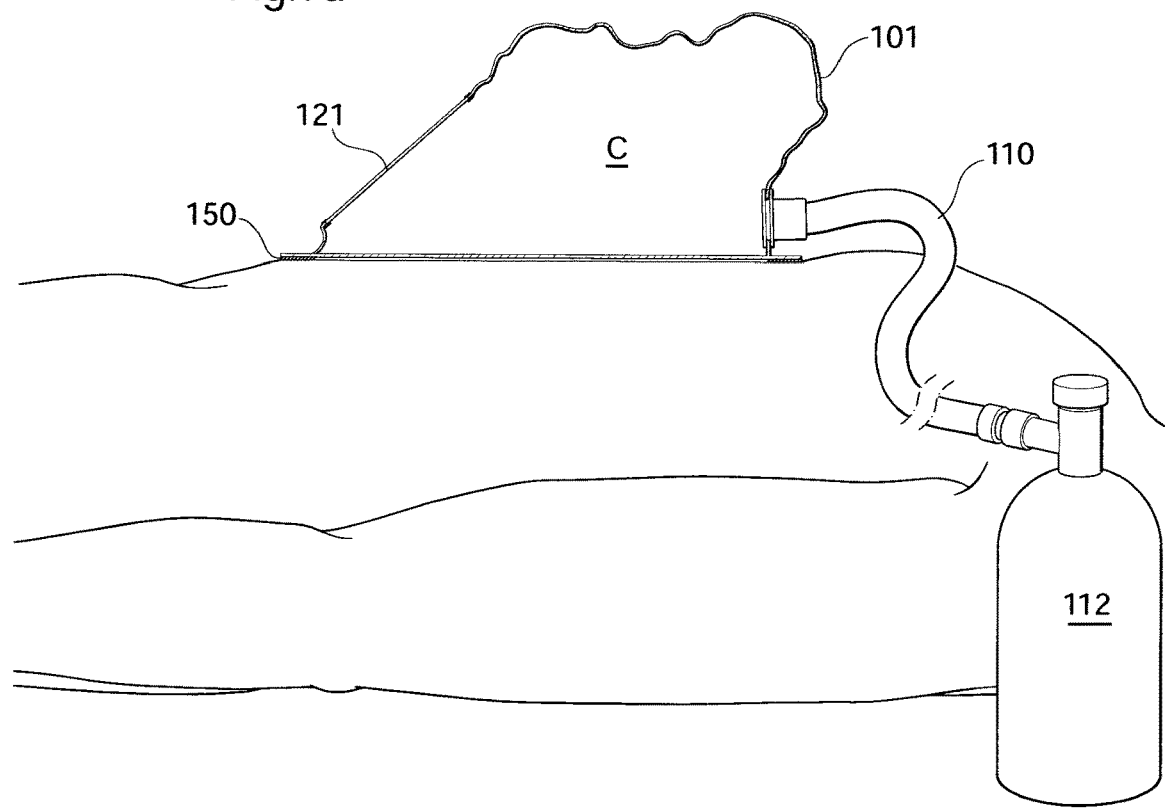
FIG. 7a shows the medical device when applied to the abdomen of a patient, in a deflated state.

FIG. 7a shows in section the medical device of FIG. 6 when fixated onto the abdominal area of the patient. The medical device is preferably attached to the patient prior to the start of the surgical procedure, such that the first incision in the patient could be performed inside the chamber C. FIG. 7a shows the medical device 100 as it is being inflated by a pressurized fluid entering the medical device through a fluid conduit 110 and according to the embodiment shown, the medical device is fixated to the abdominal region of a patient by means of an adhesive 150.

Figure 7B:
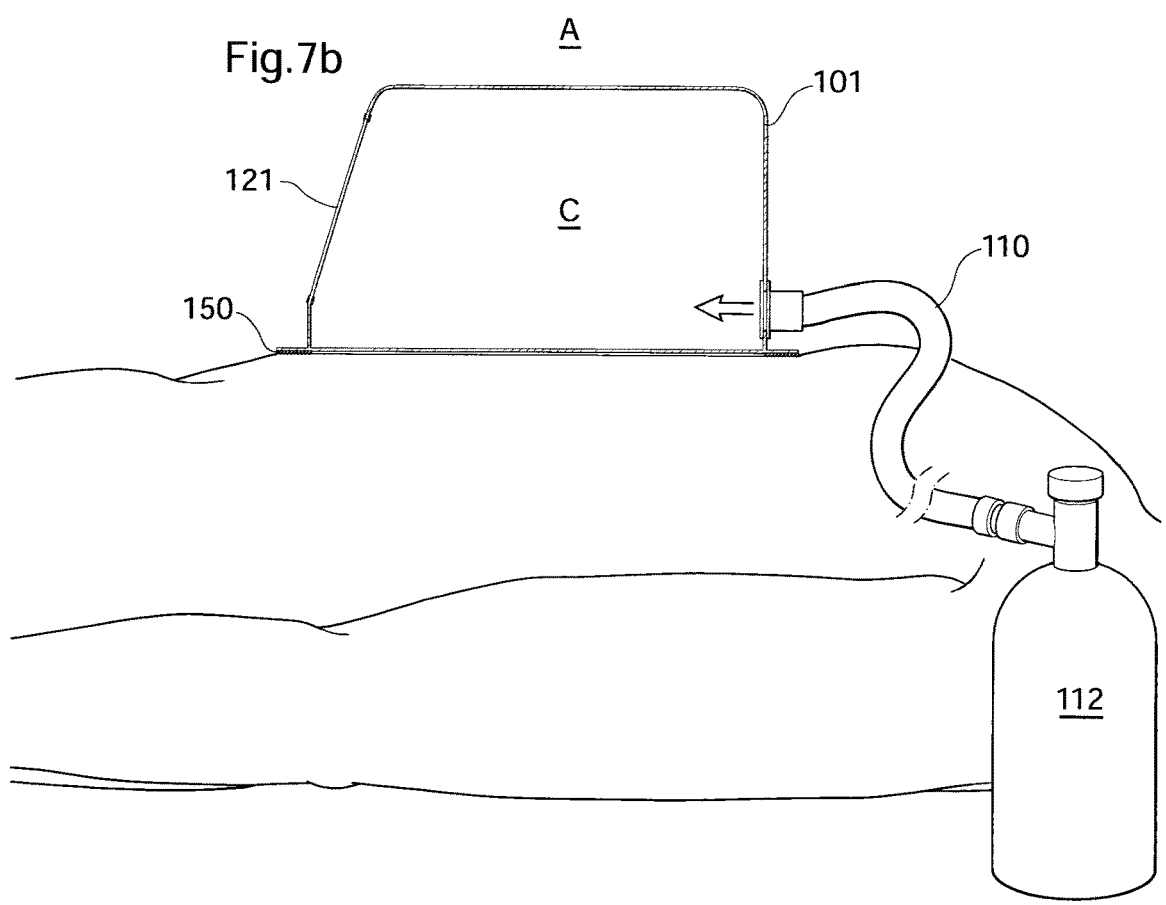
FIG. 7b shows the medical device when applied to the abdomen of a patient, in an inflated state.

FIG. 7b shows the medical device of FIG. 6 when inflated such that the wall 101 separates the camber C within the medical device 100 from the surrounding environment and thus creates an operating environment which is separated from contaminations from the ambient environment A. In some applications it is conceivable that a normal laparoscopic procedure is performed with the medical device 100 positioned but not inflated. The medical device 100 is then only inflated at the end of the procedure, for example when a specimen is to be removed.

FIG. 8 shows the medical device 100 according to an embodiment in which the medical device 100 further comprises a cleaning device for cleaning the transparent window 121 from the inside of the chamber C. The cleaning device comprises a fluid arrangement 164 for supplying a fluid adapted to assist in the cleaning of the transparent window via a fluid conduit 162 to a nozzle 163 placed in proximity to the transparent window 121. The fluid could for example be an isotonic solution, such as saline solution, or an antiseptic solution such as Chlorhexidine. The medical device 100 further comprises a window contacting member 161 for wiping the window clean after the fluid has been sprayed thereon for mechanically removing objects from the window 121.

FIG. 9 the shows the medical device 100 further comprising an airlock sluice 118 for allowing passage of objects between the chamber C and the ambient environment A. The airlock sluice 118 comprises an outer zipper 119a between the airlock sluice 118 and the ambient environment A, and an inner zipper 119b between the airlock sluice 118 and the chamber C.

FIG. 10 shows the medical device 100 according to an embodiment in which the medical device 100 is applied to the abdominal region of the patient. The medical device 100 is according to the embodiment shown here fixated to the patient by means of a sealing device comprising a vacuum sealing member 105' providing a negative pressure between the vacuum sealing member and the skin of the patient and thus providing sealing. The vacuum sealing member 105' is connected to a vacuum pump 108 by means of a vacuum conduit 106.

Figure 11:
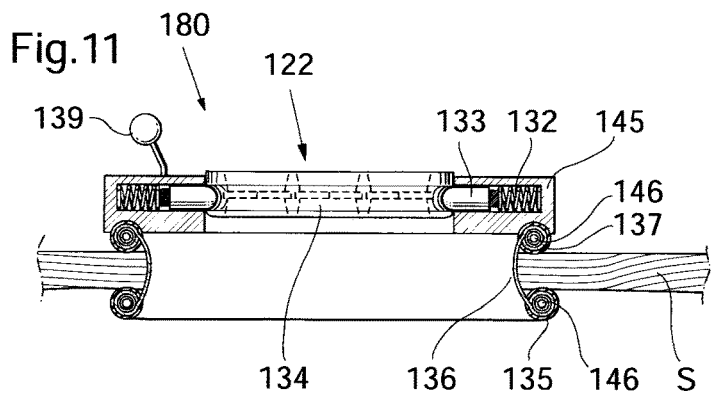
FIGS. 11, 12a, 12b shows a coupling attached to the skin of a patient, in section.

FIG. 11 shows an embodiment of a detachable body port 122 arrangement which could be positioned in the chamber of the medical device disclosed with reference to FIG. 6. The port arrangement includes an intra body ring 135 adapted to be placed at the inside of the patients skin around an incision, and an outer ring 137 adapted to be placed on the outside of the patients skin S around the incision. Between the intra body ring 135 and outer ring 137 a connecting member 136 is positioned, in the form of an annular retractor membrane 136 adapted to exert a pressure on the skin S or tissue at the incision to seal between the rings 135; 137 and the skin S or tissue and additionally for retracting the skin S and thereby keeping the incision open. The retractor membrane 136 is preferably made from a resilient or elastic polymer material. The outer and inner rings 137; 135 comprises integrated roll up systems 146, which may be spring loaded and adapted to create a suitable pressure on retractor membrane 136 to keep the incision open.

The body port 122 arrangement shown in FIG. 11 also includes a coupling 180 having a rigid annular seating 145 attached to the outer ring 137, spring loaded protruding members 133 adapted to latch the body port 122 by engaging the recess o the body port 134. The protruding members 133 being arranged in radial bores in the seating 145 and a lever 139 connected to the protruding members 133 enables the retraction thereof against the action of springs 132.

Figure 12A:
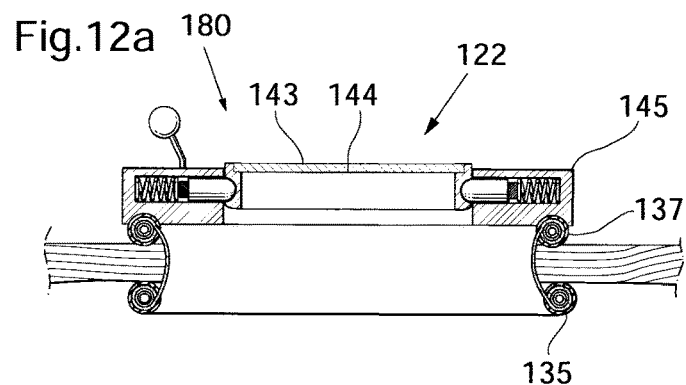

FIG. 12a shows the body port 122 comprising a disc shaped self sealing membrane 143 fixated to a rigid ring having a recess in the form of an outer circumferential groove 134 that receives the protruding members 133 of the coupling 180. The self sealing membrane 143 has a small self sealing hole 144 centrally in the membrane 143. For example, the self sealing membrane 143 may be made from a gel-type material being elastic enough to enable a deformation large enough for a person's hand to pass through the small self sealing hole 144 while still contracting enough to create an airtight seal between the chamber and the outside environment.

The coupling 180 described above enables quick exchange of the body port 122. Thus, the surgeon may release the body port 122 from the coupling 180 by simply pulling the lever 139 so that the protruding members 133 latching the rigid ring disengage from the recess 134 of the body port 122, whereby the body port 122 can be removed.

Figure 12B:
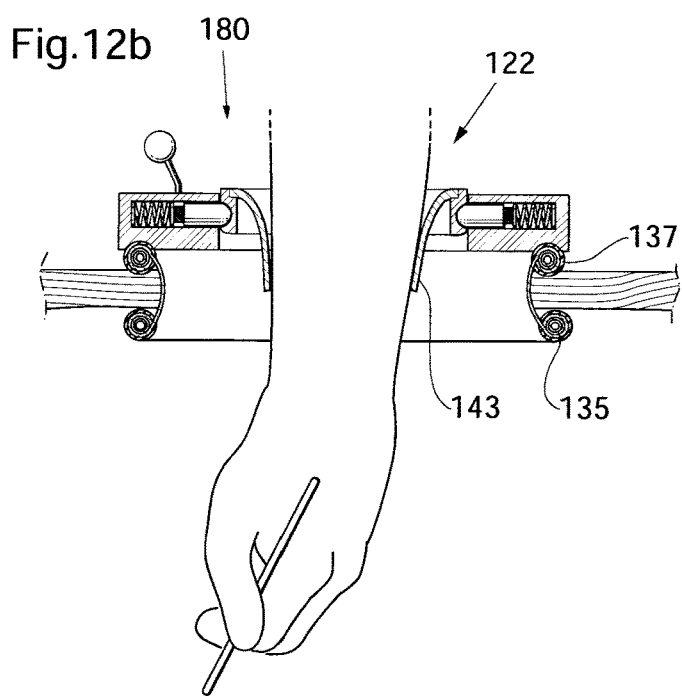

FIG. 12*b* shows the self sealing body port 122 when the hand of a surgeon is placed through the self sealing hole 144 in the membrane 143 and thus enabling manual manipulation within the body of the patient.

Figure 13A:
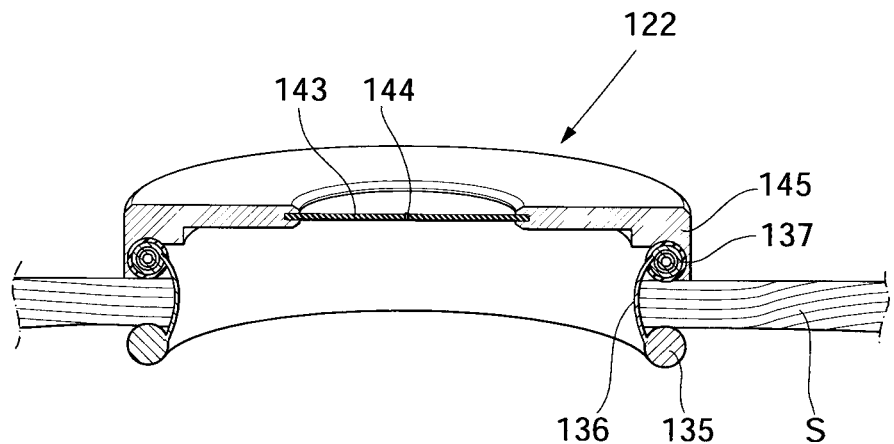
FIGS. 13a and 13b shows two different embodiments of a self sealing port.

FIG. 13*a* shows a self sealing body port 122 in a close-up, in section, where the self sealing body port 122 comprises a self sealing membrane 143 fixated to a seating part 145 of the self sealing port. The self sealing membrane 143 having a small self sealing hole 144 centrally in the membrane 143. The self sealing membrane 143 is for example made from a gel-type material being elastic enough to enable a deformation large enough for a person's hand to pass through the small self sealing hole 144 while still contracting enough to create an airtight seal between the sealed environment and the outside environment. The medical device being fixable to a sealing device in the form of a retractor comprising one intra body ring 135 adapted to be positioned on the inside of the patients skin, and an outer ring 137 adapted to be placed on the outside of the patients skin S. Between the intra body ring 135 and the outer ring 137, a retractor membrane 136 is positioned which is adapted to exert a pressure of the cut surfaces of the incision for retracting the skin and thereby keeping the incision open. The retractor membrane 136 is preferably made from a resilient of elastic polymer material. The outer ring 137 comprises an integrated roll up system which could be a spring loaded roll up system adapted to create a suitable pressure on retractor membrane 136 for keeping the incision open.

Figure 13B:
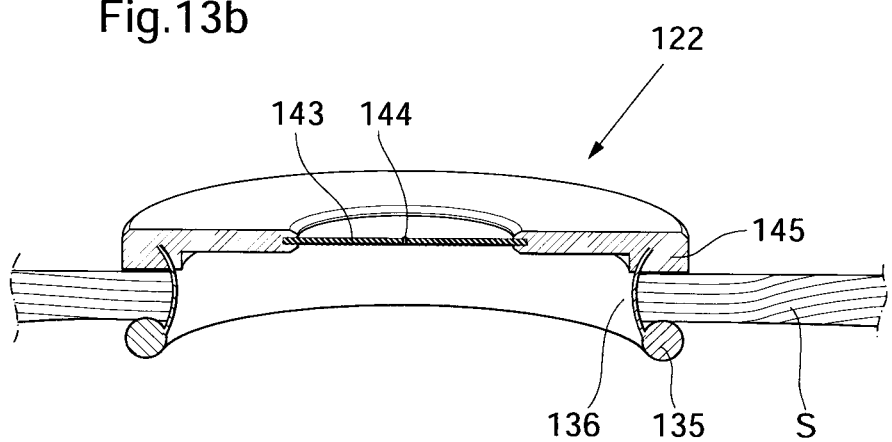

FIG. 13*b* shows an alternative embodiment of the self sealing body port 122, with the difference that the retractor membrane 136 is made from a material elastic enough such that one end of the retractor membrane 136 could be fixedly fixated to the rigid seating 145 of the port.

Figure 14:
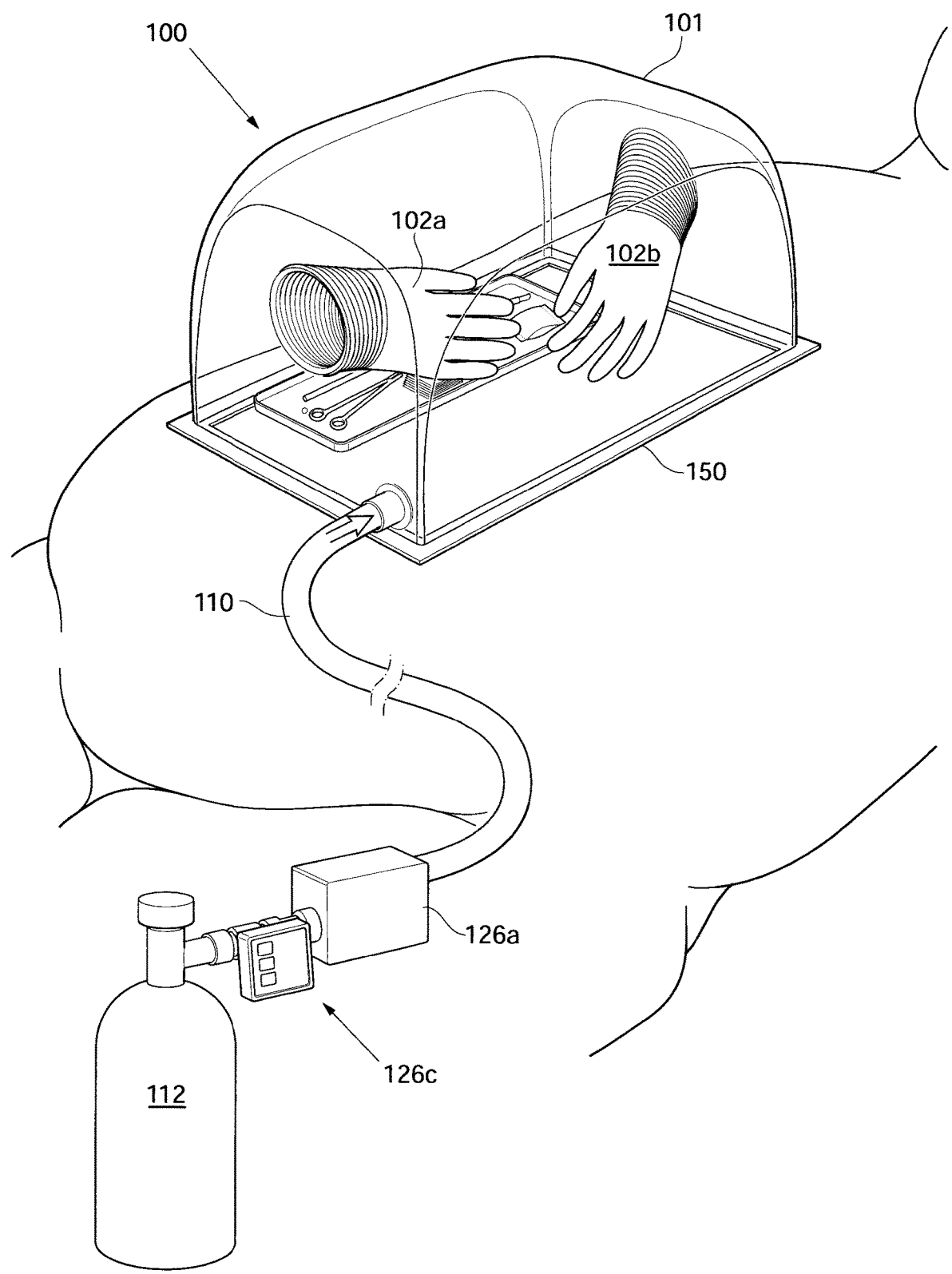
FIG. 14 shows an embodiment of the medical device when positioned on the abdomen of a patient.

FIG. 14 shows an embodiment of the medical device when positioned on the abdomen of a patient. The medical device comprises insets comprising integrated gloves 102*a*; 102*b* in the wall 101. The medical device shown in FIG. 14 further comprises a sterilizing unit 126*a* adapted to sterilize the gaseous fluid entering the medical device 100. In the embodiment disclosed herein, the gaseous fluid entering the medical device 100 originates from a pressurized tank 112 and could be pre-sterilized, however, in other embodiments, it is conceivable that the gaseous fluid is the surrounding air which is pressurized (such as further disclosed with reference to FIG. 3*e*). In the embodiments where the surrounding air is used to inflate the medical device 100 and constitute the operating environment this air needs to be properly sterilized. The medical device 100 further comprises a tempering unit 126*c* which could be provided to heat or cool the gaseous fluid inflating the medical device 100. In cases when the surrounding environment is cold the tempering unit 126*c* could be used to raise the temperature of the sealed environment to provide beneficial operating circumstances both for the patient and for the surgeon. In cases when the surrounding environment is hot, the tempering unit 126*c* can be used to lower the temperature of the to provide beneficial operating circumstances, both for the patient and for the surgeon, and for providing a temperature inhibiting bacterial and viral infections. The tempering unit 26*c* could comprise a temperature regulating portion for setting the required temperature.

Figure 15:
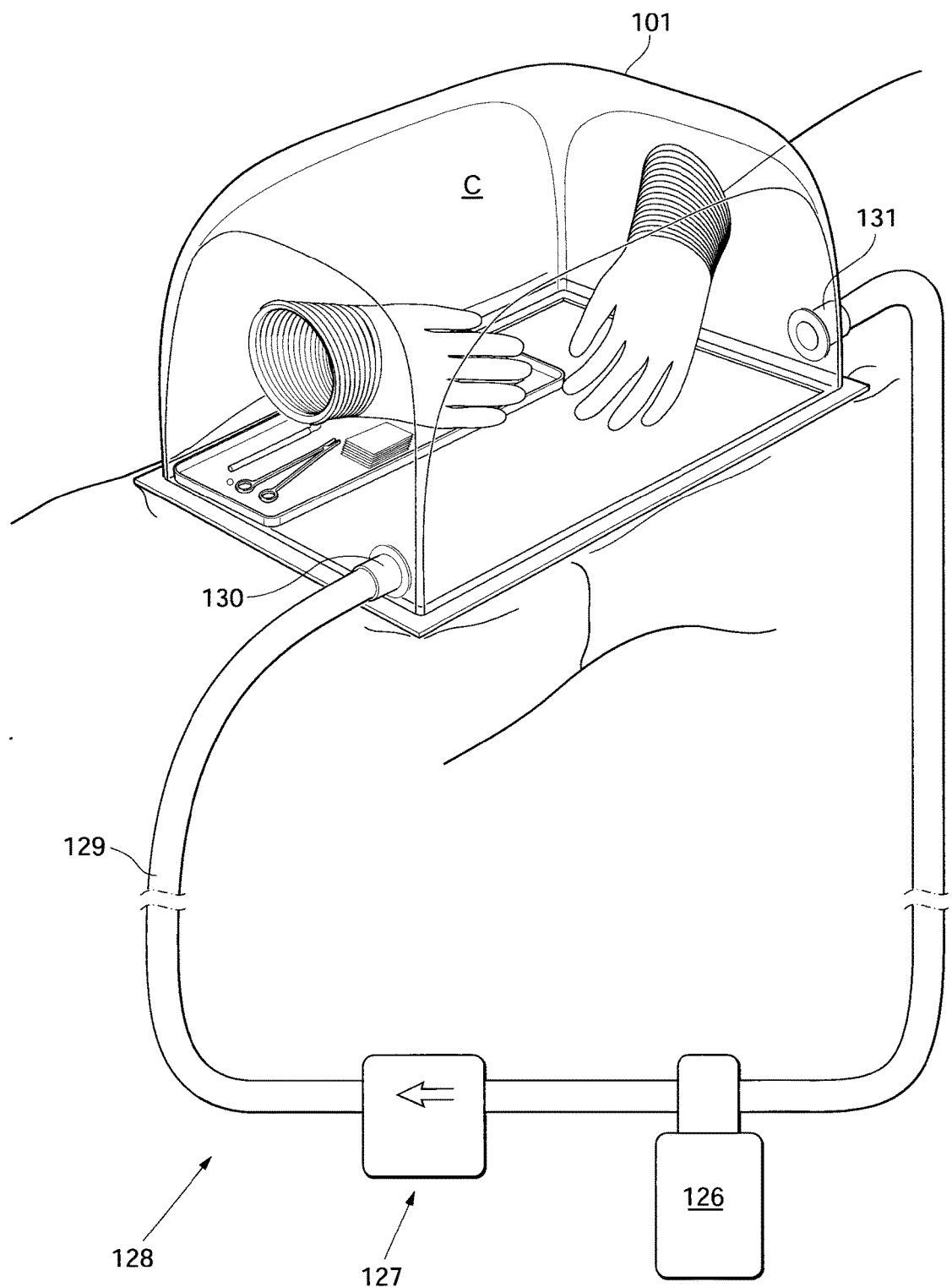
FIG. 15 shows a medical device including a circulating fluid system, when positioned on the abdomen of a patient.

FIG. 15 shows a medical device similar to the embodiment disclosed in FIG. 14 but further comprising a system 128 for circulating a fluid through the sealed environment of the medical device. The system comprises a fluid conduit 129 connected at an inlet 130 placed in the wall 101 for supplying fluid to the chamber C, and an outlet 131 for draining the fluid from the chamber C. The fluid is circled by means of a pumping unit 127 and is circled via a sterilizing/filtering/tempering unit 126 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 16:
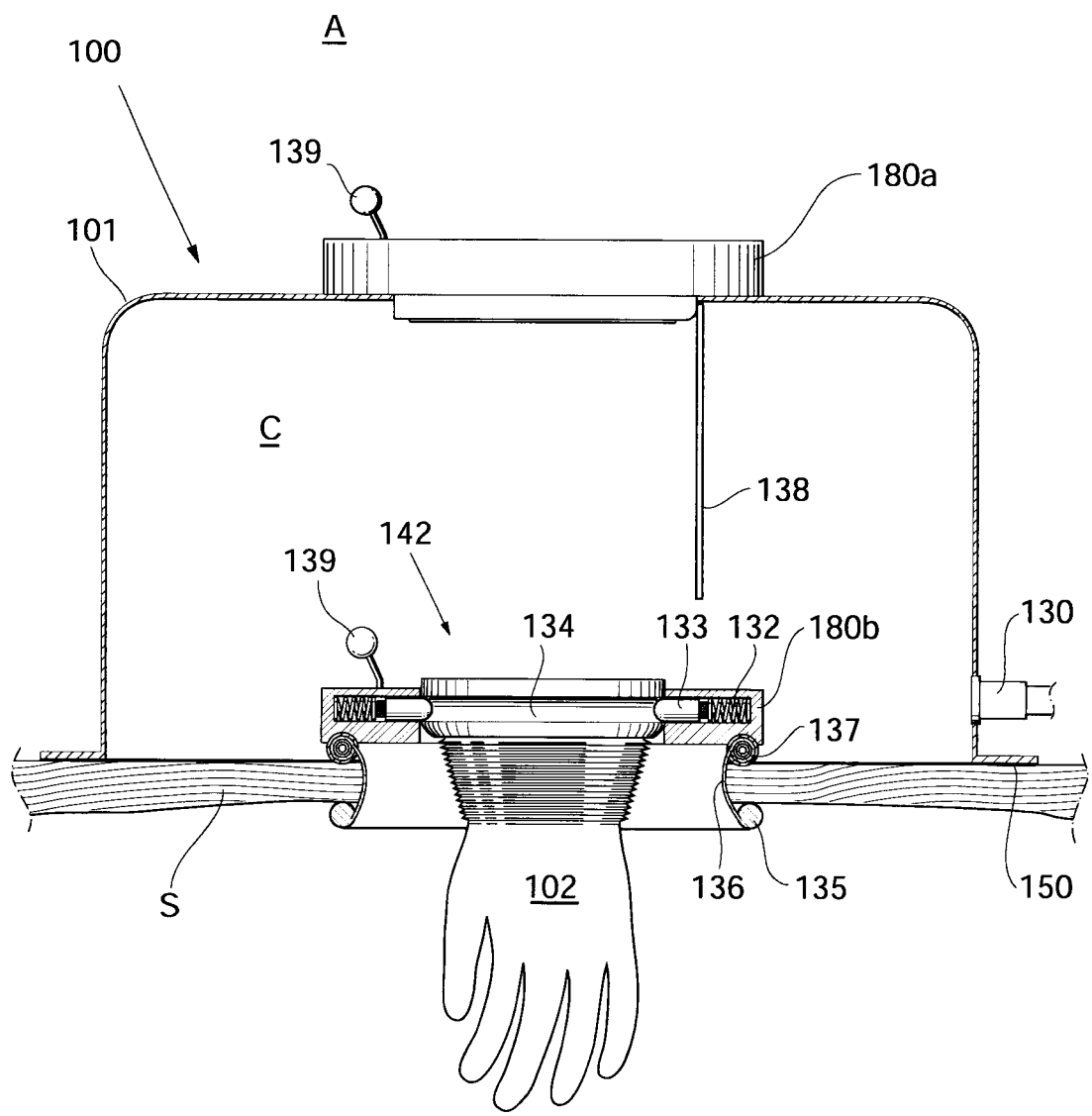
FIG. 16 shows the medical device according to one embodiment, in section.

FIG. 16 shows an embodiment similar to the embodiment disclosed with reference to FIG. 6, in section. The medical device 100 comprises a wall 101 separating the chamber C within the medical device 100 from the ambient environment A. The wall 101 is adapted to be fixated to the skin S of the patient, by means of an adhesive surface 150 or by means of a difference in pressure between the inside of the chamber C and the ambient environment A. The medical device 100 further comprises an upper 180*a* and a lower 180*b* coupling for fixating ring shaped objects which for example could be insets 142 or ports, such as the inset shown 142 comprising a surgical glove 102, or an device or instrument mount or an endoscopic port or hand access ports, such as the self sealing port disclosed with reference to FIGS. 4*a* and 4*b*. The couplings 180*a*; 180*b* comprises releasing levers 139 for releasing the ring shaped object. The lever 139 is connected to protruding members 133 which are spring loaded 132 from the rear in order to secure the recess 134 of the object. In the embodiment disclosed in FIG. 16*a*, the inset 142 fixated to the lower coupling 180*b* is a surgical glove 102 enabling manual manipulation within the body of the patient. The medical device shows in FIG. 16 further comprises a valve member 138 adapted to close the opening in the upper coupling 180*a*, when the upper coupling 180*a* is not in use. The upper coupling 180*a* is for example used for manual manipulation and preparation within the medical device 100, such that could be needed for preparing or changing an instrument or preparing an implant for implantation. The lower coupling 180*b* is for example used for laparoscopic manipulation within the body of the patient, or manual manipulation for e.g. removing a specimen or positioning an implant.

Figure 17:
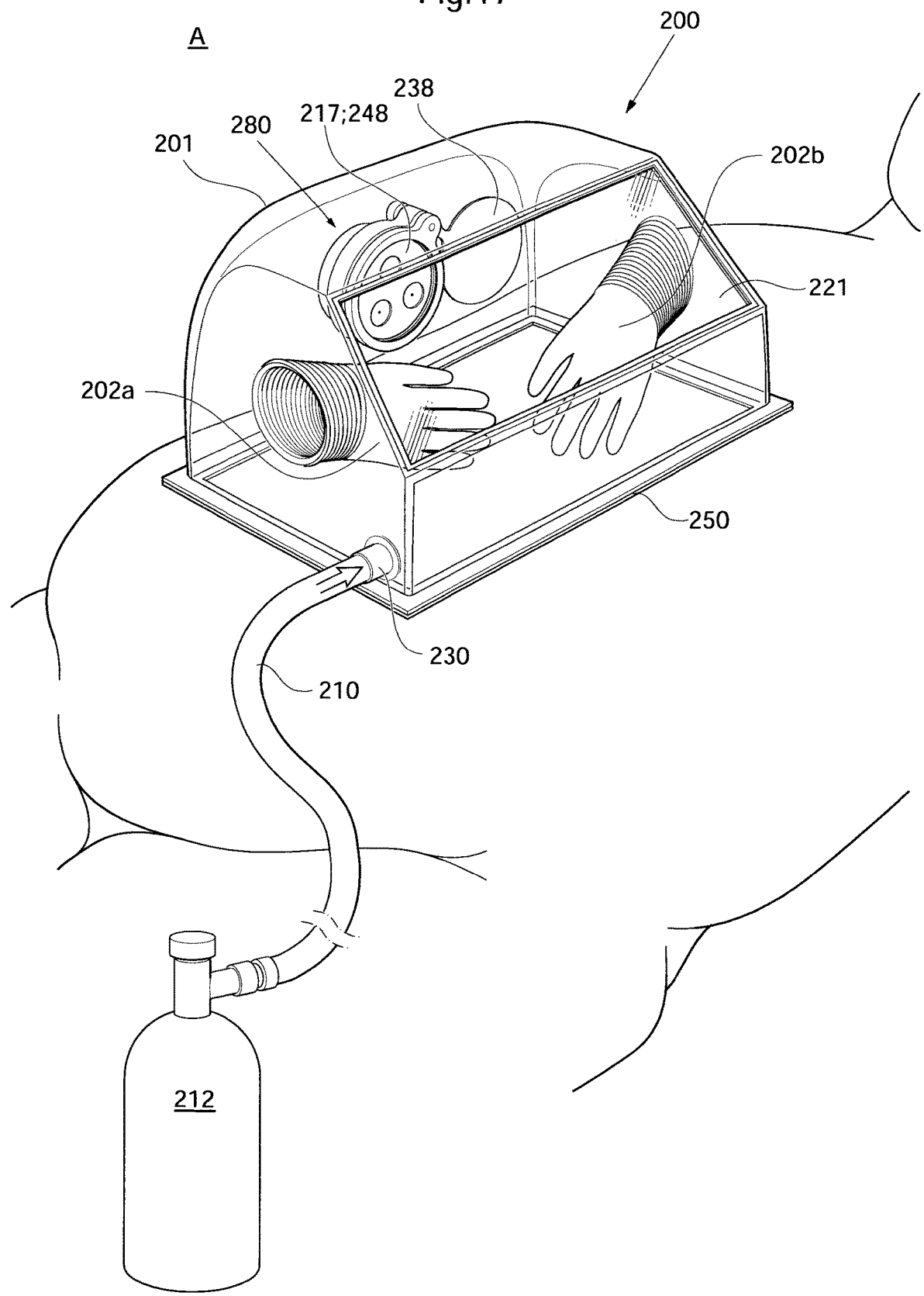
FIG. 17 shows one embodiment of the medical device, when fixated to the abdomen of a patient.

FIG. 17—shows embodiments of the medical device in which the medical device comprises a rigid transparent window for facilitating the visual inspection of the inside of the chamber.

FIG. 17 shows a medical device 200 for performing surgical procedures on a patient. The medical device 200 comprises a non-collapsible transparent window 221 for enabling viewing into the chamber C enclosed by the wall 201 of the medical device 200. The non-collapsible transparent window 221 will ensure that the surgeon has adequate visual control over the procedure since the partially collapsible wall 201, even if made from a transparent material could provide limited visibility, e.g. if the medical device 200 is not fully inflated, or in seams or bends of the wall 201. The non-collapsible transparent window 221 could for example be made from a transparent polymer, such as polycarbonate, or made from tempered glass. The medical device 200 disclosed in FIG. 17 is adapted to be attached to the patient prior to the start of the surgical procedure. In the embodiment shown in FIG. 17, but to be regarded as optionally, the medical device comprises a partially inflatable wall 201 which is adapted to be fixated to the abdominal area of a patient by means of an adhesive surface 250. By fixating the medical device 200 to the patient prior to the start of the surgical procedure the first incision in the patient could be performed inside the chamber C created by the wall 201 of the medical device 200. The medical device 200 is according to the embodiment disclosed herein connected to a source of pressurized fluid 212 which is lead into the medical device 200 through a fluid conduit 210. The medical device according to the embodiment disclosed herein is adapted to hold a gaseous fluid having a pressure exceeding 1 bar such that an endoscopic procedure could be performed partially within the medical device 200 and partially within the patient. The medical device 200 as shown in FIG. 17 comprises a wall port 217, in the form of a multi port, detachably fixated to a coupling 280 fixated to the wall 201 of the medical device. The medical device 200 further comprises a valve member 238 for closing the hole in the wall 201 while exchanging the wall port 217 to another object, such as an inset or port, such that the inset or port can be exchanged while maintaining the sealed environment within the medical device 200. In an alternative embodiment the detachable insets or ports is fixated to the wall 201 by means of the couplings further disclosed with reference to FIGS. 5a-5c. The medical device as shown in FIG. 17 further comprises surgical gloves 202a, 202b integrated in the wall 201 enabling manual manipulation within the chamber C of the medical device 200 while keeping the chamber C hermetically closed. In the embodiment shown in FIG. 17 the medical device 200 is attached to the abdomen of the patient by means of an adhesive portion 250, however, in other embodiments the medical device could be adapted to fixated to the patient by means of the pressure in the medical device 200 being different from the pressure outside of the medical device, e.g. by the pressure in the medical device 200 being lower than the pressure of the ambient environment A (atmospheric pressure), which creates a vacuum retaining the medical device 200 at the skin of the patient. The pressurized fluid tank 212 provides a pressurized fluid to the sealed environment through the fluid conduit 210, however, in alternative embodiments it is conceivable that the pressurized fluid is provided into the body of the patient through a different incision and thus enters the chamber from the inside of the patient, this particularly useful when performing laparoscopic of partially laparoscopic procedures since the abdomen needs to be inflated in these procedures.

Figure 18A:
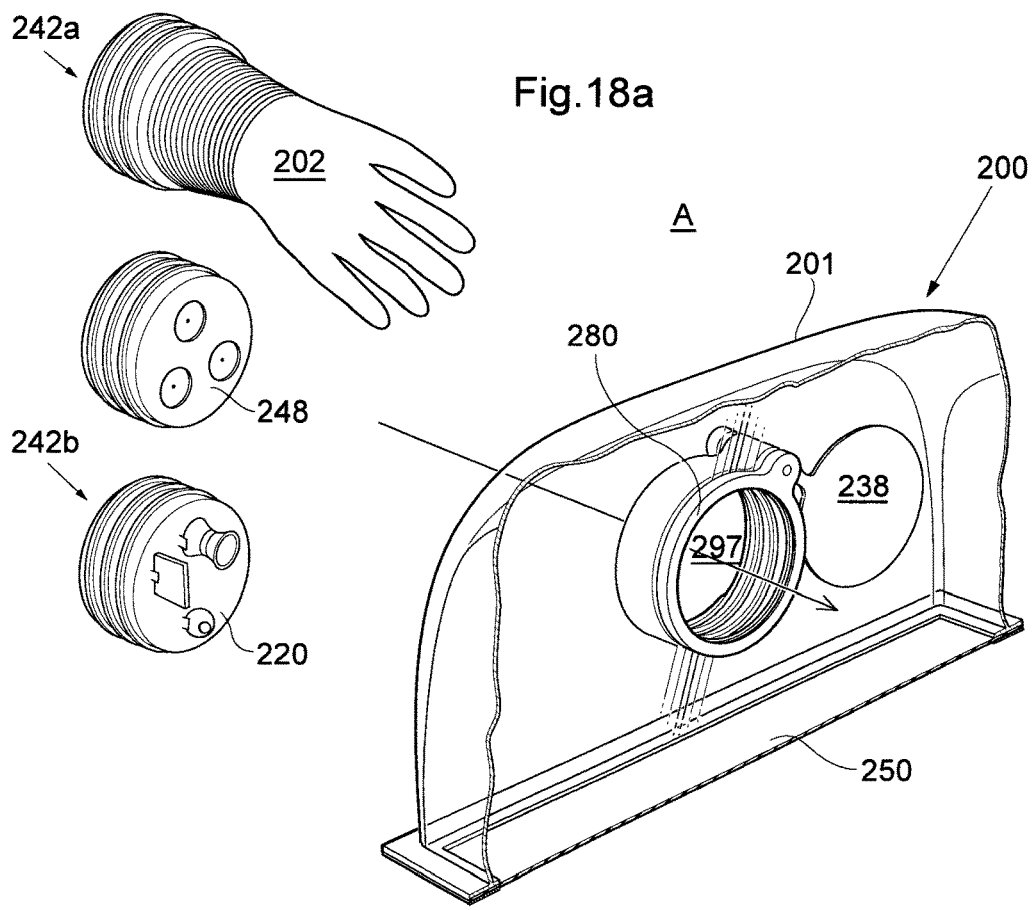
FIGS. 18a-18b shows a coupling in the wall of the medical device.

FIG. 18a shows a section of the medical device 200 of FIG. 17, showing the coupling 280 integrated in the wall 201 in further detail. The coupling 280 enables the changing of objects from for examples a multiport 248, to an inset 242a comprising a surgical glove 202 or a device or instrument mount 220. The coupling 280 comprises a valve member 238 for closing the hole in the coupling 280 when objects should be exchanged such that the environment in the medical device can remain sterile. The device or instrument mount 220 could for example be adapted to hold surgical instruments and/or implants or parts of implants. The medical device 200 is according to this embodiment adapted to be fixated to the skin of the patent by a portion of the wall of the medical device comprising an adhesive surface 250.

Figure 18B:
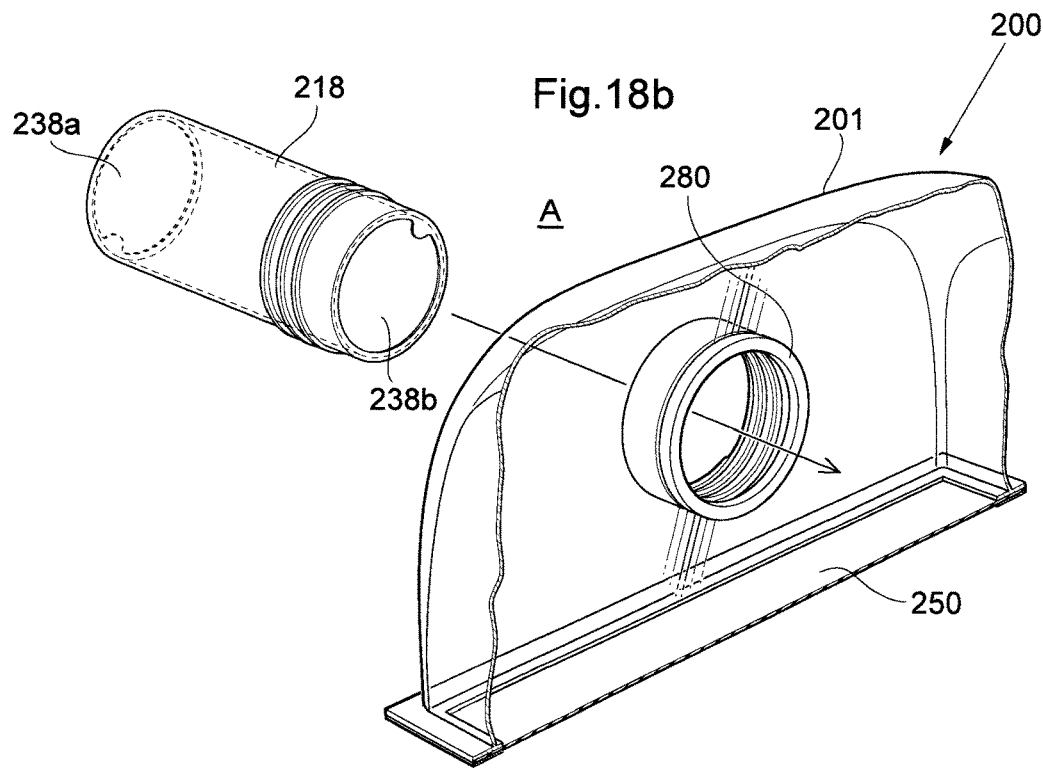

FIG. 18b shows the shows a section of the medical device 200 showing the coupling 280 integrated in the wall 201 in further detail when an airlock 270 for transferring objects between the chamber and the ambient environment is being provided. According to the embodiment shown in FIG. 18b the airlock comprises a first valve member 238a separating the airlock 218 from the ambient environment A, and e second valve 238b separating the airlock 218 from the chamber. The airlock 218 is provided between the first 238a and second 238b valve and could for example be used for passing an implant into the sealed environment, or for passing a specimen or sample out of the sealed environment.

FIG. 19a shows the medical device 200 in an embodiment when the wall 201 of the medical device 200 is inflatable, and the medical device 200 is in its inflated state. When the chamber C is deflated it has a first volume i.e. when the first 280a and second 280b couplings are interconnected, and when the chamber C is inflated and the first coupling 280a is disconnected from the second coupling 280b it has a second volume, and the second volume is larger than the first volume. According to the embodiment shown in FIG. 19a, the second volume is larger than 500 000 mm3. According to the embodiment shown in FIG. 19a, the chamber C is formed by the inflatable wall 201 and is adapted to hold a pressure exceeding atmospheric pressure.

According to the embodiment shown in FIG. 19a-19g the chamber C further comprises a pouch 282 for holding a specimen 281 removed from within the body of the patient not to contaminate any other part of the body and create the possibility of delaying the removal of the specimen until the procedure is concluded. The pouch 282 may be a pouch 282 which could be closed for creating a pouch-chamber within the chamber C for isolating the removed specimen 281 within the chamber C.

In FIG. 19a a state is illustrated in which the incision I in the patient's skin S is being created by the surgeon by means of an inset 242 latched to the first coupling 280a and comprises a glove 202 enabling manual manipulation within the chamber C. The second coupling 280b is fixated and sealed by means of the vacuum sealing member 205' since the sealing device that is provided partially within the patient's body cannot be mounted until the incision I in the patient's skin is concluded. The two different sealing devices disclosed could in some embodiments be replaced by only one of the sealing device, or by a different seal, such as the adhesive of pressure sealing device disclosed in other portions herein.

FIG. 19b shows the medical device, when the second sealing 235, 236, 237 have been placed in the incision I cut in the patient's skin S. The wall 201 enclosing the chamber C is elastic or flexible which enables the surgeon move the second part 231a in relation to the first part 231b for getting better access to different angles within the patient's body, for example for removing a specimen 281. The embodiment of FIG. 19b further comprises an iris valve 286 placed in the second coupling 280b for closing the hole in the second lower coupling 280b such that the chamber C is sealed from at least one of the ambient environment A and a cavity in the patient. The closing of the iris valve 286 enables the maintaining of a cavity within the chamber C without maintaining a pressure in the chamber C, at the same time as a pressure and/or sealed environment can be maintained within the body of the patient.

Figure 19C:
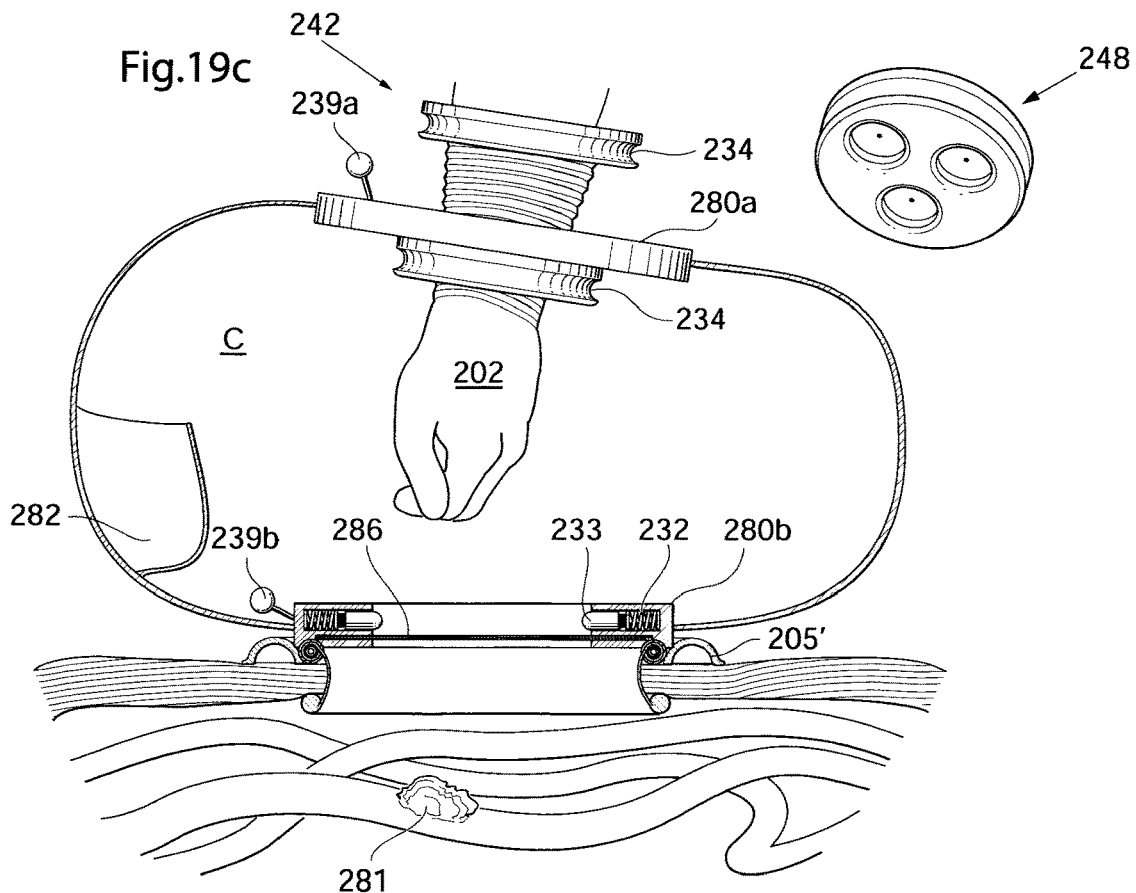

FIG. 19c shows the medical device according to FIGS. 19a and 19b when the inset 242 comprising the glove 202 is removed and replaced by a body multi-port 248 comprising a plurality of ports. The multi-port may be used for manipulating objects within the chamber C of the inflated medical device using surgical instruments 289, or within the body of the human patient, when the first and second couplings are are connected (as shown in FIG. 19d).

Figure 19D:
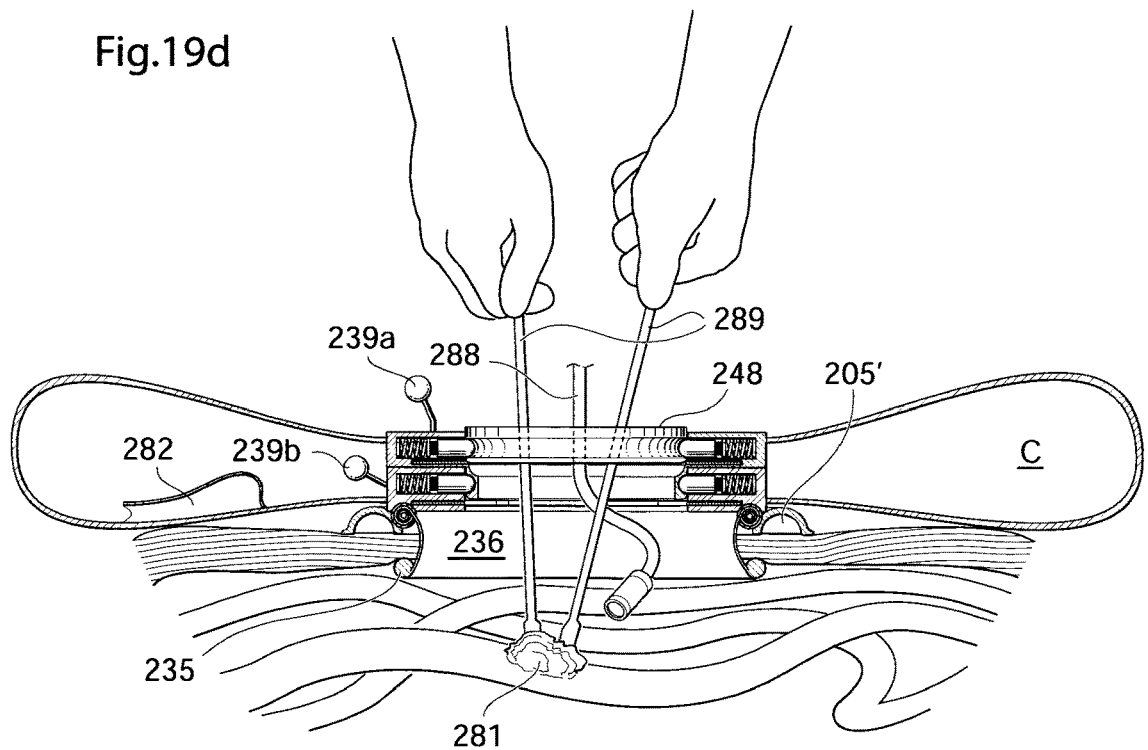

FIG. 19d shows the medical device when the first and second couplings 280a; 280b are connected such that surgical instruments 289 can be used for manipulating within the body of the patient. An endoscopic camera 288 may be provided in the multi port 248 for enabling visual inspection of the cavity within the patient's body. The process of cutting away a specimen 281 from the intestines of a patient in a laparoscopic way is shown in FIG. 19d. The first coupling 280a is connected to the second coupling 280b by the protruding members (233 in FIG. 19c) of the second coupling 280b engaging the recess (234 in FIG. 19c) of the first coupling 280a.

Figure 19E:
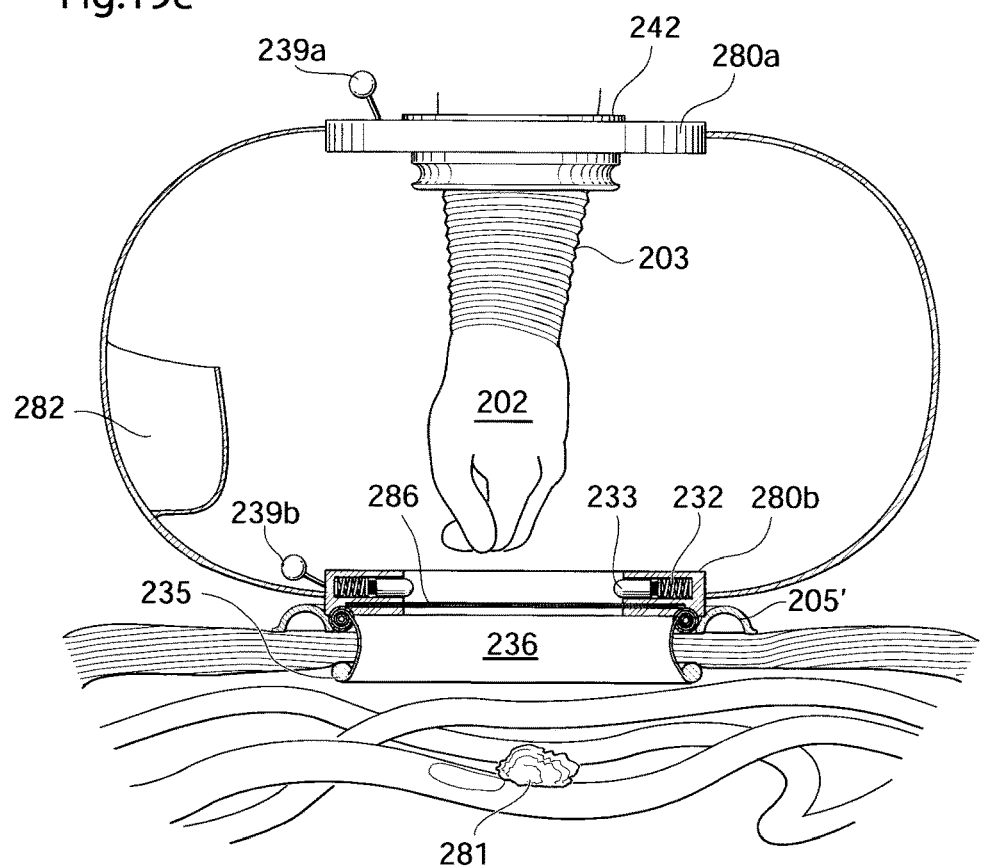

In FIG. 19e, the inset 242 comprising the glove 202 has been fixated to upper coupling 280a to enable the surgeon to operate within the cavity of the patient's body and within the chamber C enclosed by the wall 201 of the medical device. By the inset 242 comprising the glove 202 comprising a pleated portion 203, the surgeon is able to reach into the cavity of the patient for removing the specimen 281 dissected from the intestines in prior steps.

Figure 19F:
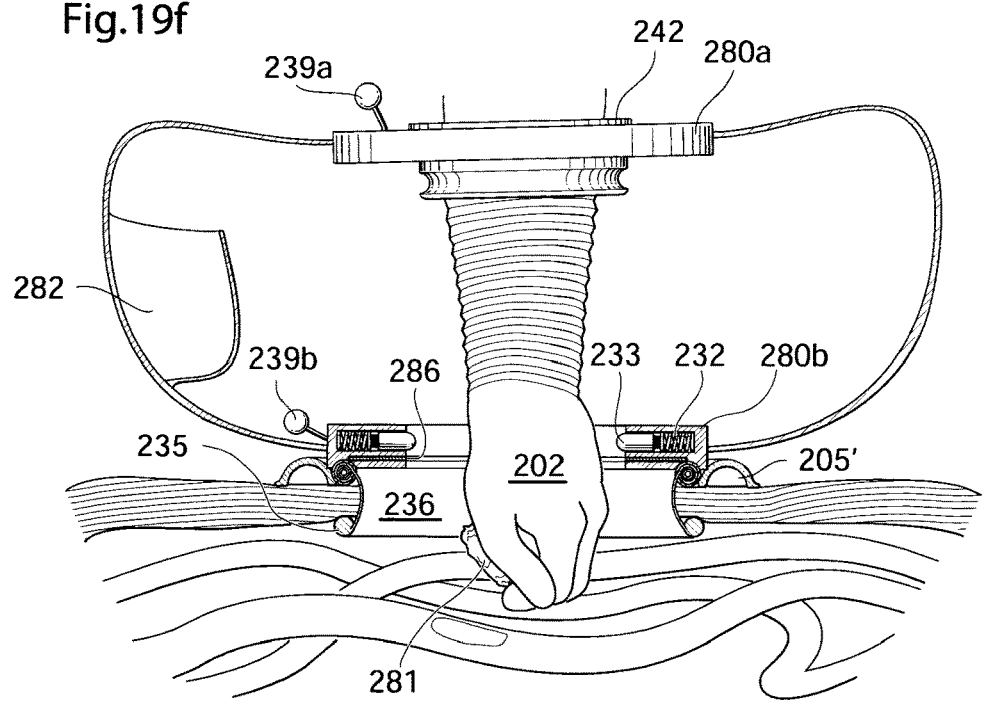

FIG. 19f shows that the wall 201 of the medical device is collapsible such that the inset comprising the glove 202 can be moved in relation to the lower coupling 280, which gives the surgeon further freedom when removing the loose specimen 281 from the intestines of the patient.

Figure 19G:
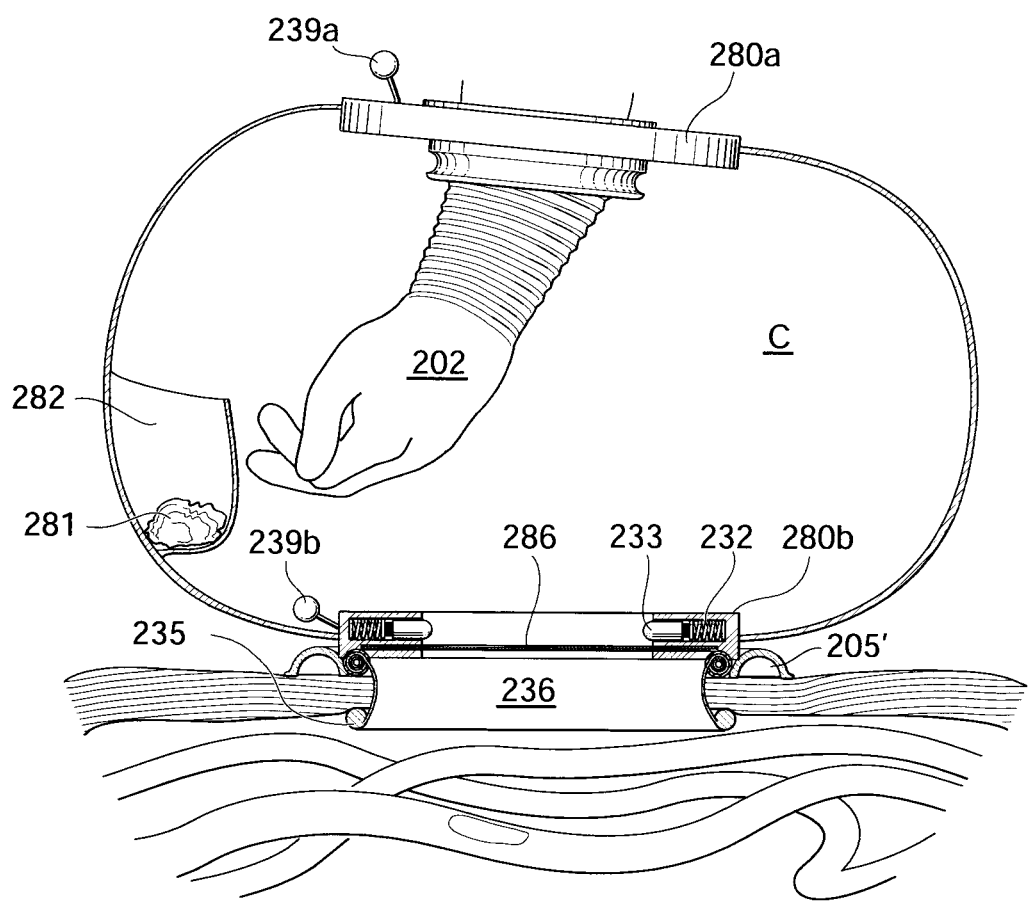

FIG. 19g shows the step of placing the removed specimen 281 in the pouch 282 such that the specimen 281 does not contaminate any other part of the body. The pouch 282 may be a pouch 282 which could be closed for creating a pouch-chamber within the chamber C for isolating the removed specimen 281 within the chamber C.

Figure 19H:
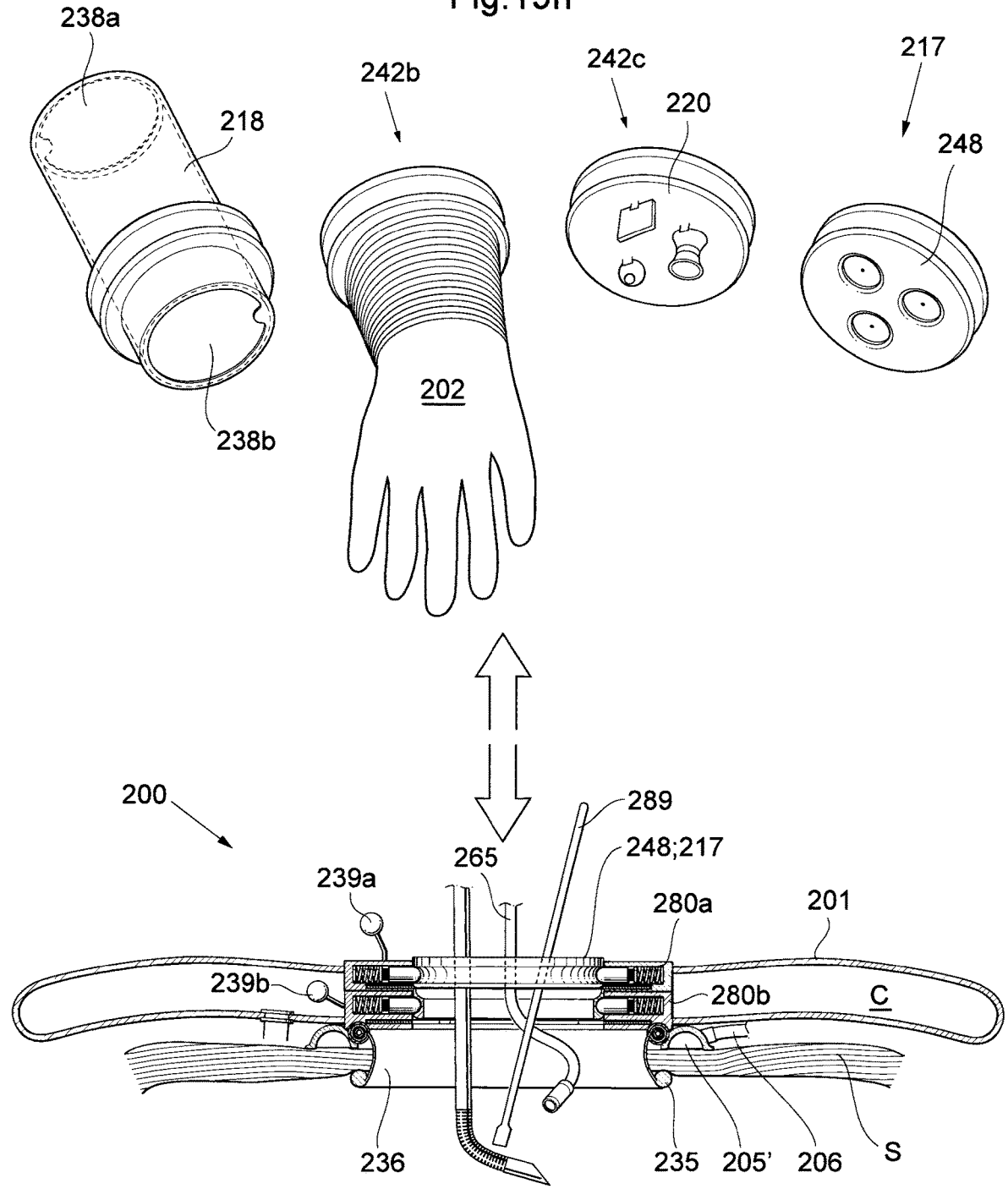
FIGS. 19h-19j shows embodiments of the medical device, in section.

FIG. 19h shows the medical device 200 adapted to be at least partially placed in an incision cut in a patient's body. The medical device 200 comprises a first 280a and second 280b coupling adapted be interconnected. The first upper coupling 280a is adapted to be disconnected from the second lower coupling 280b, and the first upper coupling 280a is connected to a first portion of the flexible wall 201, and the second lower coupling 280b is connected to a second portion of the flexible wall 201. The flexible wall 201 forms a chamber C in which a sealed environment can be maintained, the chamber C is heavily enlarged when the first coupling 280a is disengaged from the second coupling 280b, thus creating operating space within the chamber C enclosed by the wall 201. The first and second couplings comprise latching systems for locking an inset 242 or wall port 217 in the upper coupling 280a. The inset 242b; 242c may for example be a glove 202 for manual manipulation within the body of the patient, or within the enclosed chamber C, a device o instrument mount 220 for holding instruments or medical devices within the chamber C. Alternatively the insets 242b; 242c can be replaced by an airlock sluice 218 with a first 238a and second 238b valve member or a wall port 217, such as the wall multiport 248 provided in FIG. 19h, enabling the insertion of a surgical instrument 289 and a camera 265 into the cavity in the body of the patient.

In the embodiment shown in FIG. 19h the medical device is fixated to the body of the patient by means of a vacuum fixating member 205' connected to a vacuum conduit 206, which in turn is connected to a vacuum source. Furthermore, the medical device in FIG. 19h comprises a second sealing function having a first sealing member 235 in the form of an intra body ring adapted to be positioned at the inside of the patient's skin around an incision to be performed in the skin and a second sealing member 237 in the form of an outer ring adapted to be positioned at the outside of the patient's skin around the incision, and a spring-loaded or elastic connecting member 236 sealingly interconnecting the first 235 and second 237 sealing members. The spring-loaded or elastic connecting member 236 seals between at least one of the lower coupling 280b and the skin S of the patient, and the first sealing member 235 and tissue of the patient.

Figure 19I:
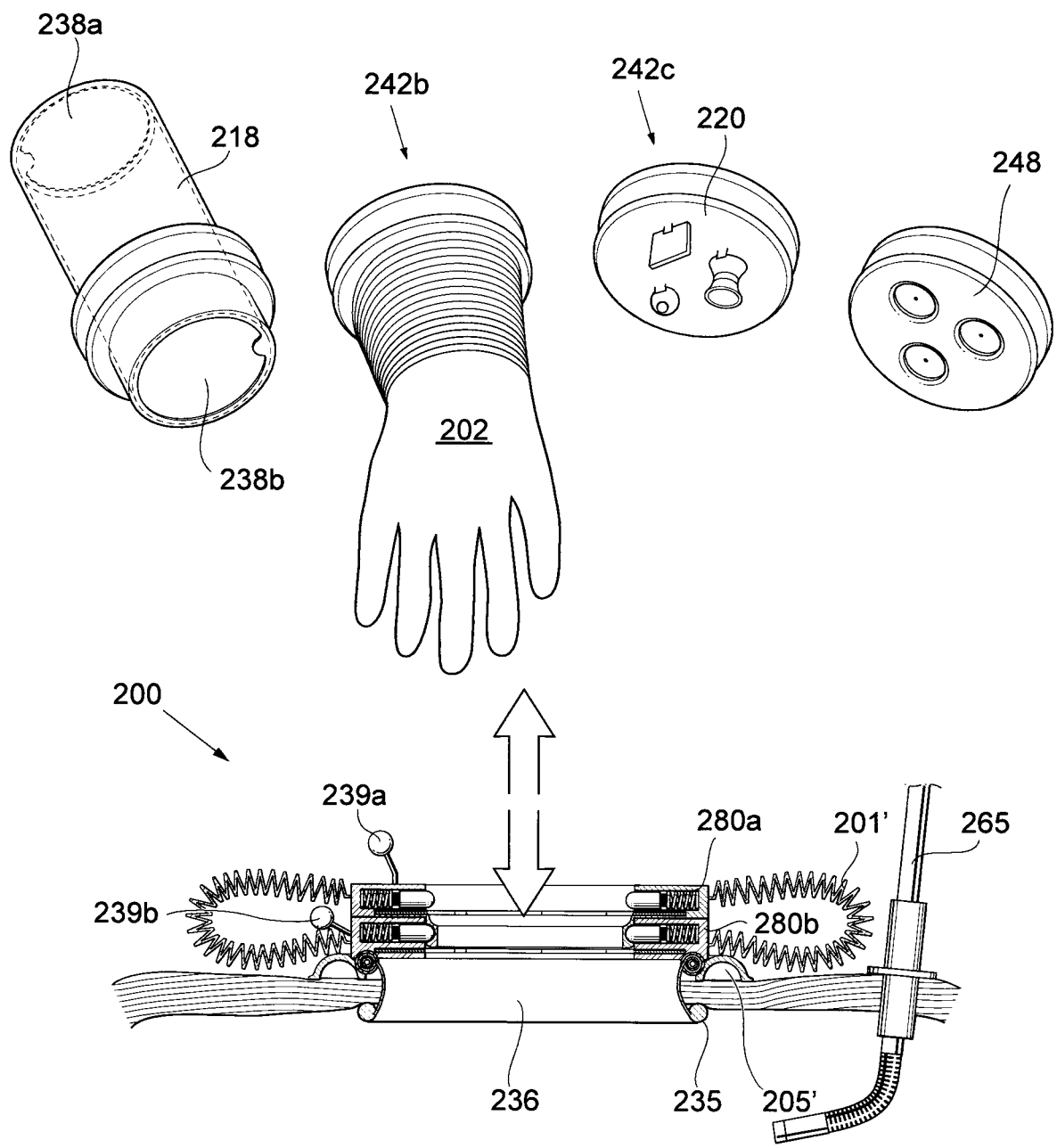

FIG. 19i shows the port in an embodiment very similar to the embodiment shown in FIG. 19h but with the difference that the wall 201' has a bellows structure and thus taking up less space when in its deflated state. The bellows structure enables the wall 201' to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. A camera 265 is also shown in FIG. 19i, placed outside of the medical device and enabling visual inspection of the cavity within the medical patient.

Figure 19J:
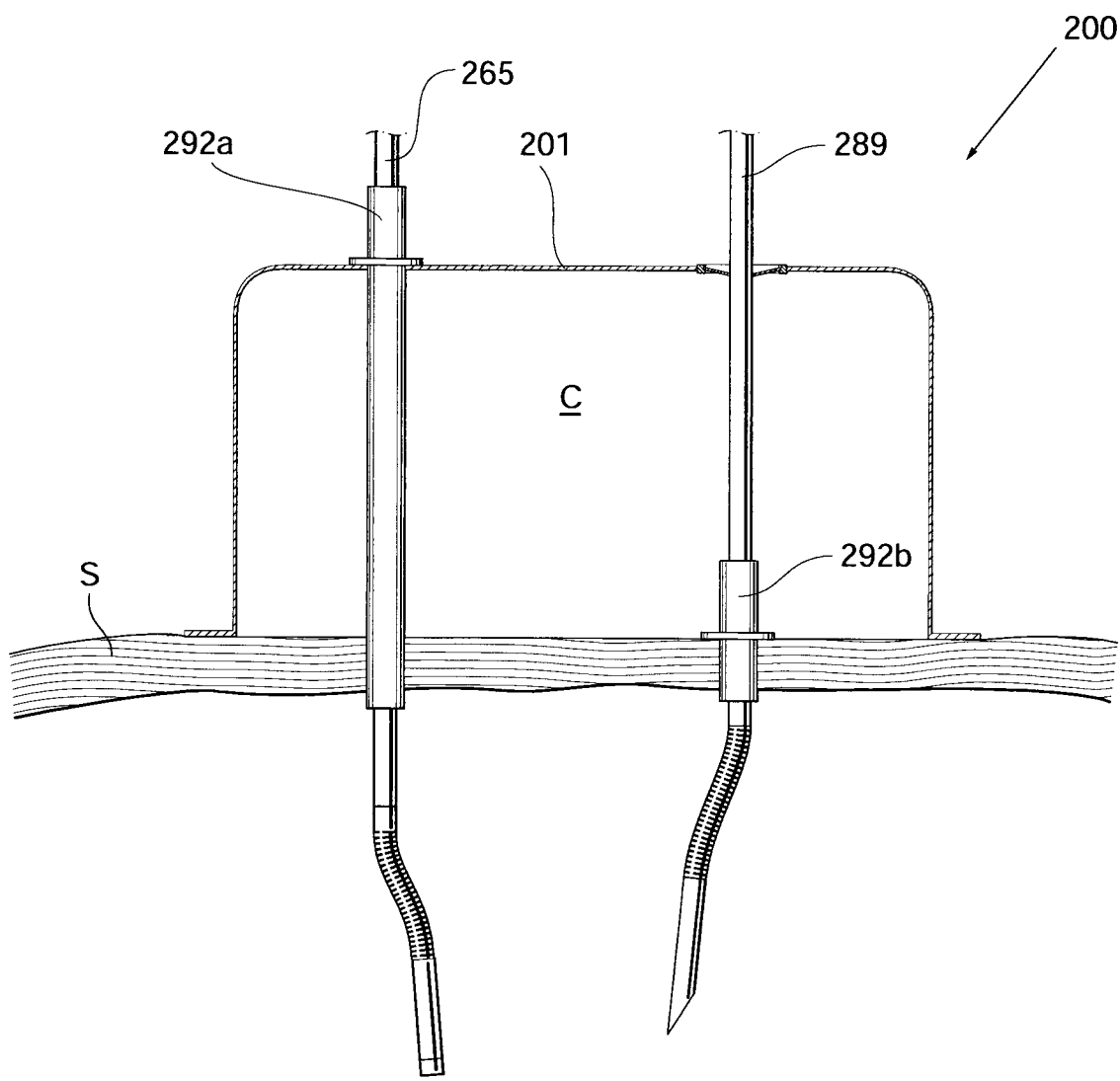

FIG. 19j shows examples of how trocars 292a; 292b may be used in combination with the medical device according to any of the embodiments shown in FIGS. 17-19i. The medical device 200 comprises a wall 201 placed on the patient's skin and thereby enclosing a chamber C for creating an enclosed environment. The medical device 200 comprises two trocars 292a; 292b, one 292a traveling through both the wall 201 of the medical device 200 and the skin S of the patient and thus enabling laparoscopic tools (in this case a camera 265) to be inserted into the patient through both the wall 201 of the medical device and the skin S of the patient through one single trocar 292a. The other trocar 292b being placed inside the chamber C and enabling a laparoscopic tool 289 to be inserted through the skin of the patient. The laparoscopic tool 289 is in this embodiment inserted into the chamber C enclosed by the wall 201 through a self sealing membrane 243 in the wall 201 sealing against the instrument 289.

Figure 19K:
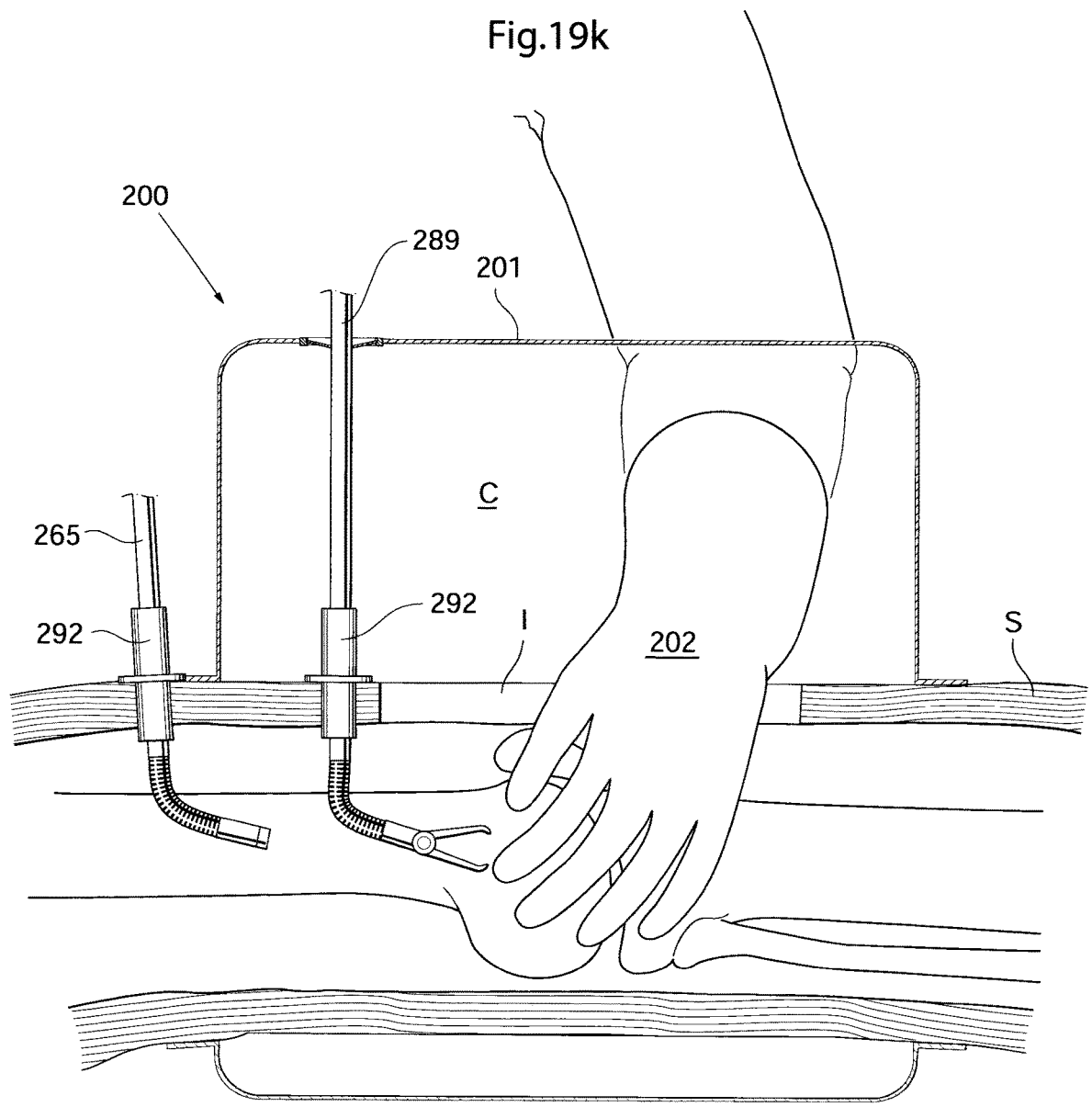
Figure 19I:
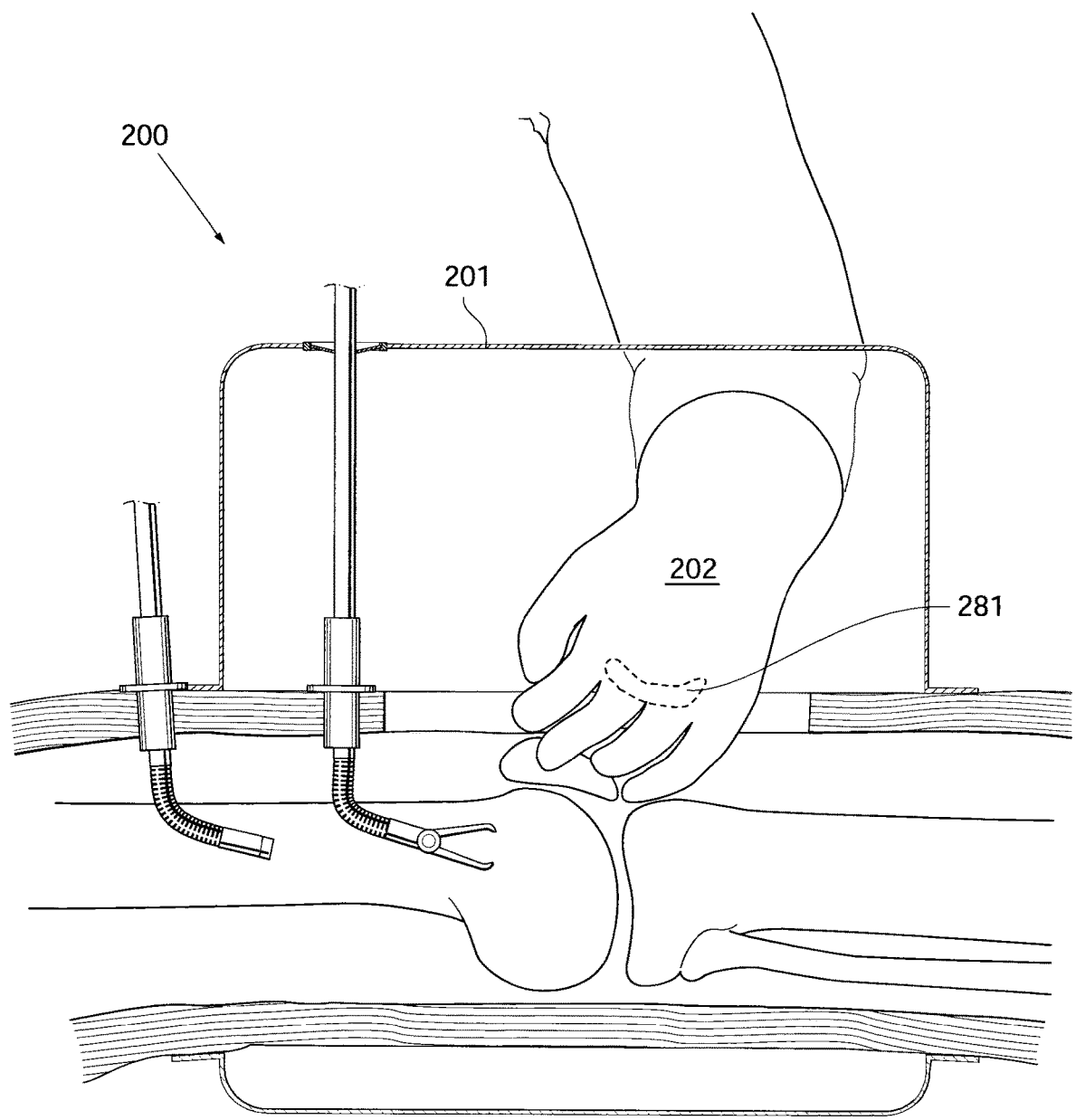

FIG. 19k shows how the medical device shown in FIGS. 17-19 may be used. The medical device 200 comprises a glove 202 integrated in the wall 201 and a camera 265 placed in the skin outside of the medical device 200. The medical device 200 further comprises a trocar 292 placed trough an opening in the wall 201 and into the chamber C and further through an opening in the skin S of the patient and into an area of the knee of the patient. FIG. 19k schematically illustrates how the surgeon manipulates the knee using the glove 202.

Figure 19M:
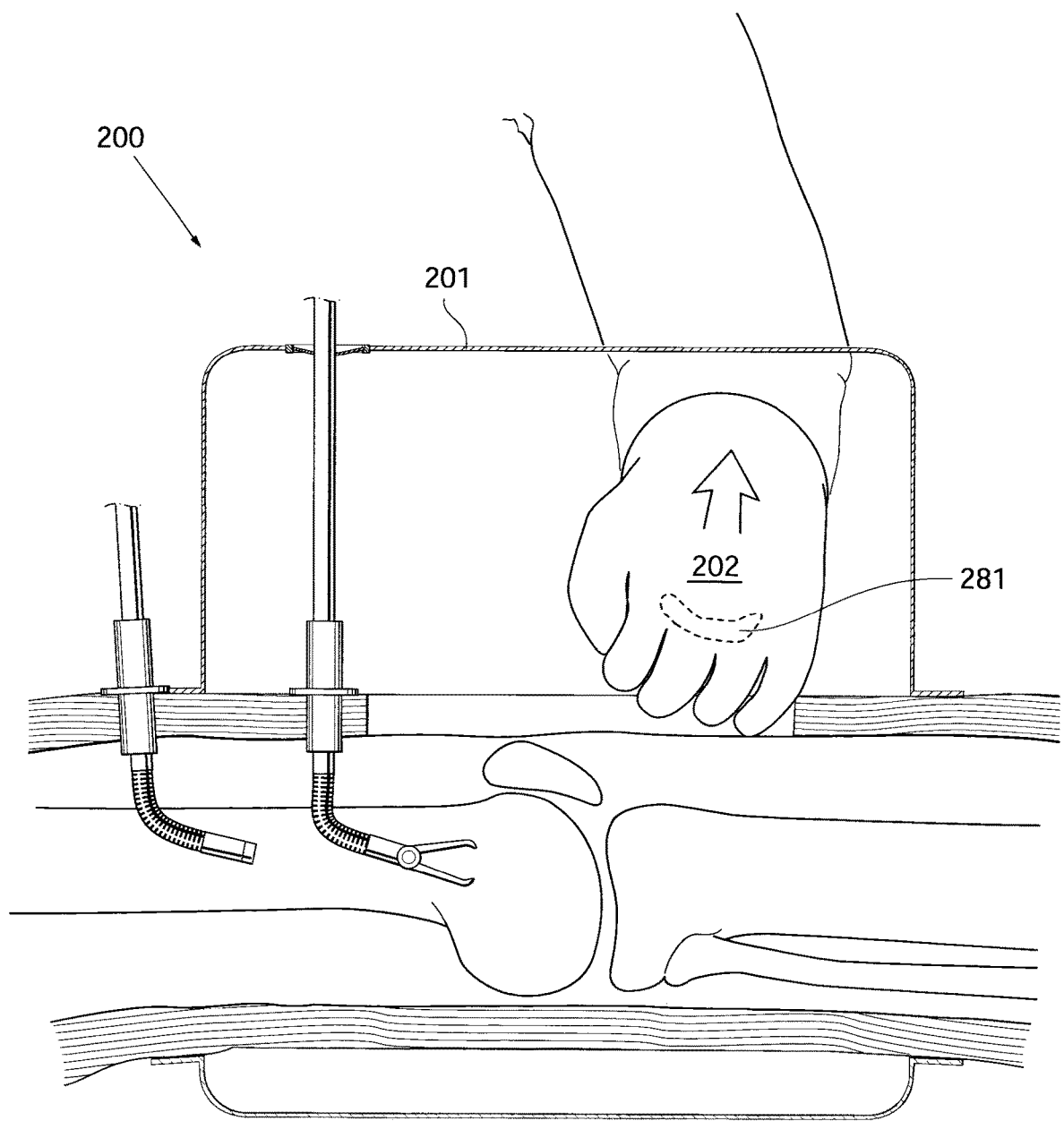

FIGS. 19l, 19m shows the medical device 200 when the surgeon removes a specimen 281 from the knee of the patient using the glove 202 integrated in the wall 201 of the medical device 200.

Figure 19N:
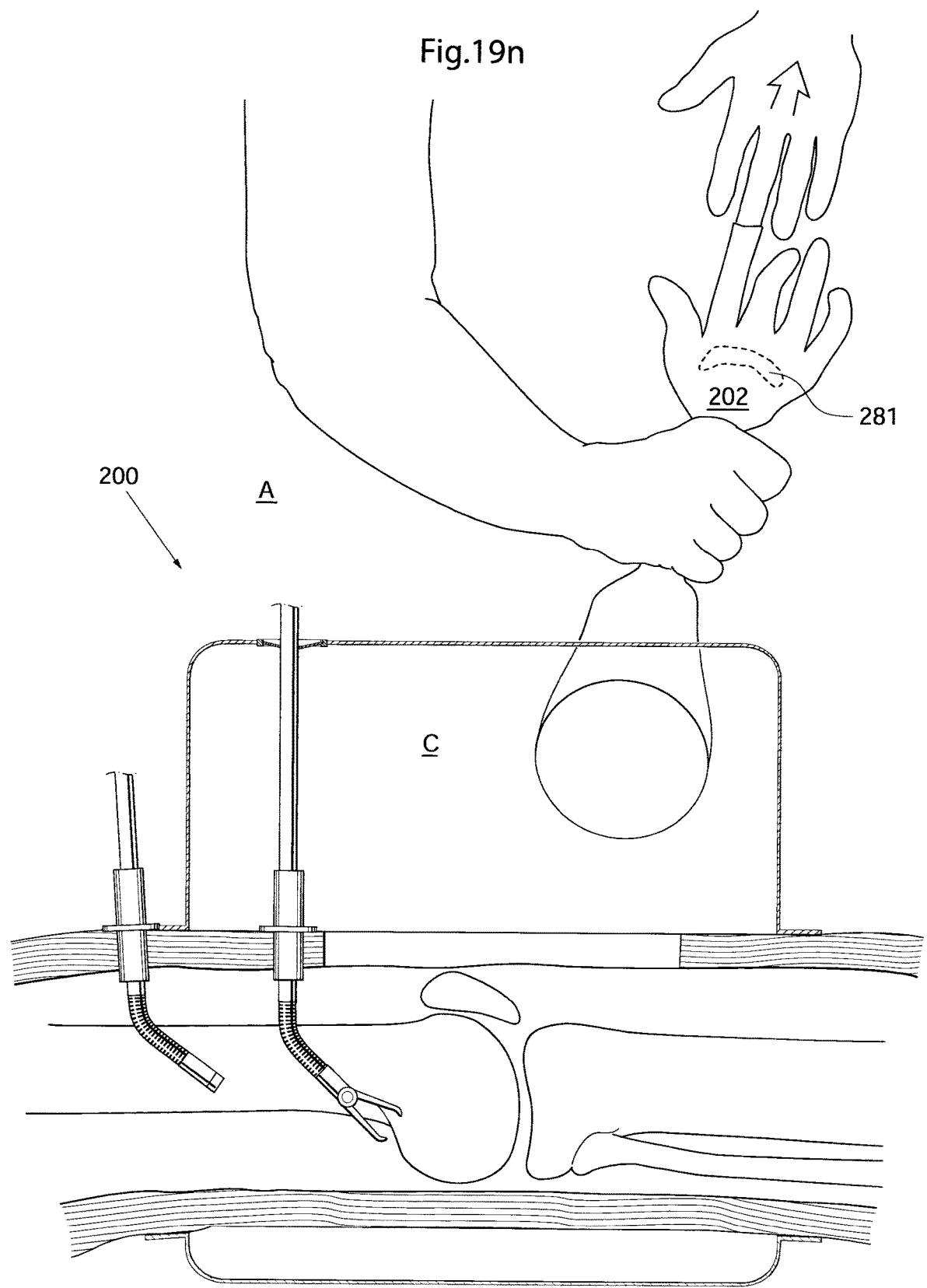

FIG. 19n shows the medical device 200, when the surgeon has turned the integrated glove 202 inside-out such that the specimen 281 can be contained within the integrated glove 202. By isolating the specimen 281 inside of the glove 202, the specimen 281 is removed both from the rest of the body of the patient and from the ambient environment A, and thereby does not risk to infect any other portion of the patient's body or medical staff with any infectious disease.

Figure 19O:
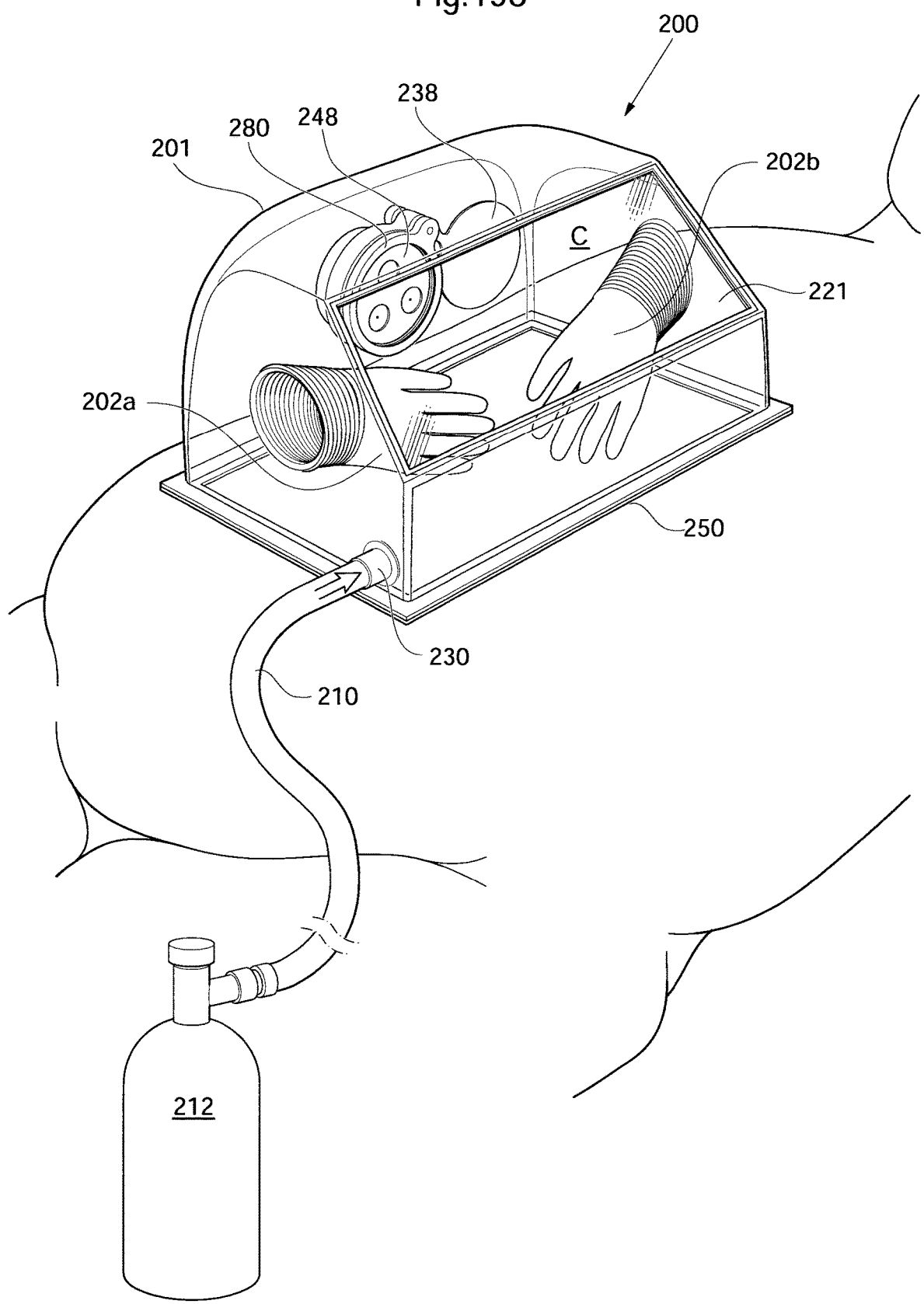
FIG. 19o shows the medical device when applied to the abdomen of a patient.

FIG. 19o shows a medical device 200 for performing surgical procedures on a patient. The medical device 200 is adapted to be attached to the patient prior to the start of the surgical procedure. In the embodiment shown in FIG. 19o the medical device 200 comprises a partially inflatable wall 201 which is adapted to be fixated to the abdominal area of a patient by means of a portion of the wall 201 comprising an adhesive surface 250. By fixating the medical device 200 to the patient prior to the start of the surgical procedure the first incision in the patient could be performed inside the chamber C enclosed by the medical device 200. The medical device 200 is according to the embodiment disclosed herein connected to a source of pressurized fluid 212 which is lead into the medical device through a fluid conduit 210. The medical device according to the embodiment disclosed herein is adapted to hold a gaseous fluid having a pressure exceeding 1 bar such that a laparoscopic procedure could be performed partially within the medical device 200 and partially within a cavity in the patient.

The medical device as shown in FIG. 19o comprises one laparoscopic wall multi port 248 detachably fixated to the wall 201. The laparoscopic wall multi port 248 is attached by means of a coupling 280 and thereby detachable. The medical device 200 further comprises a valve member 238 for closing the hole in the wall 201 while exchanging the laparoscopic wall multi port 248 to another wall port or to an inset, such that the wall port can be exchanged while maintaining the sealed environment within the medical device 200. The detachable insets or wall ports could be adapted to be fixated to the wall 201 by means of a coupling and thereby possible to quickly exchange (as disclosed above with reference to FIGS. 5a-5c). The medical device as shown in FIG. 19o further comprises insets in the form of surgical gloves 202a, 202b integrated in the wall 201 enabling manual manipulation within the sealed environment of the medical device 200 while keeping the sealed environment hermetically closed. A pressurized fluid tank 212 provides a pressurized fluid to the sealed environment through a fluid conduit 210, however, in alternative embodiments it is conceivable that the pressurized fluid is provided into the body of the patient through a different incision and thus enters the chamber C from the inside of the patient, this is particularly useful when performing laparoscopic or partially laparoscopic procedures since the abdomen needs to be inflated in these instances.

According to the embodiment shown in FIG. 19o the wall 201 is partially collapsible. The medical device 200 comprises a non-collapsible transparent window 221 for enabling viewing into the chamber C. The non-collapsible transparent window 221 will ensure that the surgeon has adequate visual control over the procedure since the partially collapsible wall 201, even if preferably made from a transparent material could provide limited visibility, e.g. if the medical device is not fully inflated, or in seams or bends of the material. The non-collapsible transparent window 221 could for example be made from a transparent polymer, such as polycarbonate, or made from tempered glass.

Figure 19P:
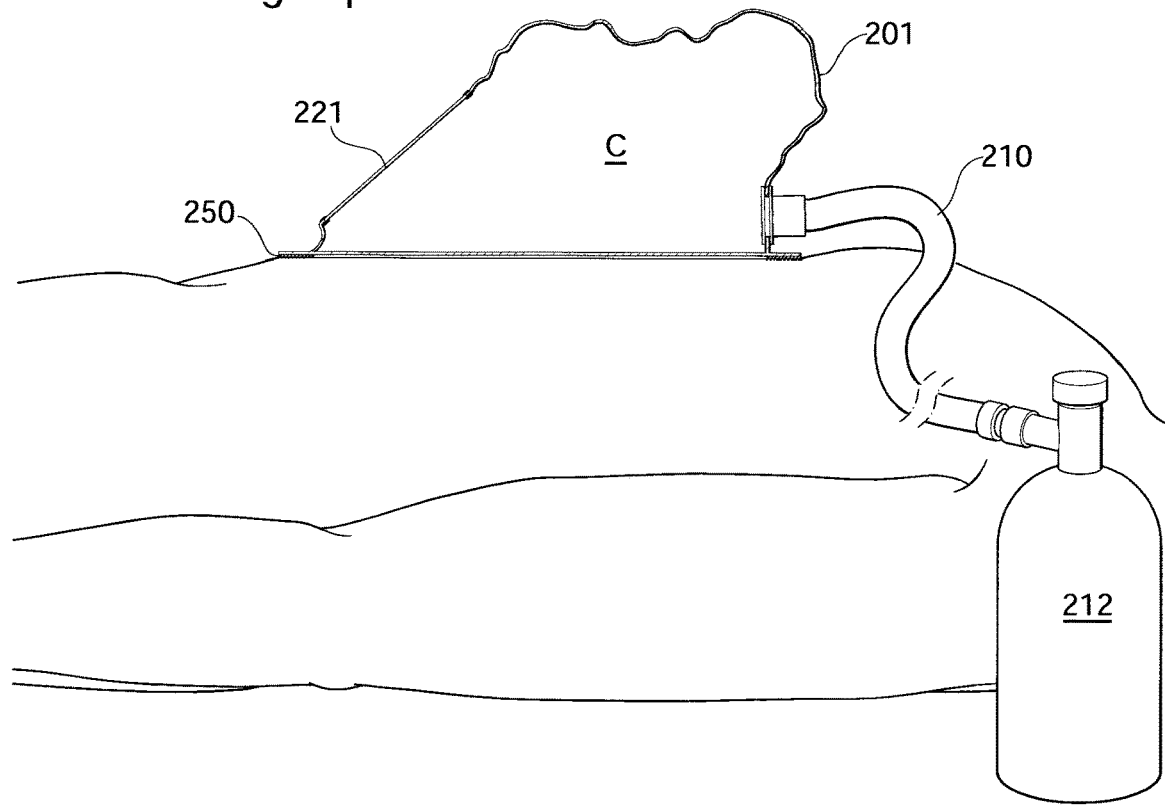
FIG. 19p shows the medical device when applied to the abdomen of a patient, in a deflated state.

FIG. 19p shows in section the medical device of FIG. 19o when fixated onto the abdominal area of the patient. The medical device is preferably attached to the patient prior to the start of the surgical procedure, such that the first incision in the patient could be performed inside the sealed environment. FIG. 19p shows the medical device as it is being inflated by a pressurized fluid entering the medical device through a fluid conduit 210 and according to the embodiment shown, the medical device is fixated to the abdominal region of a patient by means of a portion of the wall 201 being an adhesive surface 250.

Figure 19Q:
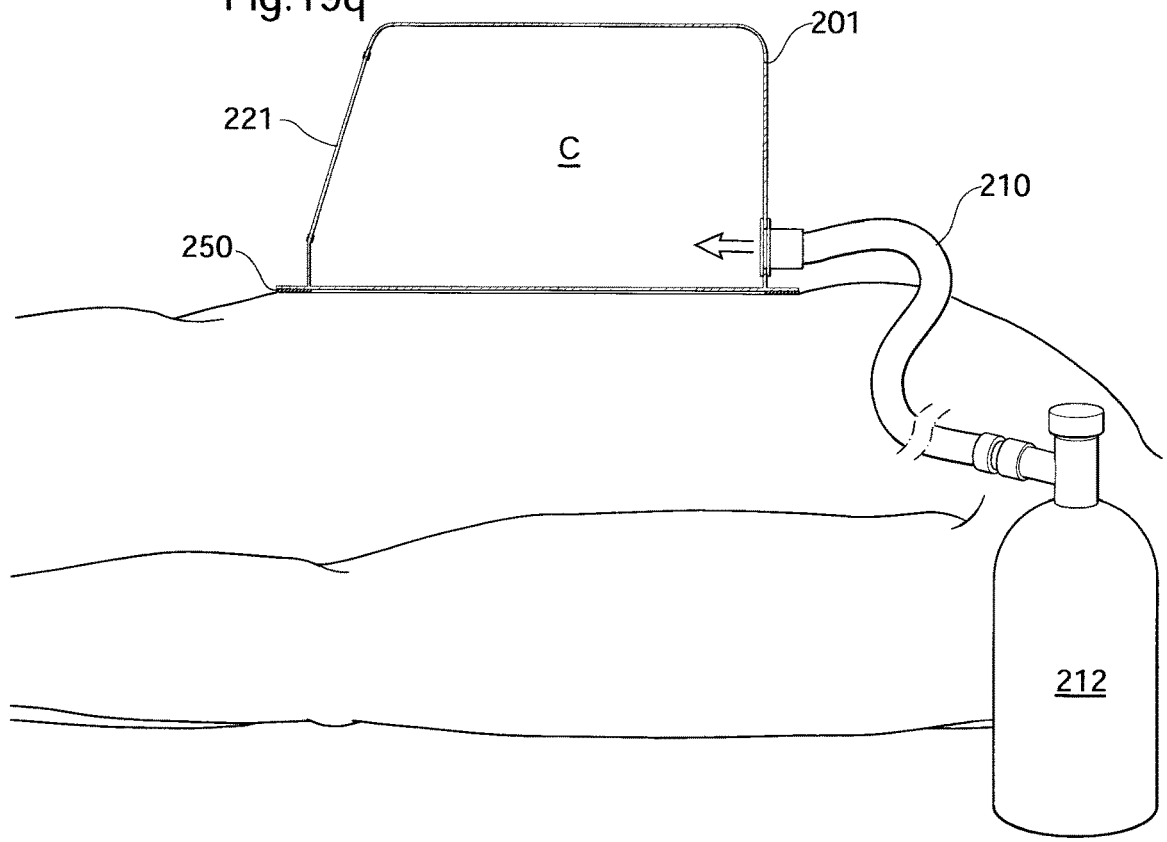
FIG. 19q shows the medical device when applied to the abdomen of a patient, in an inflated state.

FIG. 19q shows the medical device of FIG. 19o when inflated such that the wall 201 separates the sealed environment within the medical device from the surrounding environment and thus creates an operating environment which is separated from contaminations from the outside. In some applications it is conceivable that a normal laparoscopic procedure is performed with the medical device positioned but not inflated. The medical device is then only inflated at the end of the procedure, for example when a specimen is to be removed.

Figure 19R:
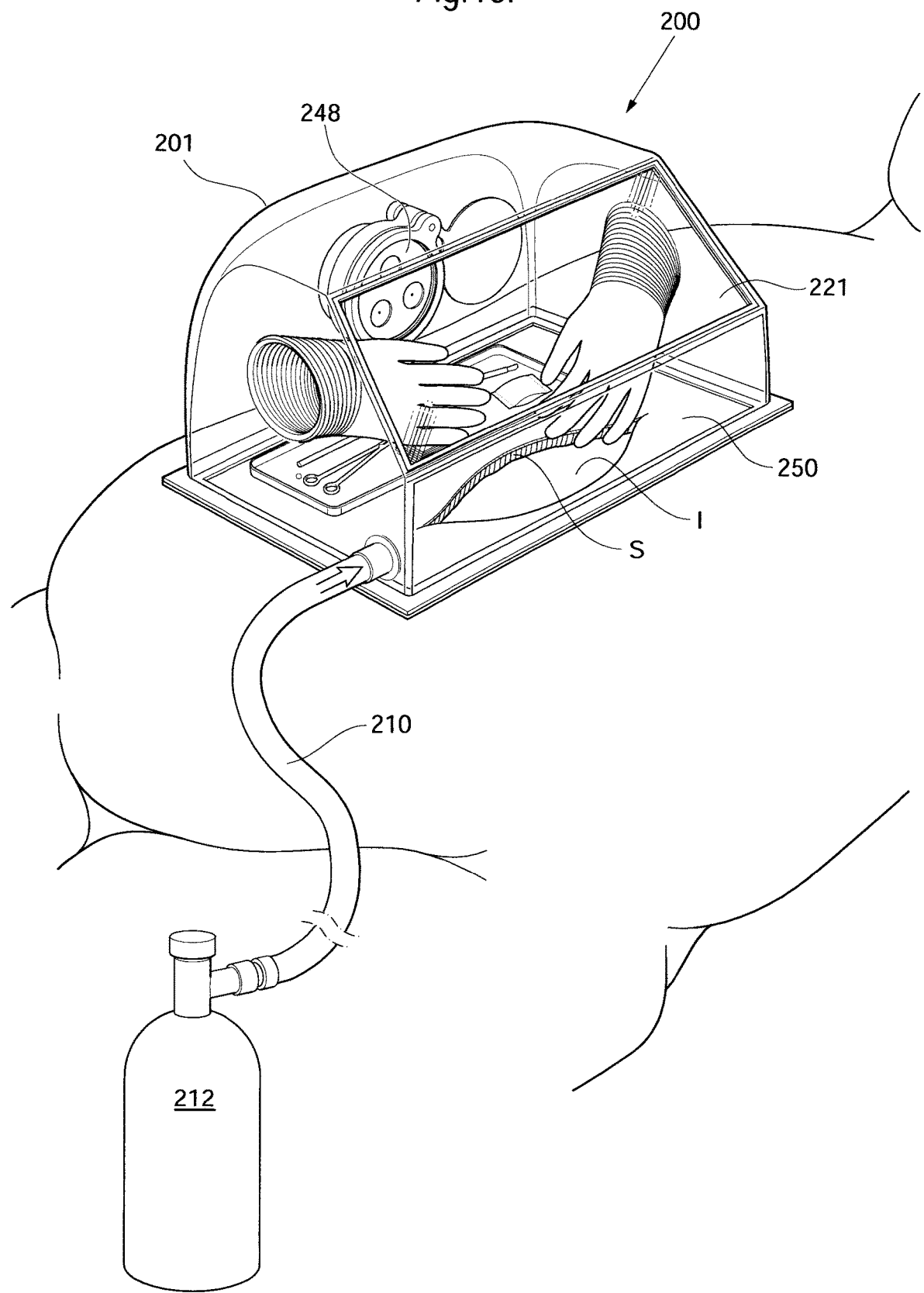
FIG. 19r shows the medical device when applied to the abdomen of a patient.

FIG. 19r shows an embodiment of the medical device 200 when the medical device 200 is placed in contact with the skin of the patient prior to the beginning of the operation and the entire portion of the wall 201 contacting the skin of the patient comprises an adhesive surface 250, such that the incision I in the patient runs through the wall 201 and further through the skin S of the patient. This reduces the risk that infectious objects can be transferred from the skin S of the patient to the incision I in the patient if the skin S of the patient is not adequately disinfected.

FIG. 19s shows a section of the medical device 200 showing the coupling 280 integrated in the wall 201 in further detail. The coupling 280 enables the changing of objects from for examples a wall multi port 248, to insets 242a; 242b; 242c in form of surgical gloves 202, a device or instrument mount 220 or the airlock sluice shown in FIG. 19t. The coupling 280 comprises a valve member 238 for closing the hole 297 in the coupling 280 when objects should be exchanged such that the sealed environment in the medical device 200 remains closed. The device or instrument mount 220 could for example be adapted to hold surgical instruments and/or implants or parts of implants. The medical device is according to this embodiment adapted to be fixated to the skin S of the patient by a large portion of the wall 201 of the medical device comprising an adhesive surface 250.

FIG. 19t shows the shows a section of the medical device 200 showing the coupling 280 integrated in the wall 201 in further detail when an airlock sluice 218 for transferring objects between the chamber and the ambient environment is being provided. According to the embodiment shown in FIG. 19t the airlock sluice 218 comprises a first valve member 238a separating the airlock sluice 218 from the ambient environment, and a second valve 238b separating the airlock sluice 218 from the chamber. The airlock sluice 218 is provided between the first 238a and second 238b valve and could for example be used for passing an implant into the chamber, or for passing a specimen or sample out of the chamber.

Figure 20:
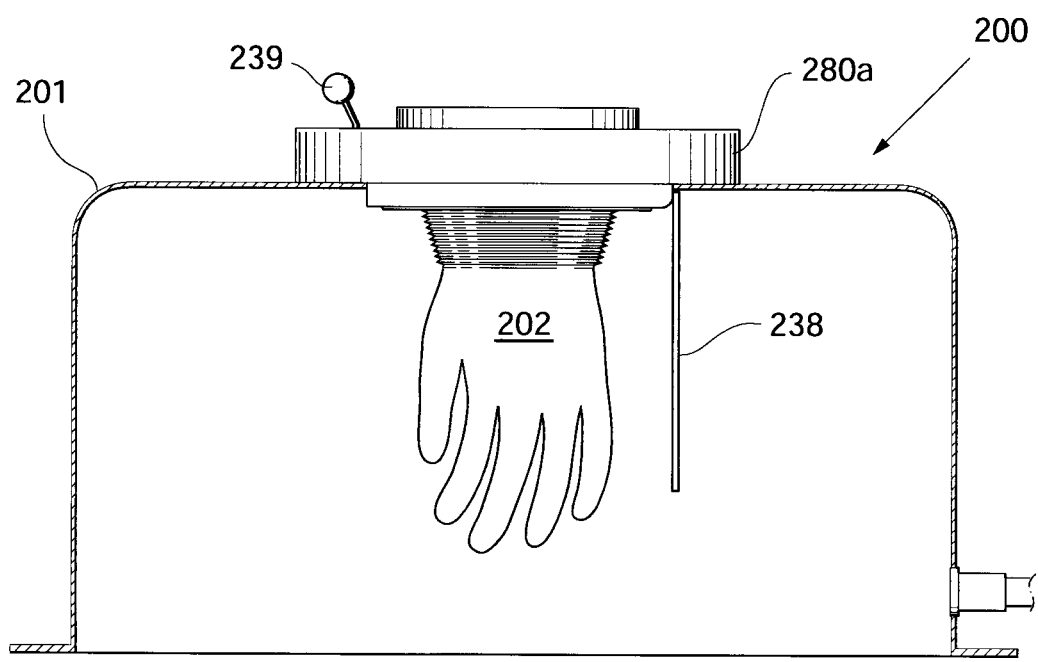
FIGS. 20-23b shows embodiments of the medical device, in section.

FIG. 20 shows an embodiment similar to the embodiment disclosed with reference to FIG. 16a but without the lower coupling. The upper coupling 280a is for example used for manual manipulation and preparation within the medical device 200, such that could be needed for preparing or changing an instrument or preparing an implant for implantation. The manual manipulation is performed by means of the inset comprising the glove 202 fixated by the coupling 280a.

Figure 21:
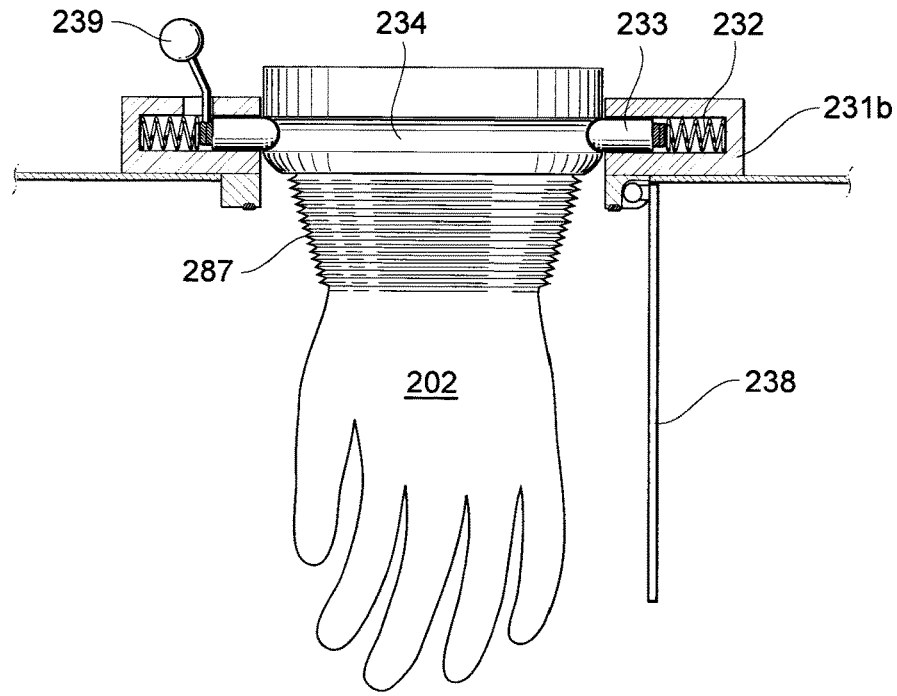

FIG. 21 shows the upper coupling 280a in further detail when an inset 242 in the form of a surgical glove 202 is fixated to the upper coupling 280a, however the surgical glove 202 could be exchanged for example for a surgical port or a device or instrument mount, as further disclosed with reference to other embodiments herein. The coupling 280a comprises a releasing lever 239 for releasing the ring shaped object latched in the coupling 280a. The lever 239 is connected to protruding members 233 which are spring loaded 232 from the rear in order to secure the recess 234 of the ring shaped object. The surgical glove 202 disclosed enables manual manipulation within the body of the patient. The coupling 280 further comprises a valve member 238 adapted to close the opening in the upper coupling 280a, when the upper coupling 280a is not in use.

Figure 22:
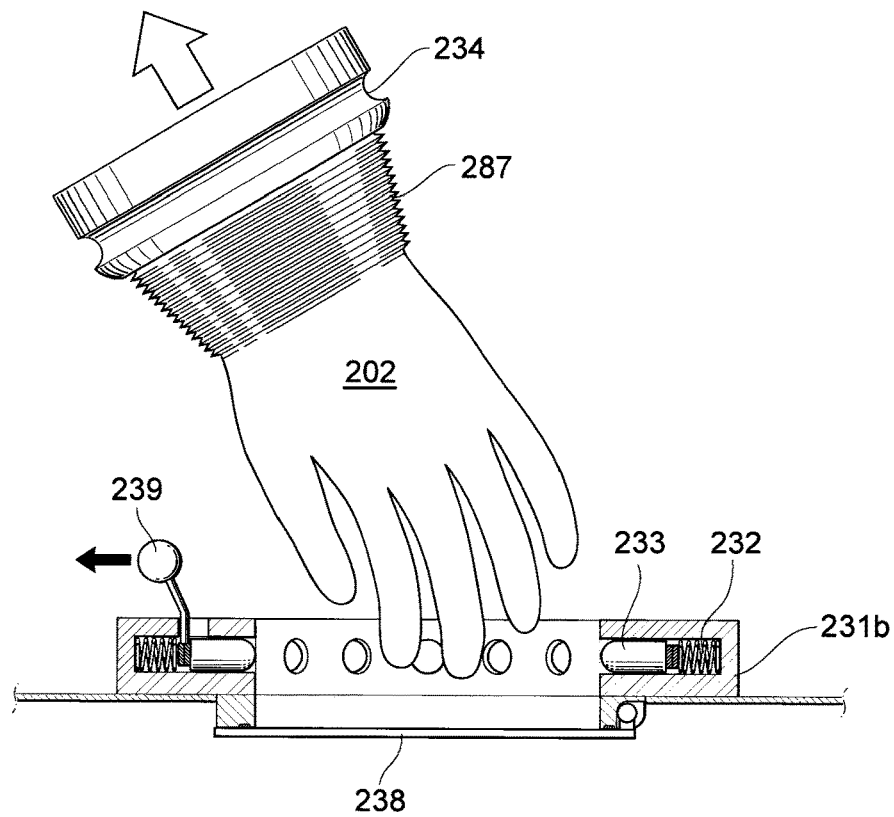

FIG. 22 shows the step of removing the surgical glove from the coupling 280a, which is necessary when switching for example from a surgical glove 202 to an endoscopic wall port. Being able to quickly switch from an endoscopic system to a hand access or manual manipulation system could be of major importance if complications arise during the procedure and could remove the need for a traditional conversion from endoscopic to open surgery, a conversion which inevitably causes problems increasing the risk of complications and/or postoperative care.

Figure 23A:
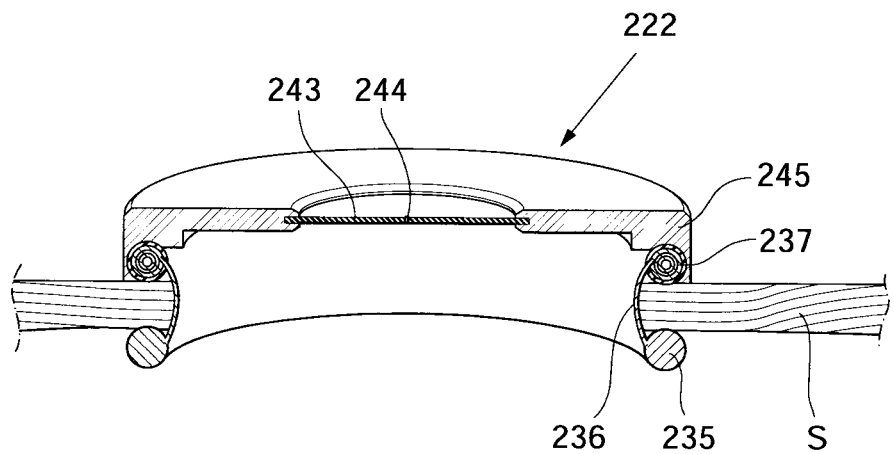
Figure 23B:
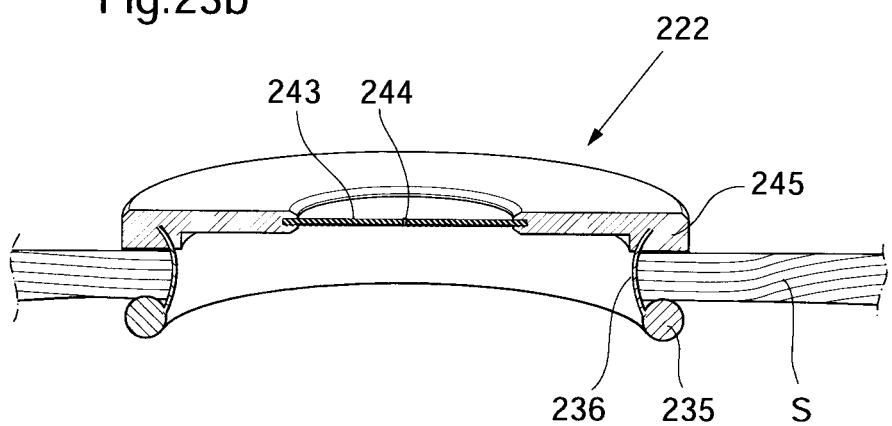

FIG. 23a shows a self sealing body port 222 in a close-up, in section. The self sealing body port 222 could be connected to a coupling, for example as disclosed as 280a with reference to FIGS. 26b and 26c or could be fixated to a retractor, as shown in FIGS. 23a and 23b. The self sealing body port 222 comprises a self sealing membrane 243 fixated to a rigid part 245 of the self sealing body port 222. The self sealing membrane 243 have a small self sealing hole 244 centrally in the membrane 243. The self sealing membrane 243 is for example made from a gel-type material being elastic enough to enable a deformation large enough for a person's hand to pass through the small self sealing hole 244 while still contracting enough to create an airtight seal between the sealed environment and the outside environment. The body port 222 is fixable to a retractor comprising one intra body ring 235 adapted to be positioned on the inside of the patients skin, and one ring 237 adapted to be placed on the outside of the patients skin S. Between the intra body ring 235 and the ring 237 adapted to be placed on the outside of the patients skin S a connecting member 236 in form of a retractor membrane 236 is positioned between the intra body ring 235 and the outer ring 237 and is adapted to exert a pressure of the cut surfaces of the incision for retracting the skin S and thereby keeping the incision open. The retractor membrane 236 is preferably made from a resilient of elastic polymer material. The outer ring comprises an integrated roll up system which could be a spring loaded roll up system adapted to create a suitable pressure on retractor membrane 236 for keeping the incision open.

FIG. 23b shows an alternative embodiment of the self sealing body port 222, with the difference that the retractor membrane 236 is made from a material elastic enough such that one end of the retractor membrane 236 could be fixedly fixated to the rigid part 245 of the port 222.

Figure 24:
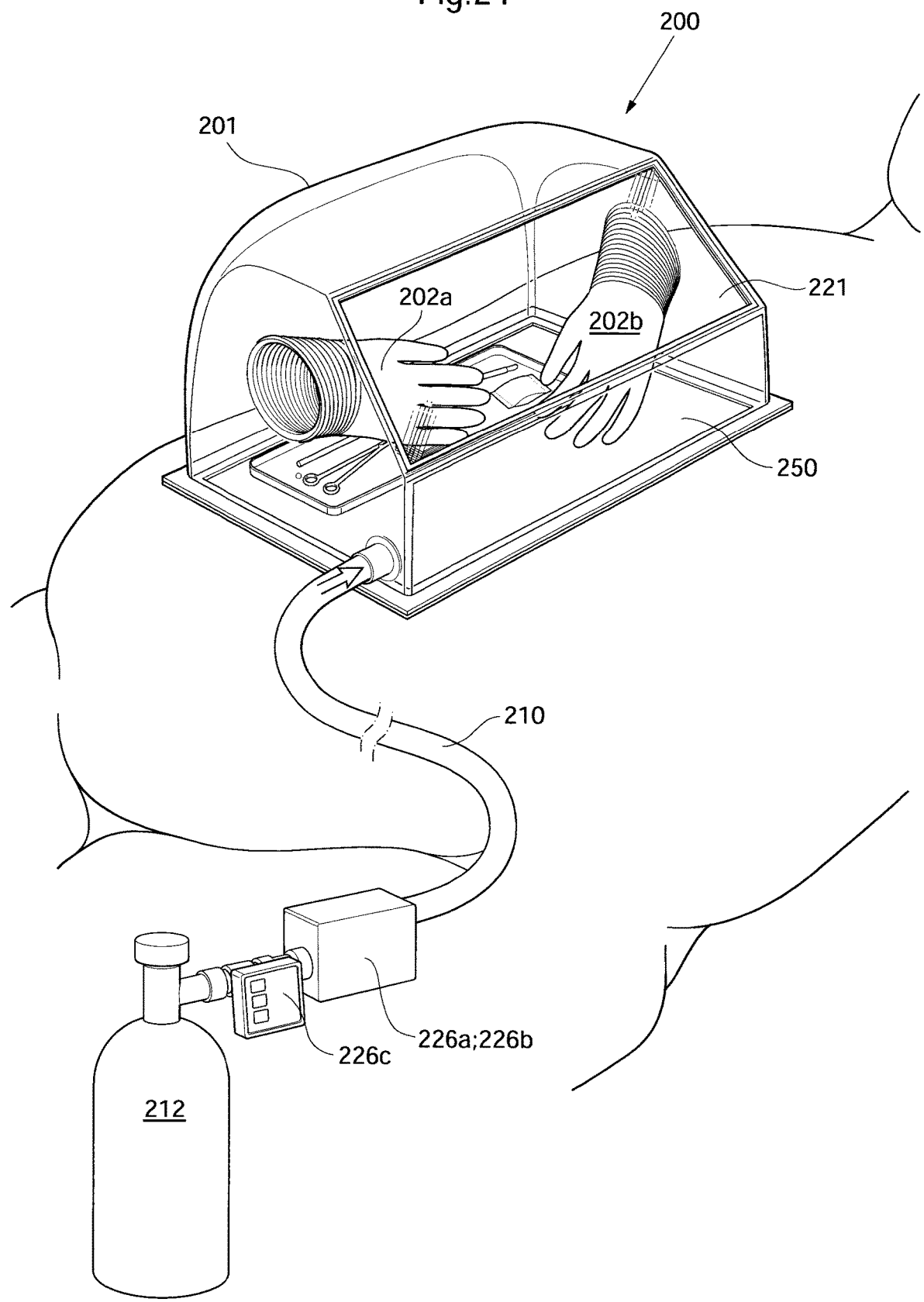
FIG. 24 shows an embodiment of a medical device, when fixated to the abdomen of a patient.

FIG. 24 shows an embodiment of the medical device 200 when positioned on the abdomen of a patient. The medical device comprises insets in the shape of integrated gloves 202a; 202b in the wall 201. The medical device 200 shown in FIG. 24 further comprises a sterilizing unit 226a adapted to sterilize the gaseous fluid entering the medical device 200. In the embodiment disclosed herein, the gaseous fluid entering the medical device 200 originates from a pressurized tank 212 and could be pre-sterilized, however, in other embodiments, it is conceivable that the gaseous fluid is the surrounding air which is pressurized (such as further disclosed with reference to FIG. 3e). In the embodiments where the surrounding air is used to inflate the medical device 200 and constitute the operating environment this air needs to be properly sterilized. The medical device 200 further comprises a tempering unit 226c which could be provided to heat or cool the gaseous fluid inflating the medical device 200. In cases when the ambient environment is cold the tempering unit 226c could be used to raise the temperature of the sealed environment to provide beneficial operating circumstances both for the patient and for the surgeon. In cases when the surrounding environment is hot, the tempering part 226c of the system could be used to lower the temperature of the sealed environment both to provide beneficial operating circumstances, both for the patient and for the surgeon, and for providing a temperature inhibiting bacterial and viral infections. The tempering unit 226c could comprise a temperature regulating device for setting the required temperature.

Figure 25:
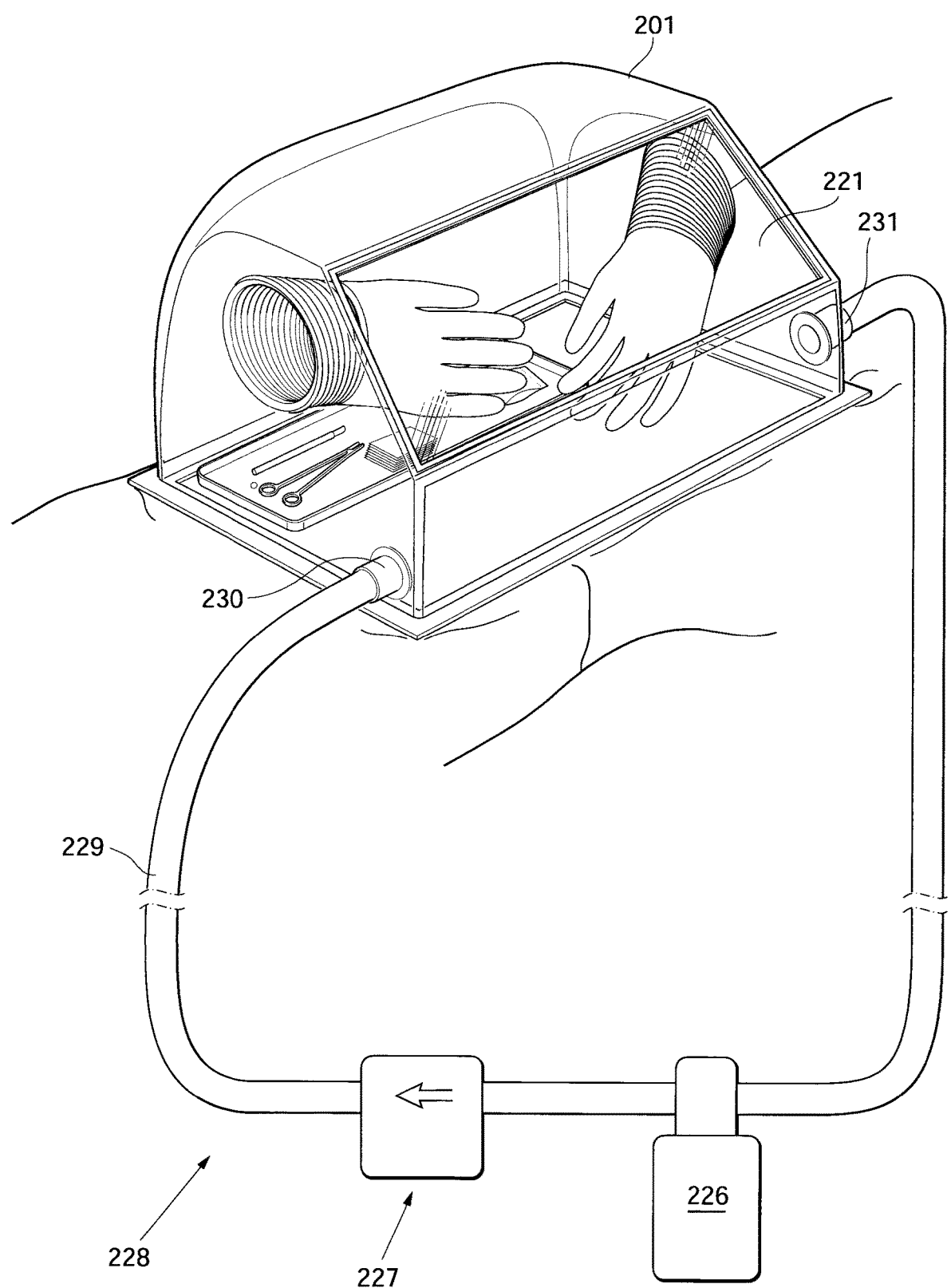
FIG. 25 shows an embodiment of the medical device, when fixated to the abdomen of a patient.

FIG. 25 shows a medical device similar to the embodiment disclosed in FIG. 24 but further comprising a system 228 for circulating a fluid through the sealed environment of the medical device. The system comprises a fluid conduit 229 connected at an inlet 230 placed in the wall 201 for supplying fluid to the sealed environment, and an outlet 231 for draining the fluid from the sealed environment. The fluid is circled by means of a pumping unit 227 and is circled via a sterilizing/filtering/tempering unit 226 adapted to remove impurities and sterilize the fluid. In embodiments where the fluid is a gaseous fluid, the filtering unit is adapted to remove fluid particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 26A:
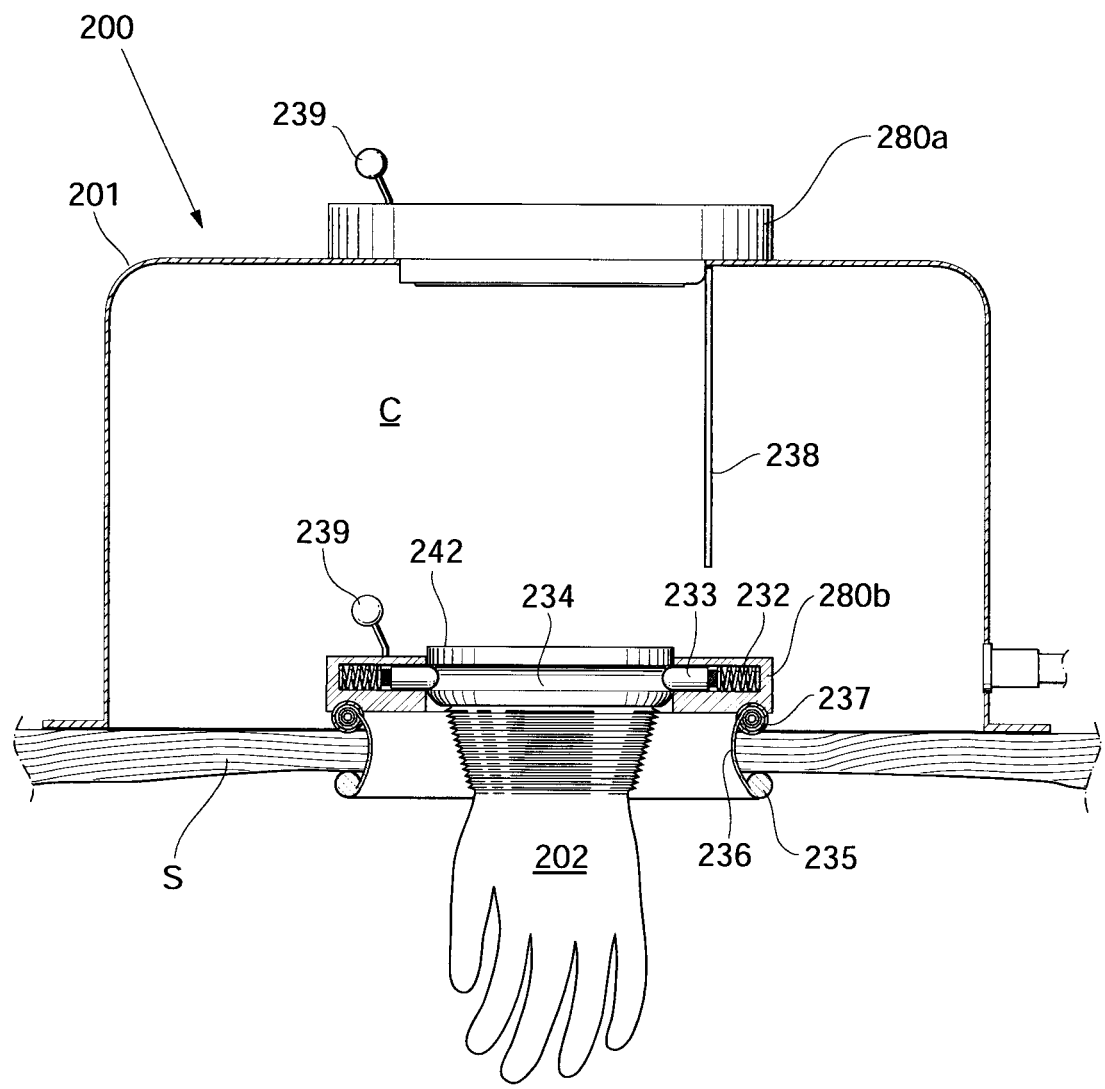
FIG. 26a shows an embodiment of the medical device, in section.

FIG. 26a comprises a medical device comprising a non-collapsible (not shown) window, in accordance with FIG. 17a, shown in section. The medical device 200 comprises a wall 201 separating the sealed environment S within the medical device from the outside environment. The wall 201 is adapted to be fixated to the skin S of the patient, by means of an adhesive or by means of a difference in pressure between the outside of the chamber C and the inside thereof. The medical device further comprises an upper 280a and a lower 280b coupling for fixating ring shaped objects which for example could be insets or ports, where insets for example could be surgical gloves 202, or device or instrument mounts and ports could be endoscopic ports or hand access ports, such as the self sealing port disclosed with reference to FIGS. 4a and 4b. The couplings 280a; 280b comprises releasing levers 239 for releasing the objects. The lever 239 is connected to protruding members 233 which are spring loaded 232 from the rear in order to secure the recess 234 of the ring shaped object. In the embodiment disclosed in FIG. 26a, the inset 242 fixated to the lower coupling 280b is a surgical glove 202 enabling manual manipulation within the body of the patient. The medical device shown in FIG. 26a further comprises a valve member 238 adapted to close the opening in the upper coupling 280a, when the upper coupling 280a is not in use. The upper coupling 280a is for example used for manual manipulation and preparation within the medical device 200, such that could be needed for preparing or changing an instrument or preparing an implant for implantation. The lower coupling 280b is for example used for endoscopic manipulation within the body of the patient, or manual manipulation for e.g. removing a specimen or positioning an implant.

Figure 26B:
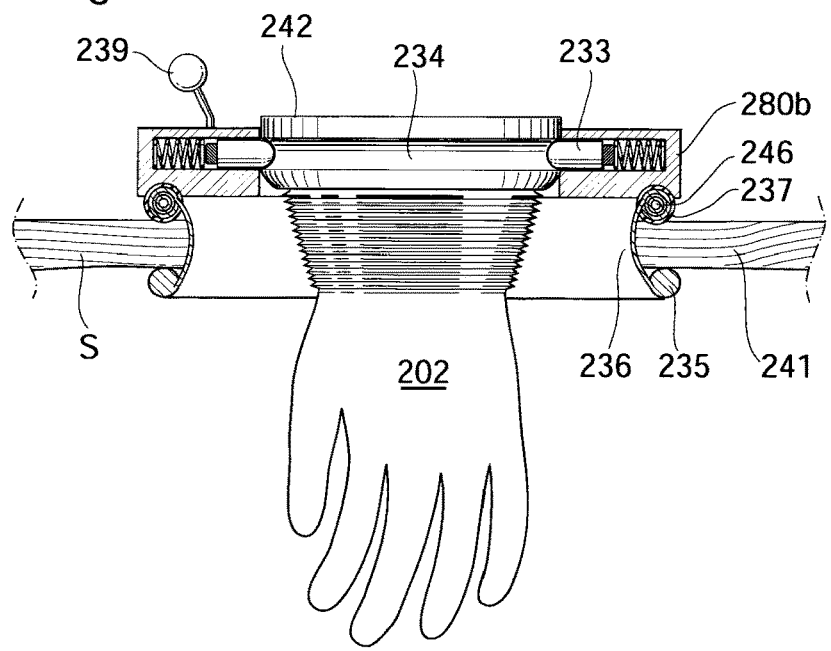
FIG. 26b shows an embodiment of the coupling, in section.

FIG. 26b shows the lower coupling 280b in further detail when an inset 242 in the form of a surgical glove 202 is fixated to the lower coupling 280b. The retractor system comprising the intra body ring 235 and the outer ring 237 adapted to be placed on the outside of the patients skin S further comprises a retractor membrane 236 positioned such that it exerts a pressure on the cut surfaces of the incision for retracting the skin and thereby keeping the incision open. The retractor membrane 236 could be rolled by a roll up system 246 inside of the ring 237 adapted to be placed on the outside of the patients skin S for tightening the retractor membrane 236 such that the incision is kept open.

Figure 26C:
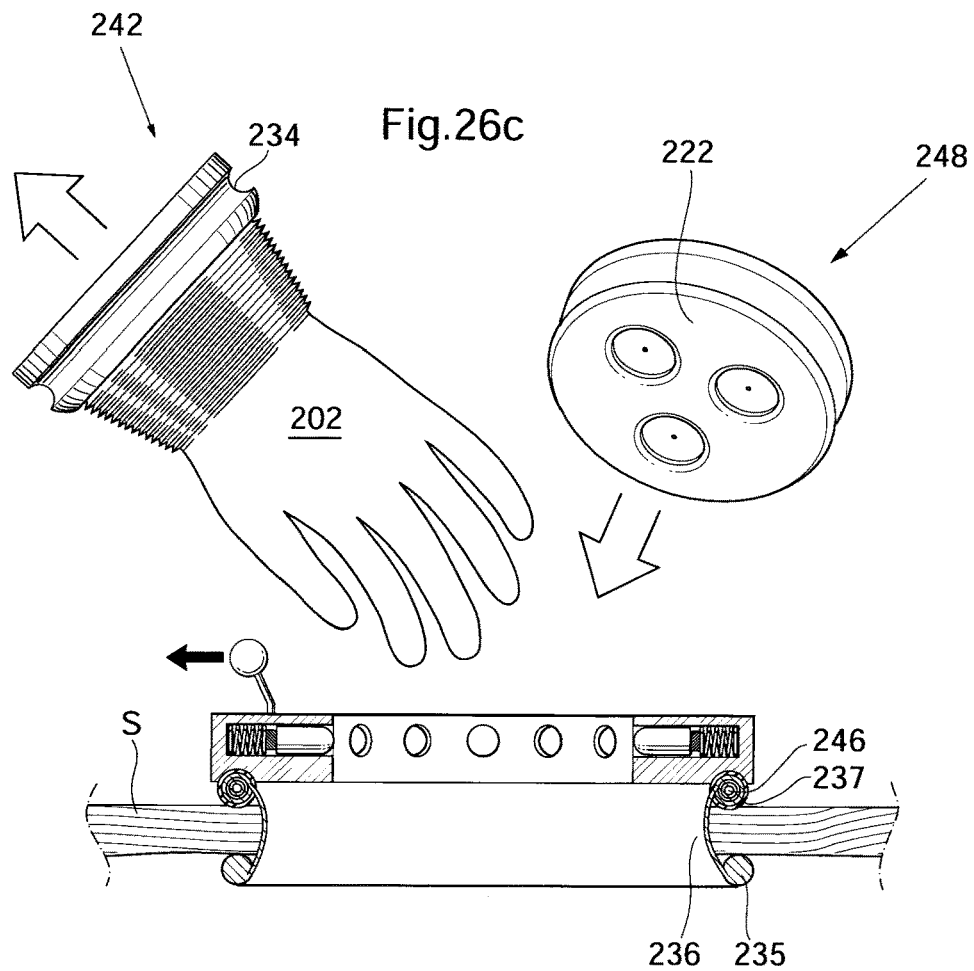
FIG. 26c shows an embodiment of the coupling, in section, when objects are being exchanged.

FIG. 26c shows the changing of objects in the coupling 280b from an inset 242 comprising a surgical glove 202, to a body port 222 in the form of a body multi-port 248 comprising three endoscopic ports 247. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the endoscopic body ports 222 and insets 242 comprising surgical gloves 202 could additionally be exchanged for device or instruments mounts, for example for holding endoscopic instruments or implants.

Figure 27:
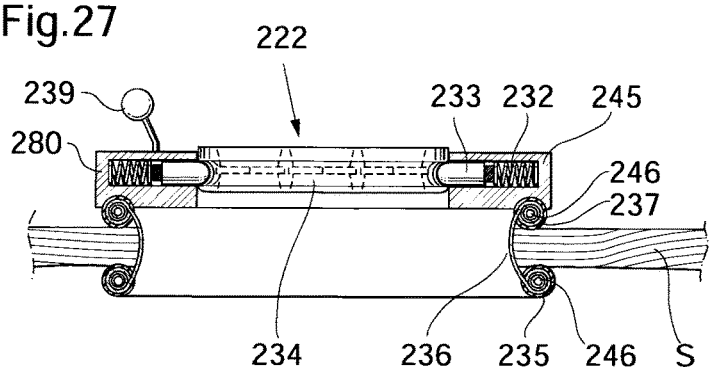
FIGS. 27, 28a and 28b shows an embodiment of a self sealing port, in section.

FIG. 27 shows an embodiment of a detachable port arrangement which could be positioned in the chamber C of the medical device disclosed with reference to FIG. 17. The port arrangement includes an intra body ring 235 adapted to be placed at the inside of the patients skin S around an incision, and an outer ring 237 adapted to be placed on the outside of the patients skin 241 around the incision. Between the intra body ring 235 and outer ring 237, a connecting member 236 in form of an annular retractor membrane 236 is positioned adapted to exert a pressure on the skin S or human tissue at the incision to seal between the rings 235; 237 and the skin S or human tissue and additionally for retracting the skin S and thereby keep the incision open. The retractor membrane 236 is preferably made from a resilient or elastic polymer material. The inner 235 and outer rings 237 comprise integrated roll up systems 246, which may be spring loaded and adapted to create a suitable pressure on retractor membrane 236 to keep the incision open.

The port arrangement shown in FIG. 27 also includes a coupling 280 having a rigid annular seating 245 attached to the outer ring 237, spring loaded protruding members 233 arranged in radial bores in the seating 245 and a hand lever 239 connected to the protruding members 233 to enable retraction thereof against the action of springs 232. The port arrangement further includes a self sealing body port 222 held by the coupling 280. The body port 222 comprises a disc-shaped self sealing membrane 243, further shown in FIG. 28a, fixated to a rigid seating 245 having an outer circumferential recess 234 that receives the protruding members 233 of the coupling 280. The self sealing membrane 243 has a small self sealing hole 244, FIG. 28a, centrally in the membrane 243. For example, the self sealing membrane 243 may be made from a gel-type material being elastic enough to enable a deformation large enough for a person's hand to pass through the small self sealing hole 244 while still contracting enough to create an airtight seal between the chamber and the ambient environment.

The coupling described above enables quick exchange of the body port 222. Thus, the surgeon may release the body port 222 from the port arrangement by simply pulling the hand lever 239 so that the protruding members 233 disengage from the recess 234 of the body port 222, whereby the body port 222 can be removed.

Figure 28A:
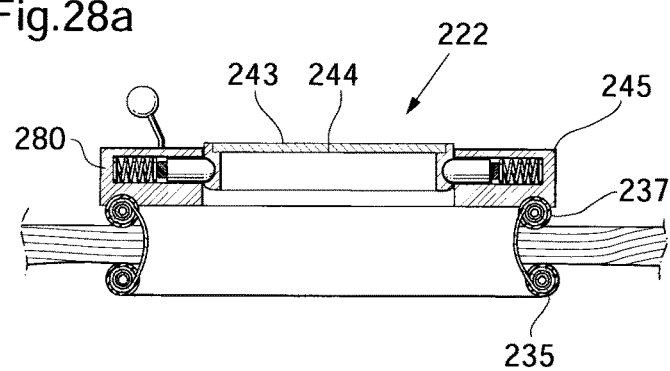

FIG. 28a is a cross-sectional view of the port arrangement shown in FIG. 27, to more clearly illustrate the body port 222 with its self sealing membrane 243 and small hole 244.

Figure 28B:
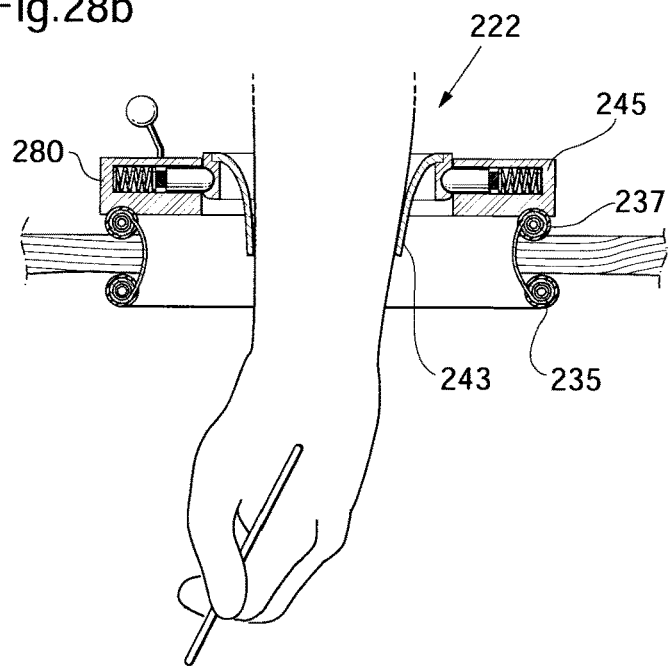

FIG. 28b shows the self sealing body port 222 when the hand of a surgeon is placed through the hole 244 in the membrane 243 and thus enabling manual manipulation within the body of the patient.

Figure 28C:
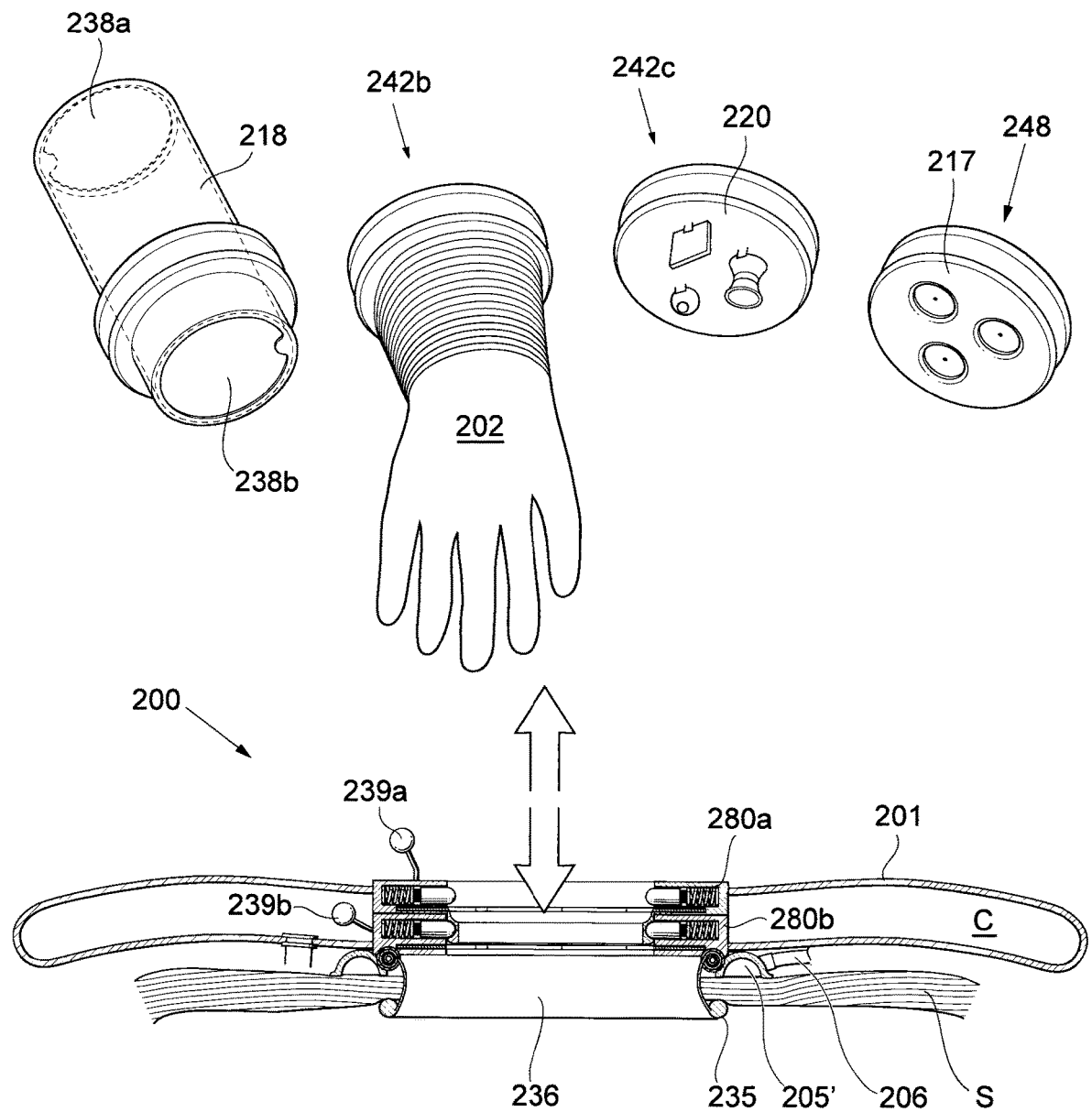
FIGS. 28c-28d shows embodiments of the medical device, in section.

FIG. 28c shows the medical device 200 adapted to be at least partially placed in an incision cut in a patient's body. The medical device 200 comprises a first 280a and second 280b coupling adapted be interconnected to form an interconnected coupling. The second lower coupling 280b is adapted to be disconnected from the first coupling 280a, and the first upper coupling 280a is connected to a first portion of a flexible wall 201, and the second coupling 280b is connected to a second portion of the flexible wall 201. The flexible wall 201 forms a chamber C in which a sealed environment can be maintained, the chamber C is heavily enlarged when the first coupling 280a is disengaged from the second coupling 280b, thus creating operating space within the chamber C enclosed by the wall 201. The first and second couplings 280a; 280b comprise latching systems for locking an inset 242 or wall port 217 (which when locked in its lower position functions as a body port). The inset 242 may for example be an inset 242b comprising a glove 202 for manual manipulation within the body of the patient, or within the enclosed chamber C, an inset 242c comprising a device or instrument mount 220 for holding instruments or medical devices within the chamber C. Alternatively the insets 242b; 242c can be replaced by an airlock sluice 218 with a first 238a and second 238b valve member or a port 217, such as the multiport 248 shown in FIG. 28c.

In the embodiment shown in FIG. 28c the medical device is fixated to the body of the patient by means of a vacuum fixating member 205' connected to a conduit 206, which in turn is connected to a vacuum source. Furthermore, the medical device in FIG. 28c comprises a second sealing function having a first sealing member 235 in form of an intra body ring 235 adapted to be positioned at the inside of the patient's skin S around an incision to be performed in the skin and a second sealing member 237 in form of an outer ring adapted to be positioned at the outside of the patient's skin S around the incision, and a spring-loaded or elastic connecting member 236 sealingly interconnecting the first 235 and second 237 sealing members. The spring-loaded or elastic connecting member 236 seals between at least one of the port and the skin of the patient, and the first sealing member and tissue of the patient.

Figure 28D:
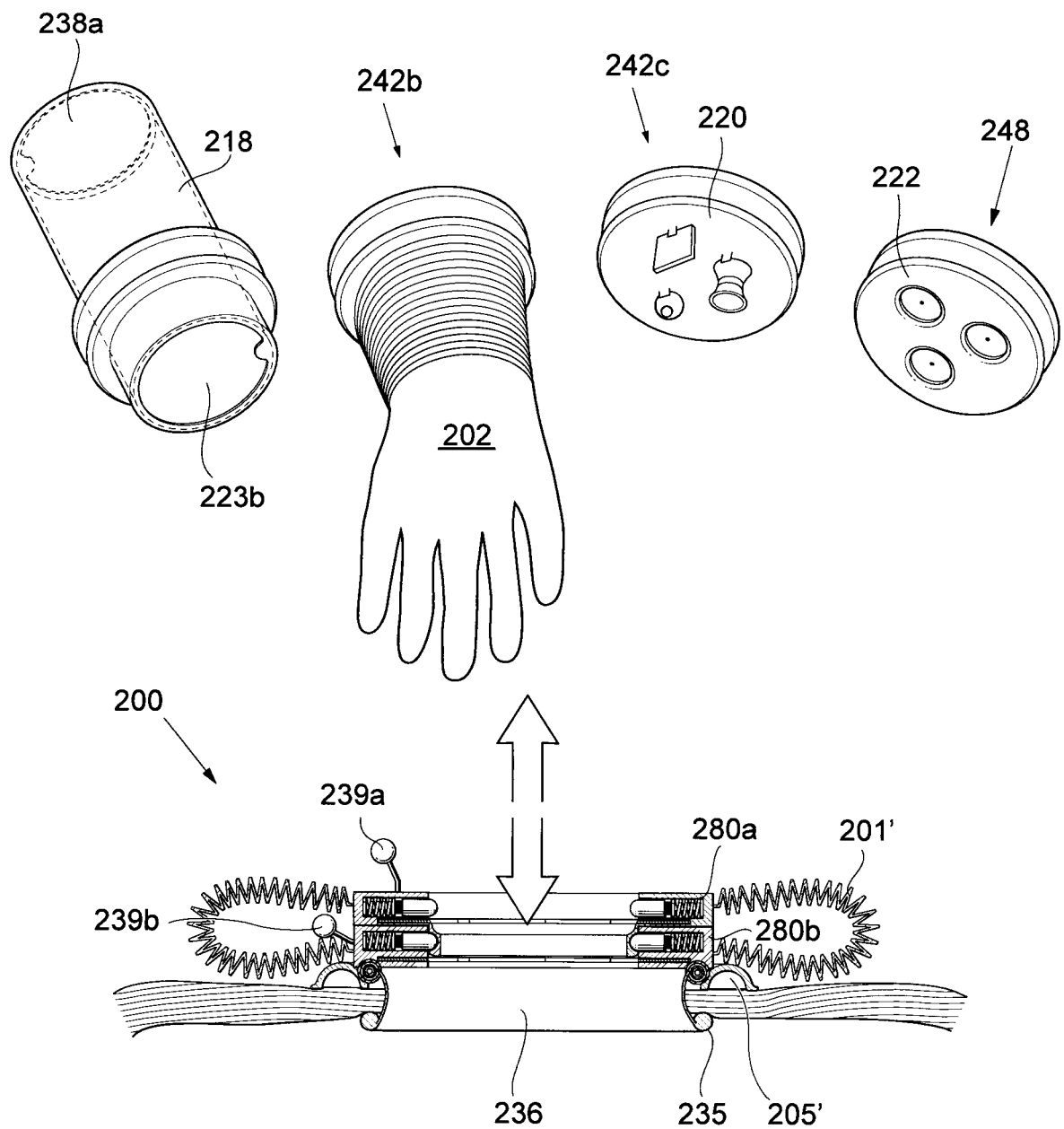

FIG. 28d shows the port in an embodiment very similar to the embodiment shown in FIG. 28c but with the difference that the wall 201' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

FIG. 28e shows the medical device in an embodiment when the wall 201 of the medical device 200 is inflatable by the fluid connection between a cavity in the patient's body and the chamber C of the medical device 200 by the incision I in the skin S of the patient, In FIGS. 28*e* and 28*f*, the medical device 200 is in its inflated state. When the chamber C is deflated it has a first volume i.e. when the first 280*a* and second 280*b* couplings are interconnected, and when the chamber C is inflated and the first coupling 280*a* is disconnected from the second coupling 280*b* it has a second volume, the second volume is larger than the first volume. According to the embodiment shown in FIG. 28*e*, the second volume is larger than 500 000 mm3 such that the surgeon can perform a step of the operation in the chamber C, such as placing a specimen in the pouch 282. According to the embodiment shown in FIG. 28*e*, the chamber C is formed by the inflatable wall 201 and is adapted to hold a pressure exceeding atmospheric pressure, such as the pressure used to expand a cavity in the patient's body during laparoscopic surgery.

According to the embodiment shown in FIG. 28*e*-28*k* the chamber C further comprises a pouch 282 for holding a specimen 281 removed from within the body of the patient not to contaminate any other part of the body and create the possibility of delaying the removal of the specimen until the procedure is concluded. The pouch 282 may be a pouch 282 which could be closed for creating a pouch-chamber within the chamber for isolating the removed specimen 281 from the rest of the chamber C of the medical device 200.

In FIG. 28*e* a state is illustrated in which the incision I in the patient's skin is being created by the surgeon by means of a glove inset 202 latched to the upper coupling 280*a*. The surgical port is fixated and sealed by means of the vacuum sealing member 205' since the seal that is provided partially within the patient's body cannot be mounted until the cut in the patient's skin is concluded. The two different seals disclosed could in some embodiments be replaced by only one of the seals, or by a different seal, such as the adhesive of pressure seals disclosed in other portions herein.

FIG. 28*f* shows the medical device, when the second sealing 235, 236, 237 have been placed in the incision cut in the patient's skin S. The wall 201 enclosing the chamber C is elastic or flexible which enables the surgeon move the upper coupling 280*a* in relation to the lower coupling 280*b* for getting better access to different angles within the patient's body, for example for removing a specimen 281.

Figure 28G:
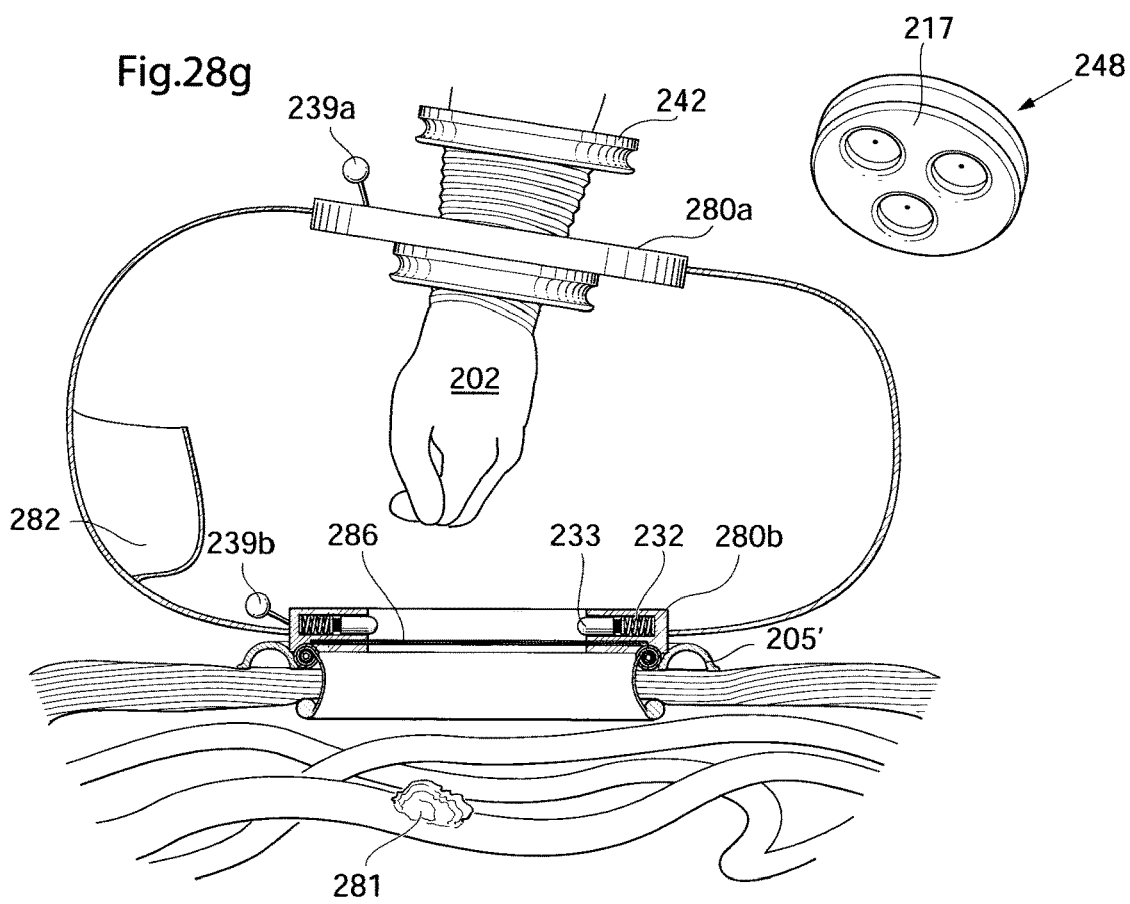

FIG. 28*g* shows the medical device when the inset 242 comprising a glove 202 is removed and replaced by a wall port 217 multi-port inset 248 comprising a plurality of ports 247. The multi-port inset may be used for manipulating objects within the chamber of the inflated medical device using surgical instruments, or within the body of the human patient, when the first and second parts are connected (as shown in FIG. 28*h*).

Figure 28H:
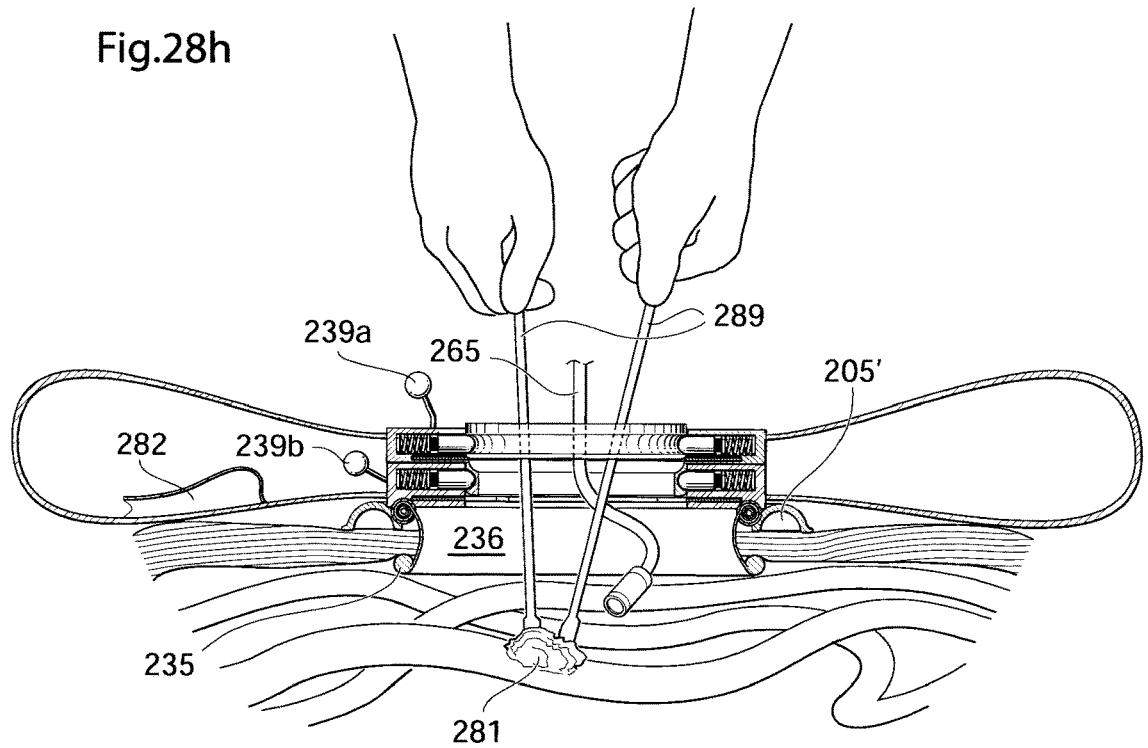

FIG. 28*h* shows the medical device when the first and second couplings 280*a*; 280*b* are connected such that surgical instruments 289 can be used for manipulating within the body of the patient. An endoscopic camera 265 may be provided in the port for enabling visual inspection of the cavity within the patient's body. The process of cutting away a specimen 281 from the intestines of a patient in a laparoscopic way is shown in FIG. 28*h*.

Figure 28I:
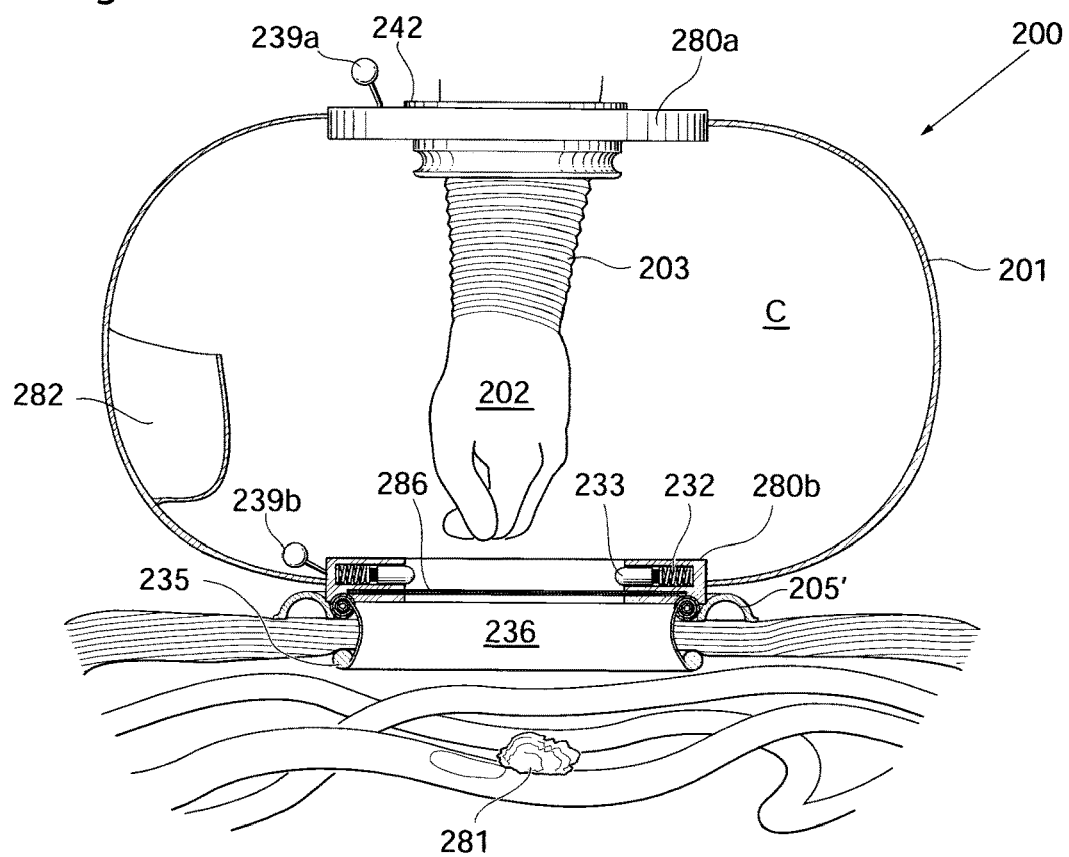

In FIG. 28*i*, the inset 242 comprising the glove 202 has been fixated to upper coupling 280*a* to enable the surgeon to operate within the cavity of the patient's body and within the chamber C enclosed by the wall 201 of the medical device 200. By the inset 242 comprising the glove 202 comprising a pleated portion 203, the surgeon is thereby able to reach into the cavity of the patient for removing the specimen 281 dissected from the intestines in prior steps.

Figure 28J:
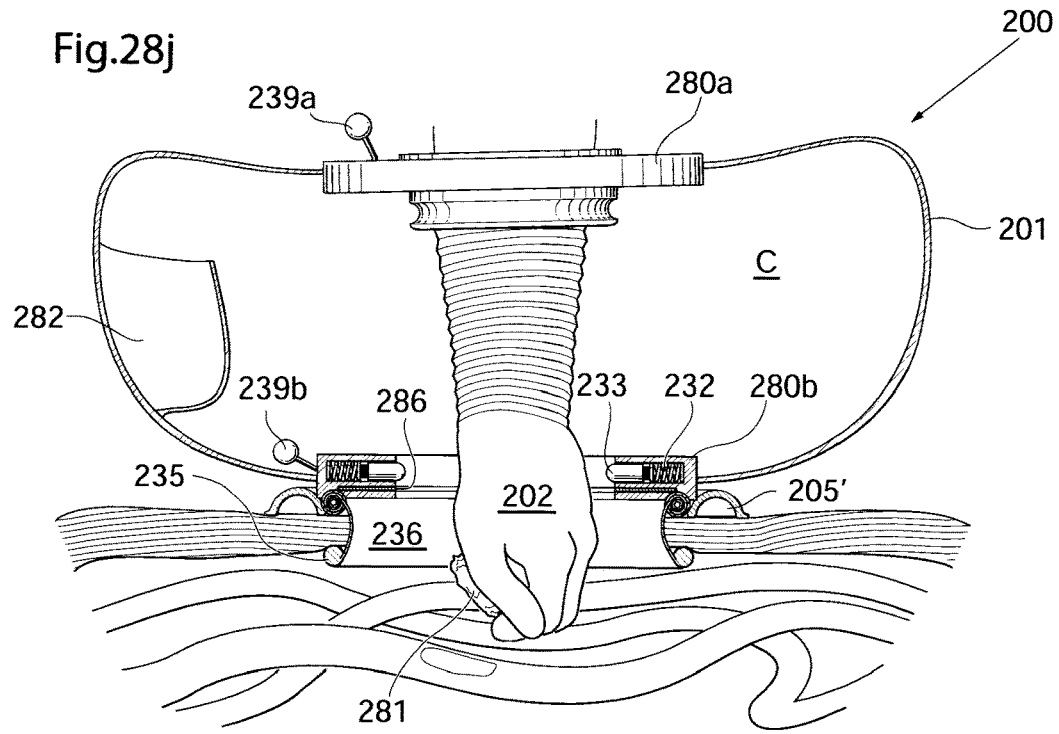

FIG. 28*j* shows that the wall of the medical device 200 is collapsible such that the inset 242 comprising the glove 202 can be moved with relation to the lower coupling 280*b*, which gives the surgeon further freedom when removing the loose specimen 281 from the intestines of the patient. The lower coupling 280*b* shown in FIGS. 28*i* and 28*j* further comprises an iris valve 286 such that the lower coupling 280*b* can be closed separating the chamber C of the medical device from the cavity of the patient.

Figure 28K:
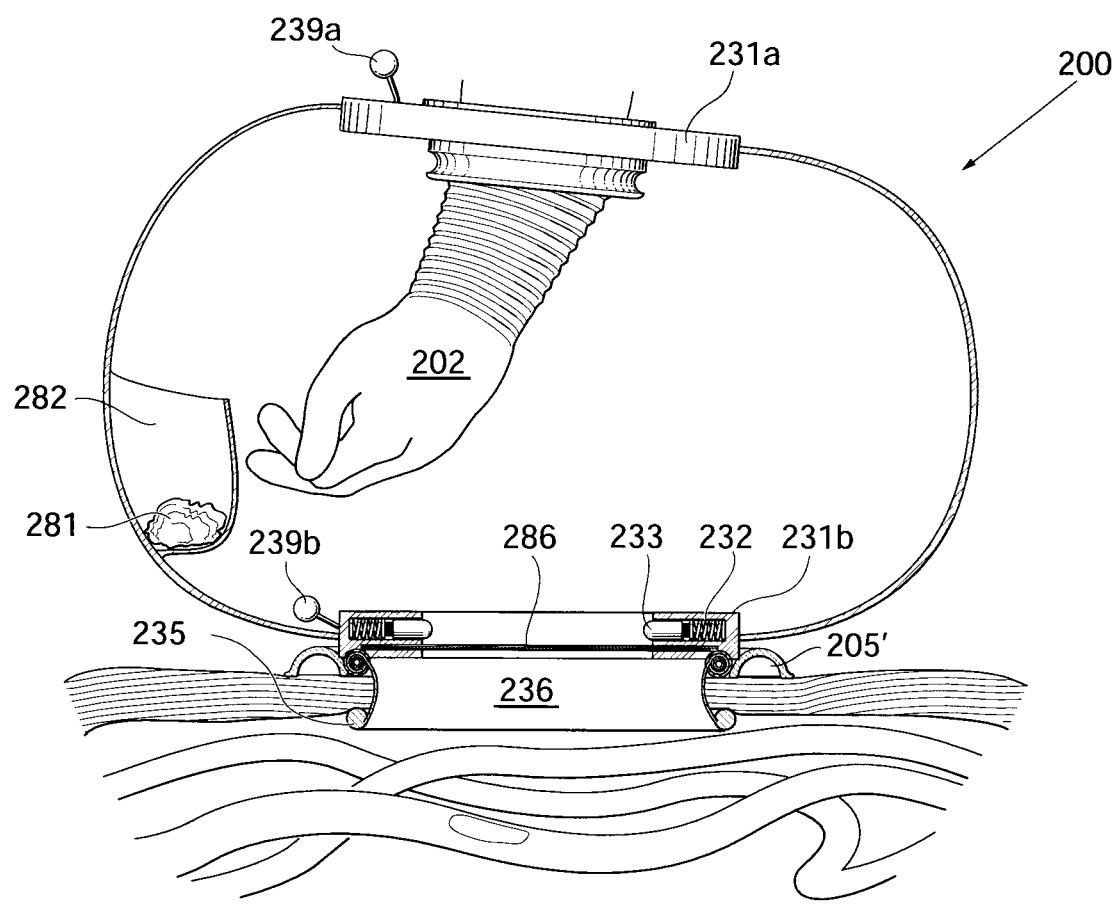

FIG. 28*k* shows the step of placing the removed specimen 281 in the pouch 282 such that the specimen 281 does not contaminate any other part of the body. The pouch 282 may be a pouch 282 which could be closed for creating a pouch-chamber within the chamber C of the medical device 200 for isolating the removed specimen 281 within the chamber C.

Figure 28L:
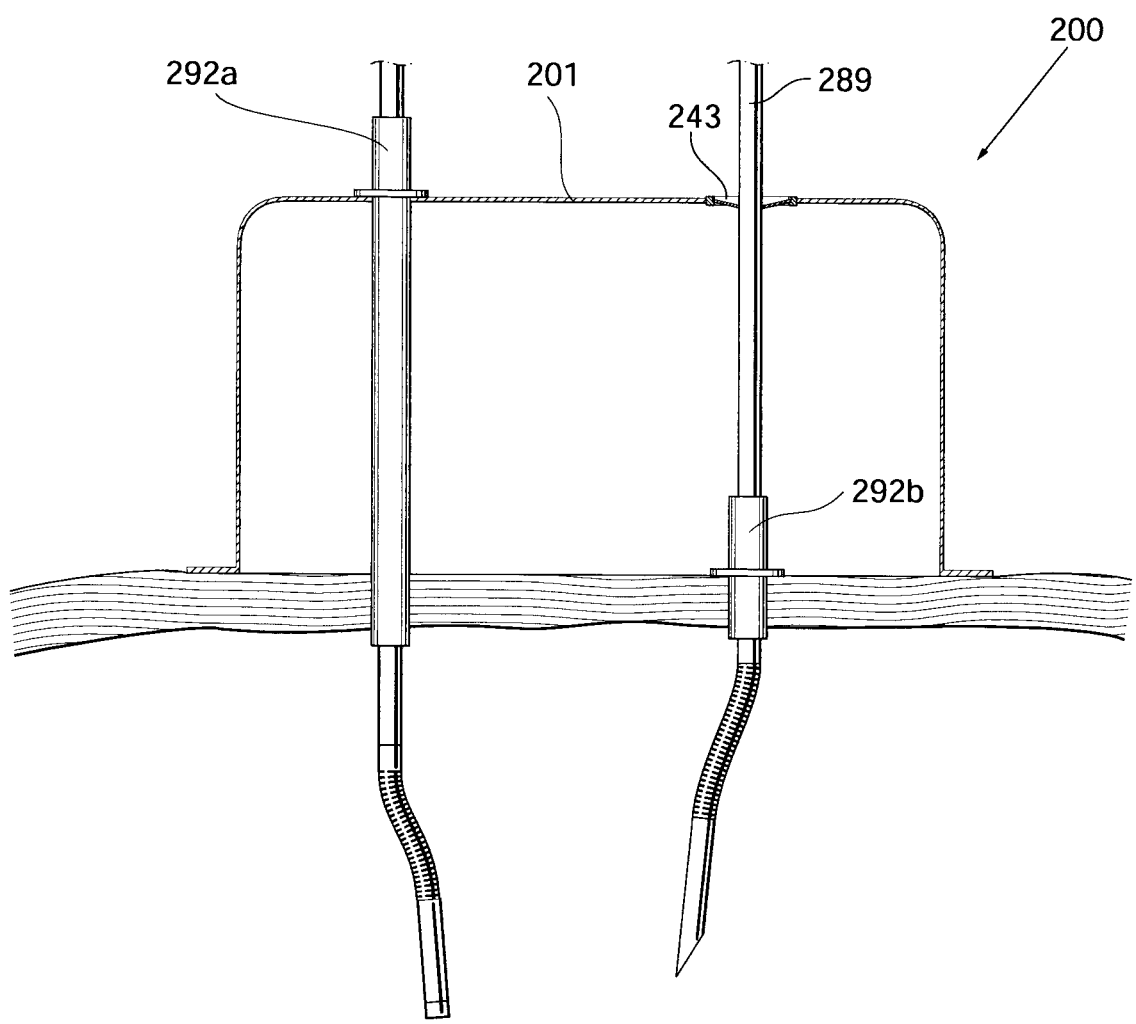
FIGS. 28l shows an embodiment of the medical device, in section.

FIG. 28*l* shows examples of how trocars may be used in combination with the medical device according to any of the embodiments shown in FIGS. 17-28*k*. The medical device comprises a wall 201 placed on the patient's skin and thereby enclosing a chamber for creating a sealed environment. The medical device comprises two trocars 292*a*; 292*b*, one 292*a* traveling through both the wall 201 of the medical device 200 and the skin S of the patient and thus enabling for example an endoscopic camera 265 to be inserted into the patient through both the wall 201 of the medical device and the skin S of the patient through one single trocar 292*a*. The other trocar 292*b* being placed inside the chamber C enables an endoscopic instrument 289 to be inserted through the skin S of the patient. The endoscopic instrument is in this embodiment inserted into the chamber C enclosed by the wall 201 through a self sealing membrane 243 in the wall 201 sealing against the instrument 289.

FIG. 28*m* shows how the medical device shown in FIGS. 17-28 may be used. The medical device 200 comprises a glove 202 integrated in the wall 201 and a camera 265 placed in the skin outside of the medical device 200. The medical device 200 further comprises a trocar 292 placed through the skin S of the patient and into an area of the knee of the patient. FIG. 28*m* schematically illustrates how the surgeon manipulates the knee in the sealed environment using the glove 202 and the endoscopic instrument 289 thus performing a hand assisted endoscopic procedure.

Figure 28N:
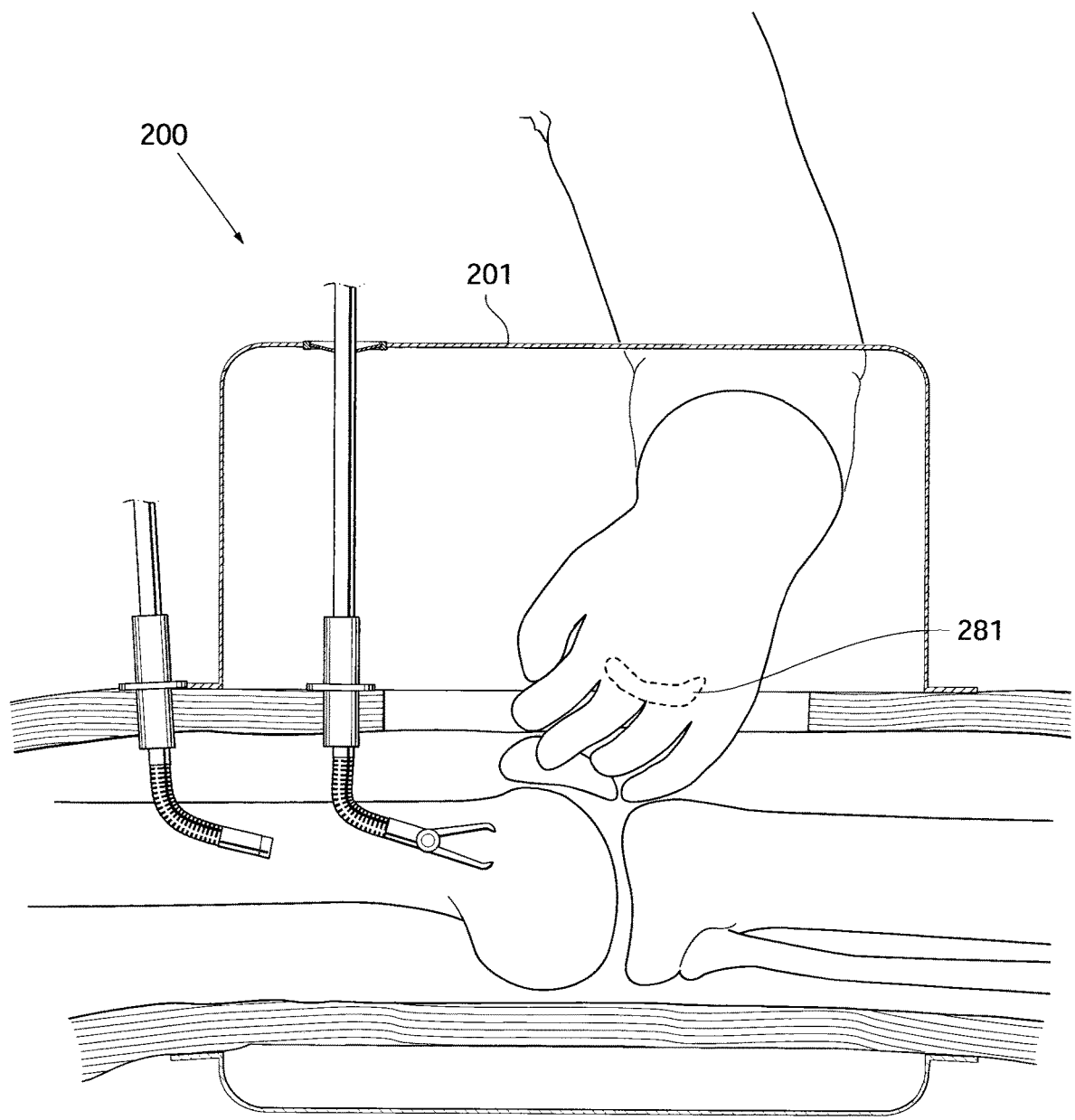
Figure 28O:
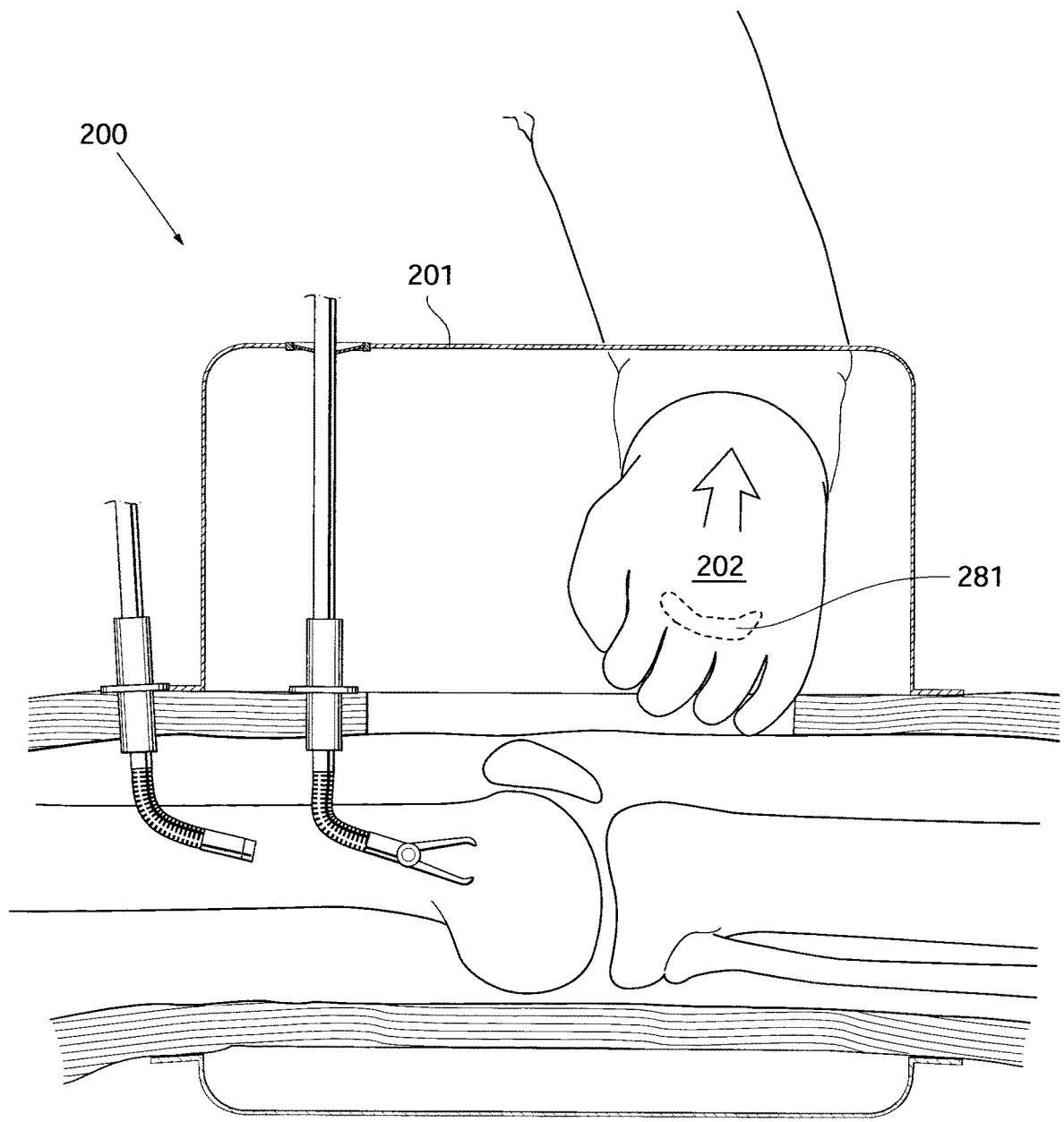

FIGS. 28*n*, 28*o* shows the medical device 200 when the surgeon removes a specimen 281 from the knee of the patient using the glove 202 integrated in the wall 201 of the medical device 200.

Figure 28P:
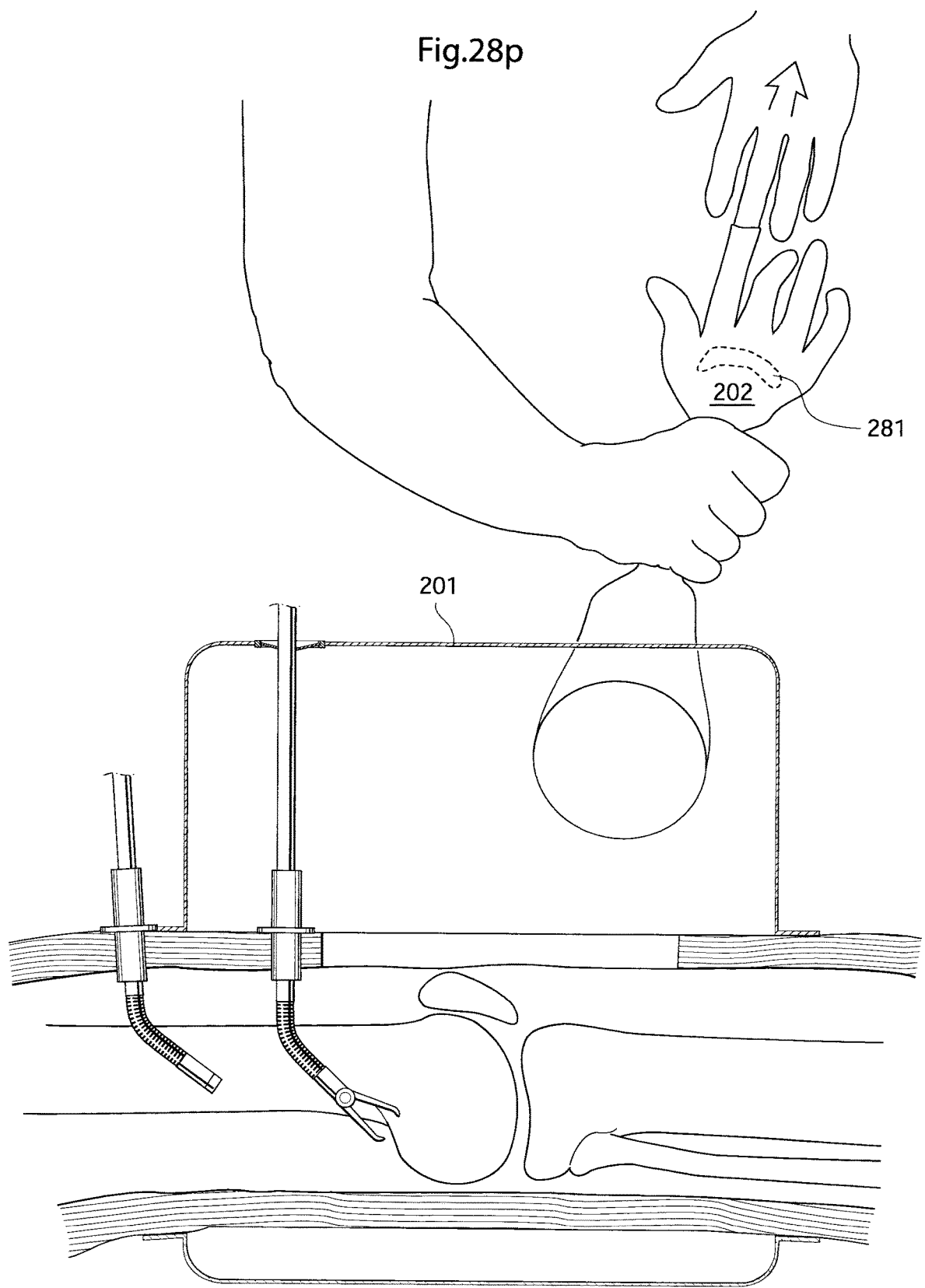

FIG. 28*p* shows the medical device 200, when the surgeon has turned the integrated glove 202 inside-out such that the specimen 281 can be contained within the integrated glove 202. By isolating the specimen 281 inside of the glove 202, the specimen 281 is removed both from the rest of the body of the patient and from the ambient environment A, and thereby does not risk to infect any other portion of the patient's body or medical staff with any infectious disease.

FIGS. 29-41*q* shows an embodiment of the medical device comprising a wall enclosing a chamber in which a portion of the surgical procedure can be performed. The wall enclosing the chamber is adapted to be pressurized before the first incision is performed inside the chamber of the medical device such that a positive pressure in the chamber reduces the risk that infectious particles can enter the chamber before an incision is performed in the skin of the patient forming a fluid connection between the chamber and a cavity in the body of the patient. All surgical instruments needed for the particular operation may be pre-placed within the chamber, such that a kit for a particular operation is created.

Figure 29:
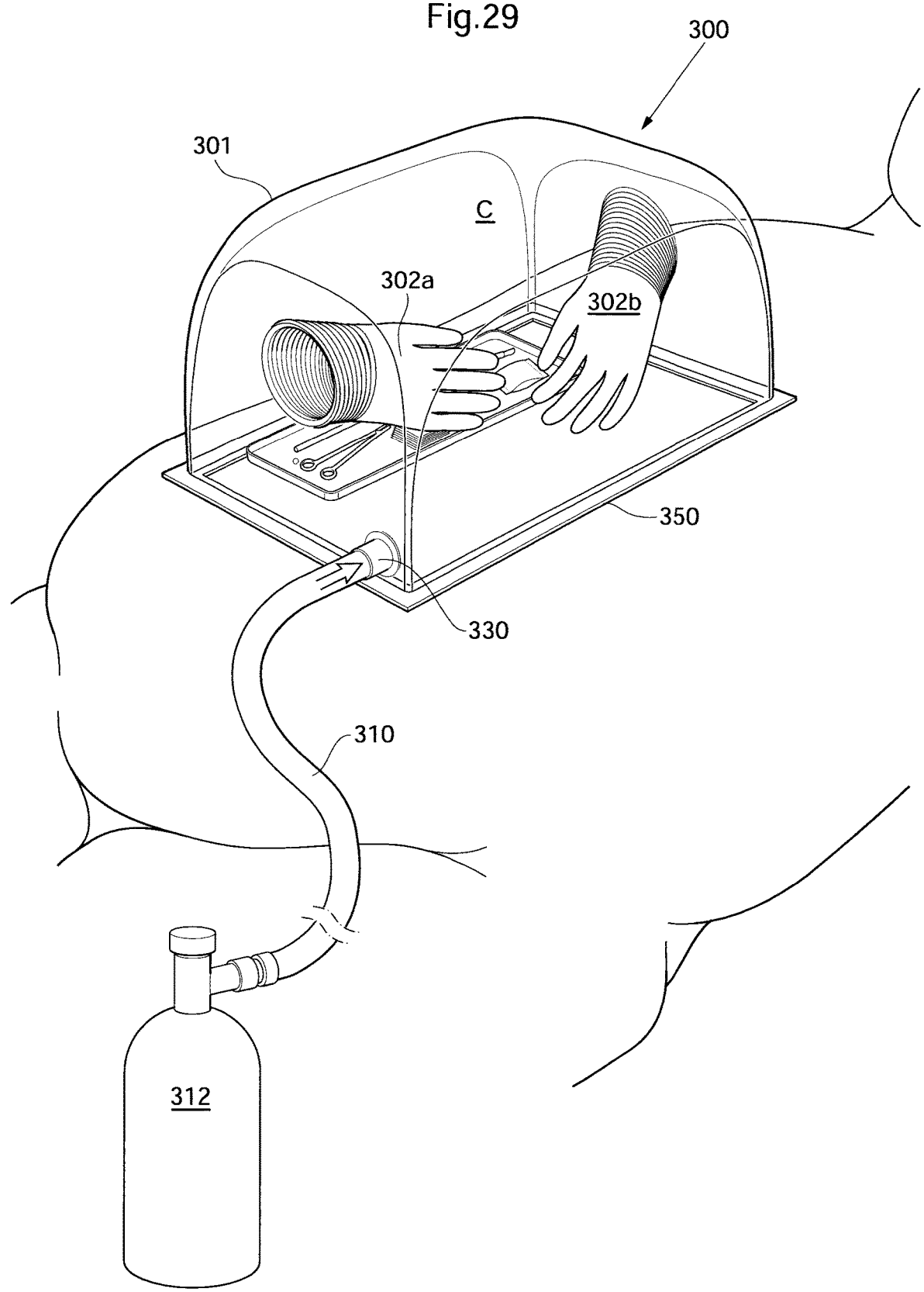
FIG. 29 shows the medical device, when fixated to the abdomen of a patient.

FIG. 29 shows a medical device 300 for performing surgical procedures. The medical device 300 comprises a wall 301 enclosing a chamber C in which a part of a surgical procedure can be performed. The chamber C is adapted to, after an incision has been created in the skin of the patient, be in fluid connection with a cavity within the patient's body via the incision in the skin of the patient. The medical device 300 is adapted to hold a pressure within the chamber C exceeding atmospheric pressure. The pressure in the chamber C is created by the injection of fluid through an inlet 330 in the wall 301 of the medical device 300. The inlet 330 being connected to a fluid conduit 310 which in turn is connected to a pressure source, in the embodiment shown in FIG. 29 in the form of a tank 312 containing a pressurized fluid. According to the embodiment shown in FIG. 29, the wall of the medical device comprises an adhesive surface 350 for fixating the medical device 300 to the skin of the patient. The medical device is adapted to be positioned in connection with the skin of the patient, for creating a substantially airtight seal between the medical device 300 and the skin of the patient prior to the incision in the skin of the patient which creates the fluid connection between the cavity within the patient and the sealed environment. According to the embodiment shown in FIG. 29 the medical device is adapted to enable manual manipulation within the chamber C enclosed by the medical device and therefore has a volume exceeding 500 000 mm3.

According to the embodiment shown in FIG. 29, the wall 301 of the medical device 300 comprises two integrated gloves 302 for enabling manual manipulation within the sealed environment, however, in other embodiments the gloves 302 could be replaced by for example ports for enabling manipulation within the chamber C using suitable instruments.

Figure 30:
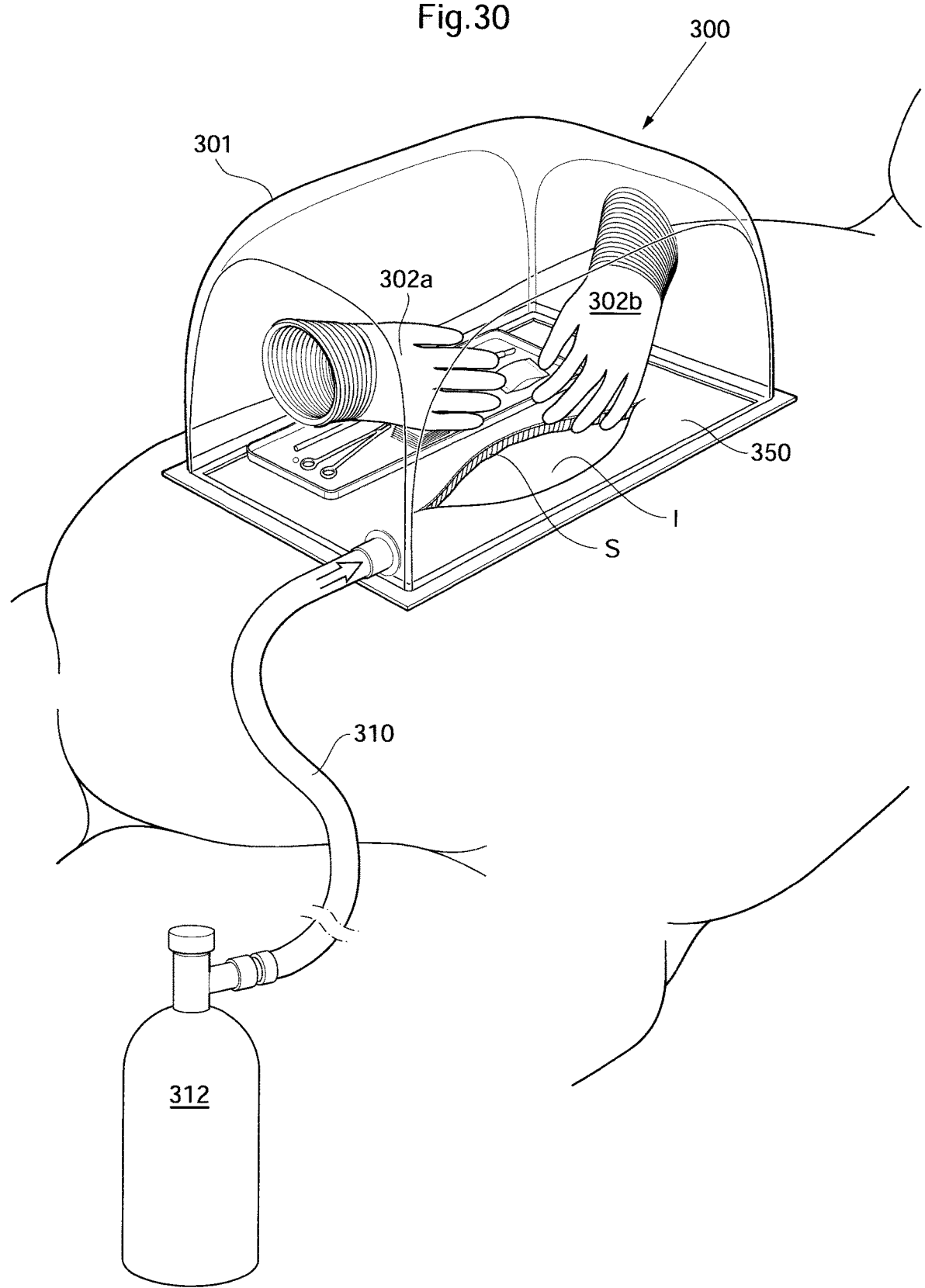
FIG. 30 shows an embodiment of the medical device, fixated to the abdomen of a patient, when an incision is performed in the medical device.

FIG. 30 shows an embodiment of the medical device 300 similar to the embodiment shown in FIG. 29 with the only difference being that the adhesive surface 350 covers the entire portion of the wall 301 adapted to be placed in connection with the skin S of the patient. The medical device 300 is adapted to be positioned prior to the beginning of the operation and as the entire portion of the wall 301 contacting the skin S of the patient comprises the adhesive surface 350, the incision I in the patient runs through the wall 301 and further through the skin S of the patient. The cutting though the wall 301 adhering to the skin S of the patient reduces the risk that infectious particles or bacteria can be transferred from the skin S of the patient to the incision I in the patient, even if the skin S of the patient is not adequately disinfected.

Figure 31:
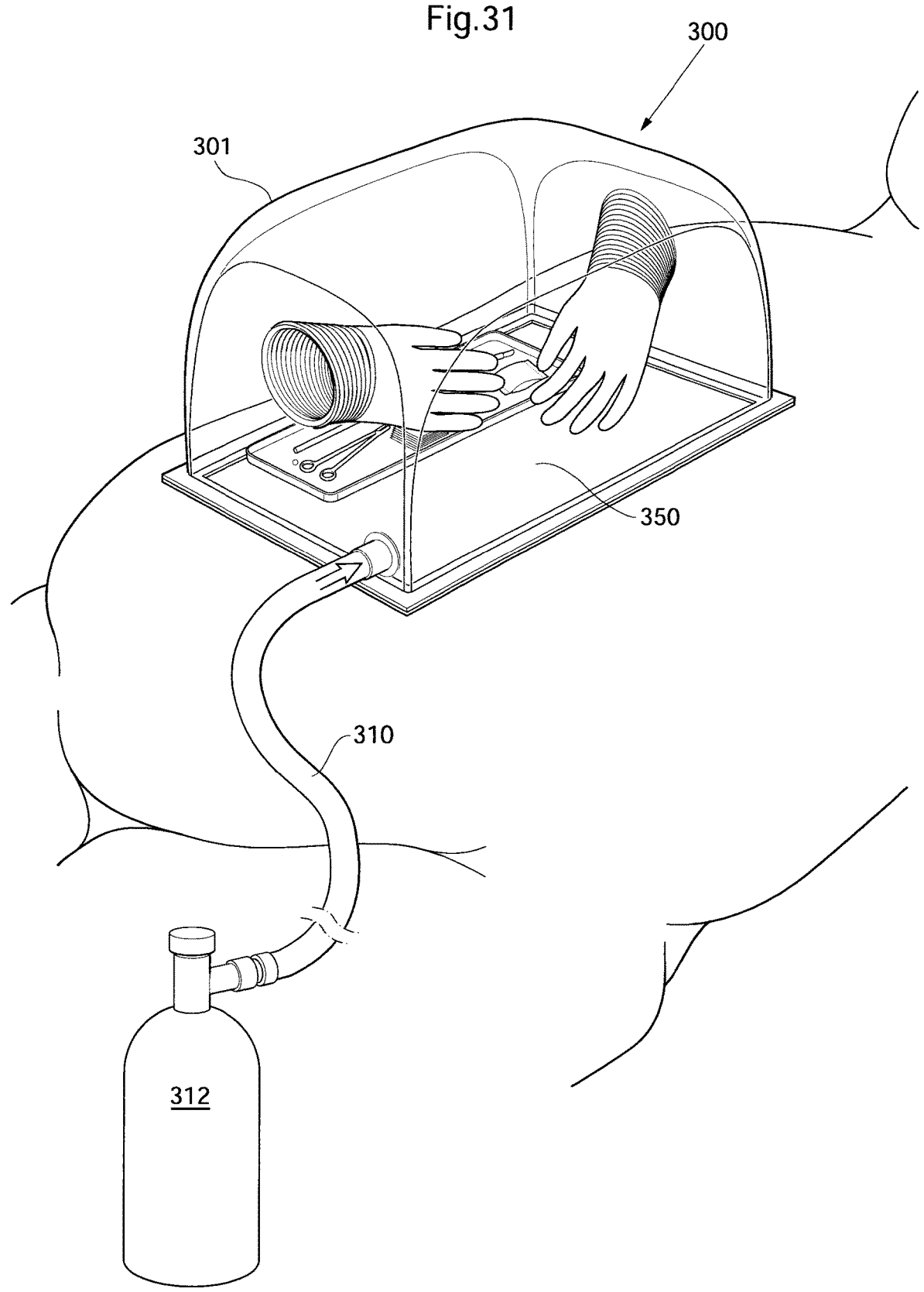
FIG. 31 shows a medical device when fixated to the abdomen of a patient.

FIG. 31 shows the medical device 300 in the embodiment where the entire portion of the wall 301 adapted to be in connection with the skin of the patient comprising an adhesive 305, prior to the incision in the wall 301.

FIG. 32 shows a medical device according to an embodiment similar to the embodiment shown with reference to FIG. 29. However, the medical device 300 according to the embodiment shown in FIG. 32 additionally comprises a sealing device comprising a vacuum sealing member 305' adapted to seal by holding a pressure less than atmospheric pressure for creating a vacuum sealing between the skin S of the patient and the medical device 300. The vacuum sealing member 305' is according to the embodiment shown in FIG. 32 fixated to the patient by means of a vacuum affecting the patient along a vacuum groove. The vacuum groove is connected to a vacuum pump 308 by means of a vacuum conduit 306. This construction enables maintaining of a pressure within the chamber C above atmospheric pressure, while having a pressure in the vacuum sealing member 305' below atmospheric pressure and thus fixating the medical device to the skin of the patient.

FIG. 33 the shows the medical device 300 according to an embodiment similar to the embodiment disclosed with reference to FIG. 29, with the addition that a portion of the wall 301 is possible to open by means of a zipper 319 such that an opening between the ambient environment and the chamber C is created for allowing passage of objects between the ambient environment A and the chamber C.

FIG. 34 shows the medical device 300 according to an embodiment similar to the embodiment disclosed with reference to FIG. 29, with the addition that the medical device 300 further comprises an airlock sluice 318 for allowing passage of objects between the chamber C and the ambient environment A whilst keeping the chamber C and the ambient environment A separated. The airlock sluice 318 enabling a pressure above atmospheric pressure to be maintained within the chamber C whilst transferring an object between the chamber C and the ambient environment A. The airlock sluice 318 comprises an outer zipper 319a, separating the airlock sluice 318 from the ambient environment A, and an inner zipper 319b separating the chamber C from the airlock sluice 318.

FIG. 35a shows the medical device 300 according to an embodiment similar to the embodiment shown with reference to FIG. 29. However, the medical device of FIG. 35a is partially collapsible, and the collapsible portion is adapted to be inflated by a gaseous fluid for defining the chamber C. The medical device 300 is inflated by a pressurized fluid entering the medical device through a fluid inlet 330 connected to a fluid conduit 310. The medical device 300 is according to the embodiment shown in FIG. 35a fixated to the abdominal region of a patient by means of a portion or the wall 301 comprising an adhesive surface 350. The medical device further comprises a rigid transparent window 321. Inflation of the wall 301 in which a window 321 is integrated, positions the window 321 in a position suitable for viewing the procedure being performed on the patient.

FIG. 35b shows the medical device 300 when inflated such that the wall 301 separates the chamber C within the medical device 300 from the ambient environment A and thus creates an operating environment which is separated from contaminations from the ambient environment A. A portion of the partially collapsible wall 301 is placed in connection with the skin of the patient, and that portion comprises an adhesive surface 350 for fixating the medical device 300 to the skin of the patient and/or sealing between the medical device 300 and the patient. The window 321 has been positioned by the inflation of the medical device 300, such as to enable viewing of the inner side being inside of the chamber C of the portion of the wall 301 comprising the adhesive surface 350. In some of the embodiments disclosed, the entire portion of the wall 301 contacting the skin of the patient comprises an adhesive, such that the incision in the patient runs through the wall 301 and further through the skin of the patient (this is further disclosed with reference to FIG. 30). This reduces the risk that infectious particles and bacteria can be transferred from the skin of the patient to the incision in the patient.

In some applications it is conceivable that a normal laparoscopic procedure is performed with the medical device 300 positioned but not inflated. The medical device 300 is then only inflated at the end of the procedure, for example when a specimen is to be removed from the body of the patient. The inflation of the medical device continues until the pressure inside the medical device exceeds atmospheric pressure.

Figure 36A:
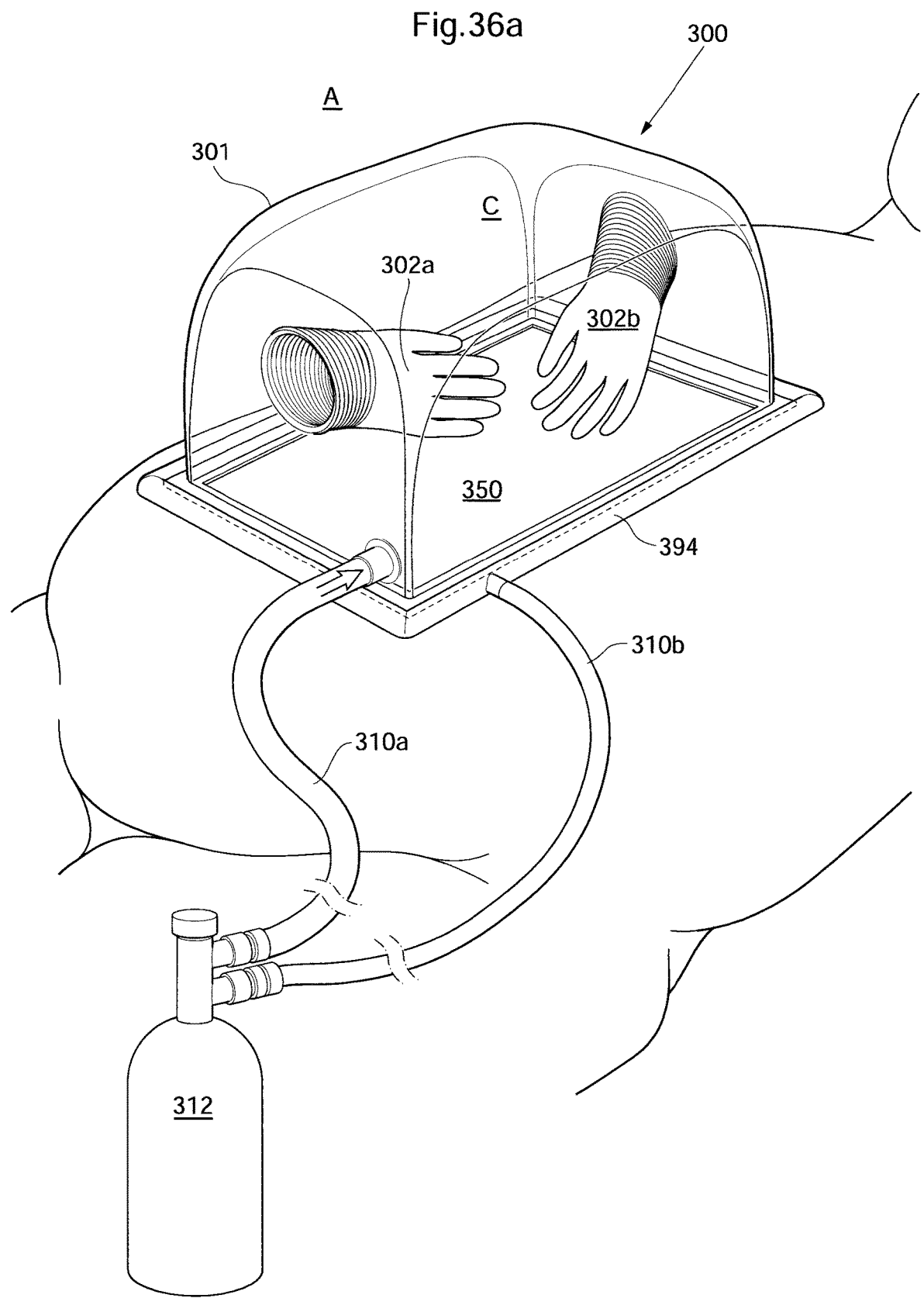
FIG. 36a shows an embodiment of the medical device having a pressure sealing.

FIG. 36a shows an embodiment of the medical device 300 similar to the embodiment shown in FIG. 29, with the difference that the embodiment shown in FIG. 36a additionally comprises a sealing device comprising a pressure sealing member 305" adapted to be inflated for pressing against the skin of the patient and thereby sealing between the chamber C within the medical device 300 and the ambient environment A. The pressure sealing member 305" is inflated though a fluid conduit 310b connected to a pressure source, in this embodiment a tank 312 containing pressurized fluid. In the embodiment shown, the medical device 300 is fixated to the patient by means of a portion of the wall 301 comprising an adhesive surface 350 adapted to withstand the force created by the inflated pressure sealing member 305".

Figure 36B:
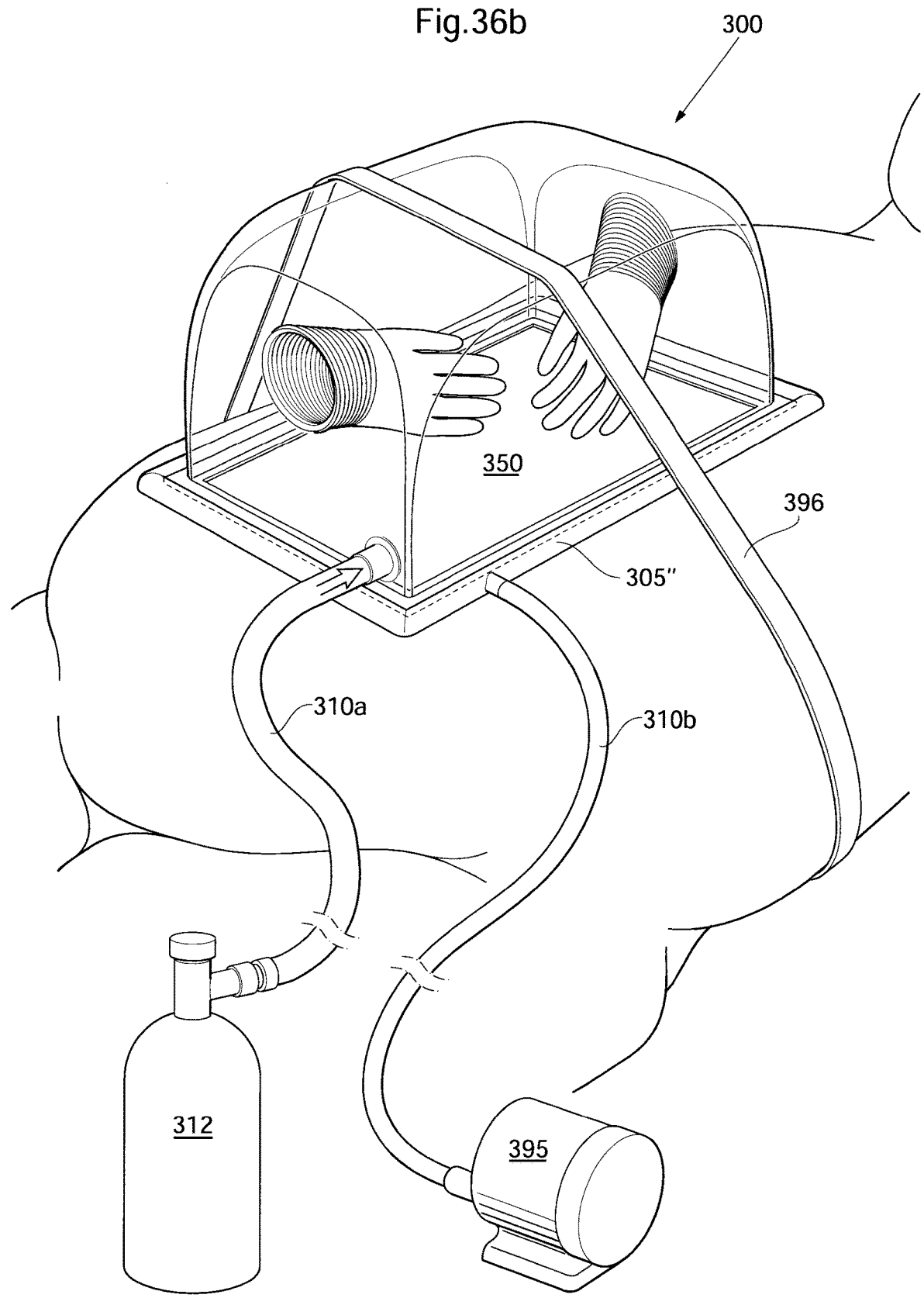
FIG. 36b shows the embodiment of FIG. 36a with a band.

FIG. 36b shows an alternative embodiment of the concept disclosed with reference to FIG. 36a. In FIG. 36b the fixation of the medical device is assisted or replaced by a holding member 396 pressing the medical device 300 against the skin of the patient. The holding member 396 could be required if the pressure needed to seal between the skin if the patient and the medical device 300 needs to be particularly large, which for example could depend on the positioning of the medical device 300. The other difference from the embodiment shown in FIG. 36a is that the source of pressure to the sealing 305" comes from a fluid pump 309 and the fluid is preferably regular air coming from the ambient environment. The use of a different pressure source for the sealing 305" could be an advantage when the available pressurized fluid is scarce or when it is important to not mix the fluid going into the chamber with the fluid adapted to be in the sealing 305".

Figure 37A:
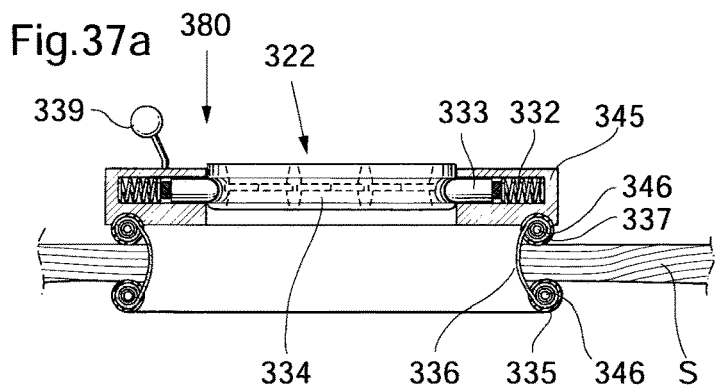
FIGS. 37a, 37b, 37c shows a coupling in section.

FIG. 37a shows an embodiment of a detachable body port 322 which could be positioned in the chamber of the medical device disclosed with reference to FIG. 29. The body port 322 is fixated to a coupling 380 comprising a sealing device comprising an intra body ring 335 adapted to be placed at the inside of the patients skin S around an incision, and an outer ring 337 adapted to be placed on the outside of the patients skin S around the incision. Between the intra body ring 335 and outer ring 337 a connecting member 336 in the form of an annular retractor membrane 336 is positioned adapted to exert a pressure on the skin S or tissue at the incision to seal between the rings 335; 337 and the skin S or tissue and additionally for retracting the skin S and thereby keeping the incision open. The retractor membrane 336 is preferably made from a resilient or elastic polymer material. The inner 335 and outer 337 rings comprise integrated roll up systems 346, which may be spring loaded and adapted to create a suitable pressure on the retractor membrane 336 to keep the incision open.

The coupling 380 has a rigid annular seating 345 attached to the outer ring 337, spring loaded protruding members 333 arranged in radial bores in the seating 345 and a hand lever 339 connected to the protruding members 333 to enable retraction thereof against the action of springs 332. The coupling latches self sealing body port 322 by means of the protruding members engaging a recess of the body port 3222. The body port 322 comprises a disc-shaped self sealing membrane 343, further shown in FIG. 37b, fixated to a rigid ring having an outer circumferential recess 334 that receives the protruding members 333 of the coupling. The self sealing membrane 343 has a small self sealing hole 344 centrally in the membrane 343. For example, the self sealing membrane 343 may be made from a gel-type material being elastic enough to enable a deformation large enough for a person's hand to pass through the small self sealing hole 344 while still contracting enough to create an airtight seal between the chamber and the ambient environment.

The coupling 380 described above enables quick exchange of the body port 322. Thus, the surgeon may release the body port 322 from the coupling 380 by simply pulling the hand lever 339 so that the protruding members 333 disengage from the recess 334 of the body port 322, whereby the body port 322 can be removed.

Figure 37B:
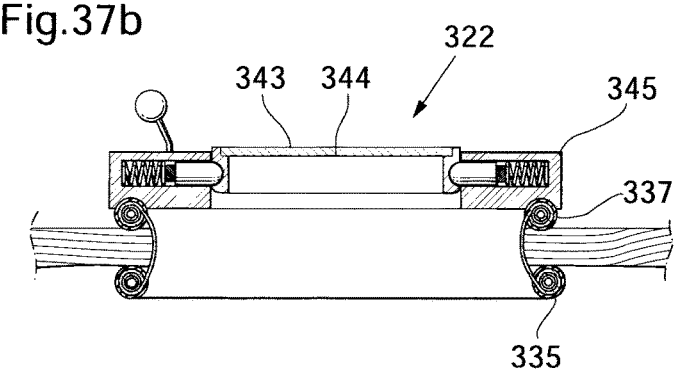

FIG. 37b is a cross-sectional view of the coupling shown in FIG. 37a, to more clearly illustrate the body port 322 with its self sealing membrane 343 and small self sealing hole 344.

Figure 37C:
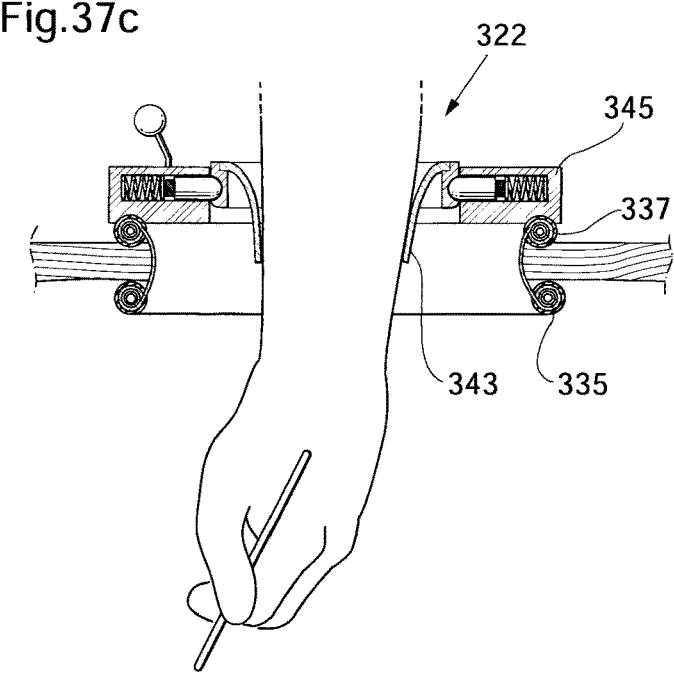

FIG. 37c shows the self sealing body port 322 when the hand of a surgeon is placed through the self sealing hole 344 in the membrane 343 and thus enabling manual manipulation within the body of the patient.

Figure 38A:
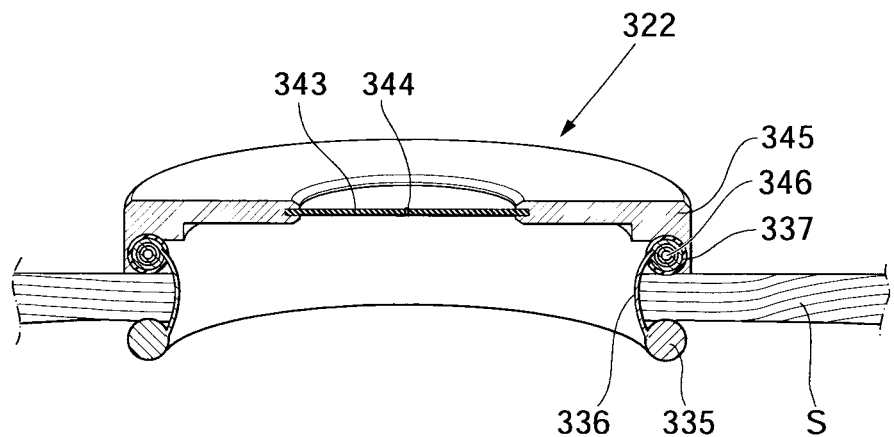
FIGS. 38a and 38b shows an embodiment of a self sealing port, in section.
Figure 38B:
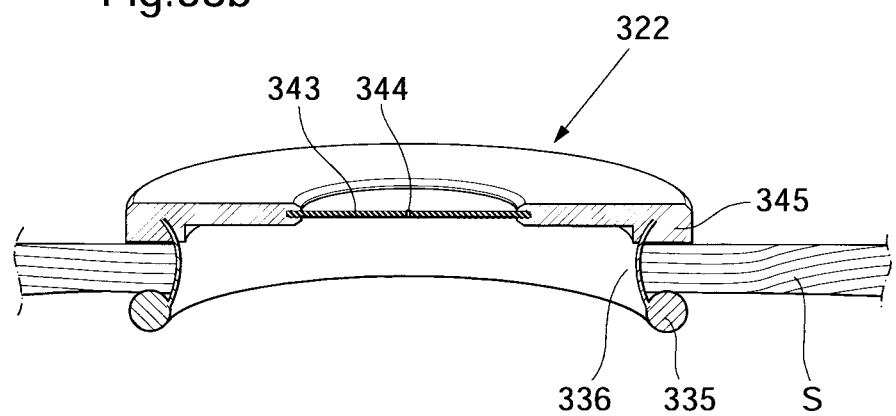

FIG. 38a shows a self sealing body port 322 in a close-up, in section. The self sealing body port 322 could be connected to the coupling, for example as disclosed with reference to FIGS. 36 and 37, which in turn is connected to the medical device disclosed with reference to FIG. 29, or the self sealing body port 322 could be fixated to a retractor, as shown in FIGS. 38a and 38b. The self sealing body port 322 comprises a self sealing membrane 343 fixated to a rigid seating 345 of the self sealing port 322. The self sealing membrane 343 having a small self sealing hole 344 centrally in the membrane 343. The self sealing membrane 343 is for example made from a gel-type material being elastic enough to enable a deformation large enough for a person's hand to pass through the small self sealing hole 344 while still contracting enough to create an airtight seal between the sealed environment and the ambient environment. The medical device being fixable to a retractor comprising one intra body ring 335 adapted to be positioned on the inside of the patients skin S, and one ring 337 adapted to be placed on the outside of the patients skin S. Between the intra body ring 335 and the outer ring 337, a connecting member in the form of a retractor membrane 336 is positioned which is adapted to exert a pressure of the cut surfaces of the incision for retracting the skin S and thereby keeping the incision open. The retractor membrane 336 is preferably made from a resilient of elastic polymer material. The outer ring 337 comprises an integrated roll up system 346 which could be a spring loaded roll up system adapted to create a suitable pressure on retractor membrane 336 for keeping the wound open.

FIG. 38b shows an alternative embodiment of the self sealing body port 322, with the difference that the retractor membrane 336 is made from a material elastic enough such that one end of the retractor membrane 336 could be fixedly fixated to the rigid seating 345 of the body port 322.

Figure 39:
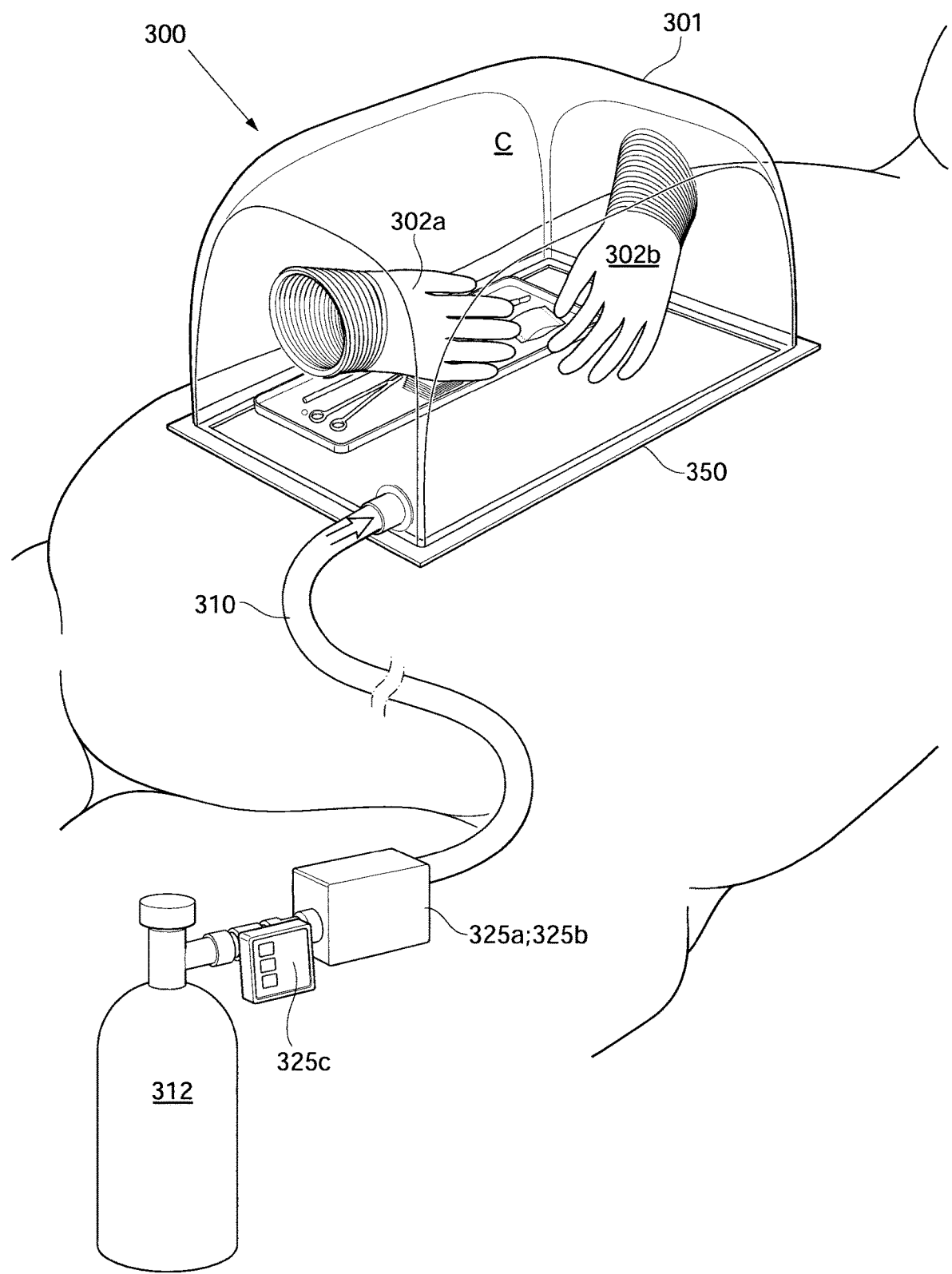
FIG. 39 shows a medical device when fixated to the abdomen of a patient.

FIG. 39 shows the medical device as shown in FIG. 29 with the addition that the embodiment comprises a sterilizing unit 326a and filtering unit 326b adapted to sterilize and filter the gaseous fluid entering the medical device 300. In the embodiment disclosed herein, the gaseous fluid entering the medical device 300 originates from a pressurized tank 312 and could be pre-sterilized, however, in other embodiments, it is conceivable that the gaseous fluid is the surrounding air which is pressurized (such as further disclosed with reference to FIG. 40). In the embodiments where the surrounding air is used to inflate the medical device 300 and constitute the operating environment this air needs to be properly sterilized. The medical device 300 further comprises a tempering unit 325c which could be provided to heat or cool the gaseous fluid inflating the medical device 300. In cases when the surrounding environment is cold the tempering unit 325c could be used to raise the temperature of the sealed environment to provide beneficial operating circumstances both for the patient and for the surgeon. In cases when the surrounding environment is hot, the tempering unit 325c could be used to lower the temperature in the chamber C to provide beneficial operating circumstances, both for the patient and for the surgeon, and for providing a temperature inhibiting bacterial and viral infections. The tempering unit 325c could comprise a temperature regulating device for setting the required temperature.

Figure 40:
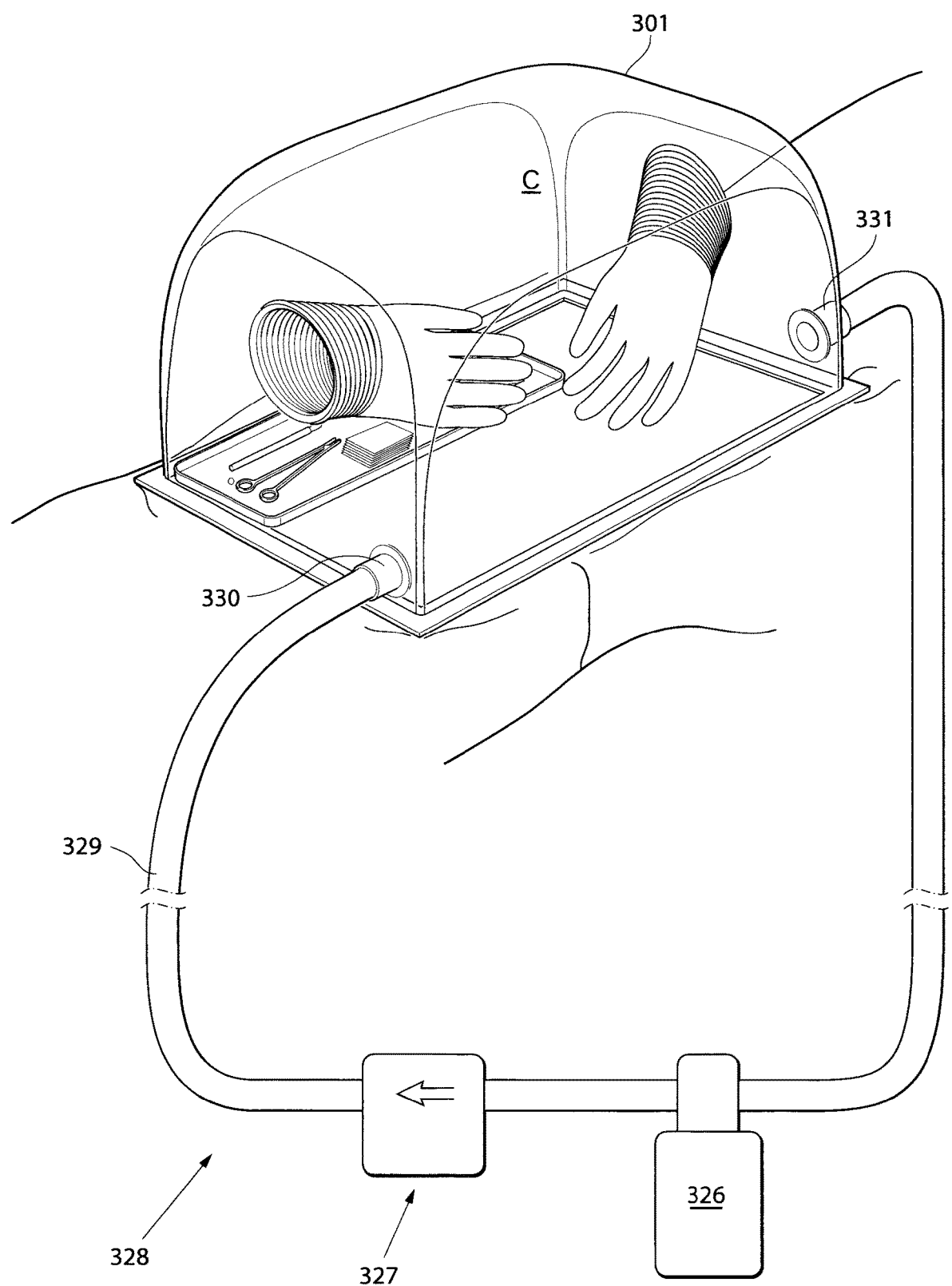
FIG. 40 shows a medical device when fixated to the abdomen of a patient.

FIG. 40 shows a medical device similar to the embodiment disclosed in FIG. 39 but comprising a system 328 for circulating a fluid through the sealed environment of the medical device. The system comprises a fluid conduit 329 connected at an inlet 330 placed in the wall 301 for supplying fluid to the sealed environment, and an outlet 331 for draining the fluid from the chamber C. The fluid is circled by means of a pumping unit 327 and is circled via a sterilizing/filtering/tempering unit 326 adapted to remove impurities, sterilize and heat the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 41A:
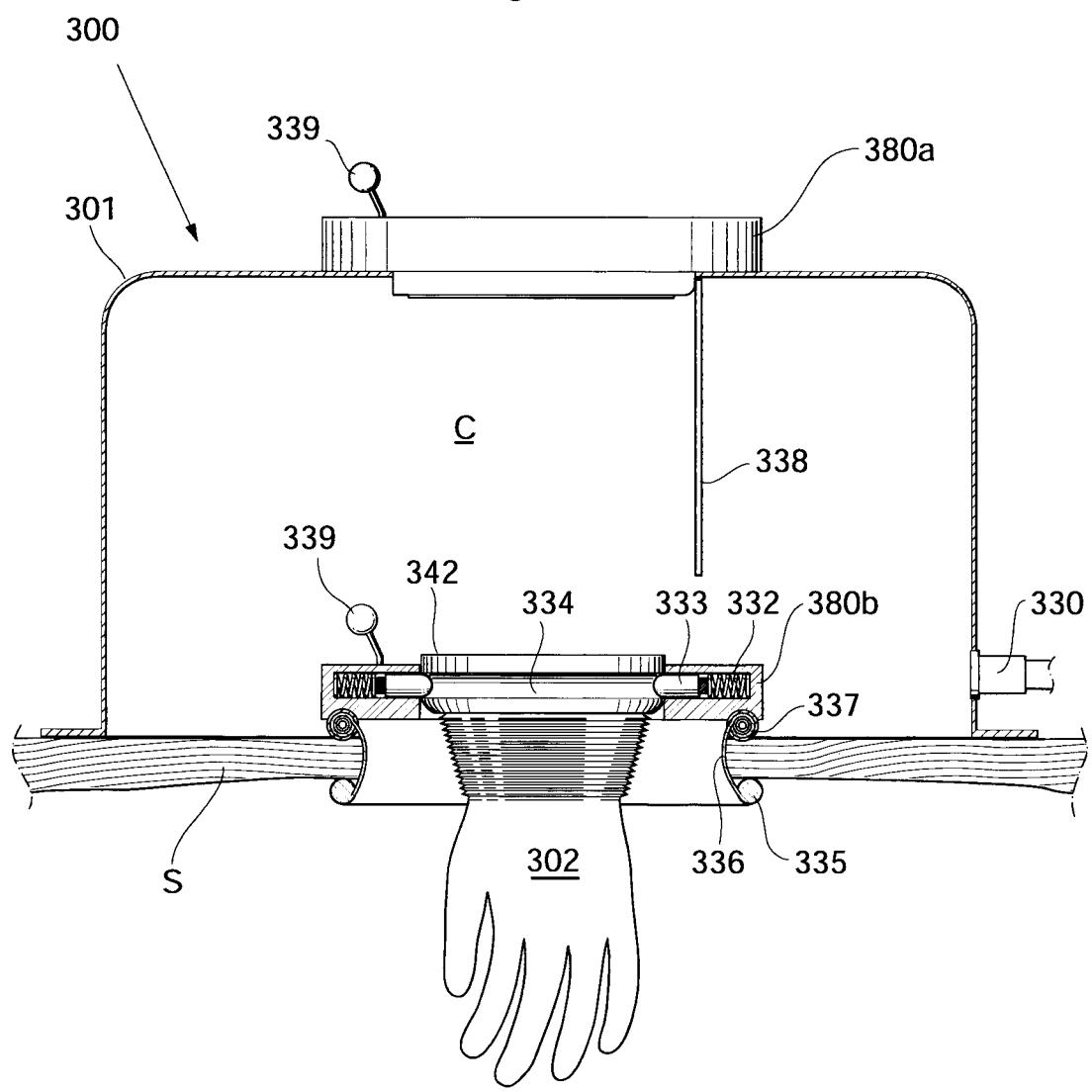
FIG. 41a shows an embodiment of a medical device, in section.

FIG. 41a shows an modification of the embodiment disclosed with reference to FIG. 29 in which the medical device 300 further comprises an upper 380a and a lower 380b coupling for fixating ring shaped objects which for example could be insets 342 or ports, where insets for example could be surgical gloves 302, or device or instrument mounts, and ports could be endoscopic ports or hand access ports, such as the self sealing port disclosed with reference to FIGS. 4a and 4b. The couplings 380a; 380b comprises releasing levers 339 for releasing the object. The lever 339 is connected to protruding members 333 which are spring loaded 332 from the rear in order to secure the recess 334 of the object. In the embodiment disclosed in FIG. 41a, the inset 342 fixated to the lower coupling 380b comprises a surgical glove 302 enabling manual manipulation within the body of the patient. The medical device 300 shown in FIG. 41a further comprises a valve member 338 adapted to close the opening in the upper coupling 380a, when the upper coupling 380a is not in use. The upper coupling 380a is for example used for manual manipulation and preparation within the medical device 300, such that could be needed for preparing or changing an instrument or preparing an implant for implantation. The lower coupling 380b is for example used for laparoscopic manipulation within the body of the patient, or manual manipulation for e.g. removing a specimen or positioning an implant.

Figure 41B:
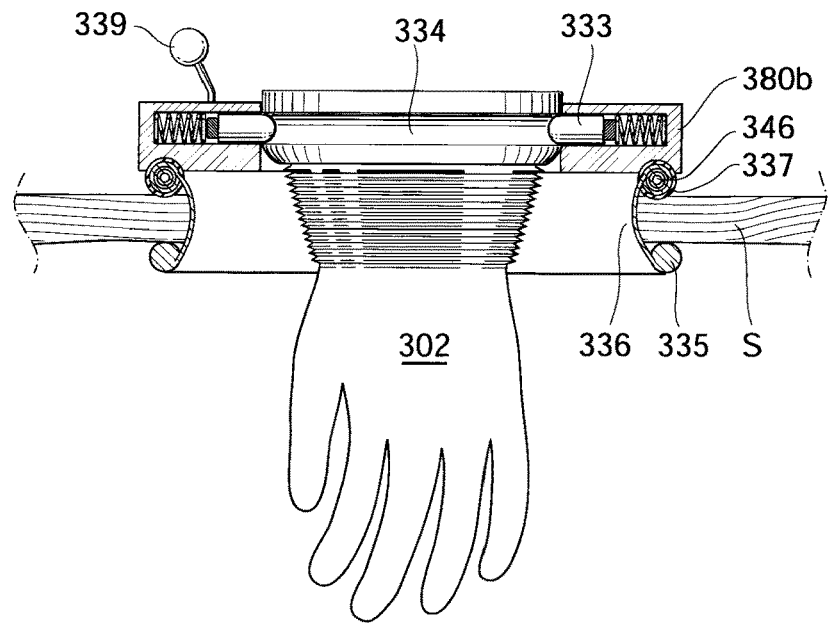
FIG. 41b shows an embodiment of a coupling, in section.

FIG. 41b shows the lower coupling 331b in further detail when an inset in the form of a surgical glove 302 is fixated to the lower coupling 331b. The retractor system comprising the intra body ring 335 and the ring 337 adapted to be placed on the outside of the patients skin S further comprises a connecting member 336 in the form of a retractor membrane 336 positioned such that it exerts a pressure on the cut surfaces of the incision for retracting the skin and thereby keeping the incision open. The retractor membrane 336 could be rolled into a roll by a roll up system 346 inside of the outer ring 337 for tightening the retractor membrane 336 such that the incision is kept open.

Figure 41C:
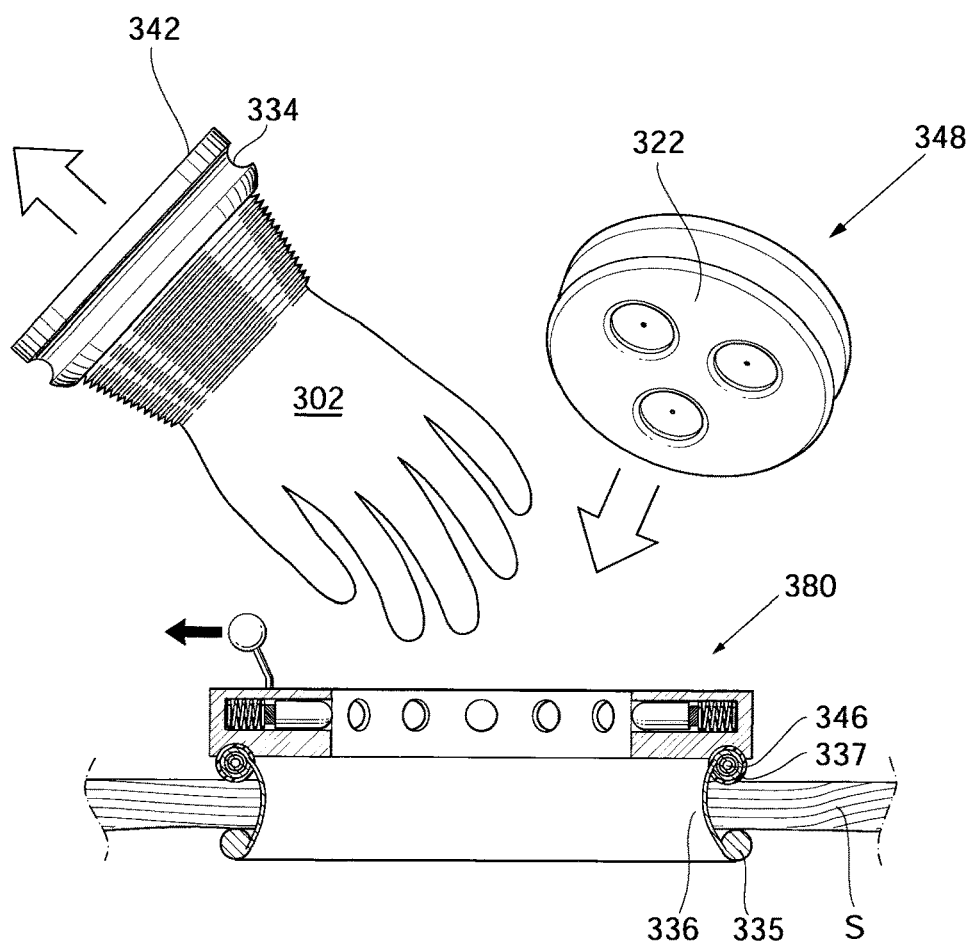
FIG. 41c shows a coupling in section, when objects are being exchanged.

FIG. 41c shows the changing of objects in the coupling 380 from an inset comprising a surgical glove 302 a body port 322 in the form of a multi-port 348 comprising three endoscopic ports. To be able to quickly switch from an endoscopic system to a hand access or manual manipulation system could be of major importance if complications arise during the procedure and could remove the need for a traditional conversion from endoscopic to open surgery, a conversion which inevitably causes problems increasing the risk of complications and/or postoperative care. In other embodiments the endoscopic ports and insets comprising surgical gloves could additionally be exchanged for device or instrument mounts, for example holding instruments or implants.

FIG. 41 d-j shows a further version of the medical device of FIG. 29. In the embodiment of FIG. 41d-j the wall 301 of the medical device 300 is inflatable, and the medical device 300 is in its inflated state. When the chamber C is deflated it has a first volume i.e. when the upper 380a and lower coupling 380b couplings are interconnected, and when the chamber C is inflated and the upper coupling 380a is disconnected from the lower coupling 380b coupling it has a second volume, and the second volume is larger than the first volume. According to the embodiment shown in FIG. 41 d, the second volume is larger than 500 000 mm3 and adapted to hold a pressure exceeding atmospheric pressure such that a surgical step can be performed inside the chamber C whilst keeping the cavity in the patient inflated.

According to the embodiment shown in FIG. 41d-28j the chamber C further comprises a pouch 382 for holding a specimen 381 removed from within the body of the patient not to contaminate any other part of the body and enabling the delaying of the removal of the specimen 381 until the procedure is concluded, such that the surgical procedure can be concluded in an endoscopic, hand assisted endoscopic and/or enclosed way. The pouch 382 may be a closeable for creating a pouch-chamber within the chamber C for isolating the removed specimen 381 within the chamber C.

In FIG. 41d a state is illustrated in which the cut in the patient's skin is being created by the surgeon by means of an inset 342 comprising a glove 302 latched to the upper coupling 380a. The medical device 300 fixated and sealed by means of a sealing device comprising a vacuum sealing member 305' since the seal that is provided partially within the patient's body cannot be mounted until the incision in the patient's skin S is concluded. The two different sealing device disclosed could in some embodiments be replaced by only one of the sealing device, or by a different sealing device for example comprising an adhesive sealing member or a pressure sealing member disclosed herein.

FIG. 41 e shows the medical device, when the second sealing device 335, 336, 337 have been placed in the incision cut in the patient's skin. The wall 301 enclosing the chamber C is elastic or flexible which enables the surgeon move the upper coupling 380a in relation to the lower coupling 380b for getting better access to different angles within the patient's body, for example for removing a specimen 381. The embodiment of FIG. 41e further comprises an iris valve 386 placed in the lower coupling 380b for closing the coupling 380b such that the chamber C is sealed from the ambient environment or the cavity in the patient. The closing of the iris valve 386 enables activity within the chamber C without maintaining a pressure in the chamber C, at the same time as a pressure and/or sealed environment can be maintained in the cavity in the body of the patient.

Figure 41F:
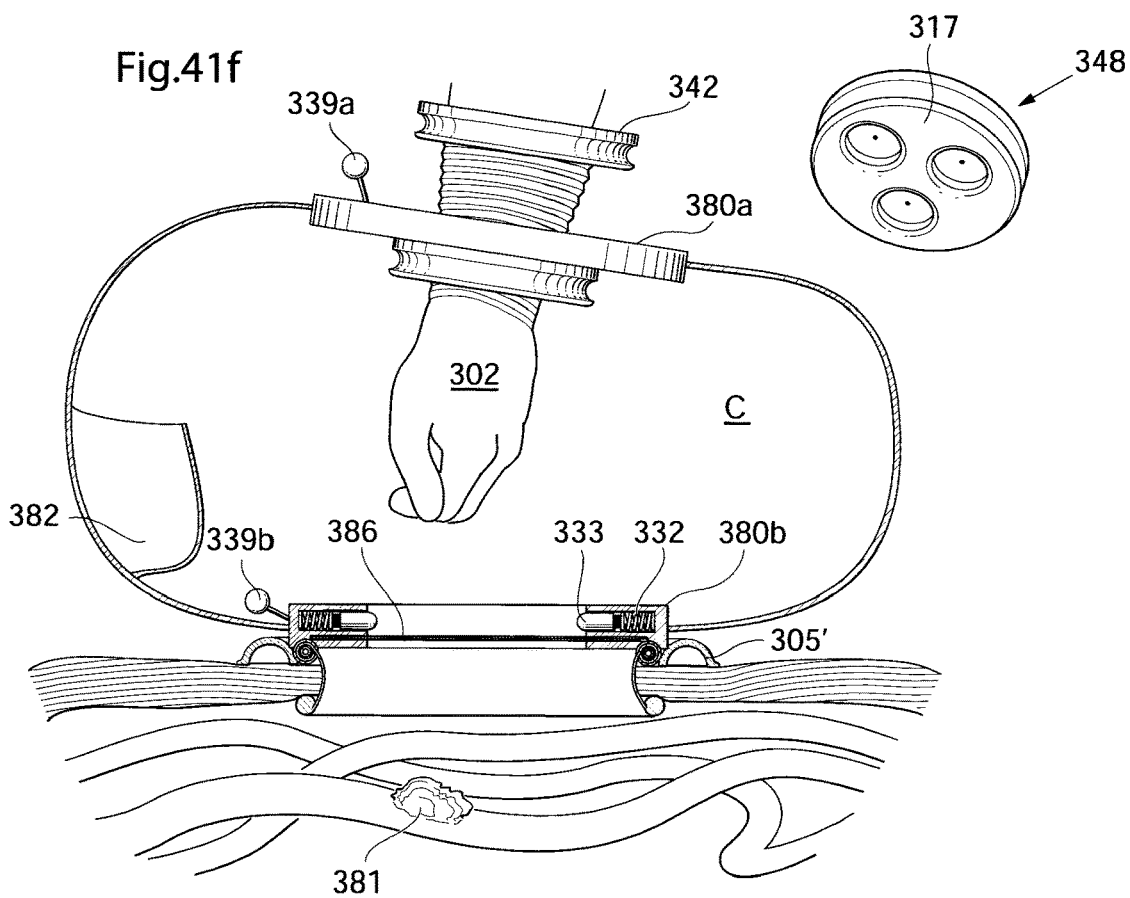

FIG. 41*f* shows the medical device when the inset 342 comprising a glove 302 is removed and replaced by a wall port 317 in the form of a multi port 348 comprising a plurality of ports 347. The multi-port 348 may be used for manipulating objects within the chamber C of the inflated medical device using surgical instruments 389, or within the body of the human patient, when the upper 380*a* and lower 380*b* couplings are connected (as shown in FIG. 41*g*).

Figure 41G:
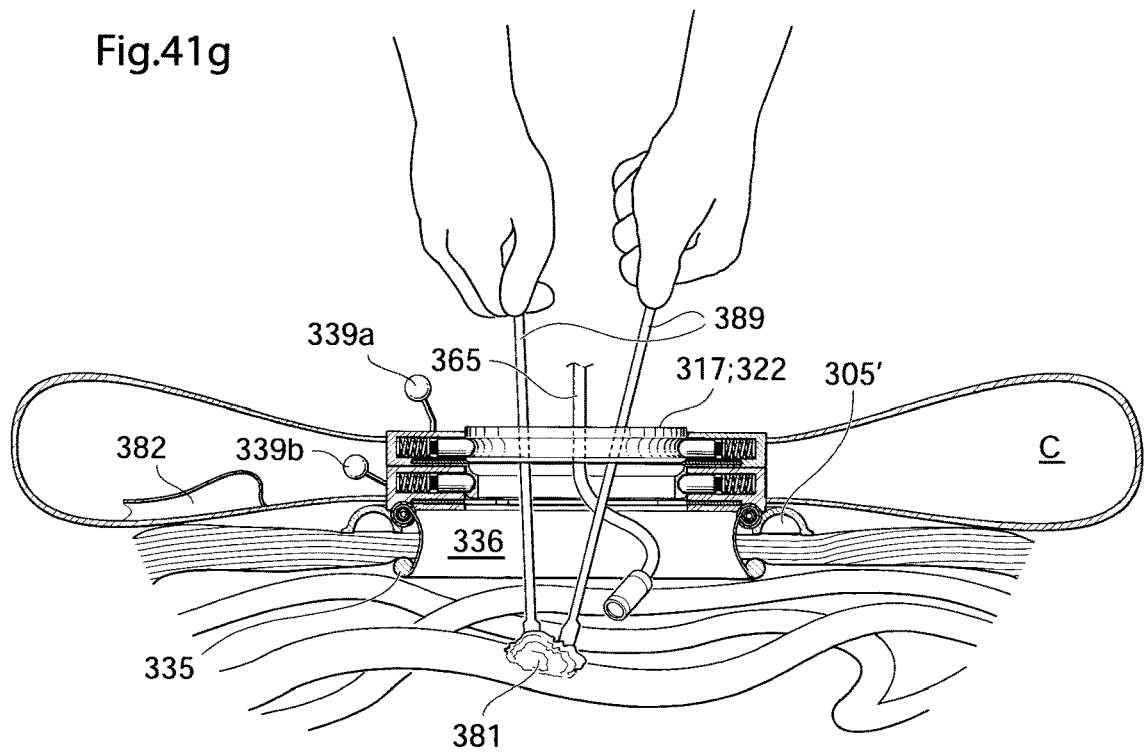

FIG. 41*g* shows the medical device 300 when the first 380*a* and second 380*b* couplings are connected such that surgical instruments 389 can be used for manipulating within the body of the patient. An endoscopic camera 365 may be provided in the wall/body port 317; 322 for enabling visual inspection of the cavity within the patient's body. The process of cutting away a specimen 381 from the intestines of a patient in a laparoscopic way is shown in FIG. 41*g*.

Figure 41H:
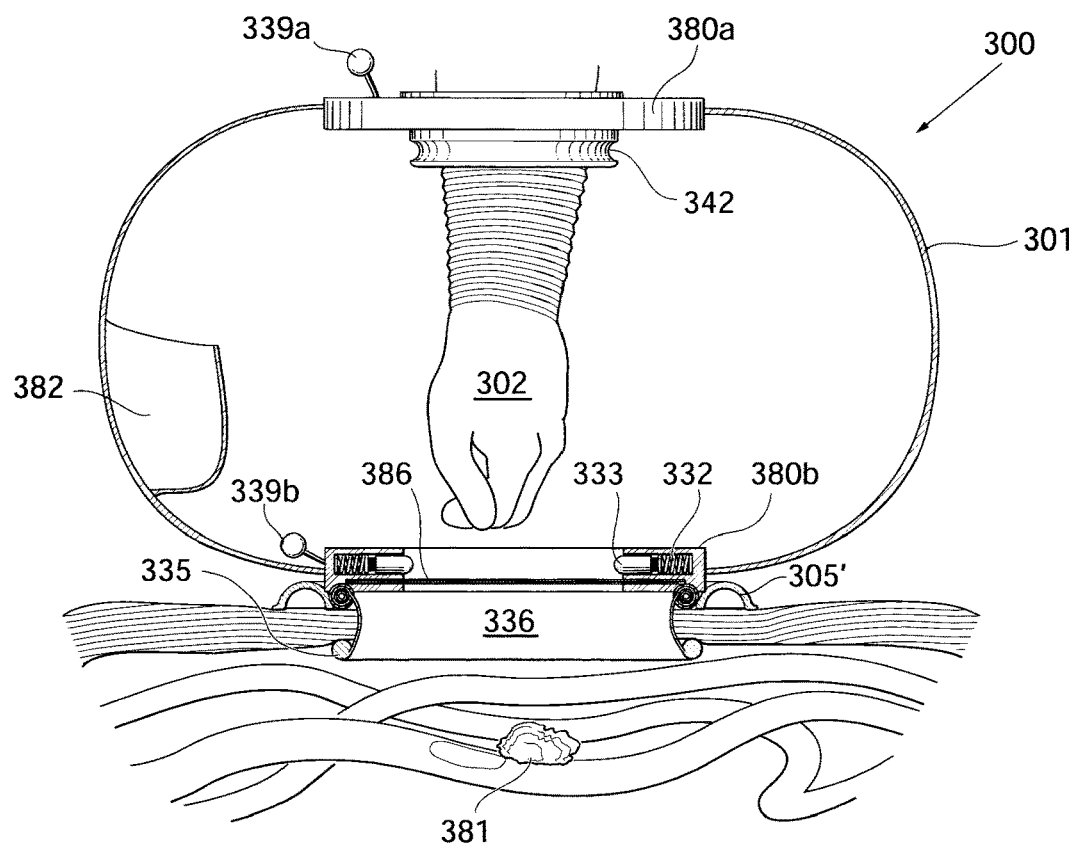

In FIG. 41*h*, the inset 342 comprising the glove 302 has been fixated to lower coupling 380*a* to enable the surgeon to operate within the cavity of the patient's body and within the chamber C enclosed by the wall 301 of the medical device 300. By the inset 342 comprising the glove 302 comprising a pleated portion 303, the surgeon is able to reach into the cavity of the patient for removing the specimen 381 cut loose from the intestines in prior steps.

Figure 41I:
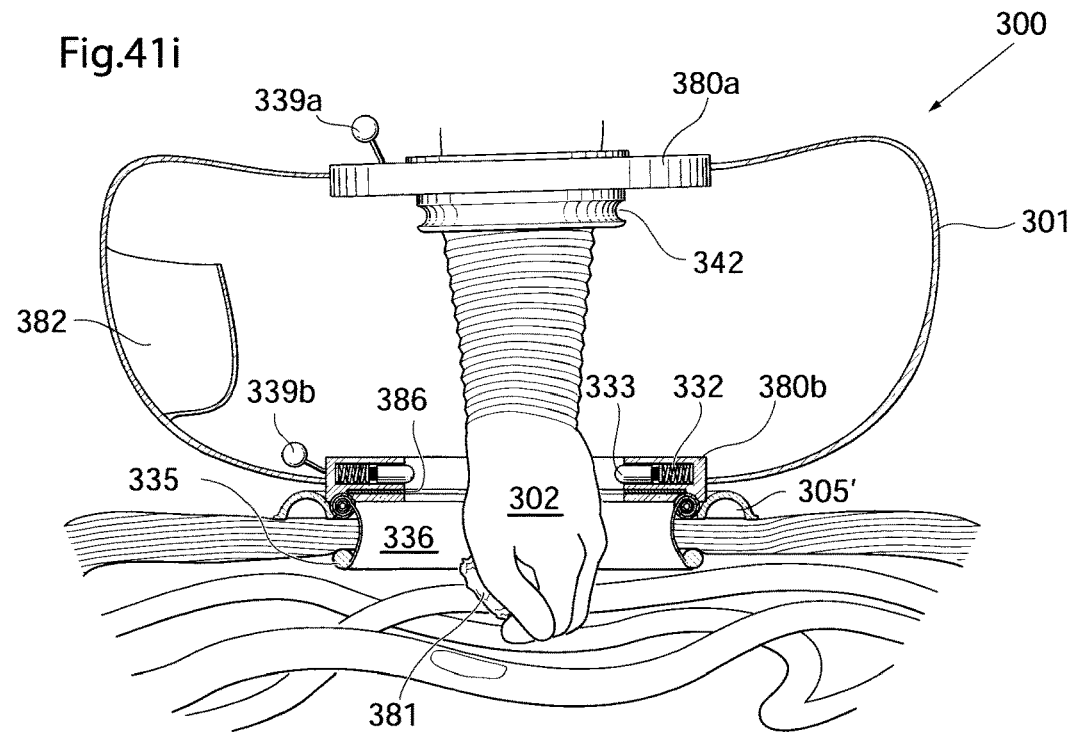

FIG. 41*i* shows that the wall 301 of the medical device 300 is collapsible such that the inset 342 comprising the glove 302 can be moved in relation to the lower coupling 380*b*, which gives the surgeon further freedom when removing the loose specimen from the intestines of the patient.

Figure 41J:
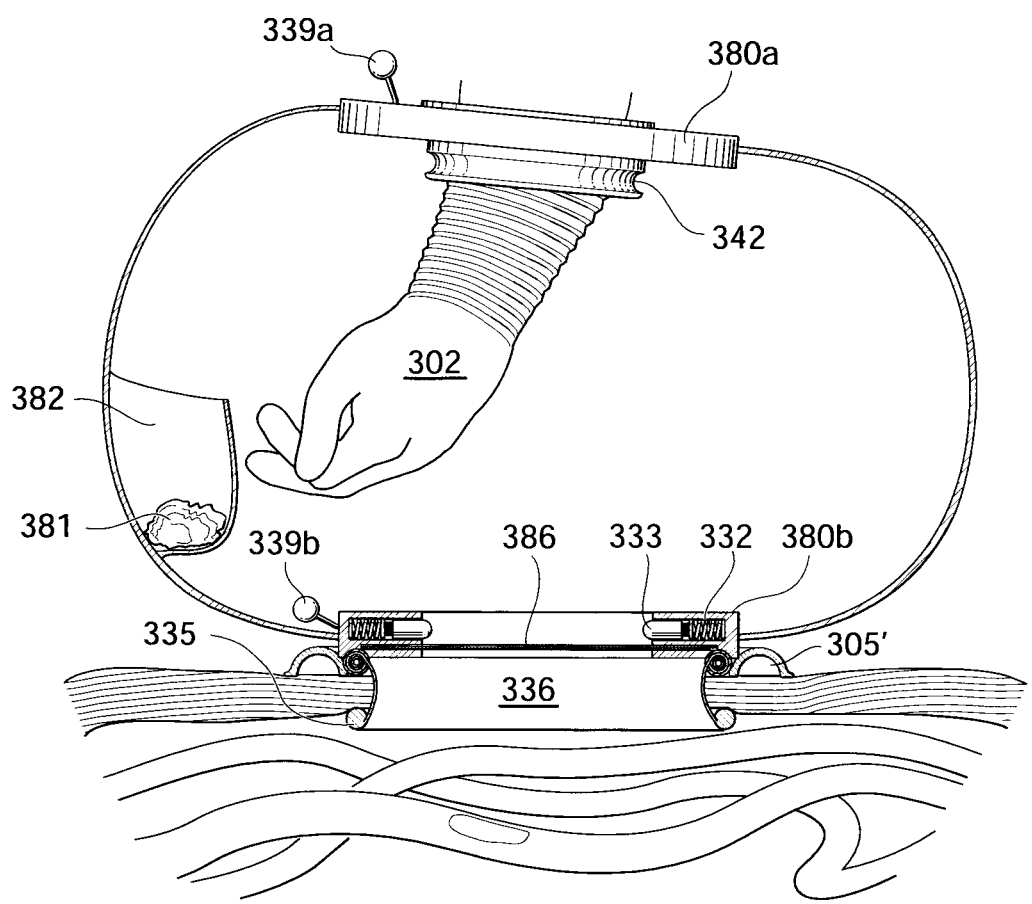
Figure 41I:
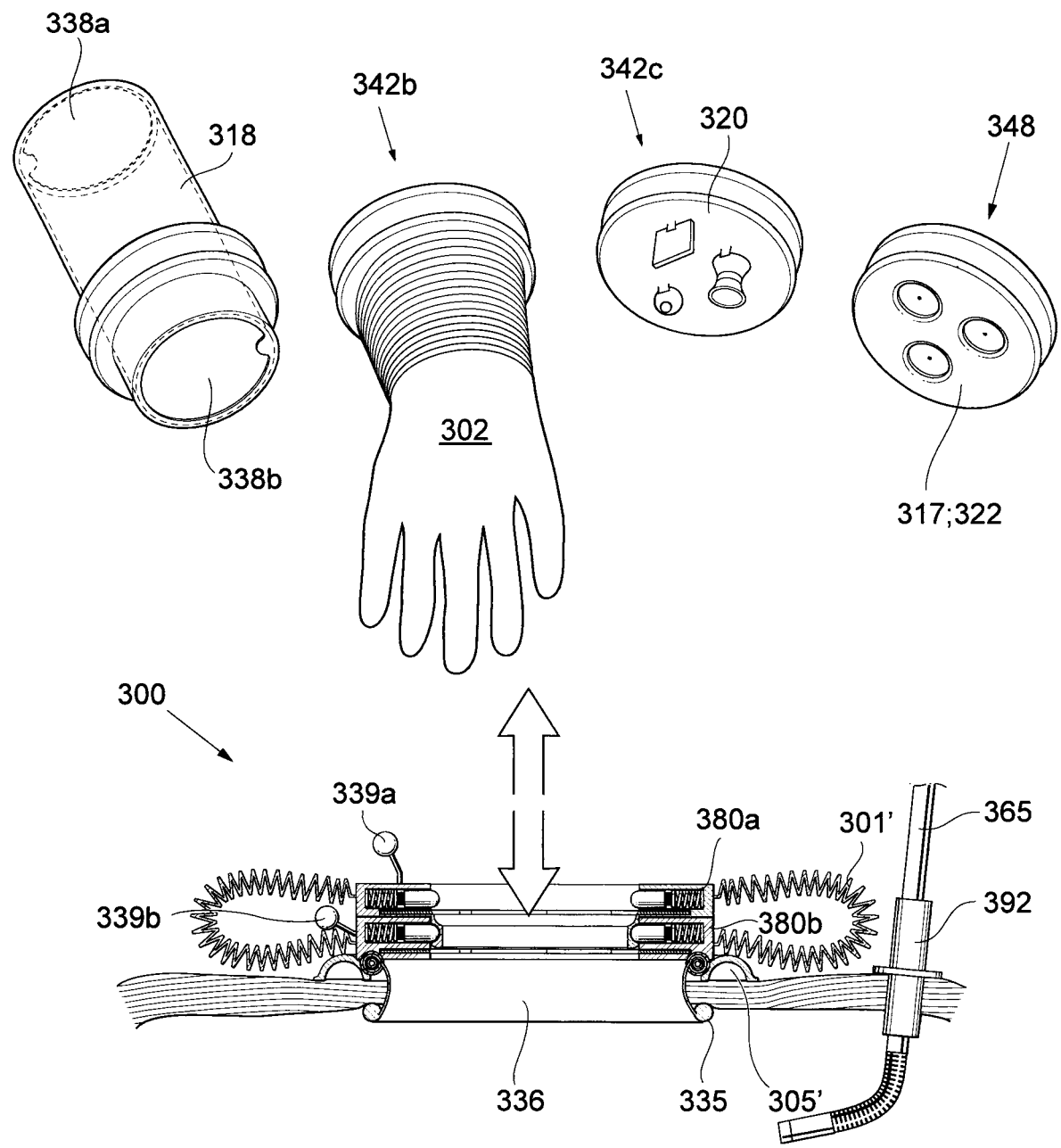

FIG. 41*j* shows the step of placing the removed specimen in the pouch 382 such that the specimen 381 does not contaminate any other part of the body. The pouch 382 may be a pouch 382 which could be closed for creating a pouch-chamber within the chamber C for isolating the removed specimen 381 within the chamber C.

FIG. 41*k* shows an alternative of the embodiment shown in FIGS. 41*d-j*. FIG. In 41*k* the medical device 300 is adapted to be at least partially placed in an incision cut in a patient's body. The medical device 300 comprises an upper 380*a* and lower 380*b* coupling adapted be interconnected to form an interconnected coupling. The upper coupling 380*a* is adapted to be disconnected from the lower coupling 380*b*, and the lower coupling 380*b* is connected to a first portion of a flexible wall 301, and the upper coupling 380*a* is connected to a second portion of the flexible wall 301. The flexible wall 301 forms a chamber C in which a sealed environment can be maintained, the chamber C is heavily enlarged when the upper coupling 380*a* is disengaged from the lower coupling 380*b*, thus creating operating space within the chamber C enclosed by the wall 301. The upper and lower couplings 380*a*; 380*b* comprise a latching system for locking an inset 342 or port 317; 322. The inset 342 may for example be an inset 342*b* comprising a glove 302 for manual manipulation within the body of the patient, or within the enclosed chamber C, an inset 342*c* comprising a device and/or instrument mount 320 for holding instruments or medical devices within the chamber C. Alternatively, the insets may be exchanged to a wall/body port 317; 322, as for example the multiport 348 shown in FIG. 41*k*.

In the embodiment shown in FIG. 41*k* the medical device is fixated to the body of the patient by means of a vacuum fixating member 305' connected to a vacuum conduit 306, which in turn is connected to a vacuum source. Furthermore, the medical device in FIG. 41*k* comprises a second sealing device having a first sealing member in the form of an intra body ring 335 adapted to be positioned at the inside of the patient's skin around an incision to be performed in the skin and a second sealing member 337 in the form of an outer ring adapted to be positioned at the outside of the patient's skin around the incision, and a spring-loaded or elastic connecting member 336 sealingly interconnecting the first 335 and second 337 sealing members. The spring-loaded or elastic connecting member 336 seals between at least one of the coupling and the skin of the patient, and the first sealing member 335 and tissue of the patient.

FIG. 41*l* shows the port in an embodiment very similar to the embodiment shown in FIG. 41*k* but with the difference that the wall 301' has a bellows structure and thus taking up less space when in its deflated state. The bellows structure enables the wall 301 to be packaged in a small package and thus not obstructing the procedure. In some applications the wall 301 can be used only on very special occasions or emergencies, such as when some part of the procedure goes wrong and conversion from endoscopic surgery to more open surgery is required. The use of the inflated chamber then enables the pressure in the cavity within the patient to be maintained since the chamber can hold a pressure. A camera 365 is also shown in FIG. 41*l*, placed in a trocar 392 outside of the medical device and enabling visual inspection of the cavity in the patient.

Figure 41M:
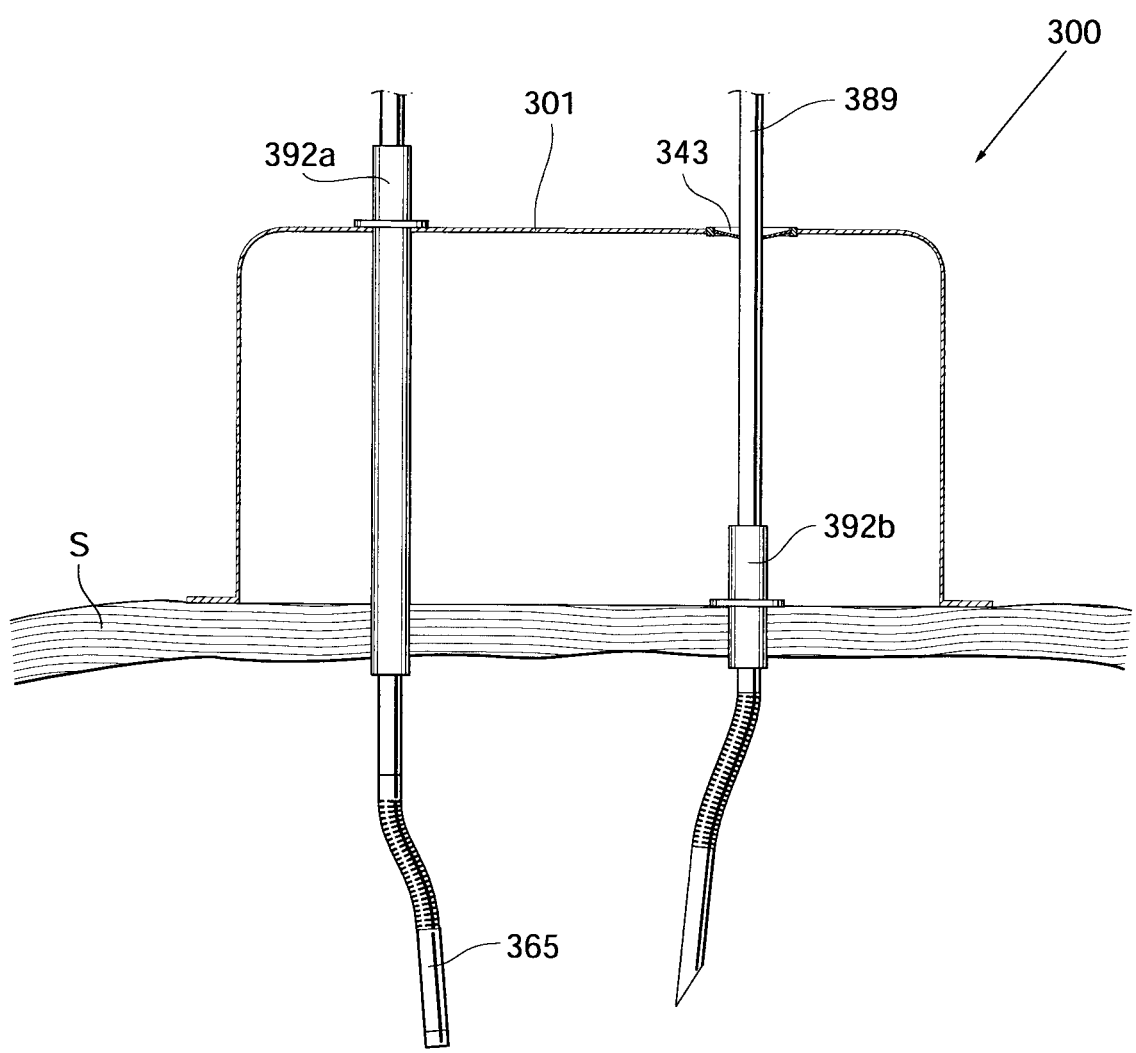
FIG. 41m shows an embodiment of a medical device, in section.

FIG. 41*m* shows examples of how trocars 392*a*; 392*b* may be used in combination with the medical device 300 according to any of the embodiments shown in FIGS. 29-41*l*. The medical device comprises a wall 301 placed on the patient's skin and thereby enclosing a chamber for creating a sealed environment. The medical device comprises two trocars 392*a*; 392*b*, one 392*a* traveling through both the wall 301 of the medical device and the skin of the patient and thus enabling endoscopic instruments (such as a camera 365) to be inserted into the patient through both the wall 301 of the medical device 300 and the skin S of the patient through one single trocar 392*a*. The other trocar 392*b* is placed inside the chamber C and enables an endoscopic instrument 389 to be inserted through the skin S of the patient. The endoscopic instrument 389 is in this embodiment inserted into the chamber C enclosed by the wall 301 through a membrane 343 in the wall sealing against the tool 392*b*.

Figure 41N:
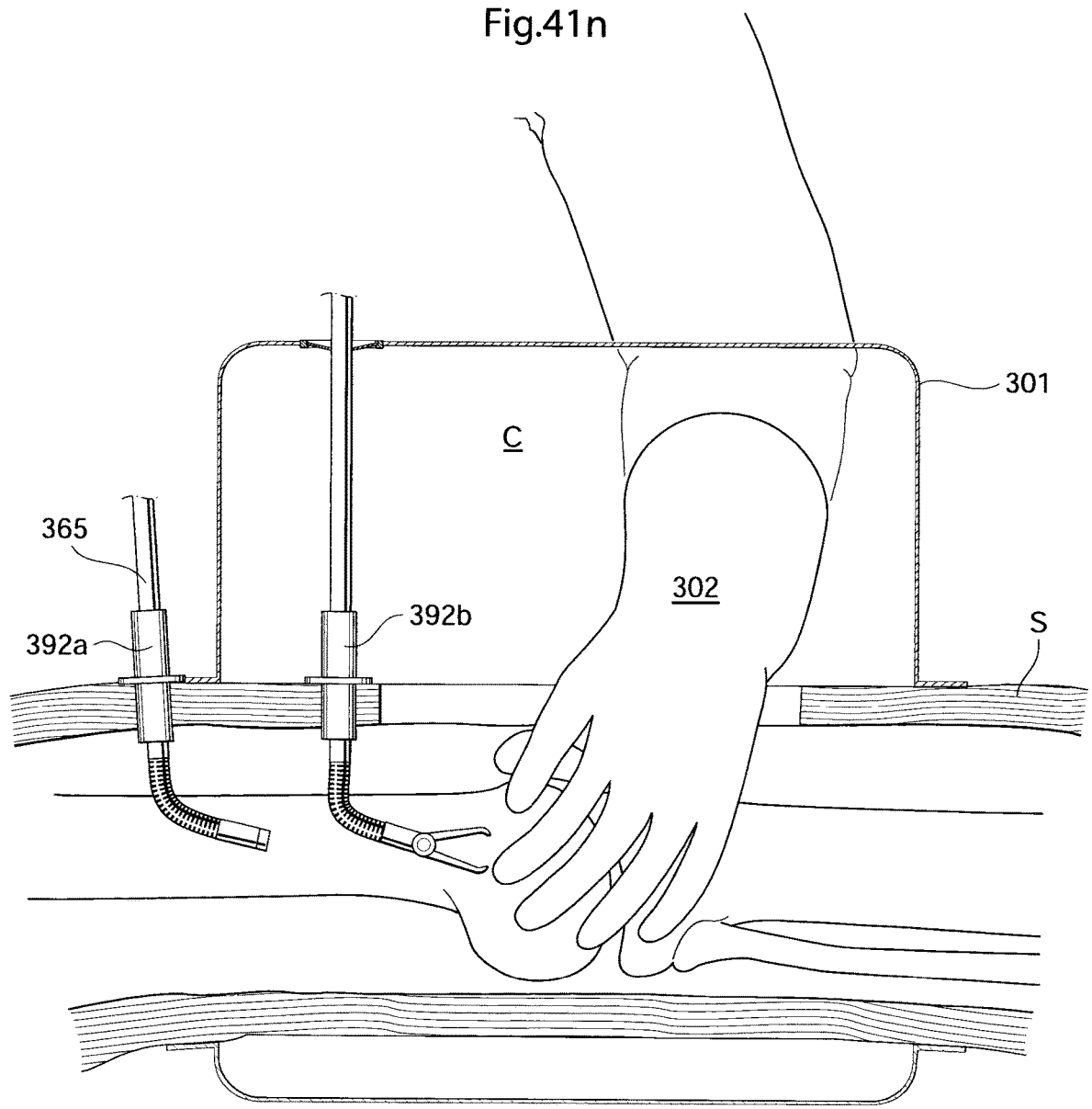

FIG. 41*n* shows how the medical device shown in FIGS. 29-41*l* may be used. The medical device 300 comprises a glove 302 integrated in the wall 301 and a camera 365 placed in a trocar placed through the skin S of the patient, outside of the medical device 300. The medical device 300 further comprises a trocar 392*a* placed inside the chamber C of the medical device 300 and into an area of the knee of the patient. FIG. 41*n* schematically illustrates how the surgeon manipulates the knee in the sealed environment using the glove 302.

Figure 41O:
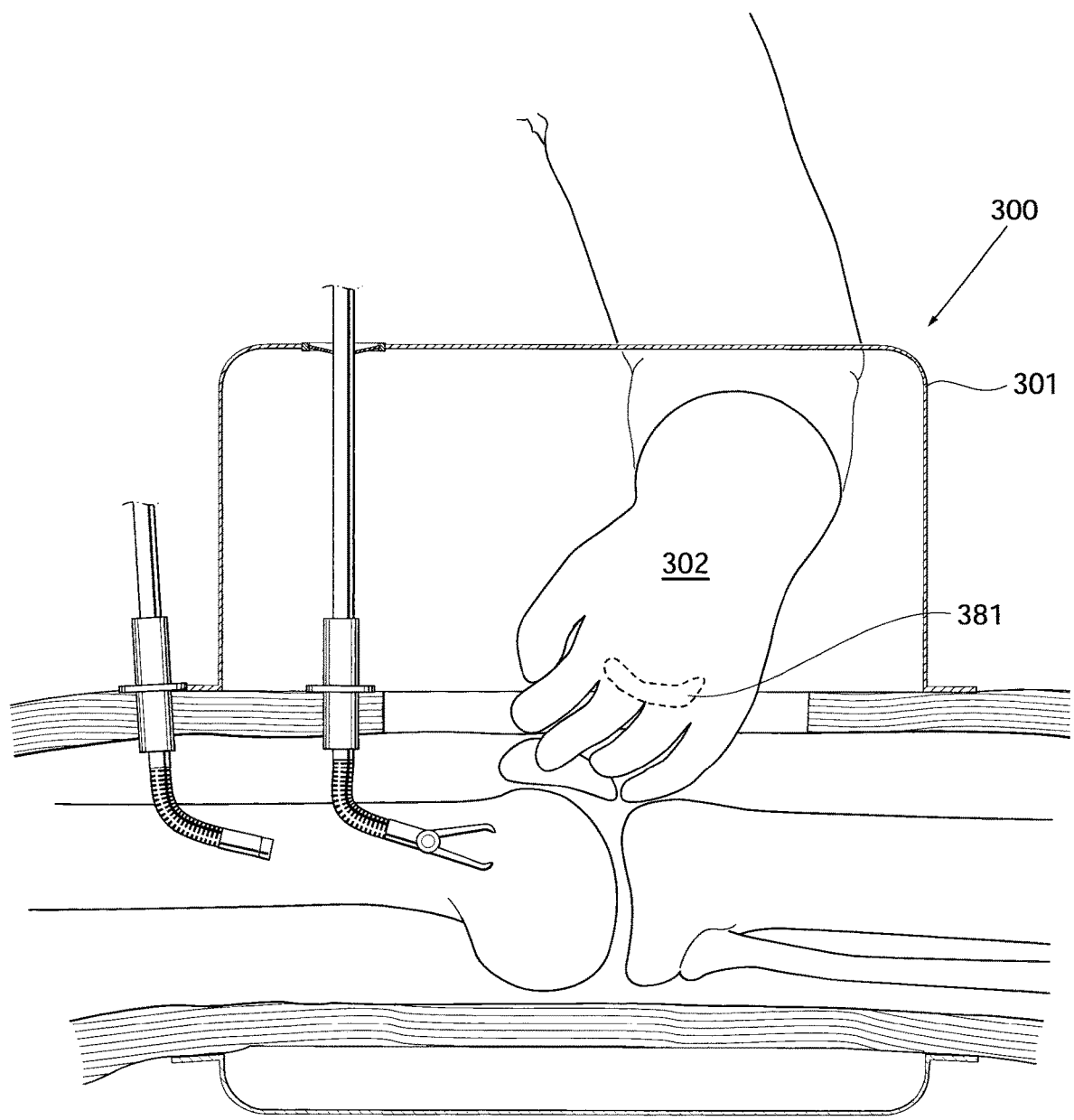
Figure 41P:
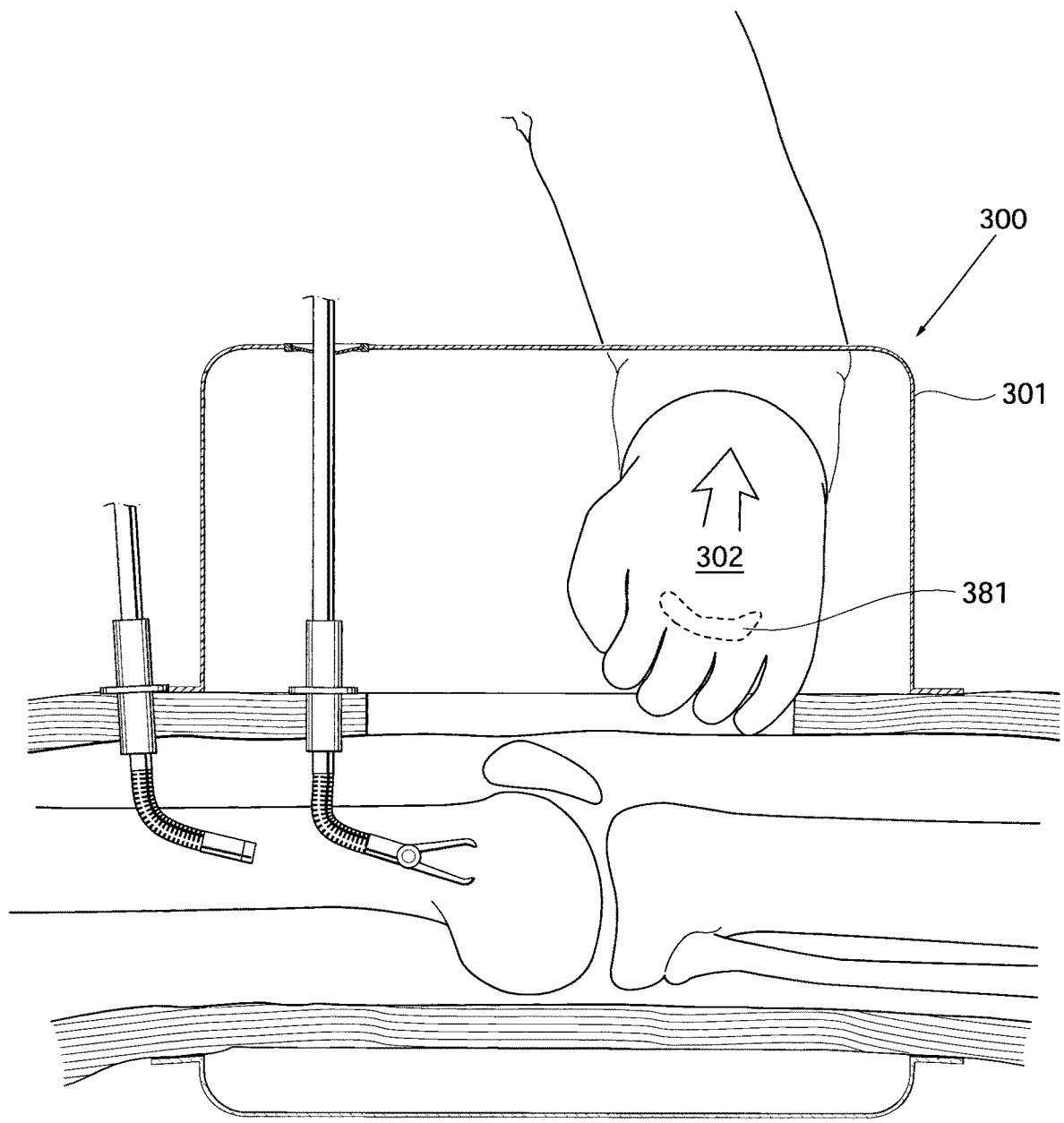

FIGS. 41*o*, 41*p* shows the medical device when the surgeon removes a specimen 381 from the knee of the patient using the glove 302 integrated in the wall 301 of the medical device 300.

FIG. 41*q* shows the medical device 300, when the surgeon has turned the integrated glove 302 inside-out such that the specimen 381 can be contained within the integrated glove 302. By isolating the specimen 381 inside of the glove 302, the specimen 381 is removed both from the rest of the body of the patient and from the ambient environment A, and thereby does not risk to infect any other portion of the patient's body or medical staff with any infectious disease.

FIGS. 42*a*-53*r* shows embodiments of the medical device in which the medical device comprises a sealing device comprising a pressure sealing member adapted to exert a force on the skin of the patient and thereby seal between the medical device and the skin of the patient.

42*a* shows a medical device 400 for performing surgical procedures. The medical device 400 comprises a wall 401 enclosing a chamber C in which a part of a surgical procedure can be performed. The chamber C is adapted to, after an incision has been created in the skin of the patient, be in fluid connection with a cavity in the patient's body via the incision in the skin of the patient. The medical device 400 is according to the embodiment shown in FIG. 42*a* adapted to hold a pressure within the chamber C exceeding atmospheric pressure, a pressure which is supplied by the pressurized fluid in the pressurized fluid tank 412 through the fluid conduit 410*a*. According to the embodiment shown in FIG. 42*a*, the medical device 400 comprises an adhesive surface 450 for fixating the medical device 400 to the skin of the patient. The medical device 400 is adapted to be positioned in connection with the skin of the patient, for creating a substantially airtight seal between the medical device 400 and the skin of the patient prior to the incision in the skin of the patient, which creates the fluid connection between the cavity within the patient and the chamber C. According to the embodiment shown in FIG. 42*a* the medical device 300 is adapted to enable manual manipulation within the chamber C enclosed by the medical device 300 and therefore has a volume being larger than 500 000 mm3. According to the embodiment shown in FIG. 42*a* the wall 401 of the medical device 400 comprises two integrated gloves 402*a*, 402*b* for enabling manual manipulation within the chamber C, however, in other embodiments the gloves 402 could be replaced by for example ports for enabling manipulation within the chamber C using suitable instruments. The embodiment shown in FIG. 42*a* additionally comprises a pressure sealing 405" adapted to be inflated for pressing against the skin of the patient and thereby sealing between the chamber C within the medical device 400 and the ambient environment. The pressure sealing 405" is inflated though a fluid conduit 410*b* connected to a pressure source, in this embodiment a pressurized fluid tank 412. In the embodiment the medical device is fixated to the patient by means of an adhesive surface 450 adapted to withstand the force created by the inflated pressure sealing 405".

Figure 42A:
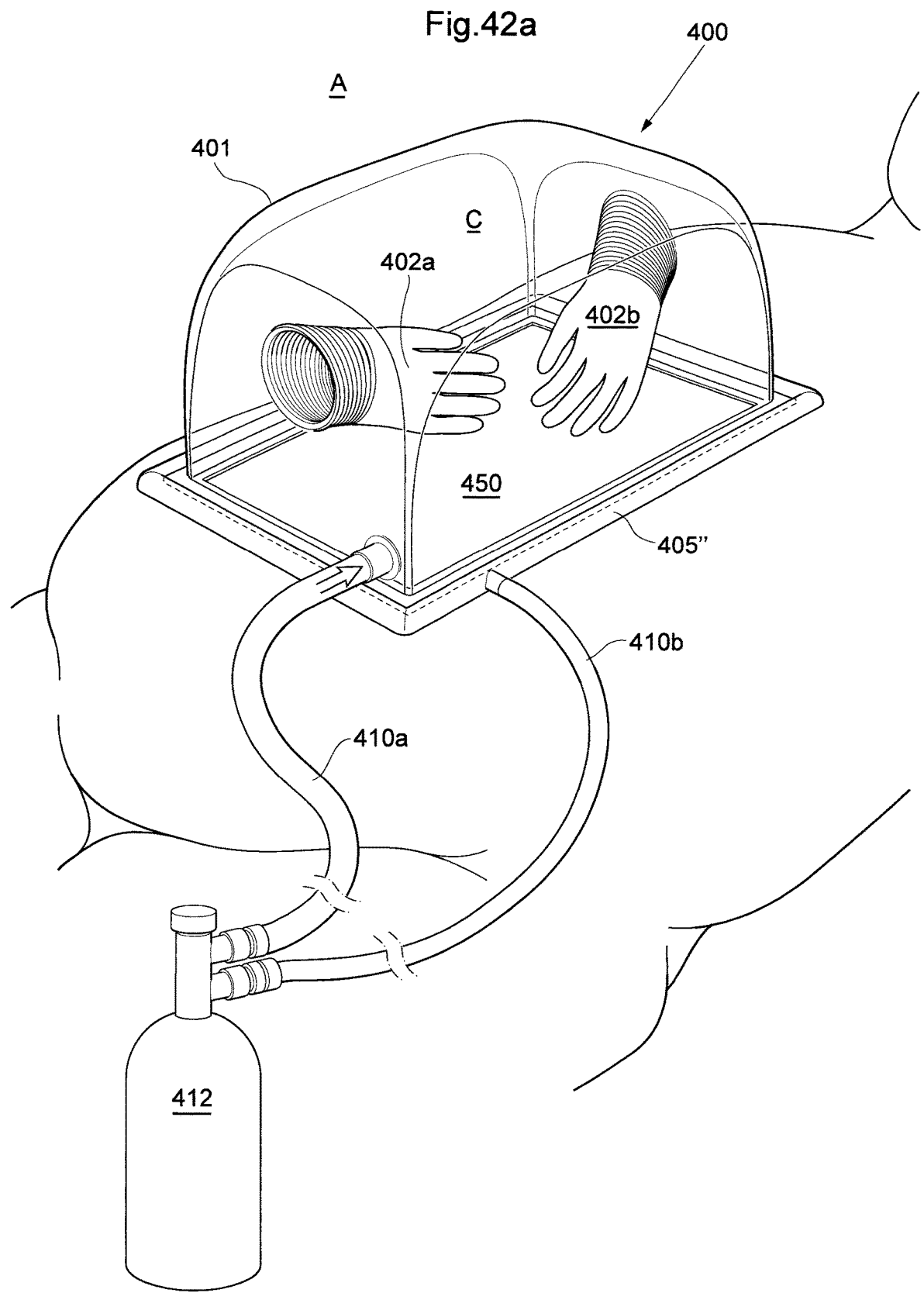
FIG. 42a shows an embodiment of the medical device having a pressure sealing.
Figure 42B:
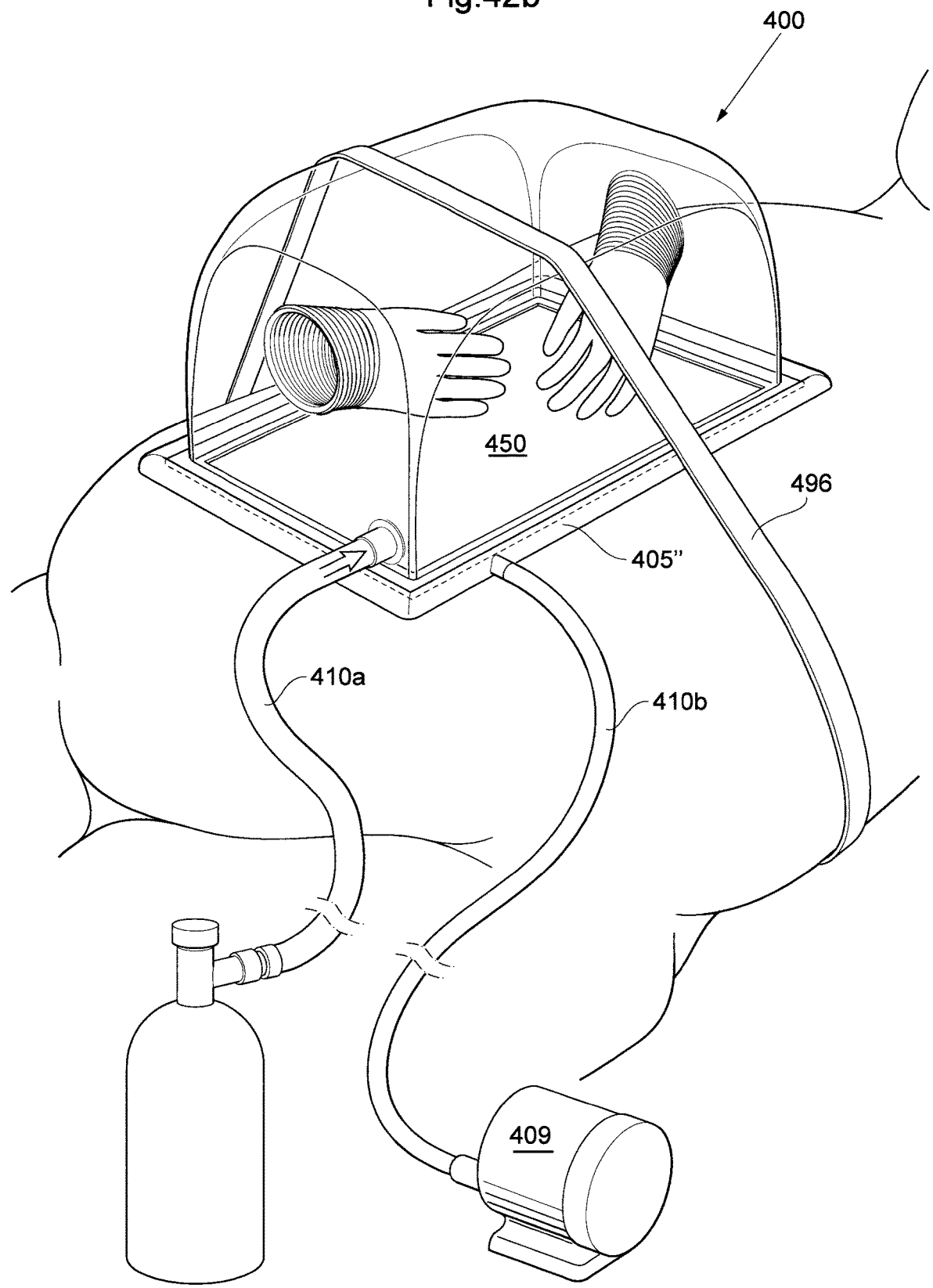
FIG. 42b shows the embodiment of FIG. 42a with a band, FIG. 42c shown an embodiment of the medical device, when an incision is performed in the medical device.

FIG. 42*b* shows an alternative embodiment of the concept disclosed with reference to FIG. 42*a*. In FIG. 42*b* the fixation of the medical device 400 is assisted or replaced by a holding member 496 pressing the medical device 400 against the skin of the patient. The holding member 496 could be required if the pressure needed to seal between the skin if the patient and the medical device 400 needs to be particularly large, which for example could depend on the positioning of the medical device 400. The other difference from the embodiment shown in FIG. 42*a* is that the source of pressure to the sealing 405" comes from a fluid pump 495 and the fluid is preferably regular air coming from the ambient environment. The use of a different pressure source for the sealing 405" could be an advantage when the available pressurized fluid is scarce or when it is important not to mix the fluid going into the chamber C with the fluid adapted to be in the sealing 405", the fluid adapted to be in the sealing 405" could be a liquid fluid while the fluid adapted to fill the chamber C could be a gaseous fluid.

Figure 42C:
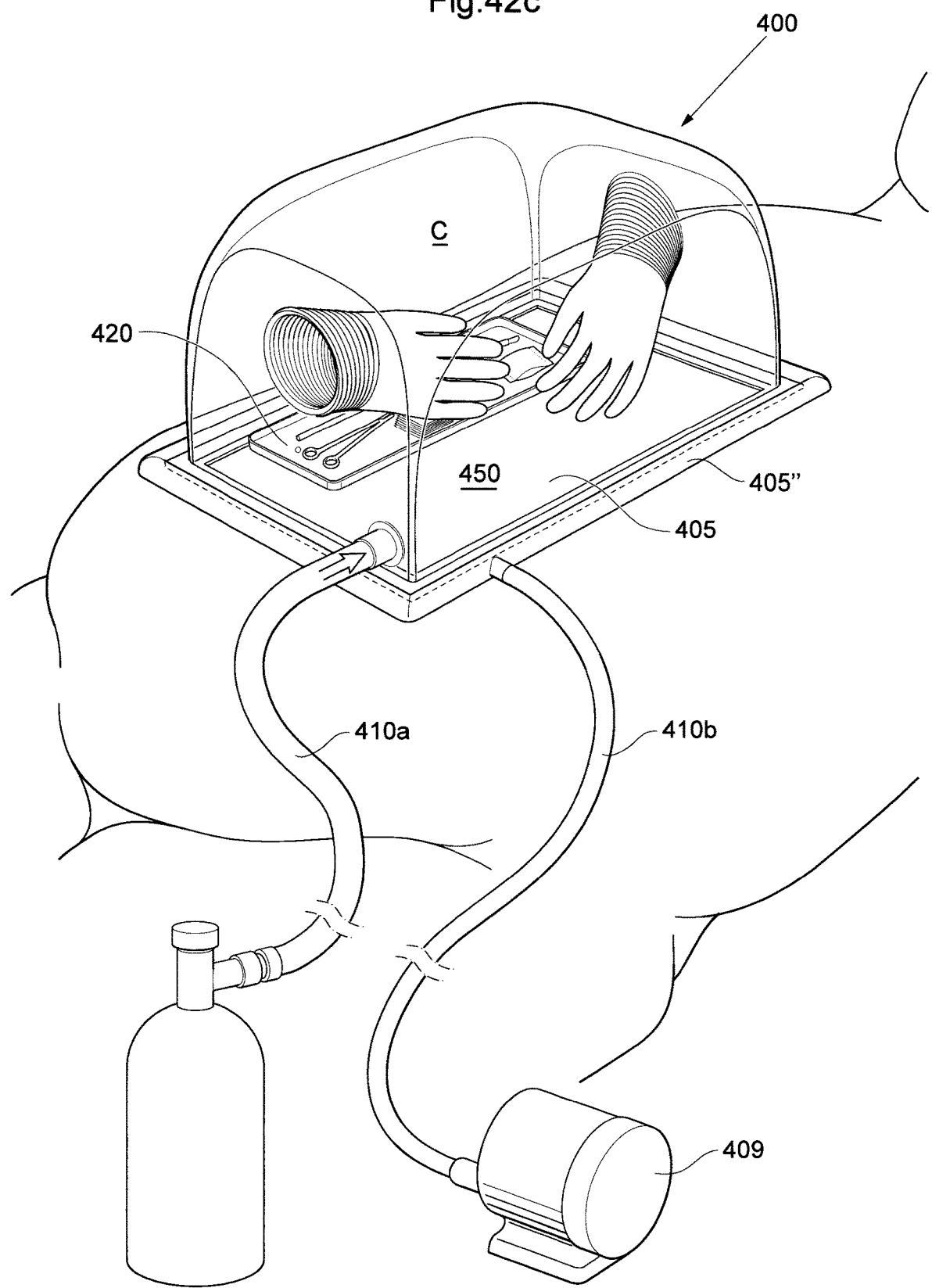

FIG. 42*c* shows the medical device according to the embodiment shown in FIG. 42*b*, when in use. The medical device 400 has been positioned in contact with the skin of the patient and fixated to the skin of the patient by means of an adhesive surface 450 applied on the entire portion of the wall 401 in connection with the skin of the patient. The positioning of the medical device 400 has taken place prior to the incision in the skin of the patient and the incision is thereby made though the wall 401 of the medical device 400 as well as through the skin of the patient, which reduces the risk that infectious bacteria or virus present on the skin of the patient enters the body of the patient and/or the chamber C of the medical device 400. The embodiment shown in FIG. 42*c* also shows a device and/or instrument mount 420 for retaining pre-inserted devices and instruments in the chamber C. In some of the embodiments of the medical device 400, the medical device 400 is adapted to be disposable and made for a specific surgery, in which case the pre-placed instruments are adapted for that specific operation and disposed of along with the rest of the medical device 400 after the surgery has been completed.

Figure 43:
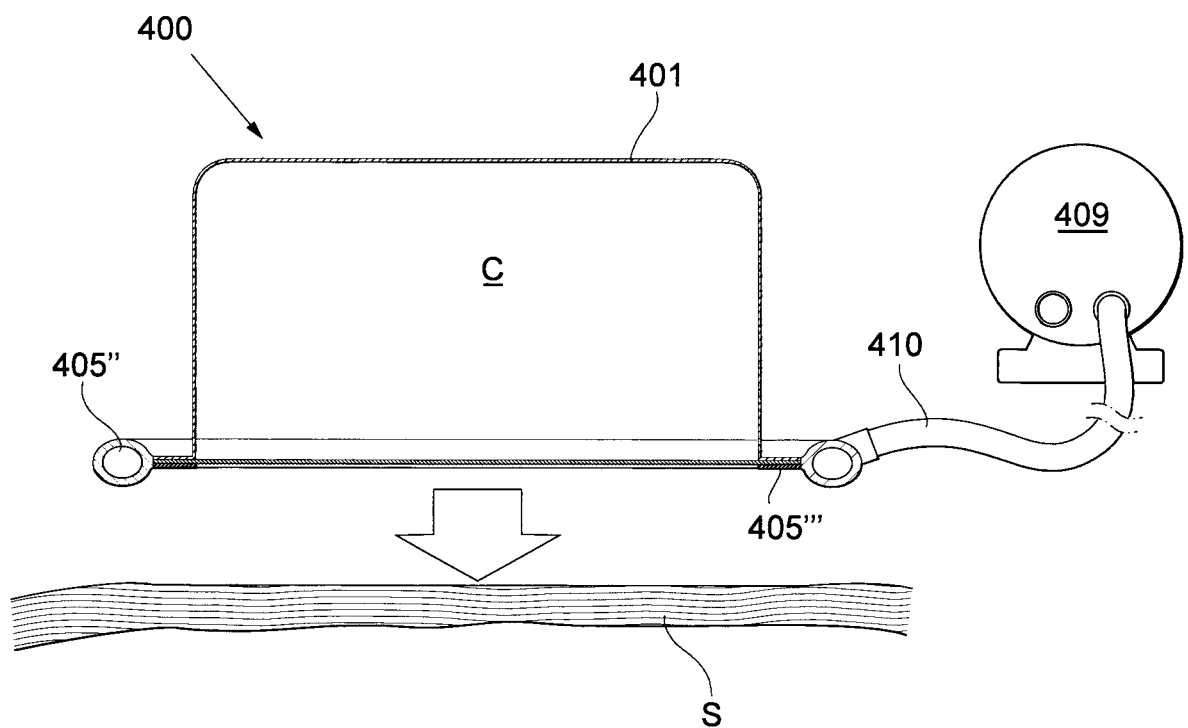
FIG. 43 shows the placing of a medical device on the skin of a patient.

FIG. 43 shows the medical device 400 in section when being applied to the skin S of the patient. The medical device 400 comprises the sealing device comprising the pressure 3 sealing member 405" connected to a fluid pump 409 by means of a pressure conduit 410. In the embodiment shown in FIG. 43 the medical device additionally comprises an adhesive seal 405"' adapted to be in connection with the skin S of the patient, however in other embodiments the adhesive 405"' could be excluded.

Figure 44:
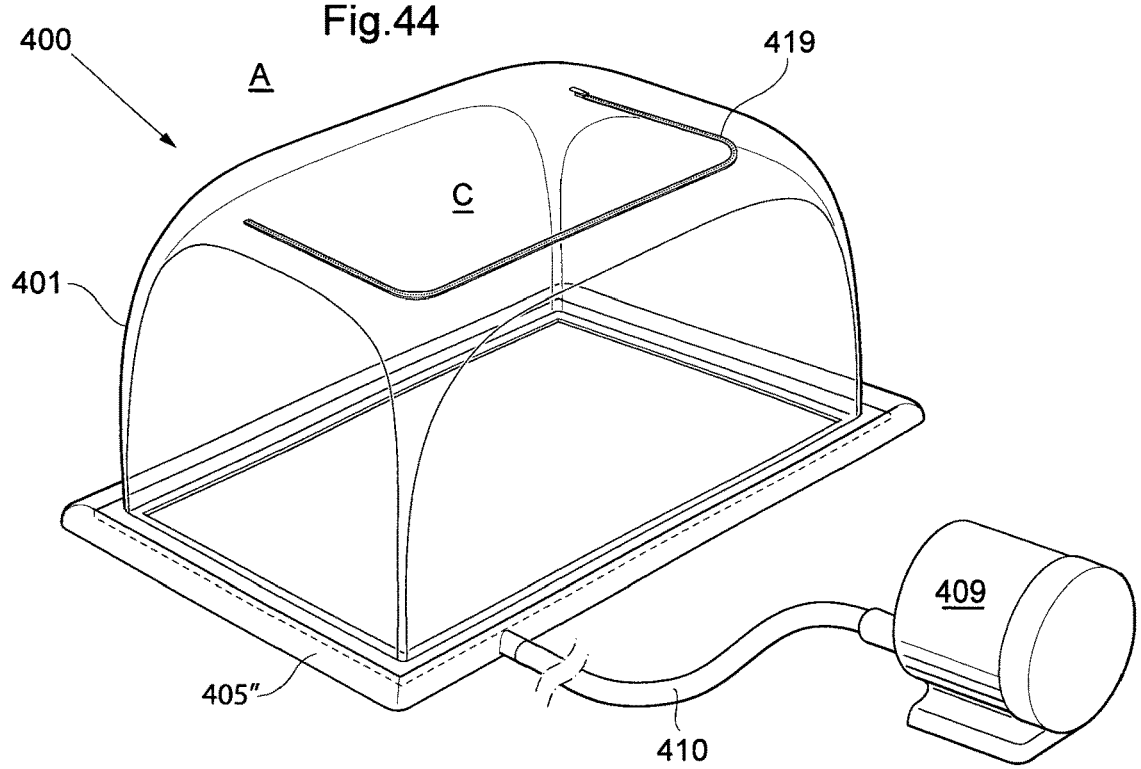
FIG. 44 shows an embodiment of the medical device having an opening.

FIG. 44 the shows the medical device 400 according to an embodiment similar to the embodiment disclosed with reference to FIG. 43, with the addition that a portion of the wall of the medical device 400 is possible to open by means of a zipper 419 between the chamber C in the medical device 400 and the ambient environment A for allowing passage of objects between the chamber C and the ambient environment A.

Figure 45:
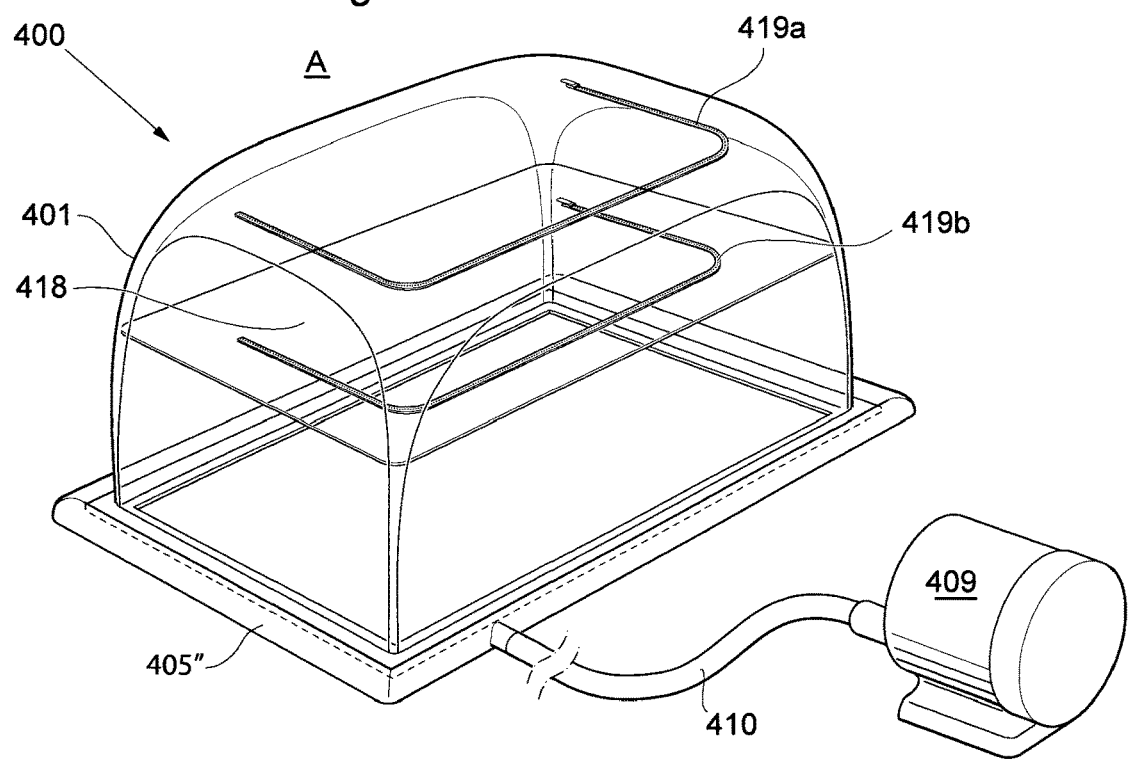
FIG. 45 shows an embodiment of the medical device having an airlock.

FIG. 45 the shows the medical device 400 according to an embodiment similar to the embodiment disclosed with reference to FIG. 43, with the addition that the medical device 400 further comprises an airlock sluice 418 for allowing passage of objects between the chamber C and the ambient environment A. The airlock sluice 418 comprises an outer zipper 419*a* between the airlock sluice 418 and the ambient environment A, and an inner zipper 419*b* between the airlock sluice 418 and the ambient environment.

FIG. 46 shows a section of an alternative to the medical device 400 shown in FIG. 42*a* having a coupling 480 integrated in the wall 401. The coupling 480 enables the changing of objects from for examples wall ports 417, to insets 442 for example comprising surgical gloves 402 or device or instrument mounts 420. The coupling 480 comprises a valve member 438 for closing the hole in the coupling 480 when objects should be exchanged such that the chamber C in the medical device 400 remains closed. The device or instrument mount 420 could for example be adapted to hold surgical instruments and/or implants or parts of implants. The medical device 400 is according to this embodiment adapted to be fixated to the skin of the patent by the pressure sealing 405", further disclosed with reference to FIG. 43 which is assisted by a large portion of the wall 401 of the medical device 400 comprising an adhesive surface 450.

FIG. 47 shows a section of the medical device 400 showing the coupling 480 integrated in the wall 401 in further detail when the an airlock 418 for transferring objects between the ambient environment A and the chamber is being provided. According to the embodiment shown in FIG. 47 the airlock sluice 418 comprises a first valve member 438*a* separating the airlock sluice 470 from the ambient environment A, and e second valve 438*b* separating the airlock sluice 418 from the chamber. The airlock sluice 418 is provided between the first 438a and second 438b valves and could for example be used for passing a medical device into the camber C, or for passing a specimen or sample out of the chamber.

Figure 48A:
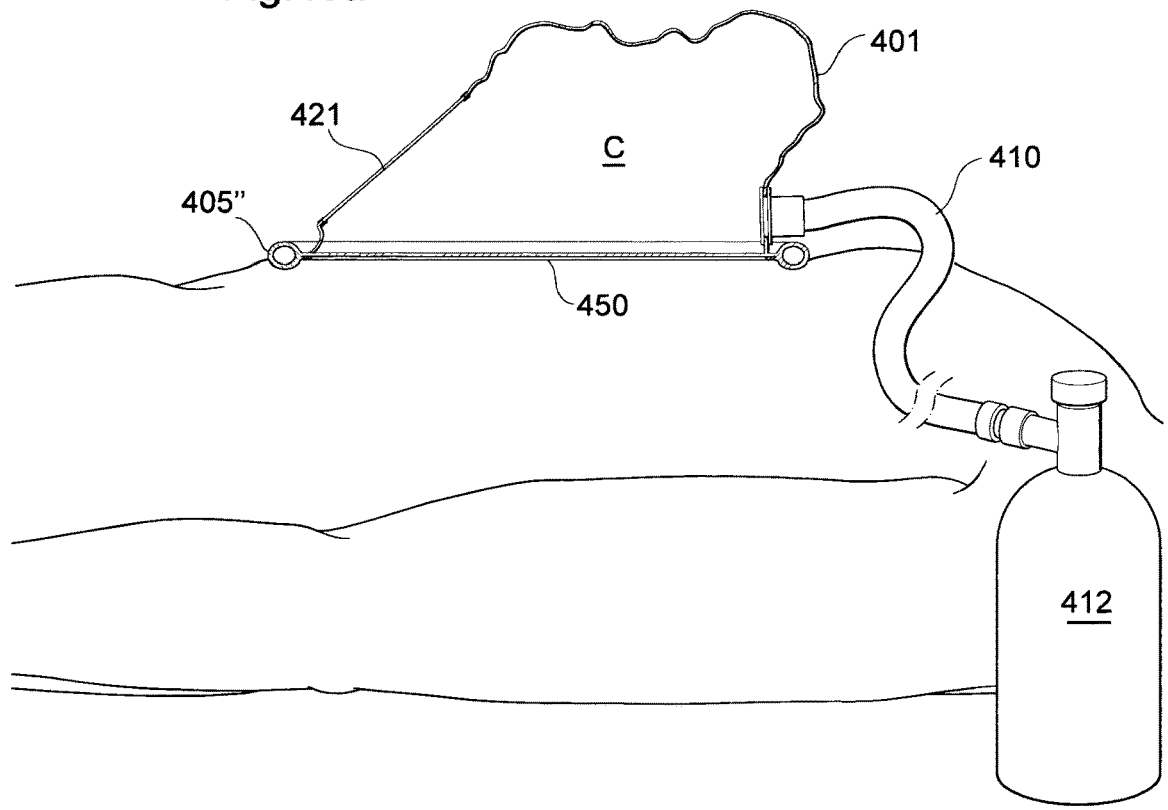
FIG. 48a shows the medical device when applied to the abdomen of a patient, in a deflated state.

FIG. 48a shows the medical device according to an embodiment similar to the embodiment shown with reference to FIG. 43. However, the wall 401 of the medical device of FIG. 48a is partially collapsible, and the collapsible portion is adapted to be inflated by a gaseous fluid for defining the chamber C. The medical device is inflated by a pressurized fluid entering the medical device 400 through a fluid conduit 410. The inflating of the wall 401 in which a window 421 is integrated, positions the window 421 in a position suitable for viewing the procedure being performed on the patient.

Figure 48B:
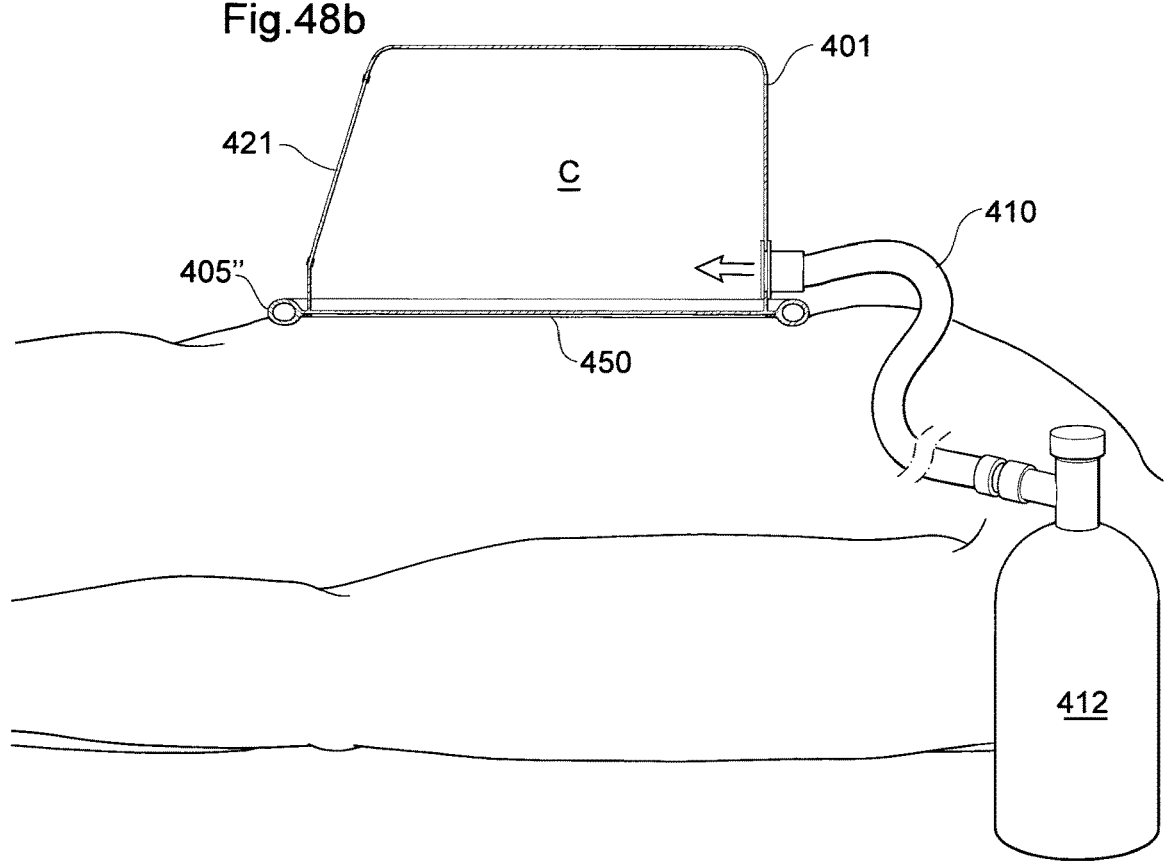
FIG. 48b shows the medical device when applied to the abdomen of a patient, in an inflated state.

FIG. 48b shows the medical device 400 when inflated such that the wall 401 separates the chamber C within the medical device 400 from the surrounding environment and thus creates an operating environment which is separated from contaminations from the outside. The window 421 has been positioned by the inflating of the medical device 400, such as to enable viewing of the portion of the wall 401 comprising the adhesive surface 450. In some of the embodiments disclosed the entire portion of the wall 401 contacting the skin of the patient comprises an adhesive surface 450, such that the incision in the patient is performed through the wall 401 and further through the skin of the patient (this is further disclosed with reference to FIG. 30). This reduces the risk that infectious objects can be transferred from the skin of the patient to the incision in the patient if the skin of the patient is not adequately disinfected. In some applications it is conceivable that a normal laparoscopic procedure is performed with the medical device positioned but not inflated. The medical device is then only inflated at the end of the procedure, for example when a specimen is to be removed from the body of the patient. The inflation of the medical device 400 could continue until the pressure inside the medical device 400 exceeds atmospheric pressure, which is required in some applications.

Figure 49A:
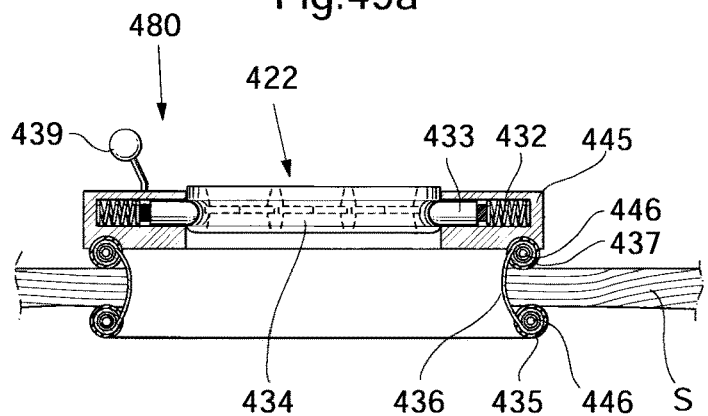
FIGS. 49a, 49b and 49c shows a coupling in section.

FIG. 49a shows an embodiment of a detachable port arrangement which could be positioned in the chamber of the medical device disclosed with reference to FIGS. 42-48. The port arrangement includes an intra body ring 435 adapted to be placed at the inside of the patients skin S around an incision, and an outer ring 437 adapted to be placed on the outside of the patients skin S around the incision. Between the intra body ring 435 and outer ring 437, a connecting member in the form of an annular retractor membrane 436 is positioned adapted to exert a pressure on the skin S or tissue at the incision to seal between the rings 335; 337 and the skin S or tissue and additionally for retracting the skin S and thereby keep the incision open. The retractor membrane 436 is preferably made from a resilient or elastic polymer material. The outer ring 437 comprises an integrated roll up system 446, which may be spring loaded and adapted to create a suitable pressure on retractor membrane 436 to keep the incision open.

The port arrangement shown in FIG. 49a also includes a coupling 480 having a rigid annular seating 445 attached to the outer ring 437, spring loaded protruding members 433 are arranged in radial bores in the seating 445 and a lever 439 is connected to the protruding members 433 to enable retraction thereof against the action of springs 432. The port arrangement further includes a self sealing body port 422 held by the coupling 480. The body port 422 comprises a disc-shaped self sealing membrane 443, further shown in FIG. 49b, fixated to a rigid ring having an outer circumferential recess 434 that receives the protruding members 433 of the coupling 480. The self sealing membrane 443 has a small self sealing hole 444 placed centrally in the membrane 443. For example, the self sealing membrane 443 may be made from a gel-type material being elastic enough to enable a deformation large enough for a person's hand to pass through the small self sealing hole 444 while still contracting enough to create an airtight seal between the chamber and the outside environment.

The coupling 480 described above enables quick exchange of the body port 422. Thus, the surgeon may release the body port 422 from the coupling 480 by simply pulling the lever 439 such that the protruding members 433 disengage from the recess 434 of the body port 422, whereby the body port 422 can be removed.

Figure 49B:
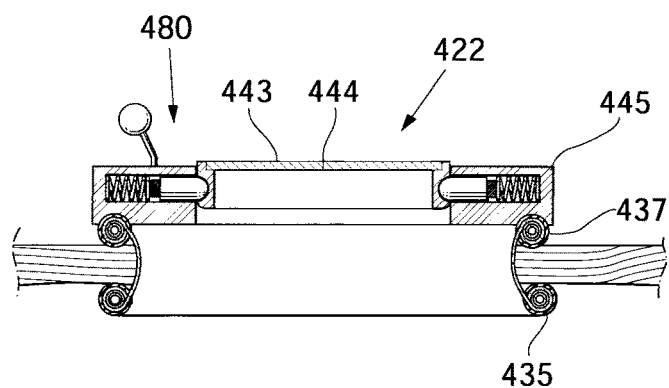

FIG. 49b is a cross-sectional view of the port arrangement shown in FIG. 49a, to more clearly illustrate the body port 422 with its self sealing membrane 443 and small hole 444.

Figure 49C:
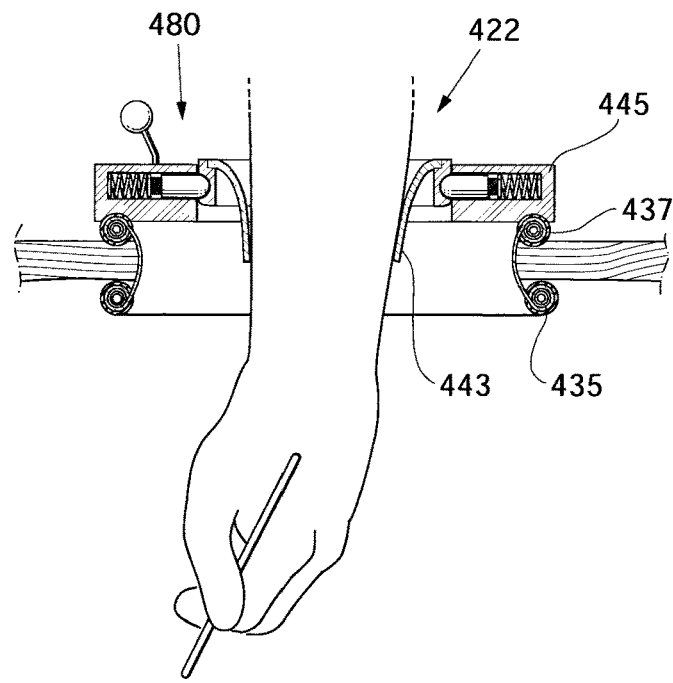

FIG. 49c shows the self sealing body port 422 when the hand of a surgeon is placed through the hole 444 in the membrane 443 and thus enabling manual manipulation within the body of the patient.

Figure 50A:
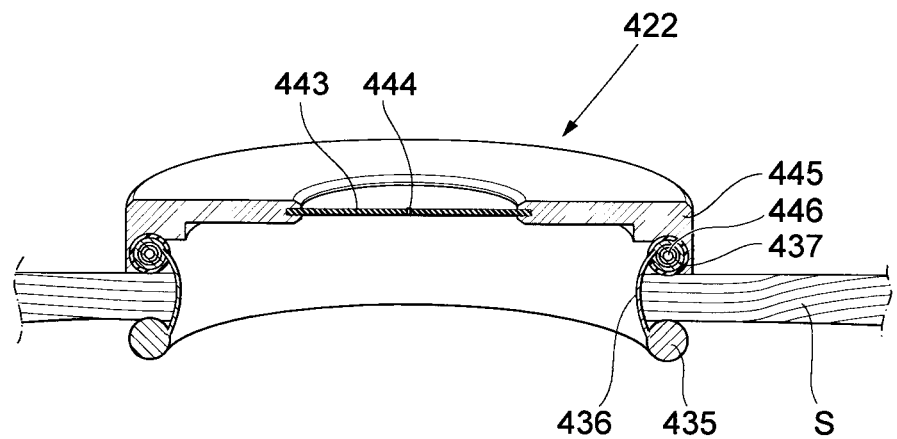
FIGS. 50a and 50b shows a self sealing port, in section.
Figure 50B:
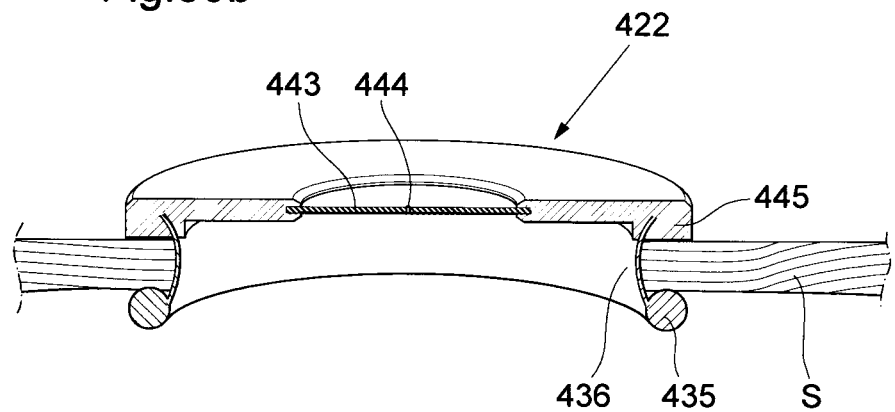

FIG. 50a shows a self sealing body port 422 in a close-up, in section. The self sealing body port 422 could be connected to the coupling 480, for example as disclosed with reference to FIGS. 49a-c, which in turn is connected to any of the medical device disclosed with reference to FIGS. 42-48, or the self sealing body port 422 could be fixated to a retractor, as shown in FIGS. 50a and 50b. The self sealing port 422 comprises a self sealing membrane 443 fixated to a rigid housing part 445 of the self sealing port. The self sealing membrane 443 having a small self sealing hole 444 centrally in the membrane 443. The self sealing membrane 443 is for example made from a gel-type material being elastic enough to enable a deformation large enough for a person's hand to pass through the small self sealing hole 444 while still contracting enough to create an airtight seal between the sealed environment and the outside environment. The medical device being fixable to a retractor comprising one intra body ring 435 adapted to be positioned on the inside of the patients skin S, and one ring 437 adapted to be placed on the outside of the patients skin S. Between the intra body ring 435 and the ring 437 adapted to be placed on the outside of the patients skin S a retractor membrane 436 is positioned which is adapted to exert a pressure of the cut surfaces of the incision for retracting the skin S and thereby keeping the wound open. The retractor membrane 436 is preferably made from a resilient of elastic polymer material, such a silicone. The outer ring 437 comprises an integrated roll up system 446 which could be a spring loaded roll up system 446 adapted to create a suitable pressure on retractor membrane 436 for keeping the wound open.

FIG. 50b shows an alternative embodiment of the self sealing port 422, with the difference that the retractor membrane 436 is made from a material elastic enough such that one end of the retractor membrane 436 could be fixedly fixated to the rigid part 445 of the port.

Figure 51:
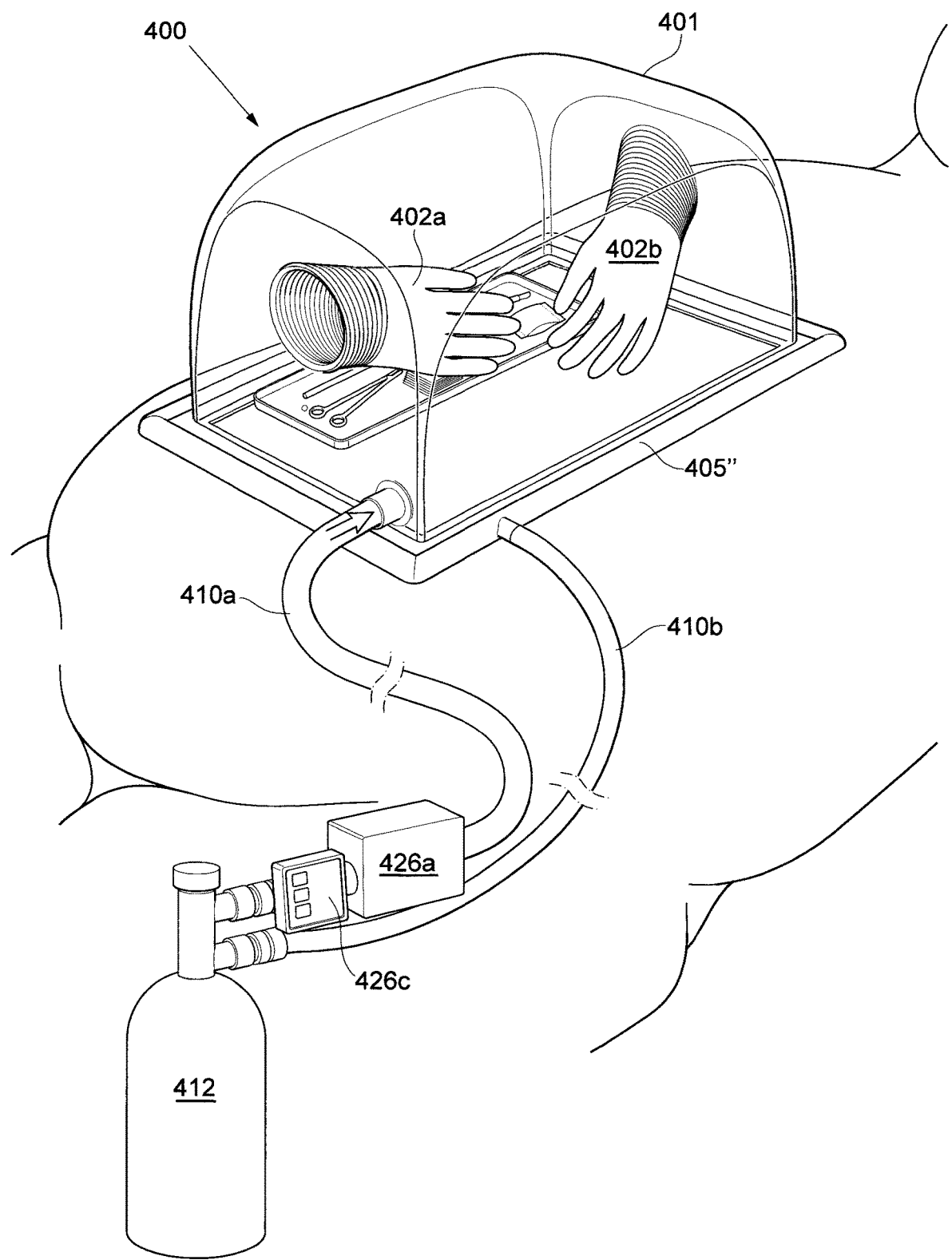
FIG. 51 shows an embodiment of the medical device comprising a pressure sealing.

FIG. 51 shows the medical device as shown in FIG. 42a with the addition that the embodiment comprises a sterilizing unit 426a adapted to sterilize the gaseous fluid entering the medical device 400. In the embodiment disclosed herein, the gaseous fluid entering the medical device 400 originates from a pressurized tank 412 and could be pre-sterilized, however, in other embodiments, it is conceivable that the gaseous fluid is the surrounding air which is pressurized (such as further disclosed with reference to FIG. 52). In the embodiments where the surrounding air is used to inflate the medical device 400 and constitute the operating environment this air needs to be properly sterilized. The medical device 400 further comprises a tempering unit 426*c* which could be provided to heat or cool the gaseous fluid inflating the medical device 400. In cases when the surrounding environment is cold the tempering unit 426*c* could be used to raise the temperature of the sealed environment to provide beneficial operating circumstances both for the patient and for the surgeon. In cases when the surrounding environment is hot, the tempering part of the system 426*c* could be used to lower the temperature of the sealed environment both to provide beneficial operating circumstances, both for the patient and for the surgeon, and for providing a temperature inhibiting bacterial and viral infections. The tempering unit 426*c* could comprise a temperature regulating device for setting the required temperature.

Figure 52:
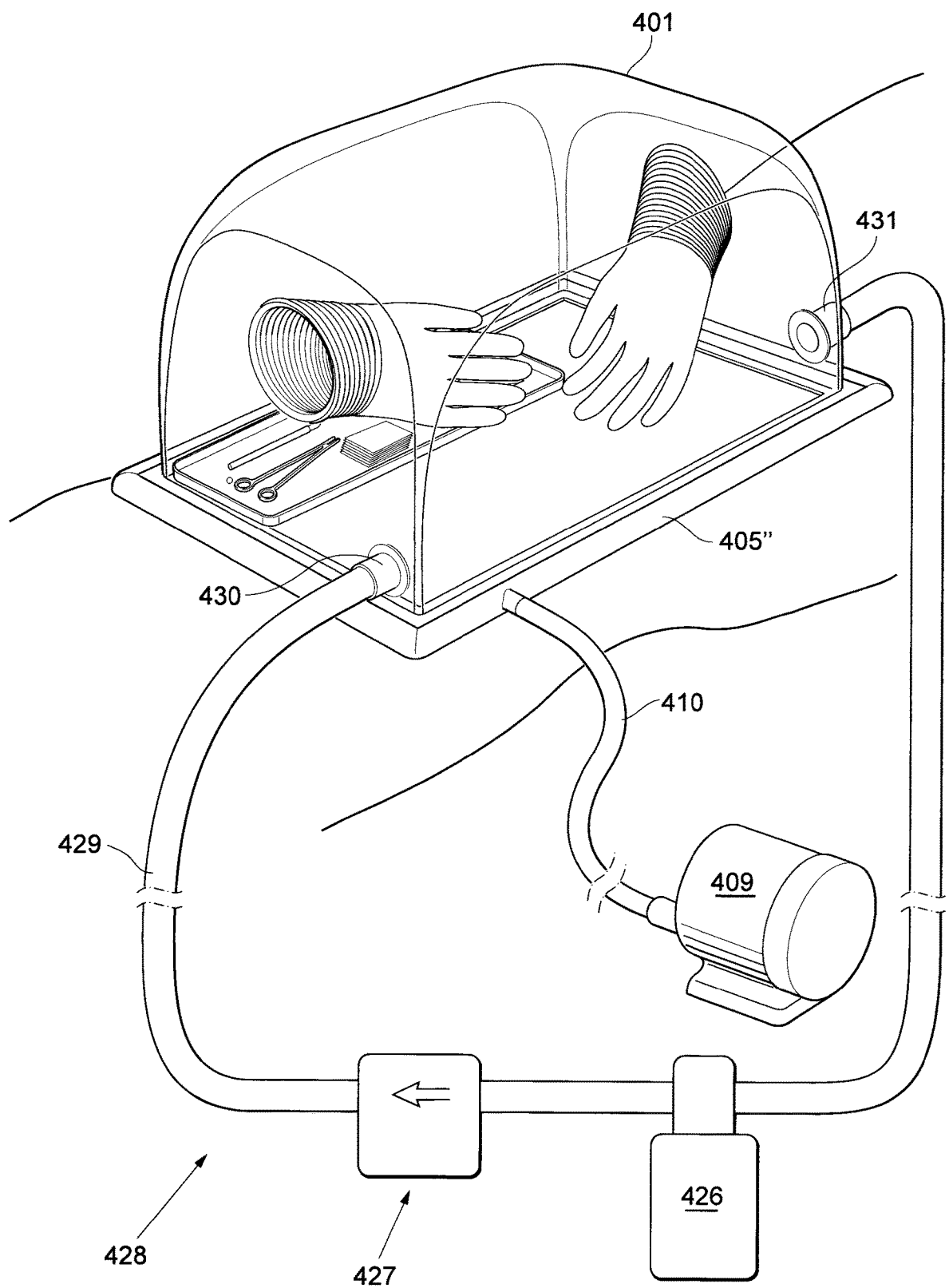
FIG. 52 shows an embodiment of the medical device comprising a pressure sealing.

FIG. 52 shows a medical device similar to the embodiment disclosed in FIG. 51 but comprising a system 428 for circulating a fluid through the sealed environment of the medical device. The system comprises a fluid conduit 429 connected at an inlet 430 placed in the wall 401 for supplying fluid to the sealed environment, and an outlet 431 for draining the fluid from the sealed environment. The fluid is circled by means of a pumping unit 427 and is circled via a sterilizing/filtering/tempering/humidifying unit 426 adapted to remove impurities, sterilize, temper and increase the humidity of the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon. The medical device according to FIG. 51 and FIG. 52 are shown with a pressure sealing members 405", however, it is equally conceivable that the medical device comprises vacuum sealing members.

Figure 53A:
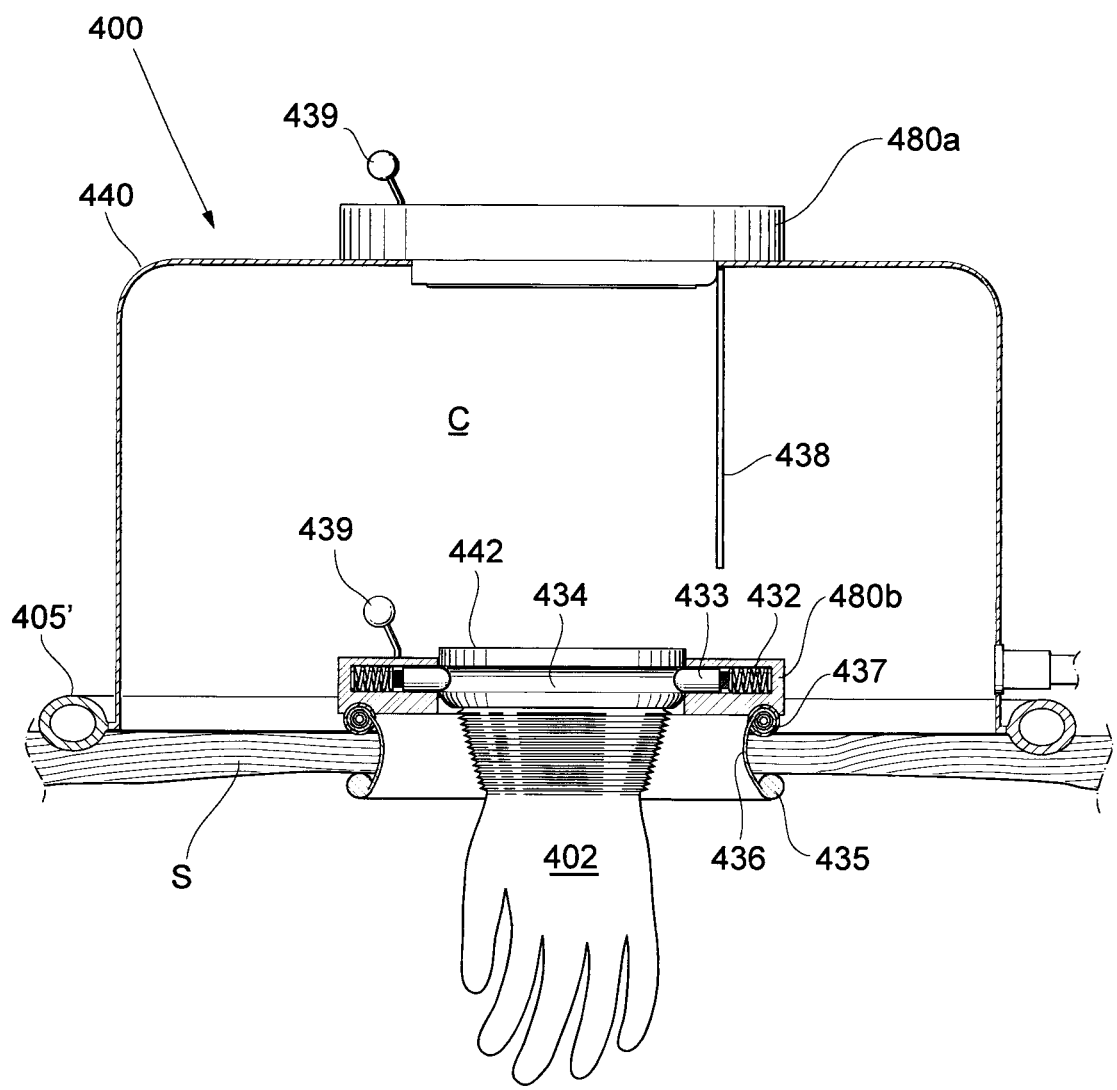
FIG. 53a shows an embodiment of the medical device, in section.

FIG. 53*a* shows a modification of the embodiment disclosed with reference to FIG. 43 in which the medical device further comprises an upper 480*a* and a lower 480*b* coupling for fixating ring shaped objects which for example could be insets 442 or ports, where insets for example could be surgical gloves 402, or device and/or instrument mounts and ports could be endoscopic ports or hand access ports, such as the self sealing port disclosed with reference to FIGS. 4*a* and 4*b*. The couplings 480*a*; 480*b* comprises a releasing levers 439 for releasing the object. The levers 439 are connected to protruding members 433 which are spring loaded 432 from the rear in order to secure the recess 434 of the object. In the embodiment disclosed in FIG. 53*a*, the inset 442 fixated to the lower coupling 480*b* is a surgical glove 402 enabling manual manipulation within the body of the patient. The medical device shown in FIG. 53*a* further comprises a valve member 438 adapted to close the opening in the upper coupling 480*a*, when the upper coupling 480*a* is not in use. The upper coupling 480*a* is for example used for manual manipulation and preparation within the medical device 400, such that could be needed for preparing or changing an instrument or preparing an implant for implantation. The lower coupling 480*b* is for example used for endoscopic manipulation within the body of the patient, or manual manipulation for e.g. removing a specimen or positioning an implant.

FIG. 53*b* shows the lower coupling 431*b* in further detail when an inset 442 in the form of a surgical glove 402 is fixated to the lower coupling 480*b*. The retractor system comprising the intra body ring 435 and the ring 437 adapted to be placed on the outside of the patients skin S further comprises a retractor membrane 436 positioned such that it exerts a pressure on the cut surfaces of the incision for retracting the skin and thereby keeping the wound open. The retractor membrane 436 could be rolled by a roll up system 446 inside of the ring 437 adapted to be placed on the outside of the patient's skin for tightening the retractor membrane 436 such that the wound is kept open.

FIG. 53*c* shows the changing of objects in the lower coupling 480*b* from an inset 442 comprising a surgical glove 402 to an endoscopic body port 422 in the form of a multiport comprising three self sealing membranes 443. To quickly being able to switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the endoscopic body port 422 and inset 442 comprising surgical gloves could additionally be exchanged for device and/or instrument mounts, for example for holding instruments or implants.

FIG. 53*d-j* shows a further version of the medical device of FIG. 42*a*. In the embodiment of FIG. 53*d-j* the wall 401 of the medical device is inflatable, and the medical device is in its inflated state. When the chamber C is deflated it has a first volume i.e. when the upper 480*a* and lower 480*b* couplings are interconnected, and when the chamber C is inflated and the upper coupling 480*a* is disconnected from the lower 431*b* coupling it has a second volume, and the second volume is larger than the first volume. According to the embodiment shown in FIG. 53*d*, the second volume is larger than 500 000 mm3 and adapted to hold a pressure exceeding atmospheric pressure.

According to the embodiment shown in FIG. 53*d*-53*j* the chamber C further comprises a pouch 482 for holding a specimen 481 removed from within the body of the patient not to contaminate any other part of the body and create the possibility of delaying the removal of the specimen 481 until the procedure is concluded. The pouch 482 may be a pouch 482 which could be closed for creating a pouch-chamber within the chamber C for isolating the removed specimen 481 within the chamber C.

Figure 53D:
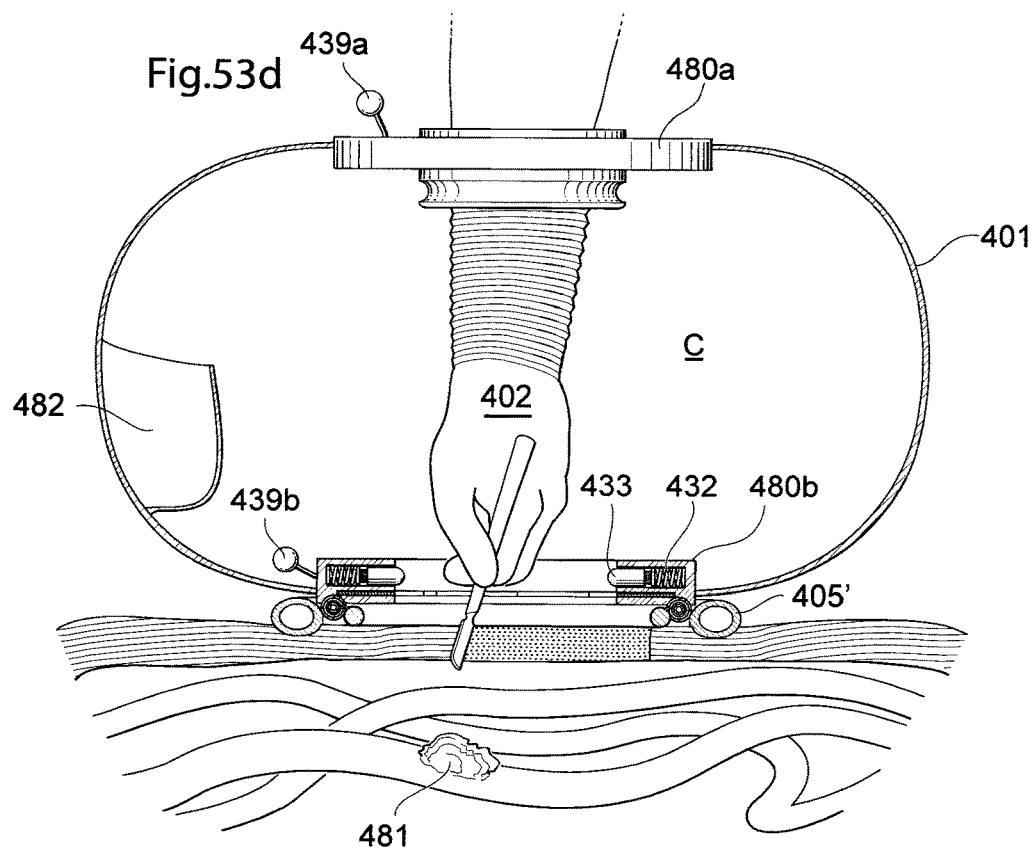
FIGS. 53d-53j shows an embodiment of the medical device being fixated to the patient and used.

In FIG. 53*d* a state is illustrated in which the cut in the patient's skin is being created by the surgeon by means of the inset 442 comprising the glove, latched to the upper coupling 480*a*. The medical device is fixated and sealed by means of the pressure sealing member 405" as the sealing device that is provided partially within the patient's body cannot be mounted until the cut in the patient's skin is concluded. The two different sealing device disclosed could in some embodiments be replaced by only one of the sealing device, or by a different sealing device, such as an adhesive sealing device.

Figure 53E:
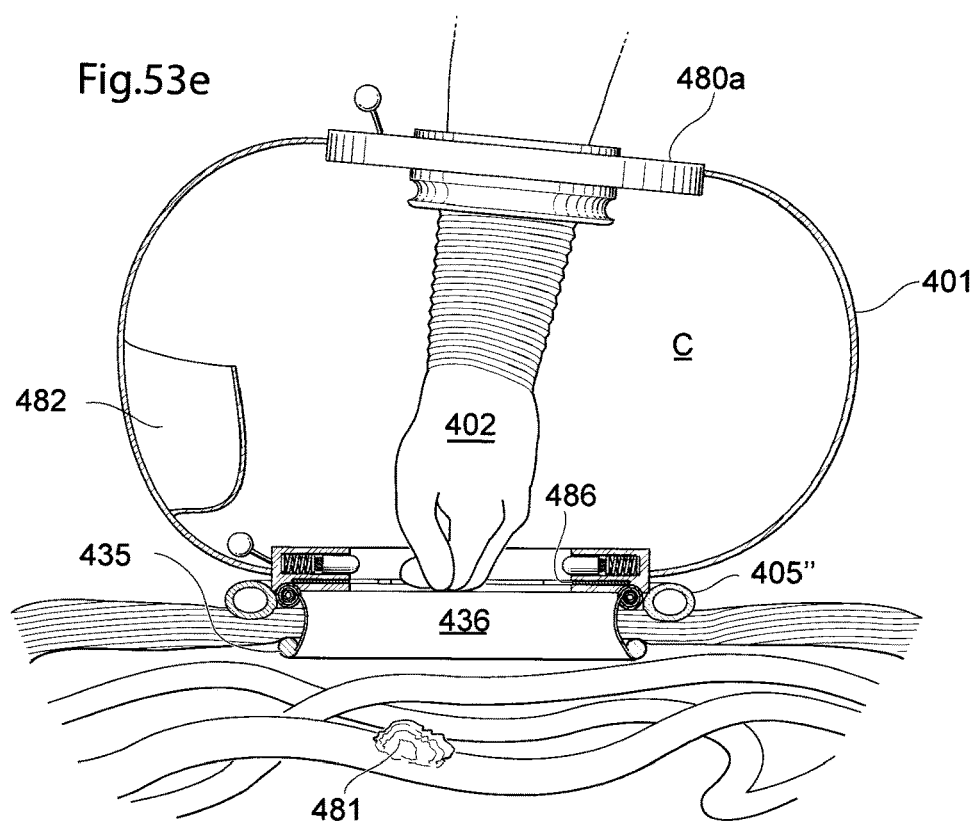

FIG. 53*e* shows the medical device, when the second sealing device 435, 436, 437 has been placed in the incision cut in the patient's skin. The wall 401 enclosing the chamber C is elastic or flexible which enables the surgeon move the upper coupling 480*a* in relation to the first part 480*b* for getting better access to different angles within the patient's body, for example for removing a specimen 481. The embodiment of FIG. 53*e* further comprises an iris valve 486 placed in the lower coupling 480b for closing the coupling 480b such that the chamber C is sealed from at least one of the ambient environment and a cavity in the patient. The closing of the iris valve 486 enables activity within the chamber C without maintaining a pressure in the chamber C, at the same time as a pressure and/or sealed environment can be maintained within the body of the patient.

Figure 53F:
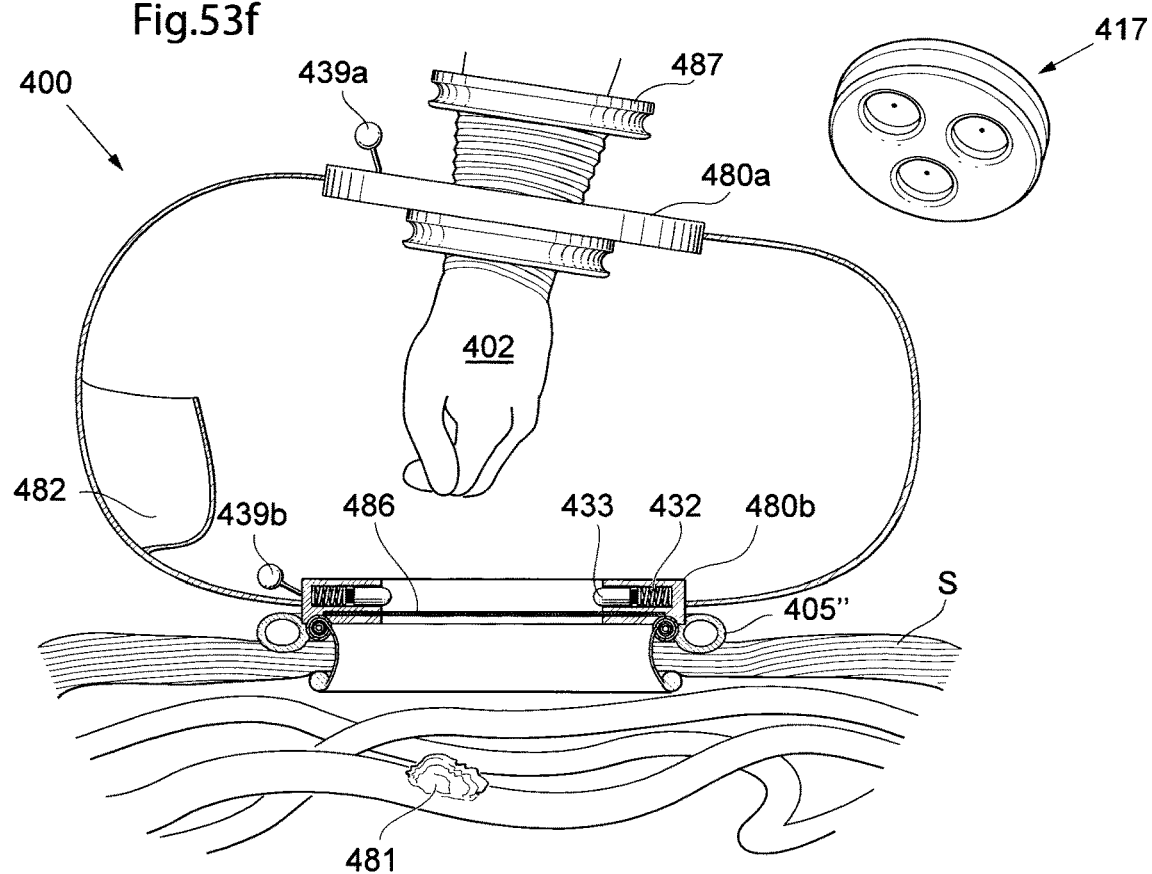

FIG. 53f shows the medical device 400 when the inset 442 comprising a glove 402 is removed and replaced by a wall port 417 in the form of a multiport. The wall port 417 may be used for manipulating objects within the chamber C of the inflated medical device using surgical instruments 489, or as a body port (422) for manipulating within the body of the human patient, when the upper and lower couplings 480a; 480b are connected (as shown in FIG. 53g).

Figure 53G:
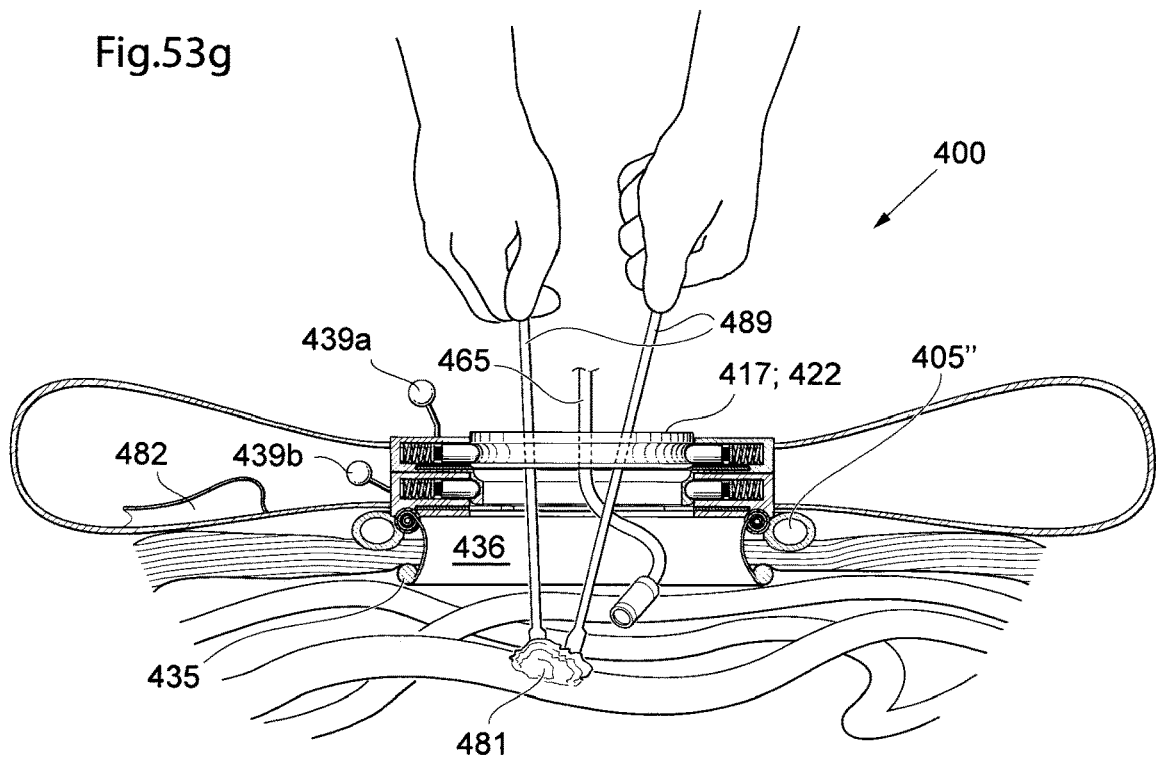

FIG. 53g shows the medical device 400 when the upper and lower couplings 480a; 480b are connected such that surgical instruments 489 can be used for manipulating within the body of the patient. An endoscopic camera 465 may be provided in the port 417; 422 for enabling visual inspection of the cavity in the patient's body. The process of cutting away a specimen from the intestines of a patient in an endoscopic way is shown in FIG. 53g.

Figure 53H:
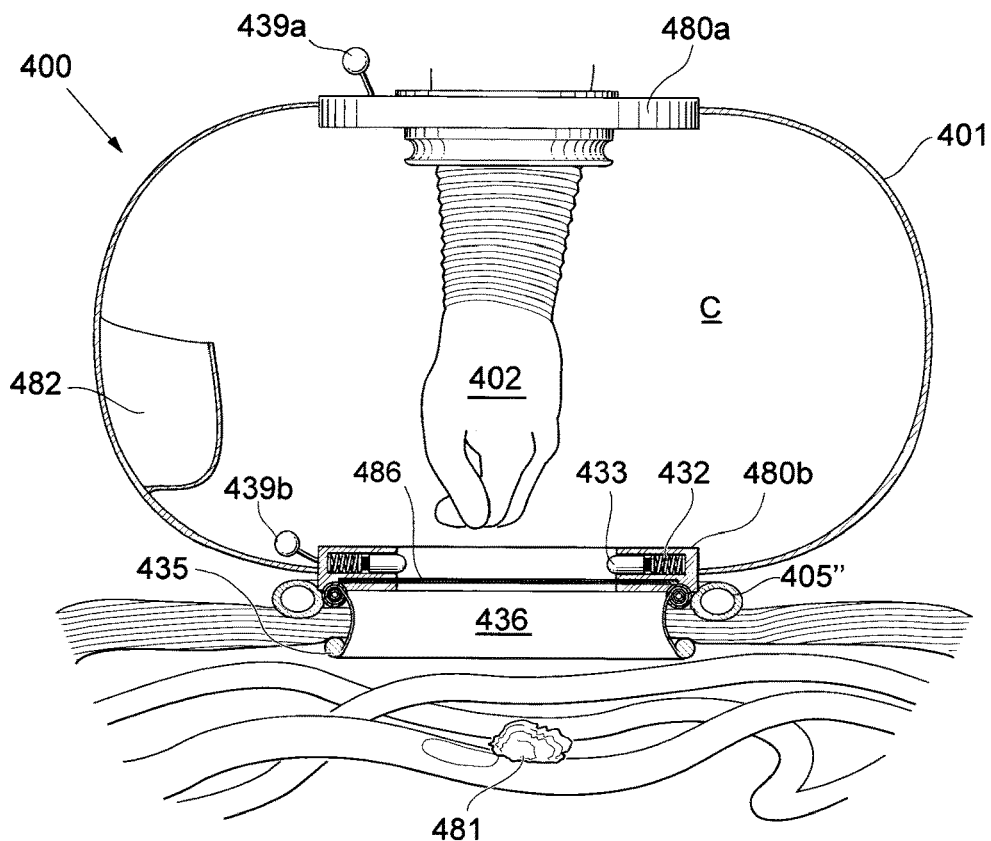

In FIG. 53h, the inset 442 comprising the glove 402 has been fixated to the upper coupling 480a to enable the surgeon to operate within the chamber C enclosed by the wall 401 of the medical device 400. By the glove inset 402 comprising a pleated portion 403, the surgeon is able to reach into the cavity of the patient for removing the specimen 481 cut loose from the intestines in prior steps.

Figure 53I:
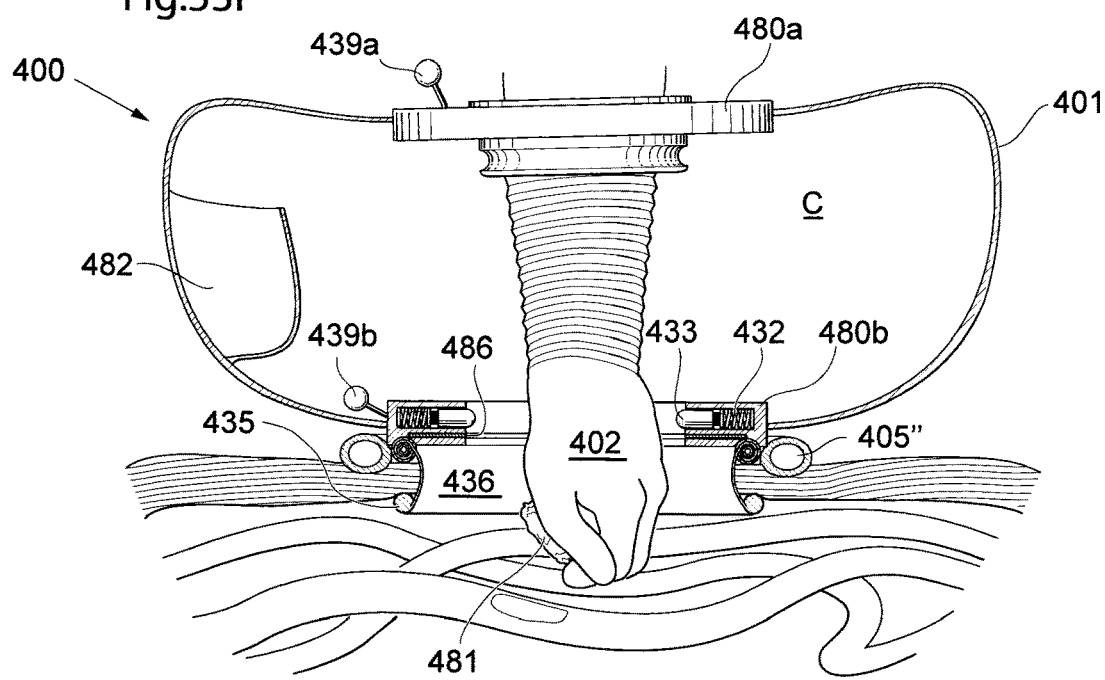

FIG. 53i shows that the wall of the medical device 400 is collapsible such that the inset 442 comprising the glove 402 can be moved in relation to the lower coupling 480b, which gives the surgeon further freedom when removing the loose specimen 481 from the intestines of the patient.

Figure 53J:
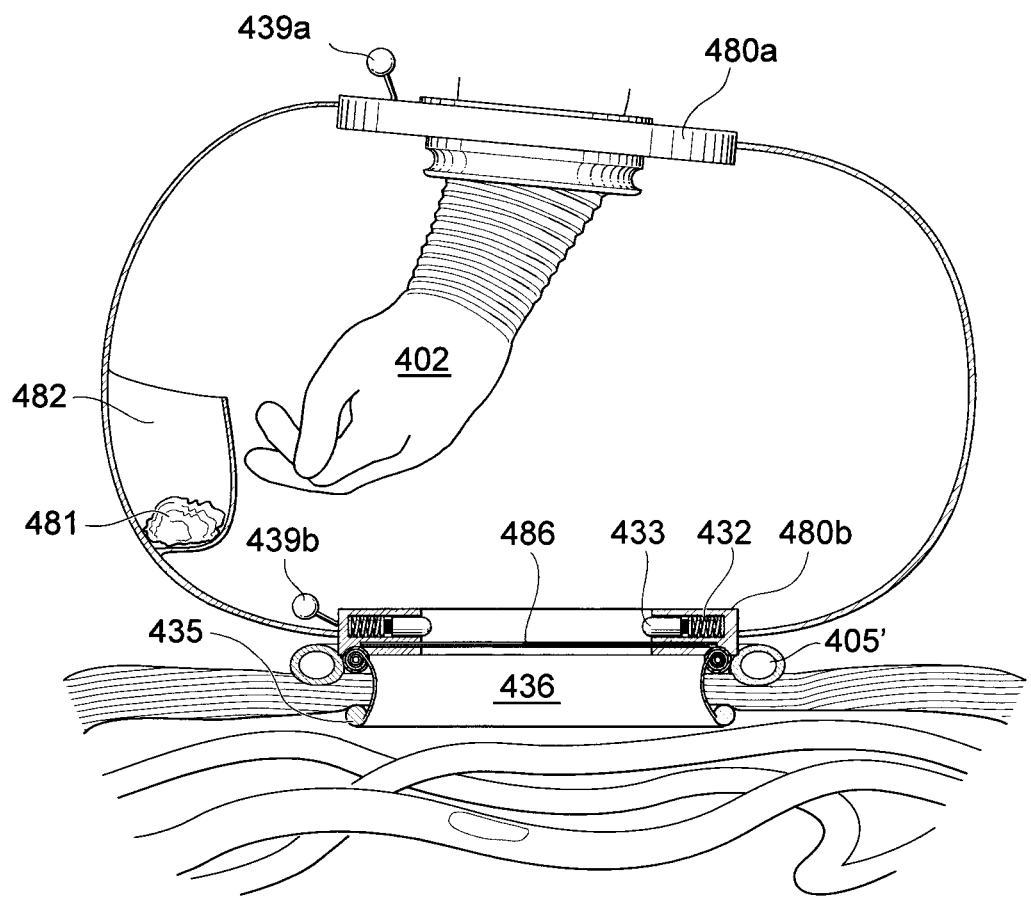

FIG. 53j shows the step of placing the removed specimen in the pouch 482 such that the specimen 481 does not contaminate any other part of the body. The pouch 482 may be a pouch 482 which could be closed for creating a pouch-chamber within the chamber C for isolating the removed specimen 481 within the chamber C.

Figure 53K:
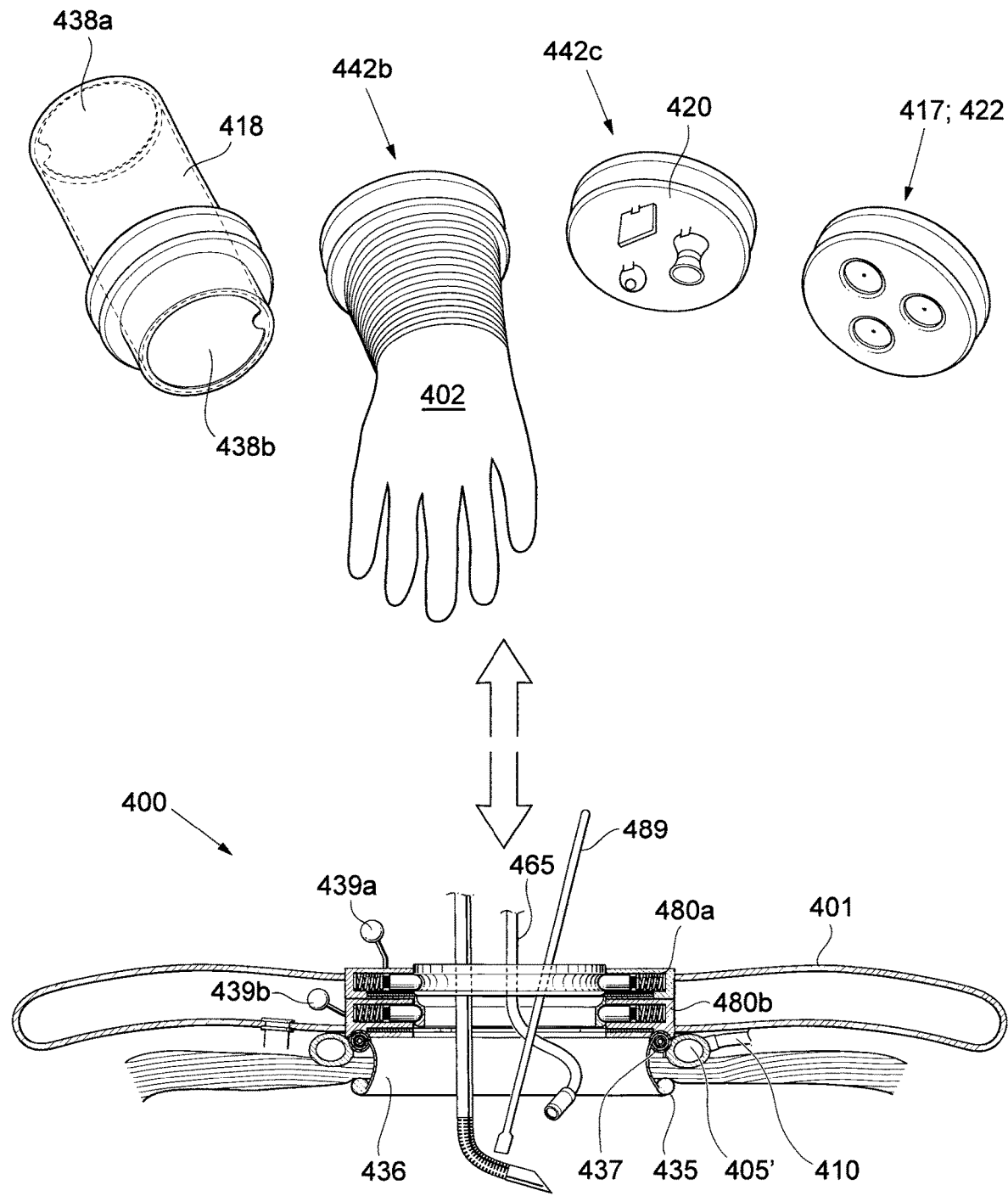
FIGS. 53k-53l shows the medical device in section, when objects are being exchanged.

FIG. 53k shows an alternative of the embodiment shown in FIGS. 53d-j. Fig. In 53k the medical device 400 is adapted to be at least partially placed in an incision cut in a patient's body. The medical device 400 comprises an upper coupling 480a and lower coupling 480b adapted be interconnected to form an interconnected coupling. The upper coupling 480a is adapted to be disconnected from the lower coupling 480b, and the upper coupling 480a is connected to a first portion of a flexible wall 401, and the lower coupling 480b is connected to a second portion of the flexible wall 401. The flexible wall 401 forms a chamber C in which a sealed environment can be maintained, the chamber C is heavily enlarged when the upper coupling 480a is disengaged from the lower coupling 480b, thus creating an operating space within the chamber C enclosed by the wall 401. The upper 480a and lower 480b couplings comprises a latching system for locking an inset 442. The inset 442 may for example be an inset 442b comprising a glove 402 for manual manipulation within the body of the patient, or within the enclosed chamber C, an inset 442c comprising a device and/or instrument mount 420 for holding instruments or medical devices within the chamber C, or a wall/body port 417; 422 comprising a plurality of self sealing membranes enabling the insertion of surgical instruments 489 or endoscopic cameras 465 into the chamber C or body of the patient.

In the embodiment shown in FIG. 53k the medical device 400 is fixated to the body of the patient by means of a pressure sealing member 405" connected to a fluid conduit 410, which in turn is connected to a source of pressurized fluid. Furthermore, the medical device 400 in FIG. 53k comprises a second sealing function having a first sealing member 435 adapted to be positioned at the inside of the patient's skin around an incision to be performed in the skin and a second sealing member 437 adapted to be positioned at the outside of the patient's skin around the incision, and a spring-loaded or elastic connecting member 436 sealingly interconnecting the first 435 and second 437 sealing members. The spring-loaded or elastic connecting member 436 seals between at least one of the outer ring 437 and the skin of the patient, and the inner ring 435 and the tissue of the patient.

Figure 53L:
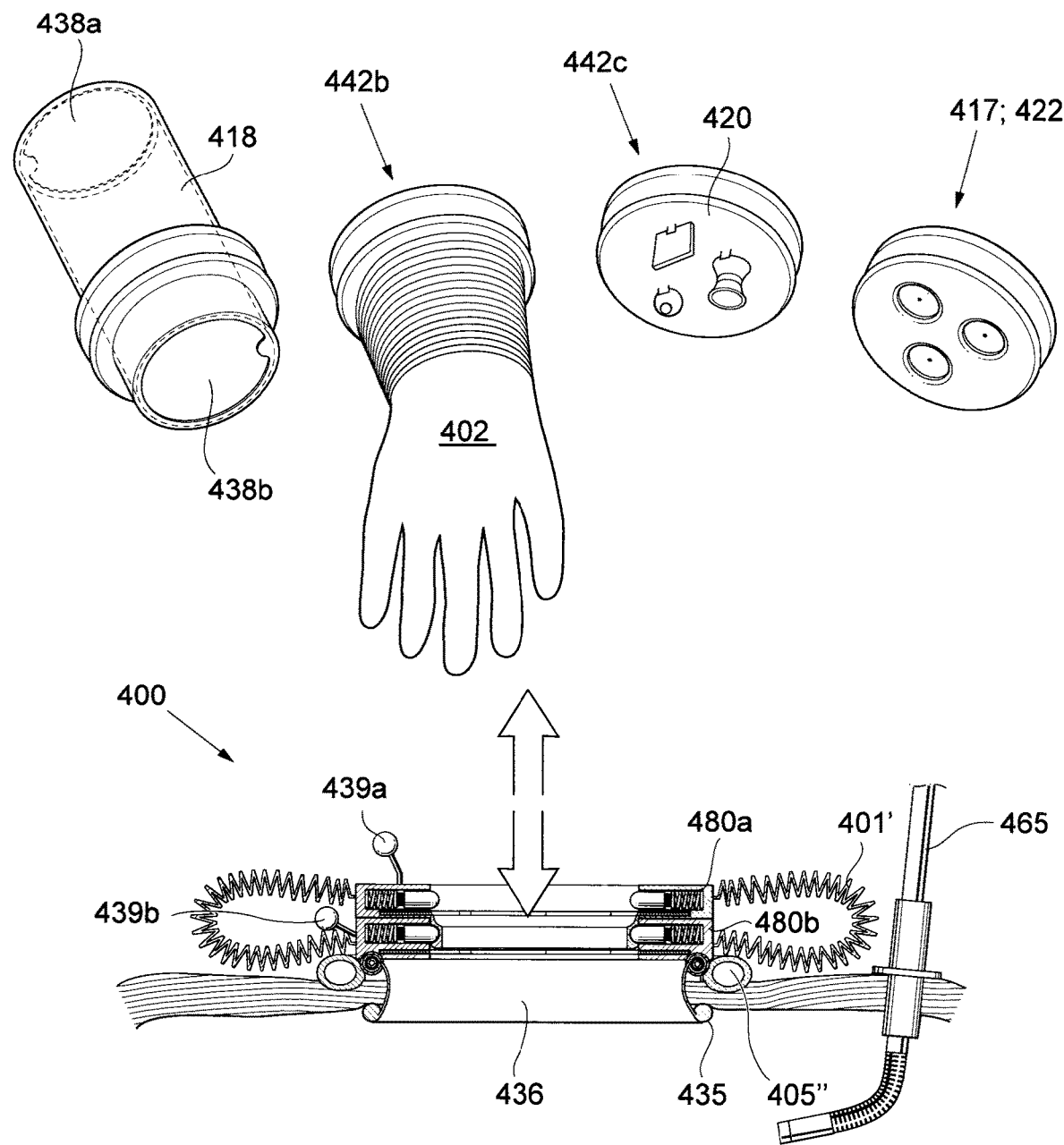

FIG. 53l shows the medical device in an embodiment very similar to the embodiment shown in FIG. 53k but with the difference that the wall 401' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. A camera 465 is also shown in FIG. 53l, placed outside of the medical device and enabling visual inspection of the cavity within the medical patient.

Figure 53M:
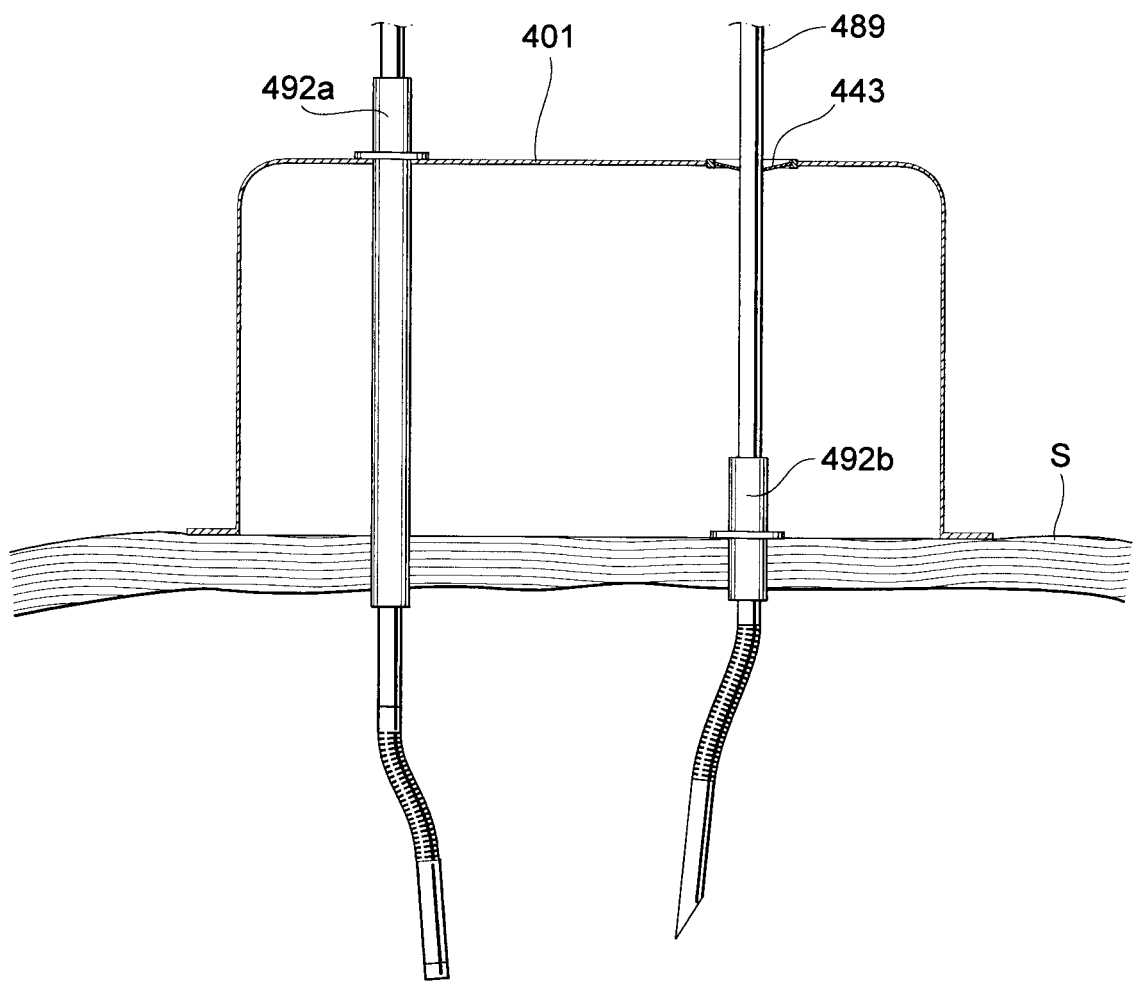
FIG. 53m shows an embodiment of the medical device, in section.

FIG. 53m shows examples of how trocars may be used in combination with the medical device according to any of the embodiments shown in FIGS. 42-53l. The medical device comprises a wall 401 placed on the patient's skin and thereby enclosing a chamber C for creating a sealed environment. The medical device comprises two trocars 492a; 492b, one 492a traveling through both the wall 401 of the medical device and the skin of the patient and thus enabling endoscopic instruments to be inserted into the patient through both the wall 401 of the medical device and the skin of the patient through one single trocar 492a. The other trocar 492b being placed inside the chamber C and enabling an endoscopic instrument to be inserted through the skin S of the patient. The endoscopic instrument is in this embodiment inserted into the chamber C enclosed by the wall 401 through a membrane 443 in the wall 401 sealing against the tool 492b.

Figure 53N:
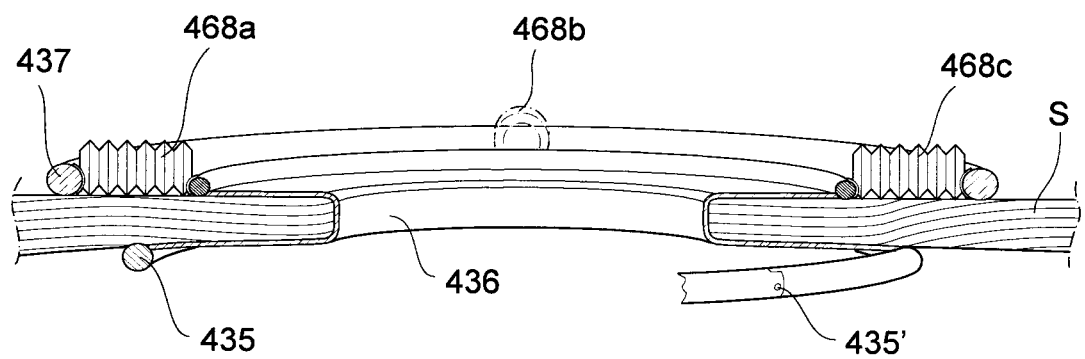
FIG. 53n shows an embodiment of a sealing device placed in the skin and tissue of the patient, in section.

FIG. 53n shows a detailed view of a body sealing device having a first sealing member 435 in the form of an intra body ring or inner retractor member adapted to be positioned at the inside of the patient's skin S around an incision to be performed in the skin S of the patient and a second sealing member or outer retractor member 437 adapted to be positioned at the outside of the patient's skin S around the incision. The sealing device further comprises a connecting member 436 sealingly interconnecting the first 435 and second 437 sealing members. The connecting member 436 seals between the second 437 sealing member and the skin S of the patient and/or the first sealing member 435 and tissue of the patient. The connecting member 436 is connected to bellows 468a;b;c adapted to pull on the connecting member 436 and thereby expand or keep the incision in the patient's body open. The bellows 468a;b;c could comprise pneumatic or hydraulic bellows that could pull on the connecting member 436 by means of vacuum force. Alternatively, the pneumatic or hydraulic bellows could comprise elastic members, such as springs, placed within the hydraulic or pneumatic retracting members such that the elastic members pulls on the connecting member 436 when the pressure in the bellows 468a;b;c is lowered.

The body sealing device could also be used as a retractor system retracting system comprising the flexible connecting member 436, an inside retracting member 435, adapted to be positioned at the inside of the patient's skin around an incision to be performed in the skin and be connected to the flexible connecting member 436, and the outside retracting member 437. The flexible connecting member 436 is interconnecting the inside 435 and outside 437 retracting members, whereby the inside 435 and outside 437 retracting members are larger than the incision allowing the flexible connecting member to retract the skin and tissue in the incision opening substantially parallel to the skin S.

I alternative embodiments, the flexible connecting member 436 is adapted to be placed in connection with at least one of; the first flexible wall of the medical device according to any of the embodiments herein, a coupling.

The retractor system is adapted to retract, substantially parallel to the skin, the skin and tissue in close relation to the incision, to enlarge the incision passage from the chamber into the body cavity, during the surgical procedure.

The retractor system may be used in a surgical method using the medical device according to any of the embodiments herein, the method comprises: creating an incision in the skin of the patient, connecting to a body cavity, placing the retracting system with its flexible connecting member through the incision, positioning the inside retracting member 435 at the inside of the patient's skin around the incision being sealingly connected to the flexible connecting member 436, positioning the outside retracting member 437 at the outside of the patient's skin around the incision. The method further comprises placing an interconnectable port (17,22 in other embodiments herein) in the incision, disconnecting the first port (17) from the second port (22), such that a chamber (C) is formed by a wall connected to the first and second ports, retracting the incision and enlarging the opening by the flexible connecting member 436 placed onto the inside 435 and outside 437 retracting members, retracting substantially parallel to the skin S, the skin and tissue in close relation to the incision, to enlarge the incision passage from the chamber into the body cavity, during the surgical procedure. The method also comprises performing a step of the surgical procedure within at least one of the chamber and the body cavity.

According to the embodiment shown in FIG. 53n, the first sealing member 435 is foldable by means of a joint 435' for inserting the first sealing member 435 through the incision in the patient's skin S. In alternative embodiments the first sealing member 435 could be elastic or flexible for enabling insertion into the body of the patient.

FIG. 53o shows how the medical device shown in FIGS. 42-53n may be used. The medical device 400 comprises a glove 402 integrated in the wall 401 and a camera 465 placed in the skin S outside of the medical device 400. The medical device 400 further comprises a trocar 492b placed inside the chamber C of the medical device into an area of the knee of the patient. FIG. 53o schematically illustrates how the surgeon manipulates the knee in the enclosed environment using the glove 402.

Figure 53P:
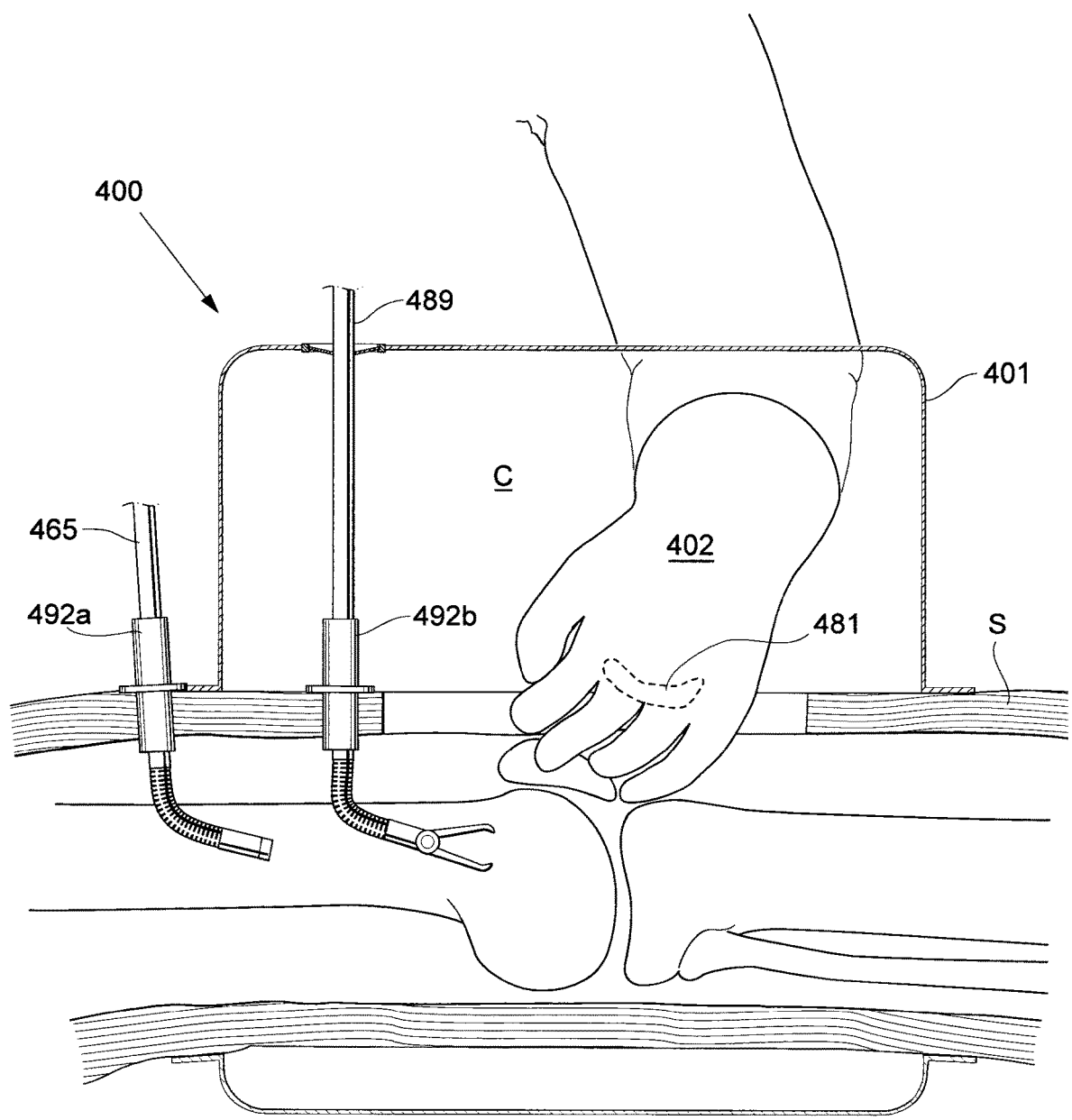
Figure 53Q:
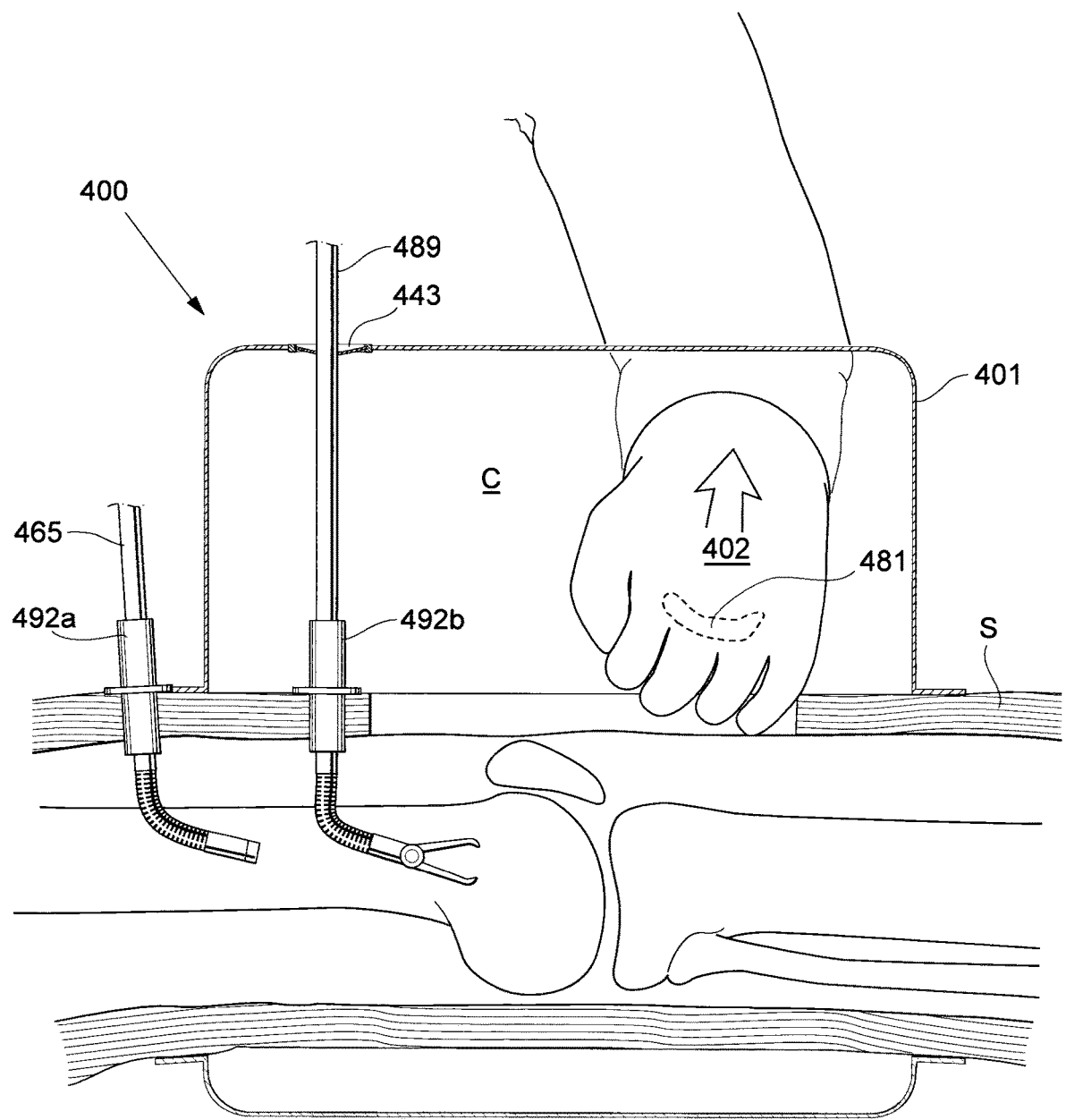

FIGS. 53p, 53q shows the medical device 400 when the surgeon removes a specimen 481 from the knee of the patient using the glove 402 integrated in the wall 401 of the medical device 400.

Figure 53R:
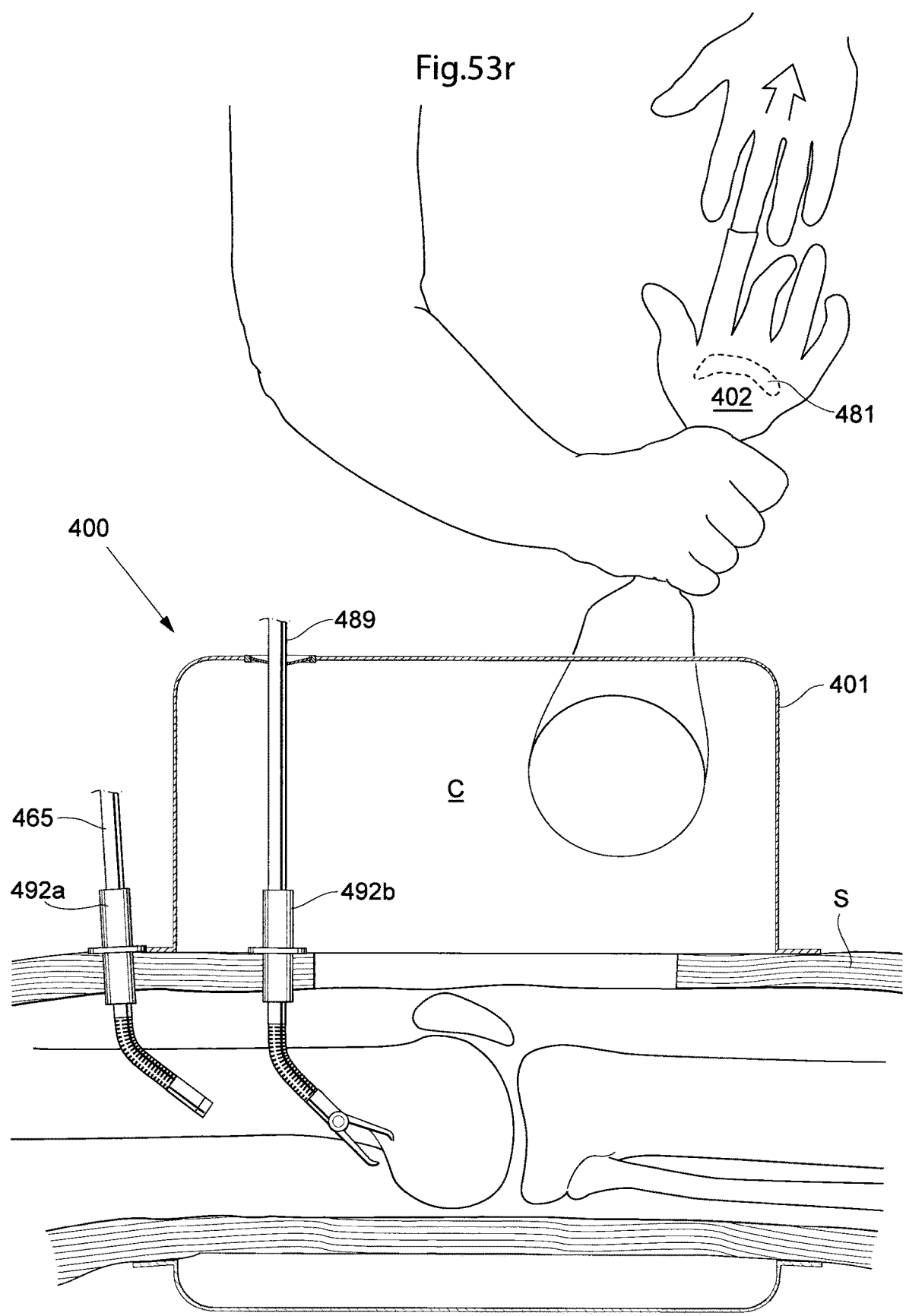

FIG. 53r shows the medical device 400, when the surgeon has turned the integrated glove 402 inside-out such that the specimen 481 can be contained within the integrated glove 402. By isolating the specimen 481 inside of the glove 402, the specimen 481 is removed both from the rest of the body of the patient and from the ambient environment, and thereby does not risk to infect any other portion of the patient's body or medical staff with any infectious disease.

FIGS. 54-65z shows an embodiment of the medical device adapted to be positioned on an extremity of the patient such that the extremity of the patient enters the medical device through a first opening thereof and exits the medical device through a second opening thereof.

Figure 54:
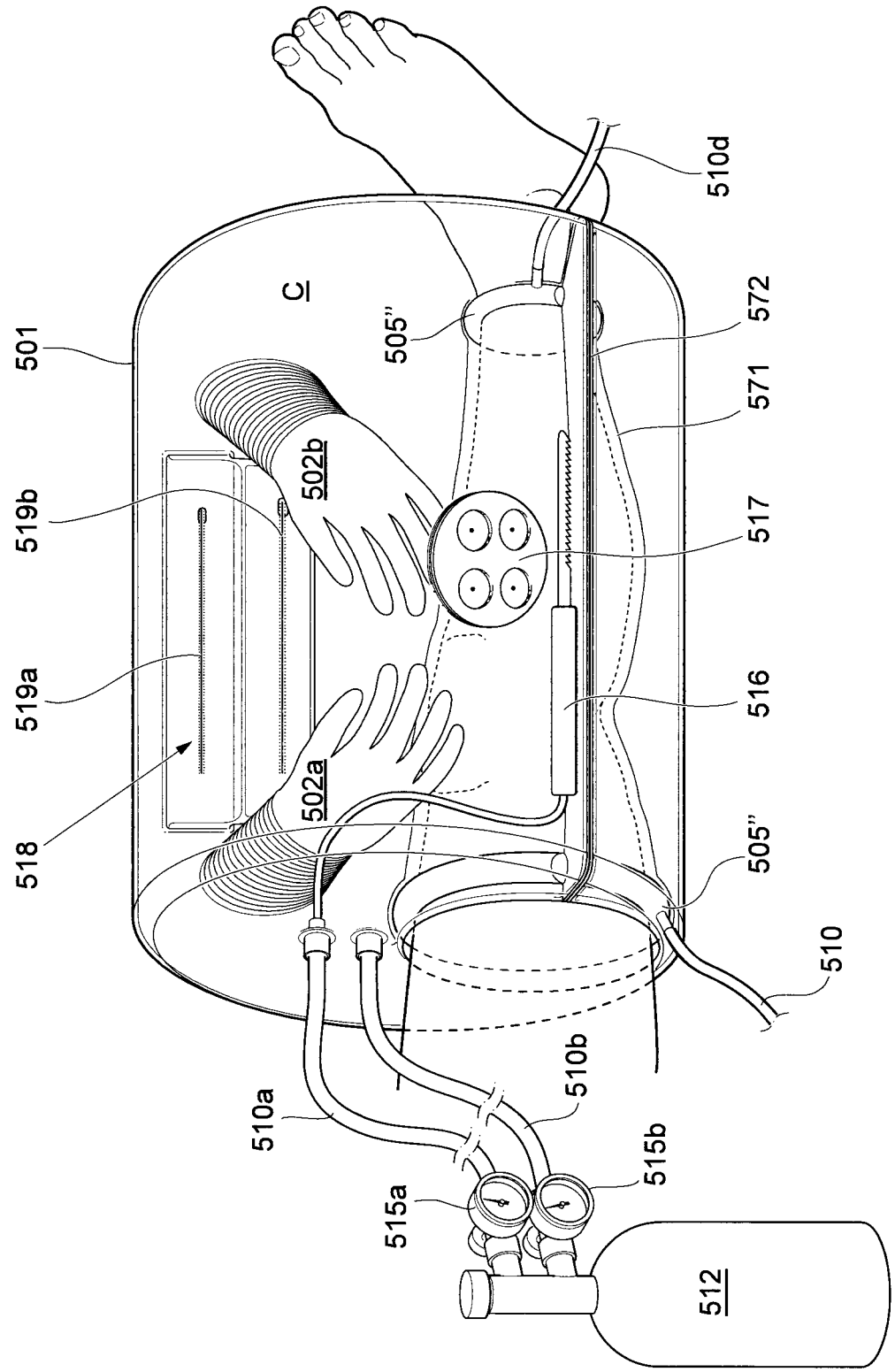

FIG. 54 shows the medical device 500 according to an embodiment in which the medical device comprises a wall 501 adapted to be at least partially applied on the patient's body to form a chamber C, in which a sealed environment can be maintained for encompassing part of a surgical procedure to be performed. An inner wall 571 forms an elongated tubular enclosure extending in the chamber C and having a first and a second open end, here equipped with pressure seals 505". The chamber C is adapted to fit a portion of an extremity of the patient, in FIG. 54 the leg of the patient, and the medical device 500 is arranged such that the portion of the extremity may be inserted into the chamber C through the first open end and exit the chamber C through the second open end and the surgical procedure is performed on the portion of the patient's extremity placed inside of the chamber C. The chamber C is inflatable by means of a fluid conduit 510b, here connected to a tank 512 containing pressurized gas. The tank 512 is further connected to a fluid conduit 510a for transferring pneumatic force into the chamber C enclosed by the wall 501 and including the operating field of the extremity. Shown in the embodiment herein, the fluid conduit 510a is connected to a pneumatic tool 516, which in the example shown as an orthopedic saw, adapted to be operated within the chamber C. The fluid pressure provided to the chamber C and to the conduit 510a is controlled and monitored by a control/monitoring system 515a, 515b connected to the pneumatic conduits 510a; 510b, respectively. In the embodiment shown, the medical device of FIG. 54 is shown incorporating the fluid pressure sealing members 505", however it is equally conceivable that the pneumatic pressure sealing members 505" are assisted or replaced by any of the other sealing members disclosed herein, such as vacuum sealing members or adhesive sealing members.

The medical device shown in FIG. 54 further comprises an airlock sluice 518 comprising two zipper-closed consecutive openings 519a, 519b, where the outer zipper 519a could be opened for placing and/or removing objects in the airlock 518 between the zippers 519a, 519b from the outside of the chamber C and the inner zipper 519b could be opened from the inside of the chamber C for placing and/or removing objects from the airlock sluice 518. For example, the airlock sluice 518 could be used to remove a specimen 581 from the chamber C while keeping the environment closed, or the airlock sluice 518 could be used to insert a medical device or an implant into the chamber C. The medical device disclosed with reference to FIG. 54 further incorporates endoscopic wall ports 517 (which are to be regarded as optional) through which endoscopic instruments could be inserted.

The medical device of FIG. 54 may further comprise at least one glove 502a, 502b integrated in the wall 501 such that a surgeon is able to use the glove 502a, 502b from outside the chamber C to make manual manipulations inside the chamber C while maintaining the closed environment in the chamber C. According to one embodiment, the wall 501 of the medical device is at least partially collapsible and may be inflated by a fluid, as is shown in FIG. 54.

The medical device may additionally comprise a non-collapsible transparent window (as for example shown in FIG. 3*b*) provided in the wall to enable viewing into the sealed environment.

In other embodiments, the medical device may comprise a device and/or instrument mount (for example shown as 20 in FIG. 3*a*) adapted to retain instruments within the chamber C.

In other embodiments, the medical device may comprise an air evacuation system adapted to evacuate air from the interior of the enclosure, when the portion of the patient's extremity is placed in the enclosure (as for example further shown in FIG. 2*b*).

The medical device shown in FIG. 54 further comprises a wall port 517 provided in the wall 501 enabling passage of an object between the chamber C and the environment outside of the chamber C. The wall port 517 comprises at least one of an elastic and flexible membrane, and the membrane is adapted to, in a non-compressed state, seal between the chamber C and the environment outside of chamber C, and in a compressed state enable a hand or an object to be inserted through the membrane.

The medical device may further comprising a body multi-port adapted to be placed inside the chamber C in an incision in the skin of the patient, wherein the body multi-port comprises at least two body ports adapted to enable passage of an object between the chamber C and the inside of the patient's body via the incision.

The medical device may further comprise a fluid tempering device and/or a sterilization device for tempering and/or sterilizing a fluid contained in the chamber C, such a system if further disclosed for example under reference to FIG. 3*c*.

In the embodiment shown in FIG. 54, the elongated tubular enclosure is formed by placing the wall 501 forming the chamber C around a portion of the extremity of the patient and closed by means of a connection 572 which is positioned between the inner wall 571, in connection with the skin of the patient, and the outer wall 501. The connection connecting one portion of the medical device with a second portion of the medical device could for example be made by means of an adhesive, a mechanical connection system, or a vacuum system.

Figure 55A:
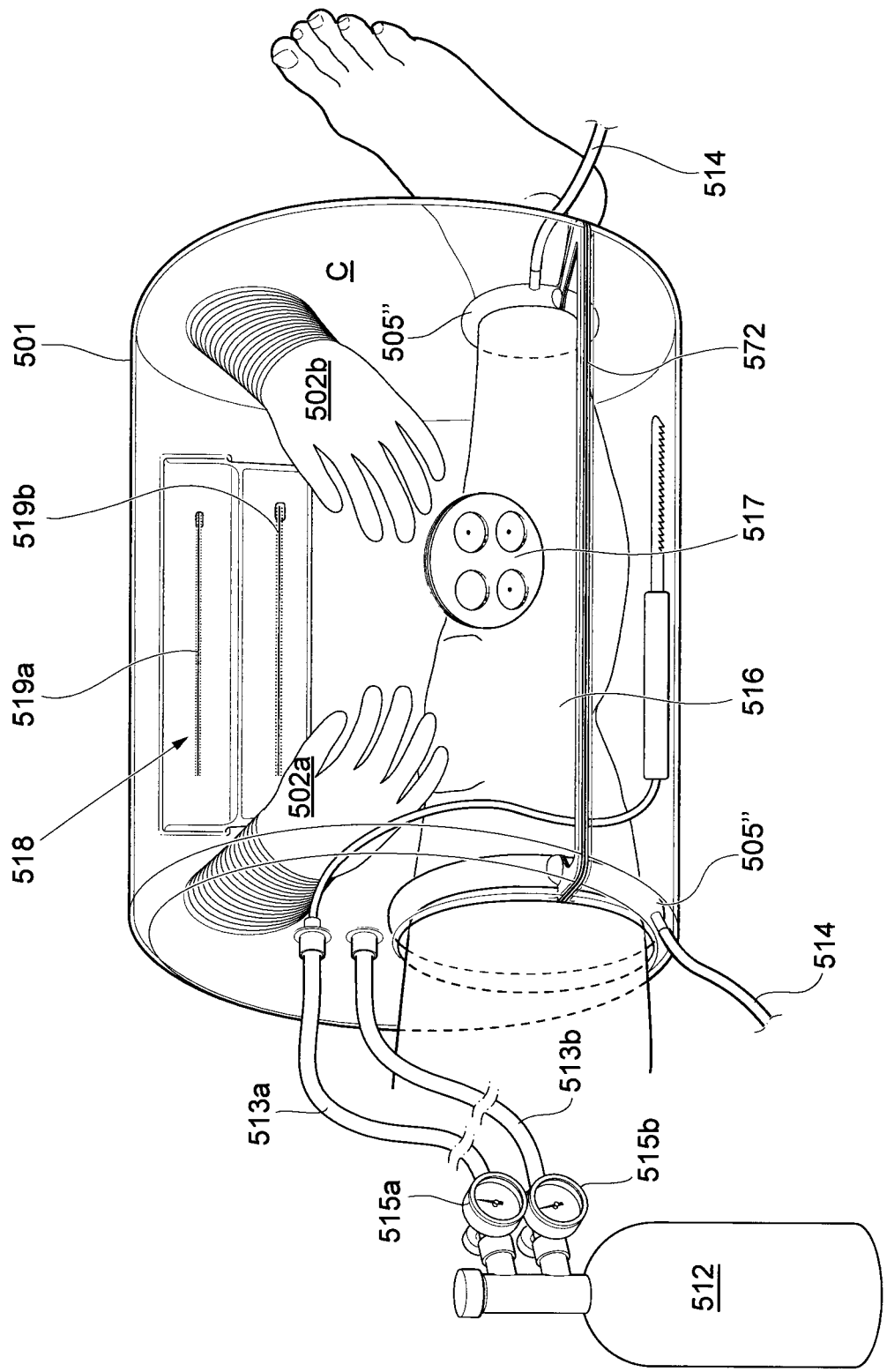

FIG. 55*a* shows the medical device according to an embodiment incorporating the features of FIG. 54 but with the difference that there is no inner wall, i.e. the enclosed environment of the chamber C is in direct connection with the skin of the patient. The connection 572 has a somewhat different design since it is only connected to the outer wall 501.

Figure 55B:
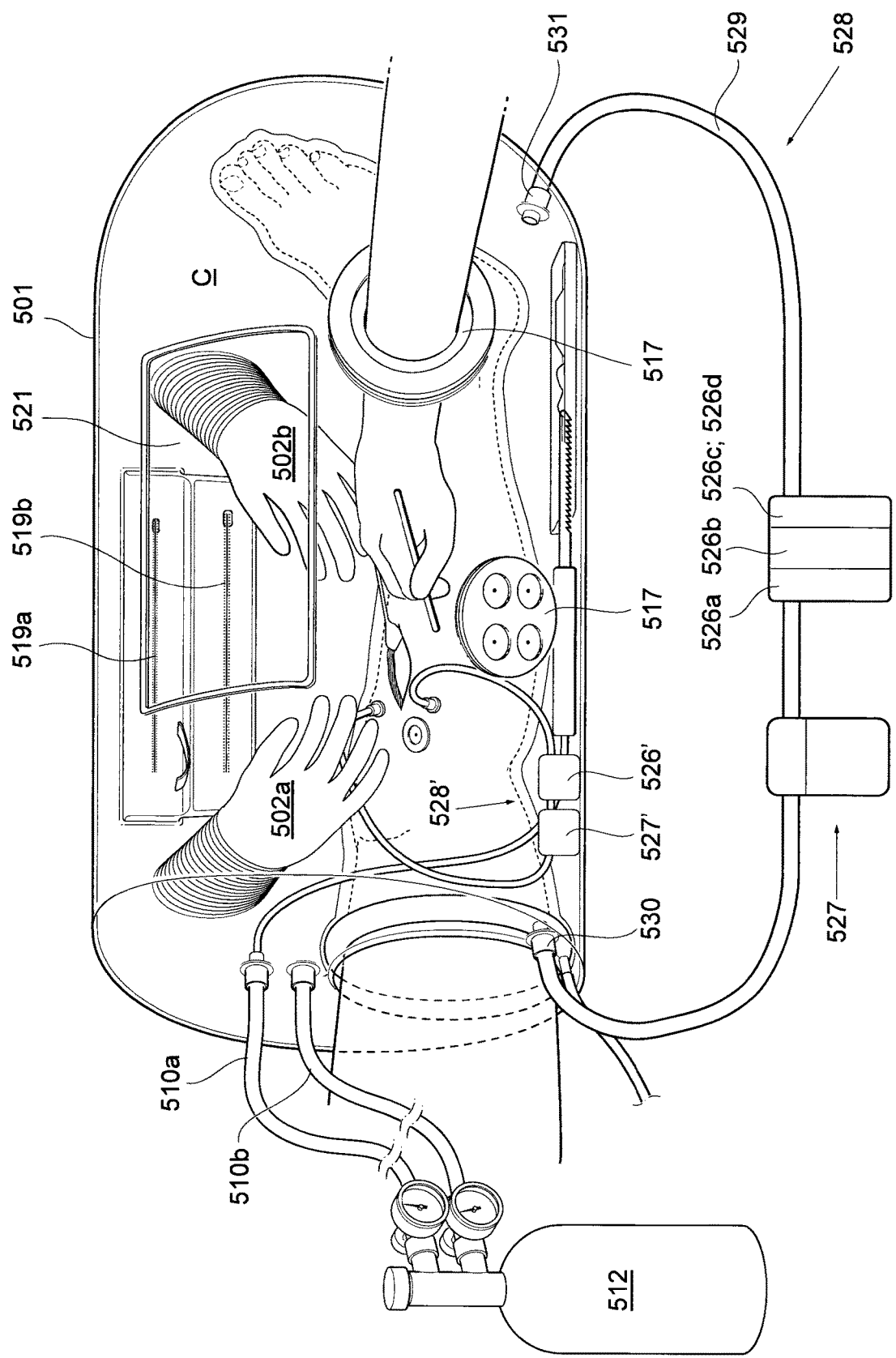

FIG. 55*b* shows the embodiment of the medical device similar to that shown in FIG. 54, with the difference that the extremity of the patient is placed in an elongated tubular enclosure within the chamber C and thus only sealed at one open end thereof, however, it is equally conceivable that the extremity of the patient is placed in a medical device comprising two seals, such that the extremity passes out of the chamber C.

In FIG. 55*b*, the arm of the surgeon is inserted through a self sealing wall port 517 in the partially collapsible wall 501 for enabling manual manipulation therein. Manual manipulation through the self sealing wall port 517 could for example be used as a last resort should complications occur during the procedure, or if additional hands are required for a specific step of the operation. FIG. 55*b* further shows an internal system 528' for fluid circulation, and an external system 528 for fluid circulation. Both systems comprises fluid conduits 529; 529', in the external system 528 connected at an inlet 530 placed in the partially collapsible wall 1 for supplying fluid to the chamber C, and an outlet 531 for draining the fluid from the chamber C, and in the internal system 528' connected to an inlet 530' in the patient's body and an outlet 531' in the patient's body for circulating fluid in a body cavity. The fluid is circulated by means pumping units 527; 527' and is circulated via a sterilizing/filtering/tempering/humidifying unit 526', in the external system disclosed as containing a sterilizing 526*a*, filtering 526*b*, and tempering/humidifying unit 526*c*; 526*d* adapted to remove impurities, sterilize, heat and humidify the fluid. In embodiments where the fluid is a gaseous fluid, the filtering unit is adapted to remove particles that could be suspended in the gas. The filtering unit 526*a* could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 526*a* could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIG. 56 shows the medical device disclosed under reference to FIG. 55 but in its open state, i.e. before it is placed around a portion of the extremity of the patient for forming the chamber C. According to the embodiment shown, the connection 572 is created by means of mechanical connecting members comprising protrusions 573 adapted to latch in corresponding key-hole recesses 583 for creating the mechanical connection. The sealing members 505'; 505" encircling the extremity when the connection is made for forming the chamber C could for example be pressure sealing members 505" connected to a fluid conduit 510 or vacuum sealing members 505' connected to a vacuum conduit (not shown).

FIG. 57 shows the medical device 400 in an embodiment where the medical device 400 comprises an inner wall 571 and an outer wall 501 both in connection with a connecting portion 572 herein adapted to connect to another connecting portion by means of a zipper 519 such that the chamber encircles the portion of the extremity.

Figure 58:
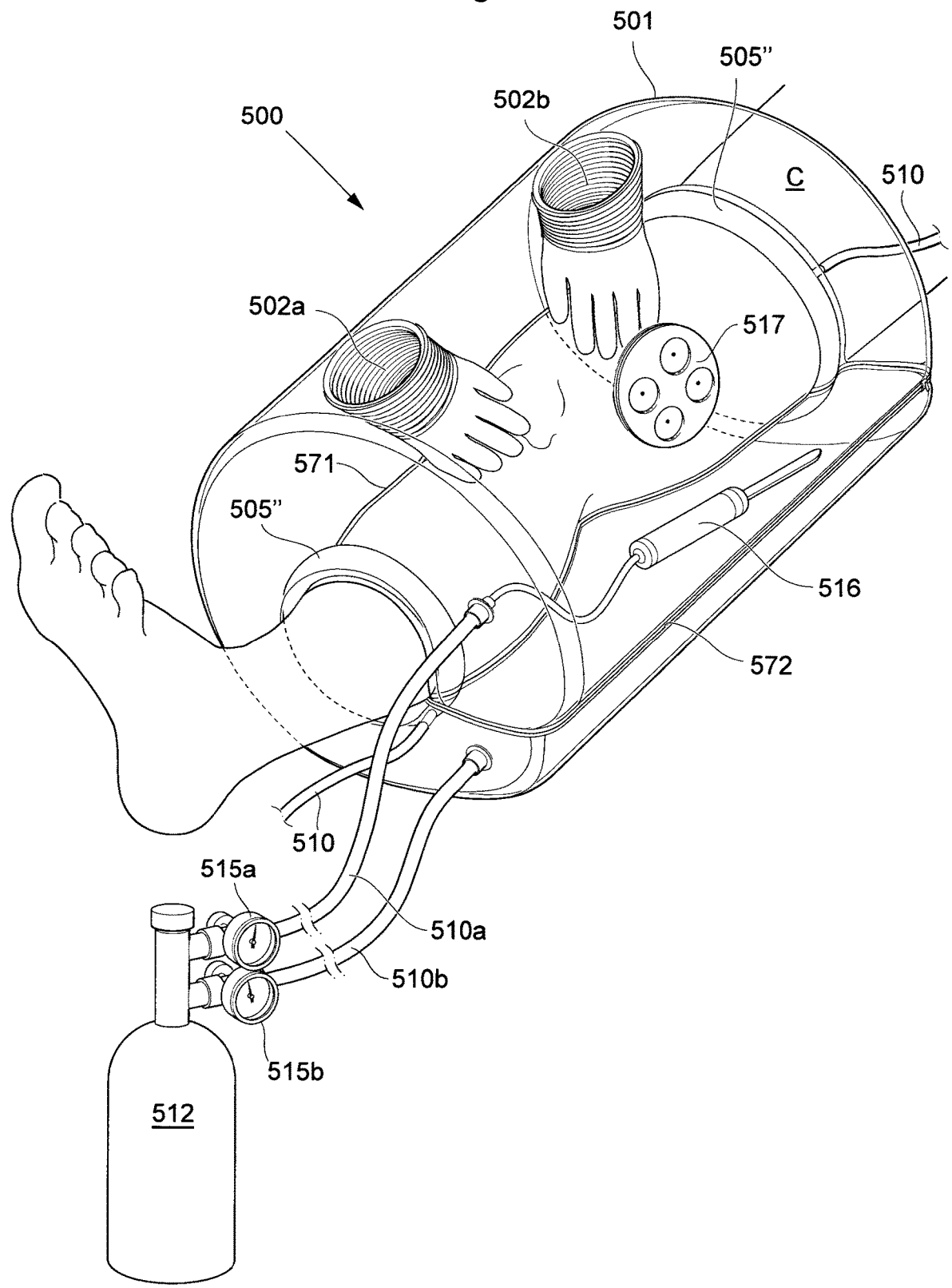

FIG. 58 shows the embodiment of the medical device 500 disclosed under reference to FIG. 57, when the connection is made such that the chamber C encircles the extremity of the patient.

Figure 59:
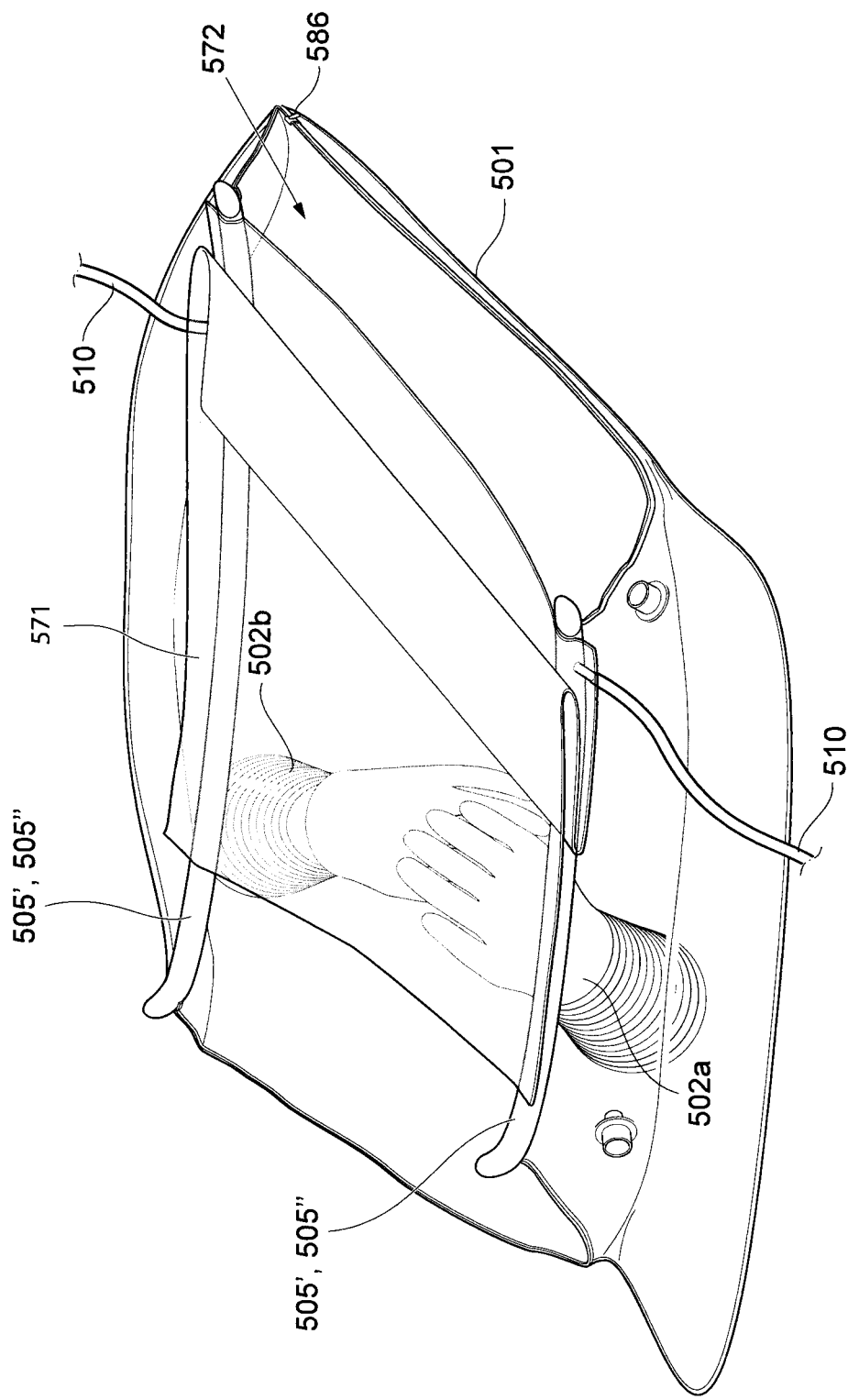

FIG. 59 shows a slightly modified version of the embodiment disclosed with reference to FIG. 57, the difference being that the inner wall 571 is made longer such as to allow an overlap of the inner wall 571 when the chamber C is placed encircling the extremity of the patient for improving the sealing between the medical device 500 and the skin of the patient.

Figure 60:
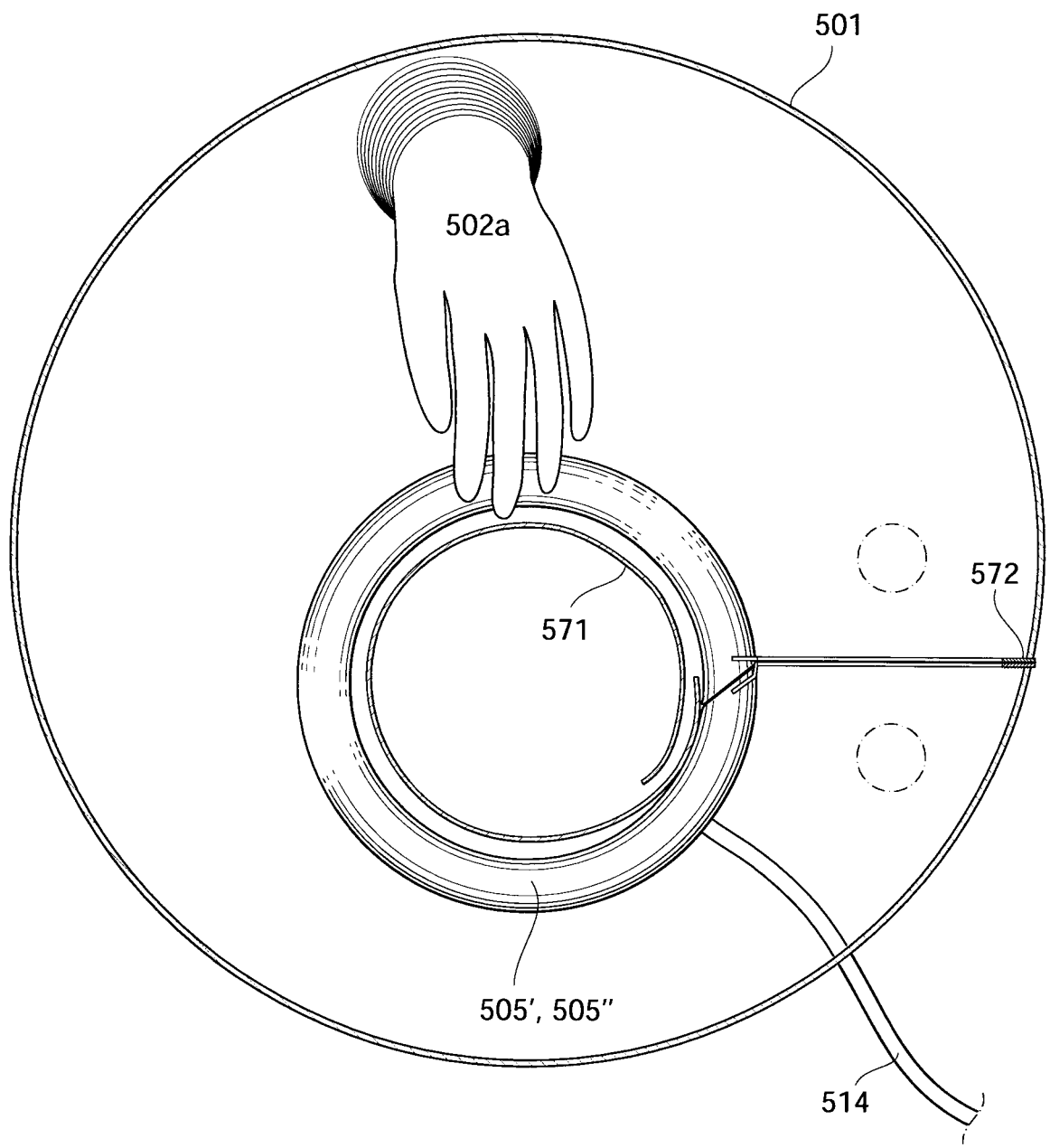
FIG. 60 shows an embodiment of the medical device, in sectional view.

FIG. 60 shows the medical device according to the embodiment shown in FIG. 60 when the chamber C is placed encircling the extremity of the patient, in a side view. The inner layer 571 is placed with an overlap and the connection is closed by means of the zipper 519. The medical device 500 is herein provided with a pressure or vacuum sealing member 505'; 505".

Figure 61:
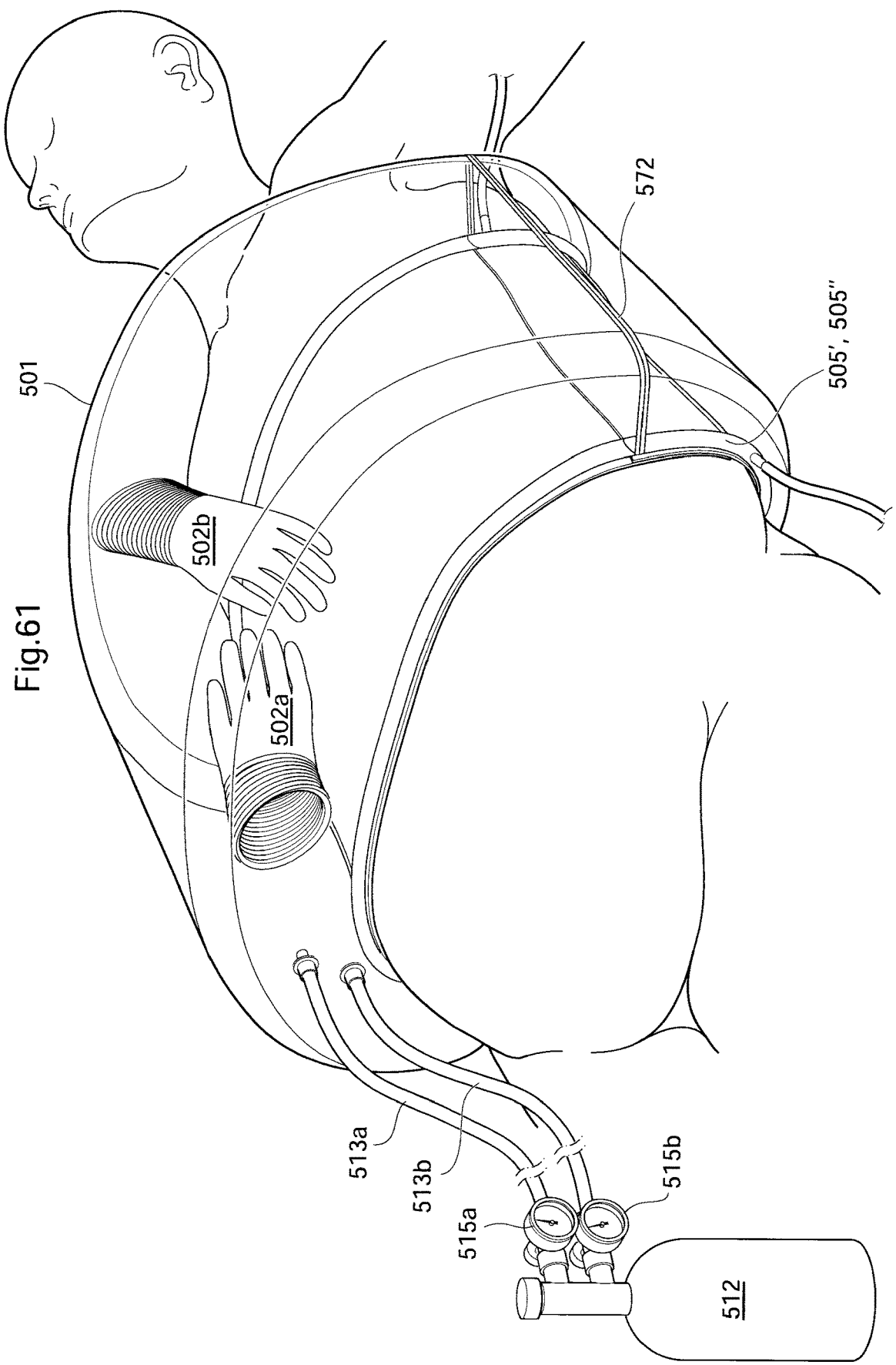
FIG. 61 shows the medical device, when applied to the abdomen of a patient.

FIG. 61 shows the medical device when applied on a portion of the upper body of a patient, thus enabling surgical procedures in the abdominal or thoracic regions. The chamber C is wrapped around the patient by means of the medical device comprising a slit and connected by means of the connection 572 and sealed against the skin of the patient by means of pressure 505" or vacuum 505' seals. The slit and the connecting members enables the placement of the chamber C around at least a portion of the extremity of the patient radially in relation to the length axis of the extremity.

Figure 62:
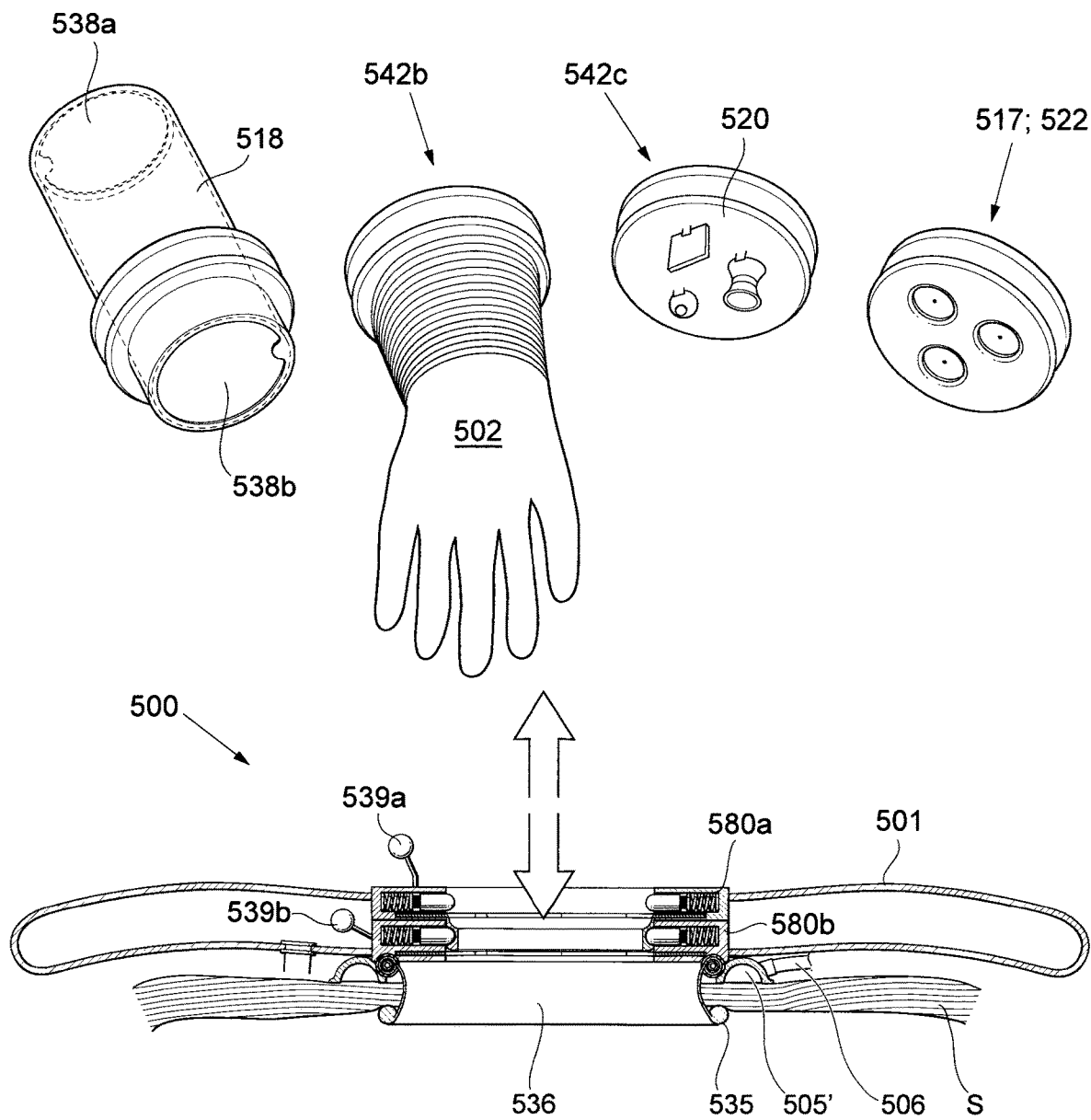
FIGS. 62-63 shows embodiments of the medical device in section, when objects are being exchanged.

FIG. 62 shows an alternative of the embodiment shown in FIGS. 54-61. In FIG. 62, the medical device 500 is adapted to be at least partially placed in an incision cut in a patient's body. The medical device 500 comprises an upper and lower coupling 580a; 580b adapted be interconnected to form an interconnected coupling. The upper coupling 580a is adapted to be disconnected from the lower coupling 580b, and the lower coupling 580b is connected to a first portion of a flexible wall 501, and the lower coupling 580b is connected to a second portion of the flexible wall 501. The flexible wall 501 forms a chamber in which a closed environment can be maintained, the chamber is heavily enlarged when the upper coupling 580a is disengaged from the lower coupling 580b, thus creating operating space within the chamber C enclosed by the wall 501. The upper and lower couplings 580a; 580b comprise a latching system for locking an inset 542a;b;c or a port 517; 522. An inset 542 could be an inset 542b comprising a glove 502 for manual manipulation within the body of the patient, or within the enclosed chamber C, or an inset 542c comprising a device/instrument mount 520 for holding instruments or medical devices within the chamber. Alternatively the insets 42b; 42c can be replaced by an airlock sluice 518 with a first 538a and second 538b valve member or a port 517; 522 enabling the insertion of a surgical instrument into the chamber or body of the patient.

In the embodiment shown in FIG. 62 the medical device is fixated to the body of the patient by means of a vacuum fixating member 505' connected to a vacuum conduit 506, which in turn is connected to a vacuum source. Furthermore, the medical device 500 in FIG. 62 comprises a second sealing device having a first sealing member 535 in the form of an intra body ring 535 adapted to be positioned at the inside of the patient's skin around an incision to be performed in the skin S and a second sealing member 537 in the form of an outer ring 537 adapted to be positioned at the outside of the patient's skin S around the incision, and a spring-loaded or elastic connecting member 536 sealingly interconnecting the first 535 and second 537 sealing members. The spring-loaded or elastic connecting member 536 seals between at least one of the outer ring 536 and the skin S of the patient, and the intra body ring 535 and the tissue of the patient.

Figure 63:
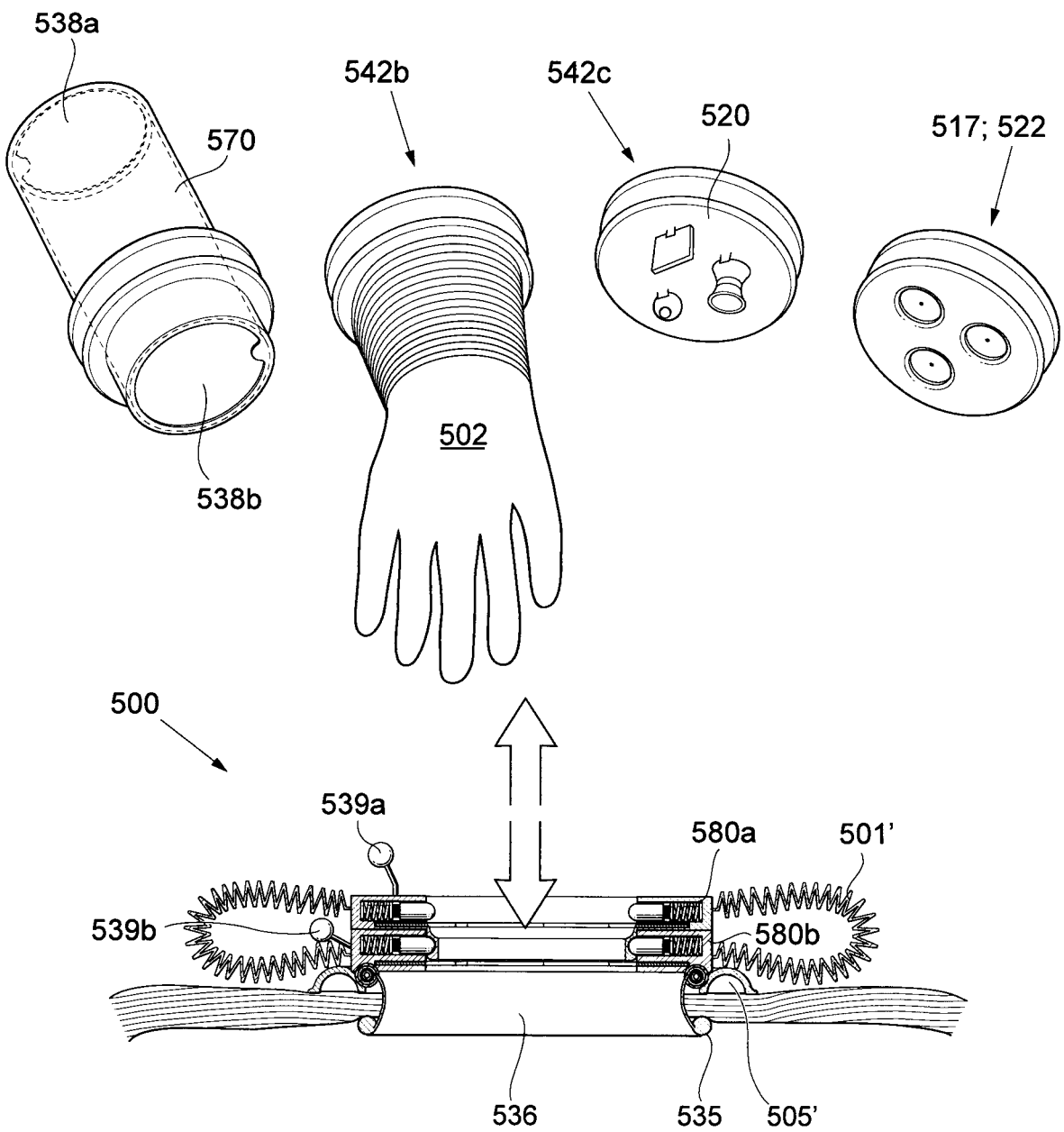

FIG. 63 shows the port in an embodiment very similar to the embodiment shown in FIG. 62 but with the difference that the wall 501' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

Figure 64:
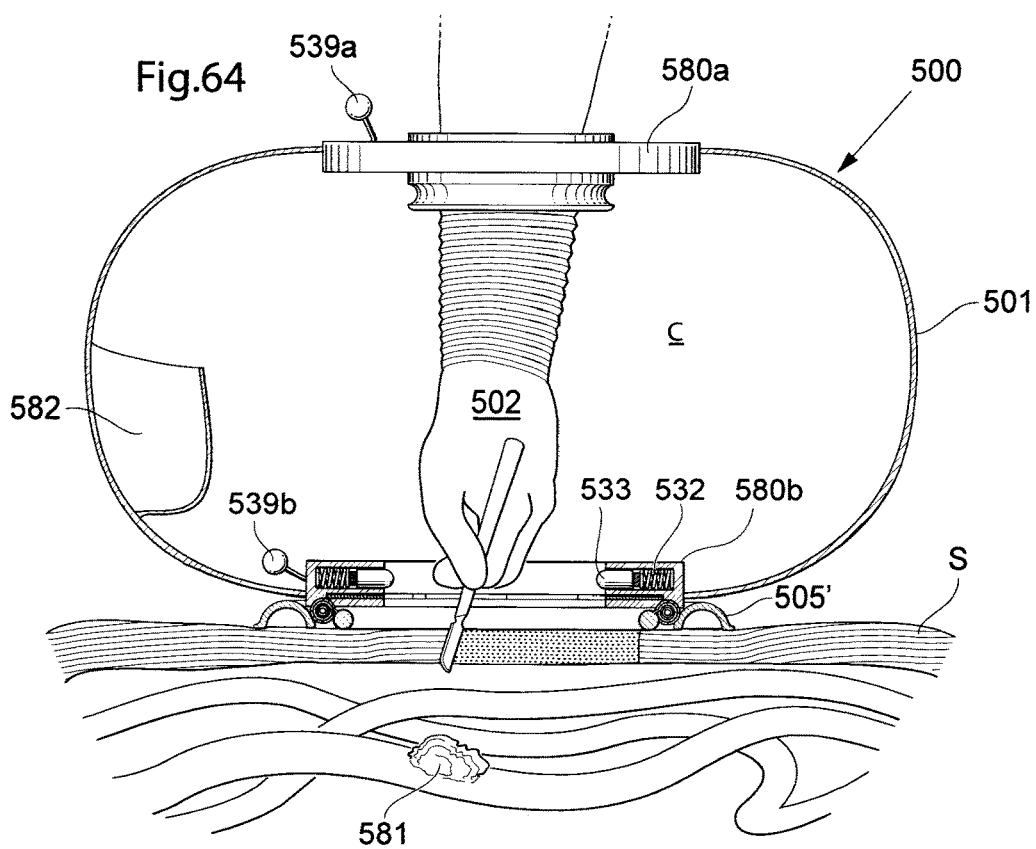
FIGS. 64-65f shows an embodiment of the medical device in section, being fixated to the patient and used.
Figure 65A:
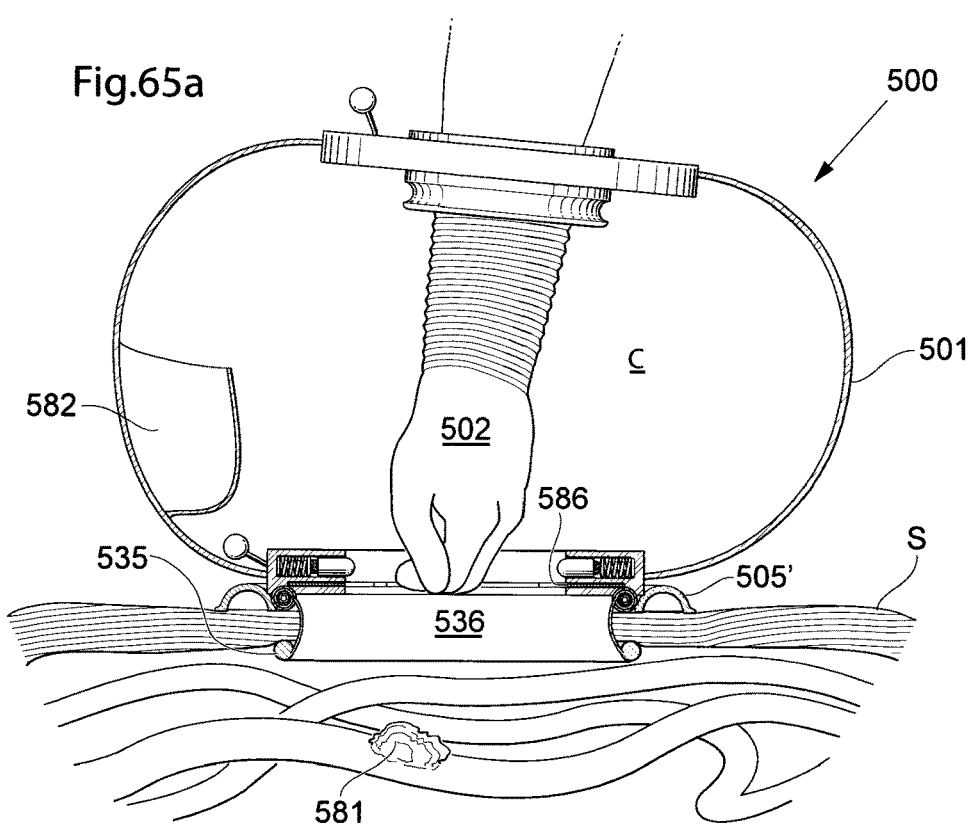
FIGS. 65g-65h shows embodiments of the medical device in section, when objects are being exchanged.
FIG. 65i shows an embodiment of the medical device, in sectional view.
FIGS. 65j-65k shows embodiments of the medical device, in perspective.
FIGS. 65l-65n shows embodiments of the medical device, in sectional view.
FIGS. 65o-65s shows embodiments of the medical device, in perspective.
FIG. 65t shows a coupling, in section.
FIG. 65u shows the exchange of objects in a coupling, FIG. 65v-65v' shows a body port, in section.
FIGS. 65w-65z shows an embodiment of the medical device in section, being fixated to the patient and used.
Figure 65D:
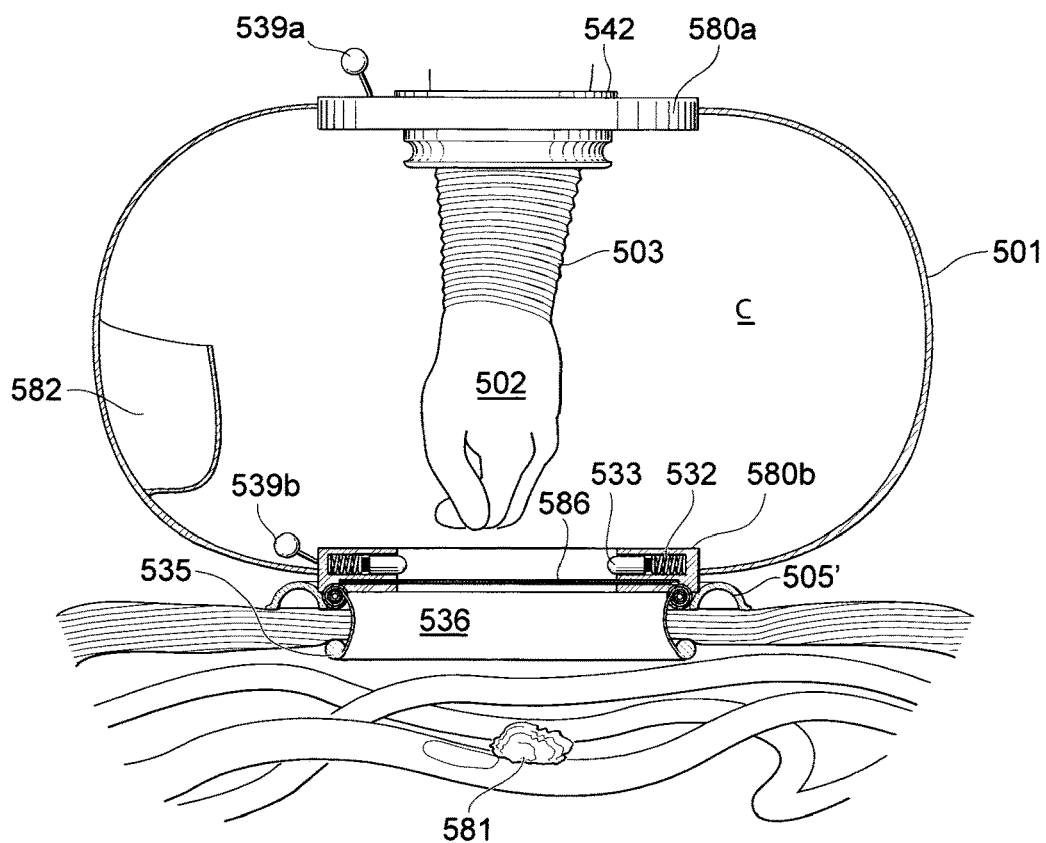
Figure 65E:
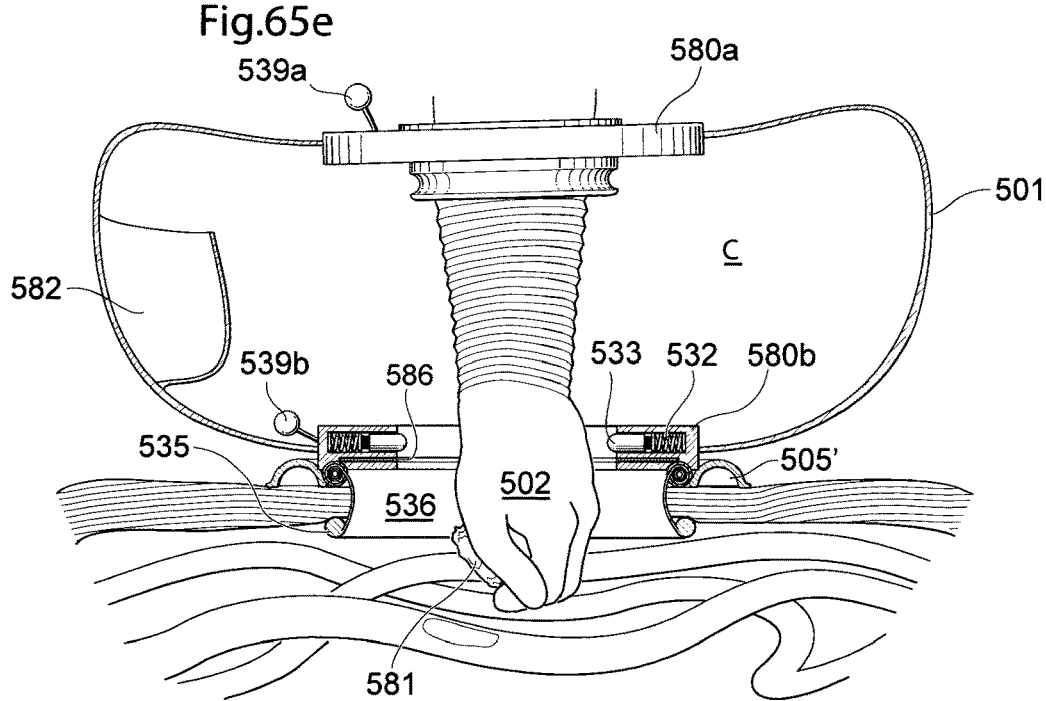
Figure 65F:
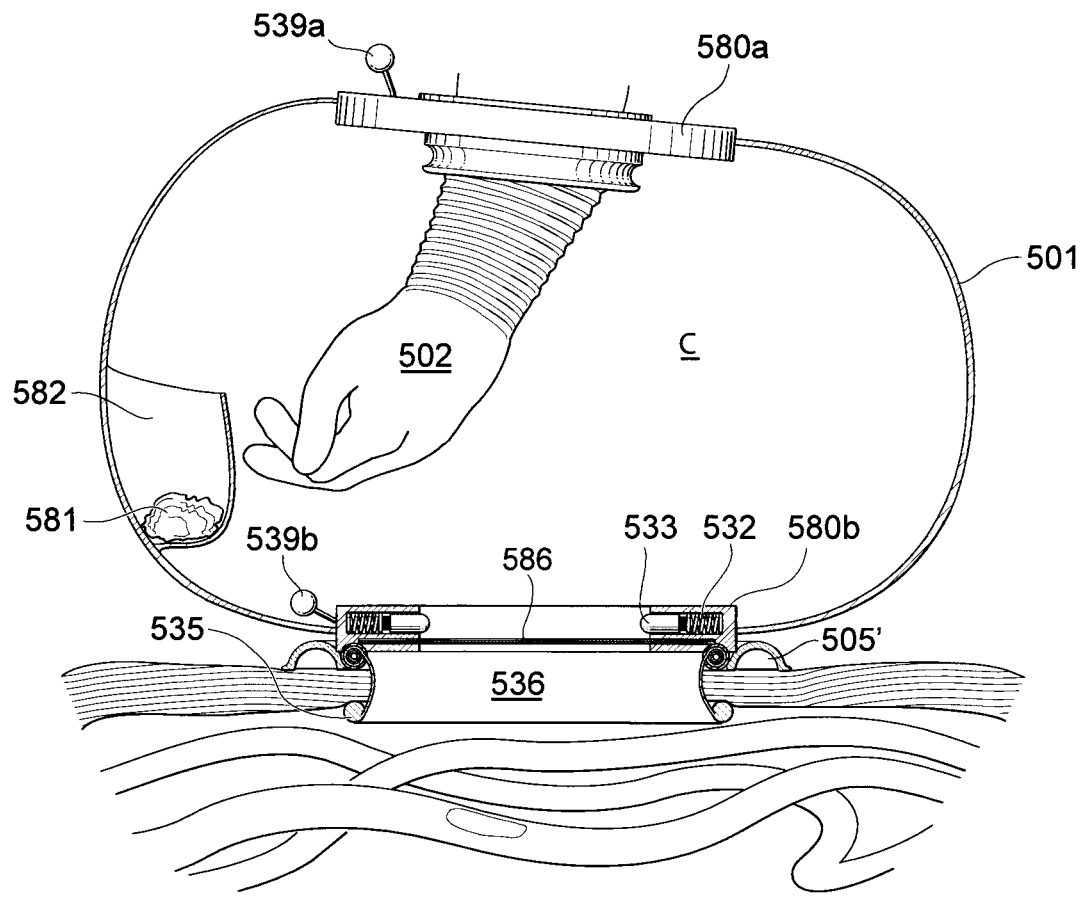

FIG. 64-65f shows a feature which could be implemented in the embodiments disclosed with reference to FIGS. 54-63. In the embodiment of FIGS. 64-65f, the wall 501 of the medical device 500 is inflatable, and the medical device is in its inflated state. When the chamber C is deflated it has a first volume i.e. when the upper 580a and lower 580b coupling are interconnected, and when the chamber C is inflated and the upper coupling 580a is disconnected from the lower coupling 580b it has a second volume, and the second volume is larger than the first volume. According to the embodiment shown in FIG. 64, the second volume is larger than 500 000 mm3 and adapted to hold a pressure exceeding atmospheric pressure.

According to the embodiment shown in FIG. 64-65f the chamber C further comprises a pouch 582 for holding a specimen 581 removed from within the body of the patient not to contaminate any other part of the body and create the possibility of delaying the removal of the specimen 581 until the procedure is concluded. The pouch 582 may be a pouch 582 which could be closed for creating a pouch-chamber within the chamber C for isolating the removed specimen 581 within the chamber C.

In FIG. 64, a state is illustrated in which the cut in the patient's skin S is being created by the surgeon by means of a glove inset 502 latched to the upper coupling 580a. The medical device is fixated and sealed by means of the vacuum sealing member 505' since the sealing device that is provided partially within the patient's body cannot be mounted until the cut in the patient's skin S is concluded. The two different sealing device disclosed could in some embodiments be replaced by only one of the sealing device, or by a different sealing device, such as the adhesive or pressure sealing device disclosed in other portions herein.

FIG. 65a shows the medical device, when the second sealing device 535, 536, 537 have been placed in the incision cut in the patient's skin S. The wall 501 enclosing the chamber C is elastic or flexible which enables the surgeon move the upper coupling 580a in relation to the lower coupling 580b for getting better access to different angles within the patient's body, for example for removing a specimen 581. The embodiment of FIG. 65a further comprises an iris valve 586 placed in the lower coupling 580b for closing the coupling such that the chamber C is sealed from at least one of the ambient environment and a cavity in the patient. The closing of the iris valve 586 enables activity within the chamber C without maintaining a pressure in the chamber C, at the same time as a pressure and/or a closed environment can be maintained within the body of the patient.

FIG. 65b shows the medical device when the glove inset 502 is removed and replaced by a wall port 517 comprising a plurality of ports. The wall port 542 may be used for manipulating objects within the chamber C of the inflated medical device 500 using surgical instruments, or within the body of the patient, when the first and second couplings 580 are connected (as shown in FIG. 65c).

FIG. 65c shows the medical device when the first and second parts are connected such that surgical instruments 589 can be used for manipulating within the body of the patient. An endoscopic camera 565 may be provided in the wall/body port 517; 522 port for enabling visual inspection of the cavity within the patient's body. The process of cutting away a specimen 581 from the intestines of a patient in a laparoscopic way is shown in FIG. 65b.

In FIG. 65d, the inset 542 comprising a glove 502 has been fixated to upper coupling 580a to enable the surgeon to operate within the cavity of the patient's body and within the chamber C enclosed by the wall 501 of the medical device 500. By the inset 542 comprising the glove 502 comprising a pleated portion 503, the surgeon is able to reach into the cavity of the patient for removing the specimen 581 cut loose from the intestines in prior steps.

FIG. 65e shows that the wall 501 of the medical device 500 is collapsible such that the inset 542 comprising the glove 502 can be moved with relation to the lower coupling 580b, which gives the surgeon further freedom when removing the loose specimen 581 from the intestines of the patient.

FIG. 65f shows the step of placing the removed specimen 581 in the pouch 582 such that the specimen 581 does not contaminate any other part of the body. The pouch 582 may be a pouch 582 which could be closed for creating a pouch-chamber within the chamber C for isolating the removed specimen 581 within the chamber C.

Figure 65G:
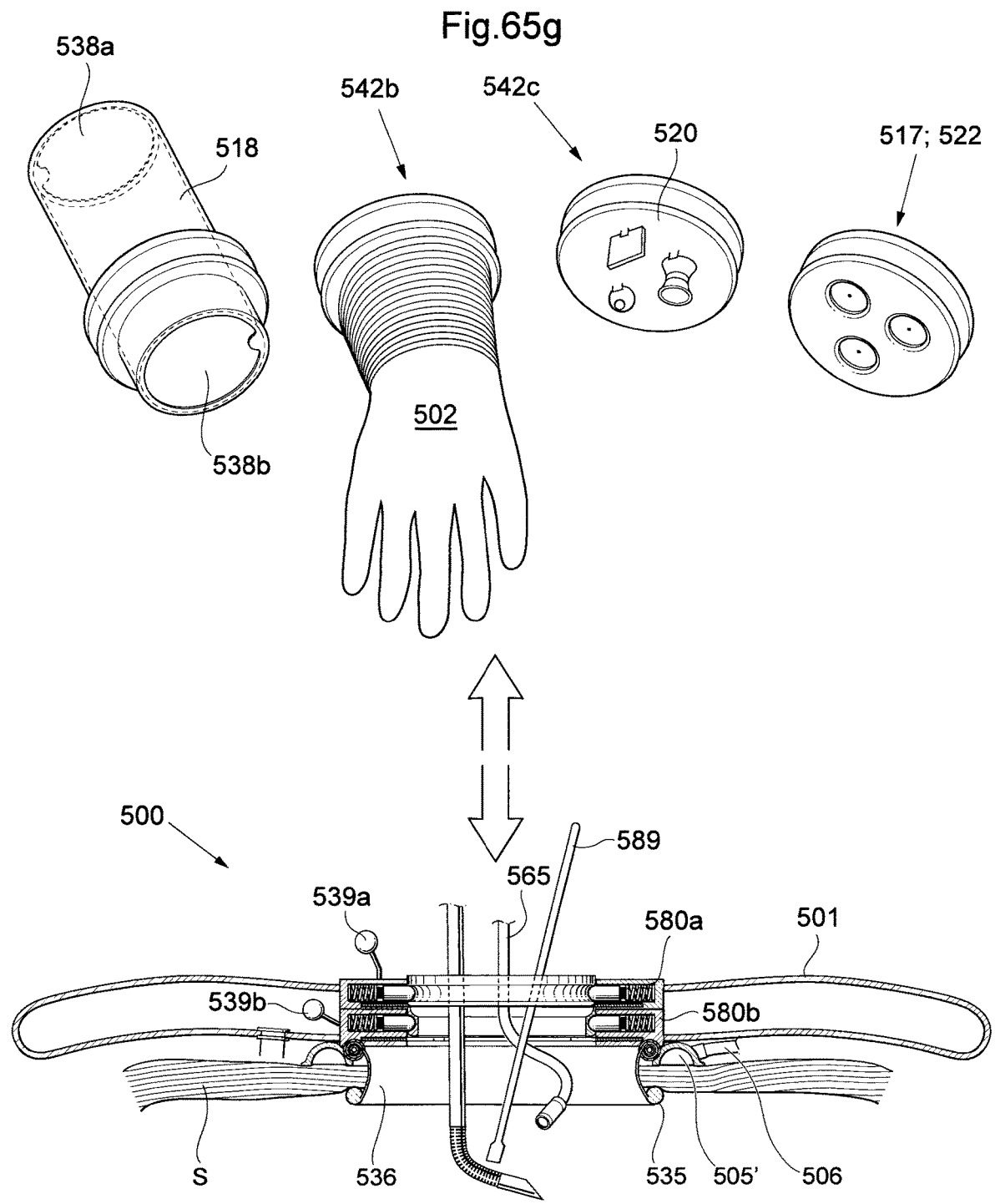

FIG. 65g shows an alternative of the embodiment shown in FIGS. 54-64. Fig. In 65g the medical device 500 is adapted to be at least partially placed in an incision cut in a patient's body. The medical device 500 comprises am upper 580a and lower 580b coupling adapted be interconnected to form an interconnected coupling. The upper coupling 580a is adapted to be disconnected from the lower coupling 580b, and the upper coupling 580a is connected to a first portion of a flexible wall 501, and the lower coupling 580b is connected to a second portion of the flexible wall 501. The flexible wall 501 forms a chamber C in which a closed environment can be maintained, the chamber C is heavily enlarged when the upper coupling 580a is disengaged from the lower coupling 580b, thus creating operating space within the chamber C enclosed by the wall 501. The upper 580a and lower 580b couplings comprises a latching system for locking an inset 542. The inset 542 could be an inset 542b comprising a glove 502 for manual manipulation within the body of the patient, or within the enclosed chamber C, a device or instrument mount 520 for holding devices or instruments within the chamber C. Alternatively the insets 542b; 542c can be replaced by an airlock sluice 518 with a first 538a and second 538b valve member or a port a wall port 517 or body port 522, which could be a multi port comprising a plurality of ports enabling the insertion of surgical instrument 589 into the chamber C or body of the patient.

In the embodiment shown in FIG. 65g the medical device 500 is fixated to the body of the patient by means of a vacuum fixating member 505' connected to a vacuum conduit 510, which in turn is connected to a vacuum source. Furthermore, the medical device in FIG. 65g comprises a second sealing device having a first sealing member in the form of an intra body ring 535 adapted to be positioned at the inside of the patient's skin S around an incision to be performed in the skin S and a second sealing member 537 in the form of an outer ring 537 adapted to be positioned at the outside of the patient's skin S around the incision, and a spring-loaded or elastic connecting member 536 sealingly interconnecting the first 535 and second 537 sealing members. The spring-loaded or elastic connecting member 536 seals between at least one of the outer ring 537 and the skin S of the patient, and the intra body ring and the tissue of the patient.

Figure 65H:
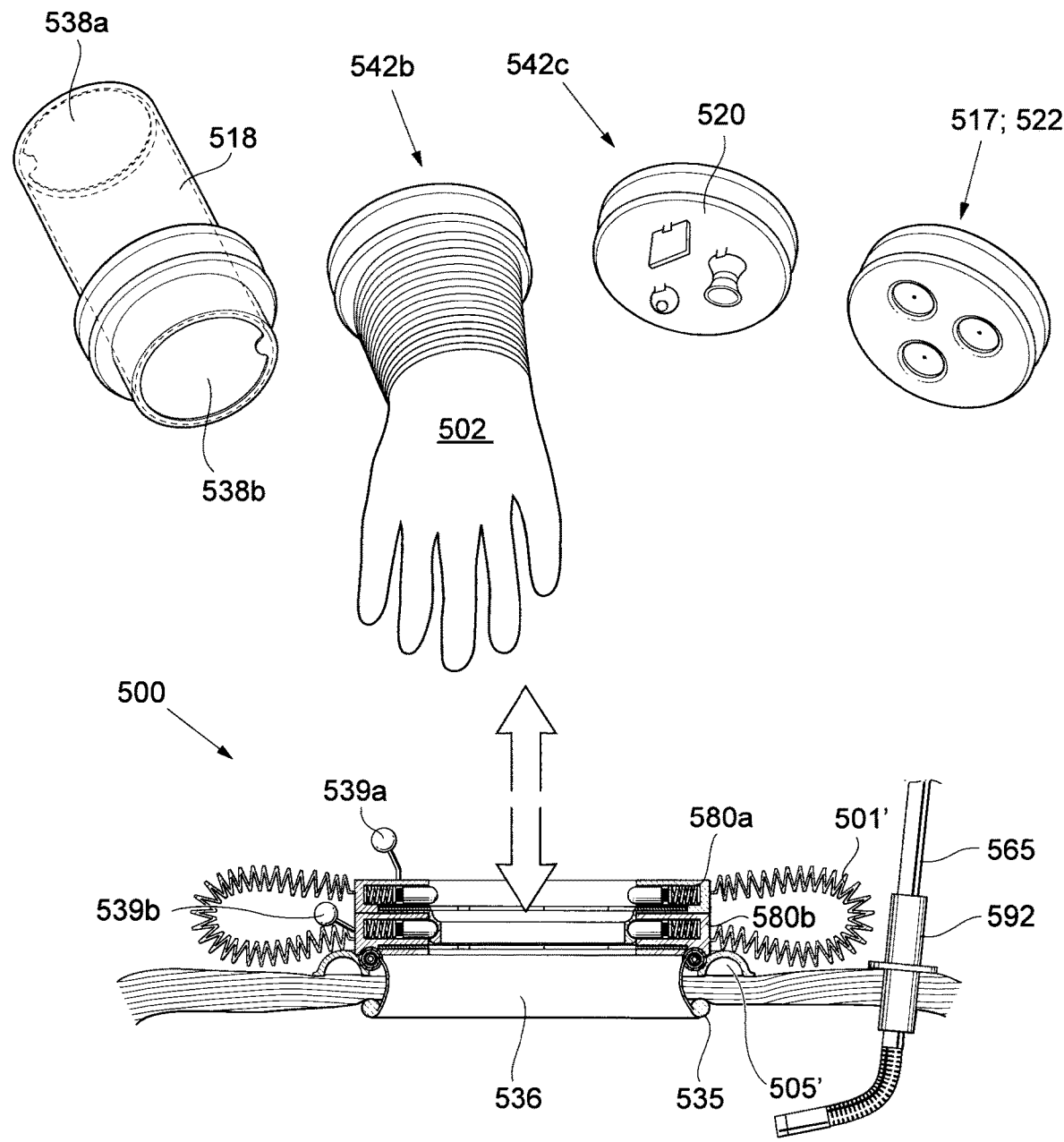

FIG. 65h shows the port in an embodiment very similar to the embodiment shown in FIG. 62 but with the difference that the wall 501' has a bellows structure and thus taking up less space when in its deflated state. The bellows structure enables the wall to be packaged in a small package and thus not obstructing the procedure. In some applications the wall 501 can be used only on very special occasions or emergencies, such as when some part of the procedure goes wrong and conversion from endoscopic surgery to more open surgery is required. The use of the inflated chamber C then enables the pressure in the cavity within the patient to be maintained since the chamber C can hold a pressure. A camera 565 is also shown in FIG. 65h, placed outside of the medical device 500 through a trocar 592 and enabling visual inspection of the cavity within the patient.

Figure 65I:
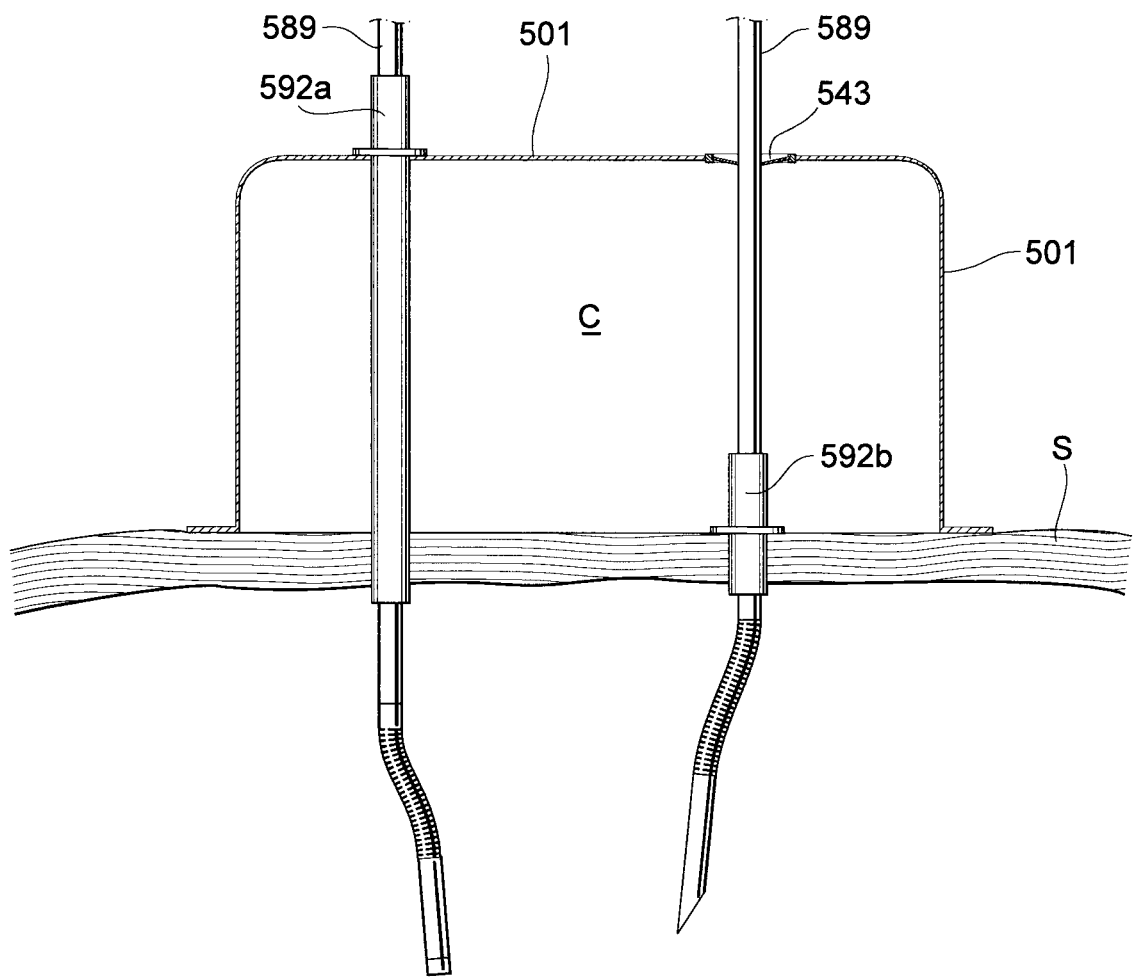

FIG. 65i shows examples of how trocars 592a; 592b may be used in combination with the medical device according to any of the embodiments shown in FIGS. 54-65h. The medical device comprises a wall 501 placed on the patient's skin and thereby enclosing a chamber C for creating a closed environment. The medical device comprises two trocars 592a; 592b, one 592a traveling through both the wall 501 of the medical device 500 and the skin S of the patient and thus enabling endoscopic instruments 589 to be inserted into the patient through both the wall 501 of the medical device and the skin S of the patient through one single trocar 592a. The other trocar 592b is placed inside the chamber C and enables an endoscopic instrument 589 to be inserted through the skin S of the patient. The endoscopic instrument 589 is in this embodiment inserted into the chamber C enclosed by the wall 501 through a membrane 543 in the wall sealing against the tool 592b.

Figure 65J:
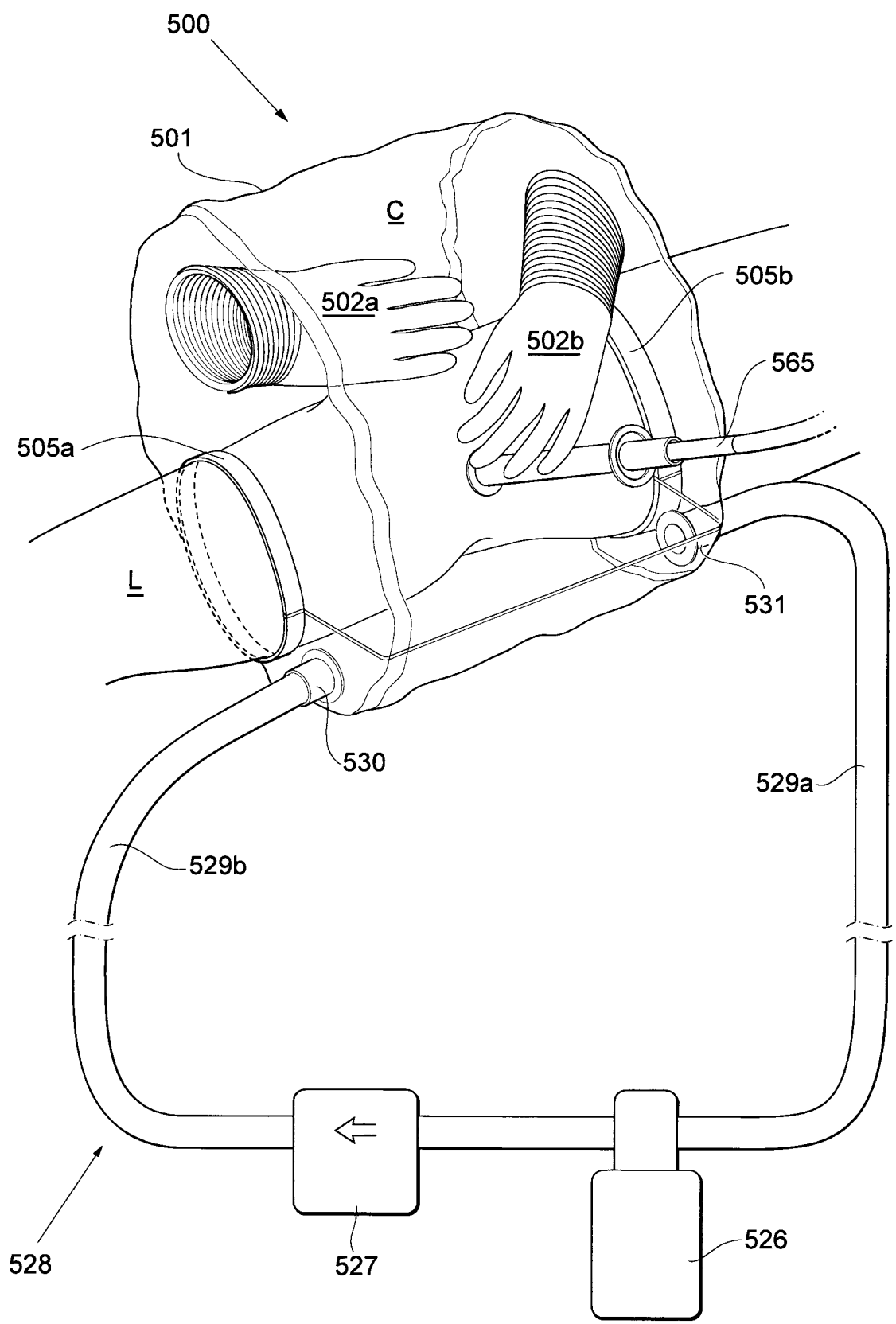

FIG. 65j shows an embodiment of the medical device 500 where the wall 501 is collapsible such that it can be collapsed for package and/or transportation and inflated when put to use in a surgical procedure. In the embodiment of FIG. 65j, the layer 501 is made from a flexible material, such as a flexible polymer material or a woven material. The material could be transparent or translucent for enabling viewing into the chamber C. The medical device 500 is shown with a system 528 for circulating a liquid or gaseous fluid. The fluid is circled form an outlet 531 in the wall 501 through a first conduit 529a via a pump 527 and via a system 526 for sterilization/filtering/tempering and humidification, through a second conduit 529b to an inlet 530.

Figure 65K:
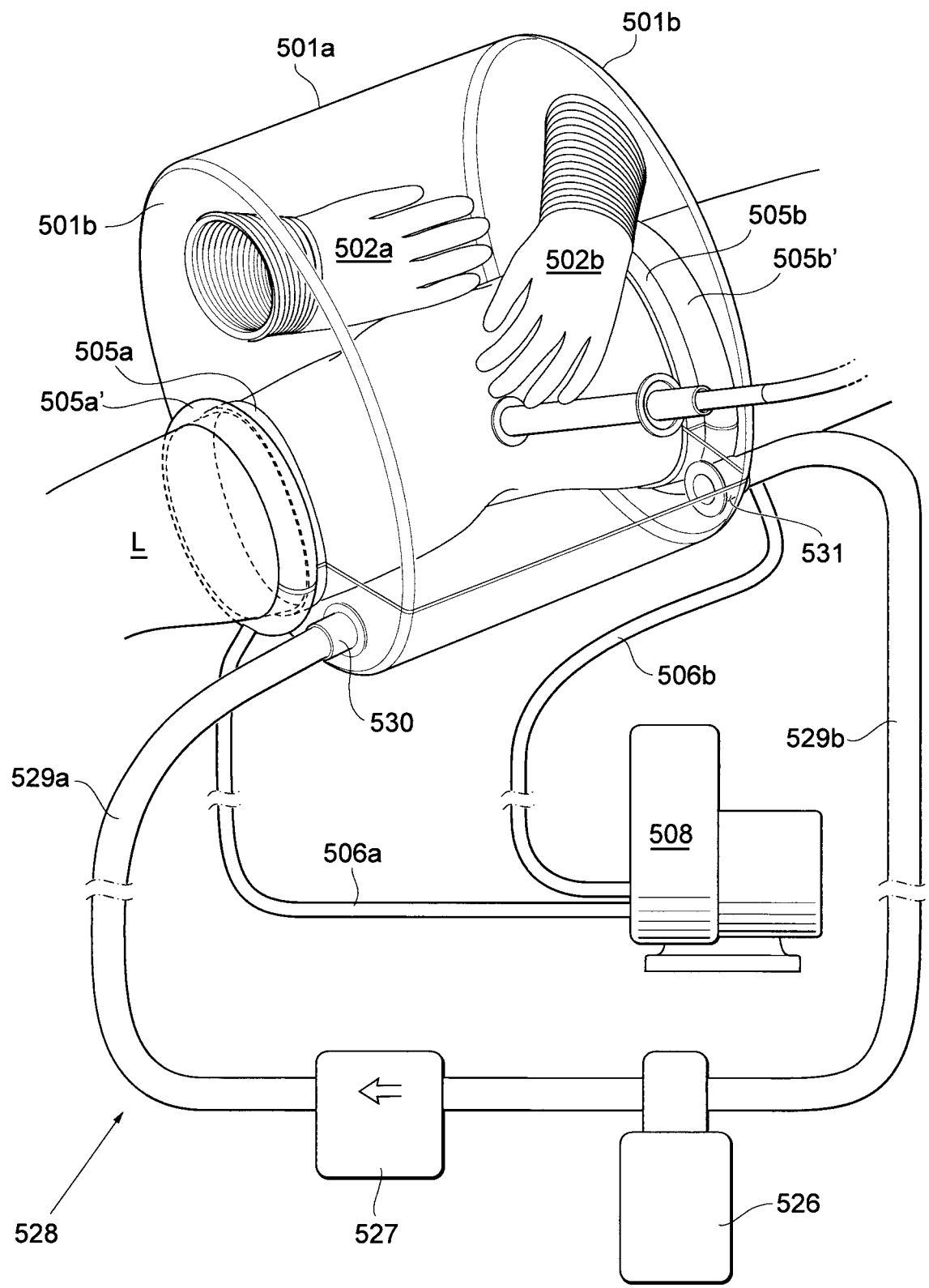
Figure 65I:
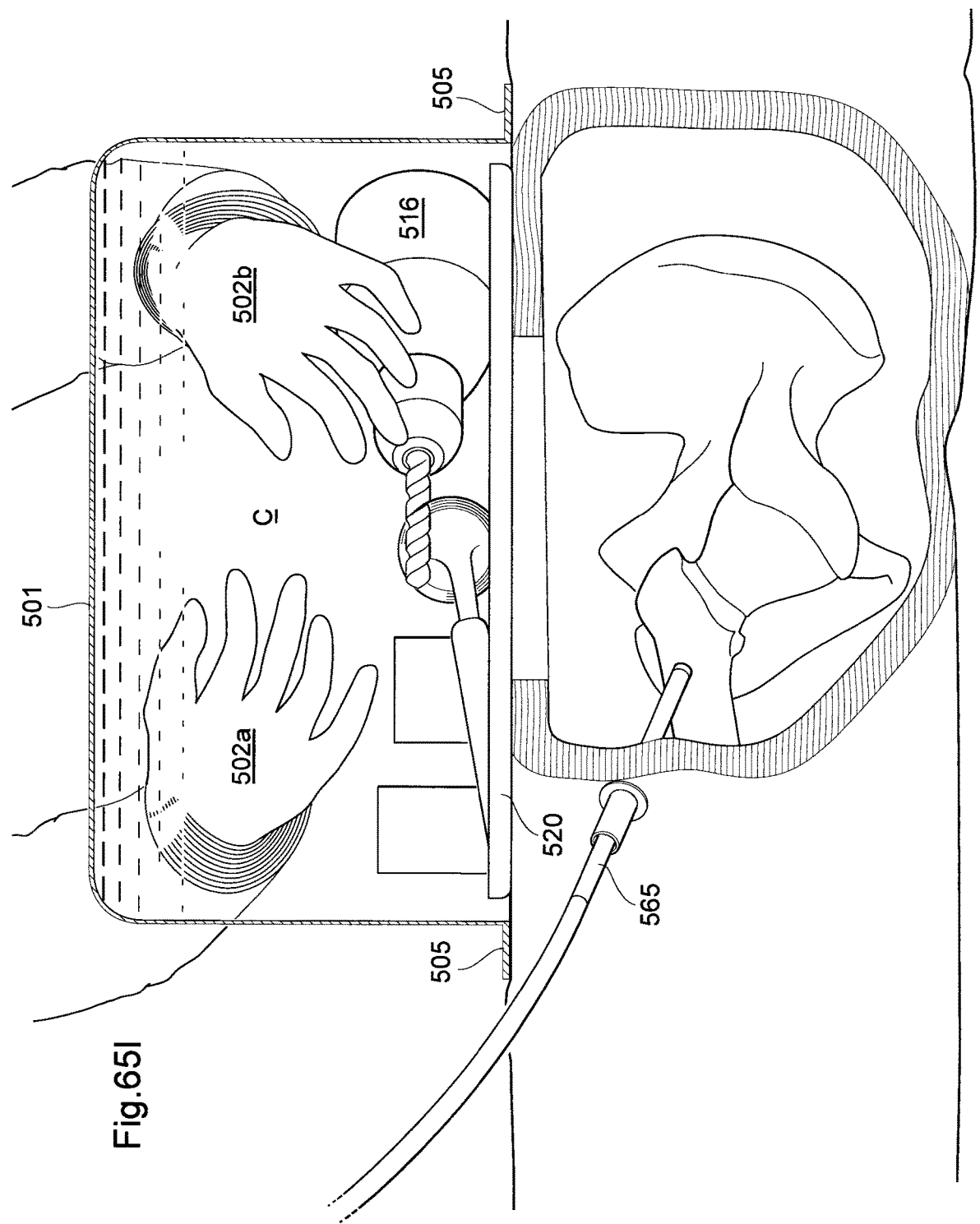

FIG. 65k shows the medical device according to an embodiment comprising the features of the embodiment disclosed with reference to FIG. 65j and further comprising a sealing device comprising vacuum sealing members 505a', 505b' encircling the leg L of the patient for sealing between the medical device 500 and the skin S of the patient. The vacuum sealing members 505a', 505b' are connected to a vacuum pump 508 through vacuum conduits 506a, 506b transferring the vacuum from the vacuum pump 508 to the vacuum sealing members 505a', 505b'. The vacuum sealing members 505a'; 505b' described with reference to FIG. 65k could be used in combination with the sealing members 505a, 505b which for example could comprise two elastic ring shaped members 505a, 505b, sealing by pressing against the skin of the patient, or without the seals 505a, 505b, in which case the vacuum sealing members 505a'; 505b' could be materially integrated in the two second portions 501b of the layer 501.

FIG. 65l shows the medical device according to an embodiment in which the medical device is adapted for performing hip joint procedures. The medical device comprises a wall 501 enclosing a chamber C adapted to be at least partially filled with a liquid when performing a surgical procedure therein. According to the embodiment shown in FIG. 65l the wall 501 is made of a rigid transparent material for example glass or a transparent polymer material such as an acrylic glass, a polycarbonate, polyethylene terephthalate, an acrylic fiber material or a copolymer containing polyacrylonitrile. However, in other embodiments the layer 501 could be partially translucent or opaque and have a transparent window for enabling viewing into the sealed environment. The medical device according to the embodiment described with reference to FIG. 65*l* is comprises a device/instrument mount 520 adapted to hold a pre-placed implant within the chamber C before the medical device is connected to the patient. The medical device is further adapted to hold equipment to be used in performing the surgical procedure and a powered tool 516, which in this embodiment is represented by a drill. The medical device is adapted to be fixated to the skin of the patient by means of a sealing device 505 contacting the skin of the patient and the medical device. The sealing device comprises an adhesive sealing member 505'" which could comprise a pressure sensitive adhesive such as 3M's pressure sensitive adhesive Scotch-Grip 4268-NF. The medical device further comprises two gloves 502*a*, 502*b* integrated in the wall 501 of the medical device, enabling manual manipulation within the chamber C, such as placement of the implant in the hip joint of the patient, without penetrating the layer 501, thus keeping the chamber C hermetically closed and reducing the risk that bacteria and/or virus potentially causing infectious diseases can enter the chamber C. A camera 565 for visual inspection is further provided.

FIGS. 65*m* and 65*n* shows an embodiment of the medical device comprising the features of the embodiment described with reference to FIG. 65*l* and additionally comprising an inlet 530 through which the liquid or gaseous fluid in the chamber C enters, and en outlet 531 through which the liquid in the chamber C exits. The inlet 530 and outlet 531 could be connected to a liquid circulating system, for example as disclosed with reference to FIG. 65*k* which could comprise a pumping unit, a tempering unit, a sterilization unit and a filtering unit. In other embodiments the liquid is not circulated but instead only used once in which case new liquid enters the sealed environment at the inlet 530 and exits the device at the outlet 531 after which the liquid is disposed of. The embodiment described with reference to FIG. 65*m* further comprises a pneumatic system 513 adapted to supply an tool consuming pneumatic energy inside of the chamber C with energy. The pneumatic system is adapted to transfer energy from the outside of the wall 501 to the inside of the wall 501 by means of an coupling which is further disclose under reference to FIGS. 213*a*; 213*b*. In alternative embodiments, the energy transferring coupling could be adapted to transfer mechanical, electrical or hydraulic energy, which is further disclosed under reference to FIGS. 212-214 and the energy consuming tool could correspondingly be a mechanical, electrical, hydraulic or pneumatic tool. The tool 516 is in the embodiment shown illustrated by a drill, however it is equally conceivable that the tool is a saw, a reamer, a tool for fastening of orthopedic screws, or any other orthopedic or generally surgical tool requiring energy to function.

FIG. 65*o* shows the embodiment of the medical device similar to the embodiment shown in FIG. 55*b* when the arm of the surgeon is inserted through the self sealing wall port 522 in the partially collapsible wall 501 for enabling manual manipulation therein. Manual manipulation through the self sealing wall port 522 could for example be used as a last resort should complications occur during the procedure, or if additional hands are required for a specific step of the operation. FIG. 65*o* further shows an internal system 528' for fluid circulation, and an external system 528 for fluid circulation. Both systems comprises fluid conduits 529; 529', in the external system 528 connected at an inlet 530 placed in the partially collapsible wall 501 for supplying fluid to the chamber C, and an outlet 531 for draining the fluid from the chamber C, and in the internal system 528' connected to an inlet 530' in the patient's body and an outlet 531' in the patient's body for circulating fluid in a body cavity. The fluid is circulated by means pumping units 527; 527' and is circulated via a sterilizing/filtering/tempering unit 526', in the external system disclosed as containing a sterilizing 526*a*, filtering 526*b*, and tempering 526*c* unit adapted to remove impurities, sterilize and heat the fluid. In embodiments where the fluid is a gaseous fluid, the filtering unit is adapted to remove particles that could be suspended in the gas. The filtering unit 526*a* could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 526*a* could for example comprise a filter containing activated carbon.

Figure 65P:
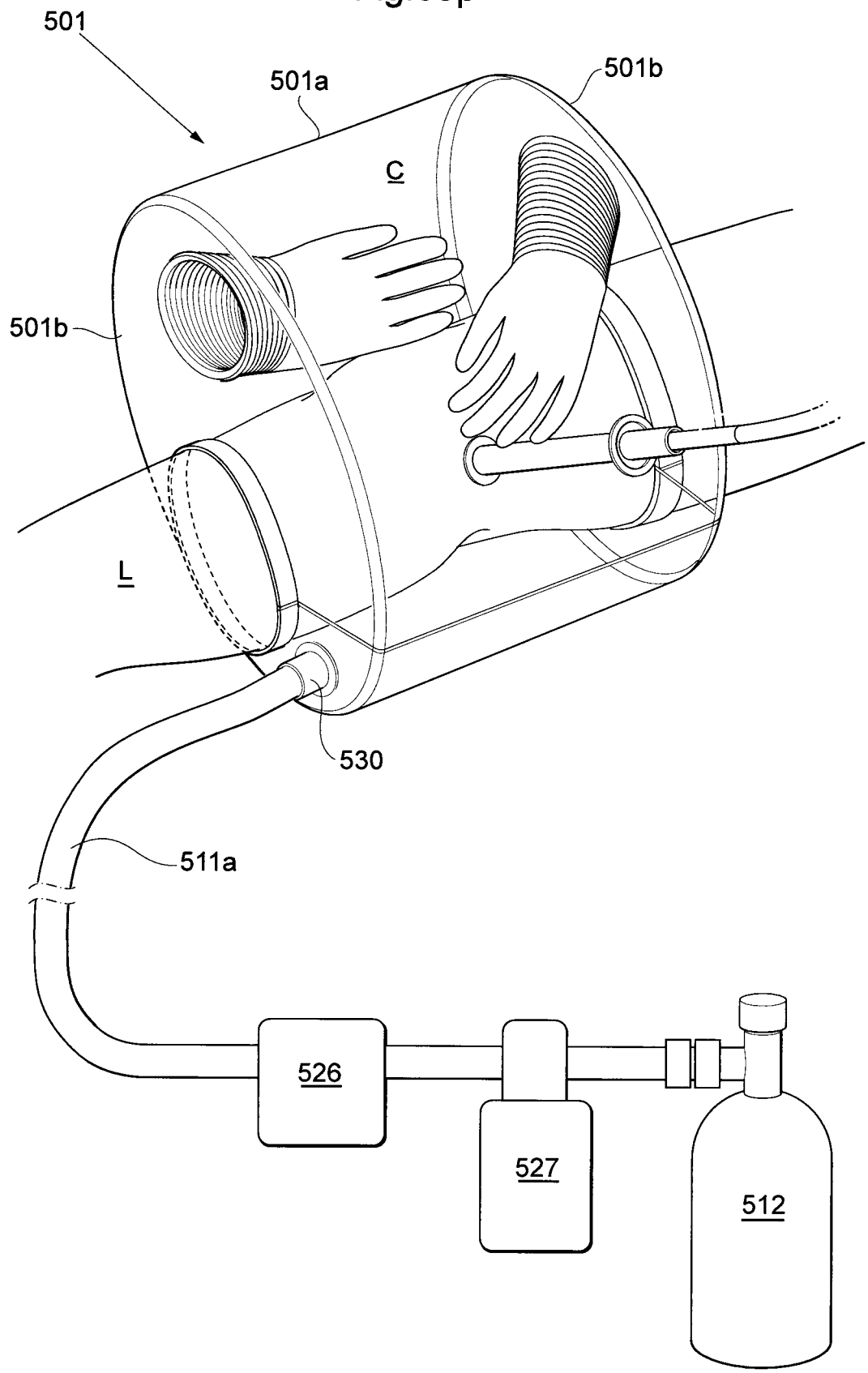
Figure 65P:
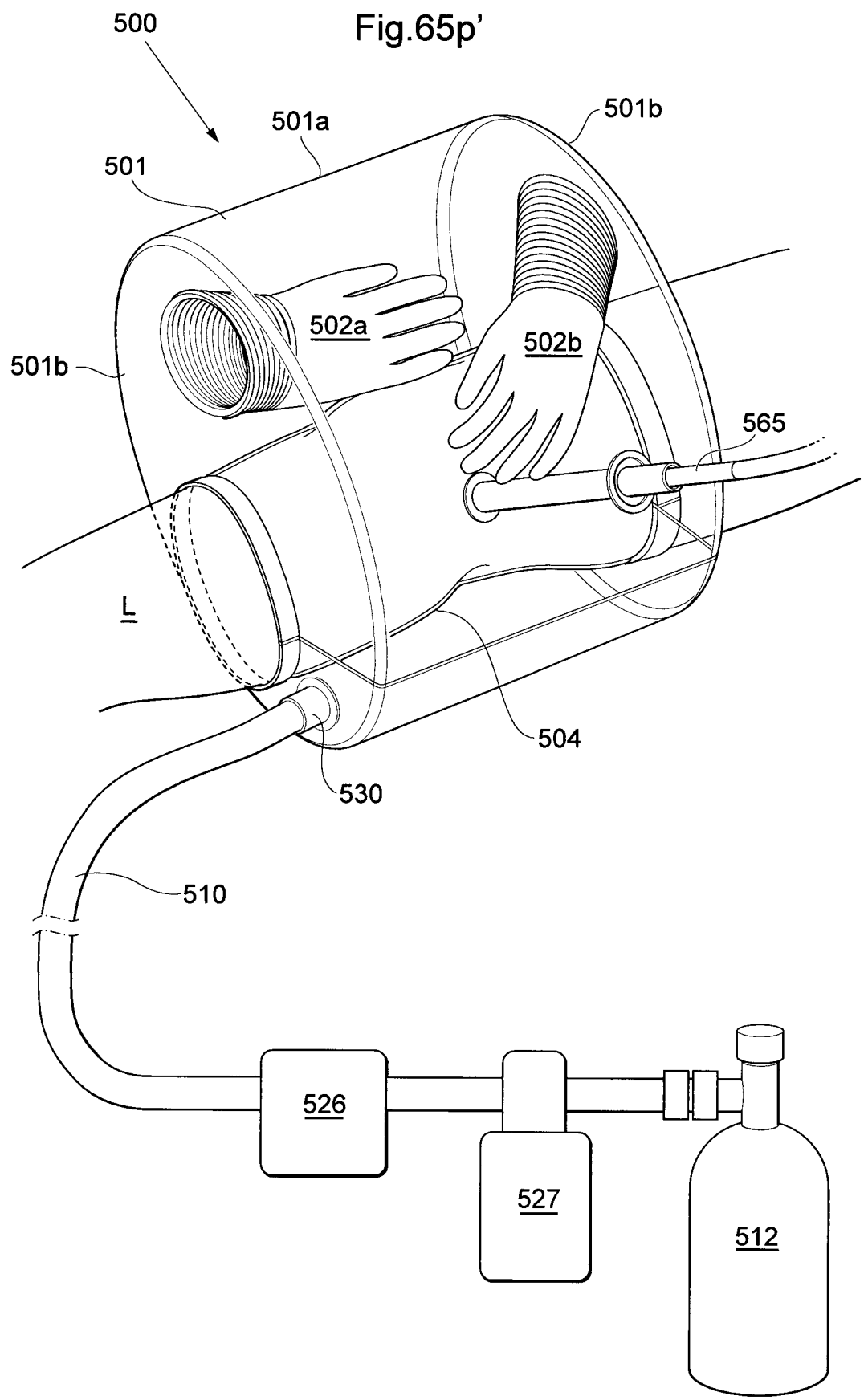

FIG. 65*p* shows an embodiment of the medical device similar to the embodiments described with reference to FIGS. 65*j* and 65*k*, in the embodiment disclosed with reference to FIG. 65*p* the medical device is adapted to be filled with a gaseous fluid, such as air or $CO_2$ gas. The system could be adapted for using the gas one time only, in which case new gas could come from a pressurized gas container and enter sealed environment through the inlet 530. In other embodiments the medical device further comprises a gas circulating system adapted to circle and thus reuse the gas, in which case the system could comprise a gas pumping unit, a gas tempering unit, a gas sterilization unit and a gas filtering unit outlined similar to the embodiments disclosed with reference to FIG. 65*q*. The system for filling the chamber C with gaseous fluid could comprise a control valve 527 and a unit 526 for sterilizing and heating the gas before it enters the chamber C.

FIG. 65*p*' shows the medical device according to an embodiment similar to the embodiment disclosed with reference to FIG. 65*p*, the difference being that an elongated tubular enclosure 504 is provided which extends within the chamber C and separates the chamber C from the skin of the patient. This reduces the amount of skin in fluid communication with the chamber C since the elongated tubular enclosure 504 only needs to be cut open where the incision in the skin of the patient should be performed.

Figure 65Q:
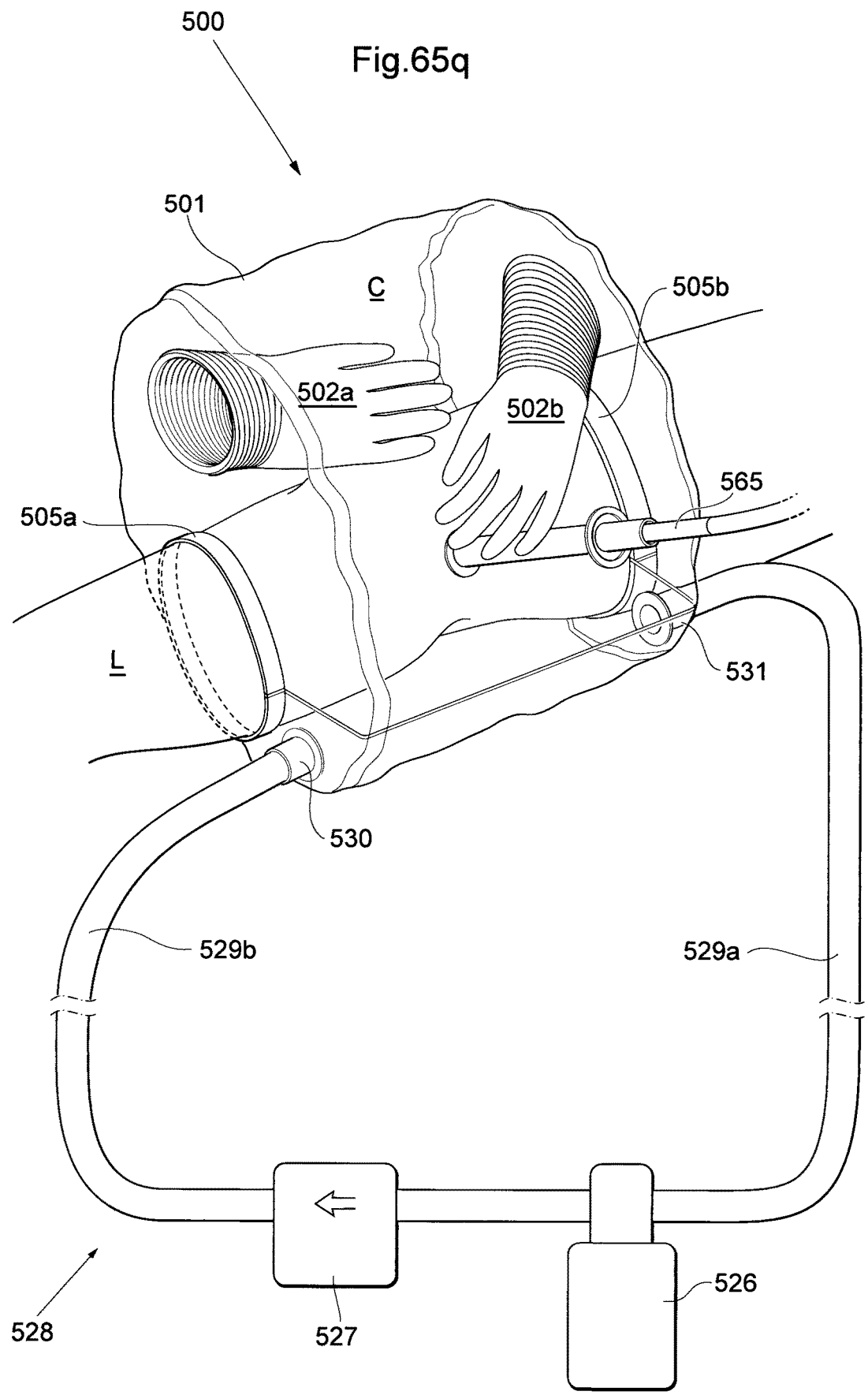

FIG. 65*q* shows an embodiment of the medical device where the wall 501 is collapsible such that it can be collapsed for package and/or transportation and inflated when put to use in a surgical procedure. In the embodiment of FIG. 65*q*, the wall 501 is made from a flexible material, such as a flexible polymer material or a woven material. The material could be transparent or translucent for enabling viewing into the chamber C of the medical device 500. The medical device 500 is shown with a system 528 for circulating a liquid or gaseous fluid. The fluid is circled form an outlet 531 in the wall 501 through a first conduit 529*a* via a pump 527 and via a system for sterilization/filtering/tempering 526, through a second conduit 529*b* to an inlet 530.

Figure 65R:
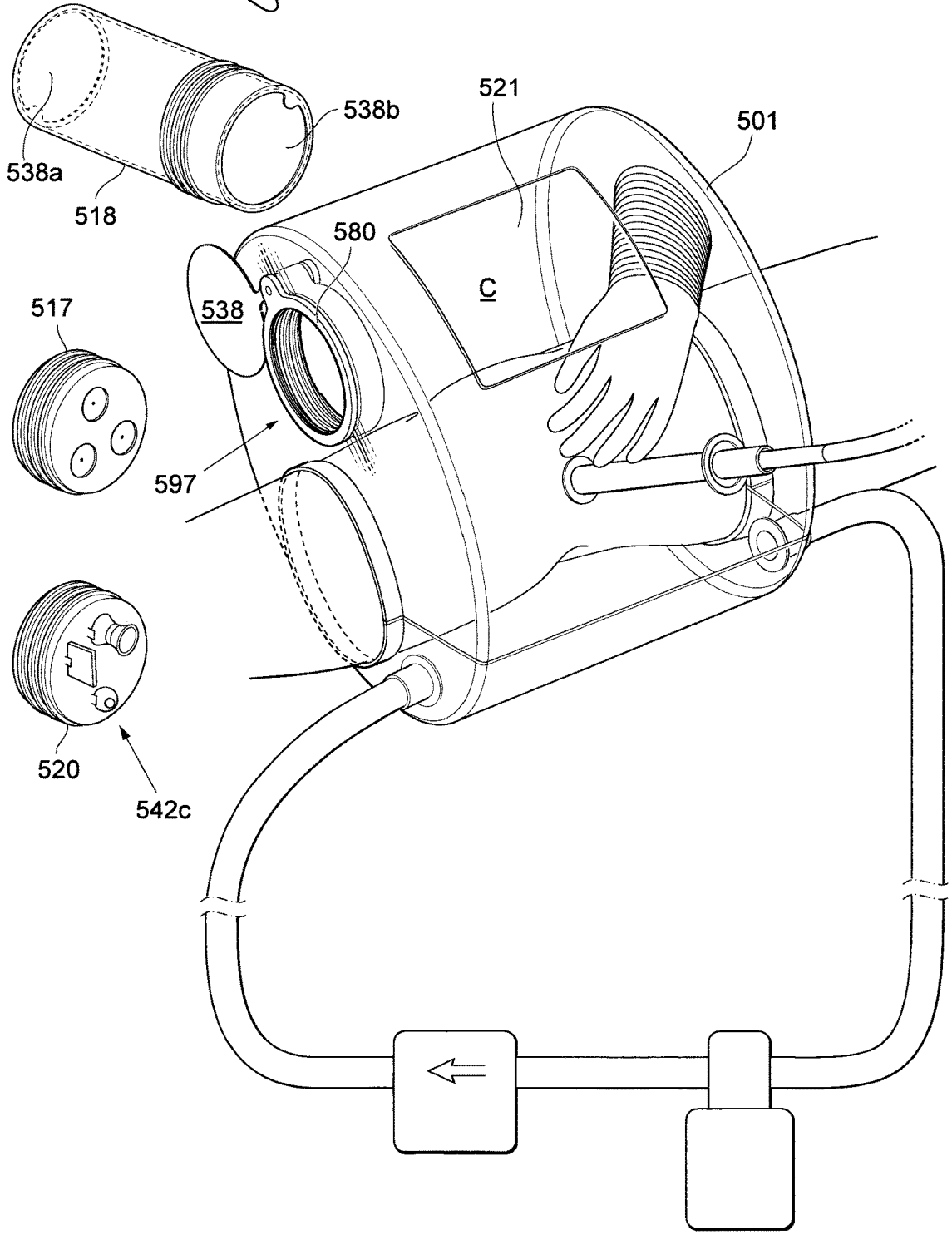

FIG. 65*r* shows the medical device according to an embodiment in which the medical device comprises a non-collapsible transparent window 521 for enabling viewing into the chamber C. The window 521 is preferably used in embodiments where the wall is a collapsible wall, as further disclosed with reference to FIG. 65*q*. The non-collapsible transparent window 521 will ensure that the surgeon has adequate visual control over the procedure since the partially collapsible layer, even if preferably made from a transparent material could provide limited visibility, e.g. if the medical device is not fully inflated, or in seams or bends of the material. The non-collapsible transparent window 521 could for example be made from acrylic glass, a polycarbonate, polyethylene terephthalate, an acrylic fiber material or a copolymer containing polyacrylonitrilea, or made from tempered glass. In other embodiments (not shown) the medical device could further comprise a cleaning device for cleaning the transparent window 521 from the inside of the sealed environment. The cleaning device could comprise an arrangement for supplying a fluid adapted to assist in the cleaning of the transparent window via a fluid conduit to a nozzle placed in proximity to the transparent window. The fluid could for example be an isotonic solution, such as saline solution, or an antiseptic solution such as Chlorhexidine. The medical device could further comprises a window contacting member for wiping the window clean after the fluid has been sprayed thereon for mechanically removing objects from the window. The embodiment shown in FIG. 65r further comprises a coupling 580 positioned in the wall 501. In the embodiment shown in FIG. 65r the coupling 580 comprise screw-threads corresponding with screw-threads of the objects 542b; 542c; 518; 517 which could be coupled to the coupling 580. The coupling 580 as shown in FIG. 65r further comprises a valve member 538 which could be closed when no objects are placed in the coupling 580 or during the process of changing objects, when otherwise the coupling 580 would be left open. Examples of objects which could be placed in the coupling 580 are shown in FIG. 65r, however, other suitable objects are also conceivable and the scope of the invention is not to be limited to the particular objects shown, rather, the concept of having changeable objects is to be regarded as part of the invention. The examples of objects shown in FIG. 65r are now further described: An inset 542a comprising a glove 502, an airlock sluice 518 is shown comprising an outer valve 538a between the ambient environment and the airlock sluice 518 and an inner valve 538b between the airlock sluice 518 and the chamber C of the medical device. The airlock sluice 518 could enable transfer between the ambient environment and the airlock sluice 518, and between the airlock sluice 518 and the chamber C of the medical device, for enabling the transfer of for example prosthesis or prosthetic parts or surgical instruments. The airlock sluice 518 could further enable transfer of objects from the chamber C, into the airlock sluice 518 and further to the ambient environment, which for example could enable the transfer of specimens from the body of the patient. Both the transferring of objects into the chamber C and out from the chamber C could by means of the airlock sluice 518 be conducted whilst keeping the chamber C hermetically closed. FIG. 65r further shows a device/instrument mount 520 for prosthetic parts or surgical instruments. By means of placing the mount 520 or exchanging the mount 520 to a different mount 520, prosthetic parts or surgical instruments could be introduced into the chamber C, which for example could be used if different steps or unexpected events in the procedure require different instruments. A wall port 517 is further shown, the wall port 517 as shown in FIG. 65r comprises three ports adapted for endoscopic instruments. In some embodiments the port unit could comprise a single larger port unit which could enable hand access into the sealed environment, the single larger port unit could for example be a gel-port type port unit.

Figure 65S:
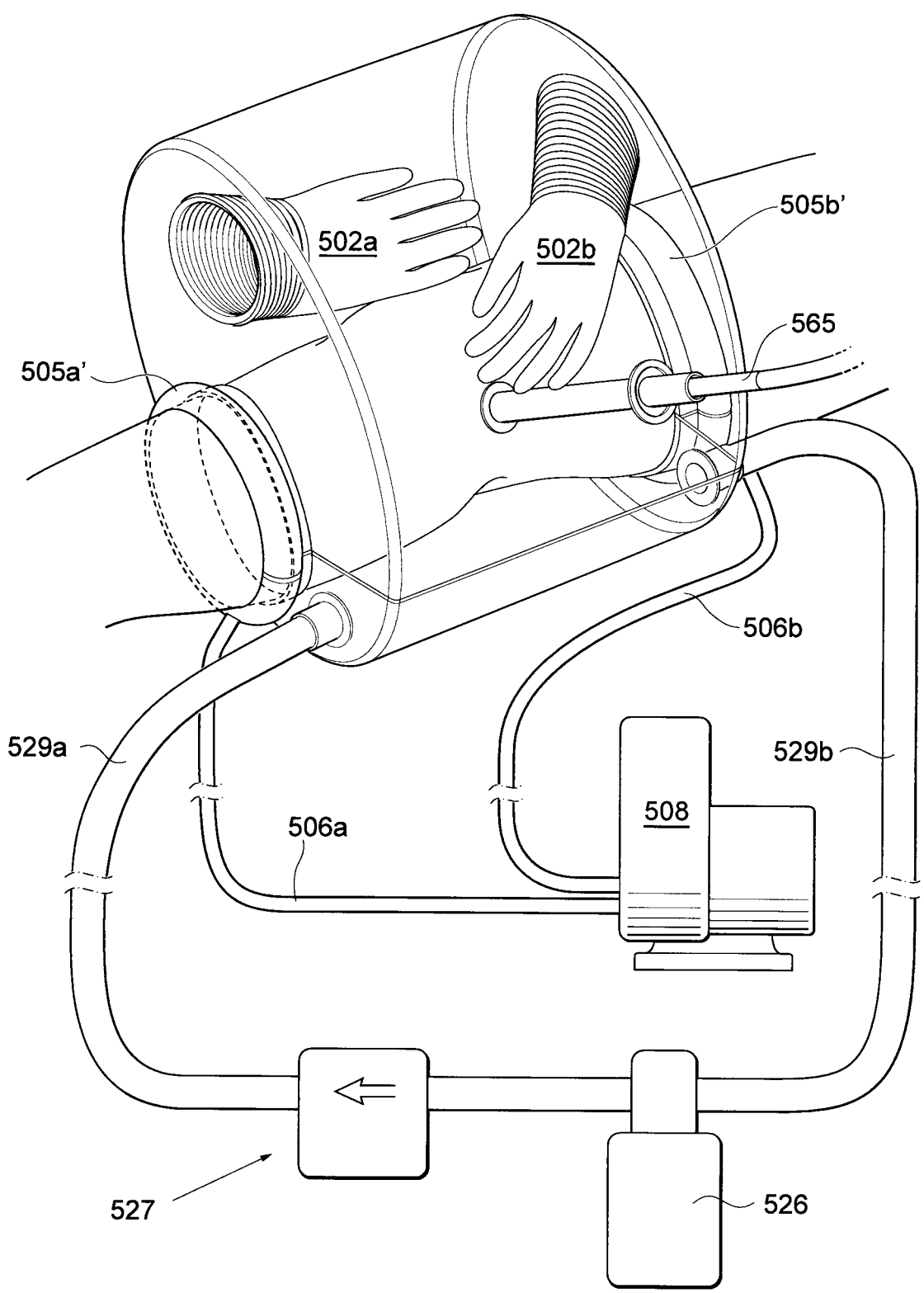

FIG. 65s shows an embodiment further comprises vacuum sealing members 505a', 505b' adapted to seal between the skin of the patient and the medical device by the vacuum sealing members 505a', 505b' being adapted to hold a pressure less than atmospheric pressure, thus creating a vacuum seal between the skin of the patient and the medical device. The vacuum sealing members 505a', 505b' are connected to a vacuum pump 508 through vacuum conduits 506a, 506b transferring the vacuum from the vacuum pump 508 to the vacuum seals 505a', 505b'. The vacuum sealing members 505a'; 505b' described with reference to FIG. 65s could be used in combination with other types of seals.

Figure 65T:
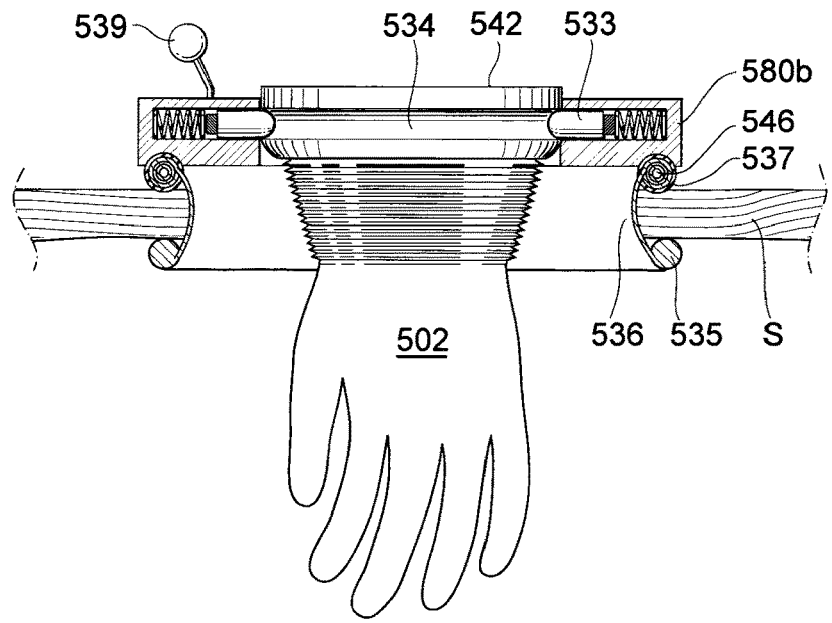

FIG. 65t shows the lower coupling 580b in further detail when an inset comprising a surgical glove 502 is fixated to the lower coupling 580b. The retractor system comprising the intra body ring 535 and s ring 537 adapted to be placed on the outside of the patients skin further comprises a retractor membrane 536 positioned such that it exerts a pressure on the cut surfaces of the incision for retracting the skin and thereby keeping the wound open. The retractor membrane 536 could be rolled up by a roll up system 546 inside of the outer ring 537 for tightening the retractor membrane 536 such that the wound is kept open.

Figure 65U:
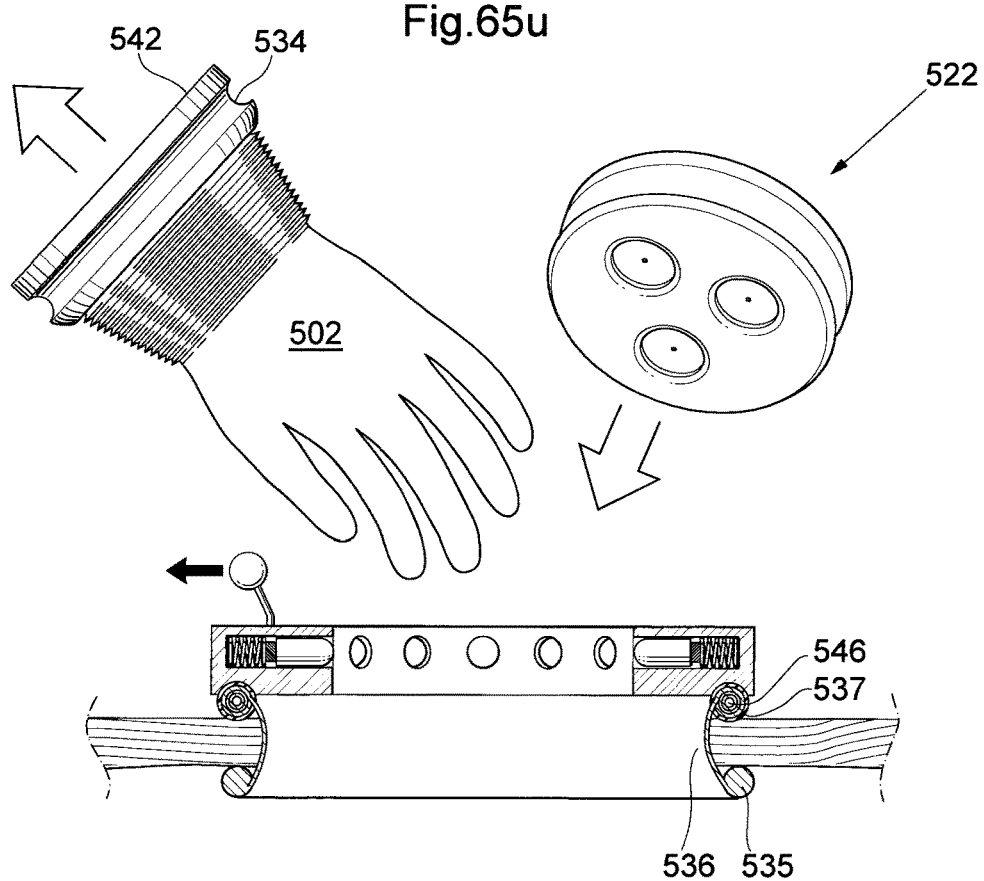

FIG. 65u shows the changing of objects in the lower coupling 580b from the inset 542a surgical glove 502 to a body port 522 in the form of a multi port 548 comprising three endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the endoscopic ports and surgical gloves could additionally be exchanged for device or instrument mounts, for example holding instruments or implants.

Figure 65V:
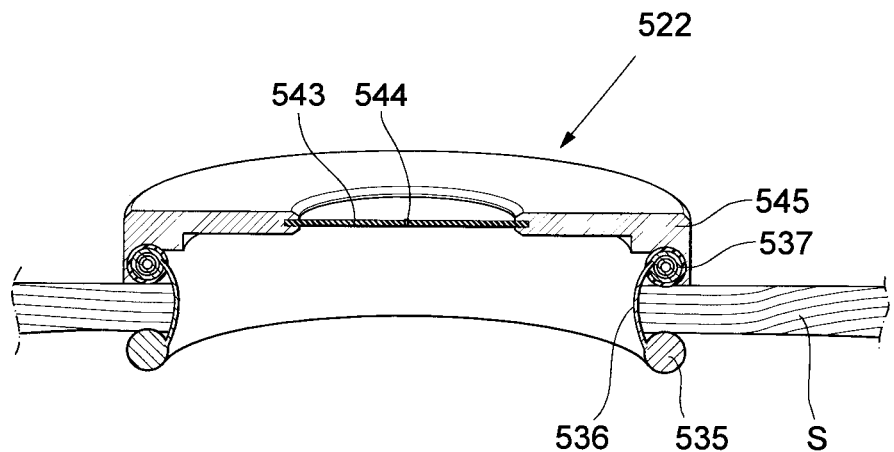
Figure 65V:
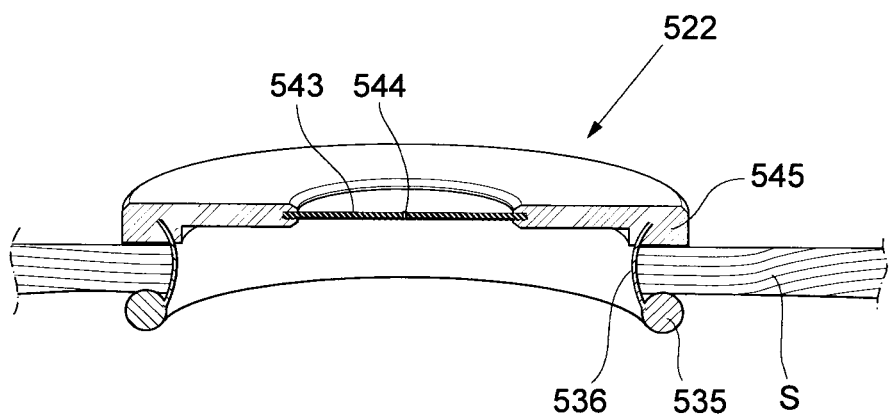

FIG. 65v shows a self sealing body port 522 in a close-up, in section. The self sealing body port 522 could be connected to the coupling for example as disclosed with reference to FIGS. 49a-c, which in turn is connected to any of the medical device disclosed with reference to FIGS. 42-48, or the self sealing body port 522 could be fixated to a retractor, as shown in FIGS. 65v and 65v'. The self sealing port 522 comprises a self sealing membrane 543 fixated to a rigid housing part 545 of the self sealing port. The self sealing membrane 543 having a small self sealing hole 544 centrally in the membrane 543. The self sealing membrane 543 is for example made from a gel-type material being elastic enough to enable a deformation large enough for a person's hand to pass through the small self sealing hole 544 while still contracting enough to create an airtight seal between the sealed environment and the outside environment. The medical device being fixable to a retractor comprising one intra body ring 535 adapted to be positioned on the inside of the patients skin S, and one ring 537 adapted to be placed on the outside of the patients skin S. Between the intra body ring 535 and the ring 537 adapted to be placed on the outside of the patients skin S a retractor membrane 536 is positioned which is adapted to exert a pressure of the cut surfaces of the incision for retracting the skin S and thereby keeping the wound open. The retractor membrane 536 is preferably made from a resilient of elastic polymer material, such a silicone. The outer ring 537 comprises an integrated roll up system 546 which could be a spring loaded roll up system 546 adapted to create a suitable pressure on retractor membrane 536 for keeping the wound open.

FIG. 65v' shows an alternative embodiment of the self sealing port 522, with the difference that the retractor membrane 536 is made from a material elastic enough such that one end of the retractor membrane 536 could be fixedly fixated to the rigid part 545 of the port.

Figure 65W:
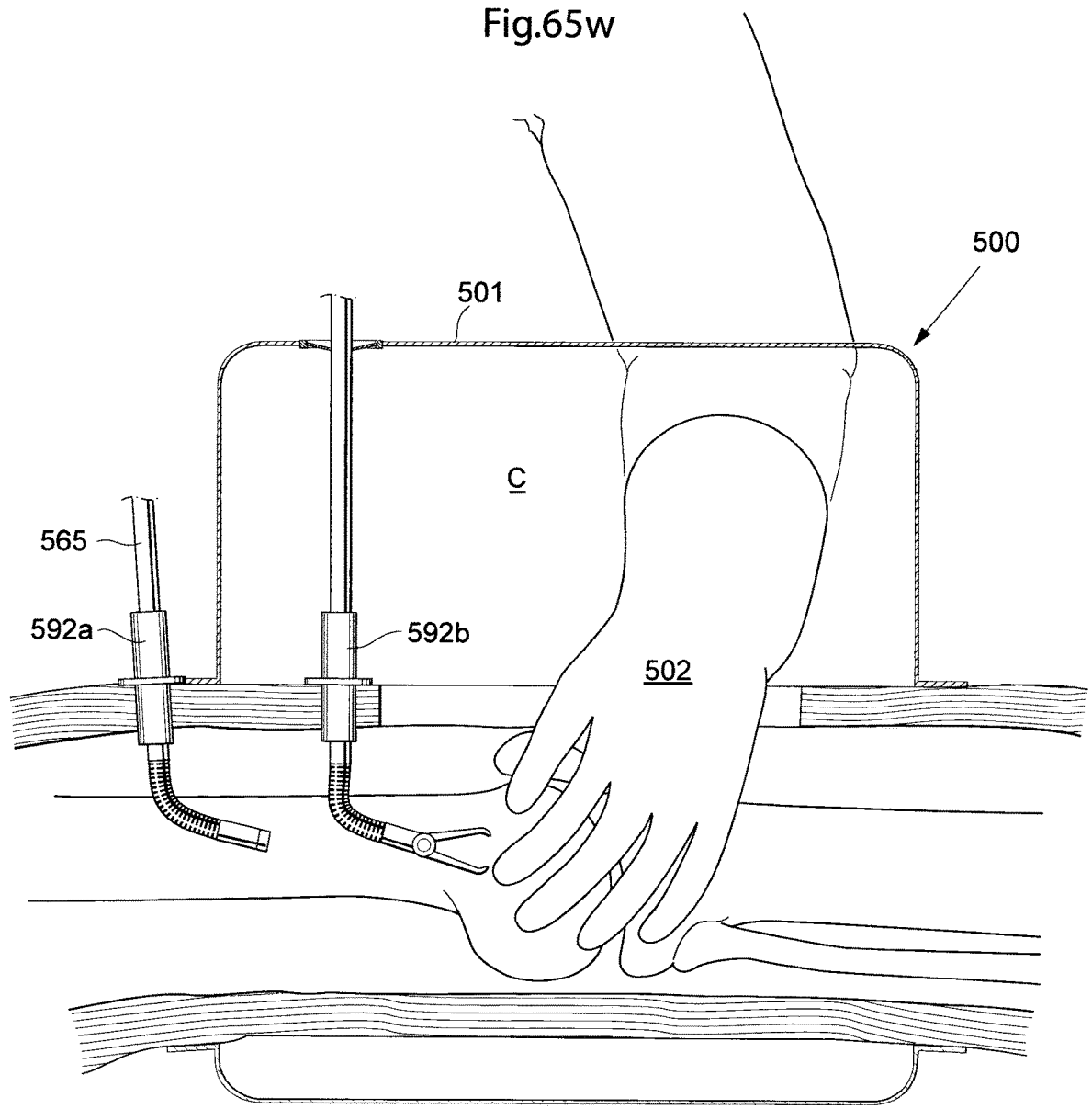

FIG. 65w shows how the medical device shown in FIGS. 64-65v' may be used. The medical device 500 comprises a glove 502 integrated in the wall 501 and a camera 565 placed in a trocar 592a in the skin outside of the medical device 500. The medical device 500 further comprises a trocar 592b placed inside the chamber C into an area of the knee of the patient. FIG. 65w schematically illustrates how the surgeon manipulates the knee in the chamber C using the glove 502.

Figure 65X:
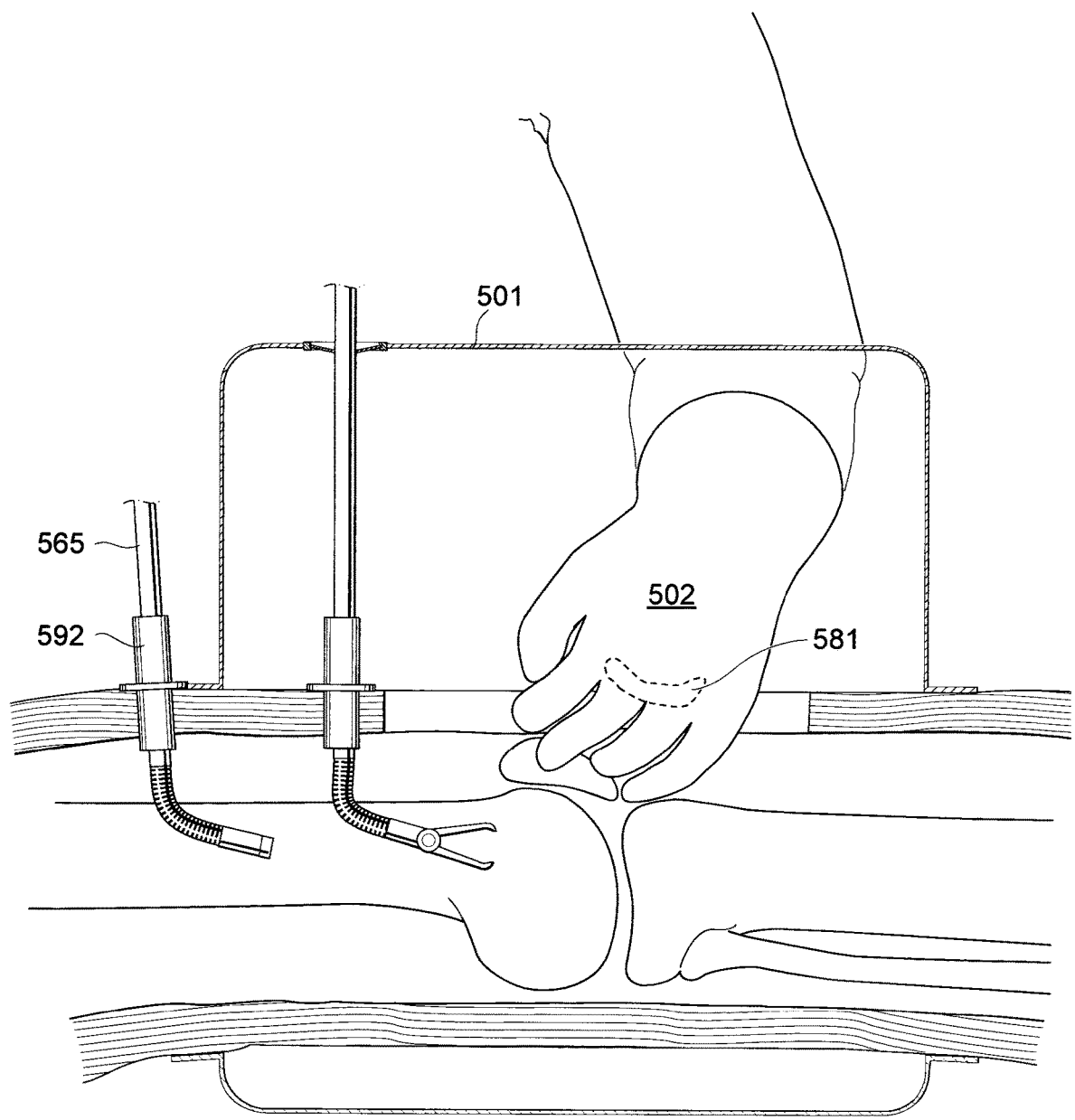
Figure 65Y:
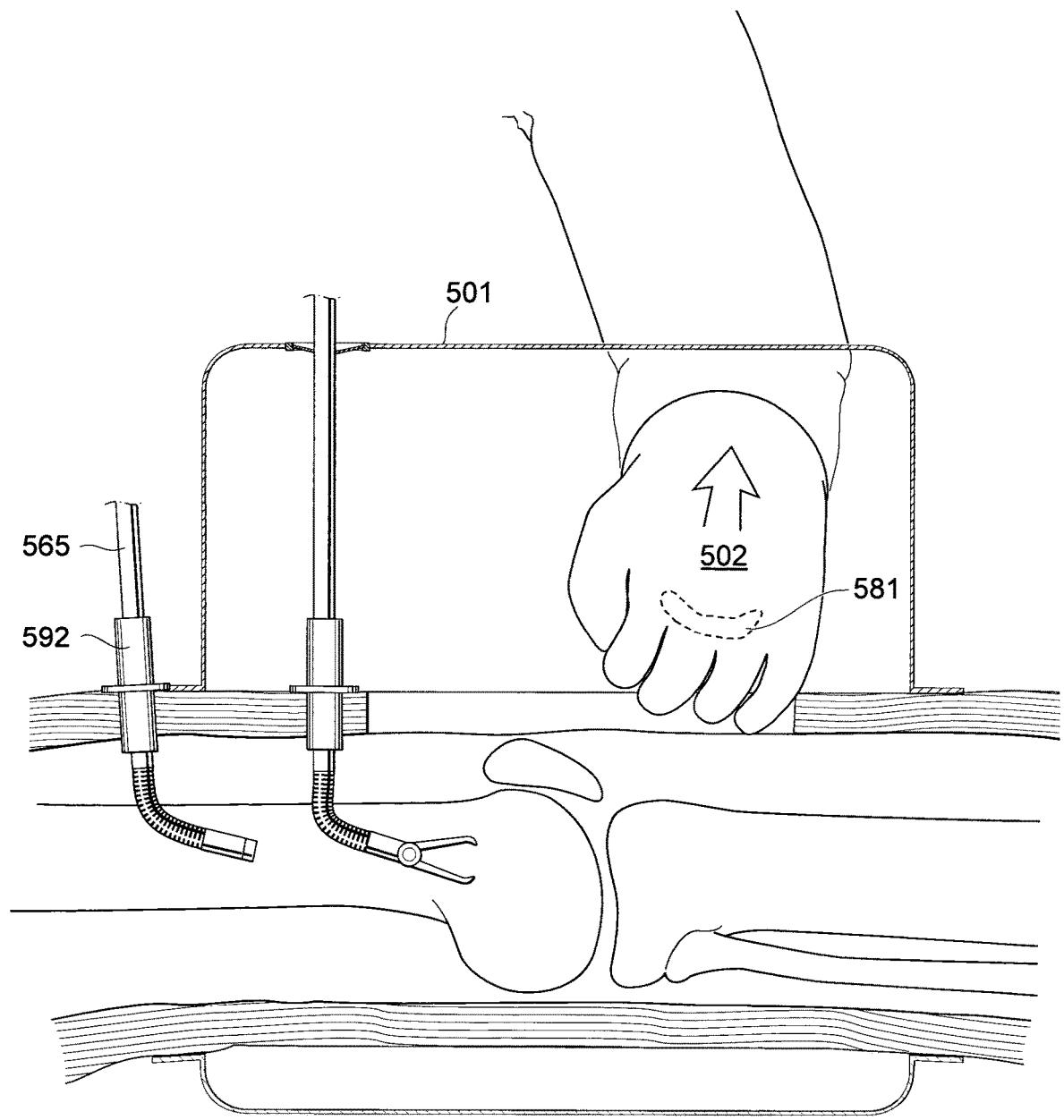

FIGS. 65x, 65y shows the medical device when the surgeon removes a specimen 581 from the knee of the patient using the glove 502 integrated in the wall 501 of the medical device.

FIG. 65z shows the medical device, when the surgeon has turned the integrated glove 502 inside-out such that the specimen 581 can be contained within the integrated glove 502. By isolating the specimen 581 inside of the glove 502, the specimen 581 is removed both from the rest of the body of the patient and from the ambient environment, and thereby does not risk to infect any other portion of the patient's body or medical staff with any infectious disease.

FIGS. 66-78o shows embodiments of the medical device comprising a sealing device comprising a vacuum sealing member adapted to seal against the skin of the patient.

Figure 66:
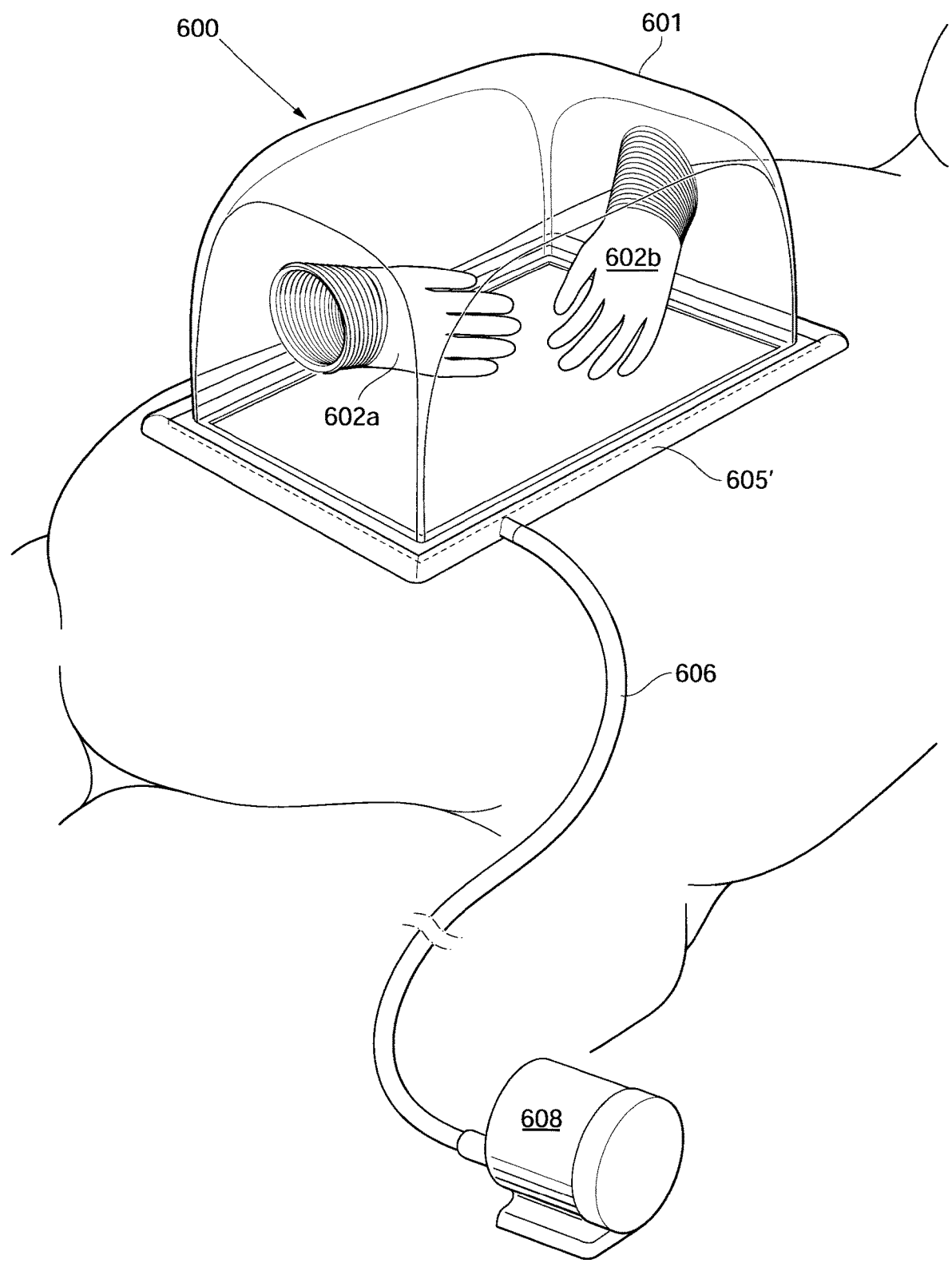
FIG. 66 shows an embodiment of the medical device.

FIG. 66 shows an embodiment of the medical device 600 for performing surgical procedures. The medical device 600 comprises a wall 601 enclosing a chamber C in which a part of a surgical procedure can be performed. The medical device 600 comprises a sealing device comprising a vacuum sealing member 605' for sealing between the medical device 600 and the patient. The vacuum sealing member 605' is adapted to hold a pressure less than atmospheric pressure for creating the vacuum seal between the skin of the patient and the medical device. The vacuum sealing member 605' is connected to a vacuum pump 608 via a vacuum conduit 606 creating a pressure less than atmospheric pressure in the vacuum sealing member 605', thereby, a seal between the medical device 600 and the skin of the patient is created. The medical device could for example, as shown in FIG. 66, comprise gloves 602a,b integrated in the wall 601 for enabling manual manipulation within the medical device while maintaining the closed environment, enclosed by the wall 601.

Figure 67:
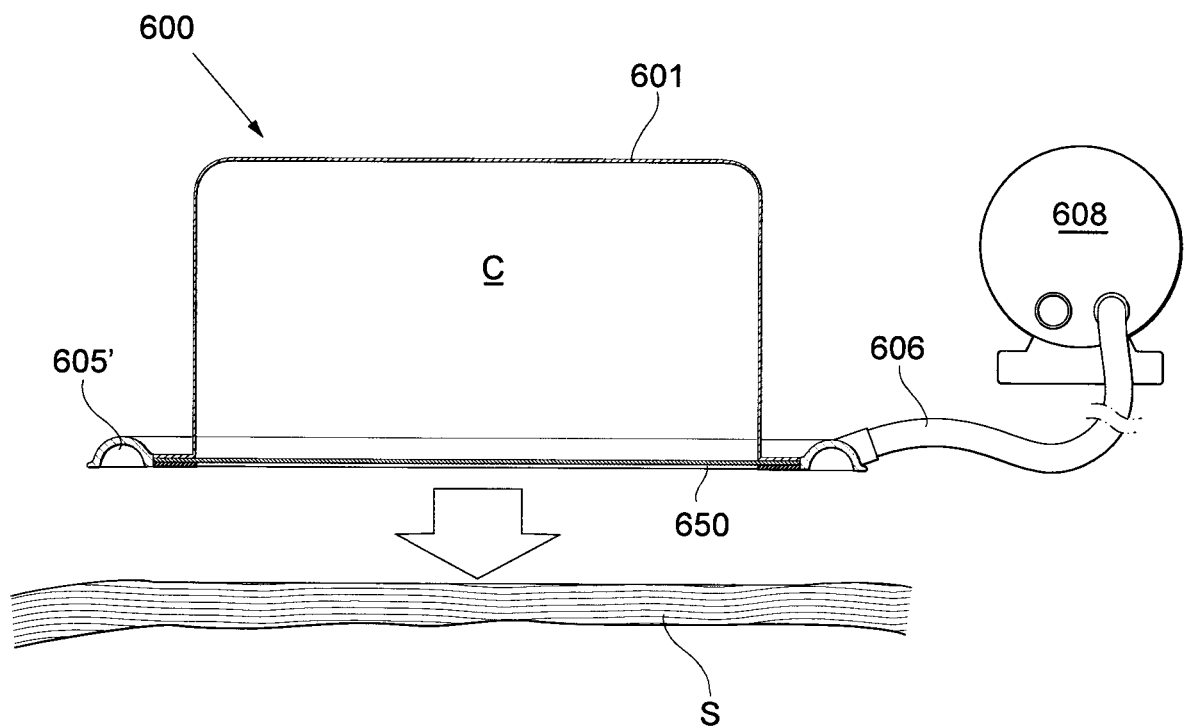
FIG. 67 shows an embodiment of the medical device, when being placed on the skin of the patient, FIG. 67' shows an embodiment of the medical device in which the medical device comprises double vacuum sealing members.
Figure 67:
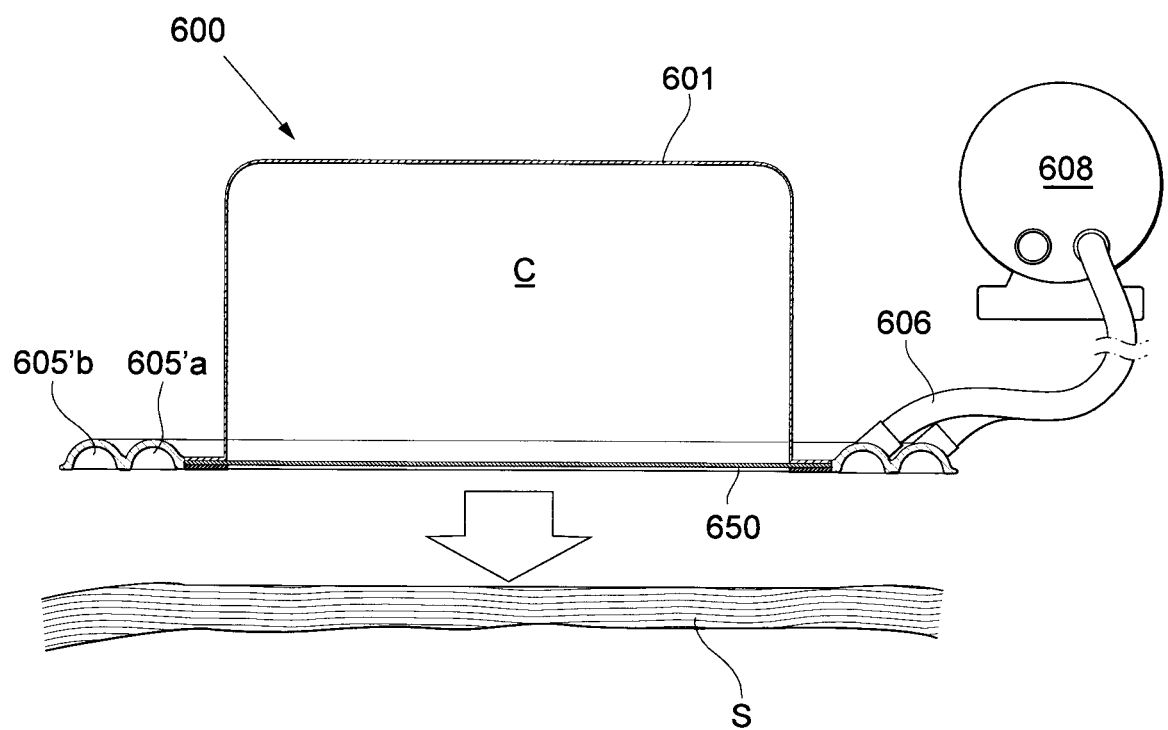

FIG. 67 shows the medical device 600 disclosed in reference to FIG. 66, in section. The medical device is adapted to be fixated to the skin 641 of the patient by means of the vacuum seal 605' connected to a vacuum conduit 606, which in turn is connected to a vacuum pump 608. The fixation to the skin of the patient is further more assisted by a portion of the wall 601 comprising an adhesive surface 650. According to the embodiment shown, the medical device 600 is adapted to be fixated to the skin S of the patient prior to making the first incision in the patient, thus enabling the surgeon to perform the entire procedure without contact with the ambient environment outside of the closed environment of the chamber C. The pressure in the vacuum sealing member 605' may be different than the pressure in the chamber C such that atmospheric pressure not affecting the skin S of the patient can be maintained in the chamber C or a pressure being above atmospheric pressure such that the pressure in the chamber C can be equal to a pressure provided in the patient's body for inflating a cavity within the patient's body for performing endoscopic surgery. By the pressure in the chamber C being the same as the pressure within the cavity of the patient, an incision can be performed in the skin of the patient forming a fluid connection between the chamber C and the cavity within the body of the patient without the cavity within the patient's body collapsing.

FIG. 67' shows a medical device 600 for performing an endoscopic surgical procedure on a patient. The medical device 600 comprising a wall 601 adapted to at least partially be applied on the patient's body to form a chamber C by itself or together with the patient's body, in which a sealed environment can be maintained for encompassing part of the surgical procedure to be performed. A portion of the wall 601 comprising an adhesive surface 650 is adapted to contact the patient's skin when the surgical procedure is to be performed. The medical device 600 further comprises a sealing device comprising a first and second vacuum seal 605'a, 605'b placed consecutively. The pressure in the first and second seals 605'a, 605'b is different than the pressure in the chamber C, and less than atmospheric pressure, for providing sealing between the wall and the patient's skin. The vacuum seals 605'a, 605'b are adapted to create a substantially airtight seal between the wall and the skin S of the patient, to enable an incision to be performed through the skin S of the patient in the closed environment in the chamber C for forming a fluid connection between a cavity within the patient and the chamber C.

Figure 68:
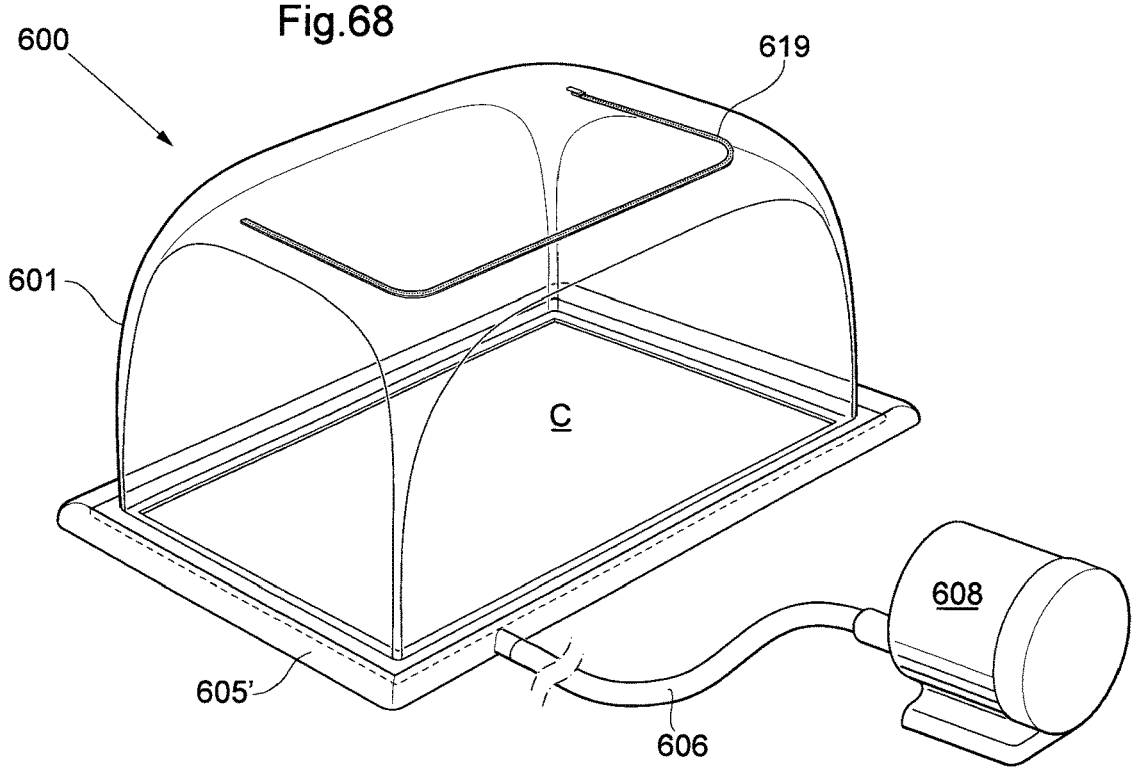
FIG. 68 shows an embodiment of the medical device comprising an opening.

FIG. 68 shows the medical device 600 according to an embodiment similar to the embodiment disclosed with reference to FIG. 66, with the addition that the a portion of the wall 601 of the medical device 600 is possible to open by means of a zipper 619. The zipper may be an airtight Ziploc® type zipper made from a polymer material such as PE. The possibility of opening a portion of the wall 601 of the medical device 600 enables passage of objects between the chamber C and the ambient environment.

Figure 69:
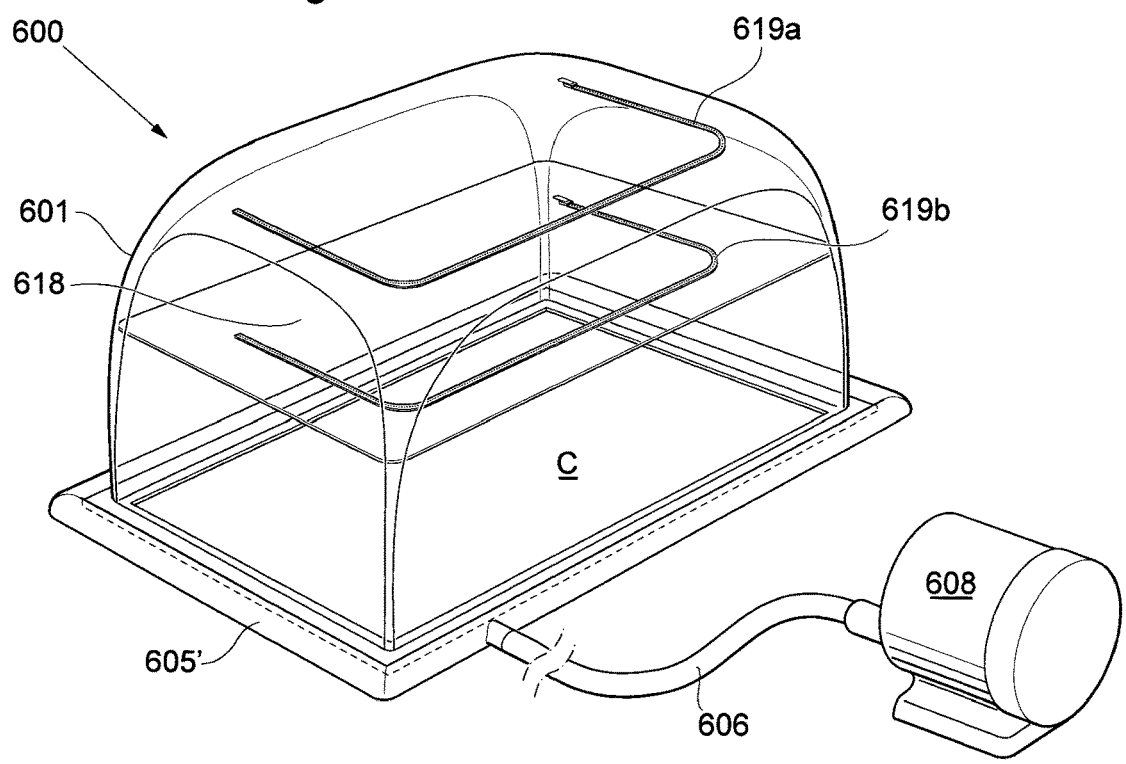
FIG. 69 shows an embodiment of the medical device comprising an airlock.

FIG. 69 shows the medical device 600 according to an embodiment similar to the embodiment disclosed with reference to FIG. 66, with the addition that the medical device 600 further comprises an airlock 618 for allowing passage of objects between the chamber C and the ambient environment. The airlock 618 comprises an outer zipper 619a between the airlock 618 and the ambient environment, and an inner zipper 619b between the airlock 618 and the chamber.

Figure 70A:
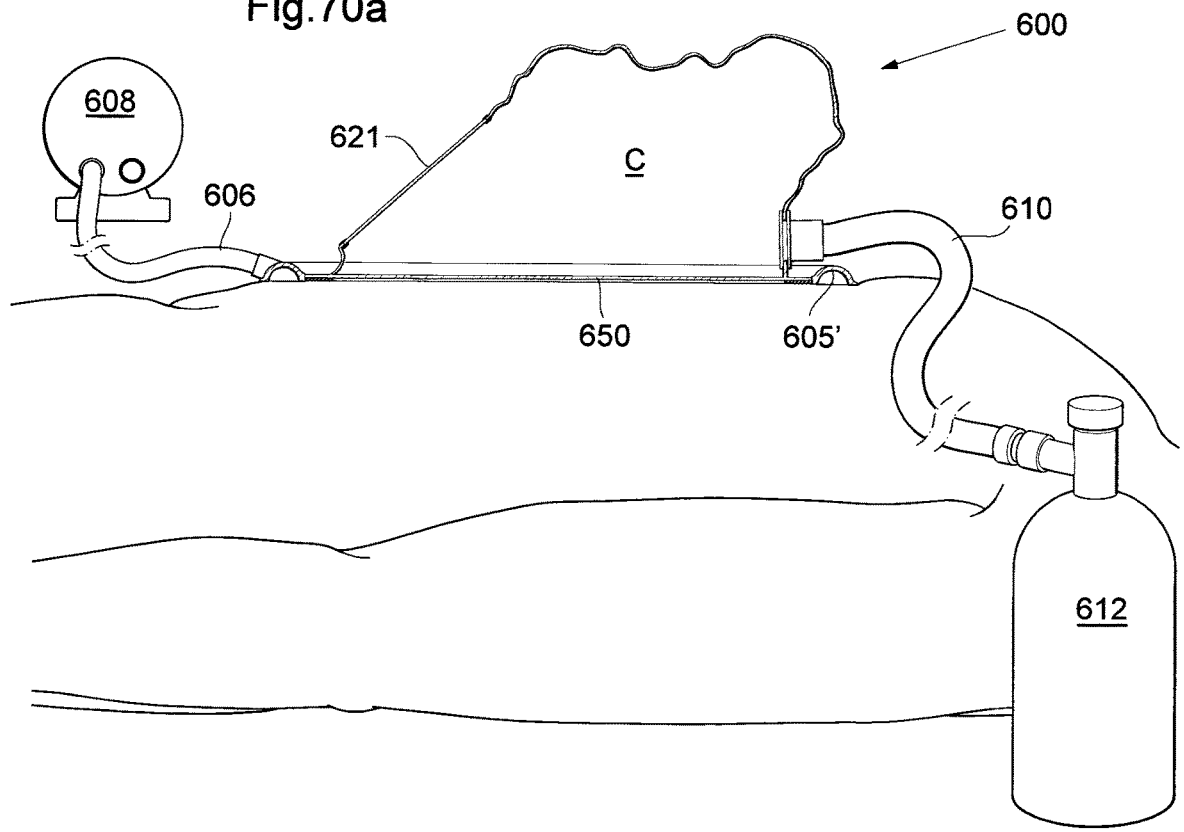
FIG. 70a shows the medical device when applied to the abdomen of a patient, in a deflated state.

FIG. 70a shows the medical device 600 in section when fixated onto the abdominal area of the patient. The medical device 600 is preferably attached to the patient prior to the start of the surgical procedure, such that the first incision in the patient could be performed inside the chamber C. FIG. 70a shows the medical device when it is being inflated by a pressurized fluid supplied by a tank 612 and entering the medical device 600 through a fluid conduit 610 and according to the embodiment shown, the medical device is fixated to the abdominal region of a patient by means of the vacuum sealing member 605' is adapted to hold a pressure less than atmospheric pressure for creating the vacuum seal between the skin of the patient and the medical device 600. The vacuum sealing member 605' is assisted by a portion of the wall of the medical device comprising an adhesive surface 650. The medical device 600 further comprising a window 621 for viewing into the chamber C of the medical device 600. Inflation of the wall 601 in which the window 621 is integrated positions the window 621 in a position suitable for viewing the procedure being performed in the chamber C.

Figure 70B:
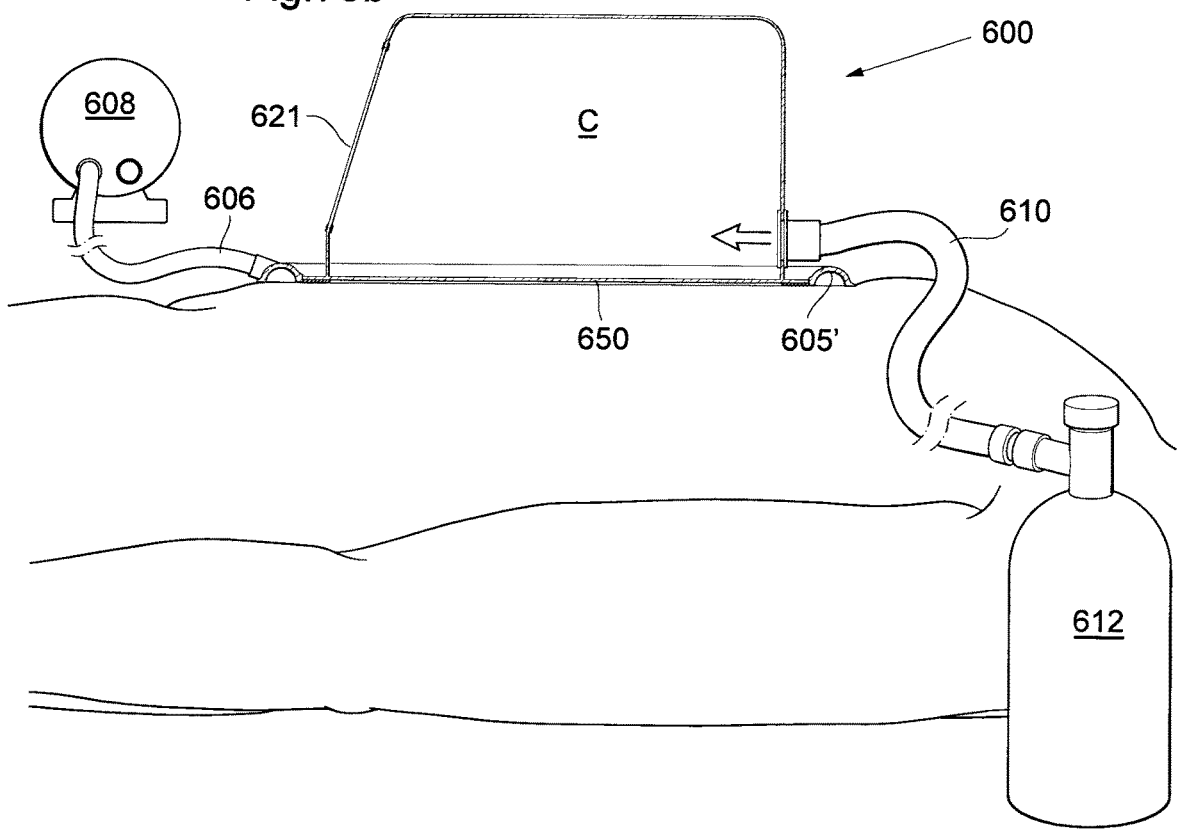
FIG. 70b shows the medical device when applied to the abdomen of a patient, in an inflated state.

FIG. 70b shows the medical device 600 when inflated such that the wall 601 separates the chamber C within the medical device 600 from the ambient environment and thus creates an operating environment which is separated from contaminations from the outside. A portion of the partially collapsible wall 601 is placed in connection with the skin of the patient, and that portion comprises an adhesive surface 650 for affixing the medical device 600 to the skin of the patient and/or sealing between the medical device 600 and the patient. The window 621 has been positioned by the inflating of the medical device 600, such as to enable viewing of the inner side being inside of the chamber C of the portion of the wall 601 comprising the adhesive surface 650. In some of the embodiments disclosed, the entire portion of the wall 601 contacting the skin of the patient comprises an adhesive surface 650, such that the incision in the patient runs through the wall 601 and further through the skin of the patient. This reduces the risk that infectious objects can be transferred from the skin of the patient to the incision in the patient if the skin of the patient is not adequately disinfected. In some applications it is conceivable that a normal laparoscopic procedure is performed with the medical device 600 positioned but not inflated. The medical device 600 is then only inflated at the end of the procedure, for example when a specimen is to be removed from the body of the patient.

FIG. 71a shows a section of an alternative to the medical device 600 with the features as shown in FIG. 66 but further having a coupling 680 integrated in the wall 601. The coupling 680 enables the changing of objects from for examples a wall port 617, to insets 642a;b;c for example comprising surgical gloves 602 or device and/or instrument mounts 620. The coupling 680 comprises a valve member 638 for closing the hole 697 in the coupling 680, when objects should be exchanged, such that the chamber C in the medical device remains closed. The mount 620 could for example be adapted to hold surgical instruments and/or implants or parts of implants. The medical device 600 is according to this embodiment adapted to be fixated to the skin of the patent by a large portion of the wall 601 of the medical device 600 comprising an adhesive surface 650, and by means of the vacuum sealing member 605'.

FIG. 71b shows the shows a section of the medical device 600 showing the coupling 680 integrated in the wall 601 in further detail when an inset 642c comprising an airlock sluice 618 for transferring objects between the chamber C and the ambient environment is being provided. According to the embodiment shown in FIG. 71b the airlock sluice 618 comprises a first valve member 638a separating the airlock 618 from the ambient environment, and a second valve 683 separating the airlock 670 from the chamber C. The airlock 618 is provided between the first 638a and second 638 valves and could for example be used for passing a medical device into the chamber C, or for passing a specimen or sample out of the chamber C.

Figure 72:
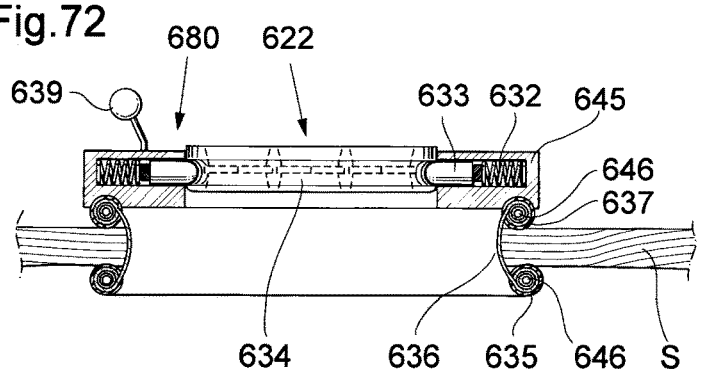
FIGS. 72, 73a and 73b shows an embodiment of a coupling, in section.

FIG. 72 shows an embodiment of a detachable port arrangement which could be positioned in the chamber C of the medical device disclosed with reference to FIGS. 66-71. The port arrangement includes an intra body ring 635 adapted to be placed at the inside of the patients skin S around an incision, and an outer ring 637 adapted to be placed on the outside of the patients skin S around the incision. Between the intra body ring 635 and outer ring 637, connecting member in the form of an annular retractor membrane 636 is positioned and adapted to exert a pressure on the skin S or human tissue at the incision to seal between the rings 635; 637 and the skin S or human tissue and additionally for retracting the skin S and thereby keeping the incision open. The retractor membrane 636 is preferably made from a resilient or elastic polymer material. The outer ring 637 comprises an integrated roll up system 646, which may be spring loaded and adapted to create a suitable pressure on retractor membrane 636 to keep the incision open.

The port arrangement shown in FIG. 72 also includes a coupling 680 having a rigid annular seating 645 attached to the outer ring 637, spring loaded protruding members 633 arranged in radial bores in the seating 645 and a hand lever 639 connected to the protruding members 633 to enable retraction thereof against the action of springs 632. The port arrangement further includes a self sealing body port 622 held by the coupling 680. The body port 622 comprises a disc-shaped self sealing membrane 643, FIG. 73a, fixated to a rigid ring having an outer circumferential recess 634 that receives the protruding members 633 of the coupling 680. The self sealing membrane 643 has a small self sealing hole 644, FIG. 73a, centrally in the membrane 643. For example, the self sealing membrane 643 may be made from a gel-type material being elastic enough to enable a deformation large enough for a person's hand to pass through the small self sealing hole 644 while still contracting enough to create an airtight seal between the chamber C and the outside environment.

The coupling described above enables quick exchange of the body port 622. Thus, the surgeon may release the body port 622 from the port arrangement by simply pulling the hand lever 639 so that the protruding members 633 disengage from the recess 634 of the body port 622, whereby the body port 622 can be removed.

Figure 73A:
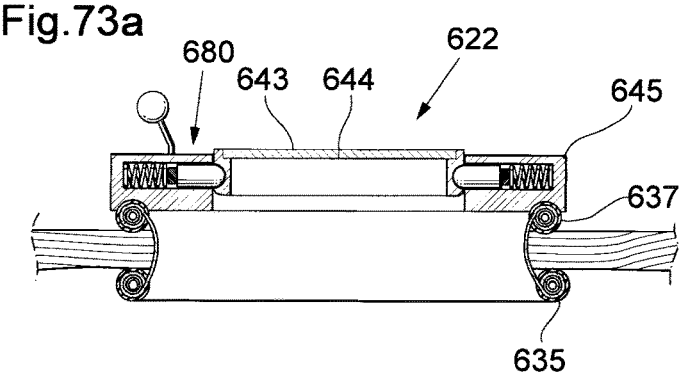

FIG. 73a is a cross-sectional view of the port arrangement shown in FIG. 72, to more clearly illustrate the body port 622 with its self sealing membrane 643 and small hole 644.

Figure 73B:
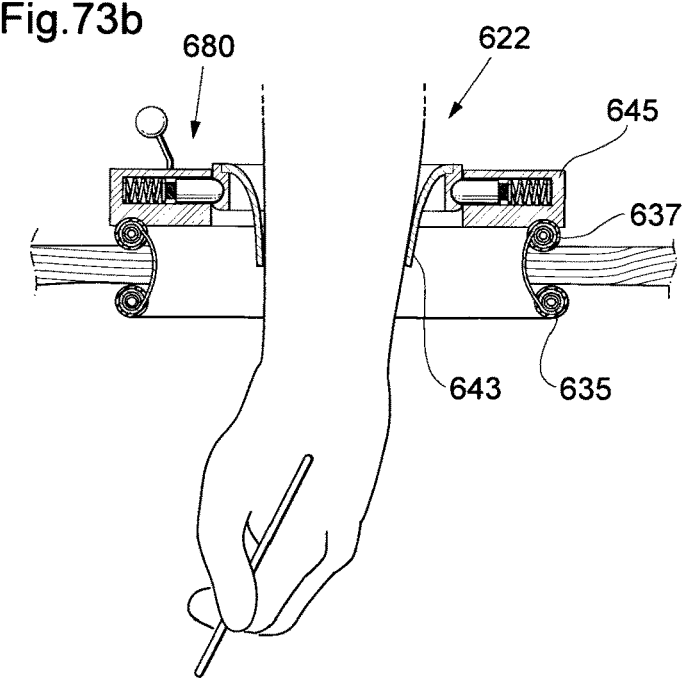

FIG. 73b shows the self sealing body port 622 when the hand of a surgeon is placed through the hole 644 in the membrane 643 and thus enabling manual manipulation within the body of the patient.

Figure 74A:
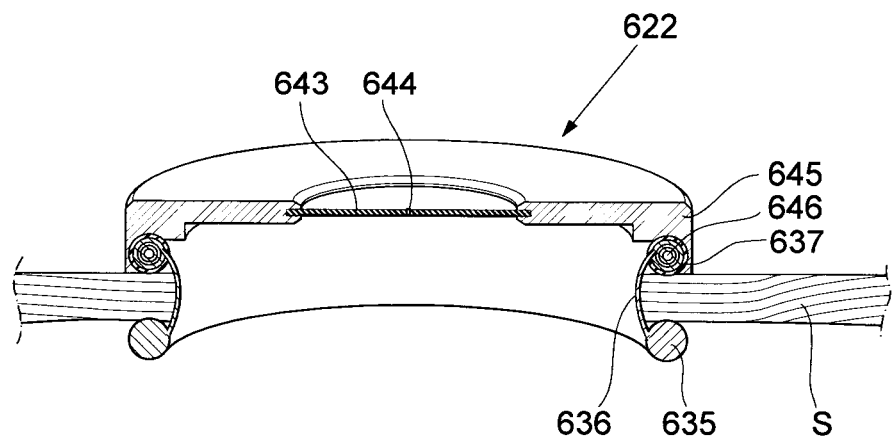
FIGS. 74a and 74b shows an embodiment of a self sealing member, in section.
Figure 74B:
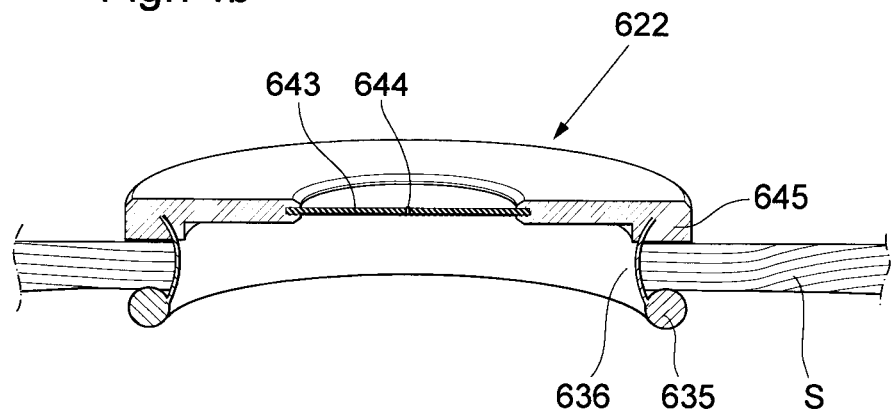

FIG. 74a shows a self sealing body port 622 in a close-up, in section. The self sealing body port 622 could be connected to the coupling, for example as disclosed with reference to FIGS. 72-73, which in turn is connected to any of the medical device disclosed with reference to FIGS. 66-69, or the self sealing body port 622 could be fixated to a retractor, as shown in FIGS. 74a and 74b. The self sealing body port 622 comprises a self sealing membrane 643 fixated to a rigid part 645 of the self sealing port 622. The self sealing membrane 643 having a small self sealing hole 644 centrally in the membrane 643. The self sealing membrane 643 is for example made from a gel-type material being elastic enough to enable a deformation large enough for a person's hand to pass through the small self sealing hole 644 while still contracting enough to create an airtight seal between the sealed environment and the outside environment. The medical device being fixable to a retractor comprising one intra body ring 635 adapted to be positioned on the inside of the patients skin, and one ring 637 adapted to be placed on the outside of the patients skin. Between the intra body ring 635 and the ring 637 adapted to be placed on the outside of the patients skin a retractor membrane 636 is positioned which is adapted to exert a pressure of the cut surfaces of the incision for retracting the skin and thereby keeping the wound open. The retractor membrane 636 is preferably made from a resilient of elastic polymer material. The ring 637 adapted to be placed on the outside of the patients skin 641 comprises an integrated roll up system 646 which could be a spring loaded roll up system adapted to create a suitable pressure on retractor membrane 636 for keeping the wound open.

FIG. 74b shows an alternative embodiment of the self sealing body port 622, with the difference that the retractor membrane 636 is made from a material elastic enough such that one end of the retractor membrane 636 could be fixedly fixated to the rigid part 645.

Figure 75:
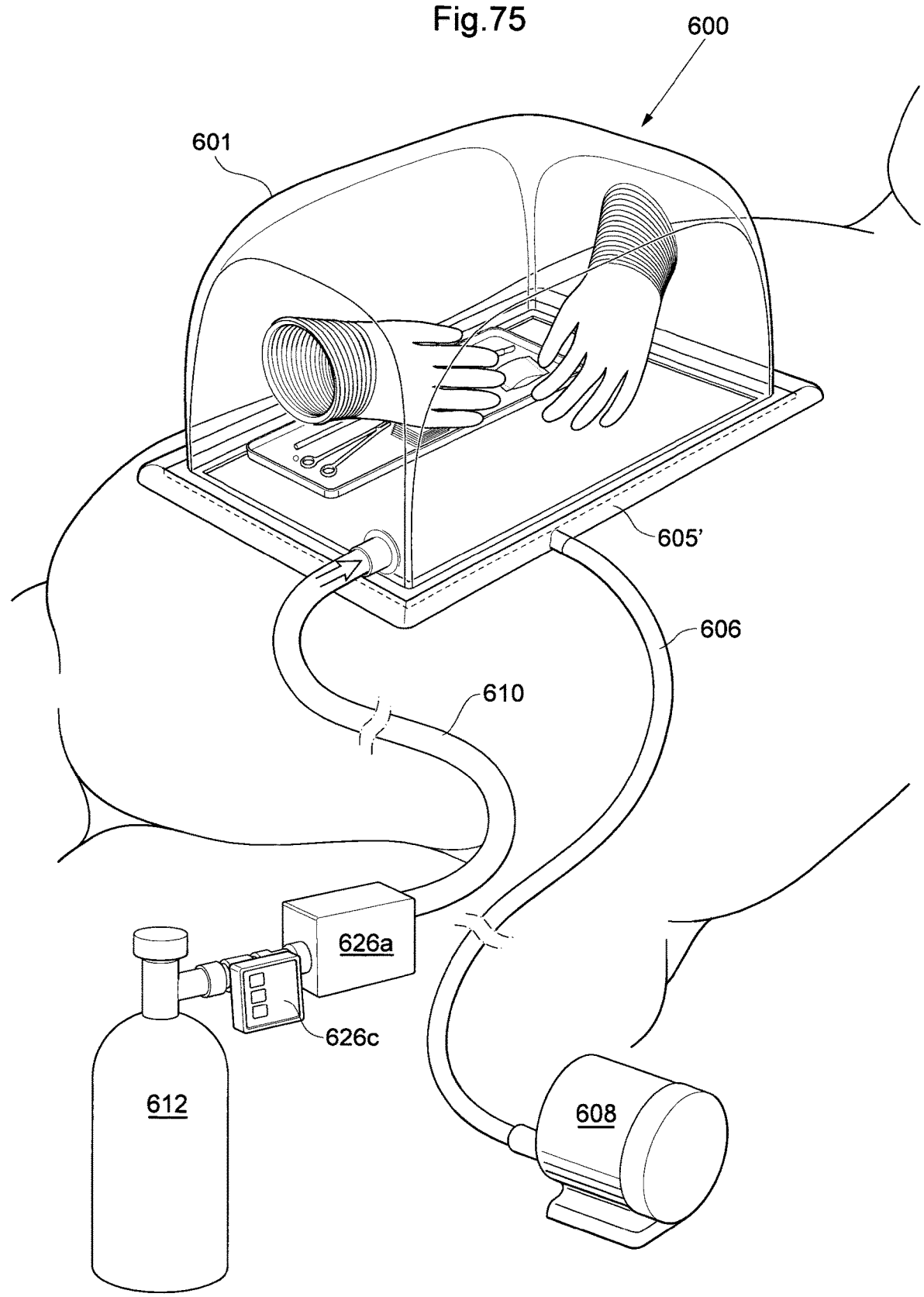
FIG. 75 shows an embodiment of the medical device comprising a vacuum sealing.

FIG. 75 shows the medical device as shown in FIG. 66 with the addition that the embodiment comprises a sterilizing unit 626a adapted to sterilize the gaseous fluid entering the medical device 600. In the embodiment disclosed herein, the gaseous fluid entering the medical device 600 originates from a pressurized tank 612 and could be pre-sterilized, however, in other embodiments, it is conceivable that the gaseous fluid is the surrounding air which is pressurized (such as further disclosed with reference to FIG. 77). In the embodiments where the surrounding air is used to inflate the medical device 600 and constitute the operating environment this air needs to be properly sterilized. The medical device 600 further comprises a tempering unit 626c which could be provided to heat or cool the gaseous fluid inflating the medical device 600. In cases when the ambient environment is cold the tempering unit 626c could be used to raise the temperature of the chamber C to provide beneficial operating circumstances both for the patient and for the surgeon. In cases when the surrounding environment is hot, the tempering part 626c of the system could be used to lower the temperature of the chamber C both to provide beneficial operating circumstances, both for the patient and for the surgeon, and for providing a temperature inhibiting bacterial and viral infections. The tempering unit 626c could comprise a temperature regulating device for setting the required temperature.

FIG. 76a shows the coupling 680 as disclosed in FIG. 72-73 in further detail when an inset 642 in the form of a surgical glove 602 is fixated to the coupling 680. The retractor system comprising the intra body ring 635 and the ring 637 adapted to be placed on the outside of the patients skin S further comprises a retractor membrane 636 positioned such that it exerts a pressure on the cut surfaces of the incision for retracting the skin S and thereby keeping the wound open. The retractor membrane 636 could be rolled by a roll up system 646 inside of the ring 637 adapted to be placed on the outside of the patients skin S for tightening the retractor membrane 636 such that the wound is kept open.

FIG. 76b shows the changing of objects in the coupling from a surgical glove 602 to a body multi-port 628 comprising three endoscopic ports 647. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the laparoscopic ports and surgical gloves could additionally be exchanged for holding devices, for example holding instruments or implants.

Figure 77:
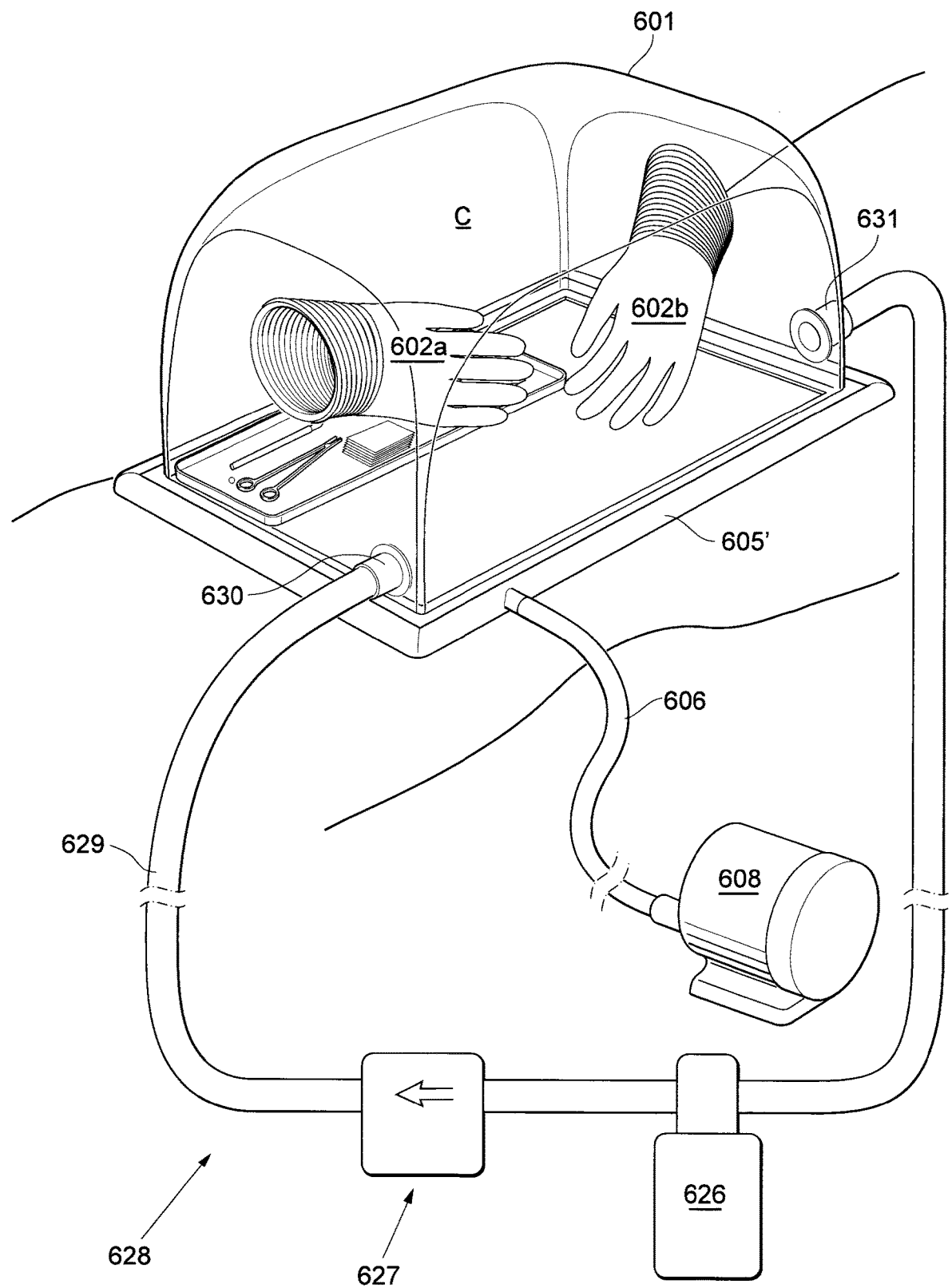
FIG. 77 shows an embodiment of the medical device comprising a vacuum sealing.

FIG. 77 shows a medical device similar to the embodiment disclosed in FIG. 66 but comprising a system 628 for circulating a fluid through the sealed environment of the medical device. The system comprises a fluid conduit 629 connected at an inlet 630 placed in the wall 601 for supplying fluid to the chamber C, and an outlet 631 for draining the fluid from the chamber C. The fluid is circled by means of a pumping unit 627 and is circled via a sterilizing/filtering/tempering/humidifying unit 626 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 78A:
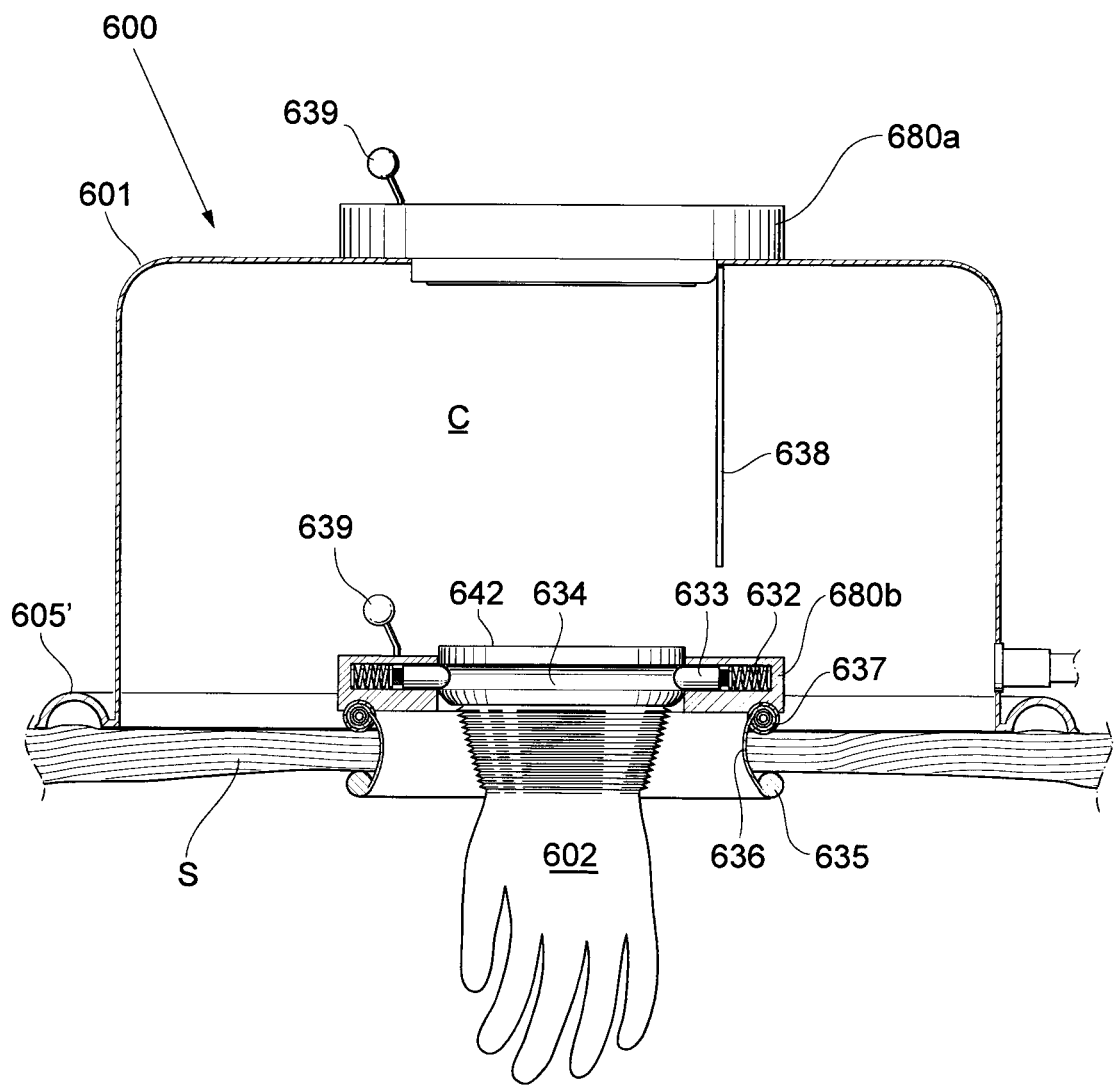
FIGS. 78a-78c shows embodiments of the medical device, in section.

FIG. 78a shows a modification of the embodiment disclosed with reference to FIG. 66 in which the medical device further comprises an upper 680a and a lower 680b coupling for fixating ring shaped objects which for example could be insets 642 or ports, where insets for example could be an insets 642 comprising a surgical glove 602, or device/instrument mounts and ports could be endoscopic ports or hand access ports, such as the self sealing port disclosed with reference to FIGS. 4a and 4b. The couplings 680a; 680b comprises releasing levers 639 for releasing the object. The levers 639 are connected to protruding members 633 which are spring loaded 632 from the rear in order to secure the recess 634 of the ring shaped object. In the embodiment disclosed in FIG. 78a, the inset 642 fixated to the lower coupling 680b is a surgical glove 602 enabling manual manipulation within the body of the patient. The medical device shown in FIG. 78a further comprises a valve member 638 adapted to close the opening in the upper coupling 680a, when the upper coupling 680a is not in use. The upper coupling 680a is for example used for manual manipulation and preparation within the medical device 600, such that could be needed for preparing or changing an instrument or preparing an implant for implantation. The lower coupling 680b is for example used for laparoscopic manipulation within the body of the patient, or manual manipulation for e.g. removing a specimen or positioning an implant. FIG. 78a is shown with the vacuum sealing 605' further disclosed with reference to FIG. 66, however, it is equally conceivable that the vacuum sealing member is assisted or replaced by an adhesive or pressure sealing member.

Figure 78B:
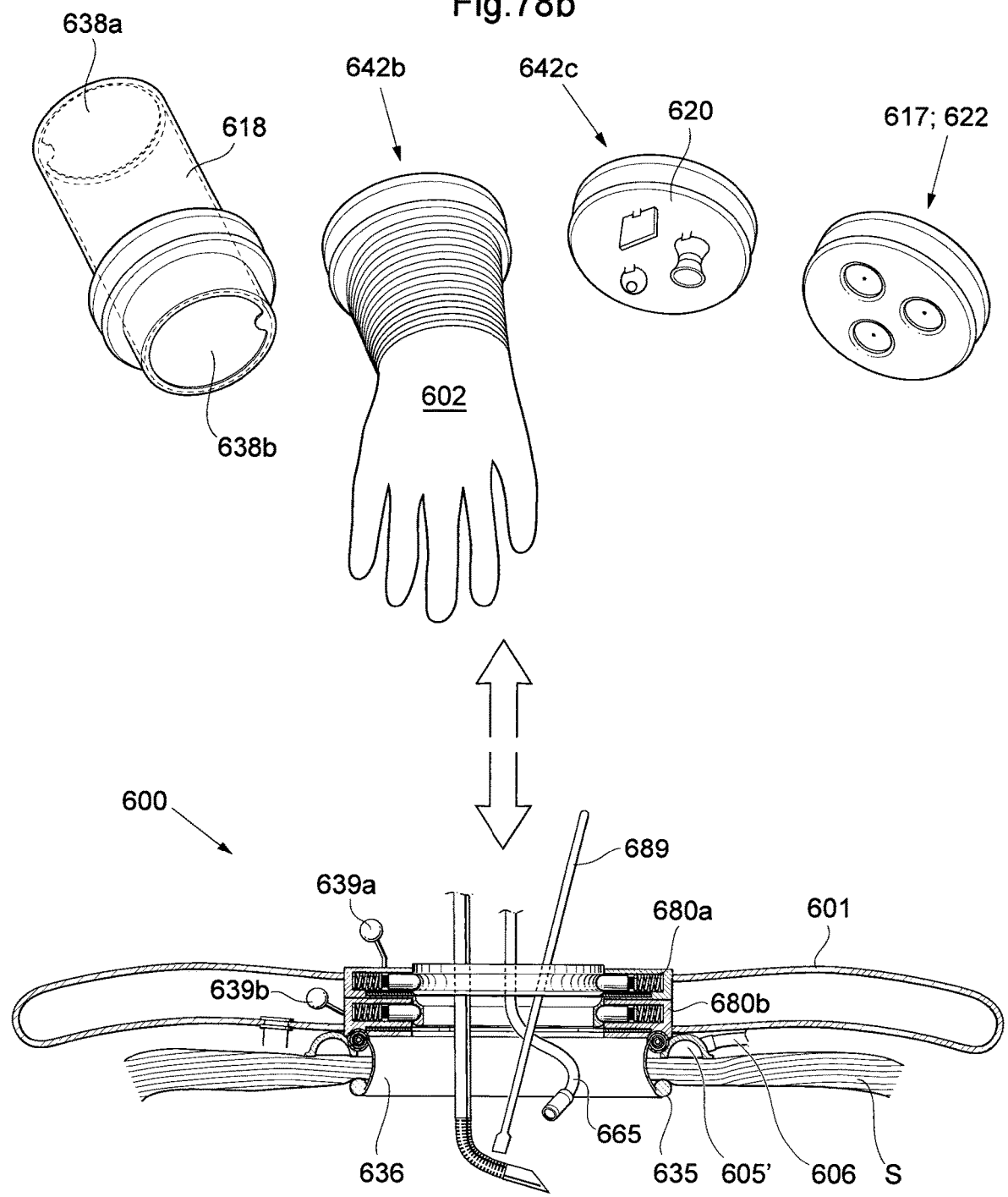

FIG. 78b shows the medical device 600 adapted to be at least partially placed in an incision cut in a patient's body. The medical device 600 comprises the upper 680a and lower 680b coupling adapted be interconnected to form an interconnected coupling. The upper coupling 680a is adapted to be disconnected from the lower coupling 680b, and the upper coupling 680a is connected to a first portion of a flexible wall 601, and the lower coupling 680b is connected to a second portion of the flexible wall 601. The flexible wall 601 forms a chamber in which a sealed environment can be maintained, the chamber is heavily enlarged when the upper coupling 680a is disengaged from the lower coupling 680b, thus creating operating space within the chamber enclosed by the wall 601. The upper 680a and lower 680b couplings comprises latching systems for locking an inset. The inset may for example be an inset 642b comprising a glove 602 for manual manipulation within the body of the patient, or within the enclosed chamber, or a device/instrument mount 620 for holding instruments or medical devices within the chamber. Alternatively the insets 642b; 642c can be replaced by an airlock sluice 618 with a first 638a and second 638b valve member, or a port 617;622, for example as shown, a multiport comprising a plurality of ports enabling the insertion of a surgical instrument 689 into the chamber or body of the patient.

In the embodiment shown in FIG. 78b the medical device is fixated to the body of the patient by means of a vacuum fixating member 605' connected to a conduit 606, which in turn is connected to a vacuum source. Furthermore, the medical device in FIG. 78*b* comprises a second sealing device having a first sealing member 635 in the form of an intra body ring 635 adapted to be positioned at the inside of the patient's skin S around an incision to be performed in the skin S and a second sealing member 637 in the form of an outer ring 637 adapted to be positioned at the outside of the patient's skin S around the incision, and a spring-loaded or elastic connecting member 636 sealingly interconnecting the first 635 and second 637 sealing members. The spring-loaded or elastic connecting member 636 seals between at least one of the outer ring 637 and the skin S of the patient, and the intra body ring 635 and the tissue of the patient.

Figure 78C:
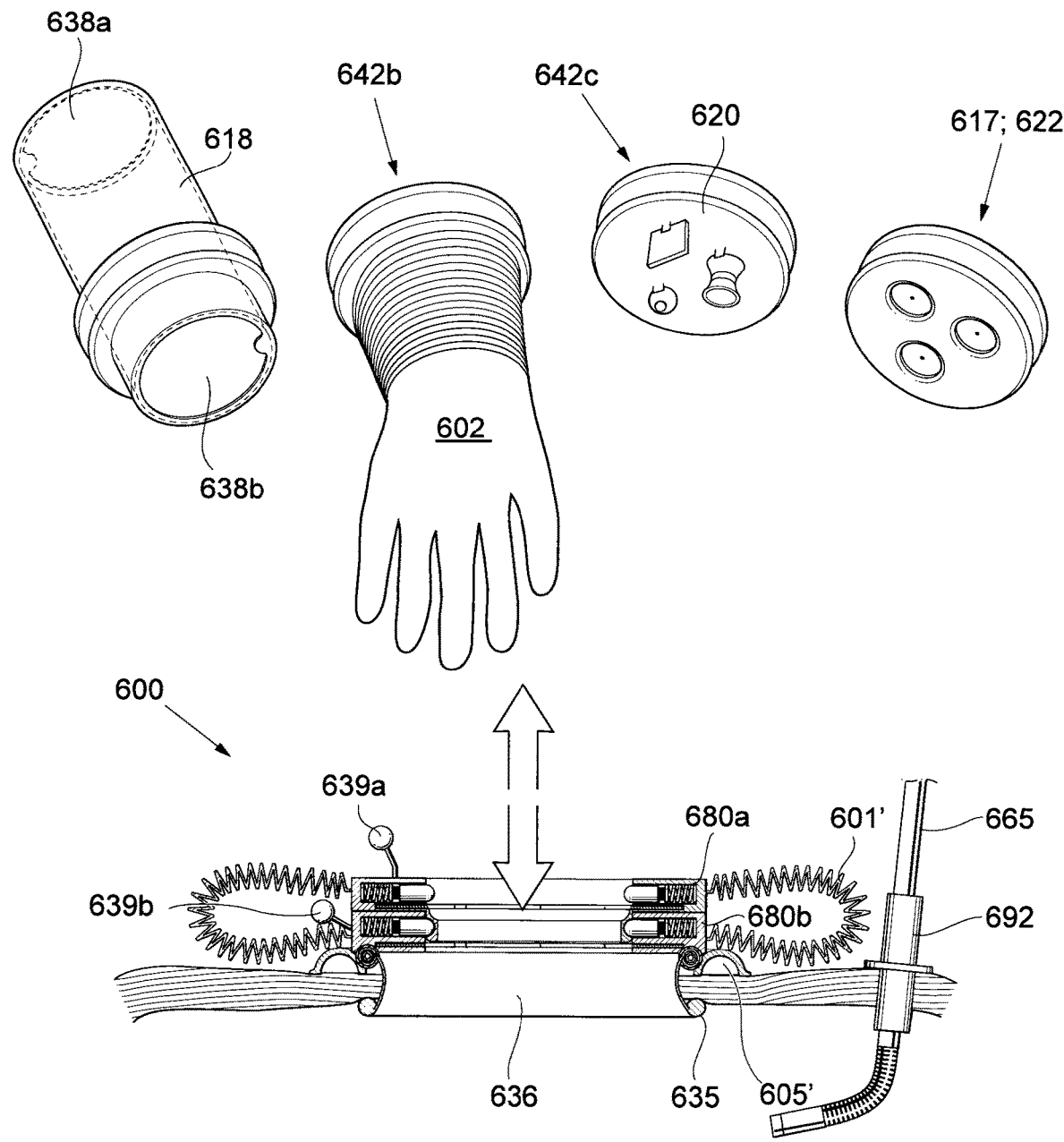

FIG. 78*c* shows the port in an embodiment very similar to the embodiment shown in FIG. 78*b* but with the difference that the wall 601' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. A camera 665 is also shown in FIG. 78*c*, placed through a trocar 692 outside of the medical device and enabling visual inspection of the cavity in the patient.

Figure 78D:
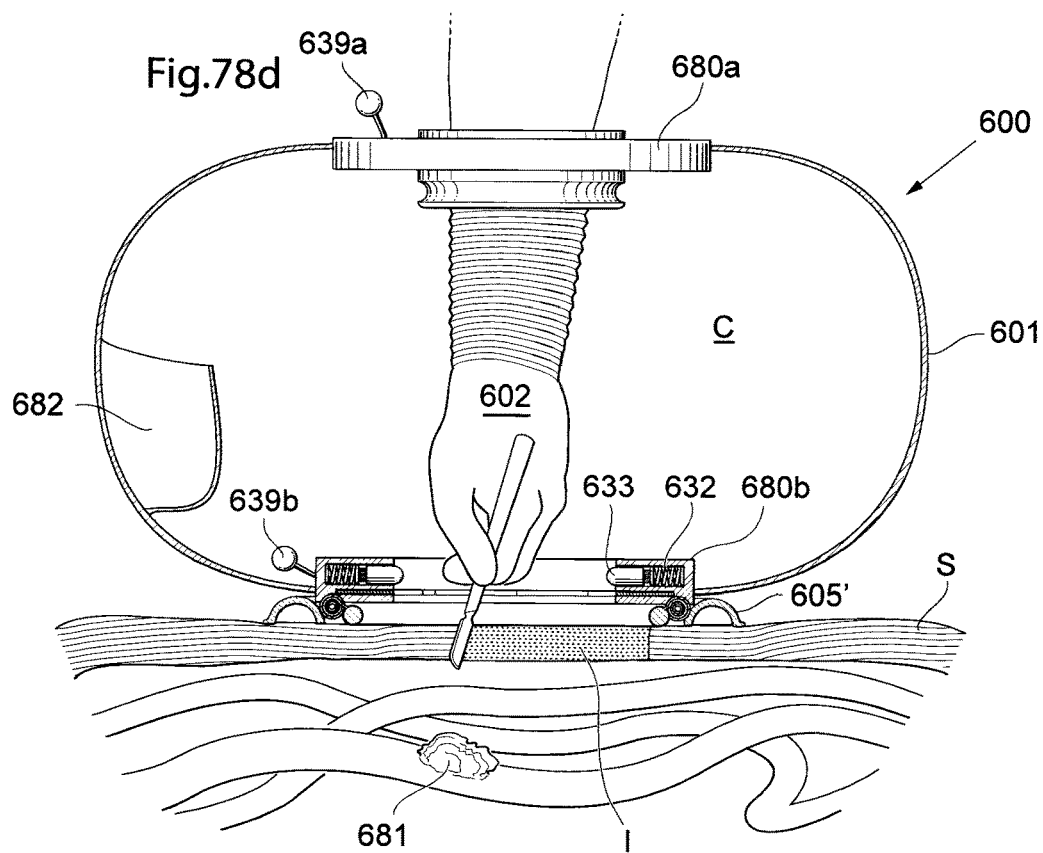
FIGS. 78d-78j shows an embodiment of the medical device in section, being fixated to the patient and used.

FIG. 78*d* shows the medical device in an embodiment when the wall 601 of the medical device is inflatable, and the medical device is in its inflated state. When the chamber C is deflated it has a first volume i.e. when the upper coupling 680*a* and lower coupling 680*b* are interconnected, and when the chamber C is inflated and the upper coupling 680*a* is disconnected from the lower coupling 680*b*, it has a second volume. The second volume is larger than the first volume. According to the embodiment shown in FIG. 78*d*, the second volume is larger than 500 000 mm3. According to the embodiment shown in FIG. 78*d*, the chamber C is formed by the inflatable wall 601 and is adapted to hold a pressure exceeding atmospheric pressure.

According to the embodiment shown in FIG. 78*d*-78*j* the chamber C further comprises a pouch 682 for holding a specimen 681 removed from within the body of the patient not to contaminate any other part of the body and create the possibility of delaying the removal of the specimen 681 until the procedure is concluded. The pouch 682 may be a pouch 682 which could be closed for creating a pouch-chamber within the chamber C for isolating the removed specimen 681 within the chamber C.

In FIG. 78*d* a state is illustrated in which the incision in the patient's skin is being created by the surgeon by means of a glove inset 602 latched to the upper coupling 680*a*. The medical device 600 is fixated and sealed by means of the vacuum sealing member 605' since the sealing device that is provided partially within the patient's body cannot be mounted until the cut in the patient's skin is concluded. The two different sealing devices disclosed could in some embodiments be replaced by only one of the sealing devices, or by a different sealing device, such as the adhesive or pressure sealing devices disclosed in other portions herein.

Figure 78E:
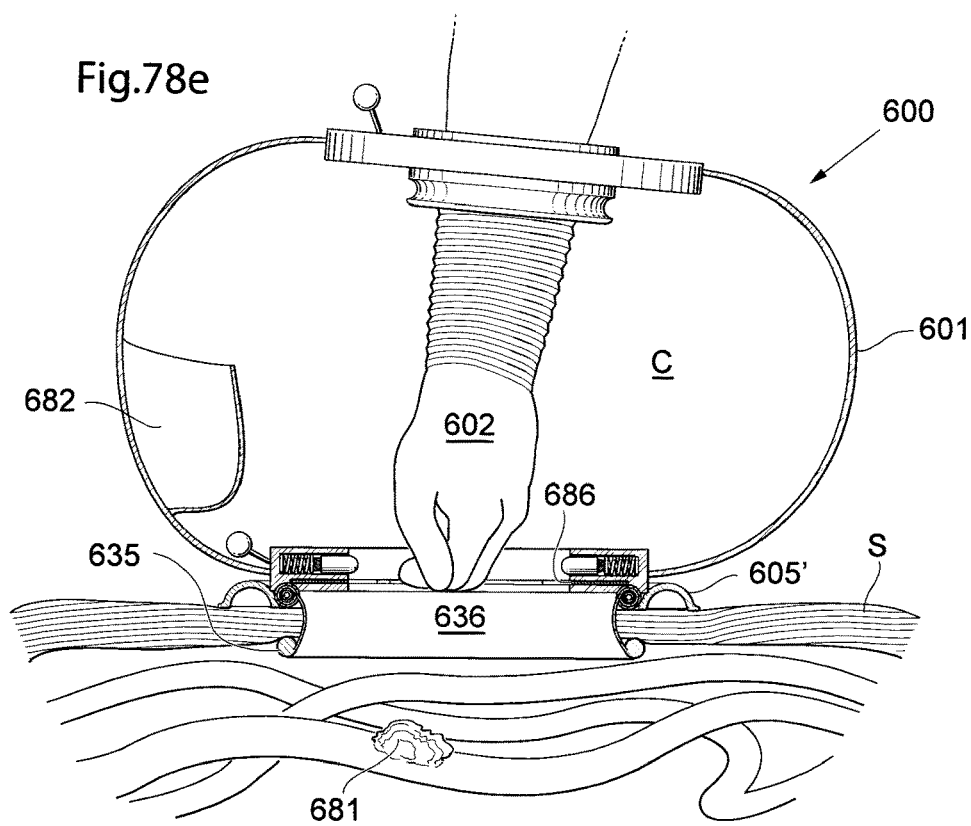

FIG. 78*e* shows the medical device 600, when the second sealing 635, 636, 637 have been placed in the incision cut in the patient's skin S. The wall 601 enclosing the chamber C is elastic or flexible which enables the surgeon move the upper coupling 680*a* in relation to the lower coupling 680*b* for getting better access to different angles within the patient's body, for example for removing a specimen 681. The embodiment of FIG. 78*e* further comprises an iris valve 686 placed in the lower coupling 680*b* for closing the coupling such that the chamber C is sealed from at least one of the ambient environment and a cavity in the patient. The closing of the iris valve 686 enables activity within the chamber C without maintaining a pressure in the chamber C, at the same time as a pressure and/or sealed environment can be maintained within the body of the patient.

Figure 78F:
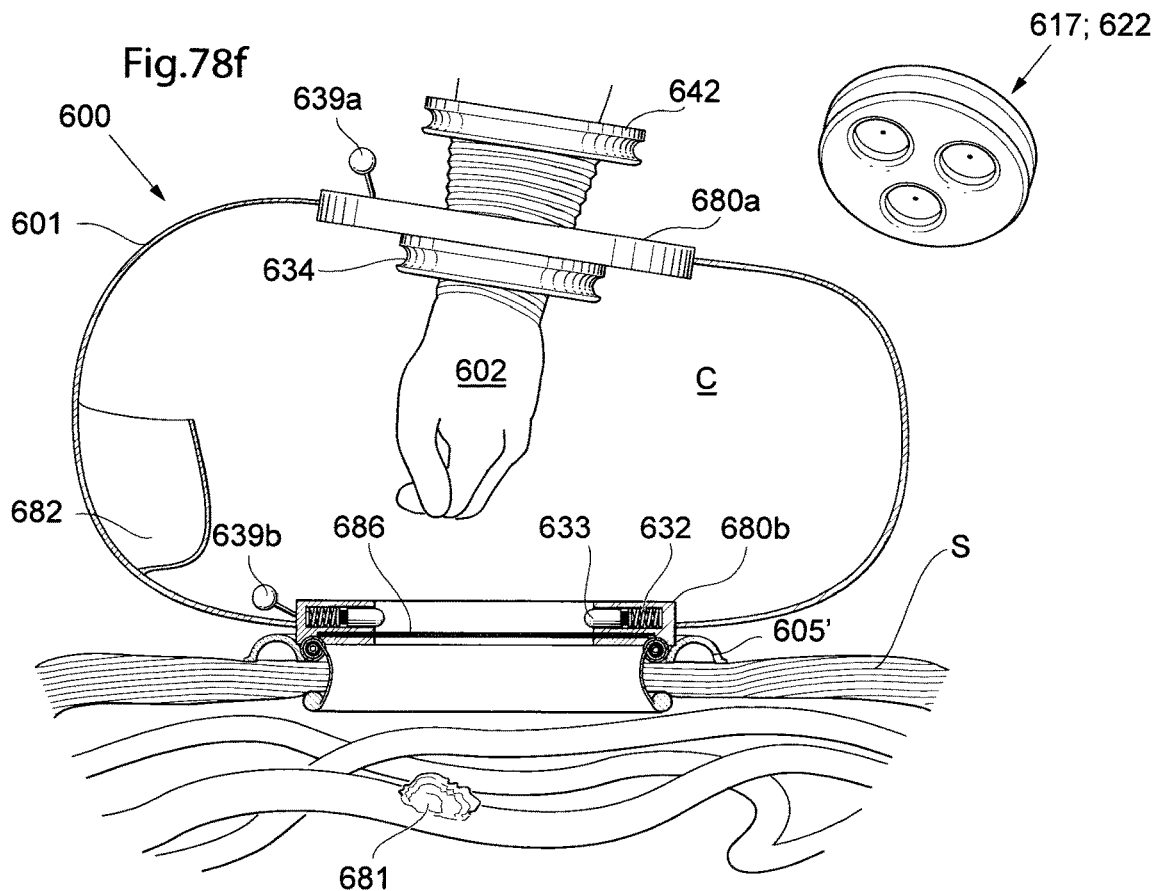

FIG. 78*f* shows the medical device 600 when the inset 642 comprising a glove 602 is removed and replaced by a port 617;622 in the form of a multiport comprising a plurality of ports. The port could be a wall port 617 for manipulating objects within the chamber C of the inflated medical device 600 using surgical instruments, or a body port 622 for manipulating within the body of the patient, when the first and second couplings 680*a*; 680*b* are connected (as shown in FIG. 78*g*).

FIG. 78*f* shows the medical device 600 when a surgical procedure is performed on a patient. The medical device comprises a wall 601 applied on the patient's body and forming a chamber C in which a sealed environment can be maintained for encompassing part of the surgical procedure to be performed. A portion of the wall 601 in form of the vacuum sealing member 605' is in contact with the patient's skin S. When the port 617; 622 is fixated to the coupling 680*a*, the port 617;622 is displaceable between a first position (shown in FIG. 78*0*) and a second position (shown in FIG. 78*g*). In the lower position (shown in FIG. 78*g*) the upper coupling 680*a* is fixated relative to the skin S or tissue of the patient, by the upper coupling 680*a* being locked to the lower coupling 680*b*. In the upper position shown in FIG. 78*f*, the upper coupling 680*a* is placed more remote from the patient's skin S than in the lower position. In the upper position, the upper coupling 680*a* is moveable relative to the skin S and tissue of the patient by the wall 601 being flexible and thus adapted to flex when the upper coupling 680*a* is moved relative to the patient, or between the upper and lower position.

The upper coupling 680*a* comprises a first interconnecting member, in the form of a recess 634. The lower coupling 680*b* comprises an interconnecting member in form of protruding latching members 633 adapted to engage in the recess (groove) 634 and thereby lock the upper coupling 680*a* to the lower coupling in the lower position.

Figure 78G:
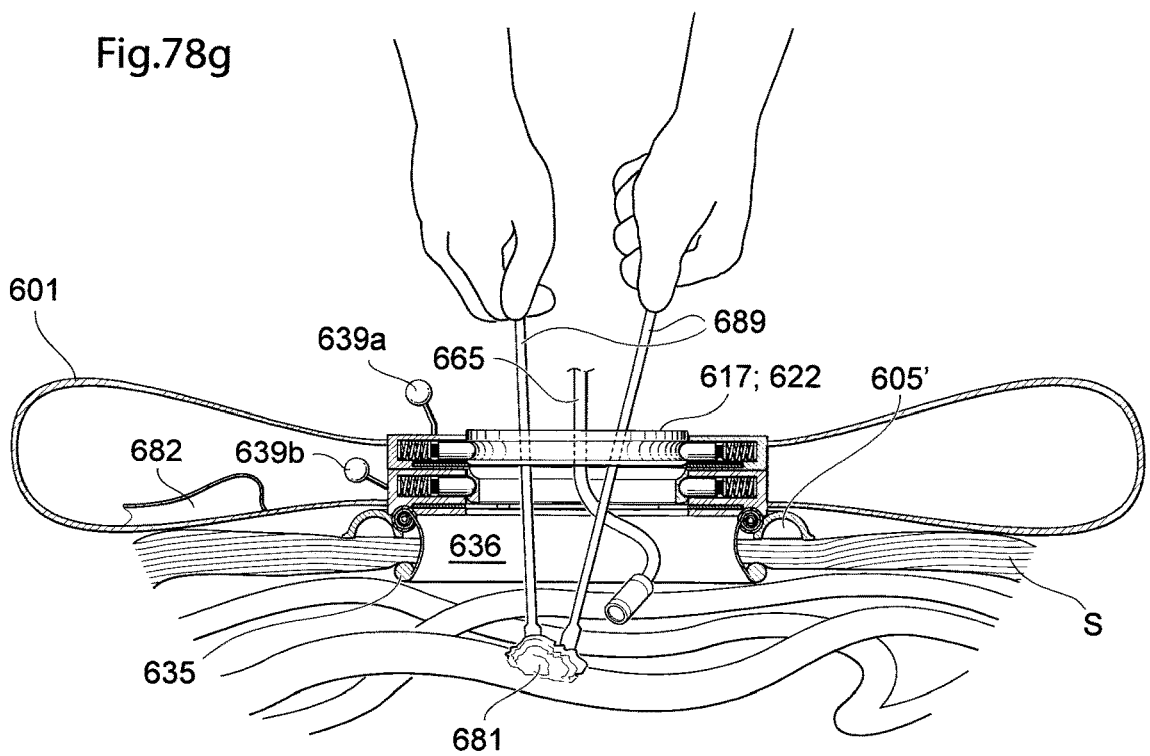
Figure 78G:
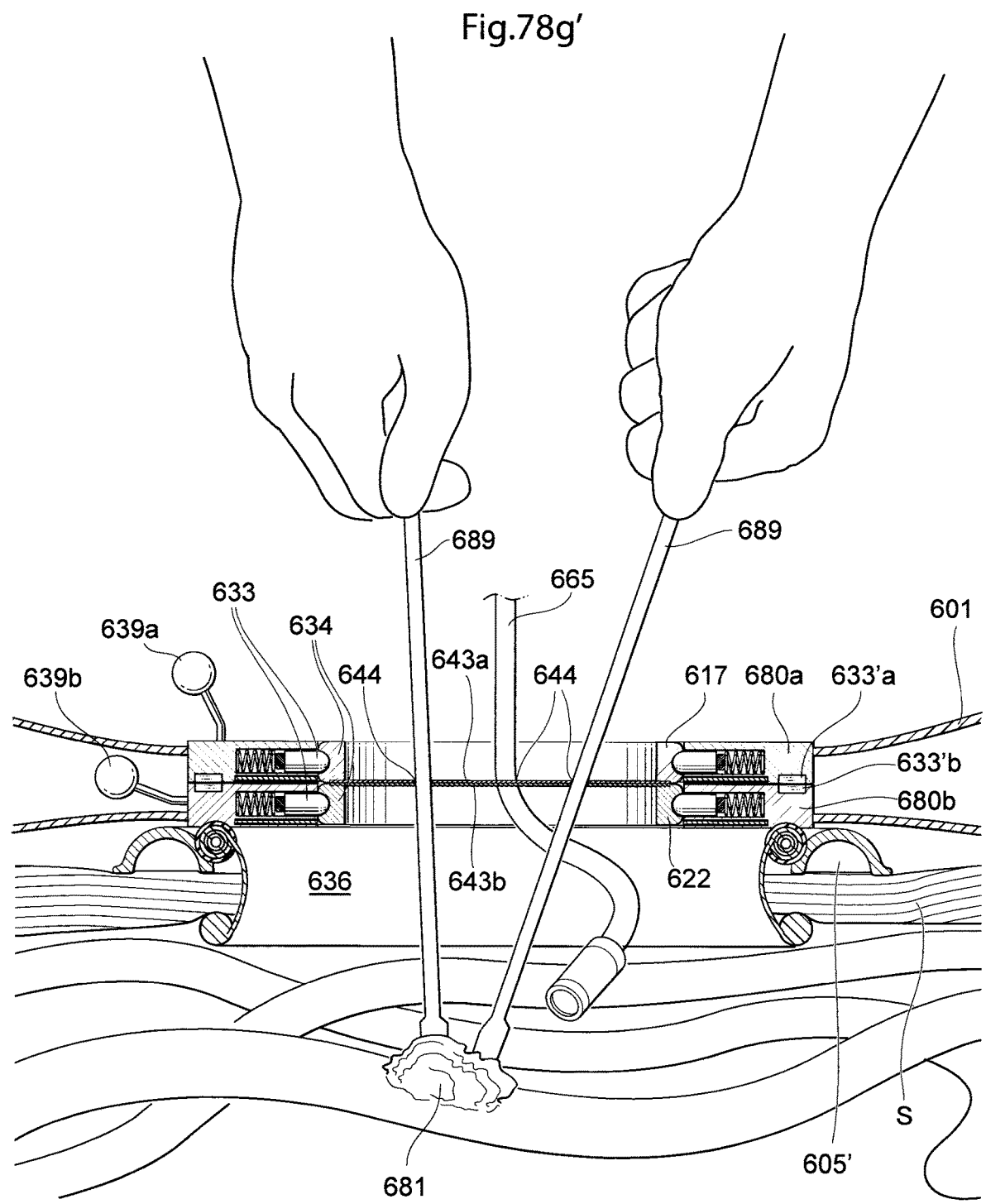

FIG. 78*g* shows the medical device when the upper 680*a* and lower 680*b* couplings are connected such that surgical instruments 689 can be used for manipulating within the body of the patient through the port now being positioned as a body port 622. An endoscopic camera 665 may be provided in the body port 622 for enabling visual inspection of the cavity in the patient's body. The process of cutting away a specimen 681 from the intestines of a patient in a laparoscopic way is shown in FIG. 78*g*.

FIG. 78*g'* shows an embodiment of the medical device in which the upper coupling comprises a wall port 617 and the lower coupling comprises a body port 622. Both the wall port 617 and the body port 622 comprises disc-shaped self sealing membranes 643*a*, 643*b*. In the body port 622, the self sealing membrane 643*b* is positioned in the top portion of the port 622, whereas in the wall port 617, the membrane 643*a* is positioned in the bottom part of the port 617. The self sealing membranes 643*a*, 643*b* have small self sealing holes 644 such that the instruments 689 or a camera can be inserted through the self sealing membranes 643*a*, 643*b*. For example, the self sealing membranes 643*a*, 643*b* may be made from a gel-type material. The wall port 617 and body port 622 forms an integrated port when the wall port 617 and body port 622 are connected, with the membranes 643a, 643b contacting each other such that the instruments 689 engage an integrated sealing membrane (made up of the first and second membrane 643a, 643b) in the integrated port. If the ports were to comprise two spaced-apart membranes, the two membranes would reduce the ability to move the instruments far more than the two integrated membranes acting as a single membrane. The sealing membranes 643a, 643b are adapted to, in a non-expanded state, provide a seal, and in an expanded state, enable an instrument 689 to be inserted through the membranes 643a, 643b.

Figure 78H:
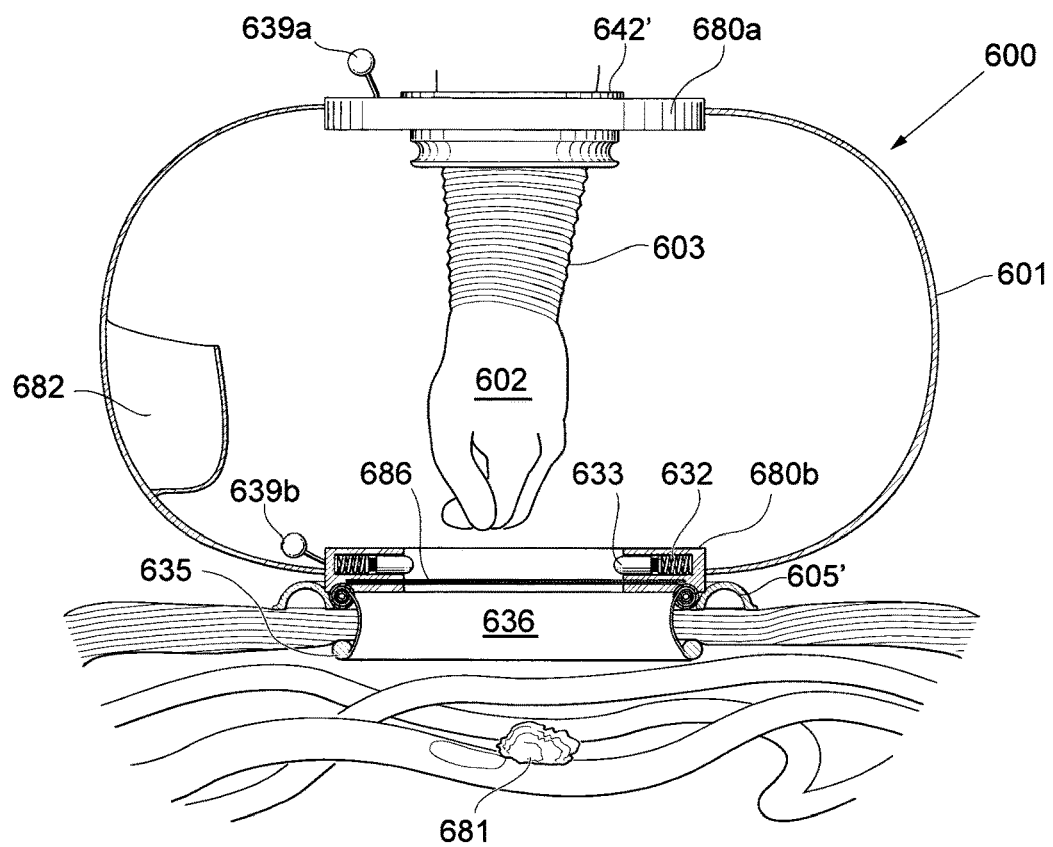

In FIG. 78h, a wall inset 642' comprising a glove 602 has been fixated to the upper coupling 680a to enable the surgeon to operate within the cavity of the patient's body and within the chamber C enclosed by the wall 601 of the medical device. By the glove inset 602 comprising a pleated portion 603, the surgeon is able to reach into the cavity of the patient for removing the specimen 681 cut loose from the intestines in prior steps.

Figure 78I:
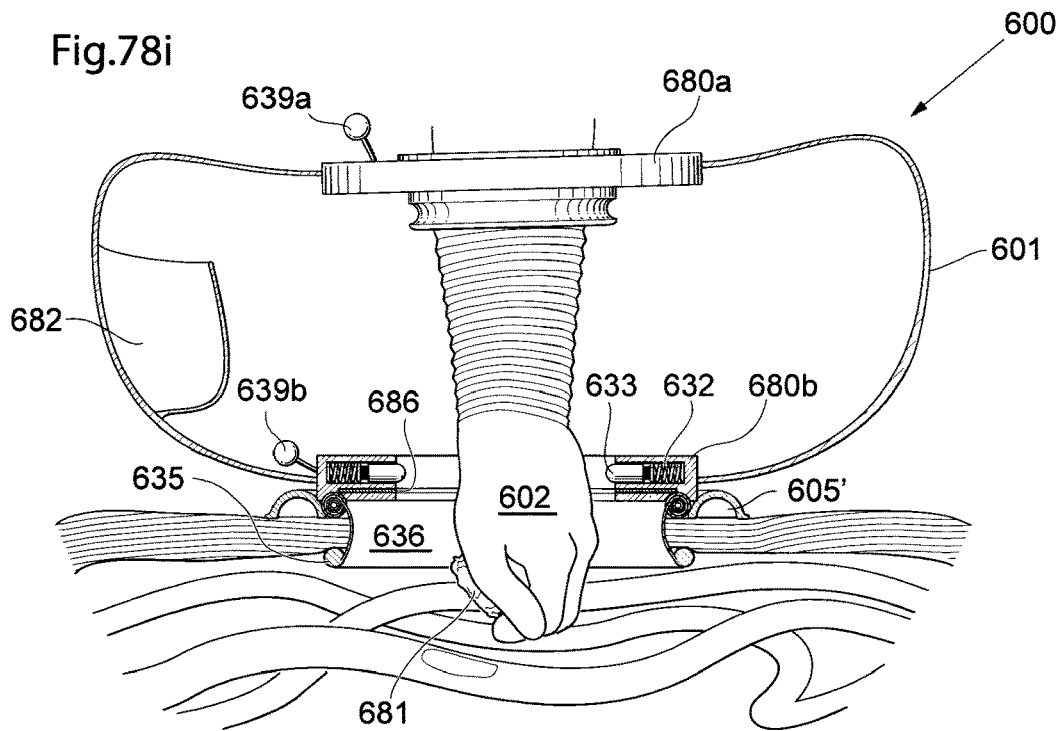

FIG. 78i shows that the wall 601 of the medical device is collapsible such that the wall inset 602 comprising the glove 602 can be moved in relation to the upper coupling 680a, which gives the surgeon further freedom when removing the loose specimen 681 from the intestines of the patient.

Figure 78J:
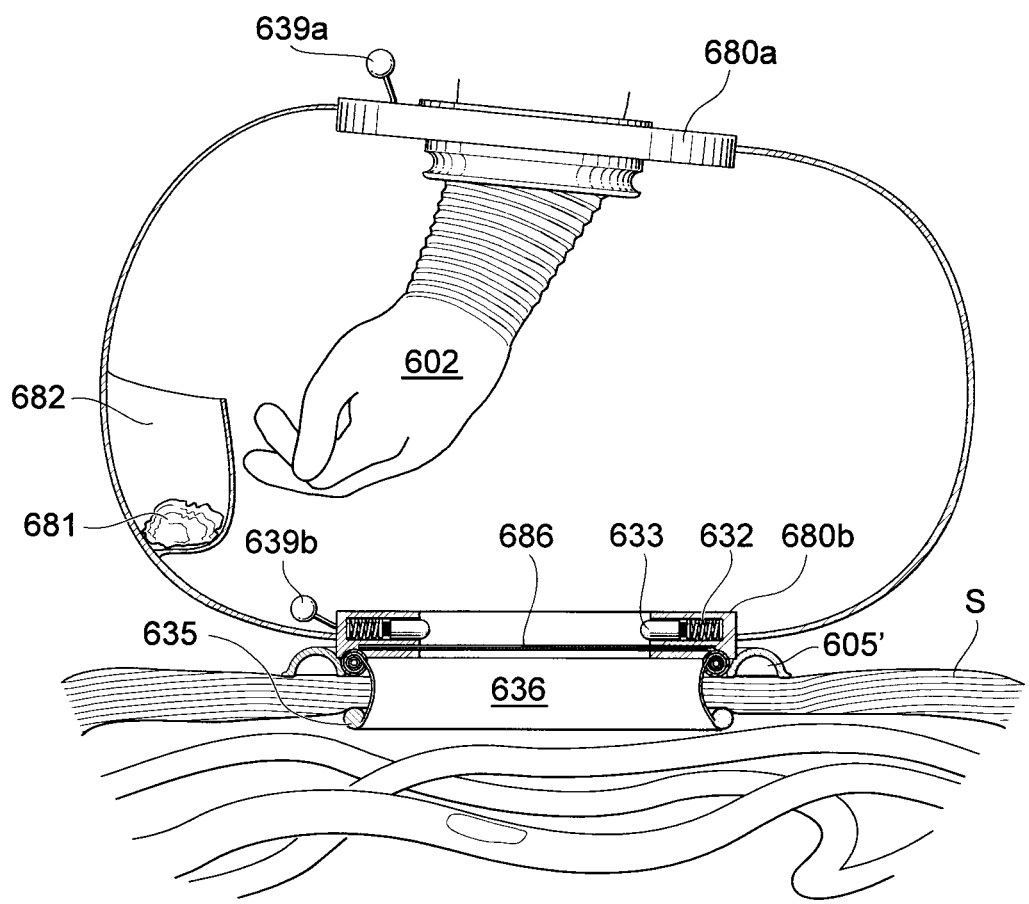

FIG. 78j shows the step of placing the removed specimen in the pouch 682 such that the specimen 681 does not contaminate any other part of the body. The pouch 682 may be a pouch 682 which could be closed for creating a pouch-chamber within the chamber C for isolating the removed specimen 681 within the chamber C.

Figure 78K:
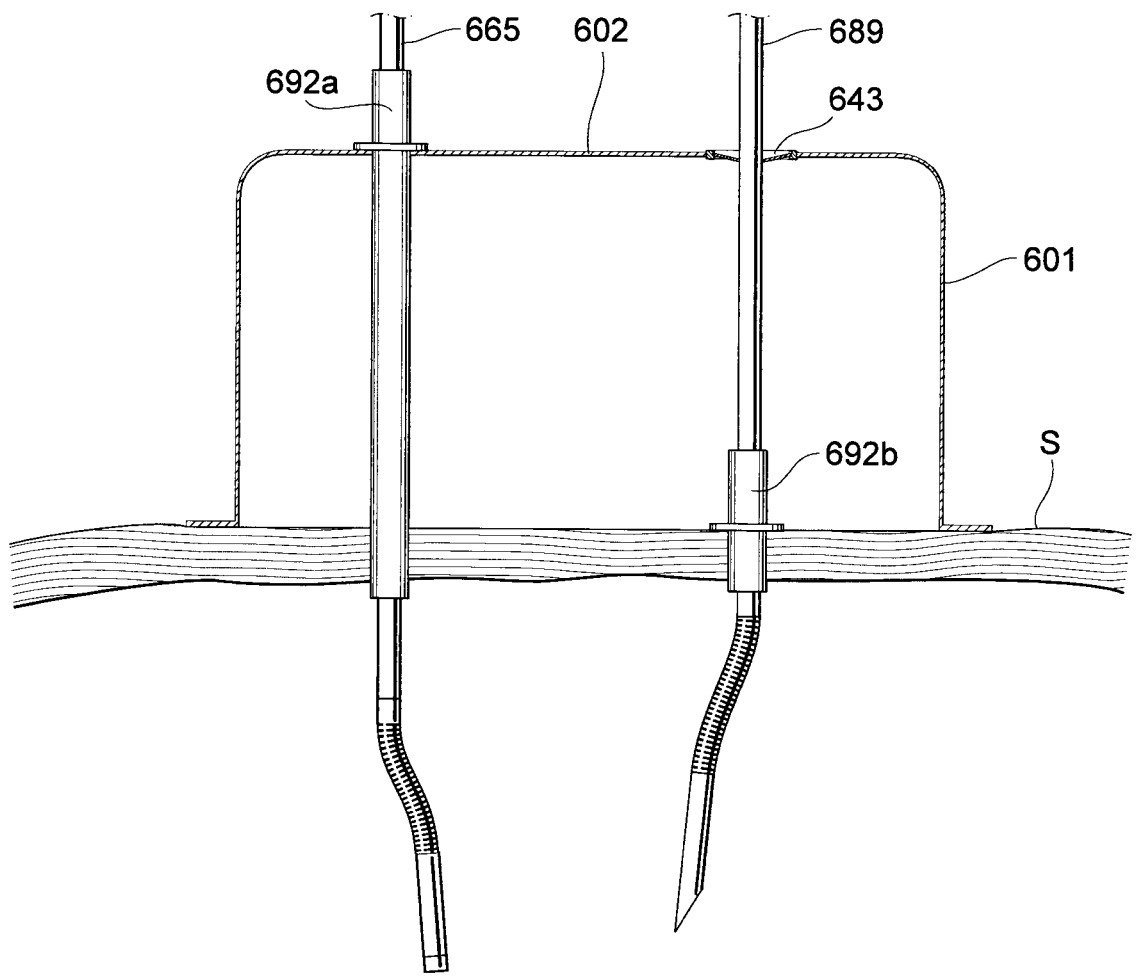
FIG. 78k shows an embodiment of the medical device, in sectional view.

FIG. 78k shows examples of how trocars 692a; 692b may be used in combination with the medical device according to any of the embodiments shown in FIGS. 66-78j. The medical device comprises a wall 601 placed on the patient's skin and thereby enclosing a chamber C for creating a sealed environment. The medical device comprises two trocars 692a; 692b, one 692a traveling through both the wall 601 of the medical device and the skin S of the patient and thus enabling endoscopic instruments 689 to be inserted into the patient through both the wall 601 of the medical device 600 and the skin S of the patient through one single trocar 692a. The other trocar 692b being placed inside the chamber C and enabling an endoscopic instrument to be inserted through the skin S of the patient. The endoscopic instrument 689 is in this embodiment inserted into the chamber C enclosed by the wall 601 through a membrane 643 in the wall 601 sealing against the instrument 689.

FIG. 78l shows how the medical device shown in FIGS. 66-78j may be used. The medical device 600 comprises a glove 602 integrated in the wall 601 and a camera 665 placed through a trocar 692a placed through the skin S outside of the medical device 600. The medical device 600 further comprises a trocar 692b placed inside the chamber C through an opening in the skin of the patient and into an area of the knee of the patient.

FIG. 78l schematically illustrates how the surgeon manipulates the knee in the sealed environment using the glove 602.

Figure 78M:
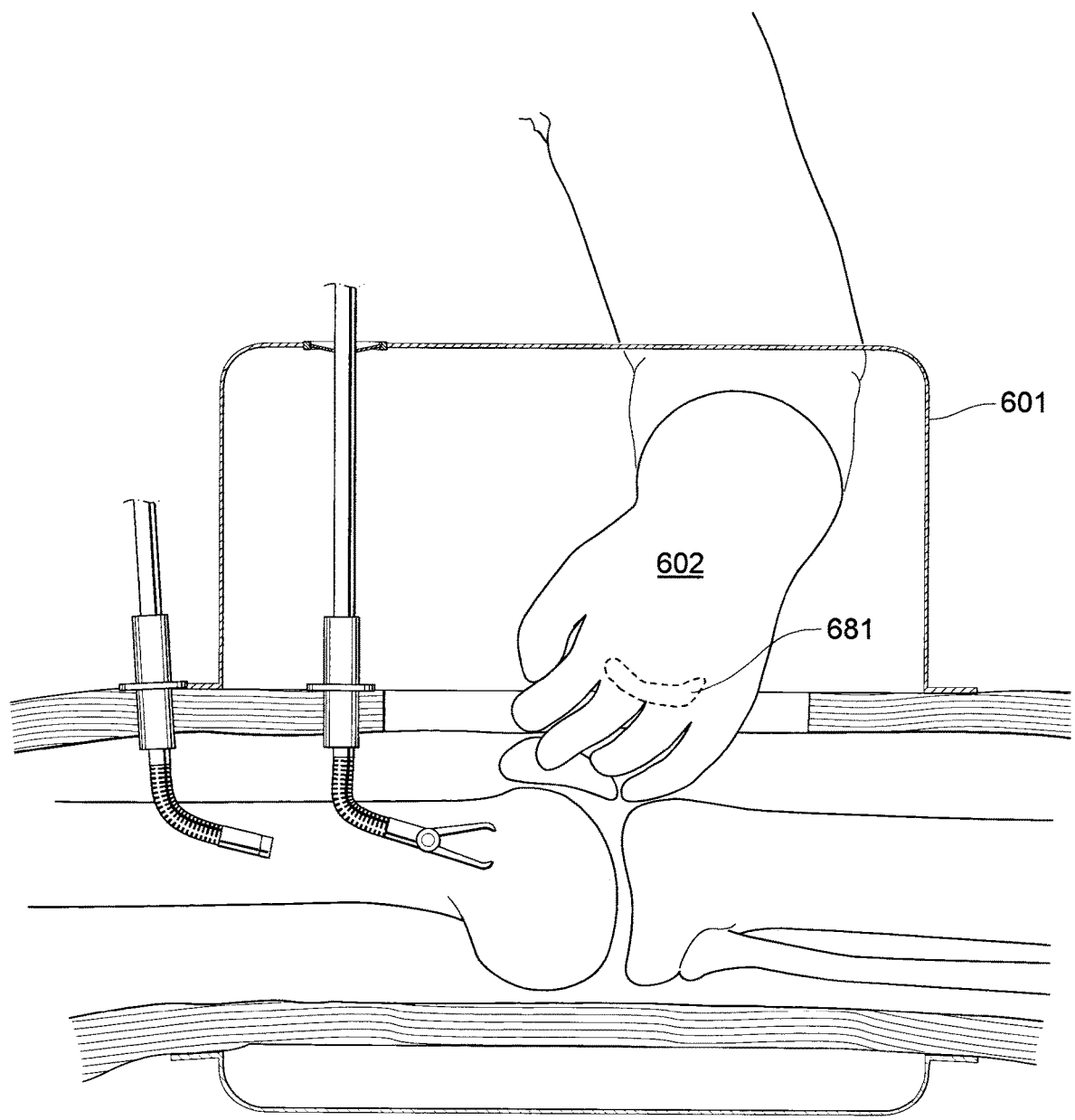
Figure 78N:
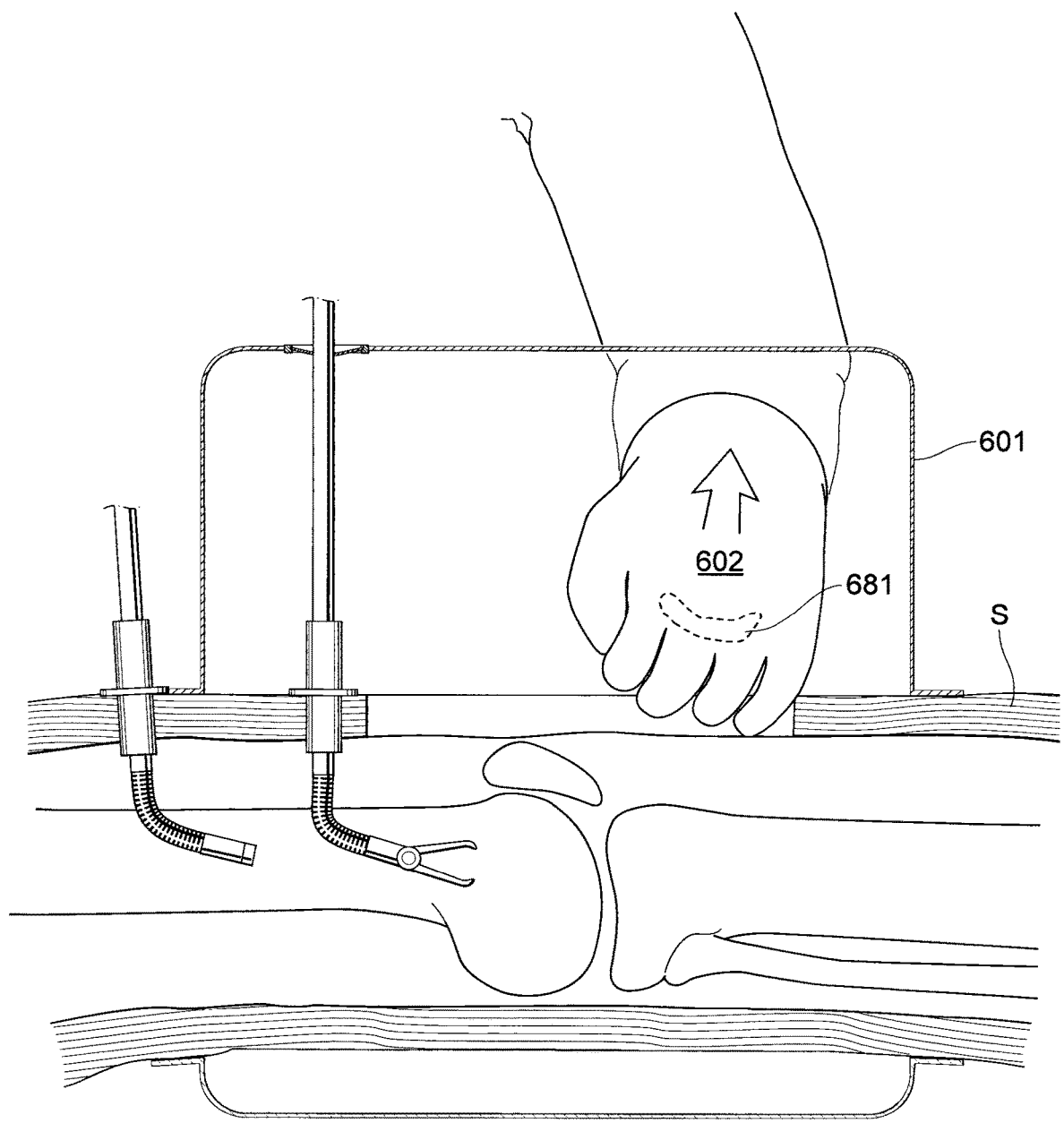

FIGS. 78m, 78n shows the medical device when the surgeon removes a specimen 681 from the knee of the patient using the glove 602 integrated in the wall 601 of the medical device.

Figure 78O:
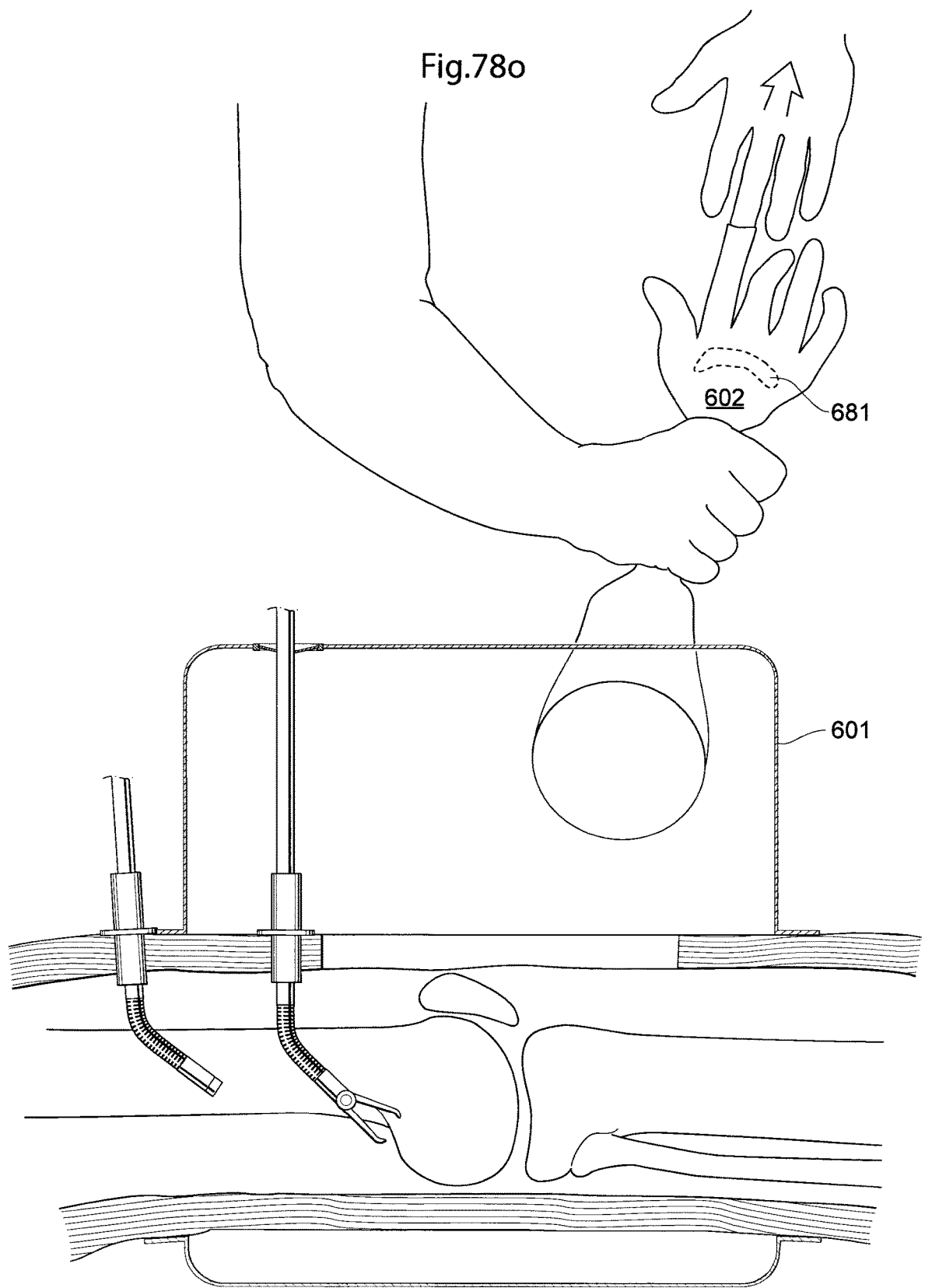

FIG. 78o shows the medical device, when the surgeon has turned the integrated glove 602 inside-out such that the specimen 681 can be contained within the integrated glove 602. By isolating the specimen 681 inside of the glove 602, the specimen 681 is removed both from the rest of the body of the patient and from the ambient environment, and thereby does not risk to infect any other portion of the patient's body or medical staff with any infectious disease.

Figure 79A:
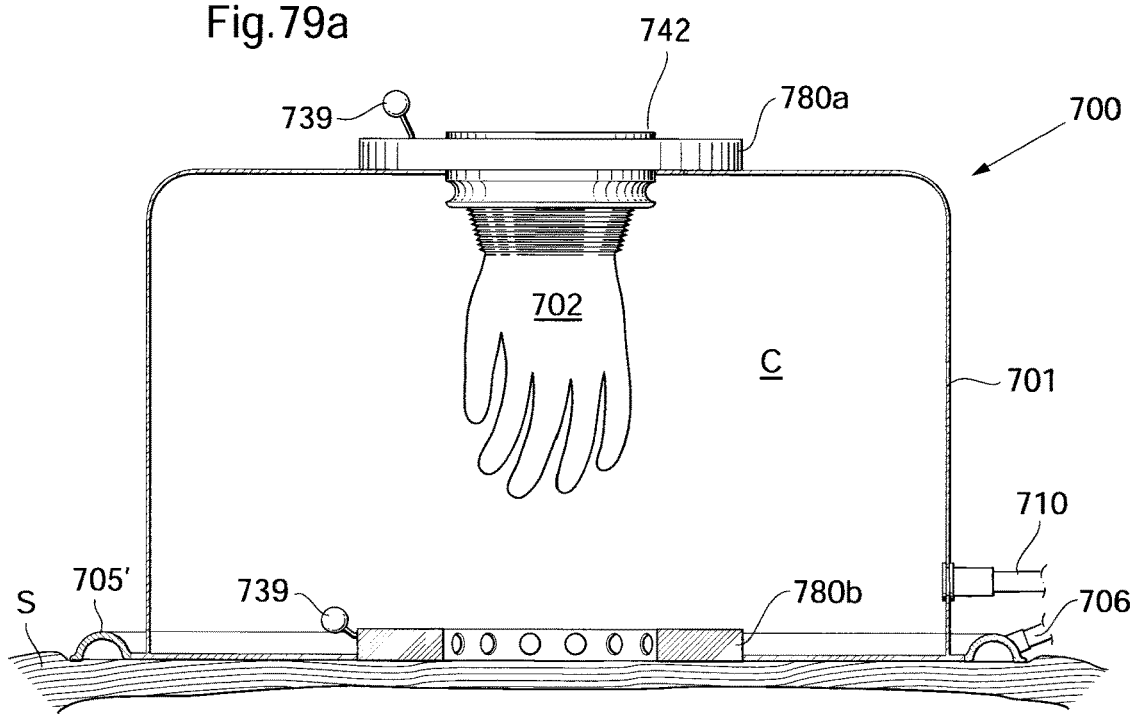

FIG. 79a shows a medical device 700 for performing surgical procedures. The medical device 700 comprises a wall 701 enclosing a chamber C for performing the surgical procedure. A portion of the wall 701 is adapted to be in contact with a patient. The medical device 700 comprises an inset 742 comprising a surgical glove 702 adapted to enable manipulation within the chamber C. The inset 742 comprising the surgical glove 702 is connected to the upper coupling 780a can be in an upper position and lower position, the upper position is disclosed in FIG. 79a, while the lower position is located closer to the skin S of the patient and disclosed in FIG. 79c. The medical device could for example be used in surgical procedures where transitions between open and laparoscopic surgery is needed. The medical device 700 could be placed in the upper position for enabling a larger freedom of motion for the surgeon within the chamber C of the medical device 700, while the lower position, with the upper coupling 780a locked to the lower coupling 780b, could enable the use of a laparoscopic trocar or hand access for further reach within the body of the patient. The medical device 700 could further be used in embodiments where manual manipulation in a sealed environment is required, e.g. for preparing a medical device for use in the surgical procedure. Other applications could for example be that the surgeon wishes to remove a specimen 781 from the body of the patient after a laparoscopic procedure has been concluded. The laparoscopic procedure could in these instances be performed with the upper coupling 780a being in the upper position (as shown in FIG. 79c), being close to the skin S of the patient, whereafter the upper coupling 780a could be placed in the lower position for enabling the specimen 781 to be removed from the body of the patient and placed in the chamber C of the medical device 700 without contacting the outside environment, and without the release of the pressure that usually fills the abdomen in laparoscopic procedures. According to the embodiment shown in FIGS. 79a-d, the wall 701 is collapsible such as to enable the transferring between the upper and lower positions. The lower coupling comprises a lever 739 for releasing and/or locking the upper coupling 780a to the lower coupling 780b, and thereby placing the upper coupling in the lower state. The medical device 700 is according to the embodiment shown in FIG. 79a fixated to the patient by means of a vacuum sealing member 705', such as for example disclosed with reference to FIGS. 66 and 67.

Figure 79B:
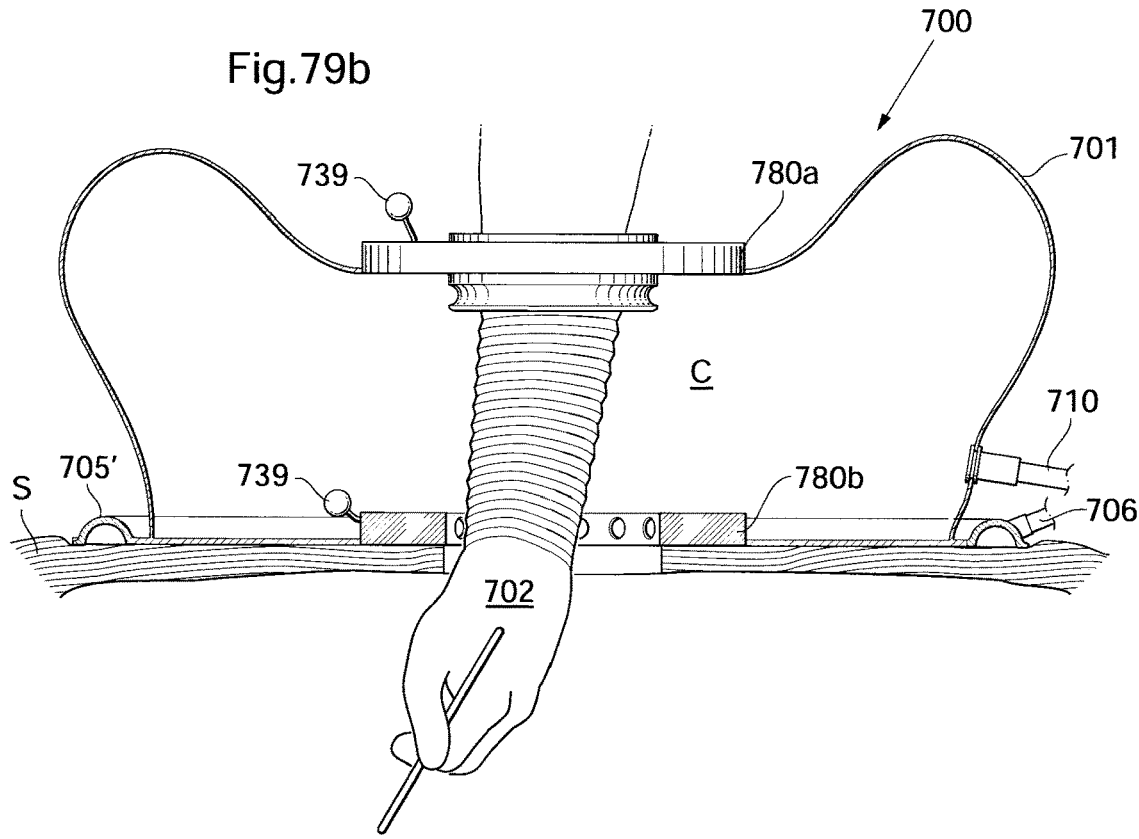

FIG. 79b shows the medical device 700 when being transferred between the upper and lower position, i.e. the upper coupling 780a is pushed towards the lower coupling 780b for enabling a lock between the upper 780a and lower 780b coupling. The integrated surgical glove 702 has been stretched such as to enable manual manipulation within the body of the patient and within the chamber C of the medical device.

FIG. 79c shows the medical device 700 when locked in the first position, i.e. the upper coupling 780a is locked to the lower coupling 780b. The integrated surgical glove 702 now enables manual manipulation with great freedom within the body of the patient. The medical device 700 comprises two levers 739a and 739b, wherein the first lever 739a is connected to the upper coupling 780a and adapted to lock the object (here being an inset 742 comprising a surgical glove 702) to the coupling 731a, while the second lever 739b is connected to the lower coupling 780b for locking the upper coupling 780a to the lower coupling 780b. The medical device 700 is according to the embodiments shown in FIG. 79 *a-d* circular when seen from above, such that the medical device 700 takes the shape of a doughnut when placed in the first position.

FIG. 79*d* shows the exchanging of objects when the upper coupling 780a has been locked to the lower coupling 780b. The object comprises the surgical glove 702 has been removed and can for example be replaced by an airlock 718 for transferring objects between the outer environment and the chamber of the medical device 700. The airlock 718 comprises a first valve 738a and a second valve 738b on each side of the airlock 718 enabling the enclosing of an object within the airlock 718. Another example of an object to which the surgical glove 702 can be exchanged is a port 717; 722 here shown as a body port 722 comprising laparoscopic ports for performing a laparoscopic procedure. In some embodiments (not shown) the upper and/or lower coupling comprises a valve member for closing the opening in the coupling when the objects should be exchanged, the valve member could for example be a flap valve.

Figure 80:
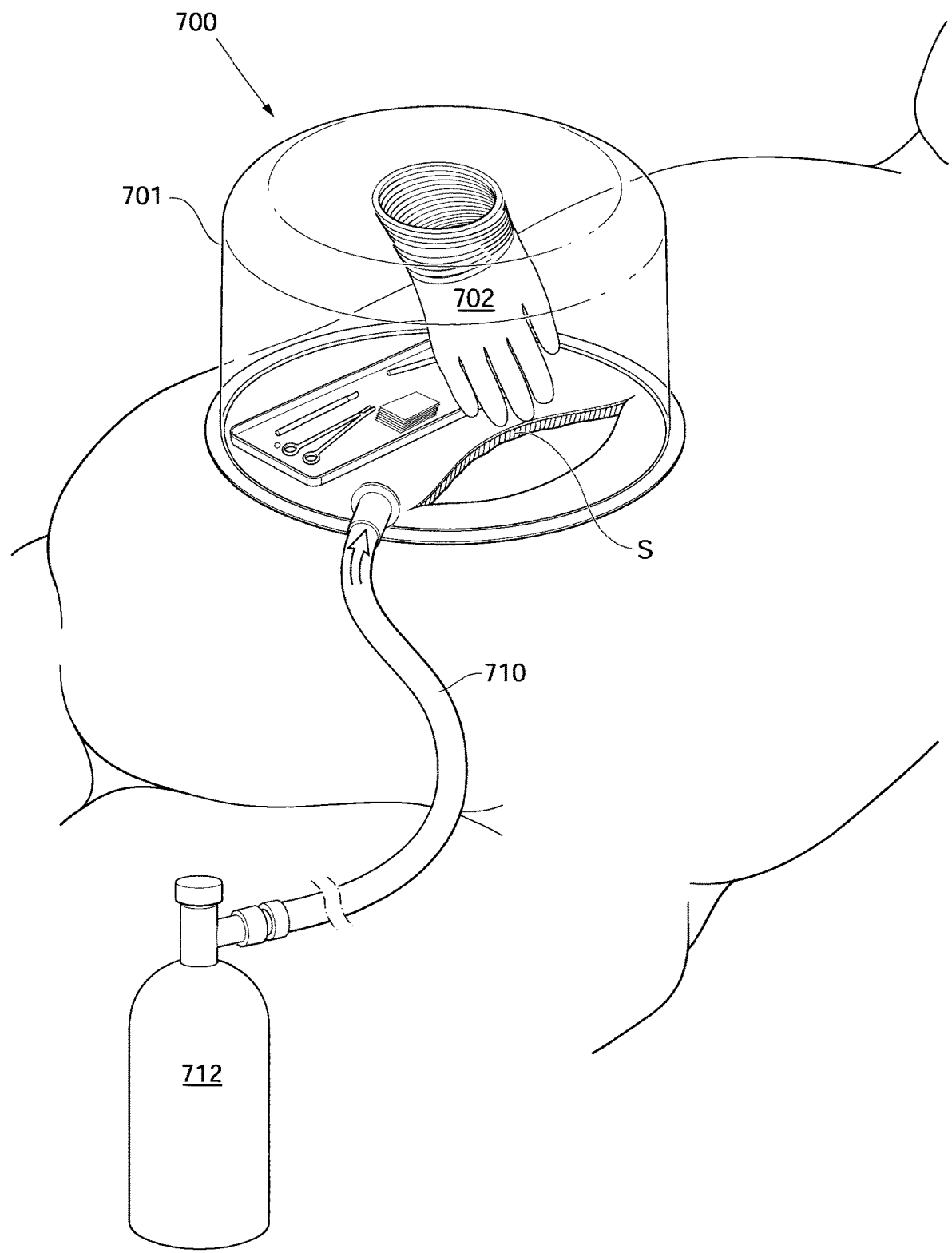
FIG. 80 shows another embodiment of the medical device when an incision is made in the medical device.

FIG. 80 shows an embodiment of the medical device 700 similar to the embodiment of FIGS. 79*a-d*. In the embodiment shown in FIG. 80, the medical device 700 is placed in contact with the skin S of the patient prior to the beginning of the operation and the entire portion of the wall 701 contacting the skin S of the patient comprises an adhesive, such that the incision in the patient runs through the wall 701 and further through the skin S of the patient. This reduces the risk that infectious objects can be transferred from the skin S of the patient to the incision in the patient if the skin S of the patient is not adequately disinfected. The body of the patient could be inflated to allow better visibility within the body from for example the fluid conduit 710 connected to the pressure tank 712, however it is equally conceivable that the body of the patient is inflated from within trough a different incision in the body of the patient.

Figure 81:
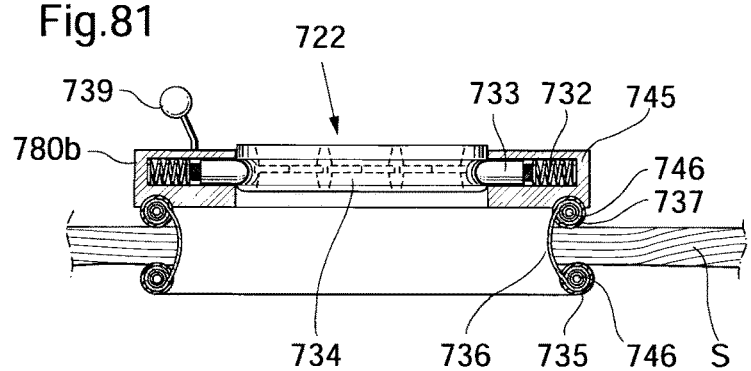
FIGS. 81, 82a and 82b shows a coupling in section.

FIG. 81 shows an embodiment of a detachable body port 722 which could be fixated to the lower coupling 780b positioned in the medical device 700 disclosed with reference to FIGS. 79*a-d*. The coupling 780b of FIG. 81 includes an intra body ring 735 adapted to be placed at the inside of the patients skin around an incision, and an outer ring 737 adapted to be placed on the outside of the patients skin S around the incision. Between the intra body ring 735 and outer ring 737 an annular retractor membrane 736 is positioned adapted to exert a pressure on the skin S or tissue at the incision to seal between the rings and the skin S or tissue and additionally for retracting the skin S and thereby keeping the incision open. The retractor membrane 736 is preferably made from a resilient or elastic polymer material. The outer ring 737 comprises an integrated roll up system 746, which may be spring loaded and adapted to create a suitable pressure on the retractor membrane 736 to keep the incision open.

The port arrangement shown in FIG. 81 also includes a coupling 780a having a rigid annular seating 745 attached to the outer ring 737, spring loaded protruding latching members 733 arranged in radial bores in the seating 745 and a hand lever 739 connected to the latching members 733 to enable retraction thereof against the action of springs 732. The coupling 780b further includes a self sealing body port 722 held by the coupling 780b. The body port 722 comprises a disc-shaped self sealing membrane 743, FIG. 82*a*, fixated to a rigid ring 45 having an outer circumferential recess or groove 734 that receives the protruding latching members 733 of the coupling 780b. The self sealing membrane 743 has a small self sealing hole 744 positioned centrally in the membrane 743. For example, the self sealing membrane 743 may be made from a gel-type material being elastic enough to enable a deformation large enough for a person's hand to pass through the small self sealing hole 744 while still contracting enough to create an airtight seal between the chamber and the outside environment.

The coupling 780b described above enables quick exchange of the port 722. Thus, the surgeon may release the body port 722 from the coupling 780b by simply pulling the hand lever 739 such that the protruding latching members 733 disengage from the groove 734 of the body port 722, whereby the body port 722 can be removed.

Figure 82A:
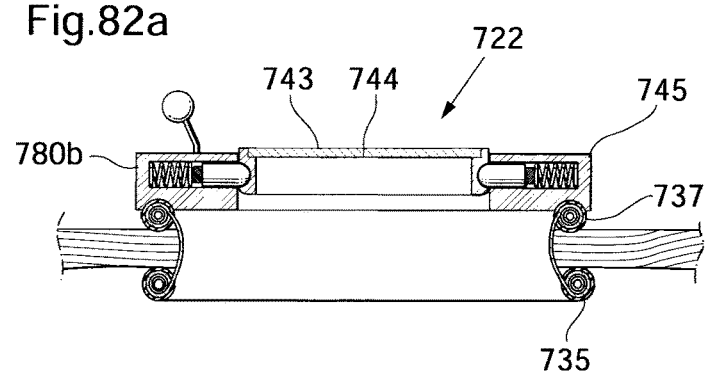

FIG. 82*a* is a cross-sectional view of the coupling 780b shown in FIG. 81, to more clearly illustrate the body port 722 with its self sealing membrane 743 and small hole 744.

Figure 82B:
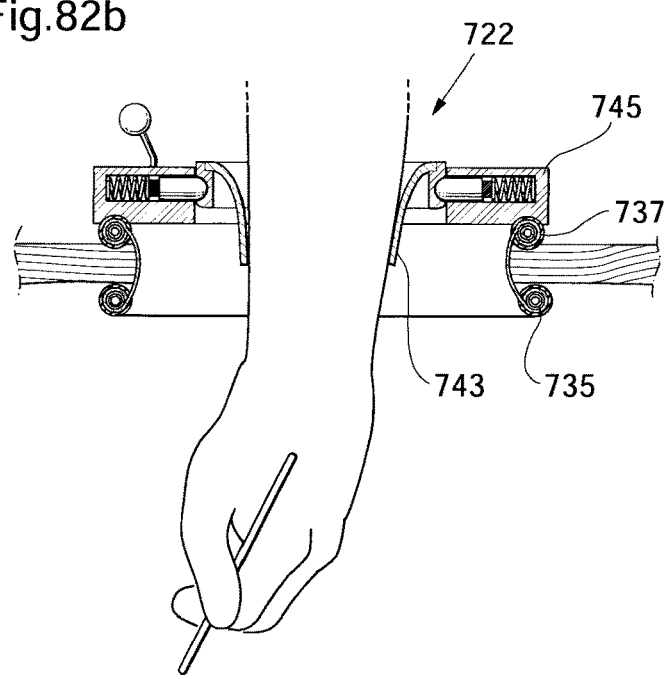

FIG. 82*b* shows the self sealing body port 722 when the hand of a surgeon is placed through the hole 744 in the membrane 743 and thus enabling manual manipulation within the body of the patient.

Figure 83A:
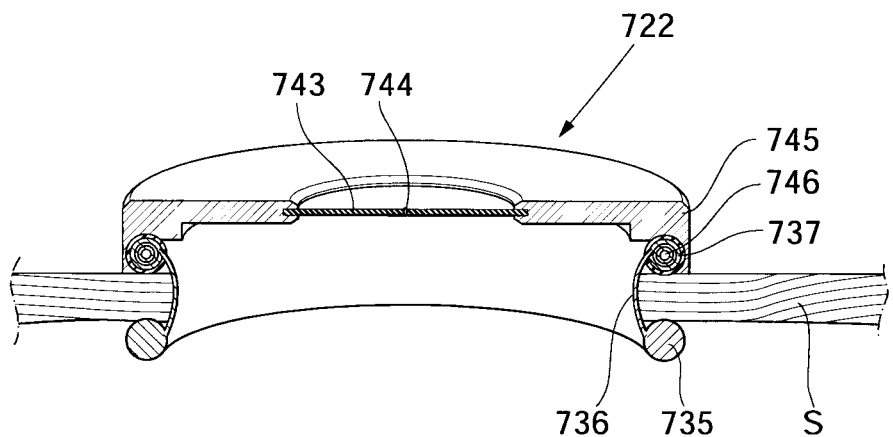
FIGS. 83a and 83b shows two different embodiments of a self sealing port.
Figure 83B:
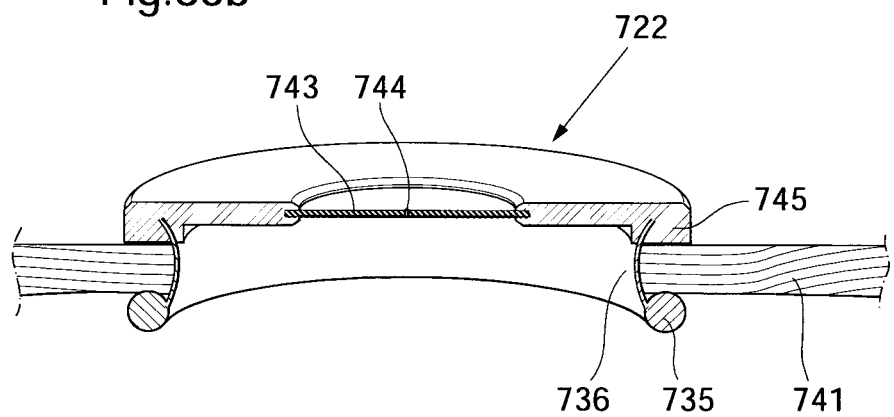

FIG. 83*a* shows a self sealing body port 722 in a close-up, in section. The self sealing body port 722 could be connected to the coupling, for example as disclosed with reference to FIGS. 81-82, which in turn is connected to any of the medical device disclosed with reference to FIGS. 79-80, or the self sealing body port 722 could be fixated to a retractor, as shown in FIGS. 83*a* and 83*b*. The self sealing body port 722 comprises a self sealing membrane 743 fixated to a rigid part 745 of the self sealing port. The self sealing membrane 743 having a small self sealing hole 744 centrally in the membrane 743. The self sealing membrane 743 is for example made from a gel-type material being elastic enough to enable a deformation large enough for a person's hand to pass through the small self sealing hole 744 while still contracting enough to create an airtight seal between the sealed environment and the outside environment. The medical device being fixable to a retractor comprising one intra body ring 735 adapted to be positioned on the inside of the patients skin, and one ring 737 adapted to be placed on the outside of the patient's skin S. Between the intra body ring 735 and the ring 737 adapted to be placed on the outside of the patients skin S a retractor membrane 736 is positioned which is adapted to exert a pressure on the cut surfaces of the incision for retracting the skin S and thereby keeping the wound open. The retractor membrane 736 is preferably made from a resilient of elastic polymer material. The ring 737 adapted to be placed on the outside of the patients skin 741 comprises an integrated roll up system 746 which could be a spring loaded roll up system adapted to create a suitable pressure on retractor membrane 736 for keeping the wound open.

FIG. 83*b* shows an alternative embodiment of the self sealing body port 722, with the difference that the retractor membrane 736 is made from a material elastic enough such that one end of the retractor membrane 736 could be fixedly fixated to the rigid part 745 of the port.

Figure 84:
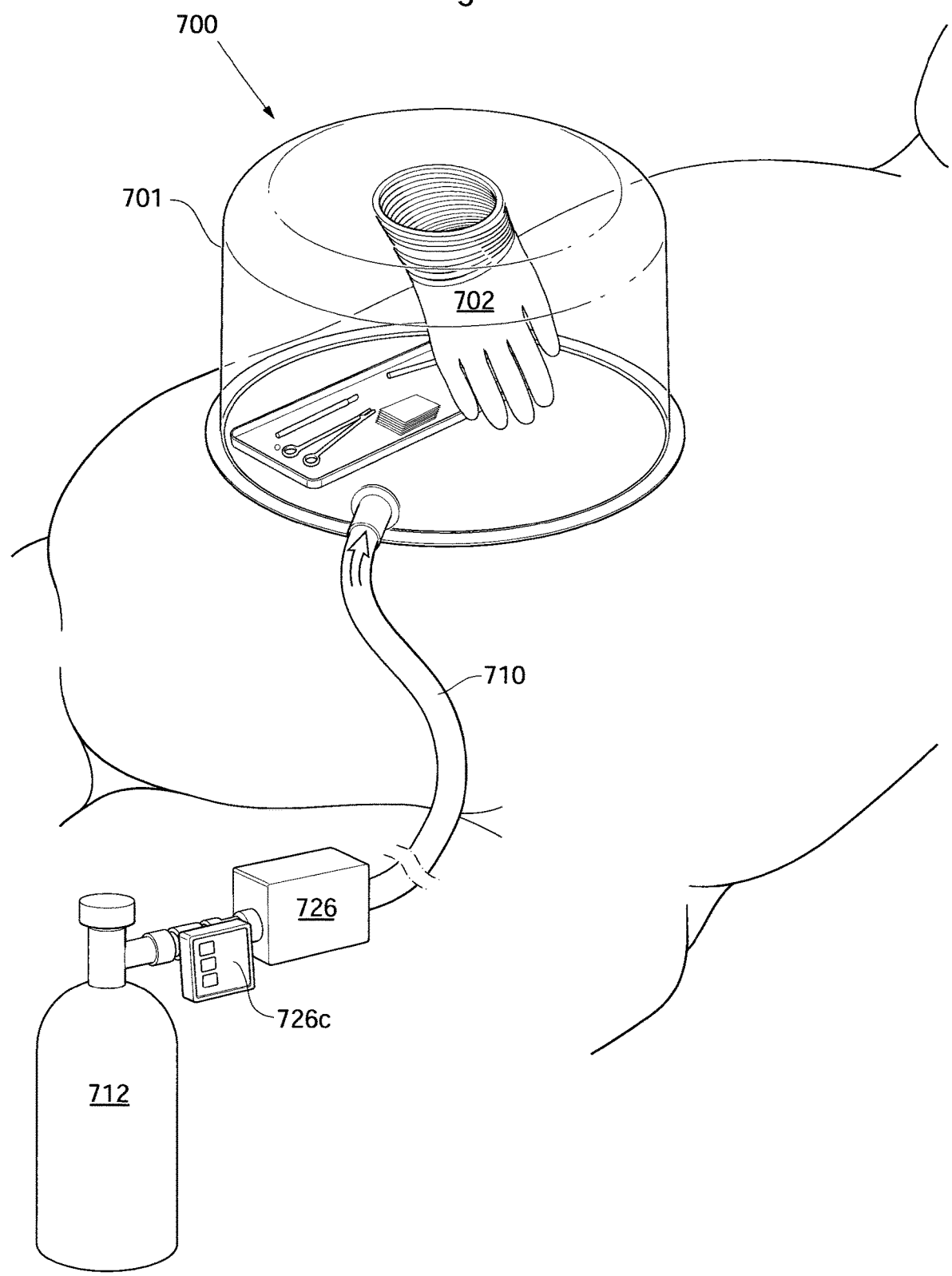
FIG. 84 shows yet another embodiment of a medical device.

FIG. 84 shows the medical device as shown in FIG. 80 with the addition that the embodiment comprises a sterilizing unit 726 adapted to sterilize the gaseous fluid entering the medical device 700. In the embodiment disclosed herein, the gaseous fluid entering the medical device 700 originates from a pressurized tank 712 and could be pre-sterilized, however, in other embodiments, it is conceivable that the gaseous fluid is the surrounding air which is pressurized (such as further disclosed with reference to FIG. 85). In the embodiments where the surrounding air is used to inflate the medical device 700 and constitute the operating environment this air needs to be properly sterilized. The medical device 700 further comprises a tempering unit 726c which could be provided to heat or cool the gaseous fluid inflating the medical device 700. In cases when the surrounding environment is cold the tempering unit 726c could be used to raise the temperature of the sealed environment to provide beneficial operating circumstances both for the patient and for the surgeon. In cases when the surrounding environment is hot, the tempering part of the system 726c could be used to lower the temperature of the sealed environment both to provide beneficial operating circumstances, both for the patient and for the surgeon, and for providing a temperature inhibiting bacterial and viral infections. The tempering unit 726c could comprise a temperature regulating device for setting the required temperature.

Figure 85A:
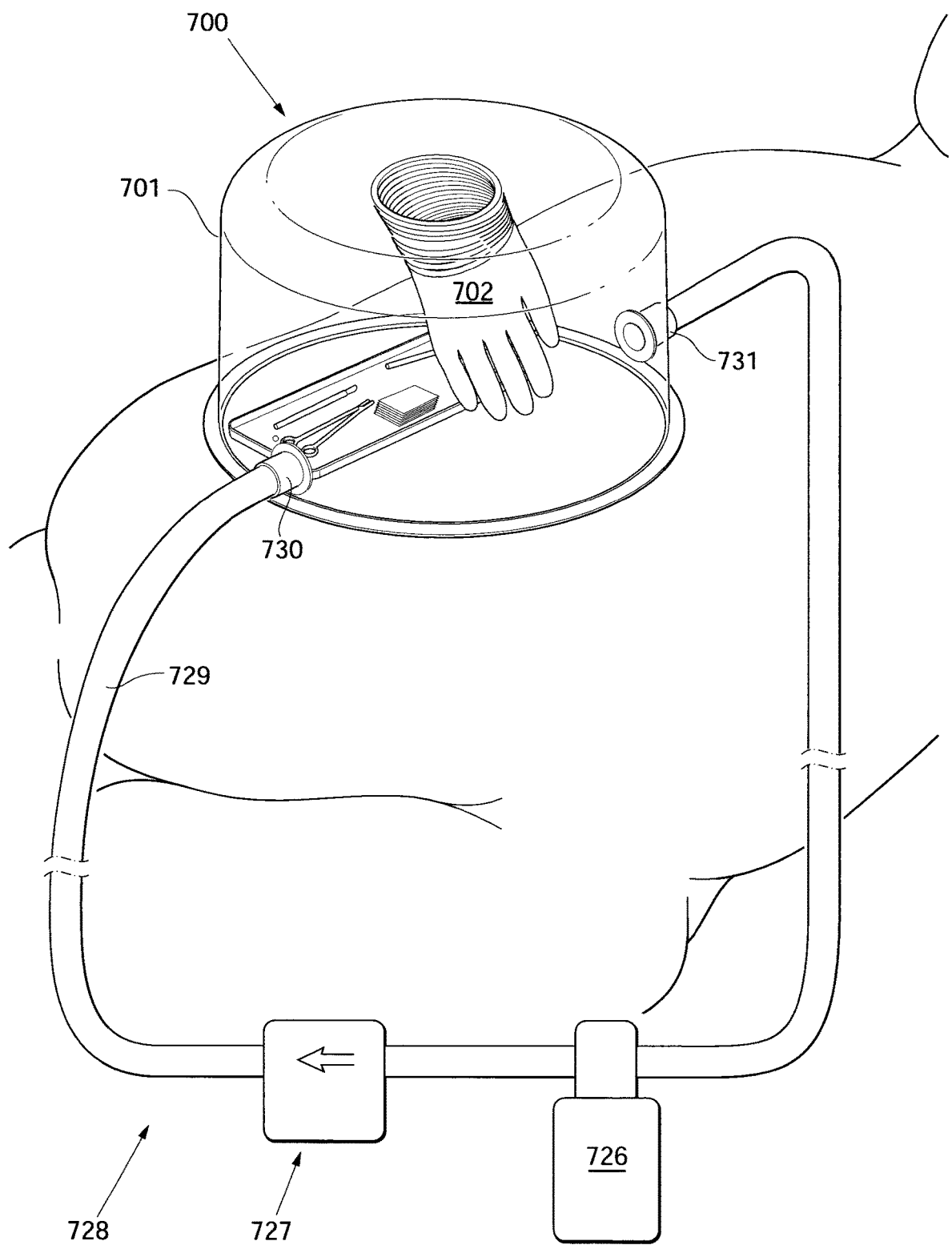
FIG. 85a shows another embodiment including a fluid circulating system.

FIG. 85a shows a medical device similar to the embodiment disclosed in FIG. 79 but comprising a system 728 for circulating a fluid through the sealed environment of the medical device 700. The system 728 comprises a fluid conduit 729 connected at an inlet 730 placed in the wall 701 for supplying fluid to the sealed environment, and an outlet 731 for draining the fluid from the sealed environment. The fluid is circled by means of a pumping unit 727 and is circled via a sterilizing/filtering/tempering unit 726 adapted to remove impurities and sterilize the fluid. In embodiments where the fluid is a gaseous fluid, the filtering unit is adapted to remove particles that could be suspended in the gas. The filtering unit 726 could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 85B:
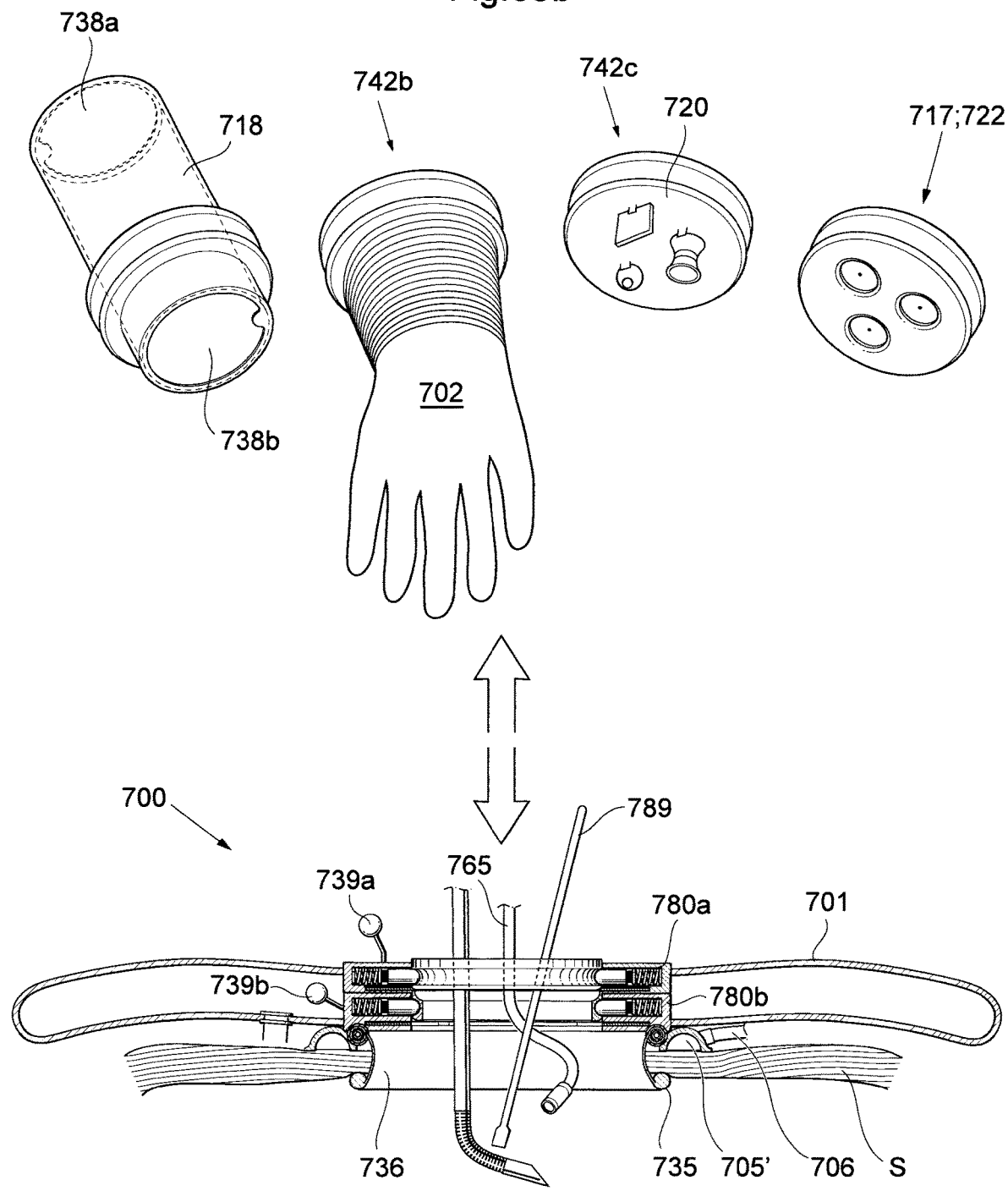
FIGS. 85b-85c shows an embodiment of the medical device, in sectional view.

FIG. 85b shows an alternative of the embodiment shown in FIGS. 79-85. Fig. In 85b the medical device 700 is adapted to be at least partially placed in an incision cut in a patient's body. The medical device 700 comprises a first 780a and second 780b coupling adapted be interconnected to form an interconnected coupling. The upper coupling 780a is adapted to be disconnected from the lower coupling 780b, and the upper coupling 780a is connected to a first portion of a flexible wall 701, and the second coupling 780b is connected to a second portion of the flexible wall 701. The flexible wall 701 forms a chamber in which a sealed environment can be maintained, the chamber is heavily enlarged when the upper coupling 780a is disengaged from the lower coupling 780b, thus creating operating space within the chamber enclosed by the wall 701. The first and second couplings 780a; 780b comprises a latching system for locking an inset 742b;c, an airlock sluice 718 or port 717;722. The inset could for example be an inset 742b comprising a glove 702 for manual manipulation within the body of the patient, or within the enclosed chamber, or an inset 742c comprising a holding device 720 for holding instruments or medical devices within the chamber. Alternatively the insets 742b; 742c can be replaced by an airlock sluice 718 with a first 738a and second 738b valve member or a port 717; 722 which could be a multiport comprising a plurality of ports enabling the insertion of a surgical instrument 789 or camera 765 into the chamber or body of the patient.

In the embodiment shown in FIG. 85b the medical device is fixated to the body of the patient by means of a vacuum fixating member 705' connected to a conduit 706, which in turn is connected to a vacuum source. Furthermore, the medical device in FIG. 85b comprises a second sealing function having a first sealing member in the form of an intra body ring 735 adapted to be positioned at the inside of the patient's skin S around an incision to be performed in the skin S and a second sealing member 737 adapted to be positioned at the outside of the patient's skin S around the incision, and a spring-loaded or elastic connecting member 736 sealingly interconnecting the first 735 and second 737 sealing members. The spring-loaded or elastic connecting member 736 seals between at least one of the coupling 780b and the skin S of the patient, and the intra body ring 735 and the tissue of the patient.

Figure 85C:
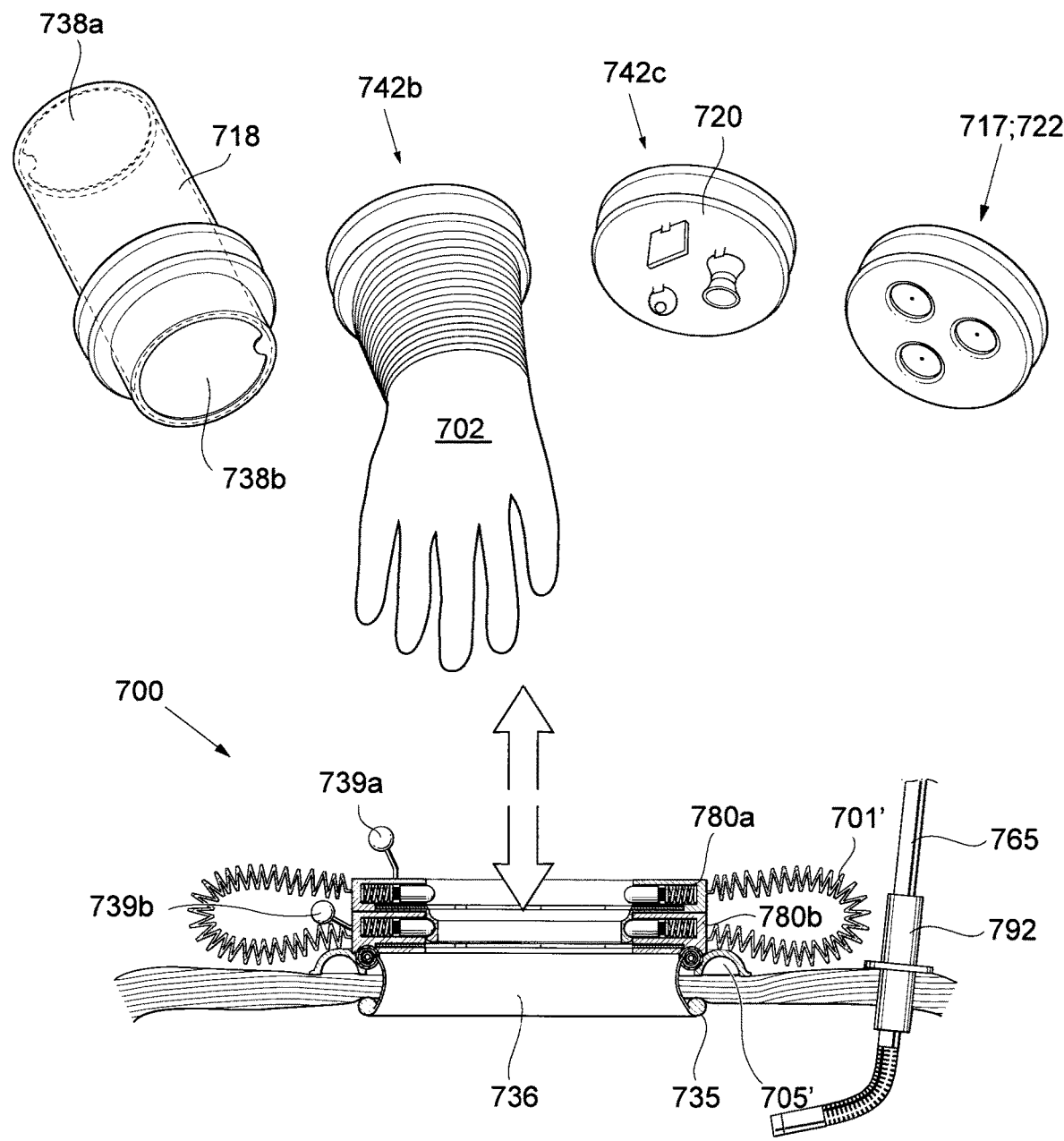

FIG. 85c shows the port in an embodiment very similar to the embodiment shown in FIG. 85b but with the difference that the wall 701' has a bellows structure and thus taking up less space when in its deflated state. The bellows structure enables the wall to be packaged in a small package and thus not obstructing the procedure. In some applications the medical device can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. A camera 765 is also shown in FIG. 85c, placed in a trocar 792 placed outside of the medical device and enabling visual inspection of the cavity within the patient.

FIG. 85d-85i shows a feature which could be implemented in the embodiments disclosed with reference to FIGS. 79-85. In the embodiment of FIGS. 85d-85i, the wall 701 of the medical device is inflatable, and the medical device 700 is in its inflated state. When the chamber C is deflated it has a first volume i.e. when the first, upper 780a and second, lower 780b couplings are interconnected, and when the chamber C is inflated and the upper coupling 780a is disconnected from the lower coupling 780b it has a second volume, and the second volume is larger than the first volume. According to the embodiment shown in FIG. 85d, the second volume is larger than 500 000 mm3 and adapted to hold a pressure exceeding atmospheric pressure.

According to the embodiment shown in FIG. 85d-85i the chamber C further comprises a pouch 782 for holding a specimen 781 removed from within the body of the patient not to contaminate any other part of the body and create the possibility of delaying the removal of the specimen until the procedure is concluded. The pouch 782 may be a pouch 782 which could be closed for creating a pouch-chamber within the chamber C for isolating the removed specimen 781 within the chamber C.

In FIG. 85d, a state is illustrated in which the cut in the patient's skin is being created by the surgeon by means of a glove inset 702 latched to the upper coupling 780a. The medical device 700 is fixated and sealed by means of the vacuum sealing member 705' since the seal that is provided partially within the patient's body cannot be mounted until the cut in the patient's skin S is concluded. The two different seals disclosed could in some embodiments be replaced by only one of the seals, or by a different seal, such as the adhesive of pressure seals disclosed in other portions herein.

FIG. 85e shows the medical device, when the second sealing 735, 736, 737 have been placed in the incision cut in the patient's skin S. The wall 701 enclosing the chamber C is elastic or flexible which enables the surgeon move the upper coupling 780a in relation to the lower coupling 780b for getting better access to different angles within the patient's body, for example for removing a specimen 781.

The embodiment of FIG. 85e further comprises a non-penetrable iris valve 786 placed in the lower coupling 780b for closing the coupling 780b such that the chamber C is sealed from at least one of the ambient environment and a cavity in the patient. The closing of the non-penetrable iris valve 786 enables activity within the chamber C without maintaining a pressure in the chamber C, at the same time as a pressure and/or sealed environment can be maintained within the body of the patient.

Figure 85F:
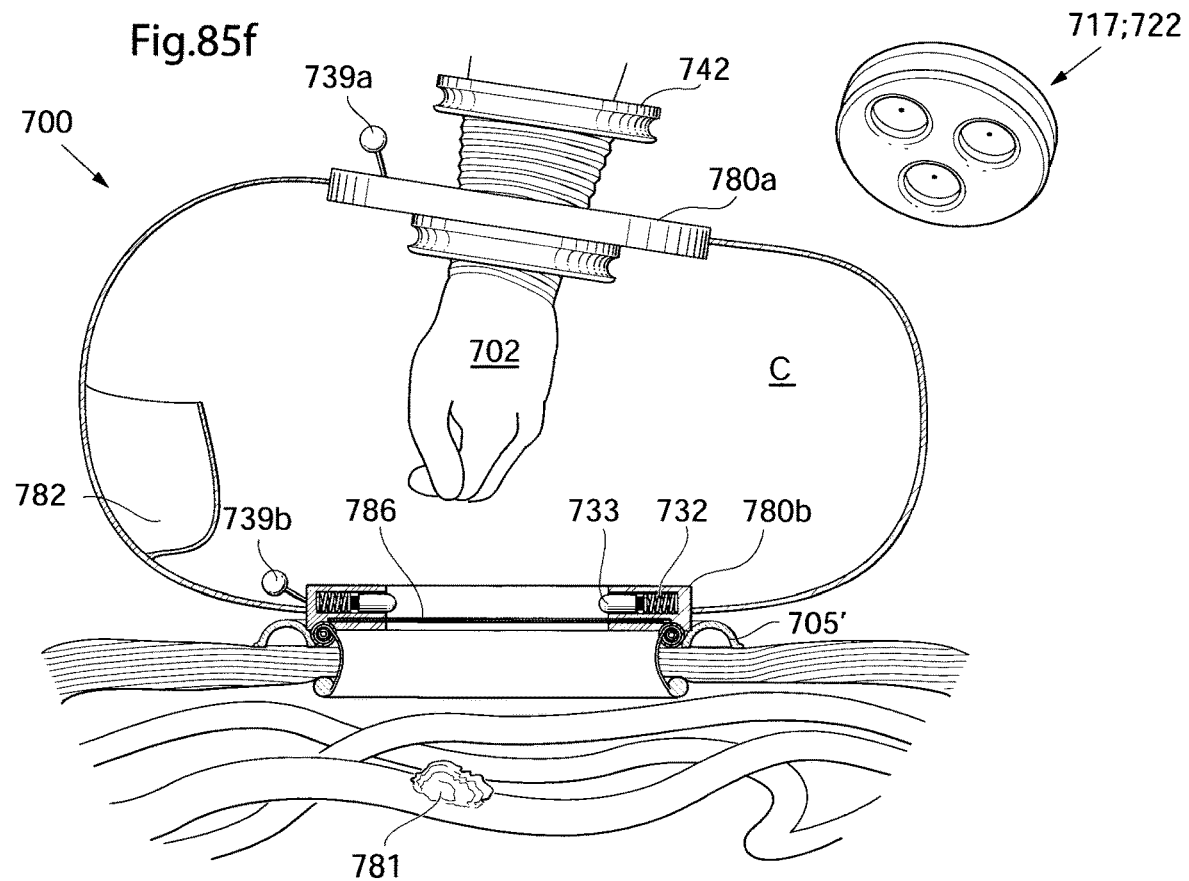

FIG. 85f shows the medical device when the glove inset 702 is removed and replaced by a port 717; 722 in the form of a multi-port comprising a plurality of ports. The multi-port may be used for manipulating objects within the chamber C of the inflated medical device 700 using surgical instruments, or within the body of the human patient, when the first and second couplings 780a; 780b are connected (as shown in FIG. 85g).

Figure 85G:
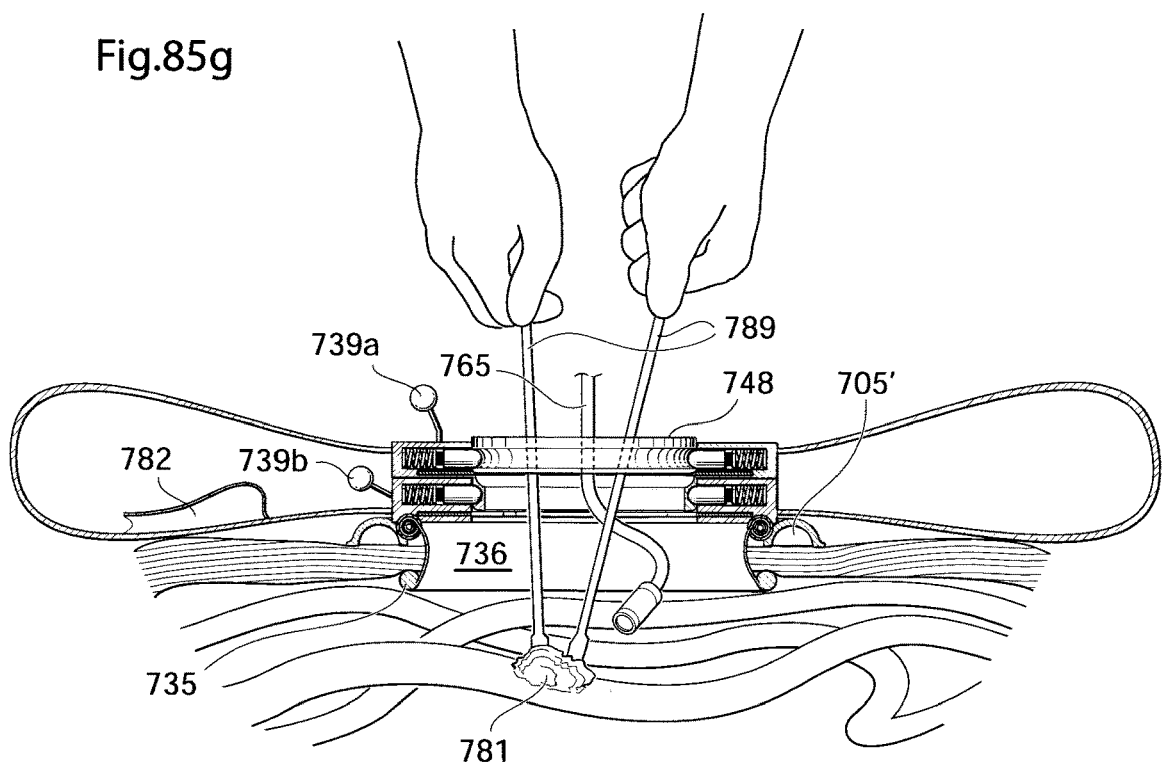

FIG. 85g shows the medical device when the first and second couplings 780a; 780b are connected such that surgical instruments 789 can be used for manipulating within the body of the patient. An endoscopic camera 765 may be provided in the port 717; 722 for enabling visual inspection of the cavity within the patient's body. The process of cutting away a specimen 781 from the intestines of a patient in a laparoscopic way is shown in FIG. 85g.

Figure 85I:
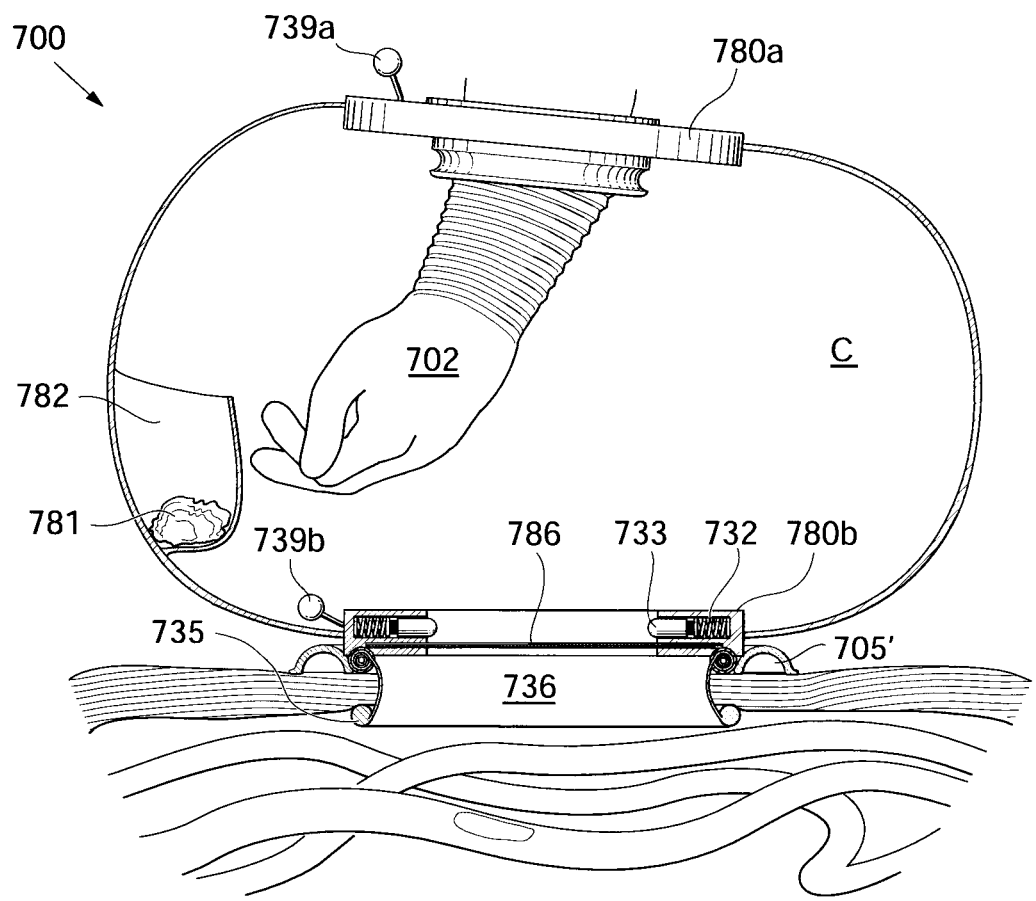

FIG. 85i shows the step of placing the removed specimen 781 in the pouch 782 such that the specimen 781 does not contaminate any other part of the body. The pouch may be a pouch 782 which could be closed for creating a pouch-chamber within the chamber C for isolating the removed specimen 781 from the rest of the chamber C.

Figure 85J:
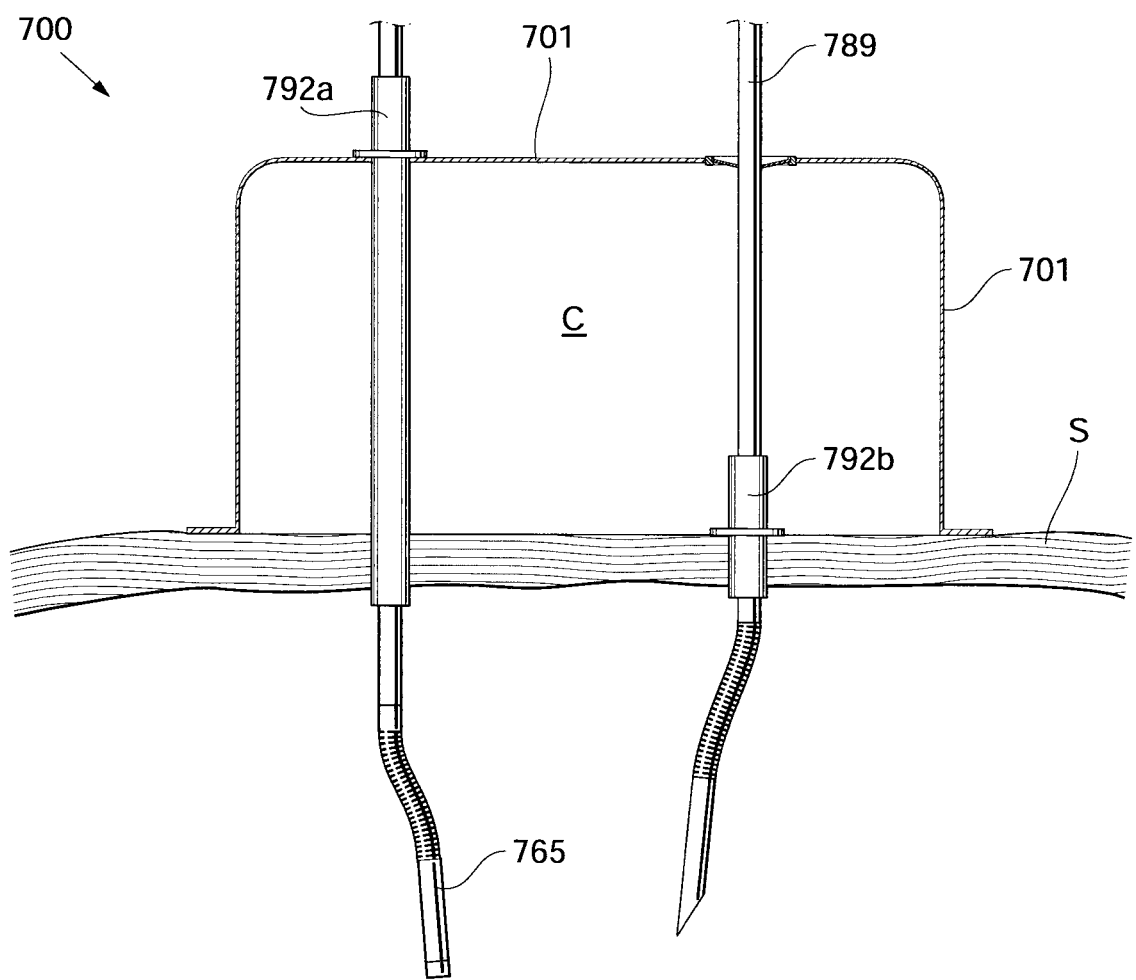
FIG. 85j shows an embodiment of the medical device, in sectional view.

FIG. 85j shows examples of how trocars 792a; 792b may be used in combination with the medical device 700 according to any of the embodiments shown in FIGS. 79-85. The medical device comprises a wall 701 placed on the patient's skin S and thereby enclosing a chamber C for creating a sealed environment. The medical device comprises two trocars 792a; 792b, one 792a traveling through both the wall 701 of the medical device 700 and the skin S of the patient and thus enabling laparoscopic instruments 789 to be inserted into the patient through both the wall 701 of the medical device 700 and the skin S of the patient through one single trocar 792a. The other trocar 792b being placed inside the chamber C and enabling an endoscopic instrument 789 to be inserted through the skin S of the patient. The endoscopic instrument 789 is in this embodiment inserted into the chamber C enclosed by the wall 701 through a membrane 743 in the wall 701 sealing against the tool 789.

Figure 85K:
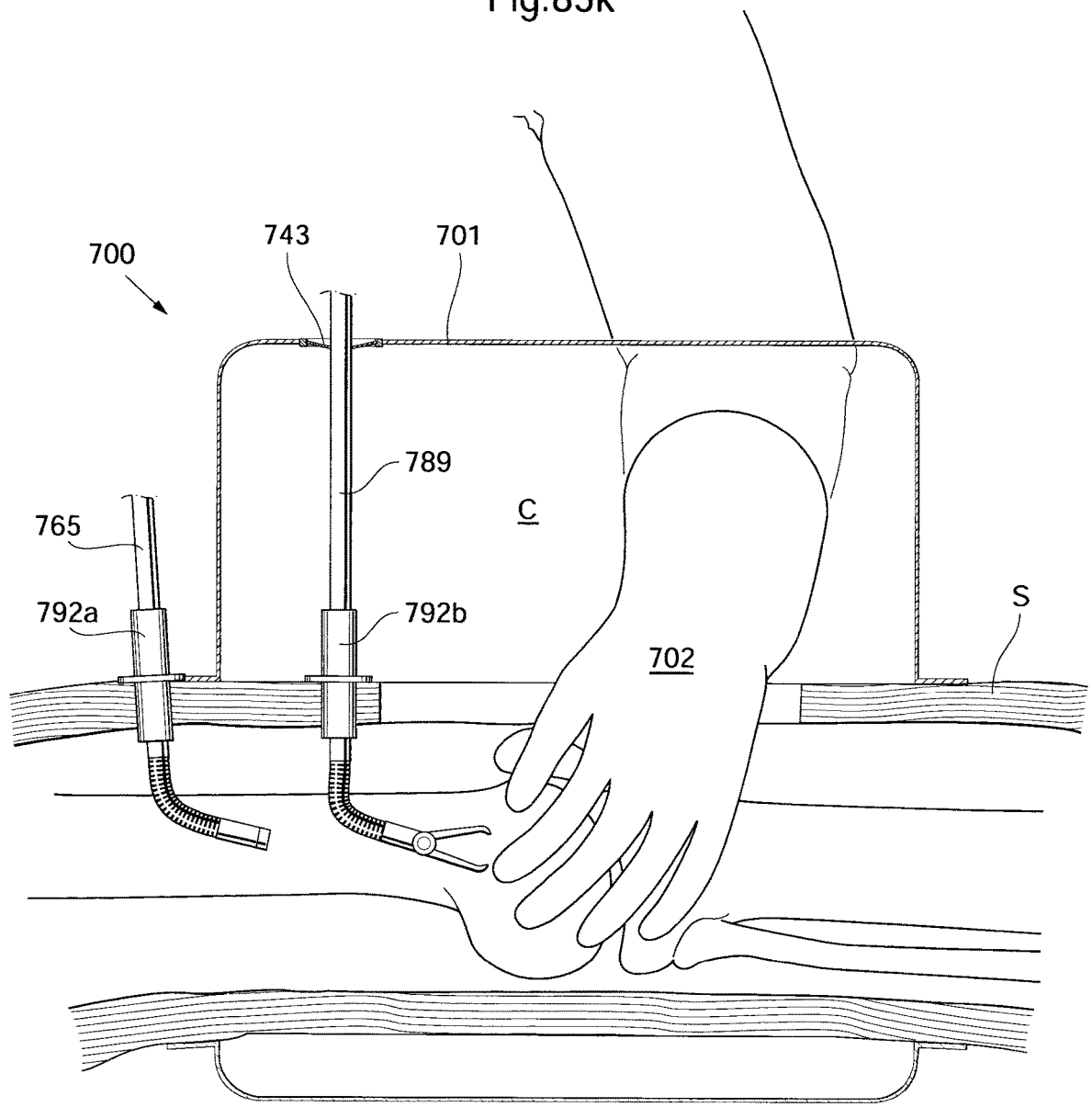
Figure 85I:
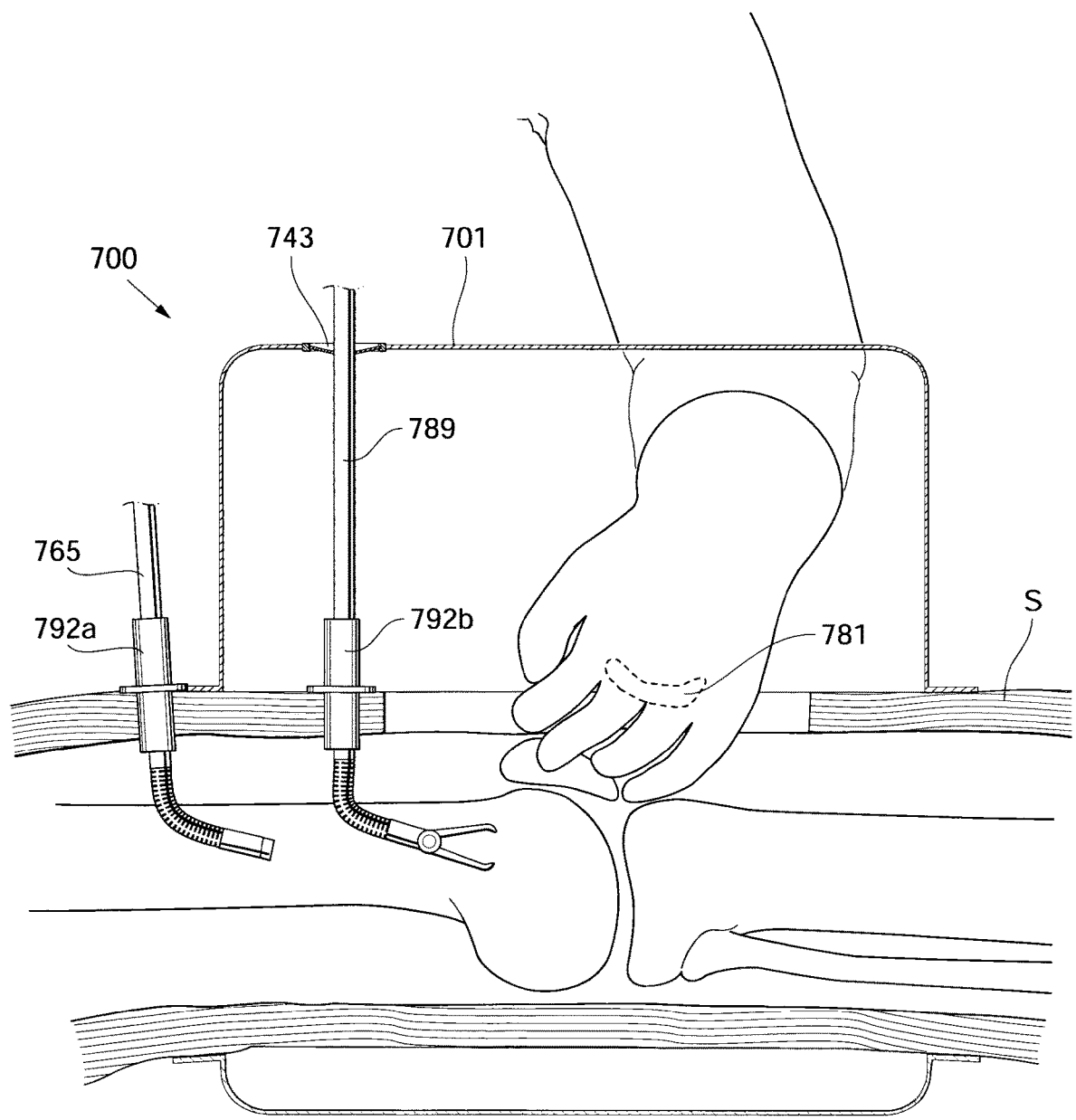

FIG. 85k shows how the medical device shown in FIGS. 75-85 may be used. The medical device 700 comprises a glove 702 integrated in the wall 701 and a camera 765 placed in the skin S outside of the medical device 700. The medical device 700 further comprises a trocar 792a; 792b placed trough an opening in the wall 701 and into the sealed environment and further through an opening in the skin S of the patient and into an area of the knee of the patient. FIG. 85k schematically illustrates how the surgeon manipulates the knee in the sealed environment using the glove 702.

Figure 85M:
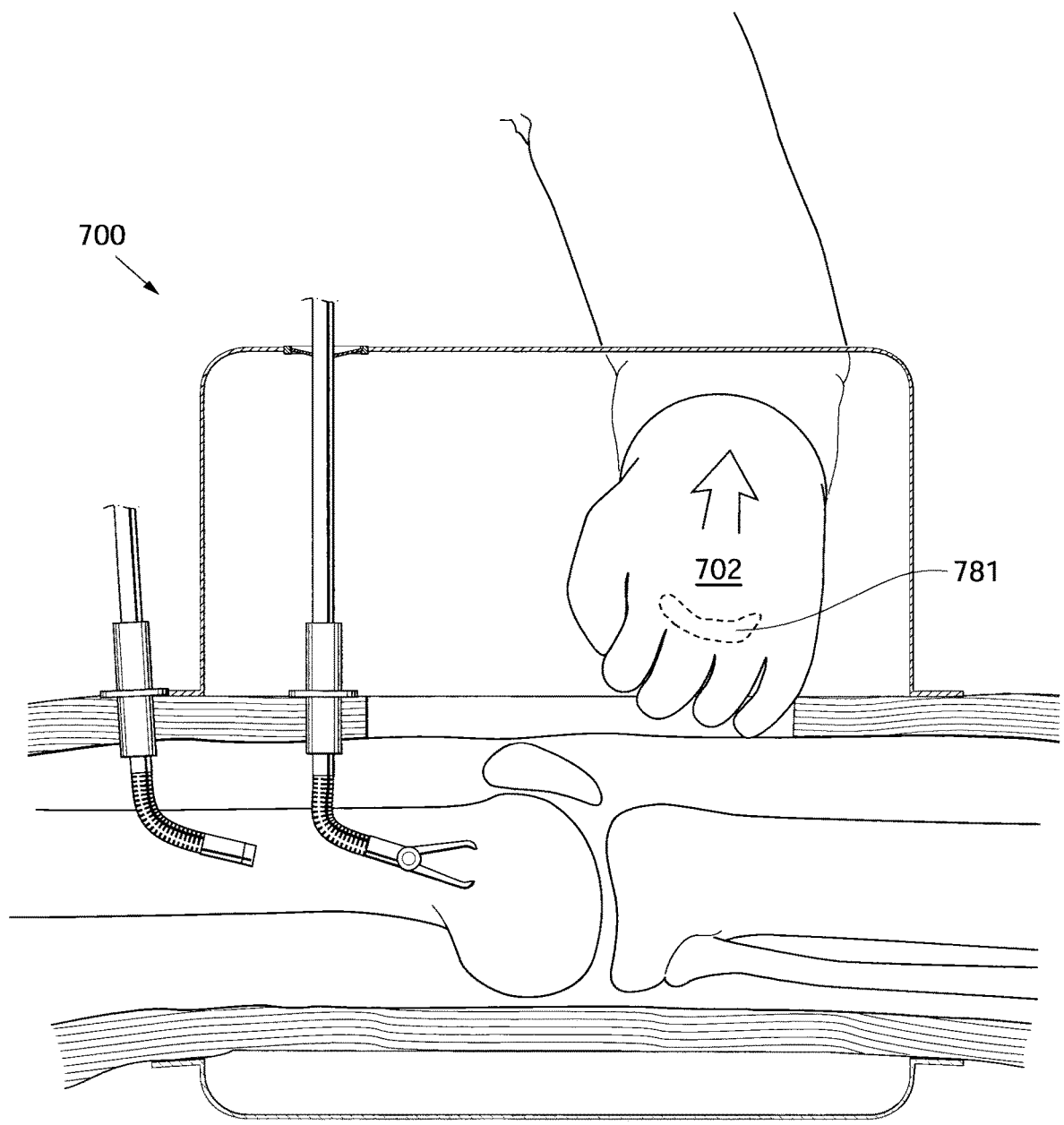
FIGS. 85m-85n shows an embodiment of the medical device in section, being fixated to the patient and used.

FIGS. 85l, 85m shows the medical device when the surgeon removes a specimen 781 from the knee of the patient using the glove 702 integrated in the wall 701 of the medical device 700.

Figure 85N:
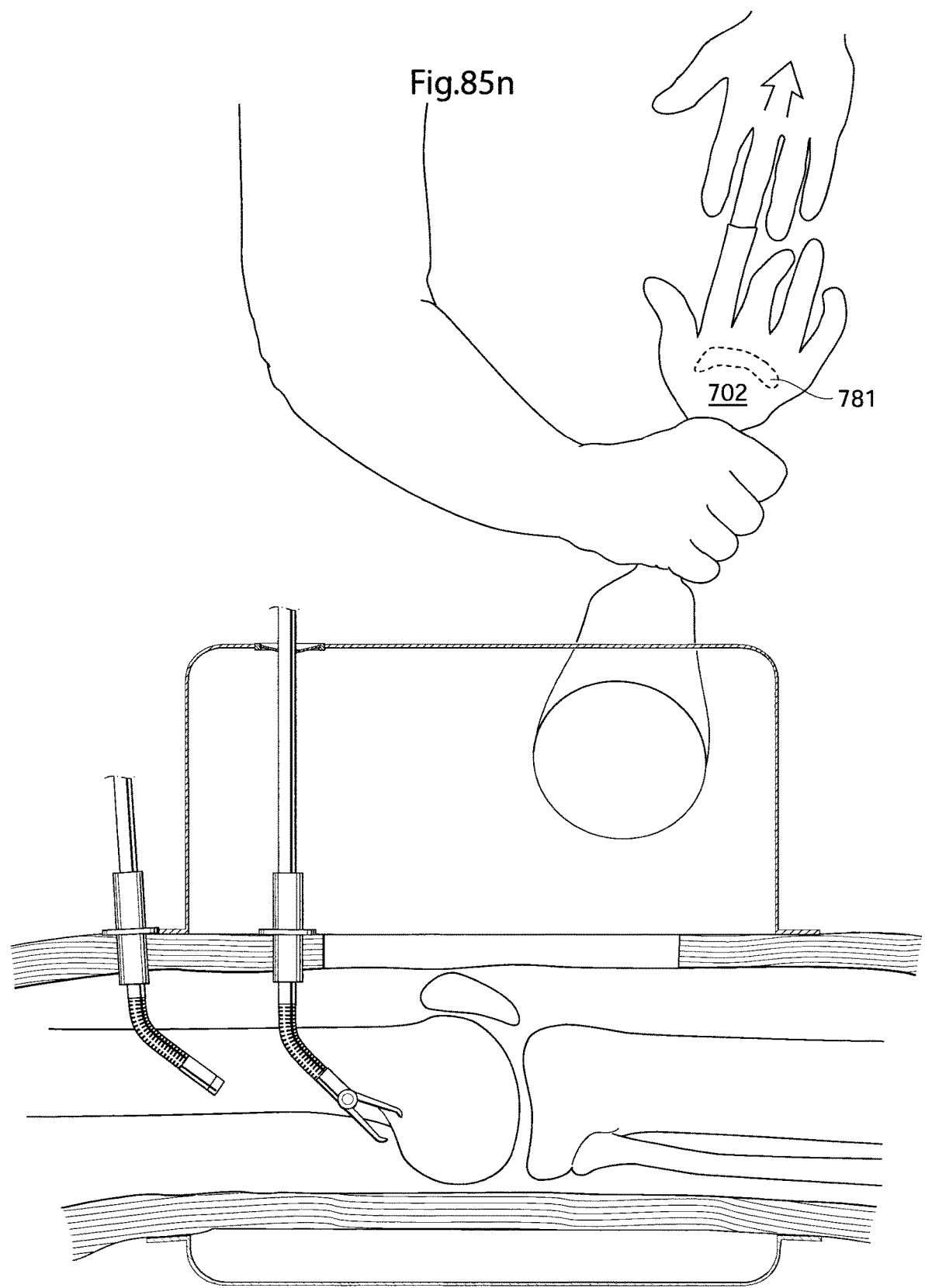

FIG. 85n shows the medical device when the surgeon has turned the integrated glove 702 inside-out such that the specimen 781 can be contained within the integrated glove 702. By isolating the specimen 781 inside of the glove 702, the specimen 781 is removed both from the rest of the body of the patient and from the ambient environment, and thereby does not risk to infect any other portion of the patient's body or medical staff with any infectious disease.

FIGS. 86-95o describes an embodiment of the medical device in which the medical device comprises an upper wall port o wall inset and a lower body port or body inset such that the chamber of the medical device can be sealed from or accessed from the ambient environment, and a cavity in the patient can be sealed from or accessed from the chamber of the medical device.

Figure 86:
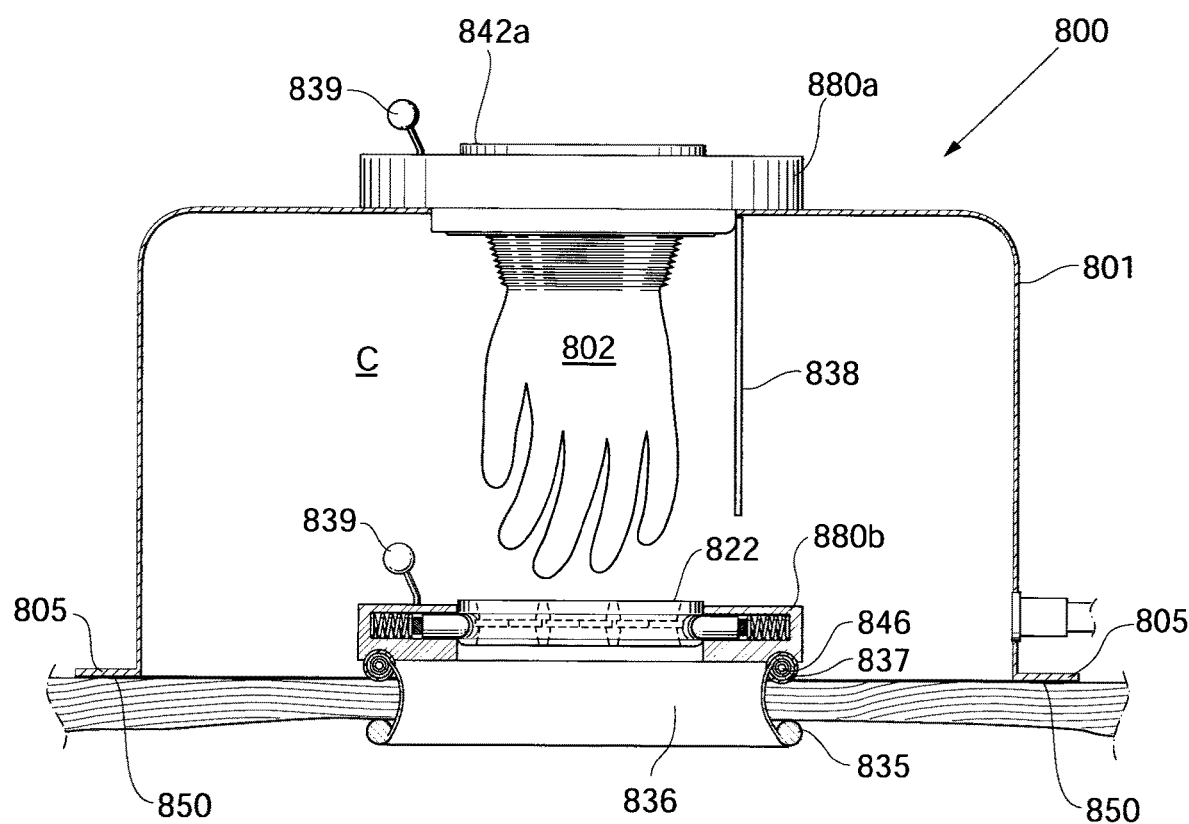
FIG. 86 shows another embodiment of the medical device, in section.

FIG. 86 shows a medical device 800 comprising a wall 801 adapted to be at least partially applied on the patient's body to form a chamber C together with the patient's body, in which a sealed environment can be maintained for encompassing part of the surgical procedure to be performed. The medical device further comprising an upper coupling 880a placed in a portion of the wall 801, an a closeable body port 822 placed in a lower coupling 880b placed in an incision in the patient's body, the medical device 800 further comprises a sealing device 805 connected to the wall 801 and adapted to seal against the skin of the patient. The sealing device disclosed in FIG. 86 is comprises an adhesive surface 850 adapted to adhere to the skin of the patient.

The upper coupling 880a, comprises a valve 838 for closing the coupling 880a when changing from a first to a second object (such as a wall port or wall inset) in the coupling 880a. According to the embodiment shown in FIG. 86, the medical device comprises a retractor comprising one intra body ring 835 adapted to be positioned on the inside of the patients skin, and one ring 837 adapted to be placed on the outside of the patients skin. Between the intra body ring 835 and the ring 837 adapted to be placed on the outside of the patients skin a retractor membrane 836 is positioned which is adapted to exert a pressure of the cut surfaces of the incision for retracting the skin and thereby keeping the wound open. The retractor membrane 836 is preferably made from a resilient of elastic polymer material. The ring 837 adapted to be placed on the outside of the patients skin comprises an integrated roll up system 846 which could be a spring loaded roll up system adapted to create a suitable pressure on retractor membrane 836 for keeping the wound open. The lower coupling 880b is fixated to the rigid part, which in some embodiments is an integral part of the wall 801 separating the sealed environment from the ambient environment. The coupling 880a comprises a releasing lever 839 for releasing the object centered therein. The lever 839 is connected to protruding latching members 833 which are spring loaded 832 from the rear in order to secure the recess or groove 834 of the port of the object. In other embodiments, the medical device 800 could be provided with a retractor 836 of a different design, or none at all.

Figure 87:
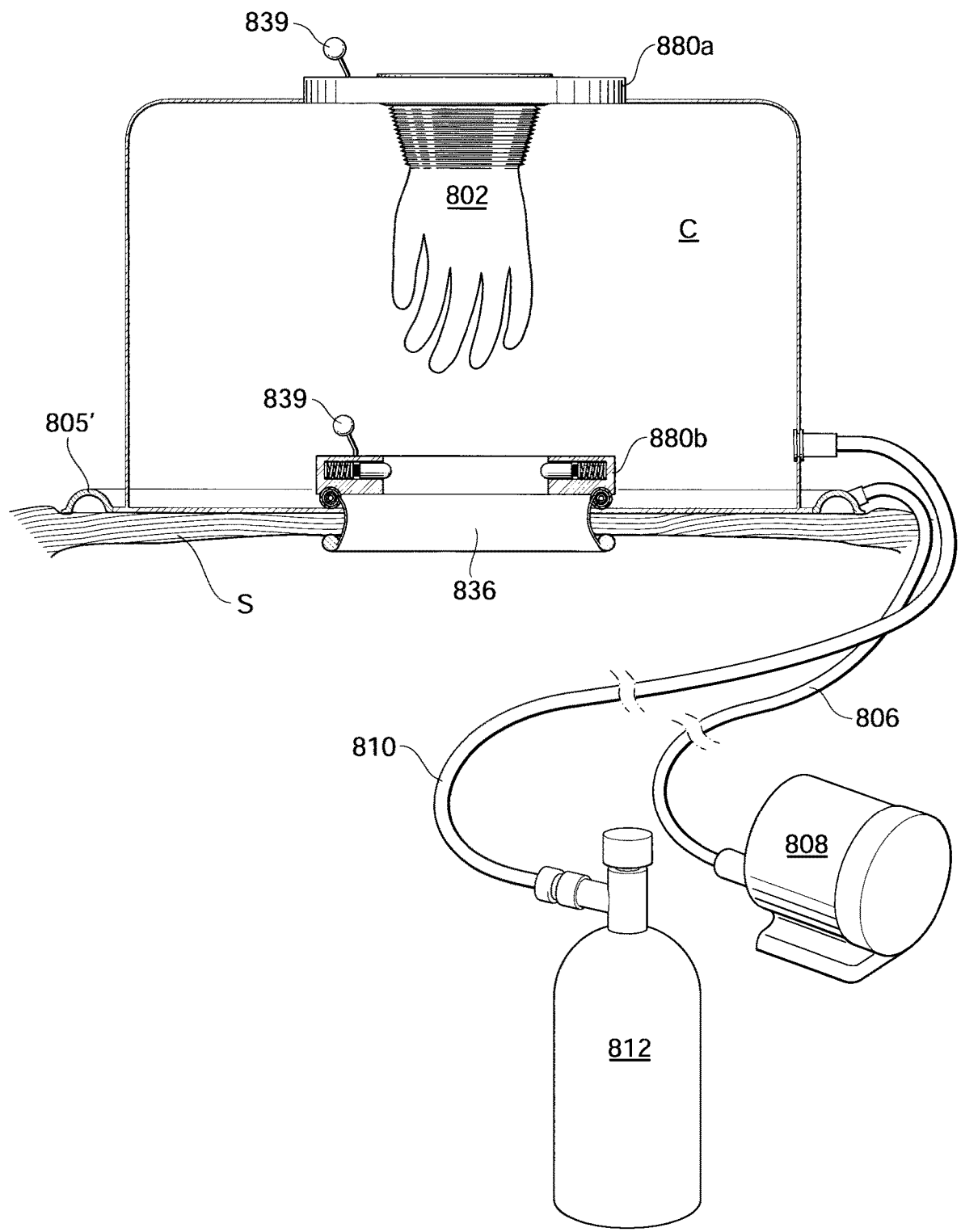
FIGS. 87, 88a, 88b, 89 and 90 shows an embodiment of the medical device comprising a vacuum sealing and a coupling to which objects could be connected.

FIG. 87 shows the medical device 800 as shown in FIG. 86, when fixated to the skin of the patient by means of a vacuum sealing member 805' connected to a vacuum pump 808 via a vacuum conduit 806. The vacuum sealing member 805' is adapted to seal between the medical device and the skin S of the patient by means of the vacuum sealing member 805' holding a pressure below atmospheric pressure. The sealed environment is here adapted to hold a pressure exceeding atmospheric pressure and is adapted to be inflated through a fluid conduit 810 connected to a pressure source, here being a pressure tank 812. The medical device is adapted to hold a pressure in the sealed environment exceeding atmospheric pressure such that the abdomen of the patient can be inflated for allowing increased visibility in the cavity thereby created. In other embodiments, the vacuum sealing member 805' could be assisted or replaced be an adhesive portion adapted to be connected to the skin S of the patient.

Figure 88A:
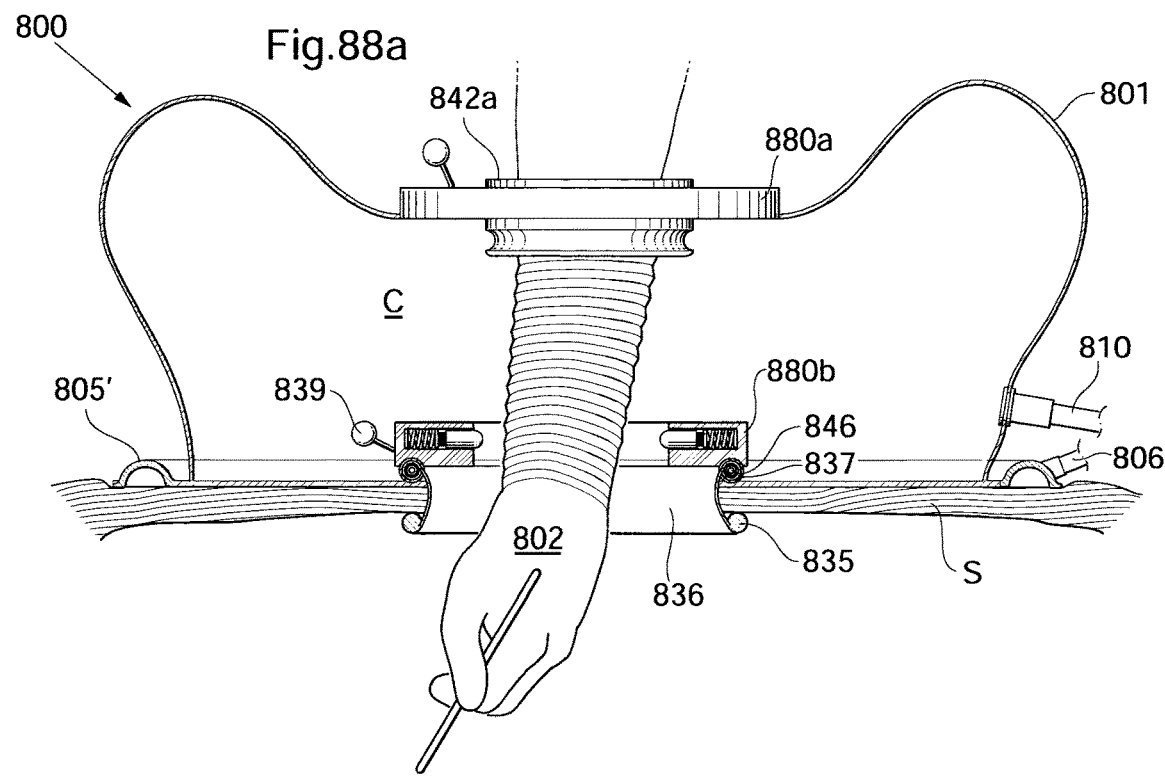
Figure 88B:
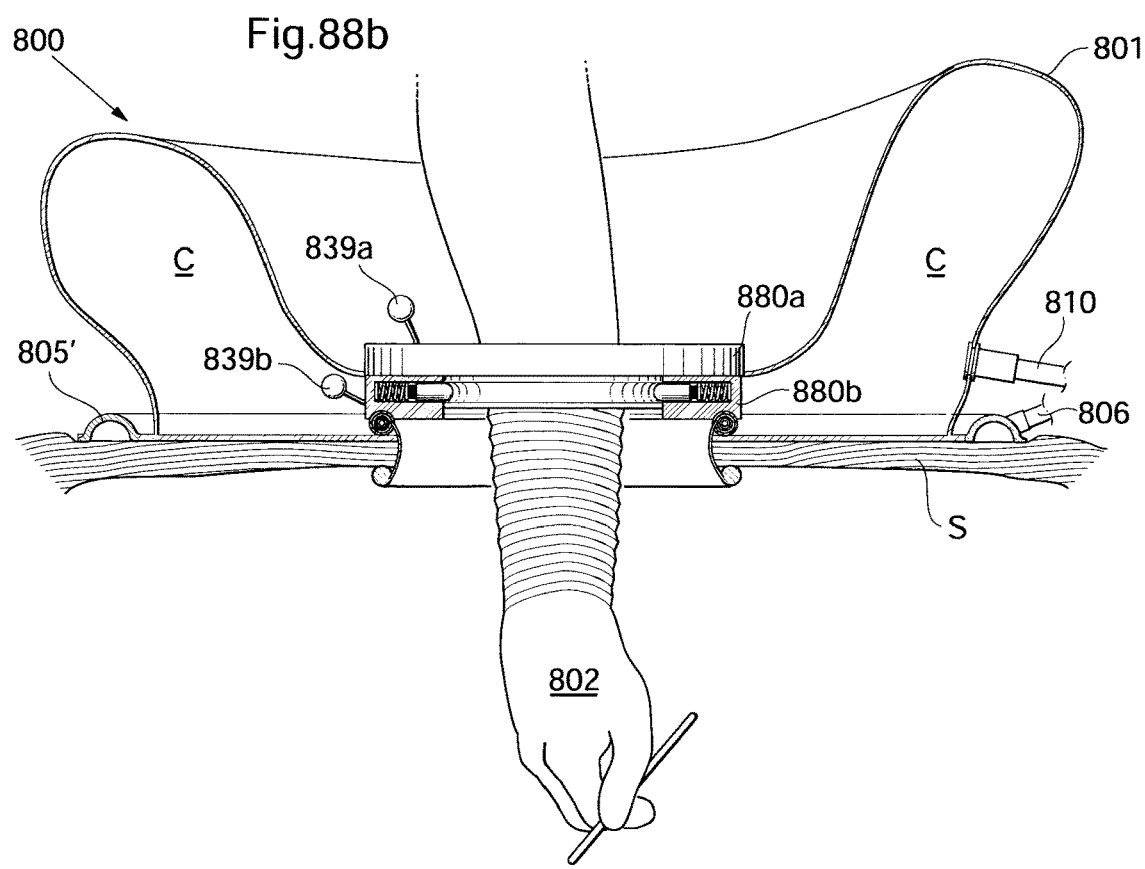

FIG. 88a shows the medical device 800 in an embodiment where the upper coupling 880a in the medical device 800 can be in a first and second position, the second position is disclosed in FIG. 88a, while the first position is located closer to the skin of the patient and disclosed in FIG. 88b. The medical device could for example be used in surgical procedures where transitions between open and laparoscopic surgery is needed. The medical device 800 could be placed in the second position such that the wall port 831a is locked to the body port 831b for enabling a larger freedom of motion for the surgeon within the chamber C of the medical device 800, while the first position could enable the use of a laparoscopic trocar or hand access for further reach within the body of the patient. The medical device could further be used in embodiments where manual manipulation in a sealed environment is required, e.g. for preparing a medical device 800 for use in the surgical procedure. Other applications could for example be that the surgeon wishes to remove a specimen form the body of the patient after a laparoscopic procedure has been concluded. The laparoscopic procedure could in these instances be performed with the medical device 800 being in the first position (as shown in FIG. 88b), being close to the skin S of the patient, whereafter the medical device 800 could be placed in the second position for enabling the specimen to be removed from the body of the patient and placed in the chamber C of the medical device 800 without contacting the ambient environment, and without the release of the pressure that usually fills the abdomen in laparoscopic procedures. According to the embodiment shown in FIGS. 88-90, the wall 801 is collapsible such as to enable the transferring between the first and second position. The lower coupling 880b comprises a lever 839 for releasing and/or locking upper coupling 880a to the lower coupling 880b. The medical device 800 is according to the embodiment shown in FIG. 88a fixated to the patient by means of a vacuum sealing member 805, such as for example disclosed with reference to FIGS. 66 and 67.

FIG. 88b shows the medical device 800 when locked in the first position, i.e. the upper coupling 880a is locked to the lower coupling 880b. The integrated surgical glove 802 now enables manual manipulation with great freedom within the body of the patient. The medical device comprises two levers 839a and 839b, wherein the first lever 839a is connected to the upper coupling 880a and adapted to lock an inset 842 or port (here being a wall inset 842a comprising a surgical glove 802) to the upper coupling 880a, while the second lever 839b is connected to the lower coupling 880b for locking the upper coupling 880a to the lower coupling 880b. The medical device 800 is according to the embodiments shown in FIGS. 88-90 circular when seen from above, such that the medical device 800 takes the shape of a doughnut when placed in the first position.

Figure 89:
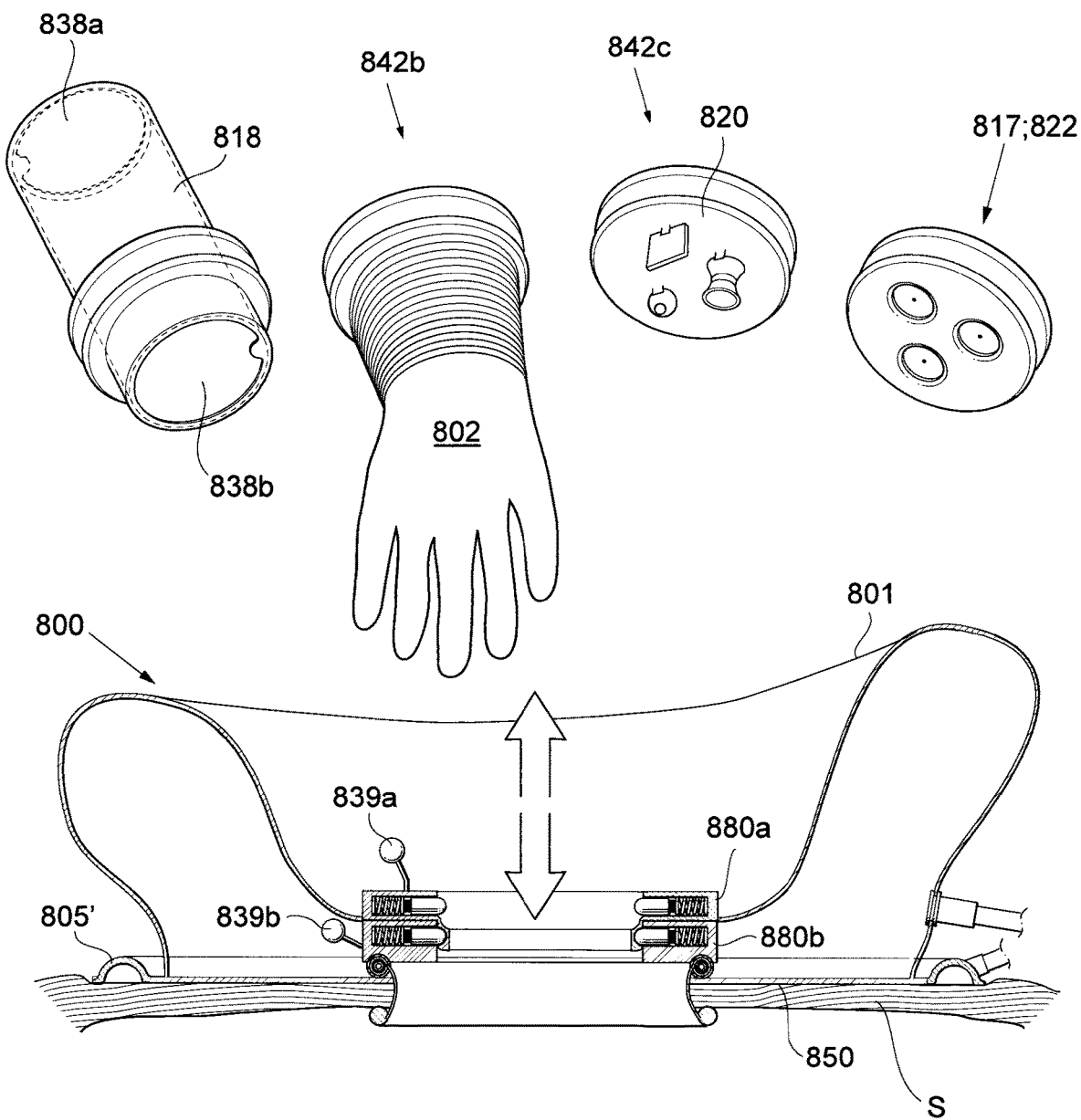

FIG. 89 shows the medical device 800 when locked in the first position, i.e. the upper coupling 880a is locked to the lower coupling 880b. The integrated surgical glove 802 disclosed with reference to the embodiments shown in FIGS. 86-88b could be exchanged by a plurality of different objects of which examples are shown in FIG. 89. FIG. 89 shows an airlock 818 comprising a first valve member 838a separating the airlock 818 from the ambient environment, and a second valve 838b separating the airlock 818 from the sealed environment of the chamber C. The airlock 818 is provided between the first 838a and second 838b valve and could for example be used for passing a medical device 800 into the sealed environment, or for passing a specimen or sample out of the sealed environment. FIG. 89 further shows an inset 842c comprising a device or instrument mount 820 which for example could be adapted to hold surgical instruments and/or parts of an implant. The insets could alternatively be exchanged for an endoscopic wall or body port (which could depend on the positioning of the upper coupling 880a), the port may be a multi-port 848 comprising a plurality of endoscopic ports. The medical device 800 is according to this embodiment adapted to be fixated to the skin S of the patient by a large portion of the medical device 800 comprising an adhesive surface 850, and by means of the vacuum sealing member 805'.

Figure 90:
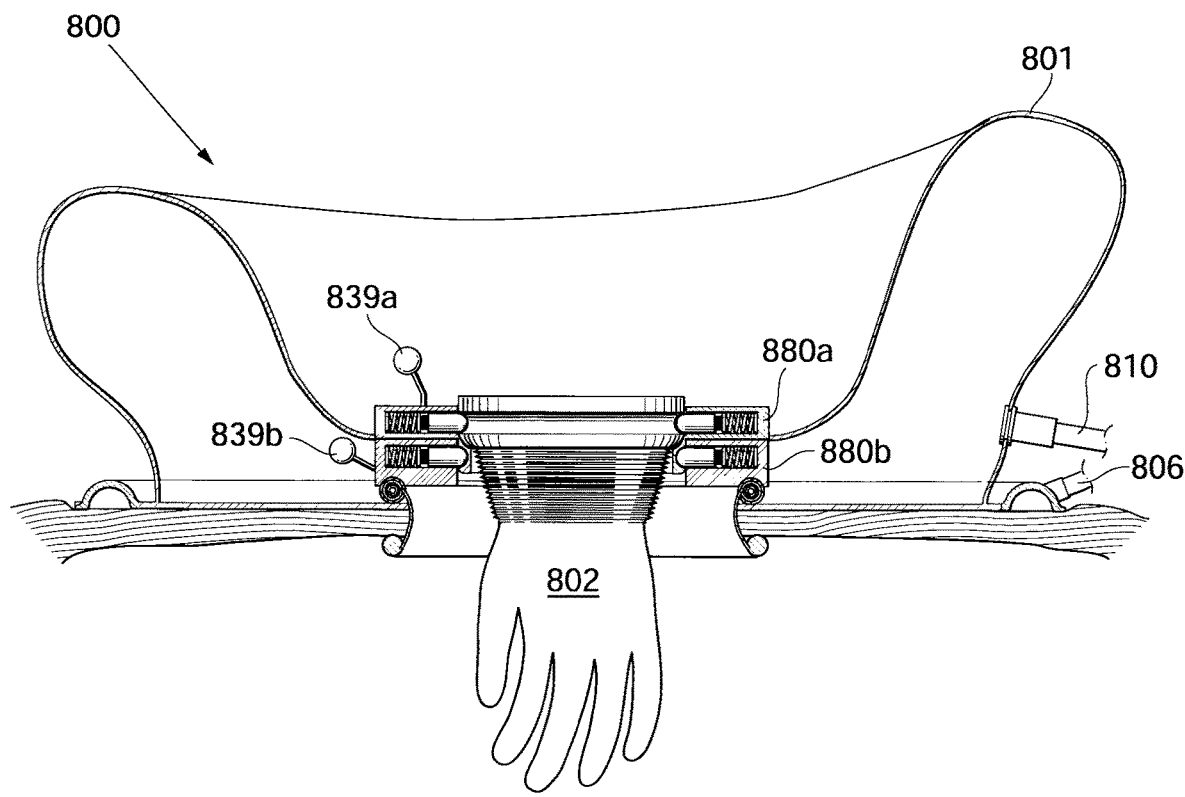

FIG. 90 shows the medical device 800 further disclosed with reference to FIGS. 86-89 when in its first position with the upper coupling of the wall port 831a locked to the lower coupling of the body port 831b. The medical device 800 comprises two levers 839a and 839b, where the first lever 839a in this case locks the inset 842a comprising the surgical glove 802 to the upper coupling 880a, and the upper coupling 880a to the lower coupling 880b.

FIG. 91 shows the medical device according to an embodiment in which the medical device comprises an retractor member 879, placed in the skin of the patient for maintaining a hole 897' forming a fluid connection between the chamber and a cavity in the patient's body enabling the passing from the sealed environment of the medical device 800 to a cavity in the body of the patient. The hole 897' enables a pressure being larger than the atmospheric pressure to be present in the in both the cavity of the patient and in the sealed environment of the chamber of the medical device 800, which enables a semi-laparoscopic procedure to be performed both using traditional trocars and by means of hand access through the use of the medical device 800. The retractor member 879 could be an incision retractor disclosed herein (for example in FIG. 92a-92c), or could be a different retractor including traditional retractors hooks. For manual manipulation within the medical device and/or the body of the patient, a wall inset 842a comprising a surgical glove 802 is attached to the wall 801 of the medical device 800, by means of an upper coupling 880a comprising a releasing lever 839, both further described throughout the application.

Figure 92A:
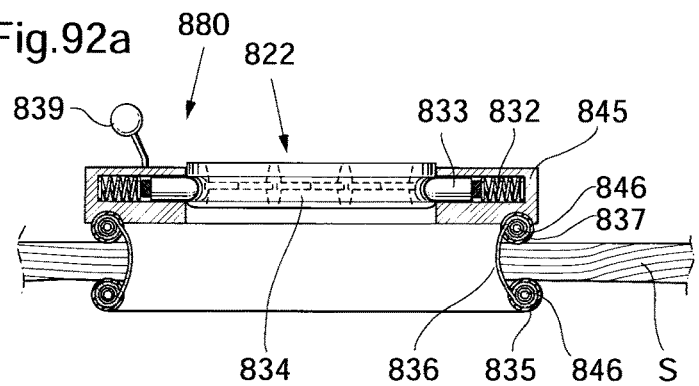
FIGS. 92a, 92b and 92c shows a coupling in section.

FIG. 92a shows an embodiment of a detachable body port 822 which could be fixated to the lower coupling 880b positioned in the medical device 800 disclosed with reference to FIGS. 86-91. The port arrangement of FIG. 92a includes an intra body ring 835 adapted to be placed at the inside of the patients skin S around an incision, and an outer ring 837 adapted to be placed on the outside of the patients skin S around the incision. Between the intra body ring 835 and outer ring 837 an annular retractor membrane 836 is positioned adapted to exert a pressure on the skin S or tissue at the incision to seal between the rings 835; 837 and the skin S or tissue and additionally for retracting the skin and thereby keeping the incision open. The retractor membrane 836 is preferably made from a resilient or elastic polymer material. The outer ring 837 comprises an integrated roll up system 846, which may be spring loaded and adapted to create a suitable pressure on retractor membrane 836 to keep the incision open.

The port arrangement shown in FIG. 92a also includes a coupling having a rigid annular seating 845 attached to the outer ring 837, spring loaded protruding latching members 833 arranged in radial bores in the seating 845 and a hand lever 839 connected to the protruding latching members 833 to enable retraction thereof against the action of springs 832.

The port arrangement further includes a self sealing body port 822 held by the coupling 880. The body port 822 comprises a disc-shaped self sealing membrane 843, FIG. 92*b*, fixated to a rigid ring having an outer circumferential groove 834 that receives the latching members 833 of the coupling 880. The self sealing membrane 843 has a small self sealing hole 844, FIG. 92*b*, centrally in the membrane 843. For example, the self sealing membrane 843 may be made from a gel-type material being elastic enough to enable a deformation large enough for a person's hand to pass through the small self sealing hole 844 while still contracting enough to create an airtight seal between the chamber and the ambient environment.

The coupling 880 described above enables quick exchange of the body port 822. Thus, the surgeon may release the body port 822 from the port arrangement by simply pulling the hand lever 839 so that the latching members 833 disengage from the recess or groove 834 of the body port 822, whereby the body port 822 can be removed.

Figure 92B:
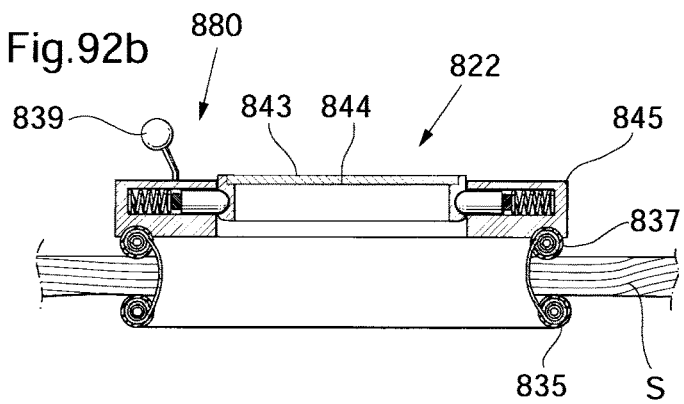

FIG. 92*b* is a cross-sectional view of the port arrangement shown in FIG. 92*a*, to more clearly illustrate the body port 822 with its self sealing membrane 843 and small hole 844.

Figure 92C:
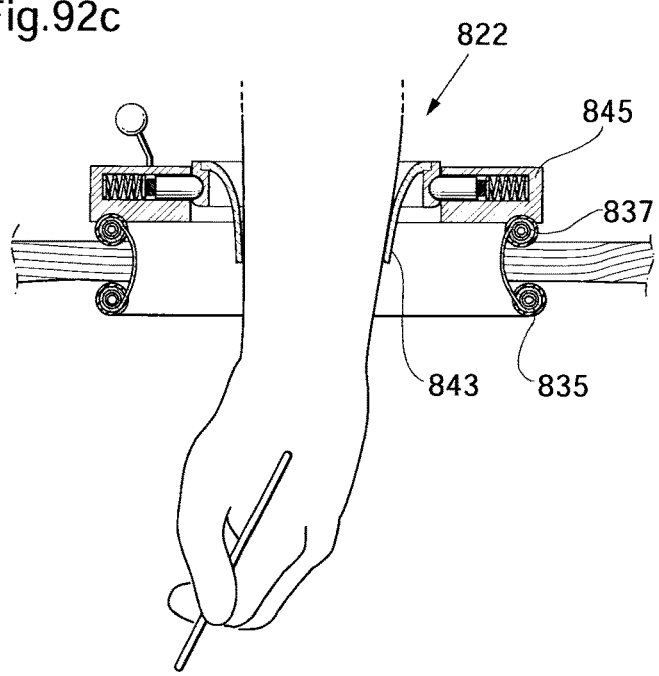

FIG. 92*c* shows the self sealing body port 822 when the hand of a surgeon is placed through the hole 844 in the membrane 843 and thus enabling manual manipulation within the body of the patient.

Figure 93A:
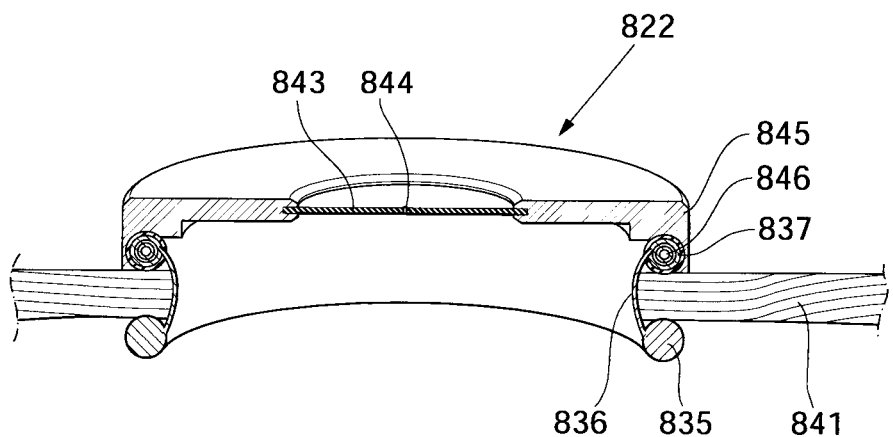
FIGS. 93a and 93b shows two different embodiments of a self sealing port.
Figure 93B:
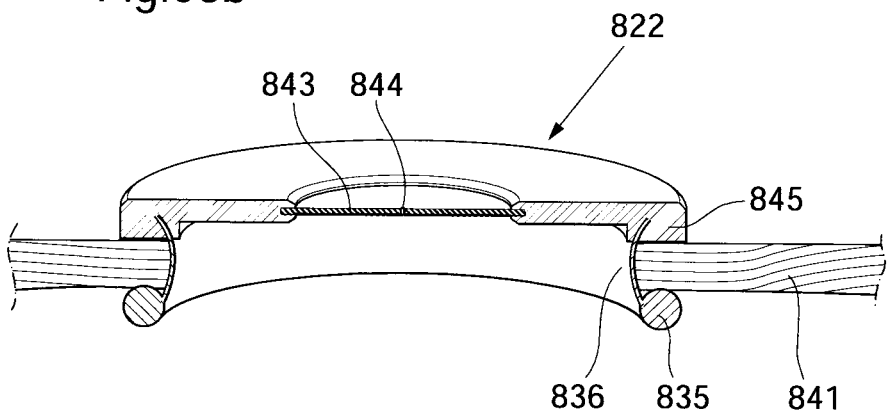

FIG. 93*a* shows a self sealing body port 822 in a close-up, in section. The self sealing body port 822 could be connected to the coupling 880, for example as disclosed with reference to FIGS. 92*a*-*c*, which in turn is connected to any of the medical device disclosed with reference to FIGS. 86-91, or the self sealing body port 822 could be fixated to a retractor, as shown in FIGS. 93*a* and 93*b*. The self sealing body port 822 comprises a self sealing membrane 843 fixated to a rigid part 845 of the self sealing port. The self sealing membrane 843 having a small self sealing hole 844 centrally in the membrane 843. The self sealing membrane 843 is for example made from a gel-type material being elastic enough to enable a deformation large enough for a person's hand to pass through the small self sealing hole 844 while still contracting enough to create an airtight seal between the sealed environment and the ambient environment. The medical device being fixable to a retractor comprising one intra body ring 835 adapted to be positioned on the inside of the patients skin, and one ring 837 adapted to be placed on the outside of the patients skin. Between the intra body ring 835 and the ring 837 adapted to be placed on the outside of the patients skin S a retractor membrane 836 is positioned which is adapted to exert a pressure of the cut surfaces of the incision for retracting the skin S and thereby keeping the wound open. The retractor membrane 836 is preferably made from a resilient of elastic polymer material. The ring adapted to be placed on the outside of the patients skin S comprises an integrated roll up system 846 which could be a spring loaded roll up system adapted to create a suitable pressure on retractor membrane 836 for keeping the incision open.

FIG. 93*b* shows an alternative embodiment of the self sealing body port 822, with the difference that the retractor membrane 836 is made from a material elastic enough such that one end of the retractor membrane 836 could be fixedly fixated to the rigid part 845 of the port.

Figure 94:
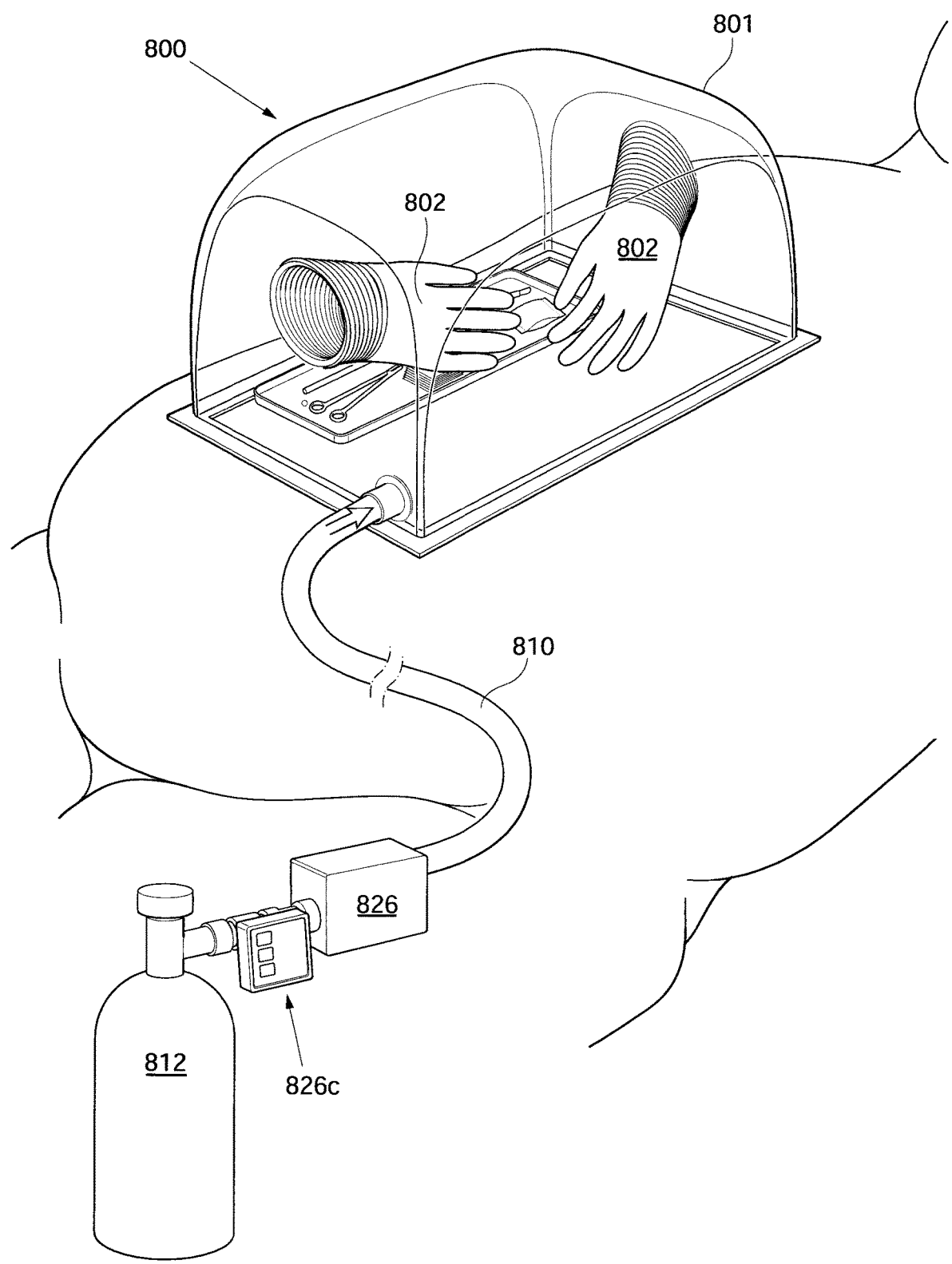
FIG. 94 shows another embodiment of the medical device, when fixated to the skin of the patient.

FIG. 94 shows the medical device as shown in FIGS. 86-90 with the addition that the embodiment comprises a sterilizing unit 826 adapted to sterilize the gaseous fluid entering the medical device 800. In the embodiment disclosed herein, the gaseous fluid entering the medical device 800 originates from a pressurized tank 812 and could be pre-sterilized, however, in other embodiments, it is conceivable that the gaseous fluid is the surrounding air which is pressurized (such as further disclosed with reference to FIG. 95). In the embodiments where the surrounding air is used to inflate the medical device 800 and constitute the operating environment this air needs to be properly sterilized. The medical device 800 further comprises a tempering unit 826*c* which could be provided to heat or cool the gaseous fluid inflating the medical device 800. In cases when the ambient environment is cold the tempering unit 826*c* could be used to raise the temperature of the sealed environment to provide beneficial operating circumstances both for the patient and for the surgeon. In cases when the surrounding environment is hot, the tempering part of the system 826*c* could be used to lower the temperature of the sealed environment both to provide beneficial operating circumstances, both for the patient and for the surgeon, and for providing a temperature inhibiting bacterial and viral infections. The tempering unit 826*c* could comprise a temperature regulating device for setting the required temperature.

Figure 95A:
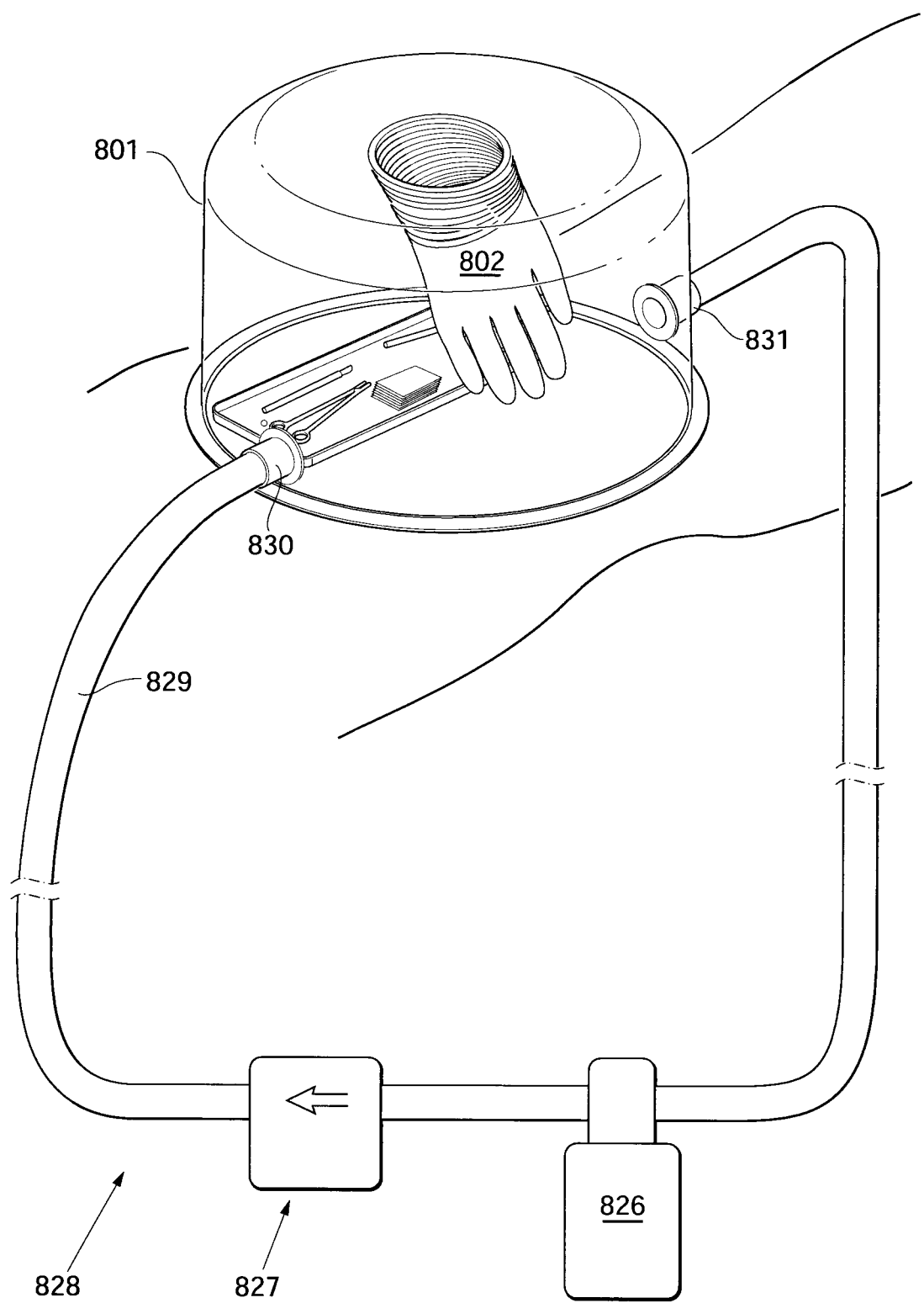
FIG. 95a shows yet another embodiment of the medical device comprising a fluid circulating system.

FIG. 95*a* shows a medical device similar to the embodiment disclosed in FIG. 94 but comprising a system 828 for circulating a fluid through the chamber of the medical device. The system 828 comprises a fluid conduit 829 connected at an inlet 830 placed in the wall 801 for supplying fluid to the chamber, and an outlet 831 for draining the fluid from the chamber. The fluid is circled by means of a pumping unit 827 and is circled via a sterilizing/filtering unit 826 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 95B:
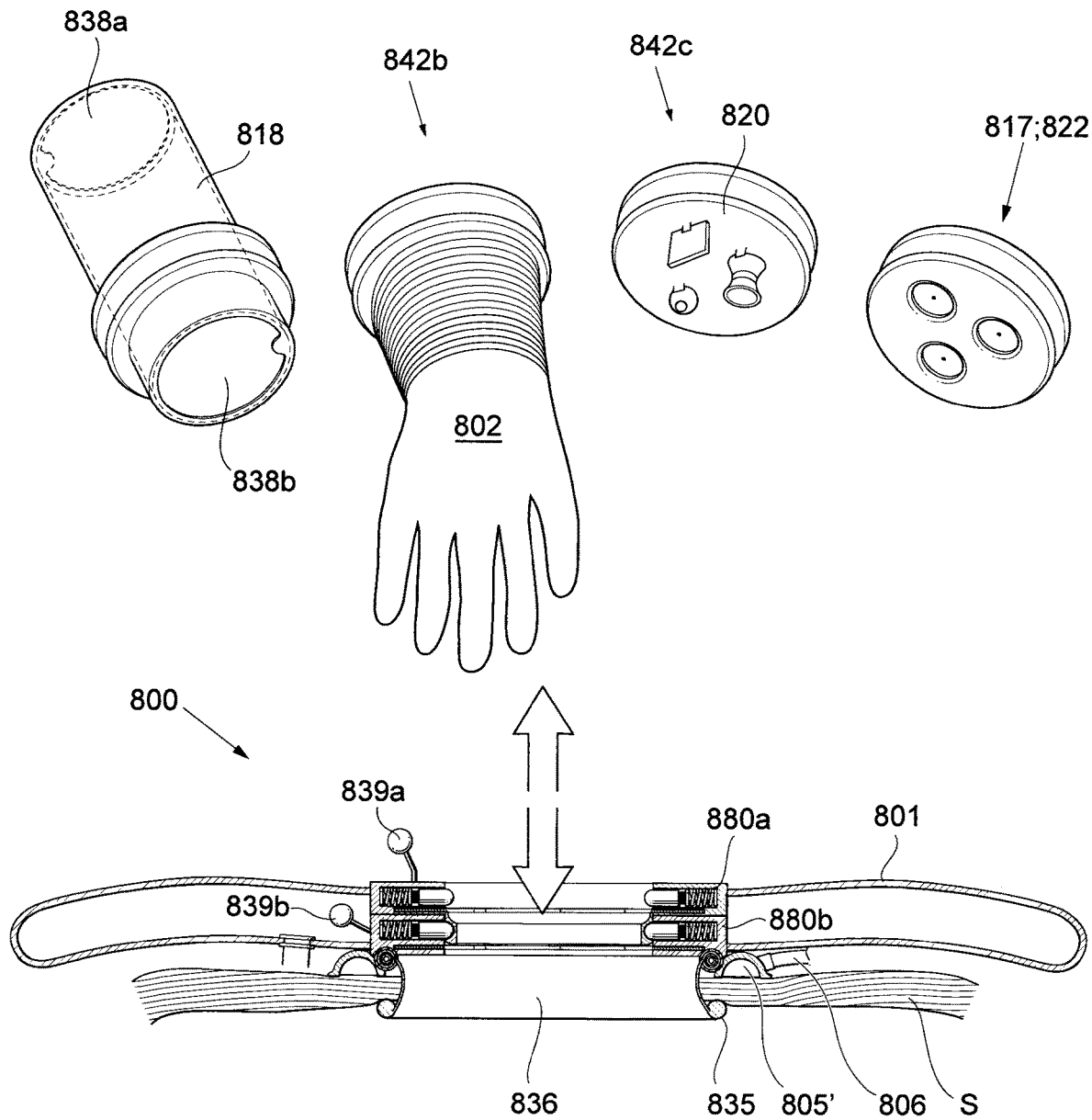
FIGS. 95b-95c shows an embodiment of the medical device, in sectional view.

FIG. 95*b* shows an alternative of the embodiment shown in FIGS. 86-95. Fig. In 95*b* the medical device 800 is adapted to be at least partially placed in an incision cut in a patient's body. The medical device 800 comprises an upper coupling 880*a* and a lower coupling 880*b* adapted be interconnected to form an integrated coupling. The upper coupling 880*a* is adapted to be disconnected from the lower coupling 880*b*. The upper and lower couplings are connected to portions of the flexible wall 801. The flexible wall 801 forms a chamber C in which a sealed environment can be maintained, the chamber C is heavily enlarged when the upper coupling 880*a* is disengaged from the lower coupling 880*b*, thus creating operating space within the chamber C enclosed by the wall 801. The couplings 880*a*; 880*b* comprises a latching system for locking an inset 842*b*;*c* in the coupling. The inset may for example be a glove 802 for manual manipulation within the body of the patient, or within the sealed chamber, or an inset 842*c* comprising a device or instrument mount 820 for holding instruments or medical devices within the chamber. Alternatively the insets 842*b*; 842*c* can be replaced by an airlock sluice 818 with a first 838*a* and second 838*b* valve member or a port 817; 822, which could comprise a multiport comprising a plurality of ports enabling the insertion of a surgical instrument into the chamber or body of the patient.

In the embodiment shown in FIG. 95*b* the medical device is fixated to the body of the patient by means of a vacuum fixating member 805' connected to a conduit 806, which in turn is connected to a vacuum source. As in other embodiments disclosed herein, it is equally conceivable that the wall is connected to the vacuum fixating member 805' instead of being fixated to the lower coupling 880*b*.

Furthermore, the medical device in FIG. 95*b* comprises a second sealing device having a first sealing member 835 adapted to be positioned at the inside of the patient's skin S around an incision to be performed in the skin S and a second sealing member 837 adapted to be positioned at the outside of the patient's skin S around the incision, and a spring-loaded or elastic connecting member 836 sealingly interconnecting the first 835 and second 837 sealing members. The spring-loaded or elastic connecting member 836 seals between at least one of the lower coupling 880*b* and the skin S of the patient, and the first sealing member and tissue of the patient.

Figure 95C:
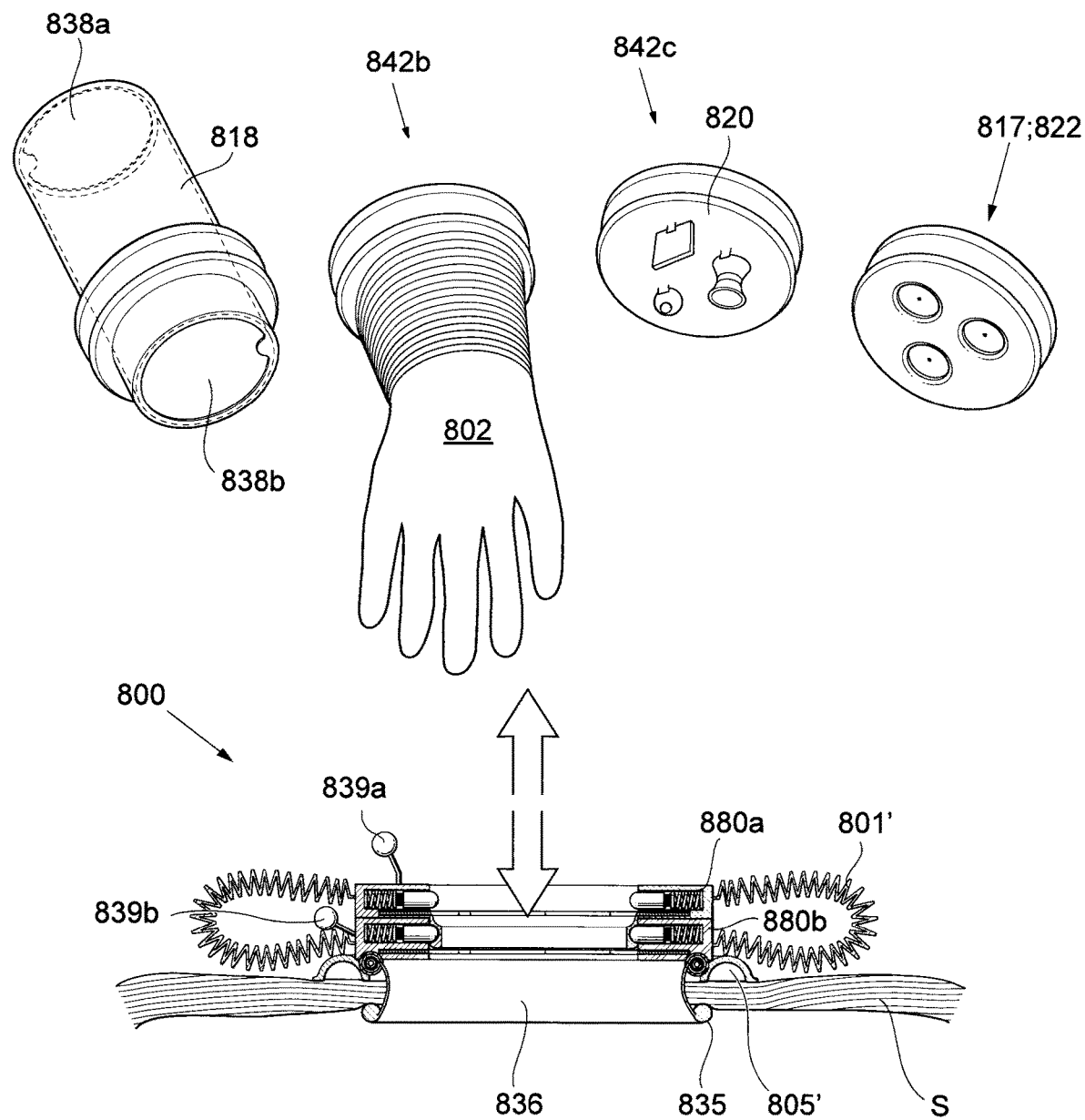

FIG. 95*c* shows the port in an embodiment very similar to the embodiment shown in FIG. 95*b* but with the difference that the wall 801' has a bellows structure and thus taking up less space when in its deflated state. The bellows structure 801' enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

FIG. 95*d*-95*i* shows a feature which could be implemented in the embodiments disclosed with reference to FIGS. 86-95. In the embodiment of FIGS. 95*d*-95*i*, the wall of the medical device is inflatable, and the medical device 800 is in its inflated state. When the chamber C is deflated it has a first volume i.e. when the body port 831*b* and wall port 831*a* are interconnected, and when the chamber C is inflated and the wall port 831*a* is disconnected from the body port 831*b* it has a second volume, and the second volume is larger than the first volume. According to the embodiment shown in FIG. 95*d*, the second volume is larger than 500 000 mm3 and adapted to hold a pressure exceeding atmospheric pressure.

According to the embodiment shown in FIG. 95*d*-95*i* the chamber C further comprises a pouch 882 for holding a specimen 881 removed from within the body of the patient not to contaminate any other part of the body and create the possibility of delaying the removal of the specimen 881 until the procedure is concluded. The pouch may be a pouch 882 which could be closed for creating a pouch-chamber within the chamber C for isolating the removed specimen 881 within the chamber C.

In FIG. 95*d*, a state is illustrated in which the cut in the patient's skin is being created by the surgeon by means of a glove inset 802 latched to the upper coupling 880*a*. The medical device is fixated and sealed by means of the vacuum sealing member 805' since the sealing device that is provided partially within the patient's body cannot be mounted until the cut in the patient's skin S is concluded. The two different sealing device disclosed could in some embodiments be replaced by only one of the sealing devices, or by a different sealing device, such as the adhesive of pressure sealing device disclosed in other portions herein.

FIG. 95*e* shows the medical device, when the second sealing 835, 836, 837 have been placed in the incision I cut in the patient's skin S. The wall 801 enclosing the chamber C is elastic or flexible which enables the surgeon move the upper coupling 880*a* in relation to the lower coupling 880*b* for getting better access to different angles within the patient's body, for example for removing a specimen 881. The embodiment of FIG. 95*e* further comprises an iris valve 886 placed in the lower coupling 880*b* for closing the coupling 880*b* such that the chamber C is sealed from at least one of the ambient environment and a cavity in the patient. The closing of the iris valve 886 enables activity within the chamber C without maintaining a pressure in the chamber C, at the same time as a pressure and/or sealed environment can be maintained within the body of the patient.

Figure 95F:
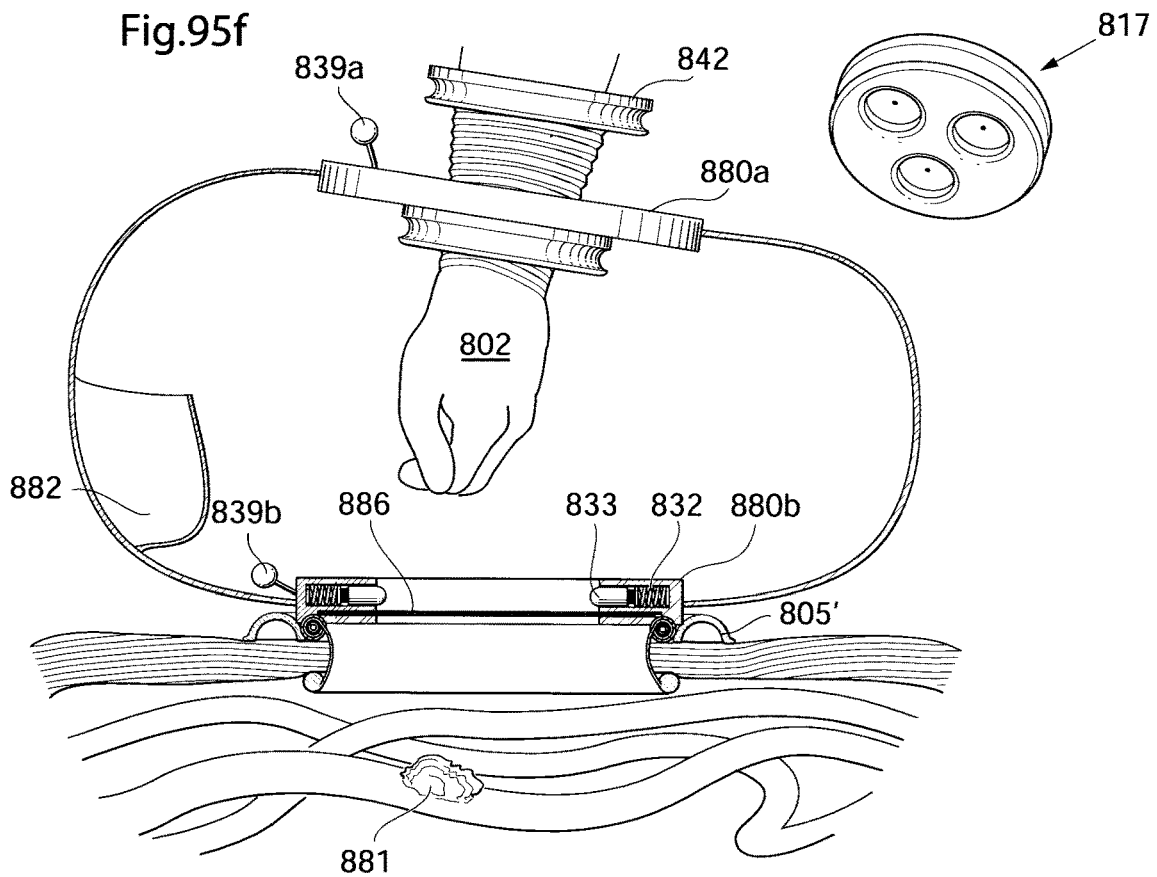

FIG. 95*f* shows the medical device when an inset 842 comprising a glove 802 is removed and replaced by a wall port 817 in the form of a multiport. The multiport may be used for manipulating objects within the chamber C of the inflated medical device using surgical instruments, or within the body of the human patient, when the wall port and body port are connected (as shown in FIG. 95*g*).

Figure 95G:
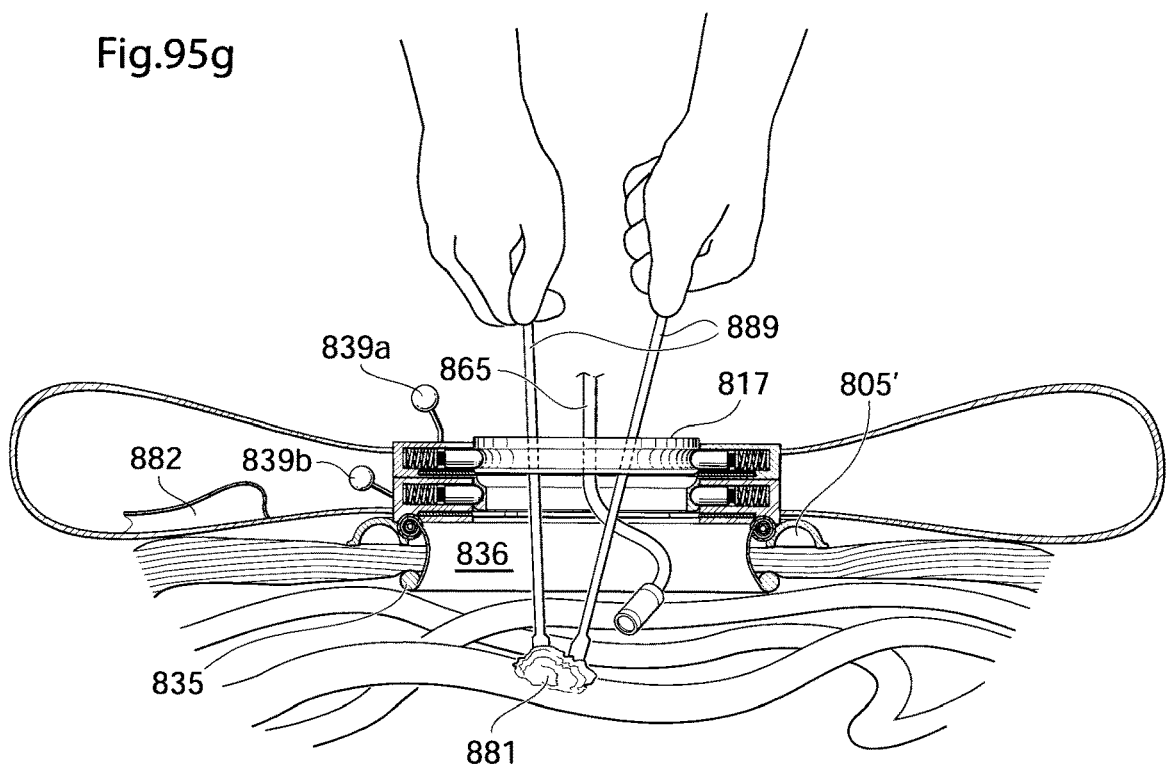

FIG. 95*g* shows the medical device when the upper coupling 880*a* and lower coupling 880*b* are connected such that surgical instruments 889 can be used for manipulating within the body of the patient. An endoscopic camera 865 may be provided in the port for enabling visual inspection of the cavity within the patient's body. The process of cutting away a specimen 881 from the intestines of a patient in a laparoscopic way is shown in FIG. 95*g*.

Figure 95H:
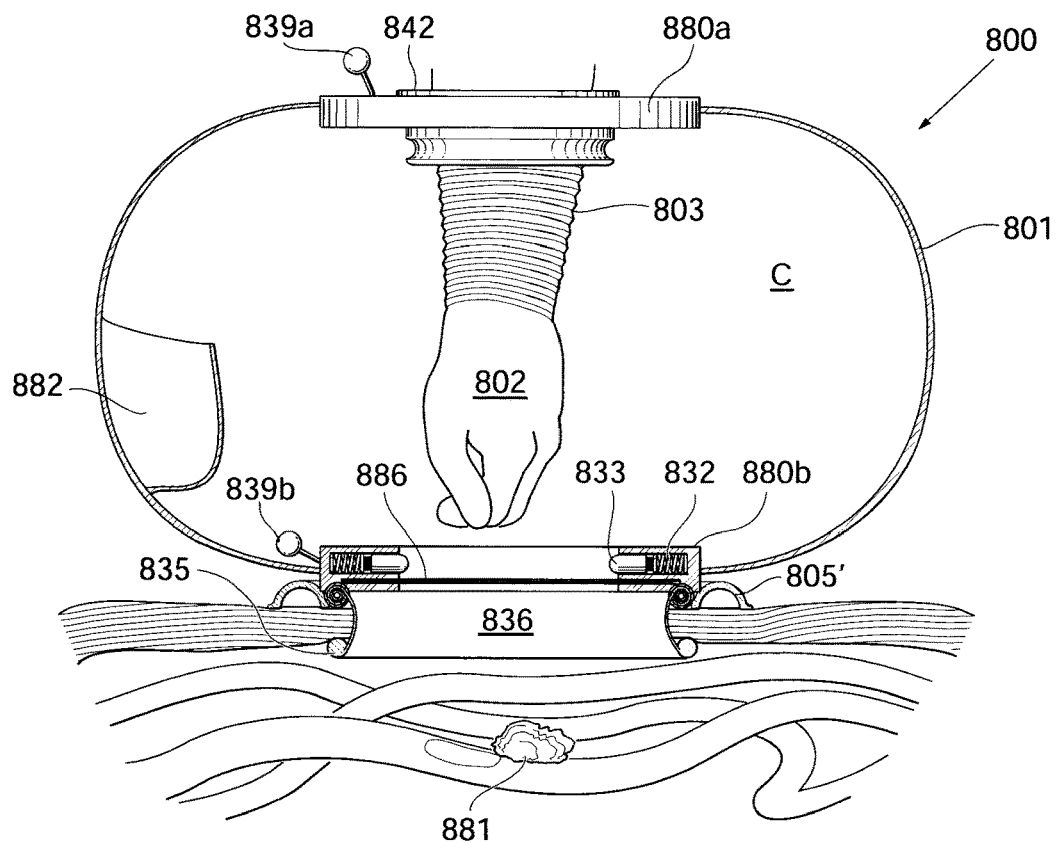

In FIG. 95*h*, the inset 842 comprising the glove 802 has been fixated to the upper coupling 880*a* to enable the surgeon to operate within the cavity of the patient's body and within the chamber C enclosed by the wall 801 of the medical device. By the glove inset 802 comprising a pleated portion 803, the surgeon is able to reach into the cavity of the patient for removing the specimen 881 cut loose from the intestines in prior steps.

Figure 95I:
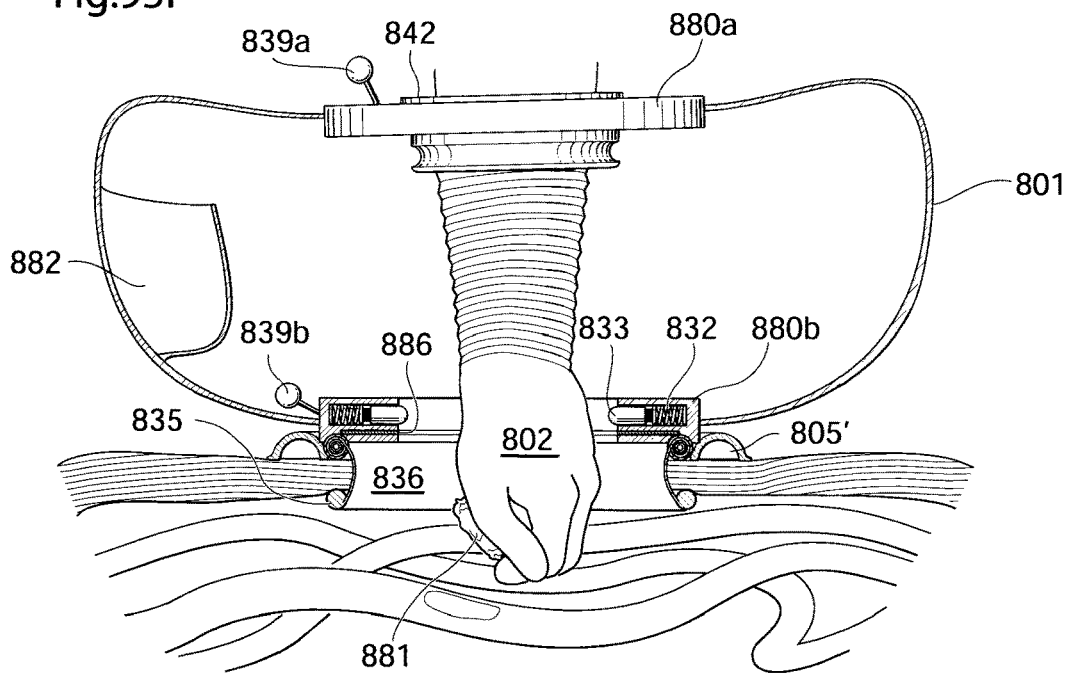

FIG. 95*i* shows that the wall 801 of the medical device is collapsible such that the inset 842 comprising the glove 802 can be moved with relation to the lower coupling 880*b*, which gives the surgeon further freedom when removing the loose specimen 881 from the intestines of the patient.

Figure 95J:
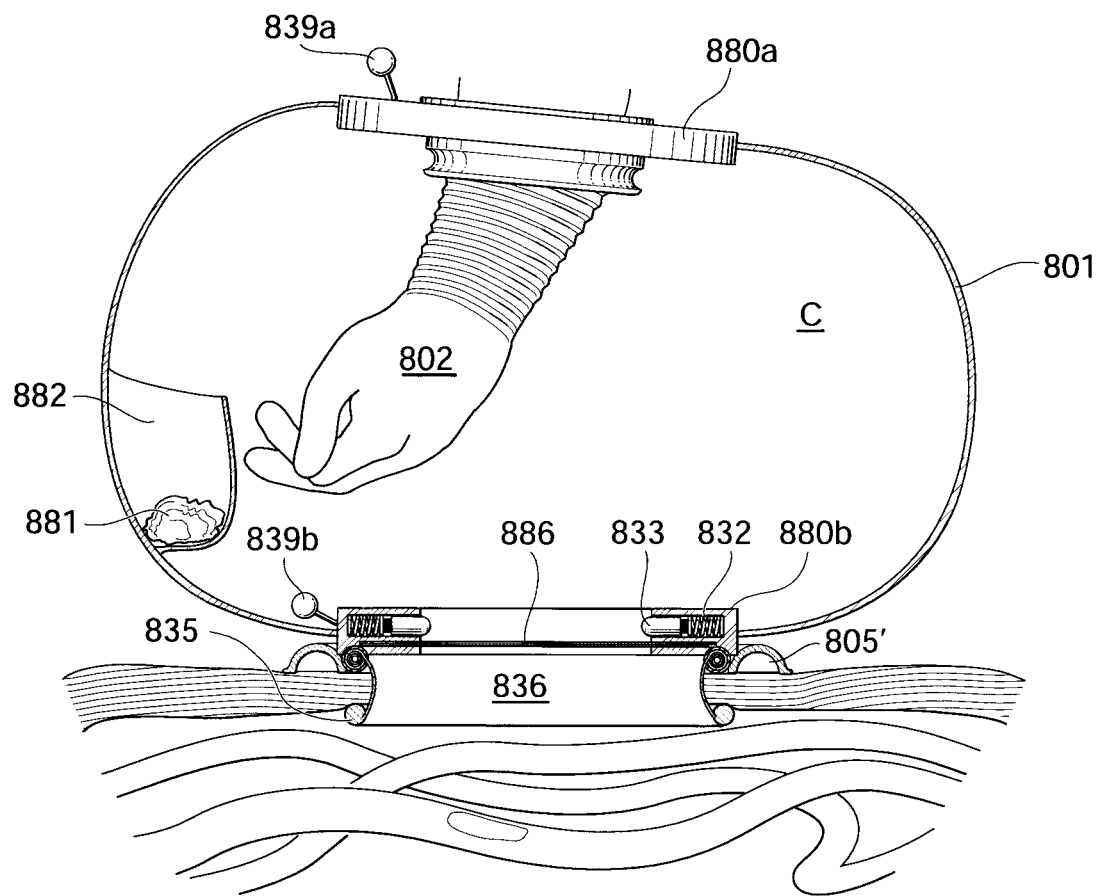

FIG. 95*j* shows the step of placing the removed specimen 881 in the pouch 882 such that the specimen 881 does not contaminate any other part of the body. The pouch may be a pouch 882 which could be closed for creating a pouch-chamber within the chamber C for isolating the removed specimen 881 within the chamber C.

Figure 95K:
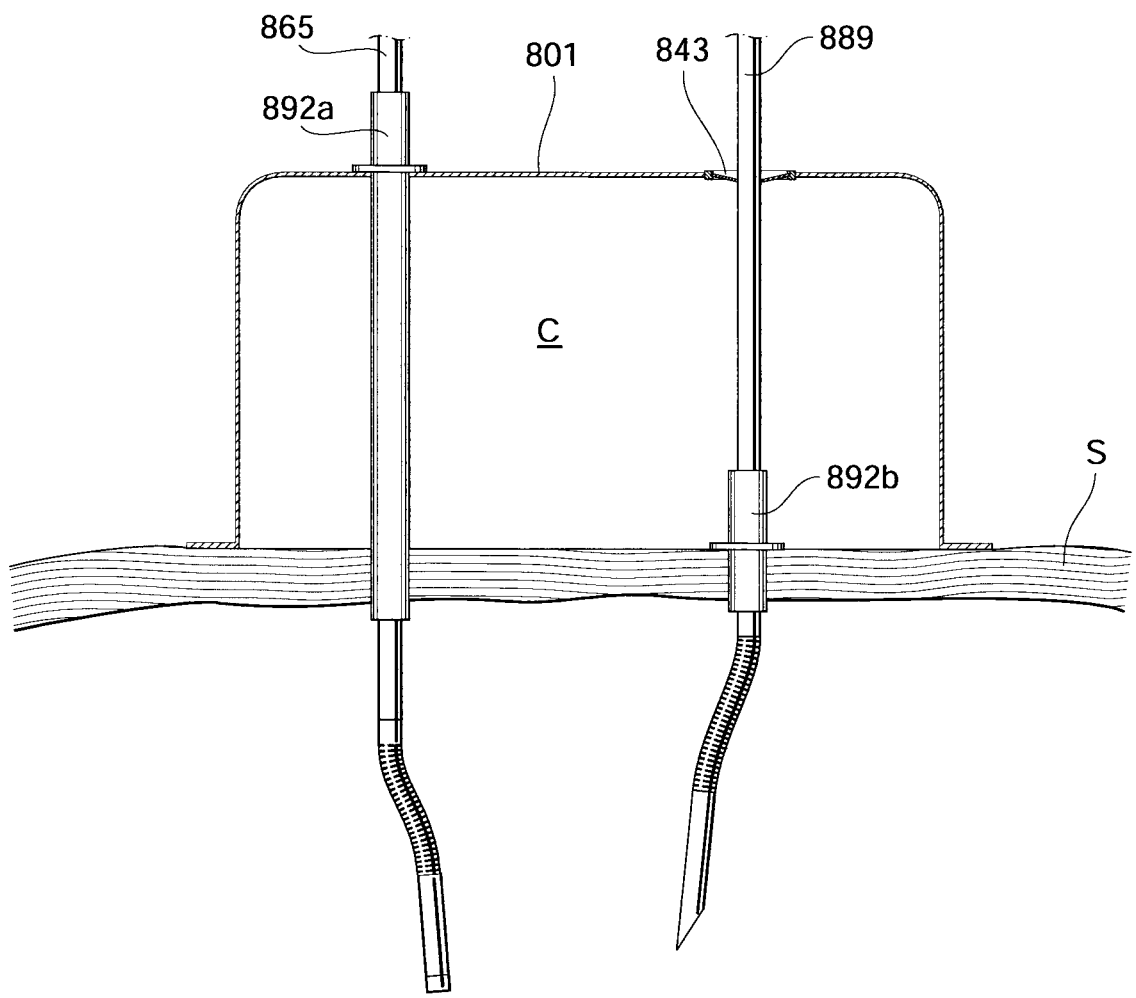
FIG. 95k shows an embodiment of the medical device, in sectional view.

FIG. 95*k* shows examples of how trocars may be used in combination with the medical device according to any of the embodiments shown in FIGS. 86-95. The medical device comprises a wall 801 placed on the patient's skin S and thereby enclosing a chamber C for creating a sealed environment. The medical device comprises two trocars 892*a*; 892*b*, one 892*a* traveling through both the wall 801 of the medical device and the skin S of the patient and thus enabling an endoscopic instrument 889 to be inserted into the patient through both the wall 801 of the medical device and the skin S of the patient through one single trocar 892*a*. The other trocar 892*b* being placed inside the chamber C and enabling an endoscopic instrument 889 to be inserted through the skin S of the patient. The endoscopic instrument 889 is in this embodiment inserted into the chamber C enclosed by the wall 801 through a membrane 843 in the wall 801 sealing against the tool 889.

FIG. 95*l* shows how the medical device shown in FIGS. 86-95 may be used. The medical device 800 comprises a glove 802 integrated in the wall 801 and a camera 865 placed through a trocar 892*a* in the skin S outside of the medical device 800. The medical device 800 further comprises a trocar 892*b* placed inside the camber C trough an opening in the wall 801 and into the sealed environment and further through an opening in the skin S of the patient and into an area of the knee of the patient. FIG. 95*l* schematically illustrates how the surgeon manipulates the knee in the sealed environment using the glove 802.

Figure 95M:
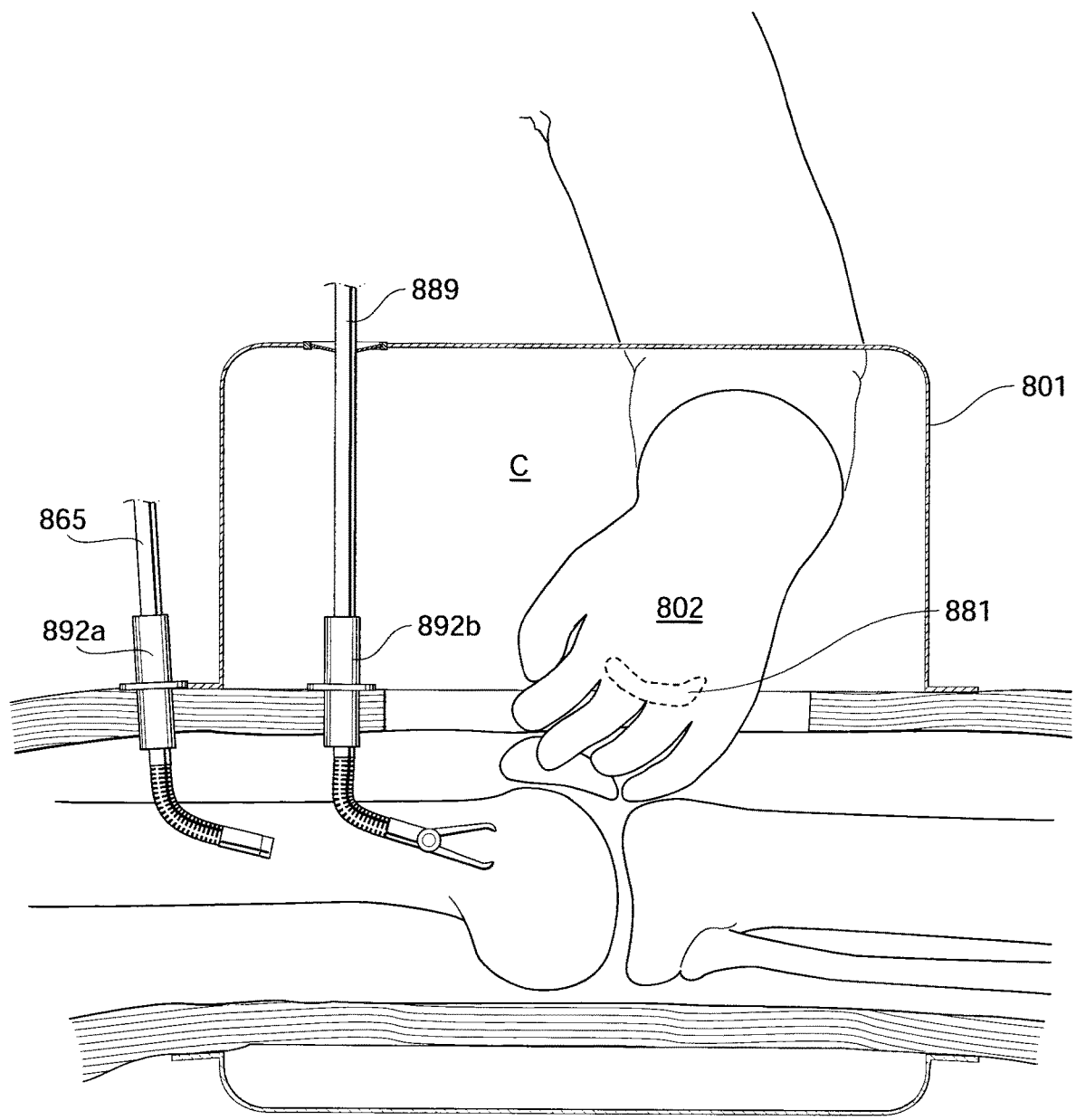
Figure 95N:
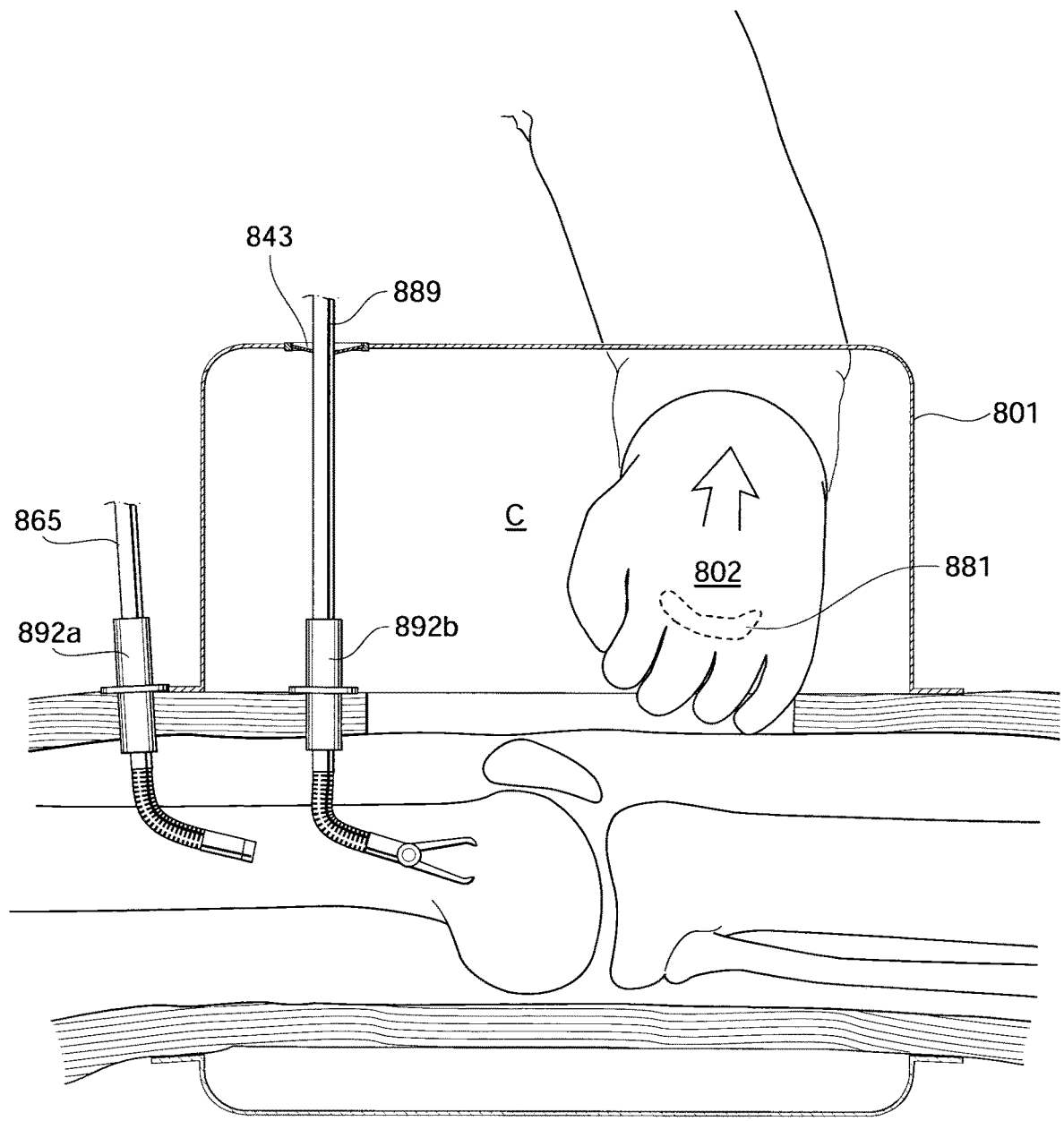

FIGS. 95*m*, 95*n* shows the medical device when the surgeon removes a specimen 881 from the knee of the patient using the glove 802 integrated in the wall 801 of the medical device 800.

Figure 95O:
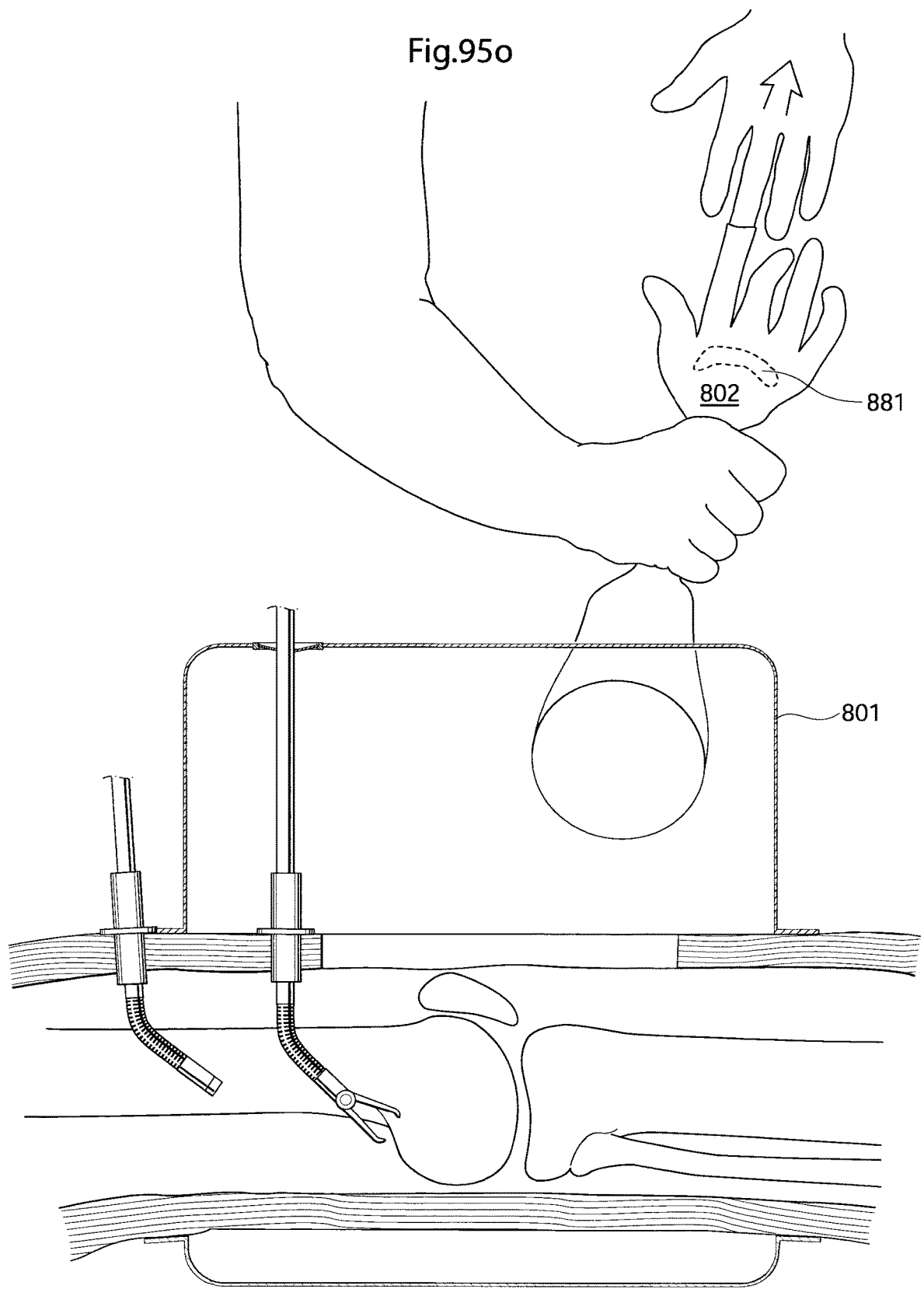

FIG. 95*o* shows the medical device, when the surgeon has turned the integrated glove 802 inside-out such that the specimen can be contained within the integrated glove 802. By isolating the specimen 881 inside of the glove 802, the specimen 881 is removed both from the rest of the body of the patient and from the ambient environment, and thereby does not risk to infect any other portion of the patient's body or medical staff with any infectious disease.

FIGS. 96-105*o* shows the medical device according to an embodiment in which the medical device comprises a closeable body port placed in the skin of the patient for establishing a closeable fluid connection between the chamber of the medical device and a cavity in the body of the patient. The medical device further comprising an airlock sluice between the ambient environment and the chamber of the medical device for enabling transfer of objects between the ambient environment and the chamber of the medical device whilst keeping the chamber sealed.

Figure 96:
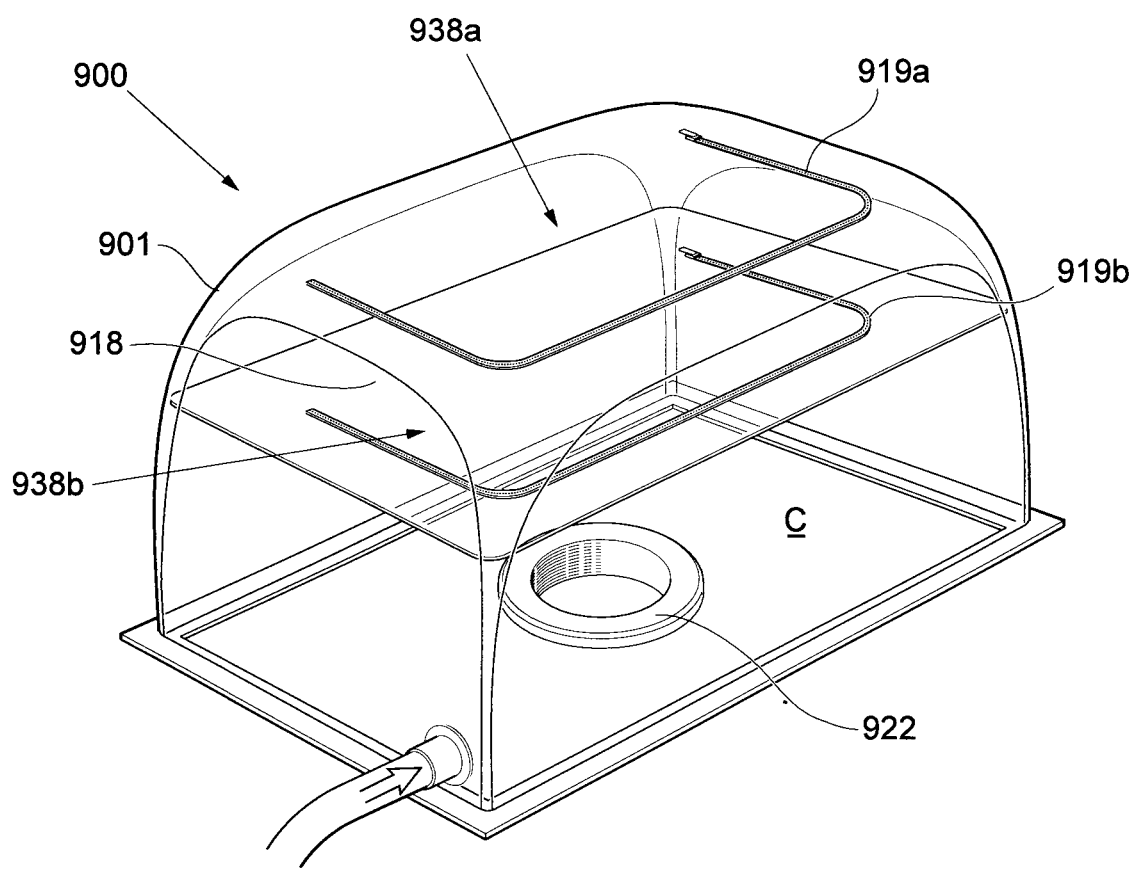
FIG. 96 shows an embodiment of the medical device comprising an airlock.

FIG. 96 shows a medical device 900 for use in surgical procedures, wherein the medical device comprises a wall 901 enclosing a sealed environment for performing the surgical procedure, wherein a portion of the wall 901 is adapted to be in contact with the skin S of the human patient when the surgical procedure is performed. The medical device further comprises an airlock 918 for allowing passage of objects between the chamber C and the environment outside of the chamber C. The airlock 918 comprises an outer zipper 919*a* for opening a portion of the wall 901 between the ambient environment and the airlock sluice 918, and in inner zipper for opening a portion of an inner wall between the chamber C and the airlock sluice 918. The airlock for examples provides the possibility to transfer an object into the sealed environment of the chamber C without releasing the pressure within the sealed environment being above atmospheric pressure, thus enabling an at least partially laparoscopic procedure to be conducted while passing objects of substantial size into the sealed environment and occasionally into the body of the patient. The airlock sluice 918 could further allow the removal of a specimen from the body of the patient via the sealed environment even if the specimen is too large for passing through regular size trocar. The airlock could for example allow the passage of objects being larger than 10 cm³ or in other embodiments larger than 20 cm³, or in other embodiments larger than 40 cm³, or in other embodiments larger than 80 cm³, or in other embodiments larger than 140 cm³, or in other embodiments larger than 180 cm³, or in other embodiments larger than 250 cm³. FIG. 96 and further figures throughout the application shows the airlock 918 construction having zipper-type closings 919*a;b*, however, it is equally conceivable that the closings throughout the application is of a different design. The medical device 900 further comprises a closeable body port 922 positioned in an incision performed in the skin of the patient such that a closeable fluid connection is established between the chamber C and a cavity in the body of the patient.

Figure 97A:
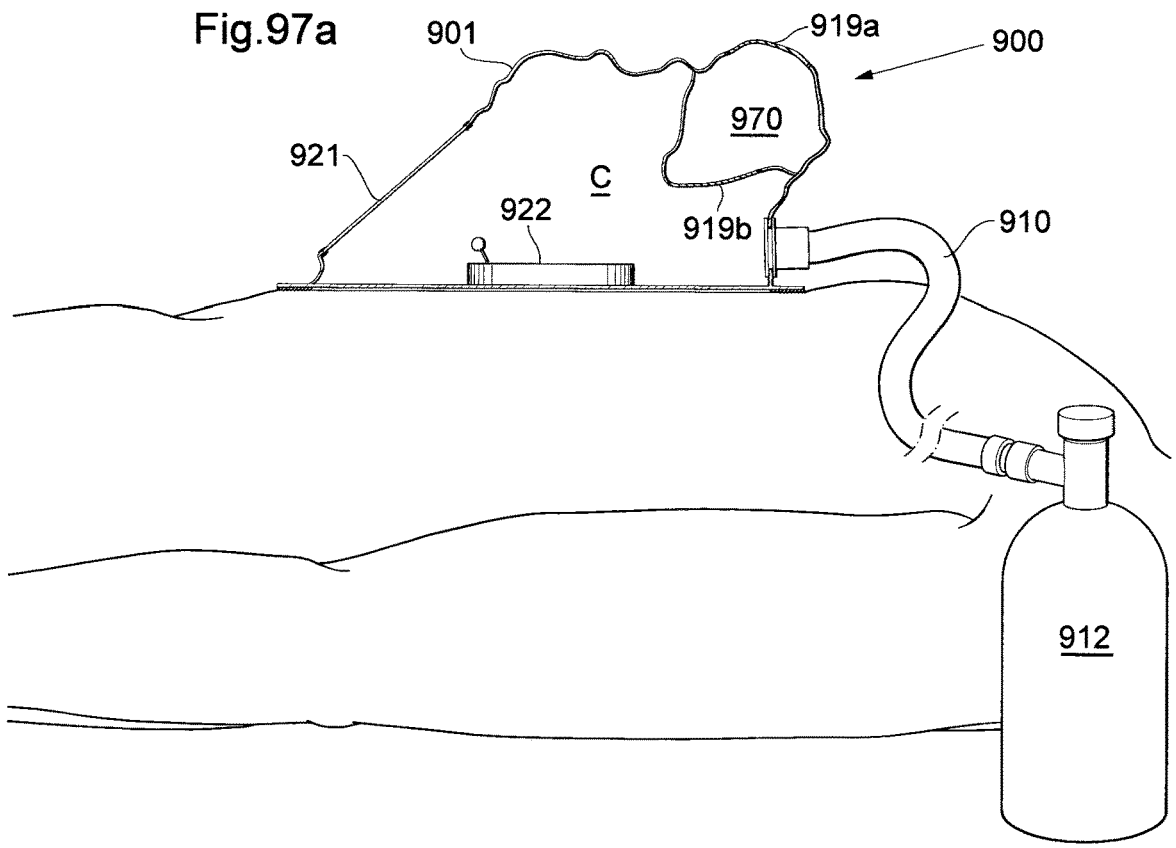
FIG. 97a shows the medical device when applied to the abdomen of a patient, in a deflated state.

FIG. 97*a* shows the medical device in an embodiment similar to the embodiment shown with reference to FIG. 96, with the difference that the medical device comprises a partially collapsible wall 901 adapted to be inflated by a gaseous fluid for defining the chamber C. In the embodiment shown the inflation is performed by means of a pressurized fluid contained in a pressurized tank 912, via a fluid conduit 910. The airlock 918 with the inner 919*b* zipper and the outer 919*a* zipper closing is according to this embodiment positioned in a corner of the medical device 900. The medical device 900 shown in FIG. 97*a* further comprises a non-collapsible transparent window 921 for enabling viewing into the chamber C.

Figure 97B:
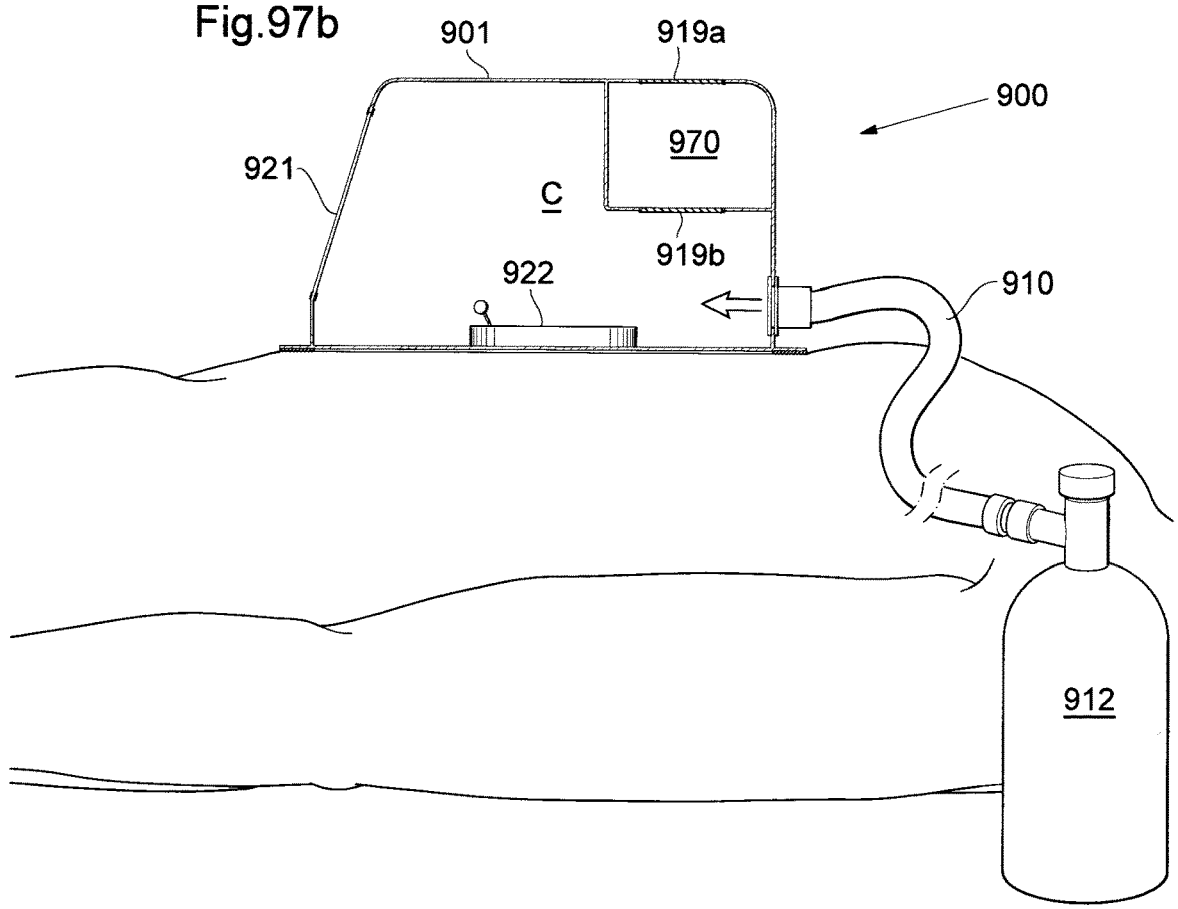
FIG. 97b shows the medical device when applied to the abdomen of a patient, in an inflated state.

FIG. 97*b* Shows the medical device of FIG. 97*a*, when the medical device 900 has been inflated such that the transparent window 921 is positioned by the wall 901 being inflated, to enable viewing into the chamber C at the area of the surgical procedure from the outside thereof.

Figure 98:
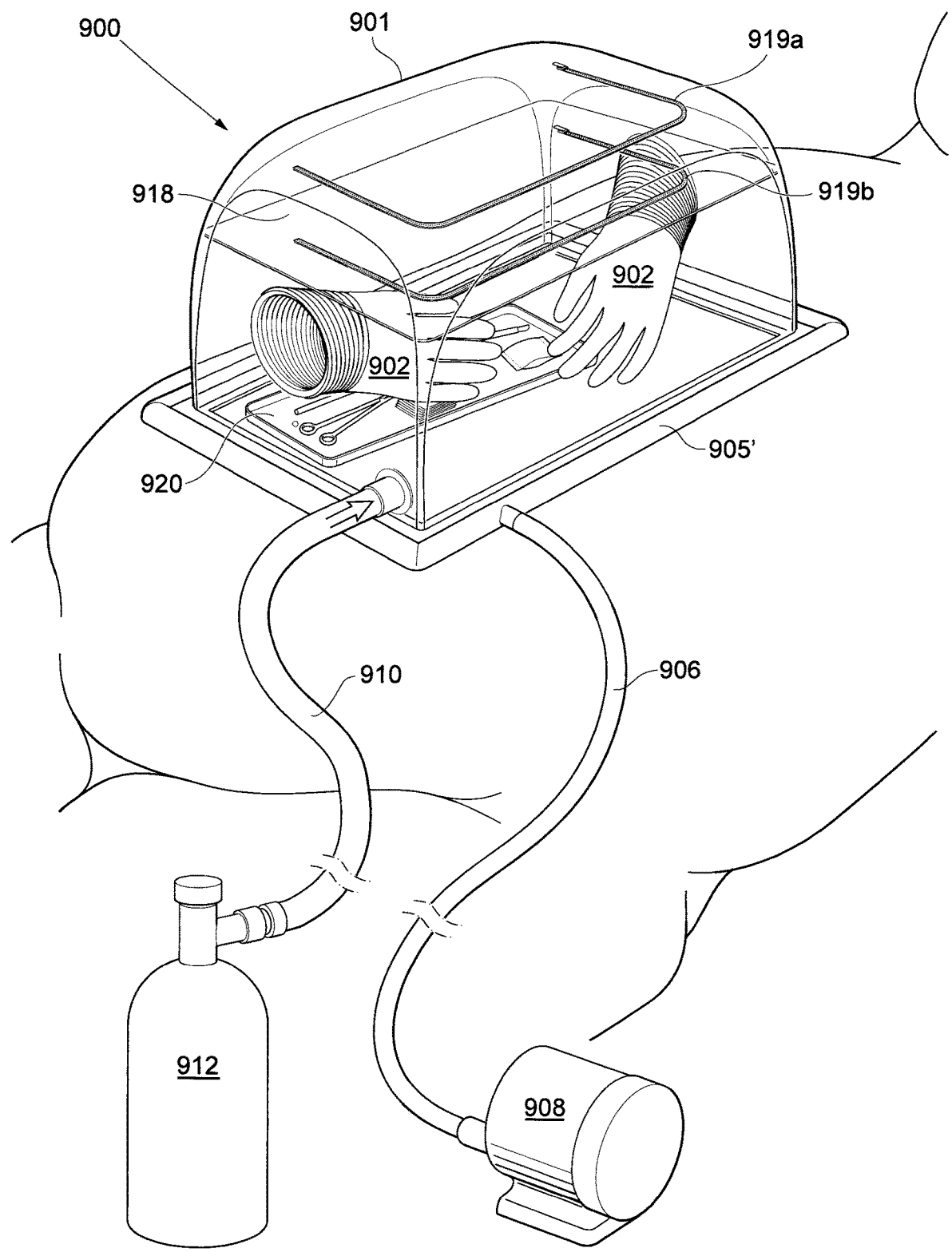
FIG. 98 shows the medical device according to yet another embodiment, when applied to the abdomen of a patient.

FIG. 98 shows the medical 900 according to an embodiment similar to the embodiment disclosed with reference to FIGS. 96-97. The medical device 900 has according to the embodiment shown in FIG. 98, a volume being larger than 500 cm³ for enabling the manipulation of objects within the sealed environment and/or placing objects of considerable size within the sealed environment of the chamber. According to the embodiment shown in FIG. 98 the partially collapsible wall 901 comprises two integrated gloves 902 for enabling manual manipulation within the chamber. The medical device 900 according as shown in FIG. 98 further comprises a device/instrument mount 920 for retaining instruments within the chamber. The instruments could be pre-placed in the chamber before positioning the medical device 900 in contact with the skin of the patient, and could be adapted for a specific operation. The medical device 900 is according to the embodiment shown in FIG. 98 adapted to be fixated to the skin of the patient by means of a vacuum sealing member 905' having a recess or groove in which a vacuum is created by means of the recess or groove being connected to a vacuum pump 908 via a vacuum conduit 906. In some embodiments the medical device 900 could further be fixated using an adhesive portion, which could be a portion of the portion of the wall in contact with the skin of the patient, or the entire portion of the wall being in contact with the skin of the patient.

Figure 99:
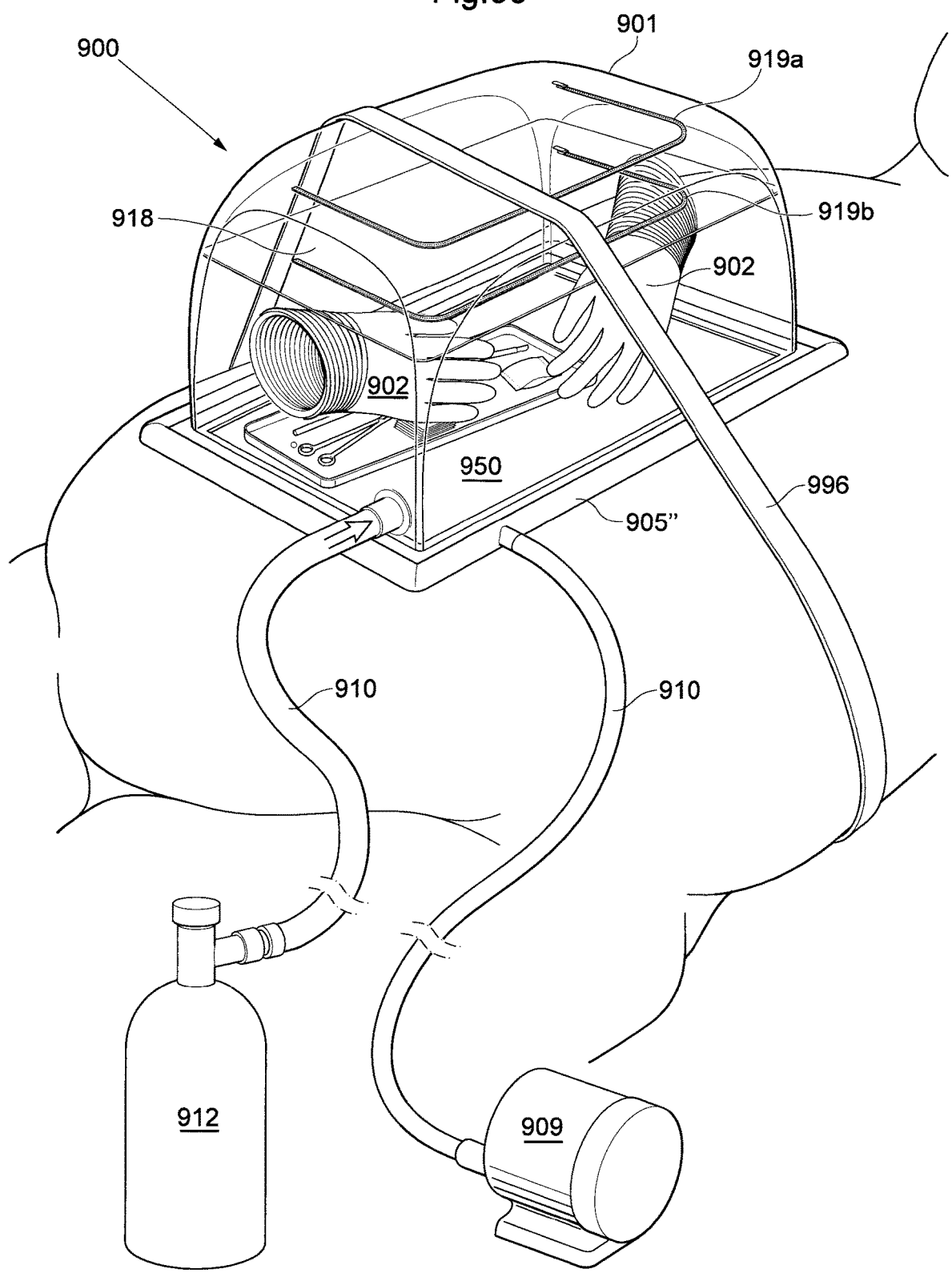
FIG. 99 shows an embodiment of the medical device comprising a pressure sealing.

FIG. 99 shows an alternative embodiment of the concept disclosed with reference to FIG. 98 with the difference that the medical device 900 additionally comprises a sealing device comprising a pressure sealing member 905" adapted to be inflated for pressing against the skin of the patient and thereby sealing between the chamber C within the medical device 900 and the ambient environment. The pressure sealing member 905" is inflated though a fluid conduit 993 connected to a pressure source, in this embodiment a pump 909. In the embodiment, the medical device 900 is fixated to the patient by means of an adhesive surface 950 adapted to withstand the force created by the inflated pressure sealing member 905", In addition, the adhesive surface 950 is assisted by a holding member 996 pressing the medical device 900 against the skin of the patient. The holding member 996 could be required if the pressure needed to seal between the skin if the patient and the medical device 900 needs to be particularly large, which for example could depend on the positioning of the medical device 900. The use of a pump 909 as pressure source for the sealing 905"

instead of a pressurized tank, as disclosed in other embodiments herein, could be an advantage if the pressurized fluid in the tank 912 is scarce or non-existing.

Figure 100A:
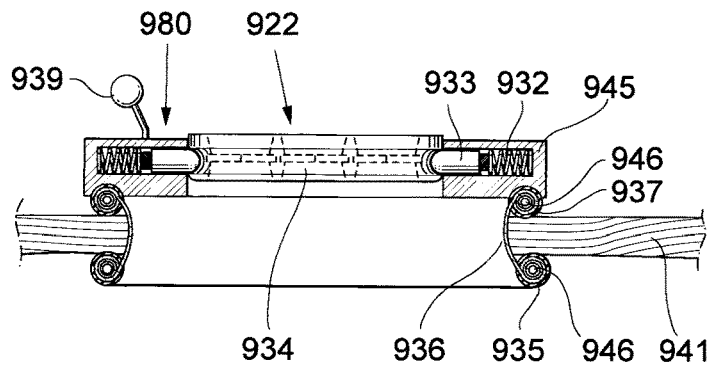
FIGS. 100a, 100b and 100c shows an embodiment of a coupling.

FIG. 100*a* shows an embodiment of a detachable body port arrangement which could be positioned in the chamber C of the medical device disclosed with reference to FIGS. 96-99. The body port arrangement includes an intra body ring 935 adapted to be placed at the inside of the patients skin around an incision, and an outer ring 937 adapted to be placed on the outside of the patients skin S around the incision. Between the intra body ring 935 and outer ring 937 an annular retractor membrane 936 is positioned adapted to exert a pressure on the skin or tissue at the incision to seal between the rings 935; 937 and the skin or tissue and additionally for retracting the skin and thereby keeping the incision open. The retractor membrane 936 is preferably made from a resilient or elastic polymer material. The outer ring 937 comprises an integrated roll up system 946, which may be spring loaded and adapted to create a suitable pressure on retractor membrane 936 to keep the incision open.

The body port arrangement shown in FIG. 100*a* also includes a coupling 980 having a rigid annular seating 945 attached to the outer ring 937, spring loaded latching members 933 arranged in radial bores in the seating 945 and a hand lever 939 connected to protruding latching members 933 to enable retraction thereof against the action of springs 932. The body port arrangement further includes a self sealing body port 922 held by the coupling. The body port 922 comprises a disc-shaped self sealing membrane 943, FIG. 100*b*, fixated to a rigid ring having an outer circumferential groove 934 that receives the protruding latching members 933 of the coupling 980. The self sealing membrane 943 has a small self sealing hole 944, FIG. 100*b*, centrally in the membrane 943. For example, the self sealing membrane 943 may be made from a gel-type material being elastic enough to enable a deformation large enough for a person's hand to pass through the small self sealing hole 944 while still contracting enough to create an airtight seal between the chamber and the outside environment.

The coupling 980 described above enables quick exchange of the body port 922. Thus, the surgeon may release the body port 922 from the port arrangement by simply pulling the hand lever 939 so that the protruding latching members 933 disengage from the recess or groove 934 of the body port 922, whereby the body port 922 can be removed.

Figure 100B:
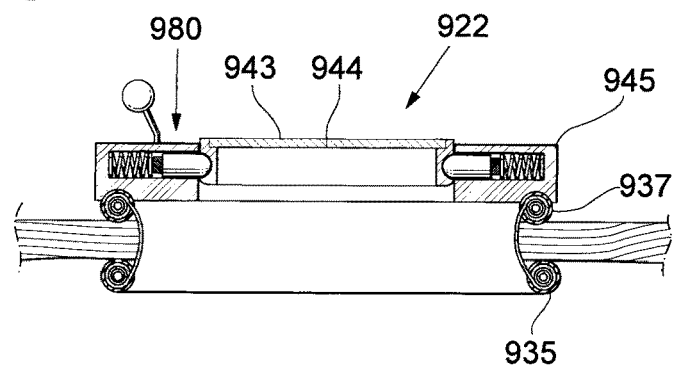

FIG. 100*b* is a cross-sectional view of the port arrangement shown in FIG. 100*a*, to more clearly illustrate the body port 922 with its self sealing membrane 943 and small hole 944.

Figure 100C:
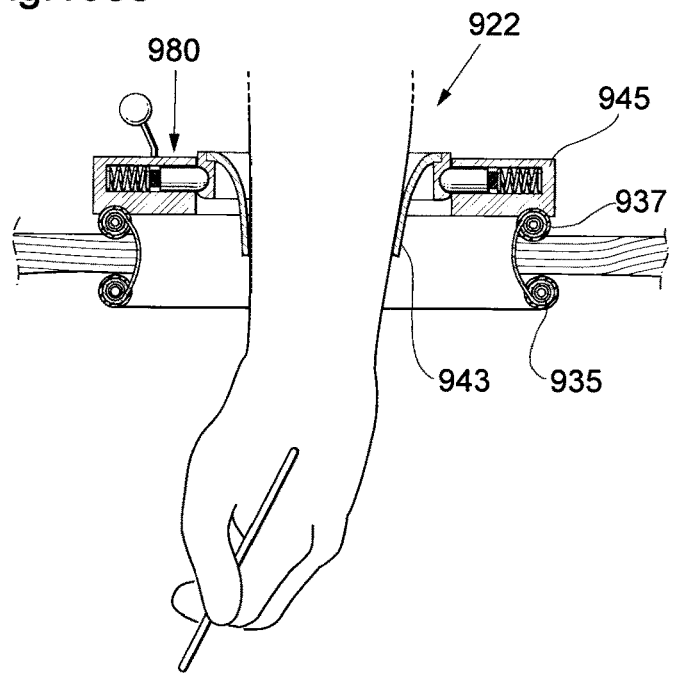

FIG. 100*c* shows the self sealing body port 922 when the hand of a surgeon is placed through the hole 944 in the membrane 943 and thus enabling manual manipulation within the body of the patient.

Figure 101A:
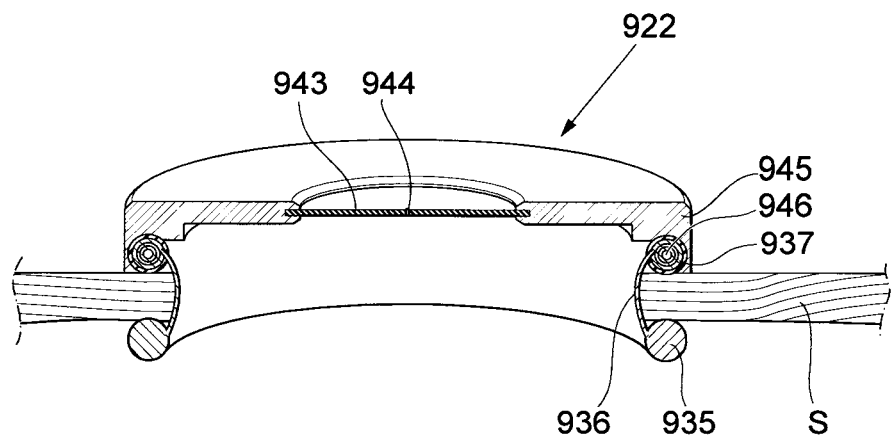
FIGS. 101a and 101b shows an embodiment of a self sealing port, in section.
Figure 101B:
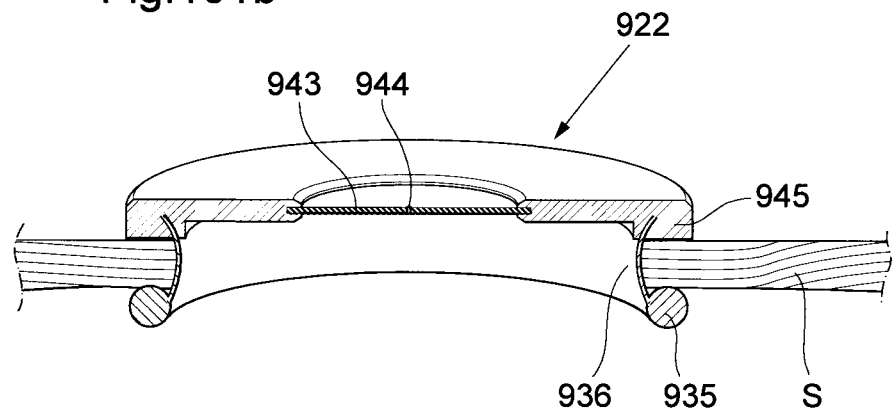

FIG. 101*a* shows a self sealing body port 922 in a close-up, in section. The self sealing body port 922 could be connected to the coupling 980, for example as disclosed with reference to FIGS. 100*a-c*, which in turn is connected to any of the medical device disclosed with reference to FIGS. 96-99, or the self sealing body port 922 could be fixated to a retractor, as shown in FIG. 101*a-b*. The self sealing body port 922 comprises a self sealing membrane 943 fixated to a rigid part 945 of the self sealing port. The self sealing membrane 943 having a small self sealing hole 944 centrally in the membrane 943. The self sealing membrane 943 is for example made from a gel-type material being elastic enough to enable a deformation large enough for a person's hand to pass through the small self sealing hole 944 while still contracting enough to create an airtight seal between the sealed environment and the outside environment. The medical device being fixable to a retractor comprising one intra body ring 935 adapted to be positioned on the inside of the patients skin, and one ring 937 adapted to be placed on the outside of the patients skin. Between the intra body ring 935 and the ring 937 adapted to be placed on the outside of the patients skin S a retractor membrane 936 is positioned which is adapted to exert a pressure of the cut surfaces of the incision for retracting the skin and thereby keeping the wound open. The retractor membrane 936 is preferably made from a resilient of elastic polymer material. The ring 937 adapted to be placed on the outside of the patients skin S comprises an integrated roll up system 946 which could be a spring loaded roll up system adapted to create a suitable pressure on the retractor membrane 936 for keeping the wound open.

FIG. 101*b* shows an alternative embodiment of the self sealing body port 922, with the difference that the retractor membrane 936 is made from a material elastic enough such that one end of the retractor membrane 936 could be fixedly fixated to the rigid part 945 of the port.

Figure 102:
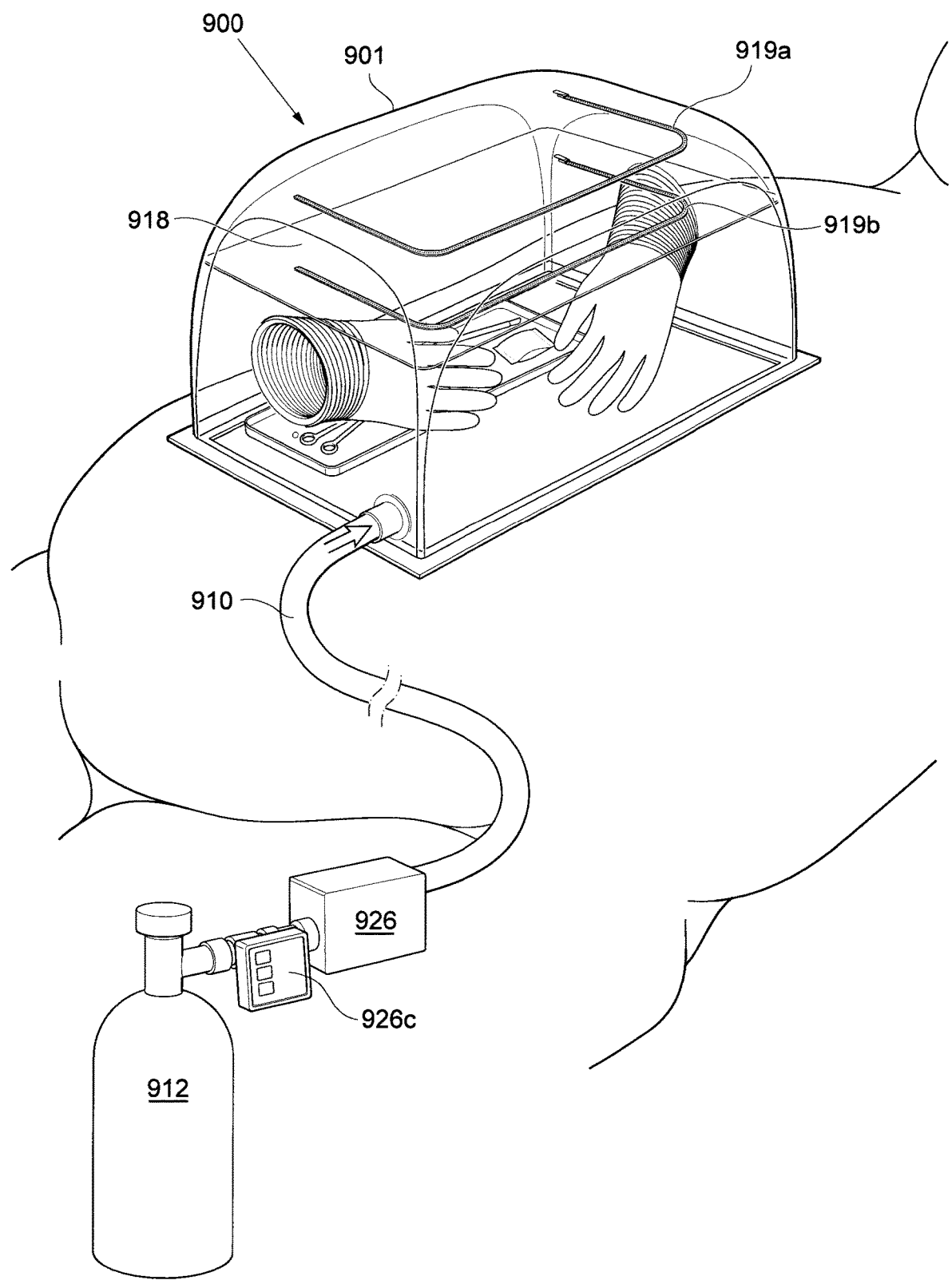
FIG. 102 shows another embodiment of the medical device, when fixated to the skin of the patient.

FIG. 102 shows the medical device 900 in an embodiment similar to that shown in FIG. 98. The embodiment shown in FIG. 102 further comprises a sterilizing unit 926 adapted to sterilize the gaseous fluid entering the medical device 900. In the embodiment disclosed herein, the gaseous fluid entering the medical device 900 originates from a pressurized tank 912 and could be pre-sterilized, however, in other embodiments, it is conceivable that the gaseous fluid is the surrounding air which is pressurized (such as further disclosed with reference to FIG. 103). In the embodiments where the surrounding air is used to inflate the medical device 900 and constitute the operating environment this air needs to be properly sterilized. The medical device 900 further comprises a tempering unit 926*c* which could be provided to heat or cool the gaseous fluid inflating the medical device 900. In cases when the surrounding environment is cold the tempering unit 926*c* could be used to raise the temperature of the chamber to provide beneficial operating circumstances both for the patient and for the surgeon. In cases when the ambient environment is hot, the tempering part of the system 926*c* could be used to lower the temperature of the sealed environment both to provide beneficial operating circumstances, both for the patient and for the surgeon, and for providing a temperature inhibiting bacterial and viral infections. The tempering unit 926*c* could comprise a temperature regulating device for setting the required temperature.

Figure 103:
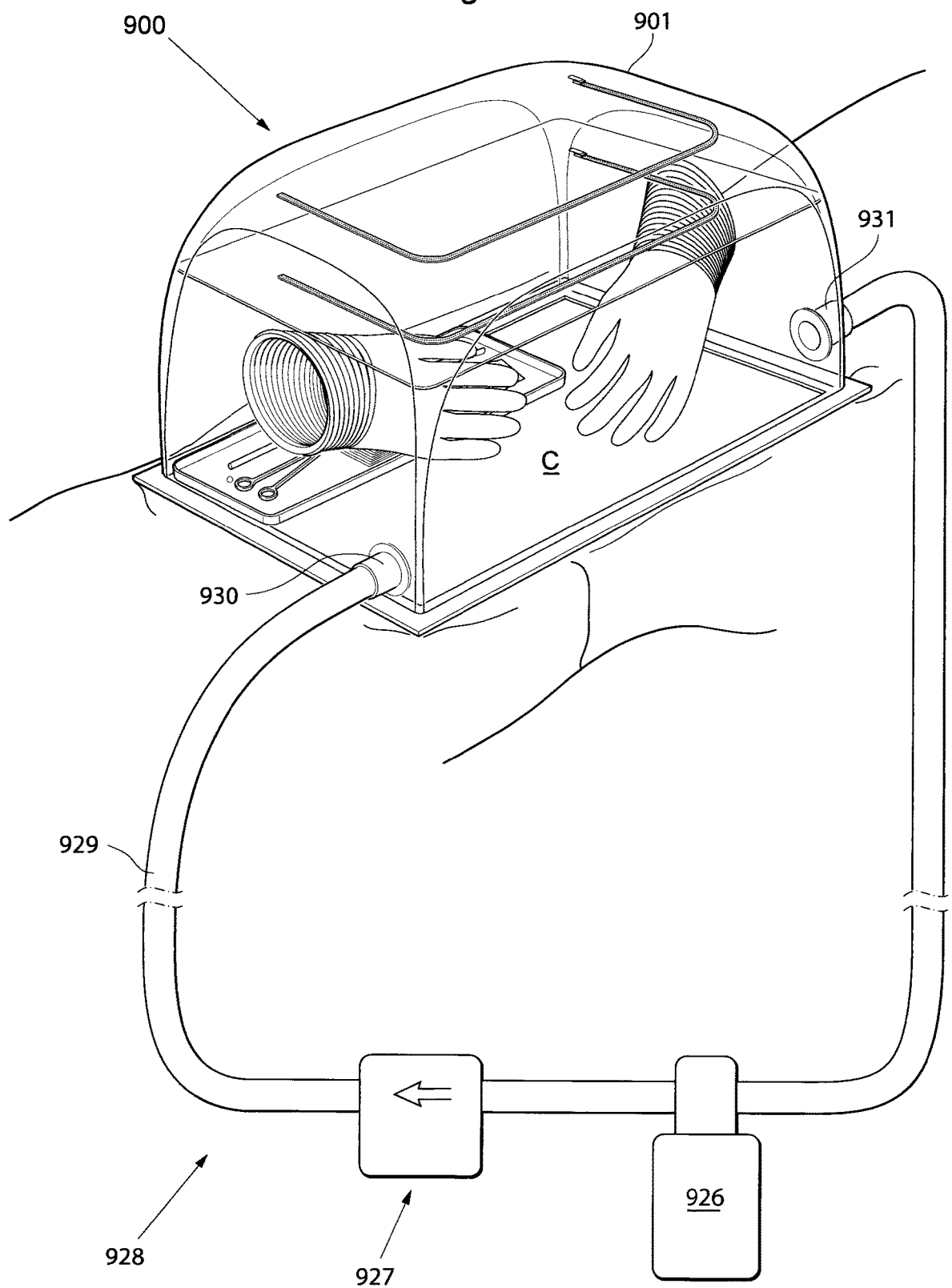
FIG. 103 shows another embodiment of the medical device, comprising a fluid circulating system, when fixated to the skin of the patient.

FIG. 103 shows a medical device similar to the embodiment disclosed in FIG. 102 but comprising a system 928 for circulating a fluid through the sealed environment of the medical device. The system comprises a fluid conduit 929 connected at an inlet 930 placed in the wall 901 for supplying fluid to the chamber C, and an outlet 931 for draining the fluid from the chamber C. The fluid is circled by means of a pumping unit 927 and is circled via a sterilizing/filtering unit 926 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 104A:
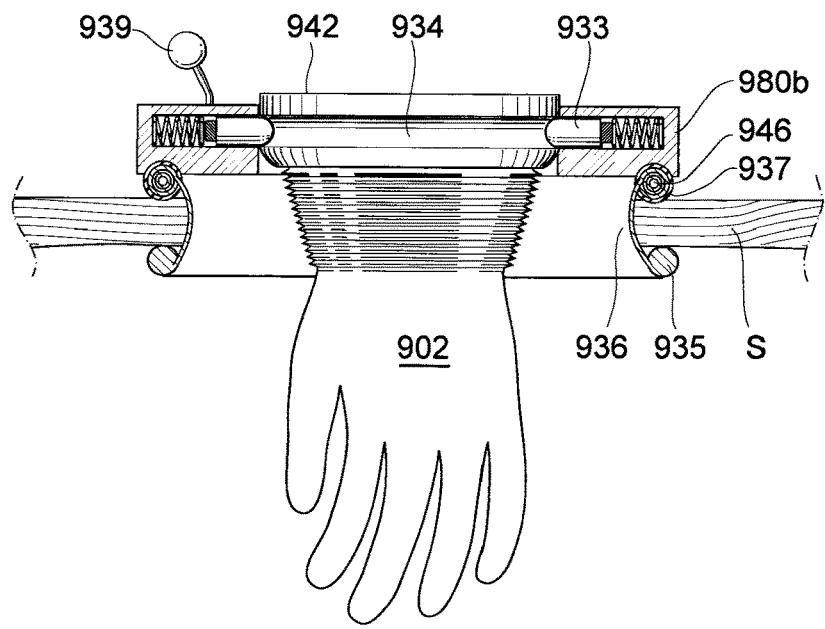
FIG. 104a shows a coupling fixated to the skin of a patient, in section.

FIG. 104a shows the coupling 980b as disclosed in FIG. 100a-100c in further detail when an inset 942 comprising a surgical glove 902 is fixated to the lower coupling 980b. The retractor system comprises an intra body ring 935 and a ring 937 adapted to be placed on the outside of the patients skin S further comprises a retractor membrane 936 positioned such that it exerts a pressure on the cut surfaces of the incision for retracting the skin S and thereby keeping the wound open. The retractor membrane 936 could be rolled up by a roll up system 946 inside of the ring 937 adapted to be placed on the outside of the patients skin S for tightening the retractor membrane 936 such that the wound is kept open.

Figure 104B:
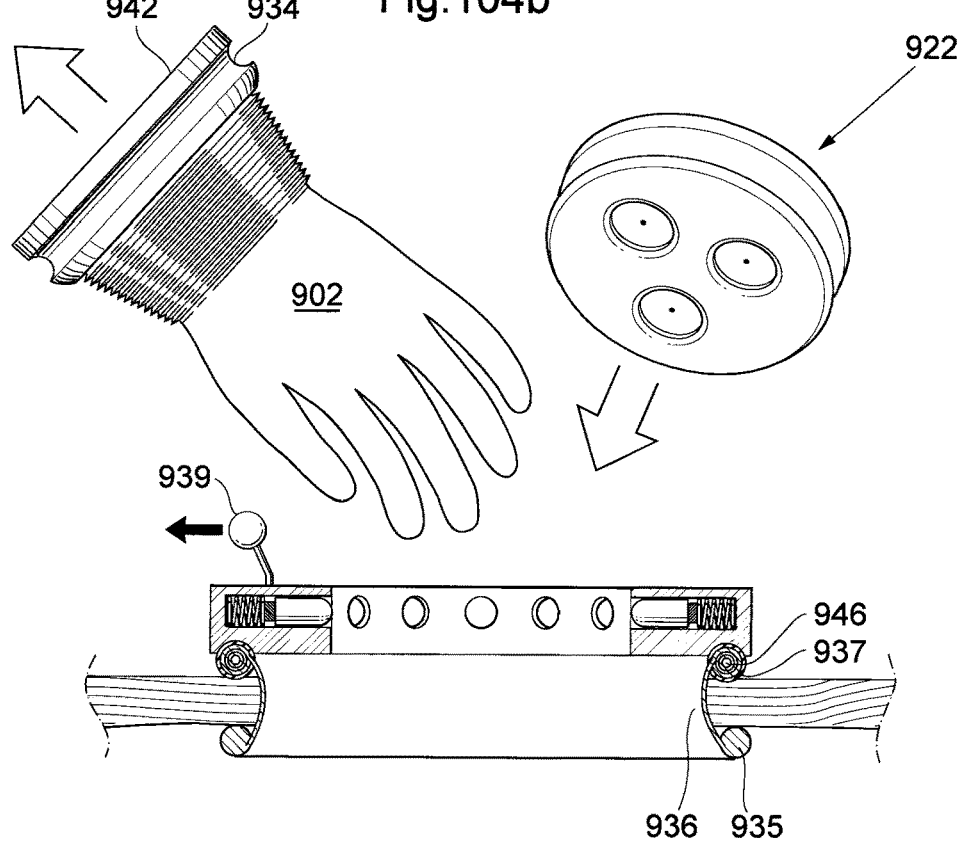
FIG. 104b shows the coupling of FIG. 104a when objects are being exchanged.

FIG. 104b shows the changing of objects in the coupling from an inset comprising a surgical glove 902 to a body port 922 in the form of a body port comprising three endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care. In other embodiments the laparoscopic ports and insets comprising surgical gloves could additionally be exchanged for insets comprising device/instrument mounts, for example holding instruments or implants.

Figure 105A:
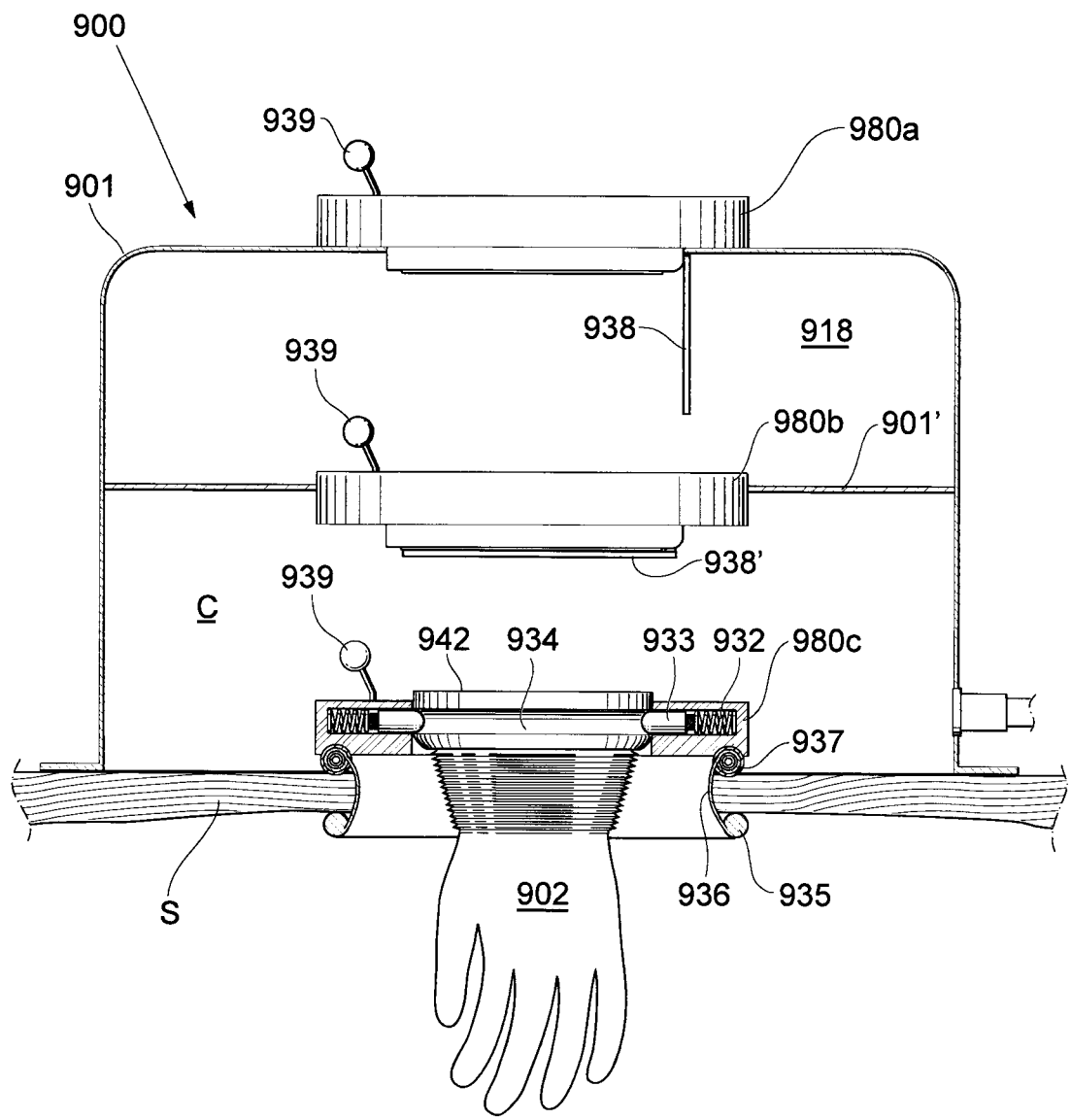
FIG. 105a shows an embodiment of the medical device, in section.

FIG. 105a shows a modification of the embodiment disclosed with reference to FIGS. 97a-b in which the medical device 900 further comprises an upper 980a, middle 980b and a lower 980c coupling for fixating ring shaped objects which for example could be insets or ports, where insets for example could be an inset 942 comprising surgical gloves 902, or devices/instrument mounts, ports could be endoscopic ports or hand access ports, such as the self sealing port disclosed with reference to FIGS. 4a and 4b. The couplings 980a;b;c comprise releasing levers 939 for releasing the object. The levers 939 are connected to protruding latching members 933 which are spring loaded 932 from the rear in order to secure the recess or groove 934 of the object. In the embodiment disclosed in FIG. 105a, the inset 942 fixated to the lower coupling 980c is a surgical glove 902 enabling manual manipulation within the body of the patient. The medical device shown in FIG. 105a further comprises a valve member 938 adapted to close the opening in the upper coupling 980a, when the upper coupling 980a is not in use. The upper coupling 980a could for example be used for manual manipulation and preparation within the medical device 900, such that could be needed for preparing or changing an instrument or preparing an implant for implantation. The lower coupling 980c is for example used for laparoscopic manipulation within the body of the patient, or manual manipulation for e.g. removing a specimen or positioning an implant. The upper coupling 980a comprises a valve 938 for closing the hole in the coupling 980a such that the chamber C is sealed. The medical device 900 further comprises an intermediary coupling 980b placed in a wall portion 901' and comprising a valve 938'. The valve 938 in the upper coupling 980a and the intermediary coupling 980b together forms an airlock sluice 918 forming part of the chamber C. The airlock sluice 918 is adapted to allow reversible passage of objects from the chamber C through the first valve 938' into the sluice 918 and further through the second valve 938 out to the ambient environment outside of the sealed environment, and vice versa, whereby the risk of contamination is reduced. The first valve 938' is adapted to be opened for an object to pass through whilst the second valve 938 remains closed by itself, thus without any object passing through the second valve 938, which enables the medical device to be hermetically sealed whilst an object passes from the chamber C of the airlock sluice 918 to the chamber C being a part of the operational area.

Figure 105B:
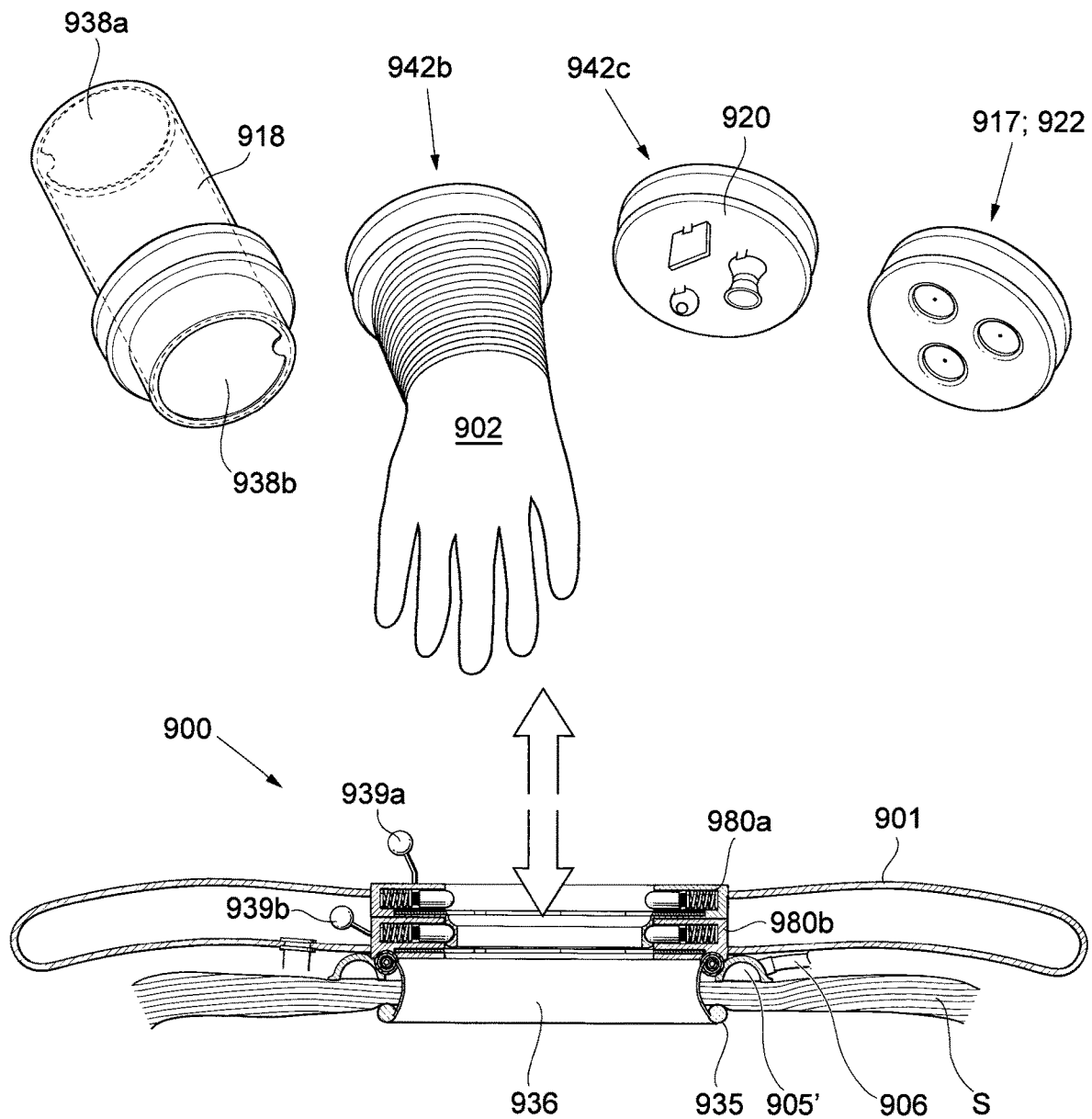
FIGS. 105b-105c shows embodiments of the medical device, in section.

FIG. 105b shows the medical device 900 adapted to be at least partially placed in an incision cut in a patient's body. The medical device 900 comprises a first upper coupling 980 and second lower coupling 980b adapted be interconnected to form an interconnected coupling. The upper coupling is adapted to be disconnected from the lower coupling 980b, and the upper coupling 980a is connected to a first portion of a flexible wall 901, and the lower coupling 980b is connected to a second portion of the flexible wall 901. The flexible wall 901 forms a chamber C in which a sealed environment can be maintained, the chamber C is heavily enlarged when the upper coupling 980a is disengaged from the lower coupling 980b, thus creating operating space within the chamber C enclosed by the wall 901. The upper 980a and lower coupling 980b comprises a latching system for locking an inset or port. The inset may for example be an inset 942b comprising a glove 902 for manual manipulation within the body of the patient, or within the enclosed chamber C, or an inset 942c comprising a device or instrument mount 920 for holding instruments or medical devices within the chamber C. Alternatively the insets 942b; 942c can be replaced by an airlock sluice 918 with a first 938a and second 938b valve member or a port 917;922, which could be in the form of a multiport comprising a plurality of ports enabling the insertion of a surgical instrument into the chamber C or body of the patient.

In the embodiment shown in FIG. 105b the medical device is fixated to the body of the patient by means of a vacuum fixating member 905' connected to a vacuum conduit 906, which in turn is connected to a vacuum source. Furthermore, the medical device in FIG. 105b comprises a second sealing device having a first sealing member 935 adapted to be positioned at the inside of the patient's skin S around an incision to be performed in the skin S and a second sealing member 937 adapted to be positioned at the outside of the patient's skin S around the incision, and a spring-loaded or elastic connecting member 936 sealingly interconnecting the first 935 and second 937 sealing members. The spring-loaded or elastic connecting member 936 seals between at least one of the port and the skin S of the patient, and the first sealing member and tissue of the patient.

Figure 105C:
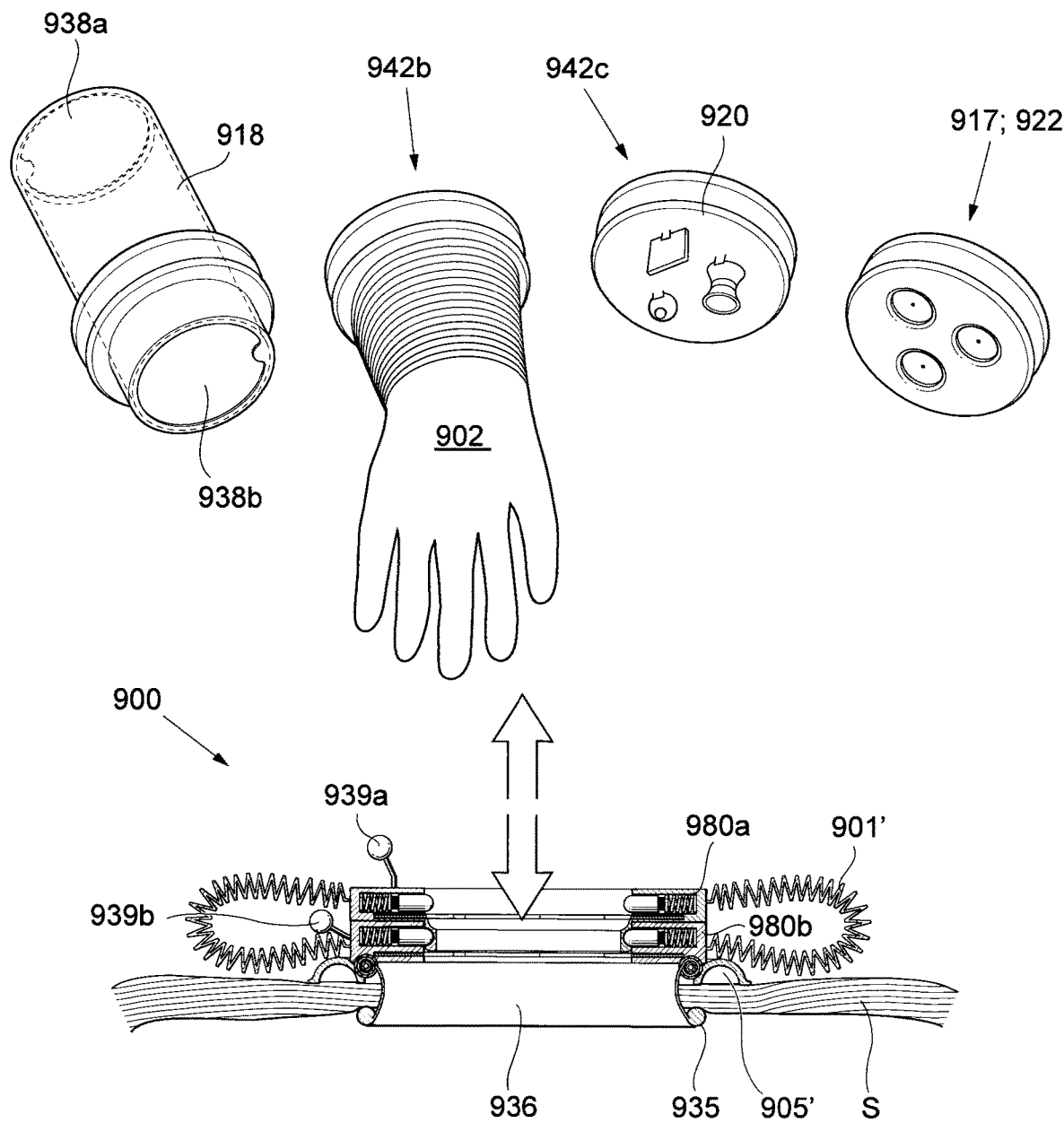

FIG. 105c shows the port in an embodiment very similar to the embodiment shown in FIG. 105b but with the difference that the wall 901' has a bellows structure and thus taking up less space when in its deflated state. The bellows structure enables the wall to be packaged in a small package and thus not obstructing the procedure. In some applications the wall 901' can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

Figure 105D:
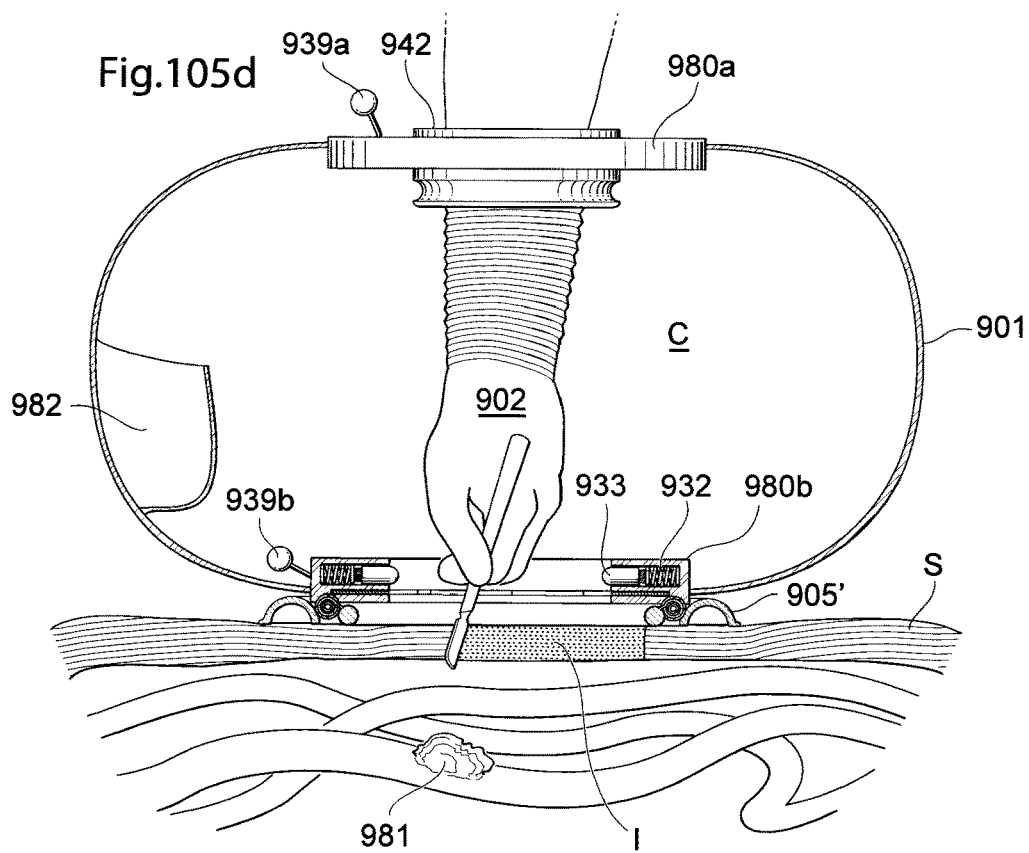
FIGS. 105d-105j shows an embodiment of the medical device in section, being fixated to the patient and used.

FIG. 105d shows the medical device in an embodiment when the wall of the medical device is inflatable, and the medical device is in its inflated state. When the chamber is deflated it has a first volume i.e. when the first, upper coupling 980a and second, lower coupling 980a parts are interconnected, and when the chamber C is inflated and the upper coupling 980*a* is disconnected from the lower coupling 980*b* it has a second volume, and the second volume is larger than the first volume. According to the embodiment shown in FIG. 105*d*, the second volume is larger than 500 000 mm3. According to the embodiment shown in FIG. 105*d*, the chamber C is formed by the inflatable wall 901 and is adapted to hold a pressure exceeding atmospheric pressure.

According to the embodiment shown in FIG. 105*d*-105*j* the chamber C further comprises a pouch 982 for holding a specimen 981 removed from within the body of the patient not to contaminate any other part of the body and create the possibility of delaying the removal of the specimen 981 until the procedure is concluded. The pouch may be a pouch 982 which could be closed for creating a pouch-chamber within the chamber C for isolating the removed specimen 981 within the chamber C.

In FIG. 105*d* a state is illustrated in which the incision in the patient's skin S is being created by the surgeon by means of an inset 942 glove inset 902 latched to the upper coupling 980*a*. The medical device is fixated and sealed by means of the vacuum sealing member 905' since the seal that is provided partially within the patient's body cannot be mounted until the incision in the patient's skin S is concluded. The two different sealing devices disclosed could in some embodiments be replaced by only one of the sealing device, or by a different sealing device, such as the adhesive or pressure sealing device disclosed in other portions herein.

Figure 105E:
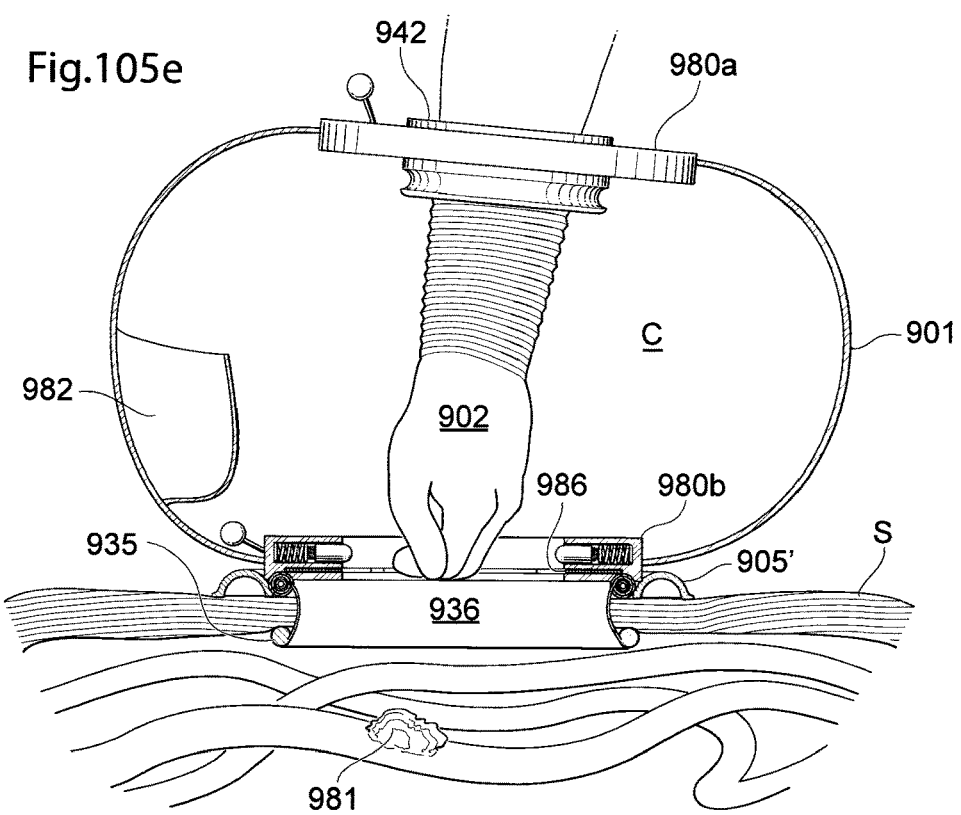

FIG. 105*e* shows the medical device, when the second sealing device 935, 936, 937 have been placed in the incision cut in the patient's skin S. The wall 901 enclosing the chamber C is elastic or flexible which enables the surgeon move the upper coupling 980*a* in relation to the lower coupling 980*b* for getting better access to different angles within the patient's body, for example for removing a specimen 981. The embodiment of FIG. 105*e* further comprises a non-penetrable valve 986 placed in the upper coupling 980*a* for closing the port such that the chamber C is sealed from at least one of the ambient environment and a cavity in the patient. The closing of the iris valve 986 enables activity within the chamber C without maintaining a pressure in the chamber C, at the same time as a pressure and/or sealed environment can be maintained within the body of the patient.

Figure 105F:
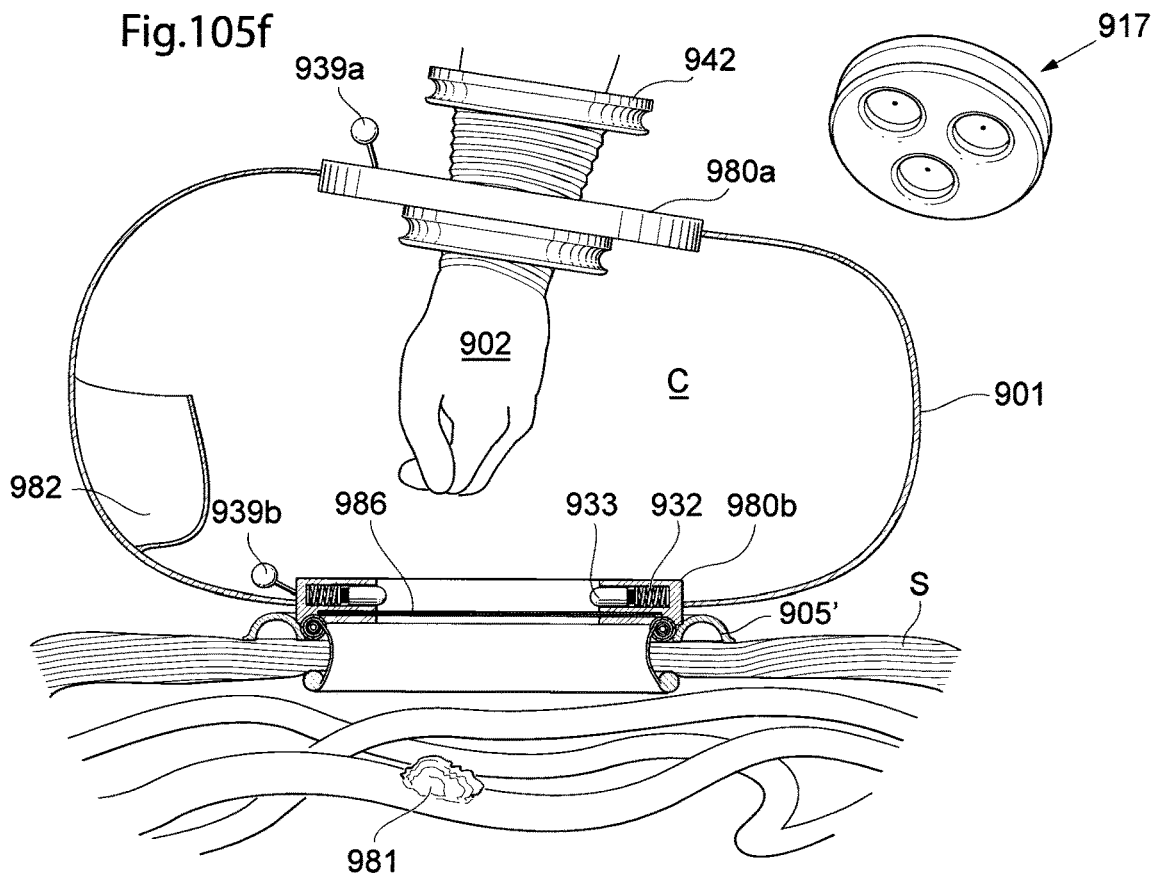

FIG. 105*f* shows the medical device when the glove inset 902 is removed and replaced by a wall port 917 comprising a plurality of ports. The multiport may be used for manipulating objects within the chamber C of the inflated medical device using surgical instruments, or within the body of the human patient, when the first and second couplings are connected (as shown in FIG. 105*g*).

Figure 105G:
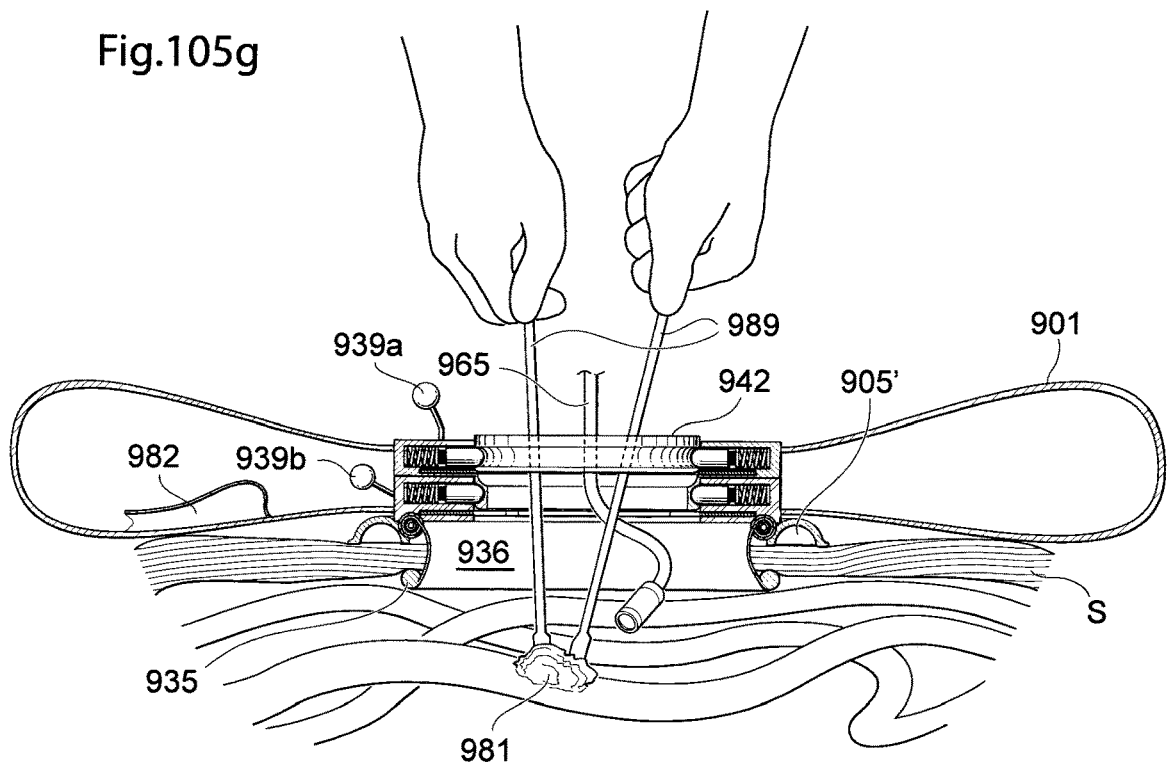

FIG. 105*g* shows the medical device when the upper and lower couplings 980*a*; 980*b* are connected such that surgical instruments 989 can be used for manipulating within the body of the patient. An endoscopic camera 988 may be provided in the port 917 for enabling visual inspection of the cavity within the patient's body. The process of cutting away a specimen 981 from the intestines of a patient in a laparoscopic way is shown in FIG. 105*g*.

Figure 105H:
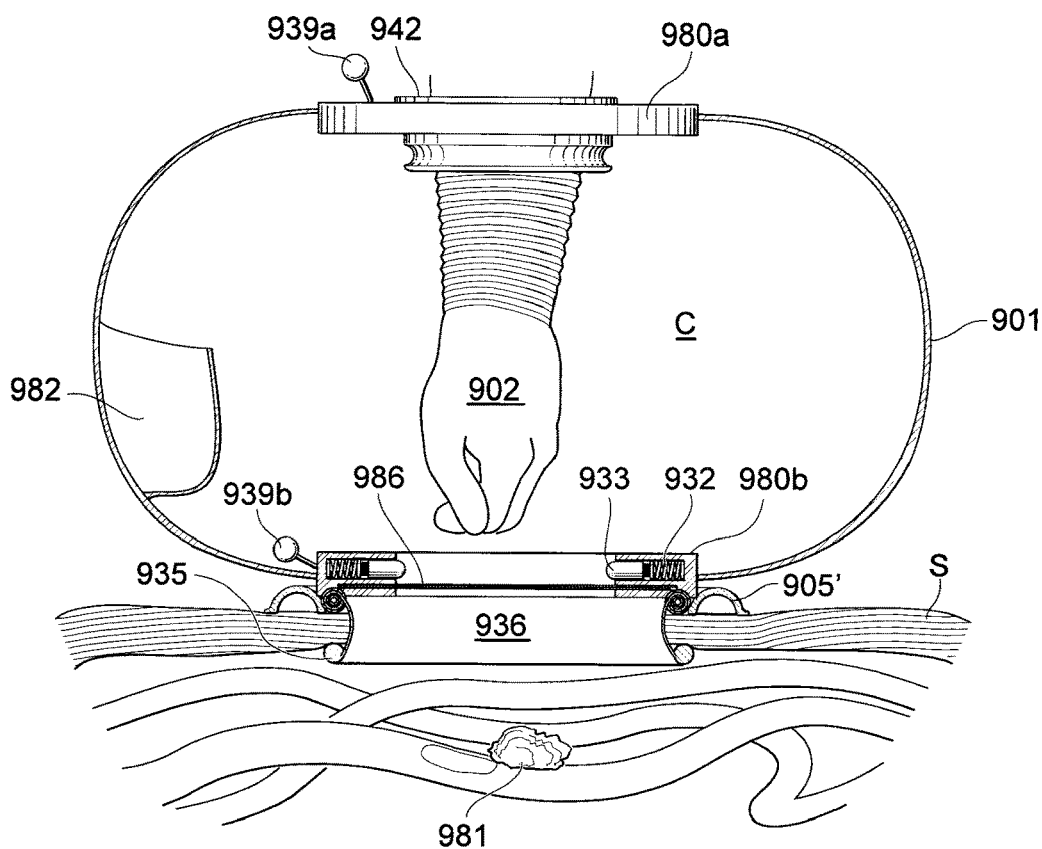

In FIG. 105*h*, the glove inset 902 has been fixated to upper coupling 980*a* to enable the surgeon to operate within the cavity of the patient's body and within the chamber C enclosed by the wall 901 of the medical device. By the glove inset 902 comprising a pleated portion, the glove surgeon is able to reach into the cavity of the patient for removing the specimen 981 cut loose from the intestines in prior steps.

Figure 105I:
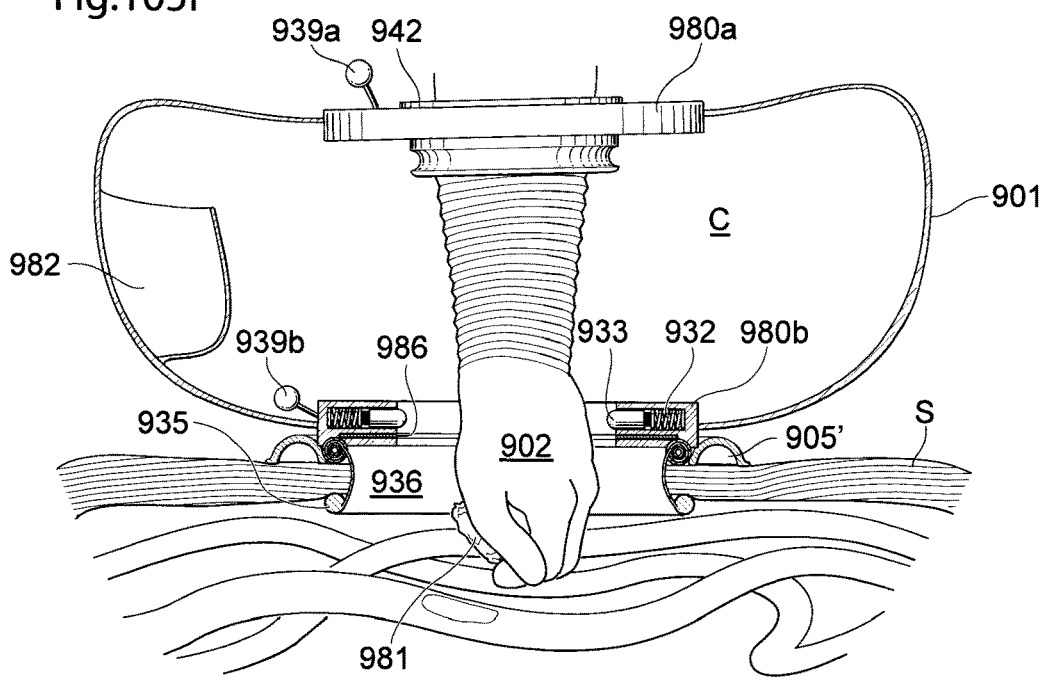

FIG. 105*i* shows that the wall of the medical device is collapsible such that the inset 942 comprising the glove 902 can be moved with relation to the lower coupling 980*b*, which gives the surgeon further freedom when removing the loose specimen 981 from the intestines of the patient.

Figure 105J:
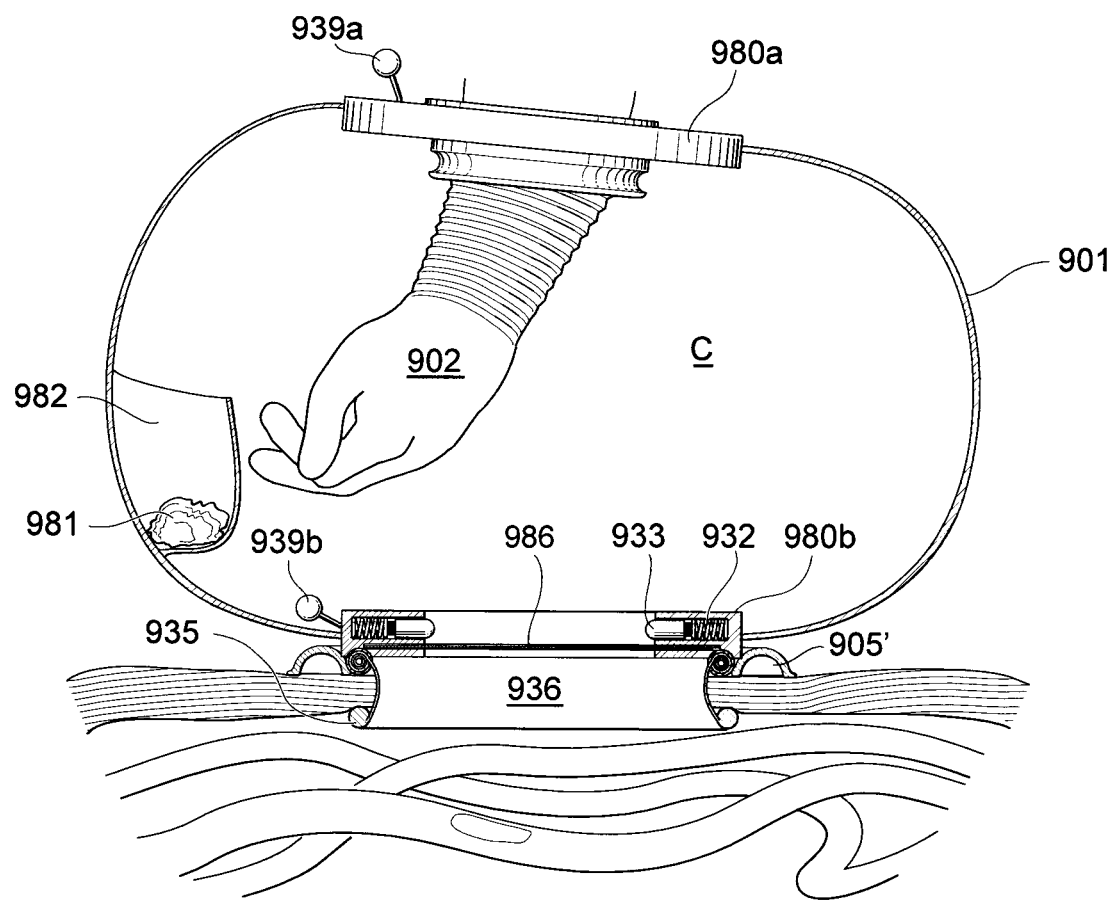

FIG. 105*j* shows the step of placing the removed specimen 981 in the pouch 982 such that the specimen 981 does not contaminate any other part of the body. The pouch may be a pouch 982 which could be closed for creating a pouch-chamber within the chamber C for isolating the removed specimen 981 within the chamber C.

Figure 105K:
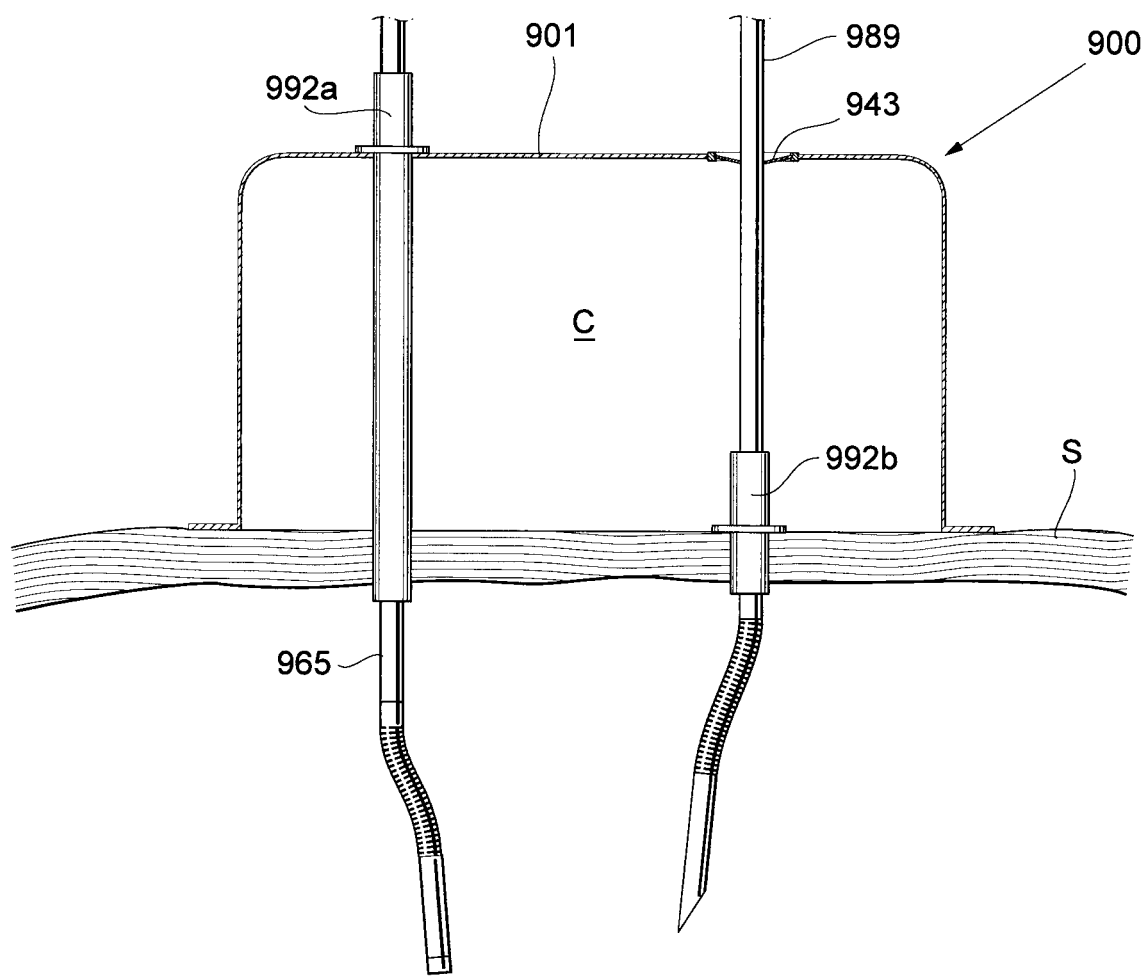
Figure 105I:
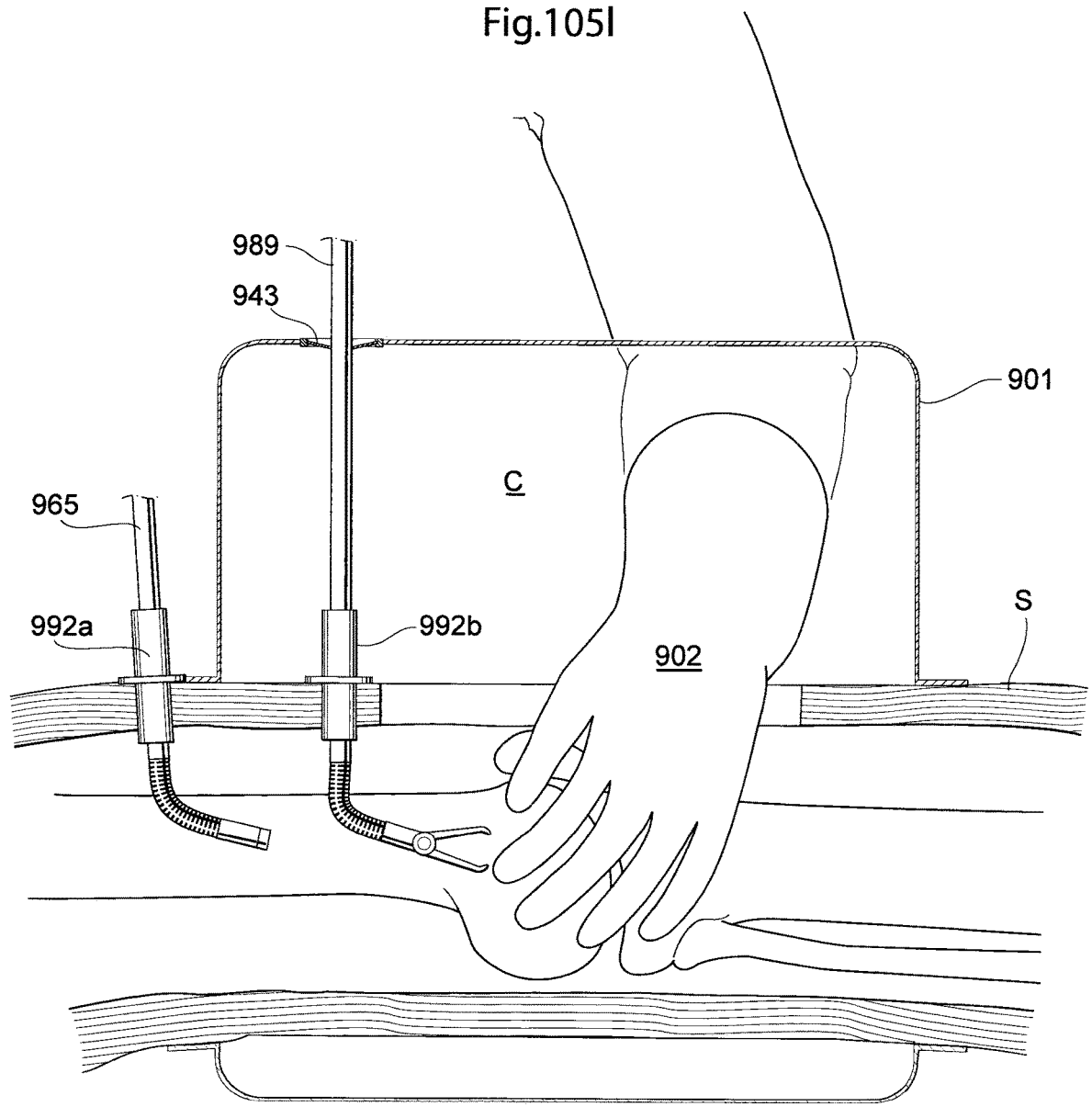

FIG. 105*k* shows examples of how trocars 992*a*; 992*b* may be used in combination with the medical device 900 according to any of the embodiments shown in FIGS. 96-105. The medical device 900 comprises a wall 901 placed on the patient's skin S and thereby enclosing a chamber C for creating a sealed environment. The medical device 900 comprises two trocars 992*a*; 992*b*, one 992*a* traveling through both the wall 901 of the medical device and the skin S of the patient and thus enabling endoscopic instruments 989 to be inserted into the patient through both the wall 901 of the medical device 900 and the skin S of the patient through one single trocar 992*a*. The other trocar 992*b* being placed inside the chamber C and enabling an endoscopic instrument to be inserted through the skin S of the patient. The endoscopic instrument 989 is in this embodiment inserted into the chamber C enclosed by the wall 901 through a membrane 943 in the wall 901 sealing against the tool 989.

FIG. 105*l* shows how the medical device shown in FIGS. 96-105 may be used. The medical device 900 comprises a glove 902 integrated in the wall 901 and a camera 965 placed in the skin outside of the medical device 900. The medical device 900 further comprises a trocar 992*b* placed inside the chamber C of the medical device 900, through an opening in the skin S of the patient and into an area of the knee of the patient. FIG. 105*l* schematically illustrates how the surgeon manipulates the knee in the chamber C using the glove 902.

Figure 105M:
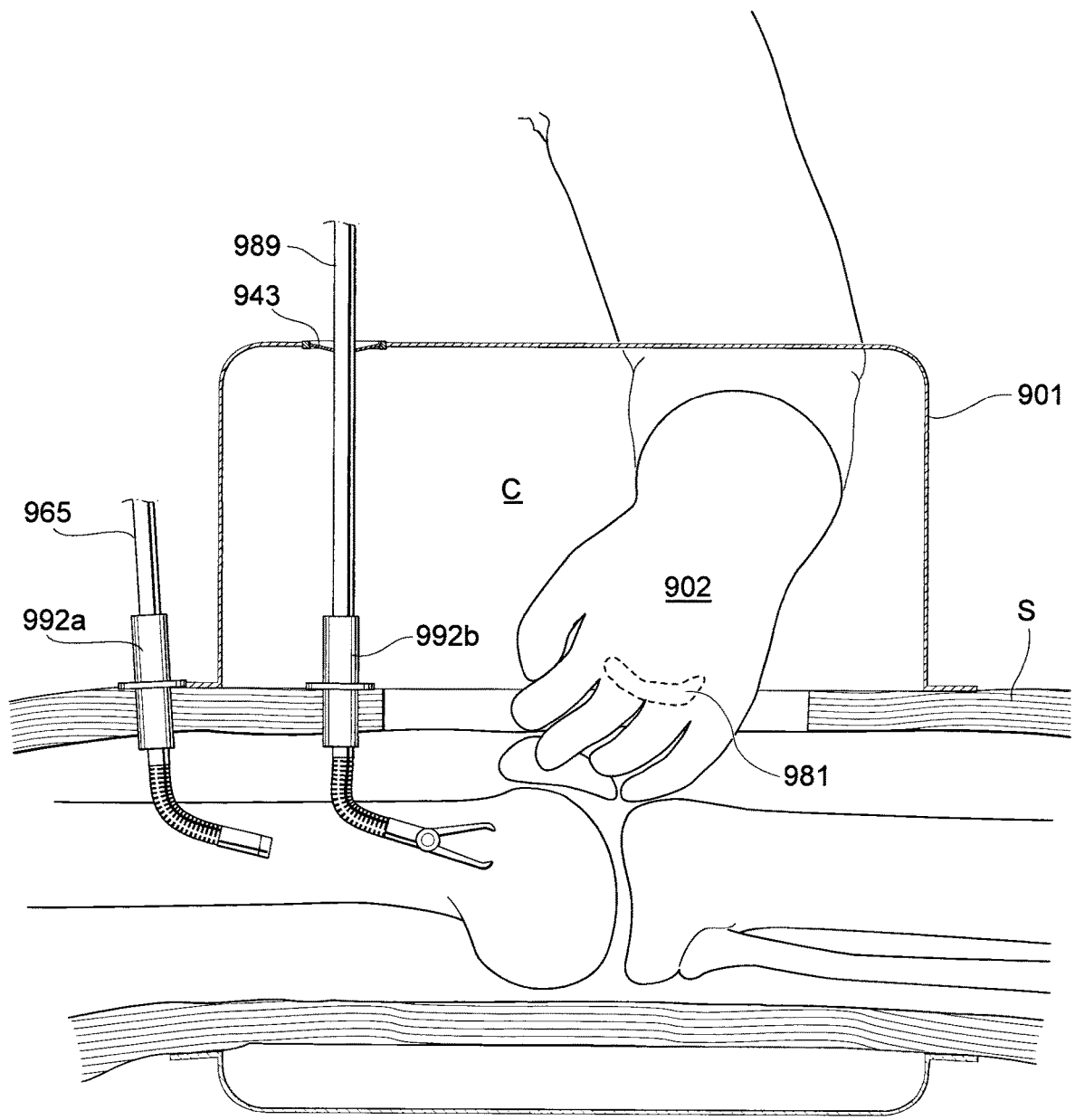
FIGS. 105m-105o shows an embodiment of the medical device in section, being fixated to the patient and used.
Figure 105N:
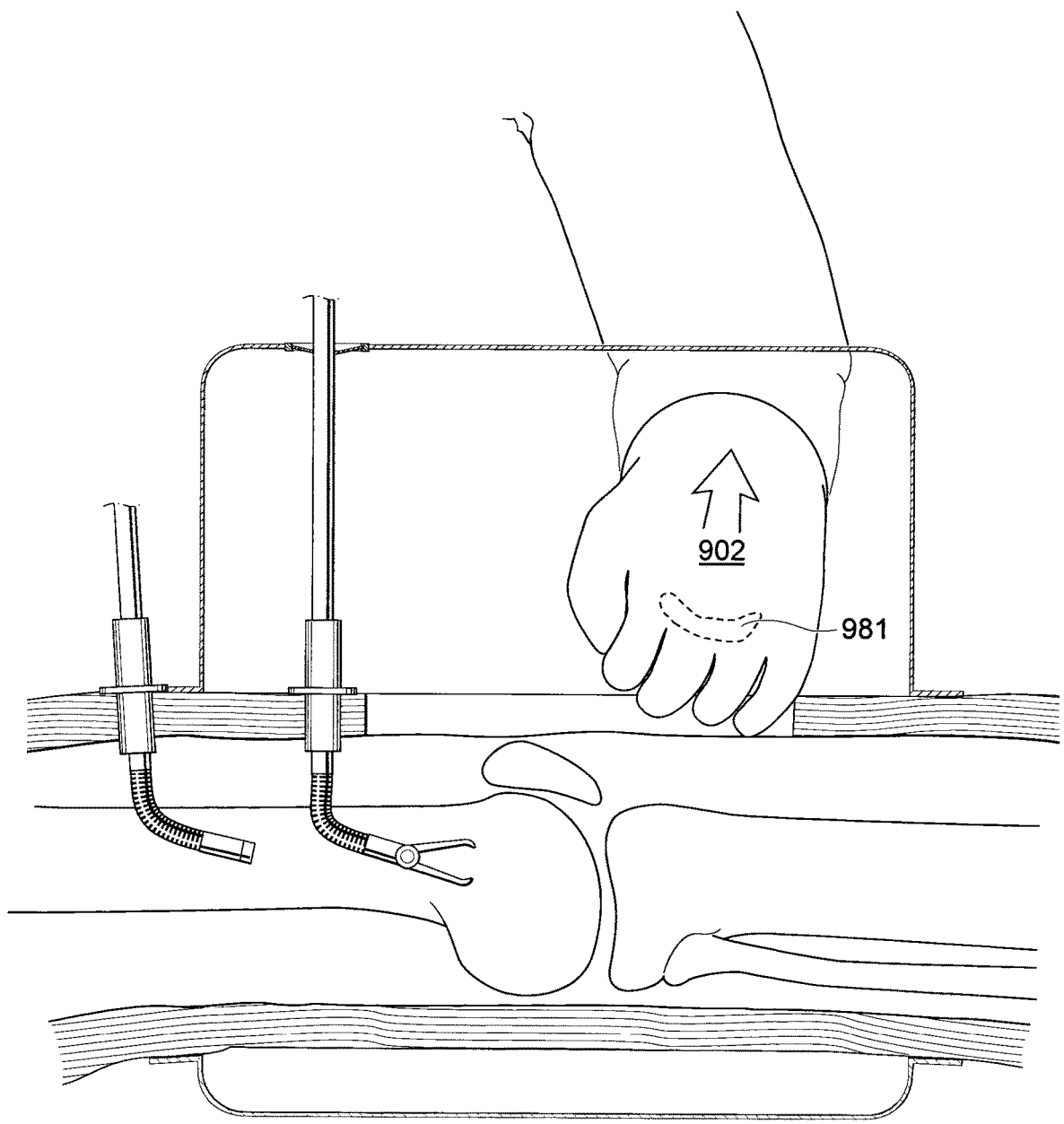

FIGS. 105*m*, 105*n* shows the medical device when the surgeon removes a specimen 981 from the knee of the patient using the glove 902 integrated in the wall 901 of the medical device 900.

Figure 105O:
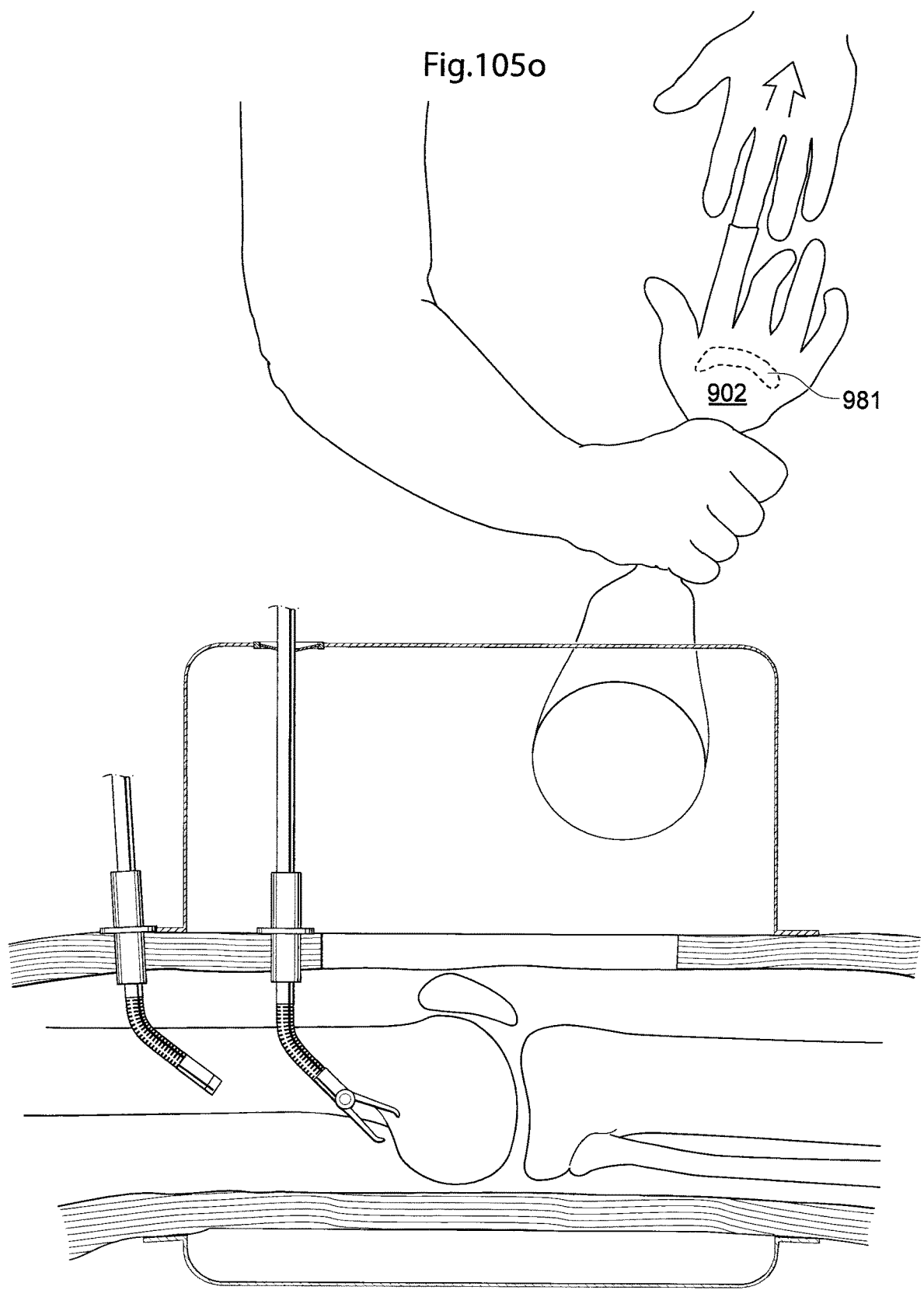

FIG. 105*o* shows the medical device, when the surgeon has turned the integrated glove 902 inside-out such that the specimen 981 can be contained within the integrated glove 902. By isolating the specimen 981 inside of the glove 902, the specimen 981 is removed both from the rest of the body of the patient and from the ambient environment, and thereby does not risk to infect any other portion of the patient's body or medical staff with any infectious disease.

Figure 106A:
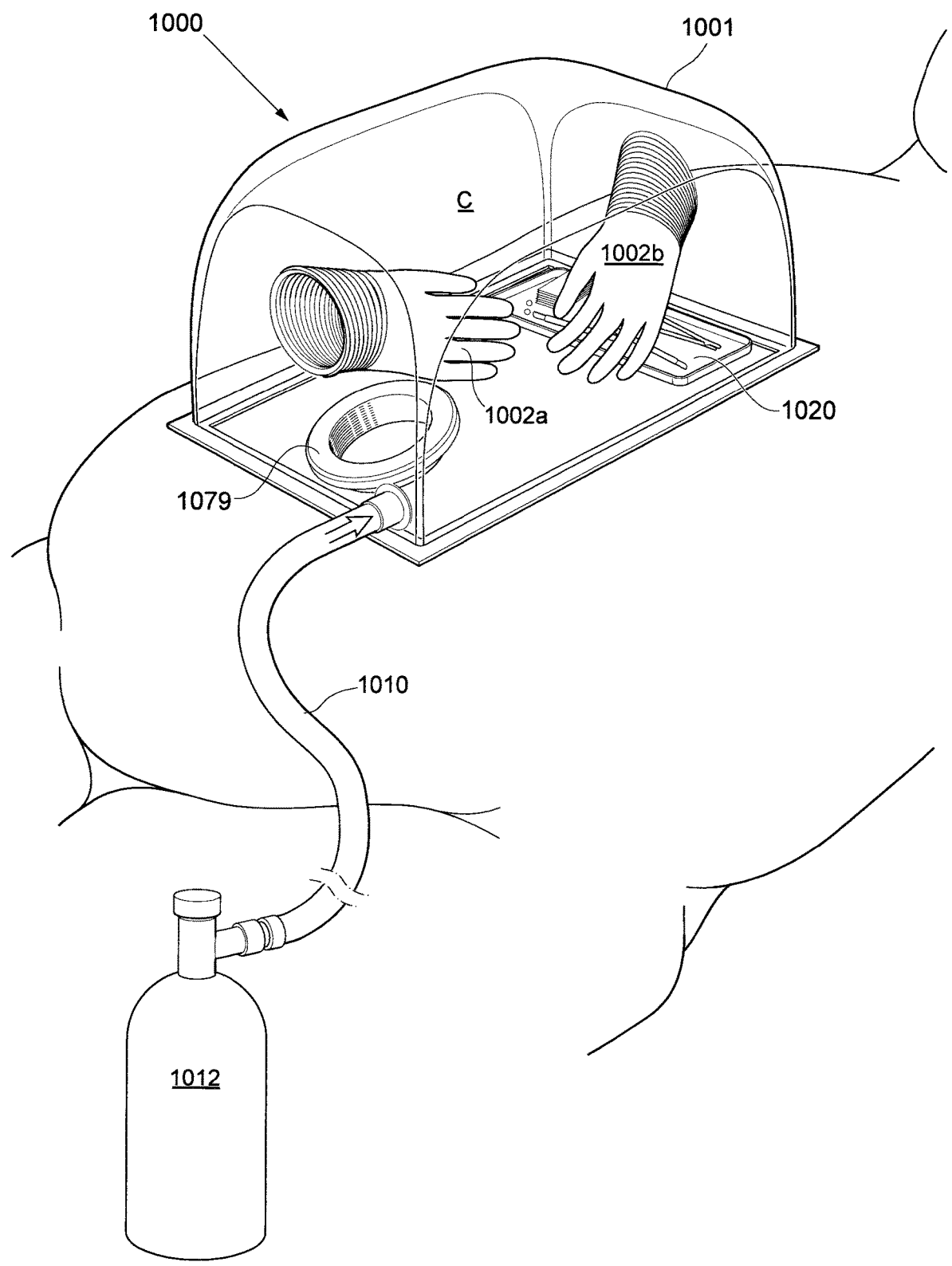
FIGS. 106a, 106b and 106c shows the process of placing a retainer in an incision made in the abdomen of the patient inside of a medical device.

FIG. 106*a* shows a medical device 1000 for performing surgical procedures. The medical device comprises a wall 1001 enclosing a chamber C for performing the surgical procedure. The chamber is adapted to be in fluid connection with a cavity within the patient's body via an incision in the skin of the patient. The medical device 1000 is adapted to be positioned in connection with the skin of the patient for creating a substantially airtight seal between the medical device and the skin of the patient prior to the incision in the skin of the patient creating the fluid connection between the cavity within the patient and the sealed environment. The medical device further comprises a retractor member 1079 adapted to be housed within the medical device 1000 prior to placing the medical device 1000 in connection with the skin of the patient. The retractor member 1079 comprises a first and second portion, the first portion is adapted to be positioned inside of the skin of the patient and the second portion is adapted to be positioned outside of the skin of the patient. The first and second portions are connected using a sealing connecting member, and the retractor member 1079 is a sealing device adapted to seal between the medical device 1000 and the skin and/or tissue of the patient. According to the embodiment shown in FIG. 106*a* the medical device 1000 further comprises a device/instrument mount 1020 for retaining medical device and/or instruments within the chamber. The instruments could be pre-placed in the chamber C before positioning the medical device 1000 in contact with the skin of the patient, and could be adapted for a specific operation. In alternative embodiments of the medical device 1000, the device/instrument mount 1020 could be excluded. In the embodiment shown in FIG. 106*a* the wall 1001 is collapsible and adapted to be inflated by a gaseous fluid for defining the sealed environment and for pressurizing the sealed environment with a pressure exceeding atmospheric pressure. The medical device as shown in FIG. 106*a* further comprises two integrated gloves 1020 for enabling manual manipulation within the chamber C.

Figure 106B:
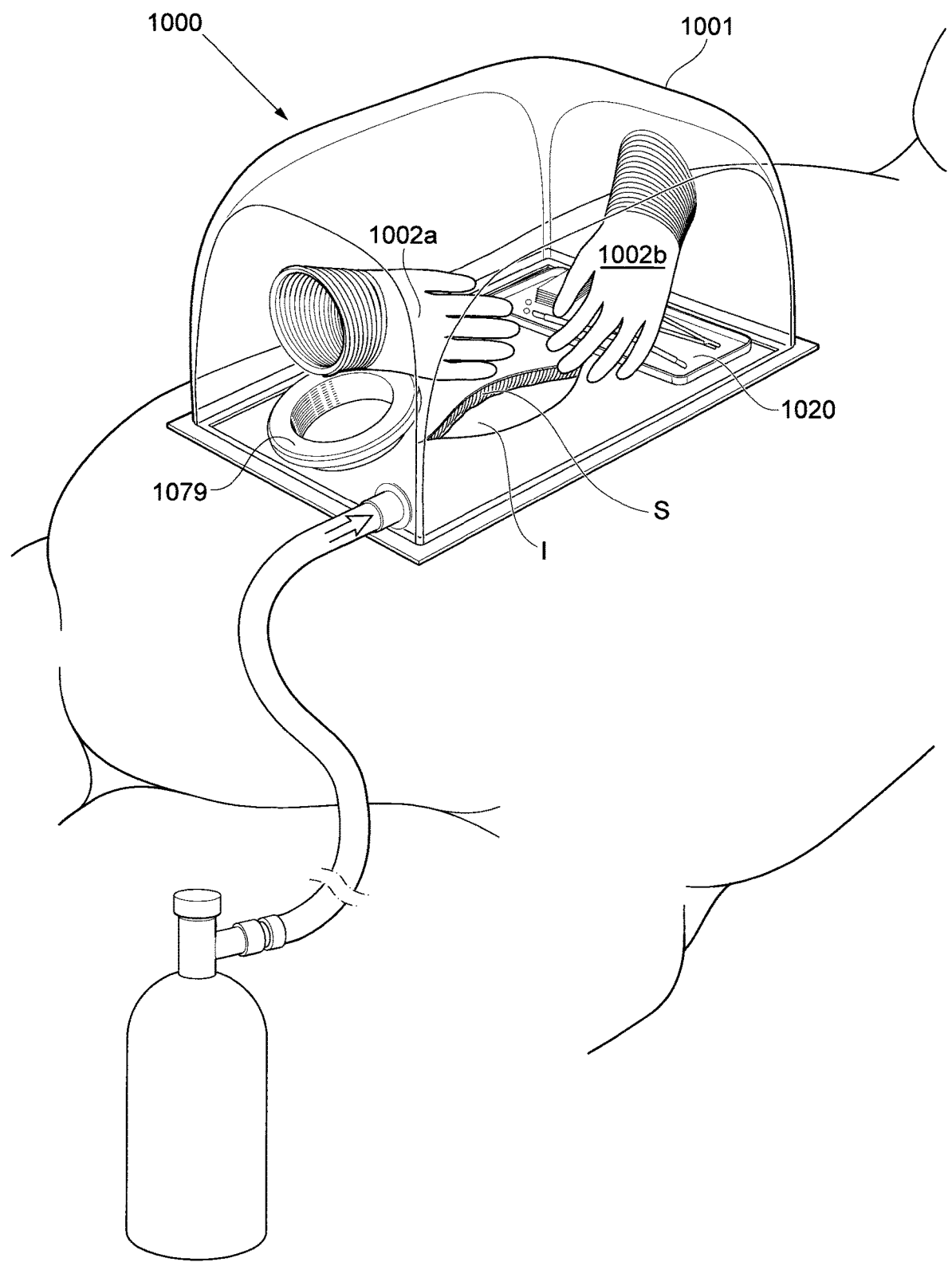

FIG. 106*b* shows the medical device 1000 when an incision in the skin S of the patient has been performed, for inserting the retractor member 1079 in the incision I. The retractor member 1079 when placed in the incision I, defines the fluid connection between the cavity within the patient and the chamber C of the medical device 1000.

Figure 106C:
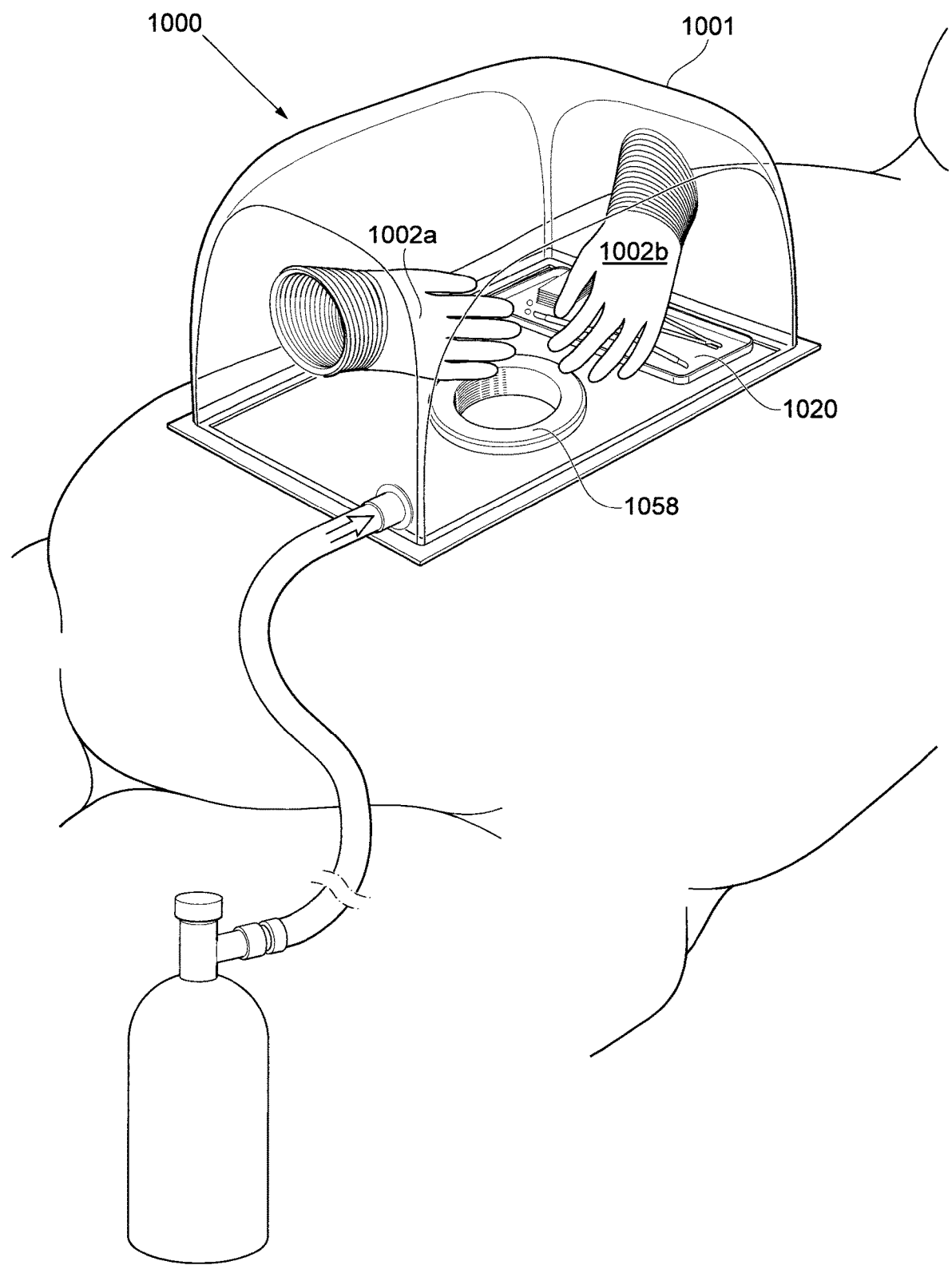

FIG. 106*c* shows the medical device 1000 when the retractor member 1079 has been placed in the incision in the skin of the patient such that the first portion is positioned on the inside of the skin of the patient and the second portion is positioned on the outside of the skin of the patient. The retractor member 1079 thus defines the fluid connection between the cavity within the patient and the chamber C of the medical device 1000.

Figure 107A:
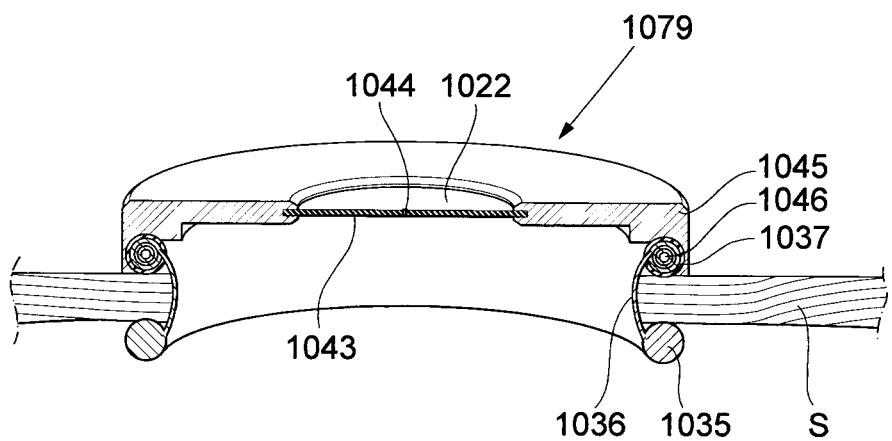
FIGS. 107a and 107b shows two different embodiments of a self sealing port.
Figure 107B:
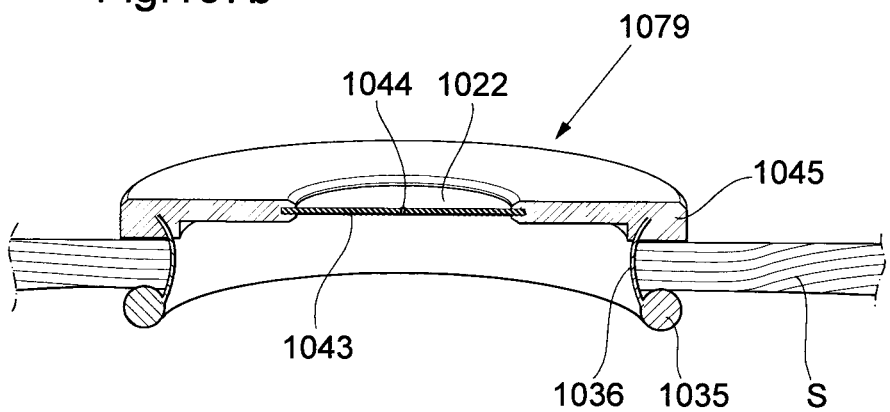

FIG. 107*a* shows the retractor member 1079 as for example disclosed with reference to FIGS. 106*a-c*. According to the embodiment shown in FIG. 107*a-b* the retractor member 1079 comprises a self sealing body port 1022 in a close-up, in section. The self sealing body port 1022 could be connected to the coupling, for example as disclosed with reference to FIGS. 111*a-c*, which in turn is connected to any of the medical device disclosed with reference to FIGS. 106*a-c*, or the self sealing body port 1022 could be fixated to the retractor 1079, as shown in FIGS. 107*a* and 107*b*. The self sealing body port 1022 comprises a self sealing membrane 1043 fixated to a rigid part 1045 of the self sealing port 1022. The self sealing membrane 1043 having a small self sealing hole 1044 centrally in the membrane 1043. The self sealing membrane 1043 is for example made from a gel-type material being elastic enough to enable a deformation large enough for a person's hand to pass through the small self sealing hole 1044 while still contracting enough to create an airtight seal between the sealed environment and the ambient environment. The medical device being fixable to the retractor 1079 comprising one intra body ring 1035 adapted to be positioned on the inside of the patients skin, and one ring 1037 adapted to be placed on the outside of the patients skin. Between the intra body ring 1035 and the ring 1037 adapted to be placed on the outside of the patients skin a retractor membrane 1036 is positioned which is adapted to exert a pressure of the cut surfaces of the incision for retracting the skin and thereby keeping the wound open. The retractor membrane 1036 is preferably made from a resilient of elastic polymer material. The ring adapted to be placed on the outside of the patients skin 1041 comprises an integrated roll up system 1049 which could be a spring loaded roll up system 1046 adapted to create a suitable pressure on retractor membrane 1036 for keeping the wound open.

FIG. 107*b* shows an alternative embodiment of the self sealing body port 1022, with the difference that the retractor membrane 1036 is made from a material elastic enough such that one end of the retractor membrane 1036 could be fixedly fixated to the rigid part 1045 of the port.

Figure 108A:
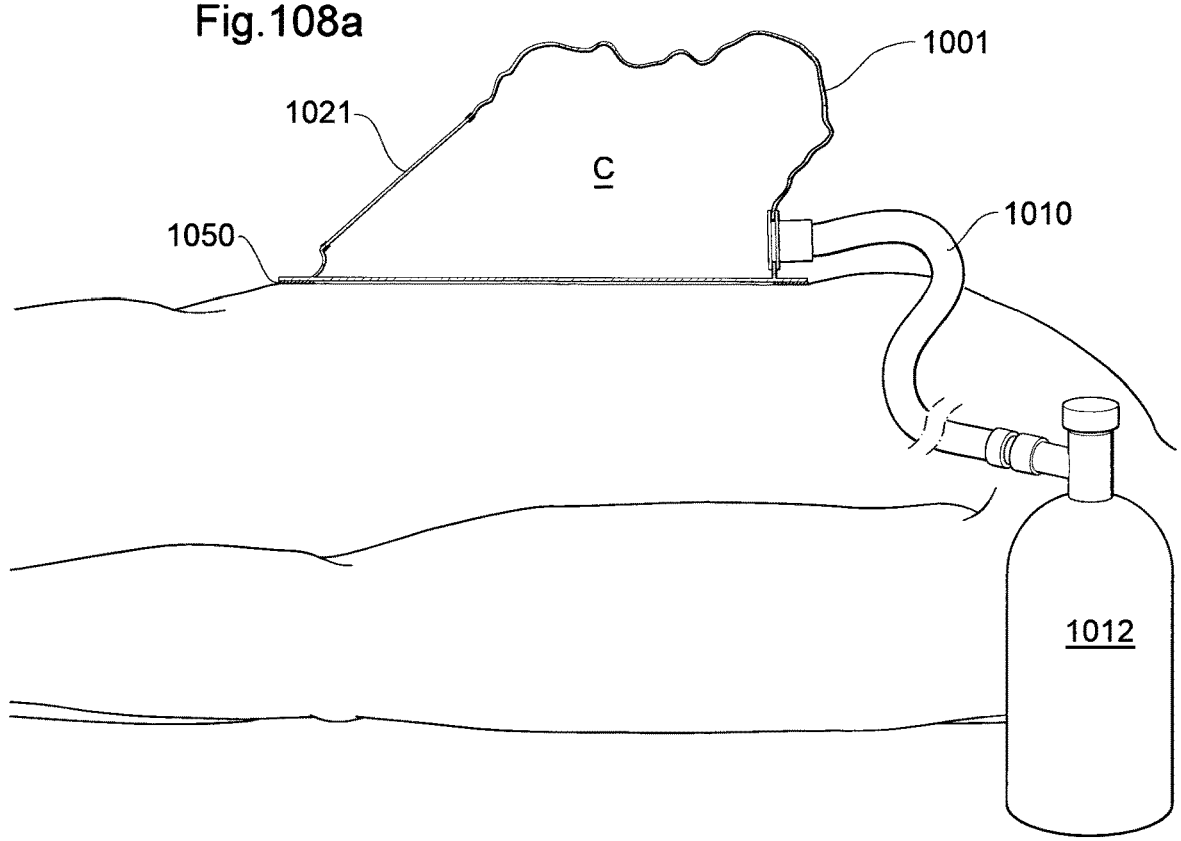
FIG. 108a shows the medical device when applied to the abdomen of a patient, in a deflated state.

FIG. 108*a* shows the medical device in an embodiment similar to the embodiment shown with reference to FIGS. 106*a-c*, with the difference that the medical device comprises a partially collapsible wall 1001 adapted to be inflated by a gaseous fluid for defining the chamber C. In the embodiment shown the inflation is performed by means of a pressurized fluid contained in a pressurized tank 1012, via a fluid conduit 1010. The medical device shown in FIG. 108*a* further comprises a non-collapsible transparent window 1021 for enabling viewing into the chamber C.

Figure 108B:
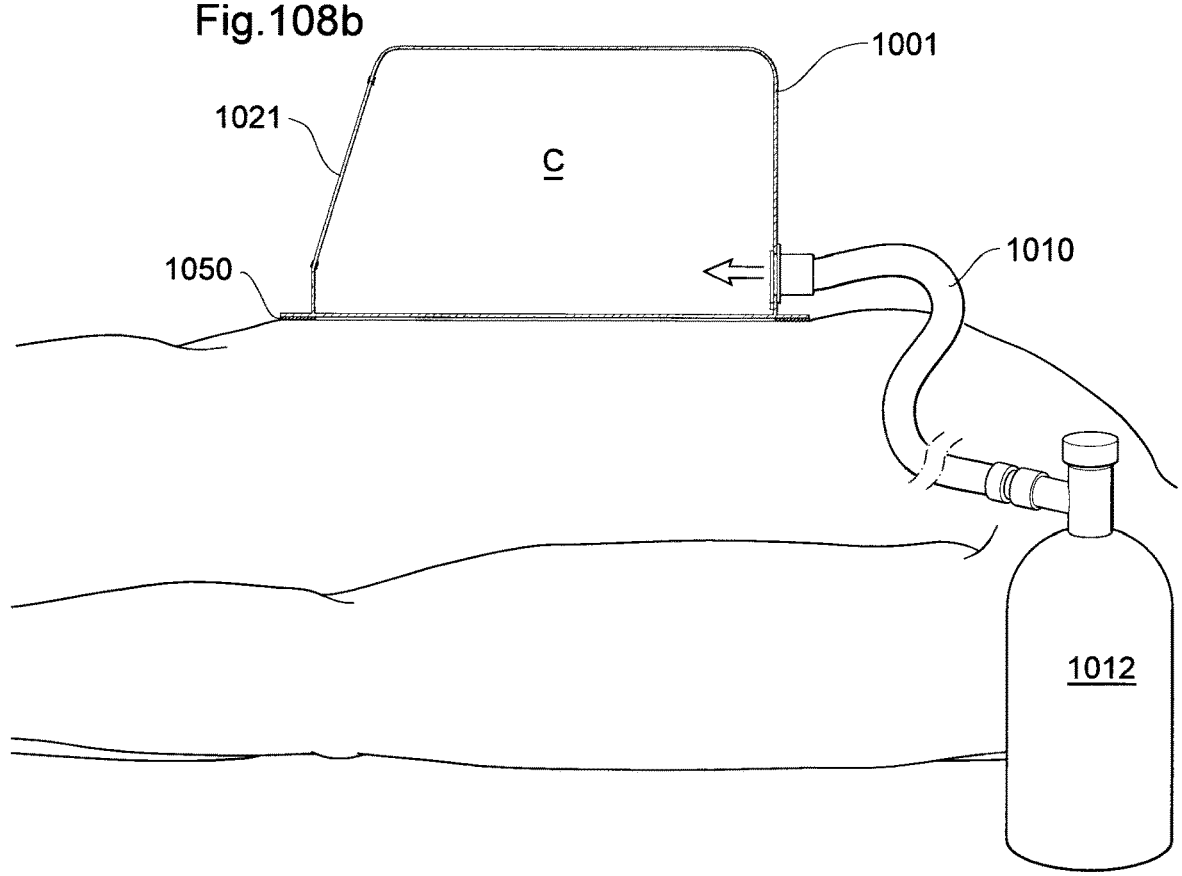
FIG. 108b shows the medical device when applied to the abdomen of a patient, in an inflated state.

FIG. 108*b* Shows the medical device of FIG. 108*a*, when the medical device 1000 has been inflated such that the transparent window 1021 is positioned by the wall 1001 being inflated, to enable viewing into the chamber C at the area of the surgical procedure from the outside thereof. In the embodiments shown in FIG. 108*a-b* the medical device 1000 is fixated to the patient by means of an adhesive surface 1050, which could be a portion of, or the entire portion contacting the skin of the patient. However, it is equally conceivable that the medical device is fixated to the skin of the patient by means of a pressure or vacuum sealing, as disclosed in relation to other embodiments herein.

Figure 109:
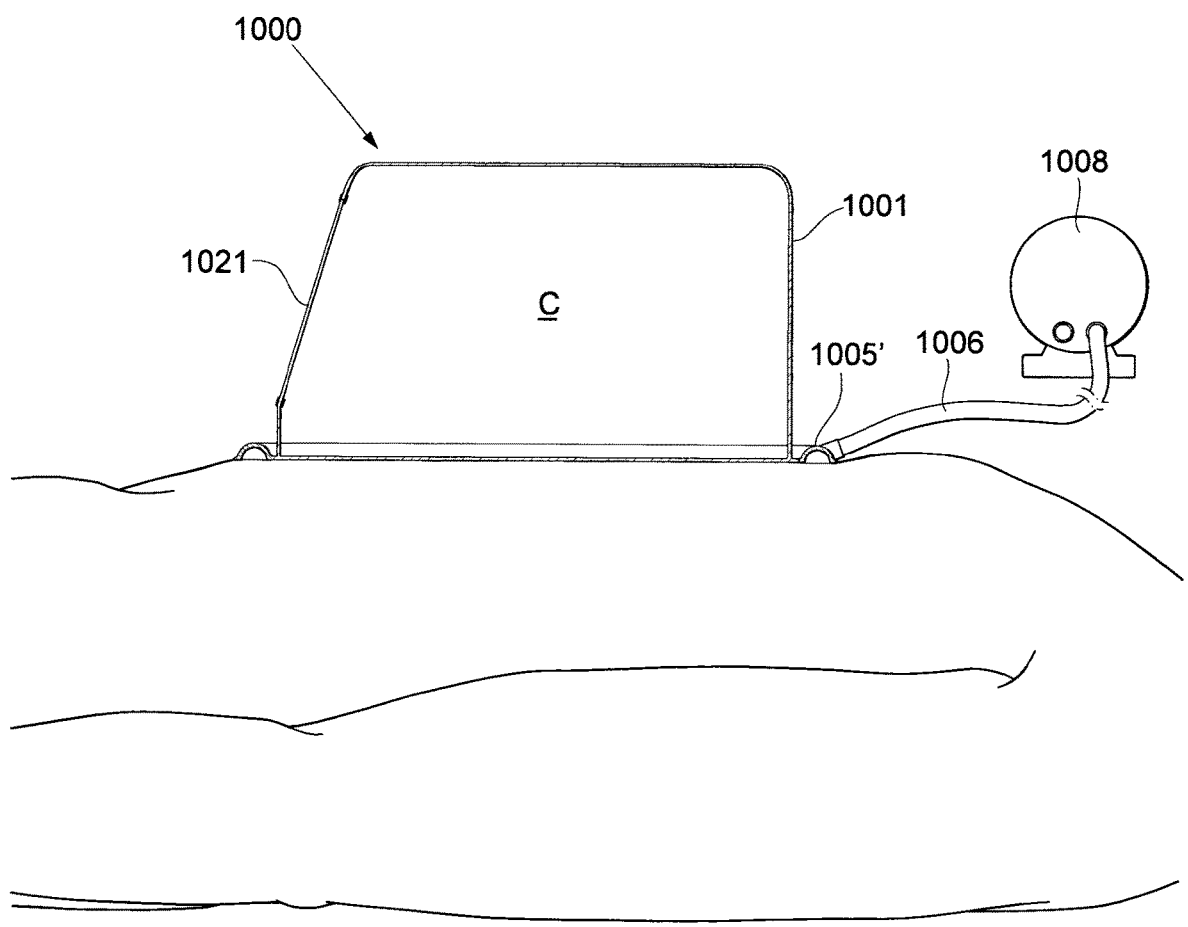
FIG. 109 shows an embodiment of the medical device comprising a vacuum sealing, when applied to the abdomen of a patient.

FIG. 109 shows an embodiment of the medical device 1000 similar to the embodiments of FIGS. 106*a*-108*c* for performing surgical procedures. The medical device comprises a wall 1001 enclosing a chamber C for performing the surgical procedure. The medical device comprises 1000 a vacuum sealing member 1005' for sealing between the medical device 1000 and the patient, wherein the vacuum sealing member 1005' is adapted to hold a pressure less than atmospheric pressure for creating the vacuum sealing between the skin of the patient and the medical device 1000. The vacuum sealing member 1005' is connected to a vacuum pump 1008 via a vacuum conduit 1006 creating a pressure less than atmospheric pressure in the vacuum sealing member 1005' and thereby creating the seal between the medical device 1000 and the skin of the patient. In some embodiments the vacuum sealing member 1005' could be assisted by an adhesive portion covering a portion of, or the entire portion of the medical device contacting the skin of the patient.

Figure 110:
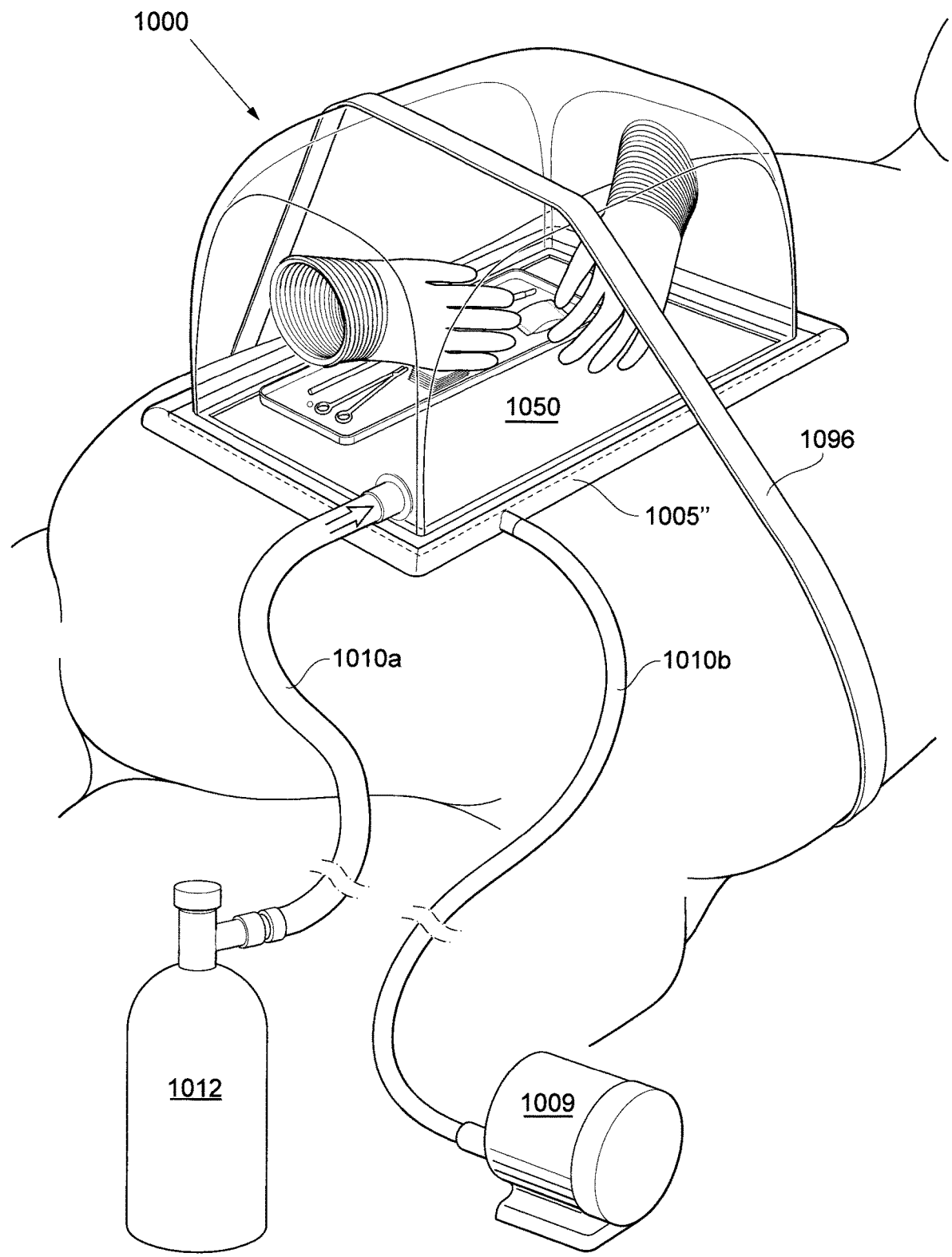
FIG. 110 shows an embodiment of the medical device comprising a pressure sealing.

FIG. 110 shows an embodiment of the medical device 1000 similar to the embodiments of FIGS. 106*a*-109 for performing surgical procedures. The difference in the embodiment disclosed in FIG. 110 is that the medical device 1000 additionally comprises a pressure sealing 1005" adapted to be inflated for pressing against the skin of the patient and thereby sealing between the chamber within the medical device and the ambient environment. The pressure sealing 1005" is inflated though a fluid conduit 1010 connected to a pressure source, in this embodiment a fluid pump 1009. In this embodiment, the medical device 1000 is fixated to the patient by means of an adhesive surface 1050 adapted to withstand the force created by the inflated pressure sealing 1005", In addition, the adhesive is assisted by a holding member 1096 pressing the medical device 1000 against the skin of the patient. The holding member or band 1096 could be required if the pressure needed to seal between the skin if the patient and the medical device needs to be particularly large, which for example could depend on the positioning of the medical device 1000. The use of a fluid pump 1009 as pressure source for the sealing 1005" instead of a pressurized tank, as disclosed in other embodiments herein, could be an advantage if the pressurized fluid in the tank is scarce or non-existing.

Figure 111A:
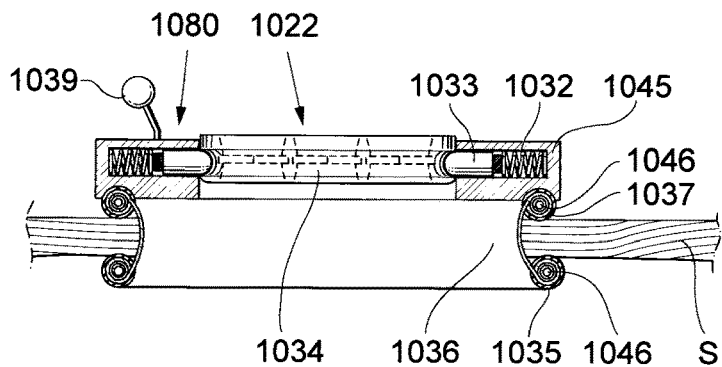
FIGS. 111a, 111b and 111c shows an embodiment of a coupling, in section.

FIG. 111*a* shows an embodiment of a detachable body port 1022 mounted to a retractor 1079, which could be used as sealing device (for example described with reference to FIGS. 106*a-c*). The detachable port arrangement of FIG. 111*a* could be positioned in the chamber of the medical device 1000. The port arrangement includes an intra body ring 1035 adapted to be placed at the inside of the patients skin around an incision, and an outer ring 1037 adapted to be placed on the outside of the patients skin 1041 around the incision. Between the intra body ring 1035 and outer ring 1037 an annular retractor membrane 1036 is positioned adapted to exert a pressure on the skin or human tissue at the incision to seal between the rings and the skin or human tissue and additionally for retracting the skin and thereby keep the incision open. The retractor membrane 1036 is preferably made from a resilient or elastic polymer material. The outer ring 1037 comprises an integrated roll up system 1046, which may be spring loaded and adapted to create a suitable pressure on retractor membrane 1036 to keep the incision open.

The port arrangement shown in FIG. 111*a* also includes a coupling 1080 having a rigid annular seating 1045 attached to the outer ring 1037, spring loaded latching members 1033 arranged in radial bores in the seating 1045 and a hand lever 1039 connected to the latching members 1033 to enable retraction thereof against the action of springs 1032. The port arrangement further includes a self sealing body port 1022 held by the coupling 1080. The body port 1022 comprises a disc-shaped self sealing membrane 1043, FIG. 111*b*, fixated to a rigid ring having an outer circumferential recess or groove 1034 that receives the latching members 1033 of the coupling 1080. The self sealing membrane 1043 has a small self sealing hole 1044, FIG. 111*b*, centrally in the membrane 1043. For example, the self sealing membrane 1043 may be made from a gel-type material being elastic enough to enable a deformation large enough for a person's hand to pass through the small self sealing hole 1044 while still contracting enough to create an airtight seal between the chamber C and the outside environment.

The coupling 1080 described above enables quick exchange of the body port 1022. Thus, the surgeon may release the body port 1022 from the port arrangement by simply pulling the hand lever 1039 so that the protruding latching members 1033 disengage from the recess or groove 1034 of the body port 1022, whereby the port 1022 can be removed.

Figure 111B:
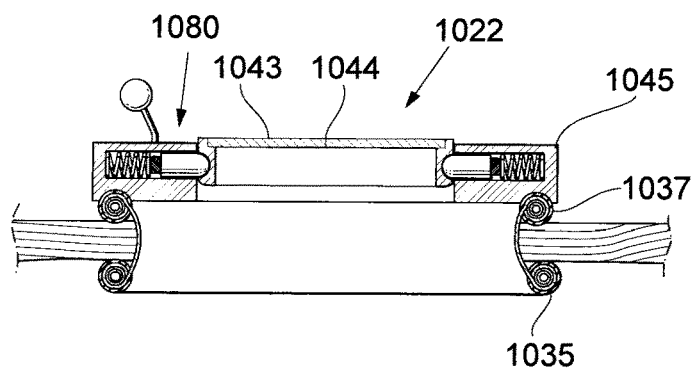

FIG. 111*b* is a cross-sectional view of the port arrangement shown in FIG. 111*a*, to more clearly illustrate the body port 1022 with its self sealing membrane 1043 and small hole 1044.

Figure 111C:
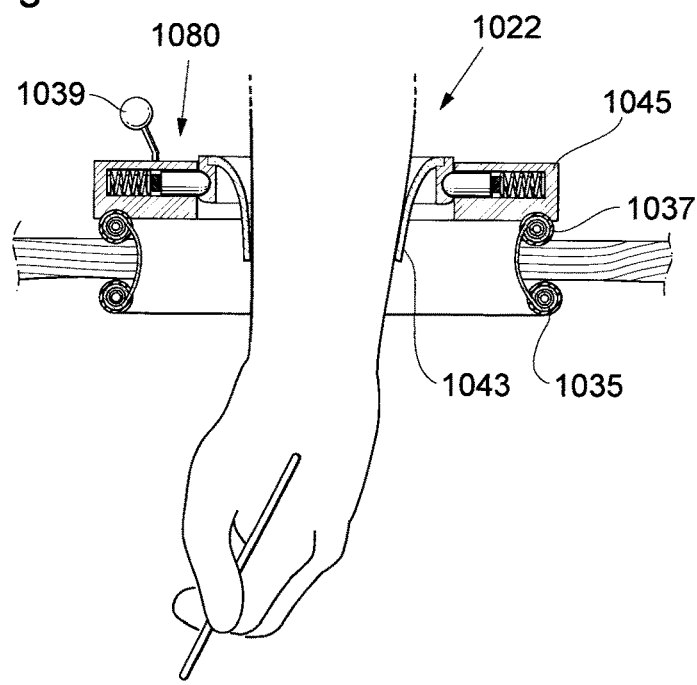

FIG. 111*c* shows the self sealing body port 1022 when the hand of a surgeon is placed through the hole 1044 in the membrane 1043 and thus enabling manual manipulation within the body of the patient.

Figure 112:
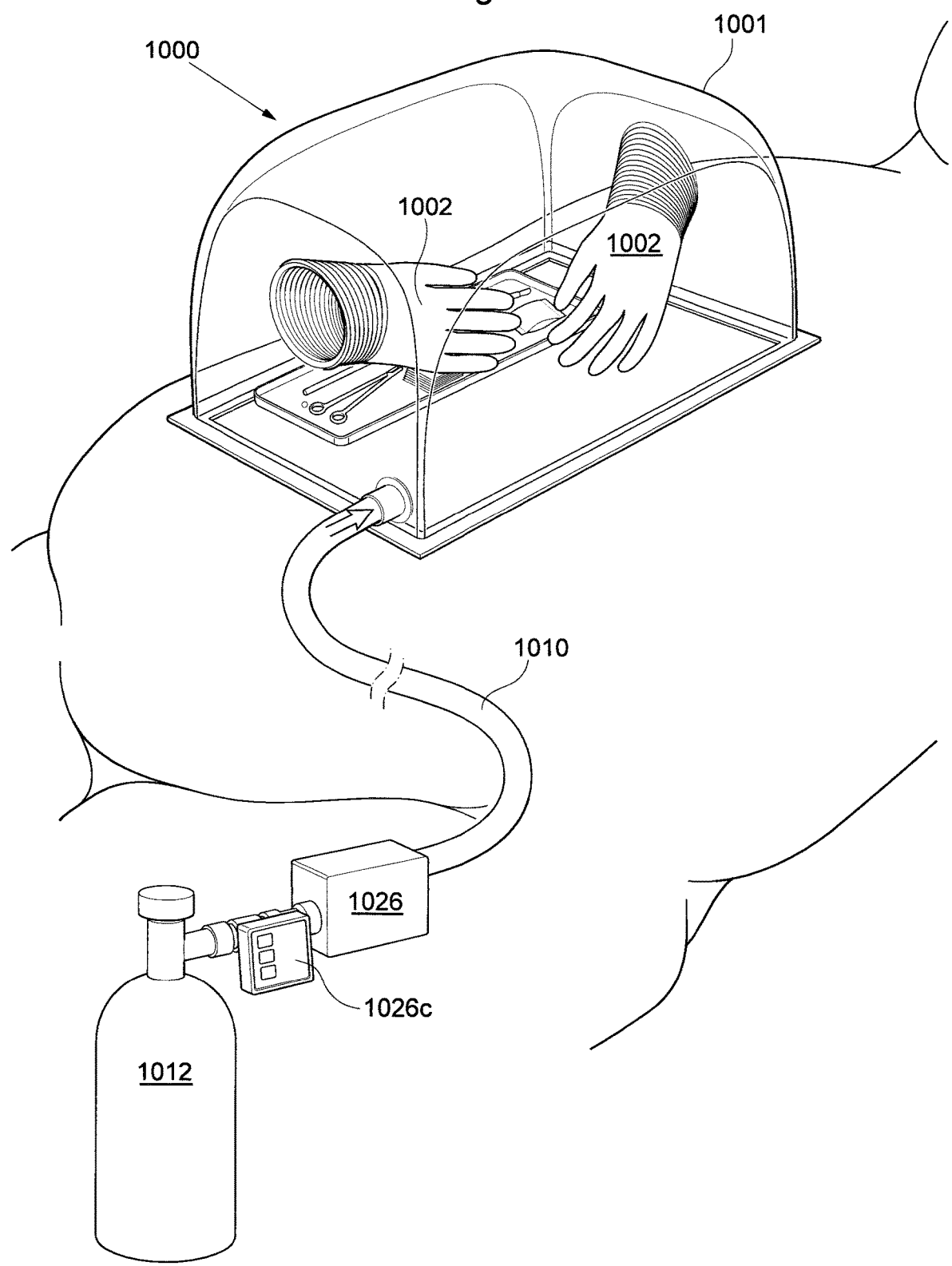
FIG. 112 shows an embodiment of the medical device, when positioned on the abdomen of a patient.

FIG. 112 shows the medical device as shown in FIGS. 106-111 with the addition that the embodiment comprises a sterilizing unit 1026 adapted to sterilize the gaseous fluid entering the medical device 1000. In the embodiment disclosed herein, the gaseous fluid entering the medical device 1000 originates from a pressurized tank 1012 and could be pre-sterilized, however, in other embodiments, it is conceivable that the gaseous fluid is the surrounding air which is pressurized (such as further disclosed with reference to FIG. 113). In the embodiments where the surrounding air is used to inflate the medical device 1000 and constitute the operating environment this air needs to be properly sterilized. The medical device 1000 further comprises a tempering unit 1026*c* which could be provided to heat or cool the gaseous fluid inflating the medical device 1000. In cases when the surrounding environment is cold the tempering unit 1026*c* could be used to raise the temperature of the camber to provide beneficial operating circumstances both for the patient and for the surgeon. In cases when the surrounding environment is hot, the tempering part of the system 1026*c* could be used to lower the temperature of the sealed environment both to provide beneficial operating circumstances, both for the patient and for the surgeon, and for providing a temperature inhibiting bacterial and viral infections. The tempering unit 1026*c* could comprise a temperature regulating device for setting the required temperature.

Figure 113:
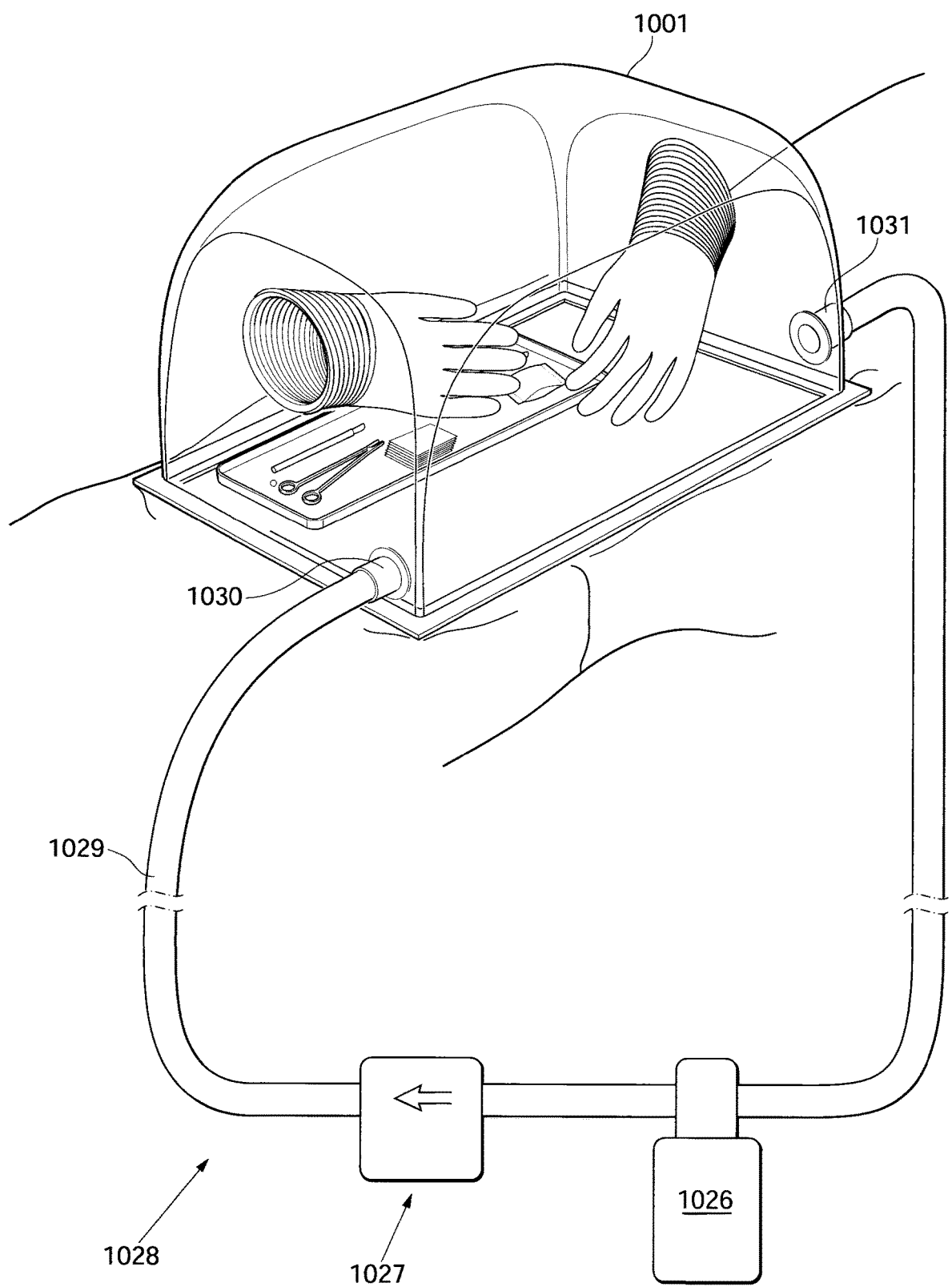
FIG. 113 shows an embodiment of the medical device, comprising a fluid circulating system, when positioned on the abdomen of a patient.

FIG. 113 shows a medical device similar to the embodiment disclosed in FIG. 112 but comprising a system 1028 for circulating a fluid through the sealed environment of the medical device. The system comprises a fluid conduit 1029 connected at an inlet 1030 placed in the wall 1001 for supplying fluid to the chamber, and an outlet 1031 for draining the fluid from the chamber. The fluid is circled by means of a pumping unit 1027 and is circled via a sterilizing/filtering/tempering/humidification unit 1026 adapted to remove impurities, sterilize, temper and humidify the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 114A:
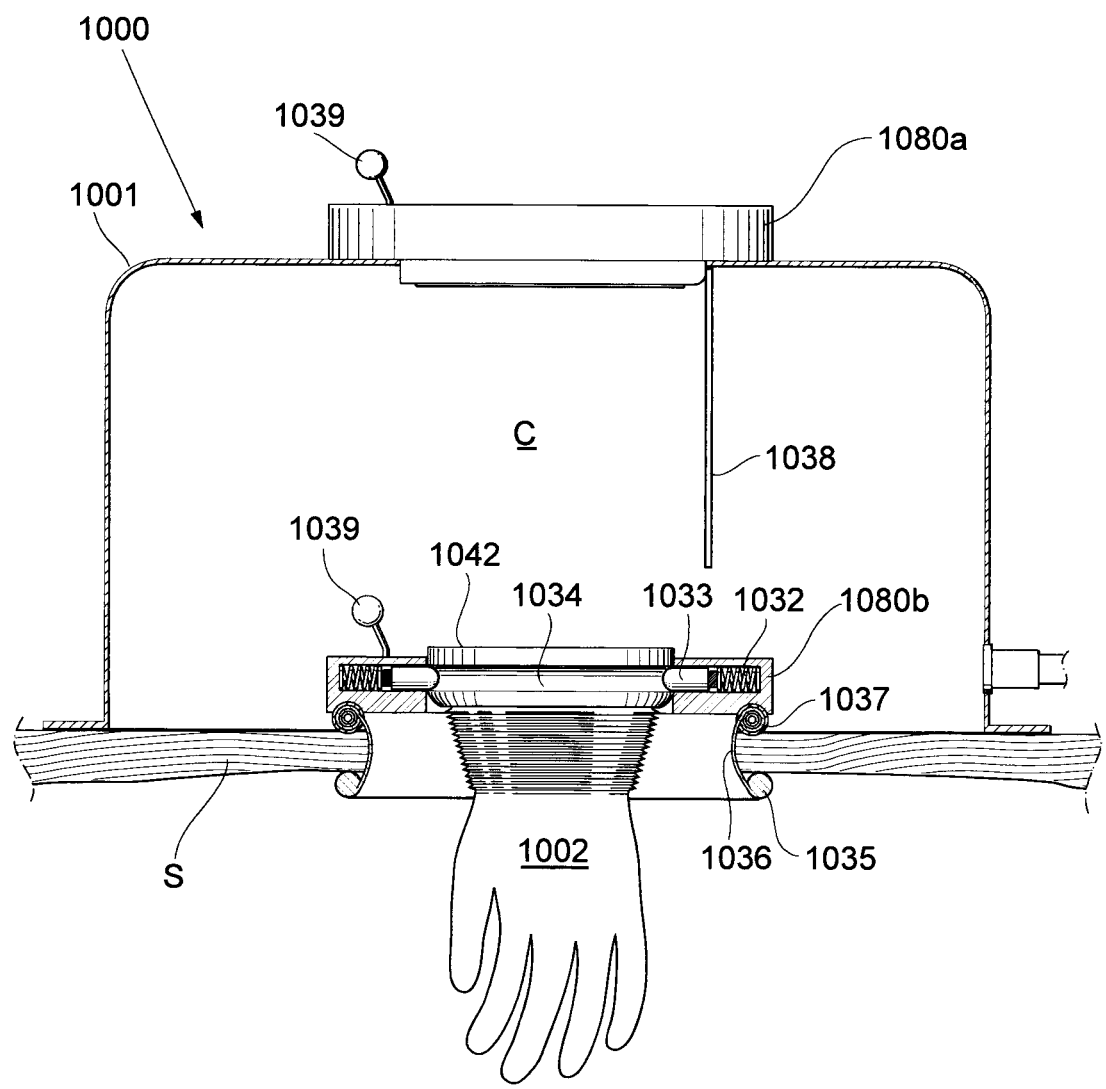
FIG. 114a shows an embodiment of the medical device in section.

FIG. 114*a* shows a modification of the embodiment disclosed with reference to FIGS. 106*a-c* in which the medical device further comprises an upper 1080*a* and a lower 1080*b* coupling for fixating ring shaped objects which for example could be insets or ports, where insets for example could be an inset 1042 comprising a surgical glove 1002, or an inset comprising a device/instrument mount. Ports could be endoscopic ports or hand access ports, such as the self sealing port disclosed with reference to FIGS. 4*a* and 4*b*. The coupling comprises a releasing lever 1039 for releasing the object. The lever 1039 is connected to latching protruding members 1033 which are spring loaded 1032 from the rear in order to secure the recess or groove 1034 of the object. In the embodiment disclosed in FIG. 114*a*, the inset 1042 fixated to the lower coupling 1080*b* comprises a surgical glove 1002 enabling manual manipulation within the body of the patient. The medical device shown in FIG. 114*a* further comprises a valve member 1038 adapted to close the opening in the upper coupling 1080*a*, when the upper coupling 1080*a* is not in use. The upper coupling 1080*a* is for example used for manual manipulation and preparation within the medical device 1000, such that could be needed for preparing or changing an instrument or preparing an implant for implantation. The lower coupling 1080*b* is for example used for endoscopic manipulation within the body of the patient, or manual manipulation for e.g. removing a specimen or positioning an implant.

Figure 114B:
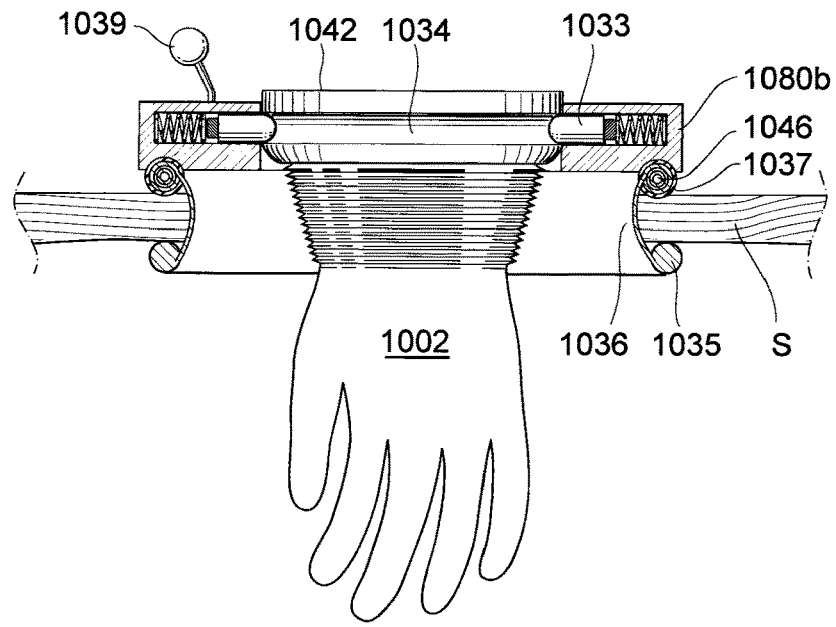
FIG. 114b shows a coupling fixated to the skin of a patient, in section.

FIG. 114b shows the coupling 1031b as disclosed in FIG. 111a-111c and FIG. 114a in further detail when an inset in the form of a surgical glove 1002 is fixated to the lower coupling 1080b. The retractor system comprising the intra body ring 1035 and the ring 1037 adapted to be placed on the outside of the patients skin S further comprises a retractor membrane 1036 positioned such that it exerts a pressure on the cut surfaces of the incision for retracting the skin S and thereby keeping the wound open. The retractor membrane 1036 could be rolled into a roll 1046 inside of the ring 1037 adapted to be placed on the outside of the patients skin S for tightening the retractor membrane 1036 such that the wound is kept open.

Figure 114C:
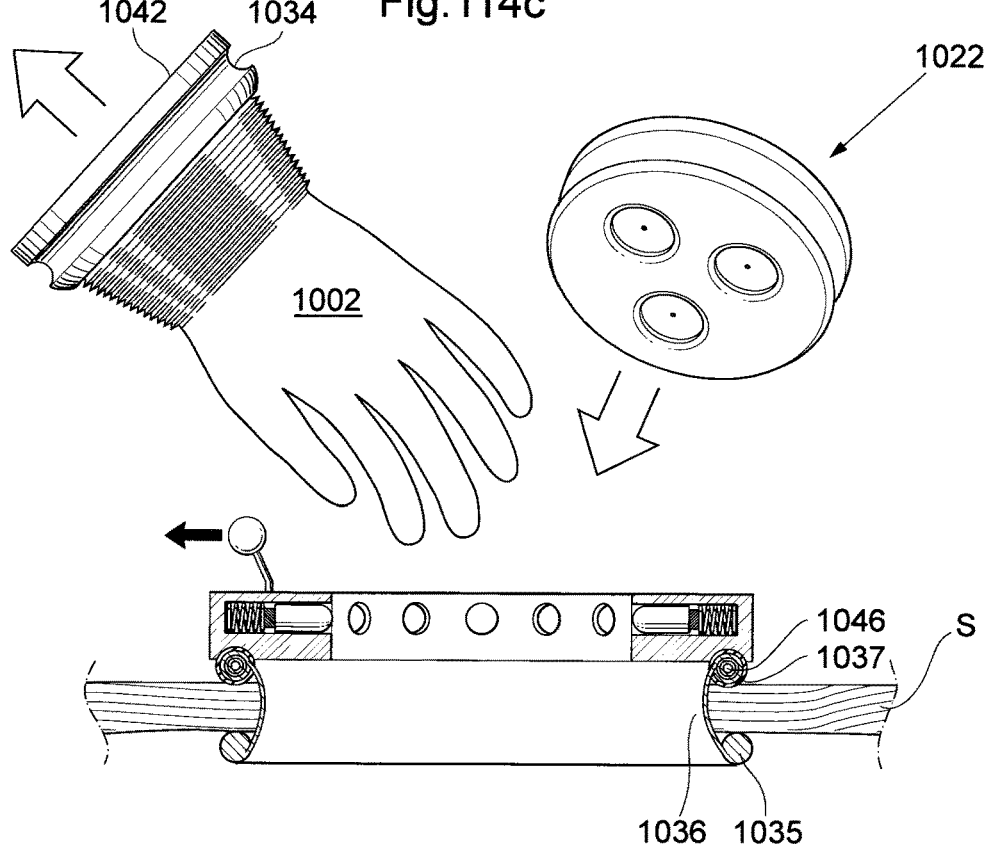
FIG. 114c shows the coupling of FIG. 114a when objects are being exchanged.

FIG. 114c shows the changing of objects in the coupling from an inset 1042 comprising a surgical glove 1002 to a body port 1022 in the form of a multiport. To be able to quickly switch from an endoscopic system to a hand access or manual manipulation system could be of major importance if complications arise during the procedure and could remove the need for a traditional conversion from endoscopic to open surgery, a conversion which inevitably causes problems increasing the risk of complications and/or post-operative care. In other embodiments the laparoscopic ports and surgical gloves could additionally be exchanged for holding devices, for example holding instruments or implants.

Figure 114D:
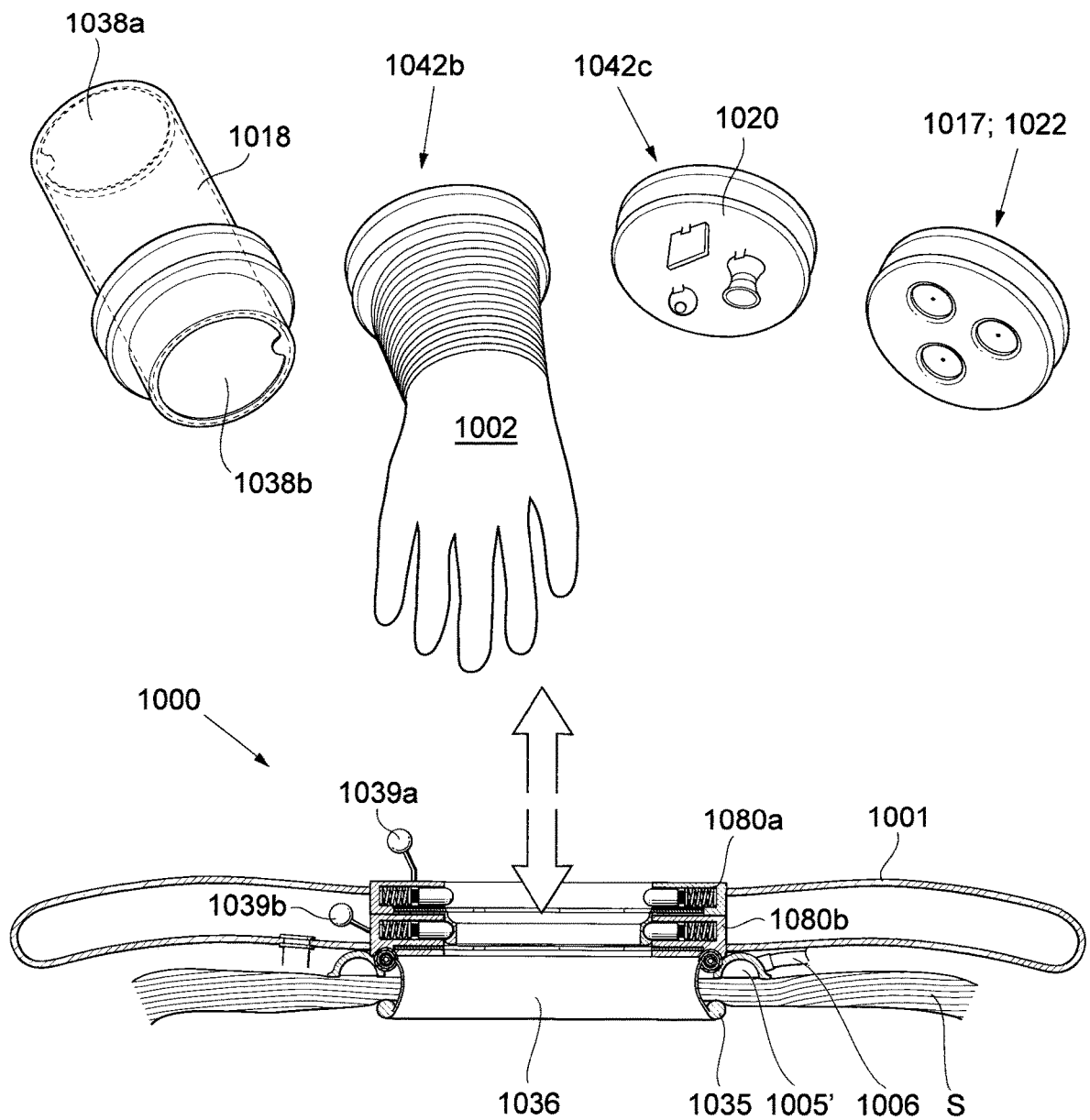
FIG. 114d shows an embodiment of the medical device, in section.

FIG. 114d shows the medical device 1000 adapted to be at least partially placed in an incision cut in a patient's body. The medical device 1000 comprises an upper coupling 1080a and lower coupling 1080b adapted be interconnected to form an interconnected coupling. The upper coupling 1080a is adapted to be disconnected from the lower coupling 1080b, and the upper coupling 1080a is connected to a first portion of a flexible wall 1001, and the lower coupling 1080b is connected to a second portion of the flexible wall 1001. The flexible wall 1001 forms a chamber C in which a sealed environment can be maintained, the chamber is heavily enlarged when the upper coupling 1080a is disengaged from the lower coupling 1080b, thus creating operating space within the chamber enclosed by the wall 1001. The upper and lower coupling 1080a; 1080b comprises a latching system for locking an inset 1042a;b;c. The inset may for example be an inset 1042a comprising an airlock sluice 1018 with a first 1038a and second 1038b valve member, an inset 1042b comprising a glove 1002 for manual manipulation within the body of the patient, or within the enclosed chamber, o an inset 1042c comprising a device/instrument mount 1020 for holding instruments or medical devices within the chamber. The insets 1042a;b;c may additionally be exchanged for a wall/body ports 1022;1017 enabling manipulation within the chamber or a cavity in the patient.

In the embodiment shown in FIG. 114d the medical device is fixated to the body of the patient by means of a vacuum fixating member 1005' connected to a vacuum conduit 1006, which in turn is connected to a vacuum source. Furthermore, the medical device in FIG. 114d comprises a second sealing device having a first sealing member 1035 adapted to be positioned at the inside of the patient's skin S around an incision to be performed in the skin S and a second sealing member 1037 adapted to be positioned at the outside of the patient's skin S around the incision, and a spring-loaded or elastic connecting member 1036 sealingly interconnecting the first 1035 and second 1037 sealing members. The spring-loaded or elastic connecting member 1036 seals between at least one of the lower coupling 1080b and the skin S of the patient, and intra body ring 1035 and tissue of the patient.

Figure 114E:
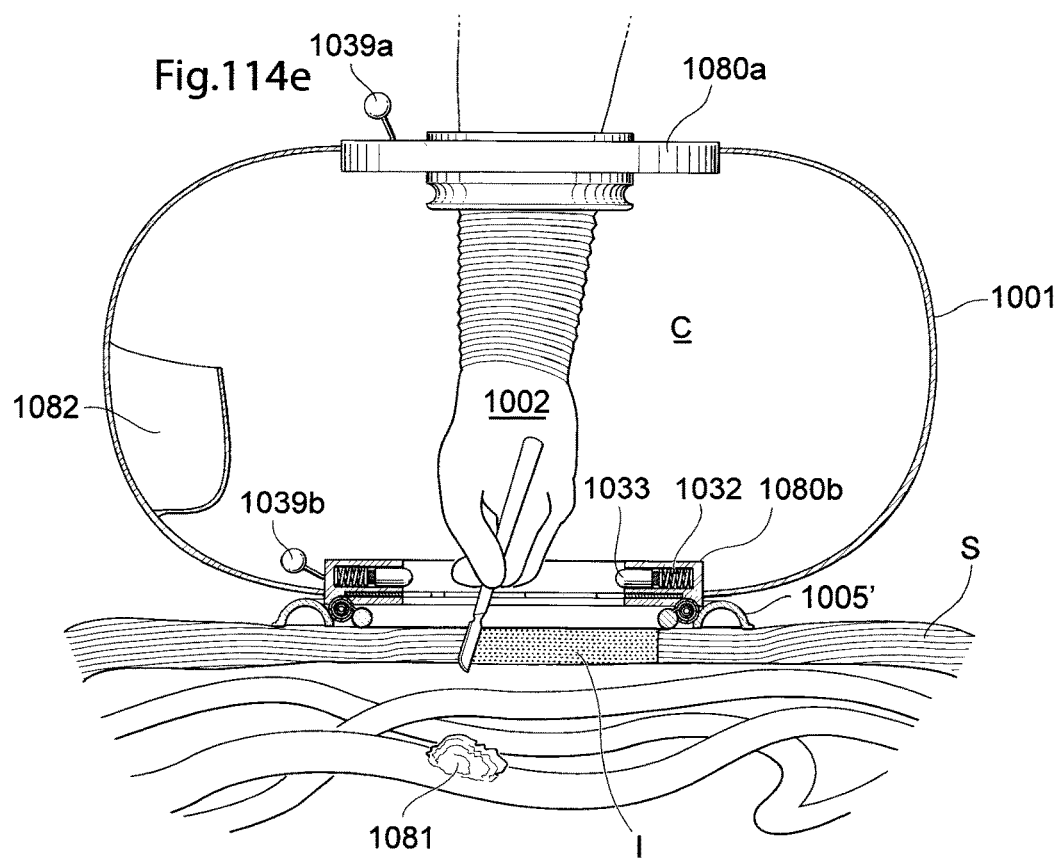
FIGS. 114e-114k shows an embodiment of the medical device in section, being fixated to the patient and used.

FIG. 114e shows the medical device in an embodiment when the wall of the medical device is inflatable, and the medical device is in its inflated state. When the chamber C is deflated it has a first volume i.e. when the upper 1080a and lower 1080b couplings are interconnected, and when the chamber C is inflated and the upper coupling 1080a is disconnected from the lower coupling 1080b it has a second volume, and the second volume is larger than the first volume. According to the embodiment shown in FIG. 114e, the second volume is larger than 500 000 mm3. According to the embodiment shown in FIG. 114e, the chamber C is formed by the inflatable wall 1001 and is adapted to hold a pressure exceeding atmospheric pressure.

According to the embodiment shown in FIG. 114e-114k the chamber C further comprises a pouch 1082 for holding a specimen 1081 removed from within the body of the patient not to contaminate any other part of the body and create the possibility of delaying the removal of the specimen 1081 until the procedure is concluded. The pouch may be a pouch 1082 which could be closed for creating a pouch-chamber within the chamber C for isolating the removed specimen 1081 within the chamber C.

In FIG. 114e a state is illustrated in which the incision I in the patient's skin S is being created by the surgeon by means of an inset 1042 comprising a glove 1002 latched to the upper coupling 1080a. The surgical port is fixated and sealed by means of the vacuum sealing member 1005' since the seal that is provided partially within the patient's body cannot be mounted until the incision in the patient's skin S is concluded. The two different sealing device disclosed could in some embodiments be replaced by only one of the sealing device, or by a different sealing device, such as the adhesive of pressure sealing device disclosed in other portions herein.

Figure 114F:
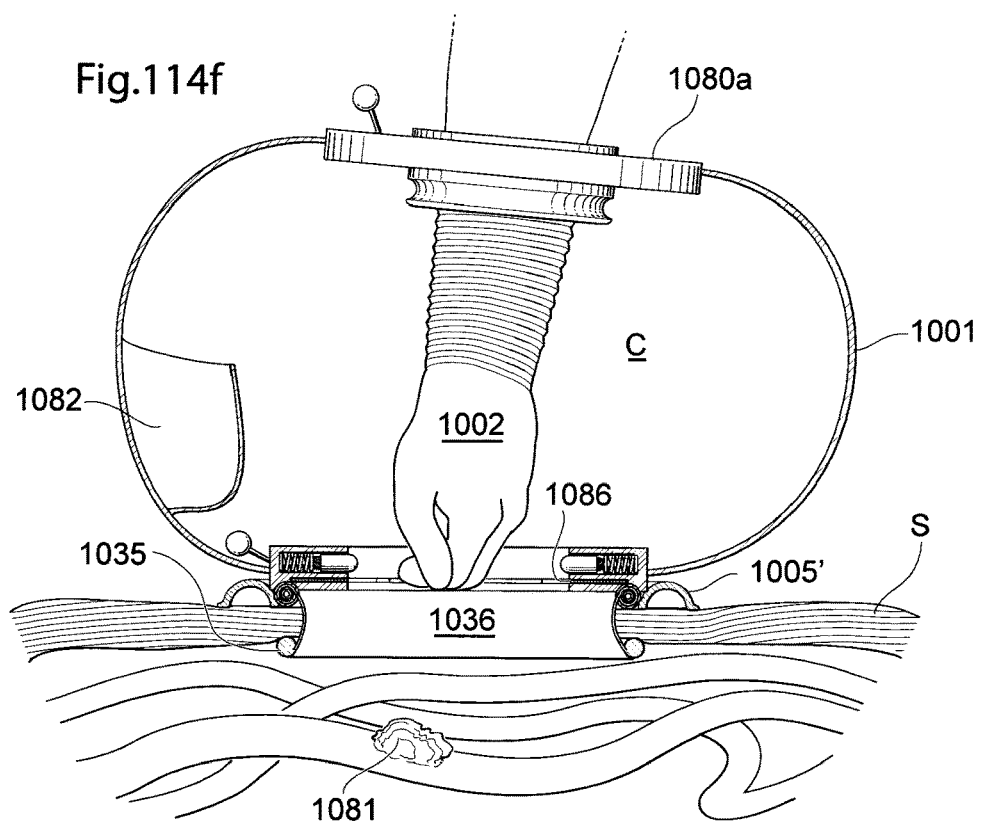

FIG. 114f shows the medical device, when the second sealing 1035, 1036, 1037 have been placed in the incision I cut in the patient's skin. The wall 1001 enclosing the chamber C is elastic or flexible which enables the surgeon move the second part 1031a in relation to the first part 1031b for getting better access to different angles within the patient's body, for example for removing a specimen 1081. The embodiment of FIG. 114f further comprises an iris valve 1086 placed in the lower coupling 1080b for closing the coupling 1080b port such that the chamber C is sealed from at least one of the ambient environment and a cavity in the patient. The closing of the iris valve 1086 enables activity within the chamber C without maintaining a pressure in the chamber C, at the same time as a pressure and/or sealed environment can be maintained within the body of the patient.

Figure 114G:
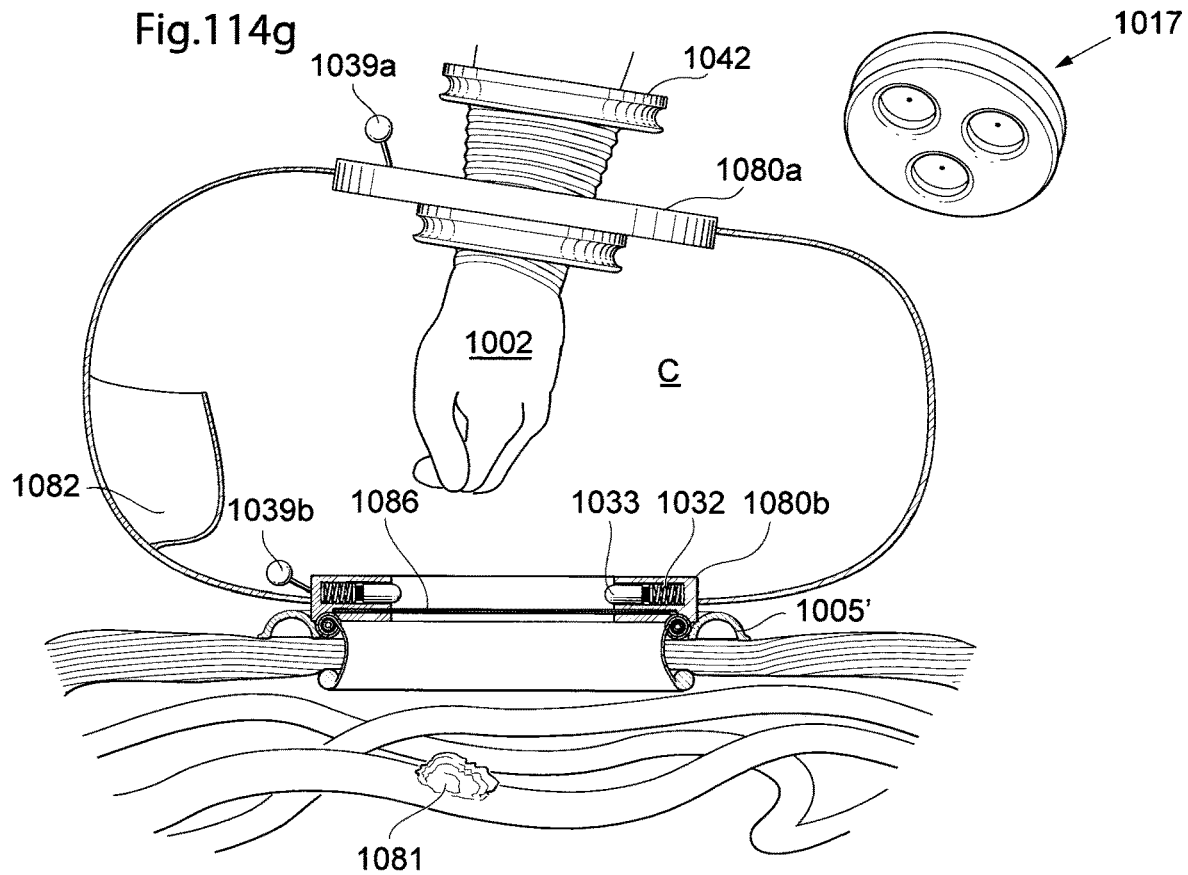

FIG. 114g shows the medical device when the glove inset 1002 is removed and replaced by a wall port 1017 comprising a plurality of ports. The multiport may be used for manipulating objects within the chamber C of the inflated medical device using surgical instruments 1089, or within the body of the human patient, when the upper and lower f couplings 1080a; 1080b are connected (as shown in FIG. 114h).

Figure 114H:
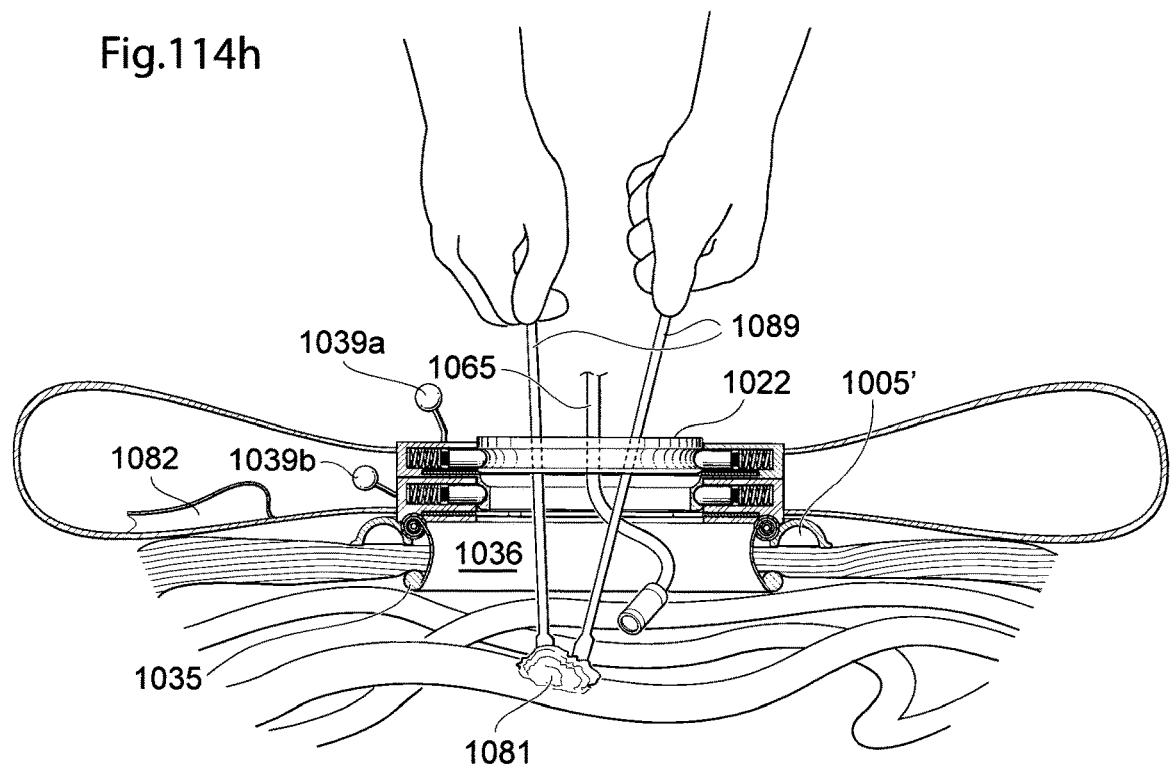

FIG. 114h shows the medical device when the upper and lower couplings 1080a; 1080b are connected such that surgical instruments 1089 can be used for manipulating within the body of the patient. The port 1017;1022 has now been transferred from a wall port 1017 to a body port 1022. An endoscopic camera 1065 may be provided in the body port 1022 for enabling visual inspection of the cavity within the patient's body. The process of cutting away a specimen 1081 from the intestines of a patient in a laparoscopic way is shown in FIG. 114*h*.

Figure 114I:
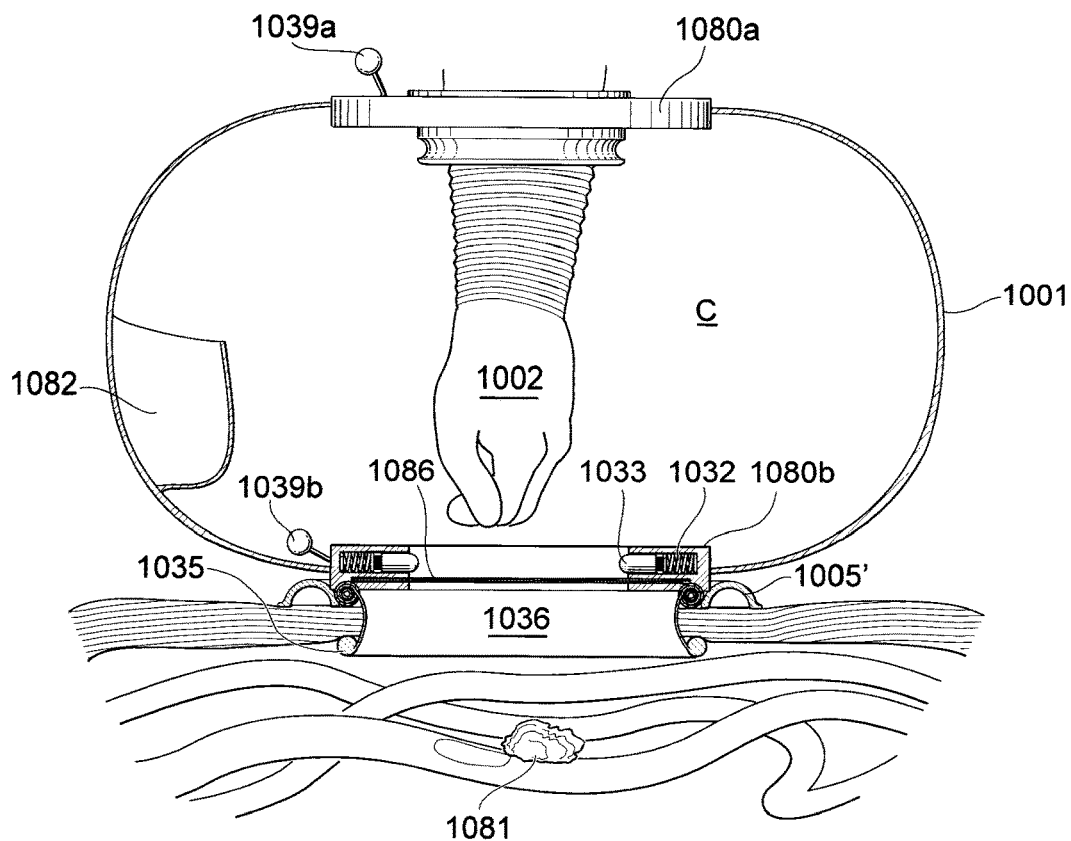

In FIG. 114*i*, the glove inset 1002 has been fixated to the upper coupling 1080*a* to enable the surgeon to operate within the cavity of the patient's body and within the chamber C enclosed by the wall 1001 of the medical device 1000. By the inset 1042 comprising the glove 1002 comprising a pleated portion 1003, the surgeon is able to reach into the cavity of the patient for removing the specimen 1081 cut loose from the intestines in prior steps.

Figure 114J:
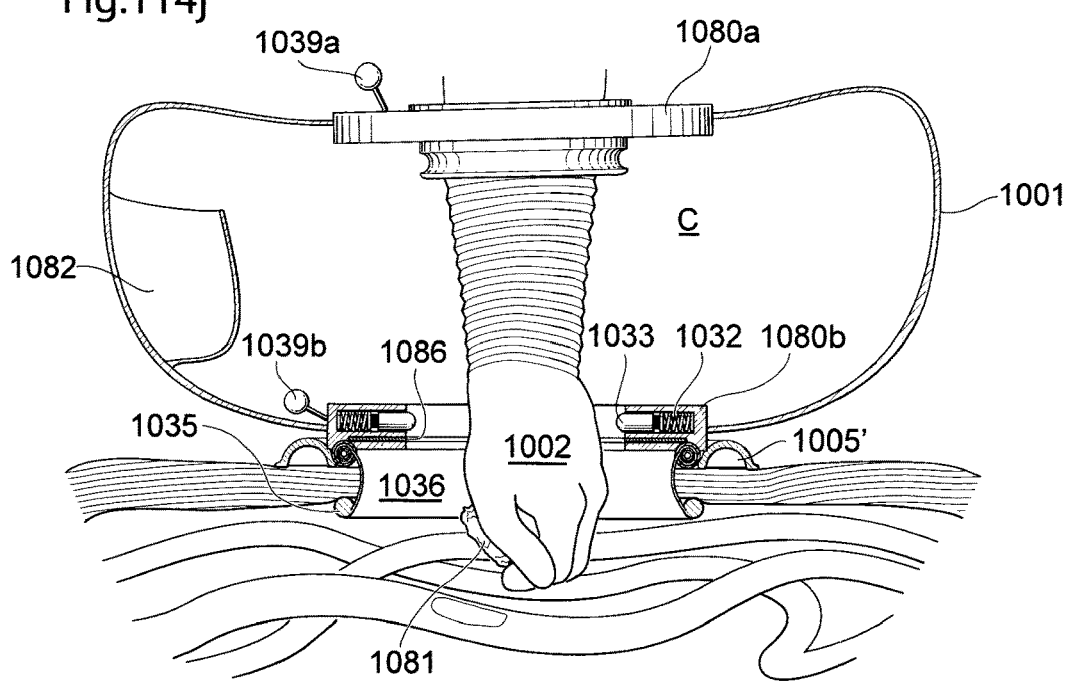

FIG. 114*j* shows that the wall 1001 of the medical device 1000 is collapsible such that the inset 1042 comprising the glove 1002 can be moved with relation to the lower coupling 1080*b*, which gives the surgeon further freedom when removing the loose specimen 1081 from the intestines of the patient.

Figure 114K:
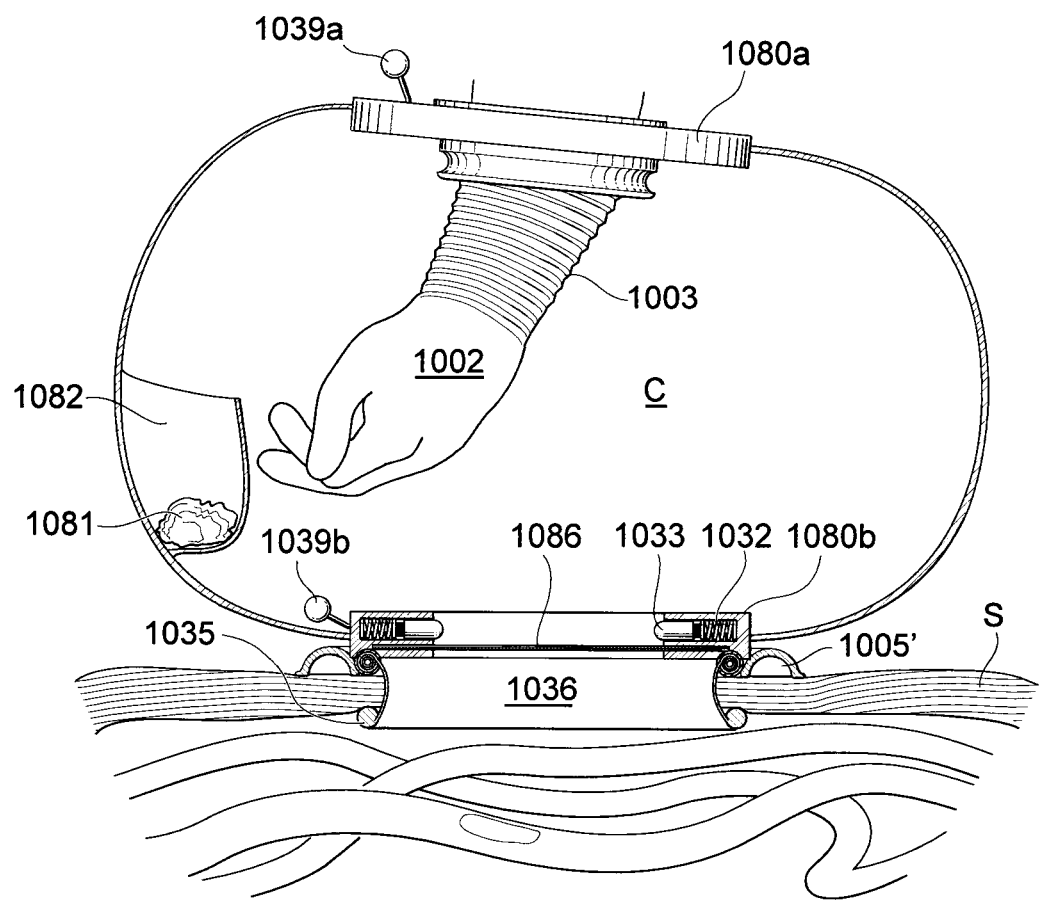
Figure 114I:
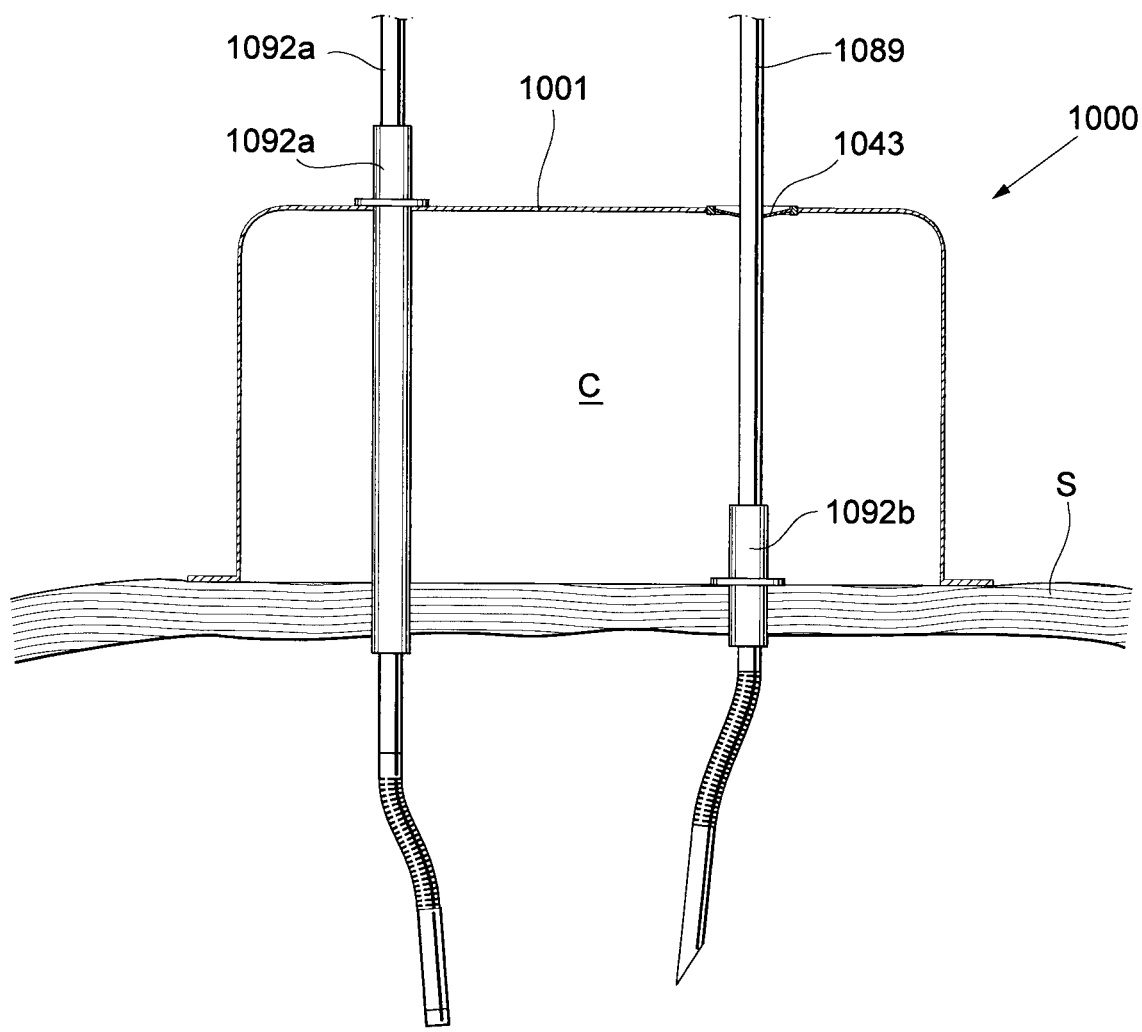

FIG. 114*k* shows the step of placing the removed specimen 1081 in the pouch 1082 such that the specimen 1081 does not contaminate any other part of the body. The pouch may be a pouch 1082 which could be closed for creating a pouch-chamber within the chamber C for isolating the removed specimen 1081 within the chamber C.

FIG. 114*l* shows examples of how trocars may be used in combination with the medical device 1000 according to any of the embodiments shown in FIGS. 106-114. The medical device 1000 comprises a wall 1001 placed on the patient's skin and thereby enclosing a chamber C for creating a sealed environment. The medical device 1000 comprises two trocars 1092*a*; 1092*b*, one 1092*a* traveling through both the wall 1001 of the medical device and the skin S of the patient and thus enabling endoscopic instruments 1089 to be inserted into the patient through both the wall 1001 of the medical device 1000 and the skin S of the patient through one single trocar 1092*a*. The other trocar 1092*b* being placed inside the chamber C and enabling an endoscopic instrument to be inserted through the skin S of the patient. The endoscopic instrument 1089 is in this embodiment inserted into the chamber C enclosed by the wall 1001 through a membrane 1043 in the wall 1001 sealing against the tool 1089.

Figure 114M:
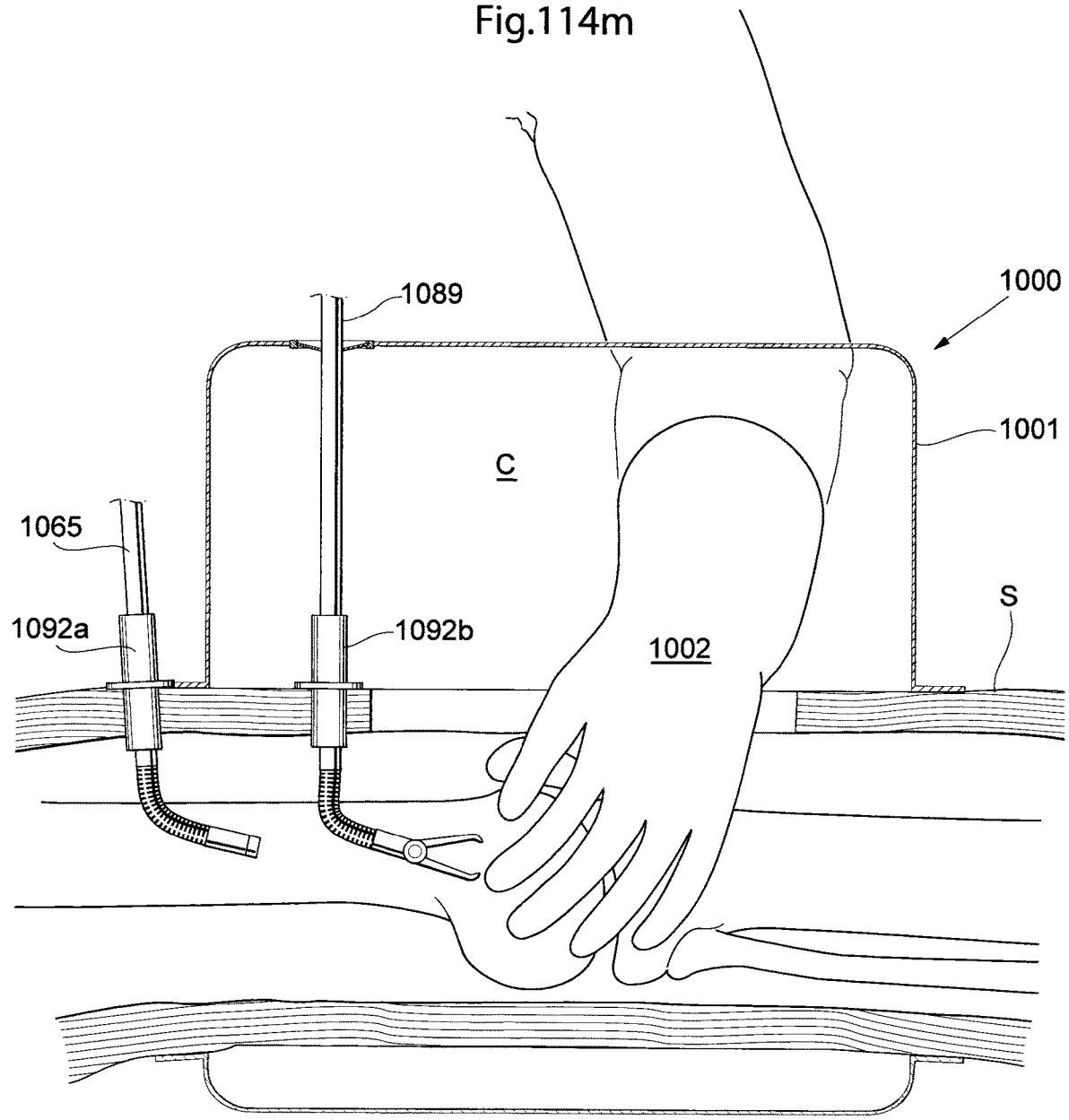
FIGS. 114m-114p shows an embodiment of the medical device in section, being fixated to the patient and used, FIGS. 115-123a' shows another embodiment of the medical device, in section.

FIG. 114*m* shows how the medical device shown in FIGS. 106-114 may be used. The medical device 1000 comprises a glove 1002 integrated in the wall 1001 and a camera 1065 placed in the skin S outside of the medical device 1000. The medical device 1000 further comprises a trocar 1092*b* placed inside the chamber C and further through an opening in the skin S of the patient and into an area of the knee of the patient. FIG. 114*m* schematically illustrates how the surgeon manipulates the knee in the chamber using the glove 1002.

Figure 114N:
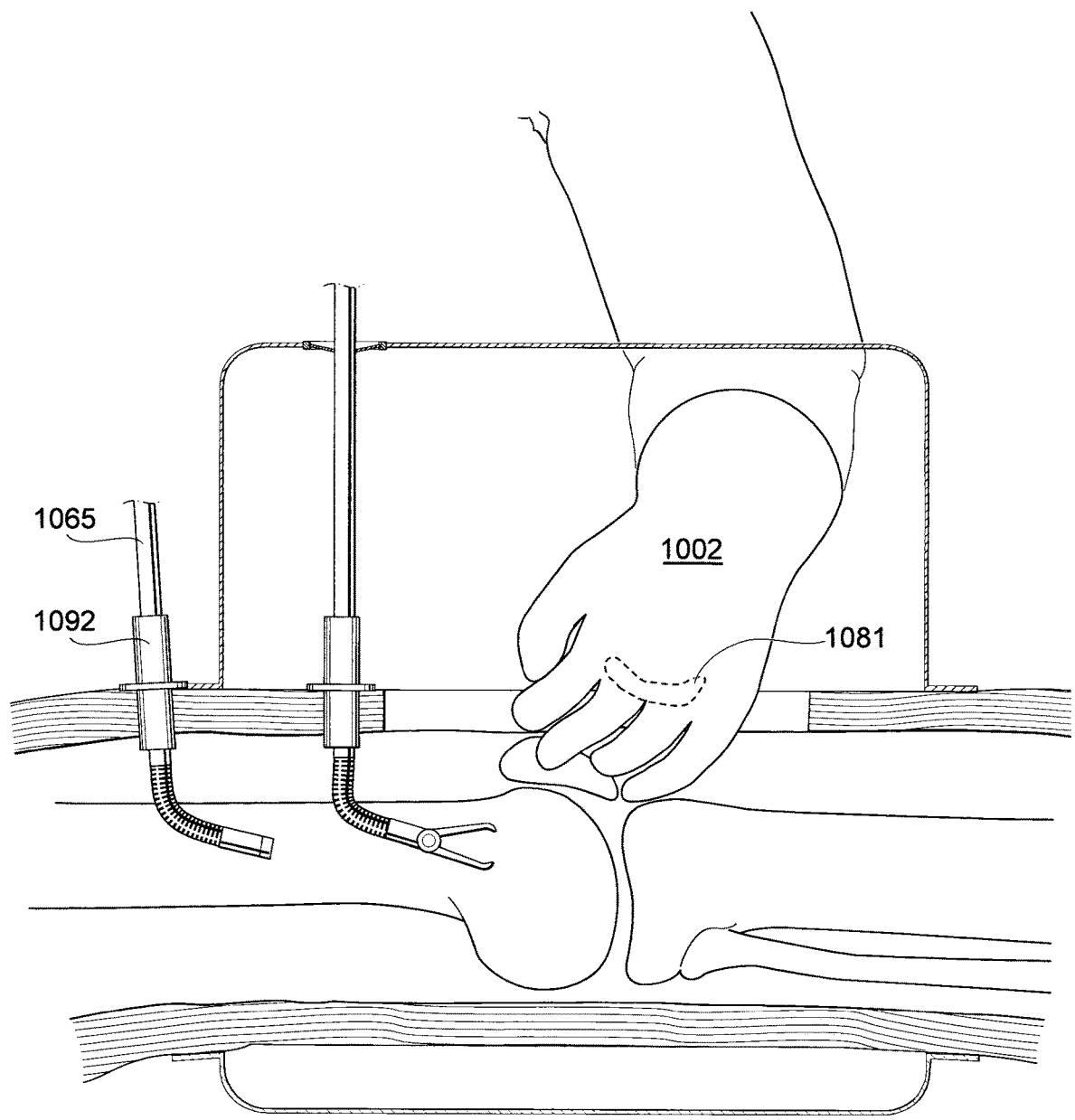
Figure 114O:
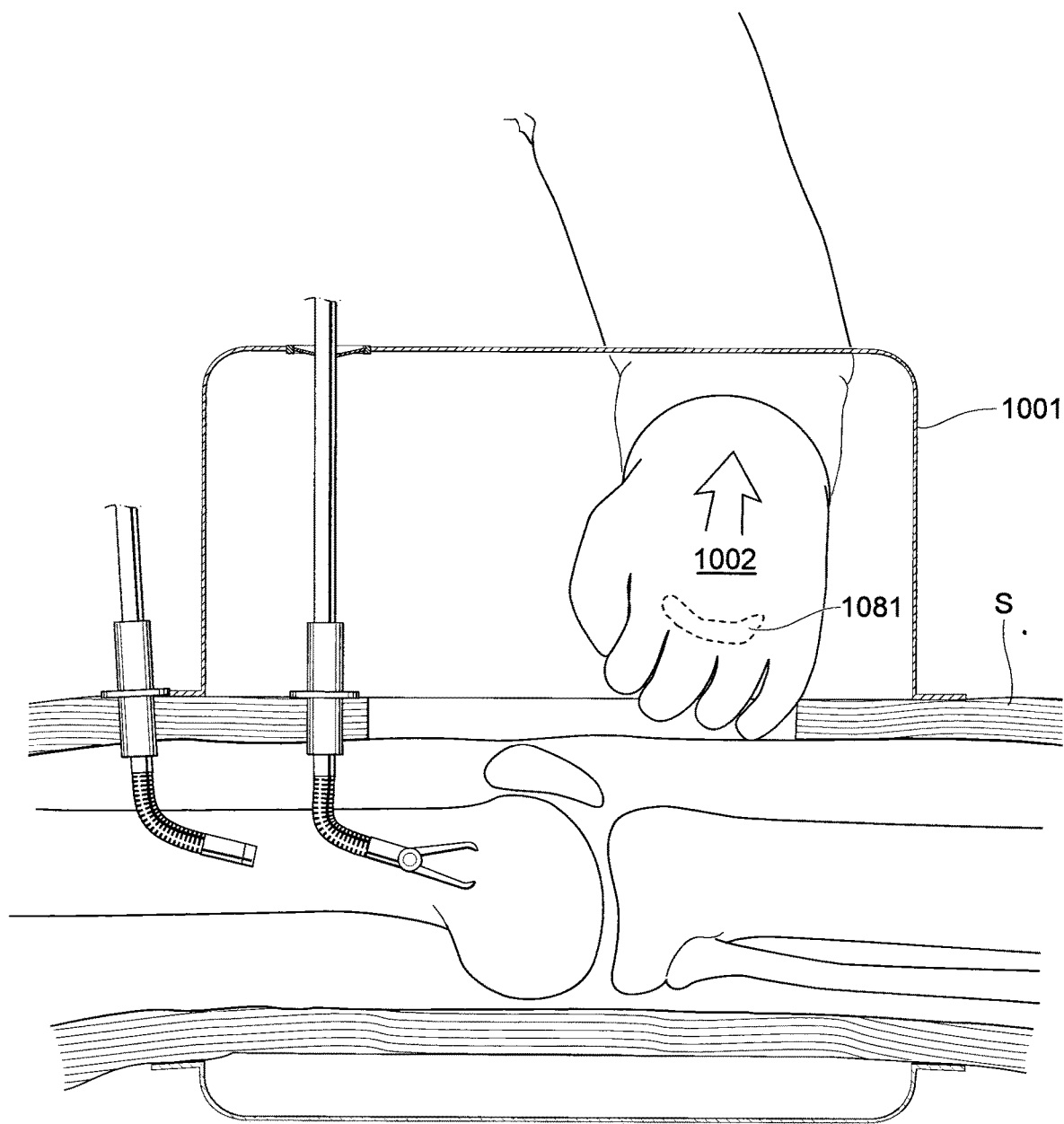

FIGS. 114*n*, 114*o* shows the medical device when the surgeon removes a specimen 1081 from the knee of the patient using the glove 1002 integrated in the wall 1001 of the medical device.

Figure 114P:
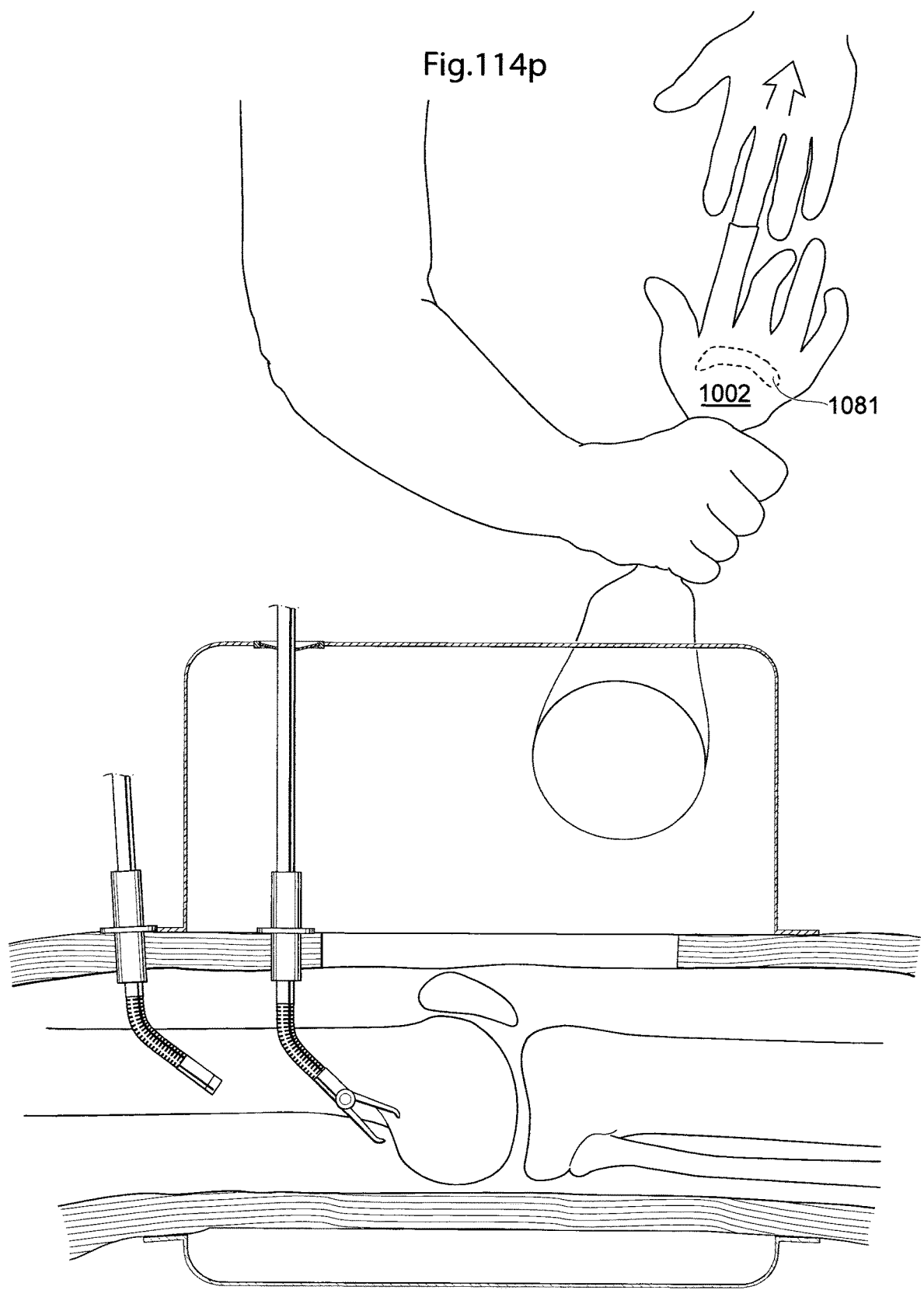

FIG. 114*p* shows the medical device 1000, when the surgeon has turned the integrated glove 1002 inside-out such that the specimen 1081 can be contained within the integrated glove 1002. By isolating the specimen 1081 inside of the glove 1002, the specimen 1081 is removed both from the rest of the body of the patient and from the ambient environment, and thereby does not risk to infect any other portion of the patient's body or medical staff with any infectious disease.

FIGS. 115-123 shows an embodiment of a medical device in which the medical device having a first state, when a first and second coupling (1180*a*, 1180*b* in the figures) are interconnected to enable a surgeon to operate through the interconnected port created, and in a second state, when the upper coupling is disconnected from the lower coupling enable the surgeon to perform steps of the procedure within the chamber C formed by the flexible wall 1101 between upper and lower couplings 1180*a;b*. The medical device is further adapted to, in the second state, enable the surgeon to remove a specimen from the body of the patient through the lower coupling (1180*b* in the figures) and into the chamber C, and to perform one of: placing the specimen within the chamber C, and removing the specimen from the chamber C through the upper coupling 1180*a*. The upper 1180*a* and lower 1180*b* couplings are then adapted to be reconnected after being disconnected such that the surgeon can continue operating through the interconnected port after the specimen has been removed for, e.g. suturing in the cavity created in the patient.

The surgical port could be used in a completely endoscopic procedure or a hand assisted endoscopic procedure. The surgical port could be a Single Incision Laparoscopic Surgery (SILS) port and could be adapted to be placed in the umbilicus of a patient such that no scars are visible after the surgical procedure is concluded.

Figure 115:
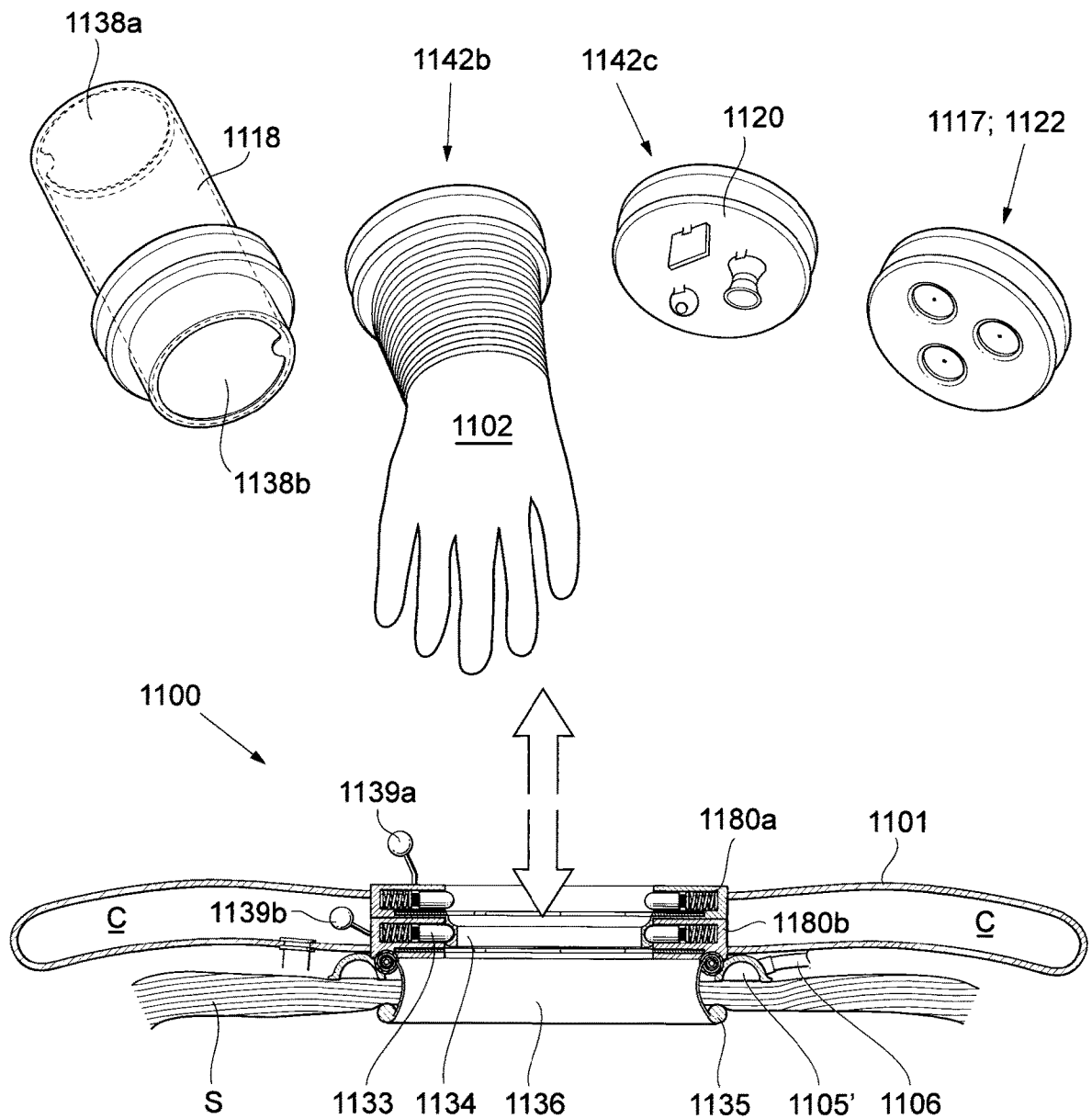

FIG. 115 shows the medical device 1100 when placed in an incision cut in a patient's body. The surgical port 1100 comprises an upper 1180*a* coupling and a lower coupling 1180*b* adapted be interconnected to form an interconnected coupling. The upper coupling is adapted to be disconnected (disconnectable) from the lower coupling 1180*b*. The first upper coupling 1180*a* is connected to a first portion of a flexible wall 1101, and the second lower coupling 1180*b* is connected to a second portion of the flexible wall 1101. The flexible wall 1101 forms a chamber C in which a sealed environment can be maintained, the chamber C is enlarged when the upper coupling is disengaged from the lower coupling 1180*b* (such as for example shown in FIGS. 117-119), thus creating operating space within the chamber C enclosed by the wall 1101. The upper coupling 1180*a* comprises a latching system for locking an inset 1142*b;c* to the upper coupling 1180*a*. The inset may for example, as disclosed in FIG. 115, be an inset comprising a glove 1102 for manual manipulation within the body of the patient, or within the enclosed chamber C or an inset comprising a device or instrument mount 1120 for holding instruments or medical devices within the chamber C. Alternatively the insets 1142*b*; 1142*c* can be replaced by an airlock sluice 1118 with a first 1138*a* and second 1138*b* valve member or a port and a port 1117; 1122 enabling the insertion of a surgical instrument into the chamber or body of the patient.

The medical device further comprises a latching system for connecting the upper coupling 1180*a* to the lower coupling 1180*b*. The latching system comprises protruding latching members 1133 in the upper coupling 1180*a* and a recess 1134 in form of a groove 1134 adapted to receive the protruding latching members 1133 for locking the upper coupling 1180*a* to the lower coupling 1180*b*.

In the embodiment shown in FIG. 115 the medical device is fixated to the body of the patient by means of a vacuum fixating member 1105' connected to a conduit 1106, which in turn is connected to a vacuum source. Furthermore, the medical device 1000 in FIG. 115 comprises a second sealing device having a first sealing member 1135 adapted to be positioned at the inside of the patient's skin around an incision to be performed in the skin S and a second sealing member 1137 adapted to be positioned at the outside of the patient's skin S around the incision, and a spring-loaded or elastic connecting member 1136 sealingly interconnecting the first 1135 and second 1137 sealing members. The spring-loaded or elastic connecting member 1136 seals between at least one of the lower coupling 1180*b* and the skin S of the patient, and the first sealing member 1135 and tissue of the patient.

Figure 116:
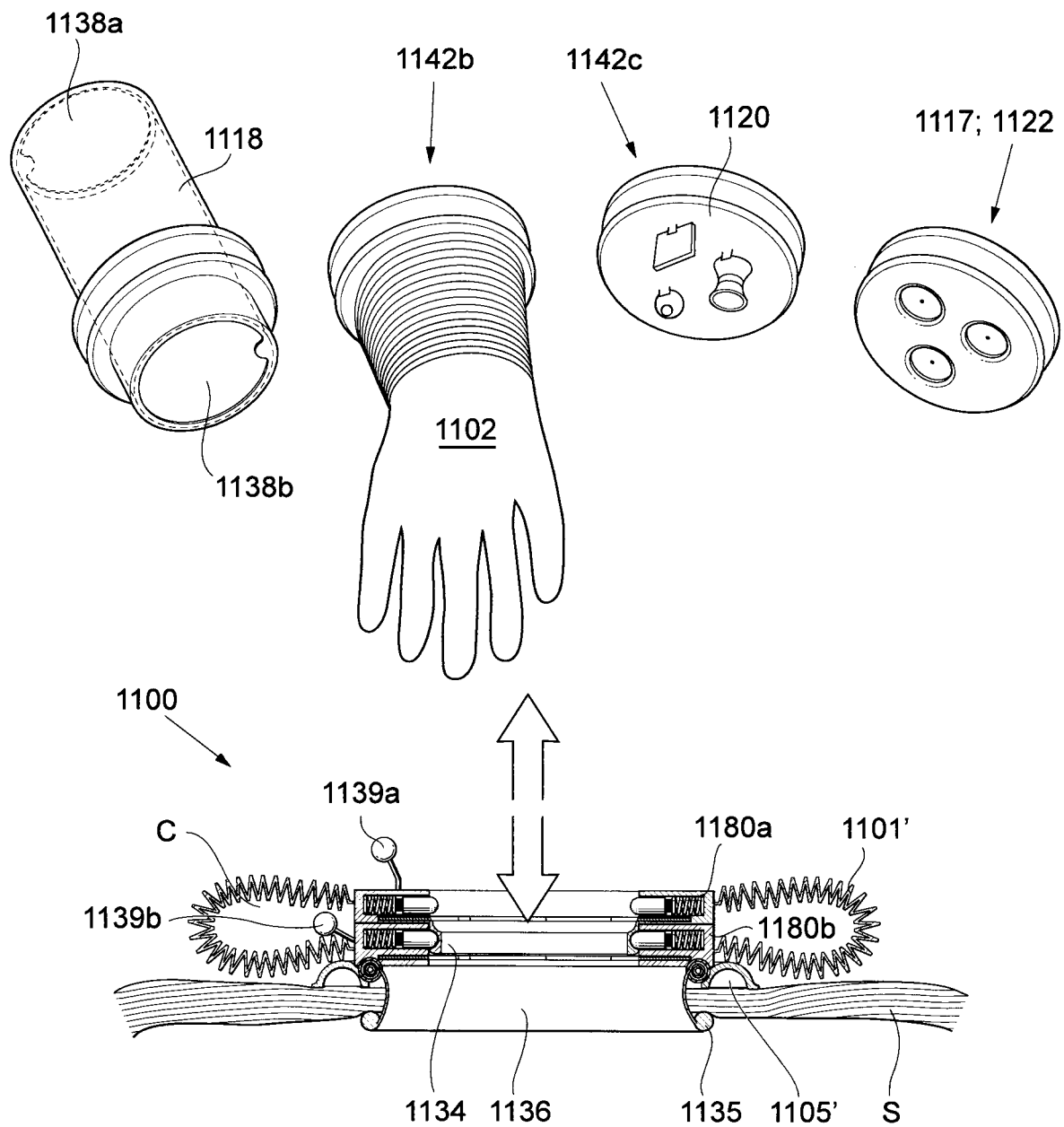

FIG. 116 shows the port in an embodiment very similar to the embodiment shown in FIG. 115 but with the difference that the wall 1101' has a pleated bellows structure and thus taking up less space when in its deflated state and enabling the wall to expand when in its inflated state. The pleated bellows structure enables the wall 1101' to be packaged in a small package and thus not obstructing the procedure thus facilitating for the surgeon. In some applications the wall 1101' can be used only in very special cases or emergencies, such as when some part of the procedure goes wrong and conversion from endoscopic surgery to more open surgery is required. The use of the surgical port 1100 with the inflated chamber C enables the pressure in the endoscopic cavity, created by inflation of the patient, to be maintained since the chamber C can hold a pressure exceeding atmospheric pressure. According to the embodiment shown in FIG. 116, the volume of the chamber C is smaller than 100 000 mm3.

Figure 117:
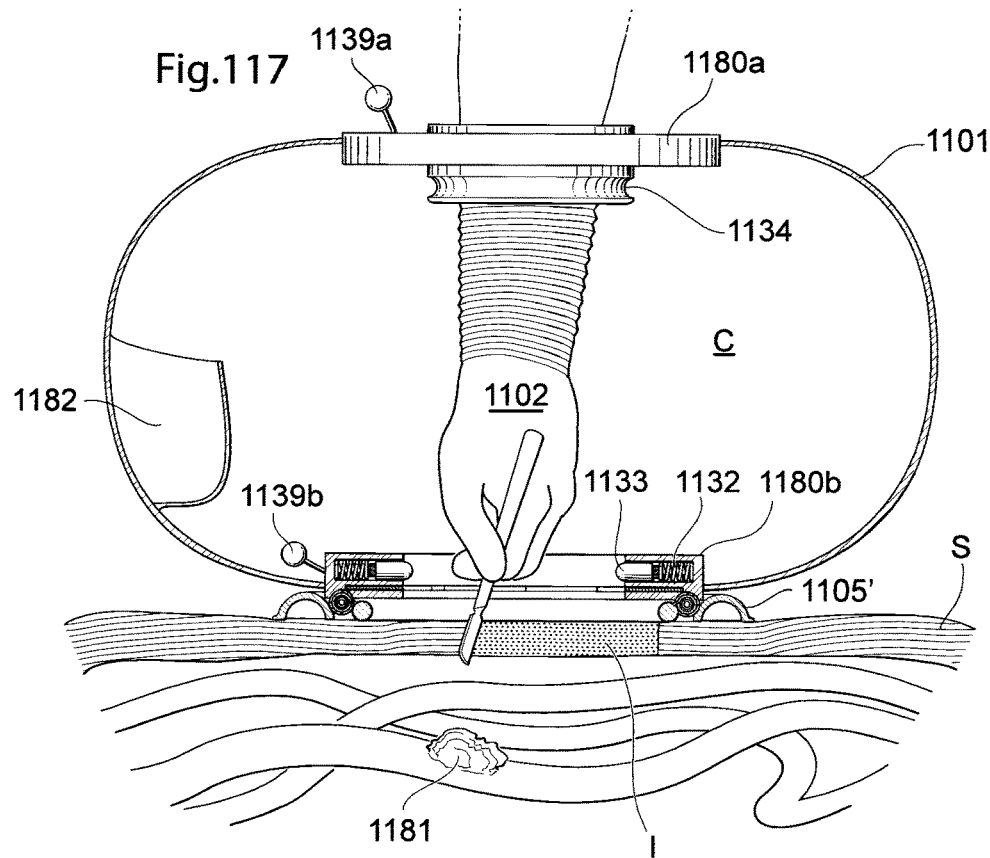

FIG. 117 shows the surgical port as disclosed with reference to FIGS. 115 and 116 when the chamber C enclosed by the wall 1101 is inflated. When the chamber C is deflated (as shown in FIGS. 115 and 116) it has a first volume i.e. when the upper coupling 1180*a* and lower coupling 1180*b* are interconnected, and when the chamber C is inflated and the upper coupling 1180*a* is disconnected from the lower coupling 1180*b* it has a second volume being larger than the first volume. According to the embodiment shown in FIG. 117, the second volume is larger than 500 000 mm3. According to the embodiment shown in FIG. 117, the chamber C is formed by the flexible wall 1101 and is adapted to hold a pressure exceeding atmospheric pressure.

According to the embodiment shown in FIG. 117-123 the chamber C further comprises a pouch 1182 for holding a specimen 1181 removed from within the body of the patient not to contaminate any other part of the body and create the possibility of delaying the removal of the specimen 1181 until the procedure is concluded. The pouch may be a pouch 1182 which could be closed for creating a pouch-chamber within the chamber C for isolating the removed specimen 1181 within the chamber C.

In FIG. 117 a state is illustrated in which the cut in the patient's skin is being created by the surgeon by means of a glove inset 1102 latched to the upper coupling 1180*a*. The medical device 1000 is fixated and sealed by means of the vacuum sealing member 1105' as the seal that is provided partially within the patient's body cannot be mounted until the incision in the patient's skin S is concluded. The two different sealing devices disclosed could in some embodiments be replaced by only one of the sealing device, or by a different sealing device, such as the adhesive of pressure seals disclosed in other portions herein.

Figure 118:
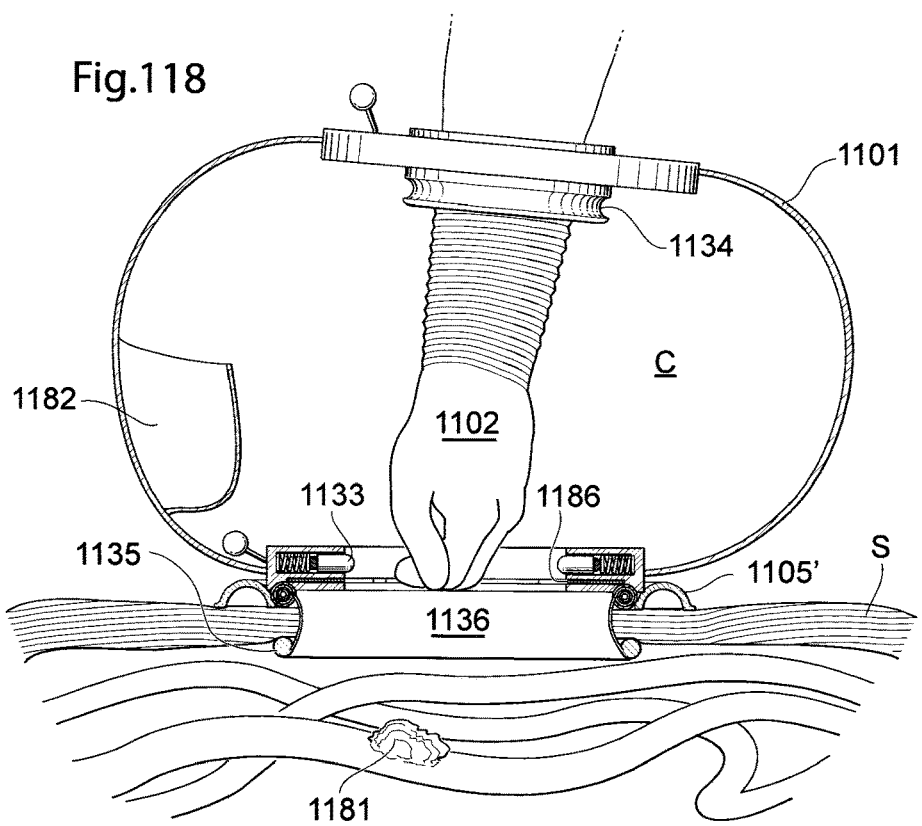

FIG. 118 shows the medical device 1000, when the second sealing 1135, 1136, 1137 has been placed in the incision I cut in the patient's skin S. The wall 1101 enclosing the chamber C is elastic or flexible which enables the surgeon move the upper coupling 1180*a* in relation to the lower coupling 1180*b* for getting better access to different angles within the patient's body, for example for removing a specimen 1181. The embodiment of FIG. 118 further comprises a non-penetrable valve 1186 (such as an iris valve) placed in the lower coupling 1180*b* for closing the coupling such that the chamber C is sealed from the cavity in the patient. The closing of the non-penetrable valve 1186 enables activity within the chamber C without maintaining a pressure exceeding atmospheric pressure in the chamber C, at the same time as a pressure and/or sealed environment can be maintained within the body of the patient.

Figure 119:
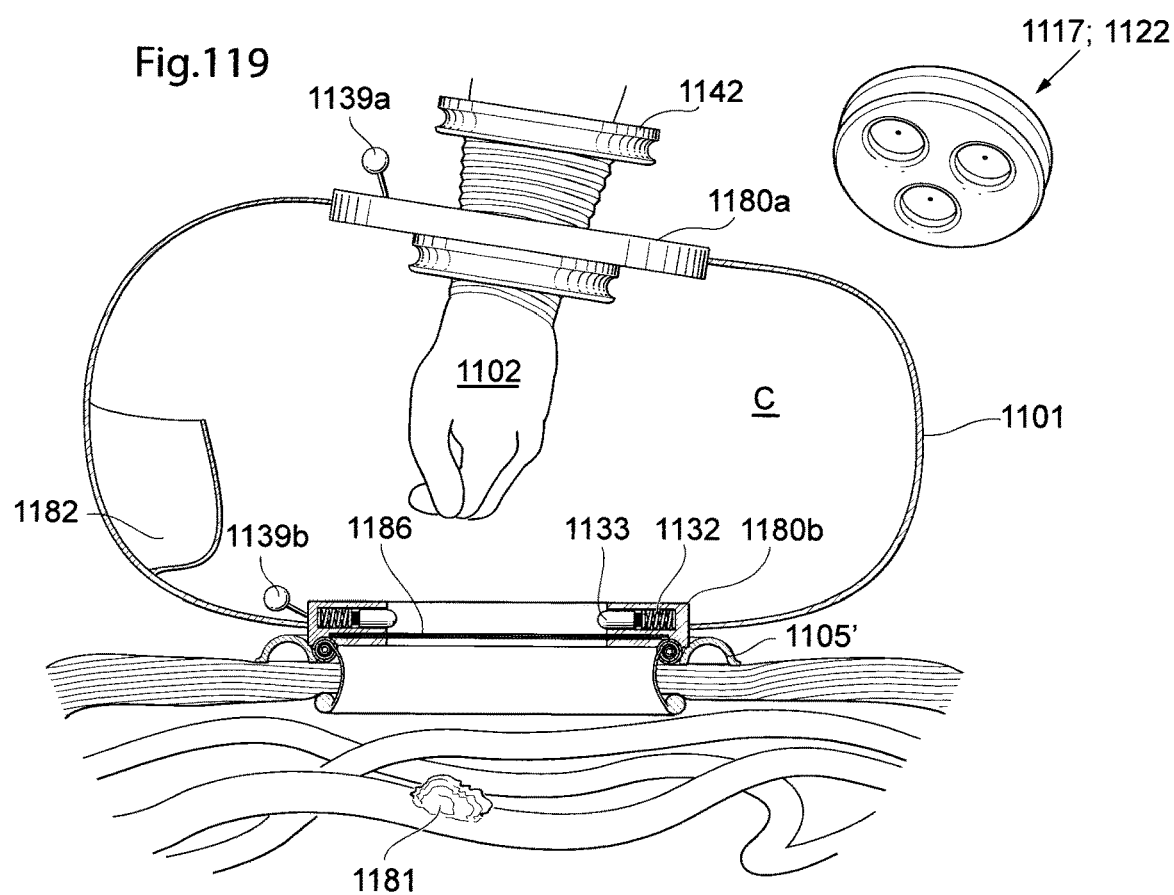
Figure 120:
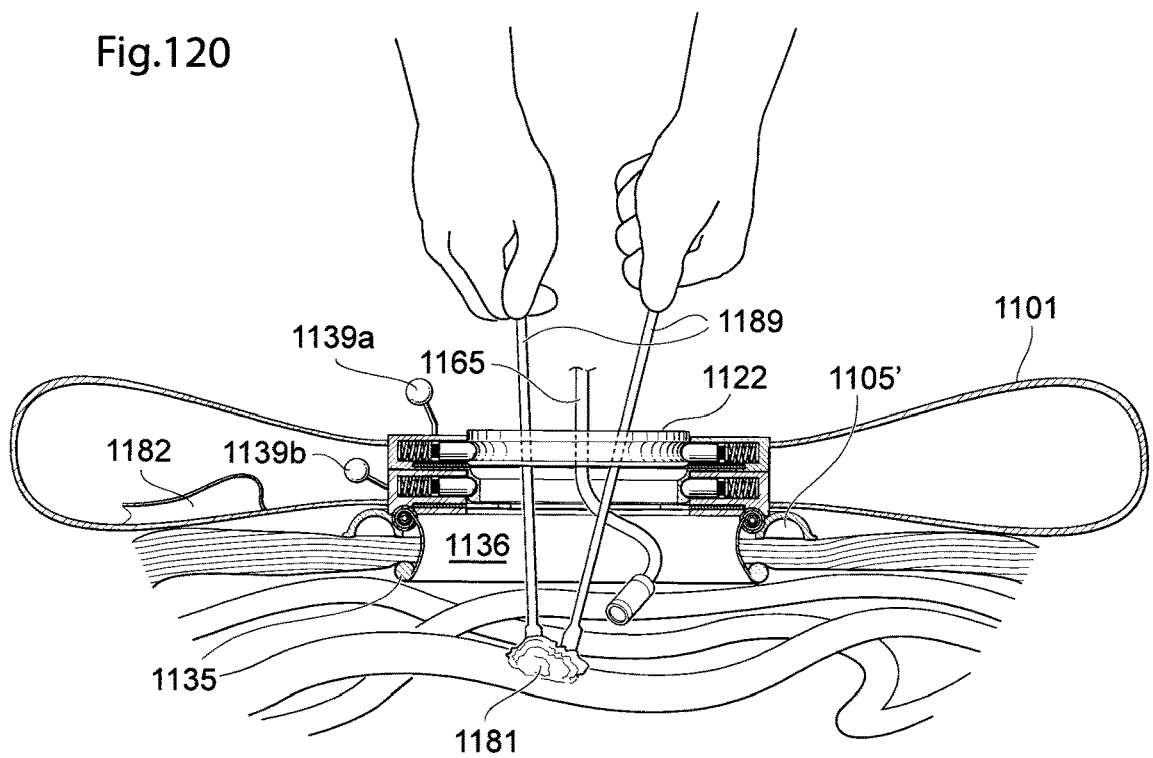
Figure 120:
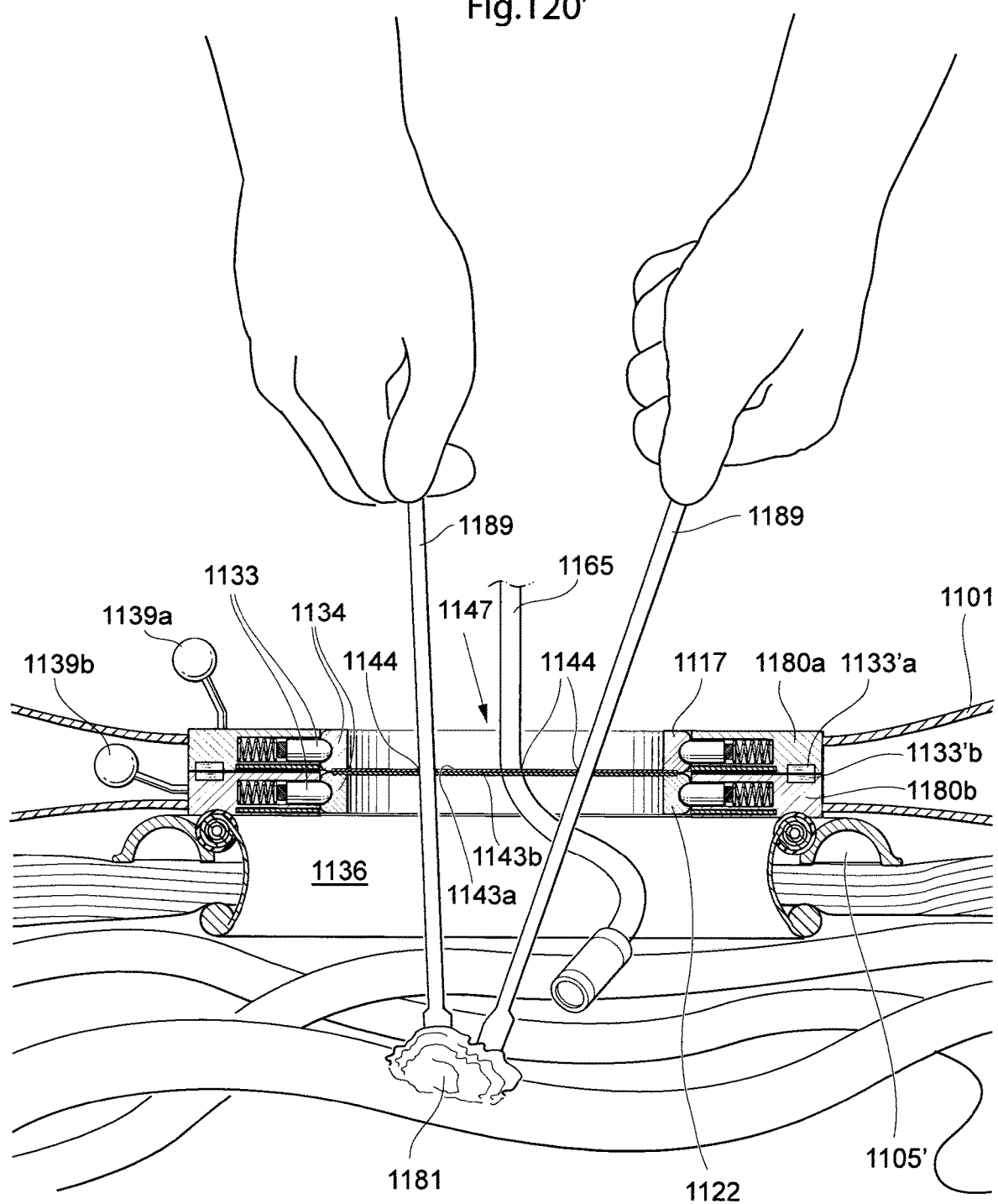

FIG. 119 shows the surgical port according to FIGS. 119 and 120 when the inset 1142 comprising the glove 1102 is placed in the upper coupling 1180*a* is removed and replaced by a wall/body port 1117; 1122 here, in the form of a multi port comprising a plurality of ports. The upper coupling 1180*a* thus forms a wall port. The wall port 1117 may be used for manipulating objects within the chamber C of the inflated medical device using surgical instruments 1189, or within the body of the human patient, when the first upper coupling 1180*a* and the lower couplings 1180*b* are connected (as shown in FIG. 120).

FIG. 120 shows the medical device when the upper and lower coupling s 1180*a;b* are connected forming an interconnected port such that surgical instruments 1189 can be used for manipulating within the body of the patient. An endoscopic camera 1165 may be provided in the body port 1122 for enabling visual inspection of the cavity within the patient's body. The process of cutting away a specimen 1181 from the intestines of a patient in a laparoscopic way is shown in FIG. 120.

FIG. 120' shows an alternative embodiment of the medical device in which a wall port 1117 is connected to an upper coupling 1180*a* and a body port 1122 is connected to the lower coupling 1180*b*. The upper and lower couplings 1180*a;* 1180*b* are connected by means of magnetic connecting members 1133'*a*, 1133'*b* such that the wall port 1117 and body port 1122 is connected, forming an interconnected port 1147. The first and second part each comprises a latching system comprising protruding latching members 1133 adapted to engage a recess in the form of a groove in 1134 in multiport insets placed in the first 1131*b* and second 1131*a* parts. The multiport insets comprise elastic membranes 1143*a*, 1143*b* adapted to, in a non-compressed state, provide sealing, and in a compressed state enable a surgical instrument to be inserted through the membrane. The elastic membrane 1143*a* of the second part 1131*a* and the elastic membrane 1143*b* of the first part 1131*b* are adapted to be placed tightly together such that they act as a single elastic membrane adapted to, in a non-compressed state, provide sealing, and in a compressed state enable the instruments 1189 to be inserted through the membranes 1143*a*, 1143*b*. The elastic membranes comprises a plurality of self sealing holes 1144 through which the instruments 1189 travel. The membranes 1143*a*, 1143*b* snuggly encircles the instruments and thus maintains the seal between the cavity in the patient and the ambient environment. In alternative embodiments similar to the embodiment shown in FIG. 120' at least one of said first and second part comprises a penetrable self sealing gel, such that an object or hand can be inserted through the surgical port while maintaining a seal. Much as in the embodiment of FIG. 120' the first part 1131*b* may comprises a first penetrable self sealing gel and the second part 1131*a* may comprise a second penetrable self sealing gel. The first and second penetrable self sealing gels may be adapted to be placed tightly together such that they act as a single penetrable self sealing gel adapted to, in a non-compressed state, provide sealing, and in a compressed state enable a hand or an object to be inserted through the self sealing gel while maintaining the seal.

Figure 121:
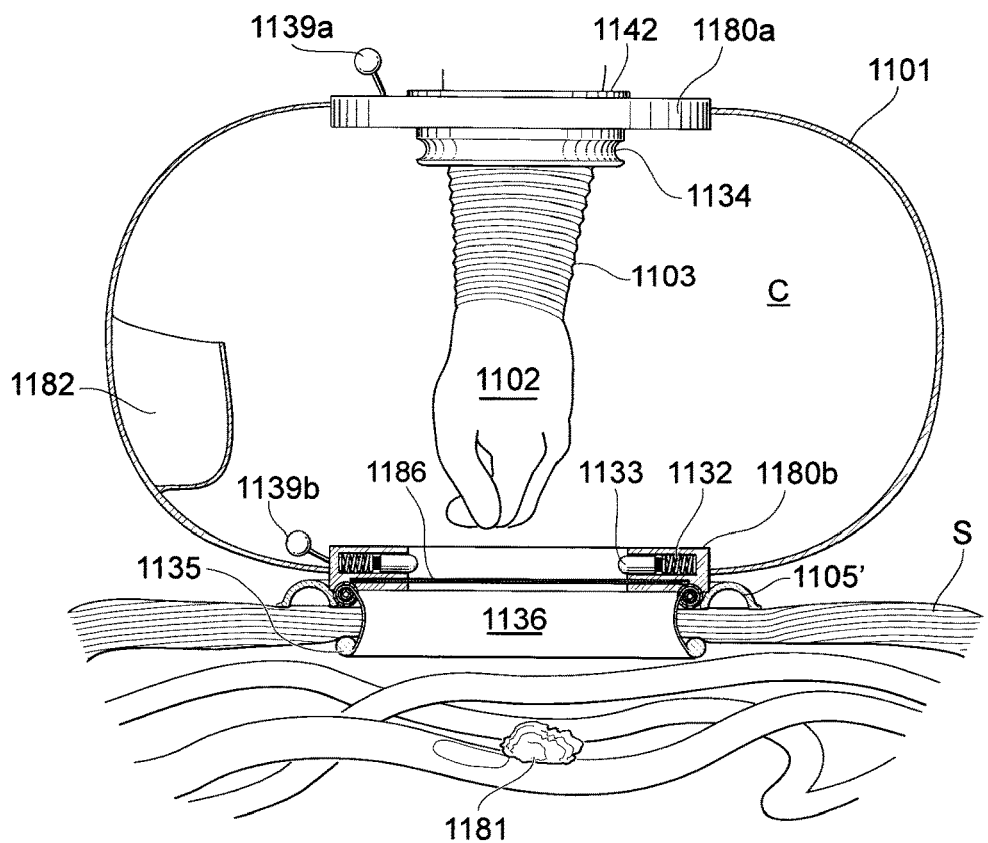

In FIG. 121, the glove inset 1102 has been fixated to second part 1131*a* to enable the surgeon to operate within the cavity of the patient's body and within the chamber enclosed by the wall of the medical device. By the glove inset 1102 comprising a pleated portion, the glove surgeon is able to reach into the cavity of the patient for removing the specimen cut loose from the intestines in prior steps.

Figure 122:
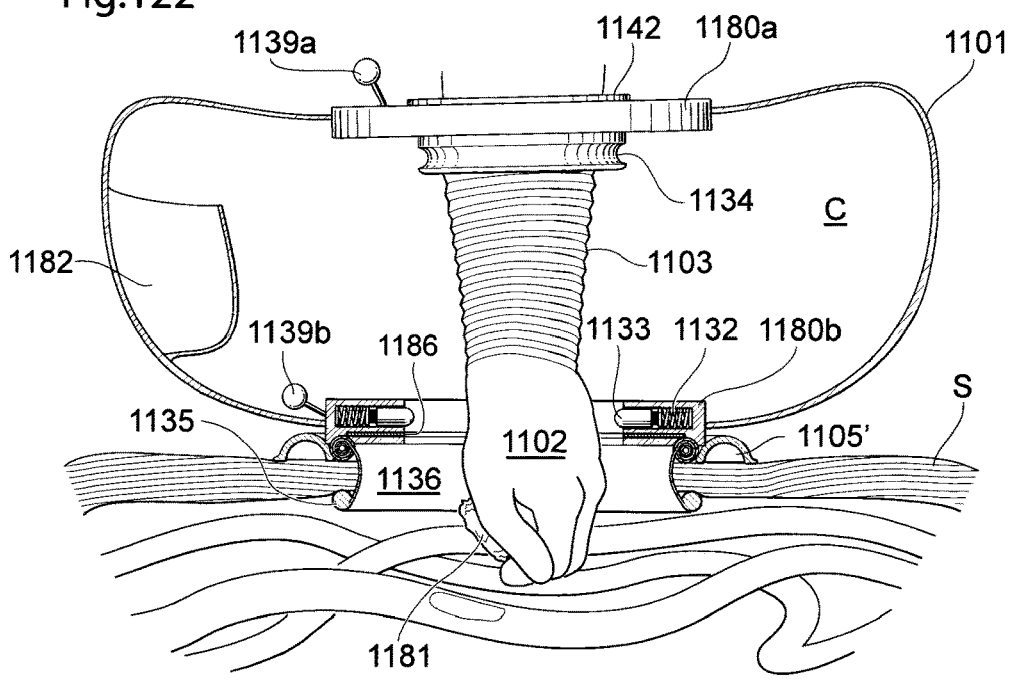

FIG. 122 shows that the wall of the medical device is collapsible such that the glove inset can be moved with relation to the first part 1131*b* of the port, which gives the surgeon further freedom when removing the loose specimen from the intestines of the patient.

Figure 123A:
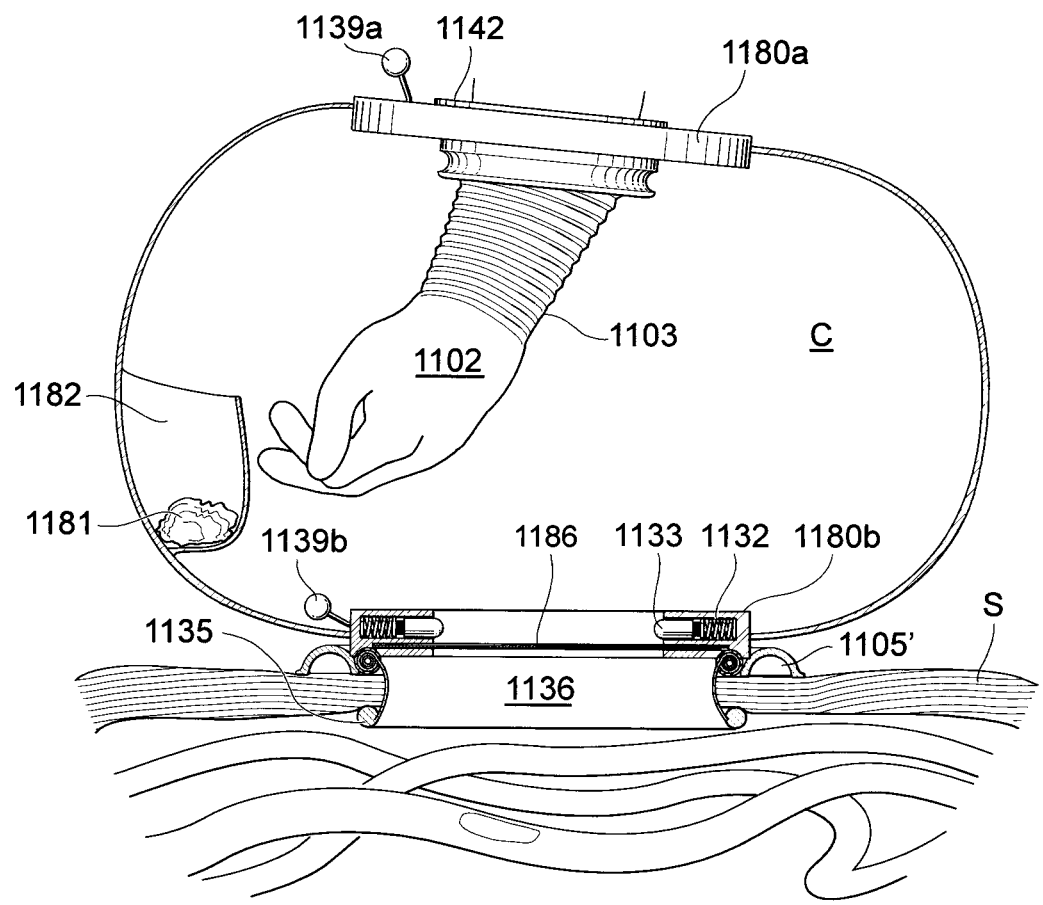
FIGS. 123b-123e shows an embodiment of the medical device in section, being fixated to the patient and used.
FIG. 123f shows an embodiment of the medical device, when positioned on the abdomen of a patient.
FIGS. 123g-123h and 123j-123k shows embodiments of body ports fixated to the tissue of the patient.
FIGS. 123l-123o shows an embodiment of the medical device, when used in performing knee joint surgery positioned on the abdomen of a patient, FIGS. 123'a-123'k shows alternative embodiments of the medical device, when fixated to the abdomen of the patient.
Figure 123A:
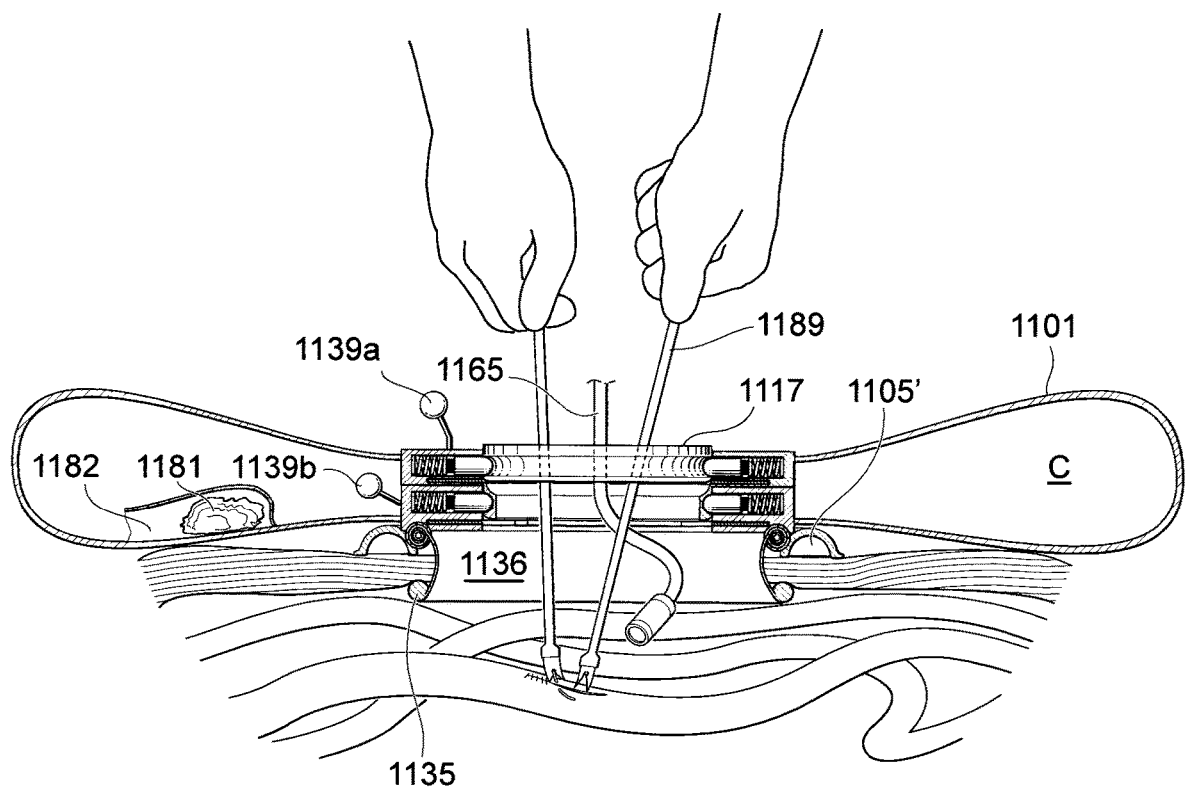

FIG. 123*a* shows the step of placing the removed specimen in the pouch 1182 such that the specimen does not contaminate any other part of the body. The pouch may be a pouch 1182 which could be closed for creating a pouch-chamber within the chamber for isolating the removed specimen 1181 within the chamber.

The first part 1131*b* and the second part 1131*a* could comprise elastic or flexible membranes, and the first and second membranes could be adapted to be placed tightly together such that they act as a single elastic or flexible membrane adapted to, in a non-compressed state, provide sealing, and in a compressed state enable a hand or an object to be inserted through the membrane. The flexible or elastic membranes could comprise a penetrable self sealing gel, such that an object or hand can be inserted through the port while maintaining a seal, and a first and second penetrable self sealing gel could be adapted to be placed tightly together such that they act as a single penetrable self sealing gel adapted to, in a non-compressed state, provide sealing, and in a compressed state enable a hand or an object to be inserted through the self sealing gel while maintaining the seal.

FIG. 123*a*' shows the step when the first 1131*b* and second 1131*a* part has been reconnected into an interconnected port after having been disconnected such that the surgeon can continue operating through the interconnected port after the specimen 1181 has been removed and securely placed in the pouch 1182. FIG. 123*a*' shows laparoscopic suturing of the wound inflicted on the intestine of the patient by the removal of the specimen 1181. By maintaining the inflated cavity in the patient even after the specimen 1181 has been removed the visual advantages of laparoscopic techniques can be maintained throughout the entire procedure.

Figure 123B:
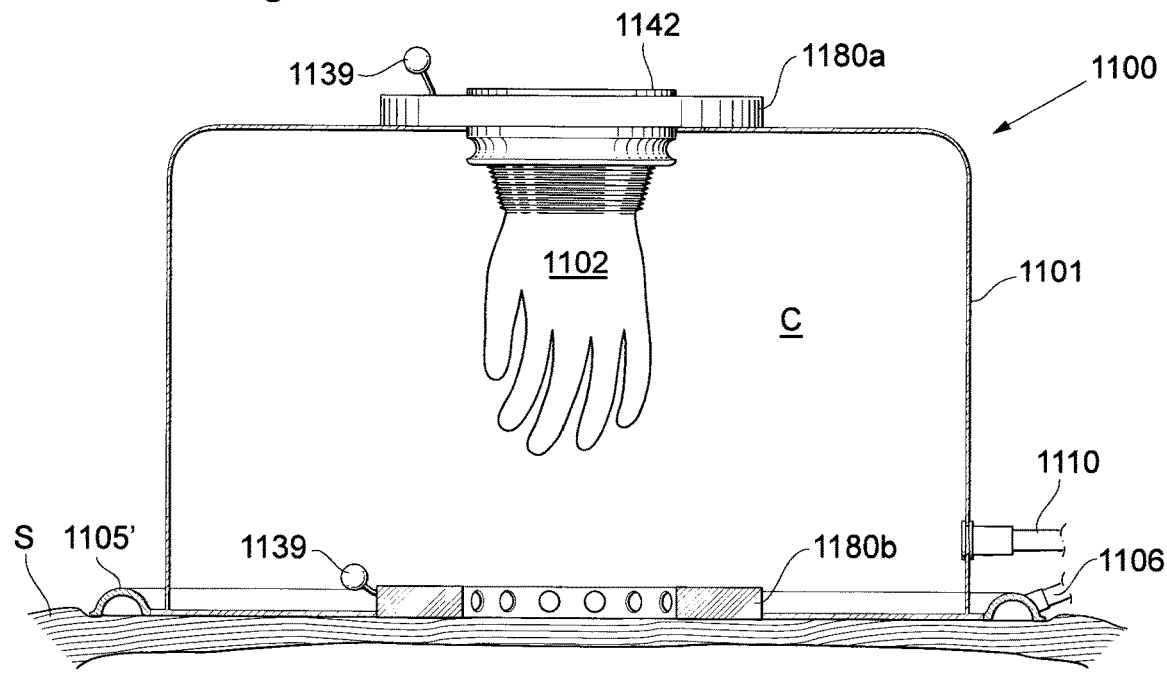

FIG. 123*b* shows an alternative embodiment of the medical device 1100 shown with reference to FIG. 115-123*a*. The medical device 1100 comprises a wall 1101 enclosing a chamber for performing the surgical procedure. A portion of the wall 1101 is adapted to be in contact with a patient. The medical device comprises an inset in the form of a surgical glove 1102 adapted to enable manipulation within the chamber. The surgical glove 1102 connected to the upper coupling (part) 1131*a* can be in a first and second position, the second position is disclosed in FIG. 123*b*, while the first position is located closer to the skin of the patient and disclosed in FIG. 123*d*. The medical device could for example be used in surgical procedures where transitions between open and laparoscopic surgery is needed. The medical device could be placed in the second position for enabling a larger freedom of motion for the surgeon within the chamber of the medical device 1100, while the first position, with the upper coupling (equivalent to the second part) 1131*a* locked to the lower coupling (equivalent to the first part) 1131*b*, could enable the use of a laparoscopic trocar or hand access for further reach within the body of the patient. The medical device could further be used in embodiments where manual manipulation in a sealed environment is required, e.g. for preparing a medical device for use in the surgical procedure. Other applications could for example be that the surgeon wishes to remove a specimen form the body of the patient after a laparoscopic procedure has been concluded. The laparoscopic procedure could in these instances be performed with the medical device being in the first position (as shown in FIG. 123*d*), being close to the skin of the patient, whereafter the medical device could be placed in the second position for enabling the specimen to be removed from the body of the patient and placed in the chamber of the medical device without contacting the outside environment, and without the release of the pressure that usually fills the abdomen in laparoscopic procedures. According to the embodiment shown in FIGS. 123*b*-*e*, the wall 1101 is collapsible such as to enable the transferring between the first and second position. The lower coupling comprises a lever 1139 for releasing and/or locking the upper coupling 1131*a* to the lower coupling 1131*b*, and thereby placing the medical device in the first state. The medical device 1100 is according to the embodiment shown in FIG. 123*b* fixated to the patient by means of a vacuum sealing member 1105', such as for example disclosed with reference to FIGS. 66 and 67.

Figure 123C:
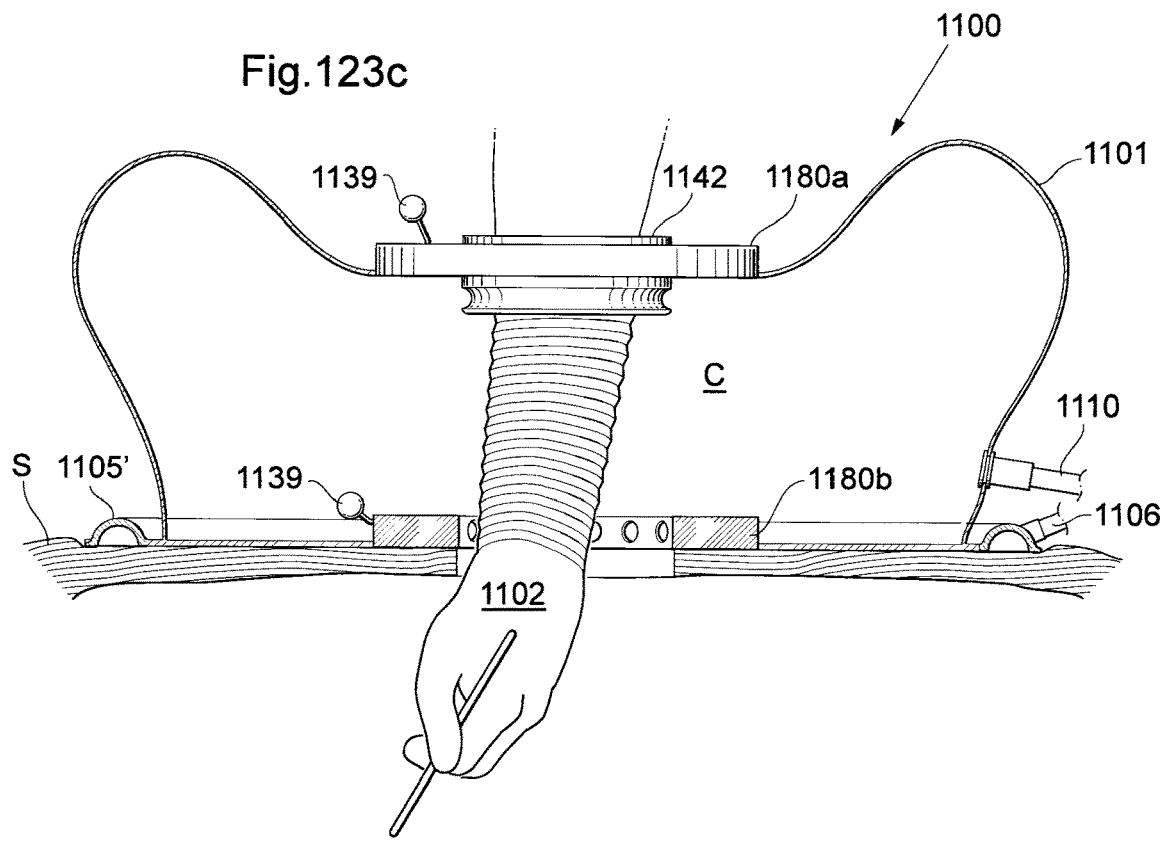

FIG. 123*c* shows the medical device 1100 when being transferred between the first and second position, i.e. the upper coupling 1131*a* is pushed towards the lower coupling 1131*b* for enabling a lock between the upper 1131*a* and lower 1131*b* coupling. The integrated surgical glove 1102 has been stretched such as to enable manual manipulation within the body of the patient and within the chamber of the medical device.

FIG. 123*d* shows the medical device 1100 when locked in the first position, i.e. the upper coupling 1131*a* is locked to the lower coupling 1131*b*. The integrated surgical glove 1102 now enables manual manipulation with great freedom within the body of the patient. The medical device comprises two levers 1139*a* and 1139*b*, wherein the first lever 1139*a* is connected to the upper coupling 1131*a* and adapted to lock the object (here being a surgical glove 1102) to the coupling 1131*a*, while the second lever 1139*b* is connected to the lower coupling 1131*b* for locking the upper coupling 1131*a* to the lower coupling 1131*b*. The medical device 1100 is according to the embodiments shown in FIG. 123 *b*-*e* circular when seen from above, such that the medical device 1100 takes the shape of a doughnut when placed in the first position.

FIG. 123*e* shows the exchanging of objects when the upper coupling 1131*a* has been locked to the lower coupling 1131*b*. The object comprises the surgical glove 1102 has been removed and can for example be replaced by an airlock 1170 for transferring objects between the outer environment and the chamber of the medical device 1100. The airlock comprises an inner wall 1182 and an outer wall 1183 on each side of the airlock 1170 enabling the enclosing of an object within the airlock 1170. Another example of an object to which the surgical glove 1102 can be exchanged is a port device 1148 here shown as a body multi-port comprising laparoscopic ports 1147 for performing a laparoscopic procedure. In some embodiments (not shown) the upper and/or lower coupling comprises a valve member for closing the opening in the coupling when the objects should be exchanged, the valve member could for example be a flap valve.

Figure 123F:
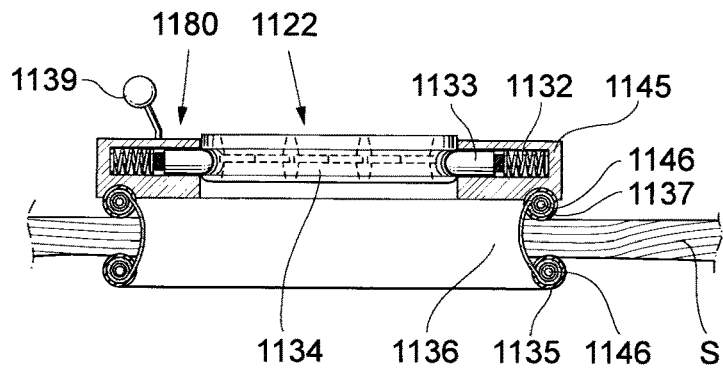

FIG. 123*f* shows an embodiment of the medical similar to the embodiment of FIGS. 123*b*-*e*. In the embodiment shown in FIG. 123*f*, the medical device is placed in contact with the skin of the patient prior to the beginning of the operation and the entire portion of the wall 1101 contacting the skin of the patient comprises an adhesive, such that the incision in the patient runs through the wall 1101 and further through the skin 1141 of the patient. This reduces the risk that infectious objects can be transferred from the skin of the patient to the incision in the patient if the skin of the patient is not adequately disinfected. The body of the patient could be inflated through a fluid inlet 1130 to allow better visibility within the body. The fluid inlet is connected to a fluid conduit 1113 connected to a pressure tank 1112. In alternative embodiments, it is equally conceivable that the body of the patient is inflated from within trough a different incision in the body of the patient.

Figure 123G:
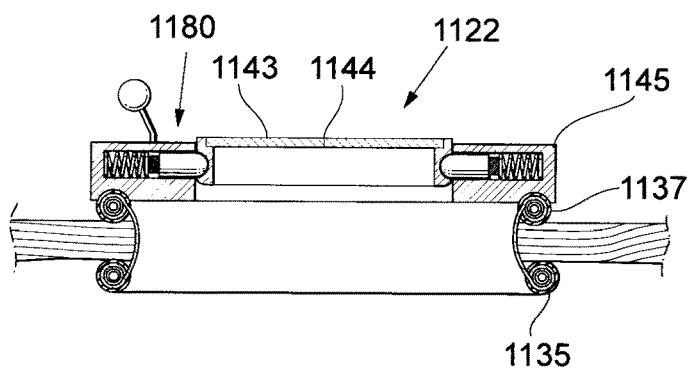

FIG. 123g shows an embodiment of a detachable body port which could be fixated to the lower coupling 1131b positioned in the medical device 1100 disclosed with reference to FIGS. 123b-e. The port arrangement of FIG. 123g includes an intra body ring 1135 adapted to be placed at the inside of the patients skin around an incision, and an outer ring 1137 adapted to be placed on the outside of the patients skin 1141 around the incision. Between the intra body ring 1135 and outer ring 1137 an annular retractor membrane 1136 is positioned adapted to exert a pressure on the skin or human tissue at the incision to seal between the rings and the skin or human tissue and additionally for retracting the skin and thereby keep the incision open. The retractor membrane 1136 is preferably made from a resilient or elastic polymer material. The outer ring 1137 comprises an integrated roll up system 1146, which may be spring loaded and adapted to create a suitable pressure on retractor membrane 1136 to keep the incision open.

The port arrangement shown in FIG. 123g also includes a coupling having a rigid annular seating 1145 attached to the outer ring 1137, spring loaded latching members 1133 arranged in radial bores in the seating 1145 and a hand lever 1139 connected to the latching members 1133 to enable retraction thereof against the action of springs 1132. The port arrangement further includes a self sealing body port 1122 held by the coupling. The body port 1122 comprises a disc-shaped self sealing membrane 1143 fixated to a rigid ring having an outer circumferential groove 1134 that receives the latching members 1133 of the coupling. The self sealing membrane 1143 has a small self sealing hole 1144, centrally in the membrane 1143. For example, the self sealing membrane 1143 may be made from a gel-type material being elastic enough to enable a deformation large enough for a person's hand to pass through the small self sealing hole 1144 while still contracting enough to create an airtight seal between the chamber and the outside environment.

The coupling described above enables quick exchange of the port 1122. Thus, the surgeon may release the body port 1122 from the port arrangement by simply pulling the hand lever 1139 so that the latching members 1133 disengage from the groove 1134 of the body port 1122, whereby the body port 1122 can be removed.

Figure 123H:
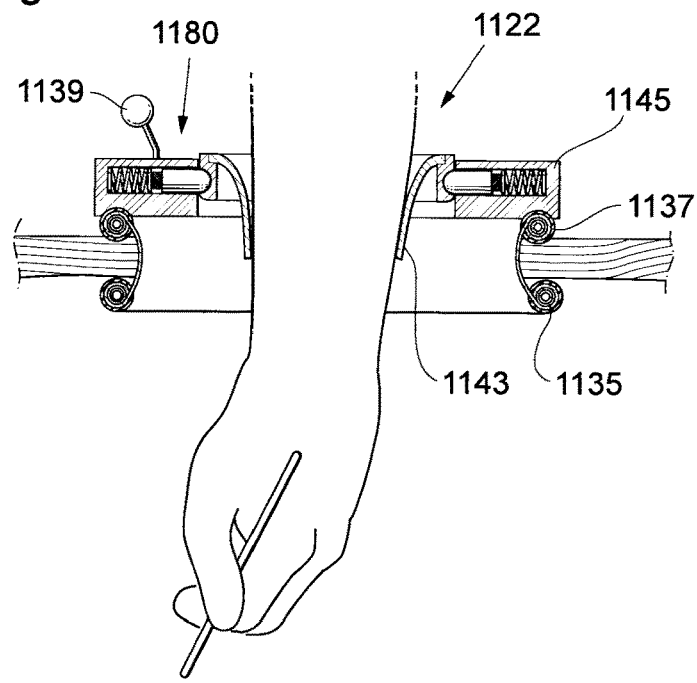

FIG. 123h is a cross-sectional view of the port arrangement shown in FIG. 123g, to more clearly illustrate the body port 1122 with its self sealing membrane 1143 and small hole 1144.

Figure 123J:
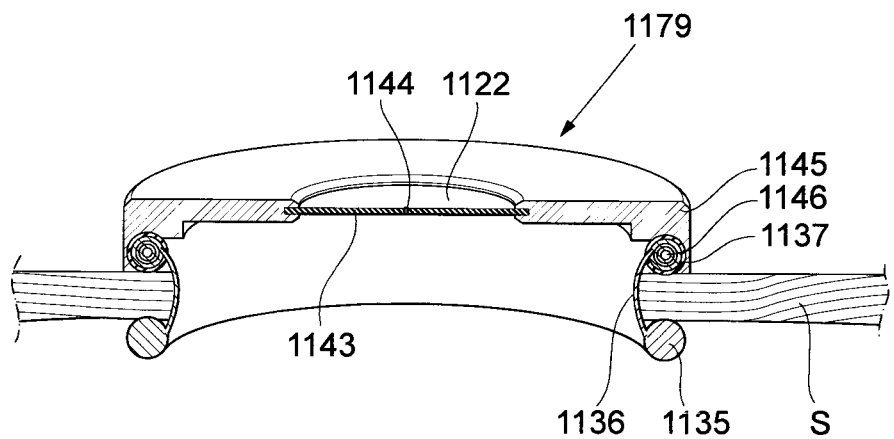
Figure 123K:
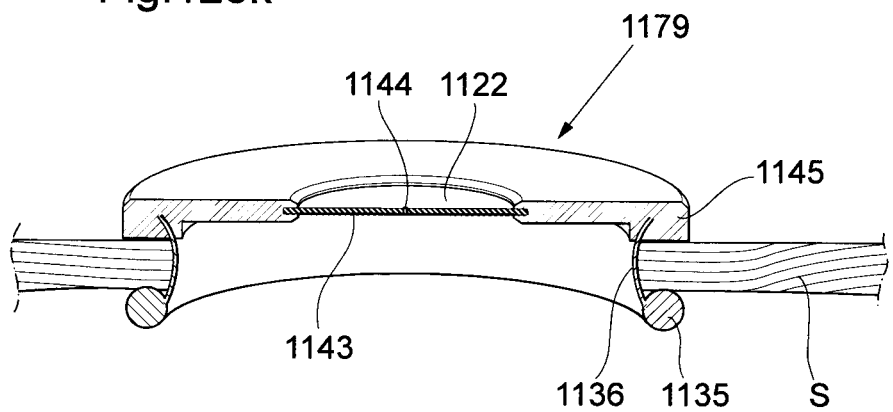
Figure 123I:
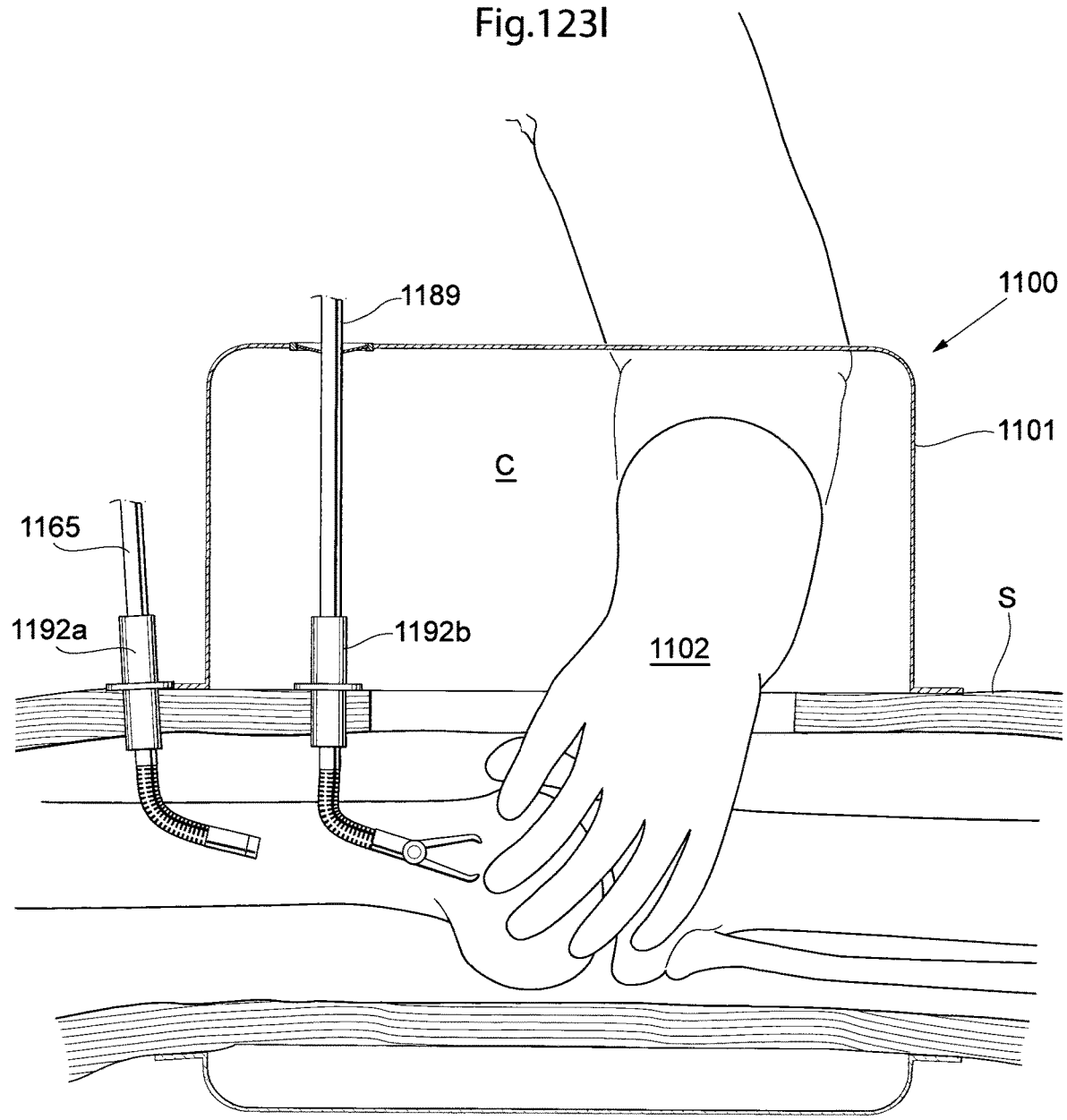

FIG. 123i shows the self sealing body port 1122 when the hand of a surgeon is placed through the hole 1144 in the membrane 1143 and thus enabling manual manipulation within the body of the patient.

FIG. 123j shows a self sealing body port 1122 in a close-up, in section. The self sealing body port 1122 could be connected to the coupling, for example as disclosed with reference to FIGS. 81-82, which in turn is connected to any of the medical device disclosed with reference to FIGS. 115-123, or the self sealing body port 1122 could be fixated to a retractor, as shown in FIGS. 123g-123i. The self sealing body port 1122 comprises a self sealing membrane 1143 fixated to a rigid part 1145 of the self sealing port. The self sealing membrane 1143 having a small self sealing hole 1144 centrally in the membrane 1143. The self sealing membrane 1143 is for example made from a gel-type material being elastic enough to enable a deformation large enough for a person's hand to pass through the small self sealing hole 1144 while still contracting enough to create an airtight seal between the sealed environment and the outside environment. The medical device being fixable to a retractor comprising one intra body ring 1135 adapted to be positioned on the inside of the patients skin, and one ring 1137 adapted to be placed on the outside of the patients skin. Between the intra body ring 1135 and the ring 1137 adapted to be placed on the outside of the patient's skin a retractor membrane 1136 is positioned which is adapted to exert a pressure of the cut surfaces of the incision for retracting the skin and thereby keeping the wound open. The retractor membrane 1136 is preferably made from a resilient of elastic polymer material. The ring adapted to be placed on the outside of the patient's skin 1141 comprises an integrated roll up system which could be a spring loaded roll up system adapted to create a suitable pressure on retractor membrane 1136 for keeping the wound open.

FIG. 123k shows an alternative embodiment of the self sealing body port 1122, with the difference that the retractor membrane 1136 is made from a material elastic enough such that one end of the retractor membrane 1136 could be fixedly fixated to the rigid part 1145 of the port.

FIG. 123l shows the medical device as shown in FIG. 123f with the addition that the embodiment comprises a sterilizing unit 1126 adapted to sterilize the gaseous fluid entering the medical device 1100 through the fluid inlet 1130. In the embodiment disclosed herein, the gaseous fluid entering the medical device 1100 originates from a pressurized tank 1112 and could be pre-sterilized, however, in other embodiments, it is conceivable that the gaseous fluid is the surrounding air which is pressurized (such as further disclosed with reference to FIG. 123m). In the embodiments where the surrounding air is used to inflate the medical device 1100 and constitute the operating environment this air needs to be properly sterilized. The medical device 1100 further comprises a tempering unit 1126c which could be provided to heat or cool the gaseous fluid inflating the medical device 1100. In cases when the surrounding environment is cold the tempering unit 1126c could be used to raise the temperature of the sealed environment to provide beneficial operating circumstances both for the patient and for the surgeon. In cases when the surrounding environment is hot, the tempering part of the system 1126c could be used to lower the temperature of the sealed environment both to provide beneficial operating circumstances, both for the patient and for the surgeon, and for providing a temperature inhibiting bacterial and viral infections. The tempering unit 1126c could comprise a temperature regulating device 1125 for setting the required temperature.

Figure 123M:
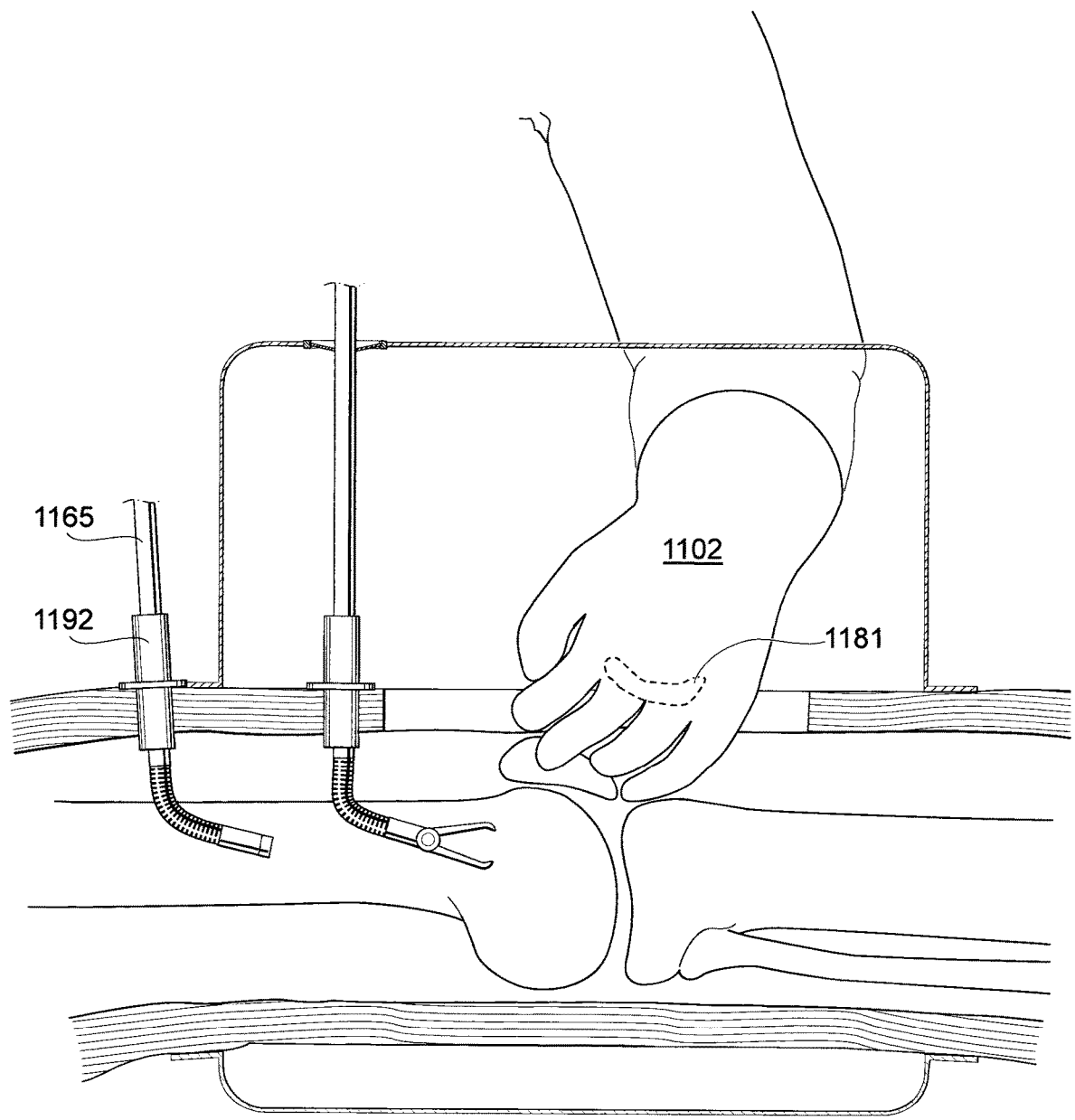

FIG. 123m shows a medical device similar to the embodiment disclosed in FIG. 123l, with the difference that the medical device comprises a system 1128 for circulating a fluid from a fluid outlet 1131 placed in the wall of the medical device 1100 to a fluid inlet 1130 placed in the medical device. The system comprises a fluid conduit 1129 connected at an inlet 1130 placed in the wall 1101 for supplying fluid to the sealed environment, and an outlet 1131 for draining the fluid from the sealed environment. The fluid is circled by means of a pumping unit 1127 and is circled via a sterilizing/filtering unit 1126 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 123N:
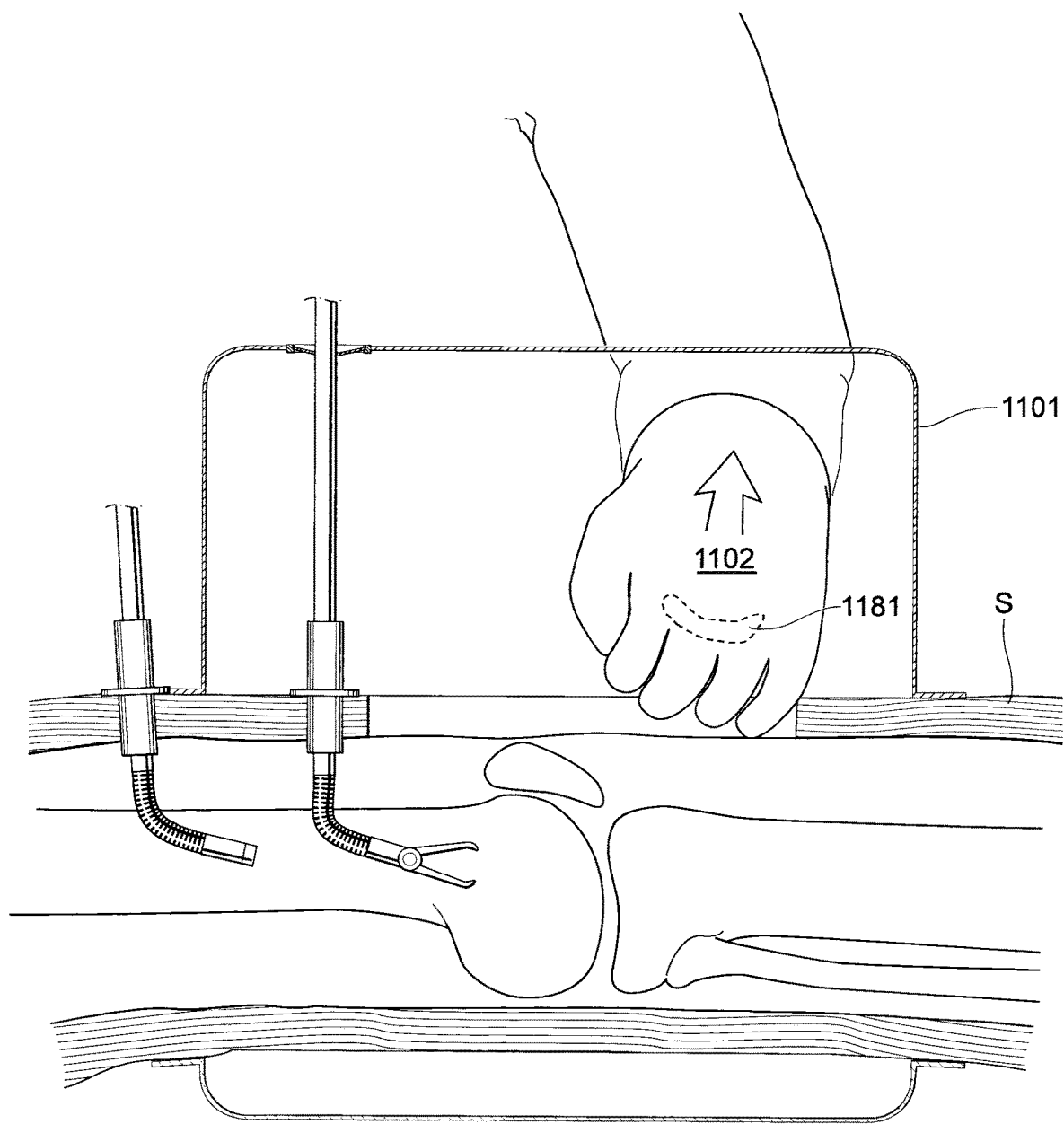

FIG. 123*n* shows an alternative of the embodiment shown in FIGS. 115-123. Fig. In 123*n* the medical device 1100 is adapted to be at least partially placed in an incision cut in a patient's body. The medical device 1100 comprises a first 1131*b* and second 1131*a* part adapted be interconnected to form a surgical port. The second part 1131*a* is adapted to be disconnected from the first part 1131*b*, and the first part 1131*b* is connected to a first portion of a flexible wall 1101, and the second part is connected to a second portion of the flexible wall 1101. The flexible wall 1101 forms a chamber in which a sealed environment can be maintained, the chamber is heavily enlarged when the second part 1131*a* is disengaged from the first part, thus creating operating space within the chamber enclosed by the wall. The first and second parts comprise a latching system for locking an inset. The inset may for example be an airlock part 1170 with a first 1182 and second 1183 valve member, a glove 1102 for manual manipulation within the body of the patient, or within the enclosed chamber, a holding device 1181 for holding instruments or medical devices within the chamber, and a multiport portion 1148 comprising a plurality of ports enabling the insertion of a surgical instrument into the chamber or body of the patient.

In the embodiment shown in FIG. 123*n* the medical device is fixated to the body of the patient by means of a vacuum fixating member 1105' connected to a conduit 1114, which in turn is connected to a vacuum source. Furthermore, the medical device in FIG. 123*n* comprises a second sealing function having a first sealing member 1135 adapted to be positioned at the inside of the patient's skin around an incision to be performed in the skin and a second sealing member 1137 adapted to be positioned at the outside of the patient's skin around the incision, and a spring-loaded or elastic connecting member 1136 sealingly interconnecting the first 1135 and second 1137 sealing members. The spring-loaded or elastic connecting member 1136 seals between at least one of the port and the skin of the patient, and the first sealing member and tissue of the patient.

Figure 123O:
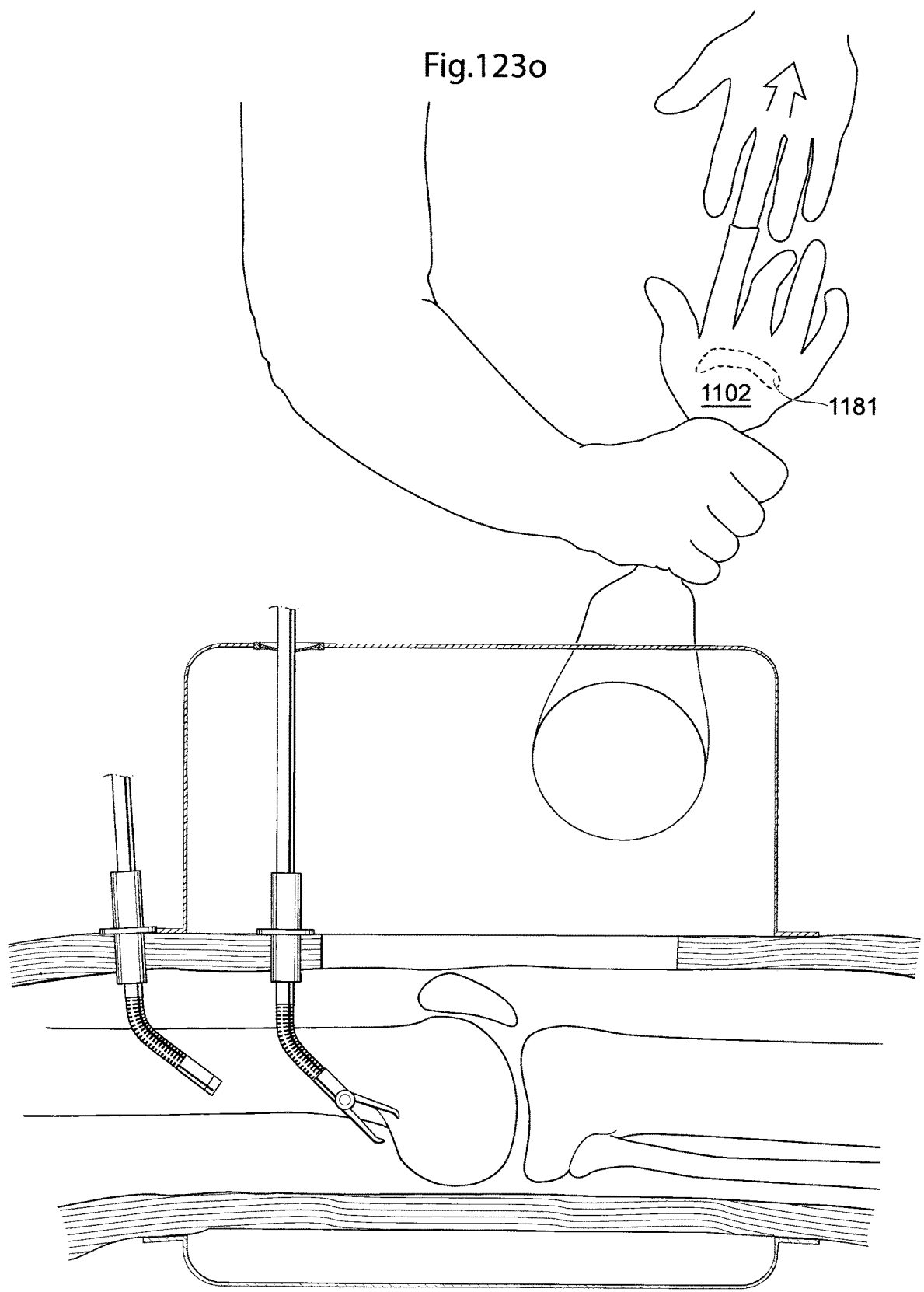

FIG. 123*o* shows the port in an embodiment very similar to the embodiment shown in FIG. 123*n*, but with the difference that the wall 1101' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure. A camera 1165 is also shown in FIG. 123*o*, placed outside of the medical device and enabling visual inspection of the cavity within the medical patient.

FIGS. 123*p*-123*s* shows how the medical device shown in FIGS. 115-123 may be used. The medical device 1100 comprises a glove 1102 integrated in the wall 1101 and a camera 1165 placed in the skin outside of the medical device 1100. The medical device 1100 further comprises a trocar 1192 placed trough an opening in the wall 1101 and into the sealed environment and further through an opening in the skin of the patient and into an area of the knee of the patient. FIG. 123*p* schematically illustrates how the surgeon manipulates the knee in the sealed environment using the glove 1102.

FIGS. 123*q*, 123*r* shows the medical device when the surgeon removes a specimen from the knee of the patient using the glove 1102 integrated in the wall of the medical device.

FIG. 123*s* shows the medical device, when the surgeon has turned the integrated glove inside-out such that the specimen can be contained within the integrated glove. By isolating the specimen inside of the glove, the specimen is removed both from the rest of the body of the patient and from the ambient environment, and thereby does not risk to infect any other portion of the patient's body or medical staff with any infectious disease.

FIG. 123'*a*-123'*e* shows an embodiment of the medical device similar to the embodiment shown in FIG. 123*b*-123*e*. The main difference being the medical device of the embodiment shown in FIGS. 123'*a*-123'*b* does not comprise a bottom portion of the wall 1101, i.e. a wall portion contacting the skin of the patient and making the wall of the medical device fully encapsulating the chamber C. In the embodiment shown in FIGS. 123'*a*-123' e, the chamber C has a circular cross-section perpendicular to the skin of the patient. However, in other embodiments, it is equally conceivable that the medical device has a cross section having a different shape.

FIG. 123' a shows a medical device for performing a surgical procedure comprising a wall 1101 adapted to enclose a chamber C together with the skin S of the patient for encompassing part of the surgical procedure. A wall port 1131*a* is placed in the wall 1101 in which an inset can be positioned (such as the glove inset 1102 shown in FIG. 123'*a*). The medical device 1100 further comprises a seal 1105' connected to the wall 1101 and adapted to seal against the patient's body, such that the chamber C is formed by the wall 1101 and the patient's body. In the embodiment shown in FIG. 123'*a* the medical device comprises a vacuum seal 1105' adapted to hold a pressure less than atmospheric pressure between the patient's skin S and the vacuum seal 1105' to seal the chamber C by sealing towards the patient's skin S. In alternative embodiments, the vacuum seal 1105' may be replaced or assisted by a pressure seal adapted to hold a pressure above atmospheric pressure between the pressure seal and the patient's skin S to seal the chamber C by sealing towards the patient's skin S (an example of a pressure seal if for example shown in FIG. 36*b*).

FIG. 123' b shows the medical device 1100 of the embodiment described with reference to FIG. 123'*a* when the wall 1101, preferably made from a transparent flexible material is compressed by the wall port 1131*a* is being moved closer to a body port 1131*b* placed in an incision in the skin S of the patient. The wall 1101 comprises an inlet 1130 for supplying a fluid to the chamber C, the wall 1101 being adapted to hold a pressure in the chamber C exceeding atmospheric pressure such that the chamber C is inflated by the fluid. In laparoscopic surgery a cavity within the patient is inflated by means of a pressurized fluid for creating an area in which the laparoscopic surgery can be performed under visual inspection. As the chamber C is adapted to hold a pressure exceeding atmospheric pressure the pressure in the cavity in the patient can be maintained even when the incision in the skin of the patient has been performed. In alternative embodiments, the medical device further comprises a fluid outlet provided in the wall 1101 for discharging the fluid from the chamber C, in which case the medical device further may comprise a pump adapted to circulate the fluid from the outlet to the inlet. The inlet 1101 may further be connected to at least one of: a filtering unit for filtering fluid supplied to the chamber C, a sterilization member for directly or indirectly sterilizing fluid supplied to the chamber C, a fluid tempering device adapted change the temperature of fluid supplied to the chamber C.

In the embodiment shown in FIG. 123' b the body port 1131b comprises protruding members 1133, and the wall port 1131a comprises a recess 1134 in the form of a groove adapted to receive the protruding members 1133. The protruding members 1133 are adapted to engage the groove 1134 for locking the wall 1131a port to the body port 1131b. The protruding members 1133 are connected to a lever 1139 for operating the protruding members 1133 such that the wall port 1131a can be quickly released from the body port 1131b after having been connected.

FIG. 123' c shows the medical device when the wall port 1131a is detachably connected to the body port 1131b placed in an incision cut in a patient's body, which enables manual manipulation within the cavity of the patient by means of the glove 1102 positioned in a glove inset fixated to the wall port 1131a. The wall port 1131a is locked to the body port 1131b by the protruding members 1133 of the body port 1131b engaging the groove 1134 of the wall port 1131a. The chamber C has a smaller volume when the wall port 1131a is connected to the body port 1131b. According to the embodiment shown in FIG. 123' c the smaller volume is smaller than 100 000 mm3, however in other embodiments, the smaller volume may be smaller than one of: 50 000 mm3, smaller than 150 000 mm3, smaller than 250 000 mm3 or smaller than 350 000 mm3, while the larger volume, when the wall port 1131a is disconnected from the body port 1131b (such as in FIG. 123'a) is larger than 500 000 mm3 for enabling manual manipulation to be made within the chamber C.

FIG. 123' d shows the medical device when the wall port 1131a has been connected to the body port 1131b and the glove 1102 shown in FIG. 123' c is replaced by either a multi port (a port comprising a plurality of ports 1147) inset 1148 adapted to enable passage of two parallel objects to the inside of the patient's body, or an airlock sluice 1170 comprising a first valve 1182 sealing between the cavity of the patient and the chamber of the airlock sluice, and a second valve 1183 sealing between the chamber of the airlock sluice 1170 and the ambient environment, such that the cavity of the patient can be sealed at all times even when an object is transferred from the ambient environment to the cavity.

FIG. 123' e shows an embodiment when both the wall port 1131a and body port 1131b comprises disc-shaped self sealing membranes 1143a, 1143b. In the body port 1131b, the self sealing membrane 1143b is positioned in the top portion of the port 1131b, whereas in the wall port 1131a, the membrane 1143a is positioned in the bottom part of the wall port 1131a. The self sealing membranes 1143a, 1143b have small self sealing holes 1144 such that the instruments 1188 can be inserted through the self sealing membranes 1143a, 1143b. For example, the self sealing membranes 1143a, 1143b may be made from a gel-type material. The wall port 1131a, and body port 1131b may form an integrated port when the wall port 1131a and body port 1131b is connected, with the membranes 1143a, 1143b contacting each other such that the instruments 1189 engage an integrated sealing membrane (made up of the first and second membranes 1143a, 1143b) in the integrated port. If the ports had two spaced-apart membranes, the two membranes would reduce the ability to move the instruments 1189 far more than the two integrate membranes acting as a single integrated membrane. The sealing membranes 1143a, 1143b are adapted to, in a non-expanded state, provide a seal, and in an expanded state, enable an instrument 1189 to be inserted through the membranes 1143a, 1143b.

FIG. 123'e further shows a fixating/sealing device for the body port 1131b. The fixating/sealing device comprises a first sealing member 1135 being an intra body ring 1135 adapted to be positioned at the inside of the patient's skin around an incision performed in the skin, and a second sealing member 1137 in form of an outer ring 1137 adapted to be positioned at the outside of the patient's skin around the incision, and a spring-loaded or elastic connecting member 1136 in form of a retractor membrane 1136 sealingly interconnecting the first 1135 and second 1137 sealing members. The spring-loaded or elastic connecting member 1136 seals between the body port 1131b and the tissue of the patient. The fixating/sealing device additionally retracts the skin and thereby keeps the incision open. The retractor membrane 1136 is preferably made from a resilient or elastic polymer material. The outer ring 1137 comprises an integrated roll up system 1146, which may be spring loaded and adapted to create a suitable pressure on retractor membrane 1136 to keep the incision open.

FIG. 123'f shows the medical device 1100 when the wall port 1131a is disconnected from the body port 1131b by the protruding members 1133 connected to the lever 1139 being disengaged from the recess 1134 (groove) of the wall part 1131a, such that a additional steps of the surgical procedure can be performed within the chamber C of the medical device 1100. For example, the disconnection could be required when a specimen has been removed from the cavity of the patient and should be removed from the cavity. The specimen may in the embodiment shown in FIG. 123'f be positioned in the chamber C while the surgical procedure is concluded, such that the environment of the chamber C can remain sealed from the ambient environment when a specimen needs to be removed from the cavity within the patient. In alternative embodiments the wall 1101 may further comprise a pouch for holding the specimen within the chamber C (such as for example the pouch disclosed under reference to FIG. 123a). The pouch can be a closeable pouch, such that a pouch-chamber can be created for isolating the removed specimen within the chamber C.

FIG. 123'g shows an embodiment of the medical device 1100 in which the medical device comprises a wall 1101 partially applied on the patient's skin S body forming a chamber C together with the patient's skin S, in which a sealed environment can be maintained for encompassing part of the surgical procedure to be performed. The medical device further comprises a closeable wall port 1147a placed in a portion of the wall 1101 and being adapted to be connected to a closeable body port 1147b, closeable by means of a self sealing membrane 1143 in the body port 1147b. The body port 1147b being placed in an incision in the patient's skin S connecting the chamber C of the medical device to a cavity of the patient's body, when the medical device is applied on the patient's skin S for performing the surgical procedure. The medical device further comprises a sealing device 1105', in the embodiment disclosed in FIG. 123'g being a vacuum seal 1105', connected to the wall 1101 and adapted to seal against the skin S of the patient. The wall port 1147a thus forming an airlock sluice together with the body port 1147b, between the cavity in the patient's body and the ambient environment, when the medical device is applied on the patient's body for performing the surgical procedure.

The closeable wall port 1147a comprises an interconnecting member comprising a recess 1134 adapted to connect to an interconnecting member of the body port 1147b in the form of protruding members such that the closeable wall port 1147a is locked to the closeable body port 1147a.

The vacuum seal 1105' shown in FIG. 123'g is connected to a vacuum conduit 1106 for supplying negative pressure to the vacuum seal 1105'. The vacuum conduit is in turn connected to a vacuum creating member, such as a vacuum pump (disclosed for example under reference to FIG. 2a).

A fluid inlet 1130 connected to a fluid conduit 1110 is furthermore shown in FIG. 123'g. The fluid inlet is adapted for supplying fluid to the chamber C for inflating the wall 1101 of the medical device 1100.

FIG. 123'h shows the medical device when an incision has been made in the skin S of the patient and the wall port 1147a is connected to the body port 1147b by means of the protruding members 1133 of the body port engaging the recess or groove 1134 of the wall port 1147b. The protruding members 1133 are connected to a releasing lever 1139b for retracting the protruding members and thereby release the wall port 1147a from the body port 1147b.

FIG. 123'i shows an alternative embodiment of the medical device disclosed with reference to FIGS. 123'a-123'h in which the body port 1147b is fixated by means of supports 1149a, 1149b attached to the sealing device 1105' and/or wall 1101 of the medical device 1100. FIG. 123'i shows the wall port 1147a when it is being displaced between a first position, in which the wall port 1147a is fixated to the body port 1147b (such as for example shown in FIG. 123'h), and a second position in which the wall port 1147a is detached from the body port 1147b and positioned more remote from the body port 1147b. The wall port 1147a and body port 1147b are closable by means of self sealing membranes 1143a, 1143b positioned in the wall port 1147a and body port 1147b.

FIG. 123j shows an embodiment of the medical device similar to the embodiment disclosed with reference to FIGS. 123'g-123'k, the difference being that the wall port 1147 comprises a portion adapted to be placed in an incision in the patient's skin for fixating and sealing the wall port in the patient's skin. The portion comprising a sealing adapted to be placed in the incision comprising a first sealing member in the form of an intra body ring 1135 adapted to be positioned at the inside of the patient's skin around the incision. The sealing further comprises a second sealing member in the form of an outer ring 1137 adapted to be positioned at the outside of the patient's skin around the incision, and a spring-loaded or elastic connecting member 1136, sealingly interconnecting the first 1135 and second 1137 sealing members, such that the spring-loaded or elastic connecting member 1136 seals between the second sealing member and the skin S of the patient and/or the first sealing member and the tissue of the patient inside of the patients skin S.

FIG. 123k shows the medical device shown in FIG. 123'j, when a portion of the wall port 1147 is placed in the incision in the skin S of the patient, such that the intra body ring 1135 fixates the wall port 1147 to the skin S of the patient. The membrane 1143 of the port 1147 now becomes a body port separating the cavity in the patient from the ambient environment and enabling laparoscopic steps to be performed through the port 1147 inside the cavity in the patient. If a specimen needs to be removed from the cavity in the patient, the portion of the wall port placed in the incision can be retracted from the incision, or the portion could be disconnected from the rest of the wall port, thus keeping the wound open whilst allowing a step of the operation to be performed in the full-size chamber of the medical device through the wall port 1147.

Figure 124A:
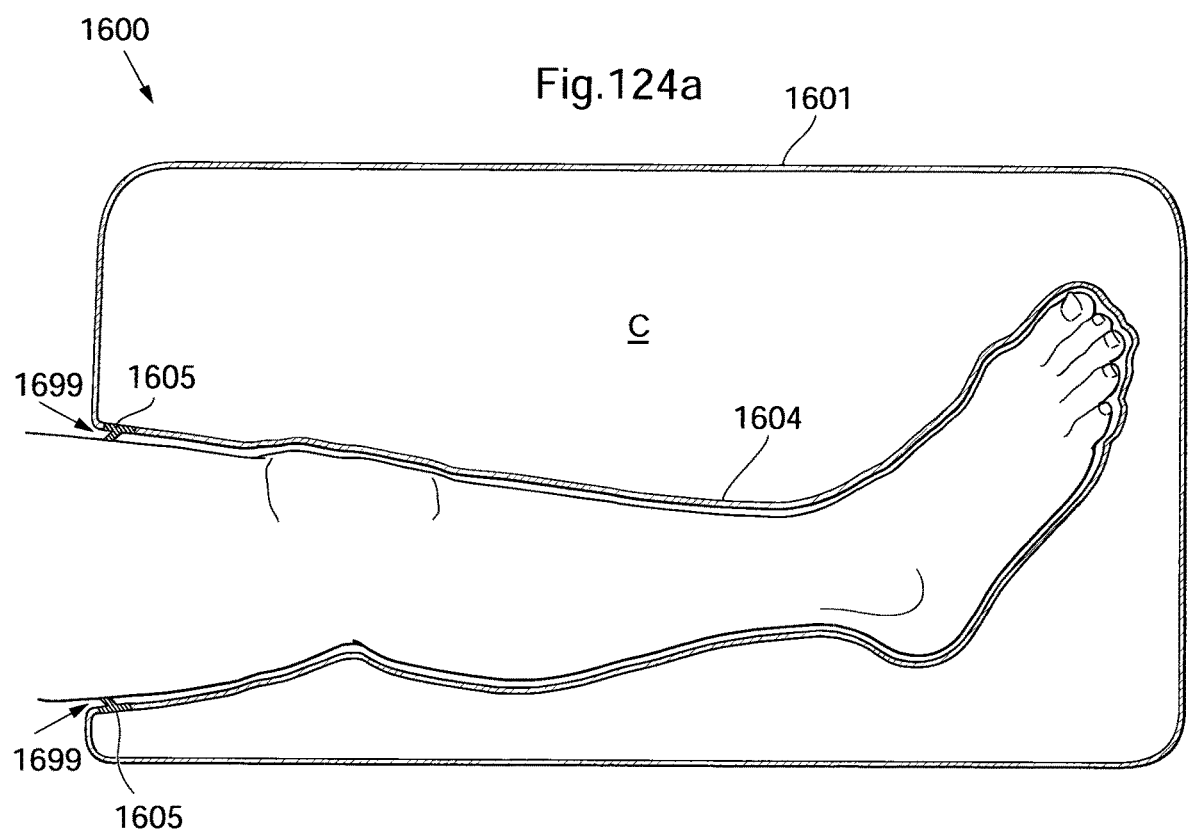
FIGS. 124a, 124b, 124d shows the medical device when applied to a leg of a patient.

FIG. 124a shows a medical device for performing surgical procedures according to an embodiment. The medical device comprises an at least partially collapsible wall 1601 enclosing a chamber in which a sealed environment can be maintained for performing the surgical procedure. The at least partially collapsible wall comprises a wall portion forming at least one elongated tubular enclosure 1604 having an open end. The enclosure 1604 extends in the chamber and is adapted to fit a portion of an extremity of a patient inserted into the enclosure through the open end thereof. In the embodiment shown in FIG. 124a the extremity is a leg of the patient. Furthermore the medical device comprises a sealing member 1605 encircling the leg of the patient and being adapted to seal between the skin of the patient and the at least partially collapsible wall 1601. According to the embodiment shown in FIG. 124a only the portion of the wall 1601 comprising the elongated enclosure 1699 is collapsible or deformable, for allowing the insertion of the extremity into the elongated enclosure 1699, whereas the rest of the wall 1601 enclosing the chamber is rigid, however, in other embodiments it is equally conceivable that the entire wall enclosing the sealed environment is collapsible.

Figure 124B:
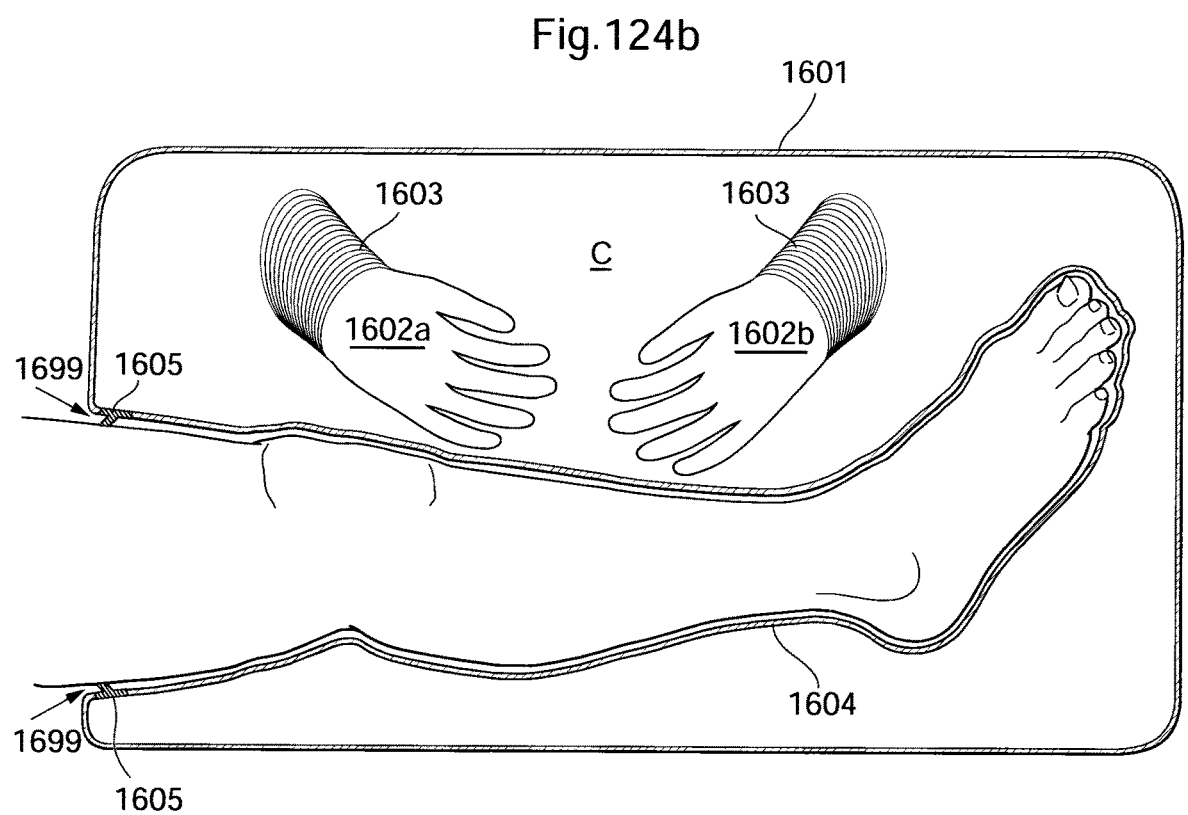

FIG. 124b shows the medical device in an embodiment similar to that of FIG. 124a with the difference that the embodiment of FIG. 124b further comprises two gloves 1602a, 1602b integrated in the wall 1601 enabling manual manipulation within the sealed environment. The gloves 1602a, 1602b are connected to the wall 1601 by means of pleated sections 1603 connecting the gloves 1602a, 1602b to the wall 1601 and enabling free movement of the gloves 1602a, 1602b within the sealed environment.

Figure 124C:
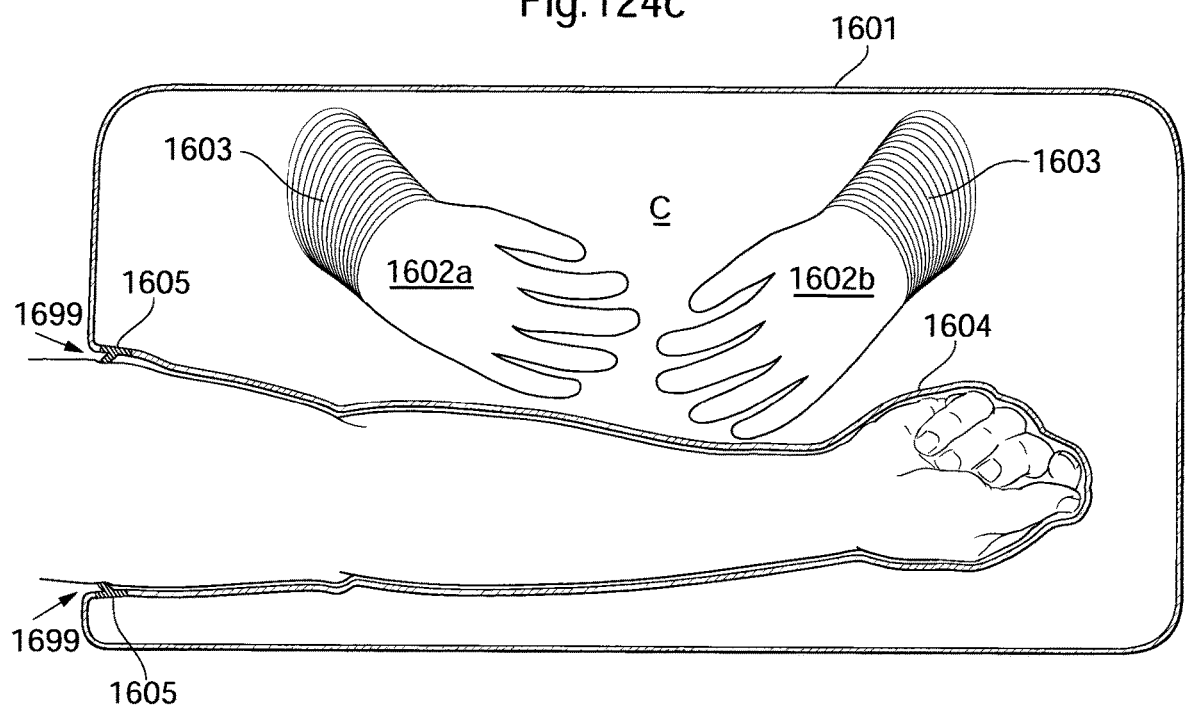
FIGS. 124c, 124e shows the medical device when applied to an arm of a patient.

FIG. 124c shows an embodiment of the medical device similar to that of FIG. 124b, the difference being that the embodiment in FIG. 124c is adapted to receive an extremity in the form of an arm.

Figure 124D:
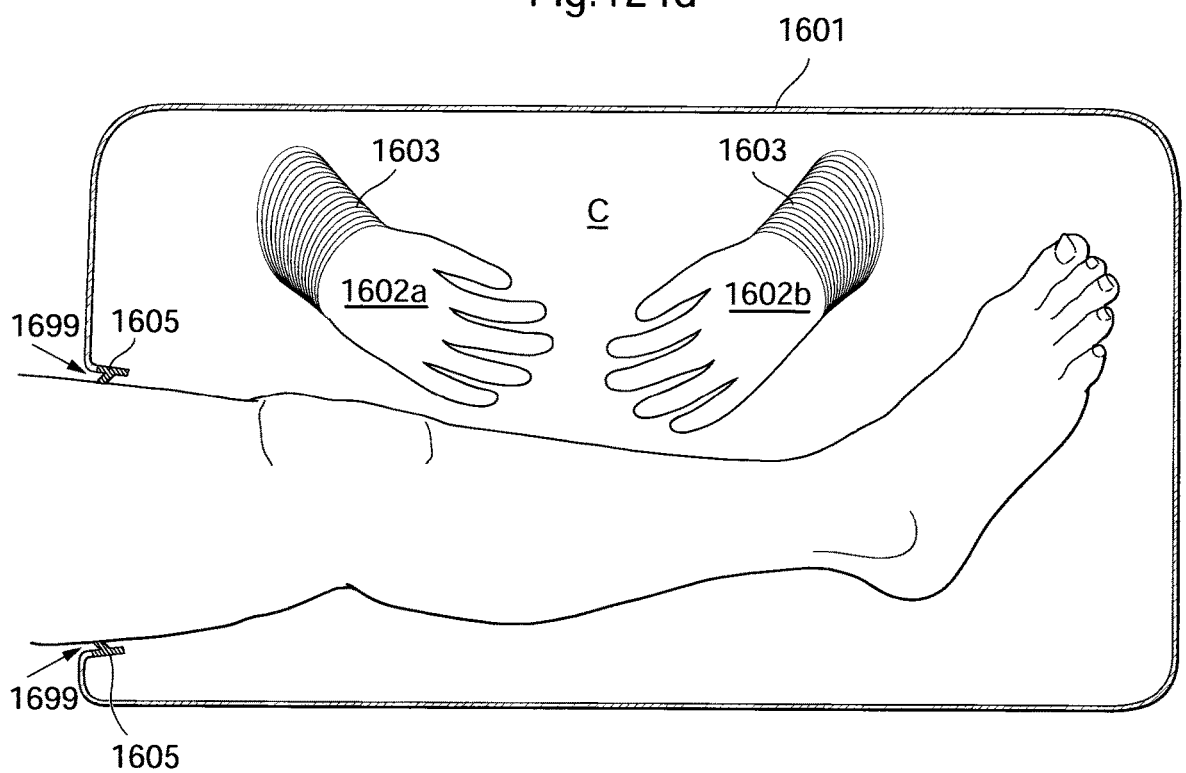

FIG. 124d shows an embodiment similar to the embodiment shown with reference to FIG. 124b, the difference being that the medical device according to the embodiment of FIG. 124d does not have the elongated enclosure, i.e. the medical device only comprises one open end for insertion of the extremity into the chamber. The chamber is thus adapted to be formed by the wall and the patient's body and the tubular enclosure is adapted to encompass the chamber, and the chamber is adapted to be sealed 1605 at the open ends by the patient's body portion (in this case the leg).

Figure 124E:
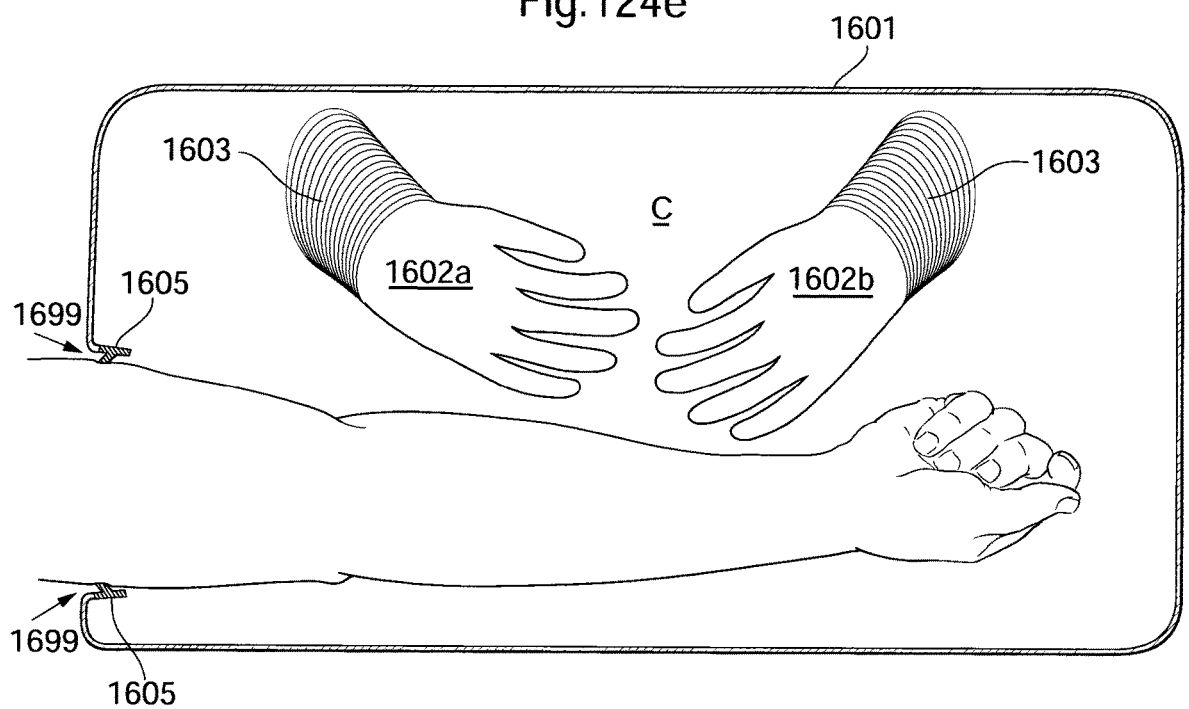

FIG. 124e shows an embodiment of the medical device similar to that of FIG. 124d, the difference being that the embodiment in FIG. 124e is adapted to receive an extremity in the form of an arm.

Figure 125A:
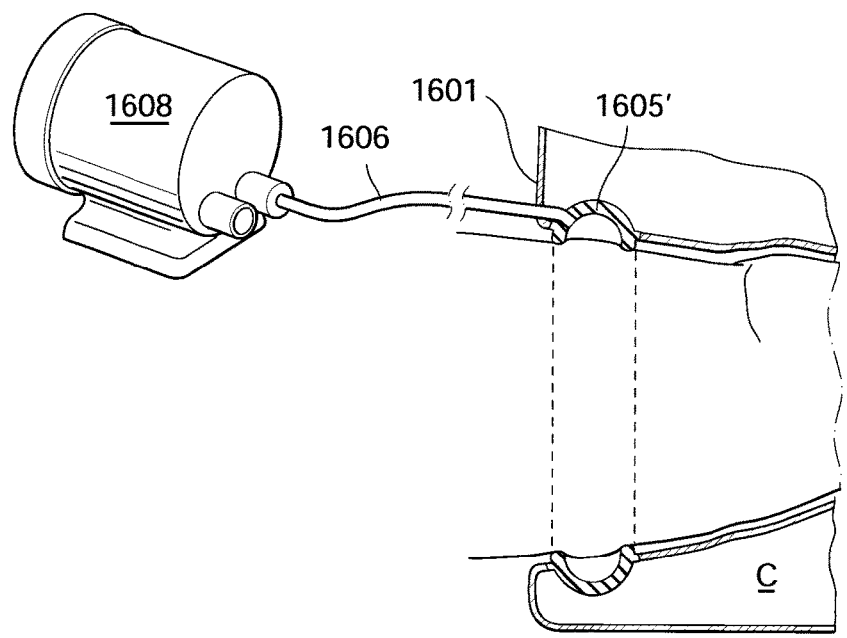
FIG. 125a shows a vacuum seal in detail.

FIG. 125a shows a sealing member in detail, in an embodiment in which the sealing member comprises a vacuum sealing member 1605' adapted to seal between an extremity of the patient and the partially collapsible wall 1601 by the vacuum sealing member 1605' being adapted to hold a pressure less than 1 bar (an under pressure) for creating a vacuum sealing between the skin of the patient and the medical device. The vacuum is created by a vacuum pump 1608 connected to the vacuum sealing member by means of a vacuum conduit 1606. The vacuum sealing member 1605' could for example be made from a semi-rigid polymer material.

Figure 125B:
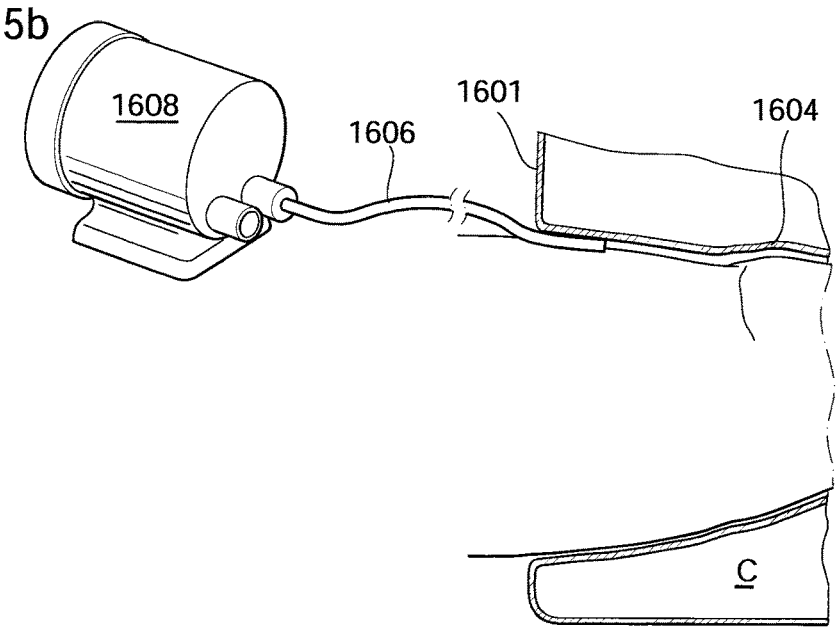
FIG. 125b shows an air evacuation pump, in detail.

FIG. 125*b* shows an embodiment of the medical device in which the medical device comprises an air evacuation system 1608 for evacuating air in the elongated enclosure 1604 after the portion of an extremity has been placed in the elongated enclosure, thereby tightening the wall around the extremity of the patient. The air evacuation system 1608 comprises a conduit 1606 in fluid connection with the elongated enclosure and thereby enabling the evacuation of the air or fluid from therein.

Figure 125C:
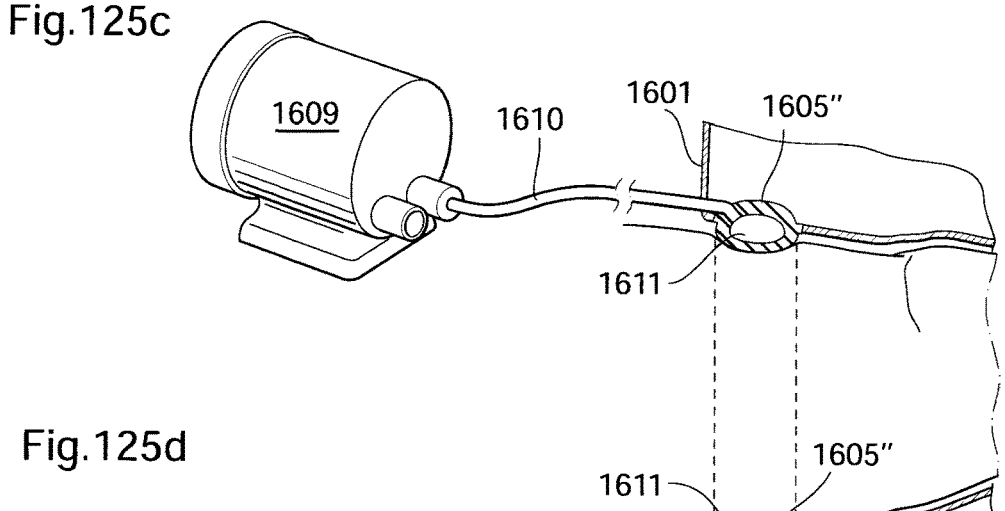
FIG. 125c shows a pressure sealing in detail.

FIG. 125*c* shows a sealing member in detail in an embodiment in which the sealing member 1605 comprises a pneumatic pressure sealing member 1605" adapted to seal between an extremity of the patient and the partially collapsible wall 1601 using a pneumatic pressure pressing against the skin of the extremity. The pneumatic pressure is created by a pneumatic pump 1609 being connected to the pneumatic pressure sealing member 1605" by means of a fluid conduit 1610 adapted to transport a pressurized gas from the pneumatic pump 1609 to a cavity 1611 within the pressure sealing member 1605", the pressure sealing member 1605" being inflatable such that the size and/or shape of the cavity 1611 can be changed for allowing the pneumatic pressure sealing member to press against the skin of the extremity and thereby sealing between the extremity and the pneumatic pressure sealing member 1605". The pneumatic pressure sealing member 1605" may for example be made from an elastic material such as an elastic polymer.

Figure 125D:
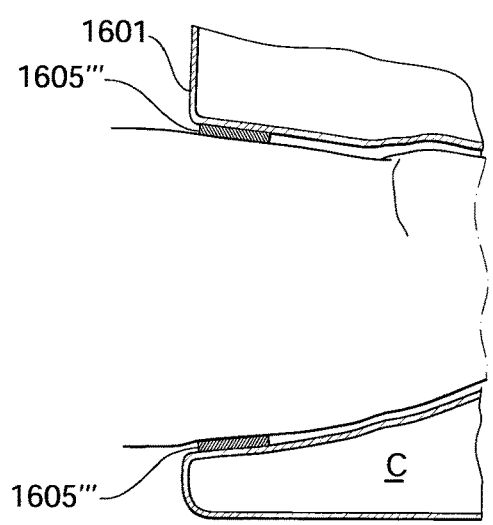
FIG. 125d shows an adhesive sealing.

FIG. 125*d* shows a sealing member in detail in an embodiment in which the sealing member comprises an adhesive sealing member 1605''' adapted to seal between an extremity of the patient and the partially collapsible wall 1601 by means of an adhesive contacting the skin of the patient and the elongated enclosure part of the medical device. In the embodiment shown in FIG. 125*d* the adhesive sealing member encircles the extremity (in this case the leg) of the patient thereby creating a seal. The adhesive may for example be a pressure sensitive adhesive such as 3M's pressure sensitive adhesive Scotch-Grip 4268-NF.

Figure 126A:
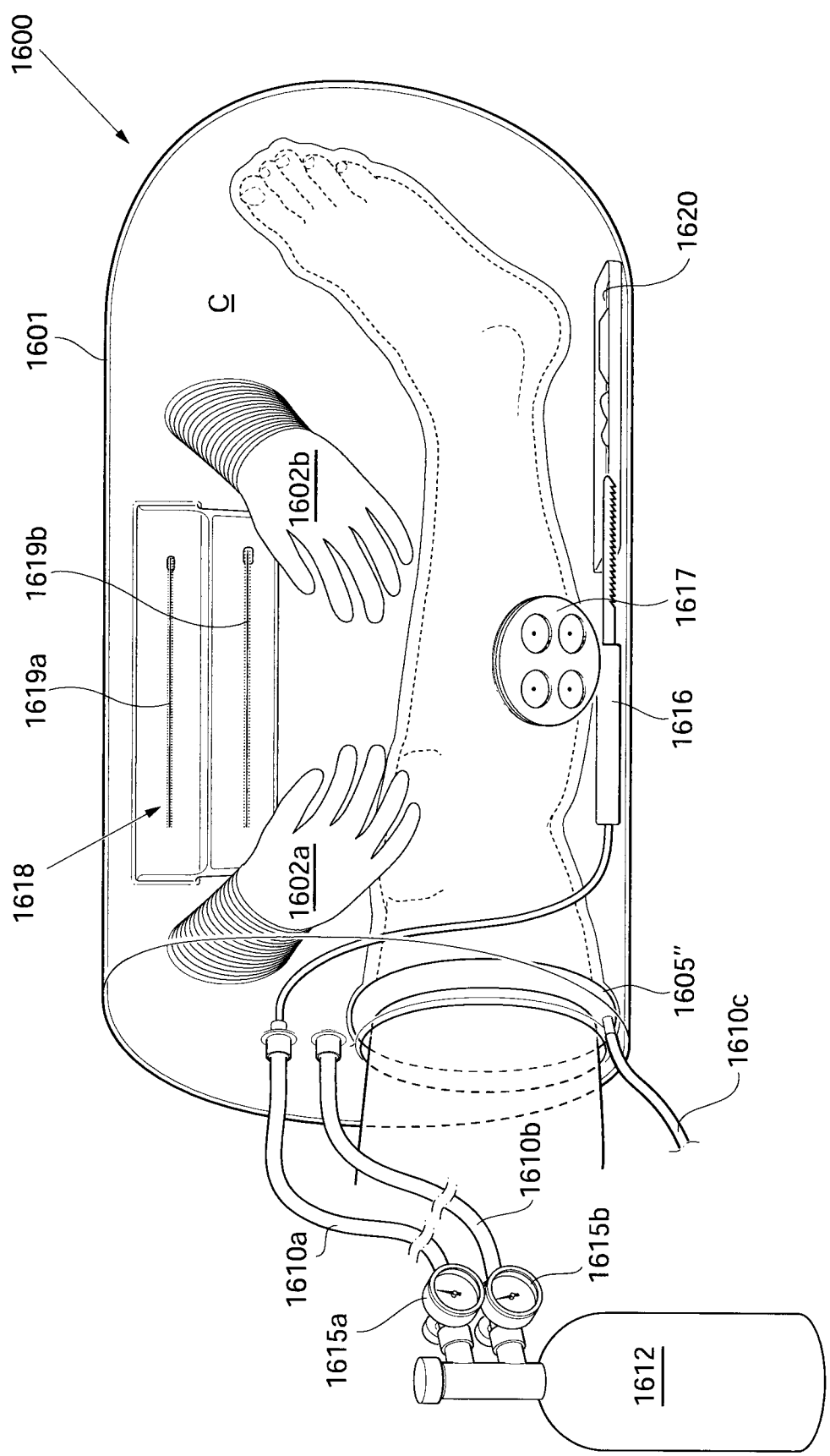
FIGS. 126a-126e shows embodiments of a medical device, in perspective.

FIG. 126*a* shows an embodiment of the medical device in which the medical device comprises a partially collapsible wall 1601 having a cylindrical or tube shaped structure. The partially collapsible wall 1601 is inflatable by means of a pneumatic conduit 1613*b*, here connected to a tank 1612 containing pressurized gas. The tank is further connected to a pneumatic system 1613*a* for transferring pneumatic force into the sealed environment enclosed by the partially collapsible wall 1601 and including the operating field of the extremity. Shown in the embodiment herein, the pneumatic system 1613*a* is connected to a pneumatic tool 1616, which in the example shown is an orthopedic saw, adapted to be operated within the sealed environment S. The pressure provided to the sterile environment and the pneumatic system 1613*a* is controlled and monitored by a control/monitoring system 1615*a*, 1615*b* connected to the pneumatic conduits, respectively. In the embodiment shown, the partially collapsible wall is sealed to the extremity of the patient by means of a pneumatic pressure sealing member 1605" (further disclosed with reference to FIG. 125*c*) encircling the extremity. In FIG. 126*a* the medical device is shown incorporating the pneumatic pressure sealing member 1605", however it is equally conceivable that the pneumatic pressure sealing member 1605" is assisted or replaced by any of the other sealing members disclosed herein. The medical device shown in FIG. 123*a* further comprises a air-lock system 1618 comprising two zipper-closed consecutive openings or valves 1619*a*, 1619*b*, where the outer zipper 1619*a* could be opened for placing and/or removing objects in the airlock or sluice chamber between the zippers 1619*a*, 1619*b* from the outside of the sealed environment or chamber and the inner zipper 1619*b* could be opened from the inside of the sealed environment for placing and/or removing objects from the airlock. For example the airlock system could be used to remove a specimen from the sealed environment while keeping the environment sterile, or the airlock could be used to insert a medical device or an implant into the sealed environment. The medical device disclosed with reference to FIG. 126*a* further incorporates laparoscopic ports 1617 (which are to be regarded as optional) through which laparoscopic trocars or endoscopic instruments could be inserted. The medical device according to the embodiment disclosed with reference to FIG. 126*a* further includes an instrument mount 1620 for retaining instruments within the sealed environment.

Figure 126B:
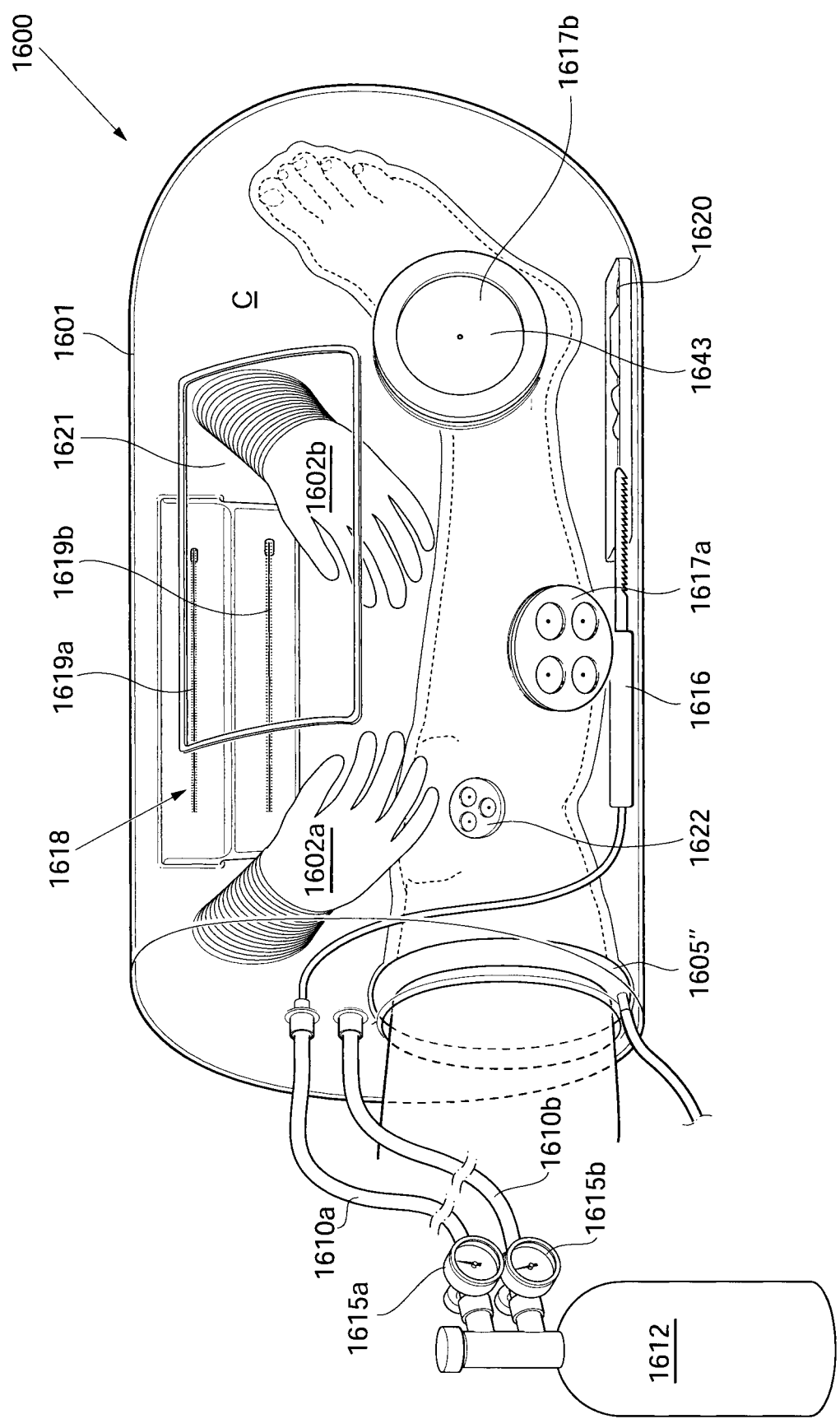
Figure 126B:
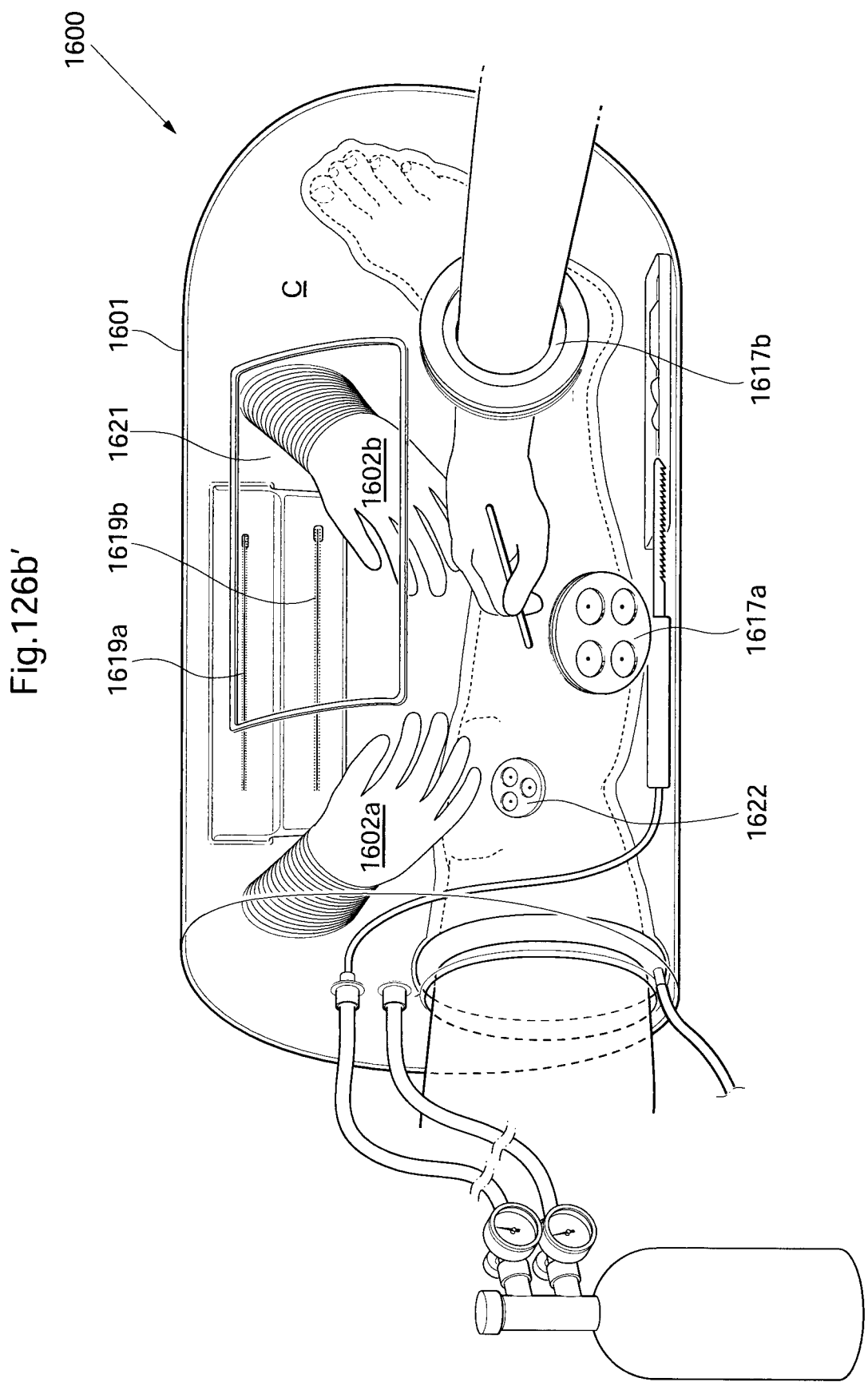

FIG. 126*b* shows the medical device similar to the embodiment shown in FIG. 126*a*, however the partially collapsible wall 1601 of the medical device according to FIG. 126*b* comprises a non-collapsible transparent window 1621 for enabling viewing into the sealed environment. The non-collapsible transparent window 1621 will ensure that the surgeon has adequate visual control over the procedure since the partially collapsible wall 1601, even if preferably made from a transparent material could provide limited visibility, e.g. if the medical device is not fully inflated, or in seams or bends of the material. The medical device shown in FIG. 126*b* further comprises a self sealing access wall port 1622, which for example could be a port comprising a material of gel type, such as the GelPort available from Applied medical inc. Rancho Santa Margarita, Calif. The self sealing access wall port 1622 enables the insertion of trocars and/or instruments as well as a persons (preferably the surgeons) hand, enabling manual manipulation within the chamber. The medical device as shown in FIG. 126*b* further comprises two body ports 1623 which incorporates endoscopic ports in direct connection with the extremity of the patient, within the sealed environment. The body ports 1623 could for example enable an arthroscopic procedure with trocars to be performed within the sealed environment and either by the instruments being manipulated from the inside of the sealed environment or by the instruments reaching from the ports 1617; 1622 in the partially collapsible wall 1601, or the self sealing wall port 1622 in the partially collapsible wall 1601 and to the body port 1623 within the sealed environment.

FIG. 126*b*' shows the embodiment of the medical device according to FIG. 126*b* when the arm of the surgeon is inserted through the self sealing wall port 1622 in the partially collapsible wall 1601 for enabling manual manipulation therein. Manual manipulation through the self sealing wall port 1622 could for example be used as a last resort should complications occur during the procedure, or if additional hands are required for a specific step of the operation. FIG. 126*b*' further shows an internal system 1628' for fluid circulation, and an external system 1628 for fluid circulation. Both systems comprises fluid conduits 1629; 1629', in the external system 1628 connected at an inlet 1630 placed in the partially collapsible wall 1601 for supplying fluid to the chamber, and an outlet 1631 for draining the fluid from the chamber, and in the internal system 1628' connected to an inlet 1630' in the patient's body and an outlet 1631' in the patient's body for circulating fluid in a body cavity. The fluid is circulated by means pumping units 1627;

1627' and is circulated via a sterilizing/filtering/tempering unit 1626', in the external system disclosed as containing a sterilizing 1626a, filtering 1626b, and heating 1626c unit adapted to remove impurities, sterilize and heat the fluid. In embodiments where the fluid is a gaseous fluid, the filtering unit is adapted to remove particles that could be suspended in the gas. The filtering unit 1626a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 1626a could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

Figure 126C:
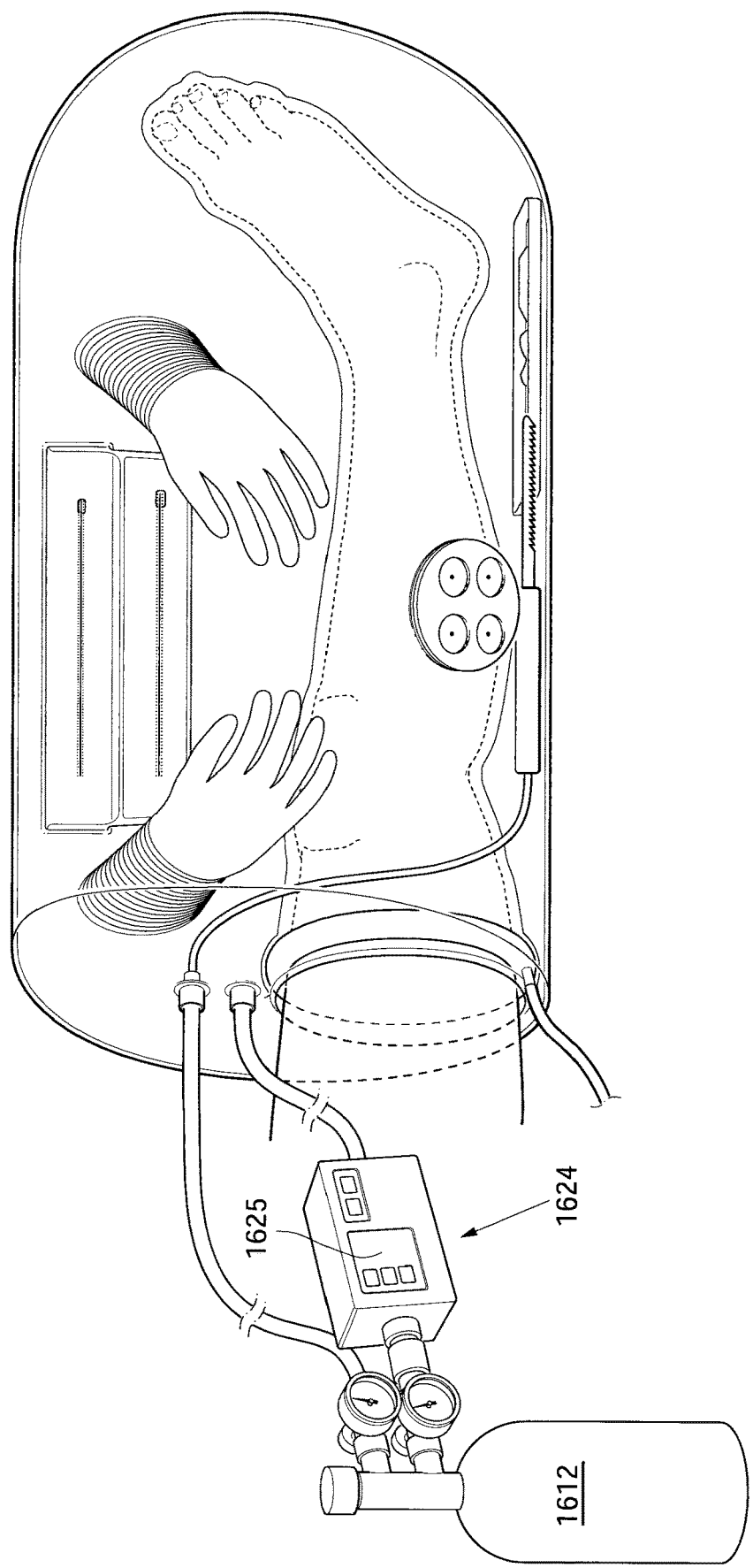

FIG. 126c shows the embodiment of the medical device also shown in FIG. 126a with the addition of a system 1626c for tempering the fluid entering the chamber. The tempering part of the system could be provided to heat or cool the gaseous fluid inflating the medical device. In cases when the surrounding environment is cold the tempering part of the system 1626c could be used to raise the temperature of the chamber to provide beneficial operating circumstances both for the patient and for the surgeon. In cases when the surrounding environment is hot, the tempering part of the system 1626c could be used to lower the temperature of the sealed environment both to provide beneficial operating circumstances, both for the patient and for the surgeon, and for providing a temperature inhibiting bacterial and viral infections. The tempering unit 1626c may comprise a temperature regulating portion 1625 for setting the required temperature.

Figure 126D:
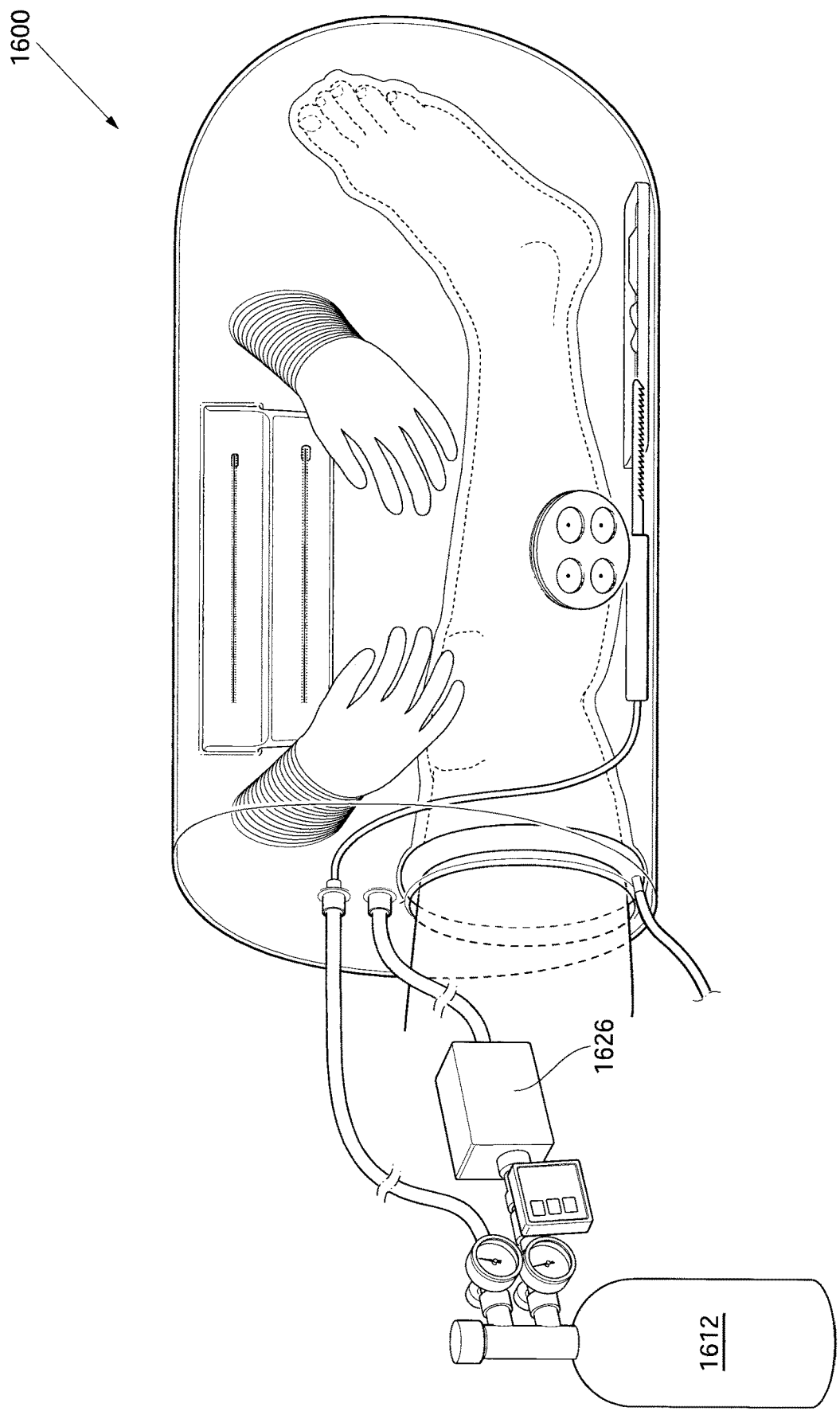

FIG. 126d shows the medical device according to FIG. 126c but further comprising a sterilizing unit 1626 adapted to sterilize the gaseous fluid entering the medical device. In the embodiment disclosed herein, the gaseous fluid entering the medical device originates from a pressurized tank 1612 and could be pre-sterilized, however, in other embodiments, it is conceivable that the gaseous fluid is the surrounding air which is pressurized (such as further disclosed with reference to FIG. 126e). In the embodiments where the surrounding air is used to inflate the medical device and constitute the operating environment this air needs to be properly sterilized.

Figure 126E:
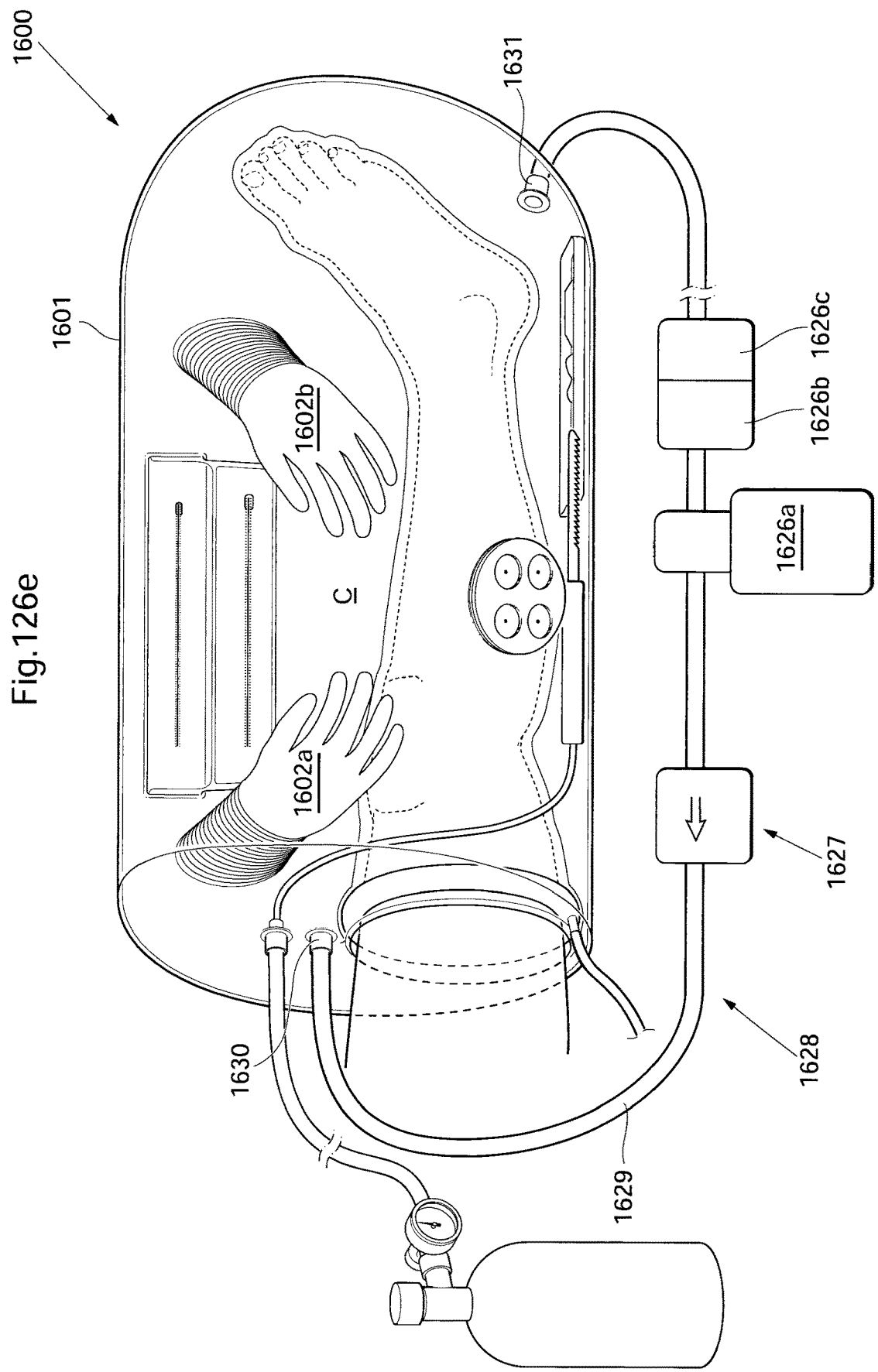

FIG. 126e shows an embodiment of the medical device in which the medical device comprise a system 1628 for circulating a fluid through the chamber of the medical device. The system comprises a fluid conduit 1629 connected at an inlet 1630 placed in the partially collapsible wall 1601 for supplying fluid to the chamber, and an outlet 1631 for draining the fluid from the chamber. The fluid is circulated by means of a pumping unit 1627 and is circulated via a sterilizing/filtering unit 1626 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIGS. 124a-126e show different embodiments of a medical device directed to an extremity of the patient e.g. a leg or an arm. The medical device could for example be used for performing an amputation both in a hospital environment and in environments where the risk of infections are considerably higher, such as in third world countries or in zones of catastrophe. The medical device disclosed enables surgical procedures to be performed in a fully enclosed environment without any risk of infection disease even in very remote locations and without the access to water or electricity.

Figure 127A:
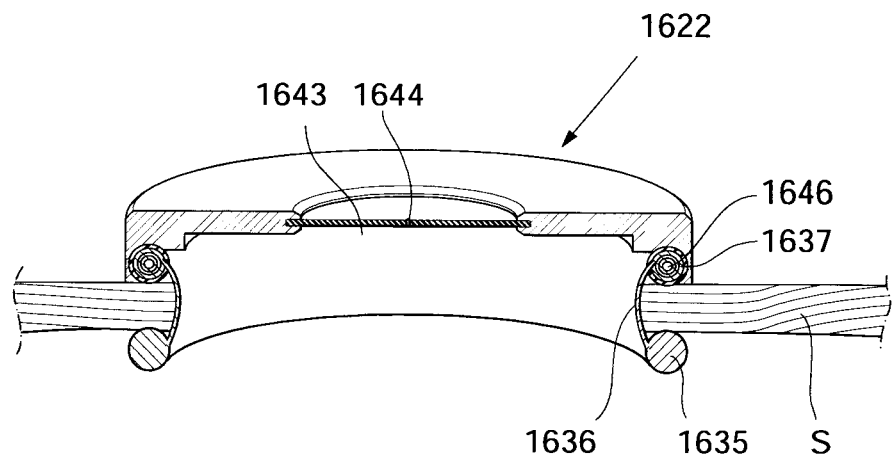
FIGS. 127a-127b shows embodiments of a self sealing port.

FIG. 127a shows the self sealing port 1622 in a close-up, in section, where the self sealing wall port 1622 comprises a self sealing membrane 1643 fixated to a rigid part 1645 of the self sealing port. The self sealing membrane 1643 having a small self sealing hole 1644 centrally in the membrane 1643. The self sealing membrane 1643 is for example made from a gel-type material being elastic enough to enable a deformation large enough for a person's hand to pass through the small self sealing hole 1644 while still contracting enough to create an airtight seal between the sealed environment and the outside environment. The medical device being fixable to a retractor comprising one intra ring 1635 adapted to be positioned on the inside of the wall 1601, and one ring 1637 adapted to be placed on the outside of the wall 1601. Between the intra ring 1635 and the ring 1637 adapted to be placed on the outside of the wall 1601a retractor membrane 1636 is positioned. The retractor membrane 1636 is preferably made from a resilient or elastic polymer material. The ring adapted to be placed on the outside of the wall 1601 comprises an integrated roll up system which could be a spring loaded roll up system adapted to create a suitable pressure on retractor membrane 1636.

Figure 127B:
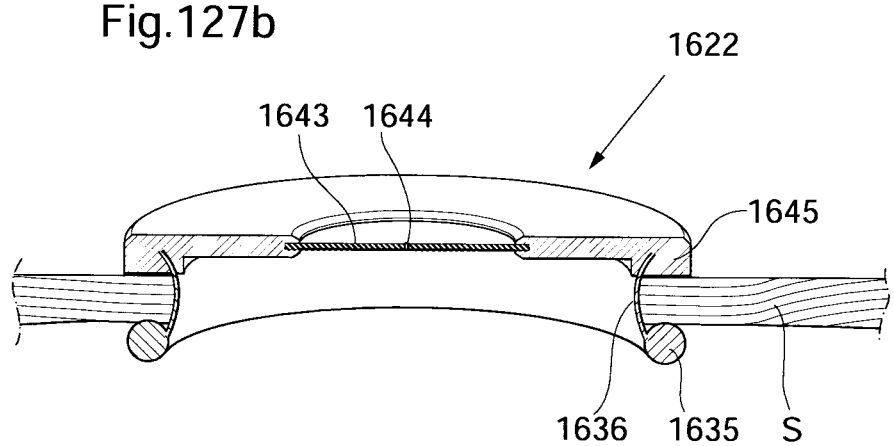

FIG. 127b shows an alternative embodiment of the self sealing port 1622, with the difference that the retractor membrane 1636 is made from a material elastic enough such that one end of the retractor membrane 1636 could be fixedly fixated to a rigid part 1645 of the port.

Figure 128A:
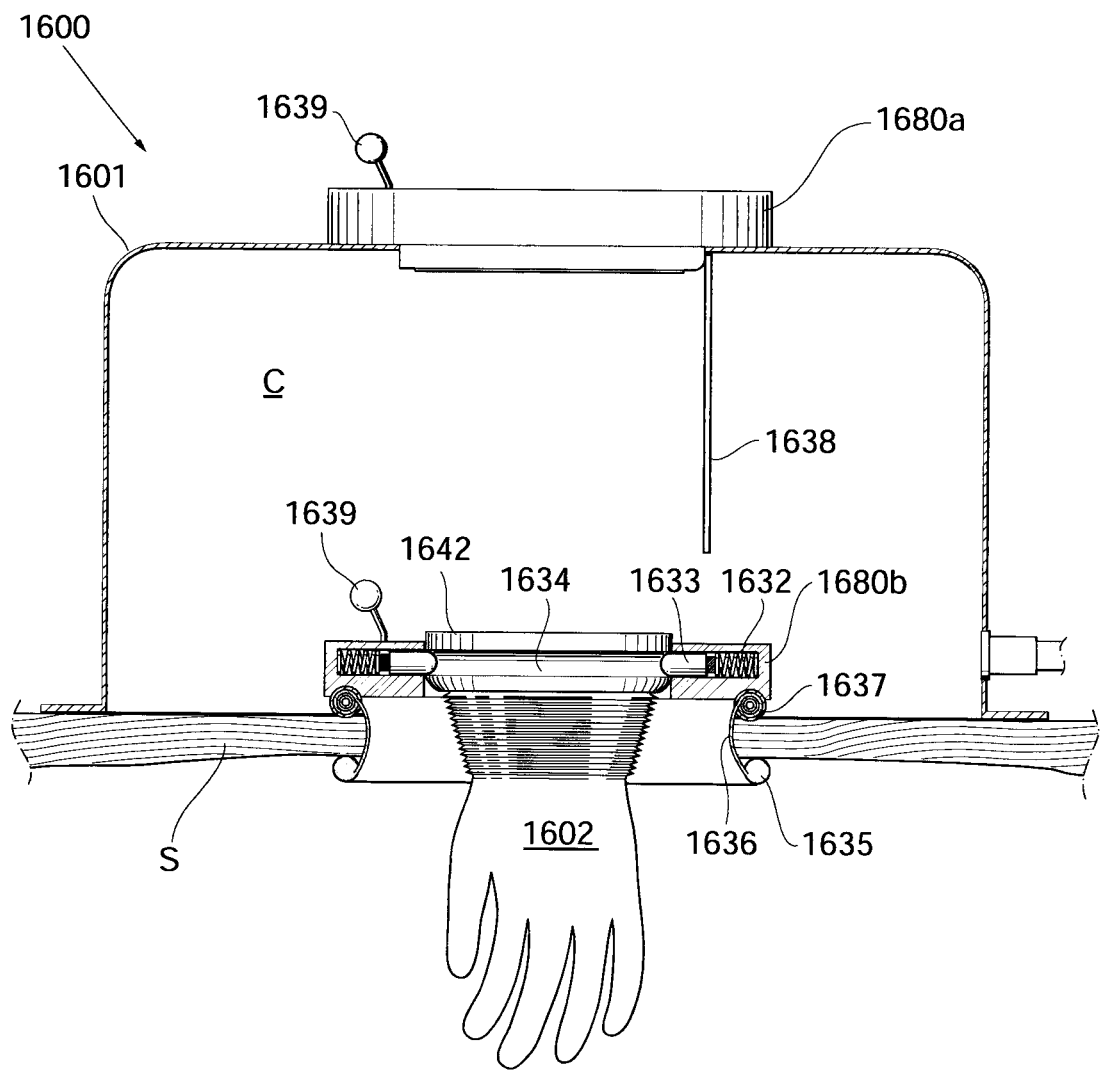
FIG. 128a shows an embodiment of the medical device, in section.

FIG. 128a shows an embodiment of the medical device in which the medical device comprises a wall 1640 separating the sealed environment within the medical device from the outside environment. The wall 1640 is adapted to be fixated to the skin 1641 of the patient, by means of an adhesive or by means of a difference in pressure between the outside of the chamber and the inside thereof. The medical device further comprises an upper 1631a and a lower 1631b coupling for fixating ring shaped objects which for example could be insets or ports. The ports may be hand access ports, such as the self sealing port disclosed with reference to FIGS. 127a and 127b. The coupling comprises a releasing lever 1639 for releasing the object. The lever 1639 is connected to latching members 1633 which are spring loaded 1632 from the rear in order to secure the groove 1634 of the object. In the embodiment disclosed in FIG. 128a, the inset fixated to the lower coupling 1631b is a surgical glove 1602 enabling manual manipulation within the body of the patient. The medical device shows in FIG. 128a further comprises a valve member 1638 adapted to close the opening in the upper coupling 1631*a*, when the upper coupling is not in use.

Figure 128B:
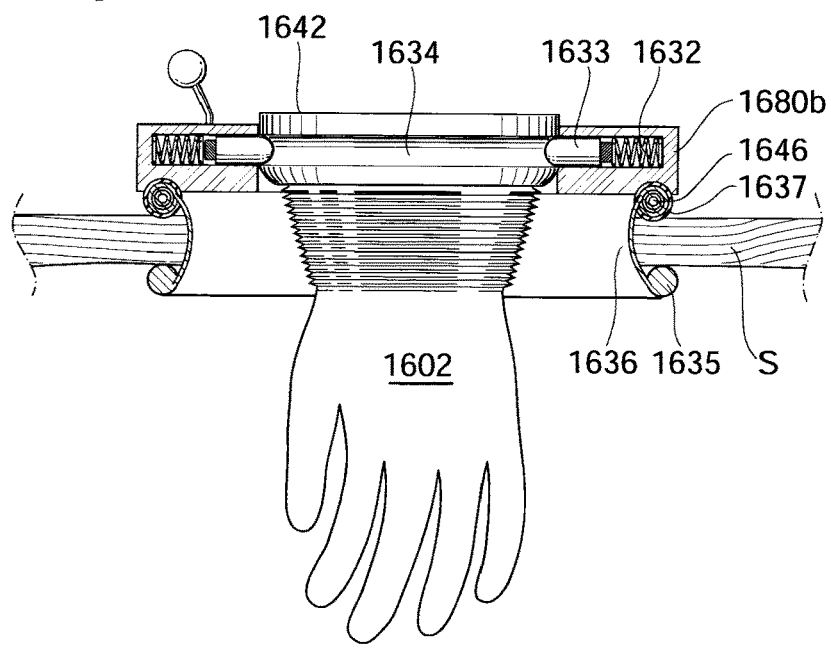
FIG. 128b shows a coupling, in section.

FIG. 128*b* shows the lower coupling 1631*b* in further detail when an inset in the form of a surgical glove 1602 is fixated to the lower coupling 1631*b*. The retractor system comprising the intra body ring 1635 and the ring 1637 adapted to be placed on the outside of the patients skin further comprises a retractor membrane 1636 positioned such that it exerts a pressure on the cut surfaces of the incision for retracting the skin and thereby keeping the wound open. The retractor membrane 1636 could be rolled into a roll 1646 inside of the ring 1637 adapted to be placed on the outside of the patients skin for tightening the retractor membrane 1636 such that the wound is kept open.

Figure 128C:
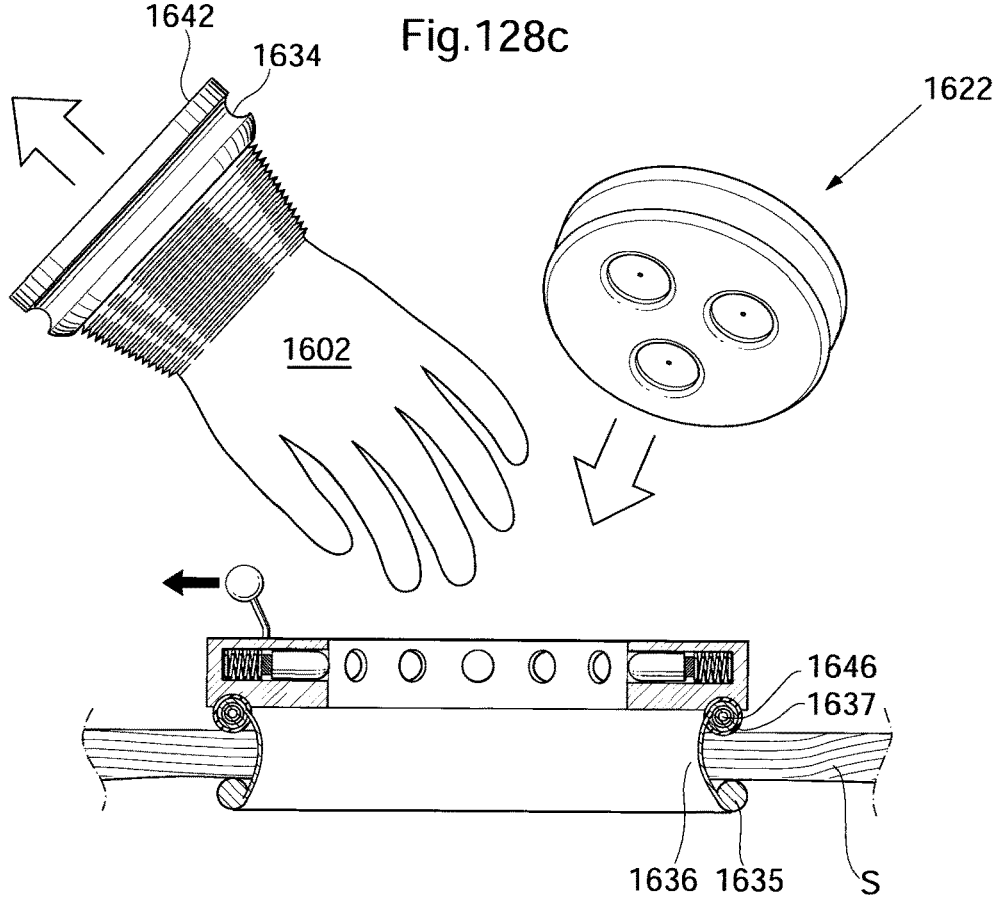
FIG. 128c shows the exchange of objects in a coupling.

FIG. 128*c* shows the changing of objects in the coupling from a surgical glove 1602 to a multi-port 1628 comprising three endoscopic ports 1647. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care.

Figure 129:
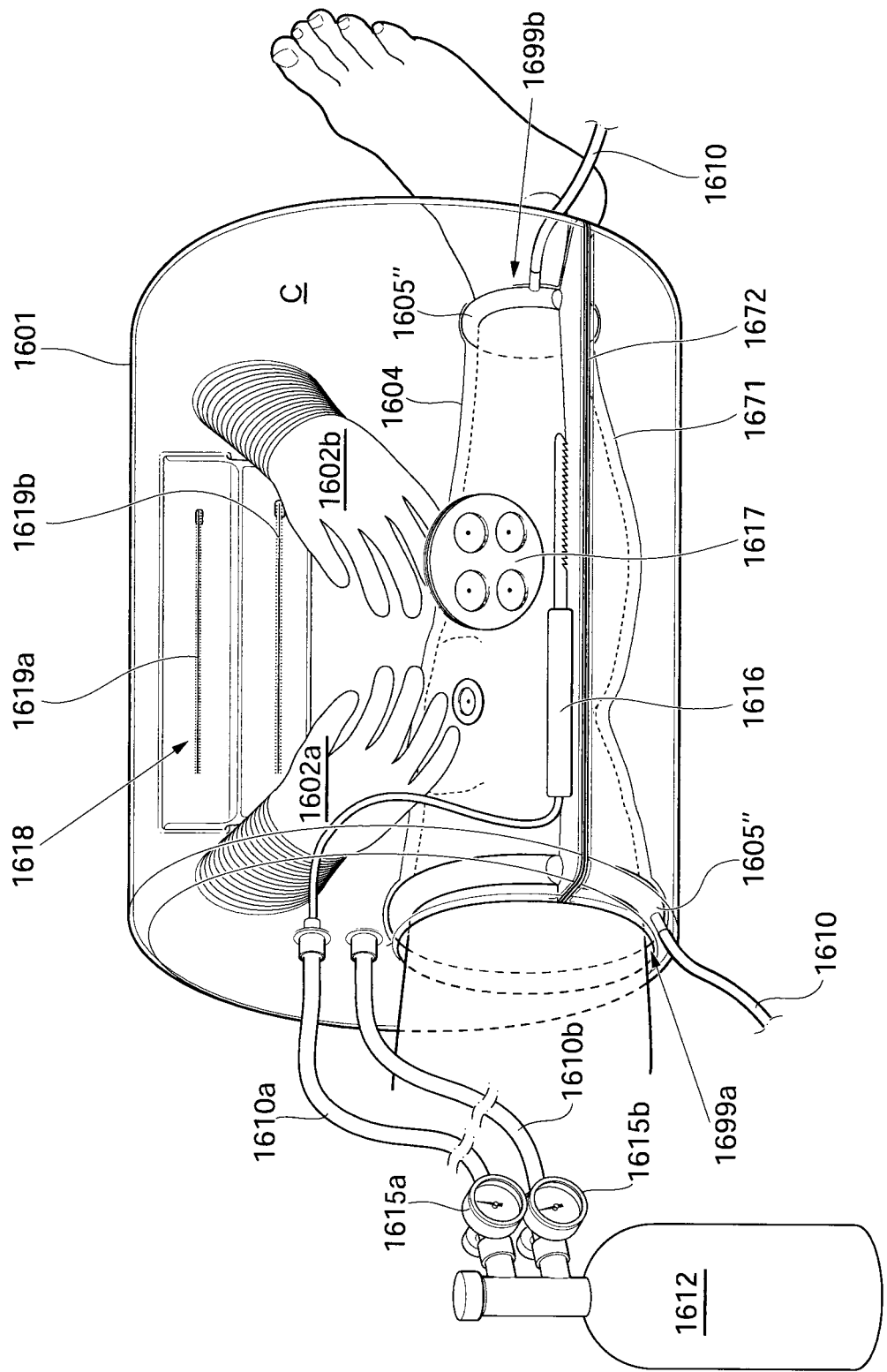

FIG. 129 shows the medical device having a wall 1601 adapted to be at least partially applied on the patient's body to form a chamber, in which a sealed environment can be maintained for encompassing part of a surgical procedure to be performed. The wall 1601 forms an elongated tubular enclosure having a first and a second open end, here equipped with pressure seals 1605". The enclosure is adapted to fit a portion of an extremity of the patient, in FIG. 129 the leg of the patient, and the medical device is arranged such that the portion of the extremity may be inserted into the enclosure through the first open end and exit the enclosure through the second open end and the surgical procedure is performed on the portion of the patient's extremity placed inside of the enclosure. The chamber is inflatable by means of a pneumatic conduit 1613*b*, here connected to a tank 1612 containing pressurized gas. The tank 1612 is further connected to a pneumatic system 1613*a* for transferring pneumatic force into the sealed environment enclosed by the wall 1601 and including the operating field of the extremity. Shown in the embodiment herein, the pneumatic system 1613*a* is connected to a pneumatic tool 1616, which in the example shown is an orthopedic saw, adapted to be operated within the sealed environment. The pressure provided to the sealed environment and the pneumatic system 1613*a* is controlled and monitored by a control/monitoring system 1615*a*, 1615*b* connected to the pneumatic conduits, respectively. In the embodiment shown. The medical device of FIG. 129 is shown incorporating the pneumatic pressure sealing members 1605", however it is equally conceivable that the pneumatic pressure sealing members 1605" is assisted or replaced by any of the other sealing members disclosed herein, such as vacuum seals or adhesive.

The medical device shown in FIG. 129 further comprises a air-lock system 1618 comprising two zipper-closed consecutive openings or valves 1619*a*, 1619*b*, where the outer zipper 1619*a* could be opened for placing and/or removing objects in the airlock between the zippers 1619*a*, 1619*b* from the outside of the sealed environment or chamber and the inner zipper 1619*b* could be opened from the inside of the sealed environment for placing and/or removing objects from the airlock or sluice chamber. For example the airlock system could be used to remove a specimen from the sealed environment while keeping the environment sealed, or the airlock could be used to insert a medical device or an implant into the sealed environment. The medical device disclosed with reference to FIG. 129 further incorporates laparoscopic ports 1617 (which are to be regarded as optional) through which laparoscopic trocars or endoscopic instruments could be inserted.

The medical device of FIG. 129 may further comprise at least one glove 1602*a*, 1602*b* integrated in the wall 1601 such that a surgeon is able to use the glove 1602*a*, 1602*b* from outside the chamber to make manual manipulations inside the chamber while maintaining the sealed environment in the chamber.

According to one embodiment, the wall 1601 of the medical device is at least partially collapsible and may be inflated by a fluid, as is shown in FIG. 129.

The medical device may additionally comprise a non-collapsible transparent window (as for example shown in FIG. 3*b*) provided in the wall to enable viewing into the sealed environment.

In other embodiments, the medical device may comprise an instrument holder adapted to retain instruments within the chamber.

In other embodiments, the medical device may comprise an air evacuation system adapted to evacuate air from the interior of the enclosure, when the portion of the patient's extremity is placed in the enclosure (as for example further shown in FIG. 2*b*).

The medical device shown in FIG. 129 further comprises a wall port 1617 provided in the wall 1601 enabling passage of an object between the chamber and the environment outside of the chamber. The wall port 1617 comprises at least one of an elastic membrane and a flexible membrane, and the membrane is adapted to, in a non-compressed state, seal between the chamber and the environment outside of the chamber, and in a compressed state enable a hand or an object to be inserted through the membrane.

The medical device may further comprising a body multi-port adapted to be placed inside the chamber in an incision in the skin of the patient, wherein the body multi-port comprises at least two body ports adapted to enable passage of an object between the chamber and the inside of the patient's body via the incision.

The medical device may further comprise a fluid tempering device and/or a sterilization device for tempering and/or sterilizing a fluid contained in the chamber, such a system if further disclosed for example under reference to FIG. 3*c*.

In the embodiment shown in FIG. 129, the elongated tubular enclosure is formed by placing the wall 1601 forming the chamber around a portion of the extremity of the patient and closed by means of a connection 1672 which is positioned between the inner wall 1671, in connection with the skin of the patient, and the outer wall 1601. The connection connecting one portion of the medical device with a second portion of the medical device could for example be made by means of an adhesive, a mechanical connection system, or a vacuum system.

Figure 130A:
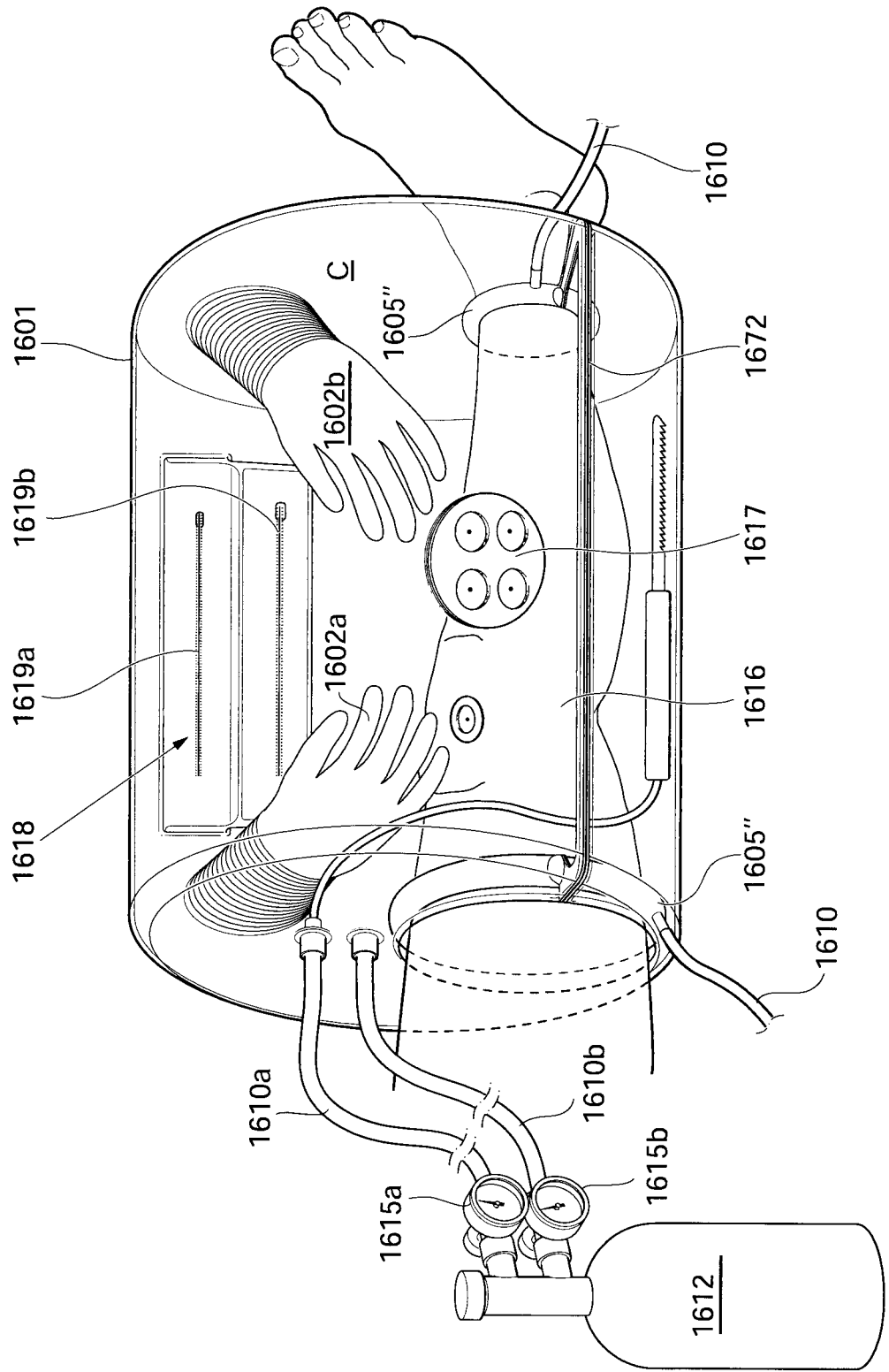

FIG. 130*a* shows the medical device according to an embodiment incorporating the features of FIG. 129 but with the difference that there is no inner wall, i.e. the sealed environment of the chamber is in direct connection with the skin of the patient. The connection 1672 has a somewhat different design since it is only connected to the outer wall 1601.

Figure 130B:
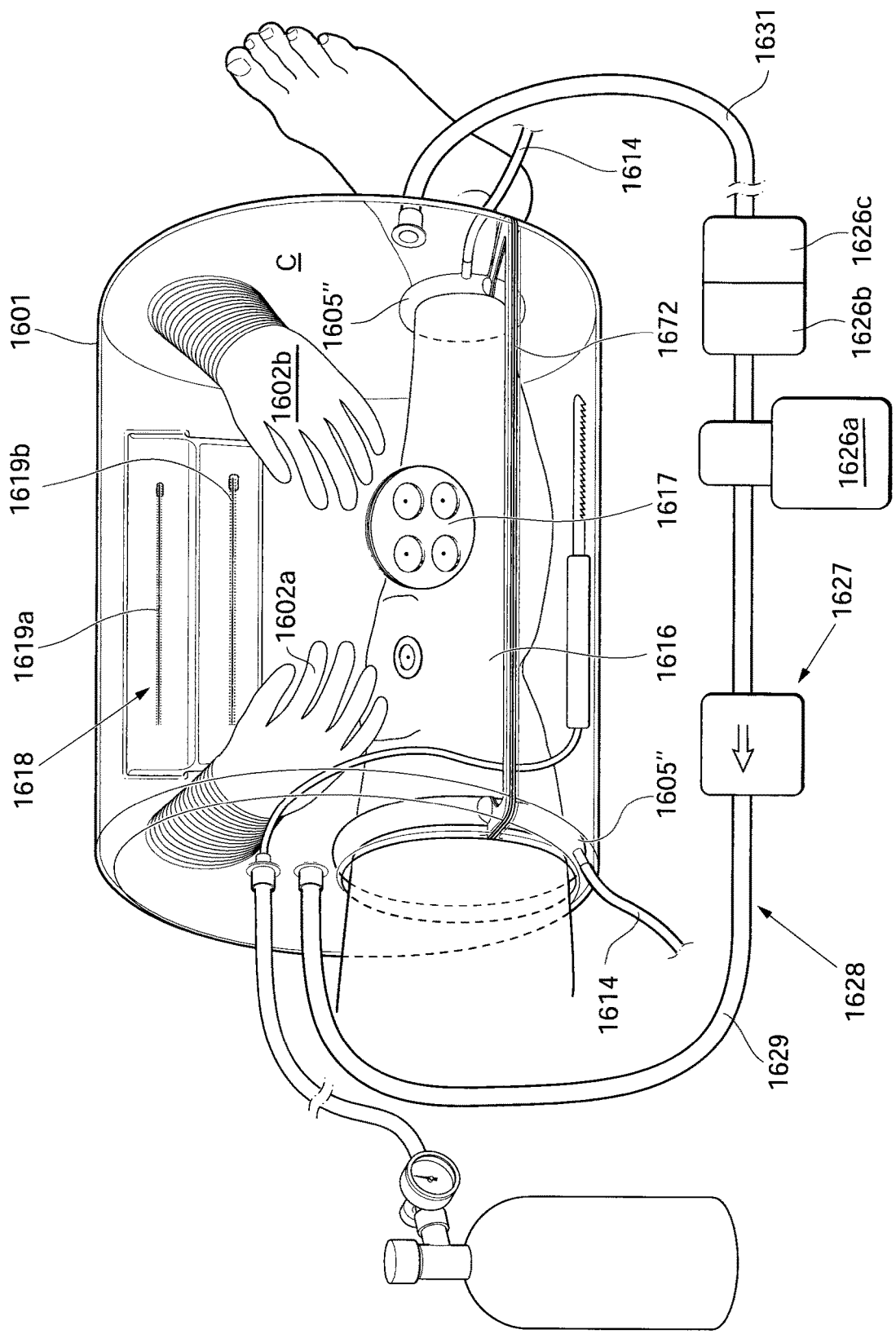

FIG. 130*b* shows the embodiment of the medical device similar to that shown in FIG. 129, with the difference that an external system 1628 for fluid circulation is provided. The system comprises fluid conduits 1629; 1629', in the external system 1628 connected at an inlet 1630 placed in the partially collapsible wall 1601 for supplying fluid to the chamber, and an outlet 1631 for draining the fluid from the chamber, the external system 1628 comprises a sterilizing 1626a, filtering 1626b, and heating 1626c unit adapted to remove impurities, sterilize and heat the fluid. In embodiments where the fluid is a gaseous fluid, the filtering unit is adapted to remove particles that could be suspended in the gas. The filtering unit 1626a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 1626a could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent. A pump 1627 for circulating the fluid is further provided.

Figure 131:
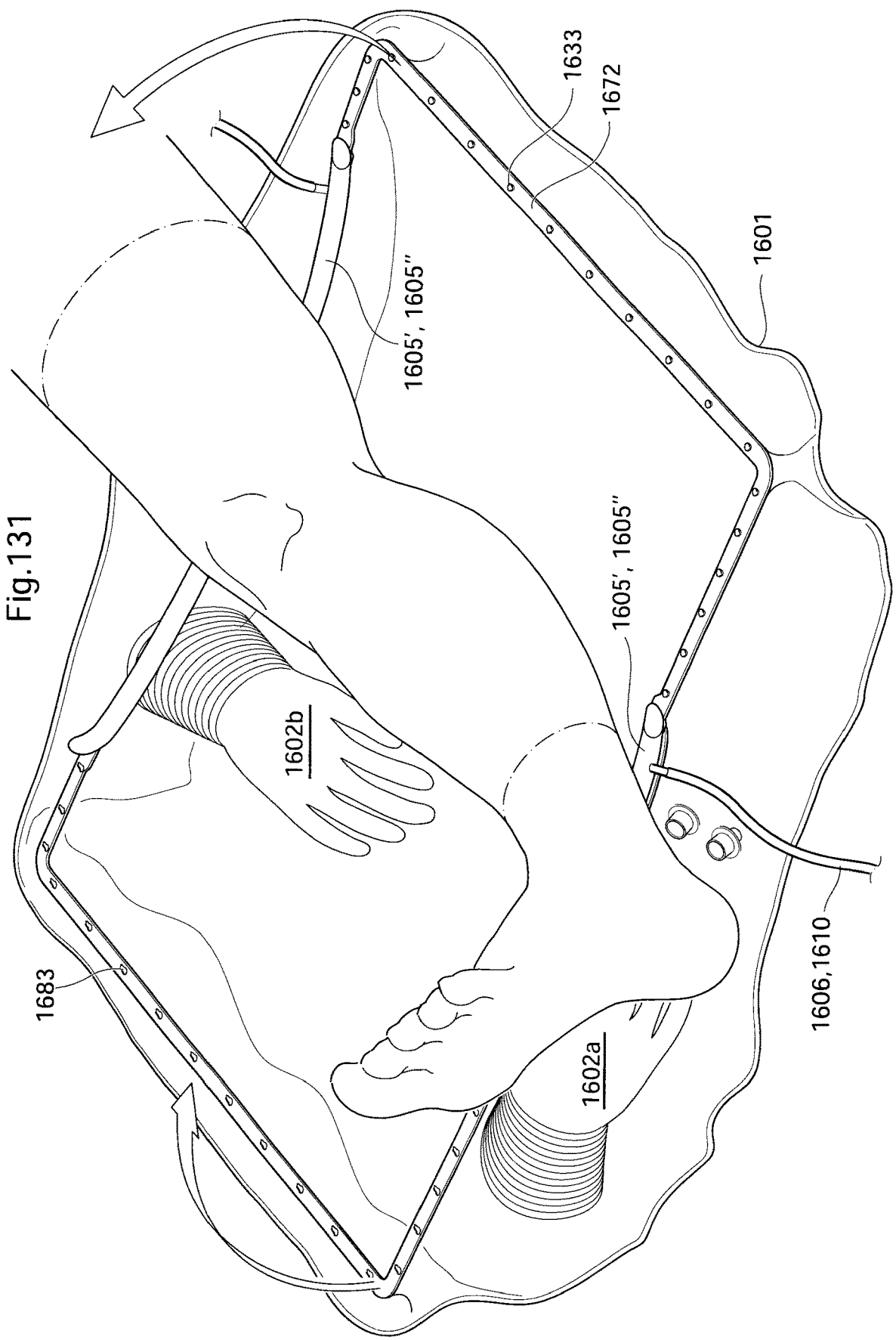

FIG. 131 shows the medical device disclosed under reference to FIG. 130b but in its open state, i.e. before it is placed around a portion of the extremity of the patient for forming the chamber. According to the embodiment shown the connection 1672 is created by means of mechanical connecting members 1673 comprising protrusions adapted to latch in corresponding key-hole recesses 1683 for creating the mechanical connection. The sealing members 1605'; 1605" encircling the extremity when the connection is made for forming the chamber could for example be pressure sealing members 1605' connected to a fluid conduit 1614 or vacuum sealing members 1605" connected to a vacuum conduit (not shown).

Figure 132:
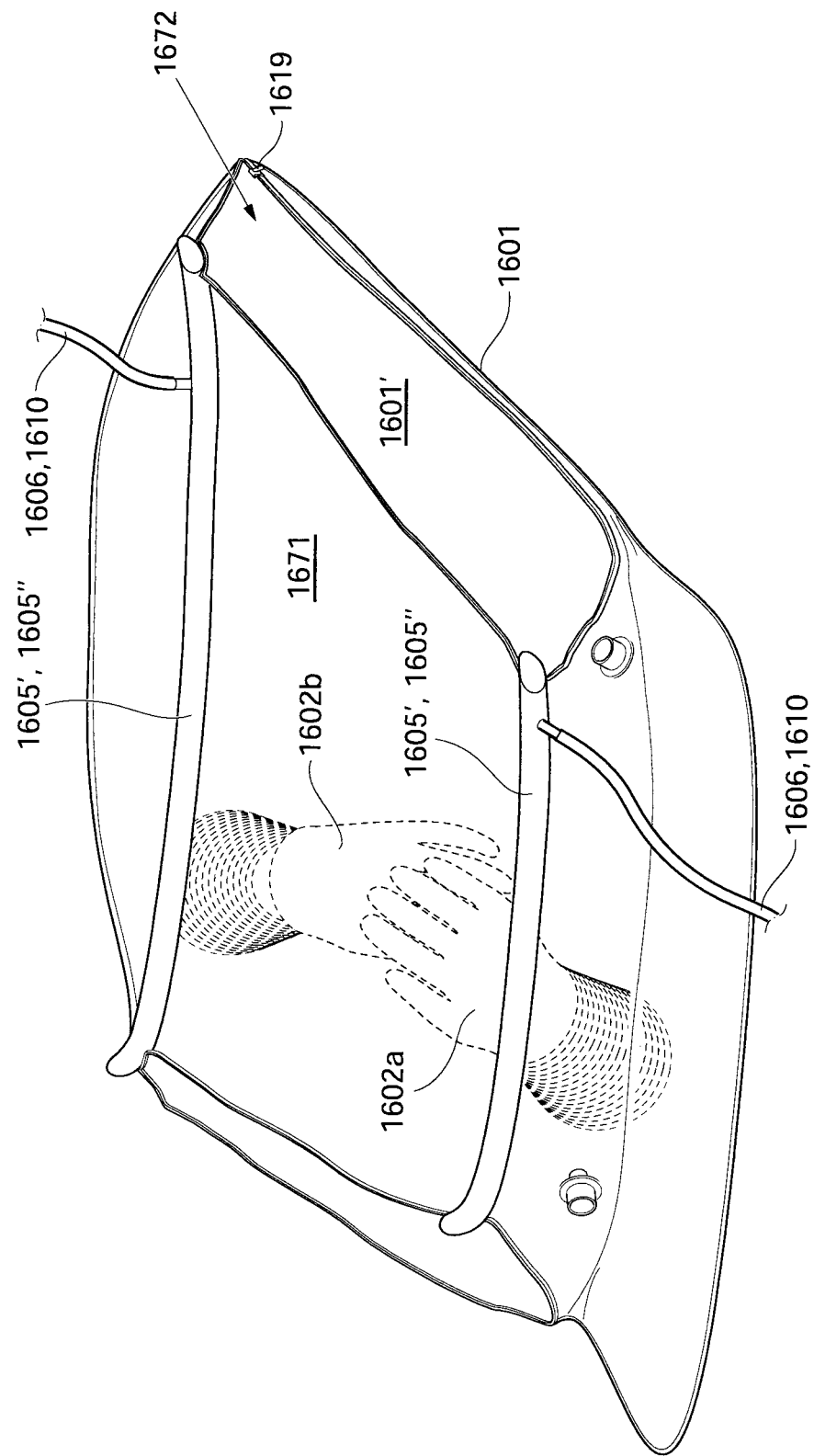

FIG. 132 shows the medical device in an embodiment where the medical device comprises an inner wall 1671 and an outer wall 1601 both in connection with a connecting portion 1672 herein adapted to connect to another connecting portion by means of a zipper 1686 such that the chamber encircles the portion of the extremity.

Figure 133A:
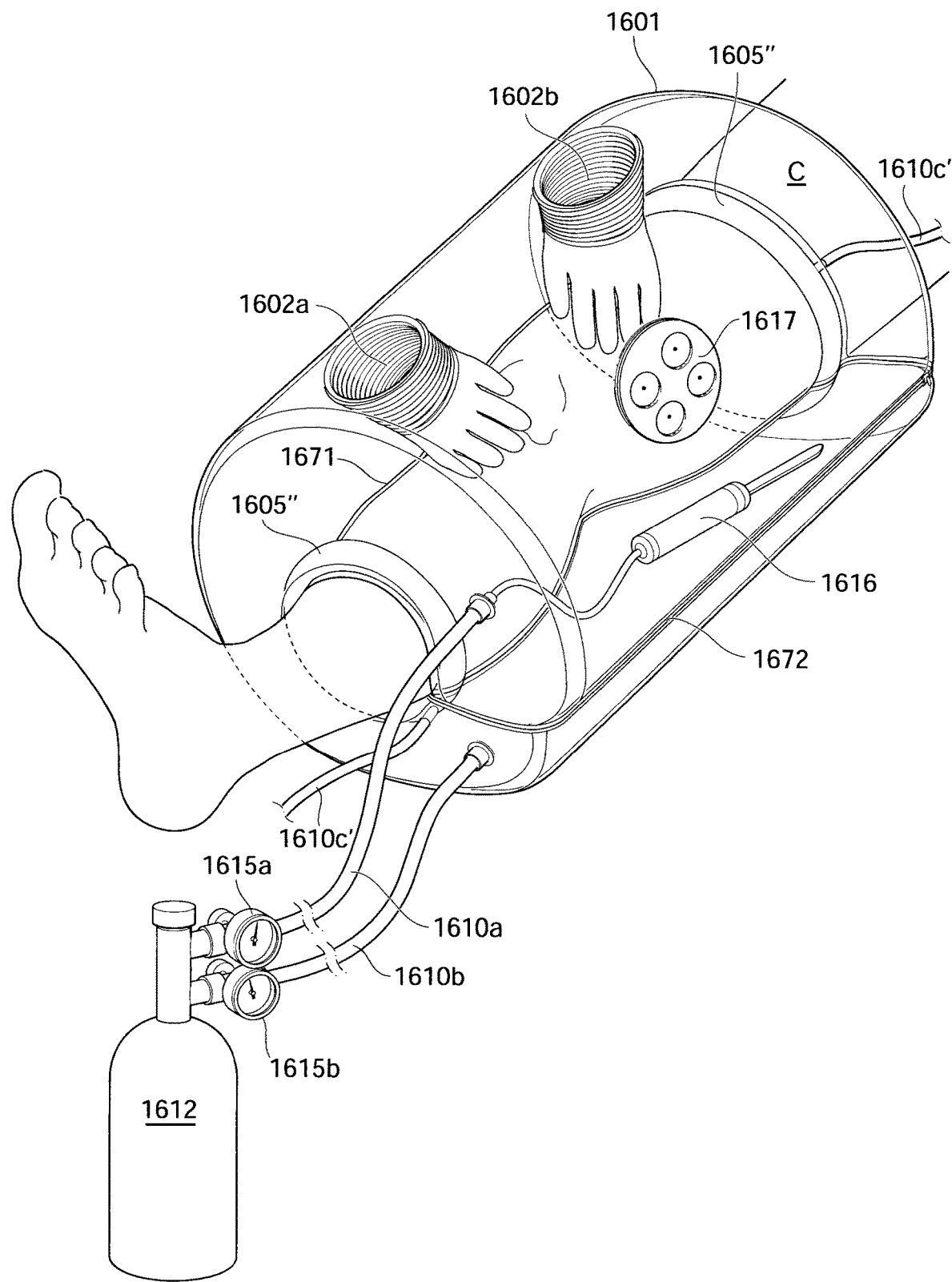

FIG. 133a shows the embodiment of the medical device disclosed under reference to FIG. 132, when the connection is made such that the chamber encircles the extremity of the patient.

Figure 133B:
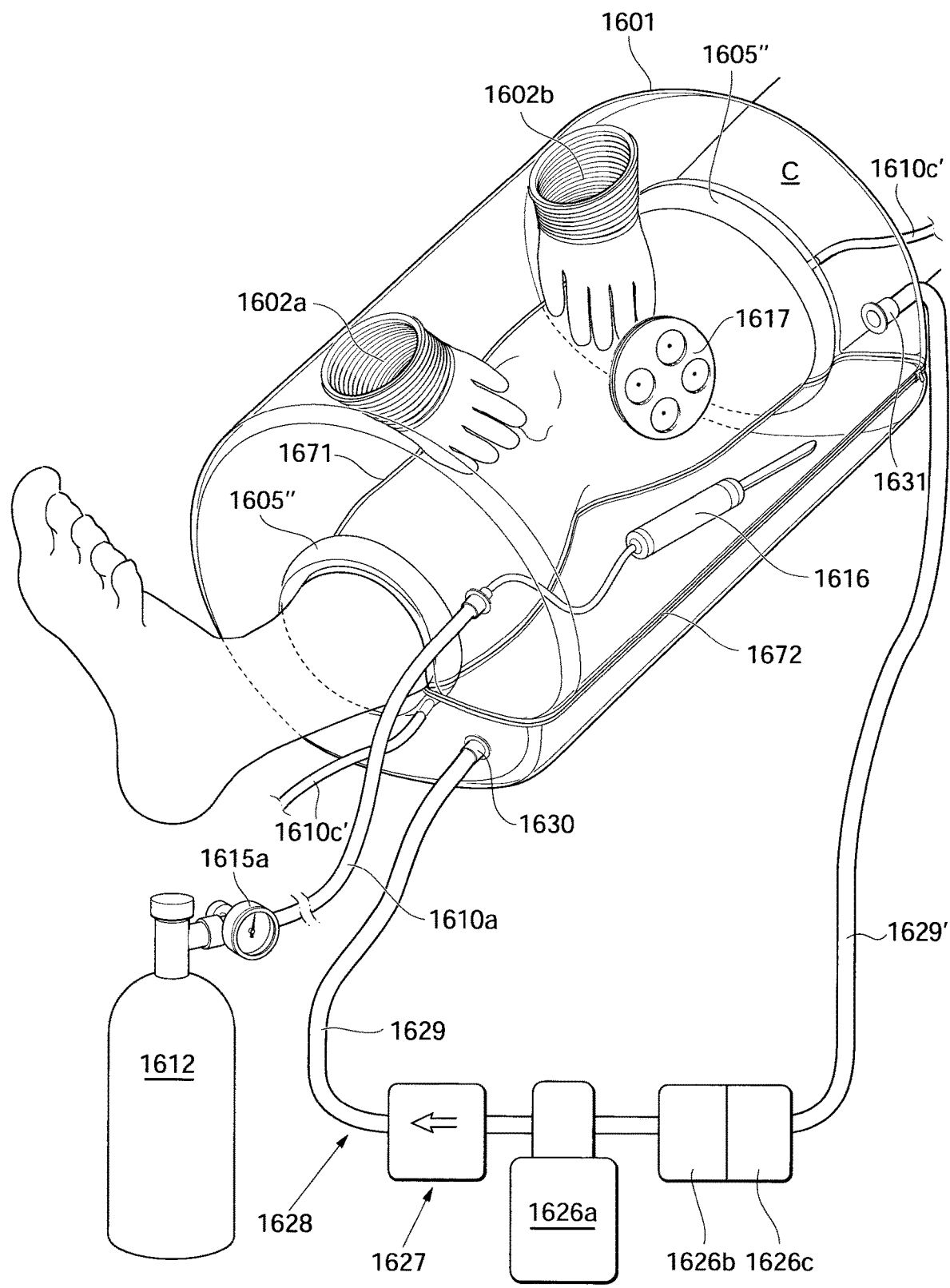

FIG. 133b shows an embodiment of the medical device similar to the embodiment shown in FIG. 133a, with the difference that the embodiment of FIG. 133b further comprises an external system 1628 for fluid circulation. The system comprises fluid conduits 1629; 1629', in the external system 1628 connected at an inlet 1630 placed in the partially collapsible wall 1601 for supplying fluid to the chamber, and an outlet 1631 for draining the fluid from the chamber, the external system 1628 comprises a sterilizing 1626a, filtering 1626b, and heating 1626c unit adapted to remove impurities, sterilize and heat the fluid. In embodiments where the fluid is a gaseous fluid, the filtering unit is adapted to remove particles that could be suspended in the gas. The filtering unit 1626a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 1626a could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent. A pump 1627 for circulating the fluid is further provided.

FIG. 134 shows a slightly modified version of the embodiment disclosed with reference to FIG. 132, the difference being that the inner layer 1671 is made longer such as to allow an overlap of the inner layer when the chamber is placed encircling the extremity of the patient for improving the sealing between the medical device and the skin of the patient.

Figure 135:
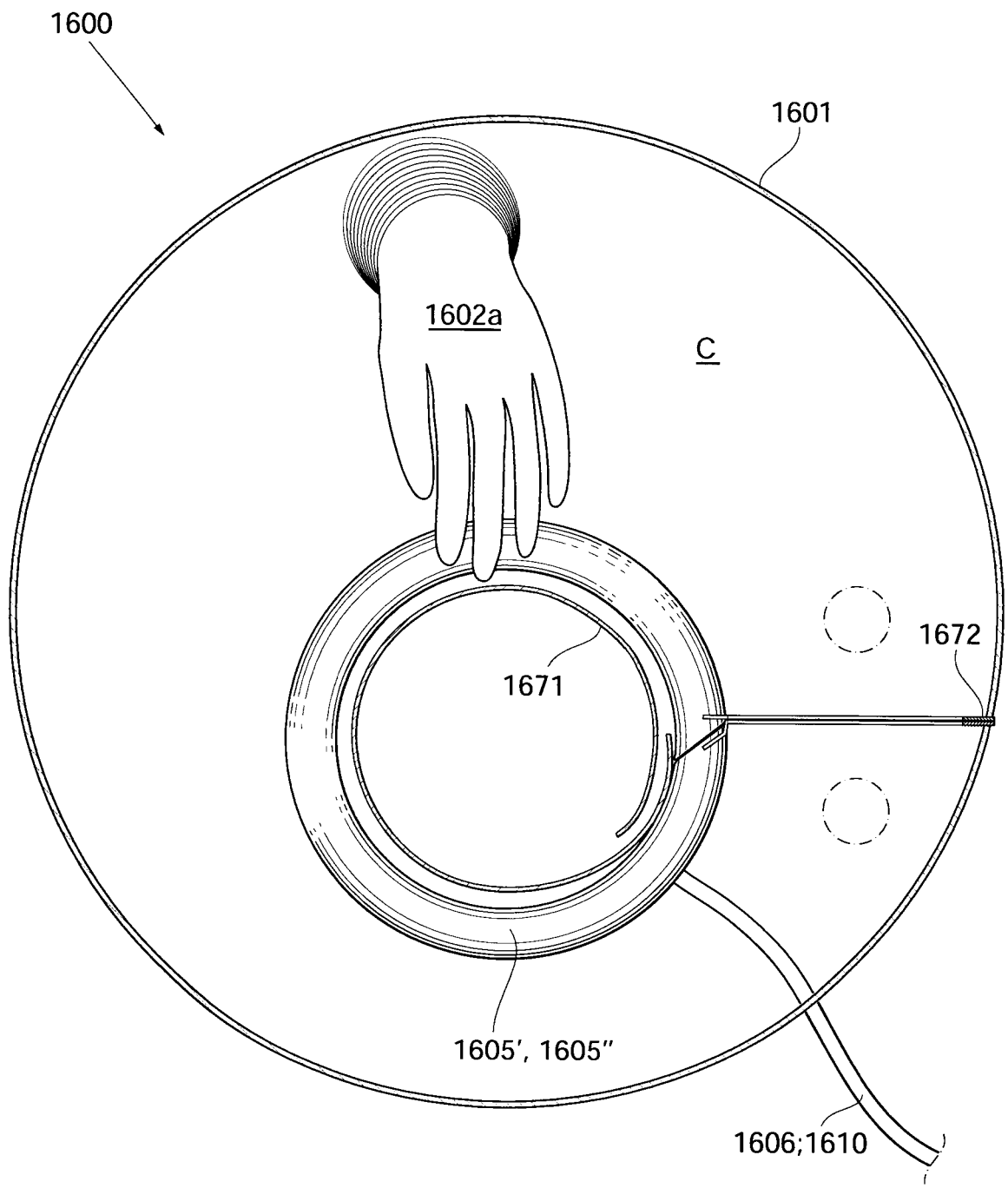
FIG. 135 shows an embodiments of the medical device, in section.

FIG. 135 shows the medical device according to the embodiment shown in FIG. 135 when the chamber is places encircling the extremity of the patient, in a side view. The inner layer 1671 is placed with an overlap and the connection is closed by means of the zipper. The medical device is herein provided with a pressure or vacuum sealing member 1605'; 1605".

Figure 136:
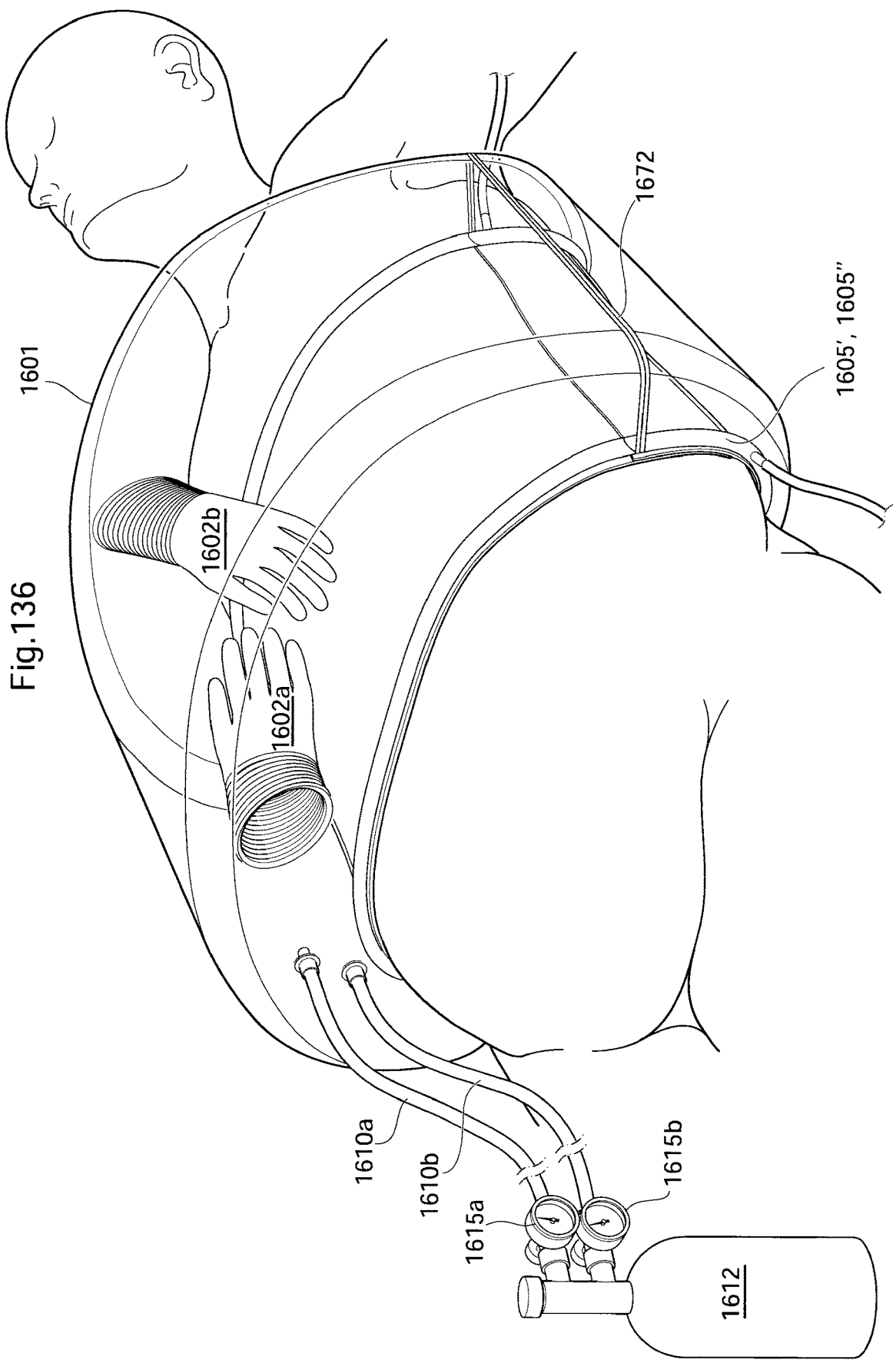
FIG. 136 shows the medical device when applied to the abdomen of a patient.

FIG. 136 shows the medical device when applied on a portion of the upper body of a patient, thus enabling surgical procedures in the abdominal or thoracic regions. The chamber is wrapped around the patient by means of the medical device comprising a slit and connected by means of the connection 1672 and sealed against the skin of the patient by means of pressure 1605' or vacuum 1605" seals. The slit and the connecting members enables the placement of the chamber around at least a portion of the extremity of the patient radially in relation to the length axis of the extremity.

Figure 137:
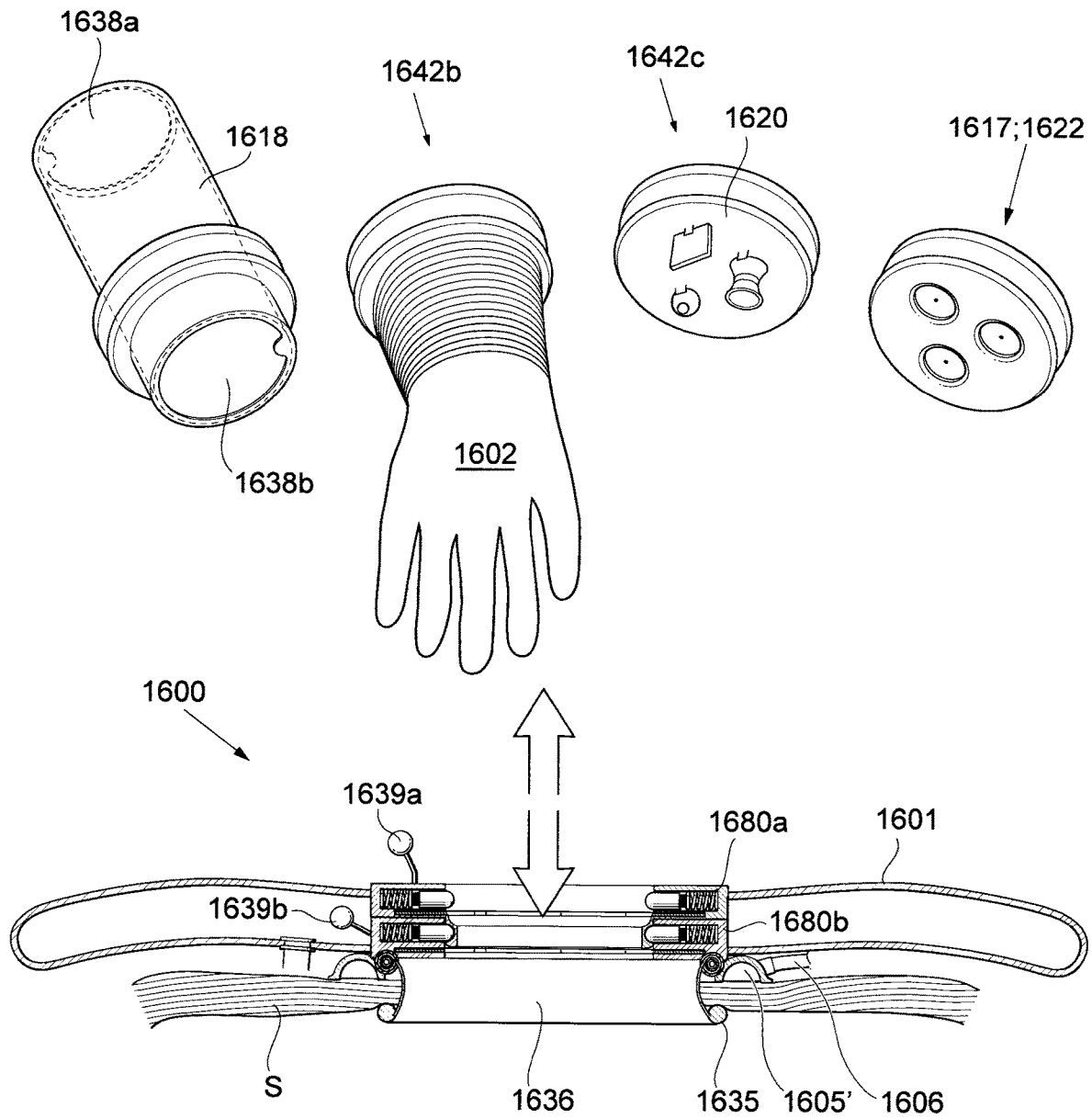
FIGS. 137-138 shows another embodiment of the medical device, in section.

FIG. 137 shows an alternative of the embodiment shown in FIGS. 124-137. Fig. In 137 the medical device 1600 is adapted to be at least partially placed in an incision cut in a patient's body. The medical device 1600 comprises a first 1631b and second 1631a part adapted be interconnected to form a surgical port. The second part 1631a is adapted to be disconnected from the first part 1631b, and the first part 1631b is connected to a first portion of a flexible wall 1601, and the second part is connected to a second portion of the flexible wall 1601. The flexible wall 1601 forms a chamber in which a sealed environment can be maintained, the chamber is heavily enlarged when the second part 1631a is disengaged from the first part, thus creating operating space within the chamber enclosed by the wall. The first and second parts comprise a latching system for locking an inset. The inset could for example be a glove 1602 for manual manipulation within the body of the patient, or within the enclosed chamber, a holding device 1681 for holding instruments or medical devices within the chamber. Alternatively the insets 1642b; 1642c can be replaced by an airlock sluice 1618 with a first 1638a and second 1638b valve member or a port, and a multiport portion 1648 comprising a plurality of ports enabling the insertion of a surgical instrument into the chamber or body of the patient.

In the embodiment shown in FIG. 137 the medical device is fixated to the body of the patient by means of a vacuum fixating member 1605' connected to a conduit 1614, which in turn is connected to a vacuum source. Furthermore, the medical device in FIG. 137 comprises a second sealing function having a first sealing member 1635 adapted to be positioned at the inside of the patient's skin around an incision to be performed in the skin and a second sealing member 1637 adapted to be positioned at the outside of the patient's skin around the incision, and a spring-loaded or elastic connecting member 1636 sealingly interconnecting the first 1635 and second 1637 sealing members. The spring-loaded or elastic connecting member 1636 seals between at least one of the port and the skin of the patient, and the first sealing member and tissue of the patient.

Figure 138:
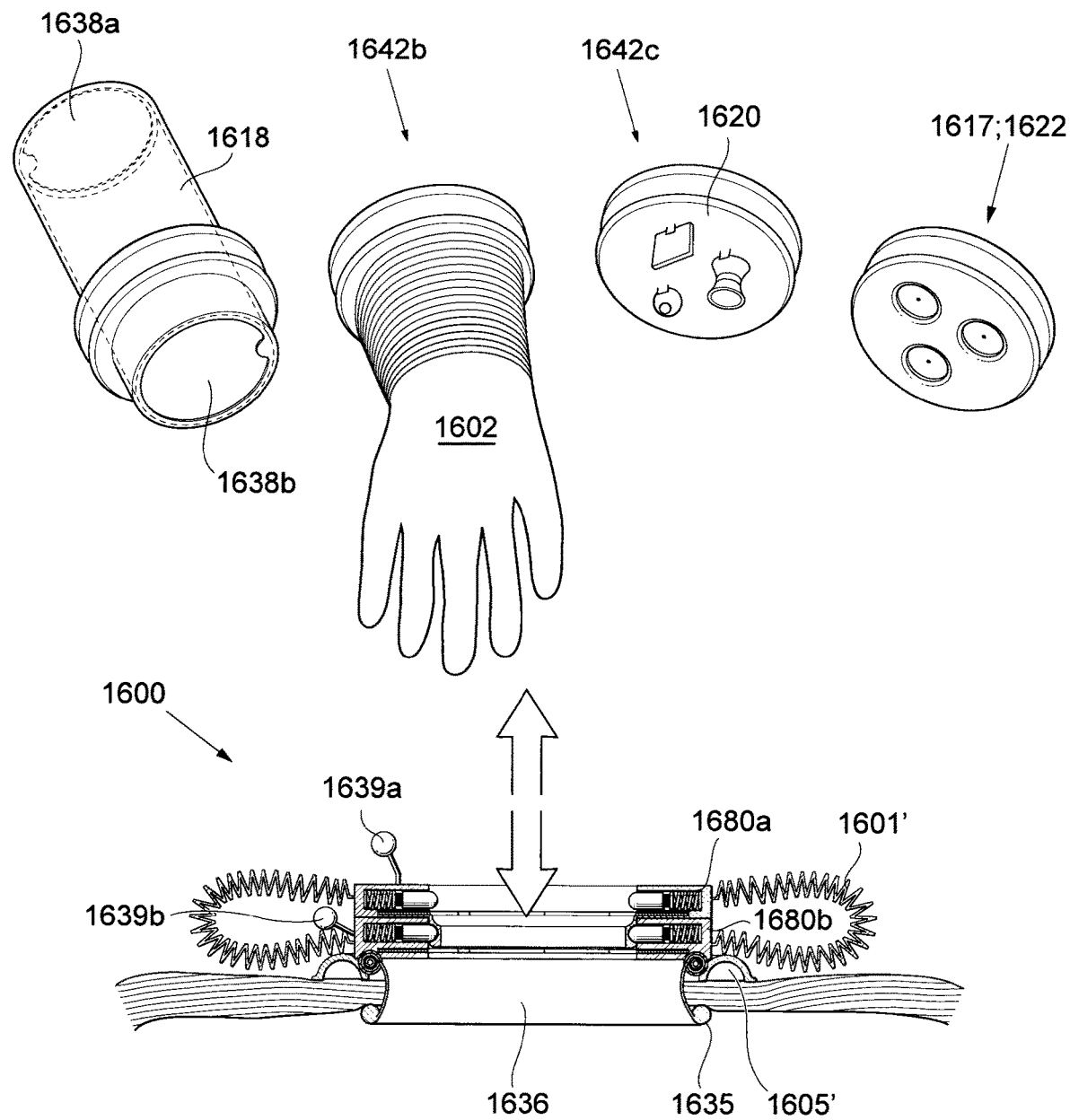

FIG. 138 shows the port in an embodiment very similar to the embodiment shown in FIG. 137 but with the difference that the wall 1601' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

Figure 140D:
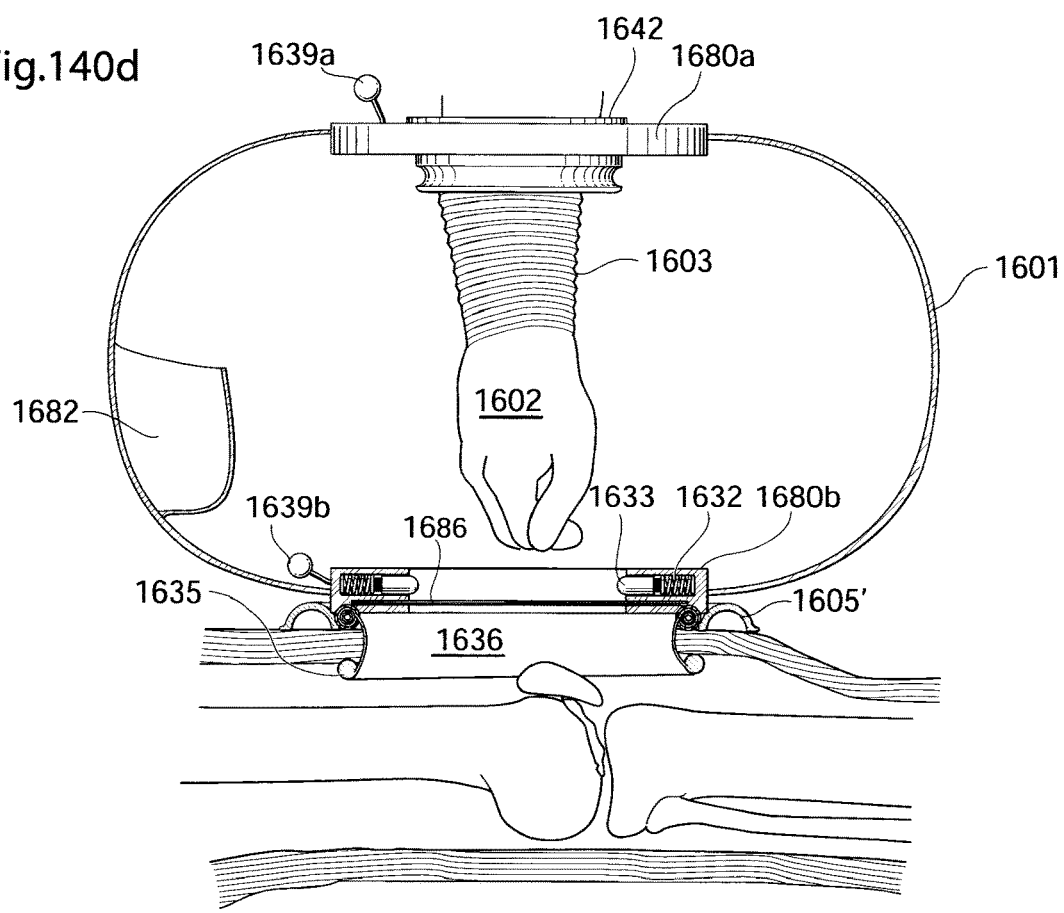
Figure 140E:
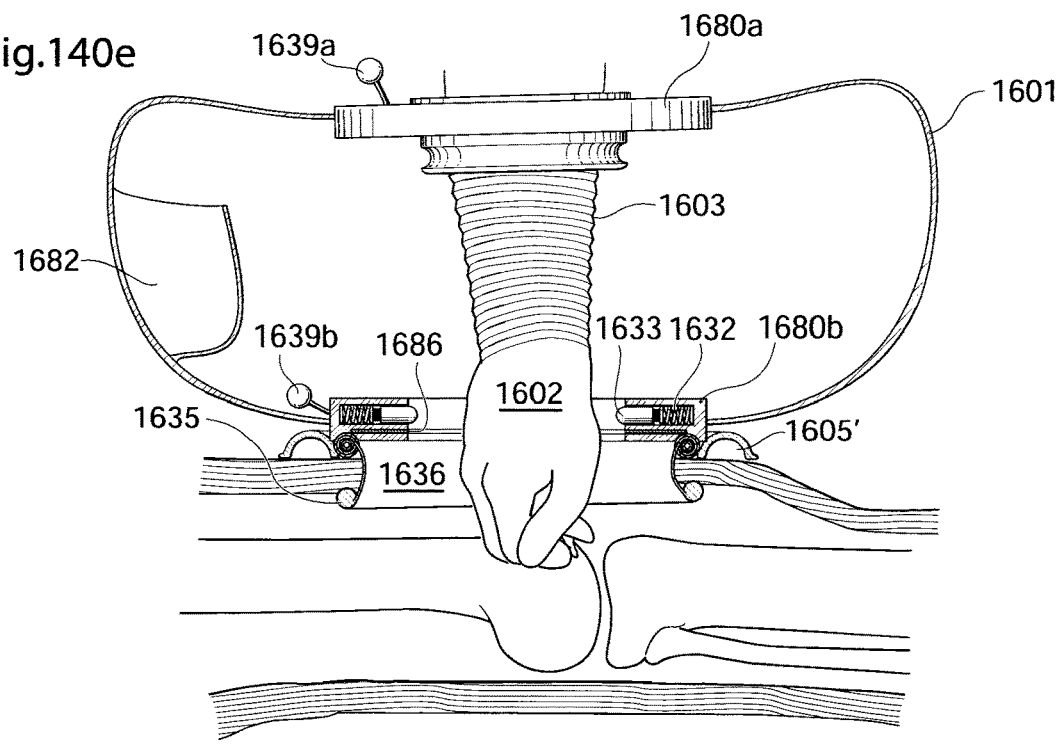
Figure 140F:
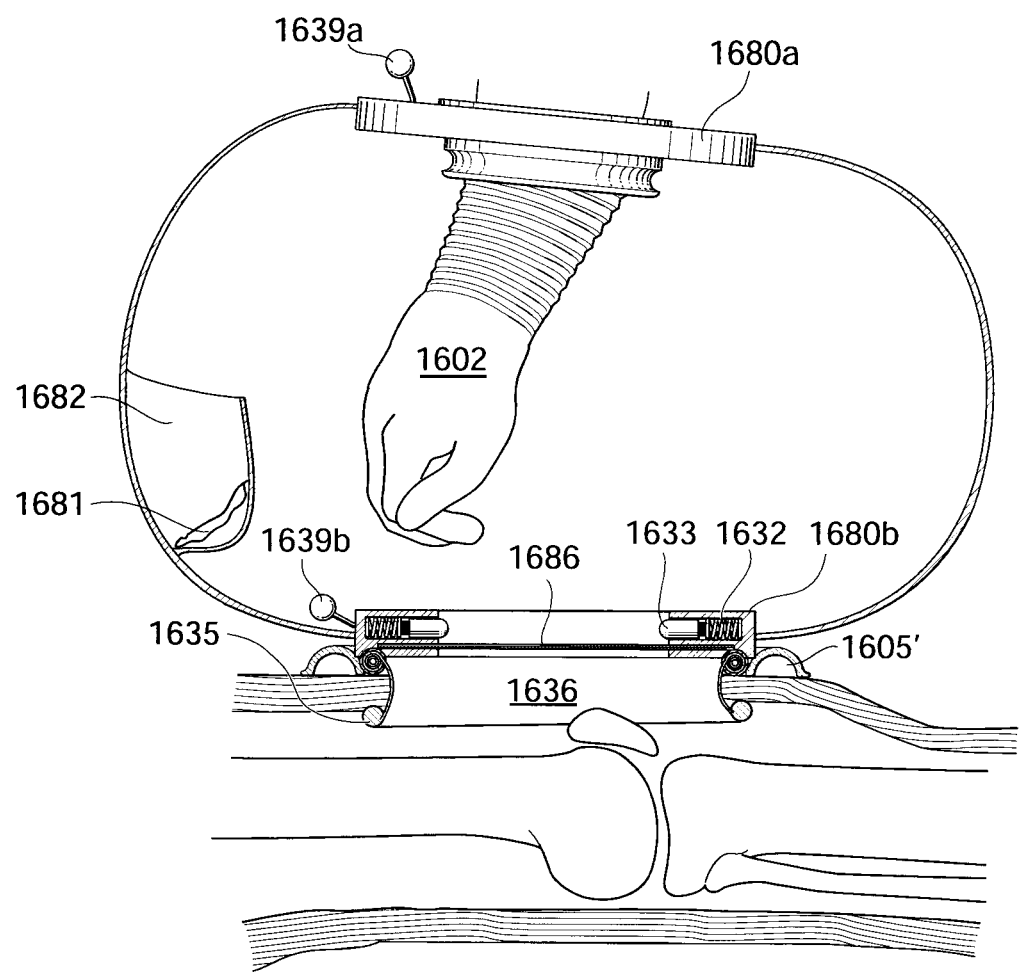

FIG. 139-140*f* shows a feature which could be implemented in the embodiments disclosed with reference to FIGS. 124-138. In the embodiment of FIGS. 139-140*f*, the wall of the medical device is inflatable, and the medical device is in its inflated state. When the chamber is deflated it has a first volume i.e. when the first 1631*b* and second 1631*a* parts are interconnected, and when the chamber is inflated and the second part 1631*a* is disconnected from the first 1631*b* part it has a second volume, and the second volume is larger than the first volume. According to the embodiment shown in FIG. 139, the second volume is larger than 500 000 mm3 and adapted to hold a pressure exceeding atmospheric pressure.

According to the embodiment shown in FIG. 139-140*f* the chamber further comprises a pouch 1682 for holding a specimen 1681 removed from within the body of the patient not to contaminate any other part of the body and create the possibility of delaying the removal of the specimen until the procedure is concluded. The pouch may be a pouch 1682 which could be closed for creating a pouch-chamber within the chamber for isolating the removed specimen 1681 within the chamber.

In FIG. 139, a state is illustrated in which the cut in the patient's skin is being created by the surgeon by means of a glove inset 1602 latched to the second part 1631*a*. The surgical port is fixated and sealed by means of the vacuum sealing member 1605' since the seal that is provided partially within the patient's body cannot be mounted until the cut in the patient's skin is concluded. The two different seals disclosed could in some embodiments be replaced by only one of the seals, or by a different seal, such as the adhesive of pressure seals disclosed in other portions herein.

FIG. 140*a* shows the medical device, when the second sealing 1635, 1636, 1637 have been placed in the incision cut in the patient's skin. The wall 1601 enclosing the chamber is elastic or flexible which enables the surgeon move the second part 1631*a* in relation to the first part 1631*b* for getting better access to different angles within the patient's body, for example for removing a specimen or placing an implant in the knee. The embodiment of FIG. 140*a* further comprises a non-penetrable valve 1686 placed in the first part 1631*b* for closing the port such that the chamber is sealed from at least one of the ambient environment and a cavity in the patient. The closing of the non-penetrable valve 1686 enables activity within the chamber without maintaining a pressure in the chamber, at the same time as a pressure and/or sealed environment can be maintained within the body of the patient.

FIG. 140*b* shows the medical device when the glove inset 1602 is removed and replaced by a multi-port inset 1648 comprising a plurality of ports 1647. The multi-port inset may be used for manipulating objects within the chamber of the inflated medical device using surgical instruments, or within the body of the human patient, when the first and second parts are connected (as shown in FIG. 140*c*).

FIG. 140*c* shows the medical device when the first and second parts are connected such that surgical instruments 1689 can be used for manipulating within the body of the patient. An endoscopic camera 1688 may be provided in the port for enabling visual inspection of the cavity within the patient's body.

In FIG. 140*d*, the glove inset 1602 has been fixated to second part 1631*a* to enable the surgeon to operate within the cavity of the patient's body and within the chamber enclosed by the wall of the medical device. By the glove inset 1602 comprising a pleated portion, the glove surgeon is able to reach into the knee joint of the patient for removing a specimen or place an implant.

FIG. 140*e* shows that the wall of the medical device is collapsible such that the glove inset can be moved with relation to the first part 1631*b* of the port, which gives the surgeon further freedom to operate within a patients joint.

FIG. 140*f* shows the step of placing a removed specimen in the pouch 1682 such that the specimen does not contaminate any other part of the body. The pouch may be a pouch 1682 which could be closed for creating a pouch-chamber within the chamber for isolating the removed specimen 1681 within the chamber.

Figure 141A:
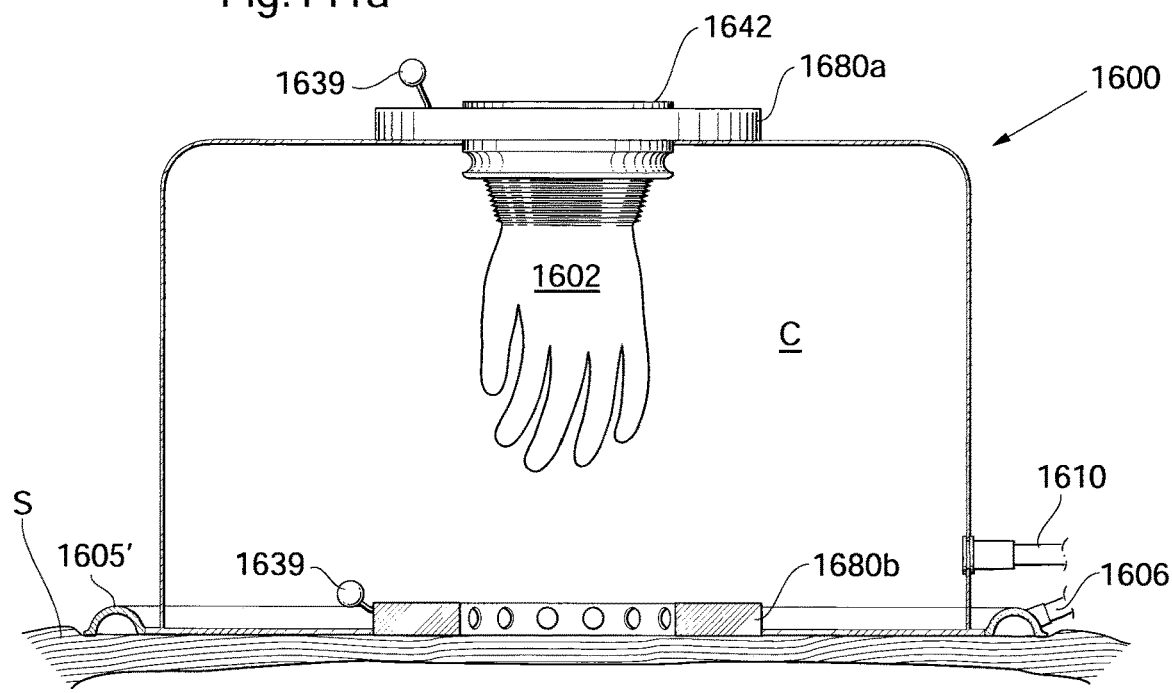

FIG. 141*a* shows another embodiment which may be implemented in or combined with the embodiments shown in FIGS. 124-140. The medical device 1600 comprises a wall 1601 enclosing a chamber for performing the surgical procedure. A portion of the wall 1601 is adapted to be in contact with a patient. The medical device comprises an inset in the form of a surgical glove 1602 adapted to enable manipulation within the chamber. The surgical glove 1602 connected to the upper coupling 1631*a* can be in a first and second position, the second position is disclosed in FIG. 141*a*, while the first position is located closer to the skin of the patient and disclosed in FIG. 141*c*. The medical device could for example be used in surgical procedures where transitions between open and laparoscopic surgery is needed. The medical device could be placed in the second position for enabling a larger freedom of motion for the surgeon within the chamber of the medical device 1600, while the first position, with the upper coupling 1631*a* locked to the lower coupling 1631*b*, could enable the use of a laparoscopic trocar or hand access for further reach within the body of the patient. The medical device could further be used in embodiments where manual manipulation in a sealed environment is required, e.g. for preparing a medical device for use in the surgical procedure. Other applications could for example be that the surgeon wishes to remove a specimen form the body of the patient after a laparoscopic procedure has been concluded. The laparoscopic procedure could in these instances be performed with the medical device being in the first position (as shown in FIG. 141*c*), being close to the skin of the patient, whereafter the medical device could be placed in the second position for enabling the specimen to be removed from the body of the patient and placed in the chamber of the medical device without contacting the outside environment, and without the release of the pressure that usually fills the abdomen in laparoscopic procedures. According to the embodiment shown in FIGS. 141*a-d*, the wall 1601 is collapsible such as to enable the transferring between the first and second position. The lower coupling comprises a lever 1639 for releasing and/or locking the upper coupling 1631*a* to the lower coupling 1631*b*, and thereby placing the medical device in the first state. The medical device 1600 is according to the embodiment shown in FIG. 141*a* fixated to the patient by means of a vacuum sealing member 1605', such as for example disclosed with reference to FIGS. 66 and 67.

Figure 141B:
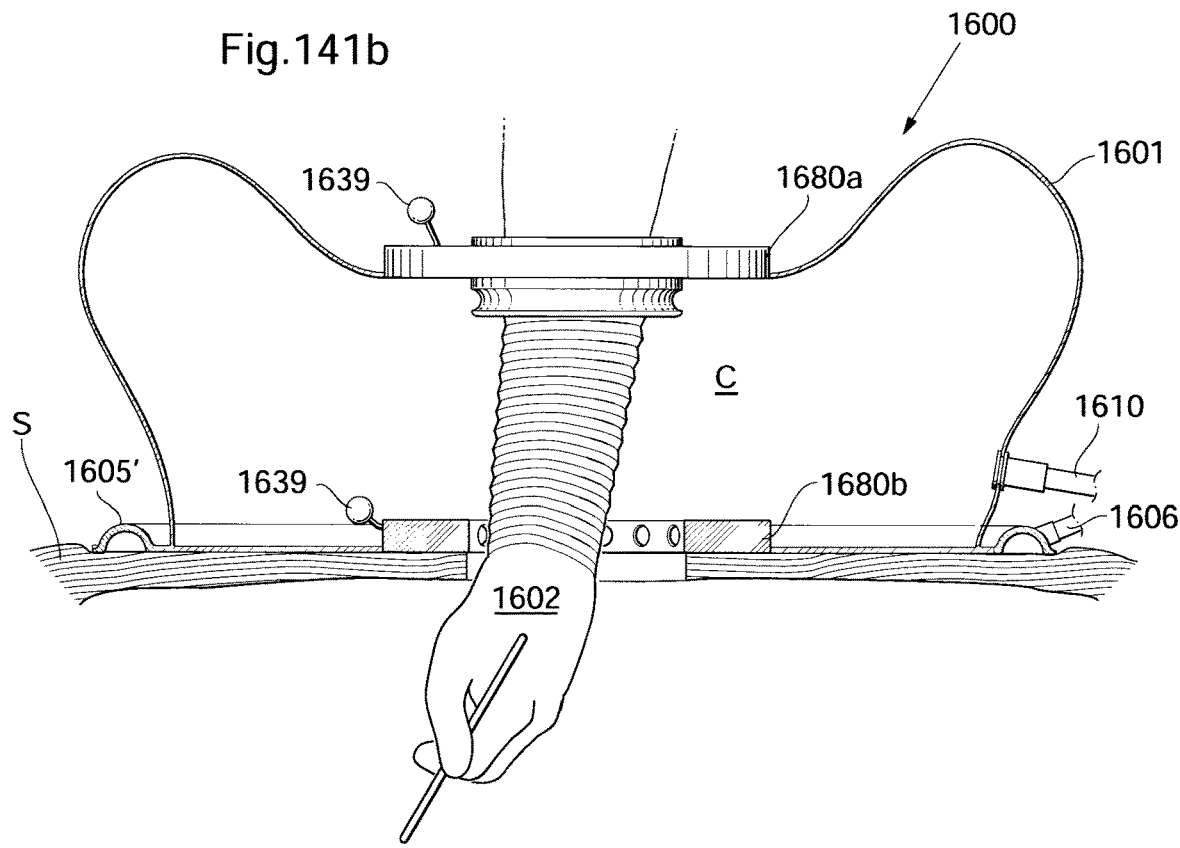

FIG. 141*b* shows the medical device 1600 when being transferred between the first and second position, i.e. the upper coupling 1631*a* is pushed towards the lower coupling 1631*b* for enabling a lock between the upper 1631*a* and lower 1631*b* coupling. The integrated surgical glove 1602 has been stretched such as to enable manual manipulation within the body of the patient and within the chamber of the medical device.

FIG. 141*c* shows the medical device 1600 when locked in the first position, i.e. the upper coupling 1631*a* is locked to the lower coupling 1631*b*. The integrated surgical glove 1602 now enables manual manipulation with great freedom within the body of the patient. The medical device comprises two levers 1639*a* and 1639*b*, wherein the first lever 1639*a* is connected to the upper coupling 1631*a* and adapted to lock the object (here being a surgical glove 1602) to the coupling 1631*a*, while the second lever 1639*b* is connected to the lower coupling 1631*b* for locking the upper coupling 1631*a* to the lower coupling 1631*b*. The medical device 1600 is according to the embodiments shown in FIG. 169 *a-d* circular when seen from above, such that the medical device 1600 takes the shape of a doughnut when placed in the first position.

FIG. 141*d* shows the exchanging of objects when the upper coupling 1631*a* has been locked to the lower coupling 1631*b*. The object comprises the surgical glove 1602 has been removed and can for example be replaced by an airlock 1670 for transferring objects between the outer environment and the chamber of the medical device 1600. The airlock comprises an inner wall 1682 and an outer wall 1683 on each side of the airlock 1670 enabling the enclosing of an object within the airlock 1670. Another example of an object to which the surgical glove 1602 can be exchanged is a port device 1648 here shown as a body multi-port comprising laparoscopic ports 1647 for performing a laparoscopic procedure. In some embodiments (not shown) the upper and/or lower coupling comprises a valve member for closing the opening in the coupling when the objects should be exchanged, the valve member could for example be a flap valve.

Figure 142:
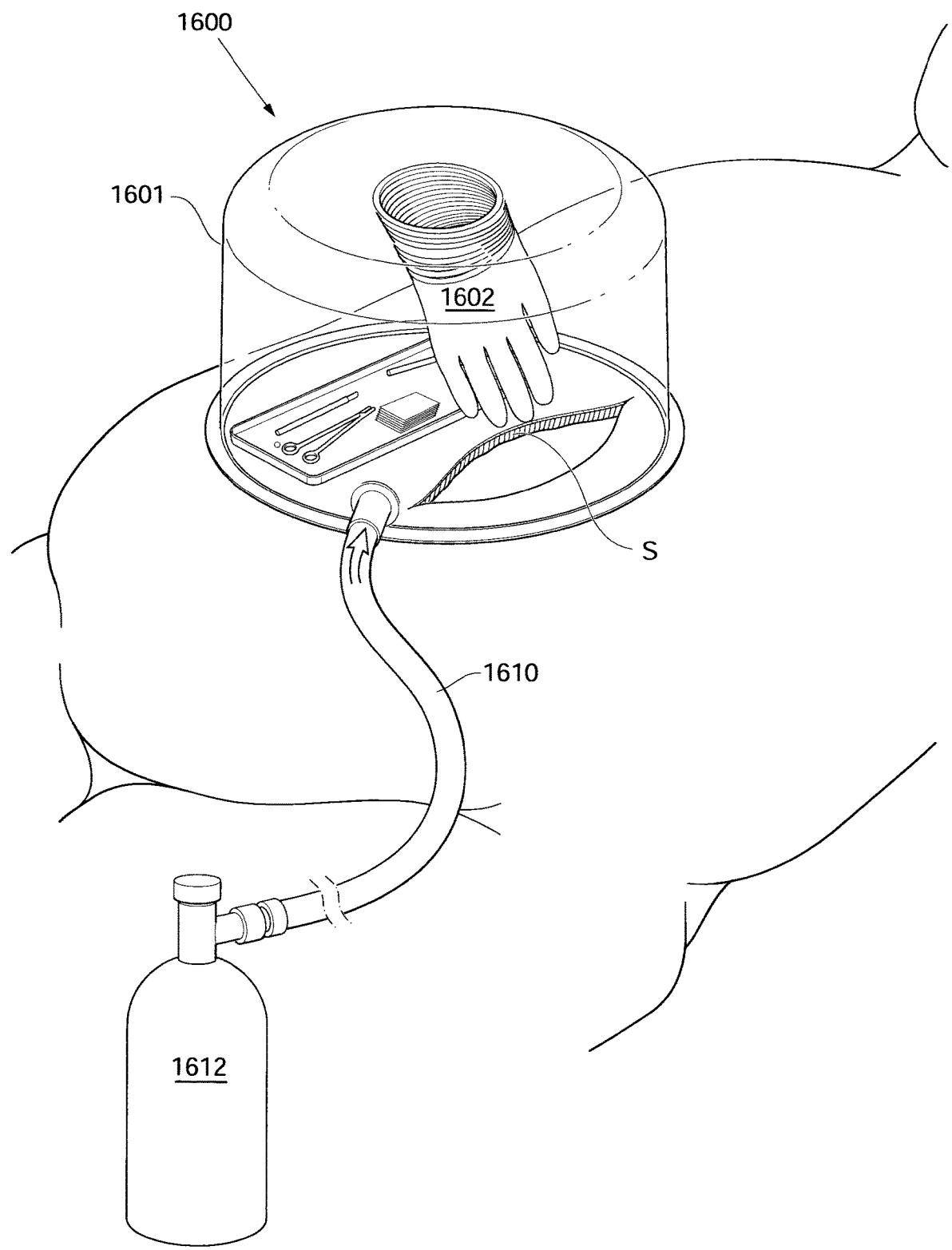
FIG. 142 shows an embodiment of the medical device, when positioned on the abdomen of a patient.

FIG. 142 shows an embodiment of the medical similar to the embodiment of FIGS. 141*a-d*. In the embodiment shown in FIG. 142, the medical device is placed in contact with the skin of the patient prior to the beginning of the operation and the entire portion of the wall 1601 contacting the skin of the patient comprises an adhesive, such that the incision in the patient runs through the wall 1601 and further through the skin 1641 of the patient. This reduces the risk that infectious objects can be transferred from the skin of the patient to the incision in the patient if the skin of the patient is not adequately disinfected. The body of the patient could be inflated to allow better visibility within the body from for example the fluid conduit 1613 connected to the pressure tank 1612, however it is equally conceivable that the body of the patient is inflated from within trough a different incision in the body of the patient.

FIG. 143 shows an embodiment of a detachable body port which could be fixated to the lower coupling 1631*b* positioned in the medical device 1600 disclosed with reference to FIGS. 141 *a-d*. The port arrangement of FIG. 143 includes an intra body ring 1635 adapted to be placed at the inside of the patients skin around an incision, and an outer ring 1637 adapted to be placed on the outside of the patients skin 1641 around the incision. Between the intra body ring 1635 and outer ring 1637 an annular retractor membrane 1636 is positioned adapted to exert a pressure on the skin or human tissue at the incision to seal between the rings and the skin or human tissue and additionally for retracting the skin and thereby keep the incision open. The retractor membrane 1636 is preferably made from a resilient or elastic polymer material. The outer ring 1637 comprises an integrated roll up system 1646, which may be spring loaded and adapted to create a suitable pressure on retractor membrane 1636 to keep the incision open.

The port arrangement shown in FIG. 143 also includes a coupling having a rigid annular seating 1645 attached to the outer ring 1637, spring loaded latching members 1633 arranged in radial bores in the seating 1645 and a hand lever 1639 connected to the latching members 1633 to enable retraction thereof against the action of springs 1632. The port arrangement further includes a self sealing body port 1622 held by the coupling. The body port 1622 comprises a disc-shaped self sealing membrane 1643, FIG. 144*a*, fixated to a rigid ring having an outer circumferential groove 1634 that receives the latching members 1633 of the coupling. The self sealing membrane 1643 has a small self sealing hole 1644, shown in FIG. 144*a*, centrally in the membrane 1643. For example, the self sealing membrane 1643 may be made from a gel-type material being elastic enough to enable a deformation large enough for a person's hand to pass through the small self sealing hole 1644 while still contracting enough to create an airtight seal between the chamber and the outside environment.

The coupling described above enables quick exchange of the port 1622. Thus, the surgeon may release the body port 1622 from the port arrangement by simply pulling the hand lever 1639 so that the latching members 1633 disengage from the groove 1634 of the body port 1622, whereby the body port 1622 can be removed.

FIG. 144*a* is a cross-sectional view of the port arrangement shown in FIG. 143, to more clearly illustrate the body port 1622 with its self sealing membrane 1643 and small hole 1644.

FIG. 144*b* shows the self sealing body port 1622 when the hand of a surgeon is placed through the hole 1644 in the membrane 1643 and thus enabling manual manipulation within the body of the patient.

Figure 145A:
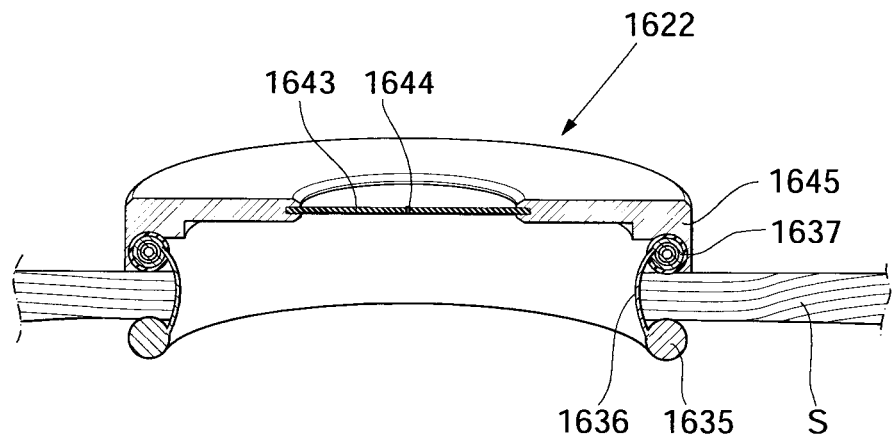
Figure 145B:
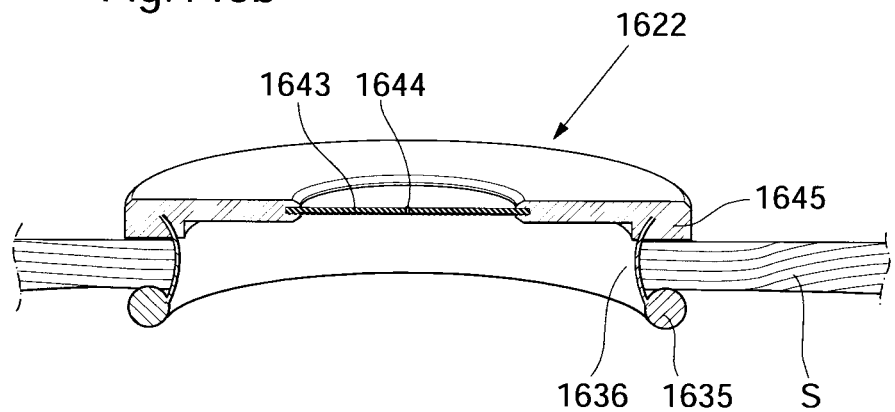

FIG. 145*a* shows a self sealing body port 1622 in a close-up, in section. The self sealing body port 1622 could be connected to the coupling, for example as disclosed with reference to FIGS. 143-144, which in turn is connected to any of the medical device disclosed with reference to FIGS. 124-145, or the self sealing body port 1622 could be fixated to a retractor, as shown in FIGS. 145*a* and 145*b*. The self sealing body port 1622 comprises a self sealing membrane 1643 fixated to a rigid part 1645 of the self sealing port. The self sealing membrane 1643 having a small self sealing hole 1644 centrally in the membrane 1643. The self sealing membrane 1643 is for example made from a gel-type material being elastic enough to enable a deformation large enough for a person's hand to pass through the small self sealing hole 1644 while still contracting enough to create an airtight seal between the sealed environment and the outside environment. The medical device being fixable to a retractor comprising one intra body ring 1635 adapted to be positioned on the inside of the patients skin, and one ring 1637 adapted to be placed on the outside of the patients skin. Between the intra body ring 1635 and the ring 1637 adapted to be placed on the outside of the patients skin a retractor membrane 1636 is positioned which is adapted to exert a pressure of the cut surfaces of the incision for retracting the skin and thereby keeping the wound open. The retractor membrane 1636 is preferably made from a resilient of elastic polymer material. The ring adapted to be placed on the outside of the patients skin 1641 comprises an integrated roll up system which could be a spring loaded roll up system adapted to create a suitable pressure on retractor membrane 1636 for keeping the wound open.

FIG. 145*b* shows an alternative embodiment of the self sealing body port 1622, with the difference that the retractor membrane 1636 is made from a material elastic enough such that one end of the retractor membrane 1636 could be fixedly fixated to the rigid part 1645 of the port.

Figure 146:
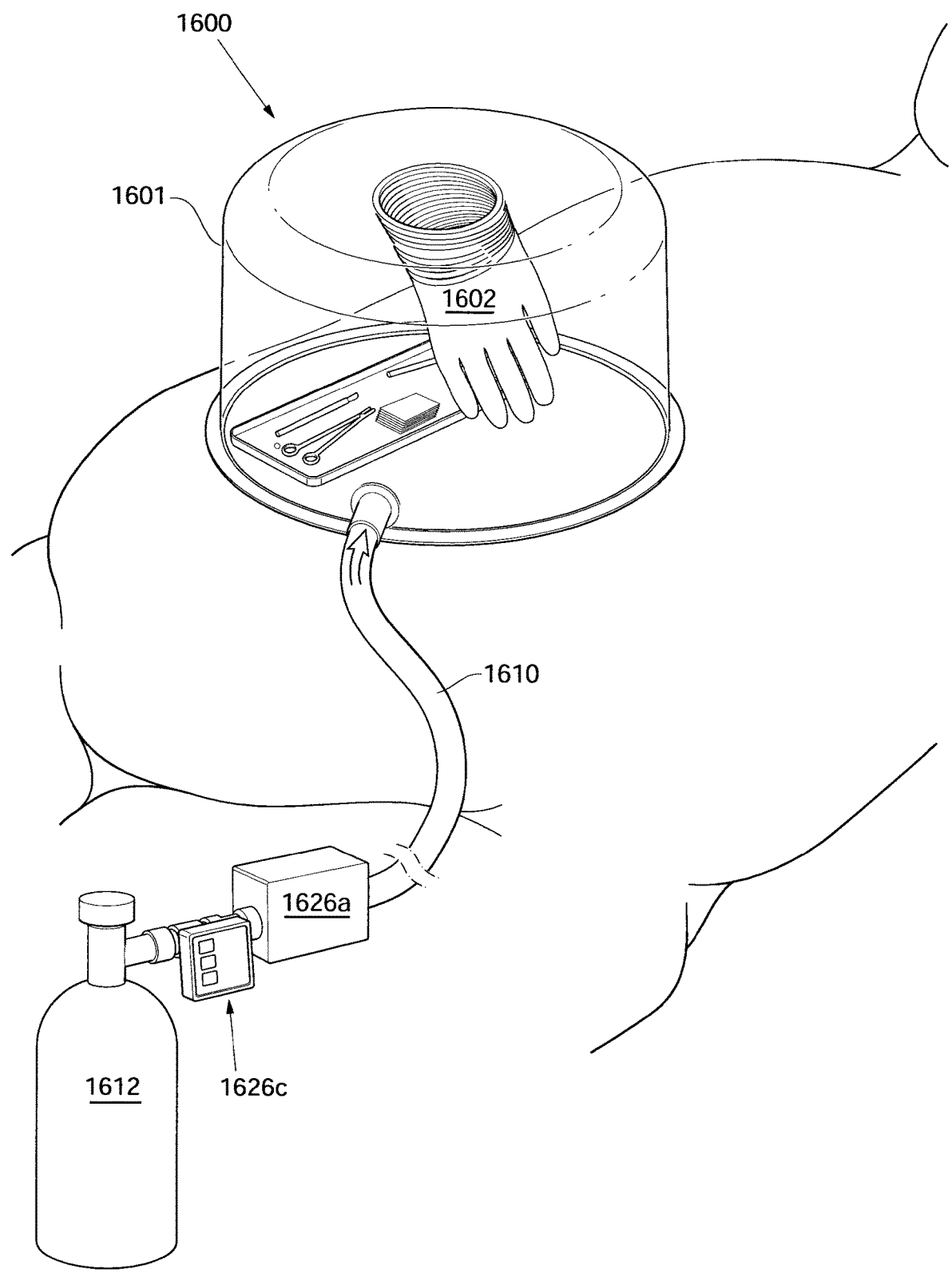
FIG. 146 shows an embodiment of the medical device, when positioned on the abdomen of a patient.

FIG. 146 shows the medical device as shown in FIG. 142 with the addition that the embodiment comprises a sterilizing unit 1626 adapted to sterilize the gaseous fluid entering the medical device 1600. In the embodiment disclosed herein, the gaseous fluid entering the medical device 1600 originates from a pressurized tank 1612 and could be pre-sterilized, however, in other embodiments, it is conceivable that the gaseous fluid is the surrounding air which is pressurized (such as further disclosed with reference to FIG. 85). In the embodiments where the surrounding air is used to inflate the medical device 1600 and constitute the operating environment this air needs to be properly sterilized. The medical device 1600 further comprises a tempering unit 1626*c* which could be provided to heat or cool the gaseous fluid inflating the medical device 1600. In cases when the surrounding environment is cold the tempering unit 1626*c* could be used to raise the temperature of the sealed environment to provide beneficial operating circumstances both for the patient and for the surgeon. In cases when the surrounding environment is hot, the tempering part of the system 1626*c* could be used to lower the temperature of the sealed environment both to provide beneficial operating circumstances, both for the patient and for the surgeon, and for providing a temperature inhibiting bacterial and viral infections. The tempering unit 1626*c* could comprise a temperature regulating device 1625 for setting the required temperature.

Figure 147:
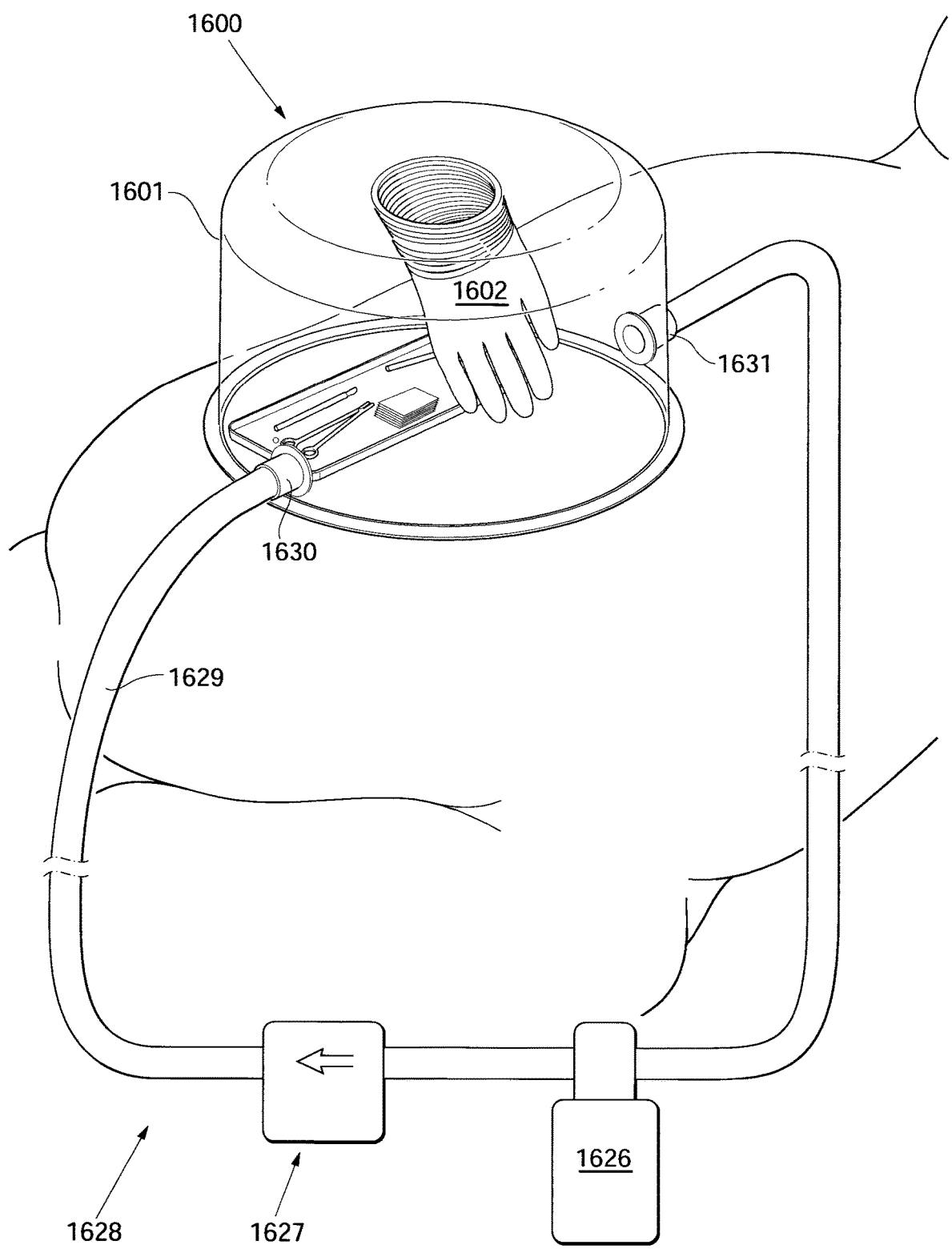
FIG. 147 shows an embodiment of the medical device, comprising a fluid circulating system, when positioned on the abdomen of a patient.

FIG. 147 shows a medical device similar to the embodiment disclosed in FIG. 142 but comprising a system 1628 for circulating a fluid through the sealed environment of the medical device. The system comprises a fluid conduit 1629 connected at an inlet 1630 placed in the wall 1601 for supplying fluid to the sealed environment, and an outlet 1631 for draining the fluid from the sealed environment. The fluid is circled by means of a pumping unit 1627 and is circled via a sterilizing/filtering unit 1626 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 148:
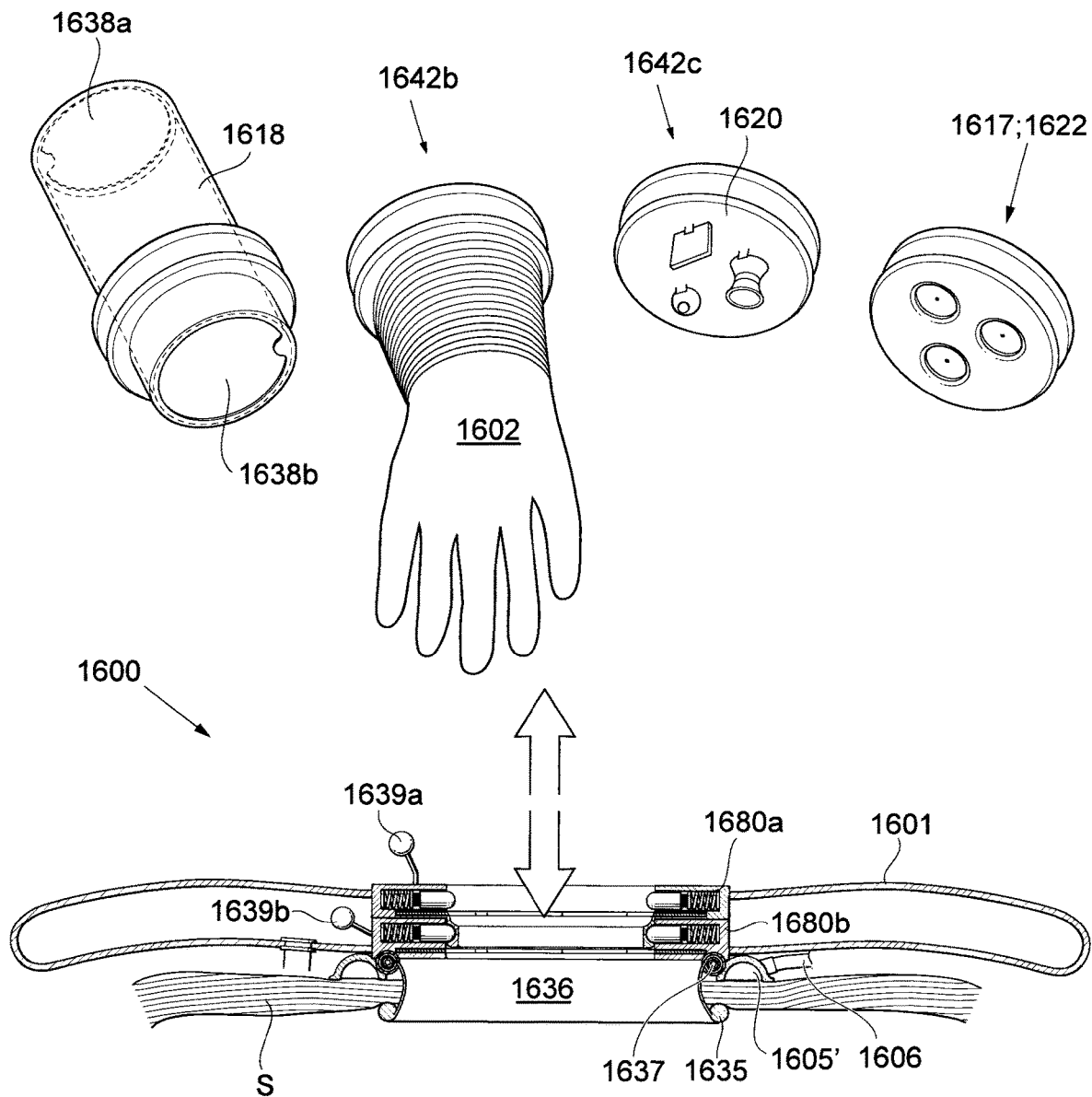
FIGS. 148-149 shows another embodiment of the medical device, in section.

FIG. 148 shows an alternative of the embodiment in which the medical device 1600 is adapted to be at least partially placed in an incision cut in a patient's body. The medical device 1600 comprises a first 1631*b* and second 1631*a* part adapted be interconnected to form a surgical port. The second part 1631*a* is adapted to be disconnected from the first part 1631*b*, and the first part 1631*b* is connected to a first portion of a flexible wall 1601, and the second part is connected to a second portion of the flexible wall 1601. The flexible wall 1601 forms a chamber in which a sealed environment can be maintained, the chamber is heavily enlarged when the second part 1631*a* is disengaged from the first part, thus creating operating space within the chamber enclosed by the wall. The first and second parts comprise a latching system for locking an inset. The inset may for example be a glove 1602 for manual manipulation within the body of the patient, or within the enclosed chamber, a holding device 1681 for holding instruments or medical devices within the chamber. Alternatively, the insets may be replaced by an airlock sluice 1618 or a port comprising a multiport portion 1648 comprising a plurality of ports enabling the insertion of a surgical instrument into the chamber or body of the patient.

In the embodiment shown in FIG. 148 the medical device is fixated to the body of the patient by means of a vacuum fixating member 1605' connected to a conduit 1614, which in turn is connected to a vacuum source. Furthermore, the medical device in FIG. 148 comprises a second sealing function having a first sealing member 1635 adapted to be positioned at the inside of the patient's skin around an incision to be performed in the skin and a second sealing member 1637 adapted to be positioned at the outside of the patient's skin around the incision, and a spring-loaded or elastic connecting member 1636 sealingly interconnecting the first 1635 and second 1637 sealing members. The spring-loaded or elastic connecting member 1636 seals between at least one of the port and the skin of the patient, and the first sealing member and tissue of the patient.

Figure 149:
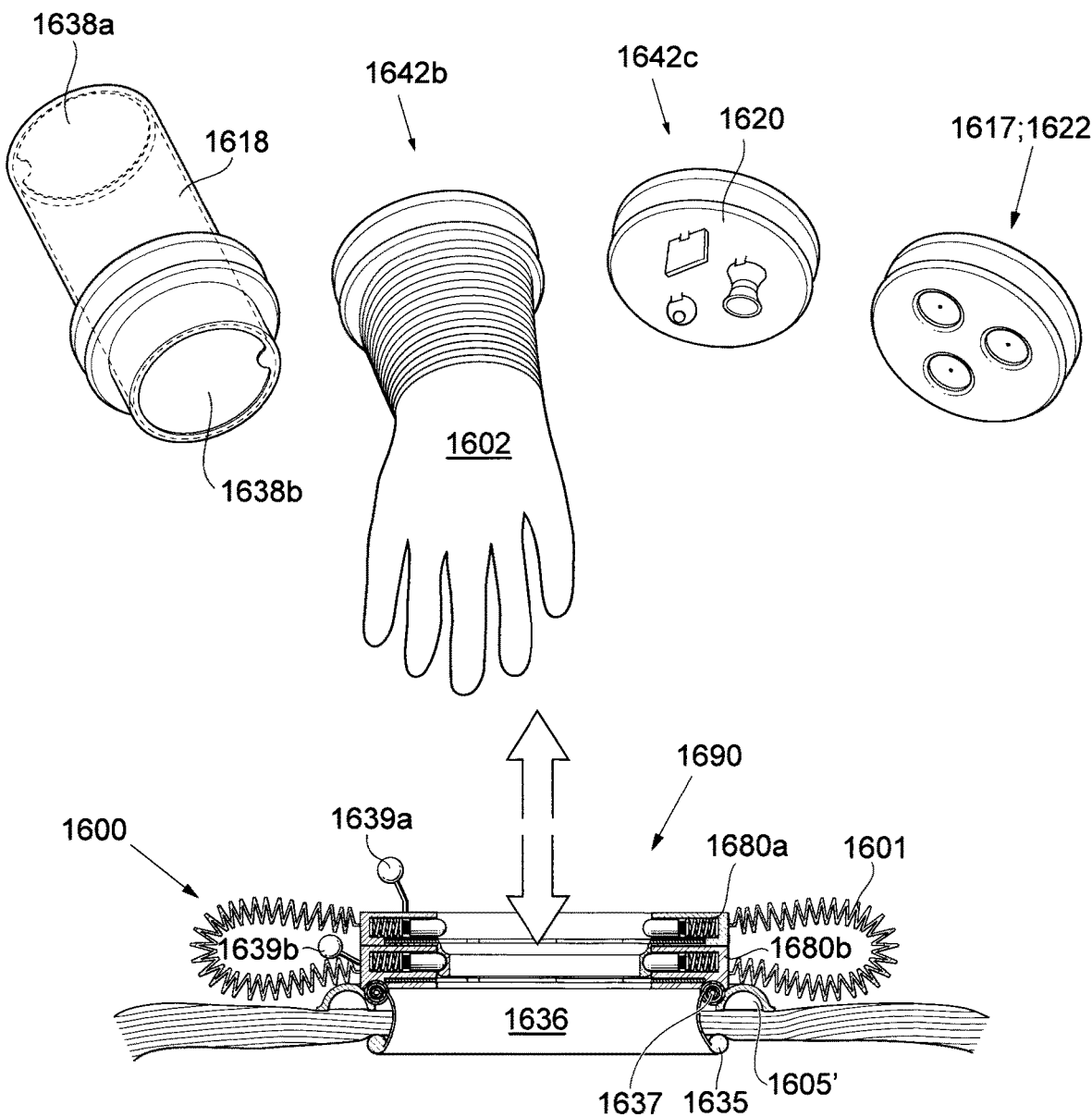

FIG. 149 shows the port in an embodiment very similar to the embodiment shown in FIG. 148 but with the difference that the wall 1601' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

FIG. 150-156 shows a feature which could be implemented in the embodiments disclosed with reference to FIGS. 124-149. In the embodiment of FIGS. 150-156, the wall of the medical device is inflatable, and the medical device is in its inflated state. When the chamber is deflated it has a first volume i.e. when the first 1631*b* and second 1631*a* parts are interconnected, and when the chamber is inflated and the second part 1631*a* is disconnected from the first 1631*b* part it has a second volume, and the second volume is larger than the first volume. According to the embodiment shown in FIG. 85*d*, the second volume is larger than 500 000 mm3 and adapted to hold a pressure exceeding atmospheric pressure.

According to the embodiment shown in FIG. 150-156 the chamber further comprises a pouch 1682 for holding a specimen 1681 removed from within the body of the patient not to contaminate any other part of the body and create the possibility of delaying the removal of the specimen until the procedure is concluded. The pouch may be a pouch 1682 which could be closed for creating a pouch-chamber within the chamber for isolating the removed specimen 1681 within the chamber.

Figure 150:
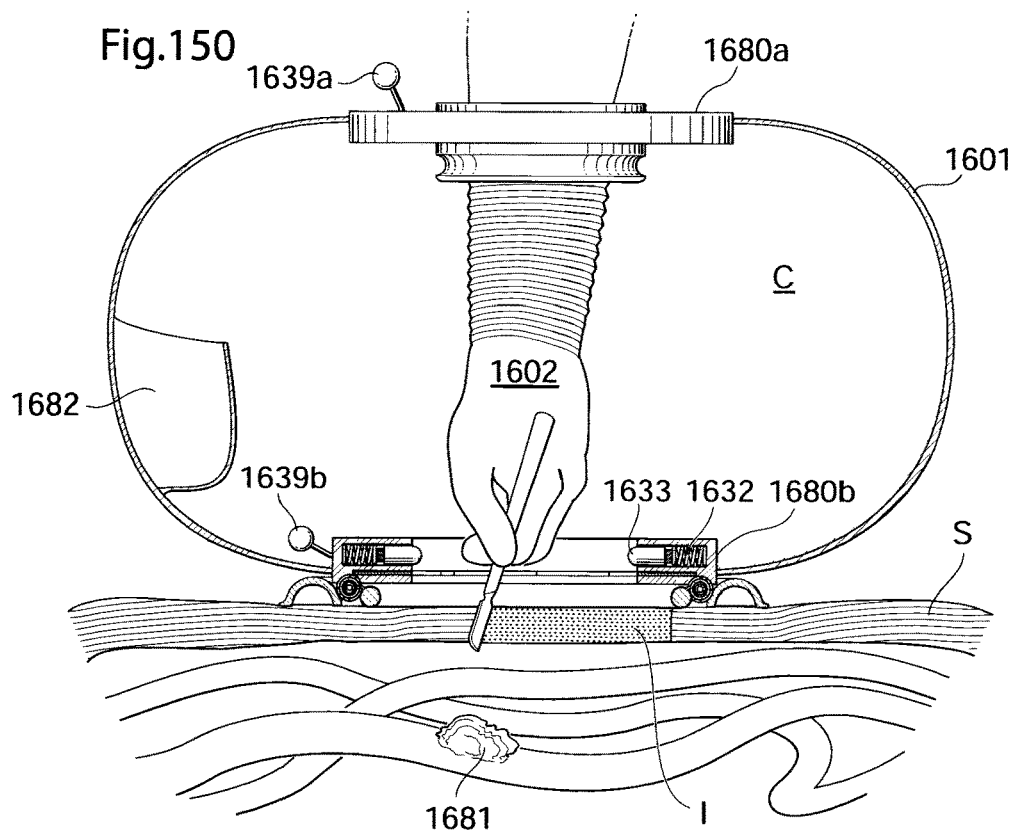
FIGS. 150-156 shows an embodiment of the medical device in section, being fixated to the patient and used.

In FIG. 150, a state is illustrated in which the cut in the patient's skin is being created by the surgeon by means of a glove inset 1602 latched to the second part 1631a. The surgical port is fixated and sealed by means of the vacuum sealing member 1605' since the seal that is provided partially within the patient's body cannot be mounted until the cut in the patient's skin is concluded. The two different seals disclosed could in some embodiments be replaced by only one of the seals, or by a different seal, such as the adhesive of pressure seals disclosed in other portions herein.

Figure 151:
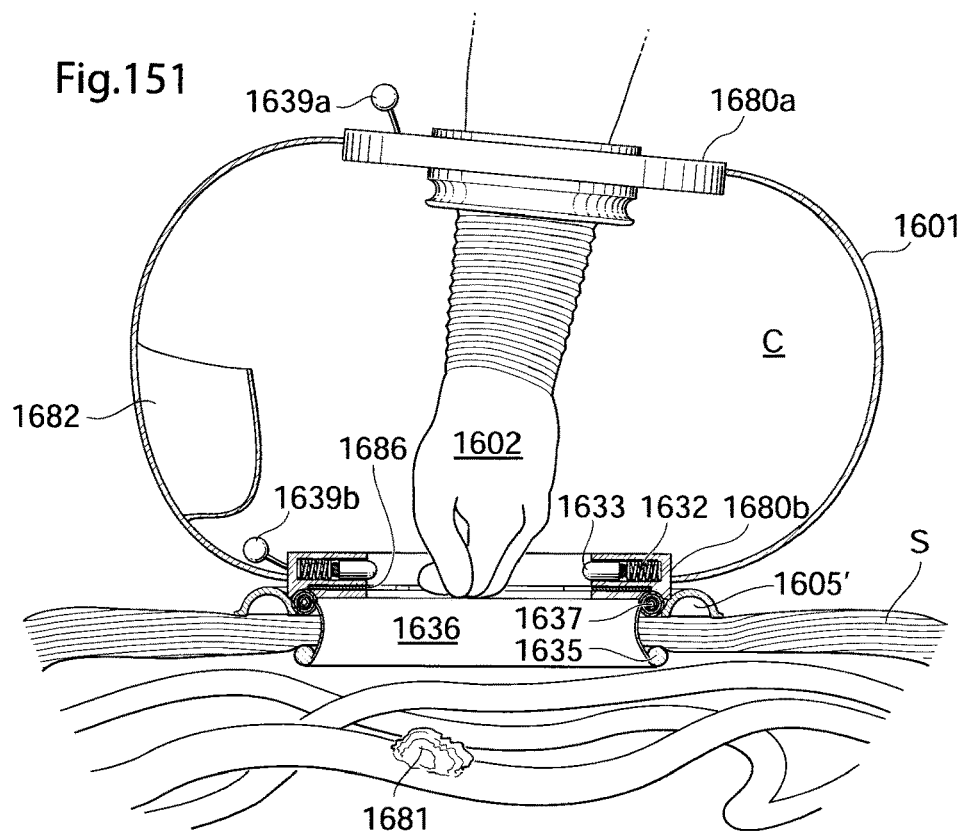

FIG. 151 shows the medical device, when the second sealing 1635, 1636, 1637 have been placed in the incision cut in the patient's skin. The wall 1601 enclosing the chamber is elastic or flexible which enables the surgeon move the second part 1631a in relation to the first part 1631b for getting better access to different angles within the patient's body, for example for removing a specimen 1681. The embodiment of FIG. 151 further comprises a non-penetrable valve 1686 placed in the first part 1631b for closing the port such that the chamber is sealed from at least one of the ambient environment and a cavity in the patient. The closing of the non-penetrable valve 1686 enables activity within the chamber without maintaining a pressure in the chamber, at the same time as a pressure and/or sealed environment can be maintained within the body of the patient.

Figure 152:
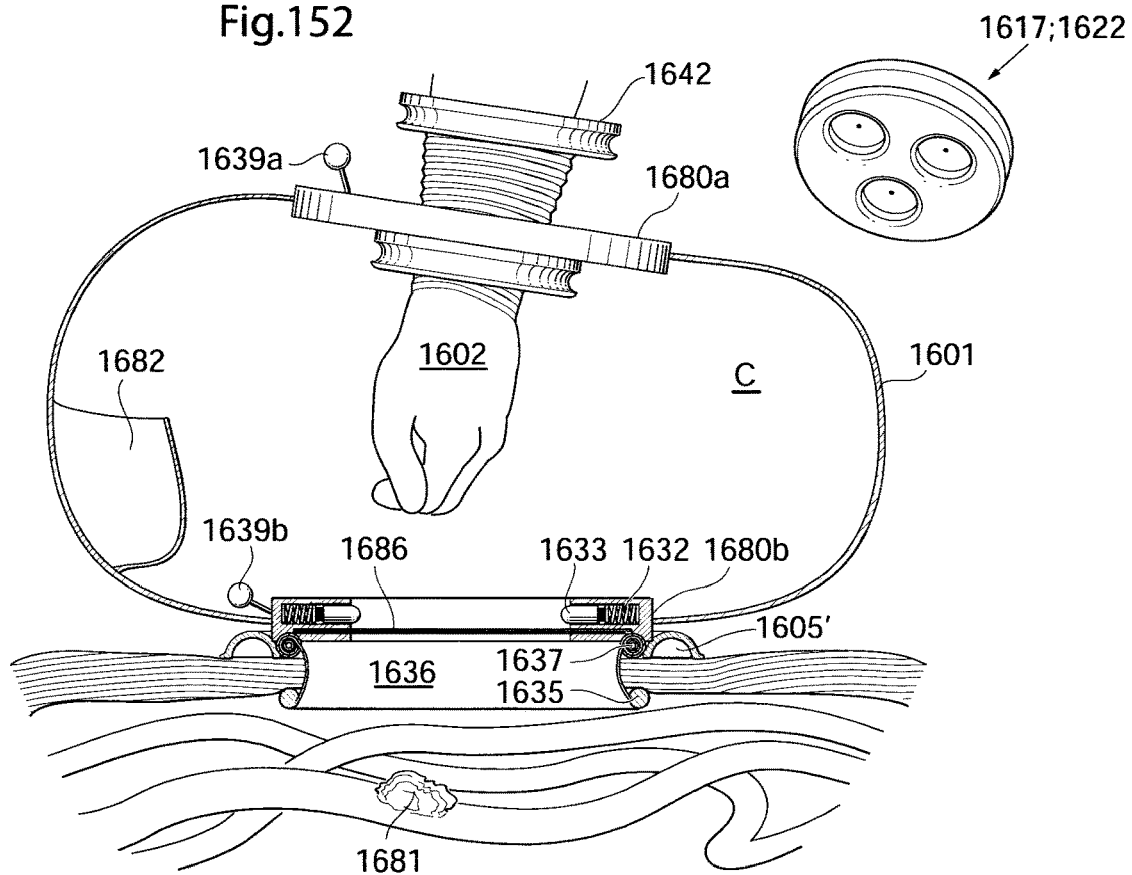

FIG. 152 shows the medical device when the glove inset 1602 is removed and replaced by a multi-port inset 1648 comprising a plurality of ports 1647. The multi-port inset may be used for manipulating objects within the chamber of the inflated medical device using surgical instruments, or within the body of the human patient, when the first and second parts are connected (as shown in FIG. 153).

Figure 153:
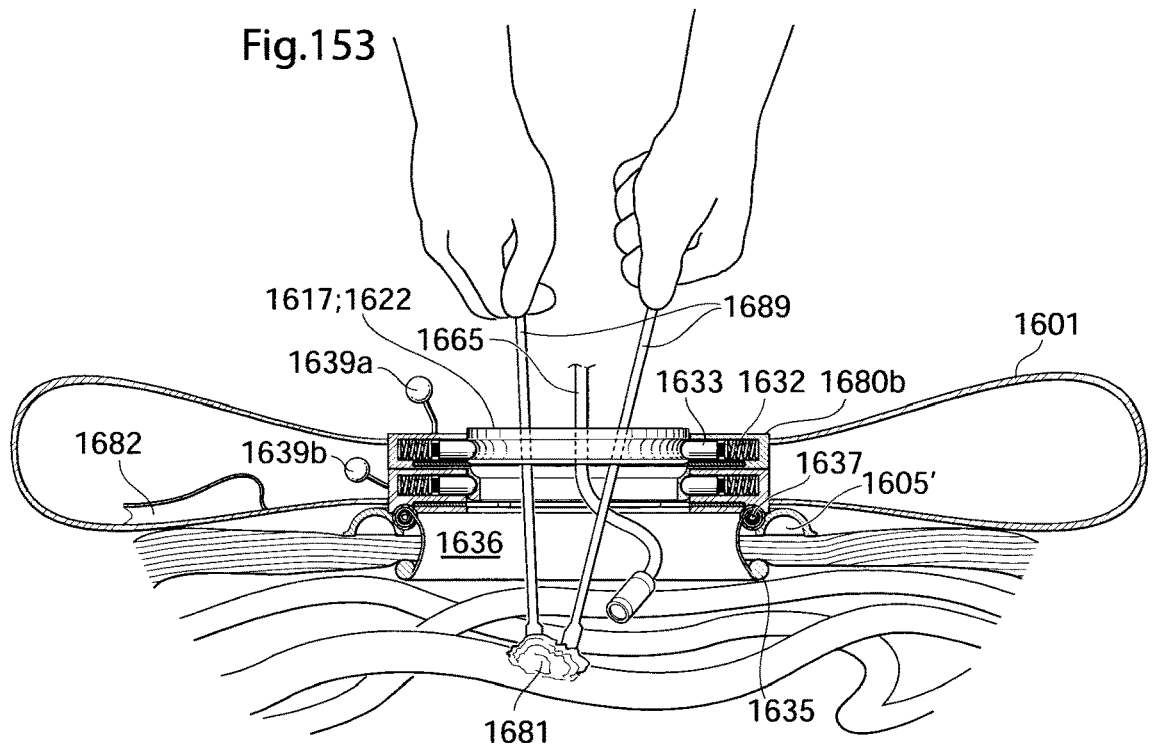

FIG. 153 shows the medical device when the first and second parts are connected such that surgical instruments 1689 can be used for manipulating within the body of the patient. An endoscopic camera 1688 may be provided in the port for enabling visual inspection of the cavity within the patient's body. The process of cutting away a specimen from the intestines of a patient in a laparoscopic way is shown in FIG. 153.

Figure 154:
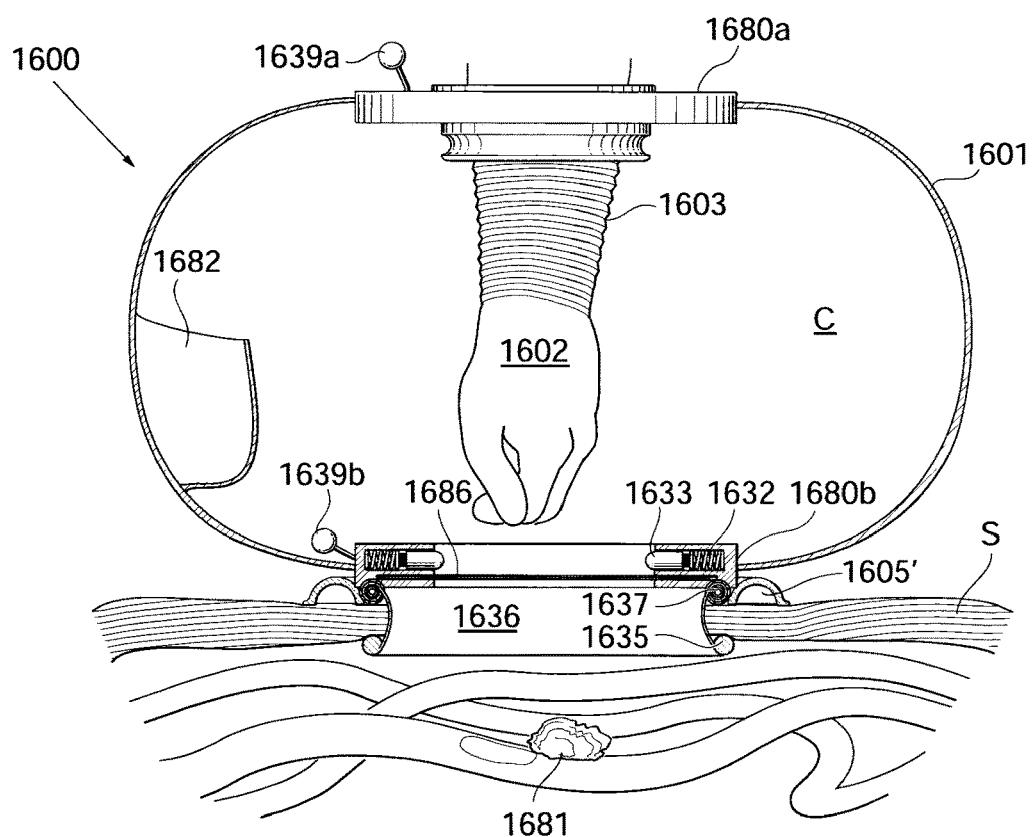

In FIG. 154, the glove inset 1602 has been fixated to second part 1631a to enable the surgeon to operate within the cavity of the patient's body and within the chamber enclosed by the wall of the medical device. By the glove inset 1602 comprising a pleated portion, the glove surgeon is able to reach into the cavity of the patient for removing the specimen cut loose from the intestines in prior steps.

Figure 155:
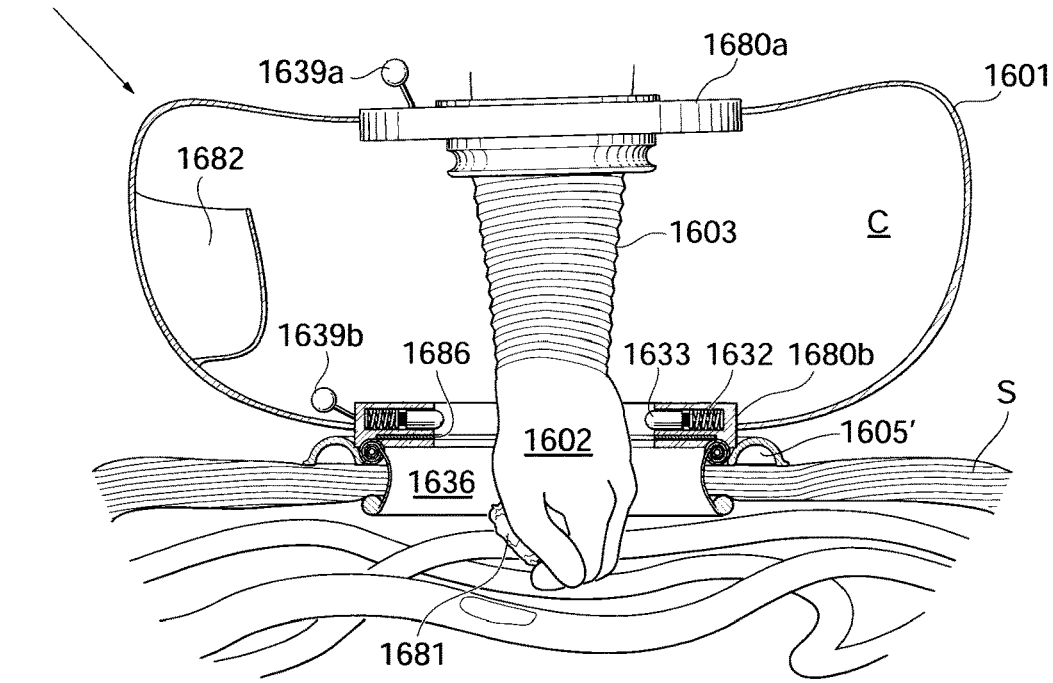

FIG. 155 shows that the wall of the medical device is collapsible such that the glove inset can be moved with relation to the first part 1631b of the port, which gives the surgeon further freedom when removing the loose specimen from the intestines of the patient.

Figure 156:
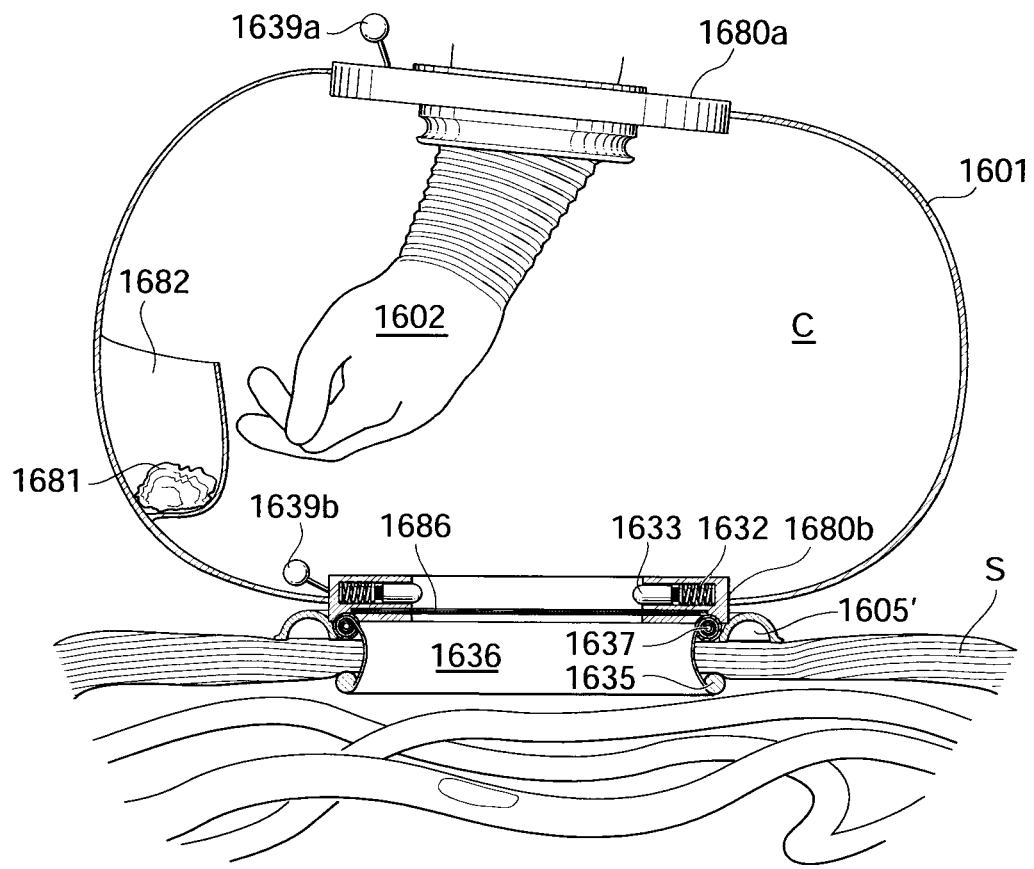

FIG. 156 shows the step of placing the removed specimen in the pouch 1682 such that the specimen does not contaminate any other part of the body. The pouch may be a pouch 1682 which could be closed for creating a pouch-chamber within the chamber for isolating the removed specimen 1681 within the chamber.

Figure 157A:
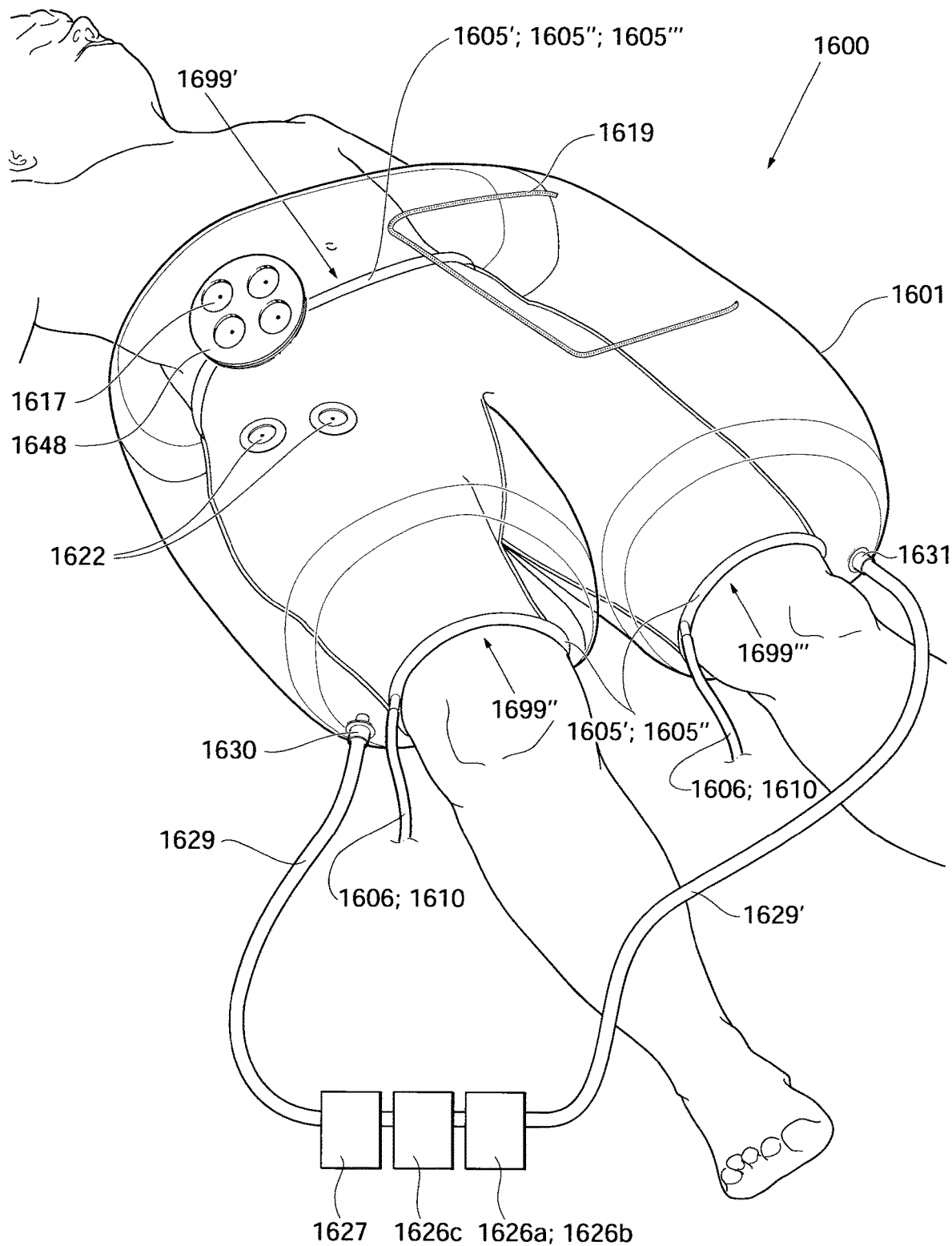
FIGS. 157a-163b shows different embodiments of the medical device in perspective, when applied to the body of the patient.

FIG. 157a shows an embodiment of the medical device in which the medical device 1600 comprises three open ends adapted to receive the two legs of the patient and the upper body, accordingly. The medical device 1600 is thus designed as a pair of pants adapted to be fitted onto the patient to provide a pants-like chamber surrounding the patient and being adapted to be inflated to provide an isolated environment in which a surgical procedure can be performed. The open ends encircling the patient's legs above the patient's knees are equipped with seals, here shown as vacuum 1605' or pressure 1605" seals adapted to be connected to vacuum 1606 or pressure 1614 conduits. The open end encircling the upper body of the patient is equipped with an adhesive seal 1605, however it is equally conceivable that the adhesive seal is supported or replaced by a vacuum or pressure seal, such as the seals disclosed encircling the legs of the patient. The medical device comprises a system for circulating a fluid inside of the camber of the medical device. The system comprises a first conduit 1629' connected to an outlet 1631 from the chamber and to a unit for heating 1626a and/or sterilizing 1626b the fluid. The system further comprises a filtering unit 1626c and a pump 1627 for circulating the fluid to a second conduit 1629 and to an inlet 1620 placed in the wall of the medical device. The medical device is also shown with a multi port 1648 placed in the wall and comprising four ports 1647 for enabling transfer between the ambient environment and the chamber. The medical device also comprises endoscopic ports 1622 placed in the skin of the patient for enabling an operation to be performed within a joint or a cavity in the patient's body. A zipper-closed opening 1619 is further provided in the wall of the medical device and adapted to enable transfer from the ambient environment into the inside of the chamber, of for example medical devices and/or implants. The medical device 1600 shown in FIG. 157a is for example ideal for use in a hip joint surgery where the entire surgical area can be isolated from the ambient environment and the operation can be performed in a sterile liquid or gas circled in the chamber.

Figure 157B:
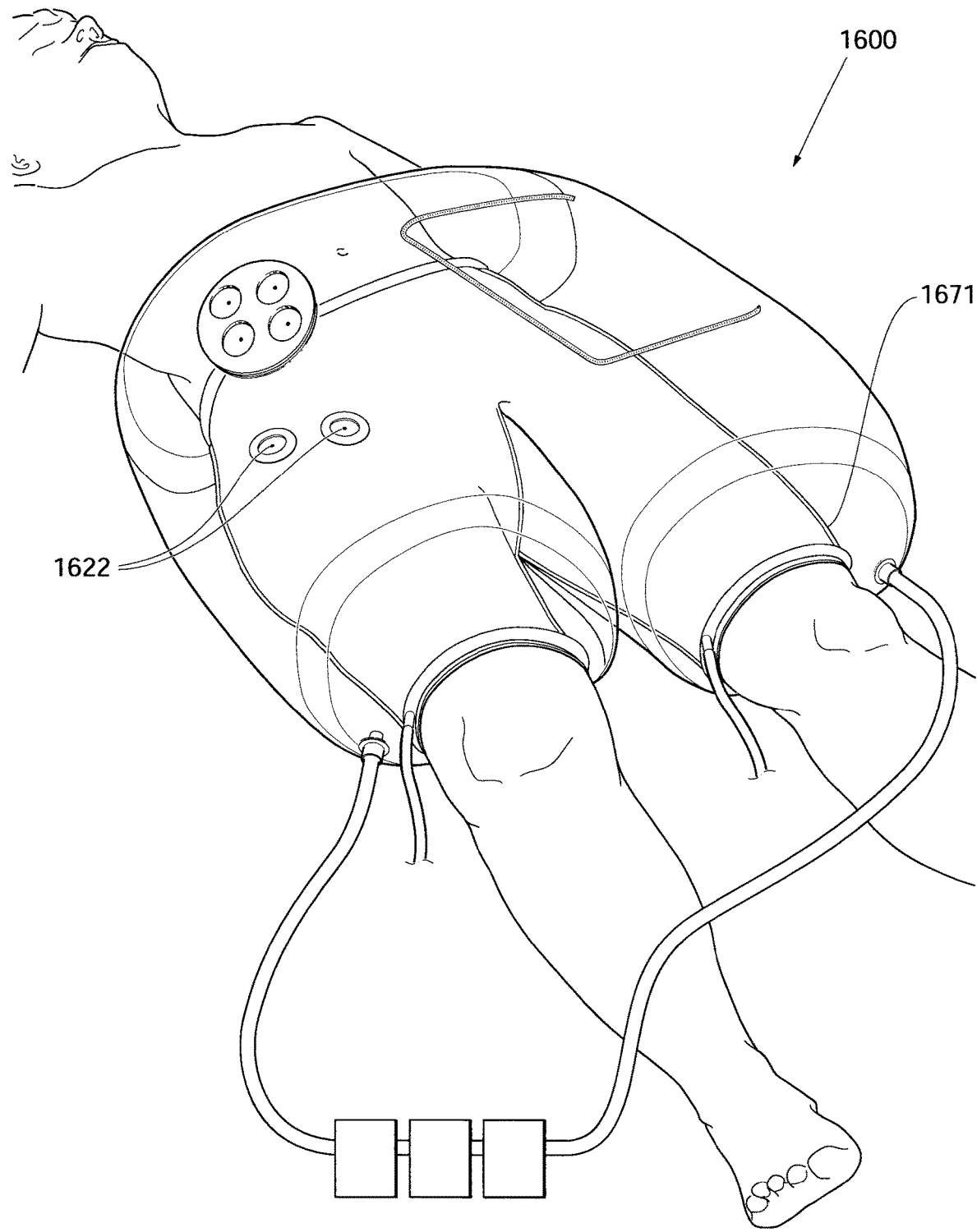

FIG. 157b shows the medical device 1600 in an embodiment comprising the features described with reference to FIG. 157a with the difference that the medical device of FIG. 157b further comprises an inner layer 1671 such that the chamber is formed by the wall 1601 without involving the patient's body. The inner layer 1671 forms a tubular enclosure formed by the wall 1601. The inner layer thus separates the chamber from the skin of the patient such that the environment in the chamber is not contaminated by for example bacteria which could reside on the patient's skin. The inner layer can be cut through when the incision is to be made in the patient's skin such that only a very small portion of the patient's skin needs to be exposed to the environment in the chamber. The inner layer 1671 could for example be an adhesive polymer layer. In the embodiments shown in FIG. 157b two body ports 1622 are placed in the wall of the inner layer. The body ports may be pre-placed in the wall, or may be placed in the wall after the medical device has been positioned with the body of the patient. The advantage with placing the ports 1622 in the inner wall 1671 and in the body of the patient after the medical device 1600 has been applied on the patient's body is that the ports 1622 can be contained within the chamber of the medical device before being placed in the skin of the patient, such that the chamber serves as a sterile package for the body ports 1622.

Figure 157C:
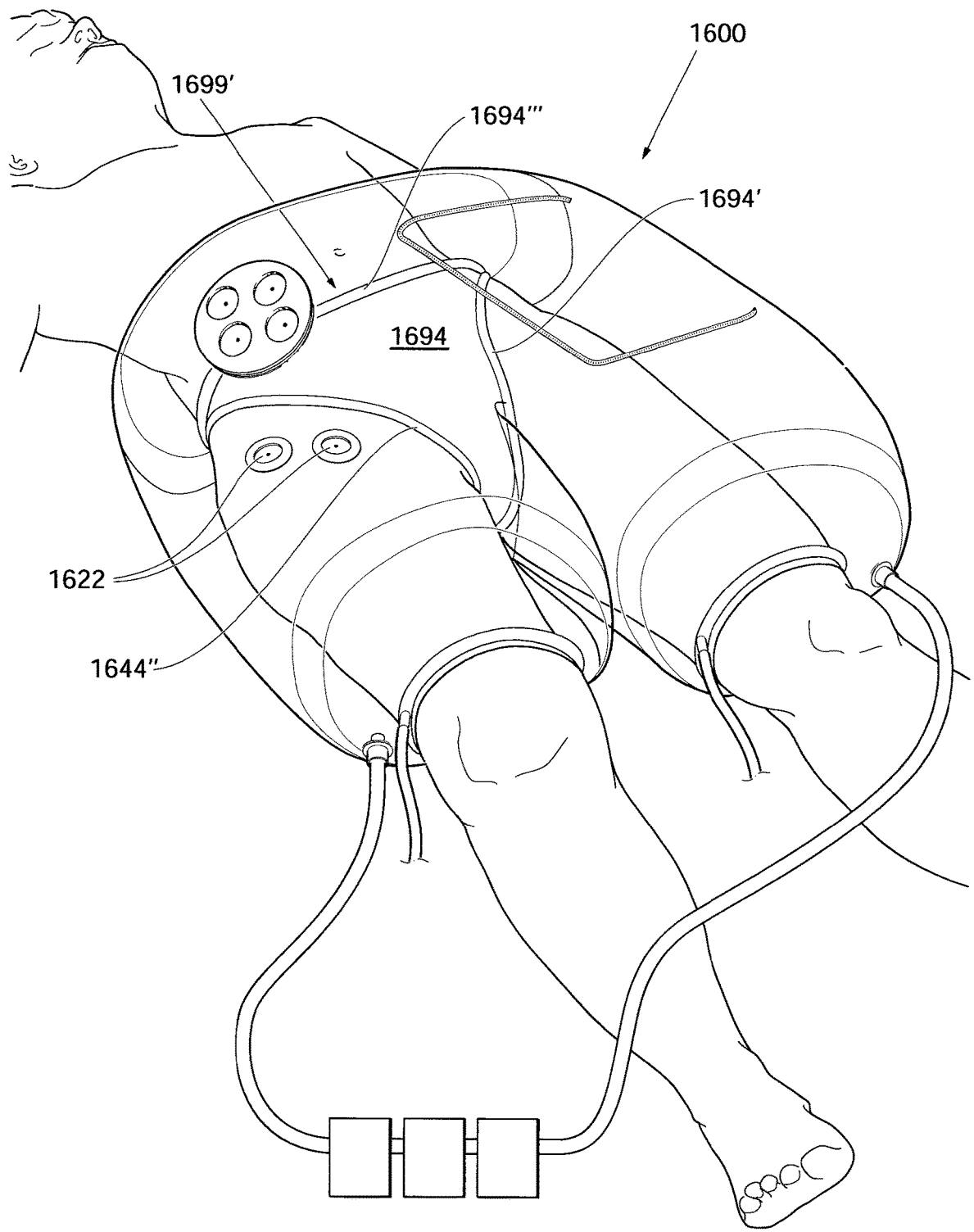

FIG. 157c shows the medical device in an embodiment including the features of the embodiment disclosed with reference to FIG. 157a. The difference being that the embodiment of FIG. 157c comprises an additional sealing subdevice 1694 comprising a wall and a sealing device adapted to be placed between the chamber and the skin of the patient. The sealing subdevice is formed to separate the anus or opening of urethra from the chamber to avoid connection between the anus or opening of the urethra and the chamber. The sealing subdevice 1694 comprises seals in the inguinal area 1694'; 1694" which could be adhesive, pressure or vacuum seals. The sealing subdevice is further connected at a connecting joint 1694''' to the open end of the medical device 1600 encircling the upper body of the patient, however it is furthermore conceivable that the sealing subdevice comprises a separate seal adapted to seal between the medical device 1600 and the skin of the patient.

Figure 158A:
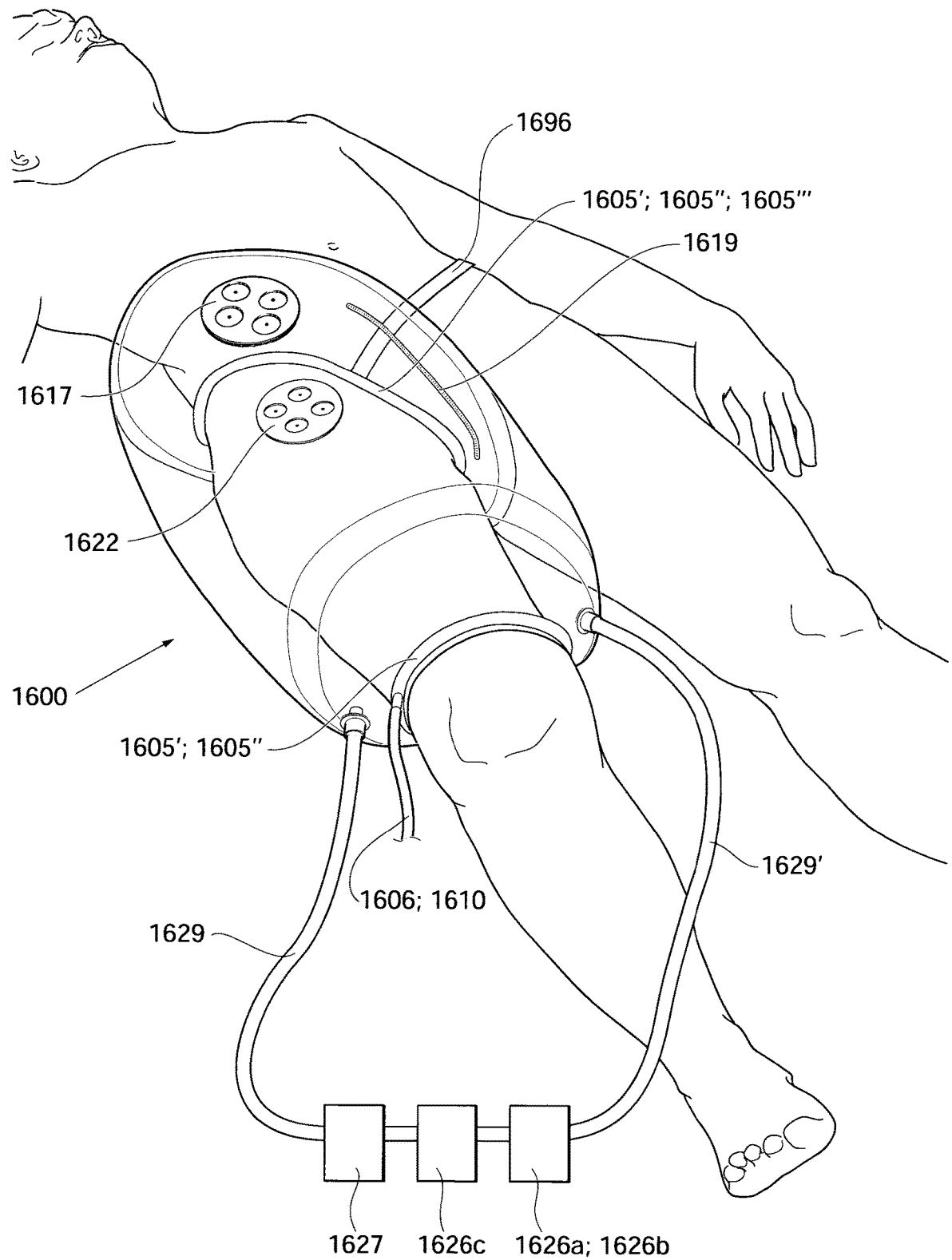

FIG. 158*a* shows a medical device similar to the medical device shown in FIG. 157*a* with the difference that the medical device of FIG. 158*a* is only adapted to be placed on one side of the patient and provide sealing 1605; 1605'; 1605" in the inguinal area. One advantage with the construction of FIG. 158*a* is that the anus and urethra openings are separated from the chamber, and the fluid volume in the device is smaller in comparison to that of the embodiment disclosed in FIG. 157*a*. The features included in FIG. 158*a* are equivalent to the features included in the embodiment disclosed in FIG. 157*a*.

Figure 158B:
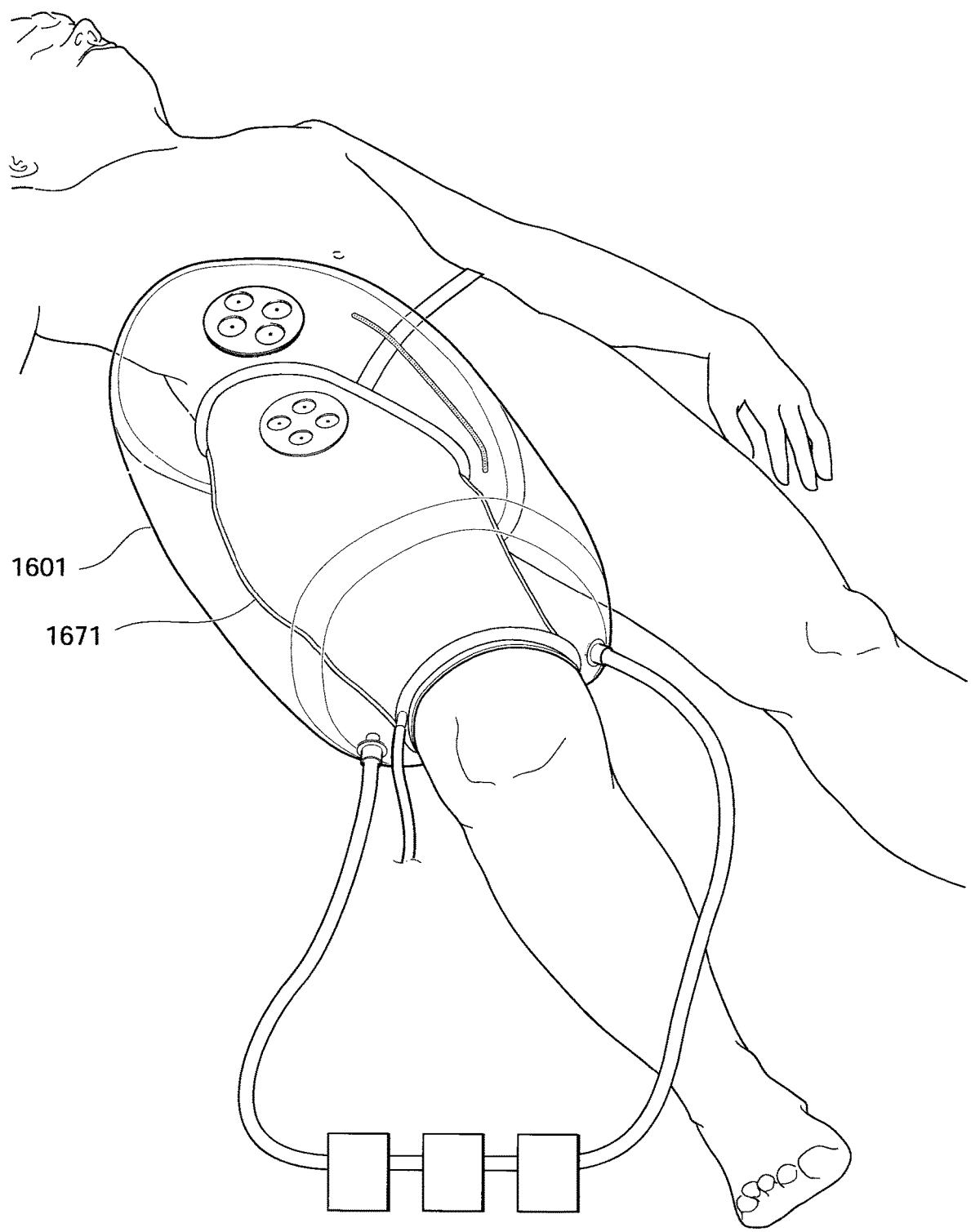

FIG. 158*b* shows the medical device in an embodiment similar to the embodiment shown in FIG. 158*a*, the difference being that in the medical device in the embodiment of FIG. 158*b* comprises an inner wall 1671 in the same way as 157*b*. The inner wall 1671 forms an elongated tubular enclosure through which the leg of the patient is placed. The inner wall 1671 forming the elongated tubular enclosure thus separates the skin of the patient from the chamber of the medical device such that the chamber is formed by the wall 1601 and the inner wall 1671 without involving the skin of the patient.

Figure 159A:
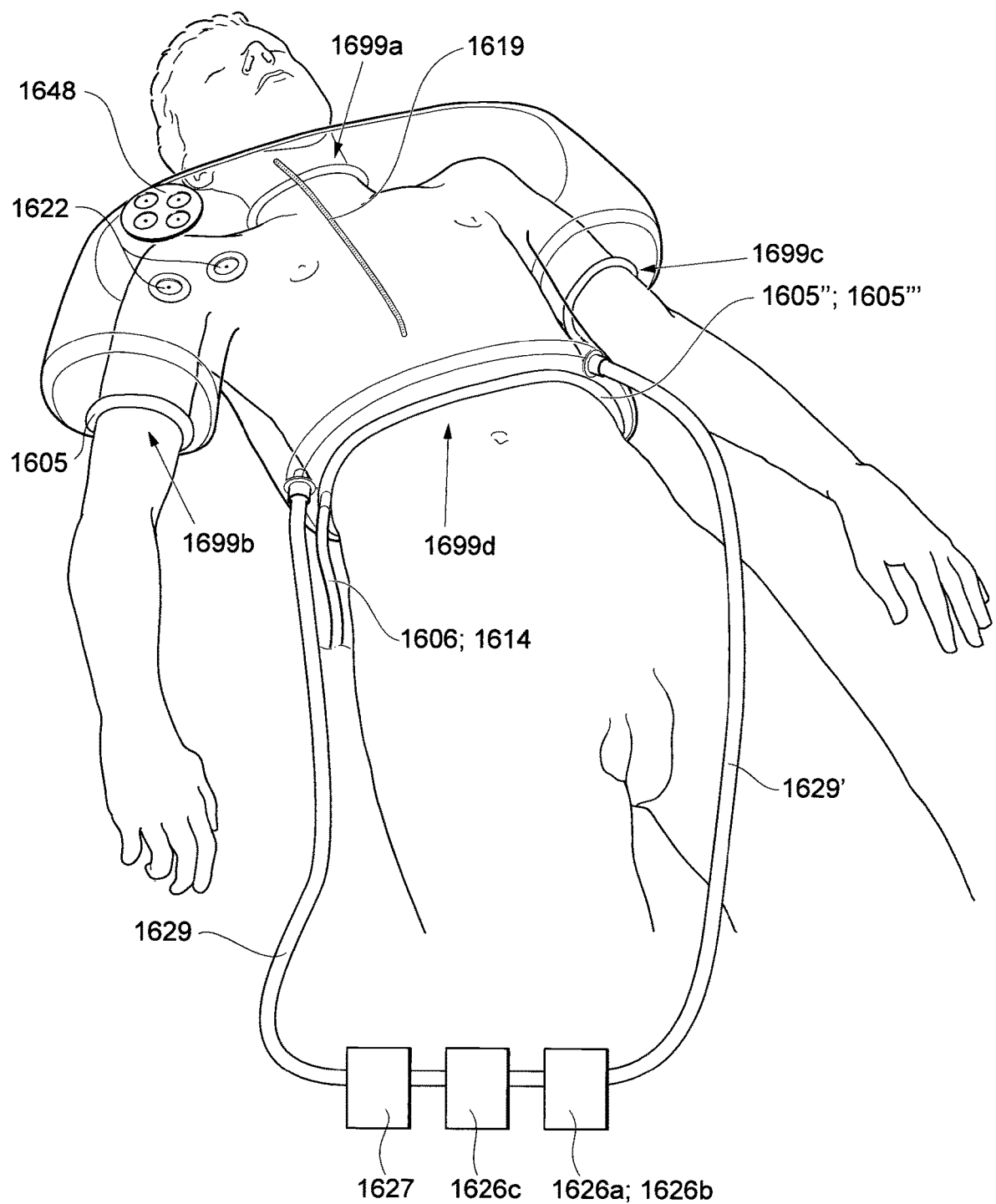

FIG. 159*a* shows an embodiment of the medical device 1600 similar to the embodiment disclosed with reference to FIG. 157*a*, the difference being that the embodiment of FIG. 159*a* comprises 4 open ends and is adapted to accommodate the upper body of the patient an seal at the arms, neck and chest of the patient. The seals could be any one of the seals 1605; 1605'; 1605" disclosed herein, i.e. adhesive, pressure or vacuum. The medical device further comprises a system for circulating a fluid, wall 1648 and body 1622 ports and zipper-closed opening 1619, all further described with reference to FIG. 157*a*. The embodiment of FIG. 159*a* is for example suitable for performing an arthroscopic shoulder joint procedure.

Figure 159B:
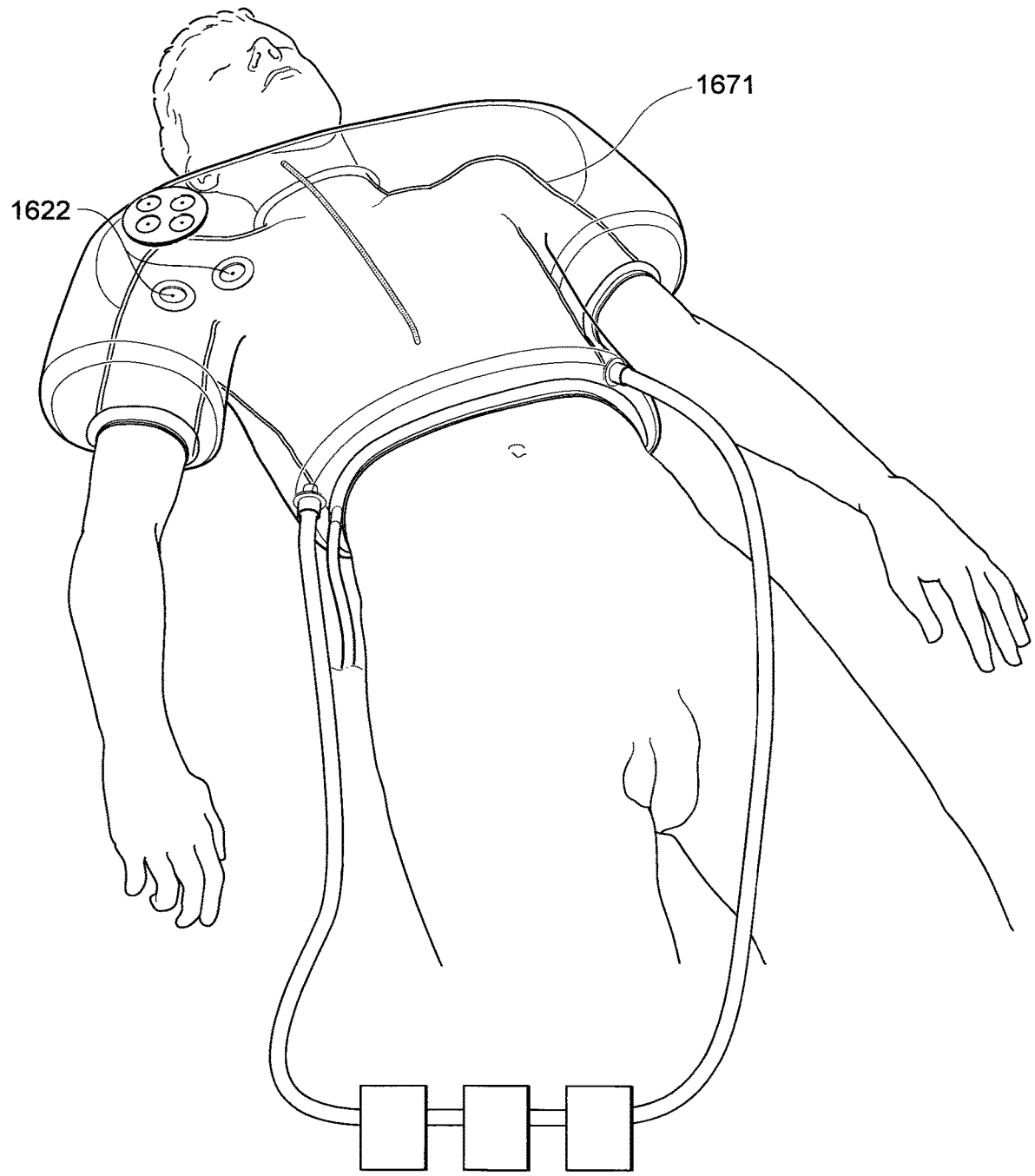

FIG. 159*b* shows an embodiment of the medical device comprising the features of the embodiment disclosed in FIG. 159*a*, with the difference that the medical device in the embodiment of FIG. 159*b* comprises an inner wall 1671, much like in the embodiment described with reference to FIG. 157*b*. The inner wall 1671 is adapted to separate the skin of the patient from the chamber of the medical device and can be cut through when the incision in the patient for performing the surgical procedure should be performed.

Figure 160A:
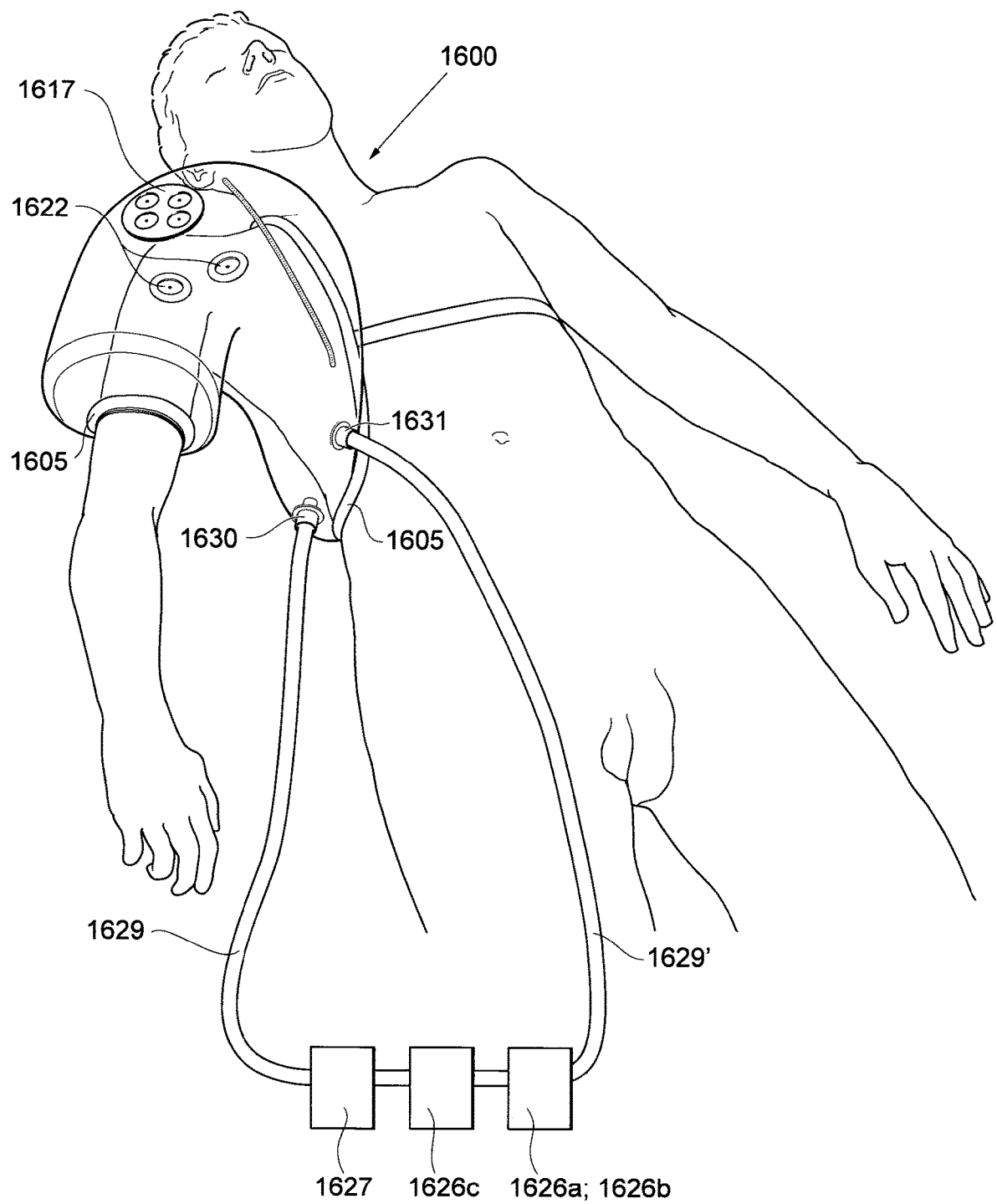

FIG. 160*a* shows a medical device 1600 similar to the medical device 1600 shown in FIG. 159*a* with the difference that the medical device of FIG. 160*a* is only adapted to be placed on one side of the patient and provide sealing 1605 along the side of the patient's chest. One advantage with the construction of FIG. 160*a* is that the fluid volume in the device is smaller in comparison to that of the embodiment disclosed in FIG. 159*a*. The features included in FIG. 160*a* are equivalent to the features included in the embodiment disclosed in FIG. 159*a*.

Figure 160B:
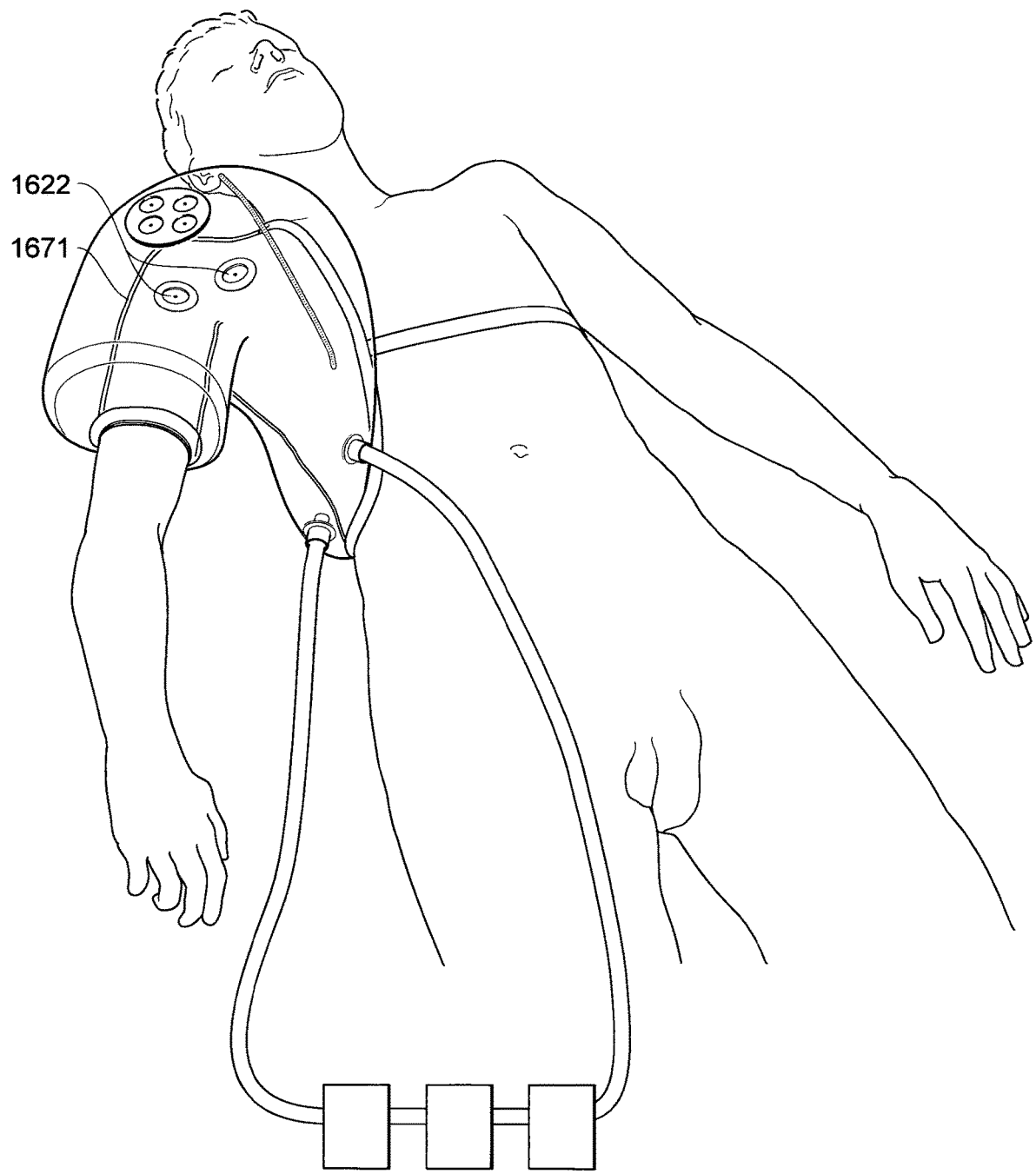

FIG. 160*b* shows an embodiment of the medical device similar to the medical device described in FIG. 160*a* with the difference that the medical device of the embodiment in FIG. 160*b* comprises an inner wall 1671, much like in the embodiment described with reference to FIG. 159*b*. The inner wall 1671 is adapted to separate the skin of the patient from the chamber of the medical device and can be cut through when the incision in the patient for performing the surgical procedure should be performed.

Figure 161A:
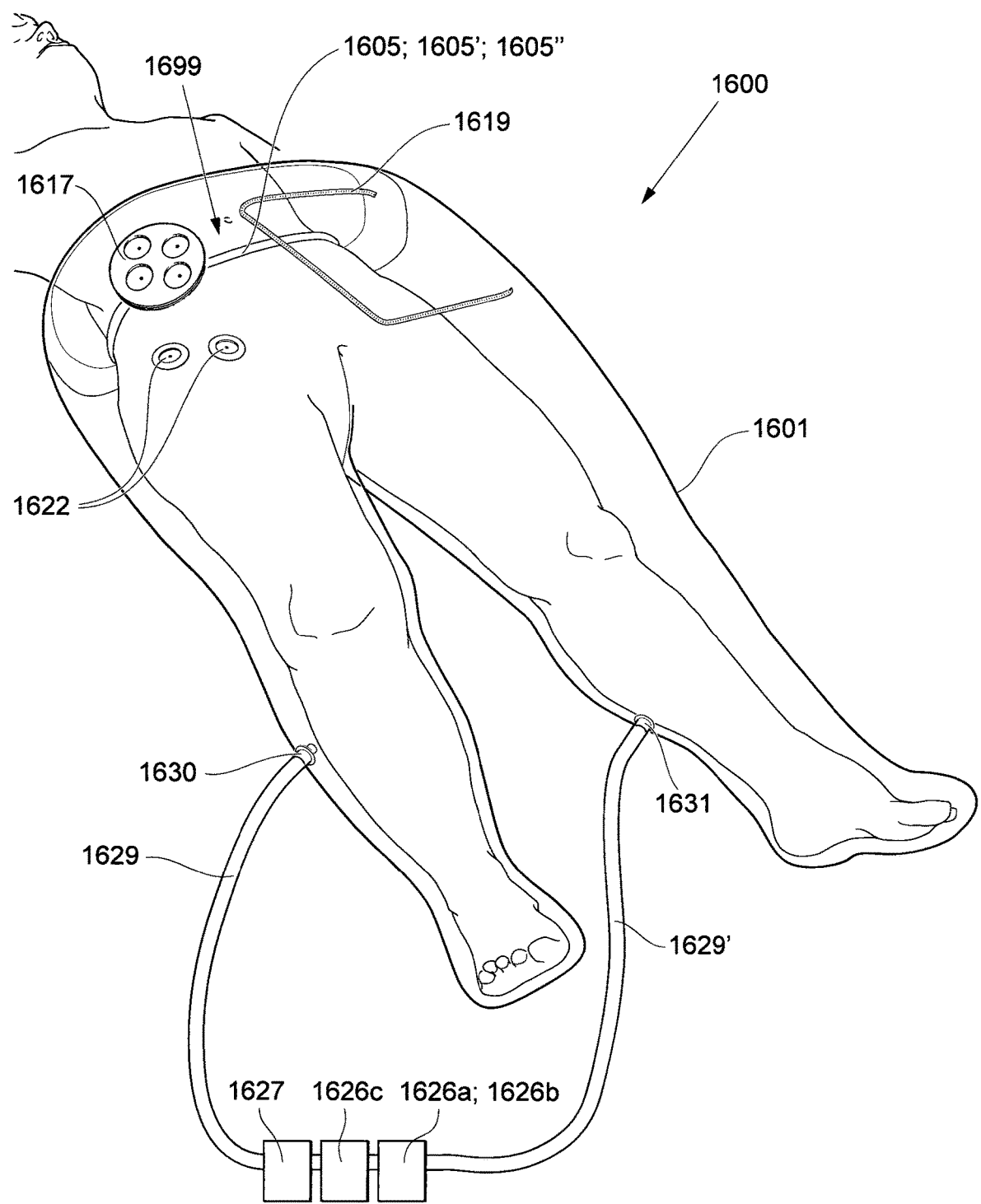

FIG. 161*a* shows an embodiment of the medical device in which the medical device only comprises one open end adapted to encircle the upper body of the patient and thereby provide sealing against the skin of the patient. The sealing could comprise any one of the seals disclosed herein, i.e. adhesive, pressure or vacuum seal. The medical device further comprises a system for circulating a fluid, wall 1648 and body 1622 ports and zipper-closed opening 1619, all further described with reference to FIG. 157*a*. The embodiment of FIG. 161*a* is for example suitable for performing an arthroscopic procedure involving the pelvis.

Figure 161B:
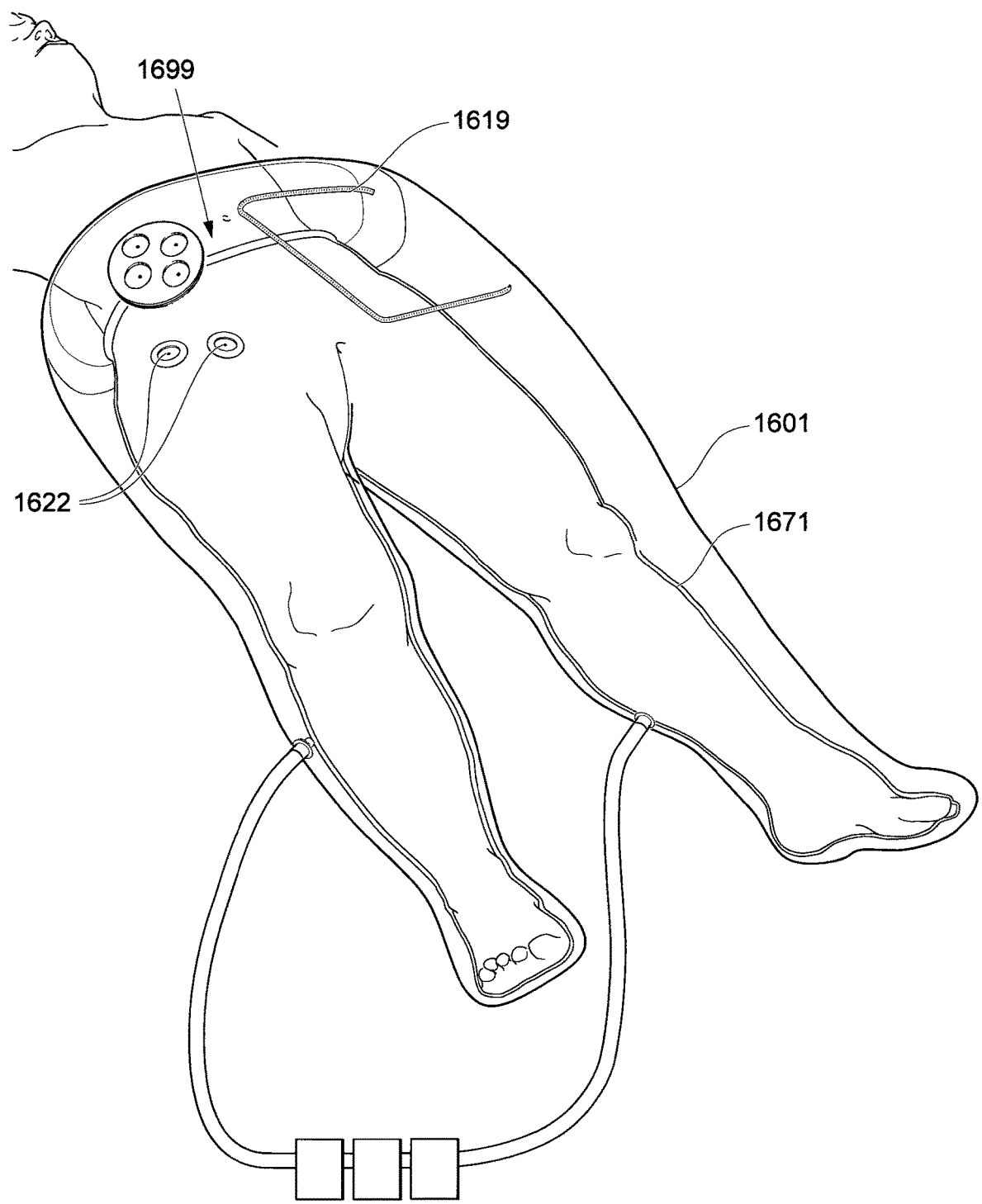

FIG. 161*b* shows an embodiment of the medical device similar to the medical device described in FIG. 161*a* with the difference that the medical device of the embodiment in FIG. 161*b* comprises an inner wall 1671, much like in the embodiment described with reference to FIG. 157*b*. The inner wall 1671 is adapted to separate the skin of the patient from the chamber of the medical device and can be cut through when the incision in the patient for performing the surgical procedure should be performed. The inner wall 1671 has the advantage of separating the feet of the patient from the chamber which is beneficial since the feet of the patient is difficult to properly sterilize.

Figure 162A:
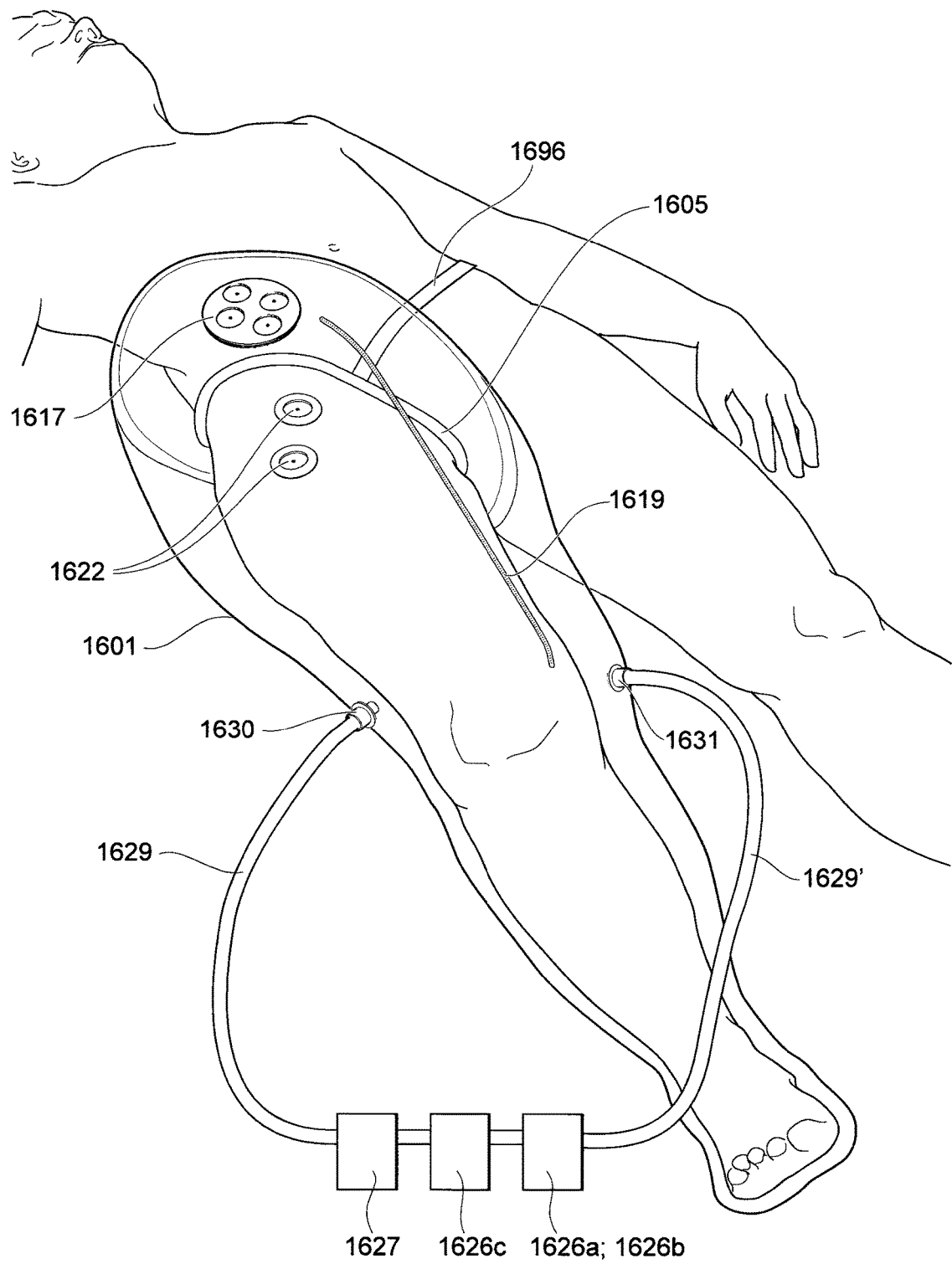

FIG. 162*a* shows a medical device similar to the medical device shown in FIG. 161*a* with the difference that the medical device of FIG. 161*a* is only adapted to be placed on one side of the patient and provide sealing 1605; 1605'; 1605" in the inguinal area. One advantage with the construction of FIG. 162*a* is that the anus and urethra openings are separated from the chamber, and the fluid volume in the device is smaller in comparison to that of the embodiment disclosed in FIG. 161*a*. The features included in FIG. 162*a* are equivalent to the features included in the embodiment disclosed in FIG. 161*a*.

Figure 162B:
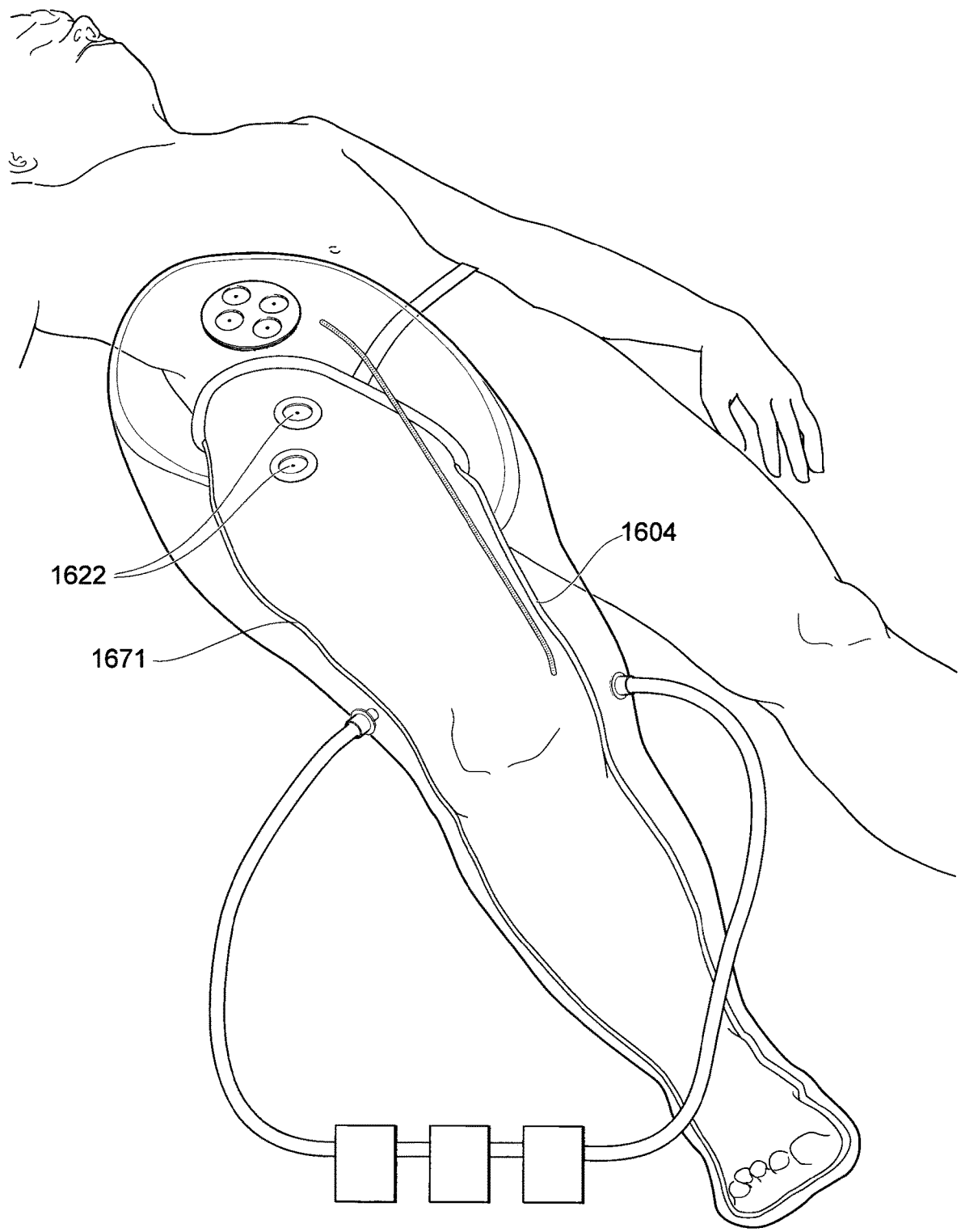

FIG. 162*b* shows the medical device in an embodiment similar to the embodiment shown in FIG. 162*a*, the difference being that in the medical device in the embodiment of FIG. 162*b* comprises an inner wall 1671 in the same way as 161*b* and 157*b*. The inner wall 1671 forms an elongated tubular enclosure through which the leg of the patient is placed. The inner wall 1671 forming the elongated tubular enclosure thus separates the skin of the patient from the chamber of the medical device such that the chamber is formed by the wall 1601 and the inner wall 1671 without involving the skin of the patient. The inner wall 1671 has the advantage of separating the feet of the patient from the chamber which is beneficial since the feet of the patient is difficult to properly sterilize.

Figure 162C:
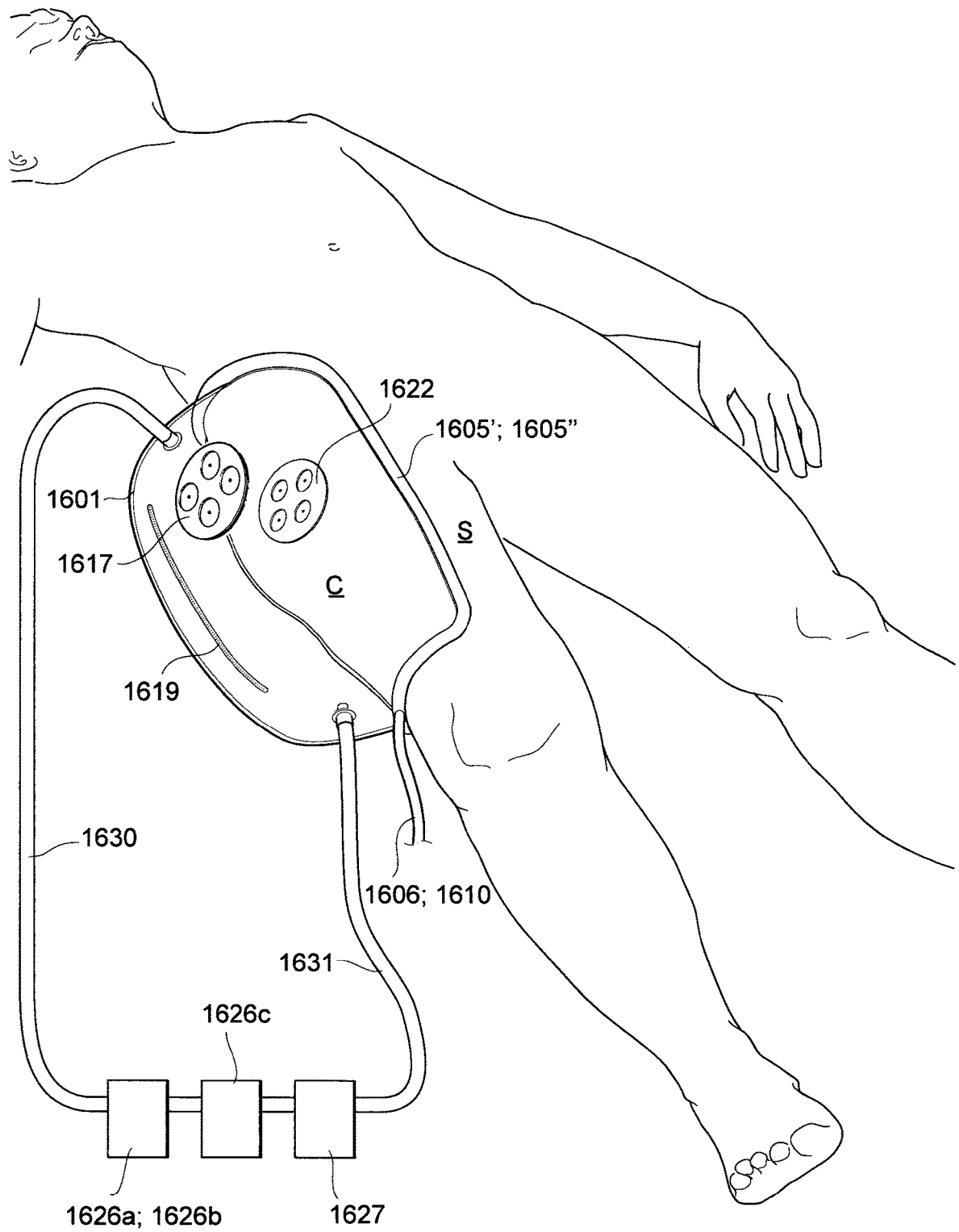
Figure 162C:
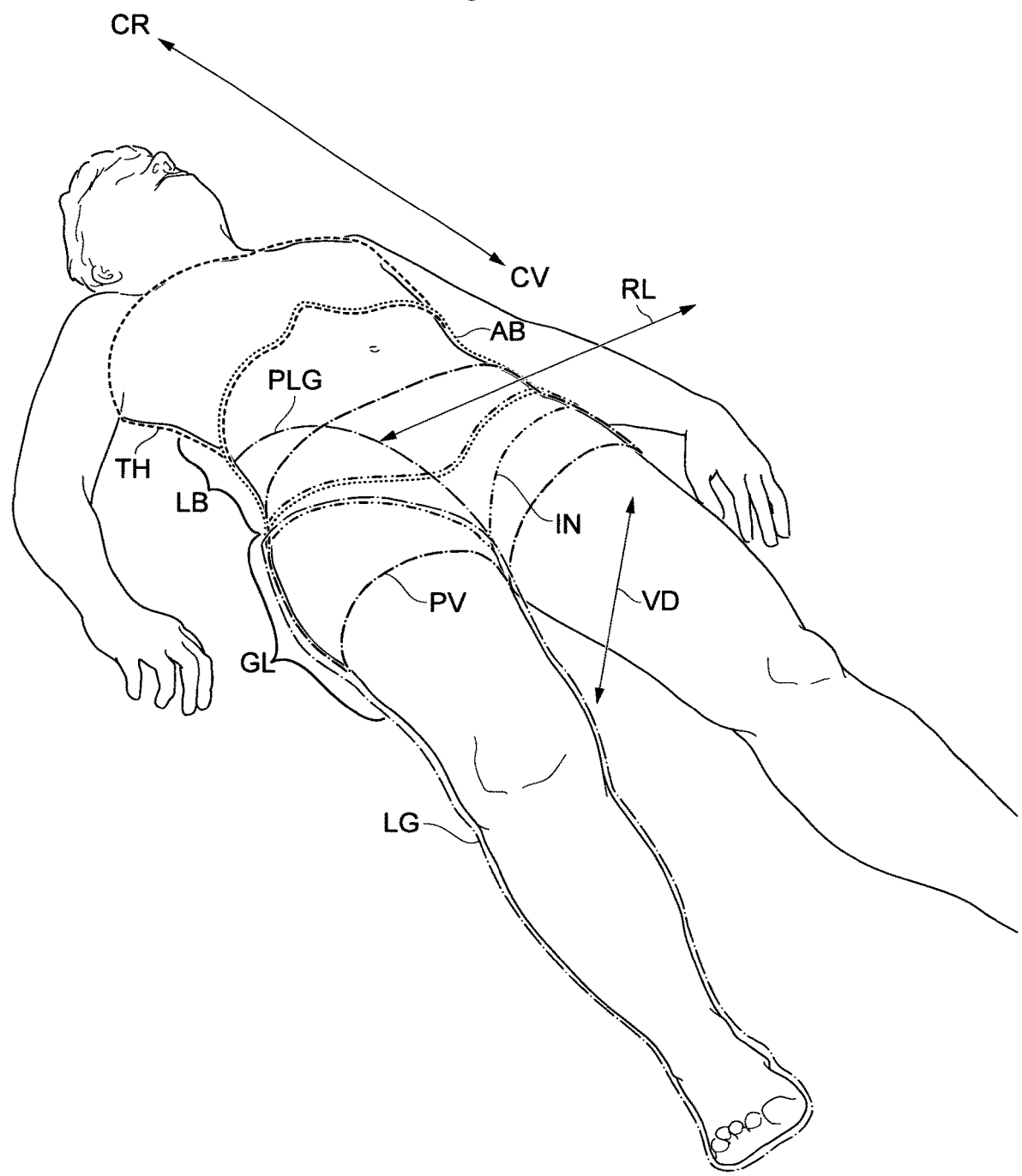
Figure 162D:
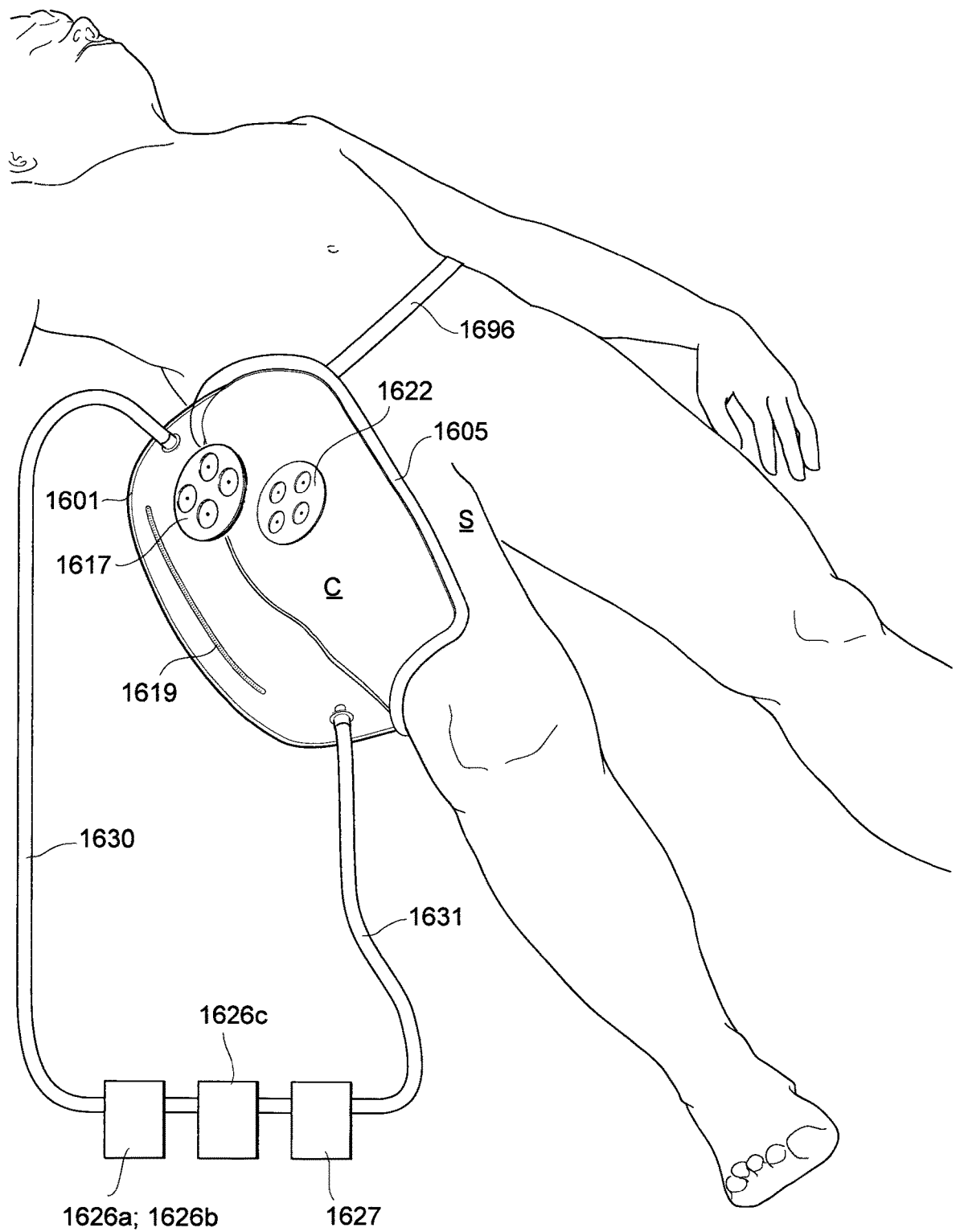

FIGS. 162*c* and 162*d* shows medical devices similar to the medical device shown in FIGS. 158*a*, 158*b*, 162*a* and 162*b*. The medical devices shown in FIGS. 162*c* and 162*d* are adapted for performing hip joint surgery on a patient in a sealed and controlled environment, such that the risk of infections can be substantially reduced. The risk of infections is particularly large when performing prosthesis surgery inside the joints of patients, which is why the maintaining of a controlled environment is of utmost importance. The medical device of FIG. 162*c* comprises a wall 1601 placed on the patient's body forming a chamber (C) together with the patient's body and is some instances together with an adhesive surface applied on against the skin S of the patient for reducing the risk that bacteria from the skin S enters the incision of the surgical procedure. The wall 1601 encloses the chamber C, such that a sealed surgical environment is created in the chamber C, in which an incision of the hip joint surgery in the skin S of the patient and at least one step of the hip joint surgery can be performed, while maintaining the sealed surgical environment. The medical device further comprises a sealing device 1605 connected to the wall 1601 and adapted to seal between the wall 1601 and the skin S of the patient. The sealing device 1605 forms a special loop encircling a portion of the leg (LG FIG. 162c'), the pelvic region (PV FIG. 162c'), the abdominal region (AB FIG. 162c'), the inguinal region (IN FIG. 162c'), the gluteal region (GL FIG. 162c'), the thoraxial region (TH FIG. 162c'), and the region of the lower back (LB FIG. 162c'), all further defined under reference to FIG. 162c', such that the sealing device 1605 seals between the incision site of the hip joint surgery and the anal orifice and/or the urethra orifice and/or the perineum region. The sealing device 1605 of the embodiment disclosed under reference to FIG. 162c seals laterally on the leg in a ventrodorsal direction to the fromtal part of the leg above the knee, the sealing thereafter turns in a cranial direction towards the cranial or proximal part of the leg, crossing the inguinal region or its prolongation, further in a cranial direction lateral of the patient's ventrodorsal midsagittal plane, on the side where the hip surgery is performed. The sealing continues cranially across the abdominal region of the patient and then turns in a laterodorsal direction crossing the lower lateral part of the thoraxial region and continuing in a medial-dorsal direction to the lower back region. Before reaching the midsagittal plane, the sealing device turns in a caudal direction across the gluteal region and continues until intersecting with the sealing device and thus forming the special loop encircling the area of the incision performed in the hip joint surgery. The placing of the sealing device 2405 forming the special loop, as shown in FIG. 162c excludes the anus, urethra and perineum regions from the sealed chamber C of the medical device which is of utmost importance as these regions are very difficult to properly disinfect.

The medical device shown in FIG. 162c further comprises a wall port 1617 (in the form of a multiport) adapted for insertion of instruments into the sealed environment of the medical device. The instruments may be equipped with couplings, such as the couplings disclosed under reference to FIGS. 220l-220q, such that the instruments can be kept sealed when not in use in the sealed environment of the medical device. The medical device further comprises a body port 1622 (in the form of a multiport) placed in an incision performed in the skin of the patient, the body port enabling manipulation in a cavity in the patient using surgical instruments. The wall port 1617 and/or body port 1622 may comprise couplings 1680 such that the wall port 1617 and body port 1622 can be connected for forming an interconnected port, for example using any of the ports adapted to be connected disclosed in other embodiments herein. The wall port 1617 may thus be fixated to a flexible and/or elastic part of the wall 1601 such that the wall port 1617 can be moved in relation to the body port 1622. The wall port 1617 or body port 1622 may be attached to the wall 1601 of the medical device 1600 by means of a coupling 1680 fixated to the wall 1601, such that the wall port 1617 and/or body port 1622 is detachably fixated to the wall 1601 and thus replaceable by an additional port or an inset (such as any of the insets disclosed herein). Different embodiments of couplings are disclosed herein and may be used in the medical device according to the embodiment disclosed in FIG. 162c.

The wall of the medical device further comprises a zipper 1619 for opening the wall 1601 of the medical device. The zipper 1619 may for example be a Ziploc-type zipper adapted to contain a fluid in the chamber C having a pressure exceeding atmospheric pressure. The wall 1601 of the medical device may be a flexible or elastic wall such that the leg of the patient can be moved during the surgical procedure, which me be required, for example in prosthesis surgery, to align and test the functionality of the implanted prosthesis.

The medical device of FIG. 162c further comprises a fluid circulating system comprising a fluid inlet 1630 and a fluid outlet 1631 connected to a sterilizing/filtering unit 1626a, 1626b and a tempering unit 1626c (further described in other embodiments of the disclosure). The fluid is circulated by means of a circulating pump 1627. The fluid contained in the chamber C of the medical device could be a gaseous fluid, such as $CO_2$ gas, or a liquid fluid, such as an isotonic or antibiotic fluid, which is used in an arthroscopic procedure in the hip joint of the patient.

The sealing member 1605 shown in the embodiment o FIG. 1662c comprises an adhesive sealing member adapted to attach and/or seal the medical device to the skin S of the patient by adhering to the skin S of the patient. However, the adhesive sealing member may be assisted or replaced by a pressure o vacuum sealing member, such as the pressure and/or vacuum sealing members disclosed in other embodiments herein.

In alternative embodiments, the wall of the medical device may further comprise an inset positioned in the wall 1601 which for example may comprises a device and/or instrument mount of a glove for enabling manual manipulation within the chamber C.

When performing a hip joint surgical procedure using the medical device disclosed in FIGS. 1662c and 1662d, the incision in the incision site of the hip joint surgery is made inside of the chamber C of the medical device, after the medical device have been placed and sealed against the skin S of the patient.

According to one embodiment, at least one of the body port, the wall port, the second wall port and the second body port, comprising a multi-port, comprising at least two ports integrated in the multi port, and adapted to enable passage of an object to the inside of the patient's body via the cut incision in the skin, when performing the surgical procedure.

The medical device of FIG. 162c may further comprise an air or liquid lock sluice fixated to the wall of the medical device and adapted to enable insertion of objects into the chamber of the medical device while maintaining the sealed environment. The air or liquid lock sluice may be an air or liquid lock sluice according to any of the embodiments described herein.

FIG. 162c' is an anatomical figure showing the thoraxial region TH, reaching from under the ribs and in cranial direction CR to the clavicles. Below the thoraxial region, the abdominal region AB reaches from below the ribs in caudal direction CV to the pubic symphysis and following the edges of pelvis, below which the inguinal region IN reaches from the lower abdomen to the upper parts of the thighs. The pelvic region PV is defined to mean the entire region encircling the body of the patient along the pelvic bone in a cranial-caudal (CR-CV) direction. The leg LG of the patient is defined as the entire leg up to the iliac crest, above which a region defined as the prolongation of the leg PLG starts and reaches further in a cranial direction. On the rear side of the patient's body the region of the lower back LB is defined as the region above the gluteal region GL, the gluteal region reaching from the lower portion of the gluteal muscles to the upper portions of the gluteal muscles in line with the lower lumbar vertebras, the region of the lower back LB then continues to mid level thoracic vertebras. The direction indicator VD indicates ventrodorsal direction and RL indicates right-left direction.

FIG. 162d shows an embodiment of the medical device identical to the embodiment shown in FIG. 162c, with the difference that the medical device comprises a holding member 1696 fixating the medical device and enabling the use of a sealing device 1605 comprising a pressure sealing member adapted to seal against the skin S of the patient by pressing on the skin S of the patient. The holding member 1696 is adapted to be placed encircling the abdominal region and the lower back of the patient (see FIG. 162c'). In alternative embodiments the holding member 1696 may be adapted to be placed encircling a single leg of the patient, or both legs of the patient, lower on the patient's body, such that the holding member encircles the gluteal region and the inguinal and pelvic regions.

Figure 163A:
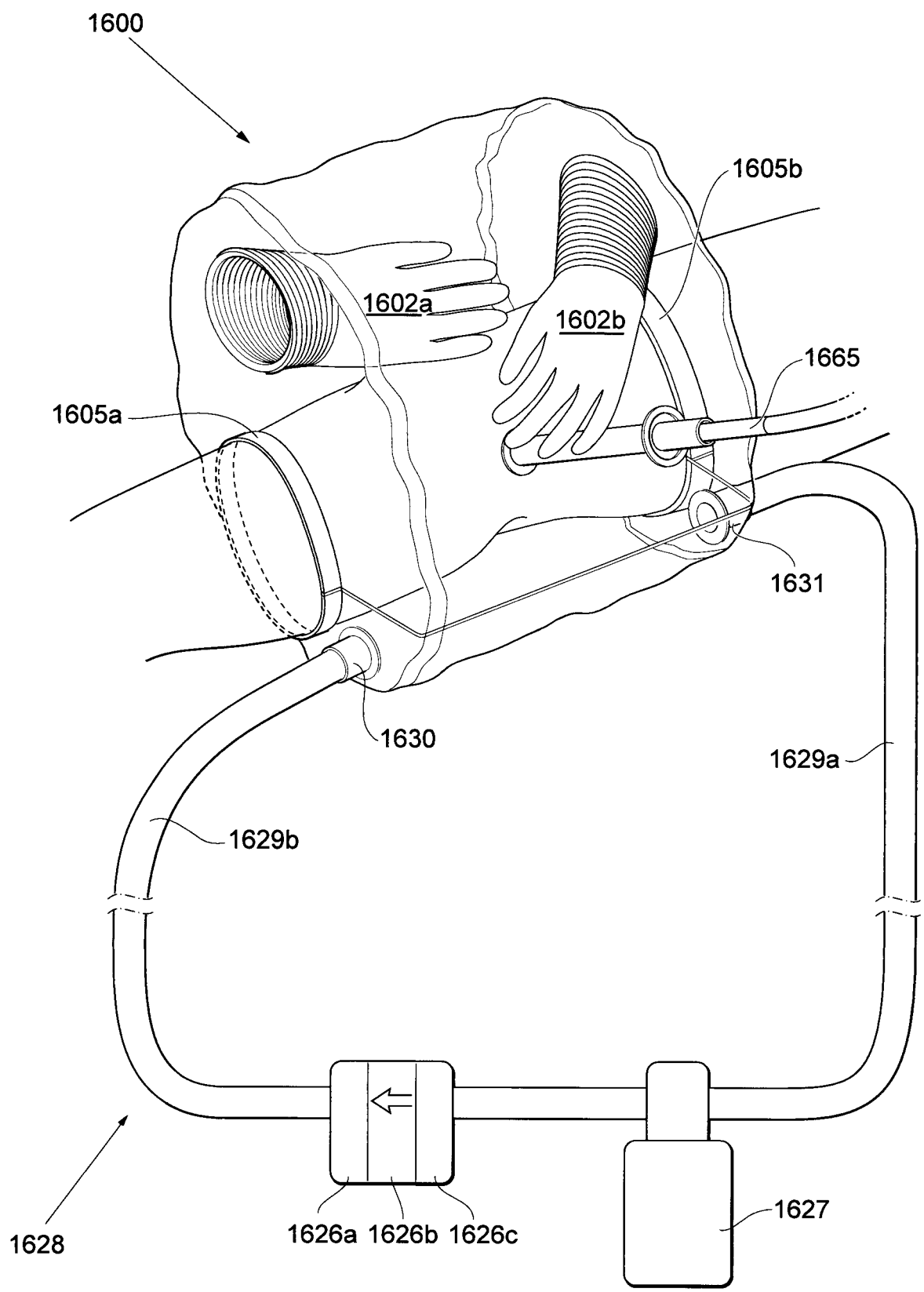

FIG. 163a shows an embodiment of the medical device where the layer 1601 is collapsible such that it can be collapsed for package and/or transportation and inflated when put to use in a surgical procedure. In the embodiment of FIG. 163a, the layer 1601 is made from a flexible material, such as a flexible polymer material or a woven material. The material could be transparent or translucent for enabling viewing into the sealed environment of the medical device. The medical device is shown with a system 1628 for circulating a liquid or gaseous fluid. The fluid is circled form an outlet 1631 in the wall 1601 through a first conduit 1629a via a pump 1626 and via a system for sterilization 1627c, filtering 1627b and heating 1627a, through a second conduit 1629b to an inlet 1630.

Figure 163B:
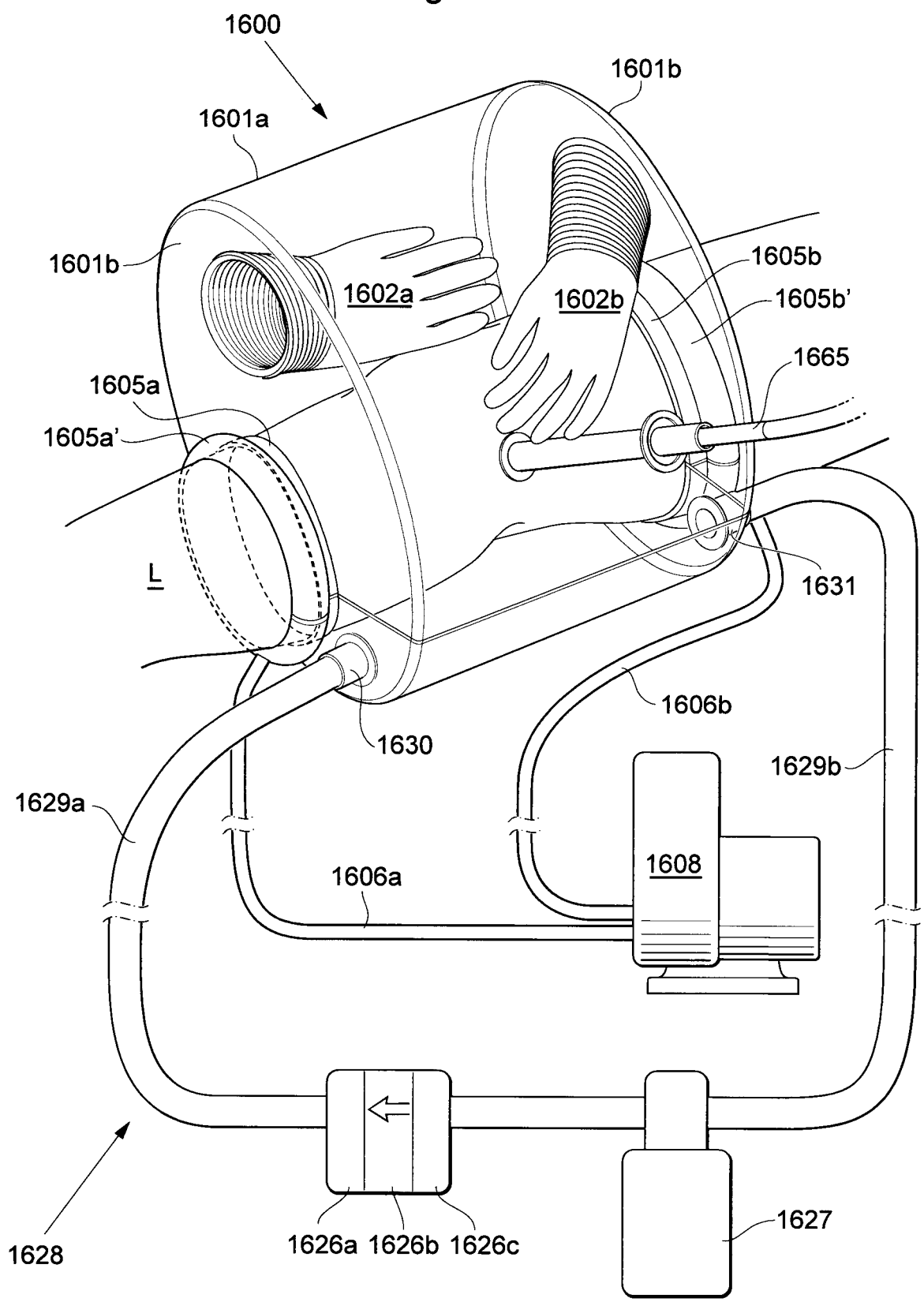

FIG. 163b shows the medical device according to an embodiment comprising the features of the embodiment disclosed with reference to FIG. 163a and further comprising vacuum seals 1605a', 1605b' encircling the leg L of the patient for sealing between the medical device and the skin of the patient. The vacuum seals 1605a', 1605b' are connected to a vacuum pump 1608 through vacuum conduits 1606a, 1606b transferring the vacuum from the vacuum pump 1608 to the vacuum seals 1605a', 1605b'. The vacuum seals described with reference to FIG. 163b could be used in combination with the seals 1605a, 1605b which for example could comprise two elastic ring shaped members 1605a, 1605b, sealing by pressing against the skin of the patient, or without the seals 1605a, 1605b, in which case the vacuum seals could be materially integrated in the second portions 1601b of the layer 1601.

FIG. 164a shows the medical device according to an embodiment in which the medical device is adapted for performing hip joint procedures. The medical device comprises a layer 1601 enclosing a sealed environment adapted to be at least partially filled with a liquid when performing a surgical procedure therein. According to the embodiment shown in FIG. 164a the layer is made of a rigid transparent layer for example made from glass or a transparent polymer material such as an acrylic glass, a polycarbonate, polyethylene terephthalate, an acrylic fiber material or a copolymer containing polyacrylonitrile. However, in other embodiments the layer 1601 could be partially translucent or opaque and have a transparent window for enabling viewing into the sealed environment. The medical device according to the embodiment described with reference to FIG. 164a is comprises a mount 1620 adapted to hold a pre-placed implant within the sealed environment before the medical device is connected to the patient. The medical device is further adapted to hold equipment to be used in performing the surgical procedure and a powered tool, which in this embodiment is represented by a drill. The medical device is adapted to be fixated to the skin of the patient by means of a seal 1605 contacting the skin of the patient and the medical device. The adhesive could for example be a pressure sensitive adhesive such as 3M's pressure sensitive adhesive Scotch-Grip 4268-NF. The medical device further comprises two gloves 1602a, 1602b integrated in the layer 1601 of the medical device, enabling manual manipulation within the sealed environment, such as placement of the implant in the hip joint of the patient, without penetrating the layer 1601, thus keeping the sealed environment hermetically enclosed and reducing the risk that bacteria and/or virus potentially causing infectious diseases can enter the sealed environment. A camera 1665 for visual inspection is further provided.

Figure 164C:
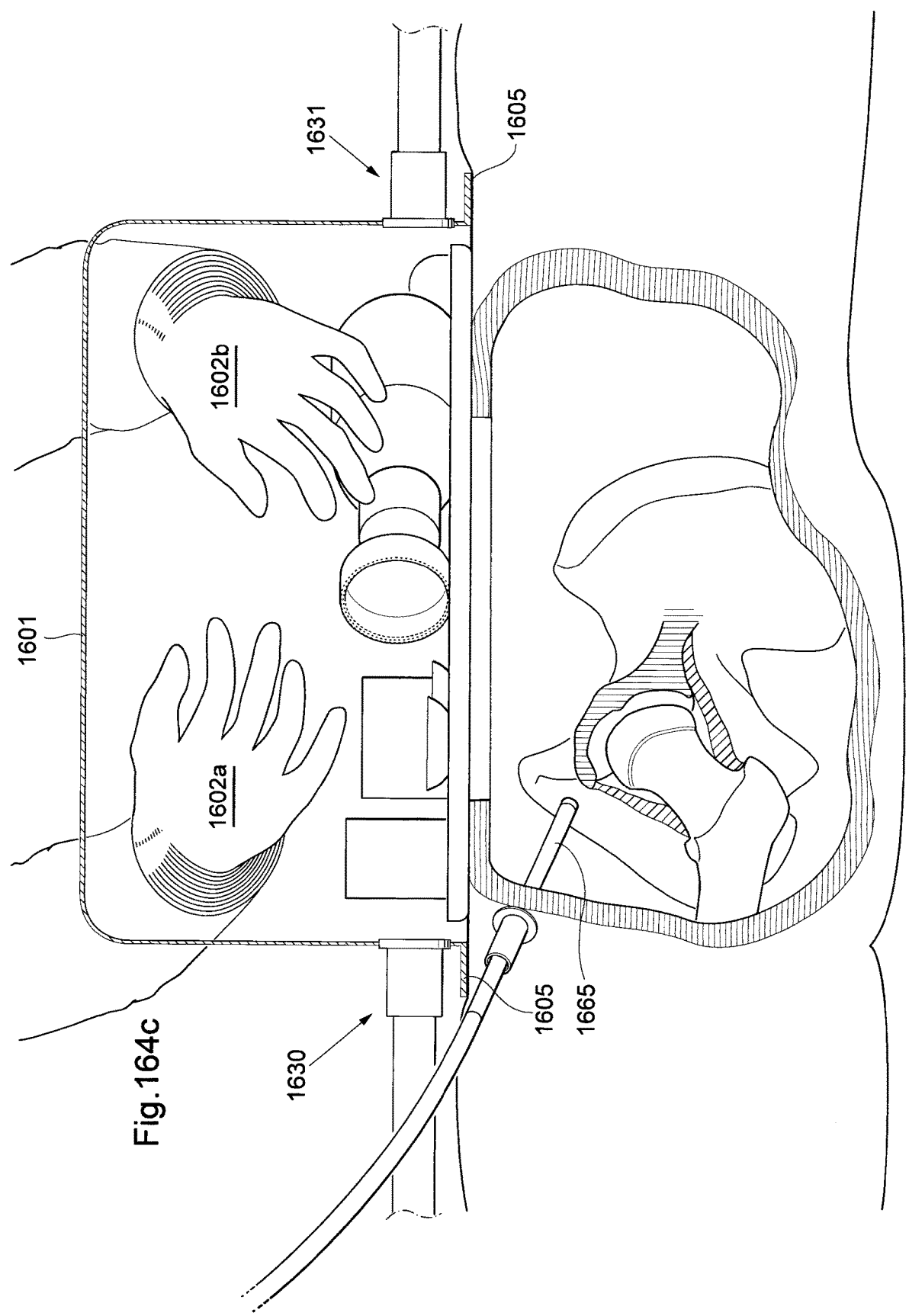

FIGS. 164b and 164c shows an embodiment of the medical device comprising the features of the embodiment described with reference to FIG. 164a and additionally comprising an inlet 1630 through which the liquid or gaseous fluid in the sealed environment enters, and en outlet 1631 through which the liquid in the sealed environment exits. The inlet 1630 and outlet 1631 could be connected to a liquid circulating system, for example as disclosed with reference to FIG. 165 which could comprise a pumping unit, a tempering unit, a sterilization unit and a filtering unit. In other embodiments the liquid is not circulated but instead only used once in which case new liquid enters the sealed environment at the inlet 1630 and exits the device at the outlet 1631 after which the liquid is disposed of. The embodiment described with reference to FIG. 164b further comprises an energy transporting member 1613a adapted to supply an energy consuming tool inside of the sealed environment with energy. The energy transporting member 1613a transfers energy from the outside of the layer 1601 to the inside of the layer 1601 by means of an energy coupling which could be a penetrating energy coupling transferring energy through a hole in the layer 1601, or an energy coupling transferring energy through the layer 1601 without penetrating the layer 1601. The non-penetrating energy coupling could for example be a magnetic mechanical coupling transferring mechanical energy, or an electrical inductive coupling transferring electrical energy.

The energy transferred could for example be mechanical, electrical, hydraulic or pneumatic energy and the energy consuming tool could correspondingly be a mechanical, electrical, hydraulic or pneumatic tool. The tool is in the embodiment shown illustrated by a drill, however it is equally conceivable that the tool is a saw, a reamer, a tool for fastening of orthopedic screws, or any other orthopedic or generally surgical tool requiring energy to function.

Figure 165:
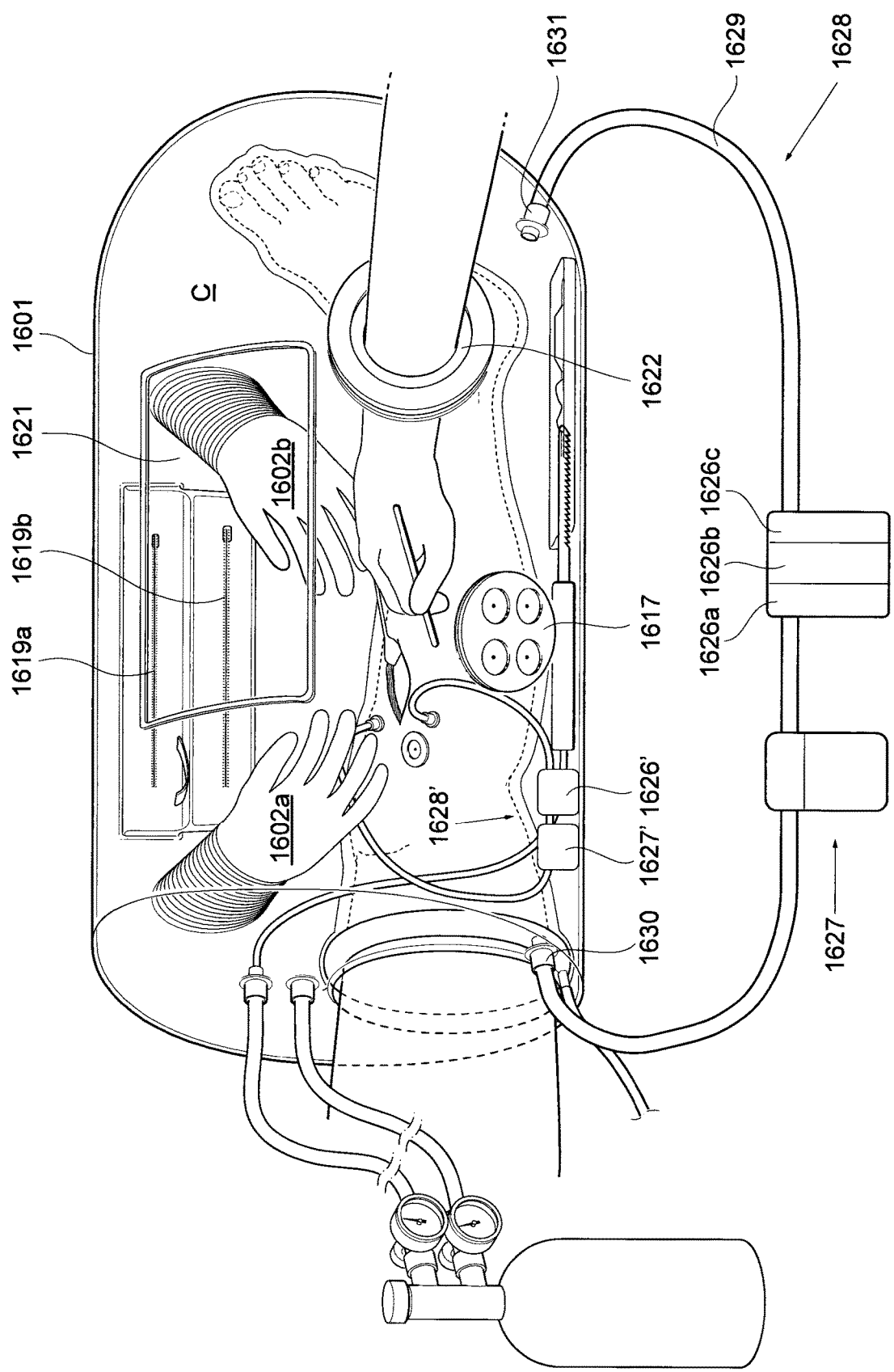
FIGS. 165-168 shows different embodiments of the medical device in perspective, when applied to the body of the patient.

FIG. 165 shows the embodiment of the medical device when the arm of the surgeon is inserted through the self sealing wall port 1622 in the partially collapsible wall 1601 for enabling manual manipulation therein. Manual manipulation through the self sealing wall port 1622 could for example be used as a last resort should complications occur during the procedure, or if additional hands are required for a specific step of the operation. FIG. 165 further shows an internal system 1628' for fluid circulation, and an external system 1628 for fluid circulation. Both systems comprises fluid conduits 1629; 1629', in the external system 1628 connected at an inlet 1630 placed in the partially collapsible wall 1601 for supplying fluid to the chamber, and an outlet 1631 for draining the fluid from the chamber, and in the internal system 1628' connected to an inlet 1630' in the patient's body and an outlet 1631' in the patient's body for circulating fluid in a body cavity. The fluid is circulated by means pumping units 1627; 1627' and is circulated via a sterilizing/filtering/tempering unit 1626', in the external system disclosed as containing a sterilizing 1626a, filtering 1626b, and tempering 1626c unit adapted to remove impurities, sterilize and heat the fluid. In embodiments where the fluid is a gaseous fluid, the filtering unit is adapted to remove particles that could be suspended in the gas. The filtering unit 1626a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 1626a could for example comprise a filter containing activated carbon.

Figure 166A:
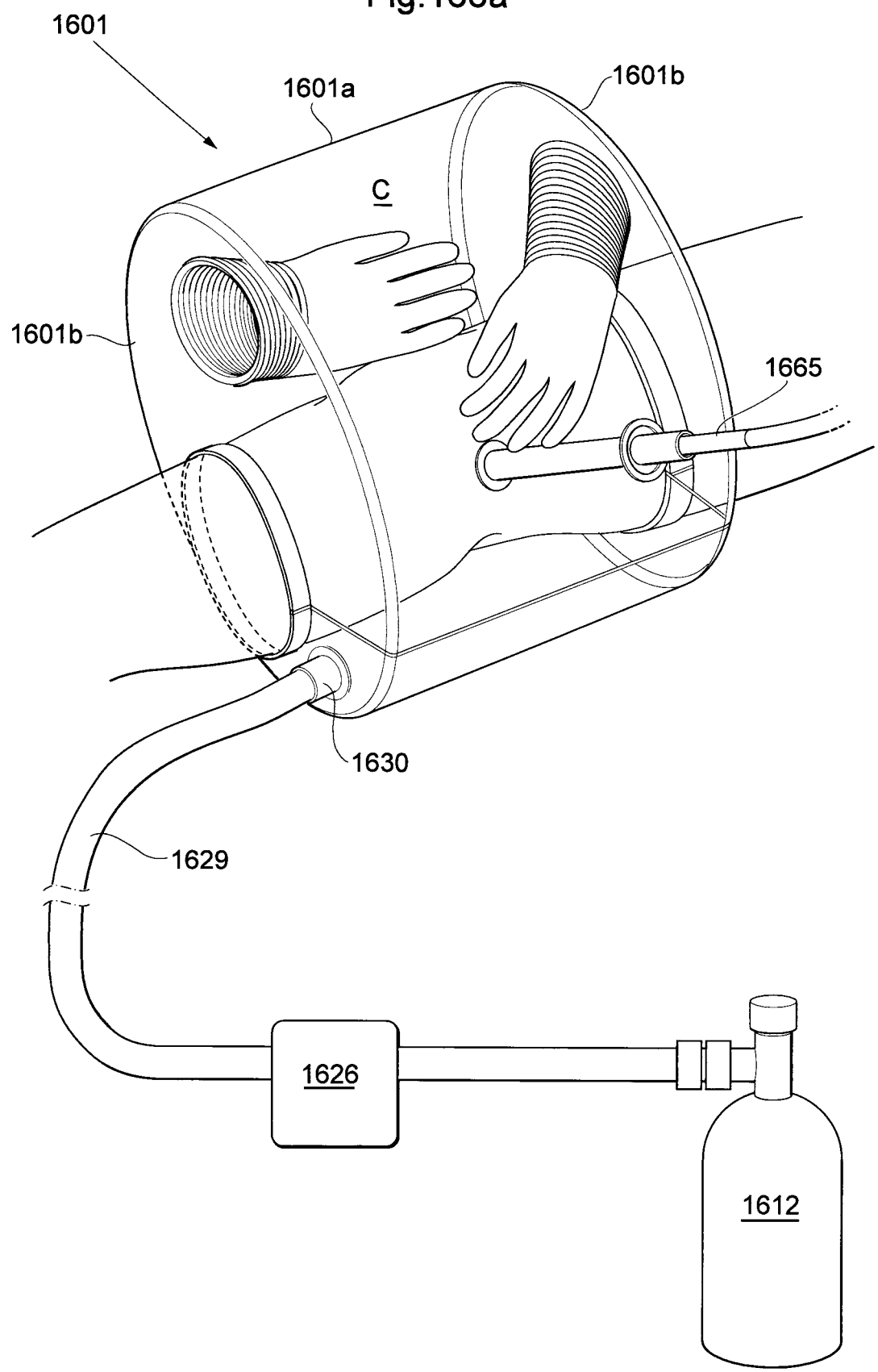

FIG. 166a shows an embodiment of the medical device similar to the embodiments described with reference to FIGS. 163a and 163b, in the embodiment disclosed with reference to FIG. 166a the medical device is adapted to be filled with a gaseous fluid such as air or CO2 gas. The system could be adapted for using the gas one time only, in which case new gas could come from a pressurized gas container and enter sealed environment through the inlet 1630. In other embodiments the medical device further comprises a gas circulating system adapted to circle and thus reuse the gas, in which case the system could comprise a gas pumping unit, a gas tempering unit, a gas sterilization unit and a gas filtering unit outlined similar to the embodiments disclosed with reference to FIG. 166b. The system for filling the chamber with gaseous fluid could comprise a control valve 1627 and a unit 1626 for sterilizing and heating the gas before it enters the chamber.

Figure 166B:
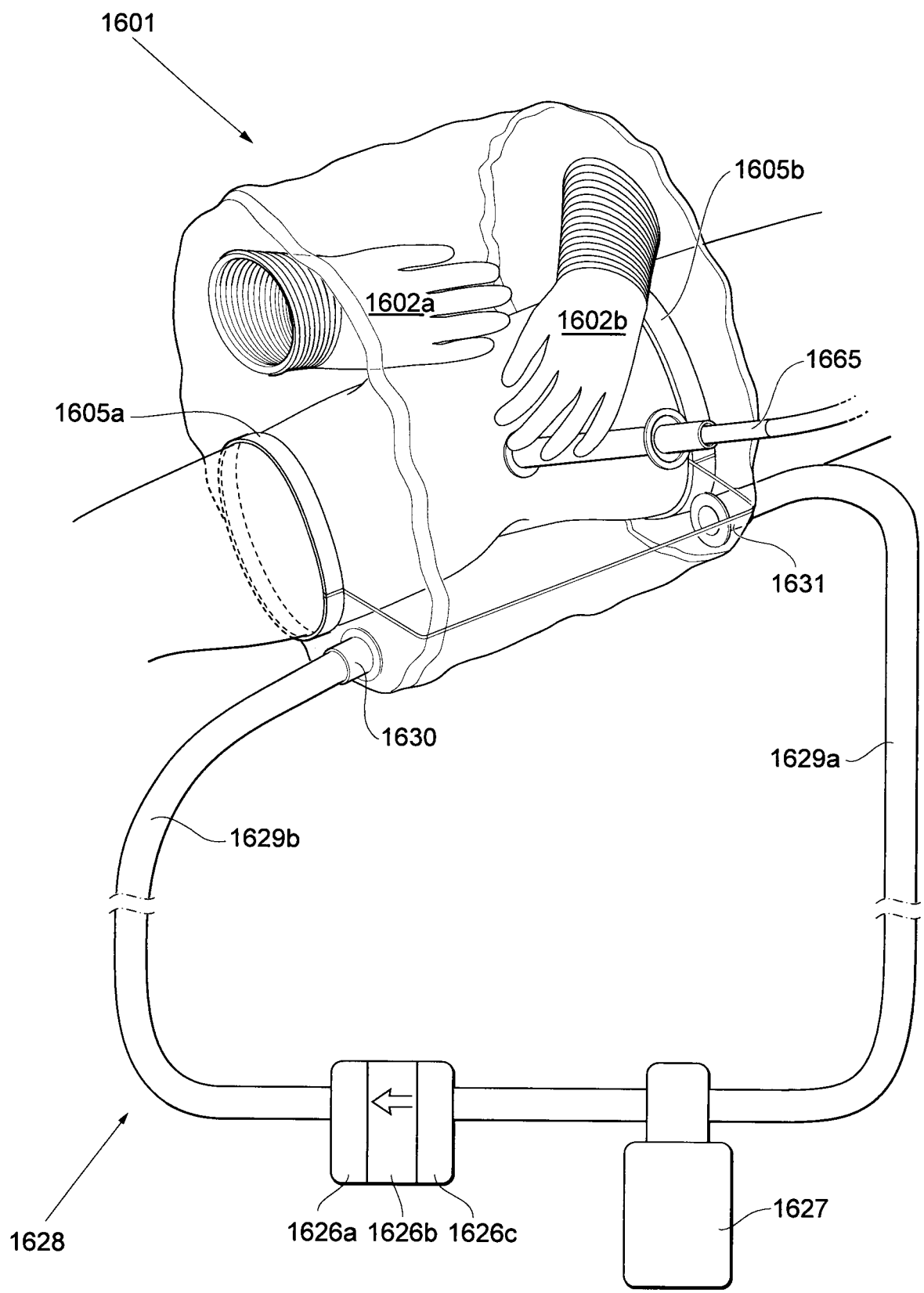

FIG. 166b shows an embodiment of the medical device where the layer 1601 is collapsible such that it can be collapsed for package and/or transportation and inflated when put to use in a surgical procedure. In the embodiment of FIG. 166b, the layer 1601 is made from a flexible material, such as a flexible polymer material or a woven material. The material could be transparent or translucent for enabling viewing into the sealed environment of the medical device. The medical device is shown with a system 1628 for circulating a liquid or gaseous fluid. The fluid is circled form an outlet 1631 in the wall 1601 through a first conduit 1629a via a pump 1626 and via a system for sterilization 1627c, filtering 1627b and heating 1627a, through a second conduit 1629b to an inlet 1630.

Figure 167:
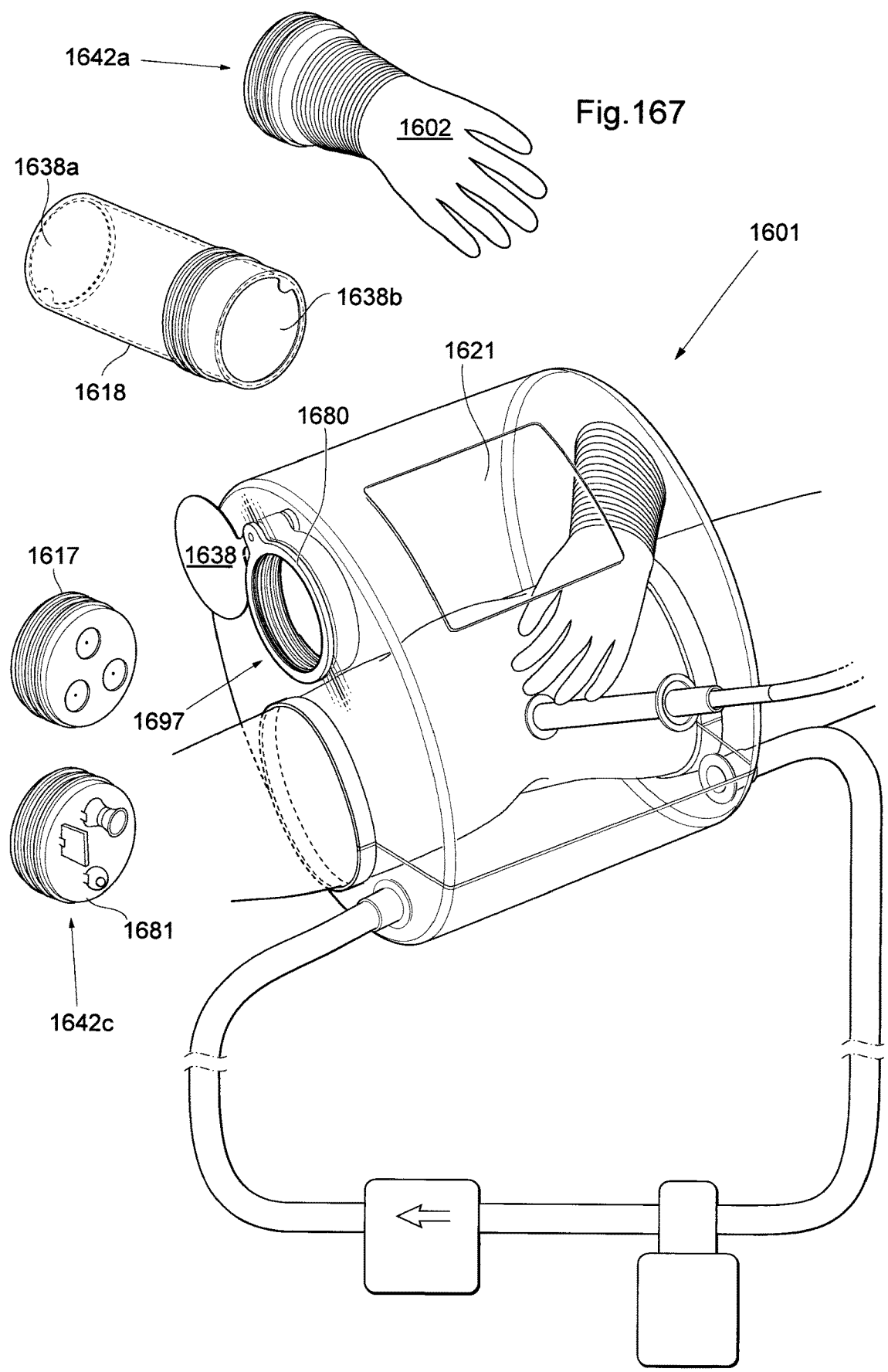

FIG. 167 shows the medical device according to an embodiment in which the medical device comprises a non-collapsible transparent window 1621 for enabling viewing into the sealed environment. The window is preferably used in embodiments where the layer is a collapsible layer, as further disclosed with reference to FIG. 166b. The non-collapsible transparent window 1621 will ensure that the surgeon has adequate visual control over the procedure since the partially collapsible layer, even if preferably made from a transparent material could provide limited visibility, e.g. if the medical device is not fully inflated, or in seams or bends of the material. The non-collapsible transparent window 1621 could for example be made from acrylic glass, a polycarbonate, polyethylene terephthalate, an acrylic fiber material or a copolymer containing polyacrylonitrilea, or made from tempered glass. In other embodiments (not shown) the medical device could further comprise a cleaning device for cleaning the transparent window 1621 from the inside of the sealed environment. The cleaning device could comprise an arrangement for supplying a fluid adapted to assist in the cleaning of the transparent window via a fluid conduit to a nozzle placed in proximity to the transparent window. The fluid could for example be an isotonic solution, such as saline solution, or an antiseptic solution such as Chlorhexidine. The medical device could further comprises a window contacting member for wiping the window clean after the fluid has been sprayed thereon for mechanically removing objects from the window. The embodiment shown in FIG. 167 further comprises a coupling 1631 positioned in the layer 1601. In the embodiment shown in FIG. 167 the coupling 1631 comprise screw-threads corresponding with screw-threads of the objects which could be coupled to the coupling 1631. The coupling 1631 as shown in FIG. 167 further comprises a valve member 1638 which could be closed when no objects are placed in the coupling 1631 or during the process of changing objects, when otherwise the coupling 1631 would be left open. Examples of objects which could be placed in the coupling 1631 are shown in FIG. 167, however, other suitable objects are also conceivable and the scope of the invention is not to be limited to the particular objects shown, rather, the concept of having changeable objects is to be regarded as part of the invention. The examples of objects shown in FIG. 167 are now further described: An airlock 1670 is shown comprising an outer opening 1638 between the surrounding environment and the airlock 1670 and an inner opening 1682 between the airlock 1670 and the sealed environment of the medical device. The airlock 1670 could enable transfer between the surrounding environment and the airlock, and between the airlock and the sealed environment of the medical device, for enabling the transfer of for example prosthesis or prosthetic parts or surgical instruments. The airlock could further enable transfer of objects from the sealed environment, into the airlock and further to the surrounding environment, which for example could enable the transfer of specimens from the body of the patient. Both the transferring of objects into the sealed environment and out from the sealed environment could by means of the airlock be conducted whilst keeping the sealed environment hermetically closed. FIG. 167 further shows a holding member 1681 for prosthetic parts or surgical instruments. By means of placing the holding member 1681, or exchanging the holding member to a different holding member, prosthetic parts or surgical instruments could be introduced into the sealed environment, which for example could be used if different steps or unexpected events in the procedure require different instruments. A port unit 1648 is further shown, the port unit as shown in FIG. 167 comprises three ports adapted for laparoscopic and/or arthroscopic instruments. In some embodiments the port unit could comprise a single larger port unit which could enable hand access into the sealed environment, the single larger port unit could for example be a gel-port type port unit.

Figure 168:
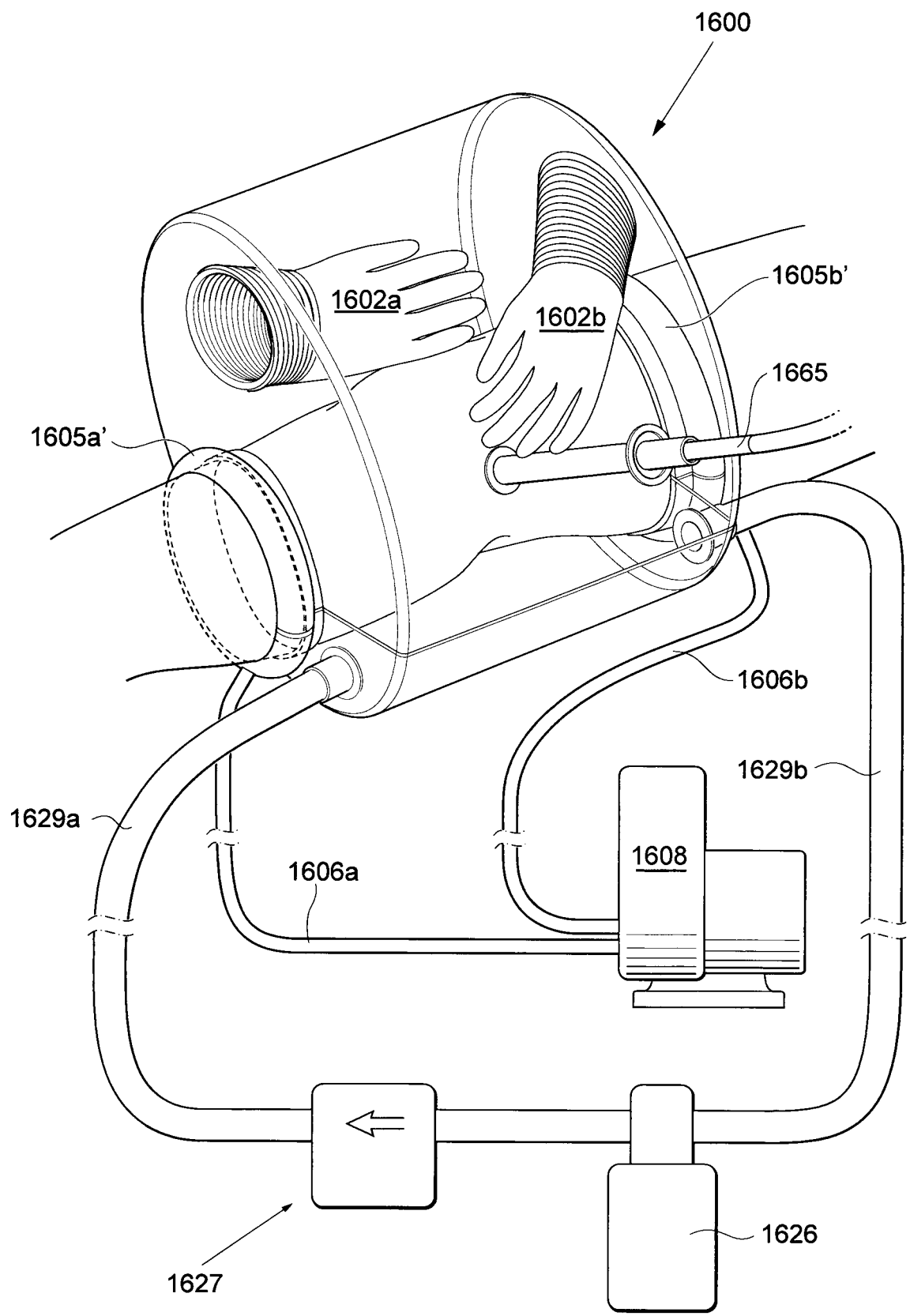

FIG. 168 shows an embodiment further comprises vacuum sealing members 1605a', 1605b' adapted to seal between the skin of the patient and the medical device by the vacuum sealing members 1605a', 1605b' being adapted to hold a pressure less than 1 bar, thus creating a vacuum seal between the skin of the patient and the medical device. The vacuum sealing members 1605a', 1605b' are connected to a vacuum pump 1608 through vacuum conduits 1606a, 1606b transferring the vacuum from the vacuum pump 1608 to the vacuum seals 1605a', 1605b'. The vacuum seals described with reference to FIG. 168 could be used in combination with other types of seals.

Figure 169A:
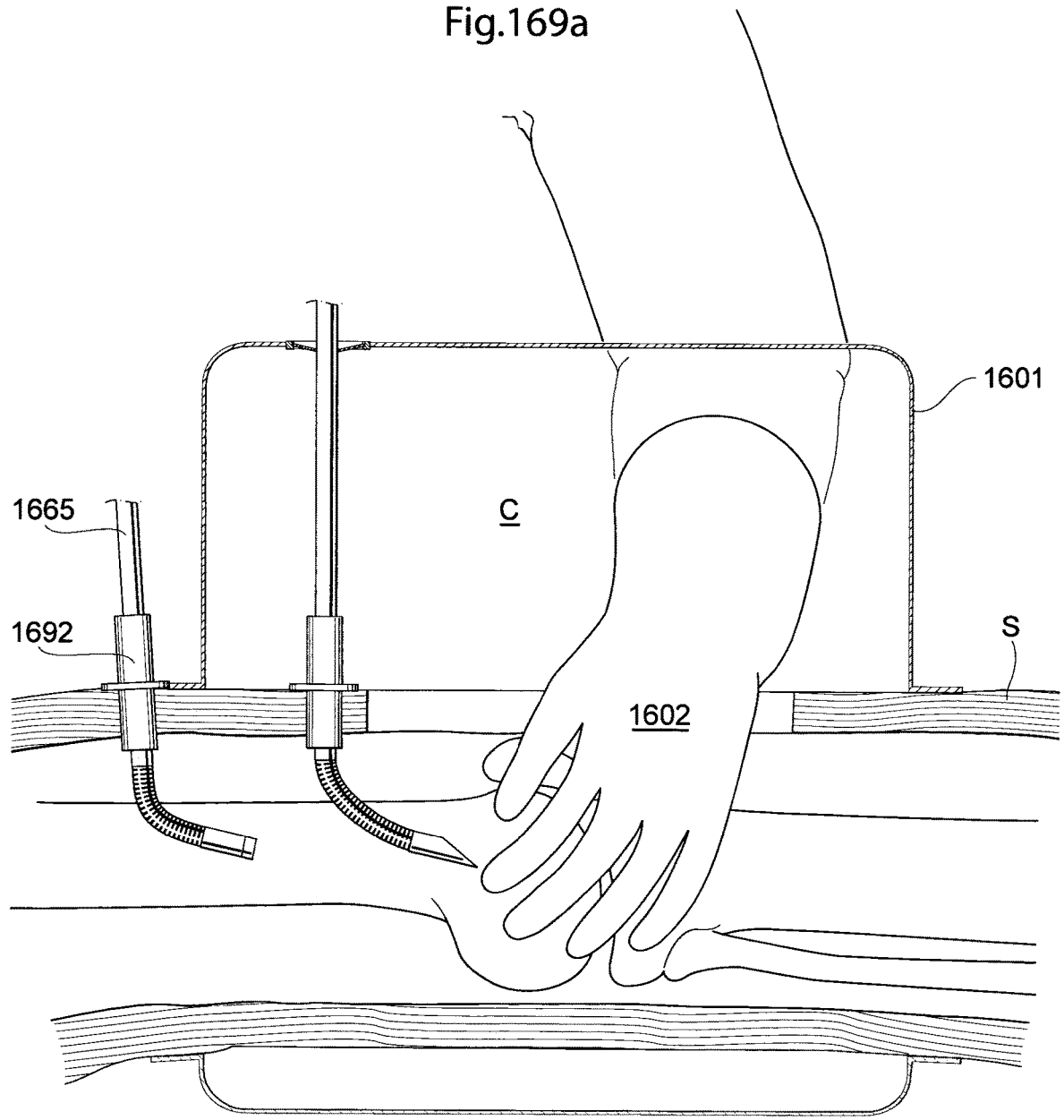
FIGS. 169a-169d shows an embodiment of the medical device in section, being fixated to the patient and used.

FIGS. 169a-169d shows how the medical device shown in FIGS. 124-169 may be used. The medical device 1600 comprises a glove 1602 integrated in the wall 1601 and a camera 1665 placed in the skin outside of the medical device 1600. The medical device 1600 further comprises a trocar 1692 placed trough an opening in the wall 1601 and into the sealed environment and further through an opening in the skin of the patient and into an area of the knee of the patient. FIG. 169*a* schematically illustrates how the surgeon manipulates the knee in the sealed environment using the glove 1602.

Figure 169B:
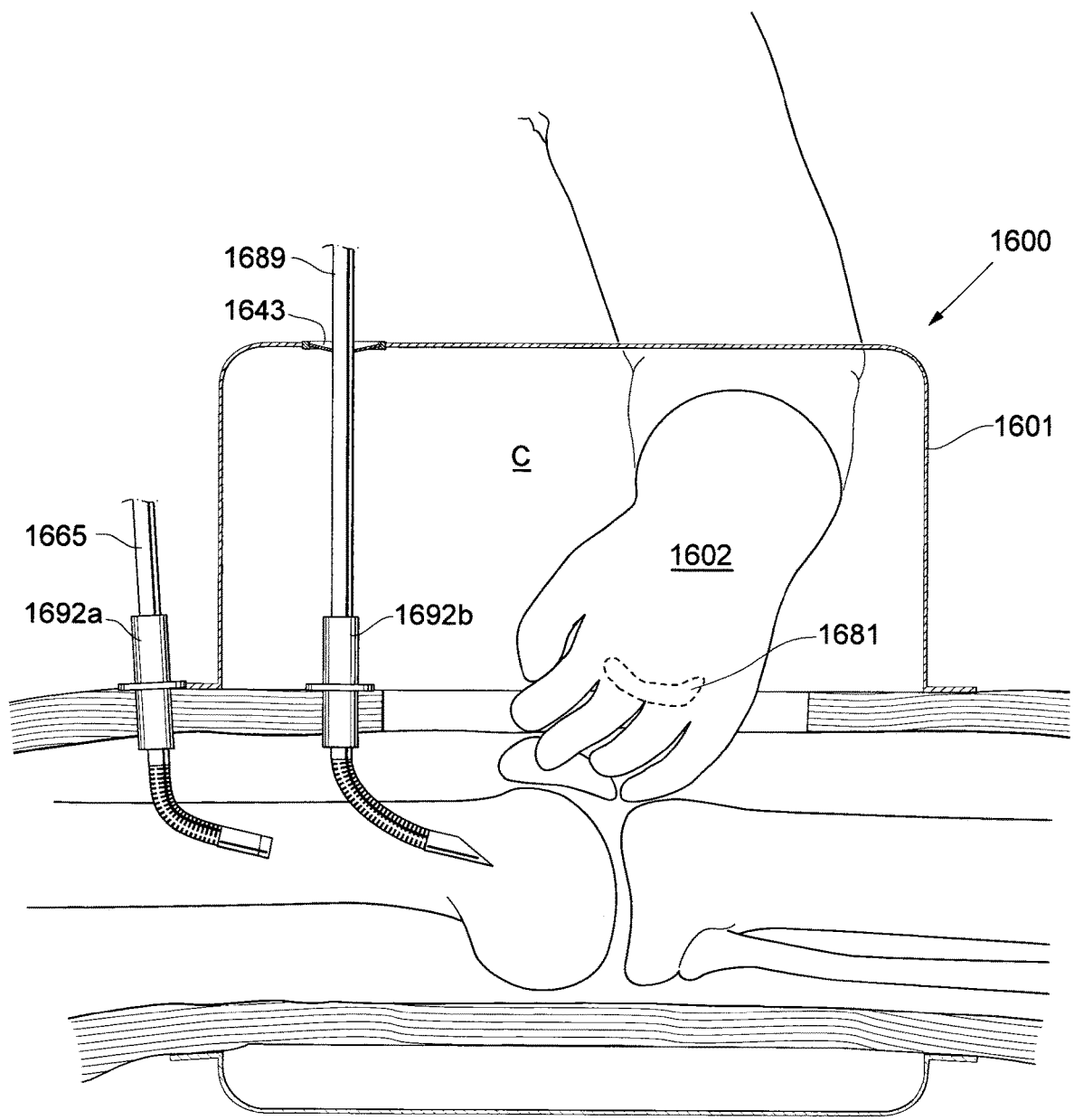
Figure 169C:
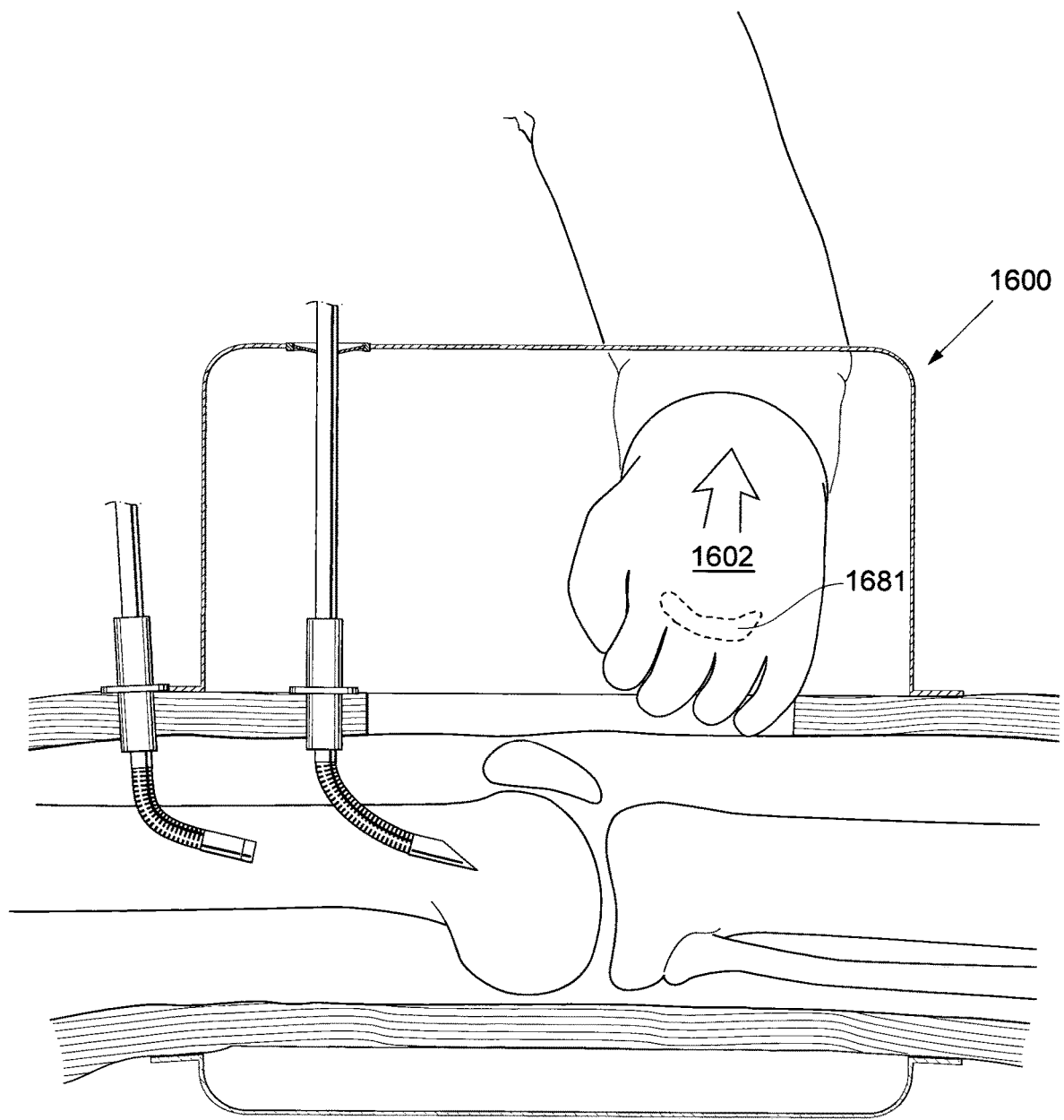

FIG. 169*b*, 169*c* shows the medical device when the surgeon removes a specimen from the knee of the patient using the glove 1602 integrated in the wall of the medical device.

Figure 169D:
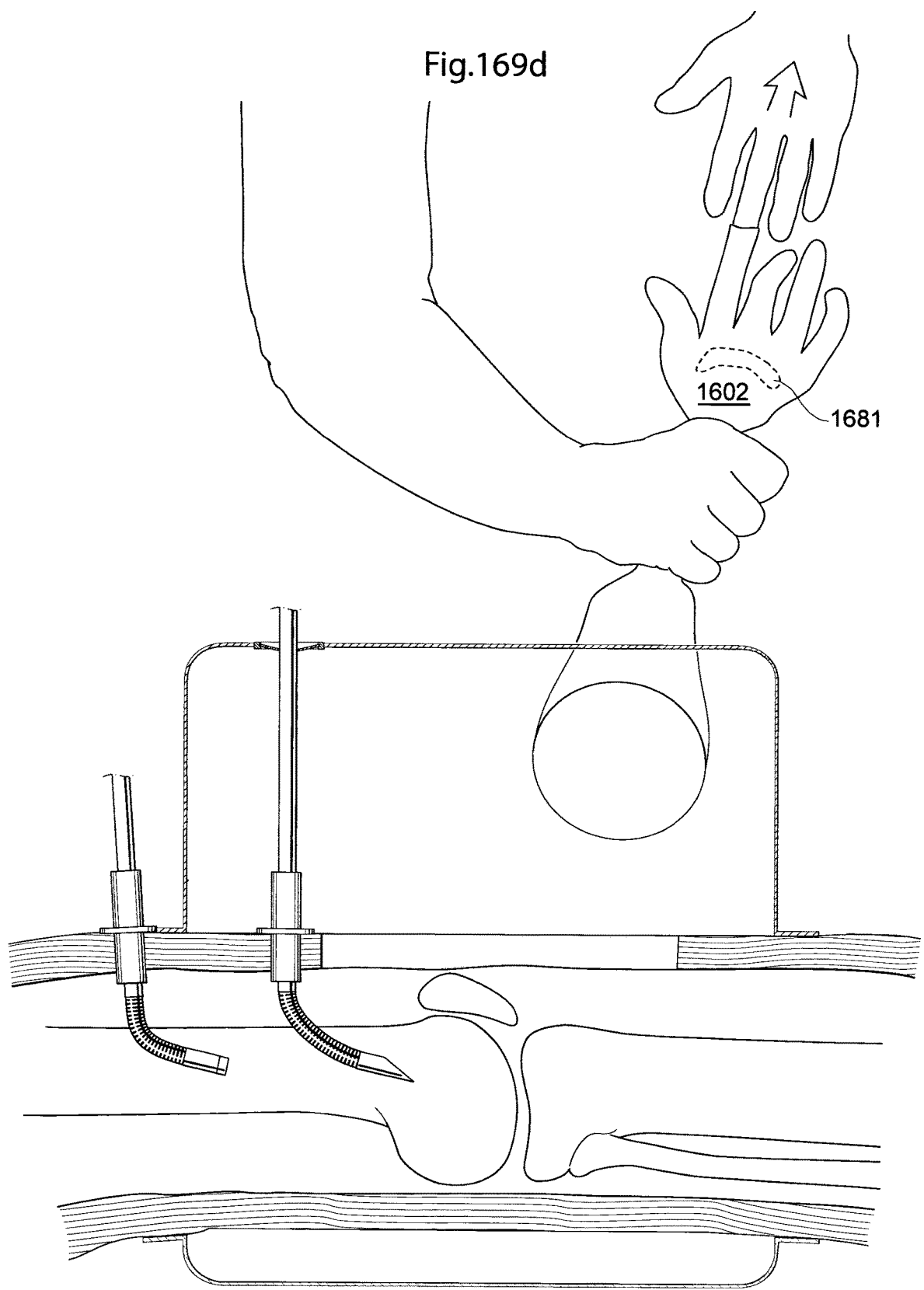

FIG. 169*d* shows the medical device, when the surgeon has turned the integrated glove inside-out such that the specimen can be contained within the integrated glove. By isolating the specimen inside of the glove, the specimen is removed both from the rest of the body of the patient and from the ambient environment, and thereby does not risk to infect any other portion of the patient's body or medical staff with any infectious disease.

Figure 170A:
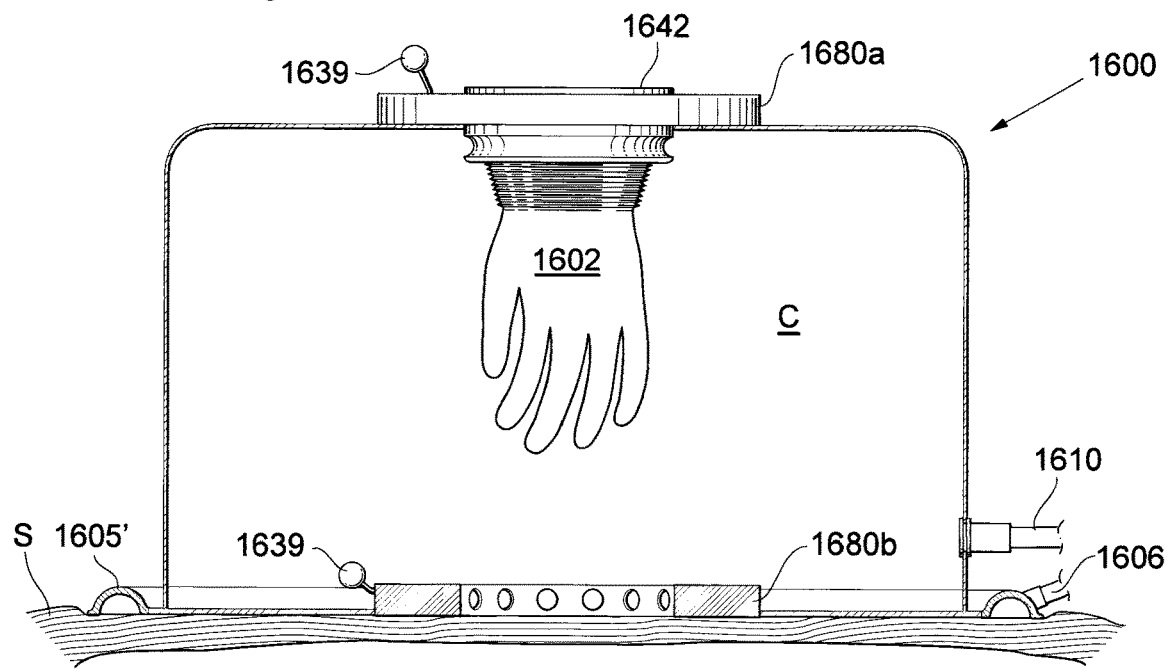
FIGS. 170a-170d shows an embodiment of the medical device in section, being fixated to the patient and used.

FIG. 170*a* shows another embodiment of the medical device in which the medical device 1600 comprises a wall 1601 enclosing a chamber for performing the surgical procedure. A portion of the wall 1601 is adapted to be in contact with a patient. The medical device comprises an inset in the form of a surgical glove 1602 adapted to enable manipulation within the chamber. The surgical glove 1602 connected to a surgical port 1631*a* can be in a first and second position, the second position is disclosed in FIG. 170*a*, while the first position is located closer to the skin of the patient and disclosed in FIG. 170*c*. The medical device could for example be used in surgical procedures where transitions between open and laparoscopic surgery is needed. The medical device could be placed in the second position for enabling a larger freedom of motion for the surgeon within the chamber of the medical device 1600, while the first position, with the surgical port 1631*a* locked to the body port 1631*b*, could enable the use of a laparoscopic trocar or hand access for further reach within the body of the patient. The medical device could further be used in embodiments where manual manipulation in a sealed environment is required, e.g. for preparing a medical device for use in the surgical procedure. Other applications could for example be that the surgeon wishes to remove a specimen form the body of the patient after a laparoscopic procedure has been concluded. The laparoscopic procedure could in these instances be performed with the medical device being in the first position (as shown in FIG. 170*c*), being close to the skin of the patient, whereafter the medical device could be placed in the second position for enabling the specimen to be removed from the body of the patient and placed in the chamber of the medical device without contacting the outside environment, and without the release of the pressure that usually fills the abdomen in laparoscopic procedures. According to the embodiment shown in FIGS. 170*a*-*d*, the wall 1601 is collapsible such as to enable the transferring between the first and second position. The body port comprises a lever 1639 for releasing and/or locking the surgical port 1631*a* to the body port 1631*b*, and thereby placing the medical device in the first state. The medical device 1600 is according to the embodiment shown in FIG. 170*a* fixated to the patient by means of a vacuum sealing member 1605', such as for example disclosed with reference to FIGS. 66 and 67.

Figure 170B:
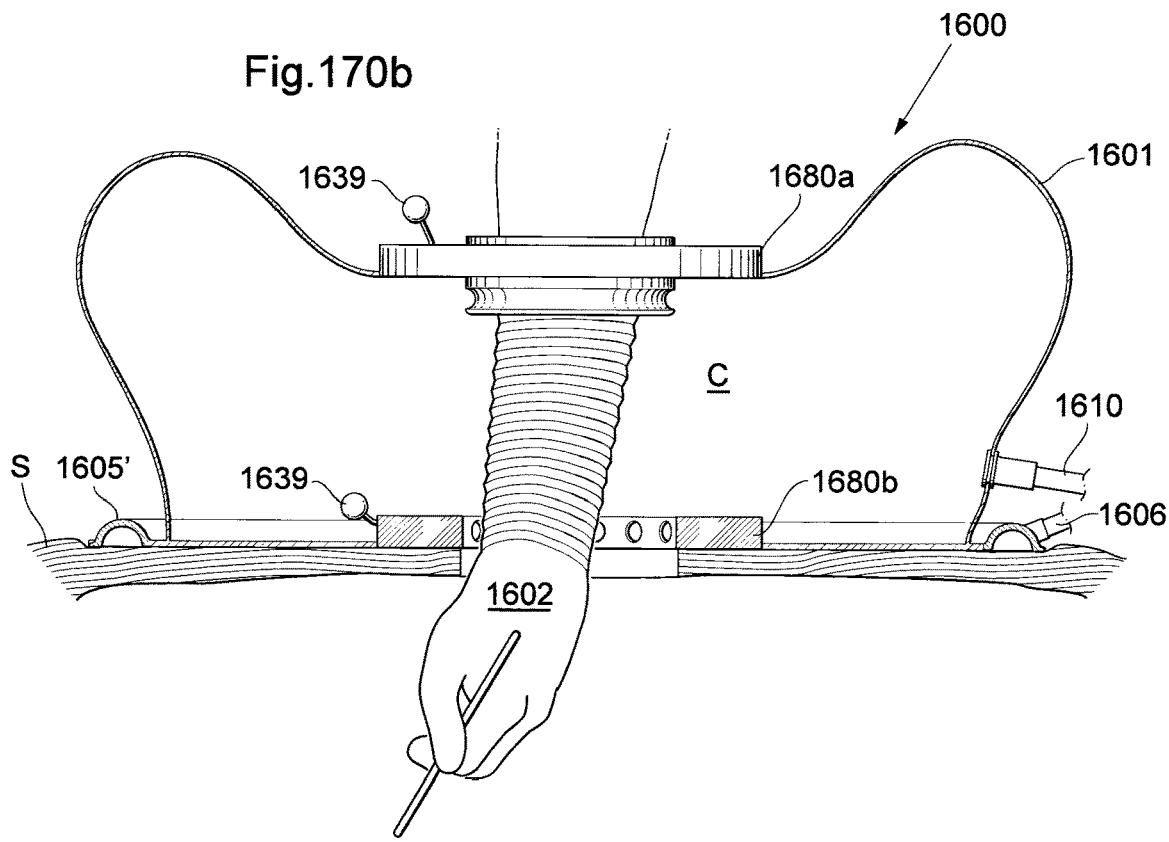
Figure 170C:
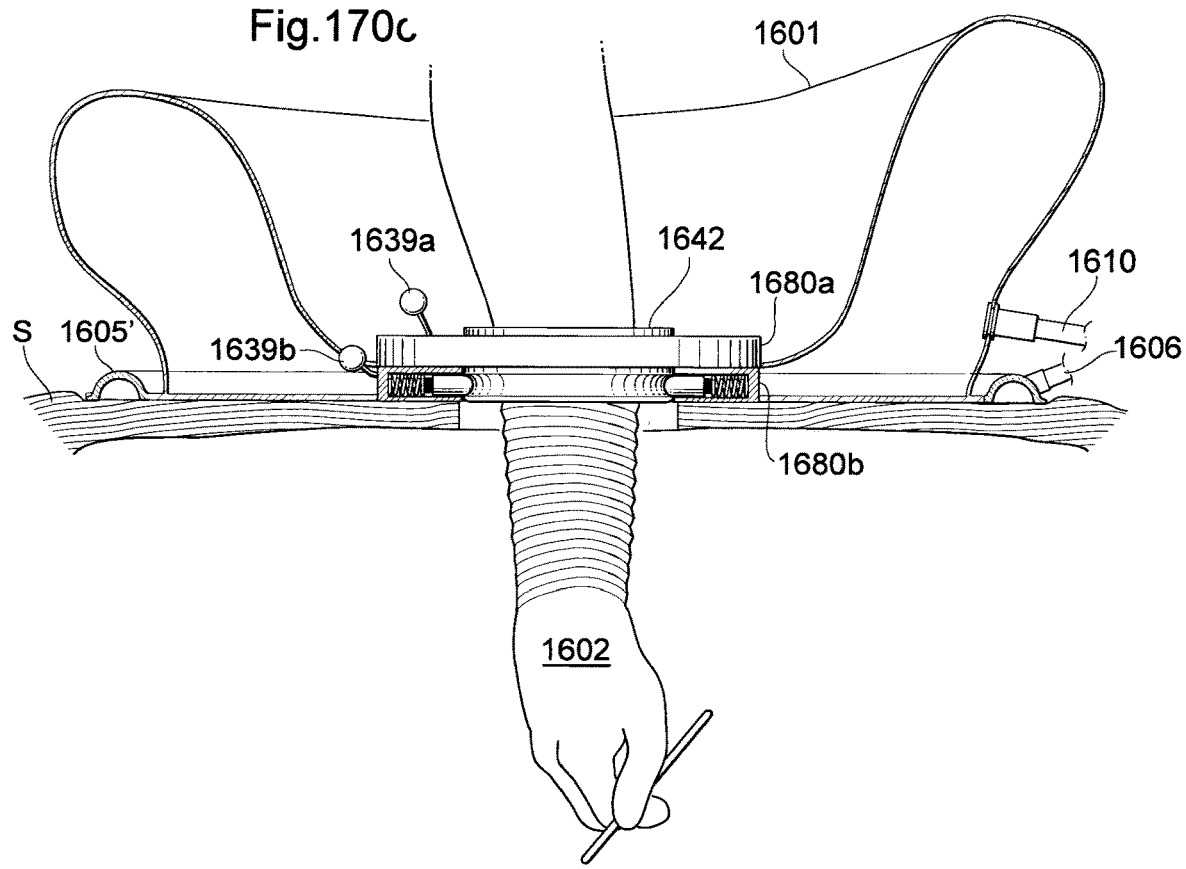

FIG. 170*b* shows the medical device 1600 when being transferred between the first and second position, i.e. the surgical port 1631*a* is pushed towards the body port 1631*b* for enabling a lock between the surgical port 1631*a* and the body port 1631*b*. The integrated surgical glove 1602 has been stretched such as to enable manual manipulation within the body of the patient and within the chamber of the medical device.

FIG. 170*c* shows the medical device 1600 when locked in the first position, i.e. the surgical port 1631*a* is locked to the body port 1631*b*. The integrated surgical glove 1602 now enables manual manipulation with great freedom within the body of the patient. The medical device comprises two levers 1639*a* and 1639*b*, wherein the first lever 1639*a* is connected to the surgical port 1631*a* and adapted to lock the object (here being a surgical glove 1602) to the surgical port 1631*a*, while the second lever 1639*b* is connected to the body port 1631*b* for locking the surgical port 1631*a* to the body port 1631*b*. The medical device 1600 is according to the embodiments shown in FIG. 169 *a*-*d* circular when seen from above, such that the medical device 1600 takes the shape of a doughnut when placed in the first position.

Figure 170D:
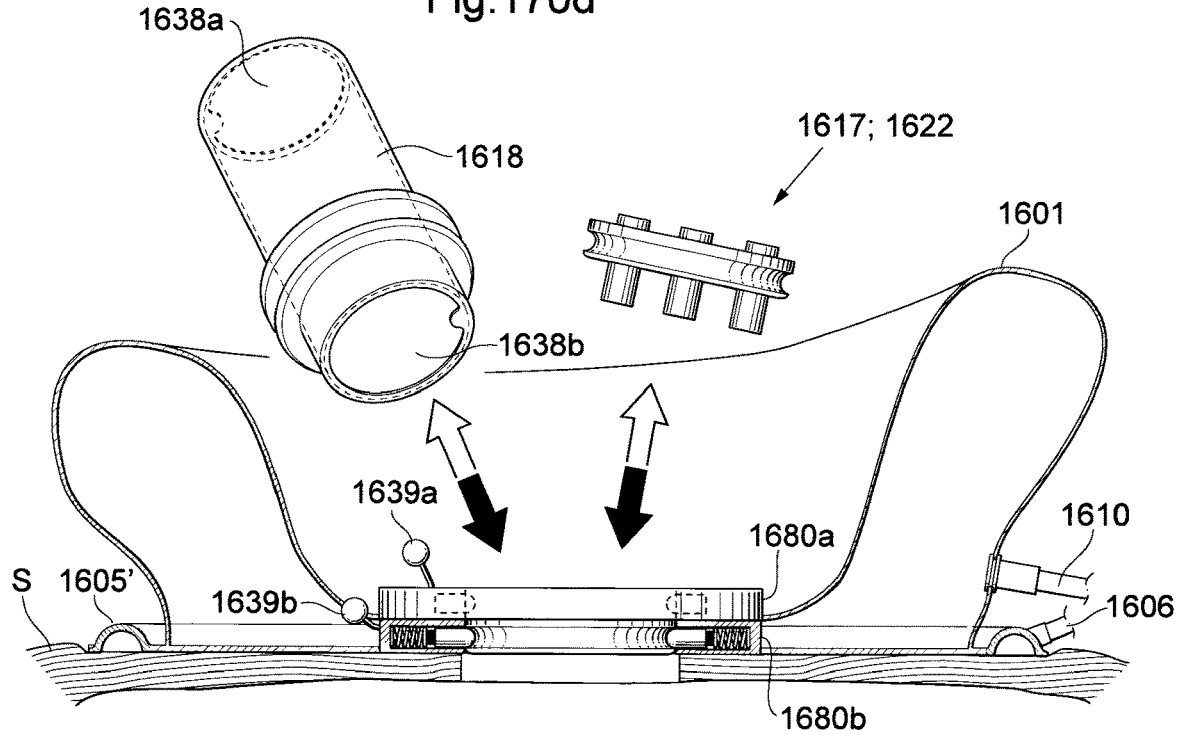

FIG. 170*d* shows the exchanging of objects when the surgical port 1631*a* has been locked to the body port 1631*b*. The object comprises the surgical glove 1602 has been removed and can for example be replaced by an airlock 1670 for transferring objects between the outer environment and the chamber of the medical device 1600. The airlock comprises an inner wall 1682 and an outer wall 1683 on each side of the airlock 1670 enabling the enclosing of an object within the airlock 1670. Another example of an object to which the surgical glove 1602 can be exchanged is a port device 1648 here shown as a body multi-port comprising laparoscopic ports 1647 for performing a laparoscopic procedure. In some embodiments (not shown) the upper and/or lower coupling comprises a valve member for closing the opening in the surgical port when the objects should be exchanged, the valve member could for example be a flap valve.

Figure 171:
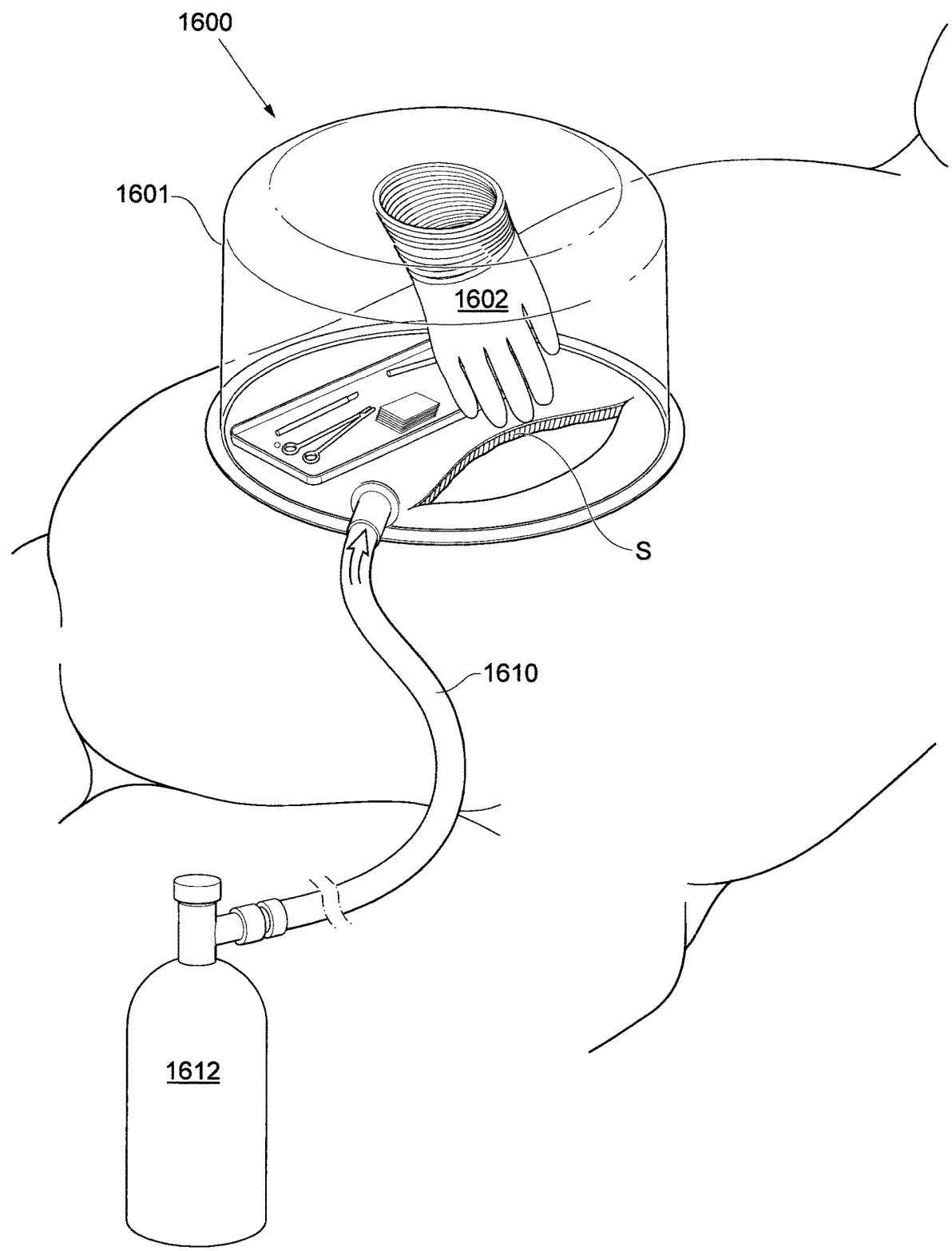
FIG. 171 shows an embodiment of the medical device, when positioned on the abdomen of a patient.

FIG. 171 shows an embodiment of the medical similar to the embodiment of FIGS. 170*a*-*d*. In the embodiment shown in FIG. 171, the medical device is placed in contact with the skin of the patient prior to the beginning of the operation and the entire portion of the wall 1601 contacting the skin of the patient comprises an adhesive, such that the incision in the patient runs through the wall 1601 and further through the skin 1641 of the patient. This reduces the risk that infectious objects can be transferred from the skin of the patient to the incision in the patient if the skin of the patient is not adequately disinfected. The body of the patient could be inflated to allow better visibility within the body from for example the fluid conduit 1613 connected to the pressure tank 1612, however it is equally conceivable that the body of the patient is inflated from within trough a different incision in the body of the patient.

Figure 172:
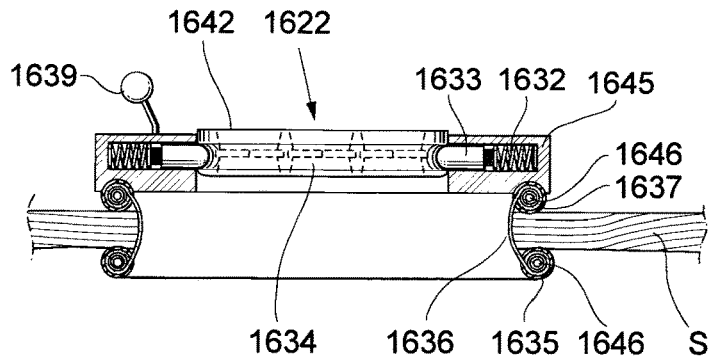
FIGS. 172-174b shows embodiments of body ports fixated to the tissue of the patient.

FIG. 172 shows an embodiment of a detachable body port 1631*b* which could be fixated to a coupling positioned in the medical device 1600 disclosed with reference to FIGS. 170*a*-*d*. The port arrangement of FIG. 172 includes an intra body ring 1635 adapted to be placed at the inside of the patients skin around an incision, and an outer ring 1637 adapted to be placed on the outside of the patients skin 1641 around the incision. Between the intra body ring 1635 and outer ring 1637 an annular retractor membrane 1636 is positioned adapted to exert a pressure on the skin or human tissue at the incision to seal between the rings and the skin or human tissue and additionally for retracting the skin and thereby keep the incision open. The retractor membrane 1636 is preferably made from a resilient or elastic polymer material. The outer ring 1637 comprises an integrated roll up system 1646, which may be spring loaded and adapted to create a suitable pressure on retractor membrane 1636 to keep the incision open.

Figure 173A:
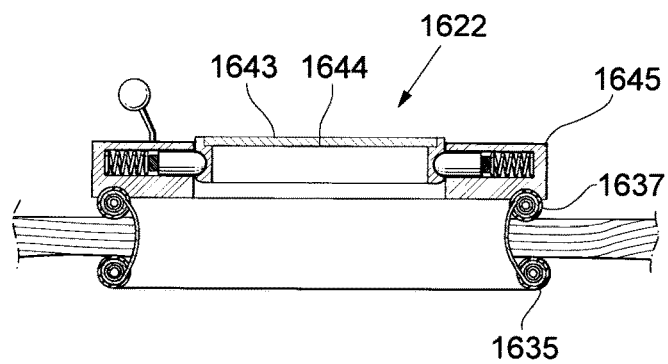

The port arrangement shown in FIG. 173*a* also includes a body port having a rigid annular seating 1645 attached to the outer ring 1637, spring loaded latching members 1633 arranged in radial bores in the seating 1645 and a hand lever 1639 connected to the latching members 1633 to enable retraction thereof against the action of springs 1632. The port arrangement further includes a self sealing body port 1622. The self sealing body port 1622 comprises a disc-shaped self sealing membrane 1643, FIG. 173*a*, fixated to a rigid ring having an outer circumferential groove 1634 that receives the latching members 1633 of the coupling. The self sealing membrane 1643 has a small self sealing hole 1644, shown in FIG. 173*a*, centrally in the membrane 1643. For example, the self sealing membrane 1643 may be made from a gel-type material being elastic enough to enable a deformation large enough for a person's hand to pass through the small self sealing hole 1644 while still contracting enough to create an airtight seal between the chamber and the outside environment.

The coupling described above enables quick exchange of the body port. Thus, the surgeon may release the body port from the port arrangement by simply pulling the hand lever 1639 so that the latching members 1633 disengage from the groove 1634 of the body port, whereby the body port can be removed.

FIG. 173*a* is a cross-sectional view of the port arrangement shown in FIG. 143, to more clearly illustrate the body port with its self sealing membrane 1643 and small hole 1644.

Figure 173B:
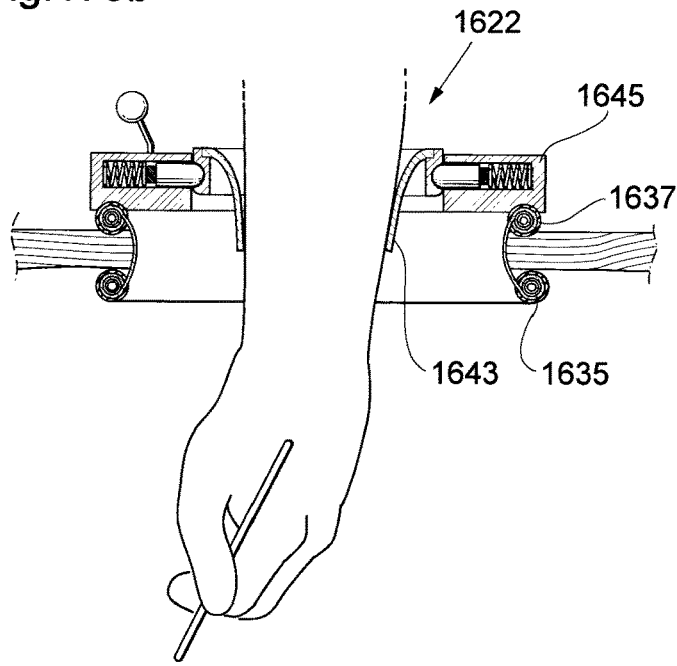

FIG. 173*b* shows the self sealing body port 1622 when the hand of a surgeon is placed through the hole 1644 in the membrane 1643 and thus enabling manual manipulation within the body of the patient.

Figure 174A:
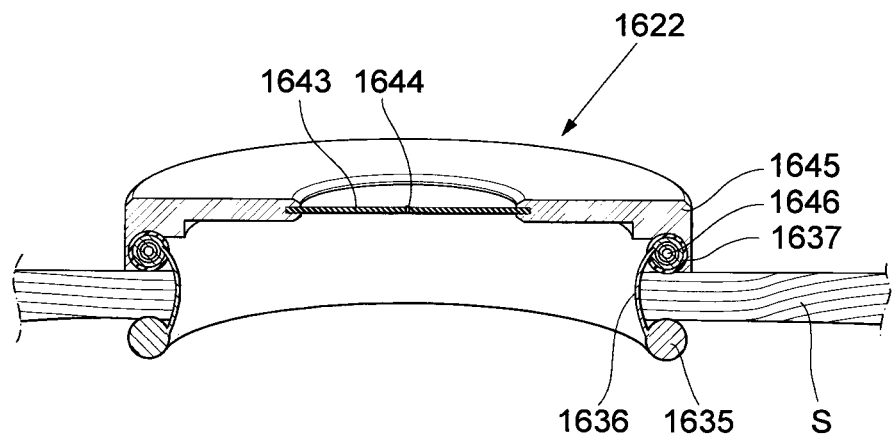
Figure 174B:
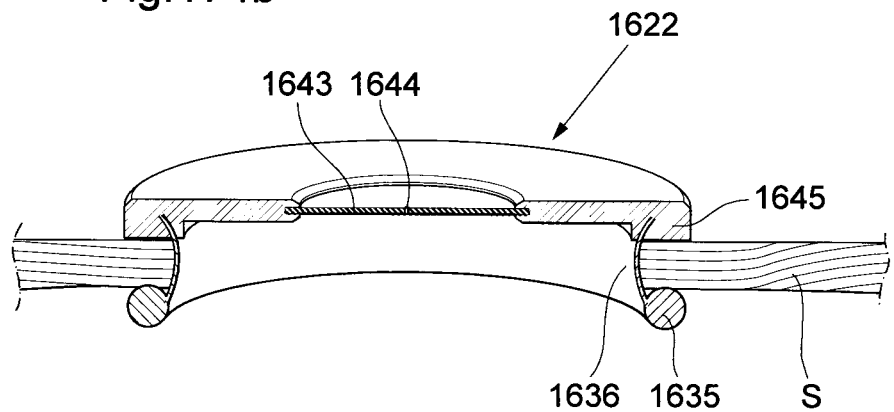

FIG. 174*a* shows a self sealing body port 1622 in a close-up, in section. The self sealing body port 1622 could be connected to the coupling, for example as disclosed with reference to FIGS. 172-173, which in turn is connected to any of the medical device disclosed with reference to FIGS. 170-174, or the self sealing body port 1622 could be fixated to a retractor, as shown in FIGS. 174*a* and 174*b*. The self sealing body port 1622 comprises a self sealing membrane 1643 fixated to a rigid part 1645 of the self sealing port. The self sealing membrane 1643 having a small self sealing hole 1644 centrally in the membrane 1643. The self sealing membrane 1643 is for example made from a gel-type material being elastic enough to enable a deformation large enough for a person's hand to pass through the small self sealing hole 1644 while still contracting enough to create an airtight seal between the sealed environment and the outside environment. The medical device being fixable to a retractor comprising one intra body ring 1635 adapted to be positioned on the inside of the patients skin, and one ring 1637 adapted to be placed on the outside of the patients skin. Between the intra body ring 1635 and the ring 1637 adapted to be placed on the outside of the patients skin a retractor membrane 1636 is positioned which is adapted to exert a pressure of the cut surfaces of the incision for retracting the skin and thereby keeping the wound open. The retractor membrane 1636 is preferably made from a resilient of elastic polymer material. The ring adapted to be placed on the outside of the patients skin 1641 comprises an integrated roll up system which could be a spring loaded roll up system adapted to create a suitable pressure on retractor membrane 1636 for keeping the wound open.

FIG. 174*b* shows an alternative embodiment of the self sealing body port 1622, with the difference that the retractor membrane 1636 is made from a material elastic enough such that one end of the retractor membrane 1636 could be fixedly fixated to the rigid part 1645 of the port.

Figure 175:
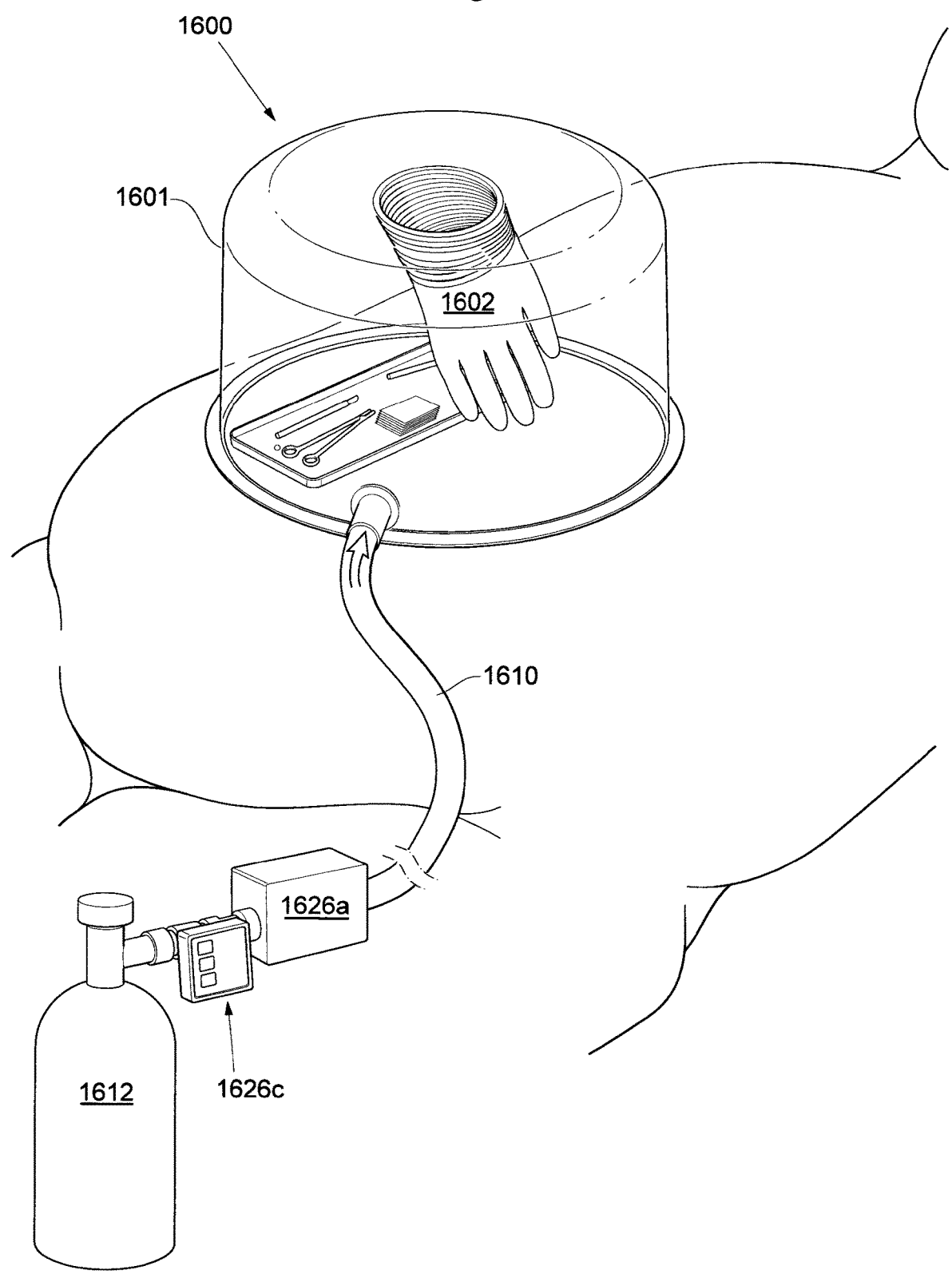
FIG. 175 shows an embodiment of the medical device, when positioned on the abdomen of a patient.

FIG. 175 shows the medical device as shown in FIG. 171 with the addition that the embodiment comprises a sterilizing unit 1626 adapted to sterilize the gaseous fluid entering the medical device 1600. In the embodiment disclosed herein, the gaseous fluid entering the medical device 1600 originates from a pressurized tank 1612 and could be pre-sterilized, however, in other embodiments, it is conceivable that the gaseous fluid is the surrounding air which is pressurized (such as further disclosed with reference to FIG. 85). In the embodiments where the surrounding air is used to inflate the medical device 1600 and constitute the operating environment this air needs to be properly sterilized. The medical device 1600 further comprises a tempering unit 1626*c* which could be provided to heat or cool the gaseous fluid inflating the medical device 1600. In cases when the surrounding environment is cold the tempering unit 1626*c* could be used to raise the temperature of the sealed environment to provide beneficial operating circumstances both for the patient and for the surgeon. In cases when the surrounding environment is hot, the tempering part of the system 1626*c* could be used to lower the temperature of the sealed environment both to provide beneficial operating circumstances, both for the patient and for the surgeon, and for providing a temperature inhibiting bacterial and viral infections. The tempering unit 1626*c* could comprise a temperature regulating device 1625 for setting the required temperature.

Figure 176:
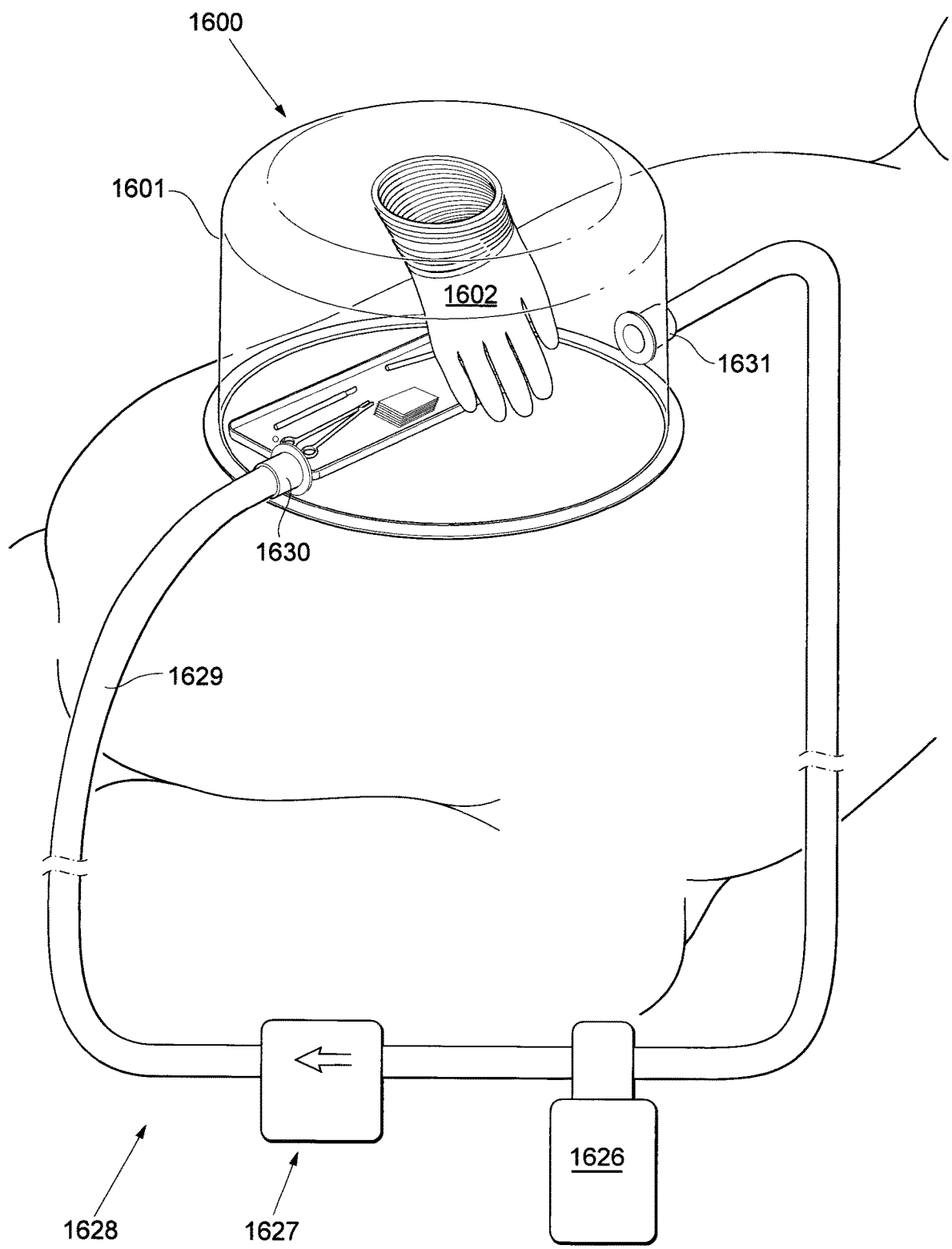
FIG. 176 shows an embodiment of the medical device, comprising a fluid circulating system, when positioned on the abdomen of a patient.

FIG. 176 shows a medical device similar to the embodiment disclosed in FIG. 175 but comprising a system 1628 for circulating a fluid through the sealed environment of the medical device. The system comprises a fluid conduit 1629 connected at an inlet 1630 placed in the wall 1601 for supplying fluid to the sealed environment, and an outlet 1631 for draining the fluid from the sealed environment. The fluid is circled by means of a pumping unit 1627 and is circled via a sterilizing/filtering unit 1626 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Figure 177:
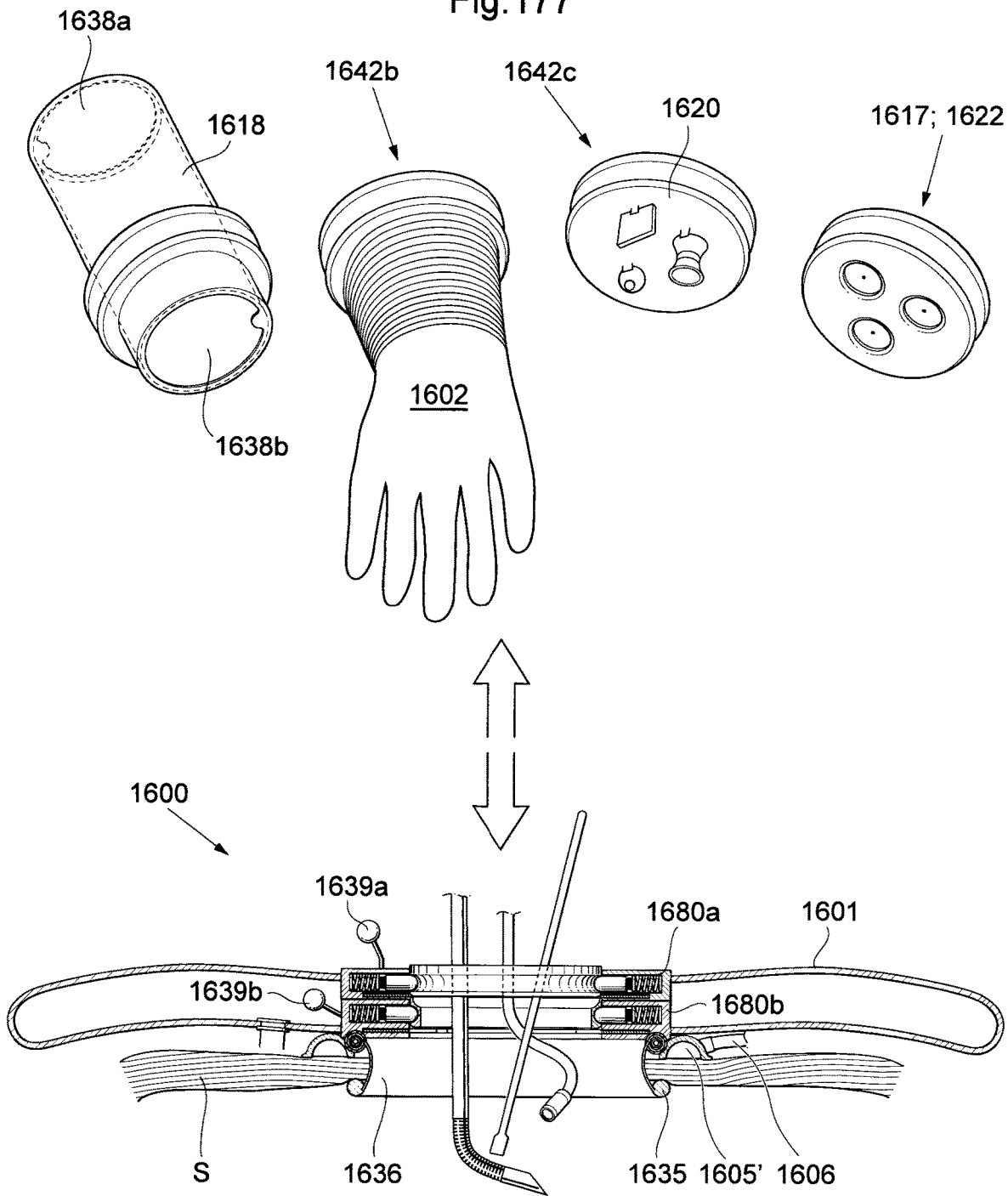
FIGS. 177-178 shows another embodiment of the medical device, in section.

FIG. 177 shows an alternative of the embodiment in which the medical device 1600 is adapted to be at least partially placed in an incision cut in a patient's body. The medical device 1600 comprises a body port 1631*b* and a surgical port 1631*a* adapted be interconnected. The surgical port 1631*a* is adapted to be disconnected from the body port 1631*b*, and the body port 1631*b* is connected to a first portion of a flexible wall 1601, and the surgical port is connected to a second portion of the flexible wall 1601. The flexible wall 1601 forms a chamber in which a sealed environment can be maintained, the chamber is heavily enlarged when the surgical port 1631*a* is disengaged from the body port, thus creating operating space within the chamber enclosed by the wall. The surgical and body ports comprise a latching system for locking an inset. The inset may for example be an airlock part 1670 with a first 1682 and second 1683 valve member, a glove 1602 for manual manipulation within the body of the patient, or within the enclosed chamber, a holding device 1681 for holding instruments or medical devices within the chamber, and a multi-port portion 1648 comprising a plurality of ports enabling the insertion of a surgical instrument into the chamber or body of the patient.

In the embodiment shown in FIG. 177 the medical device is fixated to the body of the patient by means of a vacuum fixating member 1605' connected to a conduit 1614, which in turn is connected to a vacuum source. Furthermore, the medical device in FIG. 148 comprises a second sealing function having a first sealing member 1635 adapted to be positioned at the inside of the patient's skin around an incision to be performed in the skin and a second sealing member 1637 adapted to be positioned at the outside of the patient's skin around the incision, and a spring-loaded or elastic connecting member 1636 sealingly interconnecting the first 1635 and second 1637 sealing members. The spring-loaded or elastic connecting member 1636 seals between at least one of the port and the skin of the patient, and the first sealing member and tissue of the patient.

Figure 178:
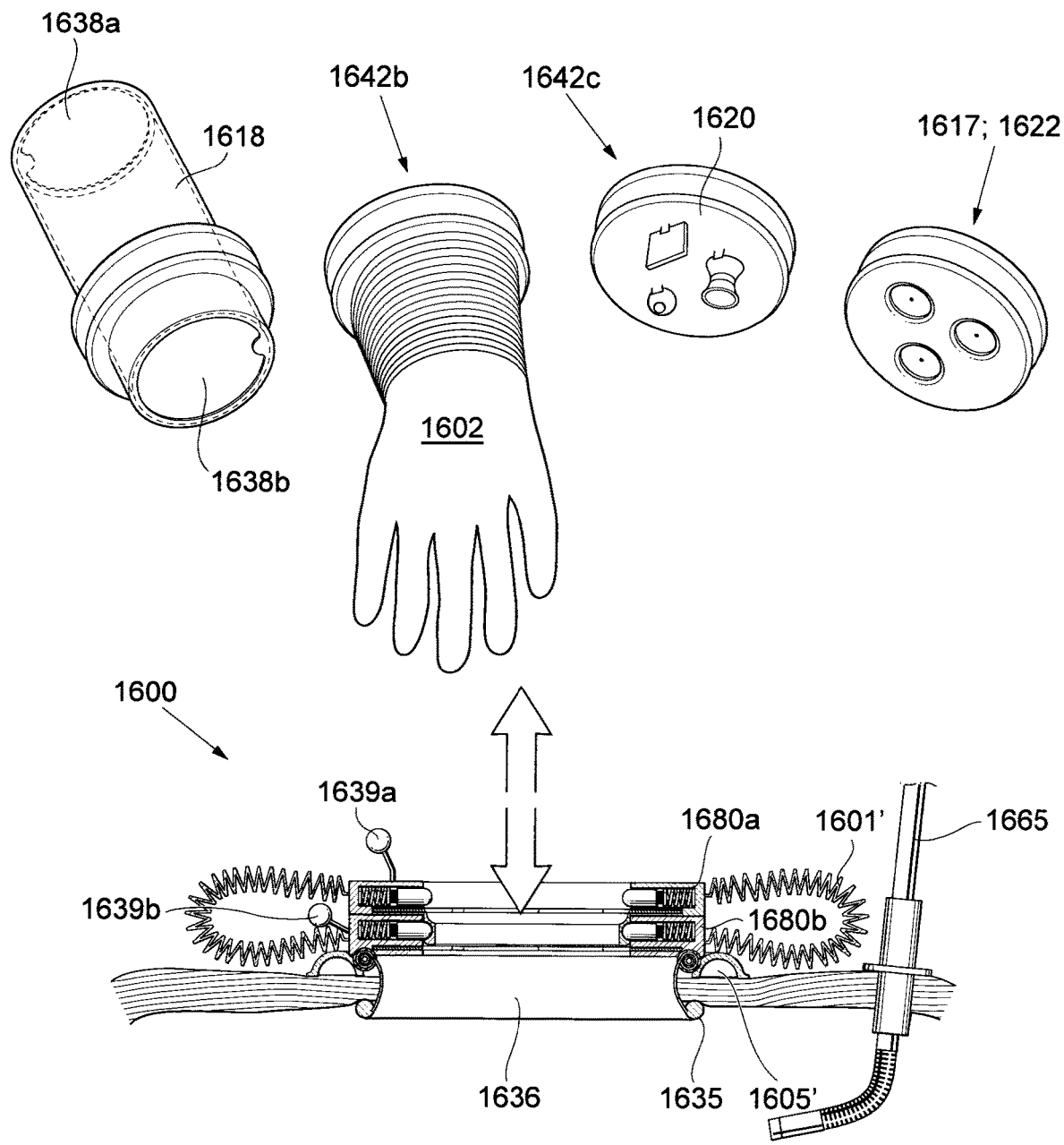

FIG. 178 shows the port in an embodiment very similar to the embodiment shown in FIG. 177 but with the difference that the wall 1601' has a bellows structure and thus taking up less space when in its deflated state. The bellows structure enables the wall to be packaged in a small package and thus not obstructing the procedure. In some applications the wall can be used only on very special occasions or emergencies, such as when some part of the procedure goes wrong and conversion from laparoscopic surgery to more open surgery is required. The use of the inflated chamber then enables the pressure in the cavity within the patient to be maintained since the chamber can hold a pressure.

FIG. 179-185 shows a feature which could be implemented in the embodiments disclosed with reference to FIGS. 170-178. In the embodiment of FIGS. 179-185, the wall of the medical device is inflatable, and the medical device is in its inflated state. When the chamber is deflated it has a first volume i.e. when the surgical port 1631*b* and body port 1631*a* are interconnected, and when the chamber is inflated and the surgical port 1631*a* is disconnected from the body port 1631*b* it has a second volume, and the second volume is larger than the first volume. According to the embodiment shown in FIG. 179*d*, the second volume is larger than 500 000 mm3 and adapted to hold a pressure exceeding atmospheric pressure.

According to the embodiment shown in FIG. 179-185 the chamber further comprises a pouch 1682 for holding a specimen 1681 removed from within the body of the patient not to contaminate any other part of the body and create the possibility of delaying the removal of the specimen until the procedure is concluded. The pouch may be a pouch 1682 which could be closed for creating a pouch-chamber within the chamber for isolating the removed specimen 1681 within the chamber.

Figure 179:
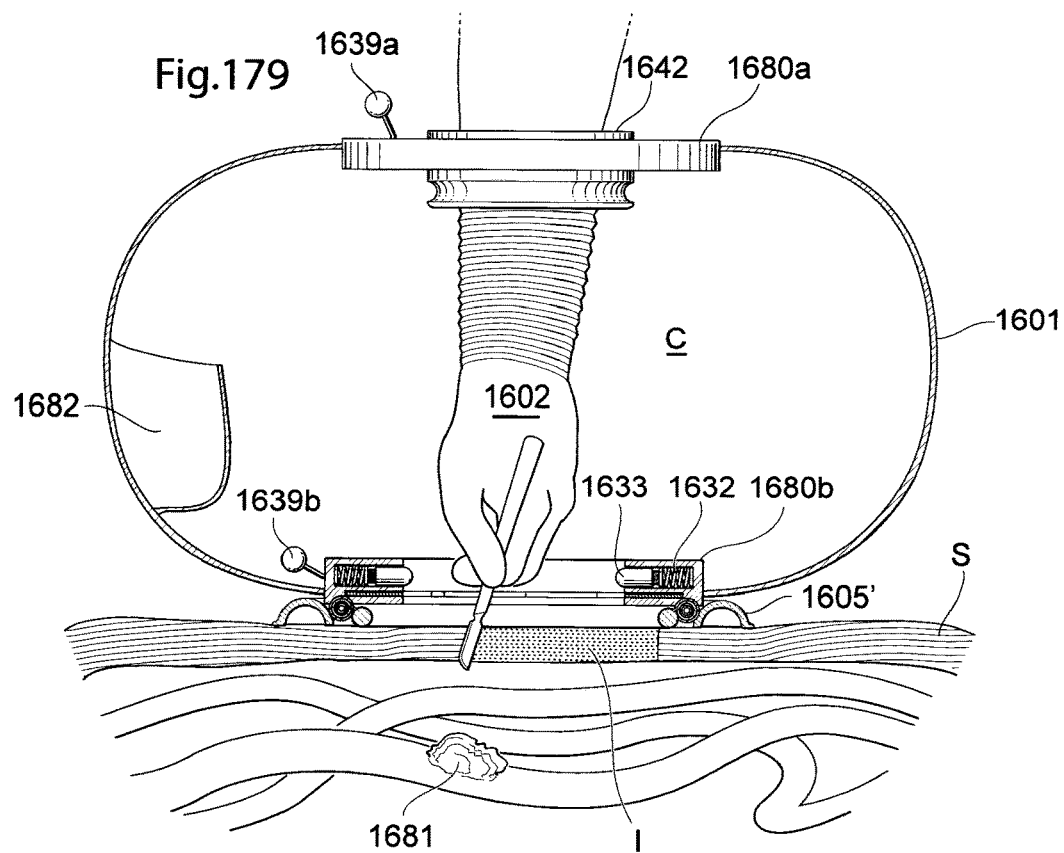
FIGS. 179-185 shows an embodiment of the medical device in section, being fixated to the patient and used.

In FIG. 179, a state is illustrated in which the cut in the patient's skin is being created by the surgeon by means of a glove inset 1602 latched to the surgical port 1631*a*. The medical device is fixated and sealed by means of the vacuum sealing member 1605' since the seal that is provided partially within the patient's body cannot be mounted until the cut in the patient's skin is concluded. The two different seals disclosed could in some embodiments be replaced by only one of the seals, or by a different seal, such as the adhesive of pressure seals disclosed in other portions herein.

Figure 180:
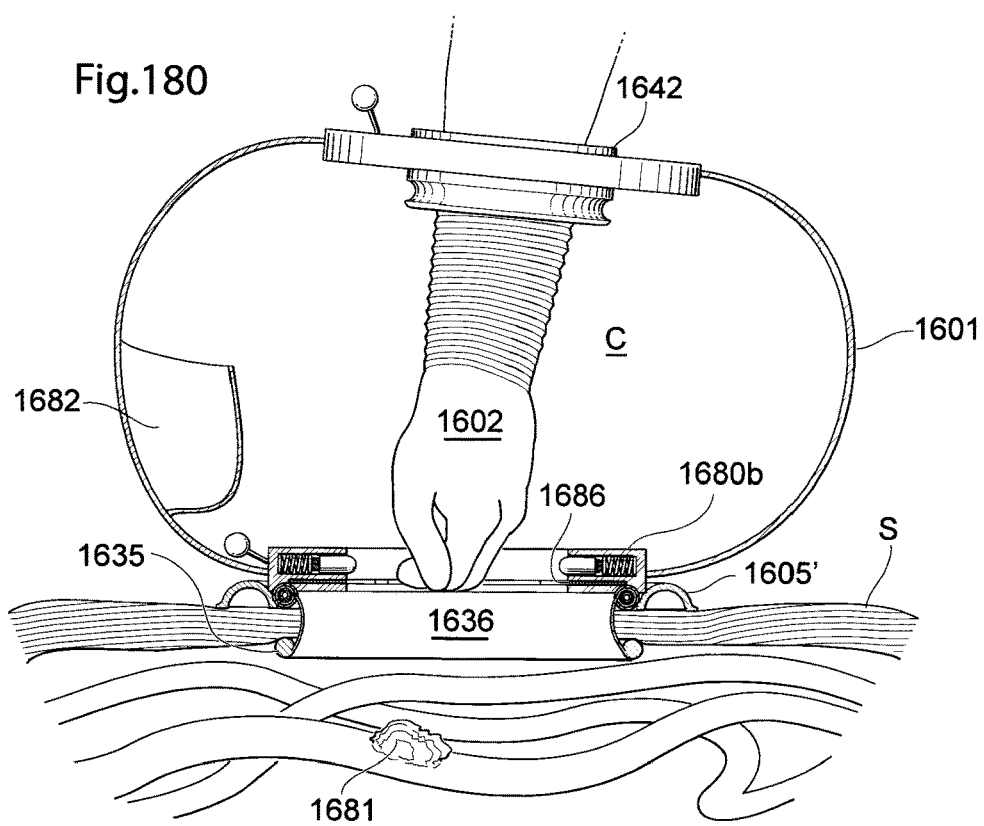

FIG. 180 shows the medical device, when the second sealing 1635, 1636, 1637 have been placed in the incision cut in the patient's skin. The wall 1601 enclosing the chamber is elastic or flexible which enables the surgeon move the surgical port 1631*a* in relation to the body port 1631*b* for getting better access to different angles within the patient's body, for example for removing a specimen 1681. The embodiment of FIG. 151 further comprises a non-penetrable valve 1686 placed in the surgical port 1631*b* for closing the port such that the chamber is sealed from at least one of the ambient environment and a cavity in the patient. The closing of the non-penetrable valve 1686 enables activity within the chamber without maintaining a pressure in the chamber, at the same time as a pressure and/or sealed environment can be maintained within the body of the patient.

Figure 181:
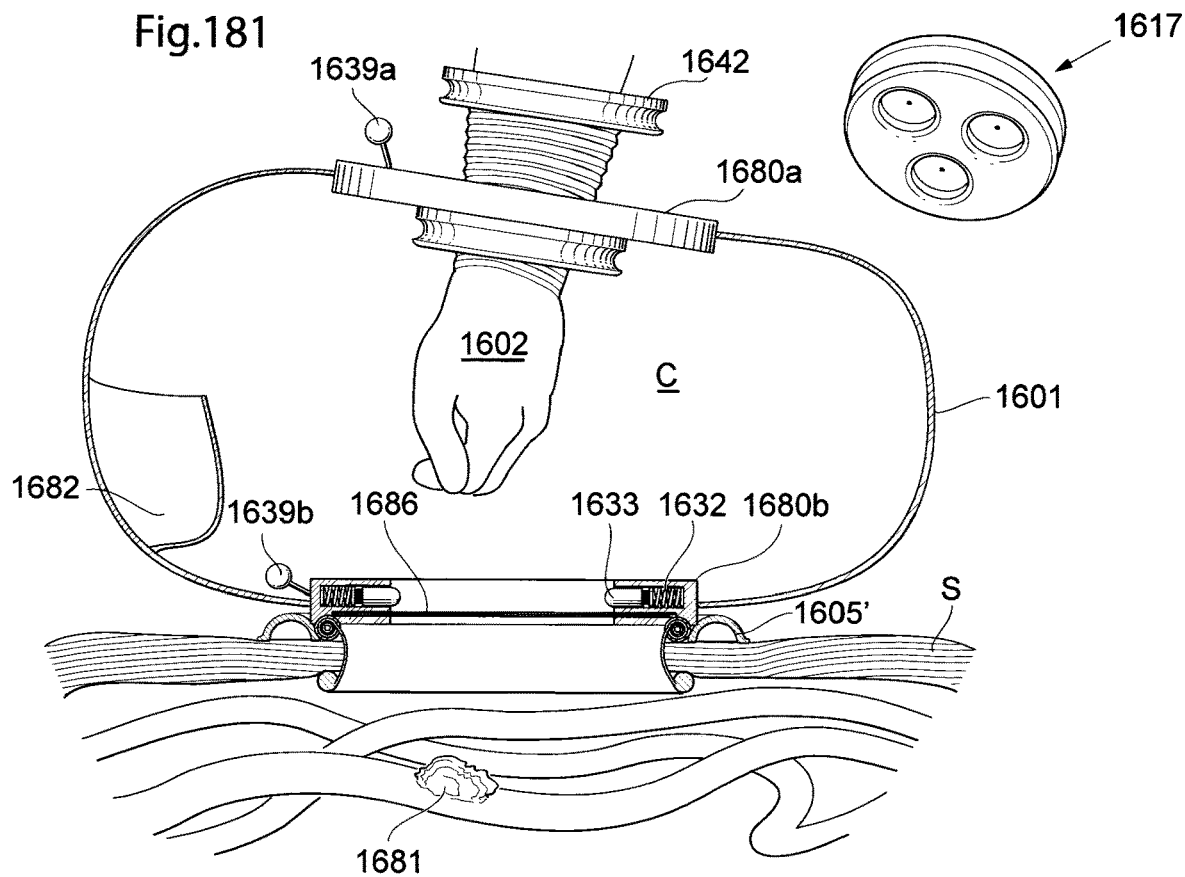

FIG. 181 shows the medical device when the glove inset 1602 is removed and replaced by a multi-port inset 1648 comprising a plurality of ports 1647. The multi-port inset may be used for manipulating objects within the chamber of the inflated medical device using surgical instruments, or within the body of the human patient, when the surgical port and body port is connected (as shown in FIG. 182).

Figure 182:
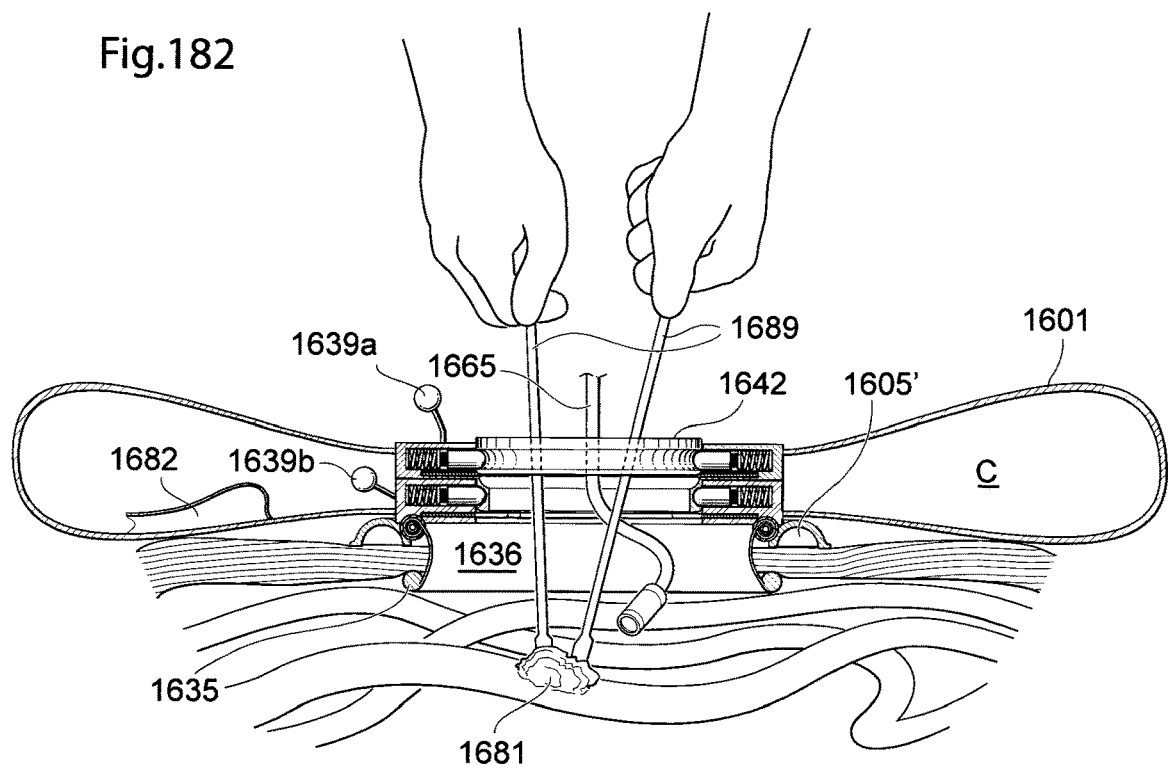

FIG. 182 shows the medical device when the first and second parts are connected such that surgical instruments 1689 can be used for manipulating within the body of the patient. An endoscopic camera 1688 may be provided in the port for enabling visual inspection of the cavity within the patient's body. The process of cutting away a specimen from the intestines of a patient in a laparoscopic way is shown in FIG. 182.

Figure 183:
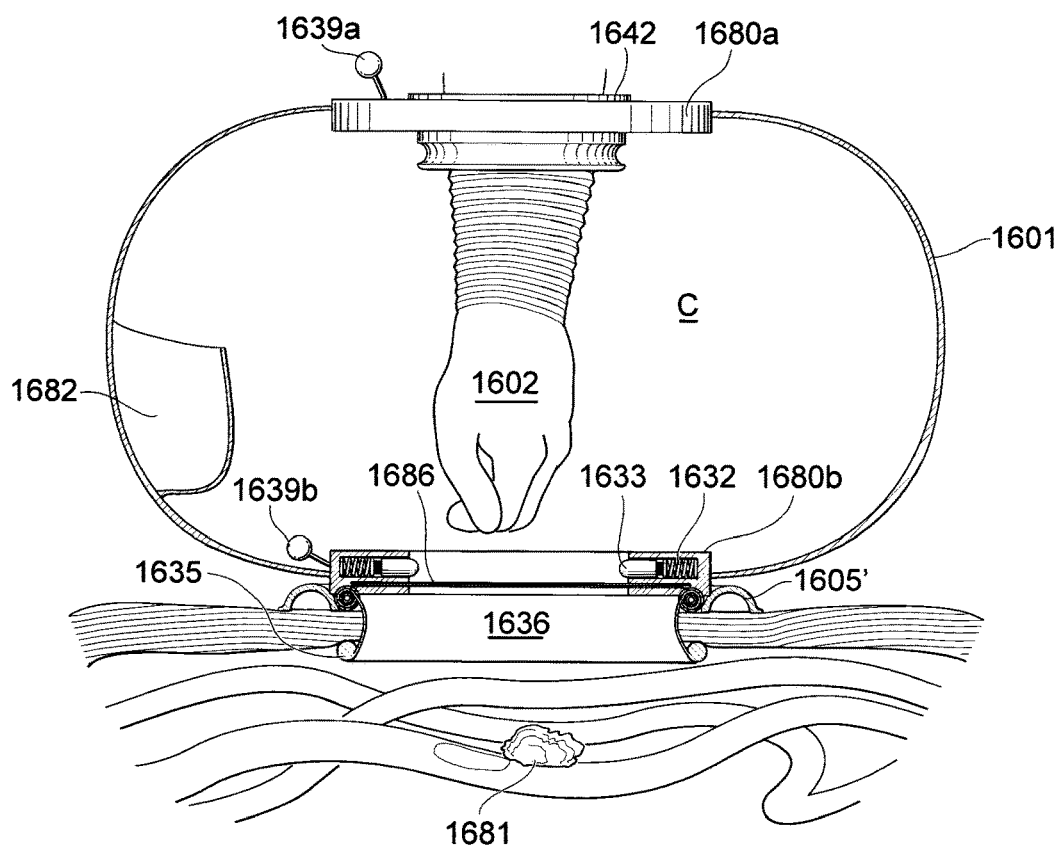

In FIG. 183, the glove inset 1602 has been fixated to second part 1631*a* to enable the surgeon to operate within the cavity of the patient's body and within the chamber enclosed by the wall of the medical device. By the glove inset 1602 comprising a pleated portion, the glove surgeon is able to reach into the cavity of the patient for removing the specimen cut loose from the intestines in prior steps.

Figure 184:
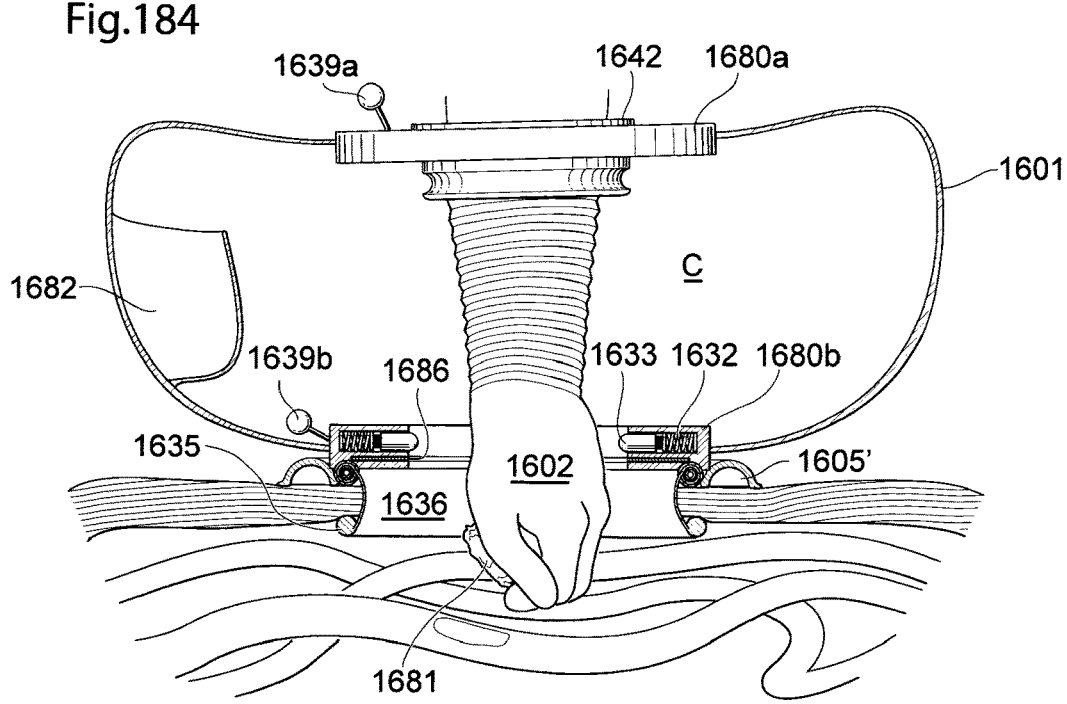

FIG. 184 shows that the wall of the medical device is collapsible such that the glove inset can be moved with relation to the first part 1631*b* of the port, which gives the surgeon further freedom when removing the loose specimen from the intestines of the patient.

Figure 185:
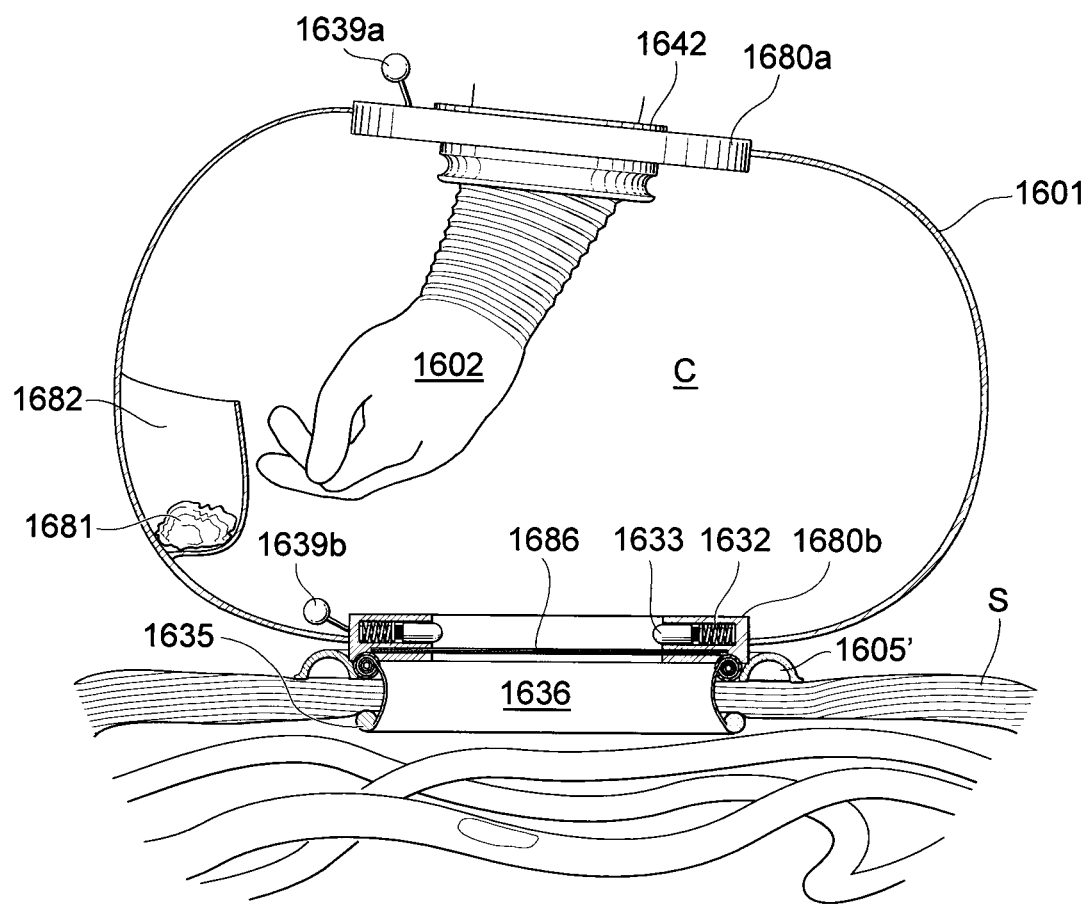

FIG. 185 shows the step of placing the removed specimen in the pouch 1682 such that the specimen does not contaminate any other part of the body. The pouch may be a pouch 1682 which could be closed for creating a pouch-chamber within the chamber for isolating the removed specimen 1681 within the chamber.

Figure 186:
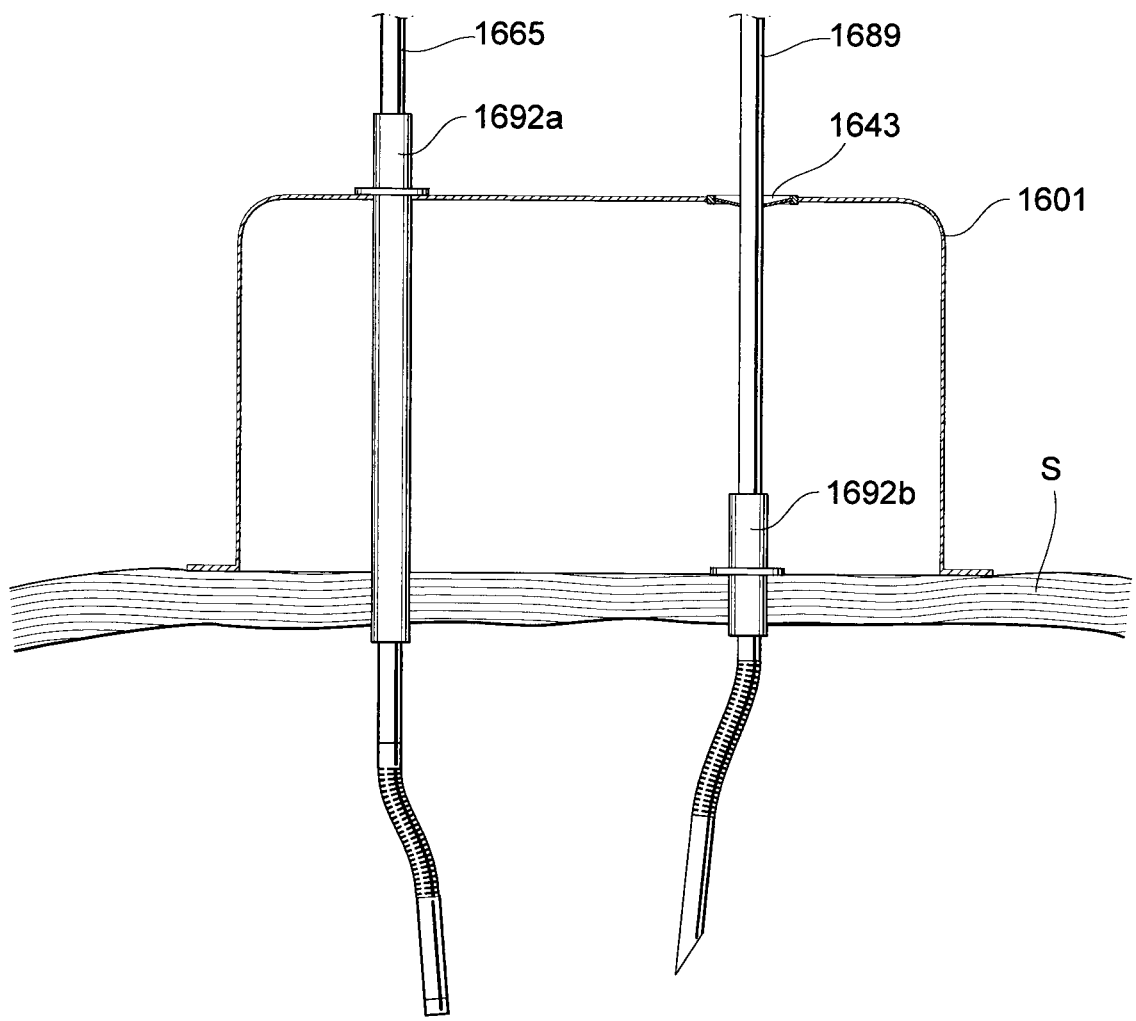
FIG. 186 shows another embodiment of the medical device comprising trocars, in section.

FIG. 186 shows examples of how trocars may be used in combination with the medical device according to any of the embodiments shown in FIGS. 170-185. The medical device comprises a wall 1601 placed on the patient's skin and thereby enclosing a chamber for creating a sealed environment. The medical device comprises two trocars 1692*a*; 1692*b*, one 1692*a* traveling through both the wall 1601 of the medical device and the skin of the patient and thus enabling endoscopic instruments to be inserted into the patient through both the wall of the medical device and the skin of the patient through one single trocar. The other trocar 1692*b* being placed inside the chamber and enabling an endoscopic instrument to be inserted through the skin of the patient. The endoscopic instrument is in this embodiment inserted into the chamber enclosed by the wall 1601 through a membrane in the wall sealing against the tool 1692*b*.

Figure 187B:
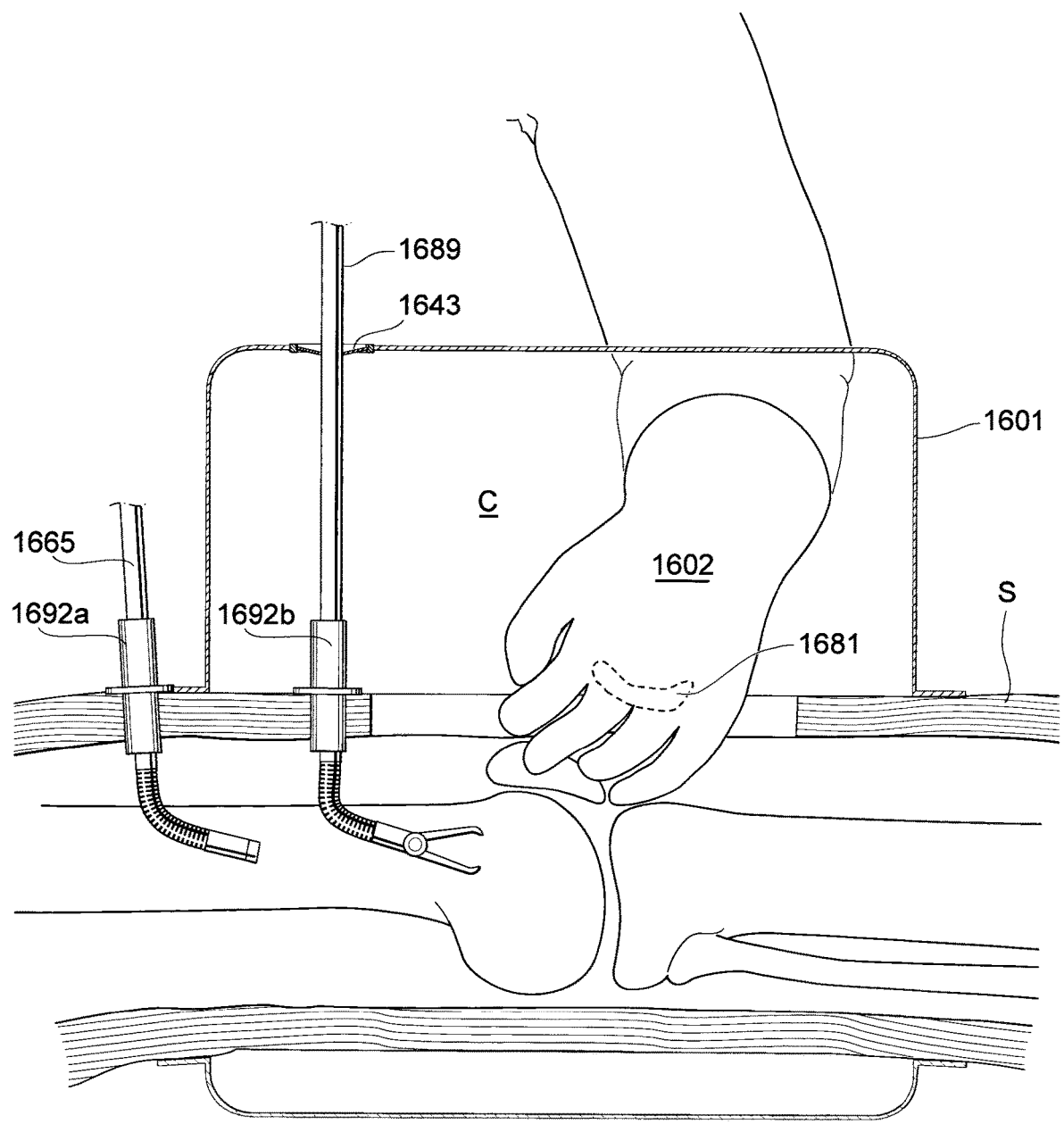

FIGS. 187*a*-187*d* shows how the medical device shown in FIGS. 170-186 may be used. The medical device 1600 comprises a glove 1602 integrated in the wall 1601 and a camera 1665 placed in the skin outside of the medical device 1600. The medical device 1600 further comprises a trocar 1692 placed trough an opening in the wall 1601 and into the sealed environment and further through an opening in the skin of the patient and into an area of the knee of the patient. FIG. 187*a* schematically illustrates how the surgeon manipulates the knee in the sealed environment using the glove 1602.

Figure 187C:
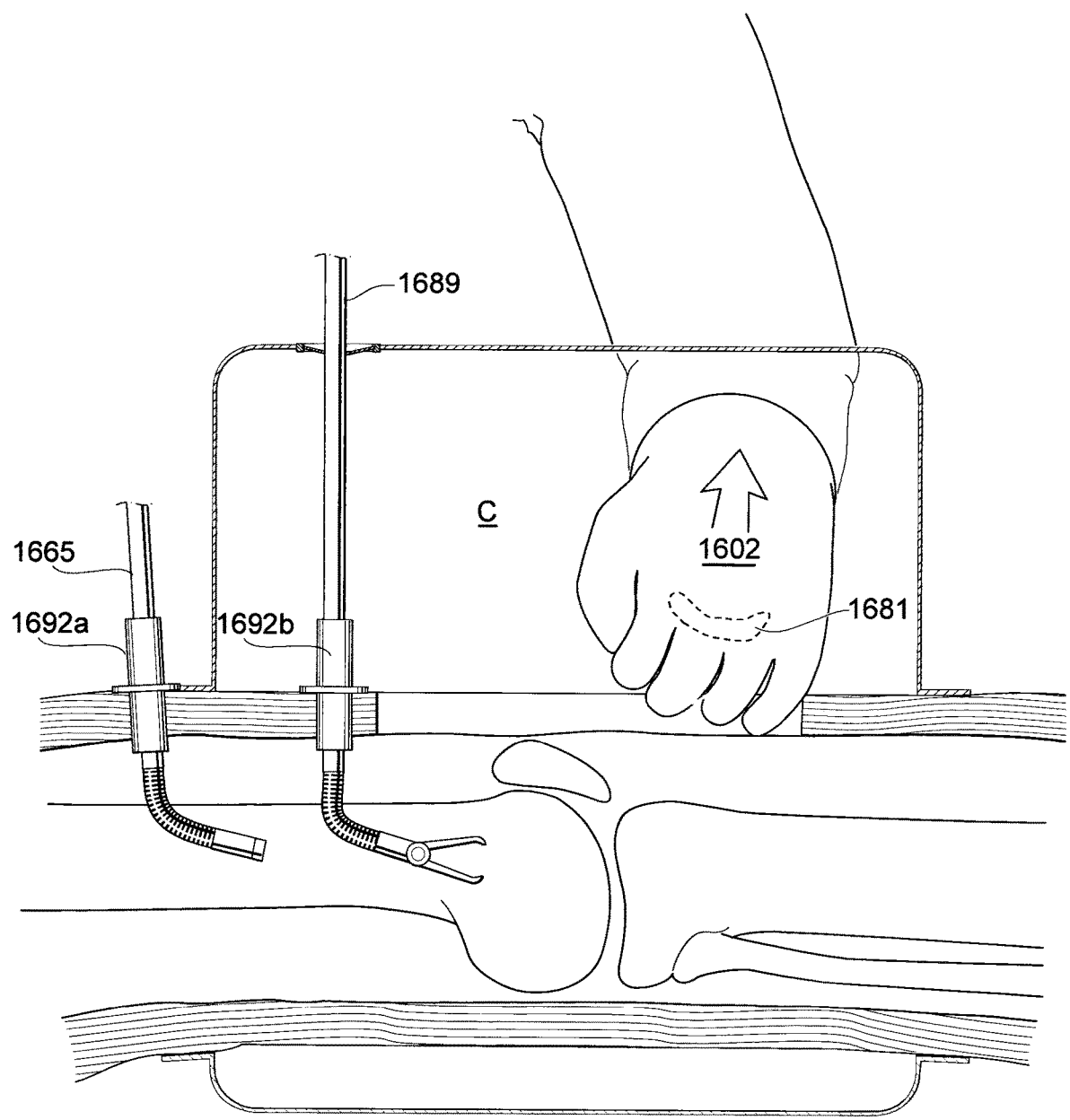

FIG. 187*b*, 187*c* shows the medical device when the surgeon removes a specimen from the knee of the patient using the glove 1602 integrated in the wall of the medical device.

Figure 187D:
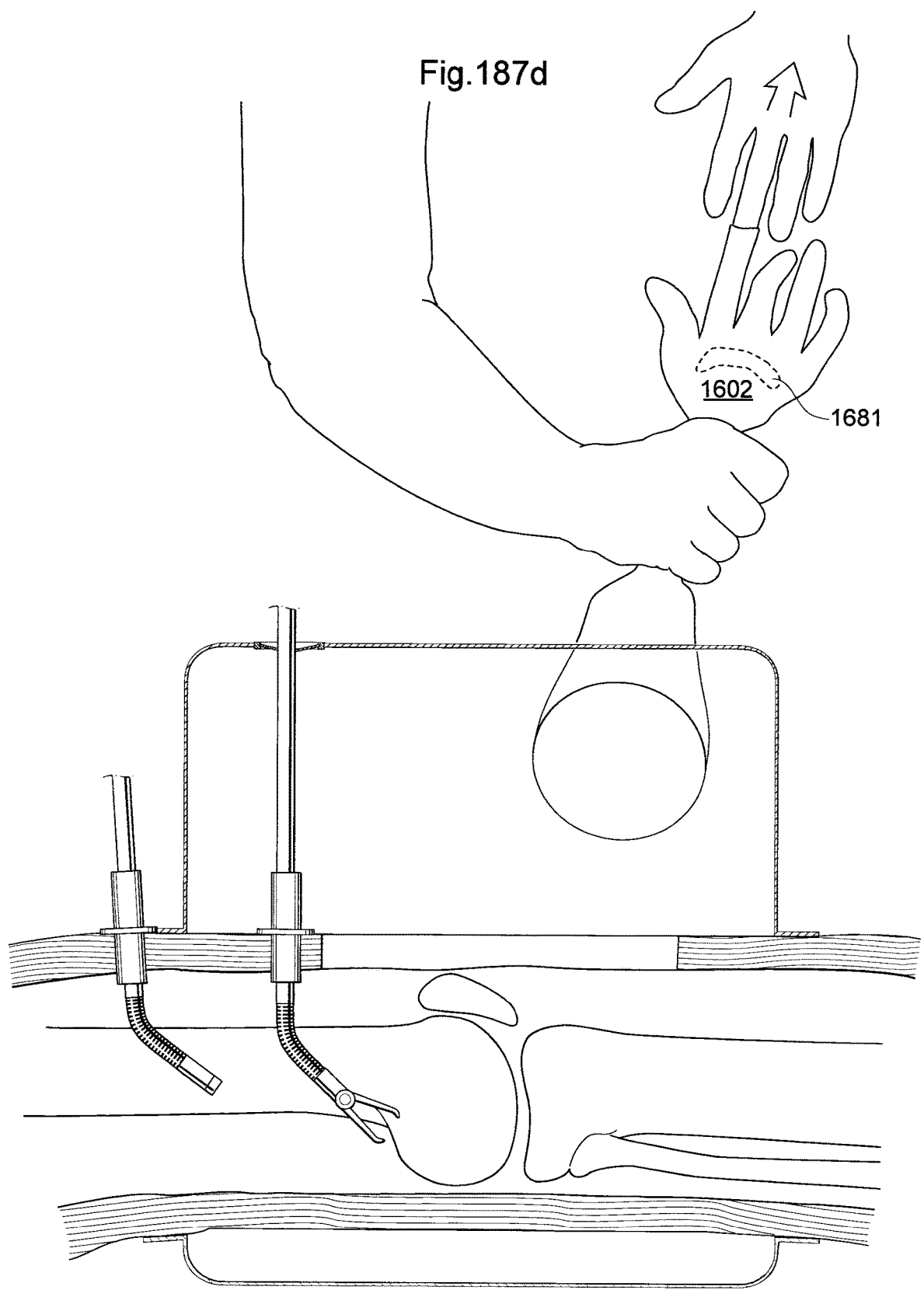

FIG. 187*d* shows the medical device, when the surgeon has turned the integrated glove inside-out such that the specimen can be contained within the integrated glove. By isolating the specimen inside of the glove, the specimen is removed both from the rest of the body of the patient and from the ambient environment, and thereby does not risk to infect any other portion of the patient's body or medical staff with any infectious disease.

Figure 188A:
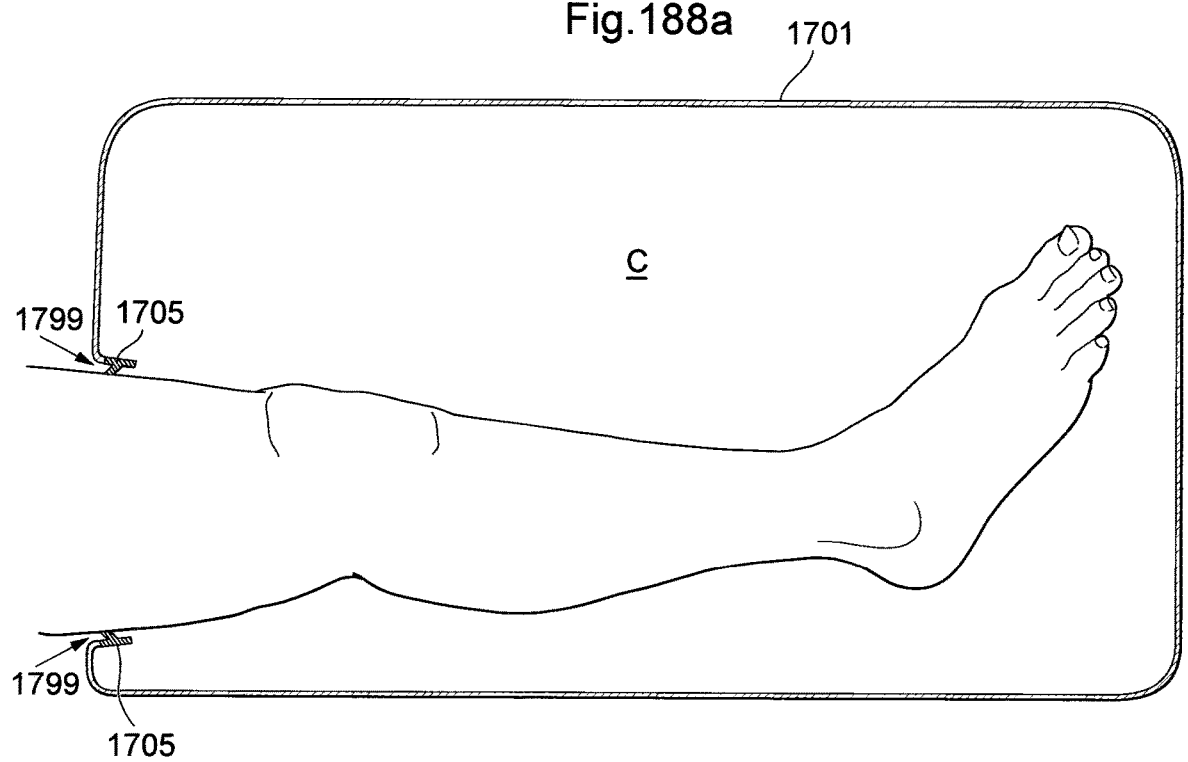
FIGS. 188a-188b shows the medical device when applied to a leg of a patient.

FIG. 188*a* shows a medical device for performing surgical procedures according to an embodiment. The medical device comprises an at least partially collapsible wall 1701 enclosing a chamber in which a sealed environment can be maintained for performing the surgical procedure. The at least partially collapsible wall comprises a hole 1797, though which the extremity can be inserted. In the embodiment shown in FIG. 188*a* the extremity is a leg of the patient. Furthermore the medical device comprises a sealing member 1705 encircling the leg of the patient and being adapted to seal between the skin of the patient and the at least partially collapsible wall 1701.

Figure 188B:
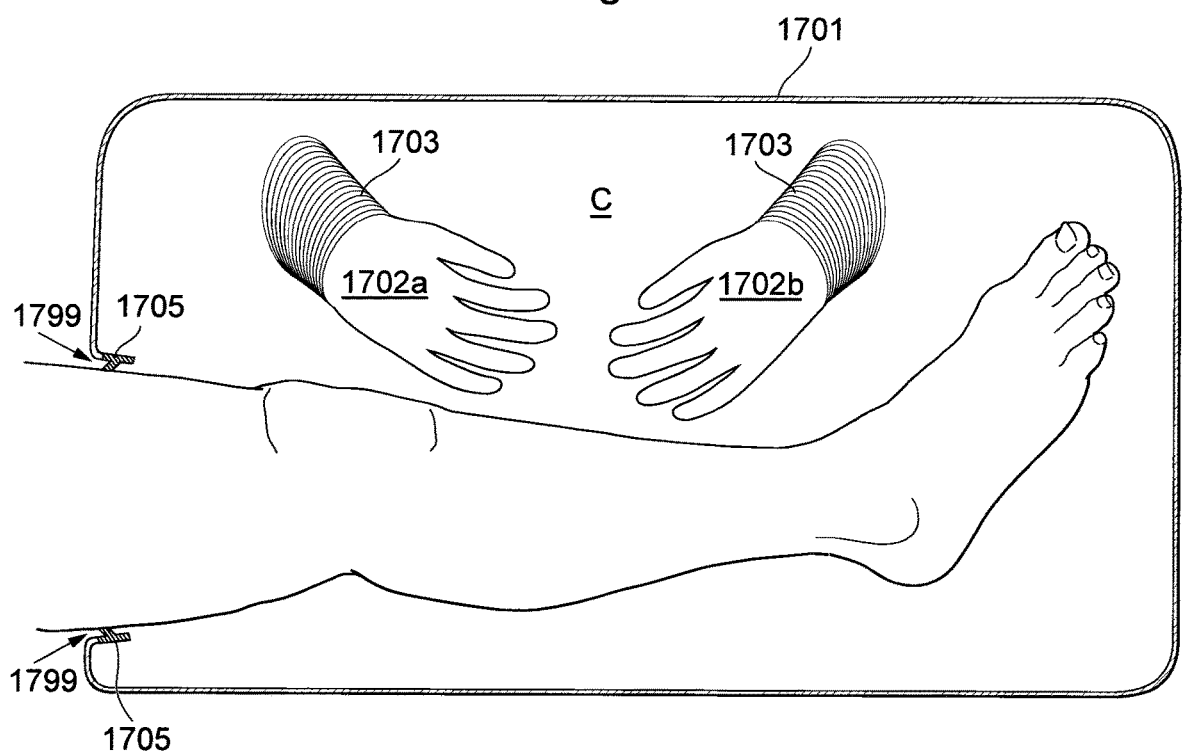

FIG. 188*b* shows the medical device in an embodiment similar to that of FIG. 188*a* with the difference that the embodiment of FIG. 188*b* further comprises two gloves 1702*a*, 1702*b* integrated in the wall 1701 enabling manual manipulation within the sealed environment. The gloves 1702*a*, 1702*b* are connected to the wall 1701 by means of pleated sections 1703 connecting the gloves 1702*a*, 1702*b* to the wall 1701 and enabling free movement of the gloves 1702*a*, 1702*b* within the sealed environment.

Figure 188C:
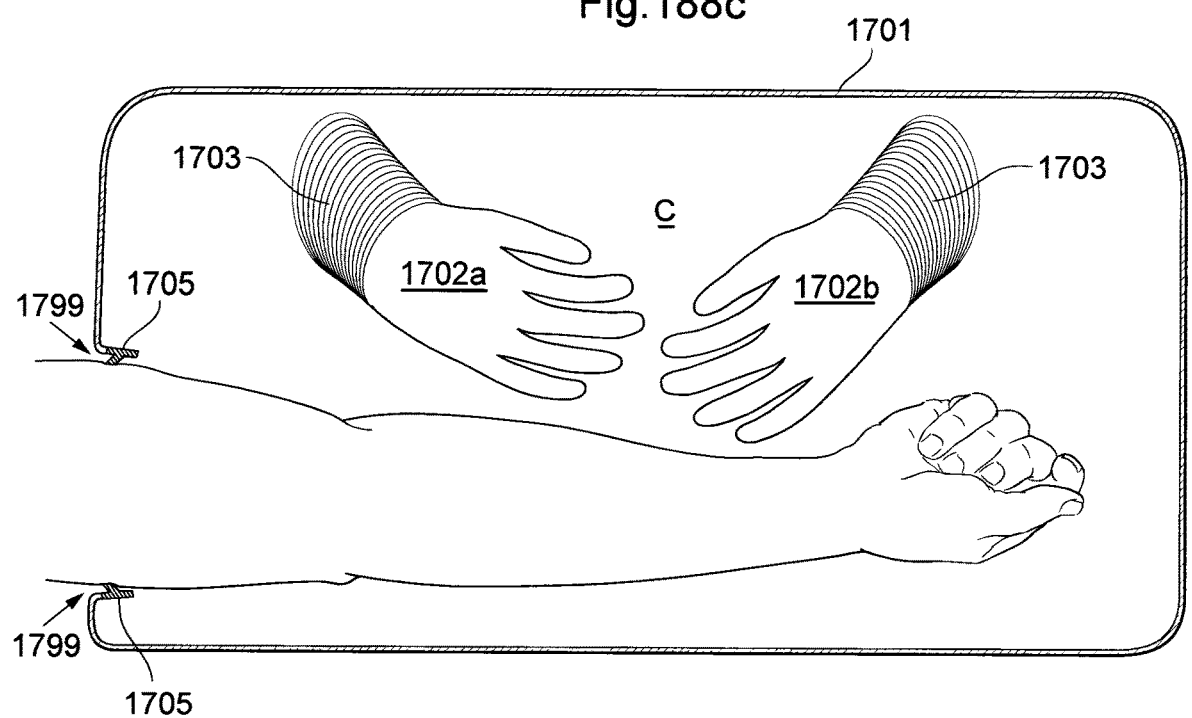
FIG. 188c shows the medical device when applied to an arm of a patient.

FIG. 188*c* shows an embodiment of the medical device similar to that of FIG. 188*b*, the difference being that the embodiment in FIG. 188*c* is adapted to receive an extremity in the form of an arm.

Figure 189A:
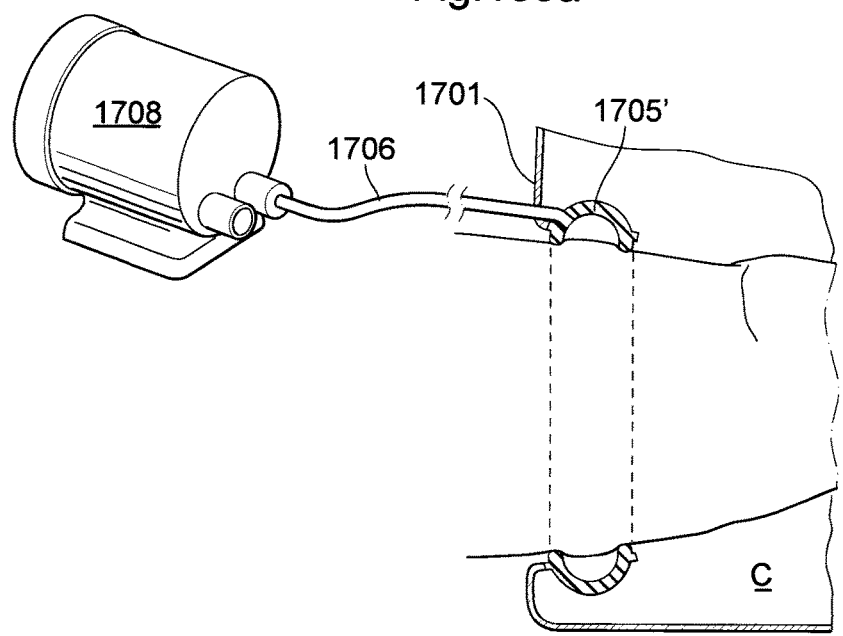
FIG. 189a shows a vacuum seal in detail.

FIG. 189*a* shows a sealing member in detail, in an embodiment in which the sealing member comprises a vacuum sealing member 1705' adapted to seal between an extremity of the patient and the partially collapsible wall 1701 by the vacuum sealing member 1705' being adapted to hold a pressure less than 1 bar (an underpressure) for creating a vacuum sealing between the skin of the patient and the medical device. The vacuum is created by a vacuum pump 1708 connected to the vacuum sealing member by means of a vacuum conduit 1706. The vacuum sealing member 5' could for example be made from a semi-rigid polymer material.

Figure 189B:
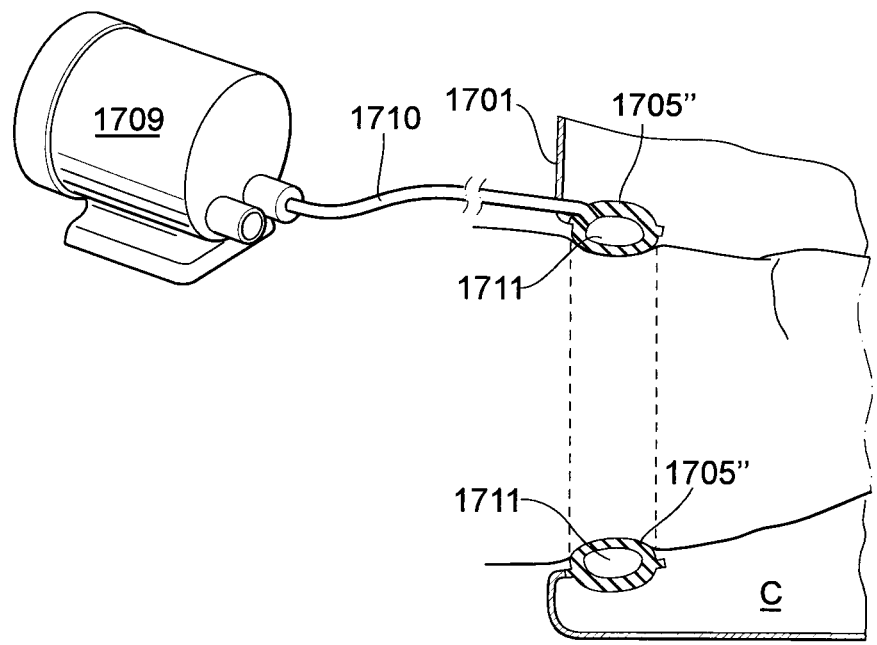
FIG. 189b shows a pressure sealing in detail.

FIG. 189*b* shows a sealing member in detail in an embodiment in which the sealing member comprises a pneumatic pressure sealing member 1705" adapted to seal between an extremity of the patient and the partially collapsible wall 1 using a pneumatic pressure pressing against the skin of the extremity. The pneumatic pressure is created by a pneumatic pump 1709 being connected to the pneumatic pressure sealing member 1705" by means of a fluid conduit 17010 adapted to transport a pressurized gas from the pneumatic pump 1709 to a cavity 1711 within the pressure sealing member 1705", the pressure sealing member 1705" being inflatable such that the size and/or shape of the cavity 1711 can be changed for allowing the pneumatic pressure sealing member to press against the skin of the extremity and thereby sealing between the extremity and the pneumatic pressure sealing member 1705". The pneumatic pressure sealing member 1705" may for example be made from an elastic material such as an elastic polymer.

Figure 189C:
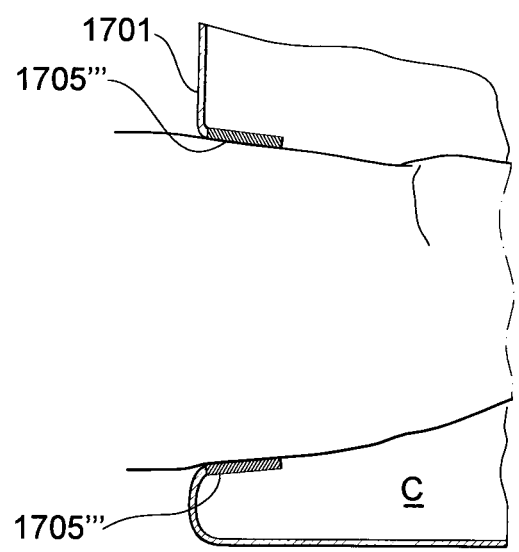
FIG. 189c shows an adhesive sealing.

FIG. 189*c* shows a sealing member in detail in an embodiment in which the sealing member comprises an adhesive sealing member 1705''' adapted to seal between an extremity of the patient and the partially collapsible wall 1701 by means of an adhesive contacting the skin of the patient and the elongated enclosure part of the medical device. In the embodiment shown in FIG. 189*c* the adhesive sealing member encircles the extremity (in this case the leg) of the patient thereby creating a seal. The adhesive may for example be a pressure sensitive adhesive such as 3M's pressure sensitive adhesive Scotch-Grip 4268-NF.

Figure 190A:
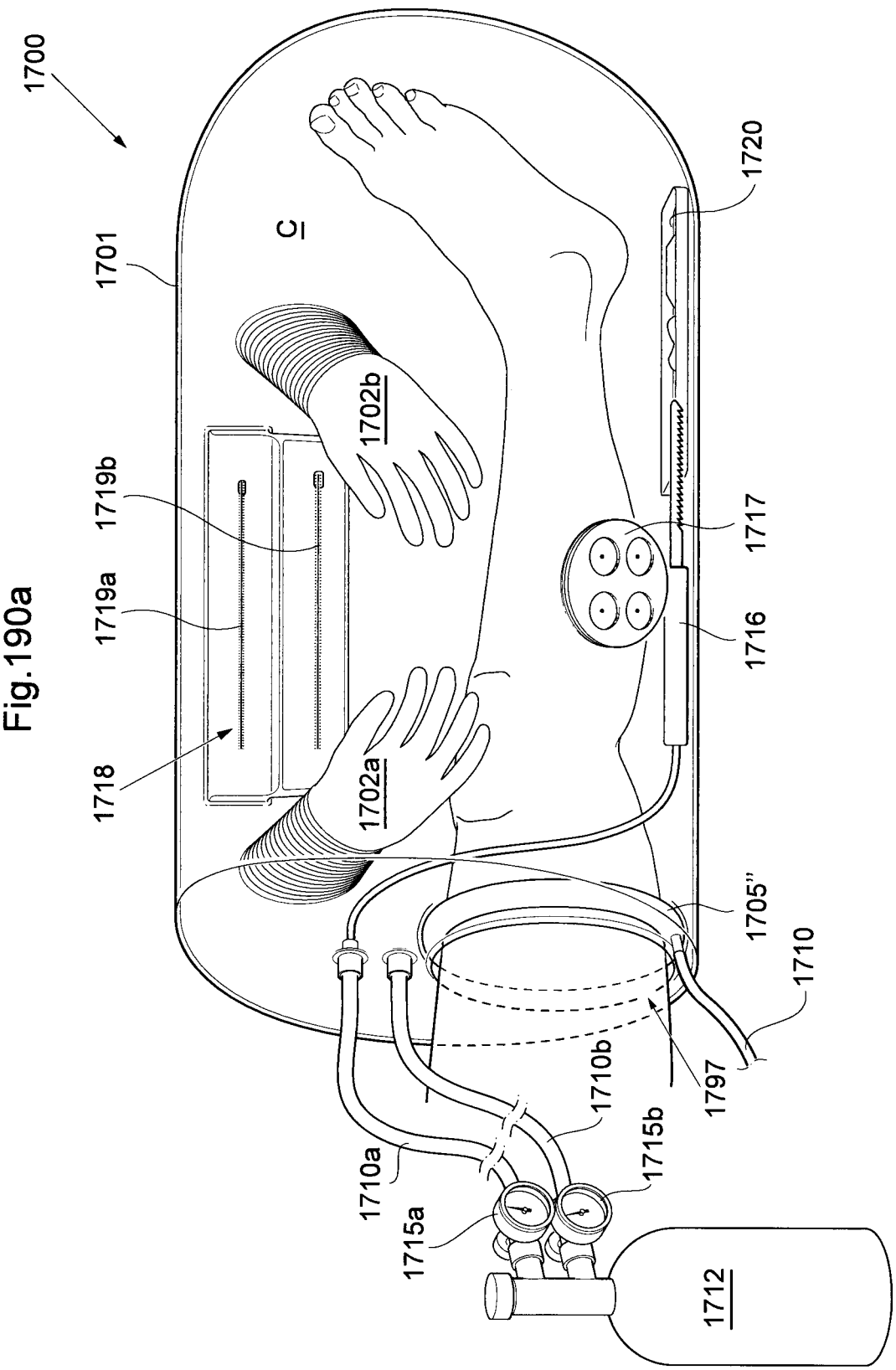

FIG. 190*a* shows an embodiment of the medical device in which the medical device comprises a partially collapsible wall 1701 having a cylindrical or tube shaped structure. The partially collapsible wall 1701 is inflatable by means of a pneumatic conduit 1713*b*, here connected to a tank 1712 containing pressurized gas. The tank is further connected to a pneumatic system 1713*a* for transferring pneumatic force into the sealed environment enclosed by the partially collapsible wall 1 and including the operating field of the extremity. Shown in the embodiment herein, the pneumatic system 1713*a* is connected to a pneumatic tool 1716, which in the example shown is an orthopedic saw, adapted to be operated within the sealed environment. The pressure provided to the sealed environment and the pneumatic system 1713*a* is controlled and monitored by a control/monitoring system 1715*a*, 1715*b* connected to the pneumatic conduits, respectively. In the embodiment shown, the partially collapsible wall is sealed to the extremity of the patient by means of a pneumatic pressure sealing member 1705" (further disclosed with reference to FIG. 189*b*) encircling the extremity. In FIG. 190*a* the medical device is shown incorporating the pneumatic pressure sealing member 1705", however it is equally conceivable that the pneumatic pressure sealing member 1705" is assisted or replaced by any of the other sealing members disclosed herein. The medical device shown in FIG. 190*a* further comprises a air-lock system 1718 comprising two zipper-closed consecutive openings 1719*a*, 1719*b*, where the outer zipper 1719*a* could be opened for placing and/or removing objects in the airlock between the zippers 1719*a*, 1719*b* from the outside of the sealed environment or chamber and the inner zipper 1719*b* could be opened from the inside of the sealed environment for placing and/or removing objects from the airlock. For example the airlock system could be used to remove a specimen from the sealed environment while keeping the environment sterile, or the airlock could be used to insert a medical device or an implant into the sealed environment. The medical device disclosed with reference to FIG. 190*a* further incorporates laparoscopic ports 1717 (which are to be regarded as optional) through which laparoscopic trocars or endoscopic instruments could be inserted. The medical device according to the embodiment disclosed with reference to FIG. 190*a* further includes an instrument mount 1720 for retaining instruments within the sealed environment.

Figure 190B:
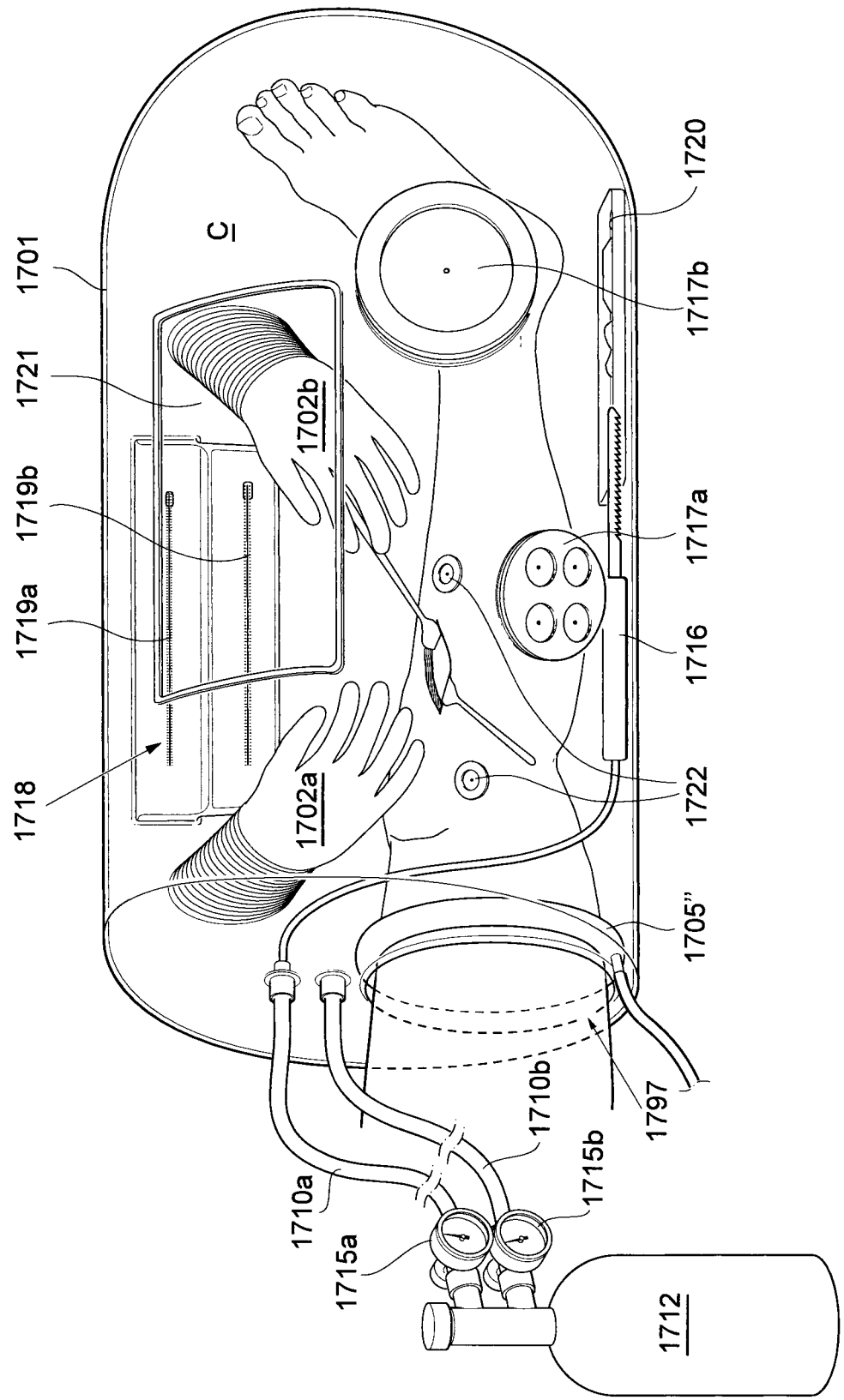

FIG. 190*b* shows a medical device similar to the medical device shown in the embodiment shown in FIG. 190*a*, however the partially collapsible wall 1701 of the medical device according to FIG. 190*b* comprises a non-collapsible transparent window 1721 for enabling viewing into the chamber C. The non-collapsible transparent window 1721 will ensure that the surgeon has adequate visual control over the procedure since the partially collapsible wall 1701, even if preferably made from a transparent material could provide limited visibility, e.g. if the medical device is not fully inflated, or in seams or bends of the material. The medical device shown in FIG. 190*b* further comprises a self sealing access wall port 1717*b*, which for example could be a port comprising a material of gel type, such as the GelPort available from Applied medical inc. Rancho Santa Margarita, Calif. The self sealing access wall port 1717*b* enables the insertion of trocars and/or instruments as well as a persons (preferably the surgeons) hand, enabling manual manipulation within the chamber C. The medical device as shown in FIG. 190*b* further comprises two body ports 1722 which incorporates endoscopic ports in direct connection with the extremity of the patient, within the chamber. The body ports 1722 could for example enable an arthroscopic procedure with trocars to be performed within the chamber C and either by the instruments being manipulated from the inside of the chamber C or by the instruments reaching from the port 1717*a* in the partially collapsible wall 1701, or the self sealing wall port 1717*b* in the partially collapsible wall 1701 and to the body port 1722 within the sealed environment of the chamber.

Figure 190C:
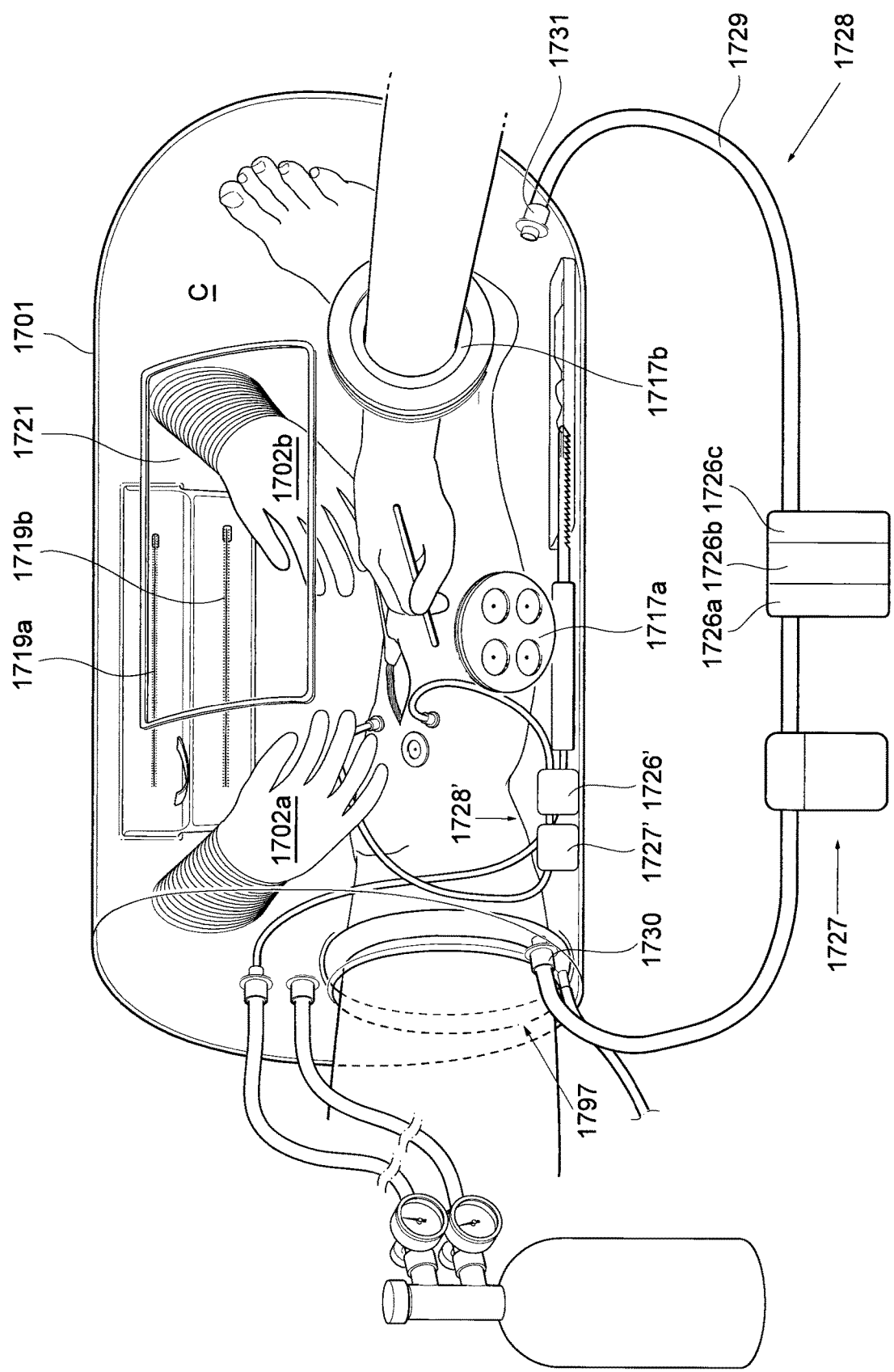

FIG. 190*c* shows the embodiment of the medical device according to FIG. 190*b* when the arm of the surgeon is inserted through the self sealing wall port 1717*b* in the partially collapsible wall 1701 for enabling manual manipulation therein. Manual manipulation through the self sealing wall port 1717*b* could for example be used as a last resort should complications occur during the procedure, or if additional hands are required for a specific step of the operation. FIG. 190*c* further shows an internal system 1728' for fluid circulation, and an external system 1728 for fluid circulation. Both systems comprises fluid conduits 1729; 1729', in the external system 1728 connected at an inlet 1730 placed in the partially collapsible wall 1701 for supplying fluid to the chamber C, and an outlet 1731 for draining the fluid from the chamber C, and in the internal system 1728' connected to an inlet 1730' in the patient's body and an outlet 1731' in the patient's body for circulating fluid in a body cavity. The fluid is circulated by means pumping units 1727; 1727' and is circulated via a sterilizing/filtering/tempering unit 1726', in the external system disclosed as containing a sterilizing 1726*a*, filtering 1726*b*, and tempering 1726*c* unit adapted to remove impurities, sterilize and heat the fluid. In embodiments where the fluid is a gaseous fluid, the filtering unit is adapted to remove particles that could be suspended in the gas. The filtering unit 1726*a* could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 26*a* could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIG. 190*d* shows the embodiment of the medical device also shown in FIG. 190*a* with the addition of a system 1726*c* for tempering the fluid entering the chamber C. The tempering part 1726*c* of the system could be provided to heat or cool the gaseous fluid inflating the medical device. In cases when the surrounding environment is cold the tempering part of the system 1726*c* could be used to raise the temperature of the chamber C to provide beneficial operating circumstances both for the patient and for the surgeon. In cases when the surrounding environment is hot, the tempering part of the system 1726*c* could be used to lower the temperature of the sealed environment both to provide beneficial operating circumstances, both for the patient and for the surgeon, and for providing a temperature inhibiting bacterial and viral infections. The tempering unit 1726*c* may comprise a temperature regulating portion for setting the required temperature. FIG. 190*d* further shows a knee joint prosthesis 1769 or a portion of a knee joint prosthesis to be implanted and being inserted into the chamber C through the air lock sluice 1718 further disclosed under reference to FIG. 190*a*.

Figure 190E:
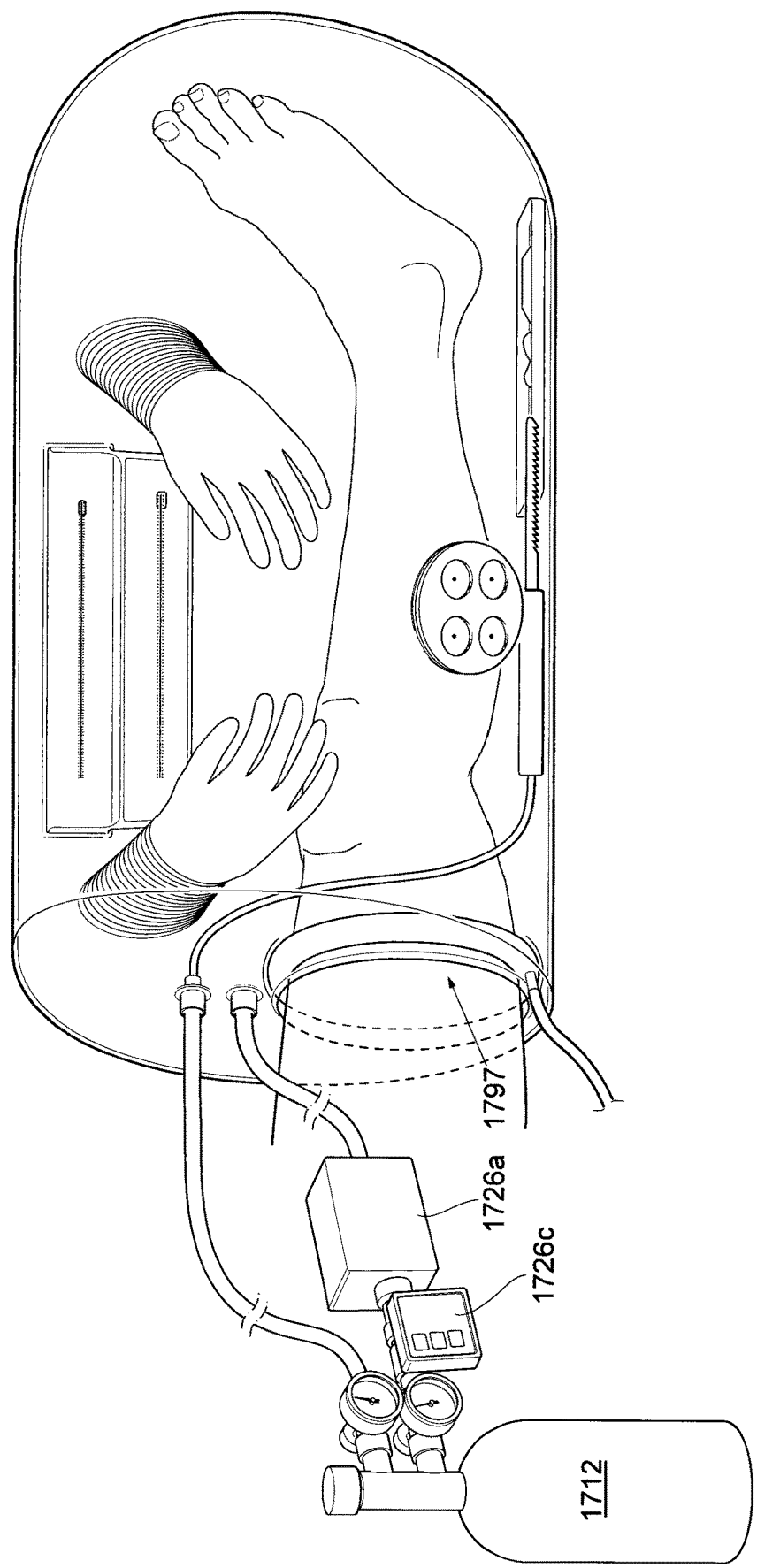

FIG. 190*e* shows the medical device according to FIG. 190*d* but further comprising a sterilizing unit 1726*a* adapted to sterilize the gaseous fluid entering the medical device. In the embodiment disclosed herein, the gaseous fluid entering the medical device originates from a pressurized tank 1712 and could be pre-sterilized, however, in other embodiments, it is conceivable that the gaseous fluid is the surrounding air which is pressurized (such as further disclosed with reference to FIG. 190*f*). In the embodiments where the surrounding air is used to inflate the medical device and constitute the operating environment this air needs to be properly sterilized.

Figure 190F:
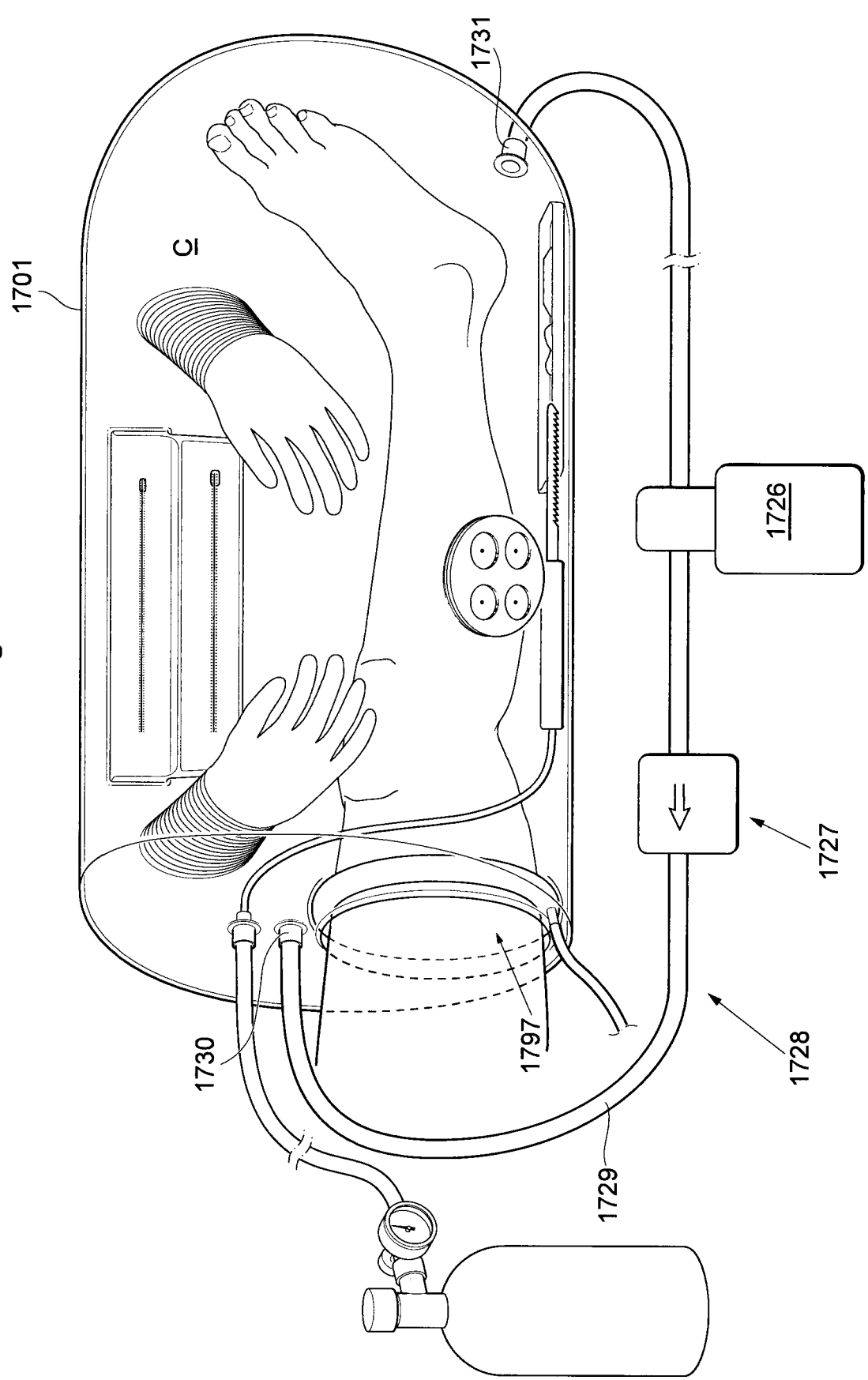

FIG. 190*f* shows an embodiment of the medical device in which the medical device comprises a system 1728 for circulating a fluid through the chamber C of the medical device. The system comprises a fluid conduit 1729 connected at an inlet 1730 placed in the partially collapsible wall 1701 for supplying fluid to the chamber C, and an outlet 1731 for draining the fluid from the chamber C. The fluid is circulated by means of a pumping unit 1727 and is circulated via a sterilizing/filtering/tempering unit 1726 adapted to remove impurities and sterilize the fluid. In embodiments where the fluid is a gaseous fluid, the filtering unit is adapted to remove particles that could be suspended in the gas. The filtering unit could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit could for example comprise a filter containing activated carbon.

Sterilizing methods could comprises the use of heat, such as electrical or chemical heat, it is furthermore conceivable that the sterilizing is performed using irradiation, such as UV-light and/or though the addition of a chemical sterilizing agent.

FIGS. 188*a*-190*f* show different embodiments of a medical device where an extremity of the patient e.g. a leg or an arm is placed in the chamber through a hole in the wall of the medical device. The medical device could for example be used for performing an amputation both in a hospital environment and in environments where the risk of infections are considerably higher, such as in third world countries or in zones of catastrophe. The medical device disclosed enables surgical procedures to be performed in a fully enclosed environment without any risk of infection disease even in very remote locations and without the access to water or electricity.

Figure 191A:
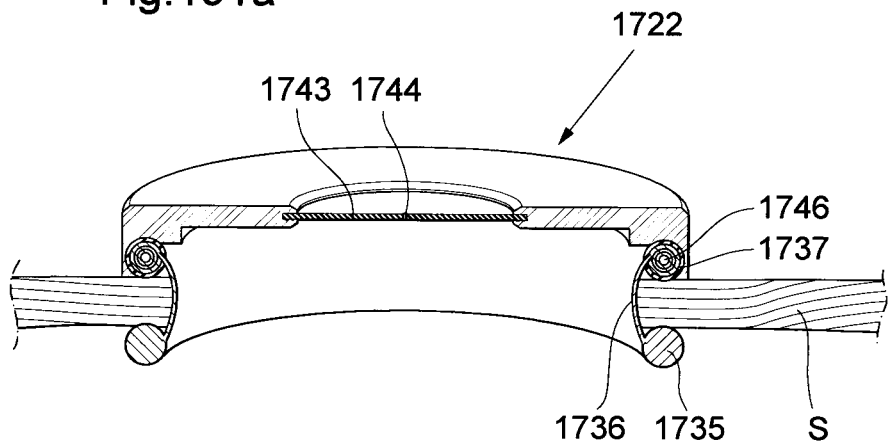
FIGS. 191a-191c shows embodiments of a self sealing port.

FIG. 191*a* shows a self sealing body port 1722 adapted to be positioned in the chamber of any of the medical devices shown in FIGS. 188*a*-190*f*, in a close-up, in section, where the self sealing body port 1722 comprises a self sealing membrane 1743 fixated to a rigid part 1745 of the self sealing port 1722. The self sealing membrane 1743 having a small self sealing hole 1744 centrally in the membrane 1743. The self sealing membrane 1743 is for example made from a gel-type material being elastic enough to enable a deformation large enough for a person's hand to pass through the small self sealing hole 1744 while still contracting enough to create an airtight seal between the sealed environment and the outside environment. The medical device being fixable to a retractor comprising one intra ring 1735 adapted to be positioned on the inside of the skin of the patient S, and one ring 1737 adapted to be placed on the outside of the wall 1701. Between the intra ring 1735 and the ring 1737 adapted to be placed on the outside of the skin of the patient a retractor membrane 1736 is positioned. The retractor membrane 1736 is preferably made from a resilient or elastic polymer material. The ring adapted to be placed on the outside of the skin S of the patient comprises an integrated roll up system 1746 which could be a spring loaded roll up system adapted to create a suitable pressure on retractor membrane 1736.

Figure 191B:
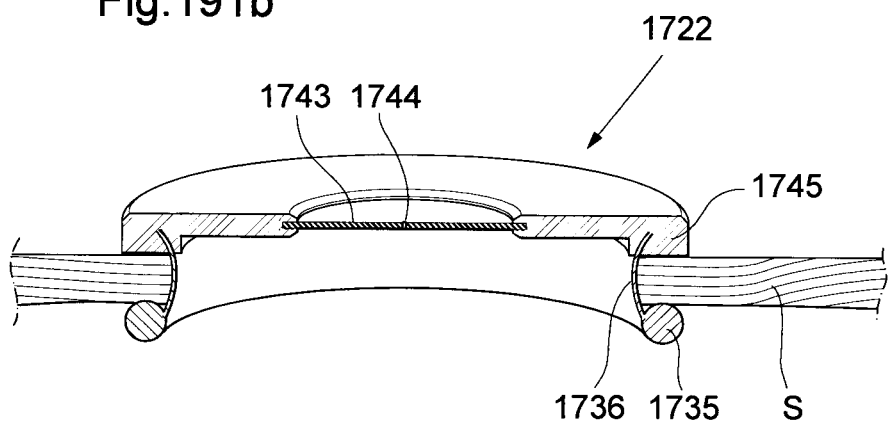

FIG. 191*b* shows an alternative embodiment of the self sealing port 1722, with the difference that the retractor membrane 1736 is made from a material elastic enough such that one end of the retractor membrane 1736 could be fixedly fixated to a rigid part 1745 of the port.

Figure 191C:
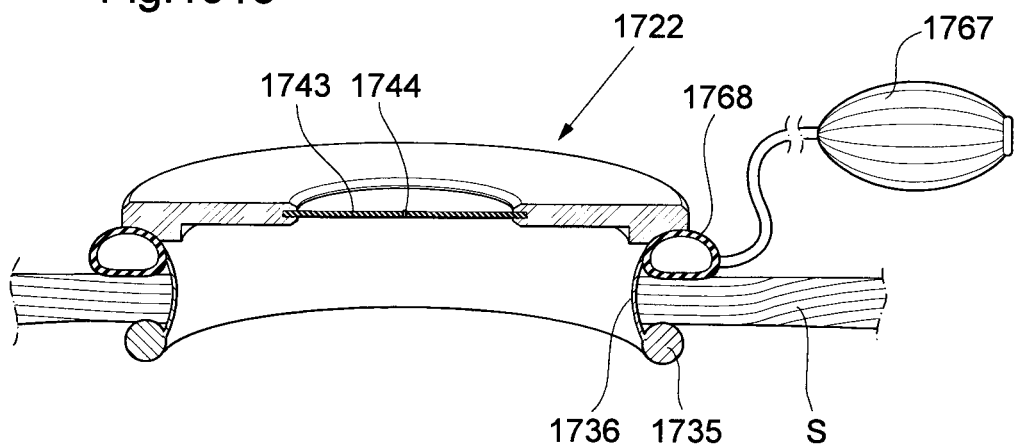

FIG. 191*c* shows an alternative embodiment of the self sealing port 1722, with the difference that the retractor membrane 1736 is connected to an inflatable bellows 1768 which in turn is connected to a pressure creating member 1767 for inflating the bellows 1768 and tighten the retractor membrane 1736 in a direction substantially perpendicular to the skin S of the patient, in line with the incision made in the patients skin S, for creating adequate sealing.

Figure 192A:
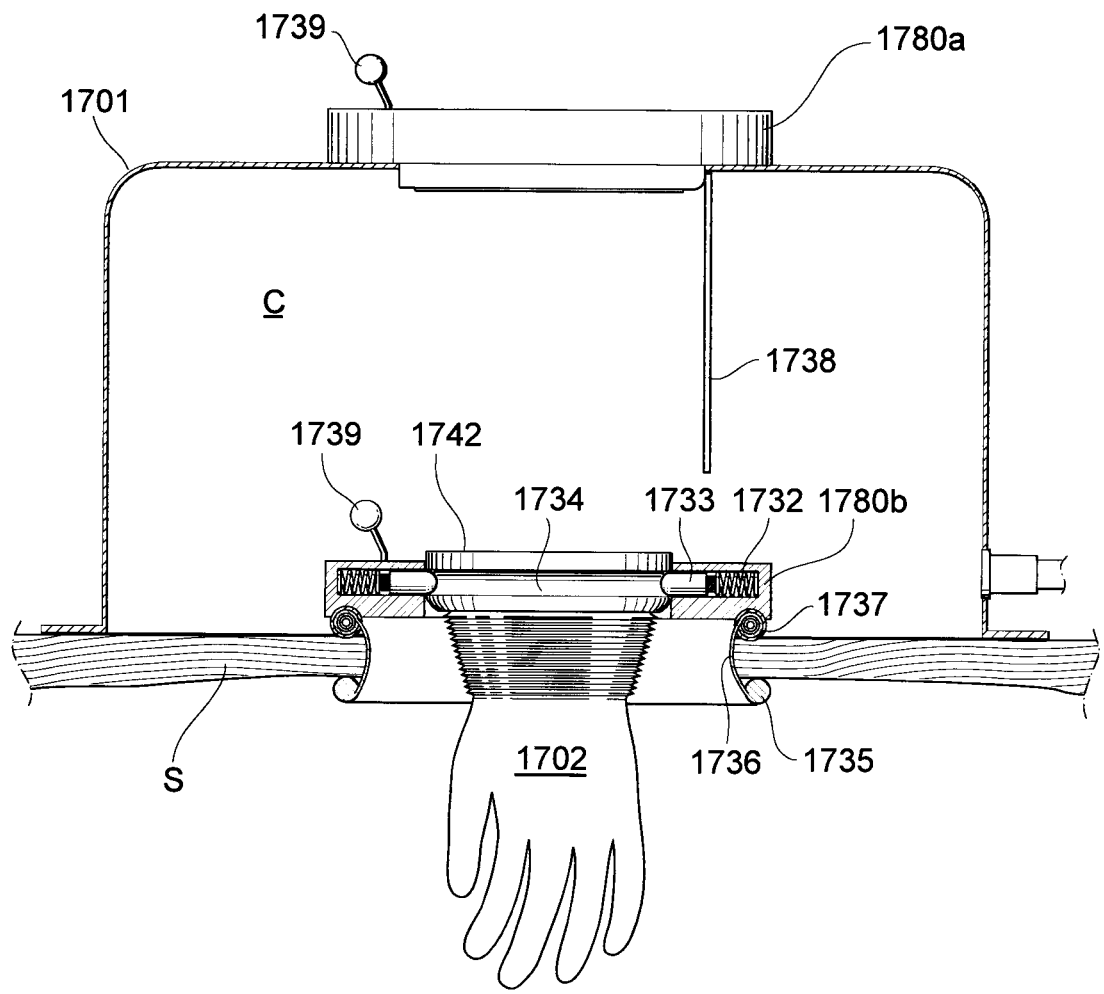
FIG. 192a shows an embodiment of the medical device, in section.

FIG. 192*a* shows an embodiment of the medical device in which the medical device comprises a wall 1701 separating the chamber C within the medical device from the ambient environment. The wall 1701 is adapted to be fixated to the skin S of the patient, by means of an adhesive or by means of a difference in pressure between the outside of the chamber C and the inside thereof. The medical device further comprises an upper 1731*a* and a lower 1731*b* coupling for fixating ring shaped objects which for example could be insets 1742 or ports. The ports may further be hand access ports, such as the self sealing port disclosed with reference to FIGS. 191*a* and 191*b*. The couplings 1731*a*; 1731*b* comprises a releasing lever 1739 for releasing the object. The lever 1739 is connected to latching members 1733 which are spring loaded 1732 from the rear in order to secure the recess or groove 1734 of the object. In the embodiment disclosed in FIG. 192*a*, the inset 1742 fixated to the lower coupling 1731*b* comprises a surgical glove 1702 enabling manual manipulation within the body of the patient. The medical device shown in FIG. 192*a* further comprises a valve member 1738 adapted to close the opening in the upper coupling 1731*a*, when the upper coupling 1731*a* is not in use.

Figure 192B:
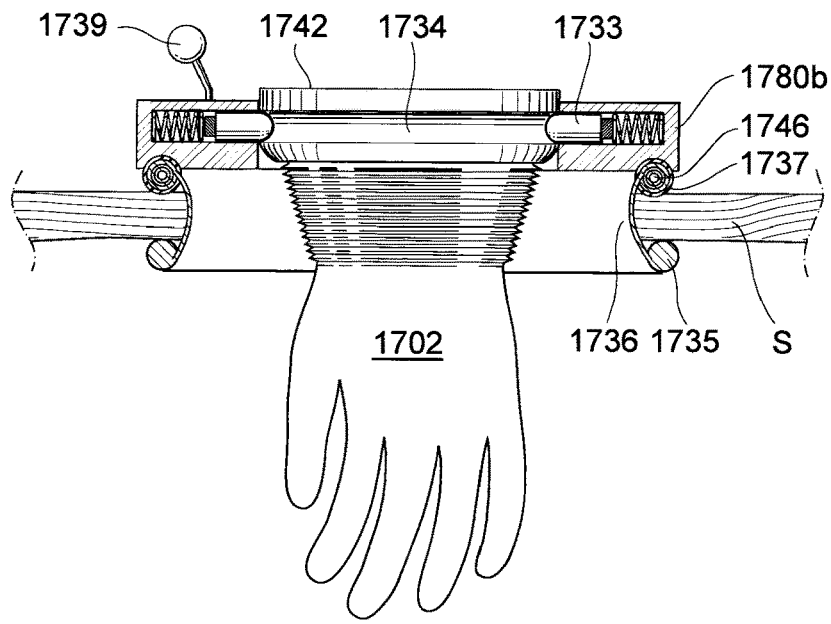
FIG. 192b shows a coupling, in section.

FIG. 192*b* shows the lower coupling 1731*b* in further detail when an inset 1742 in the form of a surgical glove 1702 is fixated to the lower coupling 1731*b*. The retractor system comprising the intra body ring 1735 and the ring 1737 adapted to be placed on the outside of the patients skin S further comprises a retractor membrane 1736 positioned such that it exerts a pressure on the cut surfaces of the incision for retracting the skin S and thereby keeping the wound open. The retractor membrane 1736 could be rolled into a roll 1746 inside of the ring 1737 adapted to be placed on the outside of the patient's skin S for tightening the retractor membrane 1736 such that the wound is kept open.

Figure 192C:
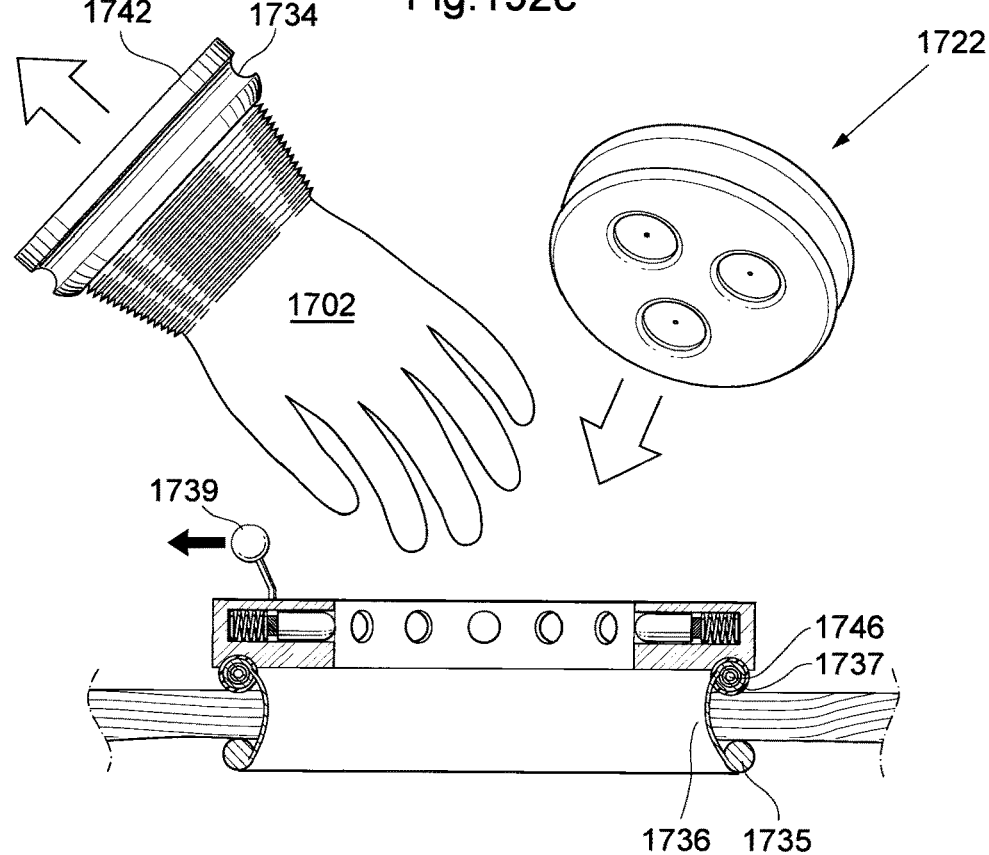
FIG. 192c shows the exchange of objects in a coupling.

FIG. 192*c* shows the changing of objects in the coupling from an inset 1742 comprising a surgical glove 1702, to a body port 1722 (multiport) comprising three endoscopic ports. To be able to quickly switch from an endoscopic system to a hand access or manual manipulation system could be of major importance if complications arise during the procedure and could remove the need for a traditional conversion from laparoscopic to open surgery, a conversion which inevitably causes problems increasing the risk of complications and/or postoperative care.

Figure 193:
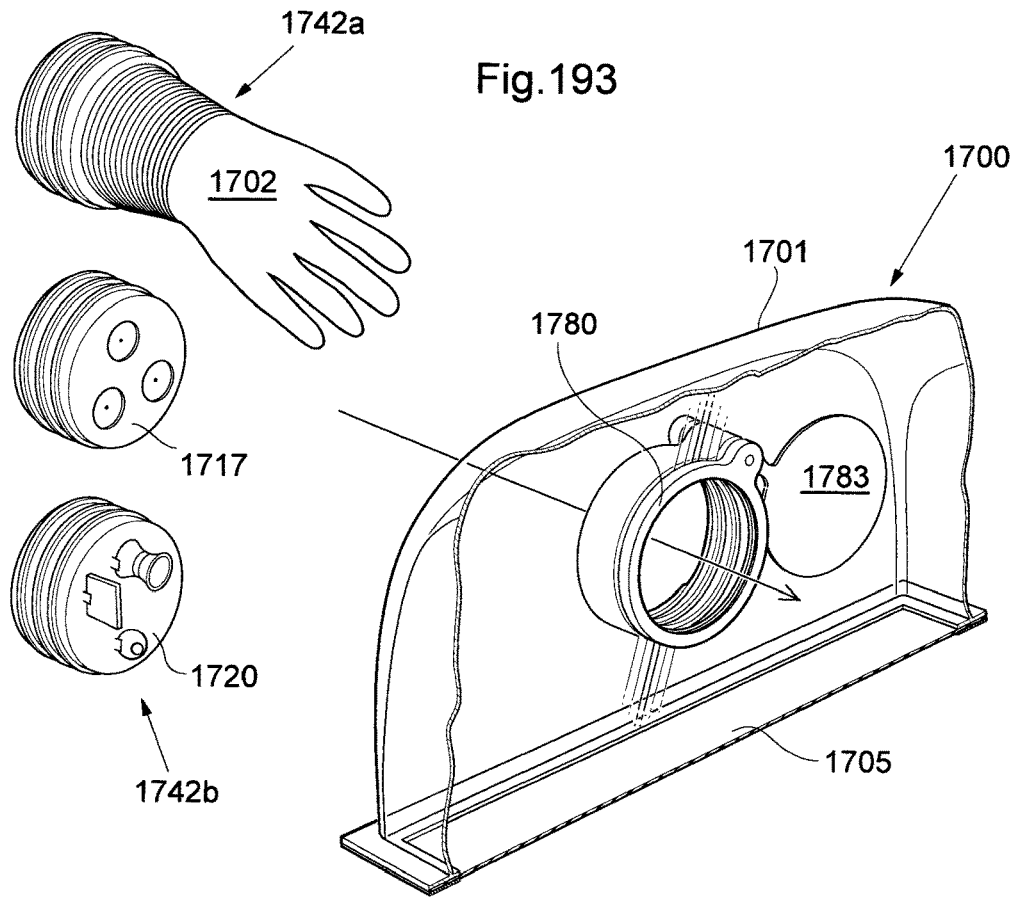
FIGS. 193-194 shows a coupling in the wall of the medical device.

FIG. 193 shows a section of the medical device 1700 showing a coupling 1780 integrated in the wall 1701. The coupling 1780 enables the changing of objects from for examples a wall port 1717, to insets 1742*a;b;c* for example comprising a surgical glove 1702 or a device or instrument mount 1720. The coupling 1780 comprises a valve member 1738 for closing the hole 1797 in the coupling 1780 when objects should be exchanged such that the sealed environment in the chamber of the medical device 1700 is maintained. The holding device 1781 could for example be adapted to hold surgical instruments and/or implants or parts of implants. The medical device is according to this embodiment adapted to be fixated to the skin of the patent by a large portion of the medical device comprising an adhesive surface 1750.

Figure 194:
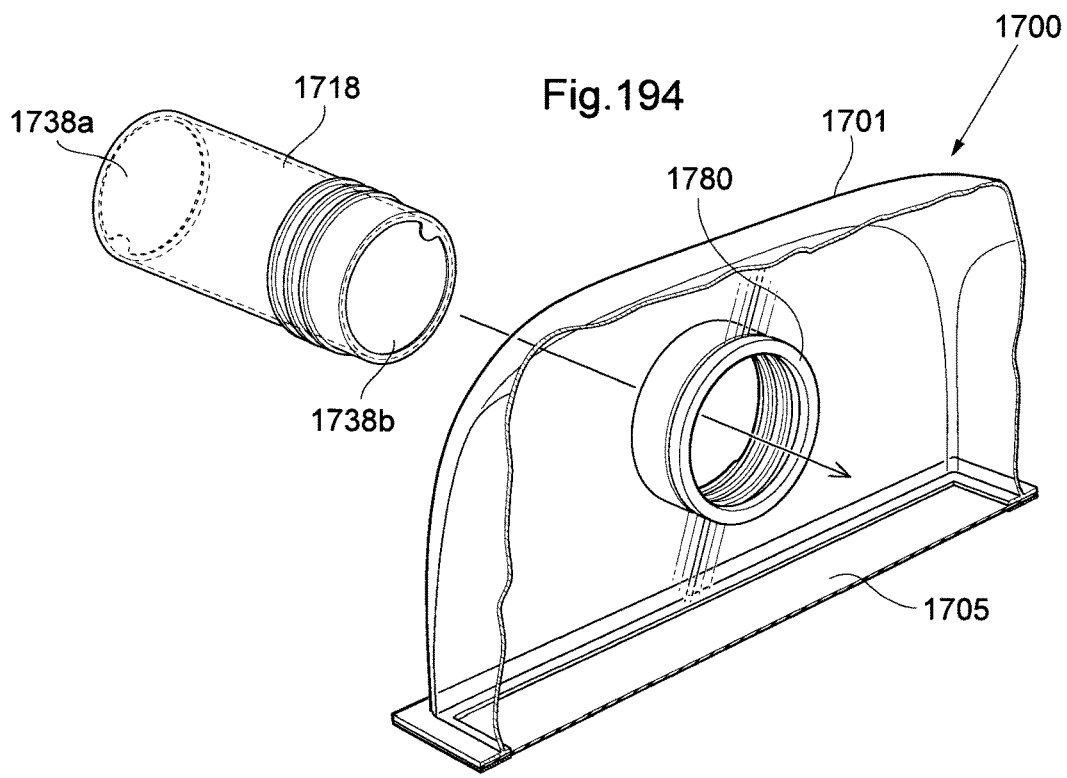

FIG. 194 shows the medical device 1700 according to the same embodiment as in FIG. 193, but when the ports of insets in the coupling 1780 have been replaced by an inset 1742*c* comprising an airlock sluice 1718 comprising a first 1738*a* and second 1738*b* valve member and a sluice chamber 1718 placed between the first 1738*a* and second 1738*b* valve members. The airlock sluice 1718 can be used to enable transfer of objects from the ambient environment to the chamber C and vice versa.

Figure 195A:
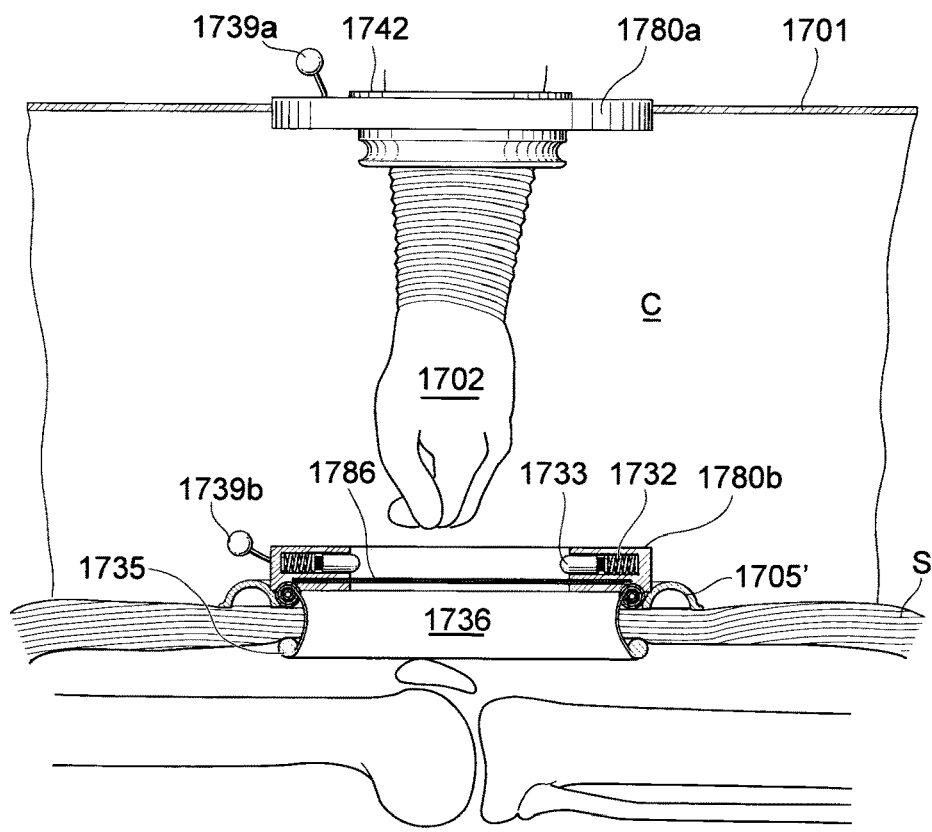
FIGS. 195a-195b shows the medical device when used.

FIG. 195*a* illustrates how a cut in the patient's skin S has been created by the surgeon by means of an inset 1742 comprising a glove 1702 latched to a upper coupling 1380*a*. The upper coupling 1780*a* is fixated and sealed by means of the vacuum sealing member 1705' since the seal that is provided partially within the patient's body 1735; 1736 cannot be mounted until the cut in the patient's skin S is concluded. The two different seals 1705'; 1735; 1736 disclosed could in some embodiments be replaced by only one of the seals, or by a different seal, such as the adhesive of pressure seals disclosed in other portions herein. The lower coupling 1780*b* comprises an iris valve 1786 which may be opened to enable the surgeon to access the inside of the patient's body, or closed to separate the patient's body from the chamber C enclosed by the medical device.

Figure 195B:
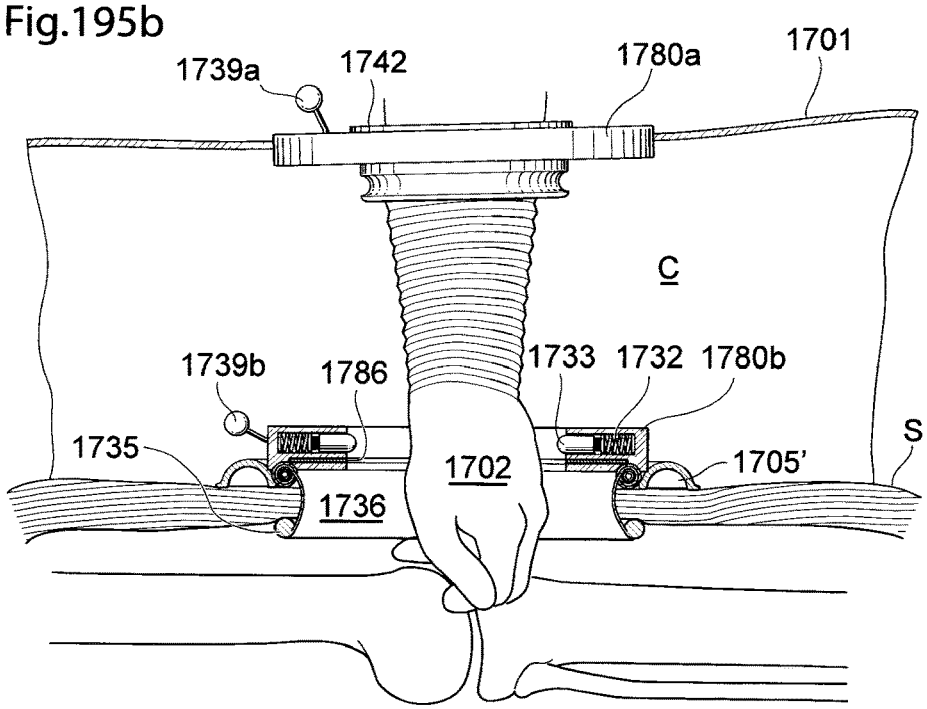

FIG. 195*b* shows the port, when the second sealing 1735, 1736, 1737 have been placed in the incision cut in the patient's skin S. The wall 1701 enclosing the chamber C is elastic or flexible which enables the surgeon to move the upper coupling 1780*a* in relation to the lower coupling 1780*b* for getting better access to different angles within the patient's body, for example for removing a specimen or placing a prosthetic part in the knee joint. The embodiment of FIG. 195b further comprises a non-penetrable valve 1786 placed in the lower coupling 1780b for closing the coupling such that the chamber C is sealed from at least one of the ambient environment and a cavity in the patient. The closing of the iris valve 1786 enables activity within the chamber C without maintaining a pressure in the chamber C, at the same time as a pressure and/or sealed environment can be maintained within the body of the patient.

Figure 196:
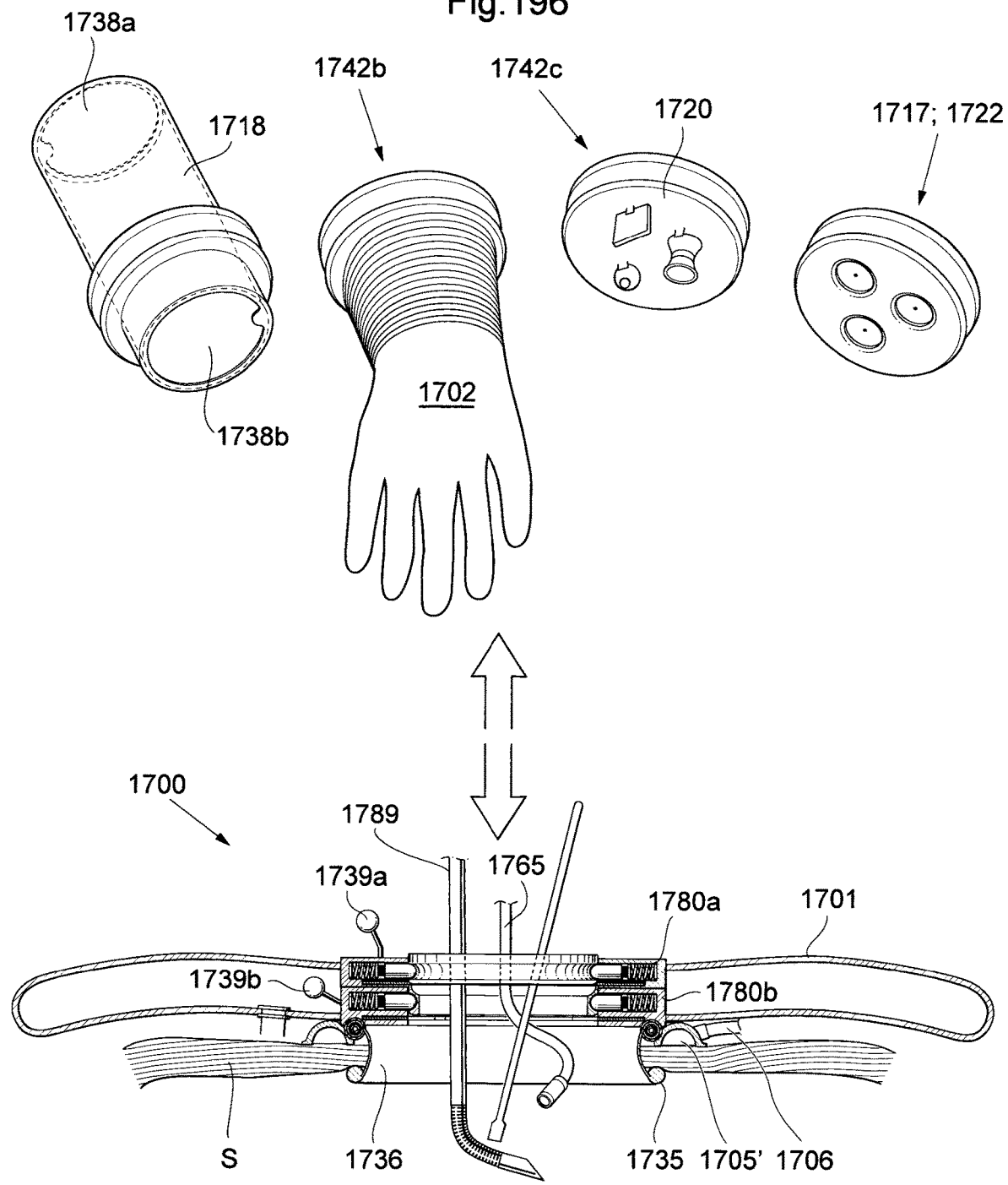
FIGS. 196-197 shows embodiments of the medical device, in section.

FIG. 196 shows the medical device 1700 adapted to be at least partially placed in an incision cut in a patient's body. The medical device 1700 comprises an upper 1780a and lower 1780b coupling adapted be interconnected to form an interconnected coupling. The upper coupling 1780a is adapted to be disconnected from the lower coupling 1780b. The upper coupling 1780a is connected to a first portion of a flexible wall 1701, and the lower coupling 1780b is connected to a second portion of the flexible wall 1701. The flexible wall 1701 forms a chamber C in which a sealed environment can be maintained, the chamber C is heavily enlarged when the upper coupling 1780a is disengaged from the lower coupling 1780b, thus creating operating space within the chamber C enclosed by the wall 1701. The upper 1780a and lower 1780b couplings comprises latching systems for locking an inset 1742b;c or port 1717;1722. The inset may for example be an inset comprising a glove 1702 for manual manipulation within the body of the patient, or within the enclosed chamber, or an inset 1742c comprising a device/instrument mount 1720 for holding instruments or medical devices within the chamber C. Alternatively, the insets may be replaced by an airlock sluice 1718 or a port 1717; 1722 comprising a plurality of ports enabling the insertion of a surgical instrument into the chamber C or body of the patient.

In the embodiment shown in FIG. 196 the medical device 1700 is fixated to the body of the patient by means of a vacuum fixating member 1705' connected to a vacuum conduit 1706, which in turn is connected to a vacuum source. Furthermore, the medical device in FIG. 196 comprises a second sealing device having a first sealing member 1735 adapted to be positioned at the inside of the patient's skin S around an incision to be performed in the skin S and a second sealing member 1737 adapted to be positioned at the outside of the patient's skin S around the incision, and a spring-loaded or elastic connecting member 1736 sealingly interconnecting the first 1735 and second 1737 sealing members. The spring-loaded or elastic connecting member 1736 seals between at least one of the medical device, and the skin S of the patient, and the first sealing member 1735 and tissue of the patient. As shown in FIG. 196 the surgeon can use the port, functioning as a body port 1722 to insert endoscopic instruments into the body of the patient.

Figure 197:
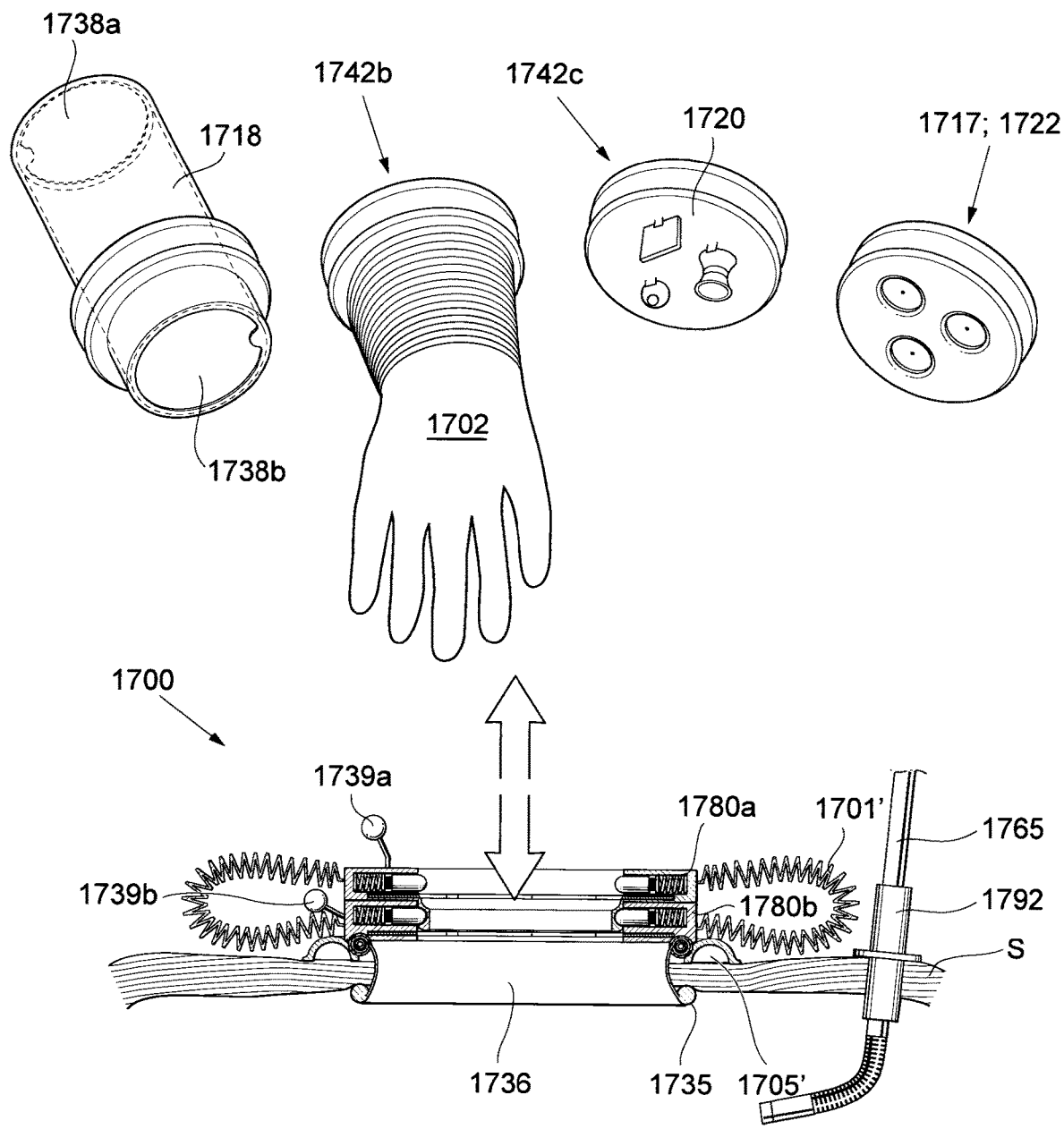

FIG. 197 shows the port in an embodiment very similar to the embodiment shown in FIG. 196 but with the difference that the wall 1701' has a bellows structure and thus taking up less space when in its deflated state. The bellows structure enables the wall 1701' to be packaged in a small package and thus not obstructing the procedure. In some applications the wall 1701' can be used only on very special occasions or emergencies, such as when some part of the procedure goes wrong and conversion from laparoscopic surgery to more open surgery is required. The use of the inflated chamber C then enables the pressure in the cavity within the patient to be maintained since the chamber C can hold a pressure. FIG. 1705i also shows a camera 1765 placed in the skin S of the patient to enable visual inspection of a cavity within the patient's body, the camera 1965 being placed outside of the ports and chamber C.

FIG. 198a shows an embodiment of the medical device 1700, in which the medical device 1700 comprises a glove 1702 integrated in the wall 1701 and a camera 1765 placed through a trocar 1792 placed in the skin S outside of the medical device 1700. The medical device 1700 further comprises a trocar 1792 placed inside the chamber C through an incision in the skin S of the patient and into an area of the knee of the patient. FIG. 198a schematically illustrates how the surgeon manipulates the knee in the chamber using the glove 1702.

Figure 198B:
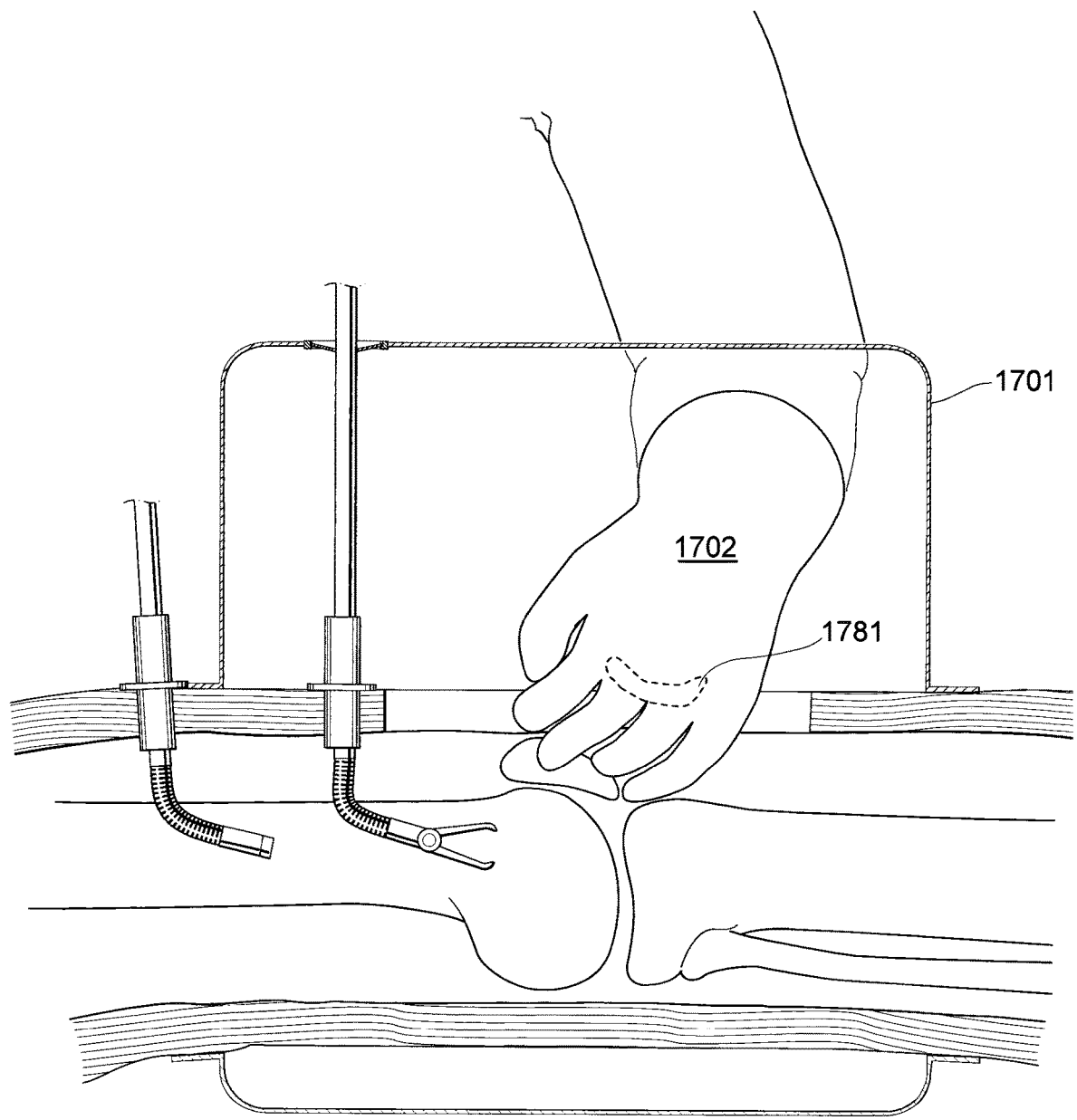
Figure 198C:
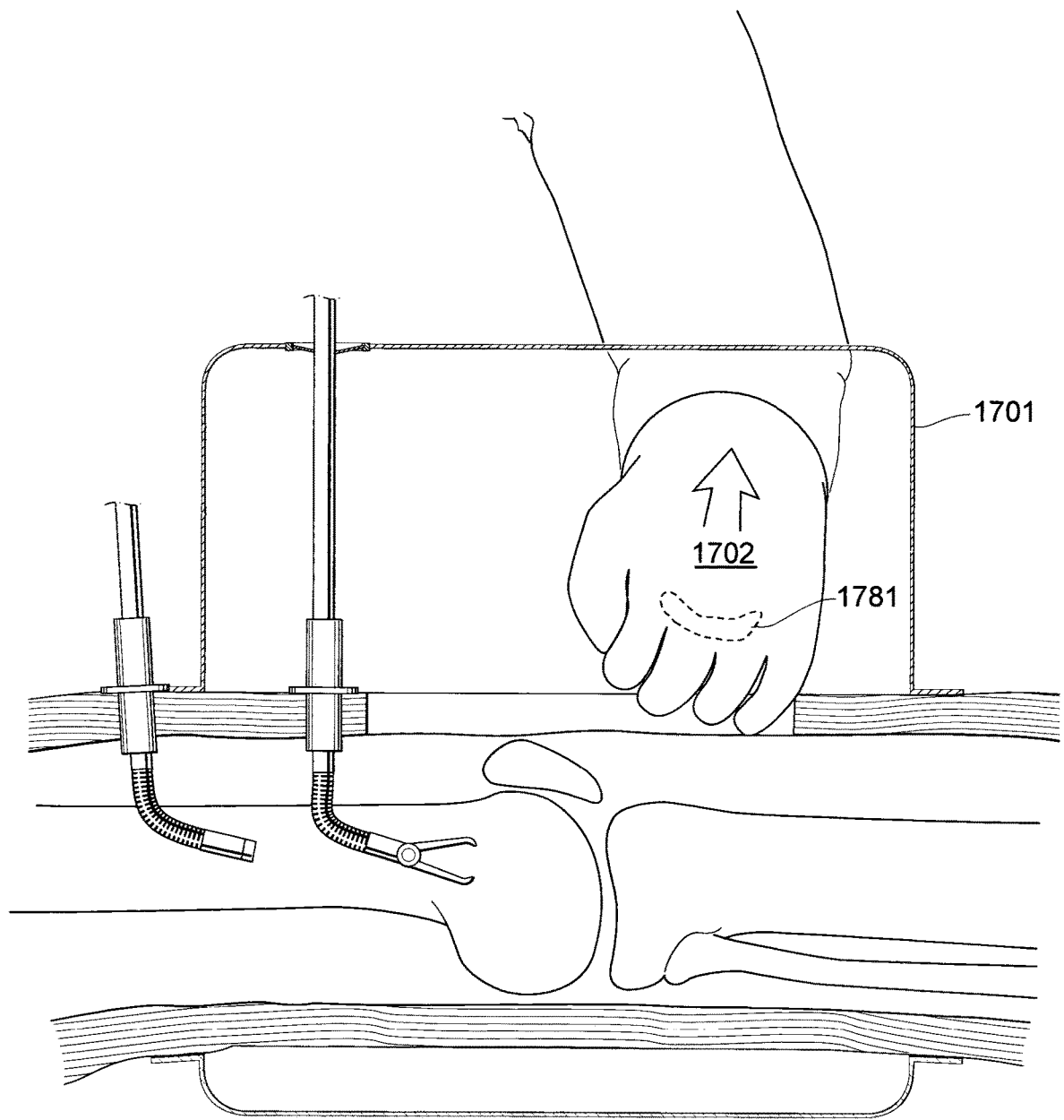

FIG. 198b, 198c shows the medical device when the surgeon removes a specimen 1781 from the knee of the patient using the glove 1702 integrated in the wall 1701 of the medical device.

Figure 198D:
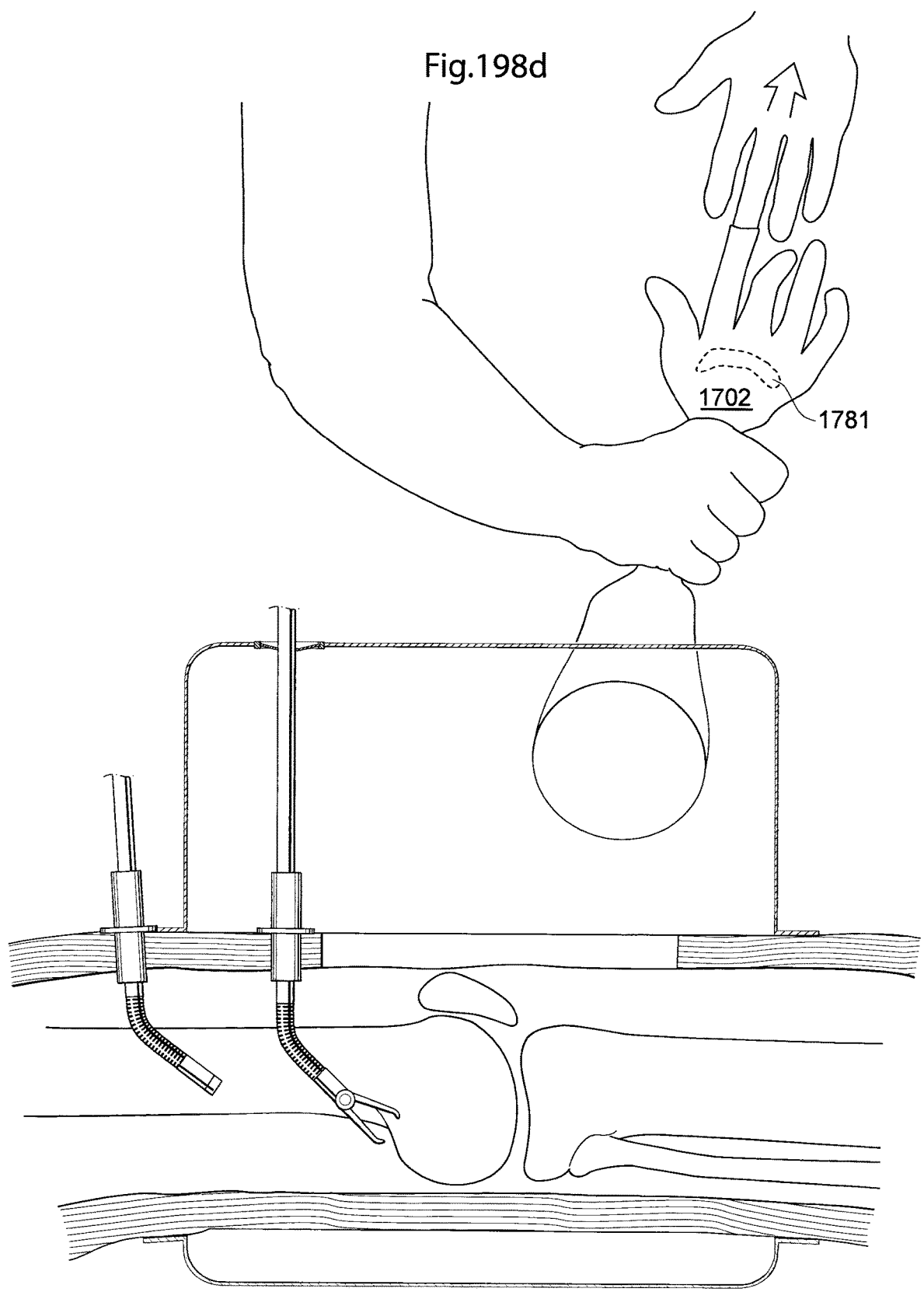

FIG. 198d shows the medical device, when the surgeon has turned the integrated glove 1702 inside-out such that the specimen 1781 can be contained within the integrated glove 1702. By isolating the specimen 1781 inside of the glove 1702, the specimen 1781 is removed both from the rest of the body of the patient and from the ambient environment, and thereby does not risk to infect any other portion of the patient's body or medical staff with any infectious disease.

Figure 199:
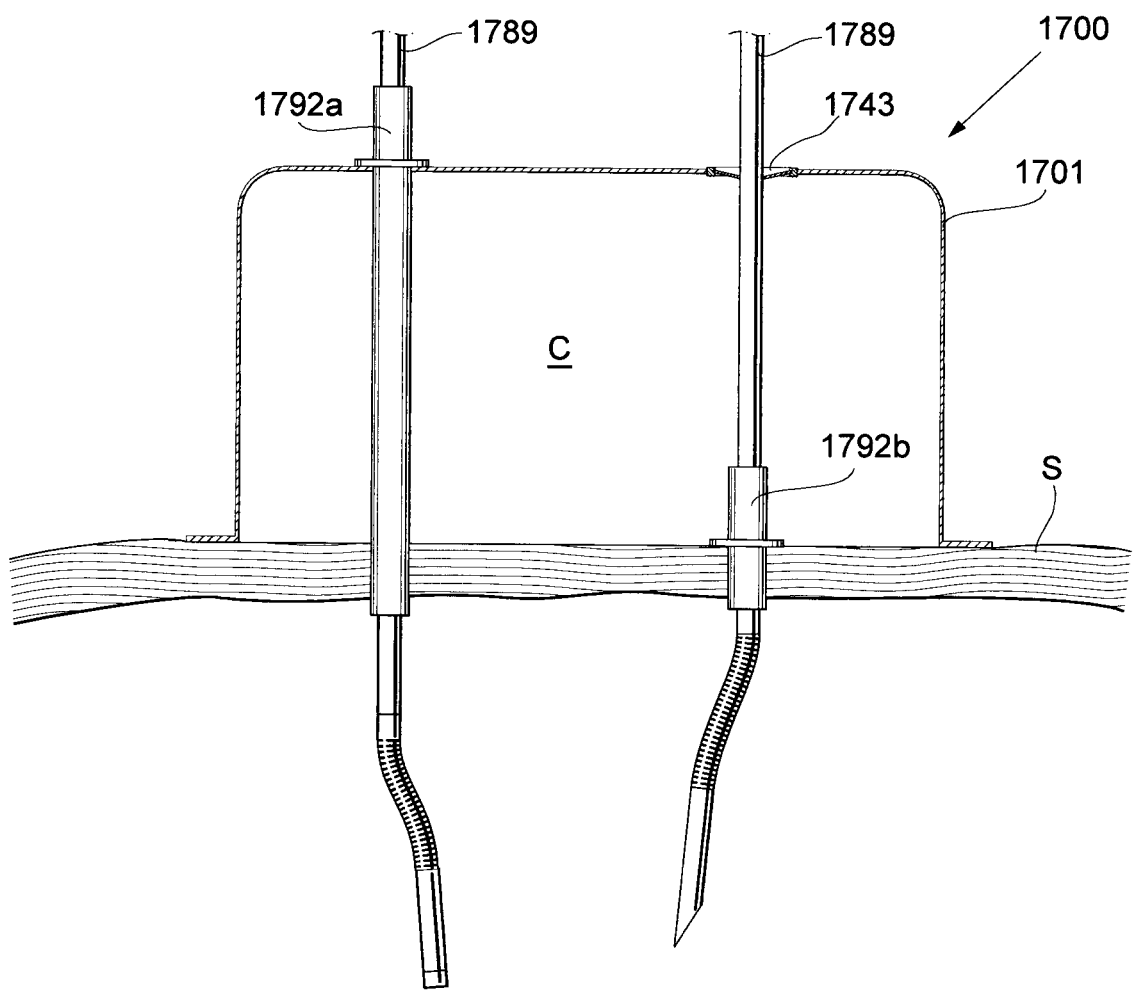
FIG. 199 shows an embodiment of the medical device comprising trocars, in section.

FIG. 199 shows the medical device 1700 according to an embodiment in which the medical device 1700 comprises a wall 1701 placed on the patient's skin S and thereby enclosing a chamber C for creating a sealed environment. The medical device 1700 further comprises two trocars 1792a; 1792b, one 1792a traveling through both the wall 1 of the medical device 1700 and the skin S of the patient and thus enabling an endoscopic instrument 1789 to be inserted into the patient through both the wall 1701 of the medical device 1700 and the skin S of the patient through one single trocar 1792a. The other trocar 1792b being placed inside the chamber C and enabling an endoscopic instrument 1789 to be inserted through the skin S of the patient. The endoscopic instrument 1789 is in this embodiment inserted into the chamber C enclosed by the wall 1 through a membrane 1743 in the wall 1701 adapted to seal against the tool 1789.

Figure 200:
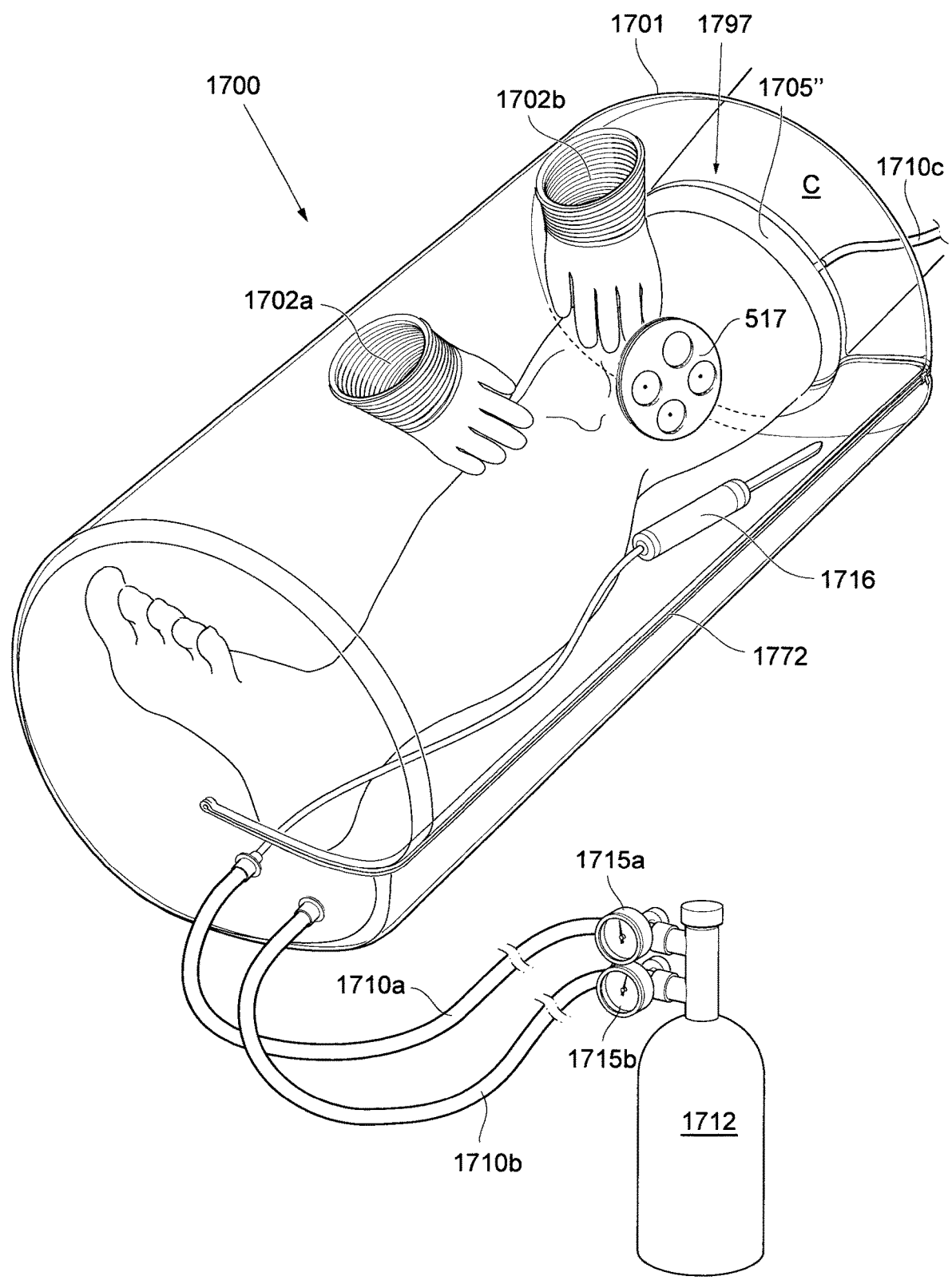
FIGS. 200-201 shows embodiments of a medical device, in perspective.

FIG. 200 shows the medical device 1700 in an embodiment similar to, and possible to adapt with the features of, the embodiments shown in FIGS. 190a-190f. The wall comprises a hole 1797 through which an extremity of the patient is inserted. The hole 1797 is surrounded by a sealing device 1705" adapted to seal against the skin S of the patient by pressing against the skin S by means of a hydraulic or pneumatic force being distributed by means of a fluid conduit 1710c. The wall 1701 is placed around the patient's extremity (in this case leg) by being possible to open by means of a connection 1772 in the wall 1701 comprising a sealing and a closing device designed as a zipper.

Figure 201:
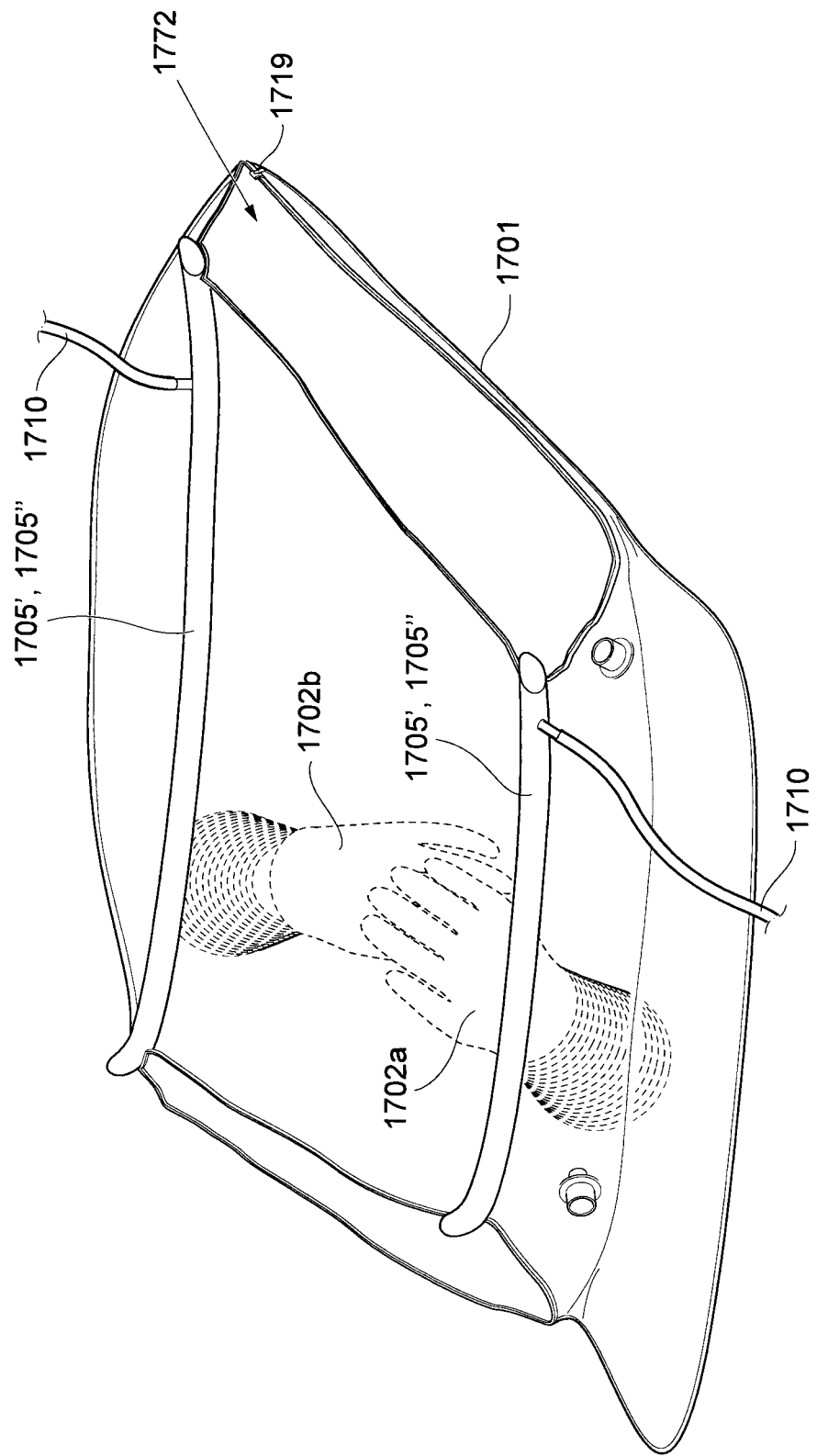

FIG. 201 shows the medical device of the embodiment shown in FIG. 200 when in its open state. The medical device comprises vacuum sealing member 1705' (which could be replaced by a pressure sealing member) adapted to encircle the extremity of the patient when the medical device is assembled. The connection 1772 between different portions of the wall is in 201 is designed as a zipper 1719 adapted for closing connecting the different portions of the wall 1701 to each other for creating the chamber C.

FIG. 202a shows the medical device in an embodiment similar to other embodiments shown herein, the difference being the medical device is adapted to contain a liquid such that an arthroscopic procedure with liquid can be performed. The embodiment shown in FIG. 202a is shown with in an embodiment where the medical device is adapted for an arthroscopic hip joint procedure and prosthetic parts and tools are pre-placed inside of the chamber C within the wall 1701 and thus within the liquid inside of the chamber C.

Figure 202B:
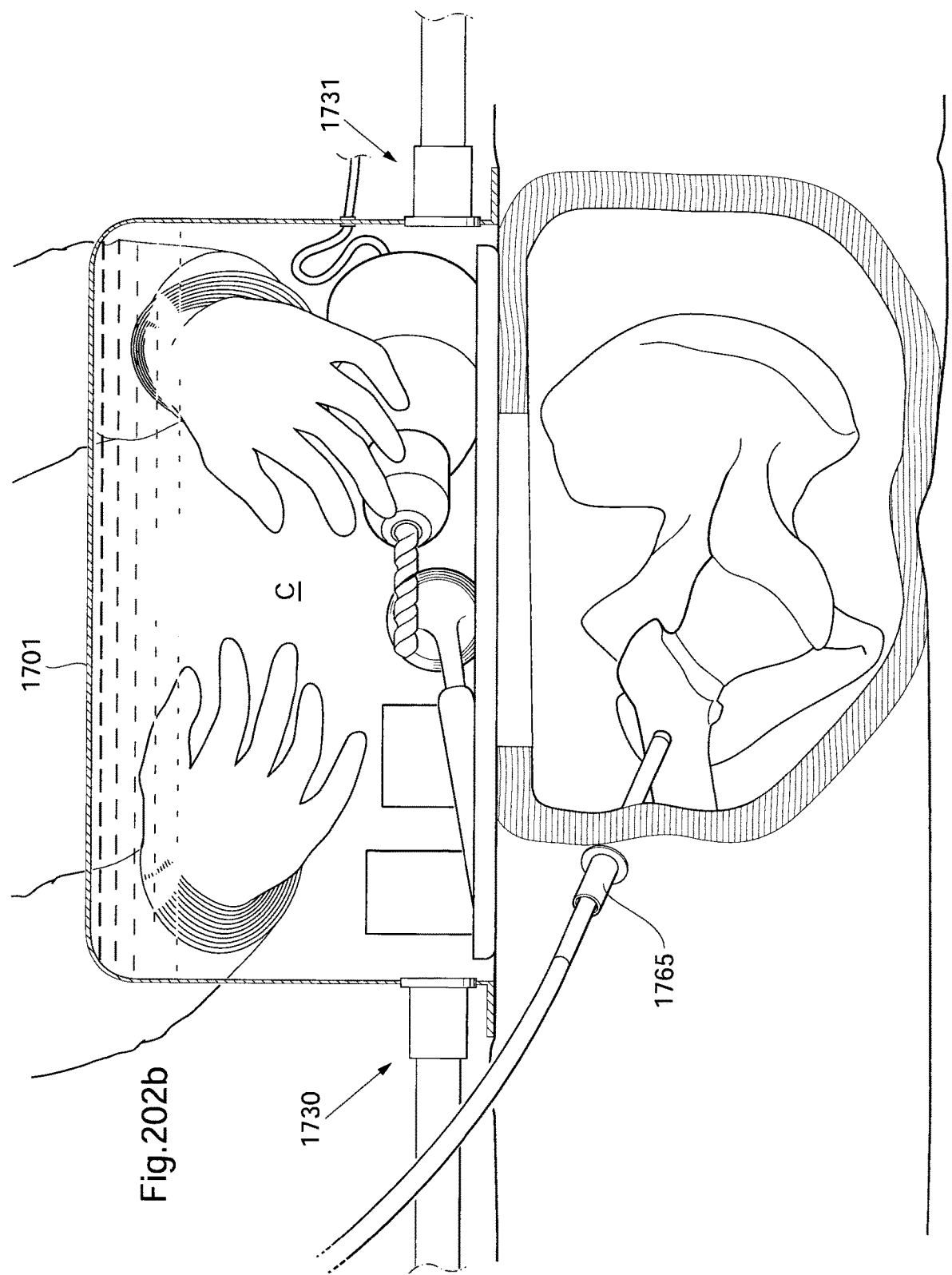

FIG. 202*b* shows the medical device according to an embodiment similar to the embodiment shown in FIG. 202*a*, the difference being that a system is provided for circulating the fluid inside of the chamber C. The liquid system comprises an inlet 1730 for injecting the liquid into the chamber C, and an outlet 1731 for enabling liquid within the chamber C to circle.

Figure 202C:
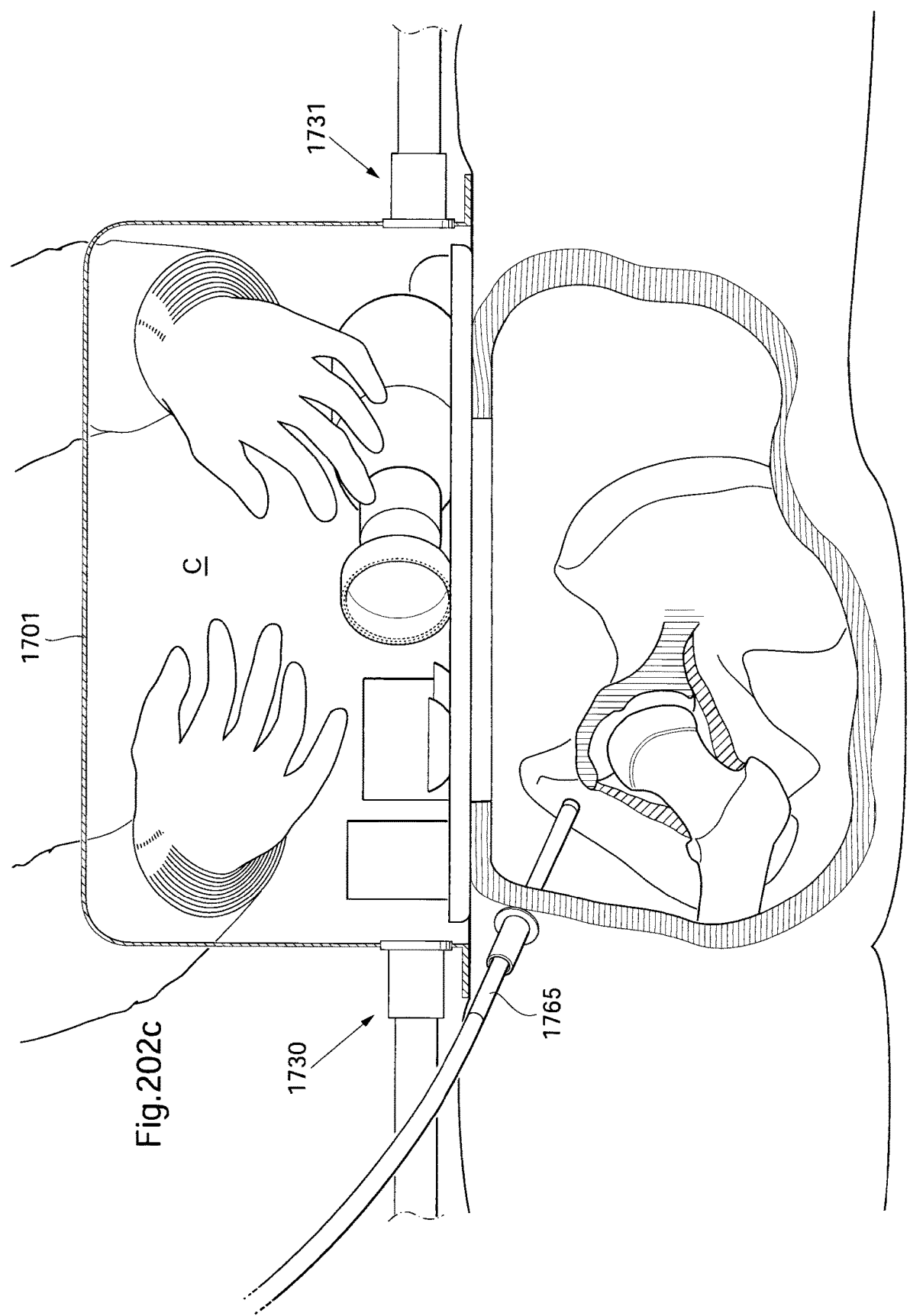

FIG. 202*c* shows the medical device according to an embodiment similar to the shown in FIG. 202*b*, the difference being that the chamber C is not adapted to hold a liquid, but rather a gaseous fluid such as CO2 gas.

Figure 203B:
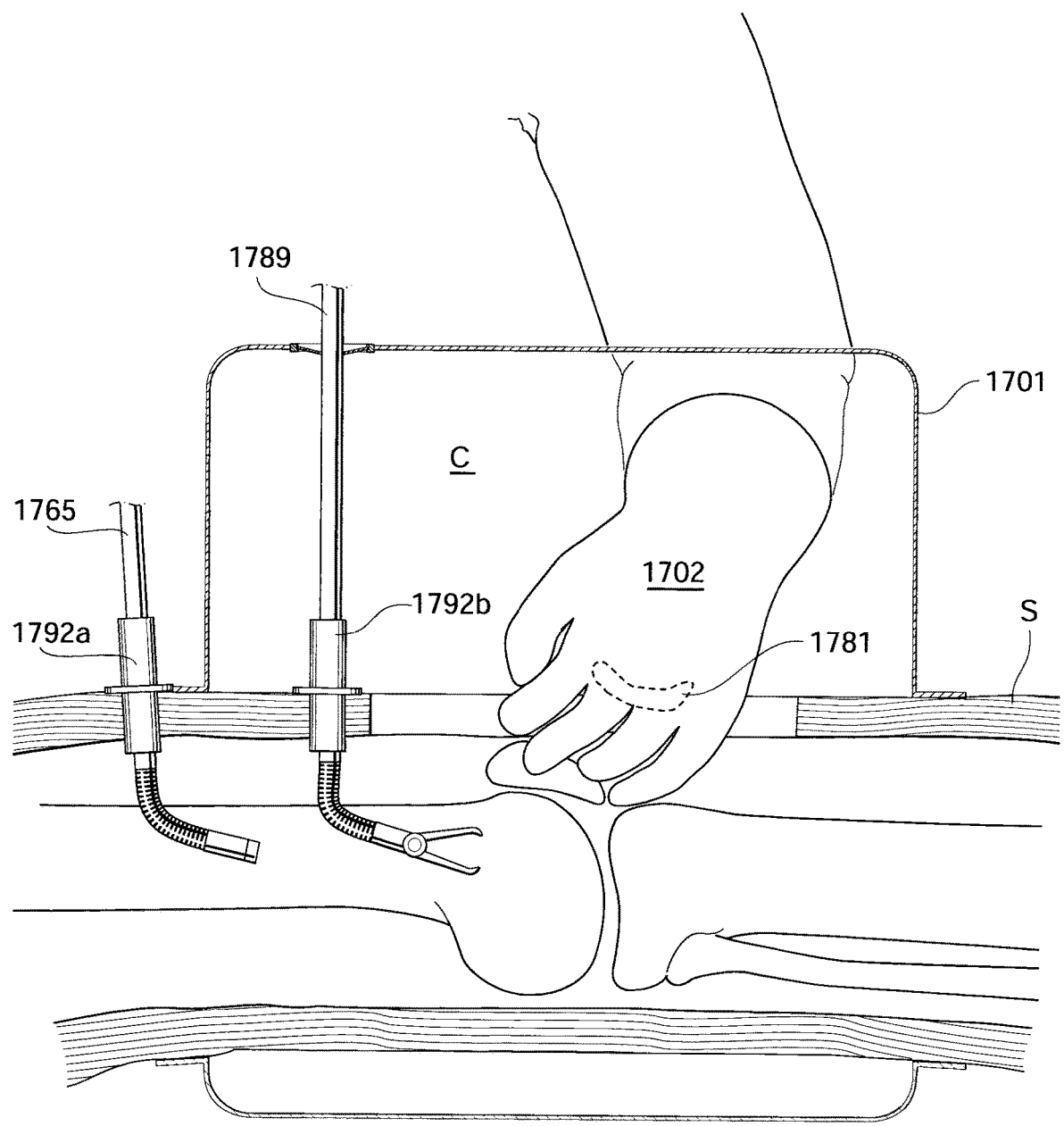

FIGS. 203*a*-203*d* shows how the medical device shown in FIGS. 188-203 may be used. The medical device 1700 comprises a glove 1702 integrated in the wall 1701 and a camera 1765 placed in the skin S outside of the medical device 1700. The medical device 1700 further comprises a trocar 1792*b* placed inside the chamber C and through an incision in the skin S of the patient and into an area of the knee of the patient. FIG. 203*a* schematically illustrates how the surgeon manipulates the knee in the chamber C using the glove 1702.

Figure 203C:
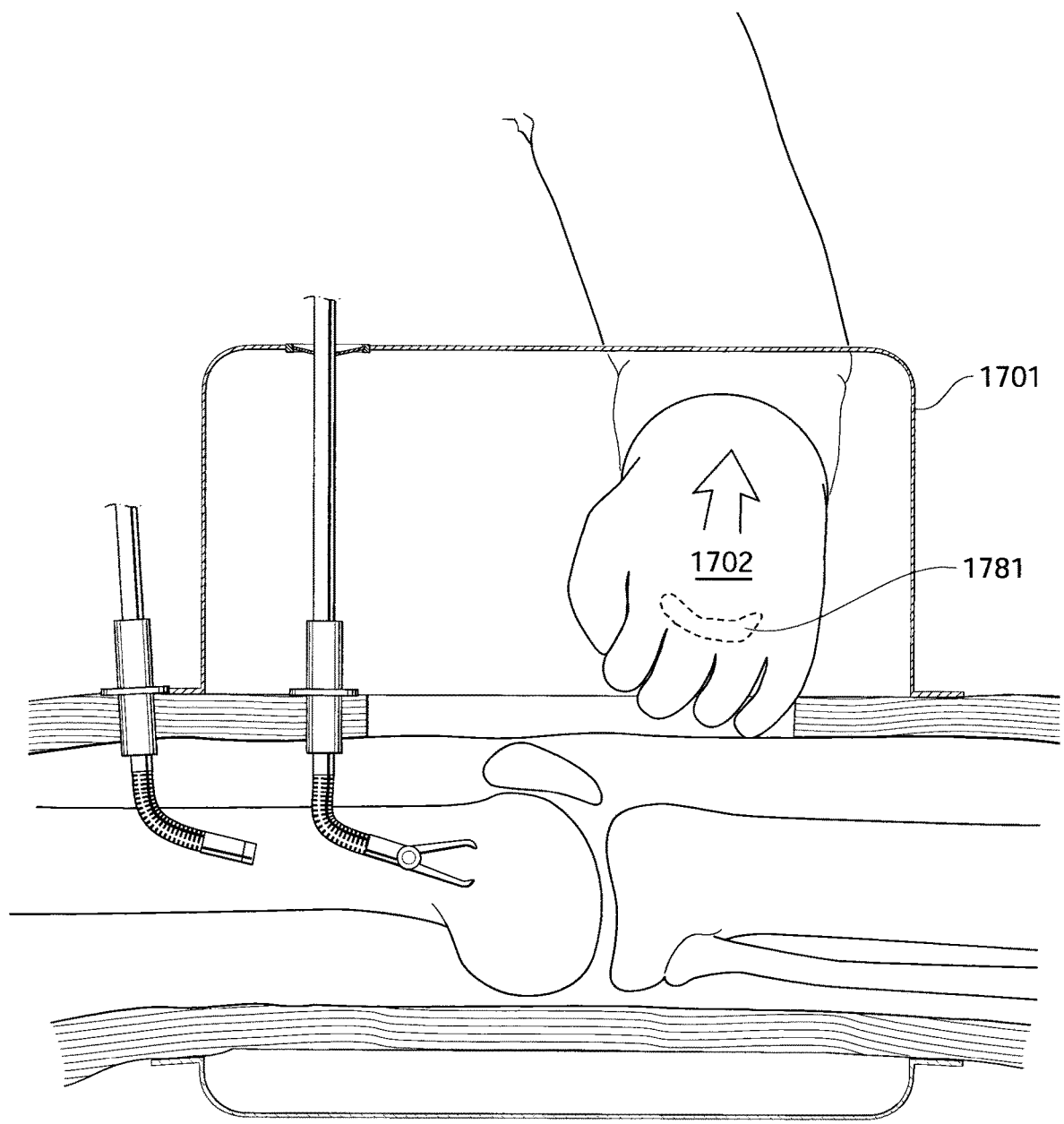

FIG. 203*b*, 203*c* shows the medical device when the surgeon removes a specimen 1781 from the knee of the patient using the glove 1702 integrated in the wall 1701 of the medical device.

Figure 203D:
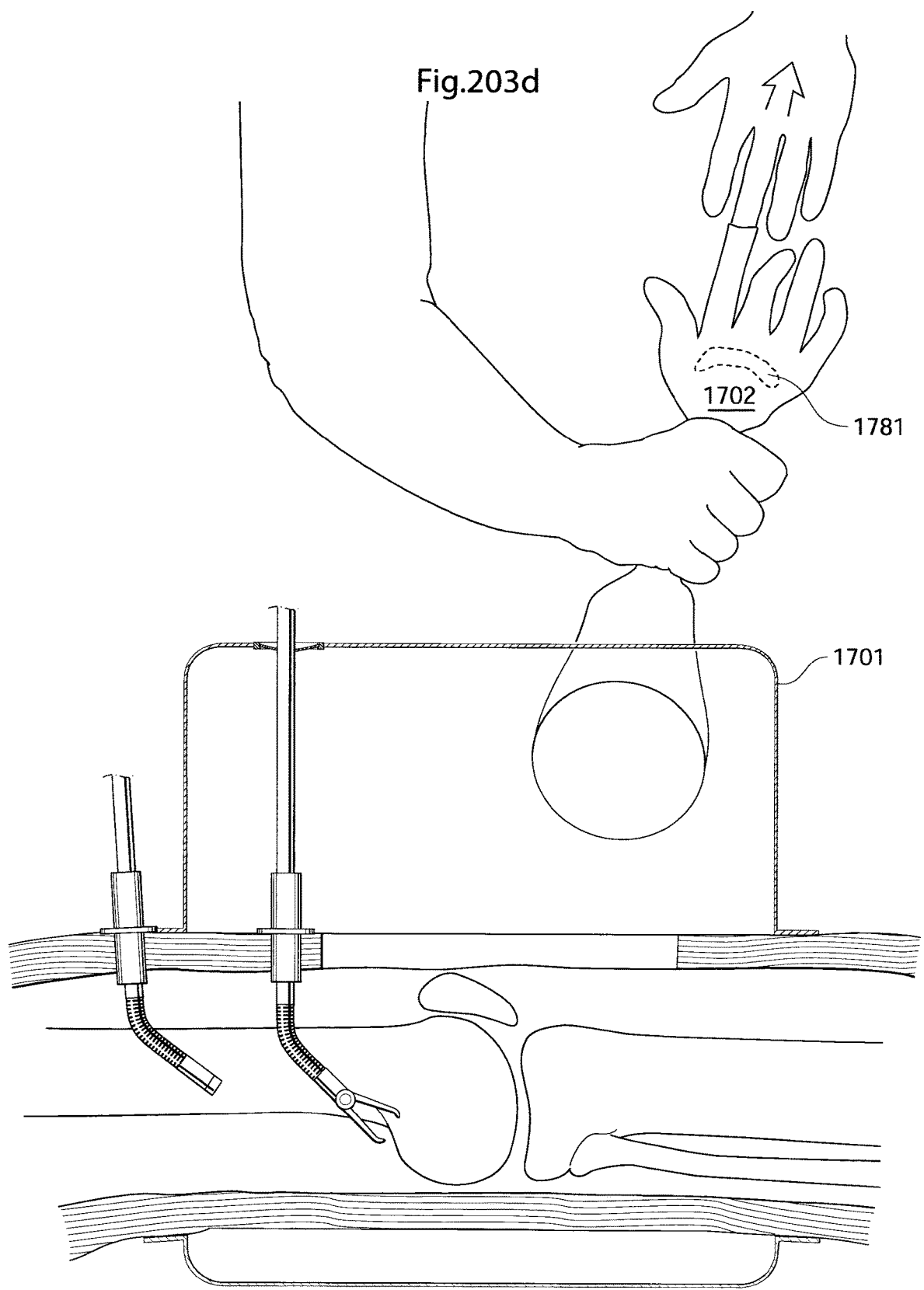

FIG. 203*d* shows the medical device, when the surgeon has turned the integrated glove inside-out such that the specimen 1781 can be contained within the integrated glove 1702. By isolating the specimen 1781 inside of the glove 1702, the specimen 1781 is removed both from the rest of the body of the patient and from the ambient environment, and thereby does not risk to infect any other portion of the patient's body or medical staff with any infectious disease.

Figure 204:
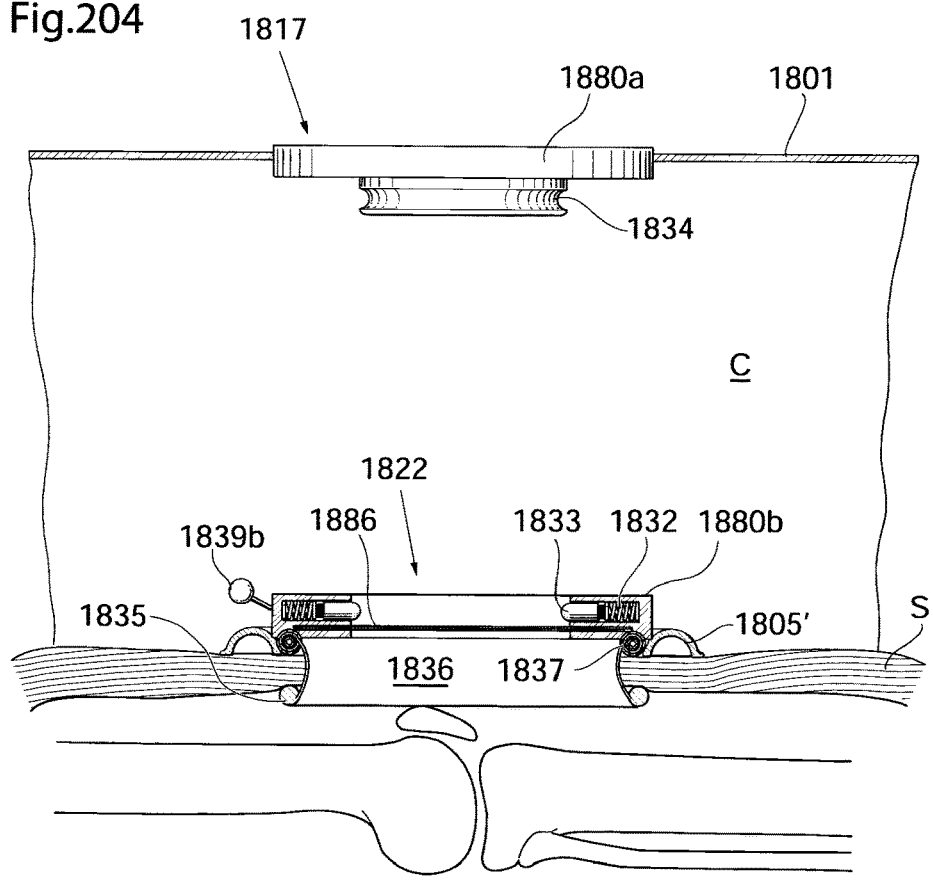
FIGS. 204-205 shows an embodiment of the medical device when being used in a knee joint surgery.

FIG. 204 shows an embodiment of a medical device for performing knee joint surgery on a patient. The knee joint surgery could be an entirely arthroscopic approach using small incisions in the skin S of the patient and a pressured circulating fluid inside of the joint for creating visibility (arthroscopy is described in further detail throughout the description). The knee joint surgery could also be a combination of an arthroscopic and an open procedure for retaining the advantages of the arthroscopic procedure, with regards to the reduced risk of infections and the enhanced visibility, whilst achieving the advantages that open surgery provides, with regards to the ability of moving larger objects in and out of the body of the patient. The medical device comprises a wall 1801 adapted to form a chamber C adapted to encapsulate an area in connection with the knee joint of the patient. The chamber C is adapted to encompass part of the knee joint surgery to be performed while maintaining a sealed environment. The medical device further comprises a closeable wall port 1817 (such as any of the wall ports disclosed herein) placed in a portion of the wall 1801 for enabling the transfer of objects from the ambient environment to the sealed environment of the chamber C. The closeable wall port 1817 comprises a connecting member 1834*a*, in the embodiment shown in FIG. 204 in the form of a recess or groove 1834*a* encircling the lower part of the port 1817. The connecting member 1834*a* is adapted to connect the closeable wall port 1817 to a connecting member 1833*b* of a body port 1822 placed in an incision in the skin S of the patient in the knee joint region. In the embodiment shown in FIG. 204, the connecting member 1833 of the body port 1822 is a spring loaded protruding member 1833 adapted to fit in the groove 1834 of the lower part of the wall port 1817.

The spring loaded protruding member 1833 being operated by a releasing lever 1839*b*. The locking of the wall port 1817 to the body port 1822 creates an interconnected port (further disclosed with reference to FIG. 206) providing mobility for an arthroscopic instrument as it creates a single operational holding position for the arthroscopic instrument. The connection of the wall port 1817 to the body port 1822 thus enables an arthroscopic knee joint procedure to be performed. The wall 1801 and the chamber C formed by the wall 1801 is adapted to hold a fluid having a pressure exceeding atmospheric pressure, such that no particles can travel from outside of the chamber C to the inside thereof. Furthermore, a pressure exceeding atmospheric pressure is useful for performing an arthroscopic procedure as the interconnecting bones of the joint may need separation, which may be performed by means of injecting a fluid having a pressure higher than atmospheric pressure into the joint.

The medical device shown in FIG. 204 further comprises a sealing device having a first sealing member 1835 adapted to be positioned at the inside of the patient's skin S around an incision to be performed in the skin S and a second sealing member 1837 adapted to be positioned at the outside of the patient's skin S around the incision, and an elastic connecting member 1836 sealingly interconnecting the first 1835 and second 1837 sealing members, wherein the elastic connecting member 1836 seals between the first 1835 and second 1837 sealing members and the skin S and tissue of the patient.

The medical device further comprises a sealing device comprising a vacuum sealing member 1805' connected to the wall 1801 and adapted to seal against the patient's body, such that the chamber C is formed by the wall 1801 and the patient's body. The wall port 1817 and body port 1822 are positioned relative to each other such that an object are displaceable from outside of the chamber C through the wall port 1817 into the chamber C, through the body port 1822 into the patient, when the surgical procedure is performed.

Figure 205:
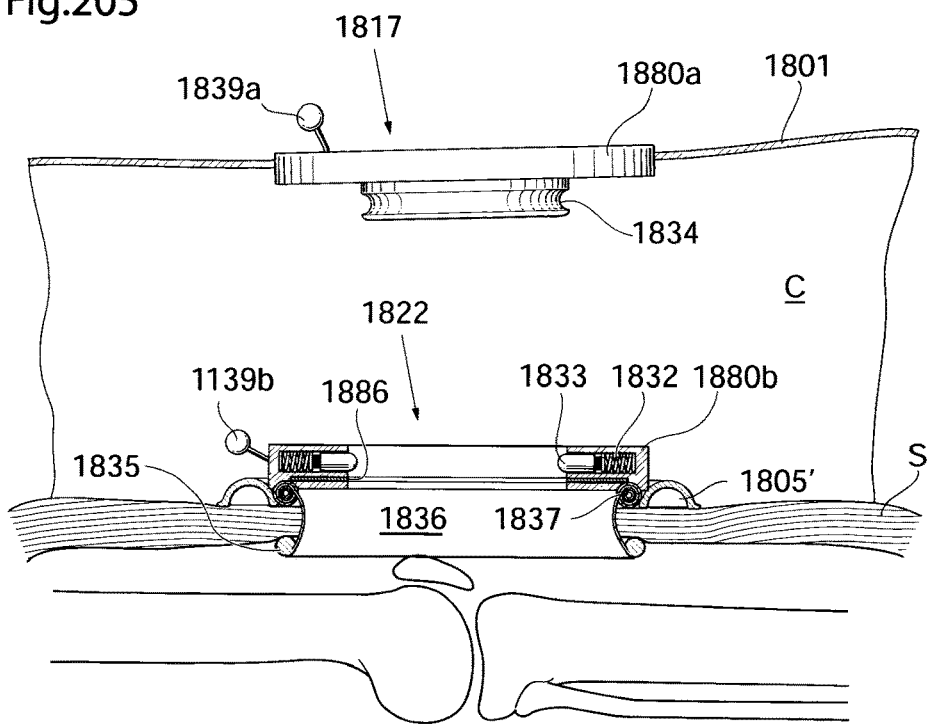

FIG. 205 shows the medical device according to the embodiment shown in FIG. 204 when the wall port 1817 has been moved from a first position situated relatively remote from the skin S of the patient to a second position closer to the tissue or skin S of the patient. The body port is closeable by means of an iris valve 1886 positioned in the lower coupling 1880 forming the body port 1822.

Figure 206:
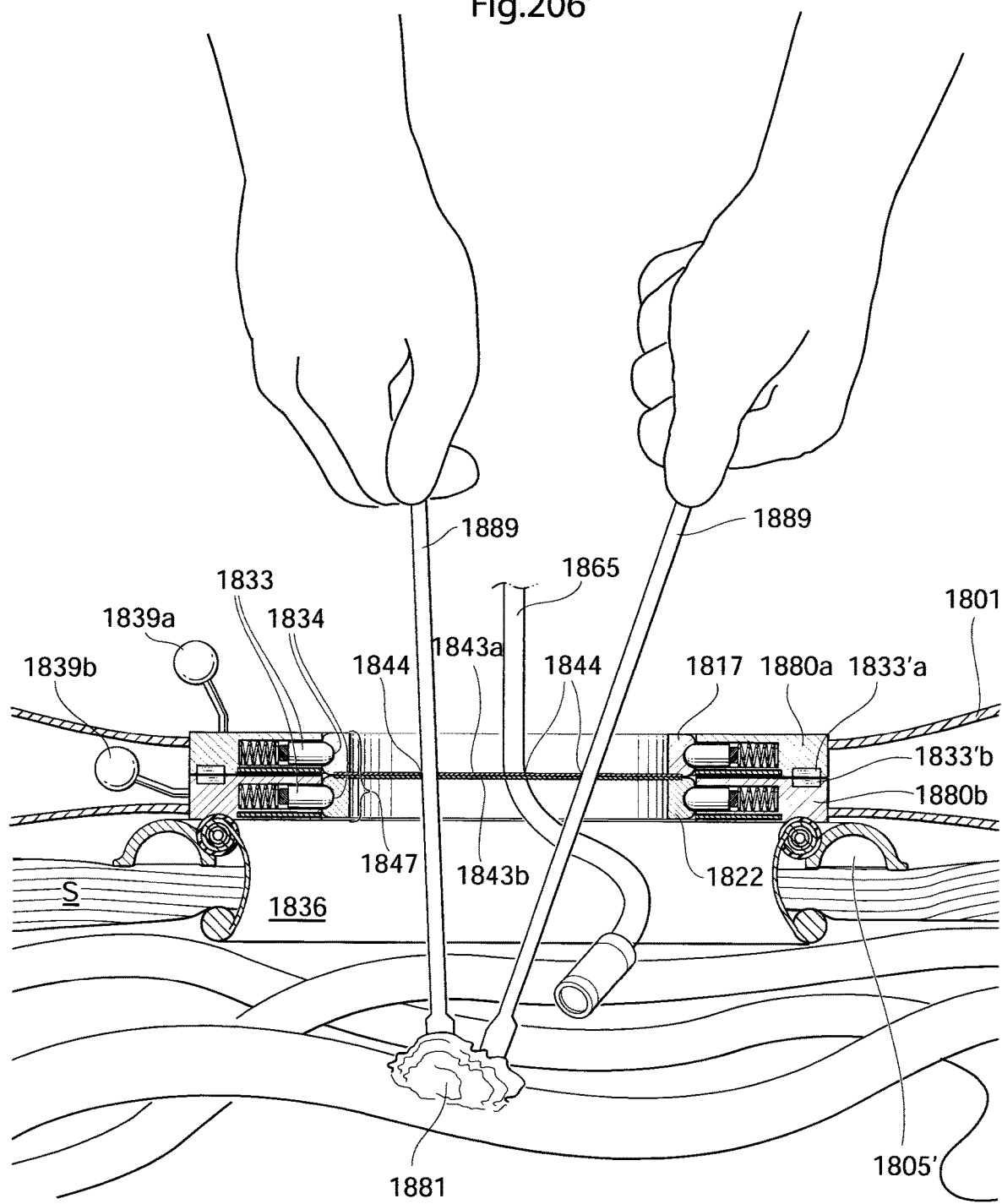
FIGS. 206-207 shows an embodiment of the medical device, when a coupling is being used.

FIG. 206 shows the medical device according to the embodiment shown in FIGS. 204 and 205, when the wall port 1817 has been connected to the body port 1822 by means of the upper coupling 1880*a* being connected to the lower coupling 1880*b*, such that an interconnected port is formed. The wall port 1817 is locked to the body port 1822 by means of the protruding connecting member 1833, further disclosed with reference to FIG. 204, being connected to the recess or groove 1834 of the upper coupling 1880*a*. The wall port 1817 is locked to the upper coupling 1880*a* by a locking member comprising protruding elements 1833 adapted to fit in a groove 1834 of the wall port 1817 portion. The protruding members 1833 are operable for releasing the wall port 1817 by means of a leaver 1839*a* connected to the spring loaded protruding members 1833. The possibility of releasing the port from the wall port 1817 enables the exchange of the wall port to alternative ports or insets 1842*b;c*, as shown in FIG. 206. The possibilities shown in FIG. 206 include an inset comprising a glove 1802 which can be placed in the wall port 1831*a* and enable the manipulation within the chamber C. An additional alternative is an inset comprising a device or instrument mount 1820 which could comprise holding portions for holding different instruments of objects which may be used within the chamber C for performing the surgical procedure. Alternatively the insets mat be exchanged to an airlock sluice 1818 enabling the transfer of objects through the couplings 1880a;b while maintaining the sealed environment of the chamber C. The airlock sluice 1818 comprises a first valve member 1838a separating the area of the airlock 1818 from the ambient environment, and a second valve member 1838b separating the area of the airlock 1818 from the sealed environment of the chamber C. FIG. 206 further shows a multi-port 1848 comprising three ports, enabling the insertion of three different instruments 1889;1865 into the chamber C of the medical device 1800. The lower coupling 1880b shown in FIGS. 204, 205 and 206 comprises an iris valve 1886 adapted to close the body port 1822.

The embodiment of the medical device shown in FIGS. 204-206 further comprises a sealing device comprising a vacuum sealing member 1805' adapted to hold a pressure less than atmospheric pressure between the first wall portion and the patient's skin S to seal between the first wall portion and the patient's skin S. The vacuum sealing member 1805' is connected to a vacuum conduit 1806, which in turn is connected to a vacuum creating member, such as a vacuum pump. In alternative embodiments the vacuum sealing member 1805' may be assisted or replaced by an adhesive portion, or a sealing member sealing by pressing against the skin or tissue of the skin. Such alternative sealing members are disclosed in further detail in other portions of this description.

FIG. 206' shows an embodiment of the medical device in which the upper coupling 1880a comprises a wall port 1817 and the lower coupling 1880b comprises a body port 1822. Both the wall port 1817 and the body port 1822 comprises disc-shaped self sealing membranes 1843a, 1843b. In the body port 1822, the self sealing membrane 1843b is positioned in the top portion of the body port 1822, whereas in the wall port 1817, the membrane 1843a is positioned in the bottom part of the port 1817. The self sealing membranes 1843a, 1843b have small self sealing holes 1844 such that the instruments 1889 or a camera 1865 can be inserted through the self sealing membranes 1843a, 1843b. For example, the self sealing membranes 1843a, 1843b may be made from a gel-type material. The wall port 1817 and body port 1822 forms an interconnected port 1847 when the wall port 1817 and body port 1822 are connected, with the membranes 1843a, 1843b contacting each other such that the instruments 1889 engage an interconnected sealing membrane (made up of the first and second membrane 643a, 643b) in the interconnected port 1847. If the ports 1817; 1822 were to comprise two spaced-apart membranes, the two membranes would reduce the ability to move the instruments far more than the two integrated membranes acting as a single membrane. The sealing membranes 1843a, 1843b are adapted to, in a non-expanded state, provide a seal, and in an expanded state, enable an instrument 1889 to be inserted through the membranes 1843a, 1843b.

Figure 207:
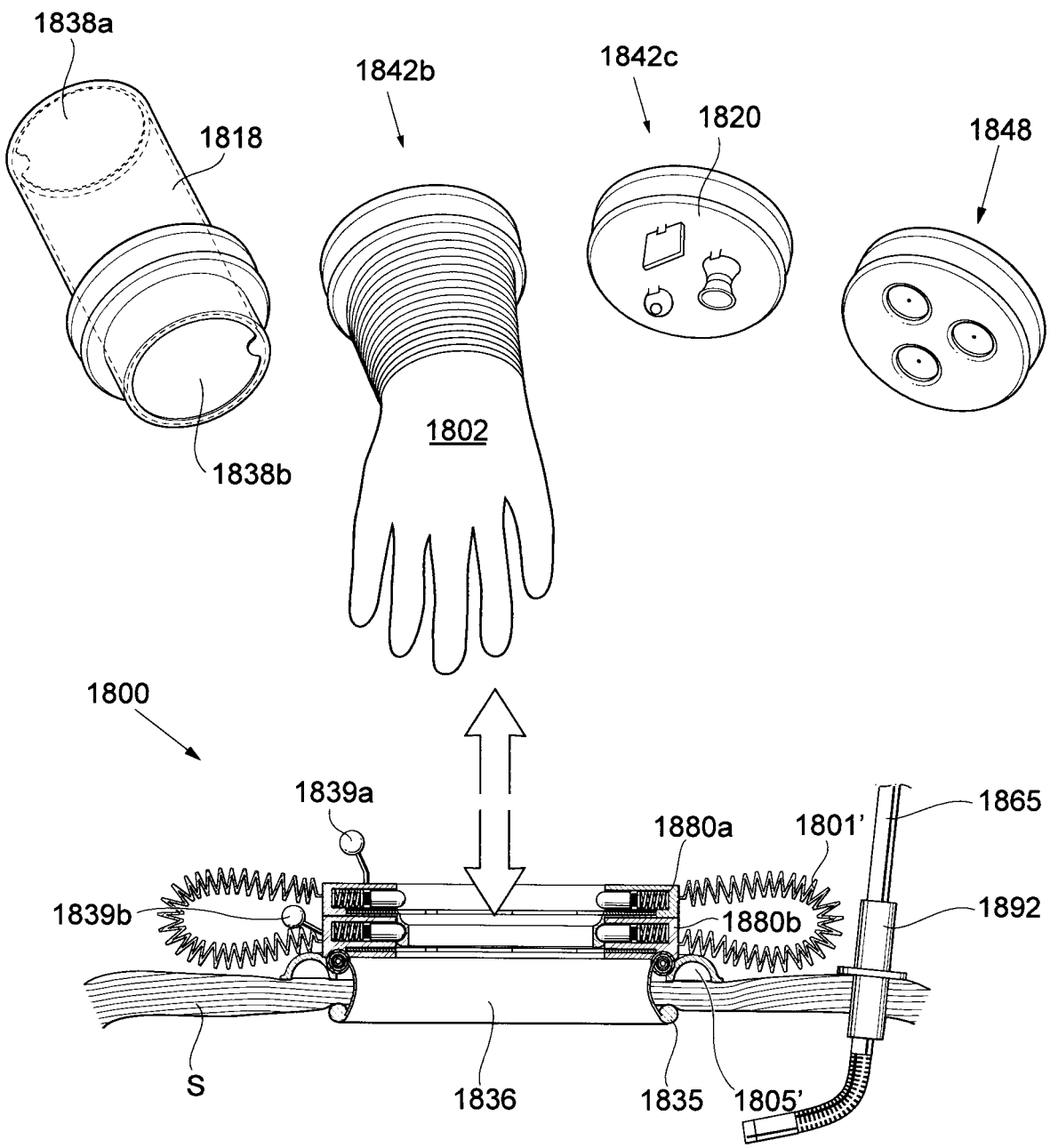

FIG. 207 shows an embodiment of the medical device 1800 similar to the embodiment disclosed with reference to FIGS. 204-206, with the difference that the wall 1801' of the medical device of FIG. 207 comprises a plurality of creases, making the wall 1801' flexible such that it takes up less space when the wall 1801' is not inflated. The creased wall 1801' makes the wall 1801' into less of an obstruction when the medical device 1800 is used in an arthroscopic approach. One further difference is that a camera 1865 placed in a trocar 1892 is placed outside of the area of the medical device 1800, which enables the visual inspection to be performed at an angle different from that available within the area of the medical device 1800.

Figure 208:
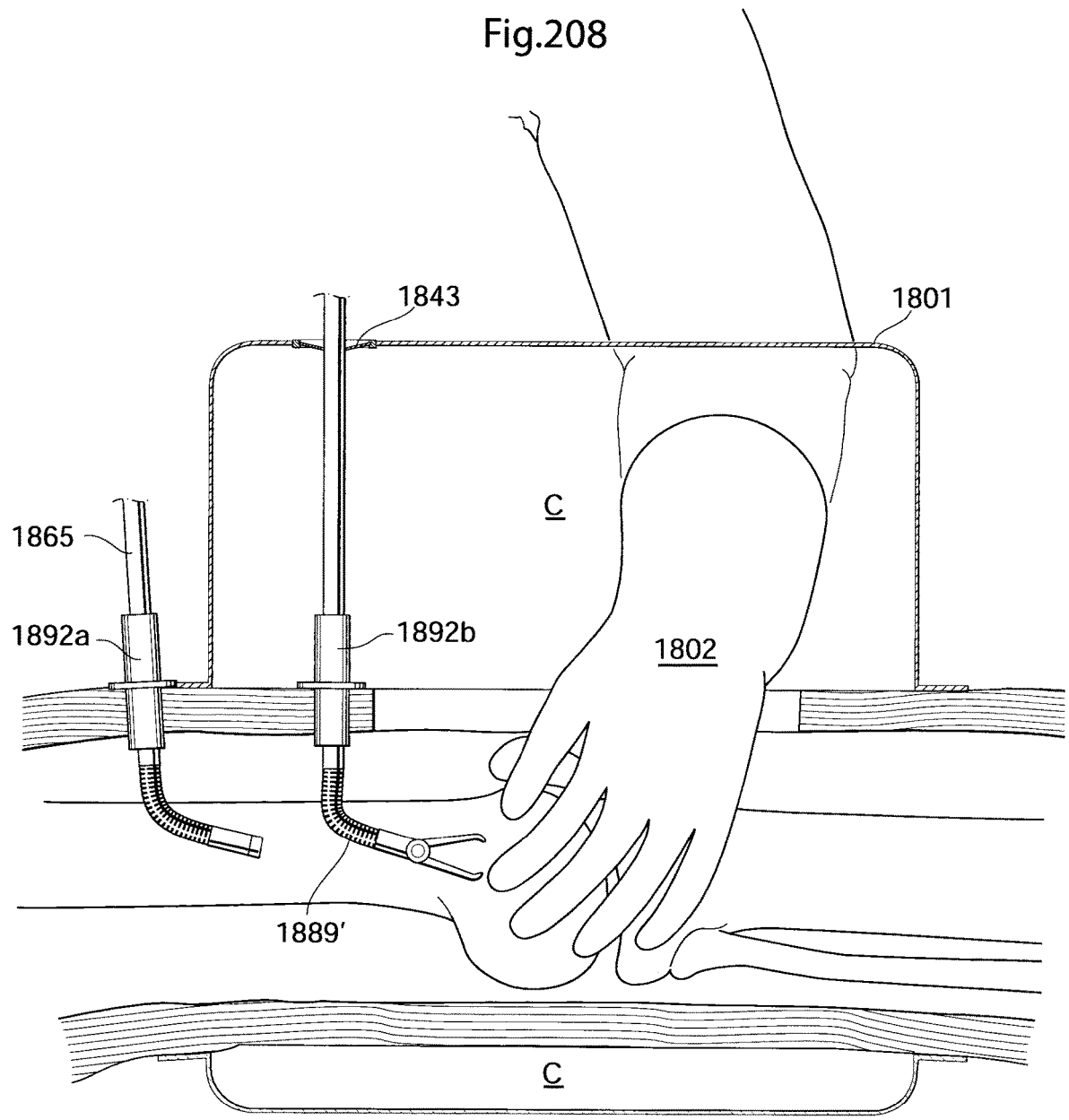
FIG. 208 shows an embodiment of the medical device in section, when being used in knee joint surgery.

FIG. 208 shows the medical device according to an embodiment in which the wall 1801 of the medical device encircles the leg of the patent such that the chamber C encircles the leg for creating a chamber C in the knee region of the patient. An arthroscopic camera 1865 is positioned outside of the medical device for providing visual inspection of the knee joint region, whereas a trocar 1892b is placed in the skin of the patient inside of the chamber C enabling the manipulation of an arthroscopic instrument 1889' in the knee joint region of the patient. The arthroscopic instrument 1889' passes through a sealing membrane 1843 in the wall 1801, further through the chamber C and through the trocar 1892 placed in the wall 1801 and into the body of the patient in the knee region. The arthroscopic instrument 1889' could for example be, as shown in FIG. 208, a gripping instrument adapted for manipulation within the joint. In other embodiments, the arthroscopic instrument could comprise a bonding instrument, such as a suturing or stapling instrument, or a severing instrument, such as a scalpel or an electromagnetic or ultrasonic diathermy.

In the embodiment shown in FIG. 208, a glove 1802 is further shown. The glove 1802 is an integrated portion of the wall 1801 and adapted to enable manual manipulation by a surgeon within the chamber C and area of the knee joint within the body of the patient. The placing of an integrated glove 1802 in the wall 1801 enables a combination of arthroscopic and open surgery which could enable the transfer of relatively large objects into the area of the joint, whilst maintaining the visual advantages and the reduced risk of infections offered by arthroscopic surgery. As an example, the surgical procedure may commence as an arthroscopic procedure, and then shift to a more open procedure when an implant should be placed in the joint, or a portion of tissue from the joint should be removed.

The medical devices shown in FIGS. 204-208 may further comprise a fluid tempering device adapted to temper a fluid within the chamber to a temperature different from the temperature of the environment outside of the chamber C and/or a sterilization device for directly or indirectly sterilizing a fluid contained in the chamber C. The tempering and sterilization device may for example be the tempering and sterilizations device disclosed in relation to other embodiments herein.

Figure 209A:
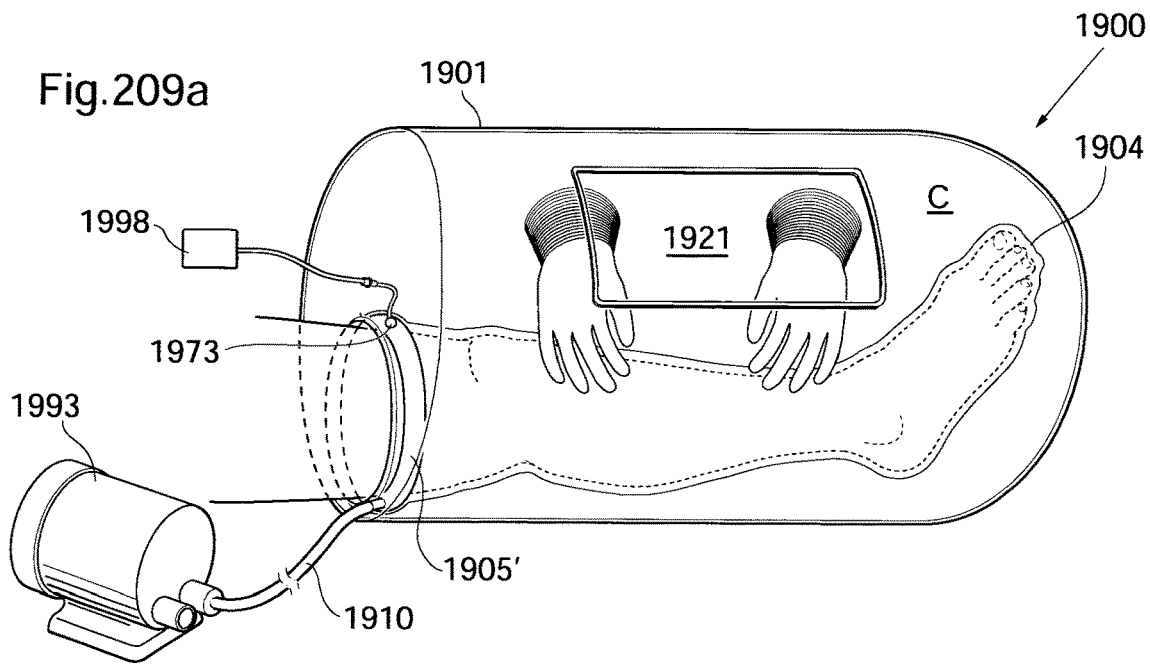
FIGS. 209a-209i shows an embodiment of the medical device, comprising pressure or vacuum sealing members being connected to monitoring units and/or adjustment devices.
Figure 209A:
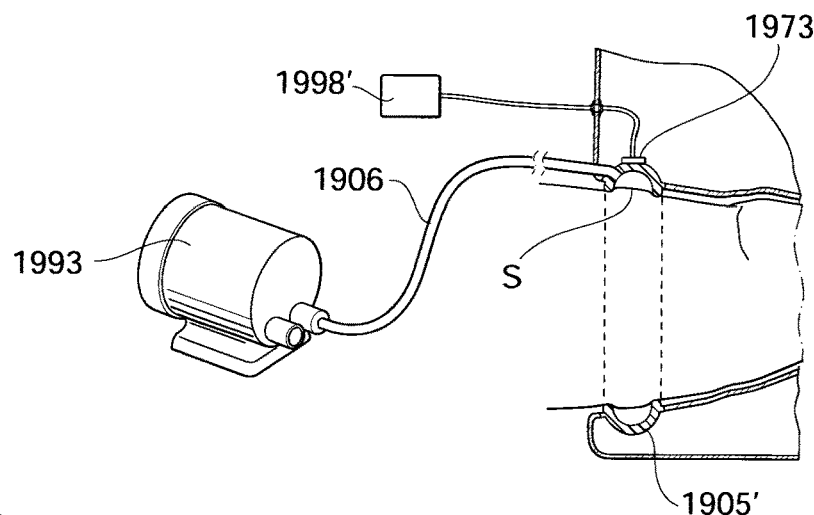

FIG. 209a shows an embodiment of the medical device 1900 for performing a surgical procedure on a patient. The medical device 1900 comprises a wall 1901 adapted to at least partially be applied on an extremity of the patient's body being a leg o the patient to form a chamber C. The chamber C may be formed, as shown in FIG. 209a, by itself, between the exterior wall 1901 and a portion of the wall 1901 forming an elongated tubular enclosure 1904 extending within the chamber C and thus forming a layer between the skin of the patient and the chamber C. The elongated tubular enclosure 1904 is fixated to the rest of the wall 1901 at the area of the wall 1901 at which a sealing member 1905" is positioned. When the surgical procedure is performed, the wall of the elongated tubular enclosure 1904 is cut through such that an incision in the skin of the patient can be made. By placing the layer in contact with the skin of the patient prior to making the incision in the skin of the patient, the risk that any bacteria present on the skin of the patient will reach the area of the incision if reduced. The layer of the wall forming the elongated tubular enclosure 1904 may comprise an adhesive surface 1950 such that the wall 1901 adheres to the skin S of the patient, which further reduces the connecting points between the chamber C and the skin S of the patient, which thus further reduces the risk that bacteria present on the skin of the patient will reach the area of the incision and cause infectious decease. In alternative embodiments, the chamber C may be formed together with the patient's body, in which case the elongated tubular enclosure 1904 is omitted.

The sealing shown in FIG. 209*a* is a pressure sealing member 1905" adapted to pneumatically or hydraulically press the wall 1901 against the body of the patient such that the chamber C is at least substantially sealed from the ambient atmosphere allowing a pressure inside the chamber C to be higher than the ambient atmospheric pressure during the surgical procedure. In other embodiments, such as other embodiments shown herein, the sealing 1905" may be mechanically powered for example by means of an adjustable band which may be combined with an elastic band.

The pressure sealing 1905" is adapted to seal the chamber C after the medical device has been applied at least partially on the patient's body such that an incision can be performed inside the chamber C for creating a fluid connection between the chamber C and a cavity in the patient. The sealing member 1905" is adapted to remain unaffected by the incision and thus sealing with unaffected force. The pressure sealing member 1905" is in fluid connection with a fluid conduit 1910 for providing a pressurized fluid to the pressure sealing member 1905". The fluid conduit 1910 is in turn connected to a pressure adjustment device 1993 in the form of a pump adapted to fill the pressure sealing 1905" with pressurized air from the ambient environment for adjusting the pressure in the sealing member 1905". The pump 1993 (further shown as 1908 in FIG. 209*g*) may in other embodiments be replaced by a tank comprising a pressurized fluid (for example the tank 2012 disclosed in the embodiment of FIG. 210).

The embodiment of FIG. 209*a* further comprises a monitoring unit 1998 connected to a lead connected to a monitoring probe 1973 fixed to the sealing member 1905". The monitoring probe 1973 comprises a pressure sensor adapted to detect change in the pressure in the sealing 1905". In alternative embodiments, the monitoring unit 1998 may be adapted to measure the blood pressure of the patient by means of measuring the blood flow in the peripheral blood vessels, by means of for example an ultra sonic flow meter. An ultrasonic flow meter measures the difference of the transit time of ultrasonic pulses propagating in and against the flow direction. This time difference is a measure of the average velocity of the fluid along the path of the ultrasonic beam. By using the absolute transit times the averaged fluid velocity can be calculated. The measurement of the blood pressure enables the adjustment of the sealing member 1905" such that the sealing member 1905" does not hinder the blood flow passing the sealing member 1905", whilst allowing the sealing member 1905" to provide sufficient pressure for sealing the chamber C from the ambient environment. The pressure adjustment device 1993 may for example be adapted to adjust the pressure in the sealing member 1905" such that the pressure in the sealing member 1905" is below the systolic blood pressure and thus do not hinder the blood flow. The systolic blood pressure varies somewhat with the age of the patient but should be within a range of 90 mmHg-160 mmHg. The pressure in the sealing member 1905" should thus not exceed the values of that range for not hindering the blood flow. The pressure could for example be in a range of 10 mmHg-160 mmHg, 20 mmHg-140 mmHg, 30 mmHg-120 mmHg, 30 mmHg-100 mmHg, 40 mmHg-100 mmHg, 40 mmHg-80 mmHg and 50 mmHg-70 mmHg.

FIG. 209*a*' shows an alternative to the pressure sealing member 1905" disclosed in FIG. 209*a* in which the pressure sealing member is replaced by a vacuum sealing member 1905' providing sealing between the wall of the medical device 1901 and the skin S of the patient by means of a pressure in the vacuum sealing member 1905' being lower than the ambient atmospheric pressure. The negative pressure in the vacuum sealing member is e.g. provided by a vacuum pump connected by means of a vacuum conduit 1906. The negative pressure in the vacuum sealing member 1905' may be monitored by means of a vacuum monitoring unit 1998' connected to a monitoring probe 1973, connected to the vacuum sealing member 1905'. The operation and effect of the vacuum sealing member 1905' is described in further detail with reference to FIG. 209*h*.

In alternative embodiments the pressure in the sealing member 1905" does not need to be monitored, only controlled such that the blood flow passed the sealing member 1905" remains substantially unaffected. The blood flow may, as previously mentioned, be measured by means of an ultra sonic flow meter. The vacuum adjustment device 1993 may in other embodiments be adapted to adjust the pressure in the vacuum sealing member 1905' as response to the blood pressure of the patient, the blood flow of the patient and/or the temperature at the skin of the patient.

The medical device may further comprise a pressure sensor for measuring the pressure inside the chamber C. By measuring the temperature inside the chamber C, fluid leakage at the sealing 1905" can be determined, which can be used as input in the control of the sealing member 1905".

Figure 209B:
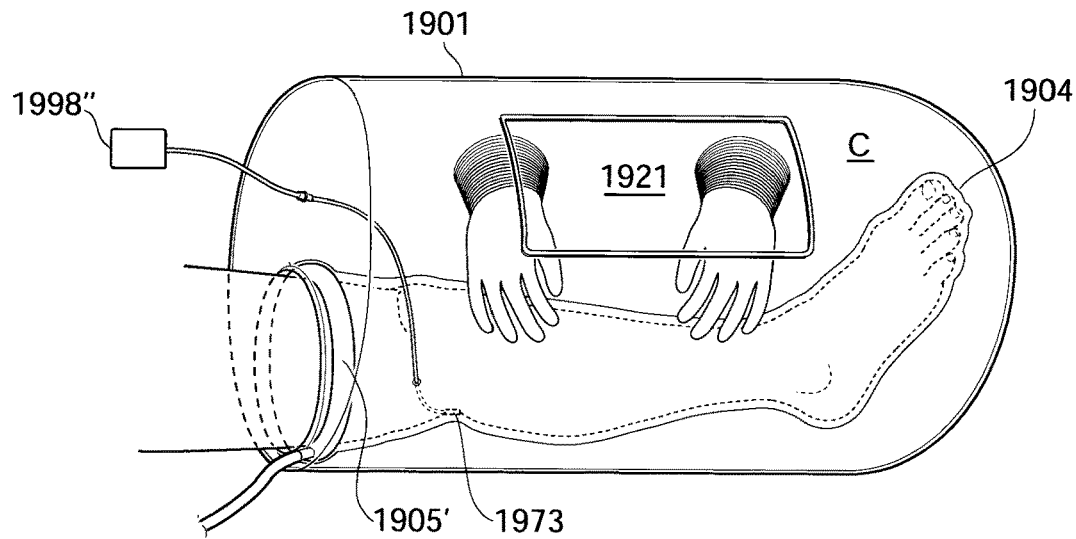

FIG. 209*b* shows an alternative embodiment of the medical device in which a probe 1973 is positioned in the knee region of the patient on the dorsal side of the leg of the patient. The probe 1973 may for example be a temperature sensing probe 1973 adapted to sense the temperature of the body of the patient for the purpose of determining that the blood flow from at that area of the patient is sufficient. When the blood flow is hindered, the temperature of the skin of the patient raises which can be used as an input variable to the pressure adjustment device shown for example as 1993 of FIG. 209*c*. In alternative embodiments the probe 1973 may be an ultra sonic flow meter for measuring the blood flow of the patient. The probe 1973 is preferably placed on the dorsal side at the knee region of the leg as the blood vessels are more superficial in this region. The probe 1973 may for example be adapted to measure the blood flow of the popliteal vein, the popliteal artery, the saphenous vein and/or the tibial artery.

Figure 209C:
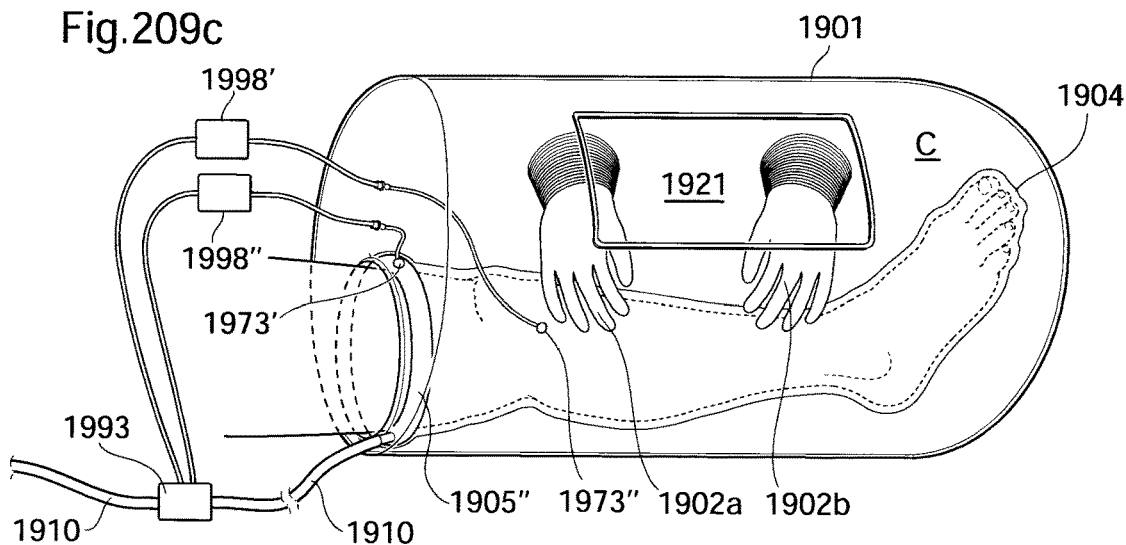

FIG. 209*c* shows an embodiment of the medical device in which the medical device comprises two monitoring units 1998'; 1998", wherein the first monitoring unit 1998' is adapted to monitor the blood flow at an area of the patient by means of an ultra sonic flow meter probe 1973", and the second monitoring unit 1998" is adapted to monitor at least one of: the pressure in the sealing device, the pressure in the chamber, and the direct or indirect leakage of fluid from the chamber by means of a pressure sensing probe 1973'.

In any of the embodiments disclosed it is equally conceivable that the medical device comprises two monitoring units 1998'; 1998", wherein the first monitoring unit is adapted to monitor the blood pressure o the patient, and the second monitoring unit 1998" is adapted to monitor at least one of: the pressure in the sealing device, the pressure in the chamber C, and the direct or indirect leakage of fluid from the chamber C.

In any of the embodiments disclosed it is equally conceivable that the medical device comprises two monitoring units 1998'; 1998", wherein the first monitoring unit 1998' is adapted to monitor a temperature of the body of the patient, and the second monitoring unit 1998" is adapted to monitor at least one of: the pressure in the sealing device, the pressure in the chamber C, and the direct or indirect leakage of fluid from the chamber C.

FIG. 209c further shows a pressure adjustment device 1993 adapted to adjust the pressure in the sealing device 1905" based on input from the first 1998' and second 1998" monitoring unit, such that the resulting pressure in the sealing member 1905" can be a mediation between providing sufficient sealing and maintaining the blood flow of the patient unaffected. The pressure adjustment device comprises an electrically controlled pressure regulating valve adapted to control pressure from a pressure source (e.g. a pump) distributed to the pressure adjustment device by means of a fluid conduit 1910.

The sealing member 1905" may be a sealing member 1905" adapted to be pressurized by means of a gaseous fluid, or by means of a liquid fluid. The liquid fluid may be pumped by means of a fluid pump. In embodiments where the sealing member 1905" is adapted to be pressurized by a gaseous fluid, the gaseous fluid may come from a pressure tank (for example shown as 2012 in FIG. 210) or may be pressurized ambient air supplied by a pneumatic pump 1908.

The sealing member 1905" in the embodiment of FIG. 209a-209g may be substituted by a vacuum sealing member 1905' as for example shown in FIG. 209a' and 209h, and further disclosed throughout the description. The vacuum sealing member 1905' is adapted to hold a pressure less than atmospheric pressure between the wall 1901 and the patient's skin to seal between the wall 1901 and the patient's skin.

Figure 209D:
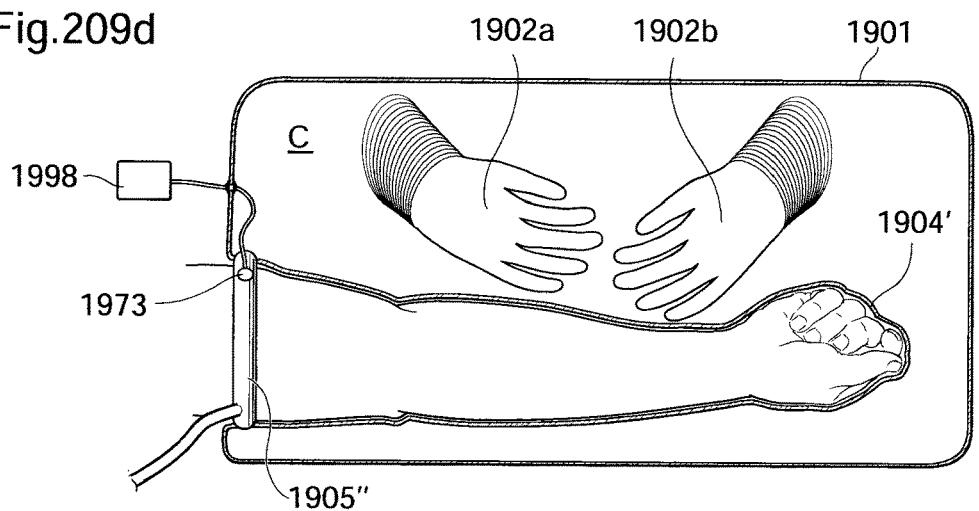

FIG. 209d shows an embodiment of the medical device similar to the embodiment shown in FIG. 209a, the difference being that the medical device with the sealing 1905" and the elongated tubular enclosure 1904' is adapted to fit an extremity being an arm of the patient.

Figure 209E:
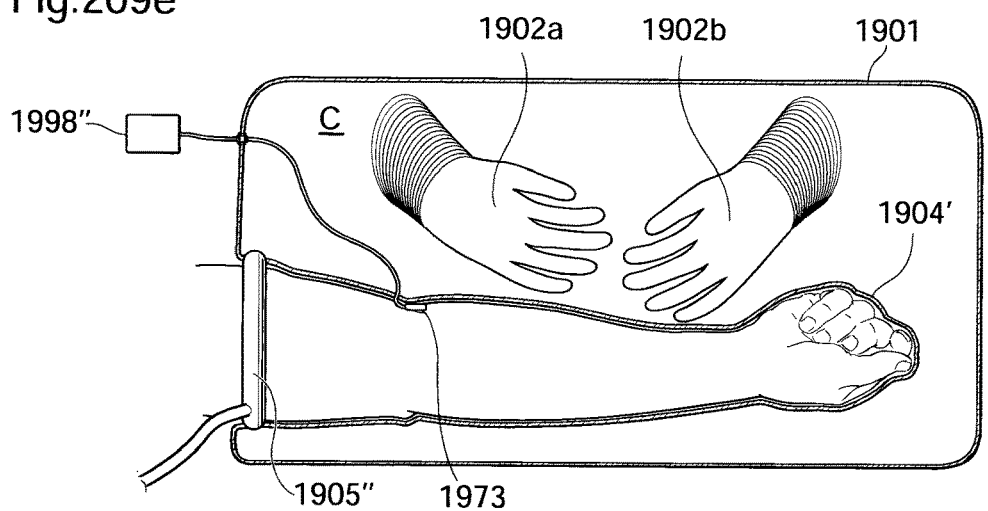

FIG. 209e shows an embodiment of the medical device similar to the embodiment shown in FIG. 209b, the difference being that the embodiment shown in FIG. 209d with the sealing 1905" and the elongated tubular enclosure 1904' is adapted to fit an extremity being an arm of the patient. The embodiment comprises an ultra sonic flow sensing probe 1973 adapted to sense the blood pressure of the patient and being adapted to be positioned on the inside of the patients arm where the blood vessels are superficial. The ultra sonic flow sensing probe 1973 may be adapted to sense the flow in one or more of the cephalic vein, the basilic vein, the median cubital vein, the brachial artery, the ulnar artery and the radial artery.

Figure 209F:
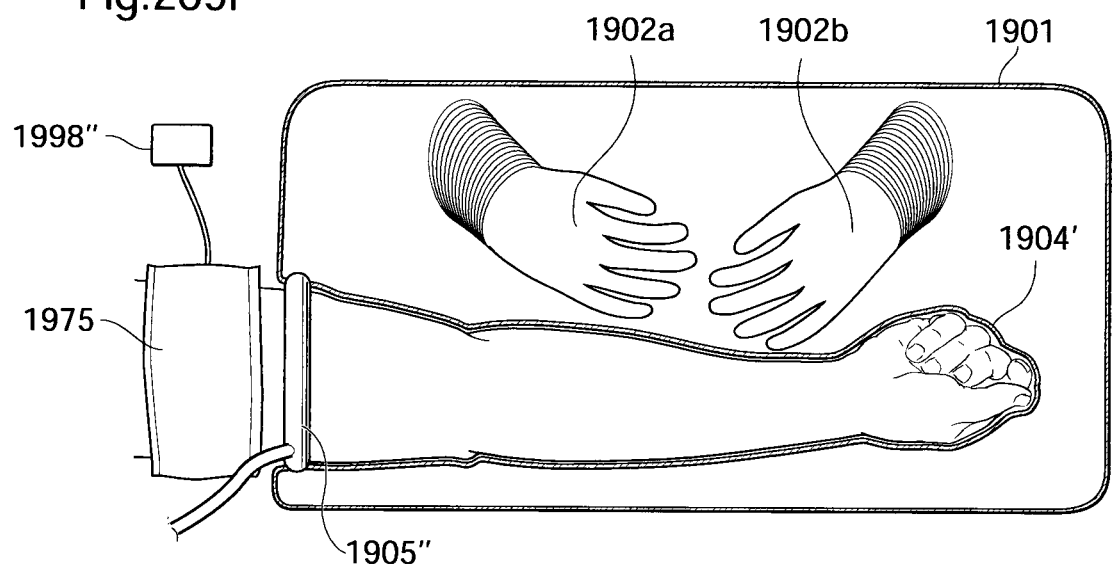

FIG. 209f shows an embodiment in which the medical device comprises a pressure sealing member 1905", equivalent to the sealing 1905" disclosed with reference to FIG. 209a-209e. The medical device further comprises a blood pressure monitoring unit 1998' operated as a sphygmomanometer. The blood pressure monitoring unit comprises an inflatable cuff 1976 which is snugly placed around the upper arm of the patient. The pressure monitoring unit 1998''' is operated by the cuff 1976 being inflated to a pressure initially in excess of the systolic arterial pressure and then reduced to below diastolic pressure over a period of about 30 seconds. When no blood is flowing passed the cuff 1976, the cuff 1976 pressure will be essentially constant. When blood flow is present, but restricted, the cuff 1976 pressure, which is monitored by a pressure sensor of the blood pressure monitoring unit 1998', will vary periodically in synchrony with the cyclic expansion and contraction of the arteries. The values of the systolic and diastolic pressure can thus be computed. In alternative embodiments the measurement of the oscillating pressure may be assisted or replaced by an ultra sonic flow meter measuring the blood flow at a relevant place of the patients arm. The blood pressure monitoring unit 1998''' may be adapted to measure the blood pressure of the patient periodically, such as for example with an interval of: 1-5 minutes, 5-10 minutes, 10-20 minutes, or 20-30 minutes. The periodical monitoring of the blood pressure enables the sealing member 1905" to be inflated/deflated such that the blood flow in the arm of the patient is substantially unaffected or periodically occluded whilst the sealing member 1905" provides sufficient sealing.

In instances when the chamber C is inflated with a pressure exceeding atmospheric pressure the sealing needs to provide a sealing force exceeding the force created by the pressure from the pressure inside the chamber C. The pressure in the sealing may then exceed the pressure in the chamber C by e.g. 10 mmHg, 20 mmHg, 30 mmHg, 40 mmHg, 50 mmHg, 60 mmHg or 100 mmHg. As an example the pressure in the sealing 1905" can be 120 mmHg, not to exceed the systolic blood pressure, and the pressure in the chamber C can be 80 mmHg such that the resulting pressure exerted on the skin of the patient and providing the sealing force is 40 mmHg.

Figure 209G:
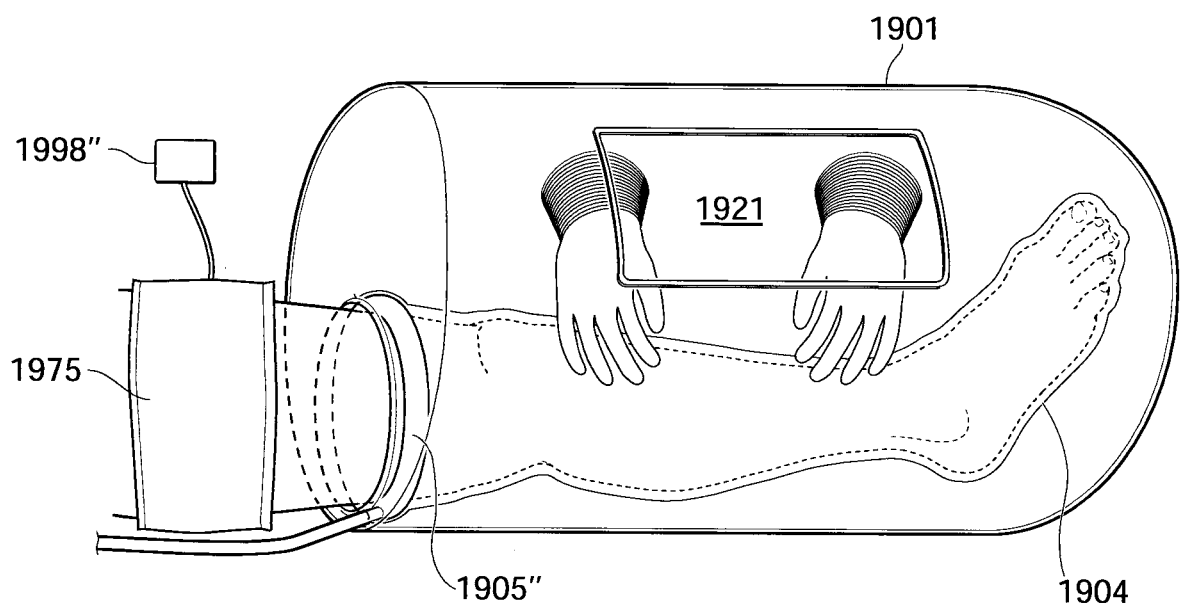

FIG. 209g shows an embodiment of the medical device similar to the embodiment described with reference to FIG. 209f, the difference being that the medical device is adapted to be positioned on an extremity of the patient being a leg of the patient, and thus the sealing member 1905" and the elongated tubular enclosure is adapted for being positioned on a leg of the patient.

Figure 209H:
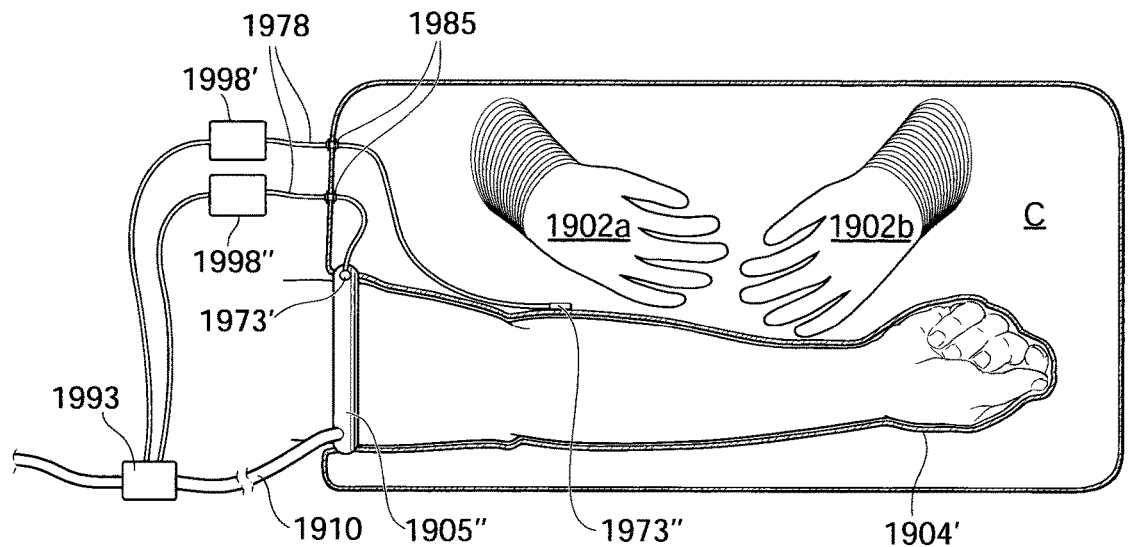
Figure 209I:
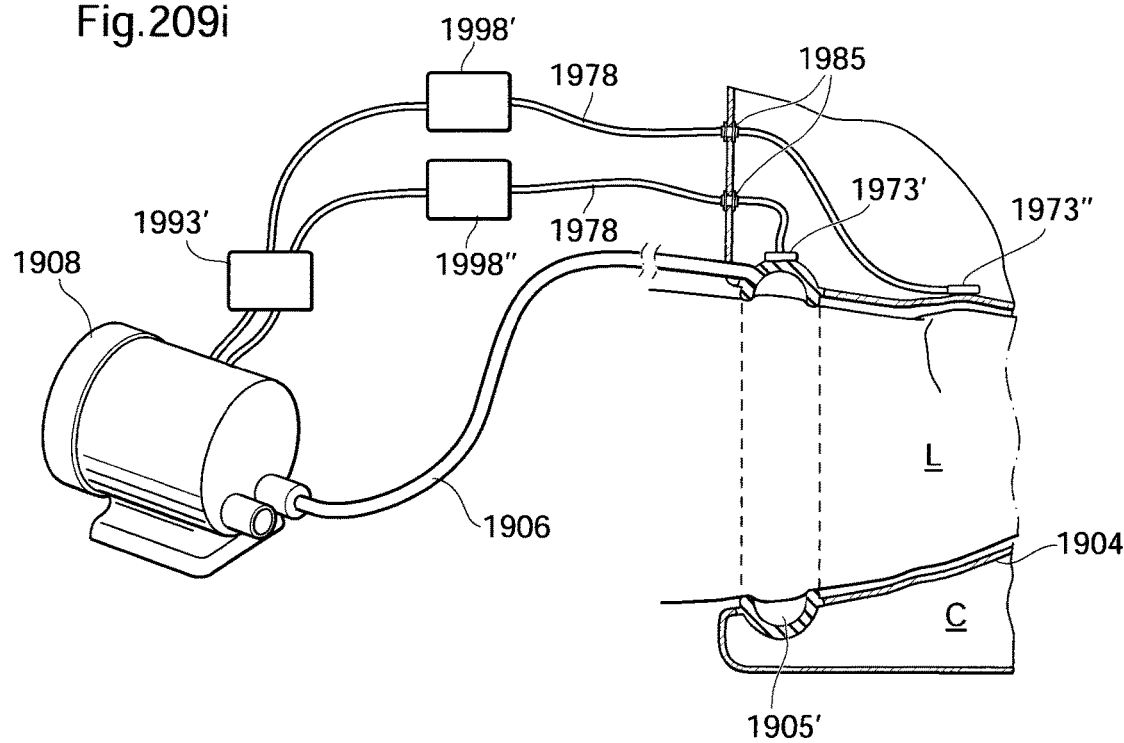

FIGS. 209h and 209i (209i being a sectional enlargement of a portion of 209h) shows an embodiment of the medical device in which the medical device further comprises a vacuum monitoring unit 1998' connected to the adjustment device 1993'. The pressure monitoring unit 1998 is connected to a pressure sensing probe 1973 via a sensing lead 1978 penetrating the wall 1901 of the medical device by means of a bushing 1985 positioned in the wall 1901. The pressure sensing probe 1973 is adapted to sense the pressure in the sealing member 1905" and to provide the pressure adjustment device 1993' with a pressure signal to be used in the adjustment of the pressure in the vacuum sealing member 1905'. The pressure adjustment device 1993' is in turn connected to a vacuum pump 1908 in connection with the vacuum sealing member 1905' by means of a vacuum conduit 1906 for adjusting the pressure in the vacuum sealing member 1905'.

The embodiment shown in FIGS. 209h, 209i also shows an alternative or complement to the vacuum monitoring unit 1998', being a probe 1973 placed inside the chamber C at an area of the leg of the patient. The alternative or complementing probe 1973 may be adapted to measure the pressure in the chamber C, the blood pressure of the patient, and the blood flow of the patient (for example by means of ultrasound).

By measuring the blood flow or blood pressure of the patient, the adjustment device 1993' could be adapted to adjust the pressure in the sealing member 1905' such that the blood flow of the patient remains unaffected.

The embodiment shown in FIGS. 209h, 209i thus shows a medical device comprising a first monitoring unit 1998' adapted to sense the pressure in the vacuum sealing member 1905' and a second monitoring unit 1998" adapted to sense the pressure in the chamber C, or the blood flow, or the blood pressure of the patient. The medical device further comprises an adjustment device 1993' adapted to adjust the pressure in the vacuum sealing member 1905' in response to the input from both the first 1998' and second 1998" monitoring unit, for mediating between keeping the chamber C sealed and keeping the blood flow of the patient un affected. The adjustment device 1993' may be adapted to adjust the pressure in the vacuum sealing member 1905' for keeping the negative pressure between at least one of: −135 mmHg and 0 mmHg, −115 mmHg and 0 mmHg, −100 mmHg and 0 mmHg, −50 mmHg and 0 mmHg, −30 mmHg and 0 mmHg, −20 mmHg and 0 mmHg, −10 mmHg and 0 mmHg, and −5 mmHg and 0 mmHg and thus keeping the blood flow of the patient substantially unaffected.

According to one embodiment, the pressure in the chamber C is between 5 mmHg and 75 mmHg above atmospheric pressure, and the negative pressure in the vacuum sealing member is between −6 mmHg and −76 mmHg.

The vacuum sealing member 1905' is adapted to create a substantially airtight seal between the wall 1901 and the skin of the patient, to enable an incision to be performed through the skin of the patient in sealed environment such that a fluid connection between a cavity within the patient and the chamber C is formed.

Figure 210:
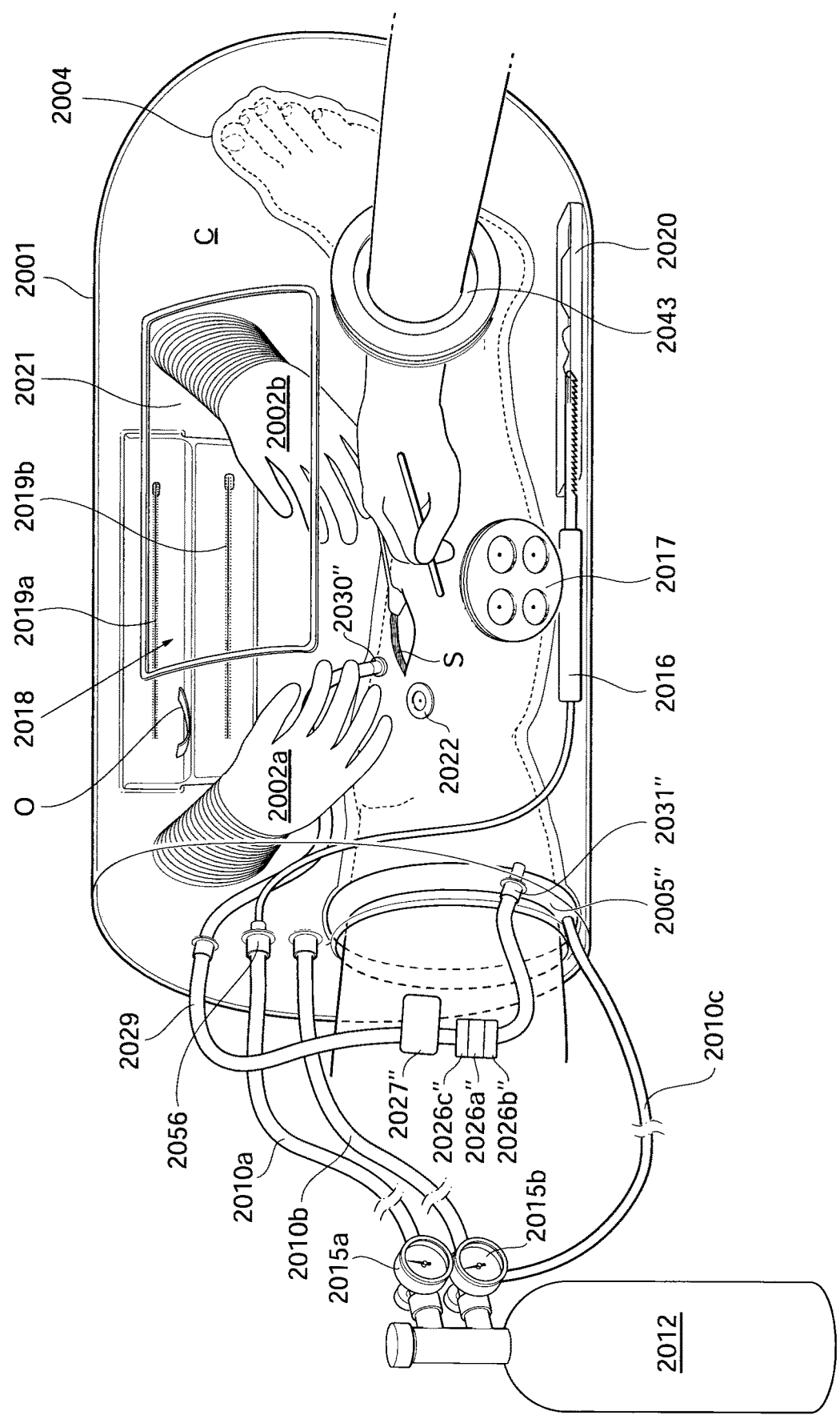
FIG. 210 shows an embodiment of the medical device applied on an extremity of the patient.

FIG. 210 shows an embodiment of the medical device further comprising an airlock sluice 2018, comprising an outer and inner zipper 2019a, 2019b provided in the wall 2001 for allowing passage of an object O between the chamber C and the environment outside of the chamber C when the sealing member 2005" is sealing between the skin of the patient and the wall 2001.

Figure 211:
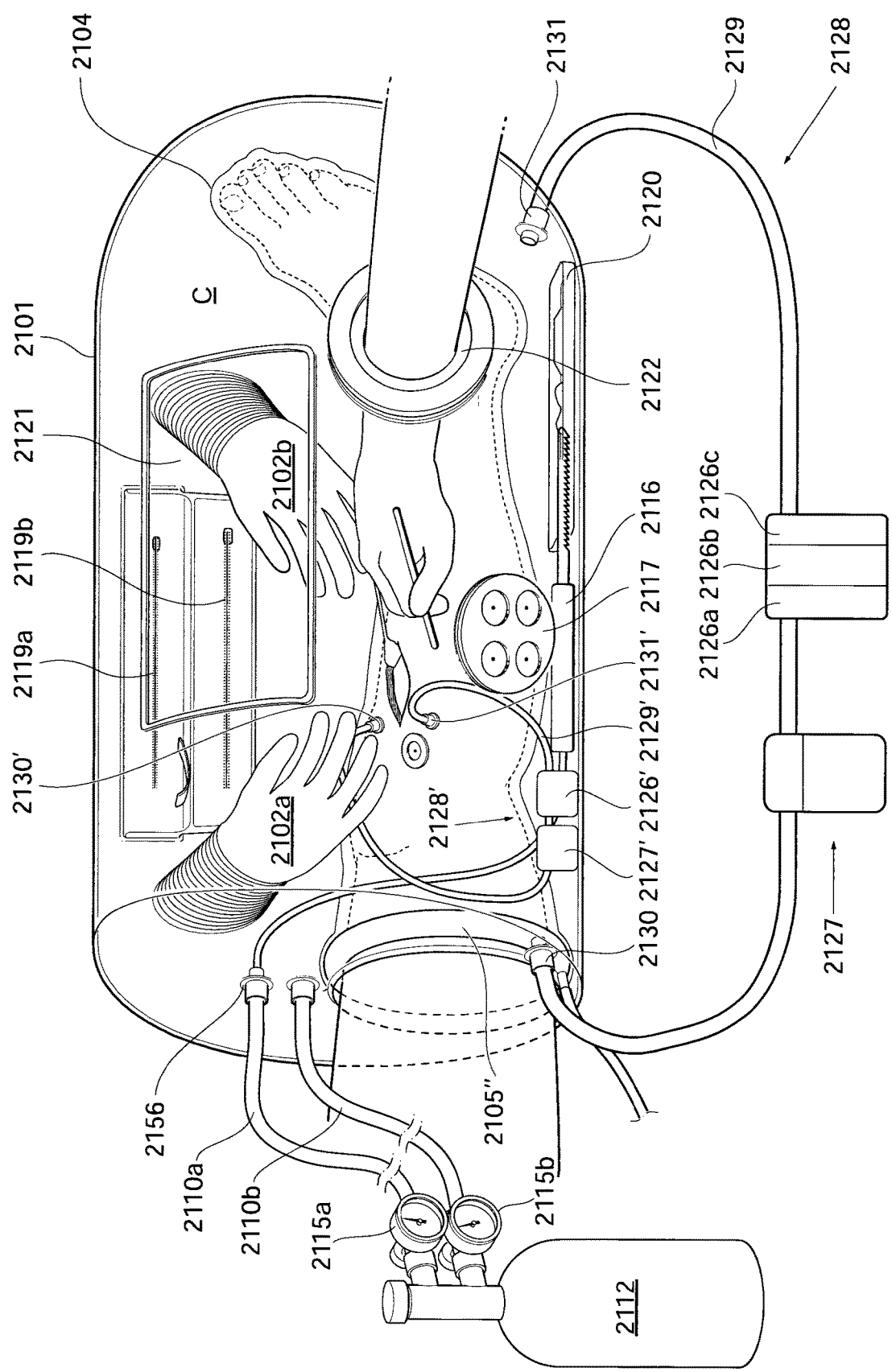
FIG. 211 shows an embodiment of the medical device applied on an extremity of the patient, comprising a fluid circulating system.

The wall 2001 of any of the embodiments described under reference to FIGS. 209-211 may be at least partially collapsible and adapted to be inflated by a fluid. According to the embodiment shown in FIG. 210, the fluid may be a compressed gaseous fluid contained in a pressure container 2012 and transported to the chamber C by means of a fluid conduit 2010b. The pressure of the pressure container and/or of the chamber C may be monitored by means of a control/monitoring device 2015b. The control/monitoring device may in other embodiments be implemented as a digital unit. In yet other embodiments, the control/monitoring unit could be adapted to measure the flow of compressed fluid in the fluid conduit 2010b for maintaining the inflation rate at a level such that the chamber or objects within the chamber is not damaged. The chamber C according to the embodiment shown in FIG. 210 is adapted to hold a pressure exceeding atmospheric pressure, and wherein the sealing member 2005" is thus adapted to seal between the wall 2001 of the medical device and the skin of the patient such that the pressure in the chamber C, exceeding atmospheric pressure, can be maintained. Having the pressure exceeding atmospheric pressure enables open and laparoscopic surgery to be combined and reduces the risk of contaminating the incision sites, as the constant overpressure will make it close to impossible for any particles to enter the sealed chamber C.

The embodiment shown in FIG. 210 further comprises two gloves 2002a, 2002b integrated in the wall 2001 such that a surgeon is able to use the glove 2002a, 2002b from outside the chamber C to make manual manipulations inside the chamber C while maintaining sealed environment in the chamber C.

The sealing member 2005", may in any of the embodiments be assisted or replaced by an adhesive adapted to provide fixation to the skin of the patient, and/or sealing between the skin of the patient and at least one of the wall 2001 and enclosure.

FIG. 210 further shows a body port 2022 positioned in the knee region of the extremity of the patient. The body port 2022 may be adapted for an optical inspection device, such as a fiber optic camera, or one or more surgical instruments suitable for an arthroscopic or laparoscopic operation.

The medical device in FIG. 210 further comprises an elongated tubular enclosure 2004 extending within the chamber C of the medical device. The tubular enclosure 2004 is contacting the skin of the patient and is adapted to separate the skin of the patient from the sealed environment of the chamber C of the medical device. The elongated tubular enclosure 2004 is for example a flexible or elastic tubular enclosure 2004 suitable for receiving a leg of a patient, and encircling the leg of the patient. The steps of the surgical procedure being performed within the chamber C thus includes cutting through the tubular enclosure 2004 for accessing the skin of the patient and thus being able to create an incision in the skin for accessing the knee of the patient. The tubular enclosure 2004 may comprise an adhesive on the side facing the skin of the patient such that the tubular enclosure 2004 can be fixated and sealed against the skin of the patient. By fixating the elongated tubular enclosure 2004 tightly against the skin of the patient, the risk of infections caused by bacteria present on the skin of the patient is reduced.

The embodiment of the medical device shown in FIG. 210 further comprises a fluid system for circulating a fluid, in particular a liquid fluid, in the chamber C of the medical device. The fluid system comprises a fluid inlet 2030" placed in the wall 2001 and adapted for supplying fluid to the chamber C. The fluid inlet 2030" is by means of a fluid conduit 2029 connected to a fluid outlet 2031" positioned in an incision in the patients skin in the knee region of the patient, for evacuating fluid from the knee joint region.

When performing an arthroscopic operation, the joint region is expanded by means of a pressurized liquid. The pressurized liquid thus fills the area of the knee joint during the surgery. For enabling visual inspection in the joint, the liquid needs to be fully transparent. However, when the surgical procedure is started the fluid is contaminated by bodily fluids, mainly blood. The fluid thus needs to be rapidly circled and filtered or replaced by new fluid for maintaining the visibility within the joint throughout the surgical procedure. By filling the chamber C with the liquid, and evacuating the chamber C via the incision in the knee region, the main part of the contaminated liquid will be evacuated through the fluid outlet 2031" and recycled into the chamber C when filtered. For the purpose of filtering the fluid, a filtering unit 2026b" is provided on the fluid conduit, the filtering unit 2026b" being adapted to remove particles by a mechanical filter, such as a filter textile, or by means of a chemical filter such as activated carbon, or by a combination of a mechanical and chemical filter. Also provided on the fluid conduit 2029 is a sterilization unit 2026a" for sterilizing the circulating fluid. The sterilization unit 2026a" could for example be a sterilization device sterilizing the fluid by means of heat, a chemical sterilization device, or a sterilization device sterilizing by means of radiation, such as UV radiation. A fluid tempering unit 2026c" may also be provided on the fluid conduit 2029 for changing the temperature of the fluid passing fluid tempering device 2026c". The fluid is for example circled by means of a pump 2027", which for example could be a peristaltic pump, a gear pump, a membrane pump or a centrifugal pump.

The liquid in the chamber C may be an isotonic solution, such as a saline solution or boric acid, or an antibiotic liquid.

In alternative embodiments of the medical device, the medical device may comprise a second opening arranged such that the leg of a patient can exit the medical device.

The medical device shown in FIG. 210 comprises a pressure sealing member 2005" adapted to seal by mechanically pressing against the skin of the patient, however it is equally conceivable that the pressure sealing member 2005" is assisted or replaced by a vacuum sealing member, such as the vacuum sealing member disclosed in any of the other embodiments herein, being adapted to hold a pressure below atmospheric pressure and thereby provide sealing.

The pressure sealing member 2005" may for example be in fluid connection with a pressure tank 2012 providing pressurized fluid for creating the pressure in the pressure sealing member 2005".

The medical device shown in FIG. 210 further comprises an energy transferring coupling 2056 adapted to transfer energy from outside the chamber C into the sealed environment C, such that a tool 2016 within the chamber C can be energized. The coupling 2056 shown in FIG. 210 is a pneumatic coupling 2056 adapted to transfer pneumatic energy for energizing a pneumatic tool 2016 within the chamber C. However, in other embodiments, it is equally conceivable that the energy transferring coupling is adapted to transfer mechanical energy, in direct, hydraulic or magnetic form, and thus the energy consuming tool being a consumer of mechanic or hydraulic energy. It is furthermore conceivable that the energy transferring coupling is adapted to transfer electric energy such that a tool consuming electrical energy can be operated within the chamber C. The tool may be an orthopedic power tool, such as an orthopedic saw or orthopedic drill, or a surgical instrument for providing light or visual inspection, i.e. a camera.

The energy consuming tool 2016 could be pre-placed within the chamber C before the medical device is placed in connection with the patient, such that nothing needs to be transferred in and out of the chamber C after the chamber C has been positioned in contact with the skin of the patient, thus maintaining the chamber C sealed from the ambient environment.

The embodiment of FIG. 210 further comprises a port 2022 positioned in the skin S of the patient for enabling manipulation within a cavity in the patient. In alternative embodiments (not shown) the port 2022 may comprise at least two ports such that multiple objects may be used simultaneously in the same port. For example, such a multiport may be adapted to receive two surgical instruments for manipulation and one camera for visual inspection of the relevant area. In alternative embodiments, a first port is adapted to handle a surgical instrument, and a second port is adapted to enable the transfer of an object from the chamber C to a cavity in the patient's body, an object may for example comprise a prosthetic part to be implanted in the patient, a part of the patients body to be removed, such as a tumor. One or more of the ports could comprise a an elastic membrane adapted to, in a non-expanded state, seal between the sealed environment and the environment outside of the sealed environment, and in an expanded state enable a hand to be inserted through the elastic membrane. The elastic membrane is for example further disclosed under reference to FIGS. 50a and 50b.

FIG. 211 shows the embodiment of the medical device similar to the embodiment disclosed under reference to FIG. 210. The arm of the surgeon is inserted through a self sealing wall port 2122 in the partially collapsible wall 2101 for enabling manual manipulation therein. Manual manipulation through the self sealing wall port 2122 could for example be used as a last resort should complications occur during the procedure, or if additional hands are required for a specific step of the operation.

The embodiment of FIG. 211 further shows two systems for fluid circulation. One internal system 2128' for fluid circulation within the joint of the patient, and one external system 2128 for fluid circulation in the chamber C. Both systems comprise fluid conduits 2129;2129'. In the external system 2128, the fluid conduits are connected at an inlet 2130 placed in the partially collapsible wall 2101 for supplying fluid to the chamber C, and an outlet 2131 for draining the fluid from the chamber C, and in the internal system 2128', the fluid conduits are connected to the inlet 2130' in the patient's body and an outlet 2131' in the patient's body for circulating fluid in a body cavity. The fluid is circulated by means pumping units 2127; 2127' and is circulated via a sterilizing/filtering/tempering unit 2126'. The external system 2128 disclosed contains a sterilizing 2126a, filtering 2126b, and tempering 2126c unit adapted to remove impurities, sterilize and temper the fluid. In embodiments where the fluid is a gaseous fluid, the filtering unit 2126b is adapted to remove particles that could be suspended in the gas. The filtering unit 2126a could further comprise an inlet for allowing the addition of gas from the surrounding environment. In cases where the circulating fluid is a liquid, the transparency of the liquid is of crucial importance for enabling the surgeon to have visual control of the procedure. The liquid is in this embodiment filtered for the removal of impurities and maintained transparency and sterilized. The filtering unit 2126a could for example comprise a filter containing activated carbon. The liquid circled could for example be an isotonic solution and an antibiotic liquid.

Sterilizing methods could comprises the use of heat, such as electrical or chemical heat, it is furthermore conceivable that the sterilizing is performed using irradiation, such as UV-light and/or though the addition of a chemical sterilizing agent.

In alternative embodiments, the medical device shown in FIG. 211 may be altered such that the medical device comprises a second opening arranged such that the leg of a patient can exit the medical device. Such an embodiment would make the medical device smaller when for example being adapted for knee joint surgery.

The medical device in FIG. 211 further comprises an elongated tubular enclosure 2104 extending within the chamber C of the medical device. The tubular enclosure 2104 is contacting the skin of the patient and is adapted to separate the skin of the patient from the chamber C of the medical device. The elongated tubular enclosure 2104 is for example a flexible or elastic tubular enclosure 2104 suitable for receiving the leg of a patient, and for encircling the leg of the patient. The steps of the surgical procedure being performed within the chamber C thus includes cutting through the tubular enclosure 2104 for accessing the skin of the patient and thus being able to create an incision in the skin for accessing the knee of the patient. The tubular enclosure 2104 may comprise an adhesive on the side facing the skin of the patient such that the tubular enclosure 2104 can be fixated and sealed against the skin of the patient. By fixating the elongated tubular enclosure 2104 tightly against the skin of the patient, the risk of infections caused by bacteria present on the skin of the patient is reduced.

The medical device shown in FIG. 211 comprises a pressure sealing member 2105" adapted to seal by mechanically pressing against the skin of the patient, however it is equally conceivable that the pressure sealing member 2105" is assisted or replaced by a vacuum sealing member, such as the vacuum sealing member disclosed in any of the other embodiments herein, being adapted to hold a pressure below atmospheric pressure and thereby provide sealing.

The pressure sealing member 2105" may for example be in fluid connection with a pressure tank 2112 providing pressurized fluid for creating the pressure in the pressure sealing member 2105".

The medical device shown in FIG. 211 further comprises an energy transferring coupling 2156 adapted to transfer energy from outside the chamber C into the sealed environment, such that a tool 2116 within the chamber C can be energized. The coupling 2156 shown in FIG. 211 is a pneumatic coupling 2156 adapted to transfer pneumatic energy for energizing a pneumatic tool 2116 within the chamber C. However, in other embodiments, it is equally conceivable that the energy transferring coupling is adapted to transfer mechanical energy, in direct, hydraulic or magnetic form, and thus the energy consuming tool being a consumer of mechanic or hydraulic energy. It is furthermore conceivable that the energy transferring coupling is adapted to transfer electric energy such that a tool consuming electrical energy can be operated within the chamber. The tool may be an orthopedic power tool, such as an orthopedic saw or orthopedic drill, or a surgical instrument for providing light or visual inspection, i.e. a camera. Couplings are further disclosed under reference to FIGS. 212a-214.

The energy consuming tool 2116 could be pre-placed within the sealed environment before the medical device is placed in connection with the patient, such that nothing needs to be transferred in and out of the chamber C after the chamber C has been positioned in contact with the skin of the patient, thus maintaining the chamber C sealed from the ambient environment.

FIGS. 212a-214 shows a system for transferring energy and/or information from the ambient environment into the chamber C of the medical device 2100 whilst maintaining the sealed environment in the chamber C. The system could be used for transferring energy and/or information to the chamber C in any of the embodiments of the medical device disclosed herein. The energy could be provided to an energy consuming tool to be used within the chamber C, or an optical or imaging instrument needed inside the chamber C for supplying visual information. An information coupling could be needed to supply information (e.g. control information) to an energized tool inside the chamber, or for providing information from within the chamber to medical personnel on the outside. Information supplied from the chamber could for example include visual information for example provided by an endoscopic camera provided inside the chamber, or sensor information provided by a sensing probe within the chamber. Sensor information could for example be sensor information related to a physiological parameter of the patient, such as temperature, blood pressure, or blood flow, or a physical parameter of the medical device, such as the pressure in seals or in the chamber.

Figure 212A:
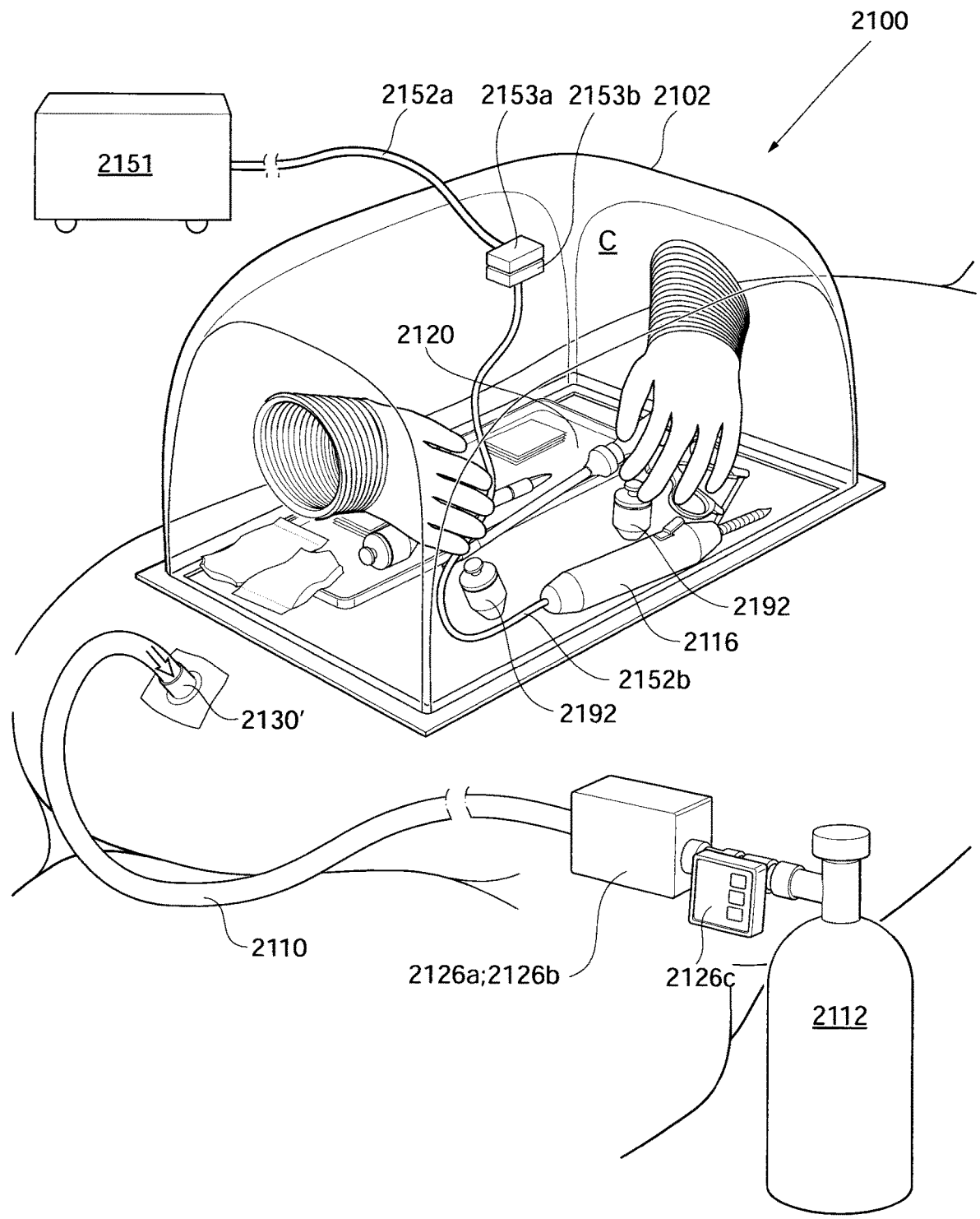
FIGS. 212-214 shows embodiments of the medical device comprising information and/or energy transferring members.

FIG. 212a shows an embodiment of the medical device 2100 similar to the embodiment disclosed under reference to FIG. 39. The difference being that the fluid inlet is a fluid body inlet 2130' adapted to inflate a cavity in the patient's body. The fluid is then transferred to a sealed chamber C of the medical device 2100 through the trocars 2192 creating a fluid connection between the cavity in the patient and the chamber C of the medical device 2100. The medical device 2100 shown in FIG. 212a comprises a wall 2101 adapted to be applied on the patient's body to form a sealed chamber C, in which a sealed environment can be maintained for encompassing part of the surgical procedure to be performed. The medical device 2100 further comprises a kinetic energy transferring member 2152a, 2152b for transferring energy from outside of the sealed chamber C to inside of the sealed chamber C. The first portion of the kinetic energy transferring member 2152a, positioned on the outside of the medical device 2100 is connected to an electric motor 2151 converting electrical energy to kinetic energy. The first portion of the kinetic energy transferring member 2152a is in the other end connected to a kinetic energy coupling 2153, comprising an external part 2153a adapted to be placed on the outside of the wall 2101 of the medical device 2100 and an internal part 2153b adapted to be placed on the inside of the wall 2101 of the medical device 2100. The kinetic energy coupling is adapted to wirelessly transfer kinetic energy from the inside of the chamber C to the outside of the chamber C wirelessly through the wall 2101 of the medical device 2100 by means of for example inductive or magnetic coupling. The internal part 2153b of the kinetic energy coupling is connected to a second portion of the kinetic energy transferring member 2152b which is connected to a kinetic energy consuming tool 2116, such as an orthopedic drill.

The fluid body inlet 2130' is connected to a fluid conduit 2110, which in turn is connected to a pressurized fluid tank 2112 via a tempering unit 2126c, a sterilizing unit 2126a and a filtering unit 2126b for filtering, sterilizing and tempering the fluid entering the cavity in the patient's body. The filtering could for example remove particles from the fluid and the tempering of the fluid could be a heating of the fluid for making the environment more suitable for the surgical procedure or the medical personnel, or a cooling of the fluid for example reducing the growth rate of bacteria in the chamber C.

Figure 212B:
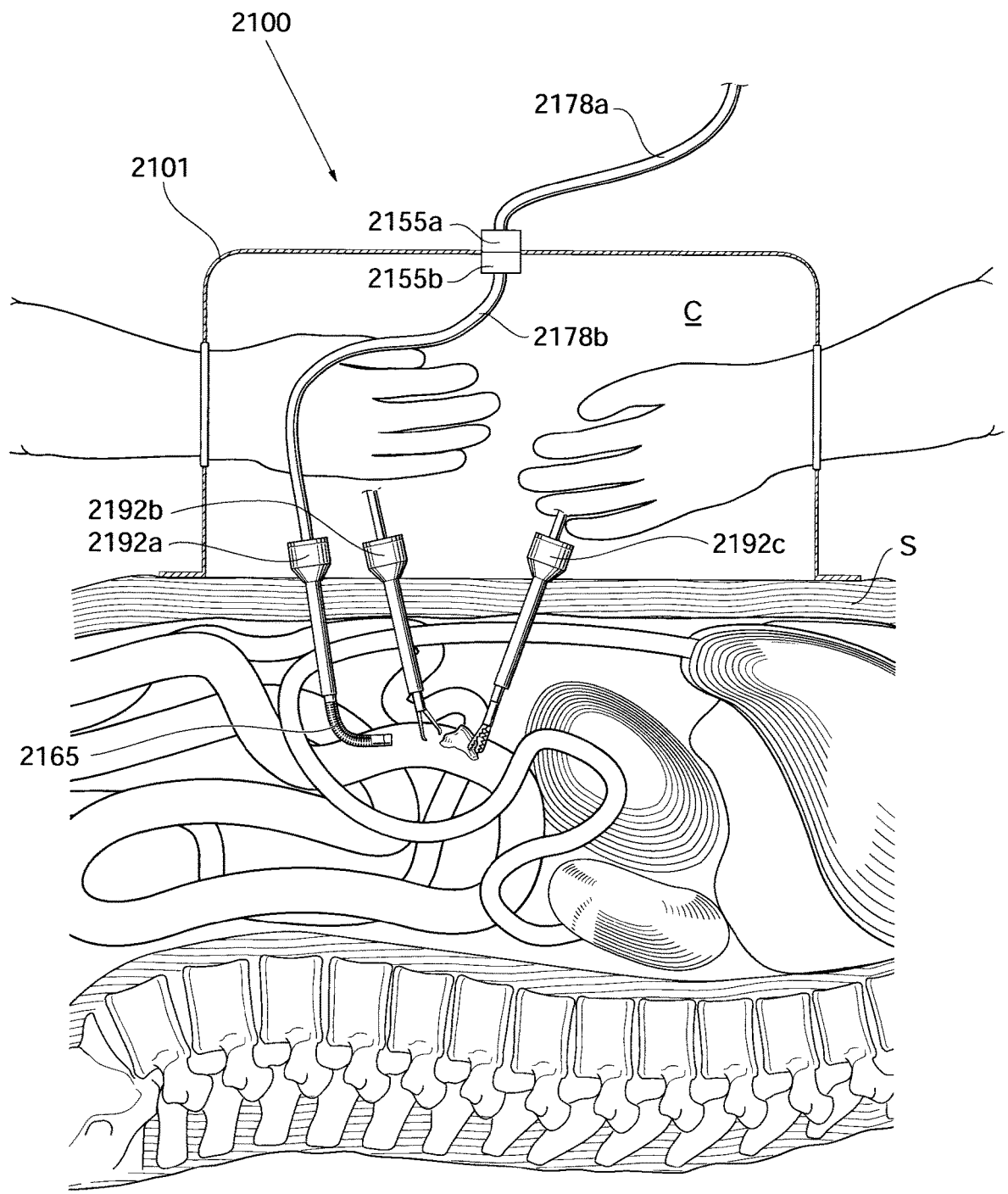

FIG. 212b shows an embodiment of the medical device 2100 placed on the abdomen of a patient. The medical device 2100 comprises three trocars 2192a, 2192b, 2192c positioned through the skin S of the patient such that a surgical procedure within the abdomen of the patient can be performed. The medical device 2100 comprises an information coupling 2155a, 2155b for transferring visual information from an endoscopic camera 2165 positioned in one of the trocars 2192a. The visual information is transferred via a lead 2178b to the interior part of the information transferring coupling 2155b to the exterior part of the information transferring coupling 2155a and further via another lead 2178a to a display device for displaying the visual information captured by the endoscopic camera 2165.

Figure 212C:
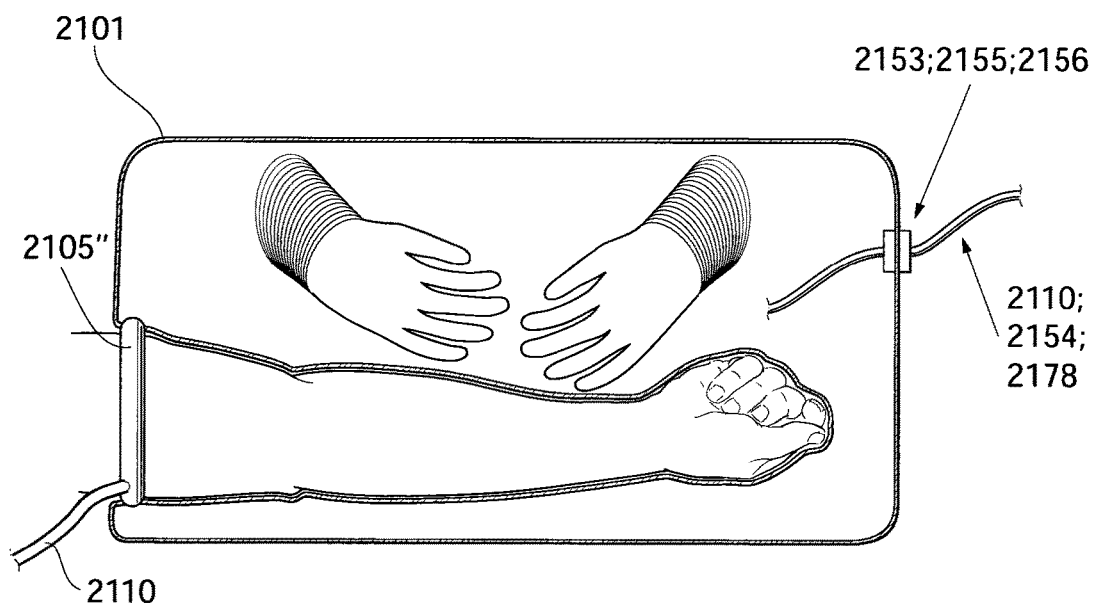

FIG. 212c shows an alternative embodiment in which the an information transferring member 2155 or energy transferring coupling 2156; 2153 is connected to an information transferring lead 2178 or energy transferring member 2110; 2154. The coupling 2153; 2155; 2156 is positioned in the side wall 2101 of the medical device 2100 adapted for surgery on an arm of a patient. The medical device 2100 is further described under reference to FIG. 1d, with the difference that the medical device of FIG. 212c comprises a pressure sealing member 2105" connected to a fluid conduit 2110, in turn connected to a pressure source (not shown).

Figure 212D:
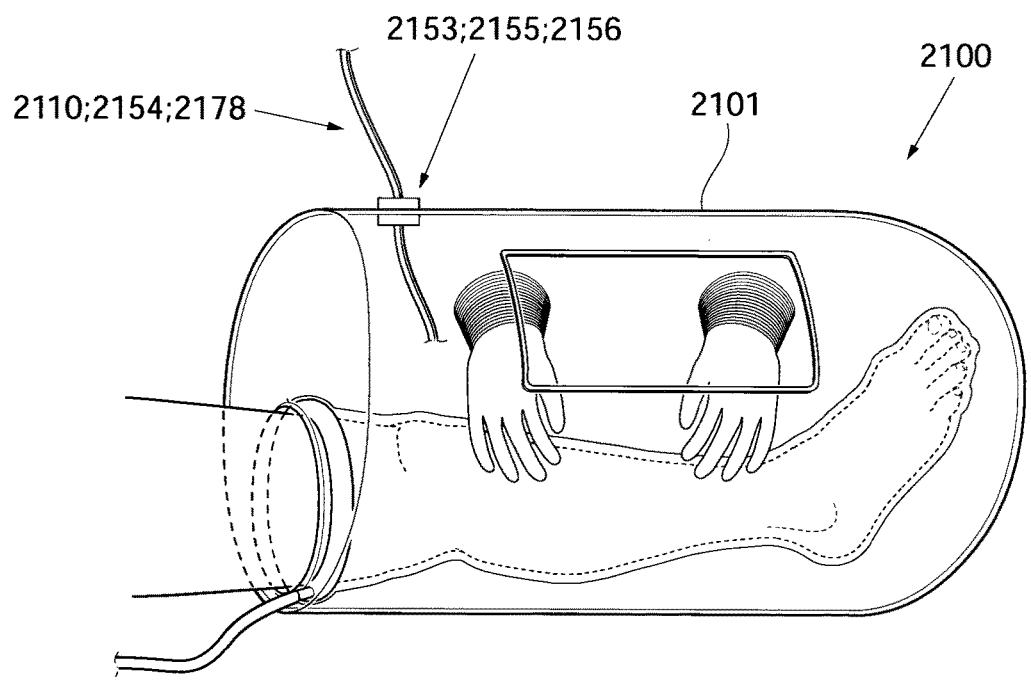

FIG. 212d shows the medical device in an embodiment further described under reference to FIG. 3b, with the difference that the medical device of FIG. 212d comprises an information transferring member 2155 or energy transferring coupling 2156; 2153 connected to an information transferring lead 2178 or energy transferring member 2110; 2154. The coupling being positioned in the top portion of the wall 2101 of the medical device 2100.

Figure 213A:
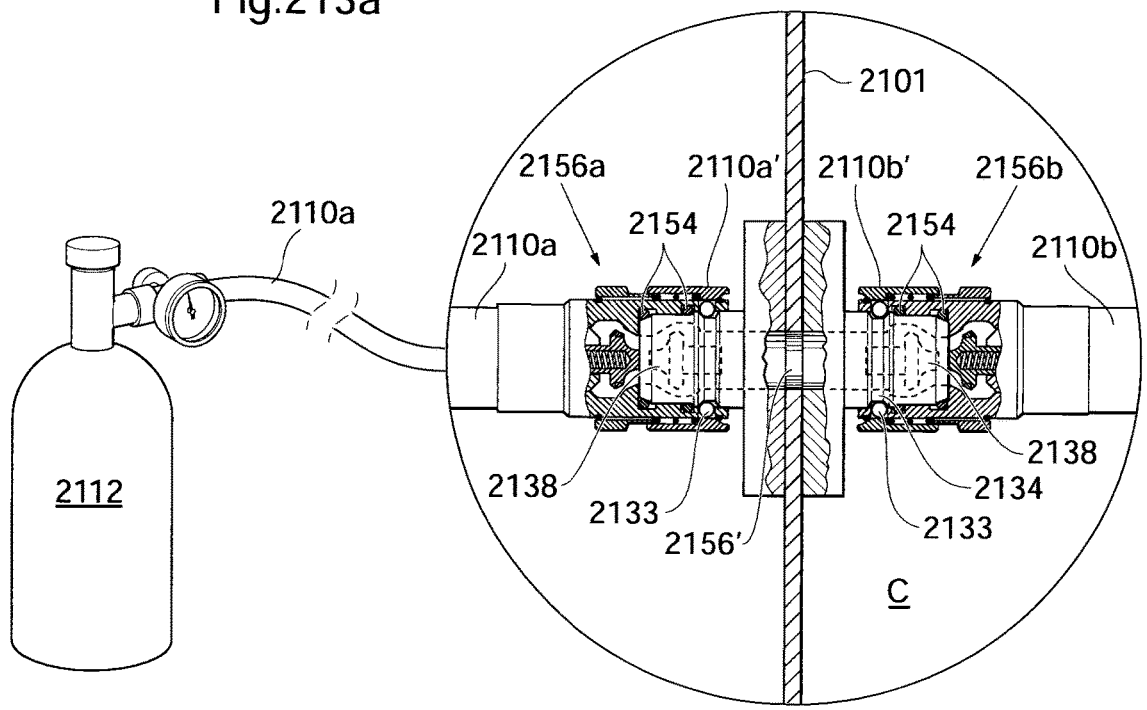

FIG. 213*a* shows a fluid energy transferring coupling 2156 in further detail. The fluid coupling 2156 enables the transfer of a pressurized fluid from a pressure source 2112 outside of the chamber C such as the pressurized fluid tank 2112 shown in FIG. 213*a* connected via a fluid conduit 2110*a* to the external portion 2156*a* of the fluid coupling. The external portion 2156*a* of the fluid coupling comprising a valve 2138 adapted to open when the fluid conduit 2110 is connected to the fluid coupling tube 2156' penetrating the wall 2101 of the medical device. When the fluid coupling 2156*a*; 2156*b* is not coupled to the fluid conduit 2110*a*, the valve 2138 remains closed, hence, fluid can only be transferred from the fluid conduit 2110*a* on the outside of the chamber C to a fluid conduit 2110*b* on to inside of the chamber C and never to the environment in the chamber C, thus can the environment of the chamber C be kept sealed. The tube 2156' comprises a recess 2134 in the form of a groove adapted to receive protruding members 2133 of the fluid conduit 2110*a* for locking the fluid conduit 2110*a* to the tube 2156'. The protruding members 2133 is small spherical balls 2133 which are pressed into the recess 2134 by a slideable external portion 2110*a*' of the fluid conduit 2110*a*. The leftwards sliding of the external portion 2110*a*' causing the spherical balls 2133 to engage a recess of the external portion 2110*a*' and thus be removed from the recess 2133 of the tube 2156', thus releasing the fluid conduit 2110*a* from the tube 2156'. The inside of the connecting portion of the fluid conduit 2110*a* comprises a plurality of O-rings 2154 providing sealing between the tube 2156' and the connecting portion of the fluid conduit 2110*a*. The internal portion of the fluid coupling 2156*b* is identical to the external portion 2156*a* and thus connects an internal portion 2110*b* of the fluid conduit to the tube 2156' enabling transfer of fluid in a corresponding way.

Figure 213B:
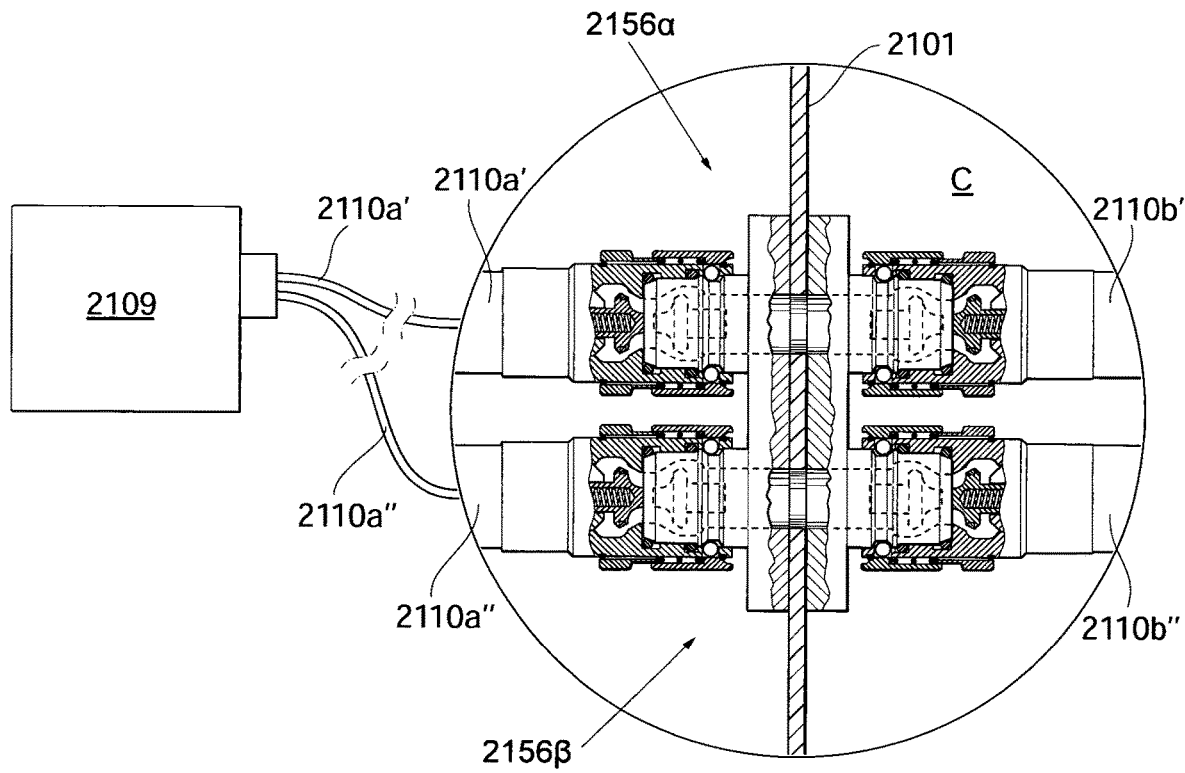

FIG. 213*b* shows an alternative embodiment of the fluid energy transferring coupling 2156 in detail. The alternative embodiment comprises two fluid energy transferring couplings 2156α, such that fluid energy can be circled. The fluid could enter the chamber C through a first fluid energy transferring coupling 2156β, and exit the chamber C through a second fluid energy coupling 2156, such that no fluid is added to the sealed environment of the chamber C.

FIG. 213*c* shows a kinetic energy transferring coupling 2153 is detail. The coupling 2153 being adapted to transfer rotational kinetic energy, contactless through the wall 2101 of the medical device. The kinetic energy transferring coupling 2153 comprises an external part 2153*a* comprising a magnet connected to a kinetic energy transferring member 2152*a* such that the magnet of the external part 2153*a* rotates as the kinetic energy transferring member 2152*a* rotates. The kinetic energy transferring coupling 2153 further comprises an internal part 2153*b* connected to a kinetic energy transferring member 2152*b*, which in turn is connected to a tool inside of the chamber C consuming kinetic energy. The internal part 2153*b* comprises a magnet or magnetic material adapted to magnetically engage with the magnet of the external part 2153*a*, such that the magnet or magnetic material of the internal part 2153*b* rotates along with the magnet of the external part 2153*a*. The coupling further comprises a holding magnet 2157 placed centrally in the coupling 2153 and adapted to hold and align the external 2153*a* and internal 2153*b* parts of the coupling 2153, such that rotational energy can be transferred contactless from the outside of the chamber C to the inside of the chamber C, through the wall 2101 of the medical device, such that the chamber C is kept sealed while transferring kinetic energy from the outside of the chamber C to the inside of the chamber C.

FIG. 213*d* shows the kinetic energy transferring coupling 2153 of the embodiment shown in FIG. 213*c* when connected by means of the holding magnets 2157*a*; 2157*b* magnetically holding and aligning the external 2153*a* and internal 2153*b* parts of the kinetic energy transferring coupling 2153, such that kinetic energy can be transferred from the outside of the chamber C to the inside of the chamber C. The external part 2153*a* of the kinetic energy transferring coupling 2153 is connected to a kinetic energy transferring member 2152*a* which in turn is connected to an electric motor 2151 transforming electrical energy to rotational kinetic energy. The internal part 2153*b* is connected to a kinetic energy transferring member 2152*b*, such as a wire adapted to transfer rotational force, which in turn is connected to a tool inside of the chamber C consuming kinetic energy, such as an orthopedic drill or an orthopedic reamer.

FIG. 213*e* shows an electric energy transferring coupling 2158 adapted to transfer energy from outside of the chamber C to the inside of the chamber C by means of induction. The energy transferring coupling 2158 comprises a first external part, comprising a first coil 2166*a* connected to a lead 2178*a* connected to some form of supply of electric energy. The second part comprises a second coil 2166*b* connected to a second lead 2178*b*, which in turn is connected to a tool within the chamber C consuming electric energy. Both the internal part and the external part further comprises magnets 2157*a*; 2157*b* adapted to hold and align the electric energy transferring coupling 2158 such that electric energy is efficiently transferred. Using the electric energy transferring coupling 2158 of FIG. 213*e*, electric energy can be wirelessly transferred from the outside of the chamber C to the inside of the chamber C, such that the chamber C can be remained sealed during the transfer of the electric energy. The tool consuming electric energy could be a mechanical tool, such as an orthopedic drill, an optical instrument, such as a camera, or an electrical instrument, such as a diathermy instrument. The electric energy transferring coupling 2158 could furthermore be adapted to transfer information, e.g. in the form of binary electric pulses. The information could for example be optical information from a camera placed on the inside of the chamber C of the medical device to the outside of the chamber C of the medical device.

Figure 213F:
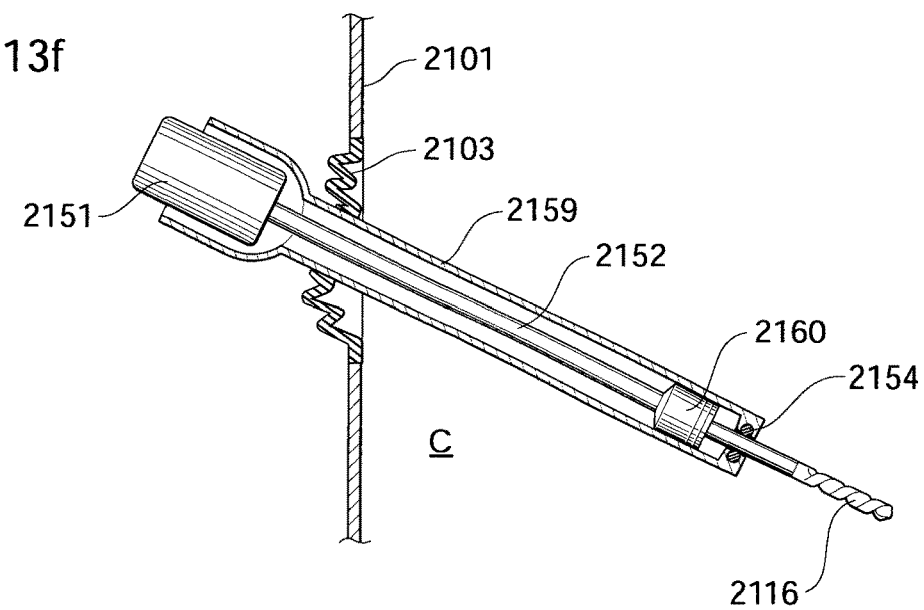

FIG. 213*f* shows an embodiment of a kinetic energy transferring member 2152 for transferring kinetic energy from outside of the chamber C to the inside of the chamber C. The device for kinetic energy transferring member comprises a sleeve 2159 adapted to be positioned through the wall 2110 of the medical device 2100. The sleeve 2159 is fixated to a pleated portion 2103 if the wall 2101 of the medical device, the pleated portion 2103 being adapted to enable movement of the sleeve 2159 in the chamber C, such that the position of the kinetic energy delivered inside the chamber C of the medical device 2100 can be changed. A motor 2151 is positioned in the sleeve 2159 and connected to an elongated kinetic energy transferring member 2152 adapted to transfer rotational kinetic energy. The elongated kinetic energy transferring member 2152 is in turn connected to a tool holder 2160 to which a tool 2116 consuming kinetic energy (such as the shown drill) can be fixated. The tool 2116 consuming kinetic energy is sealingly connected to the sleeve 2159 via an O-ring 2154 which acts as bearing and sealing between the sleeve 2159 and the tool 2116. As the O-ring 2154 provides sealing between the tool and the sleeve 2159 the hollow inside of the sleeve 2159 is sealed from the chamber C of the medical device, and thus is the chamber C sealed from the ambient environment when kinetic energy is transferred between the outside of the chamber C and the inside of the chamber C. The electric motor 2151 supplying rotational kinetic energy could be replaced by a motor supplying translating kinetic energy, in which case the kinetic energy transferring member 2152 transferring rotational kinetic energy is replaced by a kinetic energy transferring member adapted to transfer translating kinetic energy to for example a translating saw blade or a pivoting tool.

Figure 213G:
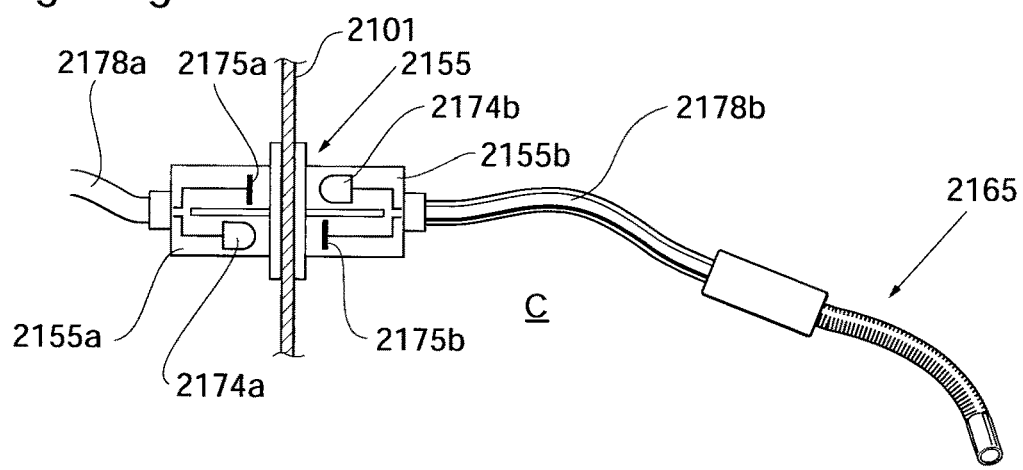

FIG. 213g shows an embodiment of an information transferring member 2155 adapted to wirelessly transfer information from inside the chamber C of the medical device to outside of the chamber C. The information transferring member 2155 comprises an external part 2155a positioned on the outside of the wall 2101 of the medical device and connected to the wall 2101. The external part 2155a comprises an Infra Red (IR) diode 2174a adapted to emit information in the form of IR light pulses, and an IR detector 2175a adapted to receive information in the form of IR light pulses. The information transferring member 2155 further comprises an internal part 2155b adapted to be placed on the inside of the wall 2101 of the medical device, connected to the wall 2101 of the medical device and aligned with the external part 2155a of the information transferring member 2155a such that the IR diode 2174a can emit information in the form of IR light pulses which can be received by the IR detector of the internal part 2155b such that information can be transferred from the external part 2155a to the internal part 2155b, through the wall 2101 of the medical device. The internal part 2155b further comprises an IR diode 2174b aligned with the IR detector 2175a of the external part 2155a, such that information can be transferred from the inside of the chamber C, through the wall 2101 of the medical device by means of IR light pulses detected by the IR detector 2175a.

Information transferred from the inside of the chamber C to the outside of the chamber C could for example be image data captured by a camera 2165 placed inside the chamber C of the medical device transferred to the internal part 2155b of the information transferring member 2155 by means of a lead 2178b. After the image data has been wirelessly transmitted through the wall 2101 of the medical device by means of the information transferring member 2155, the information is transferred to a display unit by means of a lead 2178a, such that medical personnel can see the images captured by the camera 2165 placed inside the chamber C of the medical device. Information required to be transferred into the chamber C for example includes settings for the camera 2165 placed inside the chamber C such as for example zoom level and/or resolution.

In alternative embodiments, the IR diode can be replaced by some other type of light emitting diode (LED) and a corresponding detector, without parting from the inventive concept. One advantage with having an information transferring member based on the transmission of light pulses is that no radio signals are emitted, which reduces the risk that the wireless transfer shall disturb other electronic equipment in the operating theater.

Figure 213H:
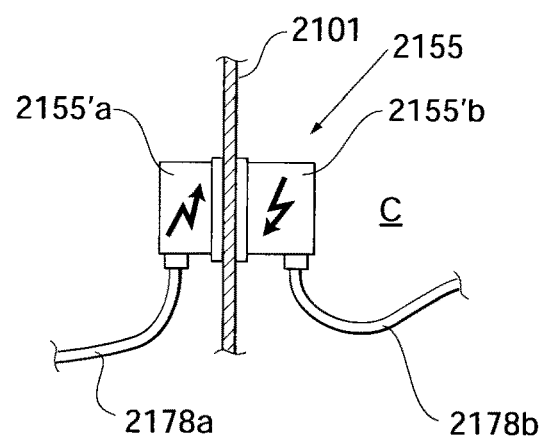

FIG. 213h shows an embodiment of the information transferring member 2155 in which the information transferring member 2155 comprises a first 2155a and second 2155b radio transceiver adapted to transmit and receive radio signals containing information from the inside of the chamber C to the outside of the chamber C, and vice versa.

The first 2155a and second 2155b radio transceiver respectively being coupled to units transmitting and/or receiving information by means of leads 2178a; 2178b. Units that transmits and/or receives information could for example be control units or monitoring equipment on the outside of the chamber C and optical instruments or sensors on the inside of the chamber C.

Figure 214:
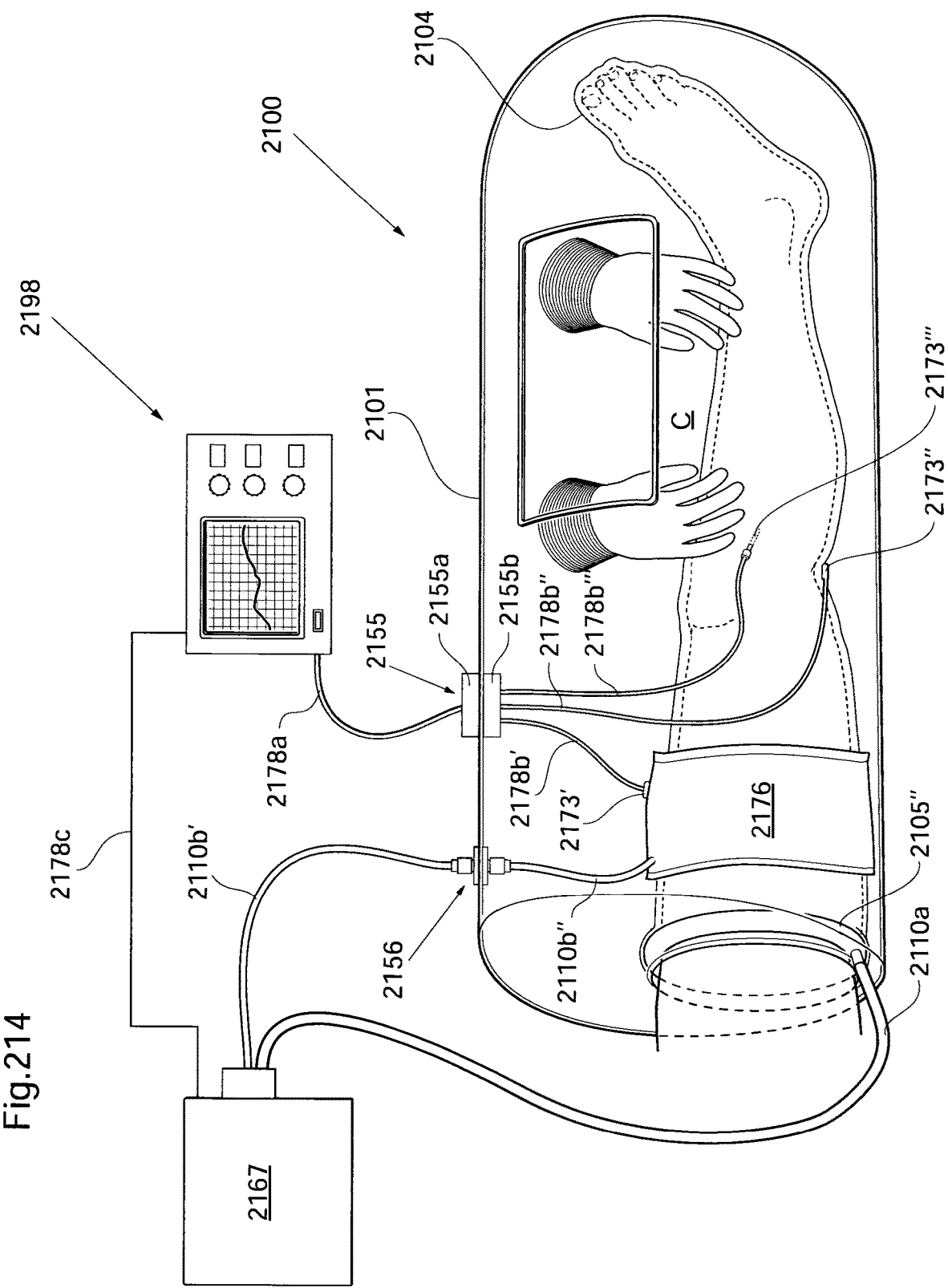

FIG. 214 shows an embodiment of the medical device 2100 in which a wall 2101 of the medical device 2100 forms a chamber C, in which a sealed environment can be maintained for encompassing part of a surgical procedure. The medical device 2100 further comprises a monitoring unit 2198 comprising a blood pressure monitoring unit operated as a sphygmomanometer. The blood pressure monitoring unit is connected to a cuff 2176 which is snugly placed around the leg of the patient. The pressure monitoring unit is operated by the cuff 2176 being inflated to a pressure initially in excess of the systolic arterial pressure and then reduced to below diastolic pressure over a period of about 30 seconds. When no blood is flowing passed the cuff 2176, the cuff 2176 pressure will be essentially constant. When blood flow is present, but restricted, the cuff 2176 pressure, which is monitored by a pressure sensing probe 2173' connected to the blood pressure monitoring unit, will vary periodically in synchrony with the cyclic expansion and contraction of the arteries. The values of the systolic and diastolic pressure can thus be computed. The flow is measured using an ultra sonic flow meter 2173" connected to a lead 2178b' and being adapted to measure the blood flow at a relevant place of the patient's leg, such as the lateral side of the knee. The blood pressure monitoring unit may be adapted to measure the blood pressure of the patient periodically, such as for example with an interval of: 1-5 minutes, 5-10 minutes, 10-20 minutes, or 20-30 minutes. The medical device 2100 further comprises a fluid energy transferring coupling 2156 (such as the fluid energy transferring coupling disclosed under reference to FIGS. 213a and 213b). The fluid energy transferring coupling 2156 connects a first portion of a fluid conduit 2110b' to a second portion of the fluid conduit 2110b". The first portion 2110b' of the fluid conduit is connected to a pressure creating member 2167 for supplying the fluid conduit 2110b' with a pressurized fluid. The second portion 2110b" of the fluid conduit is connected to the inflatable cuff 2176. The medical device further comprises a wireless information transferring member 2155 (such as the wireless information transferring members shown in FIGS. 213g and 213h, for wirelessly transferring values of the sensed blood flow through the wall 2101 of the medical device 2100 to the monitoring unit 2198. The monitoring unit is in turn connected via a lead 2178c to the pressure creating member 2167 which creates the pressure inflating the cuff 2176. By providing feedback to the pressure creating member inflating the cuff 2176 the blood flow in the leg of the patient can be regulated.

The embodiment shown in FIG. 214 further comprises an invasive sensing probe 2173''' adapted to sense a physiological parameter of the patient's body, such as saturation of the blood of the patient, or an ischemia marker such as lactate. The invasive sensor 2173''' is connected to a lead 2178b''' which in turn is connected to an internal part 2155b of the information transferring member 2155 such that the information from the invasive sensor 2173''' is wirelessly transmitted to an external part 2155a of the information transferring member 2155 and further via a lead 2178a to a monitoring unit 2198 for monitoring the sensed physiological parameter. The monitoring unit 2198 is connected to the pressure creating member 2167 for providing feedback to the pressure creating member 2167 such that the pressure in the sealing member 2105" and/or the pressure in the cuff 2176 can be regulated on the basis of input from one or more of the pressure sensor 2173' sensing the pressure in the cuff 2176, the ultra sonic blood flow sensor 2173" sensing the blood flow in a blood vessel in the leg of the patient, and the invasive sensor 2173''' sensing a physical parameter of the patient. By the described monitoring, it is possible to mediate between establishing that the leg of the patient is sufficiently saturated and that the pressure seal provides sufficient sealing between the elongated tubular enclosure 2104 and the ambient environment.

Figure 216:
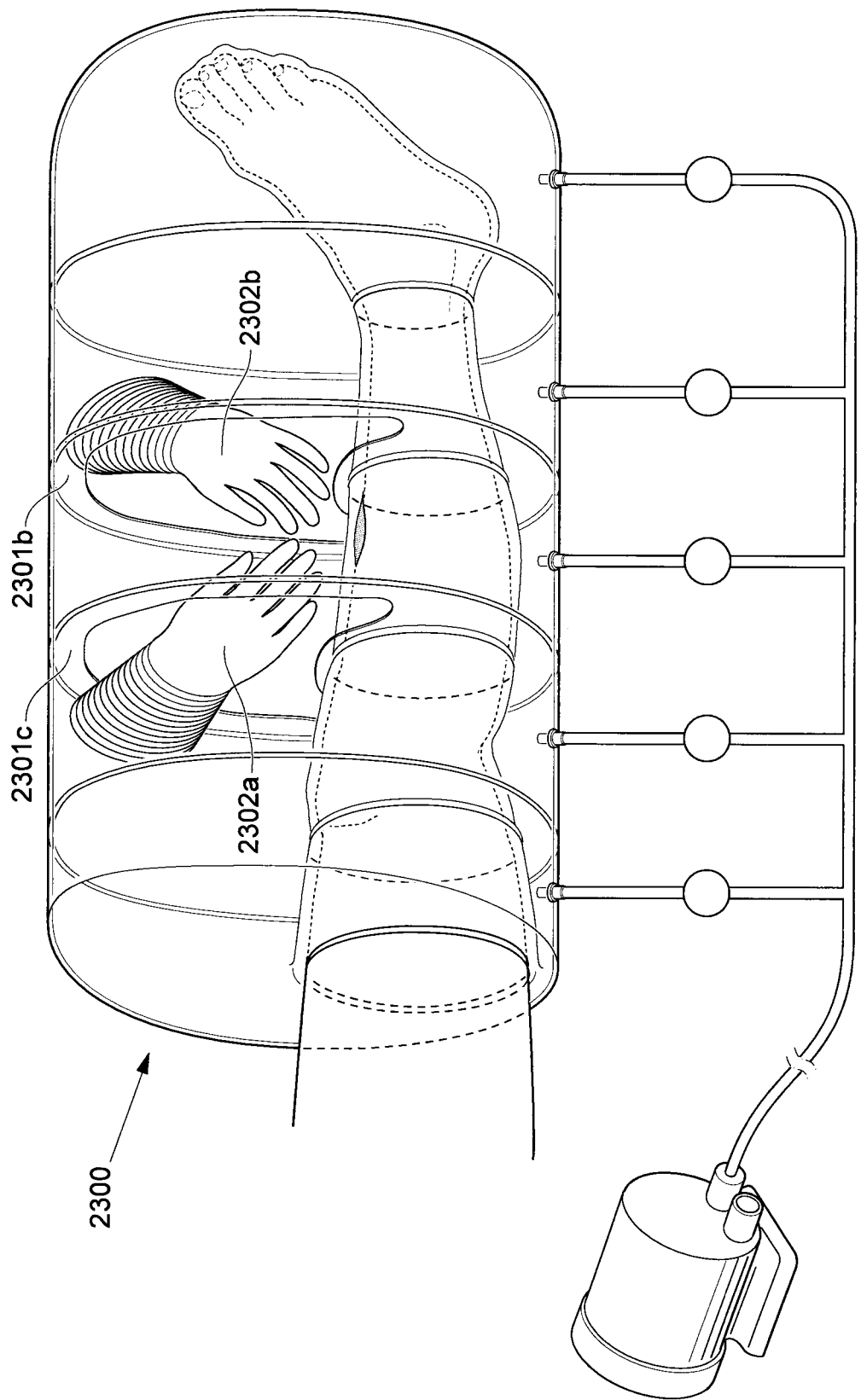
Figure 217:
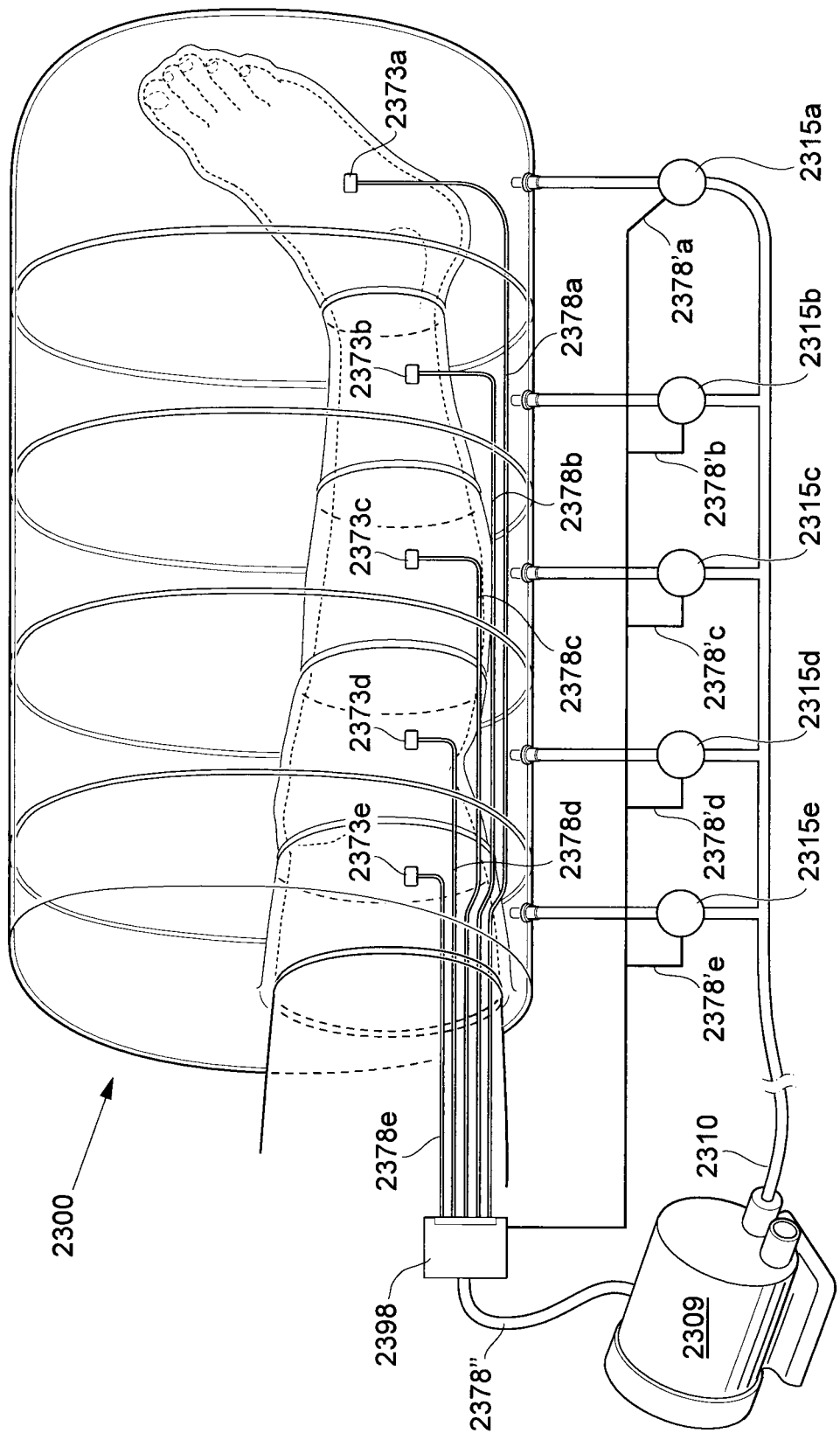

In orthopedic surgery performed on extremities of a patient it is advantageous to reduce the amount of blood present in the extremity such that heavy bleeding can be avoided. Traditionally, the blood reduction of has been performed by means of a bandage roll that the surgeon has started to roll around the most distal portion of the extremity thus pushing the blood from the most distal portion of the extremity towards more proximal portions. The surgeon continues to roll the bandage around the extremity of the patient towards the more proximal portions of the extremity. By this continuous pushing of the blood towards the proximal portions of the extremity, the amount of blood in the extremity is reduced and the surgery can be performed on the extremity of the patient with substantially less bleeding. FIG. 215-217 shows a medical device for reducing the amount of blood in an extremity of the patient. In its most simple form the medical device only comprises two compartments, reduction of blood starts with the inflation of the most distal compartment such that the blood in the extremity of the patient is pushed towards the more proximal portion of the extremity. When the volume of blood in the distal portions of the extremity is adequately reduced, the more proximal chamber is inflated such that the blood volume in the more proximal portions is reduced, whereafter the pressure in the more distal chamber can be released as the inflation of the more proximal chamber functions as tourniquets.

Figure 221A:
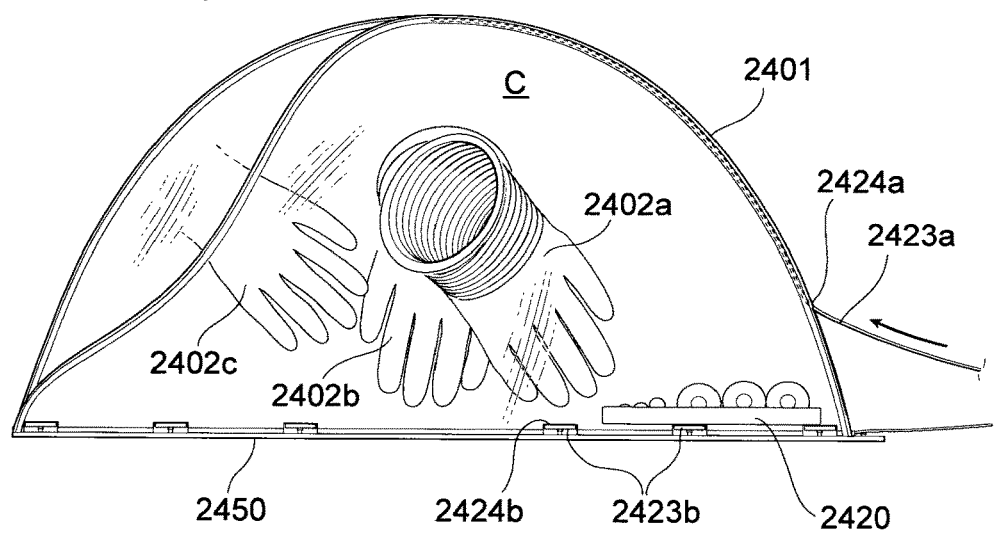
FIGS. 221*a*-221*d* shows embodiments of the medical device adapted to hold a chamber without being inflated.

FIG. 215a shows a medical device 2300 comprising a wall 2301 enclosing a compartmentalized chamber C1-C5 by means of internal compartment dividing walls 2301a-2301d. The compartmentalized chamber C1-C5 being adapted to house a step of a surgical procedure performed on an extremity, in this embodiment leg, of the patient. The medical device 2300 being adapted to reduce amount of blood in the leg of the patient, such that the surgical procedure can be performed with reduced bleeding. The compartmentalized chamber C1-C5 comprises a first inflatable compartment C1 placed around a first distal portion of the leg, the first inflatable compartment C1 being adapted to be inflated for pressing against the distal portion of the leg such that blood is pushed towards the proximal portion of the leg. The portion of the wall 2301 forming the first compartment C1 comprising a first fluid inlet 2330a connected to a first fluid conduit 2310a. The first fluid conduit 2310a is provided with a first control unit 2315a being part of a control system 2315. The first control unit 2315a is adapted to control the inflation of the first compartment C1 such that the blood is pushed out of the foot of the patient. The medical device 2300 further comprises a second inflatable compartment C2 placed around a second, more proximal portion of the leg. The second inflatable compartment C2 comprising a second fluid inlet 2330b connected to a second fluid conduit 2310b provided with a second control unit 2315b being part of the control system 2315. The second control unit 2315b being adapted to control the inflation of the second compartment C2 such that the blood is pushed further towards the more proximal portion of the leg of the patient. The medical device shown in FIG. 221a is further provided with a third, fourth and fifth inflatable compartment C3; C4; C5, each being positioned increasingly more proximal and each comprising a fluid inlet 2330c; 2330d; 2330e connected to fluid conduits 2310c; 2310d; 2310e with individual control units 2315c; 2315d; 2315e for consecutively inflating the compartments such that a peristaltic compression of the leg is created pushing the blood towards the proximal portion of the leg, reducing the amount of blood in the portion of the leg in which the surgical procedure is to be performed.

The fluid conduits 2310a-2310e are each connected to a main fluid conduit 2310 which in turn is connected to a source of pressurized fluid, in this case a fluid pump 2309. The control system 2315 may be adapted to inflate inflatable compartments C1-C5 to a pressure exceeding the systolic blood pressure by one of: 10 mmHg, 20 mmHg, 40 mmHg, 60 mmHg, 80 mmHg, 100 mmHg, 140 mmHg, for substantially stopping the blood from returning to the distal portions of the leg of the patient.

Figure 215B:
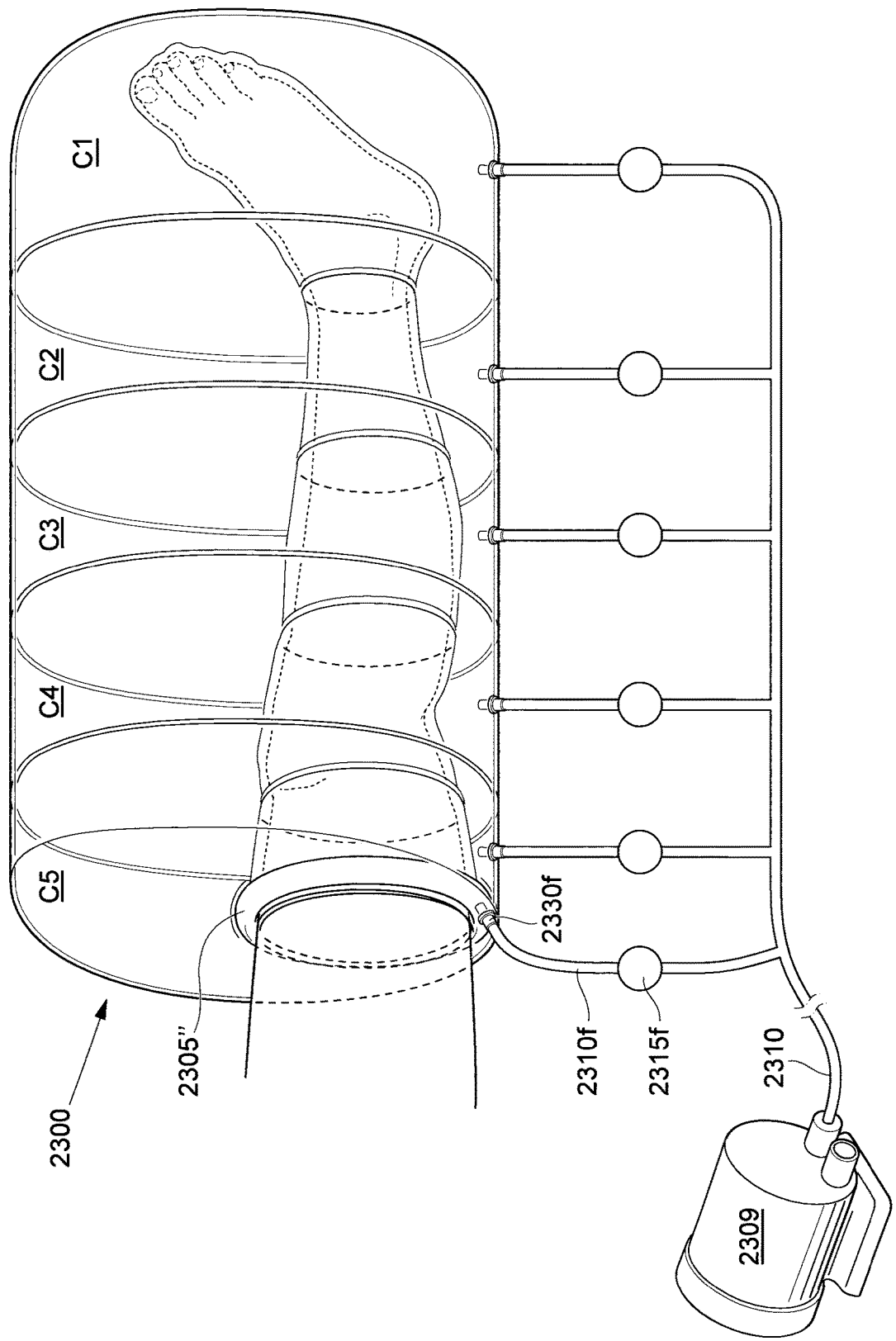
FIGS. 215a-217 shows an embodiment of the medical device comprising a compartmentalized chamber.

FIG. 215b shows an embodiment similar to the embodiment shown in FIG. 215a, the difference being that the embodiment of FIG. 215b is additionally provided with a pressure sealing member 2305" adapted to be inflated with a pressure exceeding systolic blood pressure such that the pressure in the compartments C1-C5 can be released without the blood returning to the distal portion of the leg of the patient. The pressure sealing member 2305" being connected to a fluid conduit 2310f provided with a control unit 2315f for controlling the inflation of the pressure sealing member 2305". The fluid conduit 2310f is in turn connected to a main fluid conduit 2310 connected to a pressure source in the form of a fluid pump.

Figure 215C:
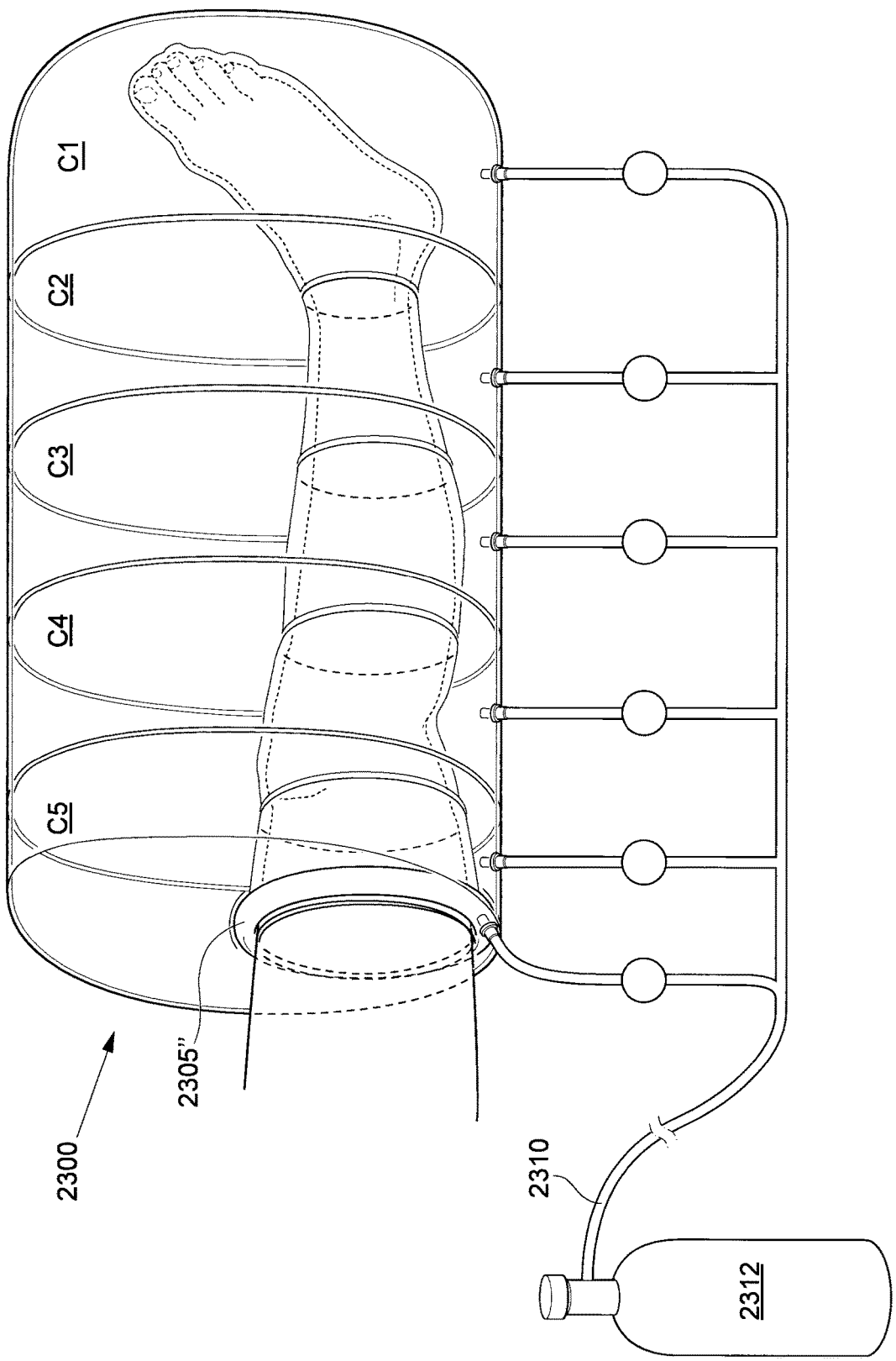

FIG. 215c shows an embodiment similar to the embodiment shown in FIG. 215b, the difference being that in the embodiment of FIG. 215c, the pressure source is a tank 2312 comprising a pressurized fluid. The pressurized fluid provided to the compartments C1-C5 and/or to the pressure seal 2305" could be a gaseous fluid or a liquid fluid, independently if the fluid is provided from a fluid pump, such as in FIGS. 215a; 215b; 216; 217 or a tank 2312 such as in FIG. 215c.

FIG. 216 shows the medical device when two of the internal compartment dividing walls 2301b; 2301c have been partially removed by means of the surgeon using a scalpel or similar sharp tool for creating large holes in the dividing walls 2301b; 2301c. By the partial removal of two of the internal compartment dividing walls 2301b; 2301c, the compartments C2-C4 have been combined to a larger compartment in which a step of the surgical procedure can be performed easier. In alternative embodiments, the dividing walls can comprise portions fixated to the dividing walls by means of Ziploc® type fastening means providing an airtight, removable portion which furthermore is possible to reconnect if necessary.

FIG. 217 shows an embodiment of the medical device 2300 in which the medical device 2300 further comprises a monitoring unit 2398 connected to the control system, 2315a-2315e. The monitoring unit 2398 is by leads 2378a-2378e connected to sensing probes 2373a-2373e adapted to sense one of: blood flow of the patient, a temperature of the patient, saturation of the blood of the patient, at least one ischemia marker of the patient and/or the skin tone of the patient and provide input to the monitoring unit, such that the monitoring unit can monitor at least one of the measured parameters. The monitoring unit 2398 is by means control signal leads 2378'a-2378'e connected to the control units 2315a-2315e such that the inflation is or the compartments C1-C5 is controlled on the basis of input from the monitoring unit. The monitoring unit 2398 may additionally be connected to the fluid pump 2309, such that the pressure in the fluid conduit 2310 can be controlled by the monitoring unit 2398 in addition to the controlling of the individual control units 2378'a-2378'e. Monitoring the pressure in the compartments C1-C5 enables mediation between providing sufficient pressure in the compartments for restricting the blood sufficiently, whilst inflicting as little harm as possible on the affected extremity as the pressing on the skin creates pressure wounds which could lead to future decreased circulation and scarring. Monitoring the pressure enables the pressure to be kept as low as possible while still obtaining the desired effect.

A medical device for performing surgery in less sealed environments is provided. Surgery in less sealed environments is in many instances necessary as the patients cannot be transferred to a regular hospital. Instances were "field surgery" is necessary, i.e. surgery performed outside of a regular hospital in a less sealed environment, includes surgery at battlefields, surgery in areas struck by natural disasters, and surgery performed in less developed countries.

Figure 218A:
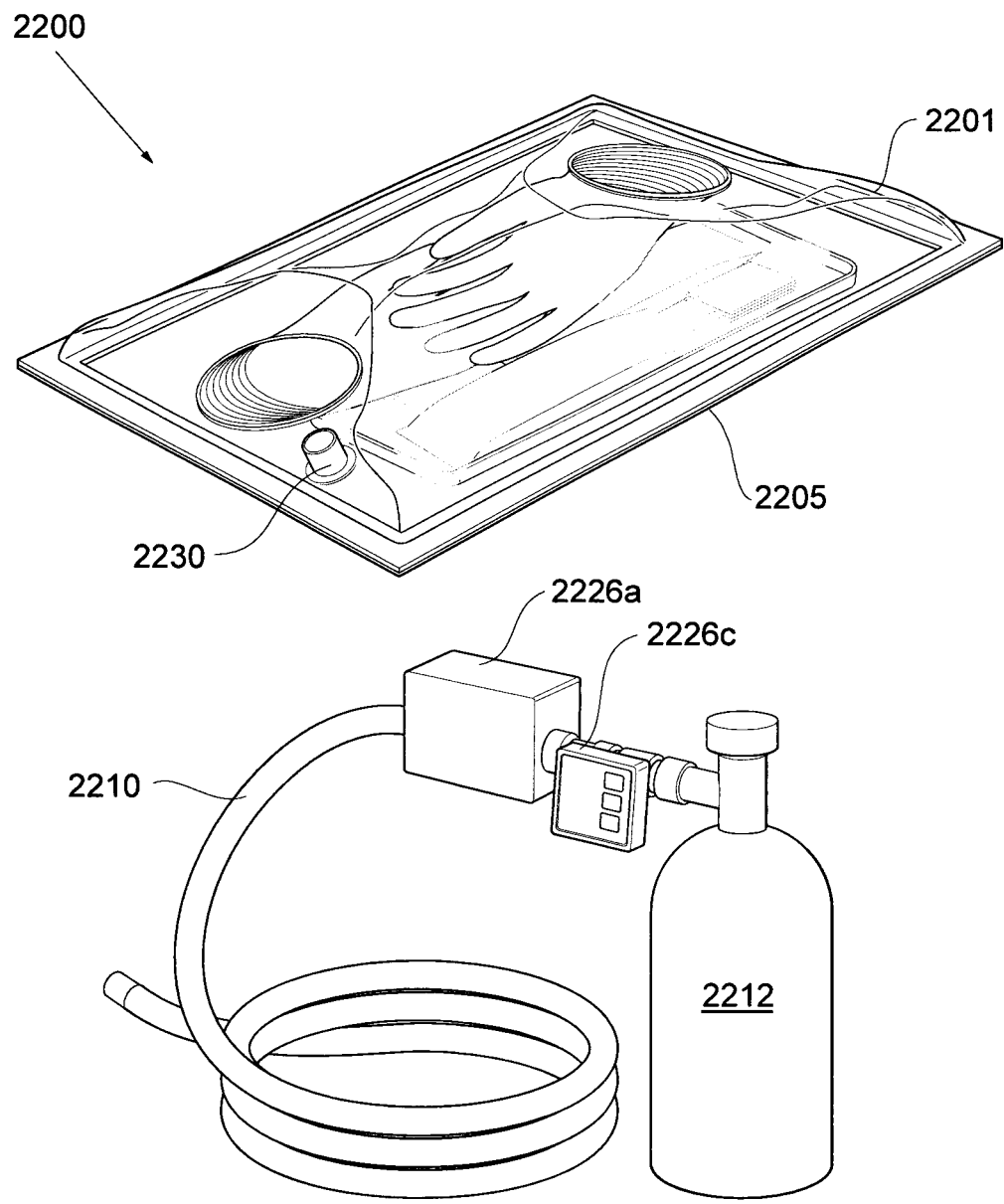

FIG. 218a shows a medical device 2200 for performing field surgery when deflated. The medical device 2200 may be packaged and shipped in its deflated and thus compact state. The medical device 2200 comprises an adhesive surface 2250 adapted to be placed in contact with the skin of the patient for providing fixation and/or sealing between the medical device 2200 and the skin of the patient. The adhesive surface 2250 may be provided with a protective sheet which is removed for affixing the medical device 2200 to the skin of the patient. The medical device 2200 further comprises a flexible inflatable layer 220l which e.g. is made from a flexible, transparent polymer material such as polyvinyl chloride (PVC) with a plasticizer additive. The flexible layer comprises an inlet 2230 adapted to be connected to a fluid source for inflating the medical device, such that a chamber within the medical device 2200 is created. FIG. 218a further shows a fluid source comprising a pressurized fluid tank 2212 connected to a fluid conduit 2210. The fluid conduit 2210 is adapted to be connected to the inlet 2230 such that the medical device 2200 can be inflated by means of the pressure source (in this case the pressurized fluid tank 2212) connected to the fluid conduit 2210. Between the pressurized fluid tank 2212 and the fluid conduit 2210 a sterilizing unit 2226a is positioned, the sterilizing unit 2226a is adapted to sterilize the fluid entering the medical device 2200. The sterilizing unit 2226a could be adapted to sterilize the fluid by the use of heat, such as electrical or chemical heat, radiation, such as UV-light and/or though the addition of a chemical sterilizing agent. A tempering unit 2226c is also provided, connected between the pressurized fluid tank 2212 and the fluid conduit 2210. The tempering unit 2226c being adapted to alter the temperature of the fluid entering the medical device 2200. The use of a tempering unit 2226c could be for the purpose of heating the fluid such that the comfort level of the patient and/or the surgeon is increased, or for the purpose of cooling the fluid e.g. for reducing bacteria growth in the area of the medical device 2200 or for the purpose of cooling the area of the incision, e.g. to cause affected blood vessels to contract and thus reduce the blood flow. The pressurized fluid may be a pressurized gas, such as pressurized CO2 gas, or a pressurized liquid, such as an isotonic or antibiotic liquid.

FIG. 218b shows an alternative embodiment of the medical device shown in FIG. 218a, the difference being that the pressurized fluid is supplied by a pump 2295 adapted to inflate the medical device 2200 using ambient air. Having a sterilizing unit 2226a and/or a unit 2226c for tempering the fluid is of great importance when the medical device 2200 is inflated by ambient air as the ambient air cannot be controlled in the same way as a pressurized fluid contained in a pressurized tank.

Figure 218C:
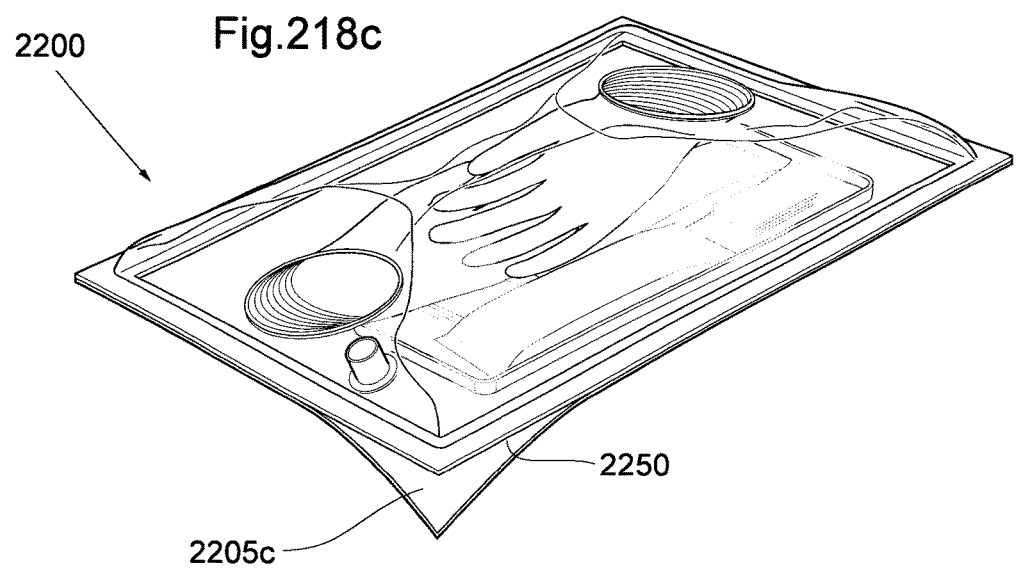

FIG. 218c shows the step of removing a protective layer 2205c covering the adhesive surface 2250 of the medical device 2200 adapted to be placed in contact with the skin of the patient for fixating and/or sealing the medical device 2200 to/against the skin of the patient.

Figure 218D:
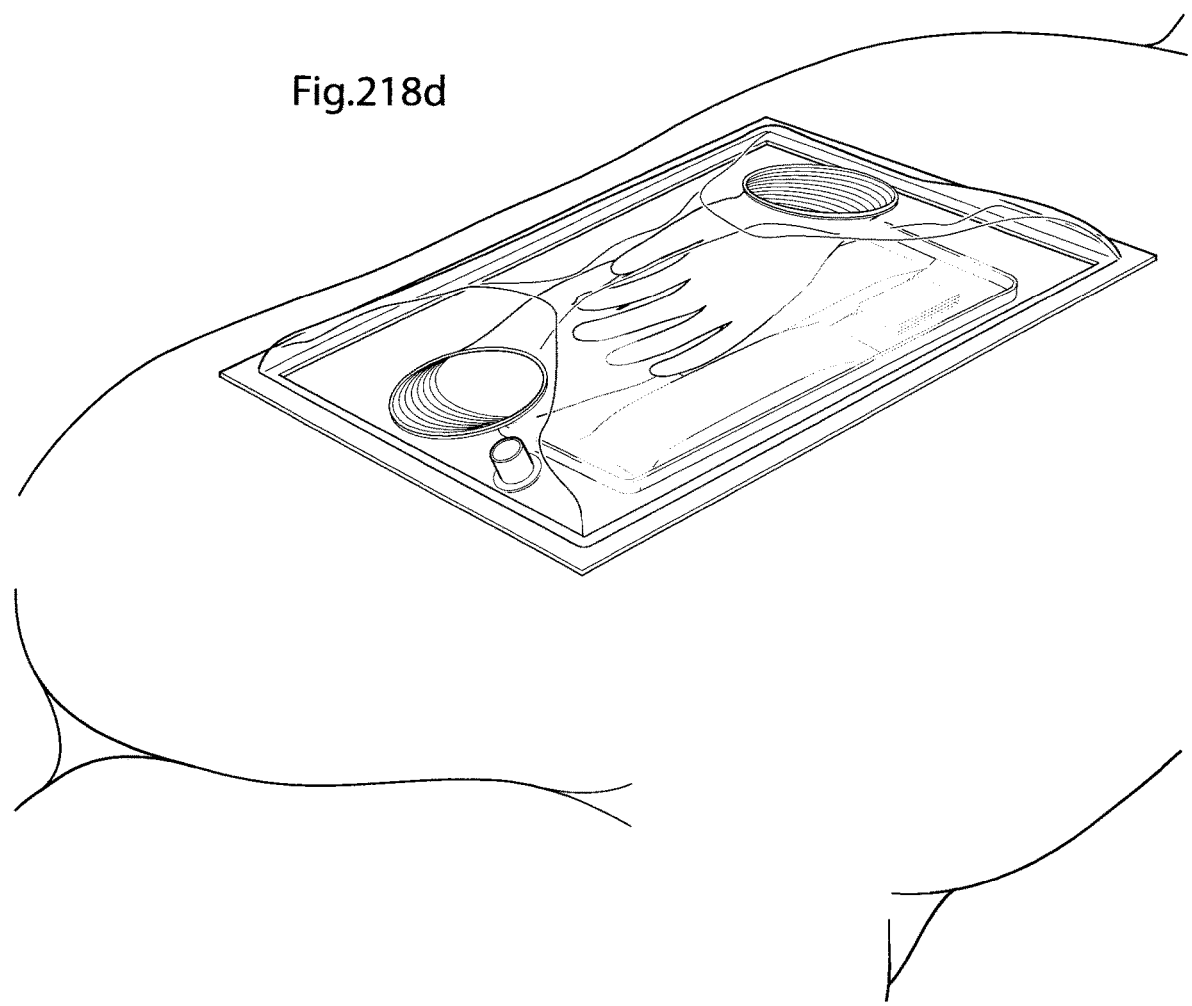

FIG. 218d shows the embodiment of the medical device shown in FIG. 218c when the protective layer has been removed, the adhesive surface has been exposed, and the medical device 2200 has been placed in contact with the skin of the patient such that a surgical procedure can be performed inside of the medical device 2200.

Figure 218E:
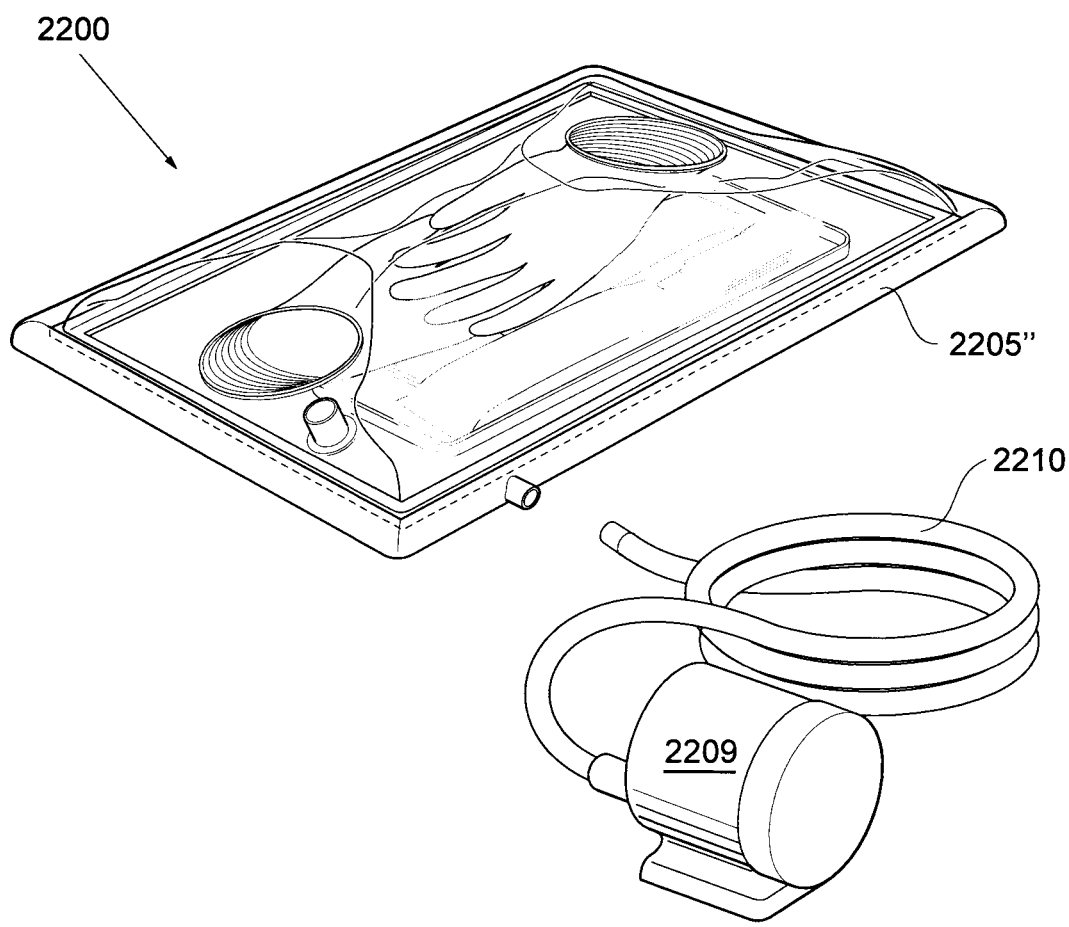

FIG. 218e shows an embodiment of the medical device 2200 similar to the embodiments shown under reference to FIGS. 218a-218d, the difference being that the medical device 2200 comprises a pressure sealing member 2205" encircling the medical device 2200 and being adapted to be inflated for pressing against the skin of the patient and thereby sealing between the medical device 2200 and the skin of the patient. The pressure sealing member 2205" is inflated through a fluid conduit 2210 connected to a pressure source, in this embodiment a pump 2208 adapted to inflate the pressure sealing member 2205" with ambient air. The pump 2208 and the fluid conduit 2210 may be the same pump and fluid conduit 2210 as used for inflating the medical device 2200, or it may be a separate pump 2208 and fluid conduit 2210. The medical device 2200 could be fixated to the patient by means of an adhesive adapted to withstand the force created by the inflated pressure sealing member 2205", or the medical device 2200 may be secured by means of a holding member, such as for example shown in FIG. 42b. The pressure sealing member 2205" could in alternative embodiments be replaced by a vacuum sealing member, such as the vacuum sealing member disclosed under reference to FIG. 43, which also may be assisted by an adhesive disposed on the wall 2201 contacting the skin of the patient.

Figure 218F:
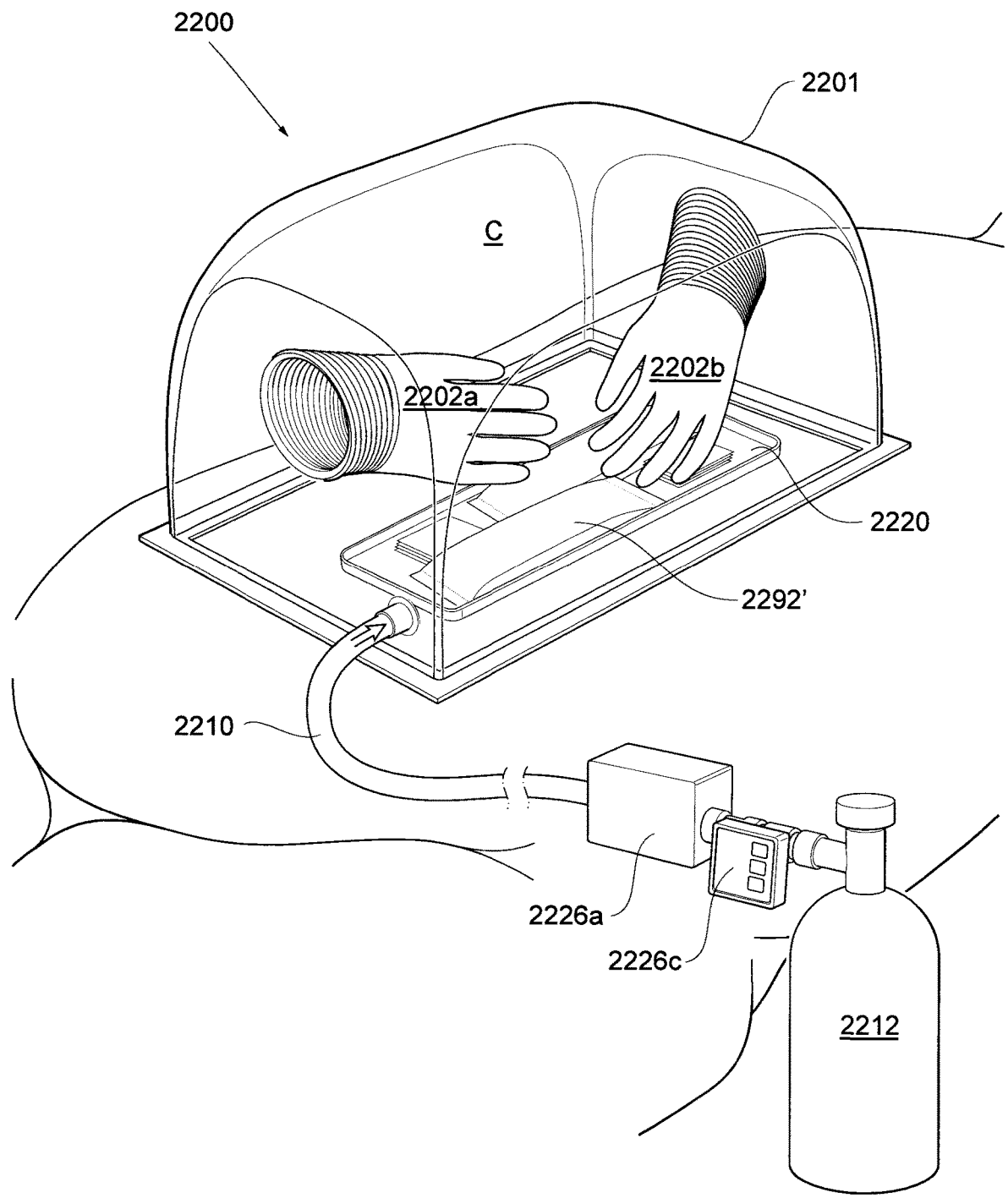
FIGS. 218f-218k shows an embodiment of the medical device when inflated and used.

FIG. 218f shows an embodiment of the medical device, when the medical device is placed in the abdominal region of the patient and inflated by means of the inflation system (2213, 2226, 2225, 2212) further described under reference to FIG. 2218a. The medical device comprises a pre-placed mount 2220 within the chamber C of the medical device 2200. The pre-placed mount 2220 comprises the instruments necessary for performing a particular surgical procedure, such that the chamber C can remain sealed during the entire surgical procedure. According to the embodiment shown in FIG. 218f the mount 2220 comprises trocars placed in trocar packages 2292' which can be used for performing a laparoscopic procedure from within the chamber C of the medical device 2200.

The medical device 2200 further comprises gloves 2202a, 2202b integrated in the wall 2201 of the medical device 2200, enabling manual manipulation within the chamber C of the medical device 2200.

Figure 218G:
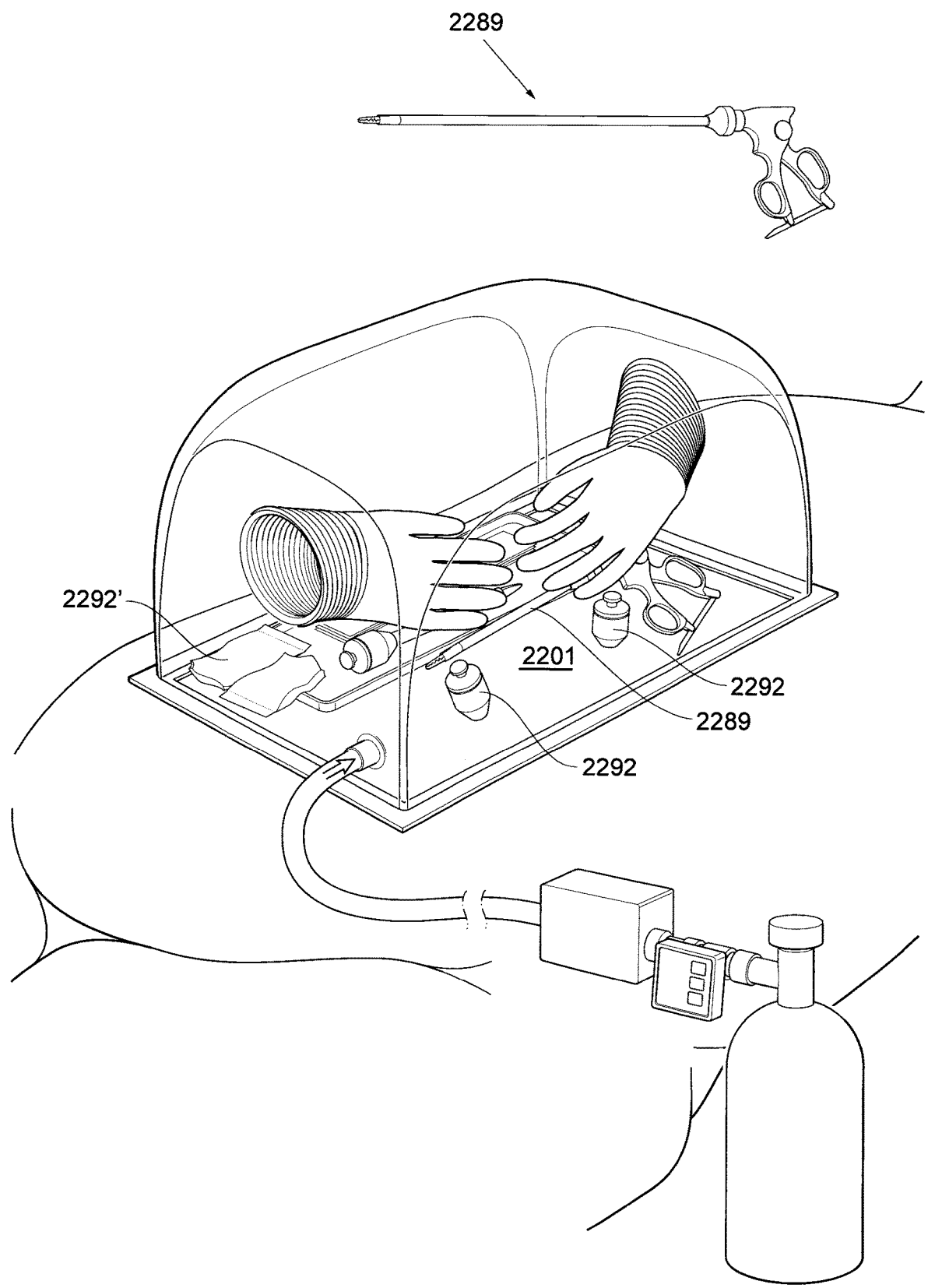

FIG. 218g shows the medical device according to the embodiment shown in FIG. 218f, when the trocar packages 2292' have been opened and trocars 2292 have been positioned through the skin of the patient, in the abdominal region of the patient, penetrating the wall of the bottom wall 2201 of the medical 2200 device. The bottom wall **220*l* being adapted to contact the skin of the patient and fixate and/or seal against the skin of the patient by means of an adhesive covering the bottom wall 2201. As shown in FIG. 218***g*, two trocars are positioned through the layer of the medical device 2200 and the skin of the patient. Generally a first and second trocar 2292 are inserted for enabling manipulation by endoscopic instruments 2289 within a cavity created in the body of the patient, and a third trocar is positioned through the skin of the patient for enabling visual inspection within the cavity created in the patient during the surgical procedure. The endoscopic instruments 2289 may, just as the trocars 2292, be pre-placed in the chamber C prior to the making of the first incision through the bottom wall 2201 of the medical device 2200 contacting the skin of the patient. The pre-placed instruments 2289 could be instruments which are adapted for the particular procedure to be made, e.g. if the surgical procedure to be made is an appendectomy, the pre-placed instruments is the instruments required for performing the entire appendectomy, including for example a suturing kit for suturing the incisions made in the skin of the patient. This way, the sealed environment is maintained throughout the surgical procedure which reduces the risk of infectious diseases. The pre-placed instruments 2289 could for example be an endoscopic grasper, an endoscopic claw grasper, an endoscopic stone grasper, an endoscopic needle holder, an endoscopic hook, an endoscopic dissector, or an endoscopic diathermy instrument.

Figure 218H:
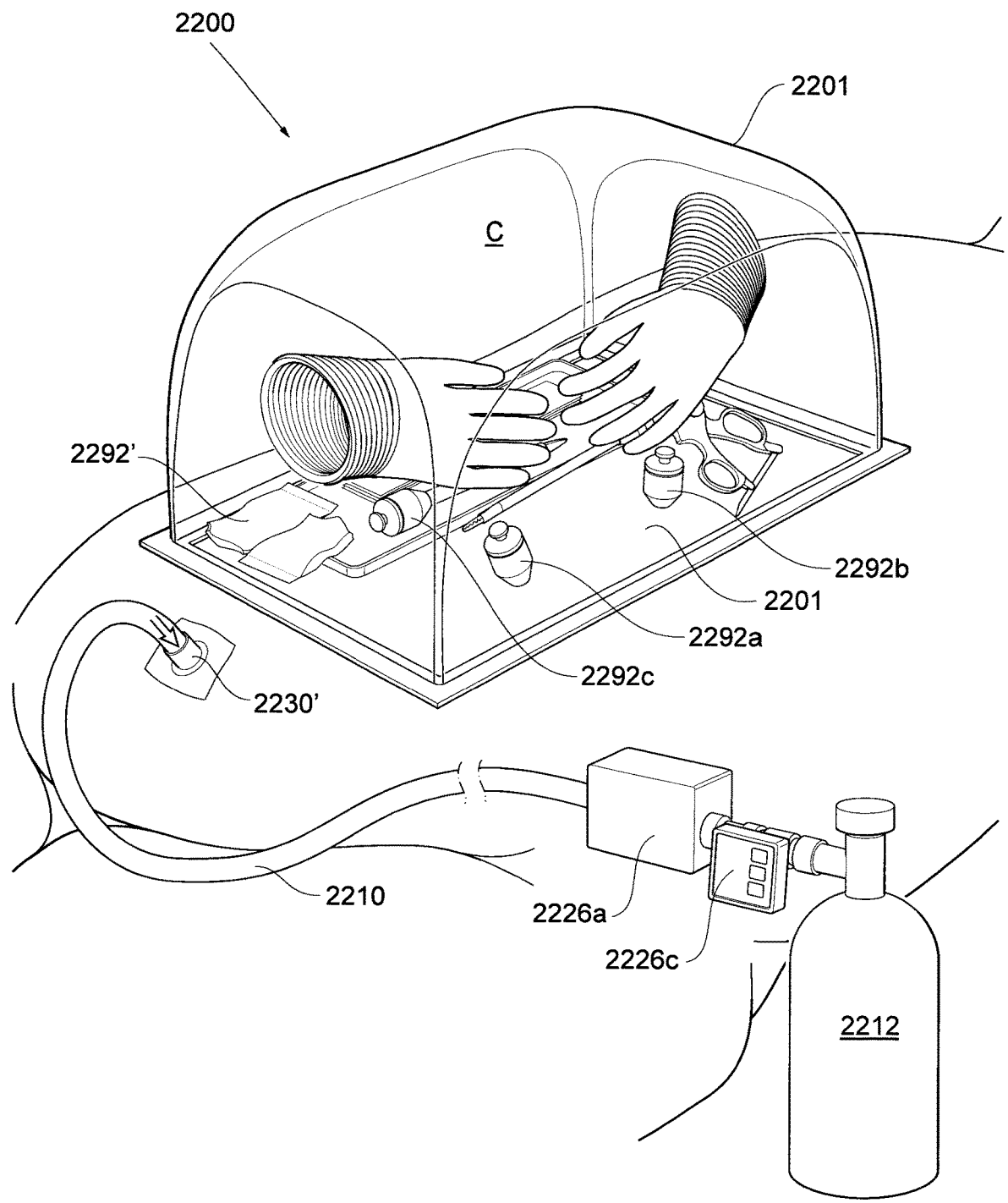

FIG. 218*h* shows an embodiment similar to the embodiment shown in FIG. 218*g*, the difference being that in the embodiment shown in FIG. 218*h*, the pressurized fluid system 2212, 2225, 2226, 2213 is adapted to supply fluid to an inlet 2230' placed in an incision made in the skin of the patient, outside of the medical device 2200 for providing a pressurized gas into the abdominal region of the patient and thereby inflating a cavity within the patient such that visual inspection of the surgical area within the patient is made possible. In the embodiment shown in FIG. 218*h*, the medical device 2200 does not have a fluid inlet for inflating the medical device 2200. The medical device 2200 is thus inflated through the incision made in the bottom wall 2201 of the medical device 2200, passing through the wall 2201 of the medical device 2200, and further though the skin of the patient into the cavity in the patient created by the injection of fluid through the inlet 2230'. By placing the medical device 2200 on an inflated area of the patient's abdomen being larger than the medical device 2200, the inflated cavity within the medical device 2200 can be maintained even when the incision is made through the skin of the patient. This enables the advantages of good visibility through the use of a fiber optic camera placed through a trocar even when a large incision is made in the medical device 2200 through the wall of the medical device 2200 and the skin of the patient.

A procedural example of the use of the embodiment shown in FIG. 218*h* for removal of a tumor in the gastrointestinal system will now be described. The inlet 2230' of the pressurized fluid system is positioned in an incision made in the abdominal region of the patient. Pressurized fluid is supplied through the fluid conduit 2213 and thereby injected into the patient via the inlet 2230', whereby a cavity is created in the abdominal region of the patient. An additional trocar may be positioned through the skin of the patient for visually inspecting the abdomen for determining where the tumor is located, such that the medical device 2200 can be accurately positioned in relation to the tumor to be removed. An alternative way is to determine the location of the tumor in a non invasive manner, by means of for example ultrasound or x-ray. The medical device is then positioned in the area in which the surgery is to be performed in its deflated state. The medical device 2200 is fixated to the skin of the patient by the help of an adhesive and/or a seal which could be the pressure seal (2205") or vacuum seal disclosed above. An incision in the skin of the patient is then created forming a fluid connection between the cavity within the patient and the chamber C of the medical device 2200. The fluid connection causes the pressurized gas filling the cavity within the patient to continue to flow through the created channel and thus inflating the layer **220*l* of the medical device 2200. At least a first 2292***a*, and second 2292*b* trocar is removed from their respective package 2292' and placed through the bottom **220*l* wall of the medical device 2200 and the skin of the patient, such that at least two endoscopic instruments 2289 can be inserted through the trocars 2292***a*, 2292*b*, for enabling manipulation within the cavity of the patient. In embodiments where no additional trocar for a camera is positioned through the skin of the patient outside of the medical device 2200, an additional trocar 2292*c* needs to be positioned through the skin of the patient inside of the medical device 2200 for inserting a camera into the medical device 2200. In embodiments where the camera is also pre-placed in the medical device 2200, the camera may be adapted to transfer the images by means of a wireless connection, or by means of a data transferring member positioned in the wall **220*l* of the patient, such as for example the data transferring member disclosed under reference to FIGS. 212-214**.

When endoscopic instruments 2289 for manipulation and at least one camera for visual inspection are positioned, the area of the tumor is dissected and the removal prepared. The tumor is then removed using endoscopic instruments, such as diathermy instruments, and the wound inflicted by the removal of the tumor is sutured by means of the endoscopic manipulation instruments, or stapled by means of an endoscopic stapler. All of the instruments used in the surgical procedure are sterilized and pre-placed in the hermitically sealed medical device 2200 prior to the fixation of the medical device 2200 to the skin of the patient. In cases where the instrument needs energy, such as the diathermy requiring electrical energy, an energy transferring member could be integrated in the wall of the medical device 2200, such as the energy transferring member disclosed under reference to FIGS. 212-214.

When the procedure inside the cavity of the abdomen is concluded, a removal incision is made through the wall 2201 and the skin of the patient having a size sufficient for the removal of the tumor from the cavity in the patient's body. As the pressure in the cavity and in the chamber C of the medical device is the same, the incision can be made without the inflated cavity within the patient's body collapsing. The tumor is then removed through the incision made and placed in the chamber C of the medical device 2200. After the removal of the tumor, the incision is sutured, either from the chamber C of the medical device, or from the inside of the inflated cavity of the medical device using the endoscopic instruments. Suturing the incision from the inside could have muscular and cosmetic advantages and is enabled by the maintaining of the inflated intra-body cavity throughout the entire procedure. Even if the suturing is performed from the outside, it may be advantageous to maintain visual inspection from the inside.

When the larger incision is sutured, the trocars are retracted and the remaining small incisions in which the trocars were placed are sutured. When all incisions in the skin of the patient, within the medical device 2200 are closed, the medical device 2200, with the removed tumor T and all the used instruments, are removed and folded such that the adhesive layer connects to itself thereby closing all incisions made in the wall 2201 of the medical device 2200, hermetically sealing the medical device 2200.

The above mentioned method has several advantages. The incisions in the patient made in the medical device 2200 are never placed in contact with the ambient environment, which minimizes the risk that bacteria will enter the body of the patient causing infectious disease. Furthermore, the removed specimen (tumor) from the patient is at all times kept within the medical device which reduces the risk that any of the assisting medical staff should get infected by any disease that the patient might have. This aspect is particularly important in countries where various blood diseases are common, such as HIV or hepatitis.

In non sterile environment the medical device makes it possible to perform a sterile operation without any possibility for the surgeon to perform proper sterilization, without the surgeon wearing mouth protection, and without means for properly sterilizing the patient.

Figure 218I:
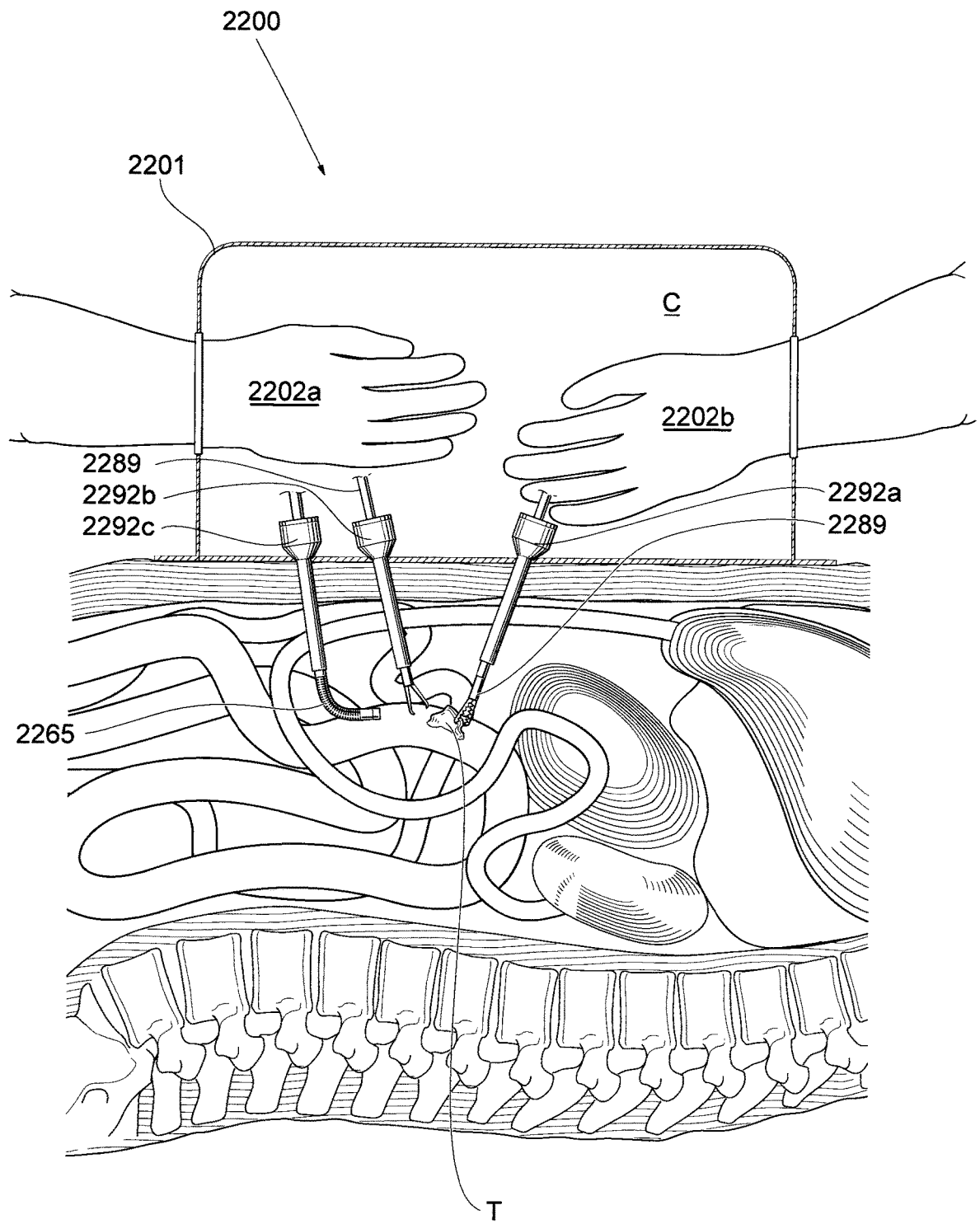

FIG. 218*i* shows the step (as described in the example above) of preparing the removal of a tumor T from the colon of the patient using the medical device according to the embodiment shown in FIG. 218*h* using two endoscopic instruments 2289 placed in a first and second trocar 2292*a*, 2292*b*. The camera 2265 enabling visual inspection is positioned in a third trocar 2292*c* which in this embodiment is positioned inside of the chamber C of the medical device 2200.

Figure 218J:
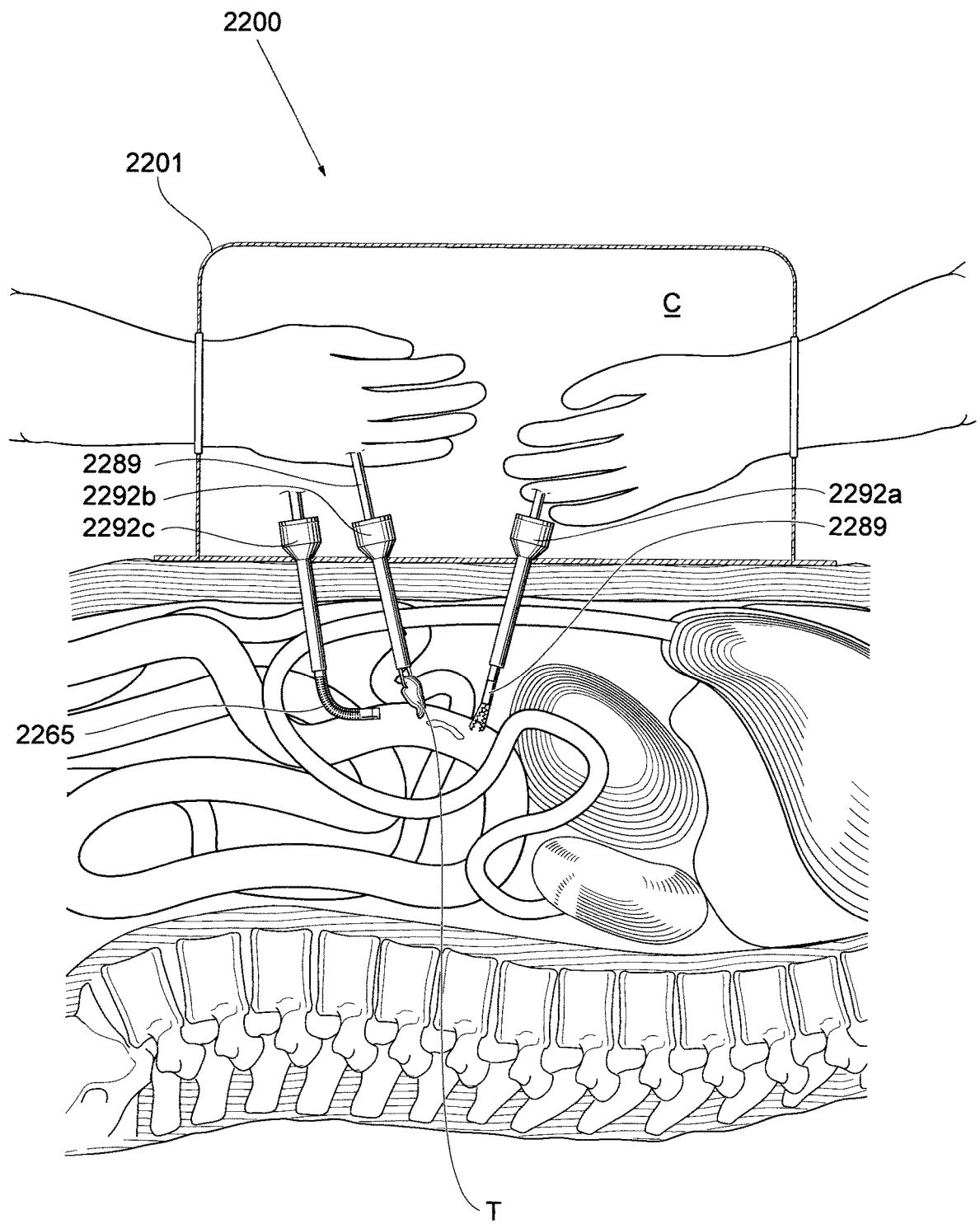

FIG. 218*j* shows the step (as described in the example above) of removing the tumor T from the colon of the patient using endoscopic instruments 2289.

Figure 218K:
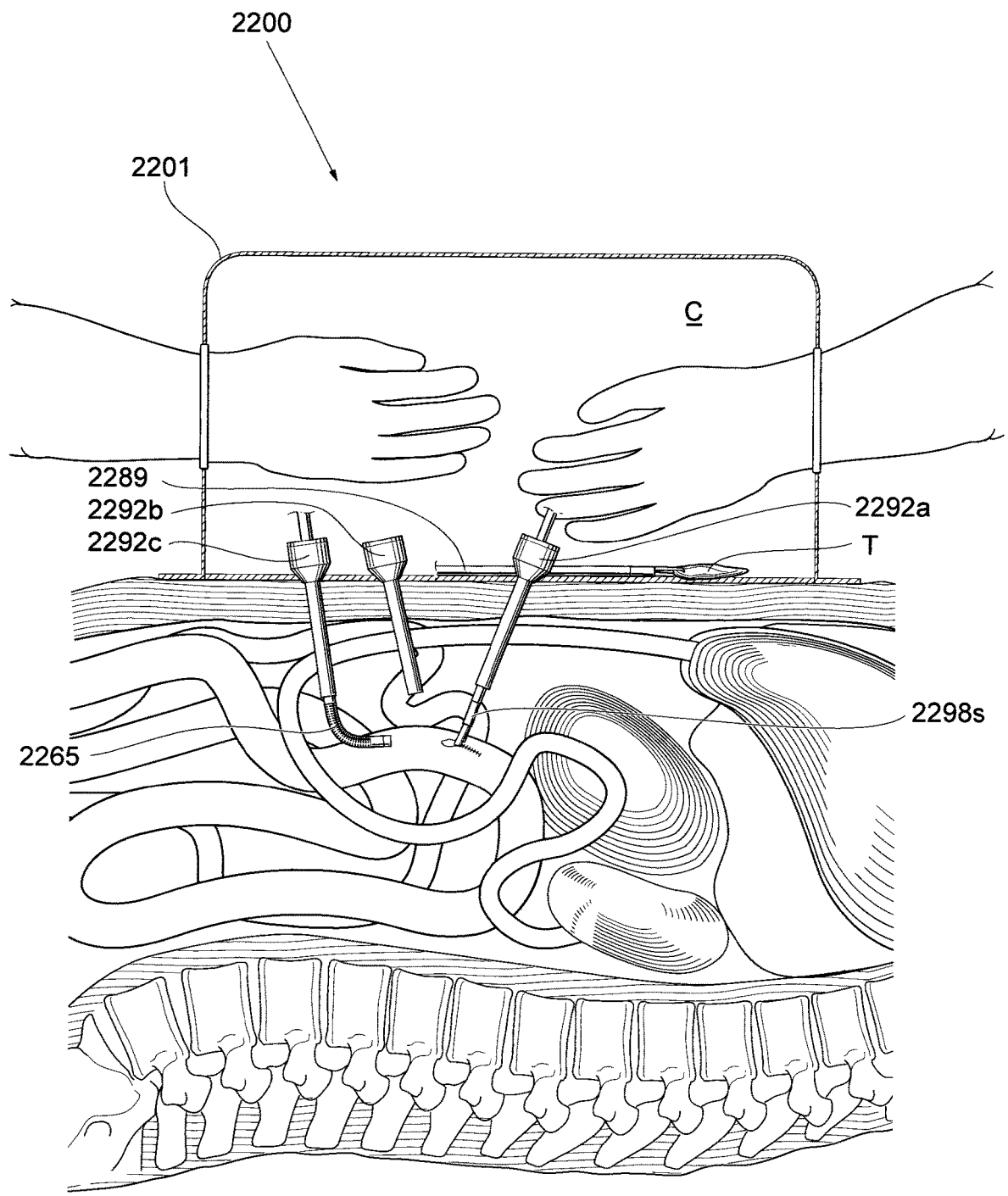

FIG. 218*k* shows the step (as described in the example above) of stapling the wound inflicted on the colon by the removal of the tumor T using an endoscopic stapler 2289*s*. The removed tumor T is securely placed within the chamber C of the medical device 2200

Figure 218L:
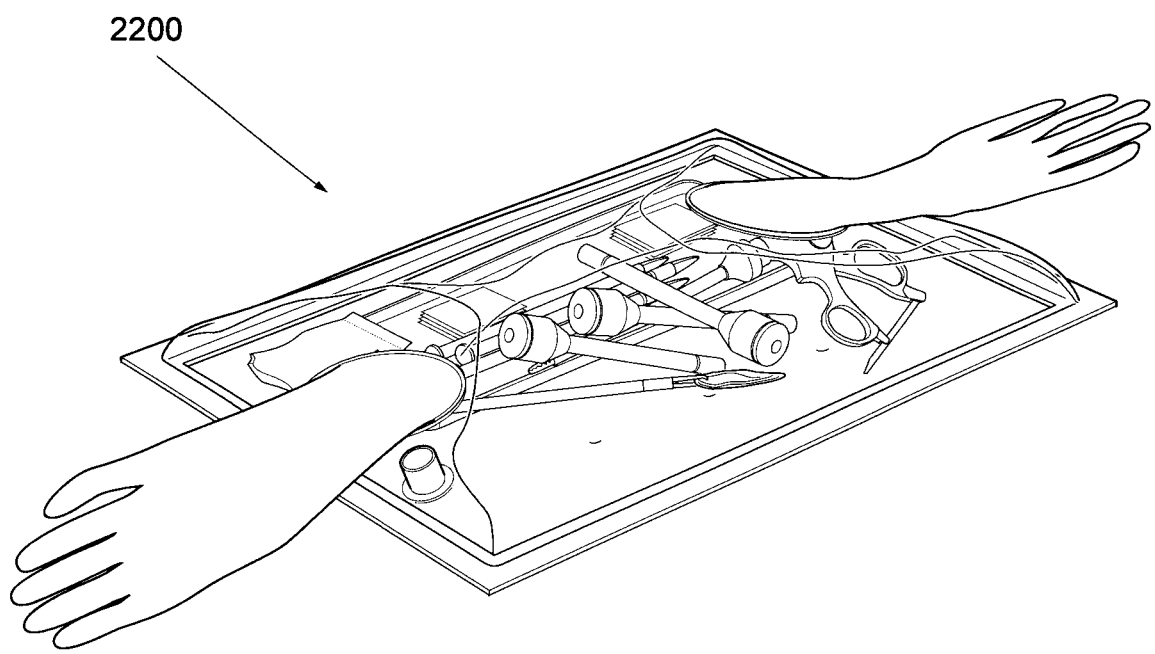
FIGS. 218*l*-218*m* shows an embodiment of the medical device when deflated after having been used.

FIG. 218*l* shows the medical device in its deflated state, all the instruments used in the surgical procedure are securely placed within the medical device 2200, and the medical device has been removed from the body of the patient.

Figure 218M:
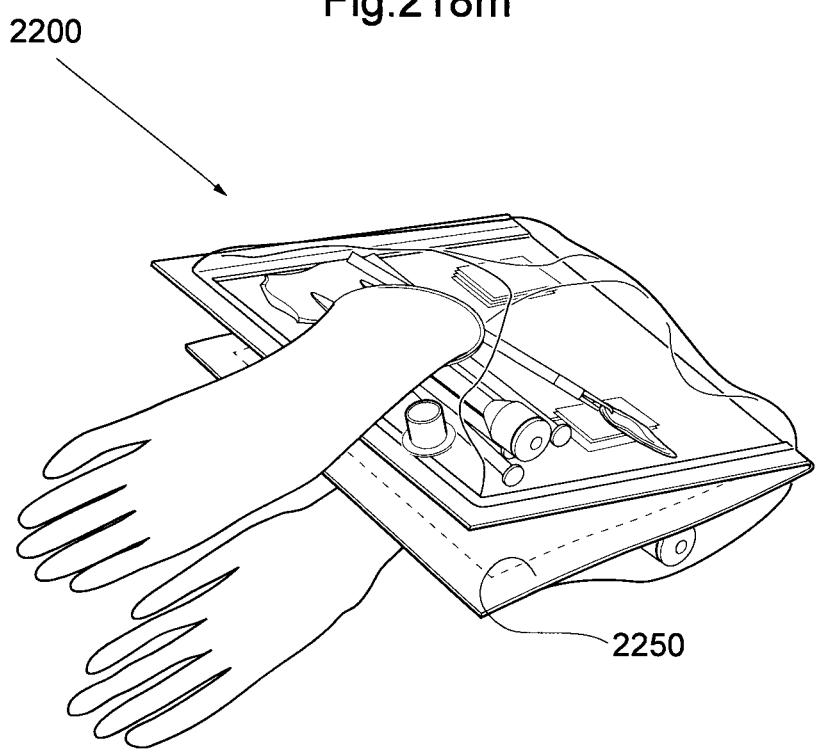

FIG. 218*m* shows the medical device when folded such that portions of the adhesive surface 2250 of the medical device is connected, such that the medical device 2200 is hermetically sealed with all the instruments and the removed specimen (tumor) secured inside.

Figure 219A:
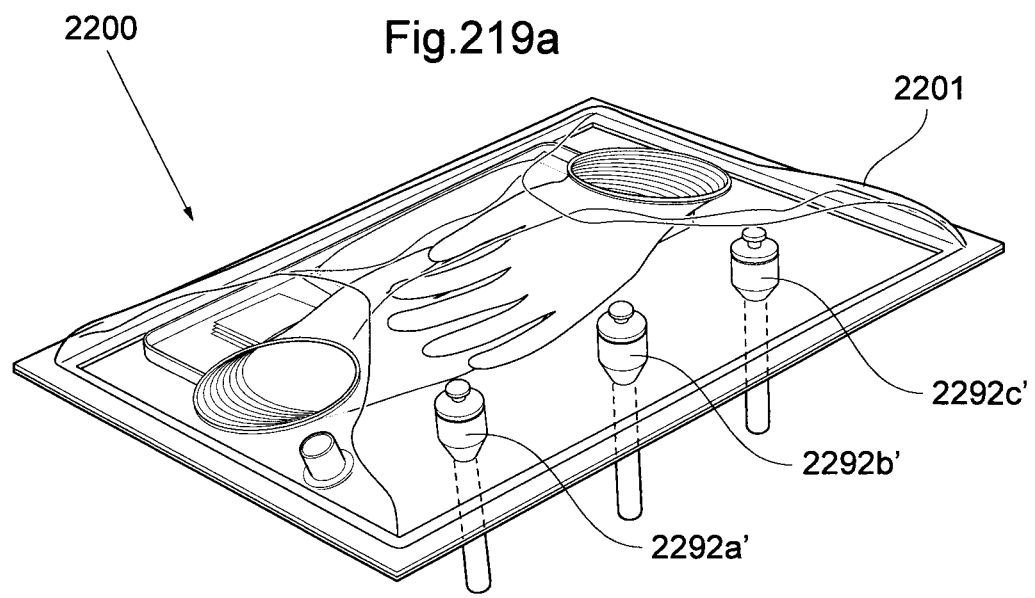
FIGS. 219*a*-219*b* shows an embodiment of the medical device when being applied on the abdomen of the patient.

FIG. 219*a* shows an embodiment of a medical device 2200 for performing a combination of open surgery and laparoscopic surgery similar to the embodiments shown in FIGS. 218*a*-218*m*, the medical device comprises a wall 2201 adapted to be inflated by a fluid for forming a chamber in which a sealed environment can be maintained for encompassing part of the surgical procedure to be performed. The medical device further comprises three laparoscopic trocars 2292*a'*, 2292*b'*, 2292*c'* positioned through the wall 220*l* of the medical device 2200, such that a first portion (shown as p1 in FIG. 218*o*) of the trocars is positioned inside of the chamber, and a second portion (shown as p2 in FIG. 218*o*) of the trocar is positioned outside of the chamber of the medical device 2200.

Figure 219B:
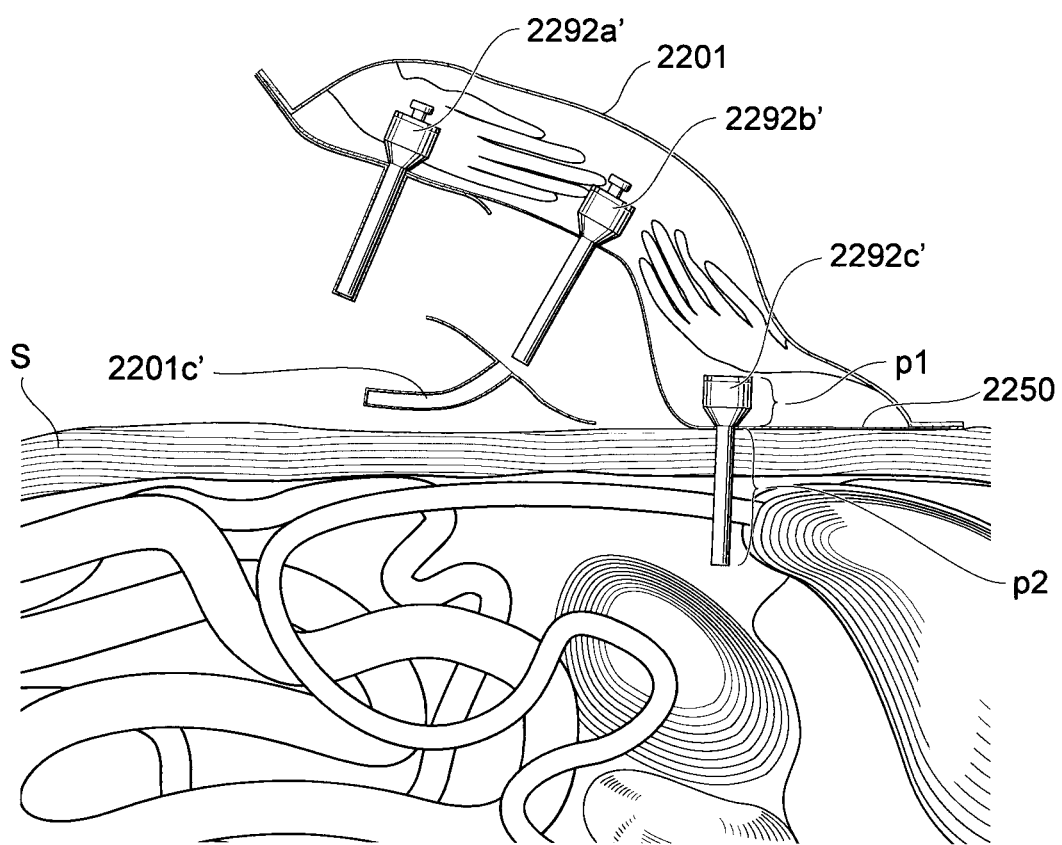

FIG. 219*b* shows the medical device when protective covers 2201*c'* are being removed and the trocars 2292*a'*, 2292*b'*, 2292*c'* are being inserted through incisions made in the skin S of the patient. The trocars 2292*a'*, 2292*b'*, 2292*c'* are placed such that a first portion p1 of the trocars 2292*a'*, 2292*b'*, 2292*c'* is positioned inside the chamber C of the medical device, whereas a second portion p2 of the trocars 2292*a'*, 2292*b'*, 2292*c'* is positioned inside the body of the patient. The protective layer 2201*c'* further serves as a protective layer for the adhesive surface 2250 of the wall 2201 of the medical device. After the trocars 2292*a'*, 2292*b'*, 2292*c'* have been positioned through the skin S of the patient, the trocars can be used for performing manipulation using endoscopic instruments within a cavity in the patient's body.

Figure 219C:
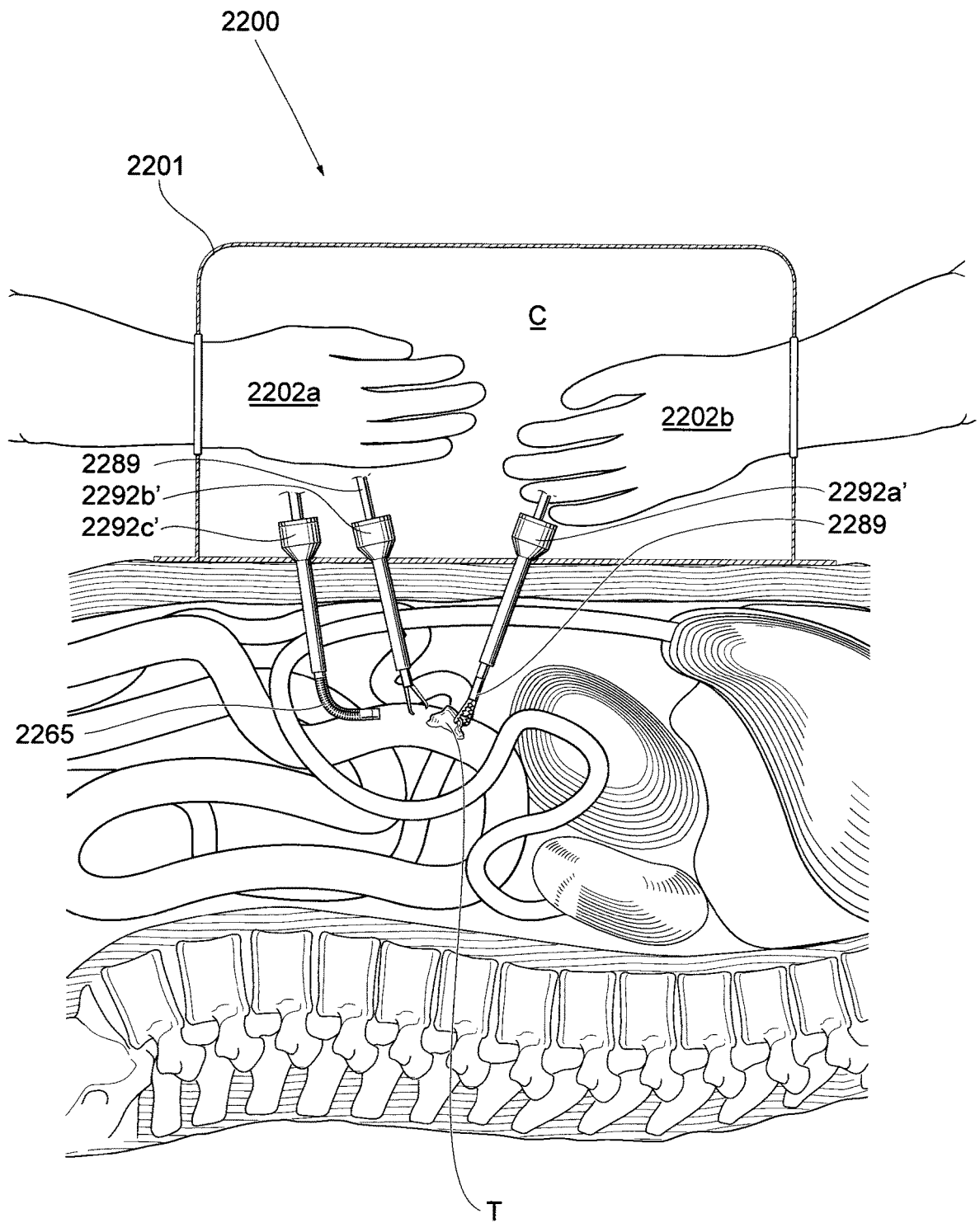
FIGS. 219*c*-219*e* shows an embodiment of the medical device when inflated and used on the abdomen of a patient.

FIG. 219*c* shows the embodiment of the medical device shown in FIG. 219*a*, 219*b* when positioned and inflated by a fluid. The fluid inflating the medical device can enter the medical device either through an inlet in the wall 2201 of the medical device (such as further disclosed with reference to FIG. 218*a*, 218*b*) or through one of the incisions by a fluid injecting member being positioned through the skin of the patient outside of the medical device (such as further disclosed with reference to FIG. 218*h*). FIG. 219*c* shows the step (as described in the example above) of preparing the removal of a tumor T from the colon of the patient using the medical device according to the embodiment shown in FIG. 219*a*, 219*b* using two endoscopic instruments 2289 placed in a first and second trocar 2292*a'*, 2292*b'*. The camera 2265 enabling visual inspection is positioned in a third trocar 2292*c'* which in this embodiment is positioned inside of the chamber C of the medical device 2200.

Figure 219D:
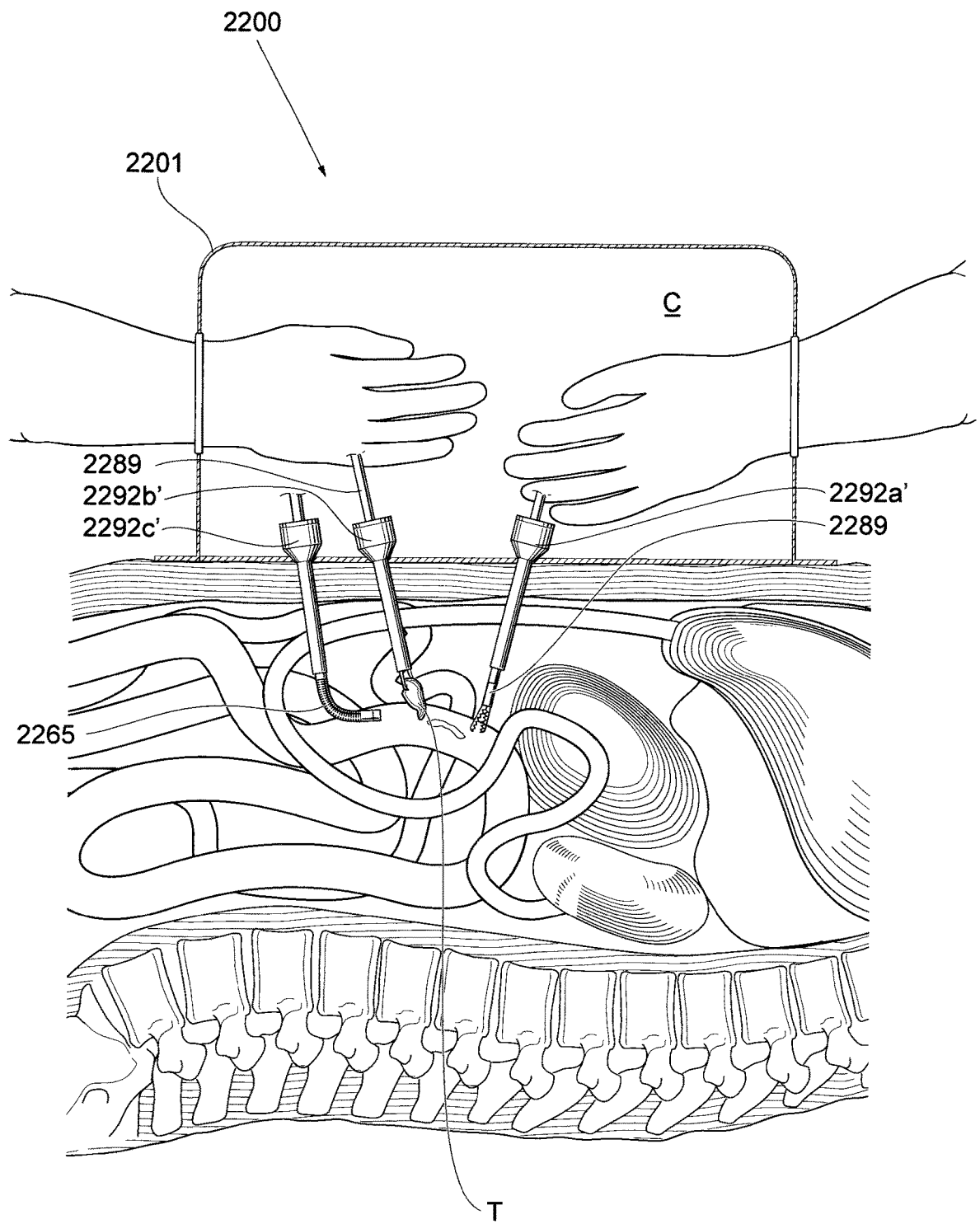

FIG. 219*d* shows the step (as described in the example above) of removing the tumor T from the colon of the patient using endoscopic instruments 2289.

Figure 219E:
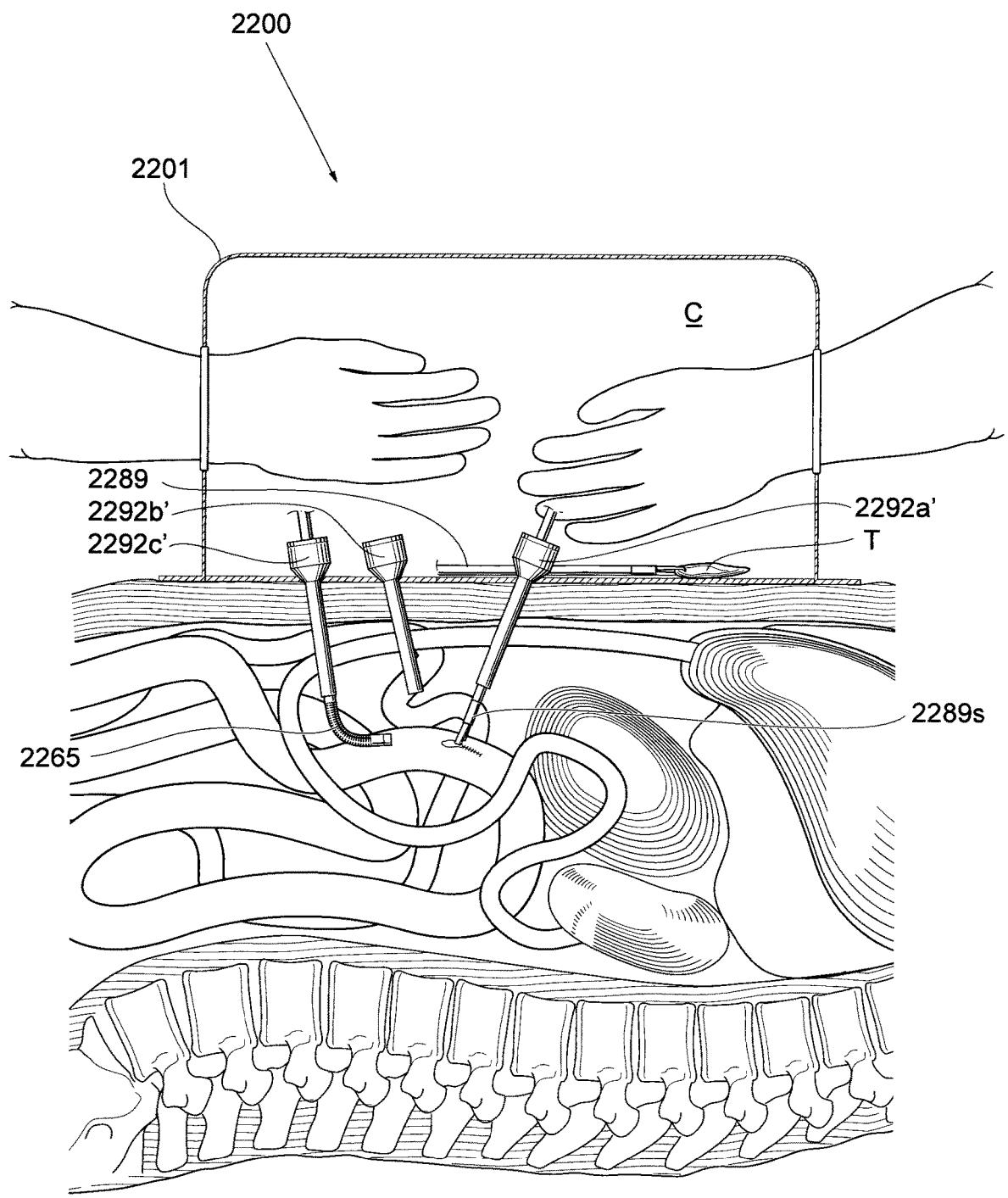

FIG. 219*e* shows the step (as described in the example above) of stapling the wound inflicted on the colon by the removal of the tumor T using an endoscopic stapler 2289*s*. The removed tumor T is securely placed within the chamber C of the medical device 2200

Figure 219F:
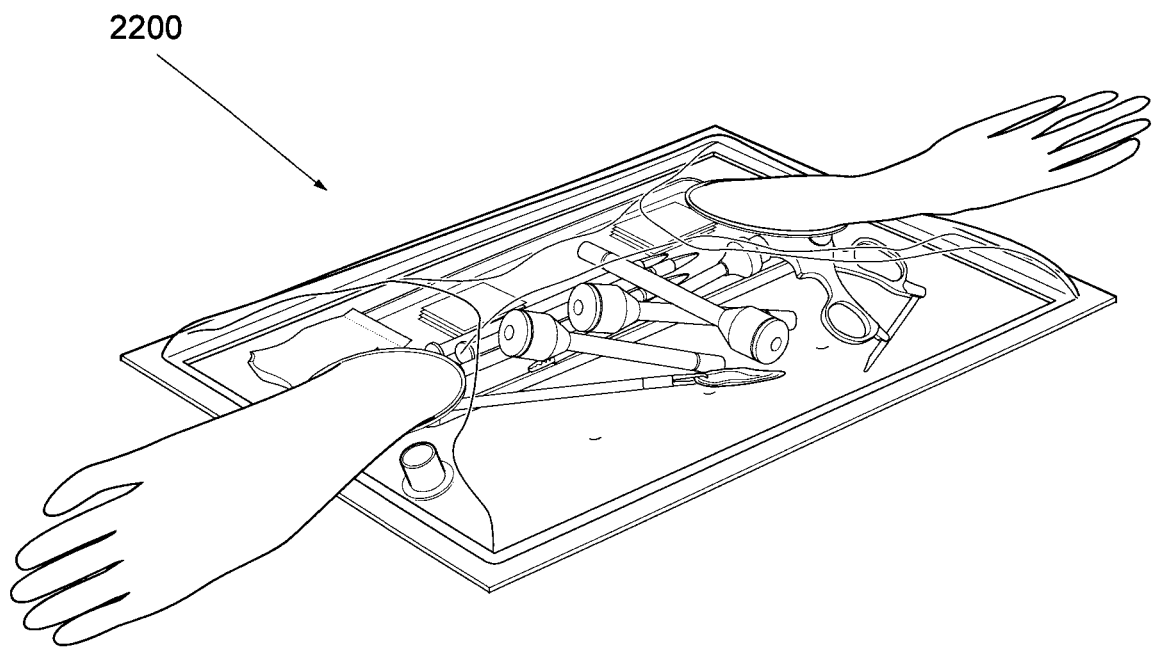
FIGS. 219*f*-219*g* shows an embodiment of the medical device when deflated after having been used.

FIG. 219*f* shows the medical device in its deflated state, all the instruments used in the surgical procedure are securely placed within the medical device 2200, and the medical device 2200 has been removed from the body of the patient.

Figure 219G:
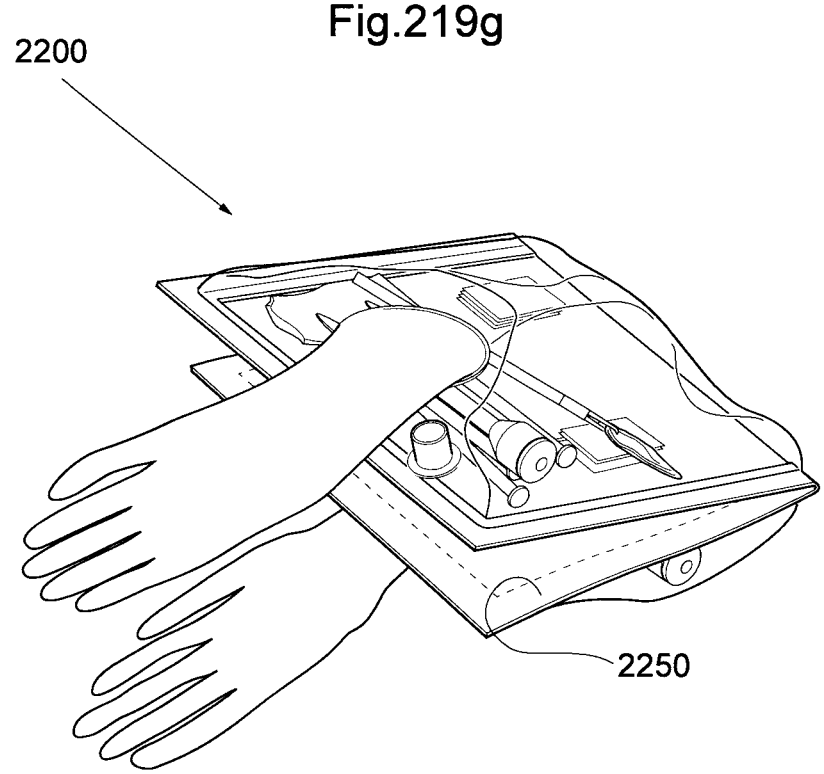

FIG. 219*g* shows the medical device when folded such that portions of the adhesive surface 2250 of the medical device is connected, such that the medical device 2200 is hermetically sealed with all the instruments and the removed specimen (tumor) secured inside.

FIG. 220*a*-220*j* shows a medical device for performing endoscopic surgery in a way such that the laparoscopic surgery can remain completely encapsulated during the entire operation. During normal laparoscopic surgery, leakage occurs in the incisions in which the trocars are placed, in the sealing membranes within the trocars and in connection with the inflation device penetrating the skin of the patient. The advantages of keeping the operation completely encapsulated includes less use of laparoscopic gas, further reduced risk of infections and reduced risk that the laparoscopic gas containing fumes from e.g. diathermy instruments used in the operation pollutes the environment of the operating theater. The advantage that the device enables a surgery which consumes less laparoscopic gas is particularly important when the medical device is used for field surgery, in which case the supply of laparoscopic gas may be limited.

In the medical device 2200 of FIGS. 220a-220d, a trocar is placed through the bottom wall of the medical device 2200 such that a first portion p1 of the trocar 2292 is placed inside of a chamber formed by the wall 2201 and a second portion p2 of the trocar 2292 is placed outside of the chamber such that the second portion p2 of the trocar can be inserted through the skin of the patient and into a cavity of the patient. The second portion p2 of the trocar 2292 is protected by a protective sheet that is removed prior to the insertion of the trocar 2292 into the patient. The inside of the trocar 2292 preferably comprises a membrane which separates the chamber enclosed by the wall 2201 form the ambient environment and the environment within the cavity of the patient when the trocar 2292 is inserted through the skin of the patient. The endoscopic instrument 2289 is entirely encapsulated by the wall 2201 and thus completely placed in the chamber when not inserted through the membrane of the trocar 2292. The endoscopic instrument 2289 can thus be positioned inside of the chamber until the trocar 2292 is positioned through the skin of the patient, thus the endoscopic instrument 2289 is positioned either inside of the chamber, or inside of the cavity formed within the patient.

FIG. 220a shows a medical device for performing endoscopic surgery. The medical device comprises a wall 2201 adapted to form a chamber in which a step of the surgical procedure can be performed. A portion of the wall 2201 comprising an adhesive portion 2250 is adapted to be fixated to the skin of the patient. The medical device 2200 comprises an endoscopic instrument 2289 enclosed within the chamber. The medical device further comprises a trocar 2292 positioned through the wall 2201 of the medical device 2200 such that a fluid connection can be established between the chamber enclosed by the wall 2201 of the medical device and a cavity in the patient. A first portion p1 of the trocar 2292 being placed inside of the chamber of the medical device 2200, and a second portion p2 of the trocar 2292 being positioned on the outside of the chamber. The medical device comprises a fluid inlet 2230 positioned in the wall 2201 adapted to be connected to a system for inflating the chamber of the medical device 2200. The system comprising a fluid conduit connected to a tank 2212 comprising pressurized fluid. The system further comprising a tempering unit 2226c for tempering the fluid entering the chamber, and a sterilizing 2226a and/o filtering system for sterilizing and/or filtering the fluid entering the chamber. The surgical instrument 2289 comprises a handle portion 2289' operably encapsulated by the wall 2201 such that the handle portion 2289' can be manipulated from outside the chamber.

Figure 220B:
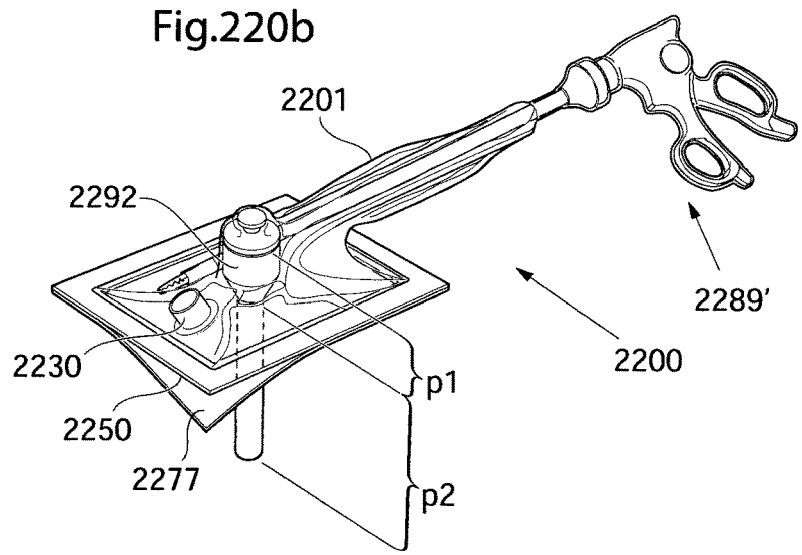
FIGS. 220*a*-220*c* shows an embodiment of the medical device comprising an integrated trocar.

FIG. 220b shows the medical device 2200 according to the embodiment shown in FIG. 220a, when a covering sheet 2277 is being removed from the adhesive surface 2250 of the medical device 2200, such that the second portion p2 of the trocar 2292 and the adhesive surface 2250 of the wall 2201 of the medical device 2200 is exposed such that the medical device 2200 can be fixated to the skin S of the patient.

Figure 220C:
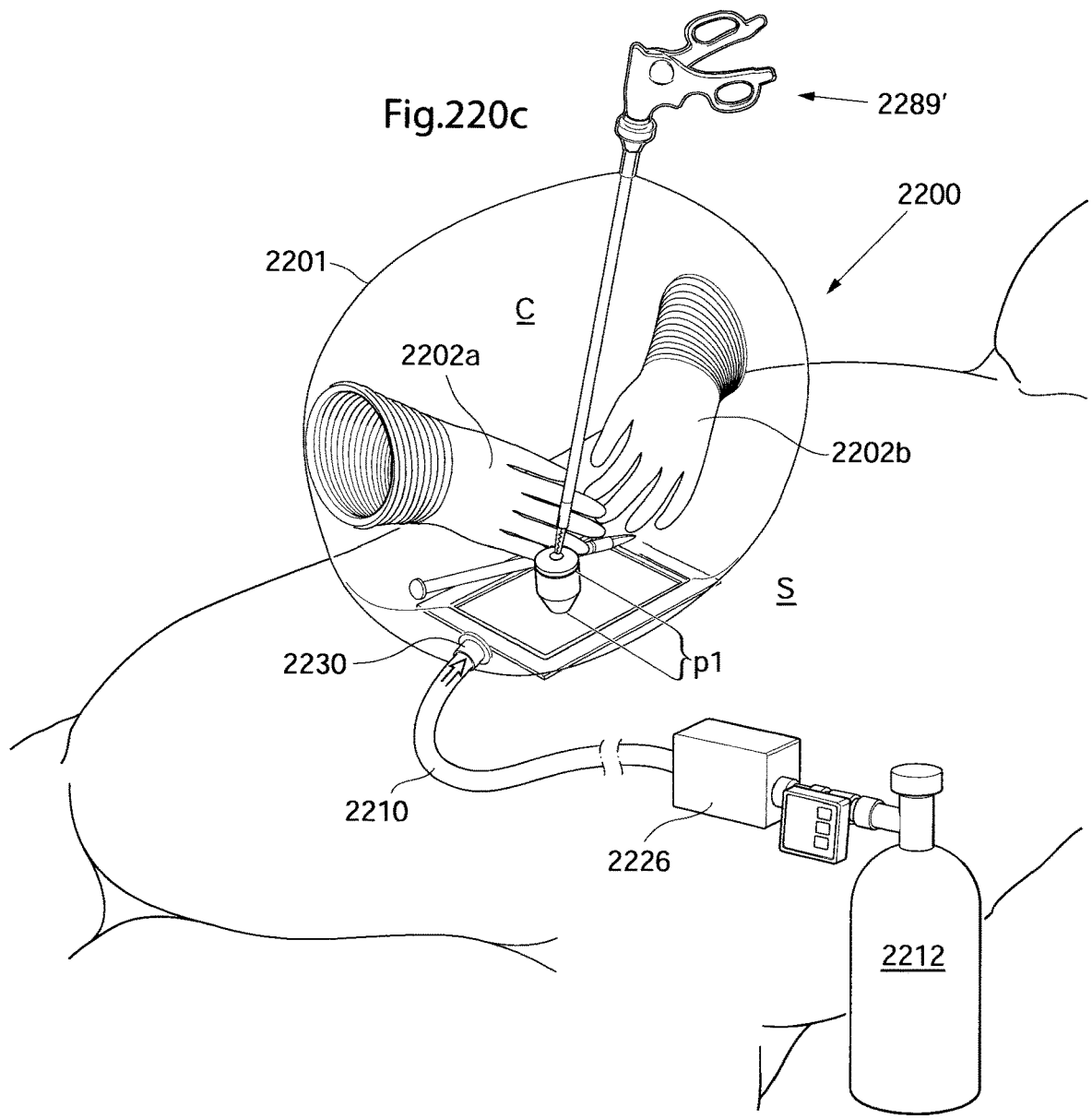

FIG. 220c shows the medical device according to the embodiment shown in FIGS. 220a and b, when the adhesive portion 2250 of the wall 2201 is fixated to the skin S of the patient and the wall 2201 is inflated such that a chamber C is created in which a part of the surgical procedure can be performed. The wall 2201 of the medical device 2200 is flexible or elastic and adapted to hold a pressure exceeding atmospheric pressure. The wall for example being made from a flexible polymer material, such as polyvinyl chloride (PVC) with a plasticizer additive, or an elastic polymer material, such as silicone. The wall 2201 of the medical device 2200 is inflated by means of the system for inflation disclosed with reference to FIG. 220a through the inlet 2230 in the wall 2201 of the medical device 2200. The medical device 2200 additionally comprises gloves 2202a; 2202b placed in the wall 220l of the medical device 2200 and enabling manipulation within the chamber C of the medical device 2200. In alternative embodiments, the medical device shown in FIGS. 220a-220c may comprise a vacuum sealing member assisting or replacing the adhesive portion 2250.

Figure 220D:
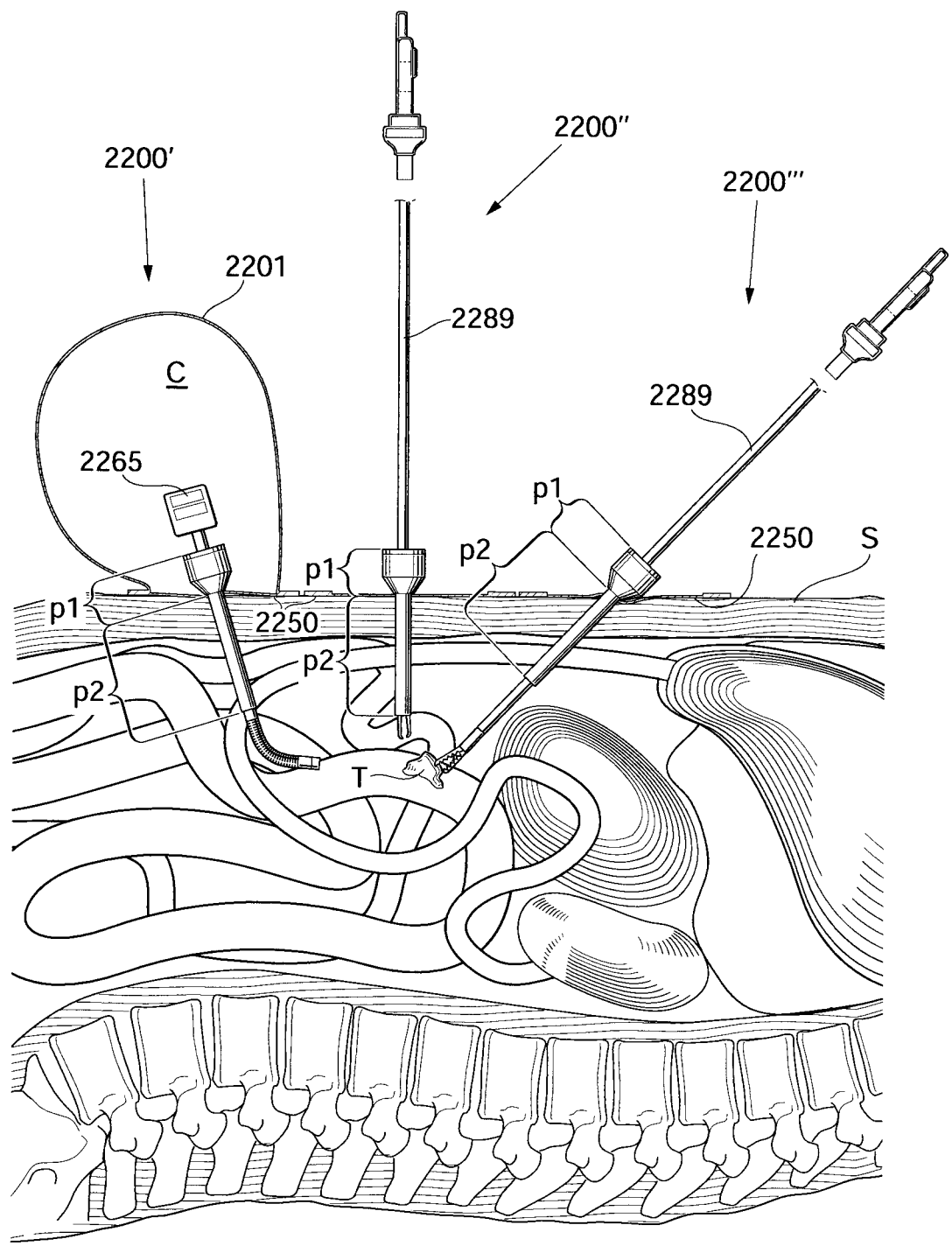
FIG. 220*d* shows an embodiment of the medical device when being used in a surgical procedure, FIGS. 220*e*-220*g"* shows different embodiments of trocars adapted to be used in combination with a medical device, FIGS. 220*h*, 220*h'* shows an embodiment of the trocar when being used with a medical device.
Figure 220H:
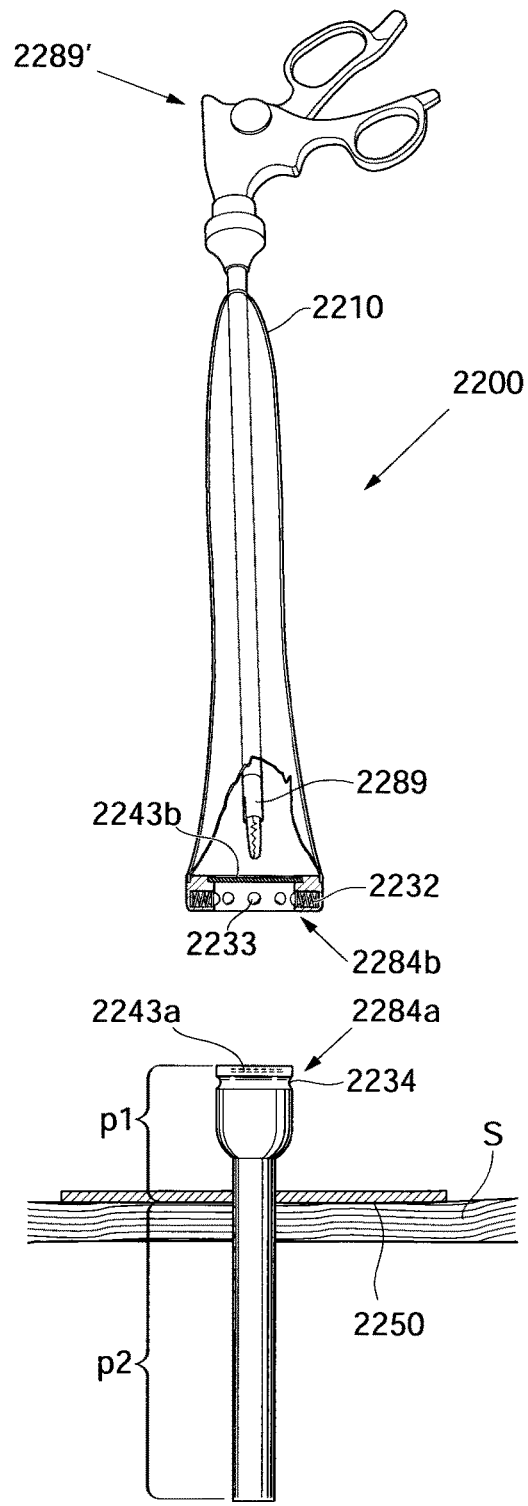
FIGS. 220*i*-220*l* shows an embodiment of an encapsulated trocar, when used, FIGS. 220*m*-220*q'''* shows embodiments of trocars and medical devices when used in combination, FIG. 220*q"* shows an alternative embodiment of a combination of a trocar and a medical device.
Figure 220H:
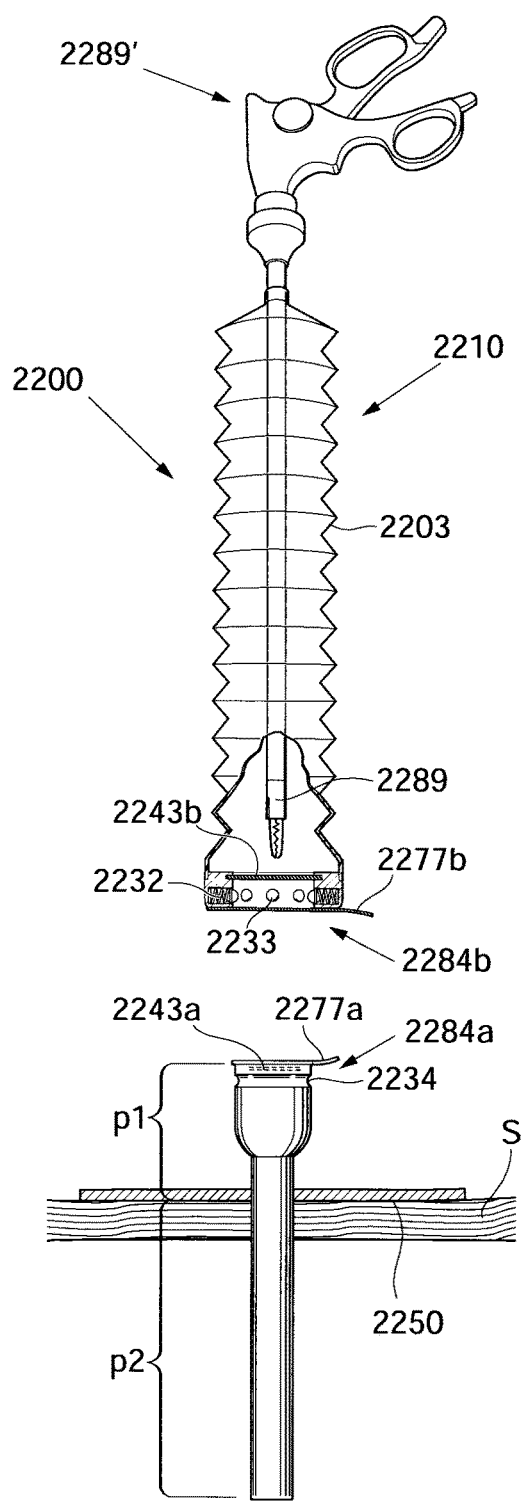
Figure 220I:
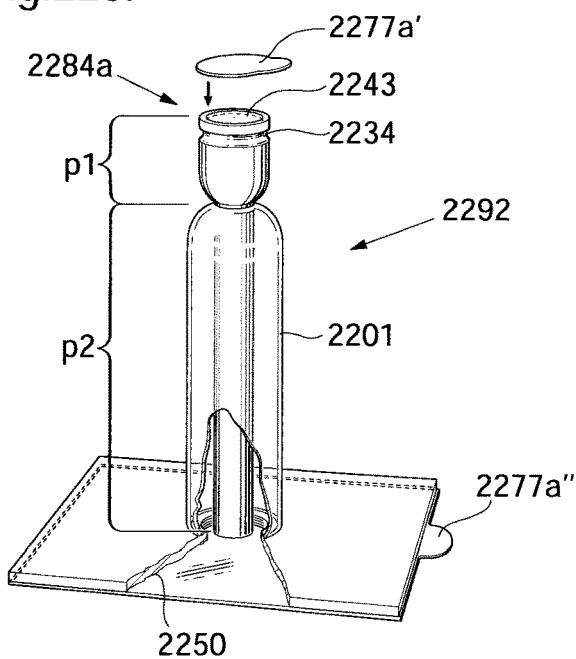
Figure 220J:
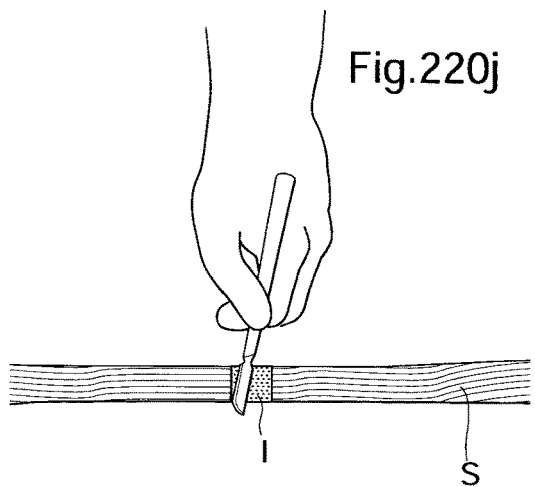
Figure 220K:
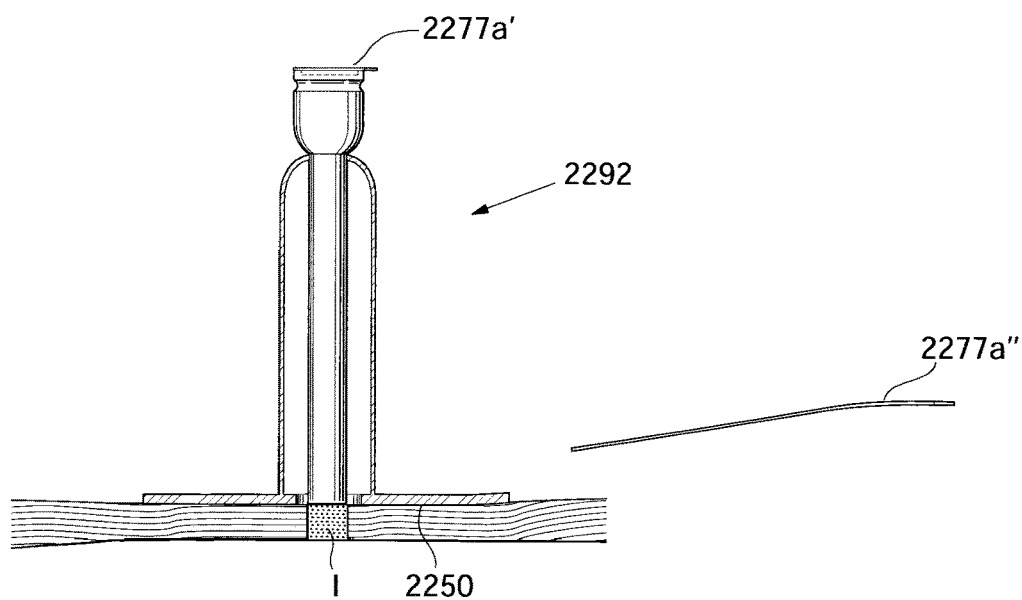
Figure 220O:
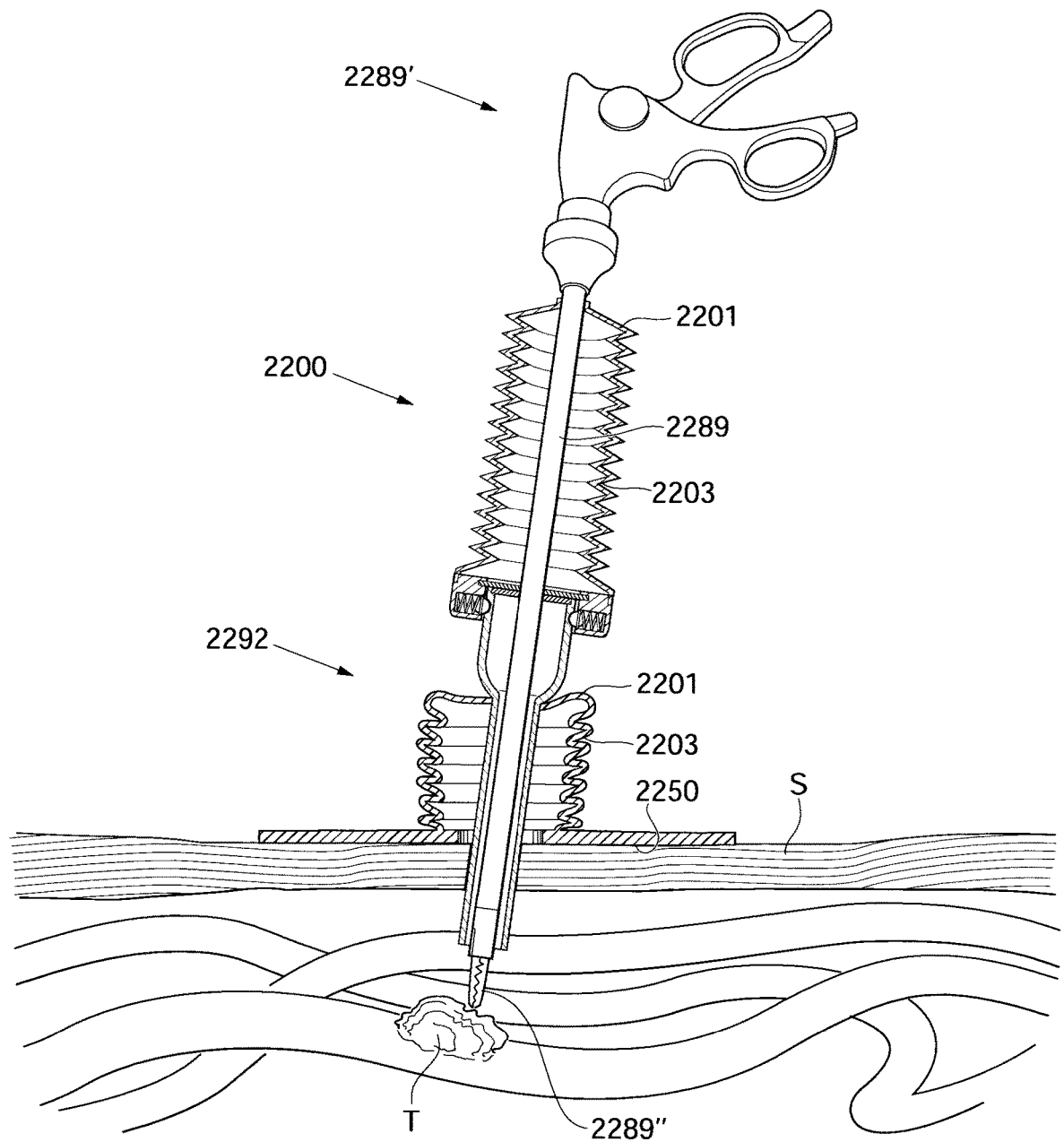
Figure 220Q:
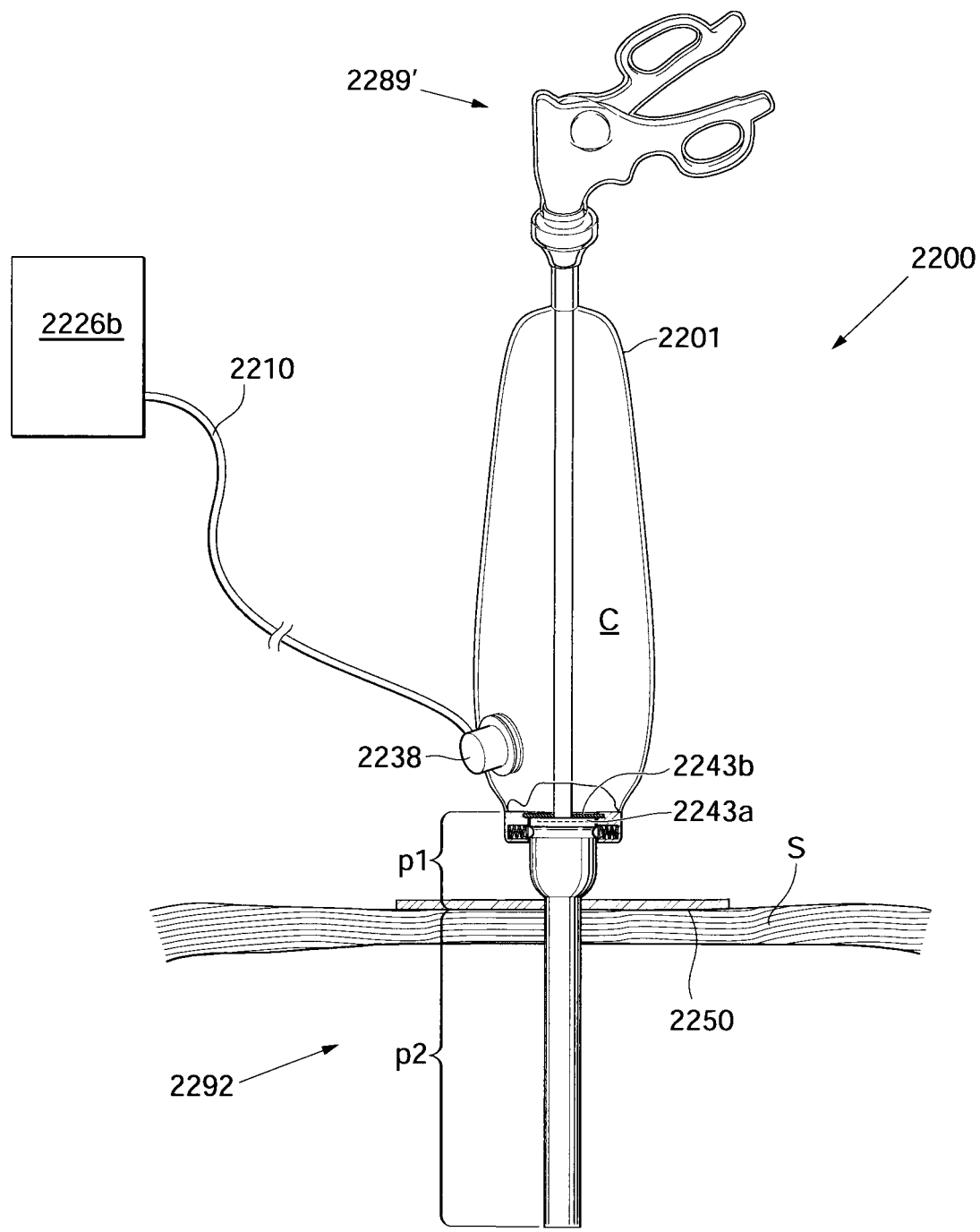

The medical device shown in FIGS. 220a-220c may additionally comprise an evacuation valve for evacuating a fluid from the chamber, such as the evacuation valve and system shown in FIG. 220q".

FIG. 220d shows and endoscopic system using the medical devices shown in FIGS. 220a-220c, when used for performing an endoscopic operation. A first medical device 2200' comprises an endoscopic camera 2265 enclosed within the wall 2201 of the medical device 2200' is used for enabling visual inspection in a cavity within the patient, a second medical device 2200". Second 2200" and third 2200''' medical devices are provided for inserting surgical instruments 2289 into the cavity in the patient for performing an endoscopic procedure, such as removing a tumor T on an intestine of the patient. Each medical device being fixated to the skin S of the patient by means of an adhesive portion 2250 of the wall 2201 of the medical device 2200. By each medical device being sealingly fixated to the skin S of the patient, a sealed endoscopic system is created which reduces the risk that bacteria will enter the FIGS. 220e-220q shows a system for performing an endoscopic procedure in a sealed environment. The system comprises an endoscopic trocar adapted to be positioned through the skin of a patient, such that an endoscopic procedure can be performed inside a cavity of the patient, and a medical device adapted to encapsulate an instrument to be inserted through the trocar. By encapsulating the instrument, the instrument can be kept sterile even when being outside of the patient's body, such that instruments used in a particular trocar can be changed without the risk that the trocar is contaminated while being on the outside of the patient's body. Encapsulated endoscopic surgery could for example be used when the risk of infections is particularly large, such as in arthroscopic surgical procedures in a joint of a patient, or in environments that are difficult to keep sterile, such as e.g. in field hospitals and in hospitals in third world countries. The embodiments of FIGS. 220e-220q shows alternative embodiments of the features needed to create a sealed endoscopic system. A further advantage with the sealed endoscopic system is that fluids used to inflate a cavity in the patient, does not leak outside of the sealed area of the endoscopic system, which keeps the consumption o the fluids at a minimum. Keeping the fluid consumption low could be of utmost importance in field applications where the fluids are a scarce resource. The features are however not limited to the particular embodiment in which it is shown and could be used in combination with any of the embodiments for creating a functioning medical device system.

FIG. 220e shows a trocar 2292 having a first portion p1 adapted to be positioned on the outside of the patient's body, and a second portion p2 adapted to be positioned through the skin S of the patient and into a cavity in the patient's body. The trocar 2292 is adapted to be fixated to the skin S of the patient by means of an adhesive surface 2250 fixated to the trocar 2292 and being adapted to seal and fixate against the surface of the skin S of the patient. The trocar 2292 further comprises a seal 2243 within the trocar 2292, in the form of a self sealing membrane 2243 adapted to seal between the cavity in the body of the patient and the ambient environment. The self sealing membrane 2243 for example comprises a silicone self sealing membrane, or a gel type self sealing membrane, such as the gel port available from Applied medical inc. The trocar 2292 further comprises a connecting portion 2284*a*, for connecting the trocar 2292 to a medical device, such as the medical devices shown in FIGS. 220*h*, 220*h'*, 220*l*-220*o*. The connecting portion 2284*a* of the embodiment shown in FIG. 220*e* comprises a recess 2234 in the form of a groove 2234 encircling the connecting portion 2284*a* of the trocar 2292. The recess 2234 is adapted to receive a protruding portion of a connecting portion of a medical device. However in alternative embodiments, the connecting portion 2284*a* could have a different configuration, the connecting portion could for example comprise a protruding portion and being adapted to be connected to a recess of a medical device.

FIG. 220*f* shows an embodiment in which the trocar 2292 comprises a vacuum sealing member 2205' adapted to hold a pressure below atmospheric pressure for providing a vacuum seal against the skin S of the patient. The vacuum sealing member 2205' is via a vacuum conduit 2206, in fluid connection with a vacuum source, such as the vacuum pump (shown as reference number xx08 in other embodiments disclosed in this application). The vacuum sealing member 2205' may be assisted by the surface contacting the skin S of the patient being adhesive.

FIG. 220*g* shows an alternative embodiment of the trocar, in which the trocar 2292 comprises a pressures seal 2205" connected via a fluid conduit 2210 to a pressure source (such as the pressurized fluid tank shown as reference number xx12 in other embodiments disclosed in this application, or the fluid pump shown as reference number xx09 in other embodiments disclosed in this application). When inflated, the pressure seal 2205" forms an inflated chamber having a first enlargement 2205"*a* on the outside of the skin S of the patient, and a second enlargement 2205"*b* on the inside of the skin S of the patient, such that the skin S (and tissue) is pressed from the outside by the first enlargement 2205"*a* and from the inside by the second enlargement 2205"*b*. The skin S (and tissue) is further pressed in a direction parallel to the skin S of the patient by the inflatable chamber 2205" being inflated, and sealing is thus provided both perpendicularly from the outside, against the skin S and tissue of the patient, and against the edges of the incision in the skin S, in a direction parallel to the skin S of the patient.

FIG. 220*g'* shows an embodiment similar to the embodiment shown in FIG. 220*g*, the difference being that the pressure seal 2205" of the embodiment in FIG. 220*g'* comprises two separate chambers 2205"*a* and 2205"*b*, wherein the first chamber 2205"*a* is adapted to press against the surface of the skin S of the patient, from the outside thereof. And the second chamber 2205"*b* of the pressure seal 2205" is adapted to press against the skin S and tissue of the patient from the inside thereof. The two separate chambers are adapted to be in fluid connection with each other by means of a fluid conduit 2210' running on the inside of the trocar 2292.

FIG. 220*g"* shows an embodiment in which the trocar 2292 comprises pivoting supports 2249*a*; 2249*b* pressing against the skin S and tissue by means of springs 2232; 2232*b* connected to the supports 2249*a*, 2249*b*. The external pivoting supports 2249*a* are adapted to press against the surface of the skin S of the patient, in a direction substantially perpendicular to the skin S of the patient and thus substantially parallel to the trocar 2292, by a spring 2232*a* being connected to the external support 2249*a* and exerting a pressing force on the external support 2249*a*. The internal pivoting supports 2249*b* are adapted to press against the inside of the skin S and tissue of the patient from the inside of the patient's body, in a direction substantially perpendicular to the skin S of the patient and thus substantially parallel to the trocar 2292, by a spring 2232*b* being connected to the internal pivoting support 2249*b* and exerting a pressing force on the internal support 2249*b*. The internal and external pivoting supports 2249*a*; 2249*b* can be folded against the trocar 2292, such that the trocar 2292 can be inserted through the incision performed in the skin S of the patient.

FIG. 220*h* shows an embodiment of a system for performing encapsulated endoscopic surgery. The system comprises the trocar 2292, further described under reference to FIG. 220*e*, and a medical device 2200 adapted to be connected to the trocar 2292. The medical device 2200 comprises a flexible wall 2201 enclosing a chamber in which an endoscopic instrument 2289 is enclosed. The medical device 2200 comprises a connecting portion 2284*b* positioned in the flexible wall 2201 and adapted to connect to a connecting portion 2284*a* of the trocar 2292, such that a fluid connection is created between the chamber enclosed by the wall 2201, and a cavity within the patient. The connecting portion 2284*b* of the medical device 2200 comprises protruding members 2233 in the form of protruding balls pressed against the edge of an orifice by a spring 2232. The balls 2233 can thus be pushed into the cavity housing the spring 2232 by a force acting on the ball 2233 from the connecting portion 2284*a* of the trocar. When the recess 2234 of the connecting portion 2284*a* of the trocar 2292 is aligned with the cavities housing the springs 2232 and balls 2233, the balls 2233 are pushed into the recess 2234 by the springs 2232 and thus connects and fixates the medical device 2200 to the trocar 2292.

The connecting portion 2284*b* of the medical device 2200 comprises a self sealing membrane 2243*b* comprising a small self sealing hole in the center through which the endoscopic instrument 2289 can be inserted. The self sealing membrane 2243*b* is positioned at the connecting portion 2284*a* of the trocar, such that the self sealing membrane 2243*b* abuts the self sealing membrane 2243*a* of the trocar 2292 when the medical device 2200 and the trocar 2292 are connected. The two self sealing membranes 2243*a*; 2243*b* thus forms an integrated self sealing membrane enabling the insertion of the endoscopic instrument 2289 through the two self sealing membranes 2243*a*; 2243*b* acting as a single membrane, such that a fluid connection between the chamber of the medical device 2200 and the cavity in the patient can be formed while the chamber and cavity of the patient is kept completely sealed from the ambient environment.

The surgical instrument 2289 shown in FIG. 220*h* comprises a handle portion 2289' for operating the surgical instrument. In the embodiment shown in FIG. 220*h* for operating the small grasping portion in the end of the surgical instrument 2289. The handle portion is operably encapsulated by the wall 2201 such that the handle portion can be manipulated from outside the chamber.

FIG. 220*h'* shows an embodiment of the medical device similar to the embodiment shown in FIG. 220*h*, the difference being that the wall 2201 of the medical device comprises a pleated 2203 portion such that it can be compressed when the handle portion 2289' is moved closer to the trocar 2292, such that the surgical instrument can perform manipulations within the cavity of the patient. The wall 2201 of the medical device is fixated to the surgical instrument just below the handle portion 2289' such that the handle portion is kept outside of the sealed environment in the chamber enclosed by the wall 2201, while the portion of the surgical instrument 2289 adapted to be inserted through the membranes 2243*a*; 2243*b* and into the cavity in the patient are encapsulated by the wall 2201 and thus kept in the sealed environment.

The embodiment of FIG. 220*h*' further shows a first and second covering sheet 2277*a*; 2277*b*, the first covering sheet 2277*a* being adapted to cover the connecting portion 2284*a* of the trocar 2292 including the self sealing membrane 2243*a*. The second covering sheet is adapted to cover the connecting portion 2284*b* of the medical device 2200, such that the self sealing membrane 2243*b* is covered. The two covering sheets 2277*a*; 2277*b* are adapted to be removed before the medical device 2200 and the trocar 2292 are connected such that the self sealing membranes 2243*a*; 2243*b* are exposed. The covering sheets 2277*a;b* are preferably made from a thin polymer material covered with a non-stick surface, such as a PTFE surface.

FIG. 220*i* shows an embodiment of the trocar 2292 similar to the embodiment shown in FIG. 220*e*, the difference being that the embodiment of FIG. 220*i* comprises a wall 2201 fixated to the trocar 2292 and being adapted to enclose the portion p2 of the trocar 2292 adapted to be inserted into the cavity of the patient, such that this portion p2 can be kept sterile. The embodiment shown in FIG. 220*i* further comprises a covering sheet 2277*a*' covering the connecting portion 2284*a* of the trocar, including the membrane 2243*a*, and a covering portion 2277*a*" covering the adhesive surface 2250 of the trocar 2292 adapted to fixate the trocar 2292 to the skin of the patient. The adhesive portion 2250 being fixated to the wall 2201.

FIG. 220*j* shows the skin S of the patient when an incision I has been performed enabling the insertion of a trocar into a cavity in the patient.

FIG. 220*k* shows when the trocar 2292 according to the embodiment shown in FIG. 220*k* when the covering sheet 2277*a*" covering the adhesive surface 2250 has been removed, thus exposing the adhesive surface 2250, and the adhesive surface 2250 has been fixated to the skin S of the patient by the adhesive surface 2250 contacting the skin S of the patient. The wall 2201 of the medical device 2200 could for example be made from a flexible polymer material, such as polyvinyl chloride (PVC) with a plasticizer additive, or an elastic polymer material, such as silicone.

FIG. 220*l* shows the trocar 2292 when a portion p2 has been inserted through the skin S of the patient and into the cavity in the patient by the flexible wall 2201 of the trocar being compressed such that a pleated portion is formed. The protective cover 2277*a*' has been removed from the connecting portion 2284*a* of the trocar, exposing the self sealing membrane 2243*a*.

FIG. 220*m* shows the trocar 2292 shown in FIG. 220*l* and a medical device 2200 comprising a connecting portion 2284*b* for connecting to the trocar 2292. The medical device being the medical device disclosed with reference to FIG. 220*h*' comprising a removable covering sheet 2277*b* for covering the connecting portion 2284*b* of the medical device 2200 and thus covering the self sealing membrane 2243*b* of the in the connecting portion 2284*b* of the medical device 2200.

FIG. 220*n*' shows the connecting portions 2284*a*; 2284*b* of the trocar 2292 and the medical device 2200, respectively. The self sealing membrane 2243*a* of the trocar 2292 comprises a small self sealing hole 2244*a* placed centrally in the membrane 2243*a* and enabling the insertion of the instrument 2289 through the self sealing membrane 2243*a* by means of the elastic properties of the material of the self sealing membrane 2243*a*. The self sealing membrane 2243*a* could for example be the self sealing membrane of the gel port available from Applied medical inc. FIG. 220*n*' further shows the connecting portion 2284*b* of the medical device 2200 in further detail. The medical device 2200 comprises a flexible wall 2201 enclosing a chamber C in which an endoscopic instrument 2289 is enclosed. The connecting portion 2284*b* positioned in the flexible wall 2201 and adapted to connect to the connecting portion 2284*a* of the trocar 2292, such that a fluid connection is created between the chamber C enclosed by the wall 2201, and a cavity within the patient. The connecting portion 2284*b* of the medical device 2200 comprises protruding members 2233 in the form of protruding balls pressed against the edge of an orifice by a spring 2232. The balls 2233 can thus be pushed into the cavity housing the spring 2232 by a force acting on the ball 2233 from the connecting portion 2284*a* of the trocar. When a recess 2234 of the connecting portion 2284*a* of the trocar 2292 is aligned with the cavities housing the springs 2232 and balls 2233, the balls 2233 are pushed into the recess 2234 by the springs 2232 and thus connects and fixates the medical device 2200 to the trocar 2292. The connecting portion 2284*b* of the medical device 2200 comprises a self sealing membrane 2243*b* comprising a small self sealing hole 2244*b* adapted to enable the insertion of an instrument 2289 through the self sealing membrane 2243*b*.

FIG. 220*n*" shows the medical device 2200 when the trocar 2292 and the medical device 2200 are connected. The balls 2233 have been pushed into the recess 2234 by the springs 2232 and thus connect and fixate the medical device 2200 to the trocar 2292. The self sealing membrane 2243*a* of the trocar abuts the self sealing membrane 2243*b* of the medical device 2200 such that an integrated self sealing membrane is formed. The small self sealing hole 2244*a* of the trocar 2292 is aligned with the small self sealing hole 2244*b* of the medical device 2200 such that the surgical instrument can be inserted through the integrated self sealing membrane by the elasticity of the material of the self sealing membranes 2243*a*; 2243*b*.

FIG. 220*n*''' shows the trocar 2292 and medical device 2292 when connected and with the instrument 2289 inserter through the expanded orifices of the self sealing membranes 2243*a*; 2243*b* from the chamber C to the inside of the trocar 2292.

FIG. 220*o* shows the medical device system, comprising the connected trocar 2292 and medical device 2200, when the surgical instrument 2289 for manipulation in the cavity within the patient is inserted through the integrated self sealing membrane and through the trocar 2292 and into the cavity on the patient such that a grasping portion 2289" of the surgical instrument 2289 can perform a step of the surgical procedure within the cavity of the patient, such as assisting in the removal of a tumor T on the intestinal system of the patient. Both the wall 2201' of the medical device 2200 and the wall 2201" of the trocar have been compressed such that pleated portions 2203 have been formed. The walls 2201'; 2201" are additionally flexible such that the surgical instrument 2289 can be moved within the cavity of the patient such that different positions within the cavity can be reached.

FIG. 220*p* shows the medical device system when a medical device 2200' is exchanged to a medical device 2200"; 2200" enclosing a different surgical instrument. The medical device 2200' enclosing a grasping surgical instrument 2289 could for example be exchanged to a medical device 2200''' enclosing an endoscopic camera 2265 or a medical device enclosing a stapling instrument 2289*s*. As the surgical instrument/camera 2289; 2289s; 2265 is retracted from the cavity of the patient and the inside of the trocar 2292, through both self sealing membranes 2243a; 2243b before the medical device 2200 is disconnected from the trocar 2292, the chamber C of the surgical instrument 2200 and the inside of the trocar 2292 is sealed from the ambient environment A during all the steps of the procedure. Surgical instruments to be used in the trocar 2292 can thus be removed from the operation site when a different instrument is needed and brought back into use without the risk that the instrument will contaminate the operation site, making the system highly suitable for use when performing endoscopic procedures in less sterile environments.

FIG. 220q' shows the medical device system according to an embodiment where the trocar shown in FIG. 220e is connected to a medical device 2200 comprising an evacuation valve 2238 for evacuating a fluid from the chamber C. The evacuated fluid could be a gas or liquid used to inflate the cavity in the patient for enabling visual inspection within the cavity. The gas or liquid could become contaminated by the steps of the surgical procedures. A laparoscopic gas, such as $CO_2$ gas could become contaminated be fumes from diathermy instruments used inside the cavity during the surgical procedure, which could affect the possibility of obtaining good visibility within the chamber C and cavity. The evacuation valve 2238 is connected to a fluid conduit 2210 which in turn is connected to a filtering unit 2226b adapted to filter the evacuated fluid such that unpleasant fumes is not released into the environment of the operating theater during the surgical procedure, such as fumes from the use of a diathermy instrument. The filtering unit 2226b could furthermore be a control system for controlling the opening of the evacuation valve 2238. The control system could control the evacuation valve on the basis of for example the pressure in the chamber C, the visibility in the chamber C, detection of smoke in the chamber C, the temperature in the chamber C, and/or a time related parameter.

FIG. 220q" shows the medical device system according to an embodiment similar to the embodiment of FIG. 220q', the difference being that the wall 2201 enclosing the chamber C is larger, such that the whole surgical instrument 2289, including the handle portion 2289', is enclosed in the chamber C. The medical device 2200 further comprises gloves 2202a; 2202b integrated in the wall 2201 of the medical device 2200 such that the handle portion 2289' of the surgical instrument 2289 can be manipulated within the chamber C by the a surgeon using the integrated gloves 2202a; 2202b. The wall 2201 of the medical device 2200 is adapted to hold a pressure exceeding atmospheric pressure which is inflated into the chamber C of the medical device 2200 by the fluid connection with an inflated cavity of the patient's body, when a surgical instrument is inserted through the seals.

FIG. 220q''' shows an alternative embodiment in which the connecting portions 2284a;2284b comprises a plurality of self sealing membranes 2243';2243";2243''' etc. which are removable such that a new sterile membrane can be exposed when the medical device 2200 is reconnected to the trocar 2292 after having been disconnected when the medical device is replaced for a different medical device for performing a specific step of the surgical procedure (the exchange of medical devices for example shown in FIG. 220p). The stack of self sealing membranes are connected to each other by means of the first 2243' self sealing membrane adhering to the next 2243" and so forth. As the stack of self sealing membranes becomes thinner as self sealing membranes 2243';2243";2243''' are removed the exposed self sealing membrane needs to be feed to the connecting position such that the exposed self sealing membrane is placed in connection with the exposed self sealing membrane of the trocar 2292 such that an interconnected self sealing membrane can be formed. The stack of self sealing membranes 2243';2243";2243''' etc. are feed by the action of springs positioned in bores in the connecting portions 2284a;2284b perpendicular to the feeding direction of the self sealing membranes 2243';2243";2243''' etc.

FIG. 220q"" shows an alternative embodiment of the medical device system where the connecting portion 2284b of the medical device 2200 comprises a sleeve 2259 adapted to connect to the connecting portion 2284a of the trocar 2292 by engaging the trocar 2292 on the outside thereof. The sleeve 2259 comprises sealing members in the form of O-rings 2254 for sealing between the sleeve 2259 and the trocar 2292. FIG. 220q''' further shows a fluid system for inflating the cavity of the patient with a fluid. The fluid system comprises a fluid inlet 2230' placed through the skin S of the patient and connected to a fluid conduit 2210, which in turn is connected to a tank 2212 comprising pressurized fluid. The fluid flow into the cavity of the patient is controlled/monitored by means of a control/monitoring system 2215 placed on a portion of the fluid conduit 2210 and for example comprising a manometer and a restriction valve for adapting the flow and/or pressure of the fluid entering the cavity of the patient.

FIGS. 221a-221e shows an alternative embodiment of the medical device in which the medical device is adapted to hold a cavity in the body of the patient and a chamber in the medical device without the inflation of the medical device. The wall of the medical device is supported by rigid mechanical elements in the bottom and/or top portion, such that the cavity in the patient and the chamber of the medical device is held in its expanded states without the use of a pressure exceeding atmospheric pressure within the chamber. Being able to hold the chamber without the use of a pressure is for example advantageous when using the product in field surgery, as compressed gas or electricity for powering a pump may hard to come by.

FIG. 221a shows an embodiment of the medical device 2400 in which the wall 2401 of the medical device comprises guide slots 2424a, 2424b adapted to guide elastic elements 2423a, 2423b. The elastic elements 2424a are adapted to hold the top portion of the wall of the medical device 2400 such that the chamber C in the medical device 2400 is created. The elastic elements 2423a are inserted into the guide slots 2424a and are thereafter fixated in the length axis of the elastic elements 2423a such that the elastic elements 2423a are confined to a particular length such that they rigidly holds the top portion of the wall 2401 of the medical device, much like the sticks of a camping tent. The medical device of FIG. 221a further shows elastic elements 2423b in guiding slots 2424b in the bottom portion of the wall 2401 of the medical device 2400 such that the central portion of the bottom portion of the medical device 2400 can be lifted in the same way as the top portion of the wall 2401 of the medical device, such that a cavity in the body of the patient can be maintained by having an adhesive surface 2450 adhering to the skin of the patient and being lifted by means of the elastic elements 2423b in the guiding slots 2424b of the bottom portion of the wall 2401 of the medical device 2400.

The medical device 2400 as shown in FIG. 221a further comprises a device/instrument mount 2420 enclosed in the chamber C of the medical device 2400, and gloves 2402 integrated in the wall 2401 of the medical device 2400 enabling manual manipulation within the chamber C of the medical device 2400. The medical device comprises a first and second glove 2402a, 2402b for use by the surgeon performing the operation, the medical device further comprises a third glove 2402c for use by the assisting surgeon, for example holding an endoscopic camera such that the operating surgeon have sufficient vision.

Figure 221B:
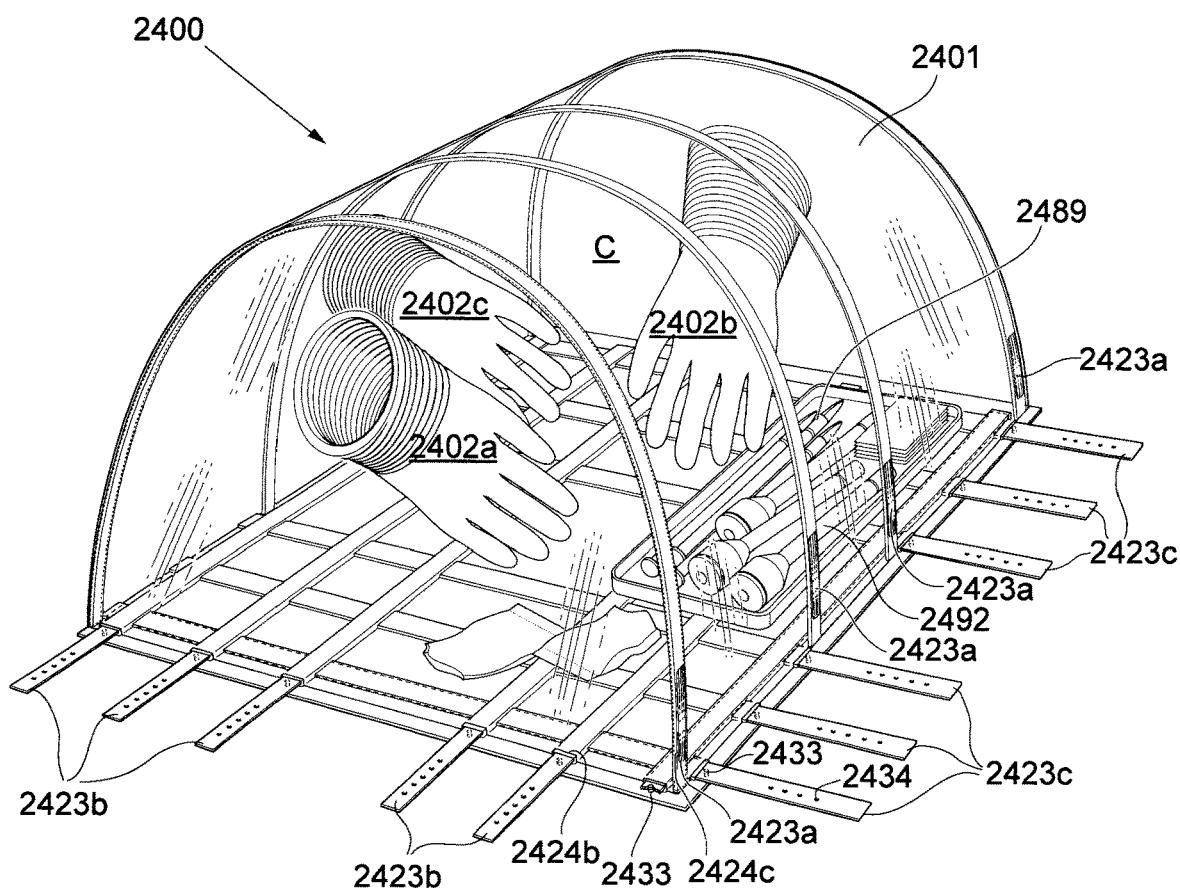

FIG. 221b shows the embodiment of the medical device according to FIG. 221a when the medical device in mounted, in perspective view. The elastic elements 2423a have been inserted into the guide slots 2424a and are fixated by holes or recesses 2434 in the elastic elements 2423 being locked by means of protruding members 2433 fixated to the bottom portion of the wall 2401 of the medical device 2400. The device/instrument mount 2420 placed in the chamber C of the medical device is shown comprising trocars 2492 for insertion through the skin S of the patient and into a cavity of the patient's body for creating a fluid connection between the chamber C of the medical device 2400 and a cavity in the body of the patient.

Figure 221C:
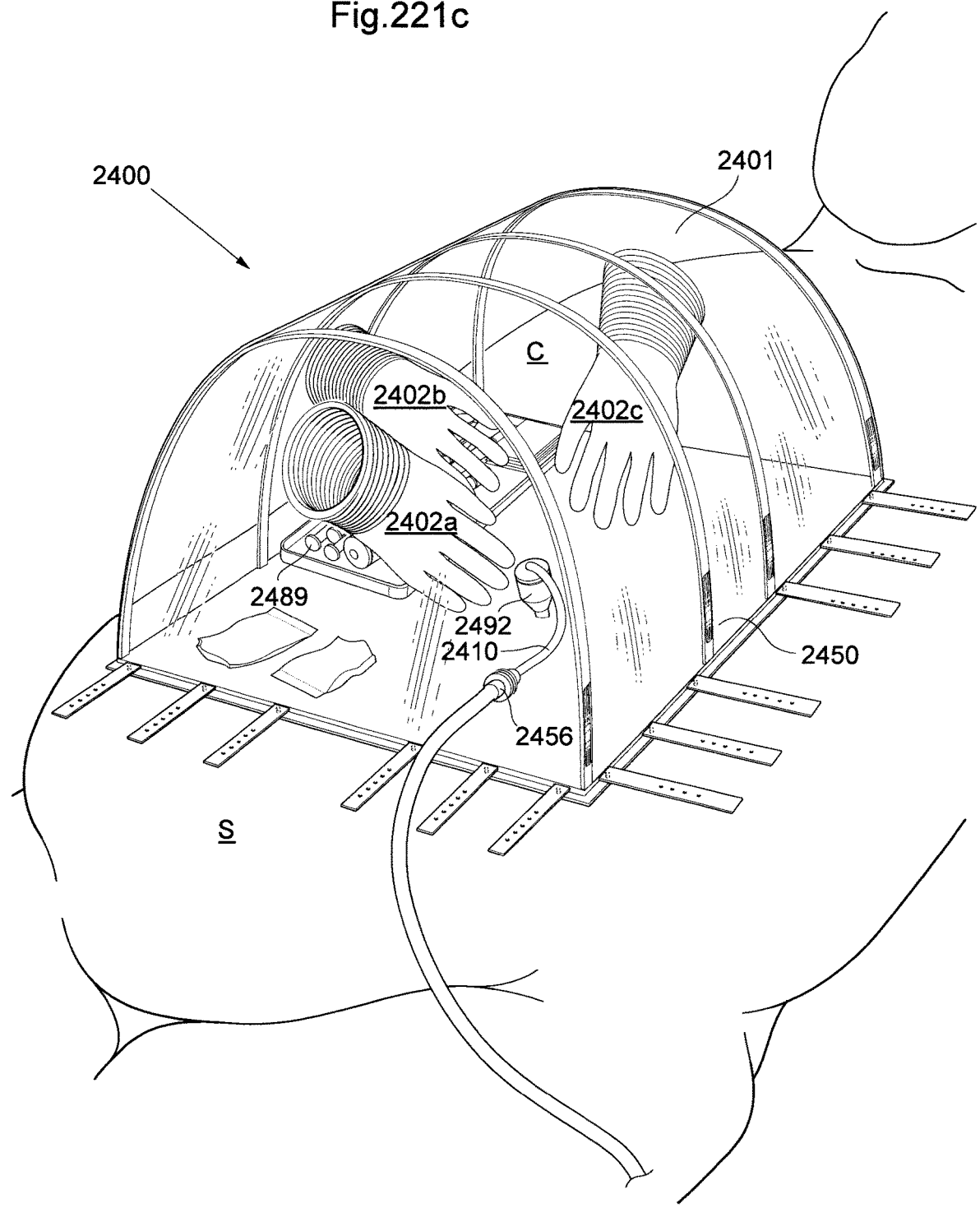

FIG. 221c shows the medical device according to the embodiment shown in FIGS. 221a and 221b when fixated by an adhesive surface 2450 to the skin S of the patient. A trocar 2492 has been placed through the bottom portion of the wall 2401 of the medical device 2400 and further through the skin S of the patient. A fluid conduit 2410 is connected to the trocar 2492. The fluid conduit 2410 runs from the ambient environment (A) through the wall 2401 of the medical device 2400 by means of a fluid coupling 2456 placed in the wall 2401 of the medical device 2400. The fluid conduit 2410 enables the inflation of a cavity in the body of the patient with a laparoscopic gas through the trocar in the skin of the patient for creating the cavity in the abdomen of the patient which could be maintained by the adhesive surface 2450 part of the wall 2401 of the medical device adhering to the skin S of the patient.

Figure 221D:
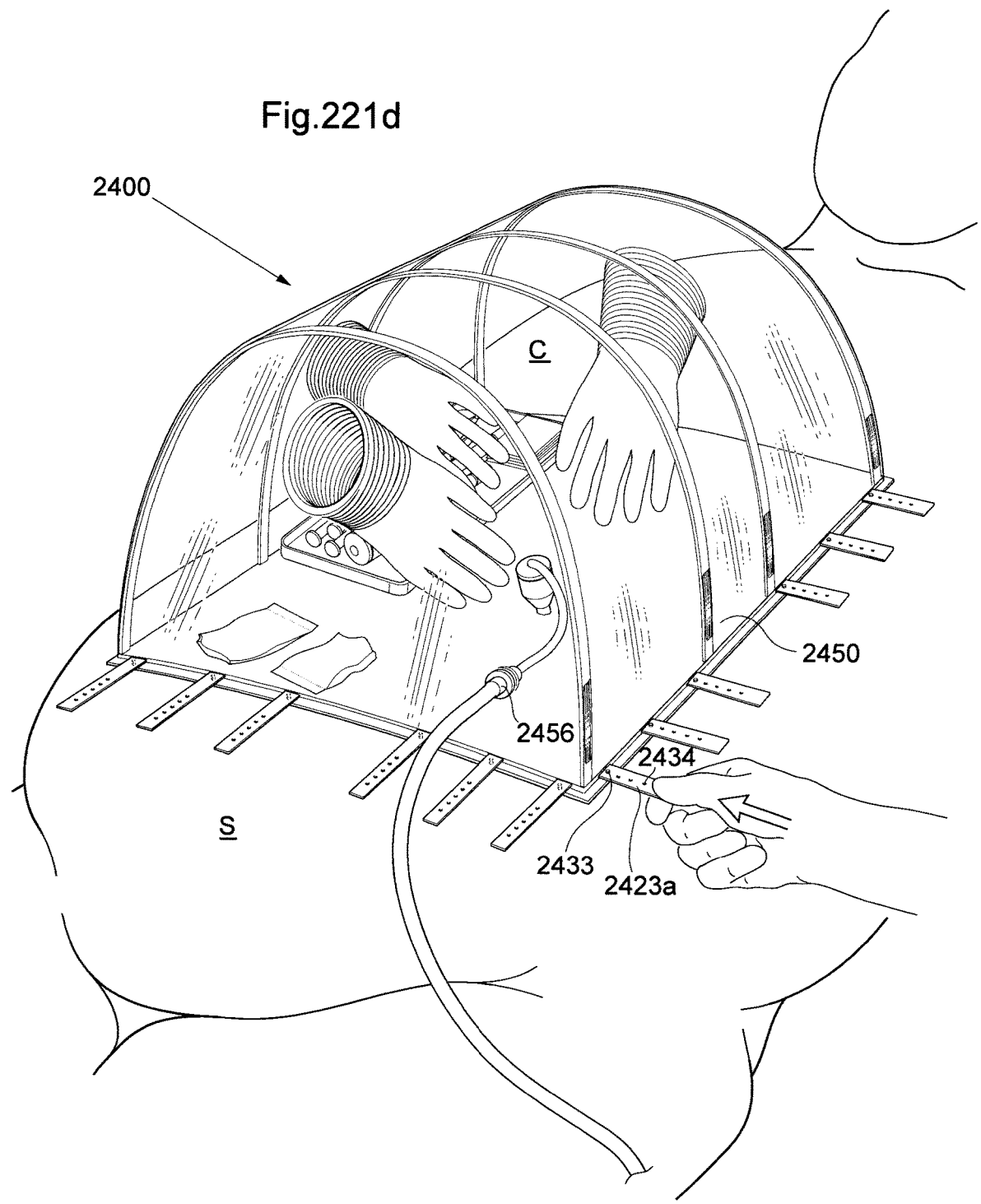

FIG. 221d shows the step of tightening the elastic elements in the guide slots and thereby raising the central portion of the wall 2401 of the medical device such that the cavity in the body of the patient created by the inflation of the abdomen is maintained even if no pressure difference between the cavity in the patient and the chamber C exists. The elastic elements 2423a are fixated in the guide slots by means of protruding members 2433 engaging holes or recesses 2434 in the elastic elements 2423a.

By using the medical device according to the embodiment disclosed in FIGS. 221a-221d, the abdominal wall is connected to the wall of the medical device by the adhesive surface 2450 of the wall of the medical device adhering to the skin S of the patient which enables laparoscopic surgery to be performed with visibility in the expanded cavity in the body of the patient whilst keeping the pressure in both the cavity in the patient's body and in the chamber C at normal atmospheric pressure.

Figure 221E:
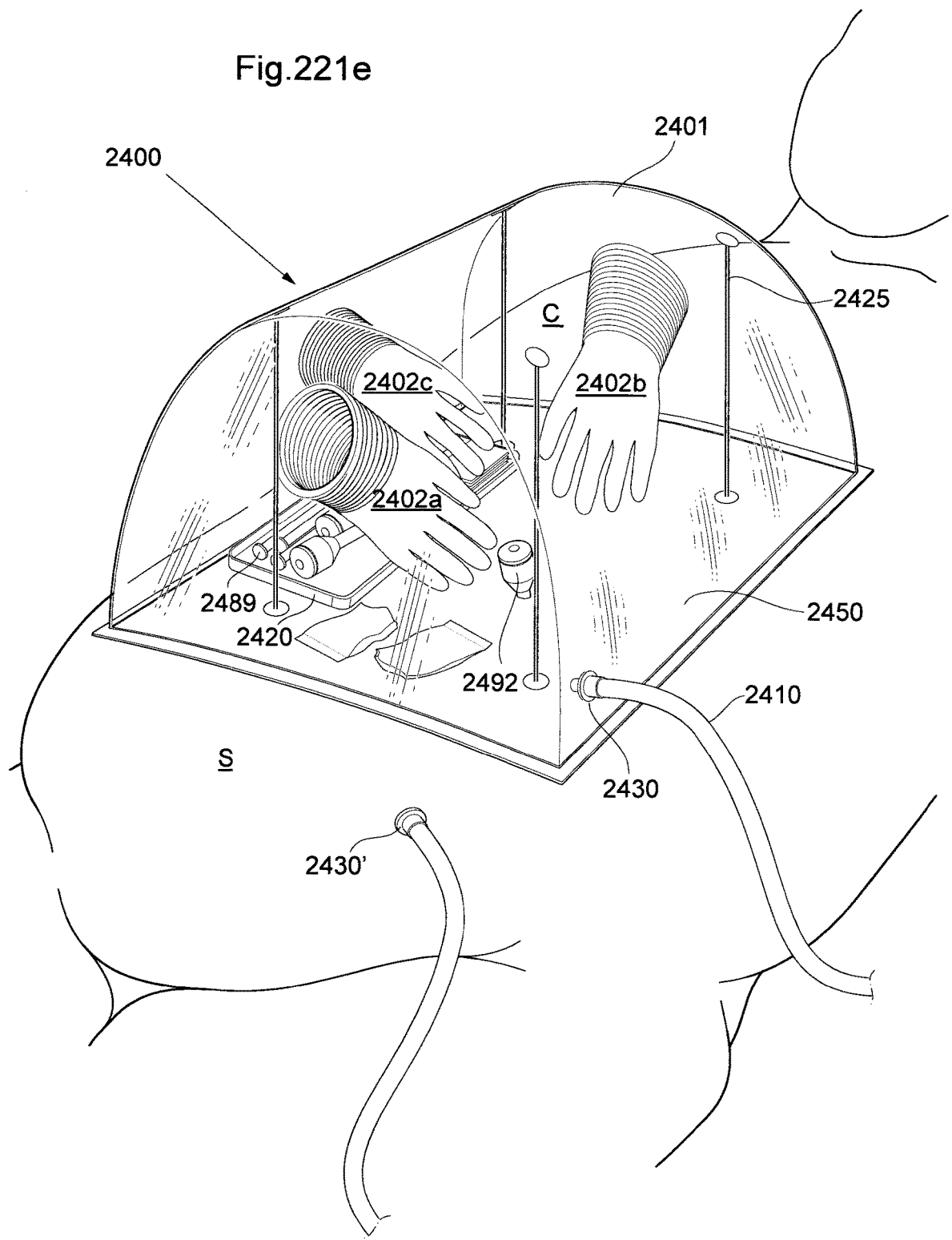
FIG. 221*e* shows an alternative embodiment of a medical device being adapted to hold a chamber without being inflated.

FIG. 221e shows an alternative embodiment of the medical device 2400 similar to the embodiments disclosed under reference to FIGS. 221a-221d. In the embodiment shown in FIG. 221e the medical device further comprises lifting members 2425 connected to the bottom portion of the wall 2401 of the medical device 2400 and to the roof portion of the wall 2401 of the medical device 2400, such the inflation of the wall 2401 of the medical device 2400 lifts the central portion of the medical device in comparison to the rigid frame of the medical device rigidly fixated to the skin of the patient by means of the adhesive surface 2450 adhering to the skin S of the patient. The cavity in the body of the patient is according to the embodiment shown in FIG. 221e expanded by inflating the abdomen of the patient through a fluid inlet 2430' positioned in the skin S of the patient, and the chamber C of the medical device is inflated through an inlet 2430 positioned in the wall 2401 of the medical device 2400. By the lifting members 2425 lifting and holding the skin of the patient in its expanded position, the cavity in the patient is maintained even if the pressure difference between the cavity in the patient and the chamber and/or the ambient environment disappears.

Figure 222:
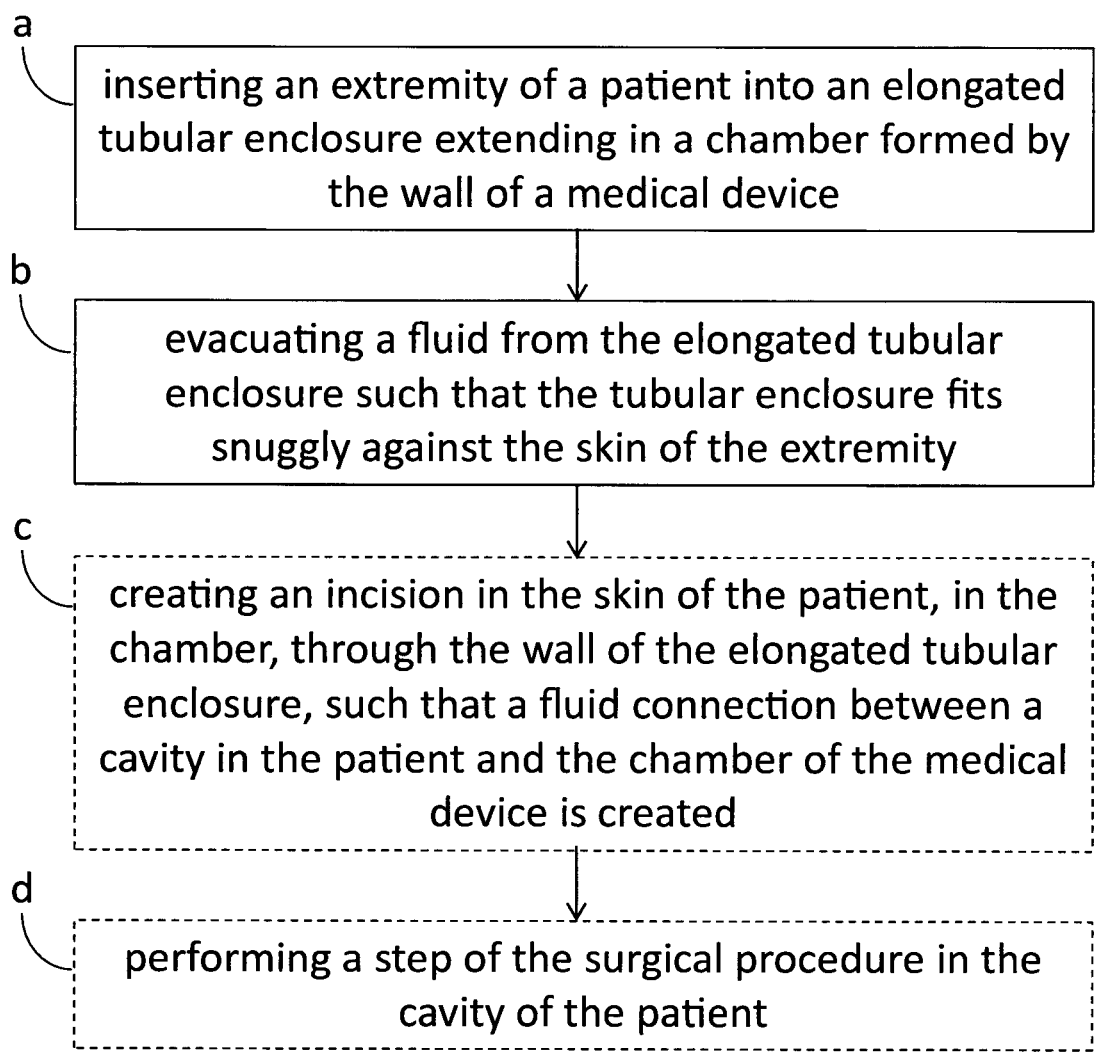

FIG. 222 is a flow chart describing a method of forming a sterile environment using a medical device. The medical device comprises a wall adapted to form a chamber in which a sealed environment can be maintained, wherein a portion of the wall directly or indirectly forms an elongated tubular enclosure extending in the chamber, having a single open end. The method comprises fitting the medical device on an extremity of a patient, such that the extremity of the patient is placed inside the elongated tubular enclosure a. The method further comprises evacuating a fluid from the elongated tubular enclosure such that the tubular enclosure fits snuggly against the skin of the extremity b. The method may further comprise the step of creating an incision in the skin of the patient, in the chamber, through the wall of the elongated tubular enclosure, such that a fluid connection between a cavity in the patient and the chamber of the medical device is created c, and the step of performing a step of the surgical procedure in the cavity of the patient.

The method may further comprise the step of inflating the wall of the medical device such that an inflated chamber is formed and/or inflating the elongated tubular enclosure prior to fitting the medical device on the extremity of the patient.

The medical device may further comprises a separating layer covering an adhesive surface of a first portion of the elongated tubular enclosure, and the method may further comprise removing the separating layer from the elongated tubular enclosure prior to fitting the medical device on the extremity of the patient.

Figure 223:
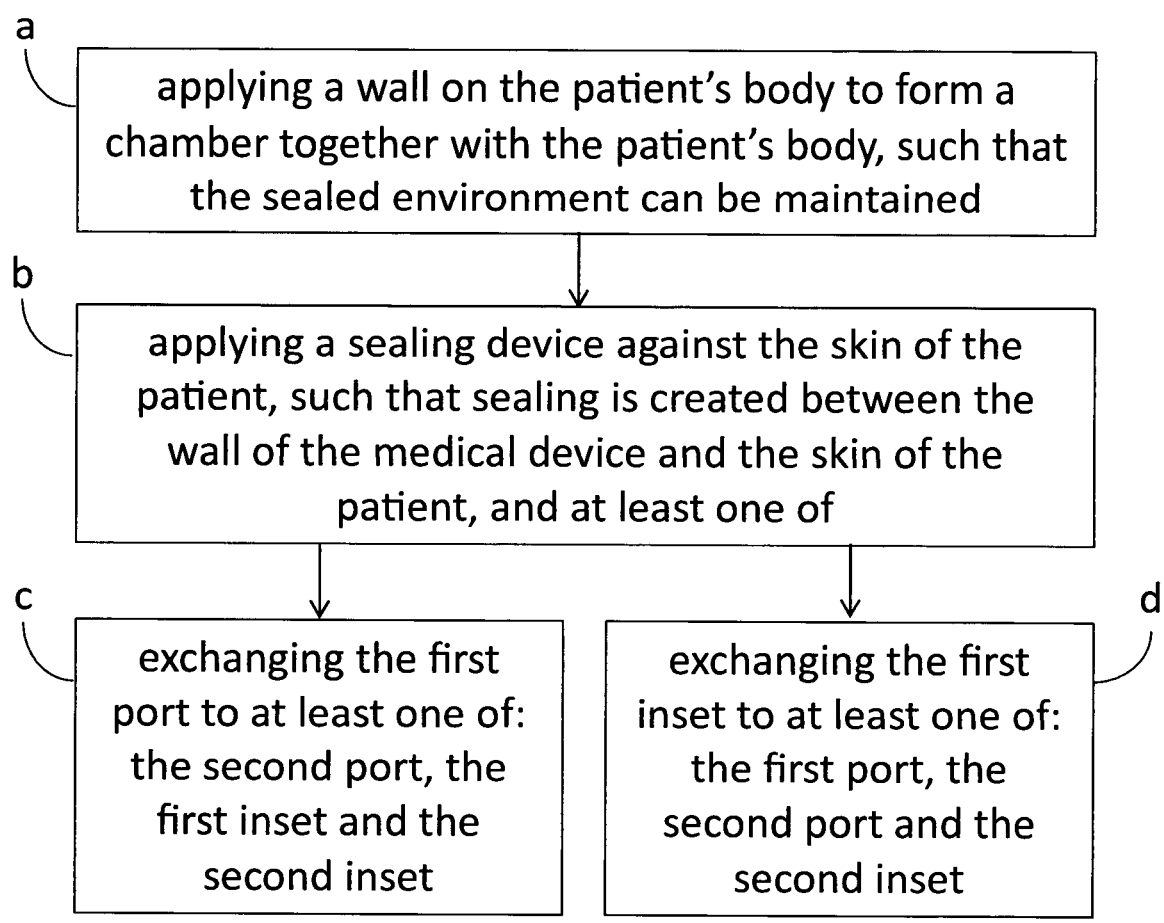

FIG. 223 is a flow chart describing a method of performing a surgical procedure on a patient using a medical device comprising a wall adapted to be applied exteriorly on the patient's body to form a chamber, in which a sealed environment can be maintained for encompassing part of the surgical procedure to be performed. The medical device further comprises a sealing device adapted to seal between the medical device and the patient's body, to allow the chamber to be in fluid connection with a cavity in the patient's body, sealed from the ambient environment. The medical device further comprises at least one first port detachably fixed to the wall for enabling access to and manipulation within the chamber, and at least one first inset detachably fixed to the wall and forming part of the chamber, and at least one of at least one second port adapted to be detachably fixed to the wall, the second port having a design different from the first port, and at least one second inset adapted to be detachably fixed to the wall, the second inset having a design different from the first inset. The method comprising the steps of applying a wall on the patient's body to form a chamber together with the patient's body, such that the sealed environment can be maintained a, applying a sealing device against the skin of the patient, such that sealing is created between the wall of the medical device and the skin of the patient b, and at least one of: exchanging the first port to at least one of: the second port, the first inset and the second inset c, and exchanging the first inset to at least one of: the first port, the second port and the second inset d.

Figure 224:
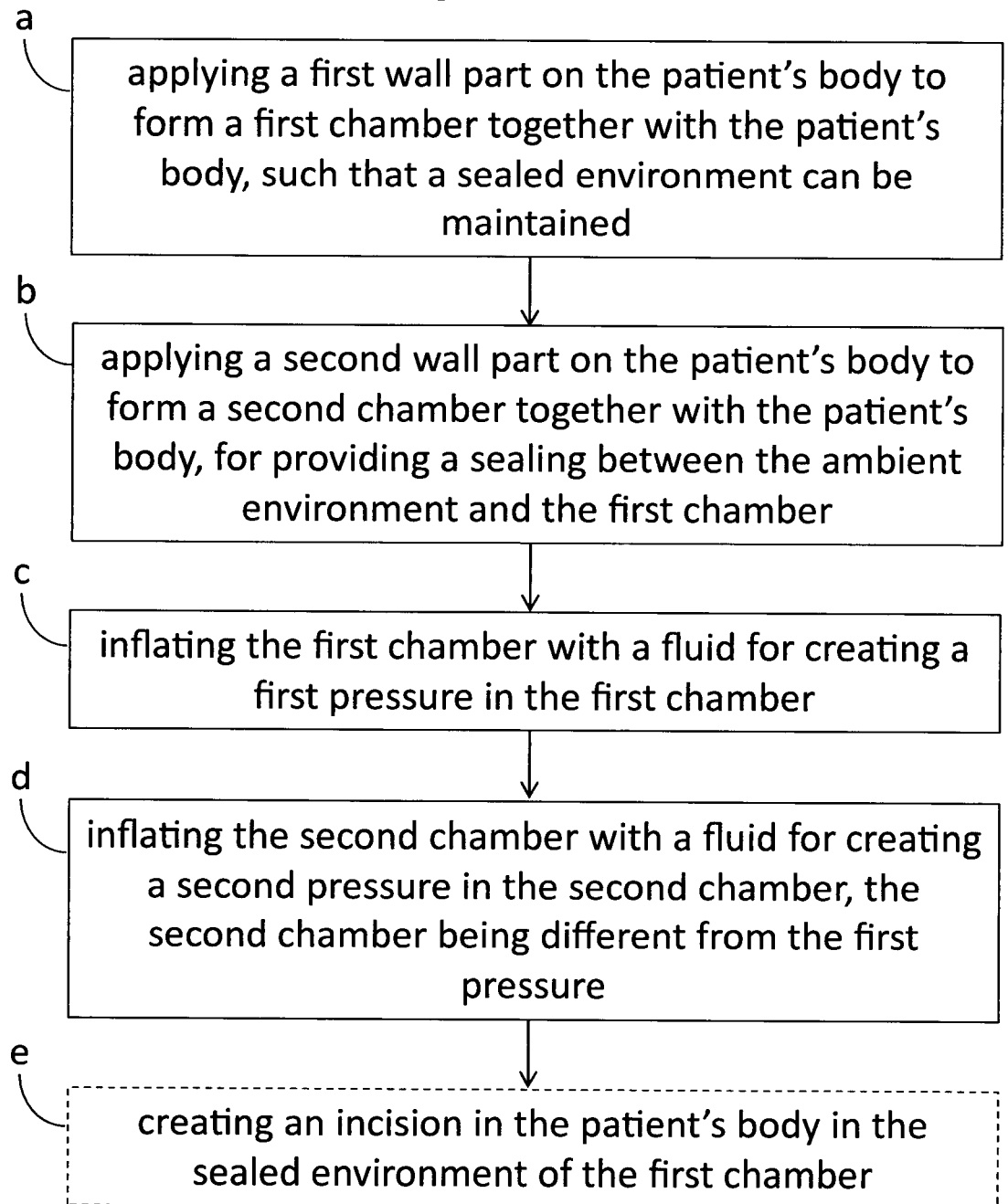

FIG. 224 is a flow chart describing a method of performing a surgical procedure in a sealed environment. The method comprises applying a first wall part on the patient's body to form a first chamber together with the patient's body, such that a sealed environment can be maintained a, applying a second wall part on the patient's body to form a second chamber together with the patient's body, for providing a sealing between the ambient environment and the first chamber b, inflating the first chamber with a fluid for creating a first pressure in the first chamber c, inflating the second chamber with a fluid for creating a second pressure in the second chamber, the second chamber being different from the first pressure d, and the method may further comprise the step of creating an incision in the patient's body in the sealed environment of the first chamber e.

Figure 225:
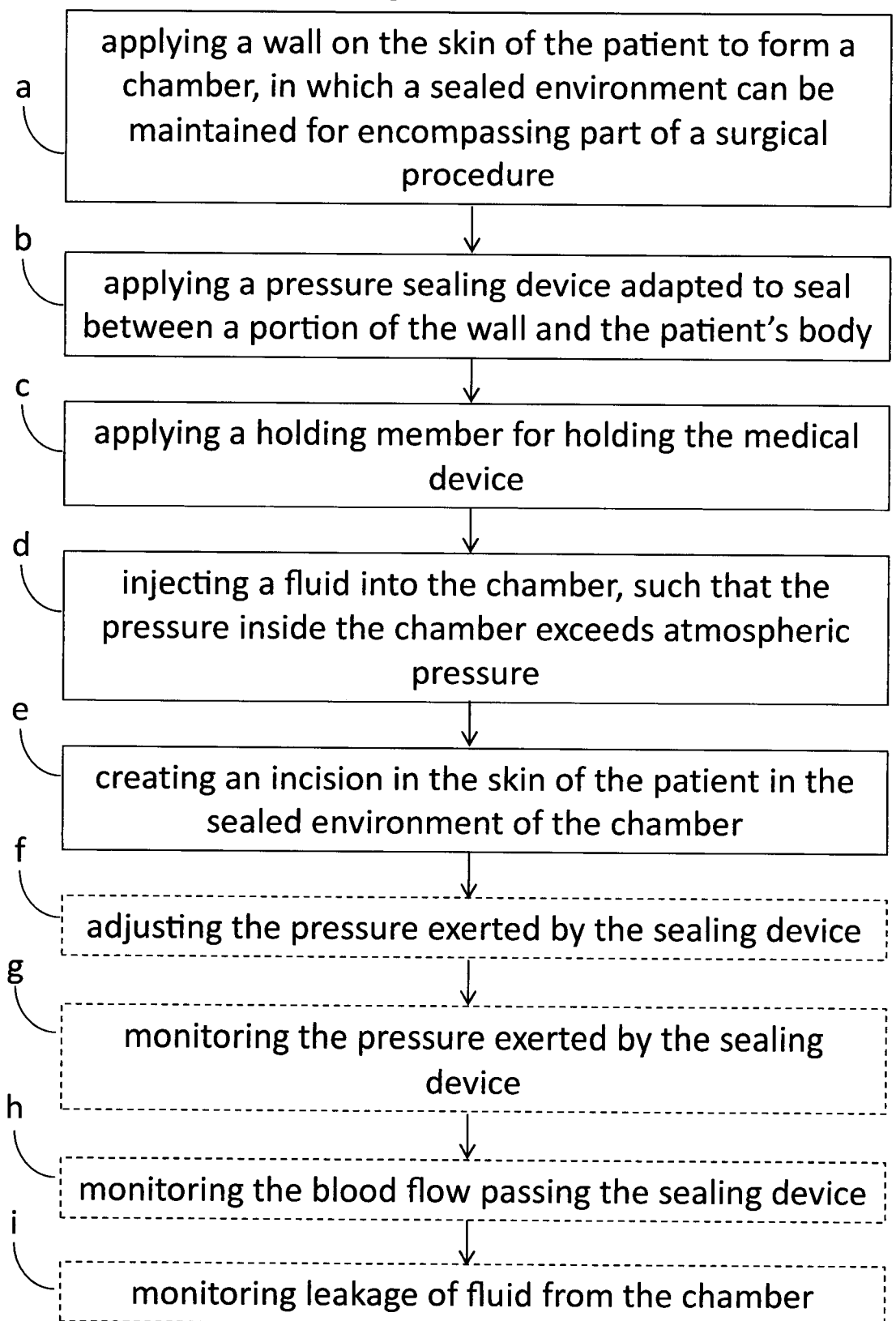

FIG. 225 is a flow chart describing a method of performing a surgical procedure on a patient using a medical device. The method comprises the steps of applying a wall of the medical device on the skin of the patient to form a chamber, in which a sealed environment can be maintained for encompassing part of the surgical procedure to be performed a, applying a pressure sealing device of the medical device adapted to seal between a portion of the wall and the patient's body b, applying a holding member of the medical device adapted to hold the medical device in a direction substantially opposite to the direction of the pressure applied from the sealing device onto the skin of the patient c, injecting a fluid into the chamber, such that the pressure inside the chamber exceeds atmospheric pressure d, creating an incision in the skin of the patient in the sealed environment of the chamber e. The method may optionally comprise at last one of the steps: adjusting the pressure exerted by the sealing device f, monitoring at least one of the pressure exerted by the sealing device g, monitoring the blood flow passing the sealing device h, monitoring the direct or indirect leakage of fluid from the chamber i.

Figure 226:
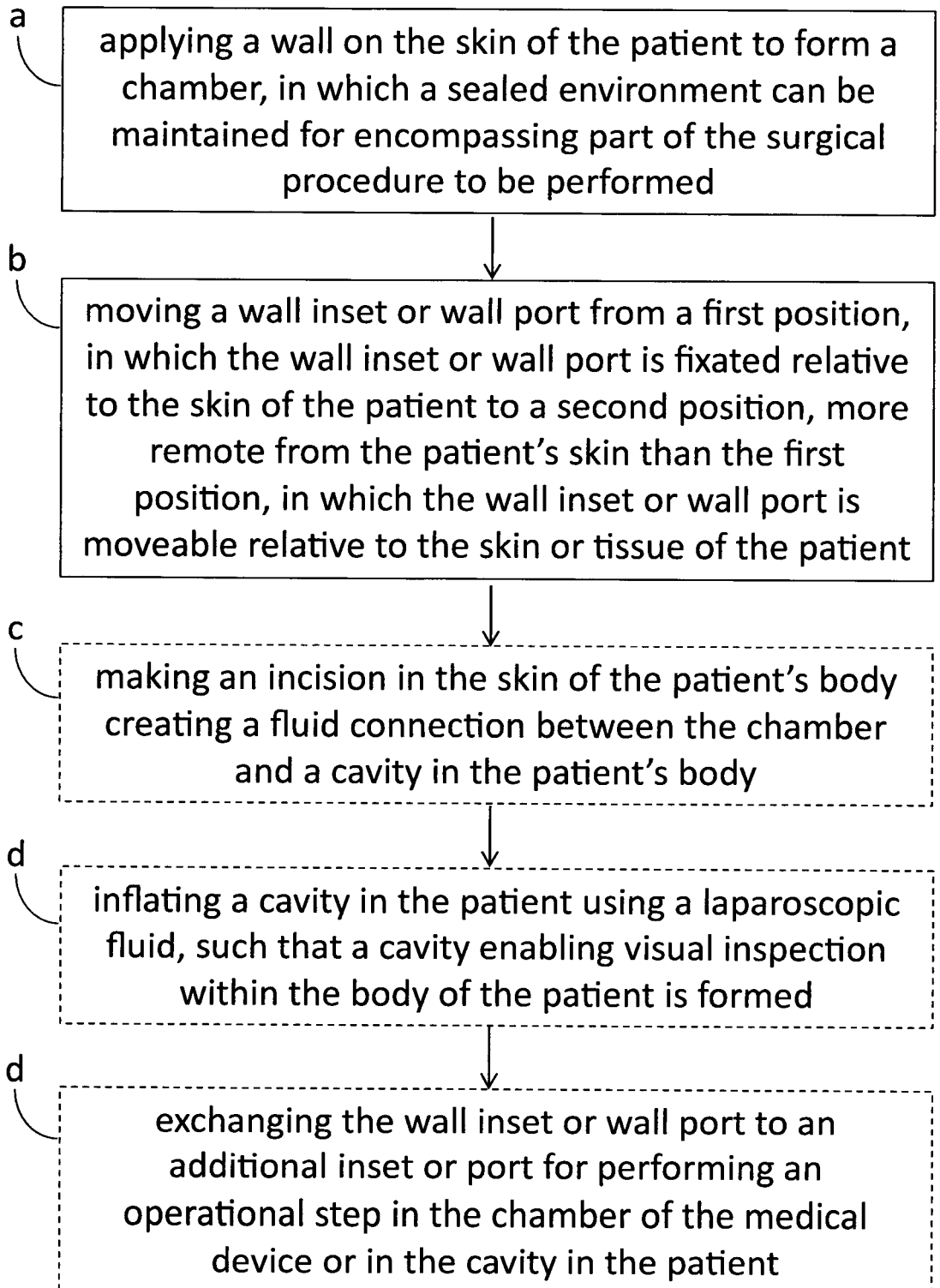

FIG. 226 is a flow chart describing a surgical method of performing a laparoscopic procedure in a sealed environment. The surgical method comprises: placing a medical device comprising a wall in connection with the patient, such that a portion of the wall of the medical device sealingly connects to the skin of the patient, such that a chamber is formed by the wall of the medical device and the skin of the patient a. The wall further comprises an wall inset or wall port. The method further comprises moving a wall inset or wall port from a first position, in which the wall inset or wall port is fixated relative to the skin of the patient to a second position, more remote from the patient's skin than the first position, in which the wall inset or wall port is moveable relative to the skin or tissue of the patient b. The surgical method may optionally comprise the step of making an incision in the skin of the patient's body creating a fluid connection between the chamber and a cavity in the patient's body c. The surgical method may optionally comprise the step of placing a portion of the wall inset or wall port in the incision made in the skin of the patient The surgical method may optionally comprise sealing the wall portion to the skin of the patient by applying a negative pressure to a sealing device.

The surgical method may optionally comprise inflating a cavity in the patient using a laparoscopic fluid, such that a cavity enabling visual inspection within the body of the patient is formed d.

The surgical method may optionally comprise exchanging the wall inset or wall port to an additional inset or port for performing an operational step in the chamber of the medical device or in the cavity in the patient d.

Figure 227:
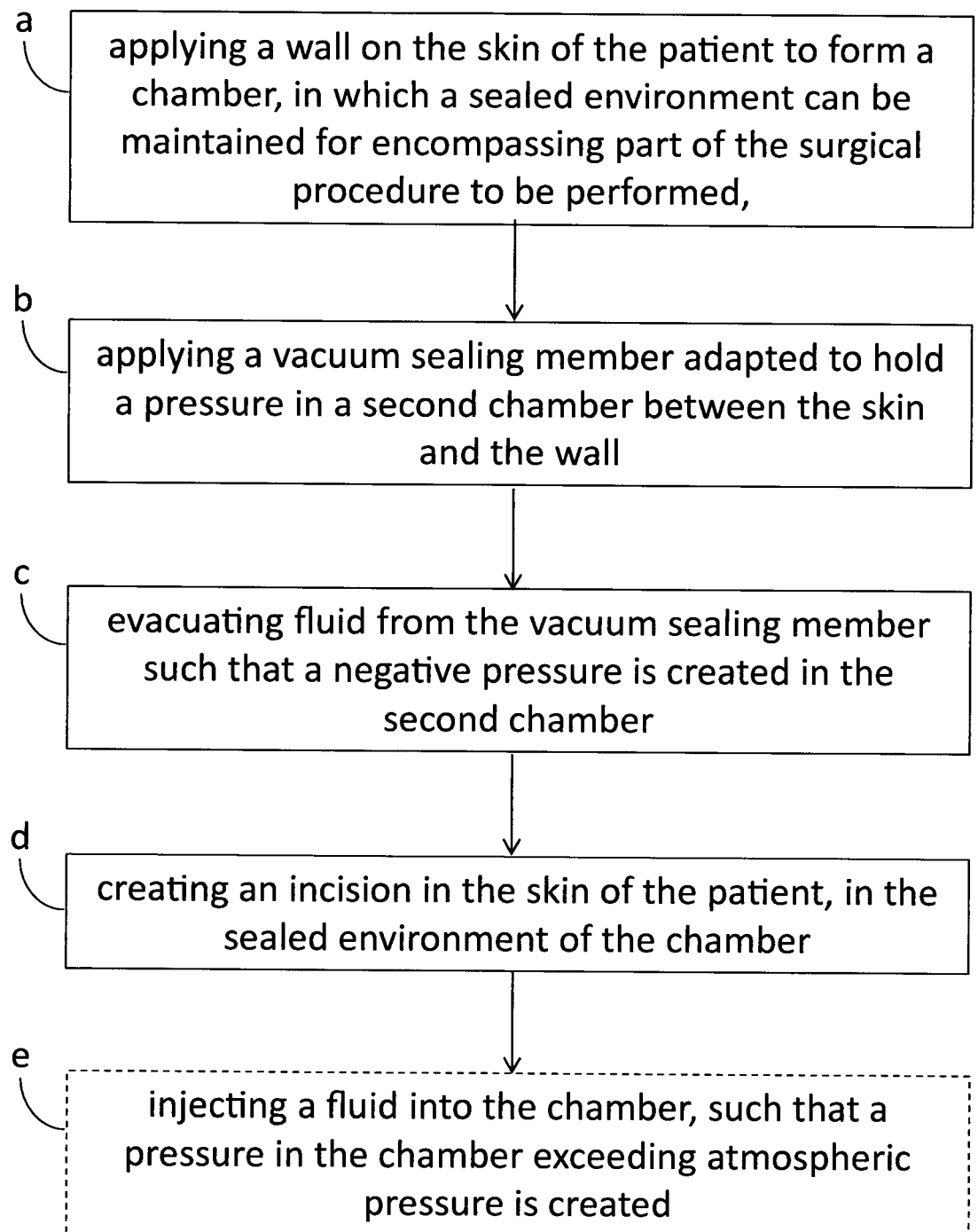

FIG. 227 is a flow chart describing a method embodiment of performing a surgical procedure on a patient using a medical device. The method comprises applying a wall on the skin of the patient to form a chamber, in which a sealed environment can be maintained for encompassing part of the surgical procedure to be performed a, applying a vacuum sealing member adapted to hold a pressure in a second chamber between the skin and the wall b, evacuating fluid from the vacuum sealing member such that a negative pressure is created in the second chamber between the skin and the wall, the pressure being different than the pressure in the chamber, and less than atmospheric pressure, such that a vacuum seal is provided c, creating an incision (I) in the skin of the patient, in the sealed environment of the chamber d. The method may optionally comprise the step of injecting a fluid into the chamber, such that a pressure in the chamber exceeding atmospheric pressure is created e.

Figure 228:
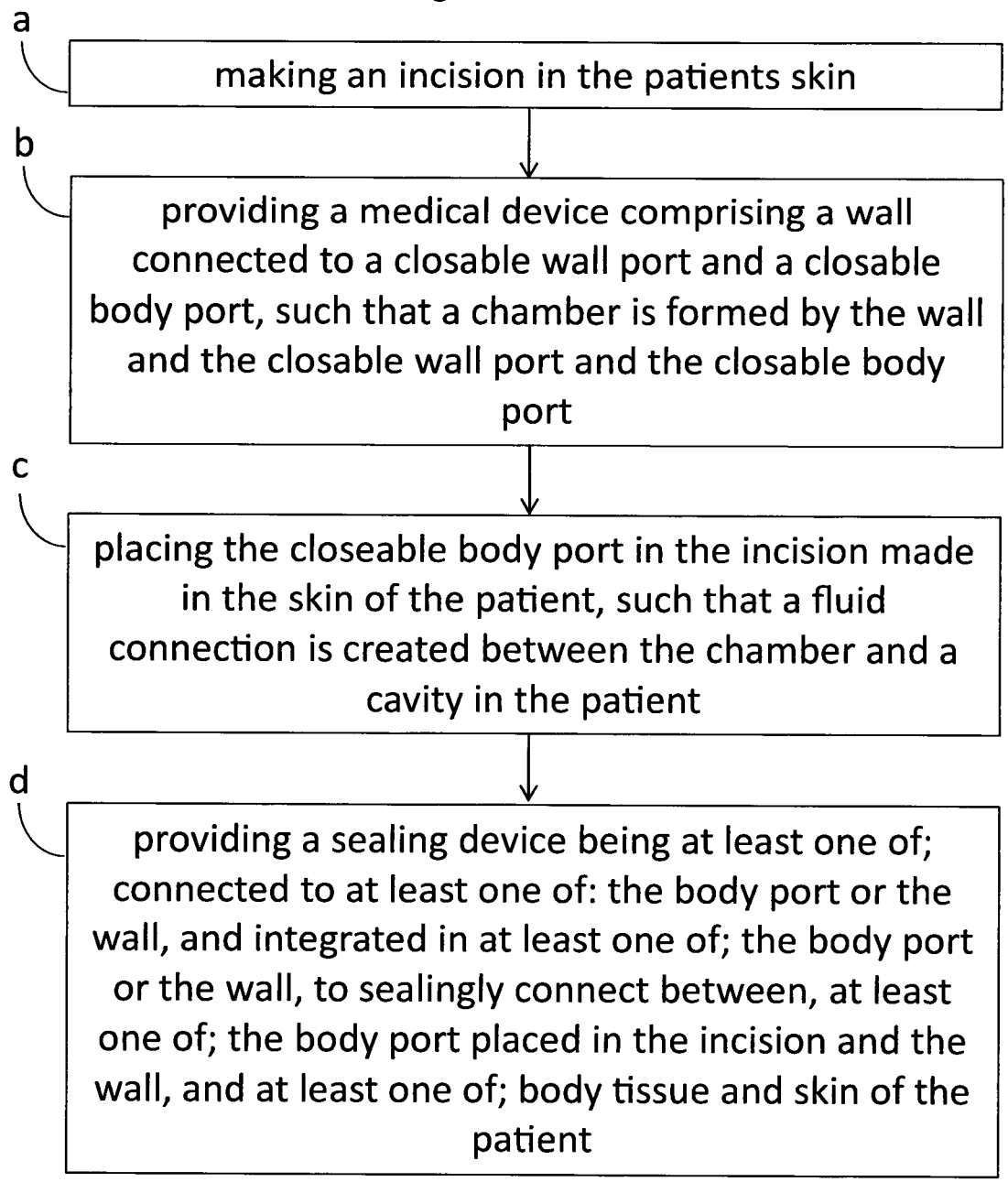

FIG. 228 is a flow chart describing a method of performing a laparoscopic procedure in a sealed environment. The surgical method comprises: making an incision in the patients skin a, providing a medical device comprising a wall connected both to a closable wall port and a closable body port, such that a chamber is formed by the wall and the closable wall port and the closable body port b, placing the closeable body port in the incision made in the skin of the patient, such that a fluid connection is created between the chamber and a cavity in the patient c, providing a sealing device being at least one of;

connected to at least one of: the body port or the wall, and integrated in at least one of; the body port or the wall, to sealingly connect between, at least one of the body port placed in the incision and the wall, and at least one of; body tissue and skin of the patient d.

Figure 229:
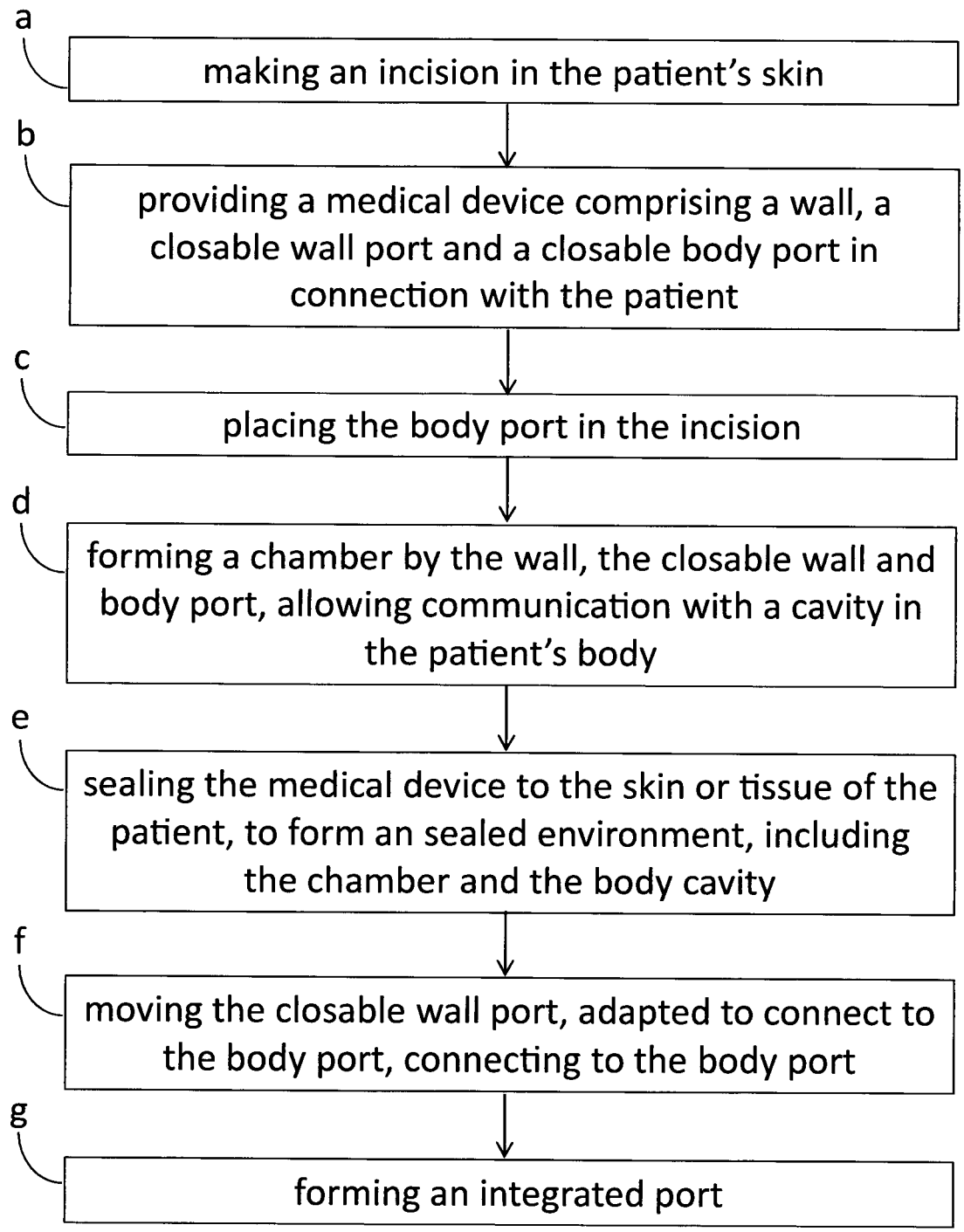

FIG. 229 is a flow chart describing a surgical method of performing a laparoscopic procedure in a sealed environment. The surgical method comprises: making an incision in the patients skin a, providing a medical device comprising a wall, a closable wall port and a closable body port in connection with the patient b, placing the body port in the incision c, forming a chamber by the wall, the closable wall and body port, allowing communication with a cavity in the patient's body d, sealing the medical device to the skin or tissue of the patient, to form an sealed environment, including the chamber and the body cavity e, moving the closable wall port, adapted to connect to the body port, connecting to the body port f, and forming an integrated port g.

The surgical method may optionally comprise the step of inflating the cavity in the patient using a laparoscopic fluid, such that a cavity enabling visual inspection within the body of the patient is formed.

The surgical method may optionally comprise the step of exchanging the closeable body port to an additional port or inset for performing an operational step in the cavity in the body of the patient.

The surgical method may optionally comprise the step of exchanging the closeable wall port to an additional port or inset for performing an operational step in the chamber of the medical device.

In another surgical method, and object is transferred through a closable wall port of the medical device, placed in the wall of the medical device, into a chamber formed by the wall of the medical device and the closable wall and body port. The method further comprising transferring the object through the closable body port placed in the incision made in the patient's skin and into the cavity in the patient.

In another surgical method, an airlock sluice between the ambient environment and a cavity in a patient is formed. The method comprising: providing a medical device comprising a wall connected to both a wall port and a body port, making an incision in the patients skin connected to a body cavity, placing the body port in the incision, forming a chamber with the wall of the medical device, the closable body port, and the closable wall port, allowing communication with the cavity, and thus forming a an airlock sluice.

Figure 230:
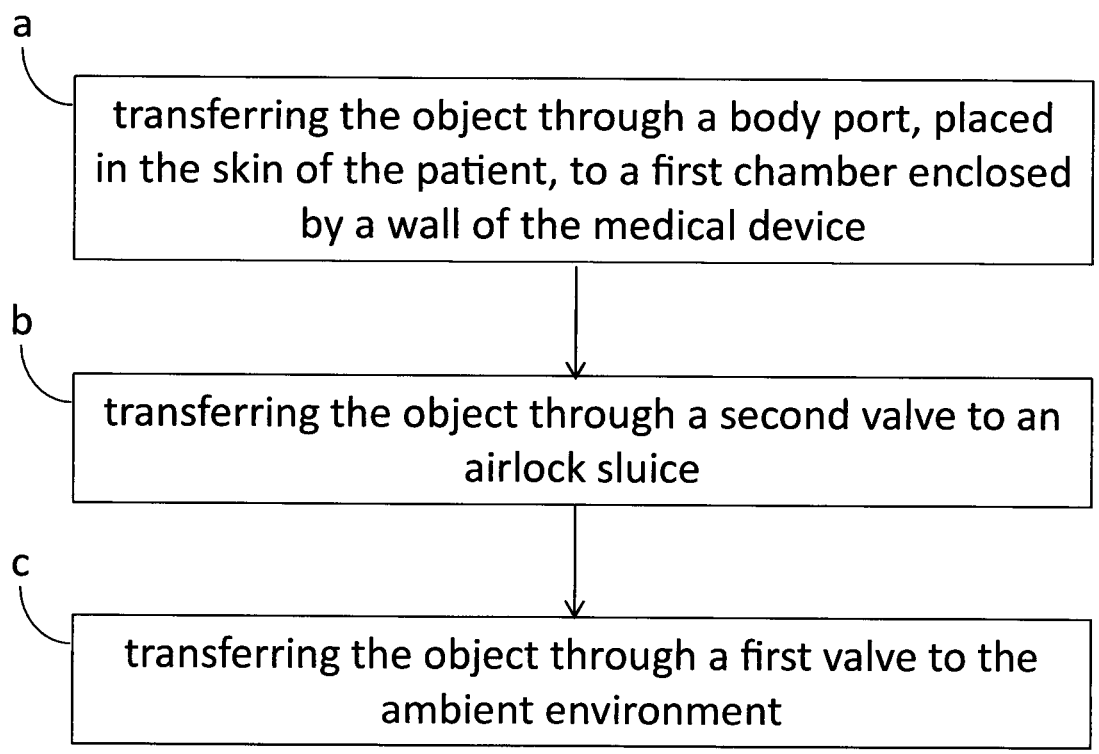

FIG. 230 is a flow chart describing a method of transferring an object from the ambient environment to a cavity in a patient, and vice versa, during a surgical procedure, using a medical device. The method comprises: transferring the object through a body port, placed in the skin of the patient, to a first chamber enclosed by a wall of the medical device a, transferring the object through a second valve to an airlock sluice b, and transferring the object through a first valve to the ambient environment c, such that the risk of contamination is reduced.

Figure 231:
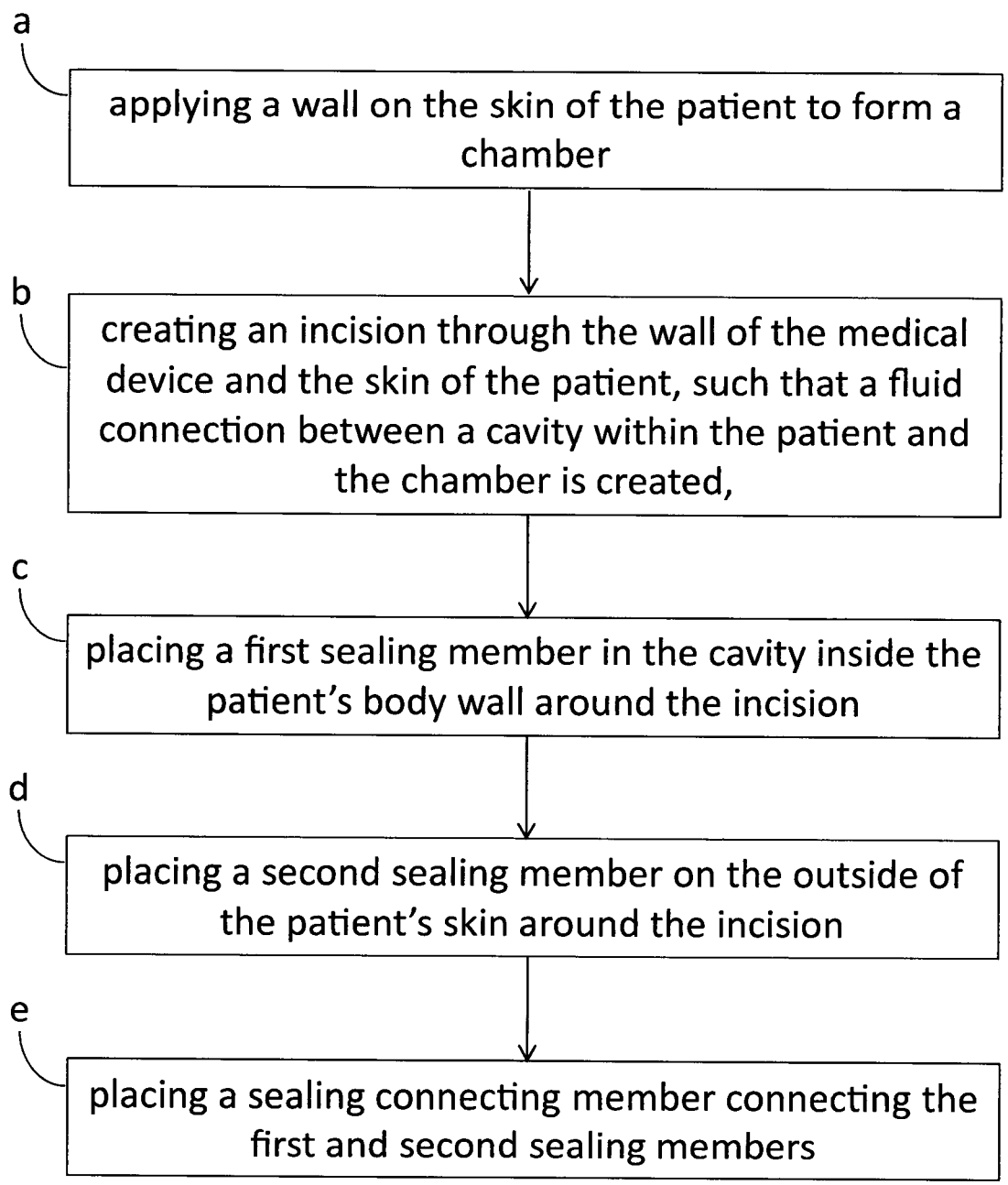

FIG. 231 is a flow chart describing a method of performing a surgical procedure on a patient using a medical device. The method comprises applying a wall on the skin of the patient to form a chamber a, in which a sealed environment can be maintained for encompassing part of the surgical procedure to be performed, creating an incision through the wall of the medical device and the skin of the patient, such that a fluid connection between a cavity within the patient and the chamber is created b, placing a first sealing member in the cavity inside the patient's body wall around the incision c, placing a second sealing member on the outside of the patient's skin around the incision d, and placing a sealing connecting member connecting the first and second sealing members e. The method enables the second sealing member to seal directly or indirectly against the skin of the patient, or the first sealing member sealing directly or indirectly against the tissue of the patient.

Figure 232:
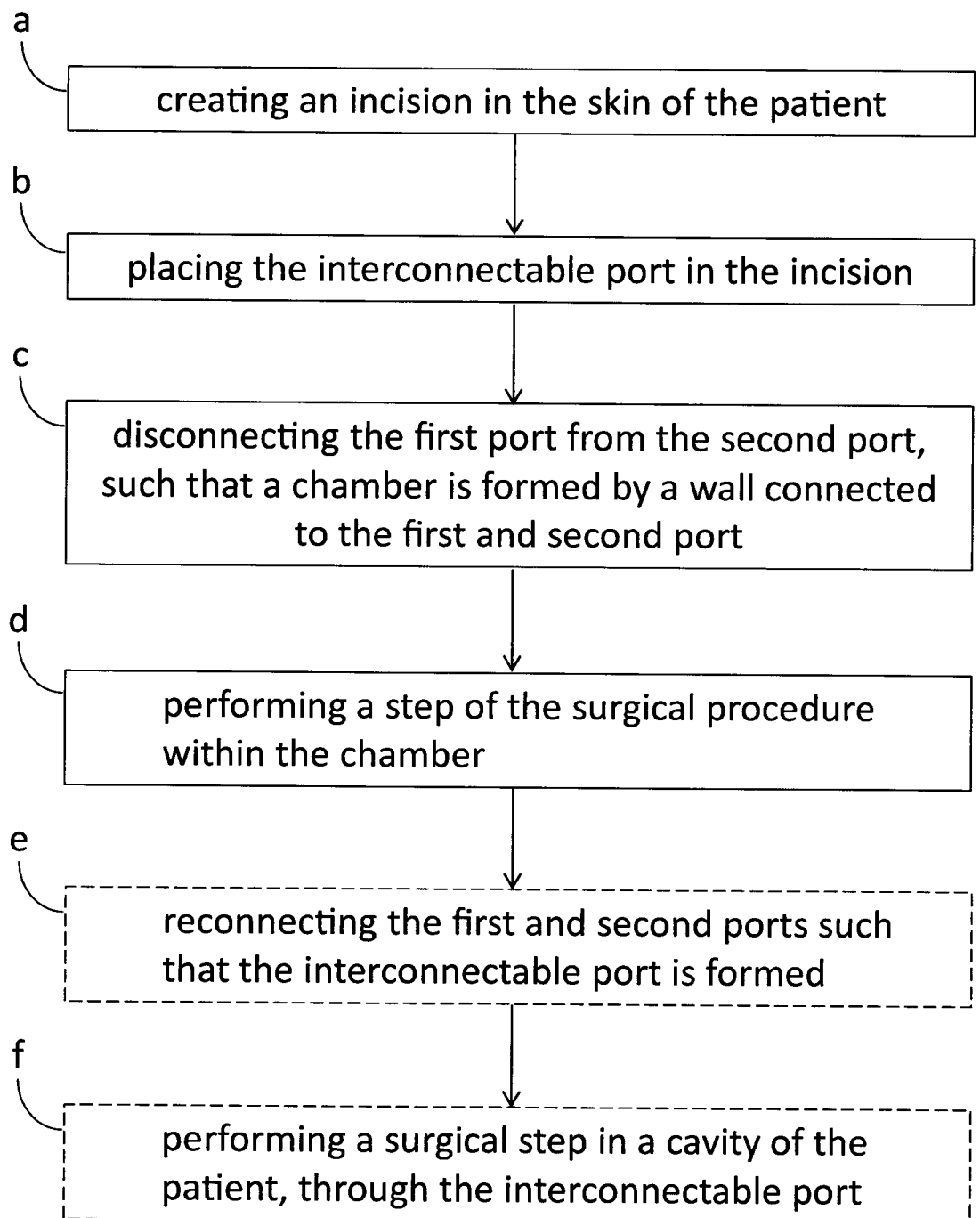

FIG. 232 is a flow chart describing a surgical method to be performed on the body of a patient using an interconnectable port. The interconnectable port comprising a first and second port. The method comprising: creating an incision in the skin of the patient a, placing the interconnectable port in the incision b, disconnecting the first port from the second port, such that a chamber is formed by a wall connected to the first and second port c, and performing a step of the surgical procedure within the chamber d.

The step of performing a step of the surgical procedure within the chamber may comprise: removing a specimen from the cavity in the body of the patient, transferring the specimen through the second port, and placing the specimen within the chamber of the medical device.

The surgical method may optionally comprise the steps of reconnecting the first and second ports such that the interconnectable port is formed, and performing a surgical step in a cavity of the patient, through the interconnectable port.

Figure 233:
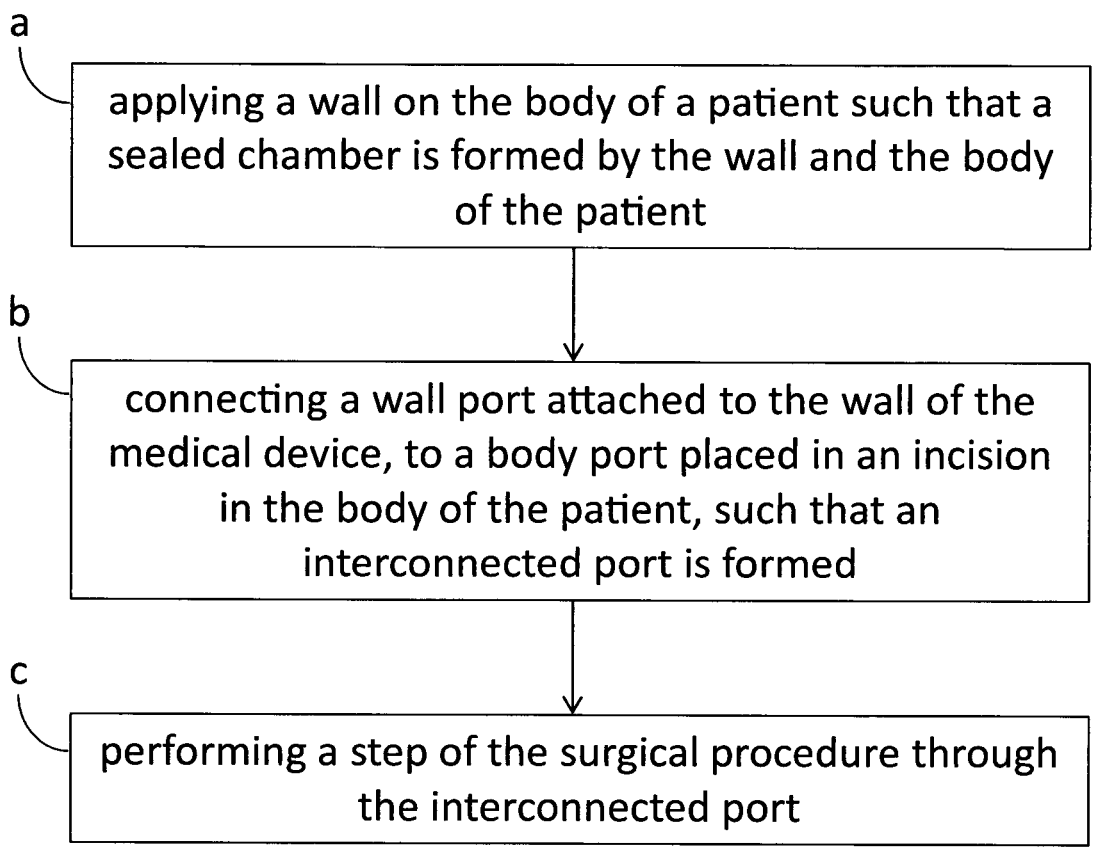

FIG. 233 is a flow chart describing a method of performing a surgical procedure on a patient using a medical device. The method comprising: applying a wall on the body of a patient such that a sealed chamber is formed by the wall and the body of the patient a, and connecting a wall port attached to the wall of the medical device, to a body port placed in an incision in the body of the patient, such that an interconnected port is formed b, and performing a step of the surgical procedure through the interconnected port c.

Figure 234:
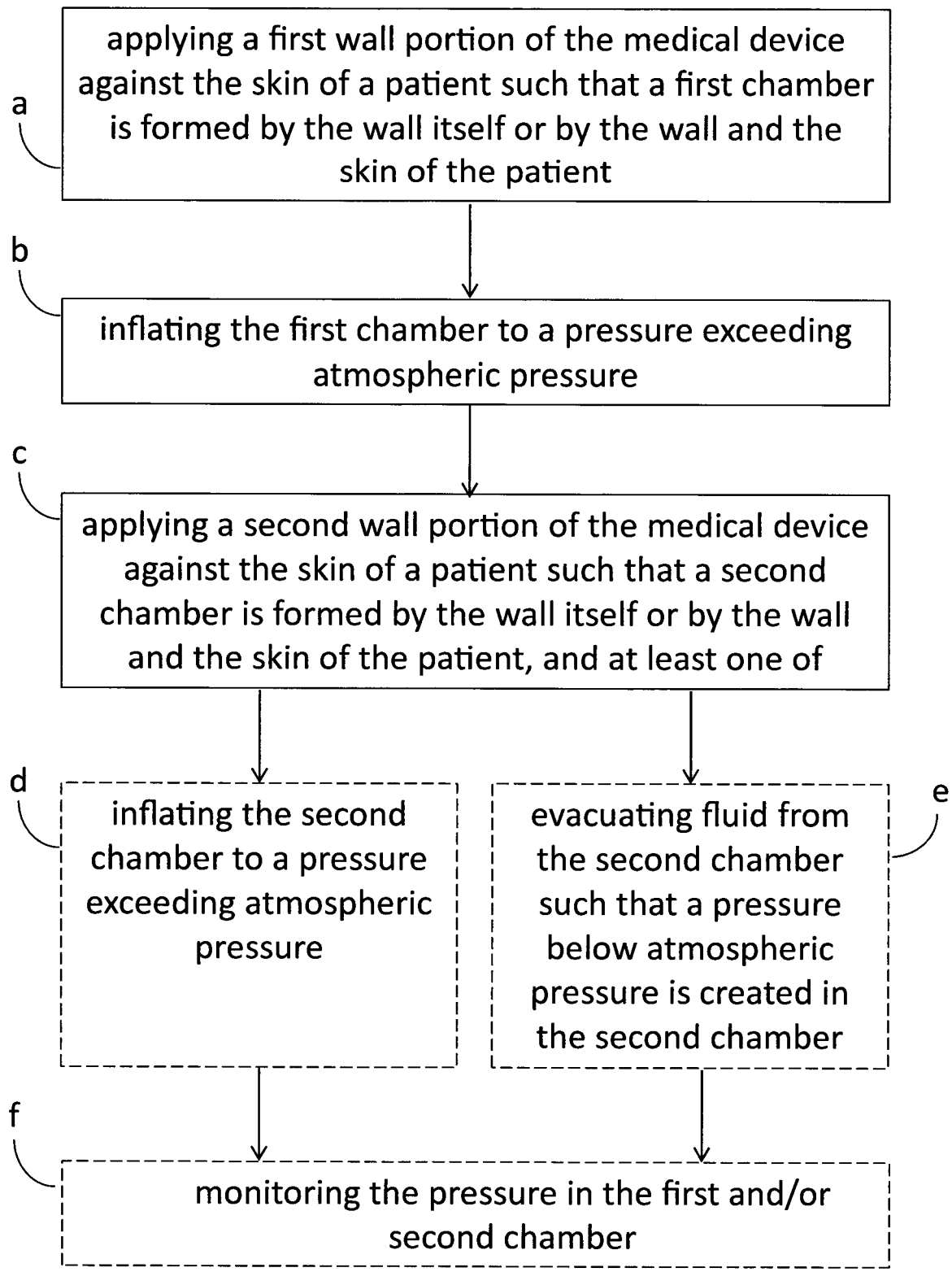

FIG. 234 is a flow chart describing a method of creating a chamber in a medical device and sealing between the medical device and the skin of a patient. The method comprising, applying a first wall portion of the medical device against the skin of a patient such that a first chamber is formed by the wall itself or by the wall and the skin of the patient a, inflating the first chamber to a pressure exceeding atmospheric pressure b, applying a second wall portion of the medical device against the skin of a patient such that a second chamber is formed by the wall itself or by the wall and the skin of the patient c.

The method may further comprise inflating the second chamber to a pressure exceeding atmospheric pressure d, such that the second wall portion is pressed against the skin of the patient and thereby provides sealing, wherein the pressure in the second chamber is different from the pressure in the first chamber, and The method may further comprise evacuating fluid from the second chamber such that a pressure below atmospheric pressure is created in the second chamber e, such that a vacuum sealing is created between the second wall portion and the skin of the patient.

The step of inflating the first chamber may comprise inflating the first chamber to a pressure between 5 mmHg and 120 mmHg.

The step of evacuating fluid from the second chamber may comprise evacuating fluid such that a negative pressure between 5 mmHg and 120 mmHg is created in the second chamber.

The step of inflating the first chamber may comprise inflating the first chamber to a pressure between 5 mmHg and 120 mmHg, and the step of inflating the second chamber may comprise inflating the second chamber to a pressure between 5 mmHg and 120 mmHg.

The method may optionally comprise the step of monitoring the pressure in as least one of the first chamber and the second chamber f.

The method may optionally comprise the step of monitoring a physiological parameter of the patient, and inflate or evacuate at least one of the first and second chambers on the basis of the monitored physiological parameter.

The method may optionally comprise the step of monitoring the blood pressure or blood flow of the patient, and inflate or evacuate fluid from at least one of the first and second chambers on the basis of the monitored blood pressure or blood flow.

The method may optionally comprise the step of creating an incision in the skin of the patient inside of the first chamber, such that a fluid connection is created between the first chamber and a cavity in the body of the patient.

Figure 235:
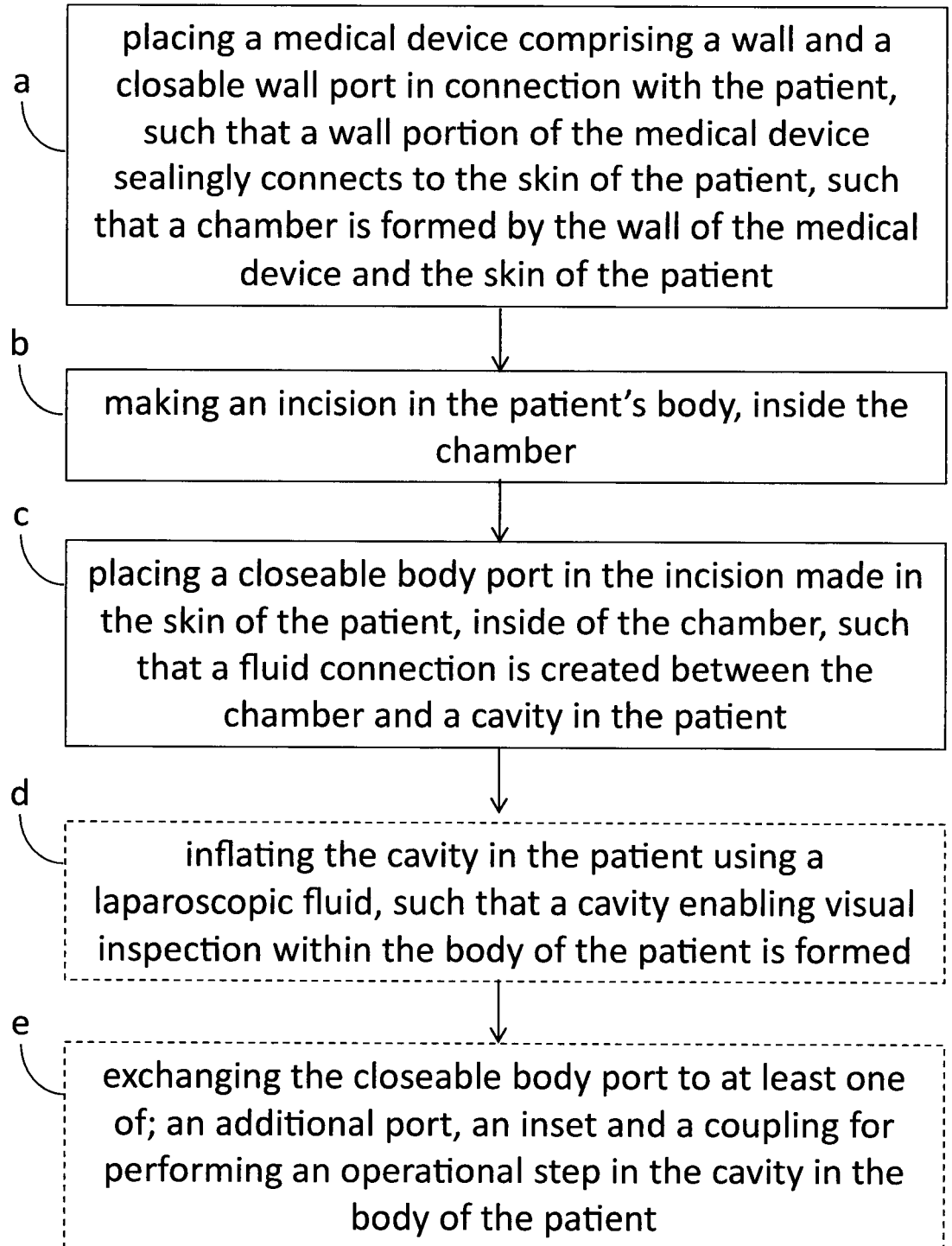

FIG. 235 is a flow chart describing a surgical method for performing a laparoscopic procedure in a sealed environment. The surgical method comprising: placing a medical device comprising a wall and a closable wall port in connection with the patient, such that a wall portion of the medical device sealingly connects to the skin of the patient, such that a chamber is formed by the wall of the medical device and the skin of the patient a, making an incision in the patient's body, inside the chamber b, and placing a closeable body port in the incision made in the skin of the patient, inside of the chamber, such that a fluid connection is created between the chamber and a cavity in the patient c.

Figure 236:
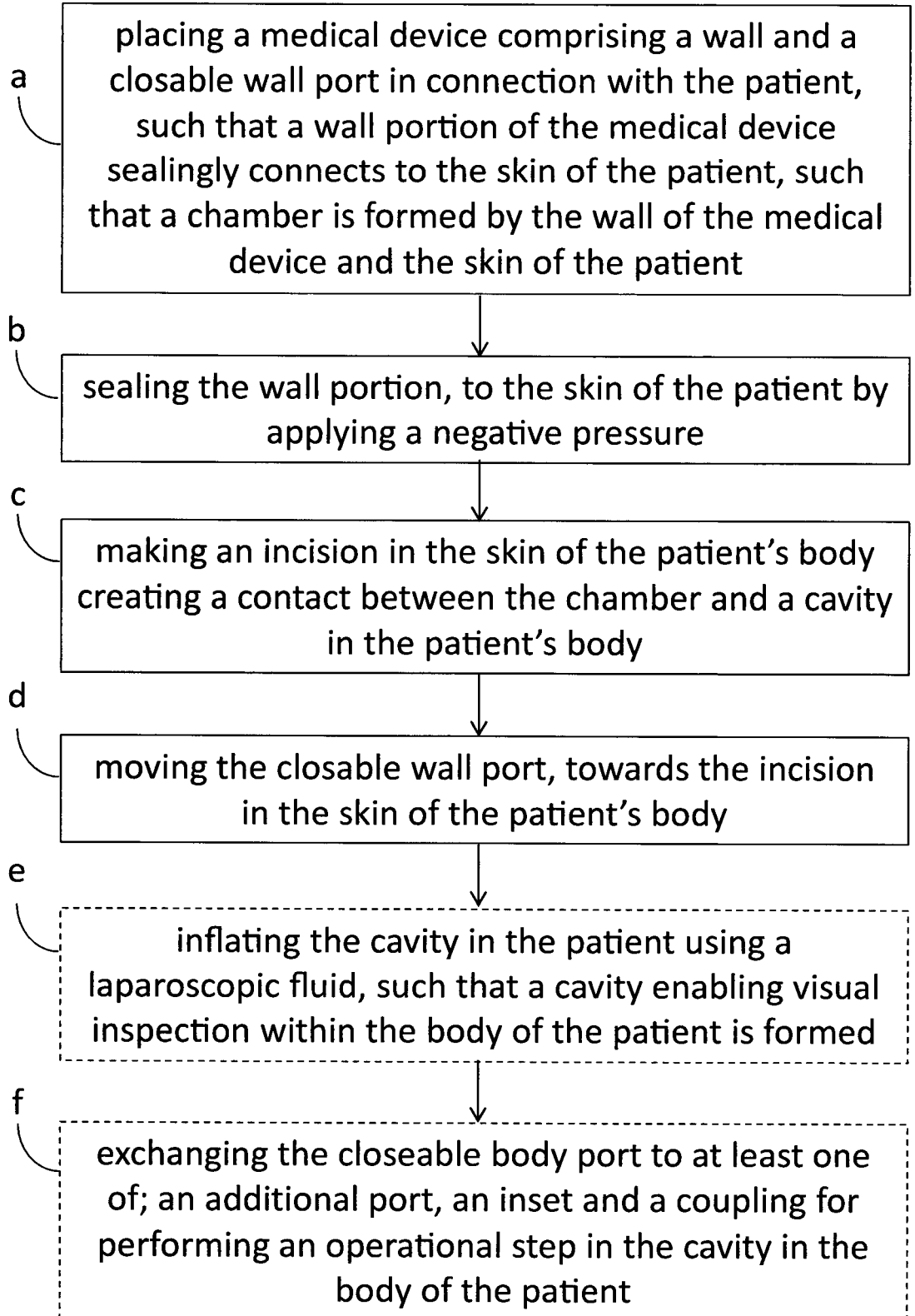

FIG. 236 is a flow chart describing a surgical method for performing a laparoscopic procedure in a sealed environment may comprise: placing a medical device comprising a wall and a closable wall port in connection with the patient a, such that a wall portion of the medical device sealingly connects to the skin of the patient, such that a chamber is formed by the wall of the medical device and the skin of the patient. Sealing the wall portion, to the skin of the patient by applying a negative pressure b, making an incision in the skin of the patient's body creating a contact between the chamber and a cavity in the patient's body c, and moving the closable wall port, adapted to connect directly or indirectly to the incision in the skin of the patient, towards the incision in the skin of the patient's body d.

The surgical method may optionally comprise inflating the cavity in the patient using a laparoscopic fluid, such that a cavity enabling visual inspection within the body of the patient is formed e, and exchanging the closeable body port to at least one of; an additional port, an inset and a coupling for performing an operational step in the cavity in the body of the patient f.

The surgical method may optionally comprise exchanging the closeable wall port to at least one of; an additional port, an inset and a coupling for performing an operational step in the chamber of the medical device.

FIG. 237 is a flow chart describing a method of transferring an object from the ambient environment to a cavity in a patient during a surgical procedure. The method comprises: transferring the object through a first closable wall port, placed in a wall of a medical device, into a chamber formed by the wall of the medical device and the skin of the patient a, and transferring the object through a closable body port placed in an incision made in the patient's skin and into the cavity in the patient b.

FIG. 237 further shows a flow chart (18(4)) describing a method of forming an airlock sluice between the ambient environment and a cavity in a patient. The method comprises two in time interchangeable steps: placing a body port in an incision made in the skin of the patient a, and placing a medical device comprising a closable wall port in connection with the patient, such that a wall portion of the medical device sealingly connects to the skin of the patient b, and forming a chamber by the wall of the medical device, the skin of the patient, and the body port c.

Figure 238:
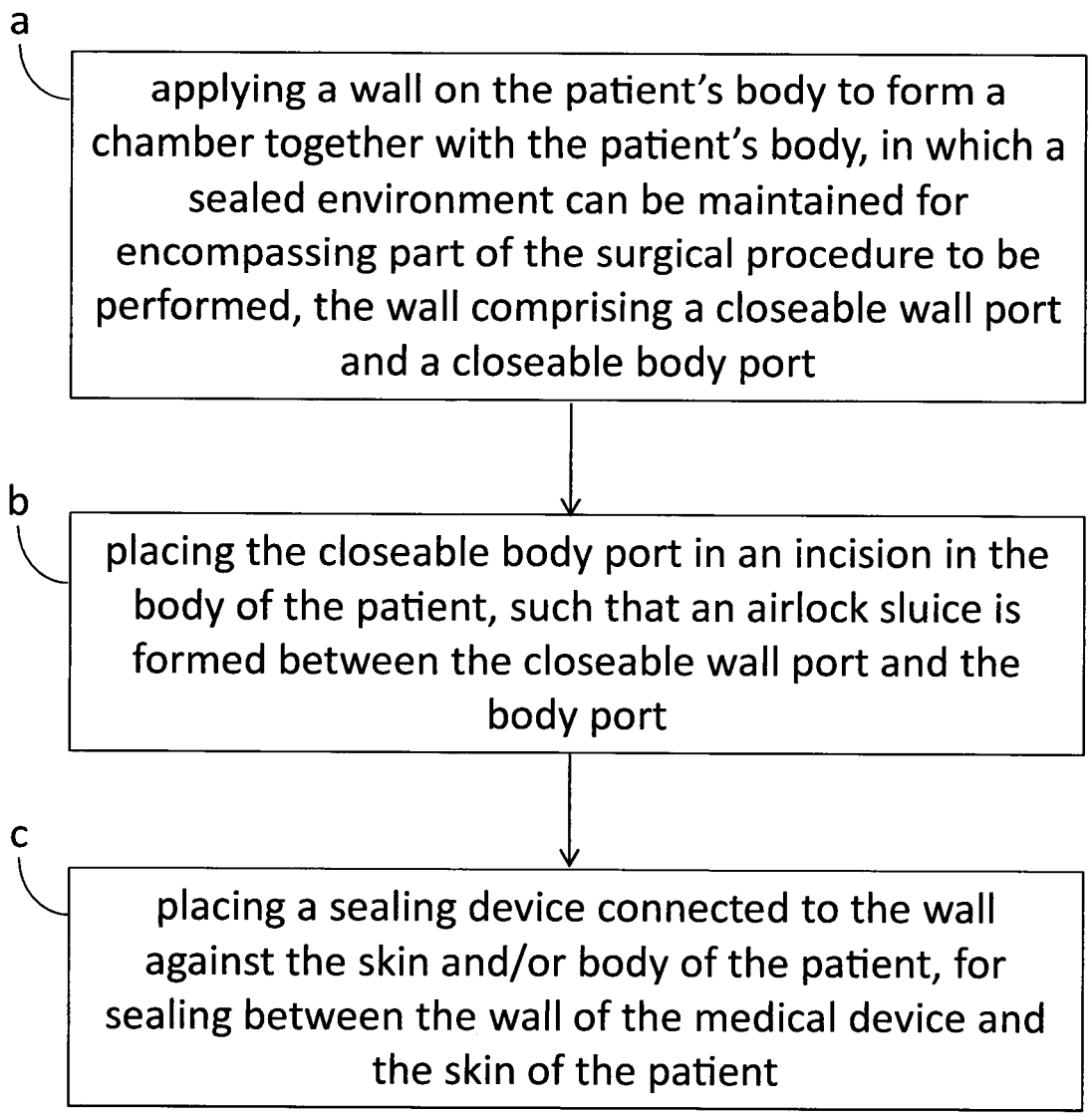

FIG. 238 is a flow chart describing a method of forming an airlock sluice for use when performing a surgical procedure on a patient. The method comprising: applying a wall on the patient's body to form a chamber together with the patient's body, in which a sealed environment can be maintained for encompassing part of the surgical procedure to be performed, the wall comprising a closeable wall port and a closeable body port a, placing the closeable body port in an incision in the body of the patient, such that an airlock sluice is formed between the closeable wall port and the body port b, and placing a sealing device connected to the wall against the skin and/or body of the patient, for sealing between the wall of the medical device and the skin of the patient c.

Figure 239:
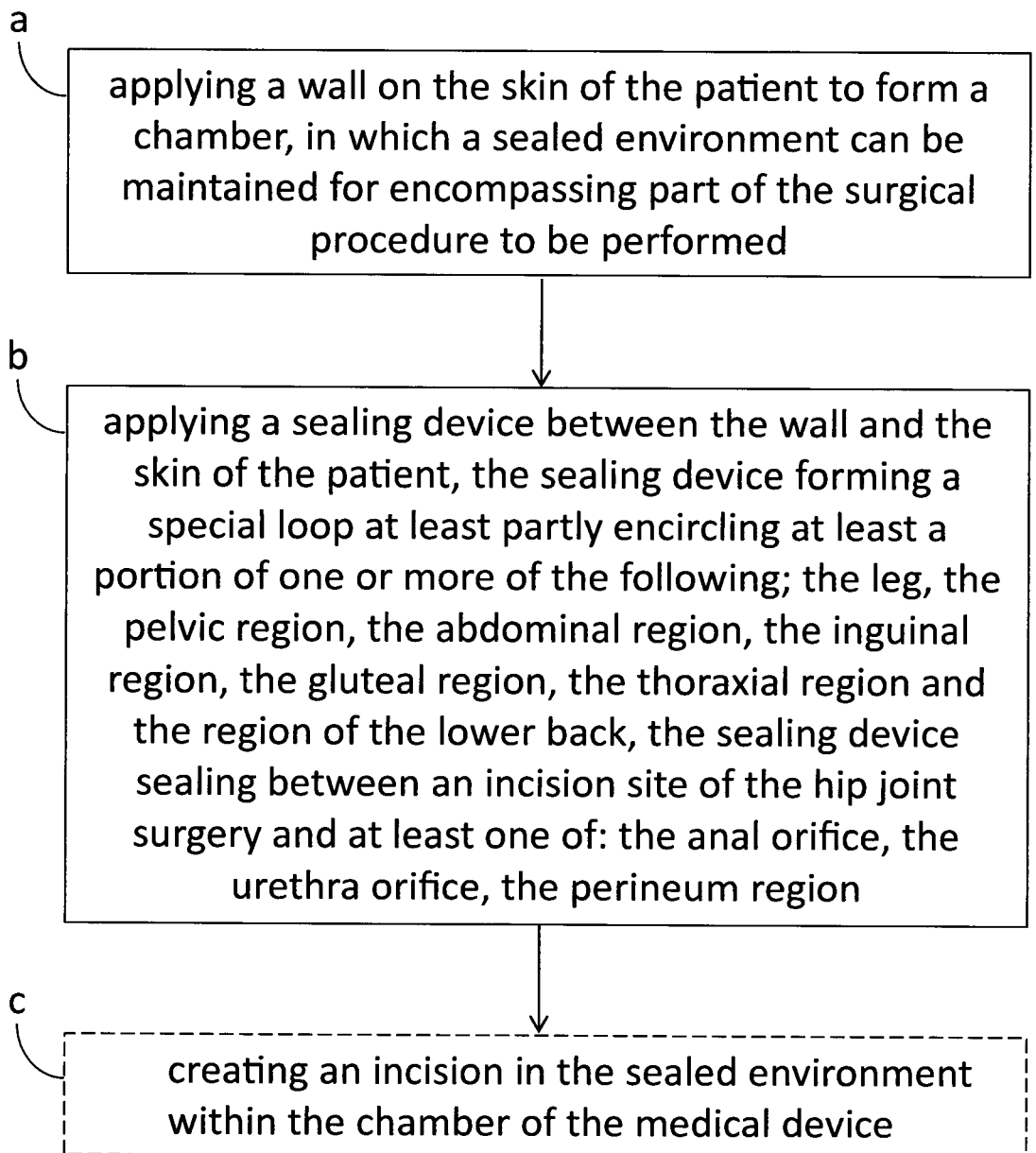

FIG. 239 is a flow chart describing a method of performing a portion of a hip joint surgery on a patient using a medical device. The method comprising: applying a wall on the skin of the patient to form a chamber, in which a sealed environment can be maintained for encompassing part of the surgical procedure to be performed a, applying a sealing device between the wall and the skin of the patient such that the sealing device forms a special loop at least partly encircling at least a portion of one or more of the following; the leg, the pelvic region, the abdominal region, the inguinal region, the gluteal region, the thoraxial region and the region of the lower back, such that the first sealing device seals between an incision site of the hip joint surgery and at least one of: the anal orifice, the urethra orifice, the perineum region b. The surgical method further comprises the step of creating an incision at the incision site in the sealed environment within the chamber of the medical device c.

Figure 240:
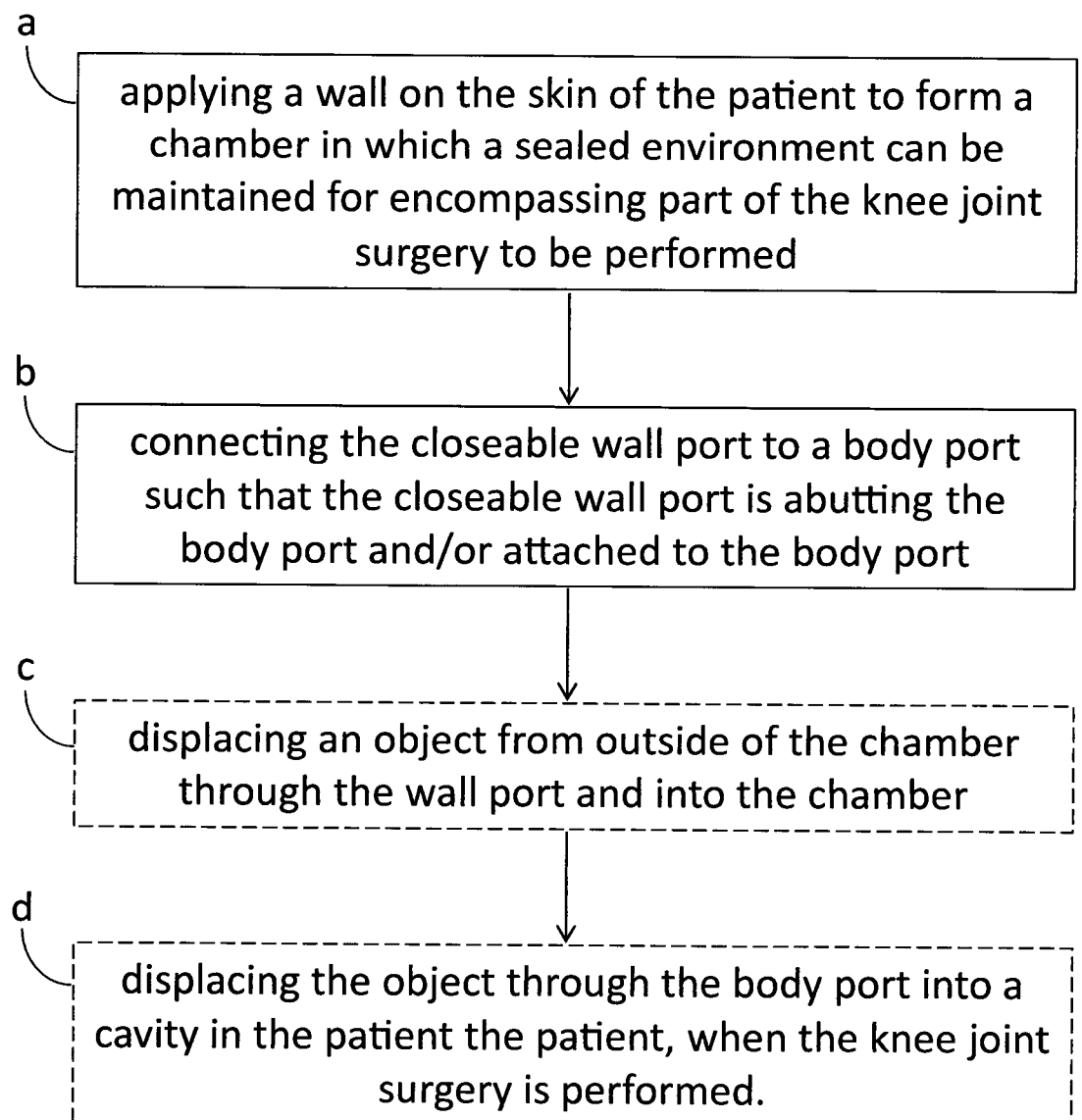

FIG. 240 is a flow chart describing a method of performing a portion of knee joint surgery on a patient using a medical device. The method comprising: applying a wall on the skin of the patient to form a chamber, in which a sealed environment can be maintained for encompassing part of the knee joint surgery to be performed a. The wall comprises a closeable wall port and the method further comprises connecting the closeable wall port to a body port, such that the closeable wall port is at least one of: abutting the body port and attached to the body port b, such that an arthroscopic step of the knee joint surgery can be performed.

The surgical method may optionally comprise the steps of displacing an object from outside of the chamber through the wall port and into the chamber c, and displacing the object through the body port into a cavity in the patient the patient, when the knee joint surgery is performed d.

The surgical method may optionally comprise displacing the wall port from a first position relatively close to the skin of the patient to a second position more remote from the skin of the patient than the first position.

Figure 241:
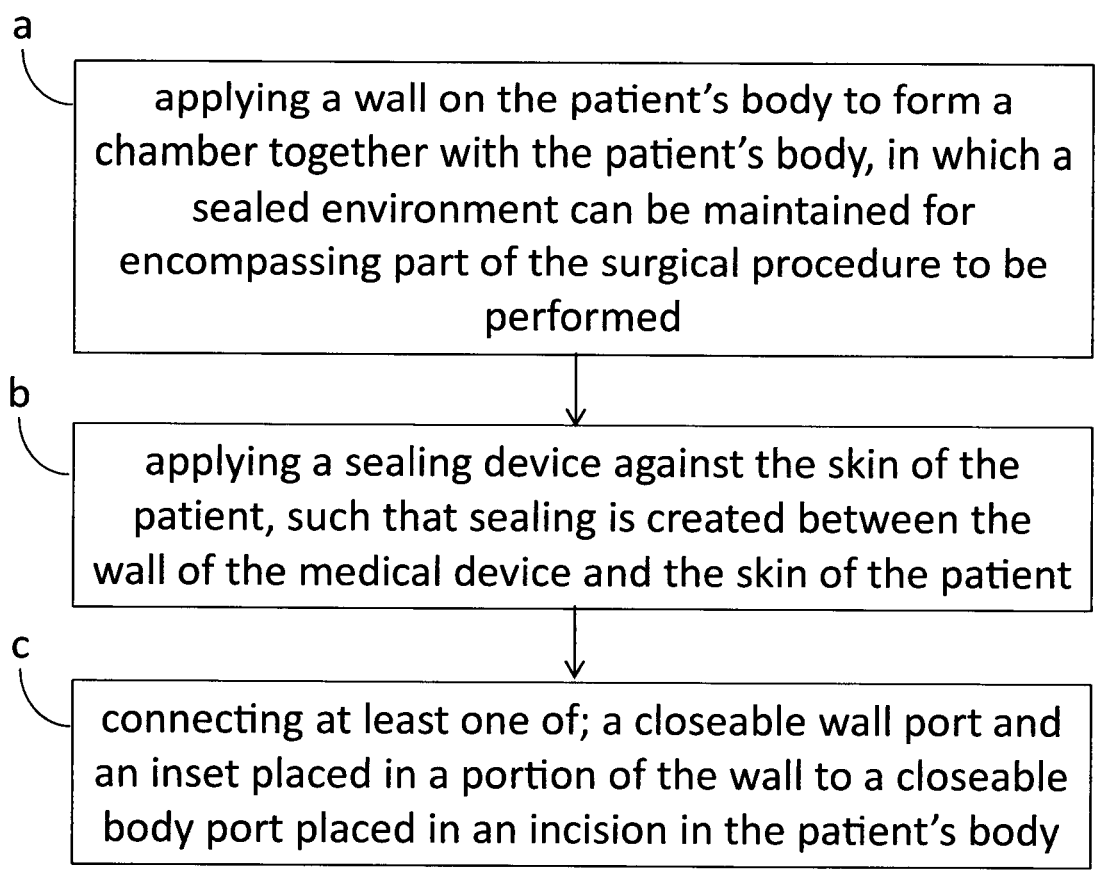

FIG. 241 is a flow chart describing a method of forming an airlock sluice for use when performing a surgical procedure on a patient. The method comprises: applying a wall on the patient's body to form a chamber together with the patient's body, in which a sealed environment can be maintained for encompassing part of the surgical procedure to be performed a, applying a sealing device against the skin of the patient, such that sealing is created between the wall of the medical device and the skin of the patient b, connecting at least one of; a closeable wall port and an inset placed in a portion of the wall to a closeable body port placed in an incision in the patient's body c.

Figure 242:
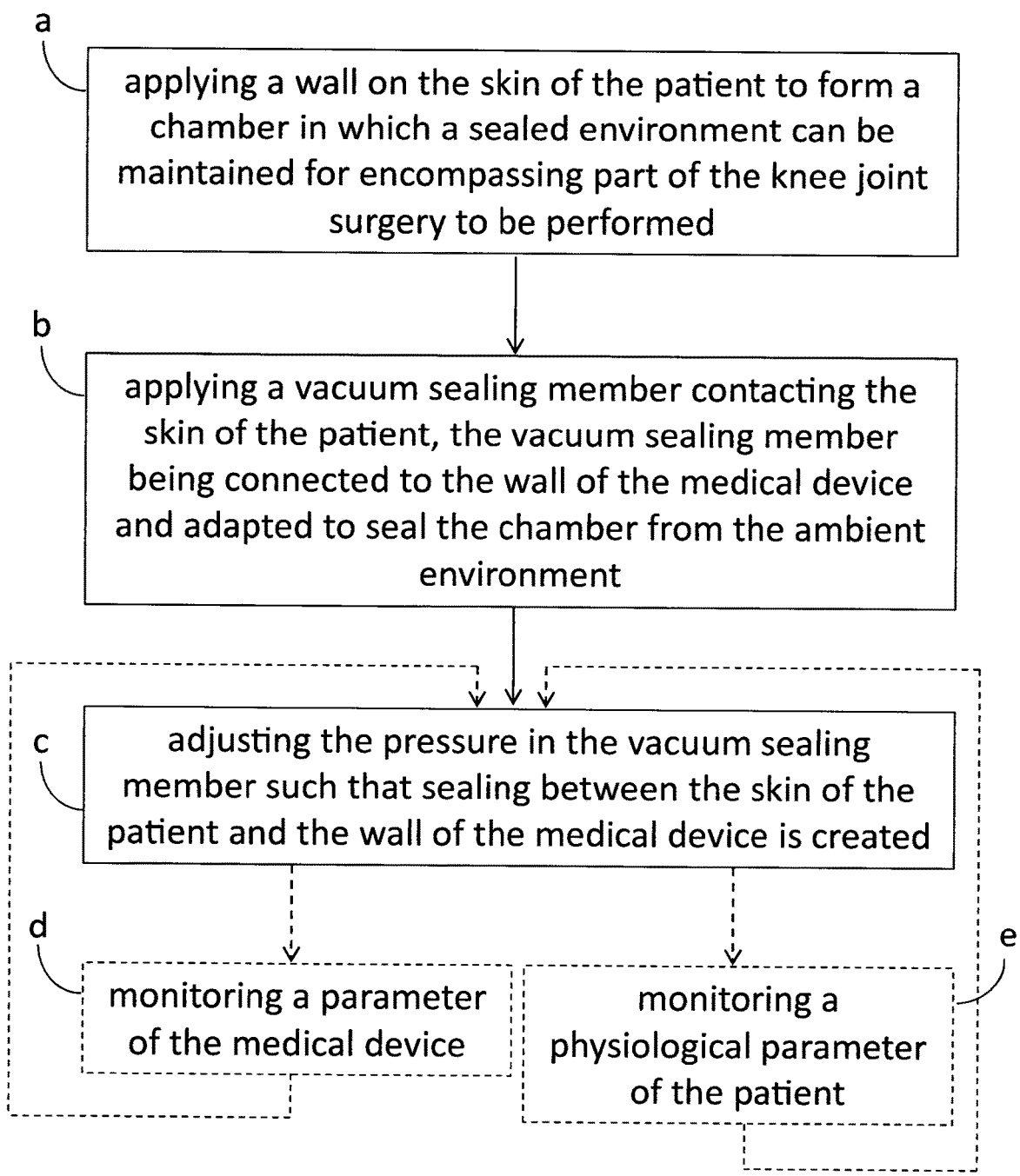

FIG. 242 is a flow chart describing a method of providing a sealed environment using a medical device, such that a surgical procedure can be performed in the sealed environment. The method comprises: applying a wall on the skin of the patient to form a chamber, in which a sealed environment can be maintained for encompassing part of the surgical procedure to be performed a, applying a vacuum sealing member contacting the skin of the patient, the vacuum sealing member being connected to the wall of the medical device and adapted to seal the chamber from the ambient environment b, and adjusting the pressure in the vacuum sealing member such that sealing between the skin of the patient and the wall of the medical device is created c.

The step of adjusting the pressure in the vacuum sealing member may comprise adjusting the pressure in the vacuum sealing member as a response to at least one of: a monitored parameter of the medical device d, and a monitored physiological parameter of the patient e.

The step of adjusting the pressure in the vacuum sealing member as a response to a monitored parameter of the medical device may comprise adjusting the pressure in the vacuum sealing member as a response to: the pressure in the chamber, the pressure in the vacuum sealing member.

The step of adjusting the pressure in the vacuum sealing member as a response to a monitored physiological parameter of the patient may comprise adjusting the pressure in the vacuum sealing member as a response to: the blood pressure of the patient, the blood flow of the patient, and a temperature of the body of the patient.

Figure 243:
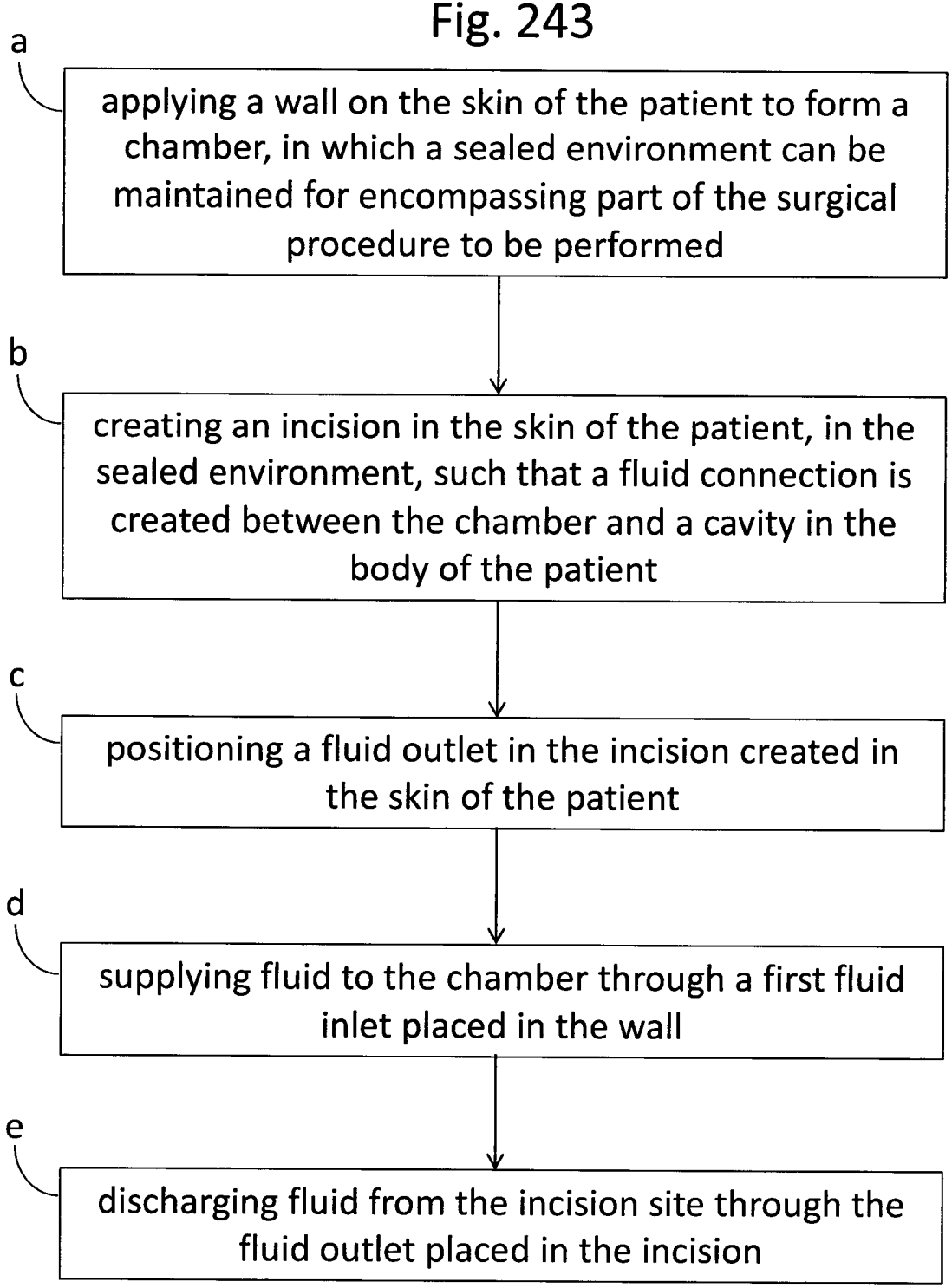

FIG. 243 is a flow chart describing a method of performing an arthroscopic surgical procedure on a patient using a medical device. The method comprises: applying a wall on the skin of the patient to form a chamber, in which a sealed environment can be maintained for encompassing part of the surgical procedure to be performed a, creating an incision in the skin of the patient, in the sealed environment, such that a fluid connection is created between the chamber and a cavity in the body of the patient b, positioning a fluid outlet in the incision created in the skin of the patient c, supplying fluid to the chamber through a first fluid inlet placed in the wall d, and discharging fluid from the incision site through the fluid outlet placed in the incision e.

Figure 244:
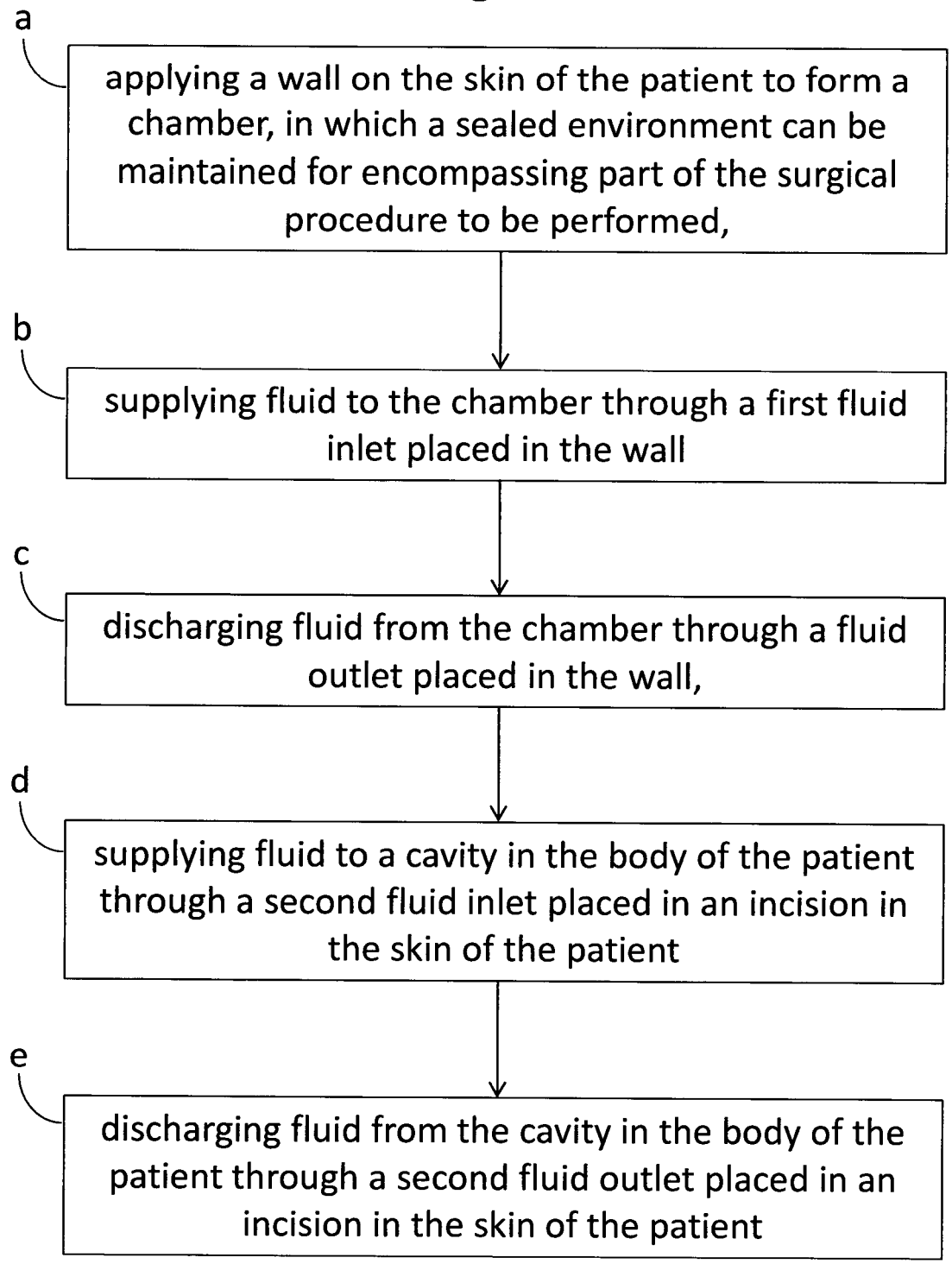

FIG. 244 is a flow chart describing a method of performing an arthroscopic surgical procedure on a patient using a medical device. The method comprises: applying a wall on the skin of the patient to form a chamber, in which a sealed environment can be maintained for encompassing part of the surgical procedure to be performed a, supplying fluid to the chamber through a first fluid inlet placed in the wall b, discharging fluid from the chamber through a fluid outlet placed in the wall c, supplying fluid to a cavity in the body of the patient through a second fluid inlet placed in an incision in the skin of the patient d, and discharging fluid from the cavity in the body of the patient through a second fluid outlet placed in an incision in the skin of the patient e.

Figure 245:
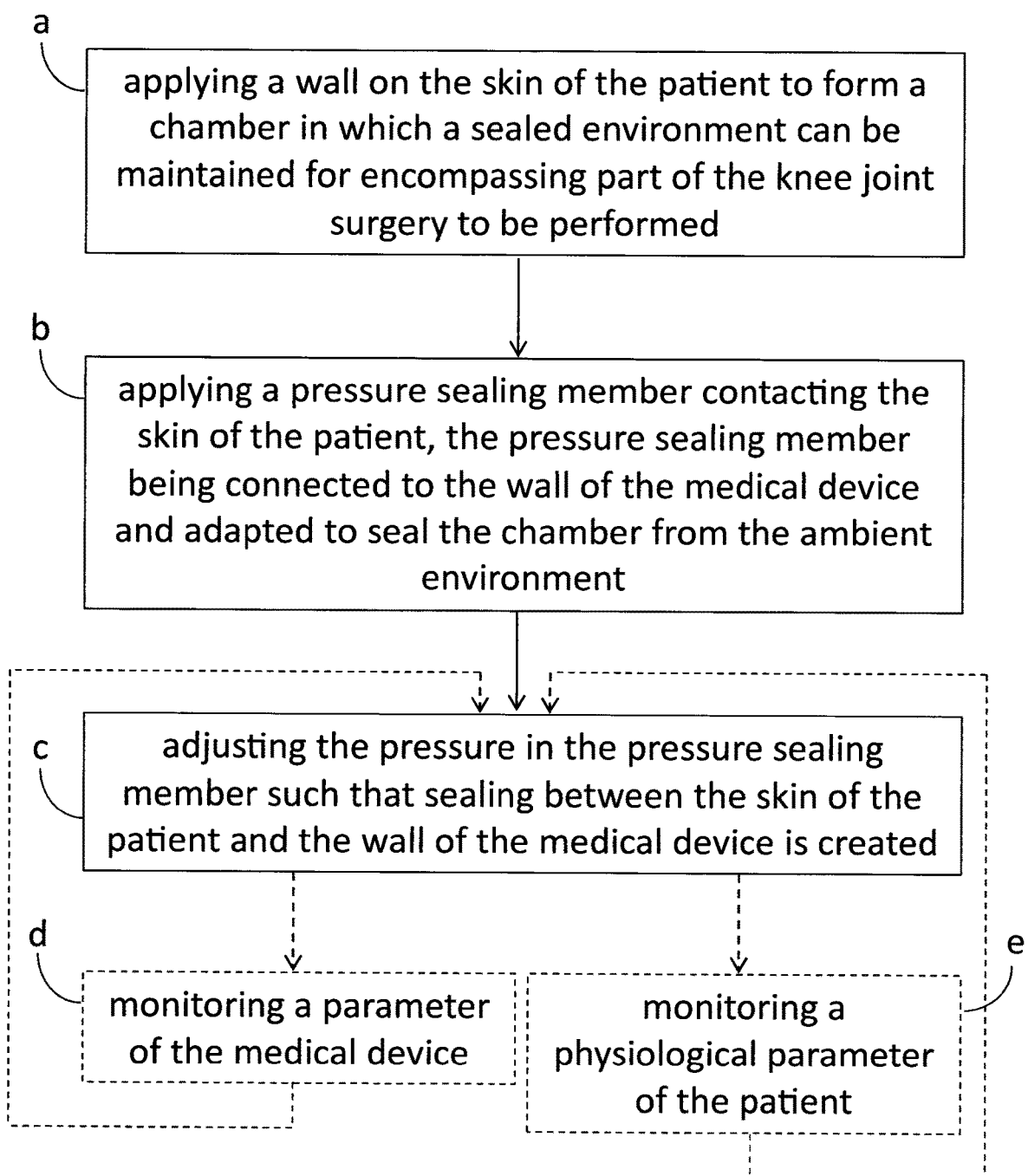

FIG. 245 is a flow chart describing a method of providing a sealed environment using a medical device, such that a surgical procedure can be performed in the sealed environment. The method comprises: applying a wall on the skin of the patient to form a chamber, in which a sealed environment can be maintained for encompassing part of the surgical procedure to be performed a, applying a pressure sealing member contacting the skin of the patient, the pressure sealing member being connected to the wall of the medical device and adapted to seal the chamber from the ambient environment b, adjusting the pressure in the pressure sealing member such that sealing between the skin of the patient and the wall of the medical device is created c.

The step of adjusting the pressure in the pressure sealing member may comprise adjusting the pressure in the pressure sealing member as a response to at least one of: a monitored parameter of the medical device d, and a monitored physiological parameter of the patient e.

The step of adjusting the pressure in the pressure sealing member as a response to a monitored parameter of the medical device may comprise adjusting the pressure in the pressure sealing member as a response to: the pressure in the chamber and the pressure in the pressure sealing member.

The step of adjusting the pressure in the pressure sealing member as a response to a monitored physiological parameter of the patient may comprise adjusting the pressure in the pressure sealing member as a response to: the blood pressure of the patient, the blood flow of the patient, and a temperature of the body of the patient.

Figure 246:
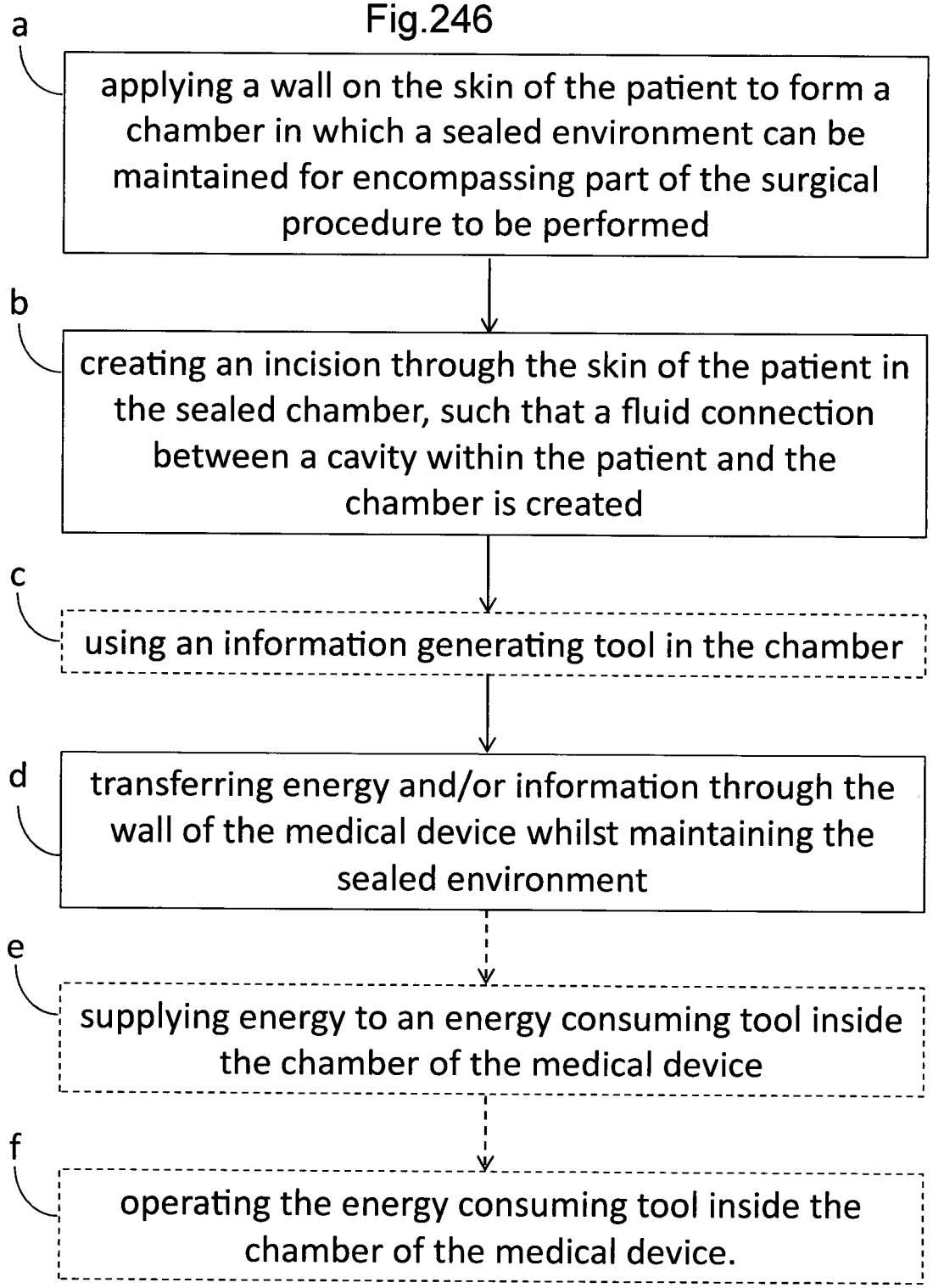

FIG. 246 is a flow chart describing a method of performing a surgical procedure on a patient using a medical device. The method comprises applying a wall on the skin of the patient to form a chamber, in which a sealed environment can be maintained for encompassing part of the surgical procedure to be performed a, creating an incision through the skin of the patient in the sealed chamber, such that a fluid connection between a cavity within the patient and the chamber is created b, transferring at least one of: energy and information through the wall of the medical device whilst maintaining the sealed environment d.

The step of transferring energy through the wall of the medical device may comprise transferring at least one of: pneumatic, hydraulic and kinetic energy through the wall of the medical device.

The step of transferring energy through the wall of the medical device may comprise: supplying energy to an energy consuming tool inside the chamber of the medical device e, and operating the energy consuming tool inside the chamber of the medical device f.

The step of transferring information through the wall of the medical device may comprise transferring data through the wall of the medical device, and the data may be image data.

The method may comprise the step of using an information generating tool in the chamber c, such as a camera or a sensor, for creating the information to be transferred through the wall of the medical device.

Figure 247:
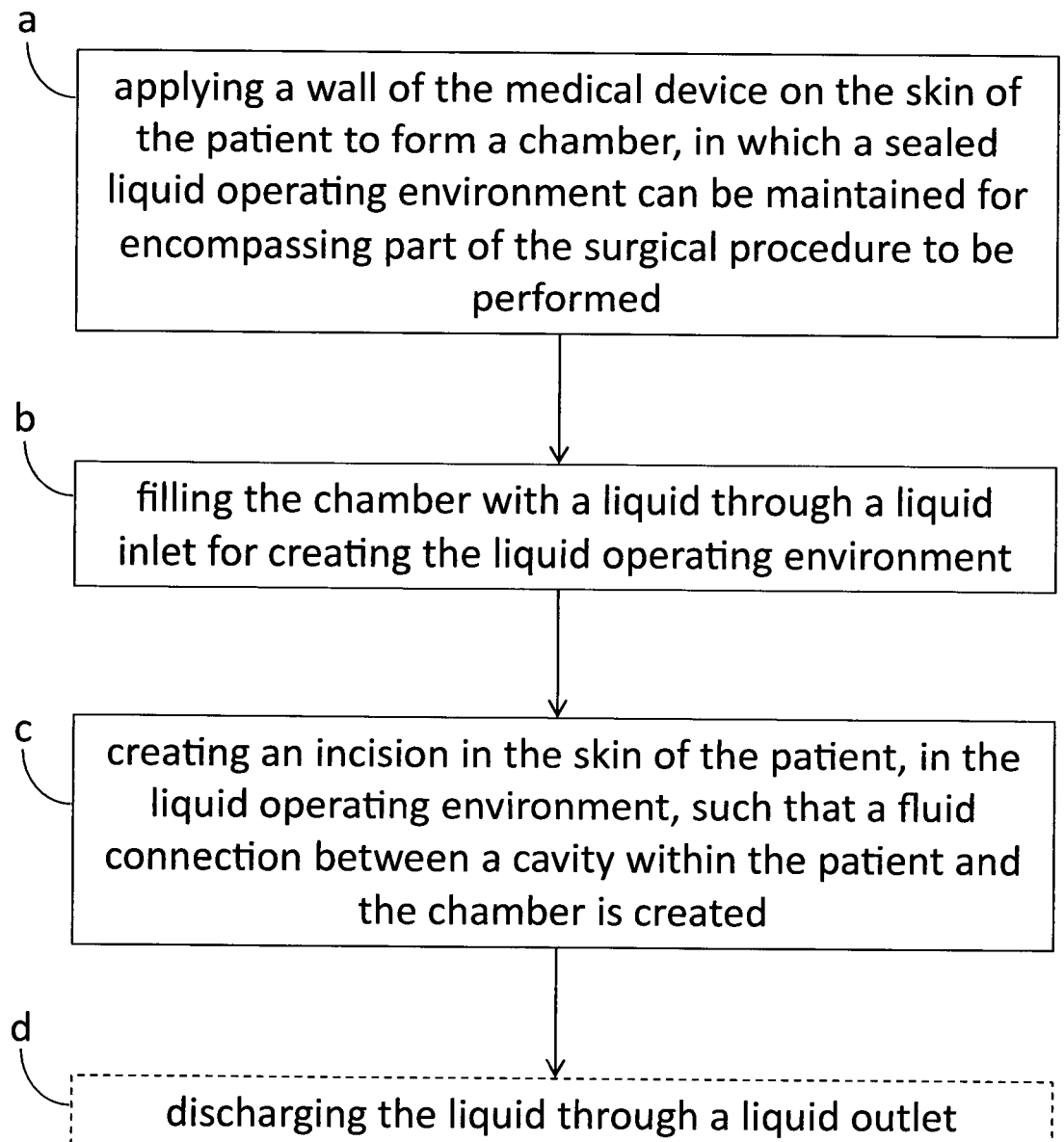

FIG. 247 is a flow chart describing a method of performing a surgical procedure on a patient using a medical device. The method comprises: applying a wall of the medical device on the skin of the patient to form a chamber in which a sealed liquid operating environment can be maintained for encompassing part of the surgical procedure to be performed a, filling the chamber with a liquid through a liquid inlet for creating the liquid operating environment b, and creating an incision in the skin of the patient, in the liquid operating environment, such that a fluid connection between a cavity within the patient and the chamber is created c.

The step of filling the chamber with a liquid through a liquid inlet may comprise filling the chamber with a liquid through a liquid inlet placed in at least one of: the wall of the medical device, and the body of the patient.

The method may optionally comprise the step of discharging the liquid through a liquid outlet d. The step of discharging the liquid through a liquid outlet may comprise discharging the liquid through a liquid outlet placed in at least one of: the wall of the medical device, and the body of the patient.

Figure 248:
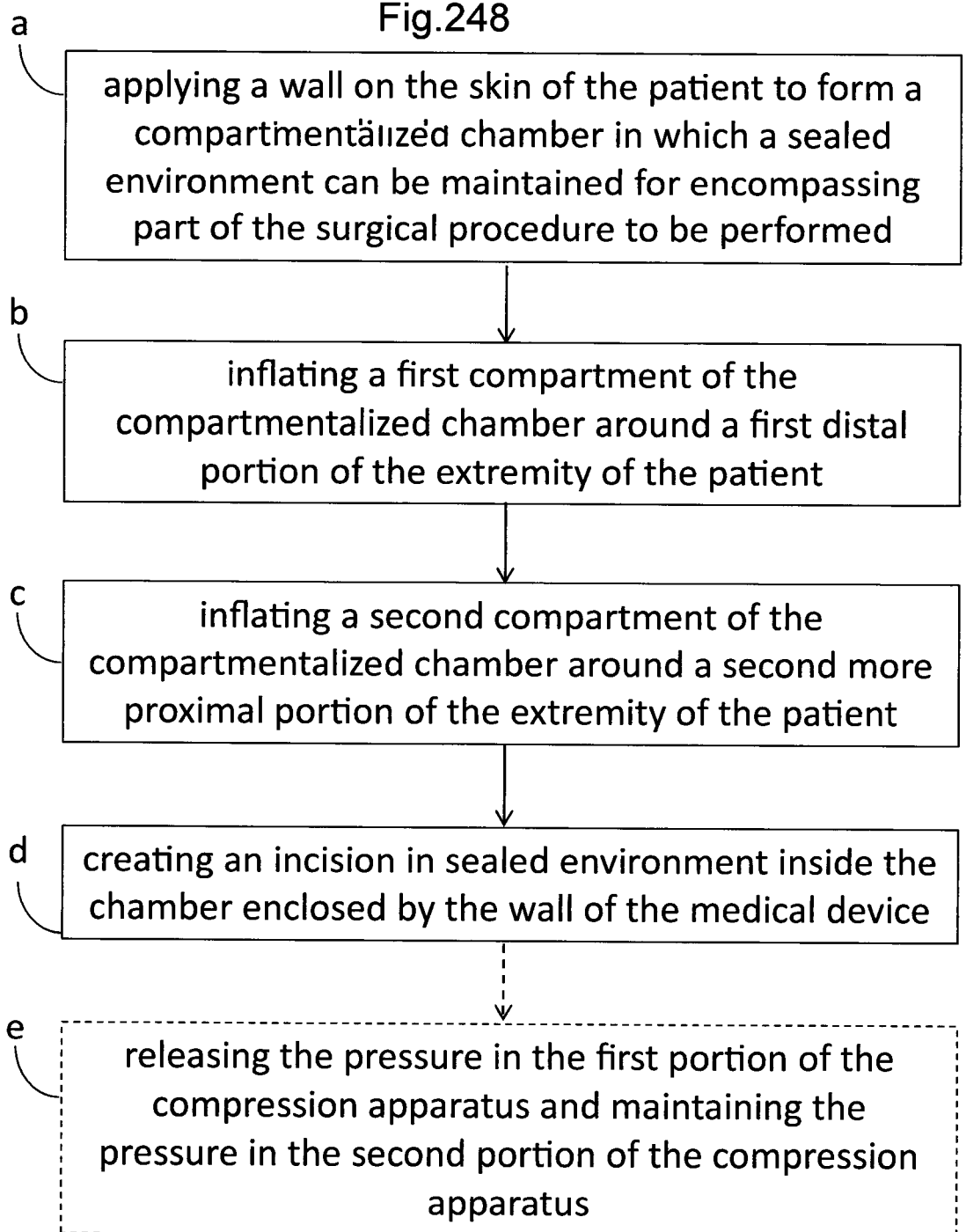

FIG. 248 is a flow chart describing a surgical method on an extremity of the patient having a reduced amount of blood using a medical device. The medical device comprises an inflatable wall enclosing a compartmentalized chamber in which a sealed environment can be maintained for encompassing part of the surgical procedure to be performed. The surgical method comprises: applying a wall on the skin of the patient to form a compartmentalized chamber in which a sealed environment can be maintained for encompassing part of the surgical procedure to be performed a, inflating a first compartment of the compartmentalized chamber around a first distal portion of the extremity of the patient, for reducing the amount of blood in the first distal portion of the extremity b, inflating a second compartment of the compartmentalized chamber around a second more proximal portion of the extremity of the patient c, for reducing the amount of blood in the second more proximal portion of the extremity, and creating an incision in sealed environment inside the chamber enclosed by the wall of the medical device d. The method may further comprise the step of releasing the pressure in the first portion of the compression apparatus and maintaining the pressure in the second portion of the compression apparatus e.

The steps of inflating the first and second chambers may comprise inflating the first and second chambers with a liquid.

Figure 249B:
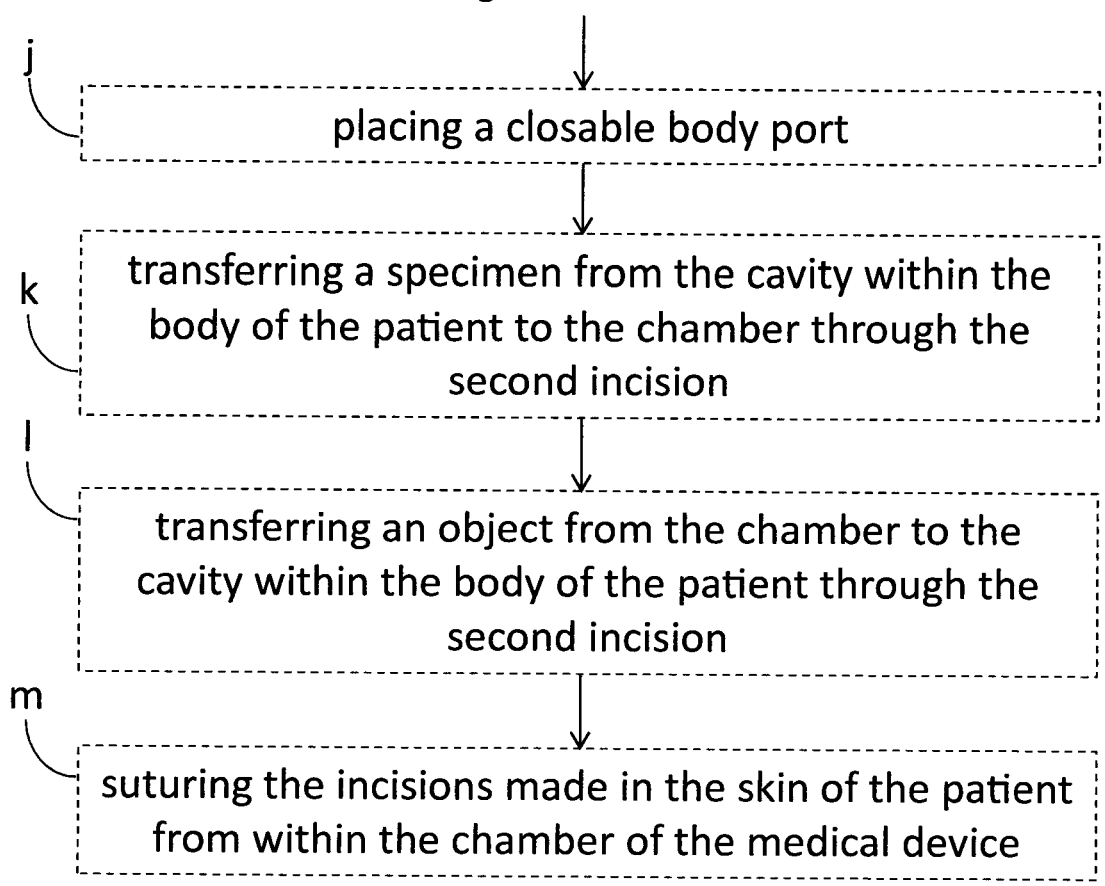

FIG. 249*a*, 249*b* are flow charts describing a surgical method of performing a combination of open and endoscopic surgery using a medical device comprising a wall adapted to be inflated by a fluid for forming a chamber in which a sealed environment can be maintained for encompassing part of the surgical procedure to be performed. The method comprises fixating a portion of the wall of the medical device to the skin of the patient a, making an incision in the skin of the patient inside or outside the chamber b, placing a fluid inlet through the incision c, supplying a fluid into the patient, thereby creating a cavity within the body of the patient d, making one or more additional incision(s) in the wall of the medical device continuing through the skin of the patient e, inserting a trocar in each of the one or more additional incision(s) made in the wall of the medical device f, inserting at least one of a camera and a surgical instrument g, through one of the one or more trocar(s), performing at least one step of endoscopic surgery through the trocar(s) h, making a second incision in the wall of the medical device continuing through the skin of the patient i. The medical device further comprises at least one of: placing a closable body port j, transferring a specimen from the cavity within the body of the patient to the chamber through the second incision k, transferring an object from the chamber to the cavity within the body of the patient through the second incision l.

The method may further comprise the step of suturing the incisions made in the skin of the patient from within the chamber of the medical device m.

FIG. 250 is a flow chart describing a method embodiment of performing endoscopic surgery using a medical device. The medical device comprises: a wall adapted to be inflated by a fluid for forming a chamber in which a sealed environment can be maintained for encompassing part of the surgical procedure to be performed, and at least one endoscopic trocar positioned through the wall of the medical device, such that a first portion of the trocar is positioned inside of the chamber, and a second portion of the trocar is positioned outside of the chamber. The method comprises: creating an incision in the skin of the patient a, inserting the endoscopic trocar through the incision in the skin of the patient into the body of the patient b, fixating a portion of the wall of the medical device to the skin of the patient c, supplying a fluid into the patient, thereby creating a cavity within the body of the patient d, and performing at least one step of endoscopic surgery through the trocar e.

The medical device may further comprise a closable body port integrated in the wall adapted to be placed in an incision in the skin, when the surgical procedure is performed, and the method may thus comprise: making a second incision through the skin of the patient f, and at least one of: placing the closable body port in the incision g, transferring a specimen from the cavity within the body of the patient to the chamber through the second incision h, transferring an object from the chamber to the cavity within the body of the patient through the second incision i.

The method may optionally comprise the step of suturing the incisions made in the skin of the patient from within the chamber of the medical device.

Figure 251:
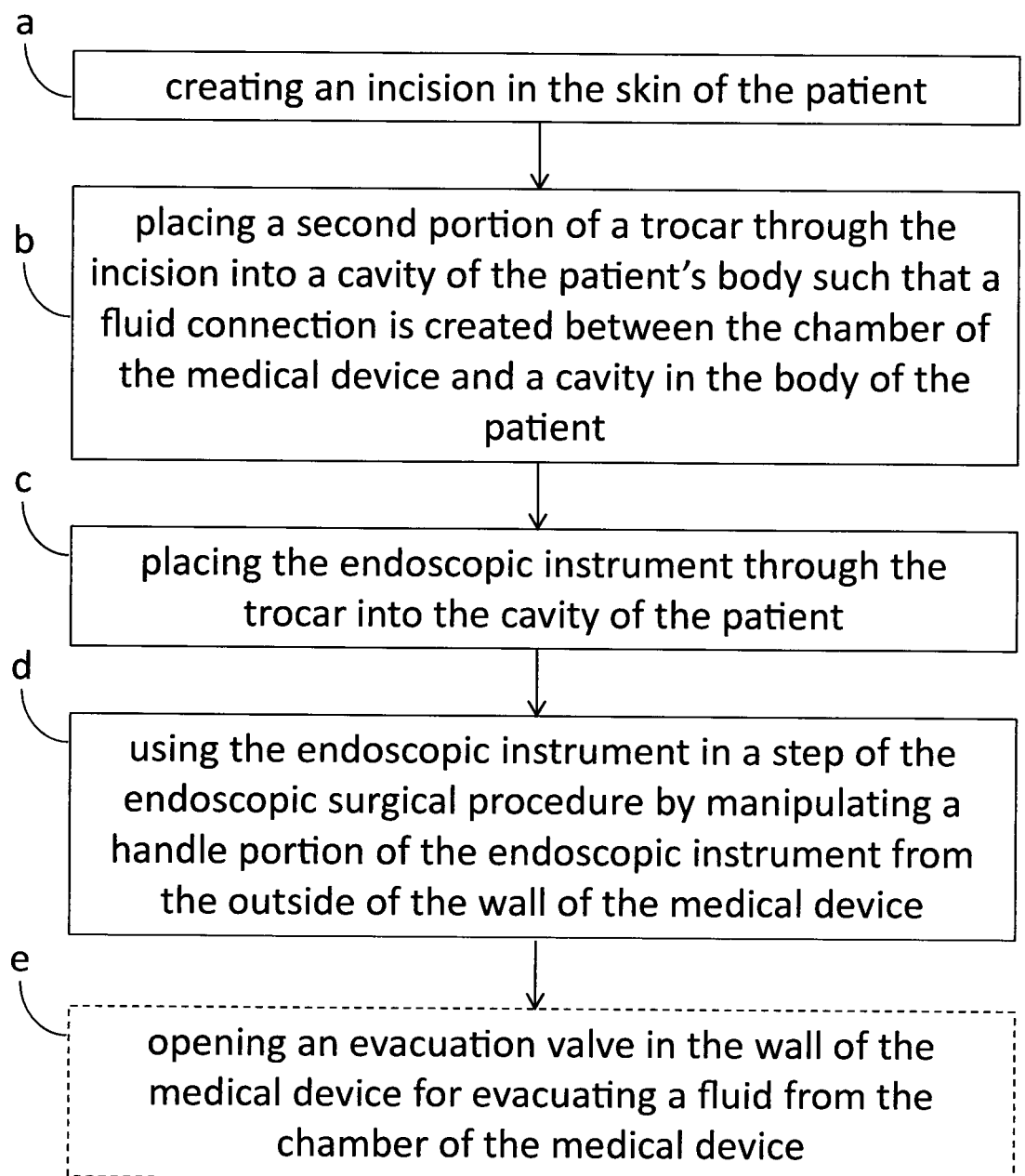

FIG. 251 is a flow chart describing a method embodiment of performing an endoscopic surgical procedure on a patient using a medical device. The medical device comprising a wall enclosing a chamber in which a sealed environment can be maintained, in which an endoscopic instrument is enclosed. The method comprises: creating an incision in the skin of the patient a, placing a second portion of a trocar through the incision into a cavity of the patient's body, wherein the first portion of the trocar is positioned inside the chamber of the medical device, such that a fluid connection is created between the chamber of the medical device and a cavity in the body of the patient b, placing the endoscopic instrument through the trocar into the cavity of the patient c, using the endoscopic instrument in a step of the endoscopic surgical procedure by manipulating a handle portion of the endoscopic instrument from the outside of the wall of the medical device d. The method may further comprise the step of opening an evacuation valve in the wall of the medical device for evacuating a fluid from the chamber of the medical device e.

Figure 252:
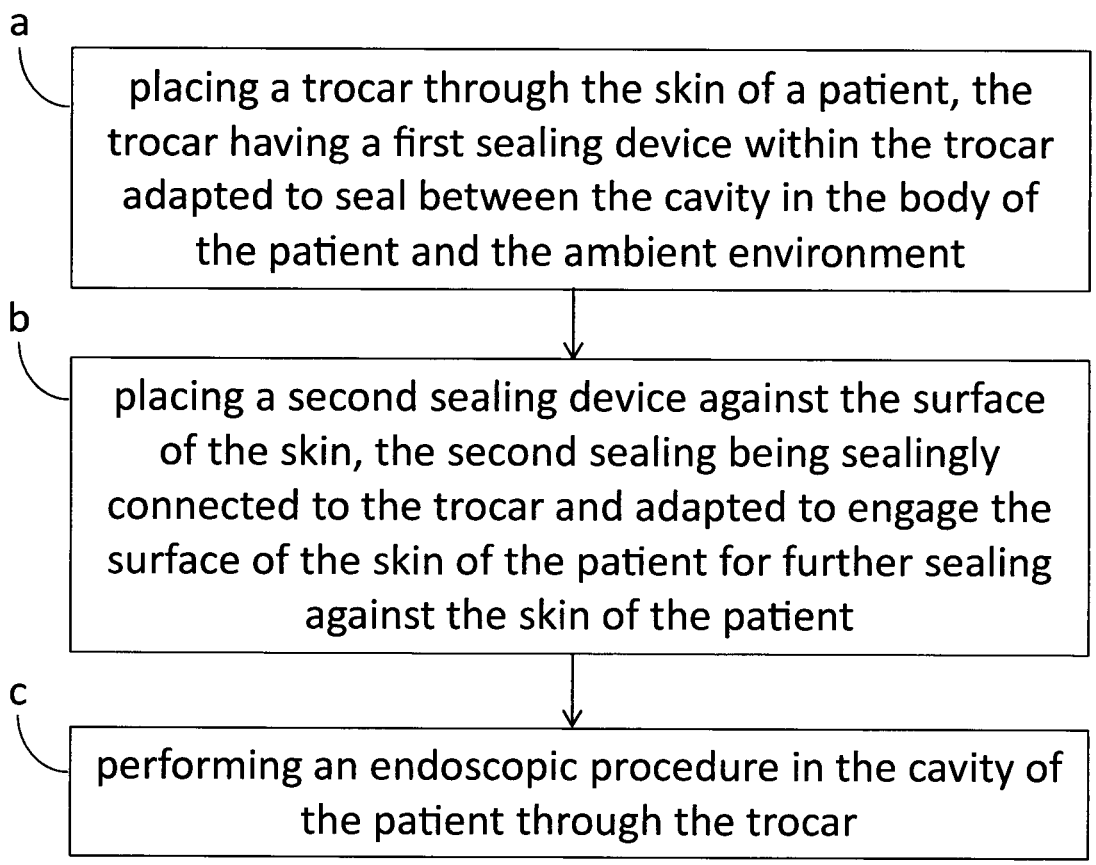

FIG. 252 is a flow chart describing an endoscopic surgical method of performing an endoscopic procedure in a cavity in a patient's body. The method comprises: placing a trocar through the skin of a patient, the trocar having a first sealing device within the trocar adapted to seal between the cavity in the body of the patient and the ambient environment a, and placing a second sealing device against the surface of the skin, the second sealing being sealingly connected to the trocar and adapted to engage the surface of the skin of the patient for further sealing against the skin of the patient b, and performing an endoscopic procedure in the cavity of the patient through the trocar c.

Figure 253:
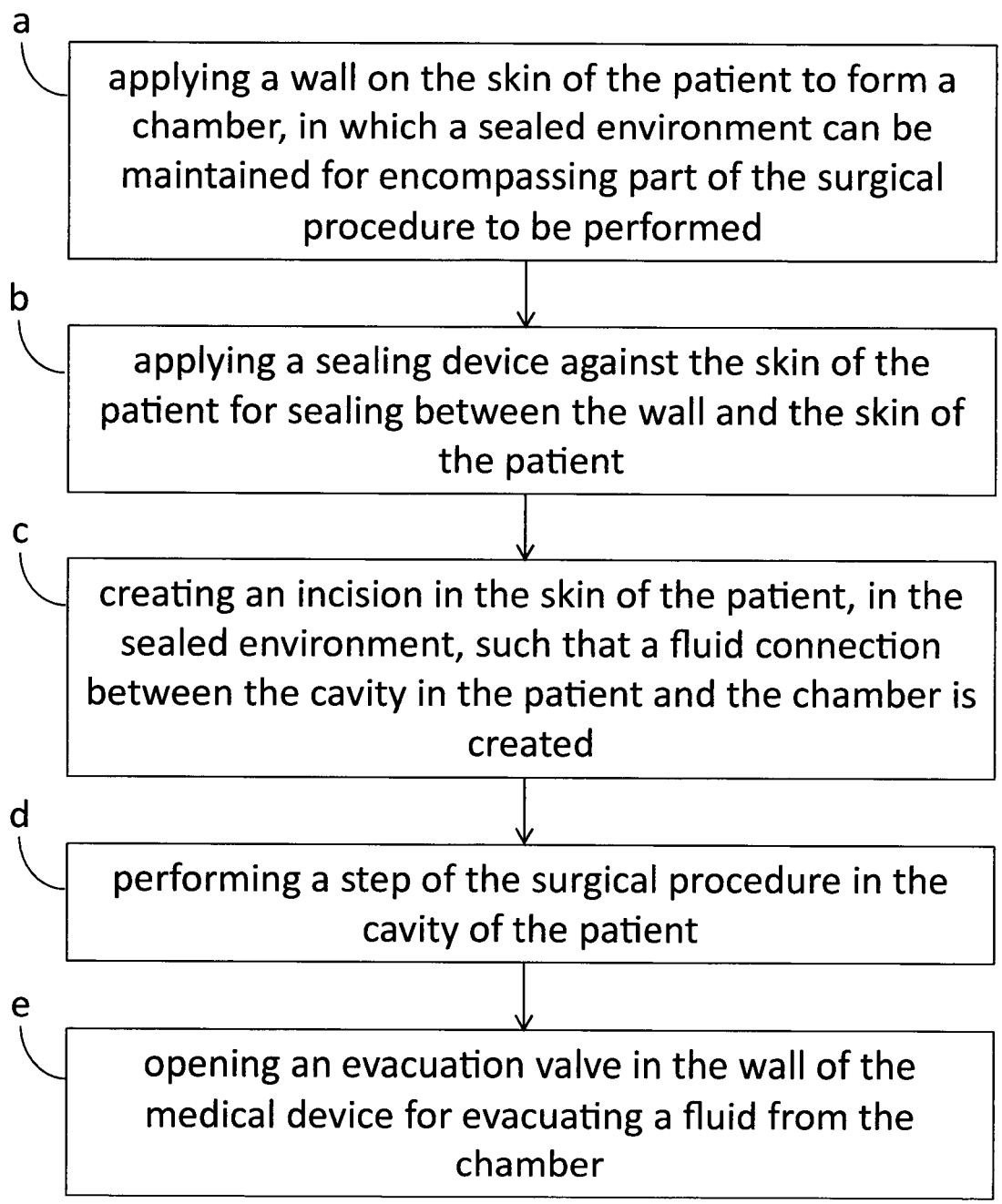

FIG. 253 is a flow chart describing a method of performing a surgical procedure on a patient using a medical device. The method comprises: applying a wall on the skin of the patient to form a chamber, in which a sealed environment can be maintained for encompassing part of the surgical procedure to be performed a, applying a sealing device against the skin of the patient for sealing between the wall and the skin of the patient b, the method may optionally comprise the step of inflating at least one of a cavity of the patient and the chamber of the medical device with a fluid. The method further comprises the step of creating an incision in the skin of the patient, in the sealed environment, such that a fluid connection between the cavity in the patient and the chamber is created c, performing a step of the surgical procedure in the cavity of the patient d, and opening an evacuation valve in the wall of the medical device for evacuating a fluid from the chamber e.

Figure 254:
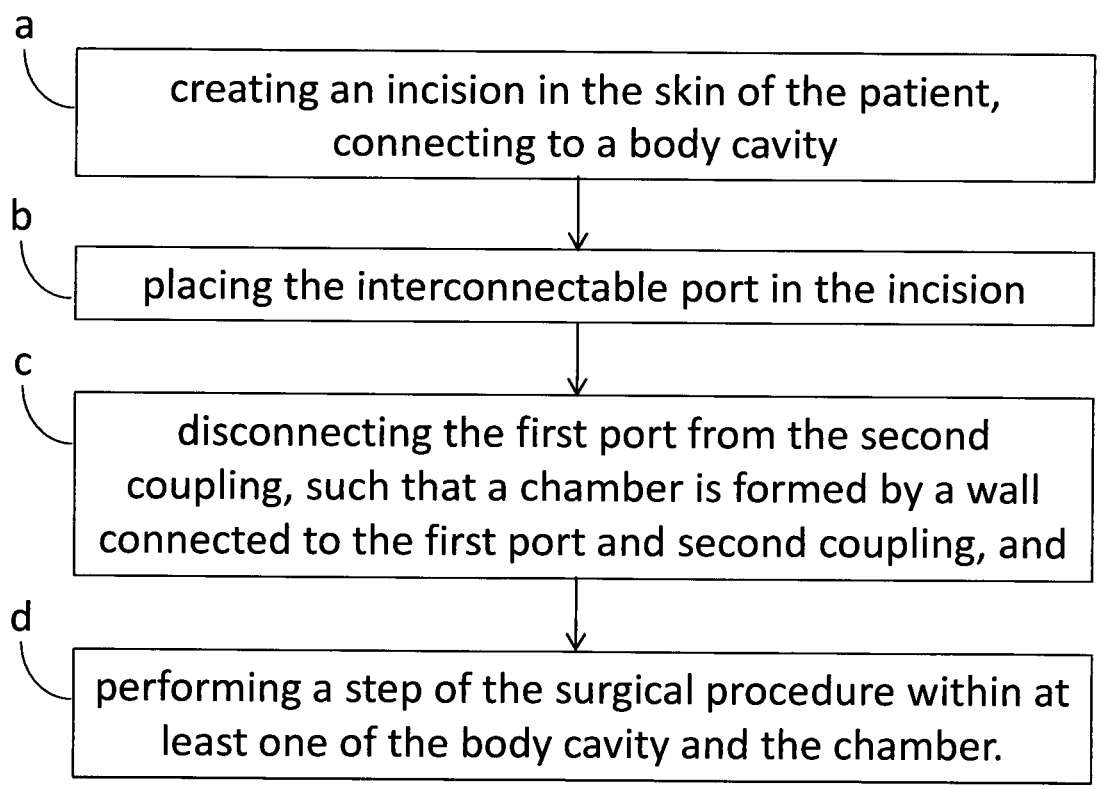

FIG. 254 is a flow chart describing a surgical method to be performed on the body of a patient using an interconnectable port comprising a first port and a second coupling. The method comprising: creating an incision in the skin of the patient, connecting to a body cavity a, placing the interconnectable port in the incision b, disconnecting the first port from the second coupling, such that a chamber is formed by a wall connected to the first port and second coupling c, and performing a step of the surgical procedure within at least one of the body cavity and the chamber d.

The surgical method may further comprise placing a sealing device in connection with at least one of the flexible wall and the second coupling, to seal between the medical device and the skin or tissue of the patient, and sealing the combined volume of the chamber and the body cavity to the outer environment, when the second coupling is open.

The surgical method may further comprise removing a specimen from the cavity in the body of the patient, transferring the specimen through the second coupling, and placing the specimen within the chamber of the medical device.

The surgical method may further comprise reconnecting the first port and second coupling such that the interconnectable port is formed, performing a surgical step in a cavity of the patient, through the interconnectable port.

Figure 255:
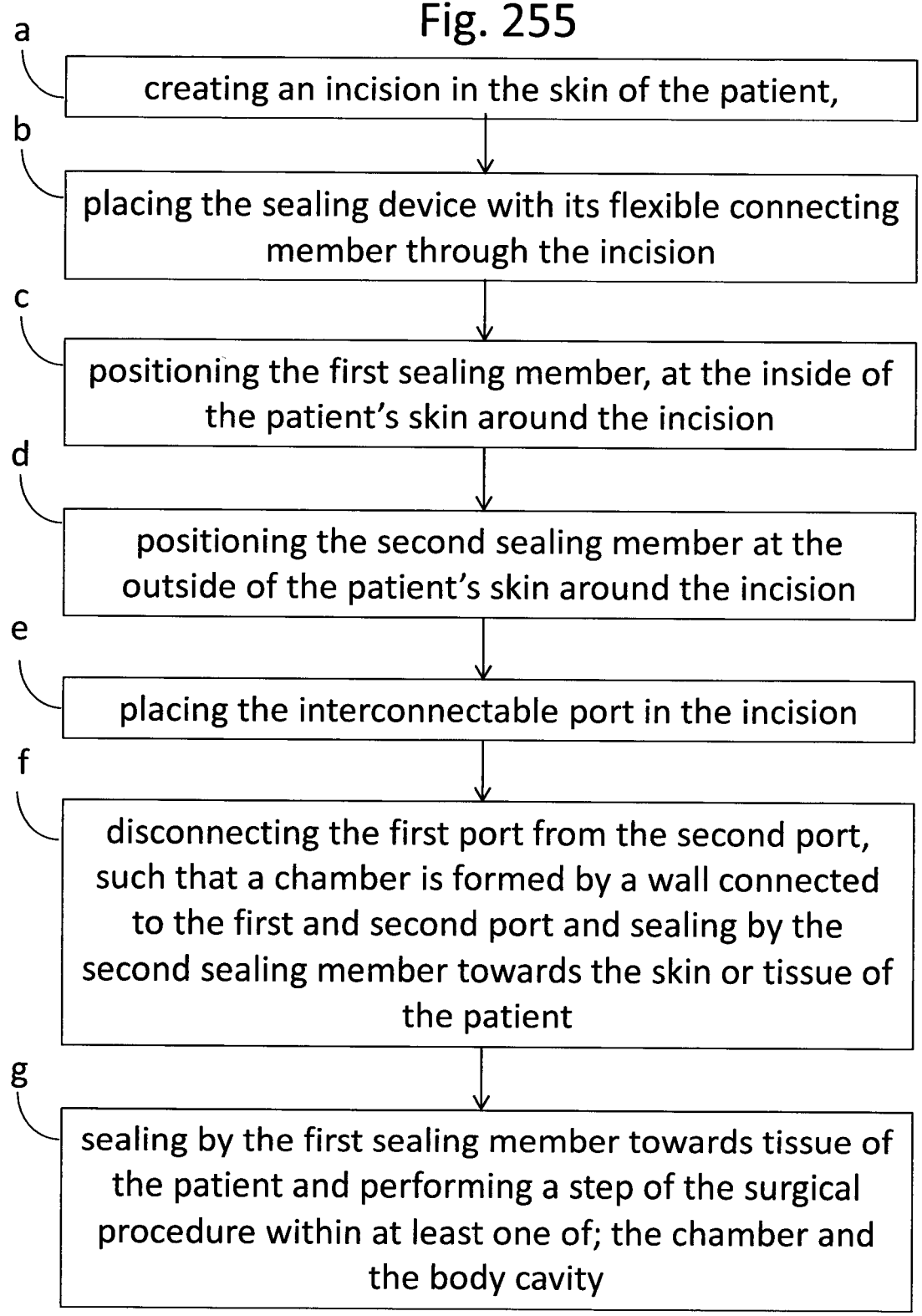

FIG. 255 is a flow chart describing a surgical method to be performed on the body of a patient using a medical device. The medical device comprising a sealing device and an interconnectable port having a first port and a second coupling, the sealing device includes a flexible connecting member and a first and second sealing member. The method comprises: creating an incision in the skin of the patient a, the incision connecting to a body cavity, placing the sealing device with its flexible connecting member through the incision b, positioning the first sealing member at the inside of the patient's skin around the incision being sealingly connected to the flexible connecting member c, positioning the second sealing member at the outside of the patient's skin around the incision d, placing the interconnectable port in the incision e, disconnecting the first port from the second port, such that a chamber is formed by a wall connected to the first and second port and sealing by the second sealing member towards the skin or tissue of the patient f. The method further comprises sealing by the first sealing member towards tissue of the patient and performing a step of the surgical procedure within at least one of the chamber and the body cavity g.

The step of performing a step of the surgical procedure within the chamber may comprise: removing a specimen from the cavity in the body of the patient, transferring the specimen through the first port, and placing the specimen within the chamber of the medical device.

The surgical method may further comprise: reconnecting the first port and second coupling such that the interconnectable port is formed, performing a surgical step in a cavity of the patient, through the interconnectable port.

Figure 256:
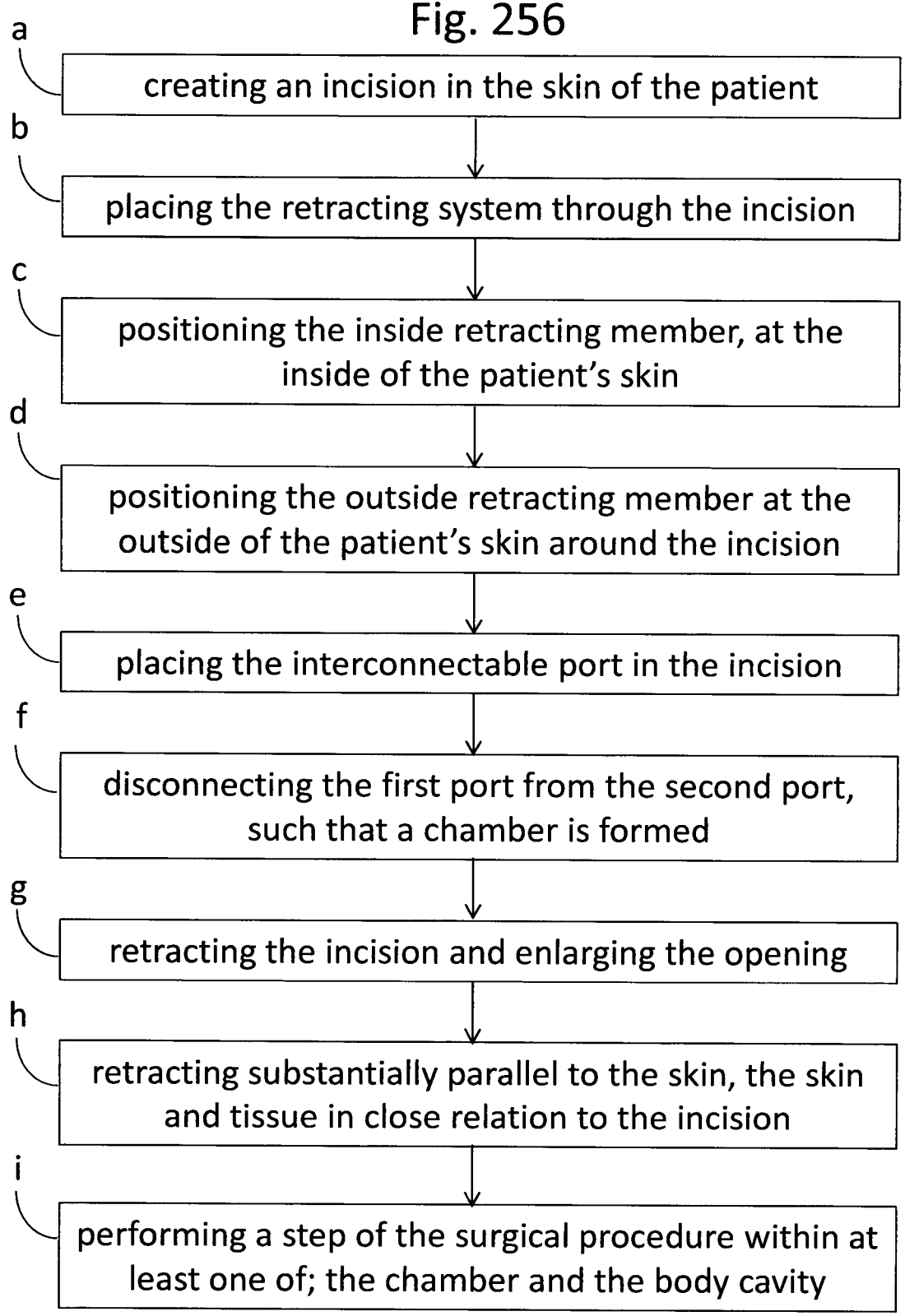

FIG. 256 is a flow chart describing a surgical method to be performed on the body of a patient using a medical device. The medical device comprises a retracting system and an interconnectable port having a first port and a second coupling, the retracting system includes a flexible connecting member and a inside and outside retracting member, the method comprising: creating an incision in the skin of the patient a, connecting to a body cavity, placing the retracting system with its flexible connecting member through the incision b, positioning the inside retracting member, at the inside of the patient's skin c around the incision being sealingly connected to the flexible connecting member, positioning the outside retracting member at the outside of the patient's skin around the incision d, placing the interconnectable port in the incision e, disconnecting the first port from the second port, such that a chamber is formed f by a wall connected to the first and second port, retracting the incision and enlarging the opening g by the flexible connecting member placed onto the inside and outside retracting members, retracting substantially parallel to the skin, the skin and tissue in close relation to the incision h, to enlarge the incision passage from the chamber into the body cavity, during the surgical procedure, and performing a step of the surgical procedure within at least one of; the chamber and the body cavity i.

The step of performing a step of the surgical procedure within the chamber may further comprise: removing a specimen from the cavity in the body of the patient, transferring the specimen through the second port, and placing the specimen within the chamber of the medical device.

The surgical method may further comprise reconnecting the first port and second coupling such that the interconnectable port is formed, performing a surgical step in a cavity of the patient, through the interconnectable port.

Figure 257:
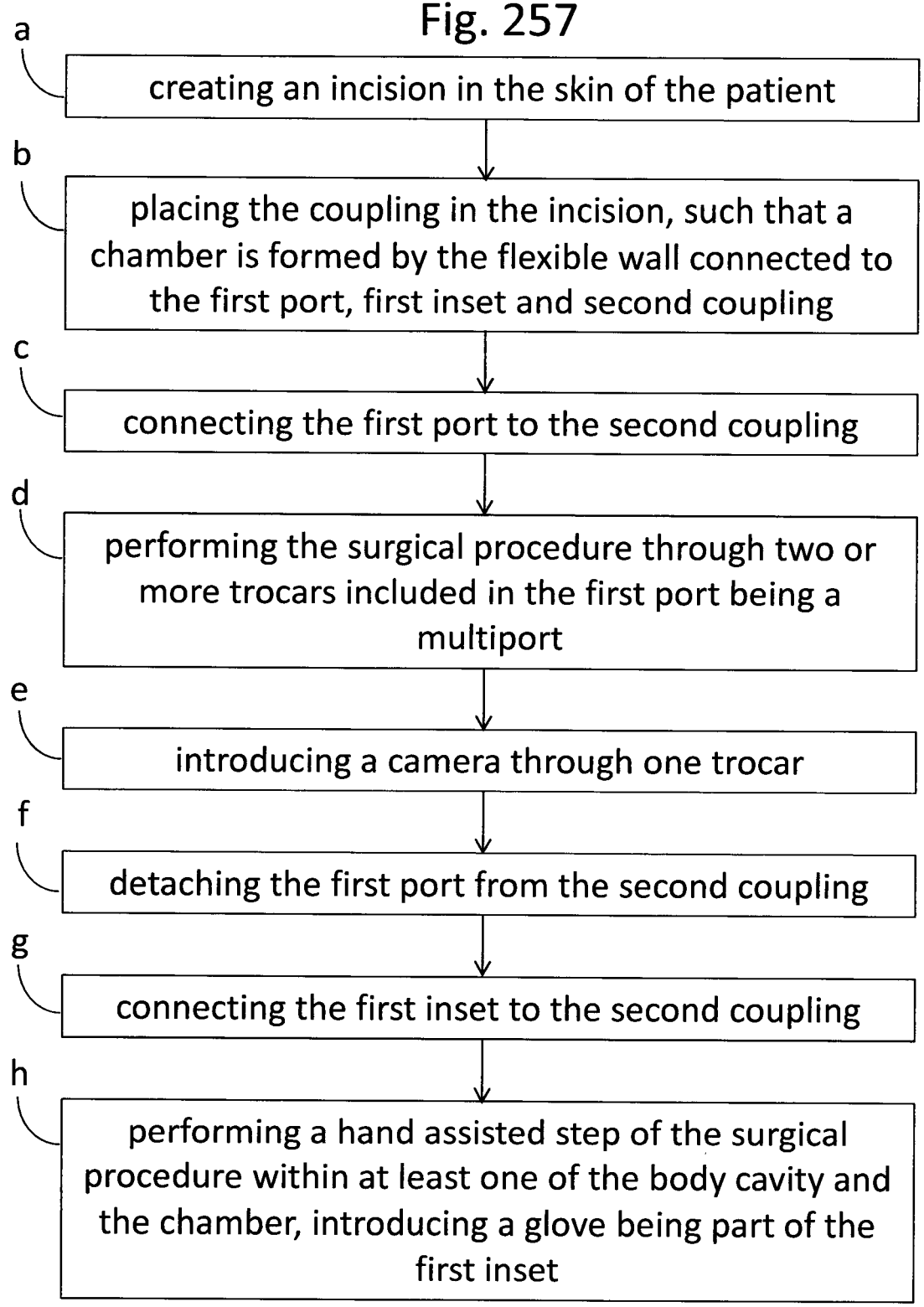

FIG. 257 is a flow chart describing a surgical method to be performed on the body of a patient using a medical device. The medical device comprises a flexible wall, a first inset and an interconnectable port, comprising a first port being a multiport, and a second coupling. The method comprises: creating an incision in the skin of the patient, connecting to a body cavity a, placing the coupling in the incision, such that a chamber is formed by the flexible wall connected to the first port, first inset and second coupling b, connecting the first port to the second coupling c, performing the surgical procedure through two or more trocars included in the first port being a multiport d, introducing a camera through one trocar e, detaching the first port from the second coupling f, connecting the first inset to the second coupling g, and performing a hand assisted step of the surgical procedure within at least one of the body cavity and the chamber, introducing a glove being part of the first inset h.

The medical device may further comprise a sealing device. The method may further comprise: placing a sealing device in connection with at least one of; the flexible wall and the second coupling, to seal between the medical device and the skin or tissue of the patient, sealing the combined volume of the chamber and the body cavity to the outer environment, when the second coupling is open.

The step of performing a step of the surgical procedure within the chamber may comprise: removing a specimen from the cavity in the body of the patient, transferring the specimen through the second coupling, and placing the specimen within the chamber of the medical device.

The surgical method may further comprise: disconnecting the first port or and second coupling such that the interconnectable port is separated and performing a surgical step in the chamber, using the first port or first inset.

Figure 258:
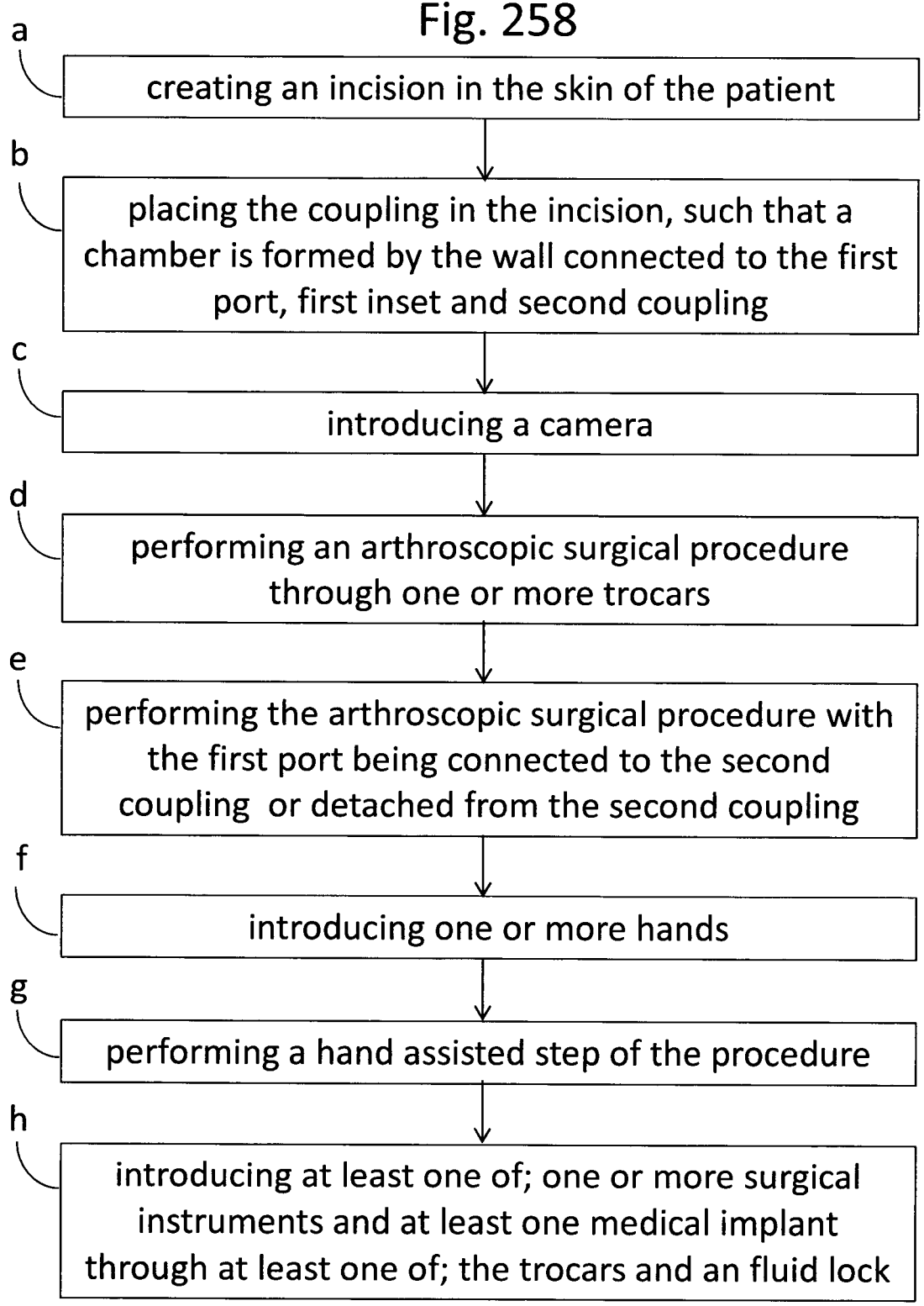
Figure 260A:
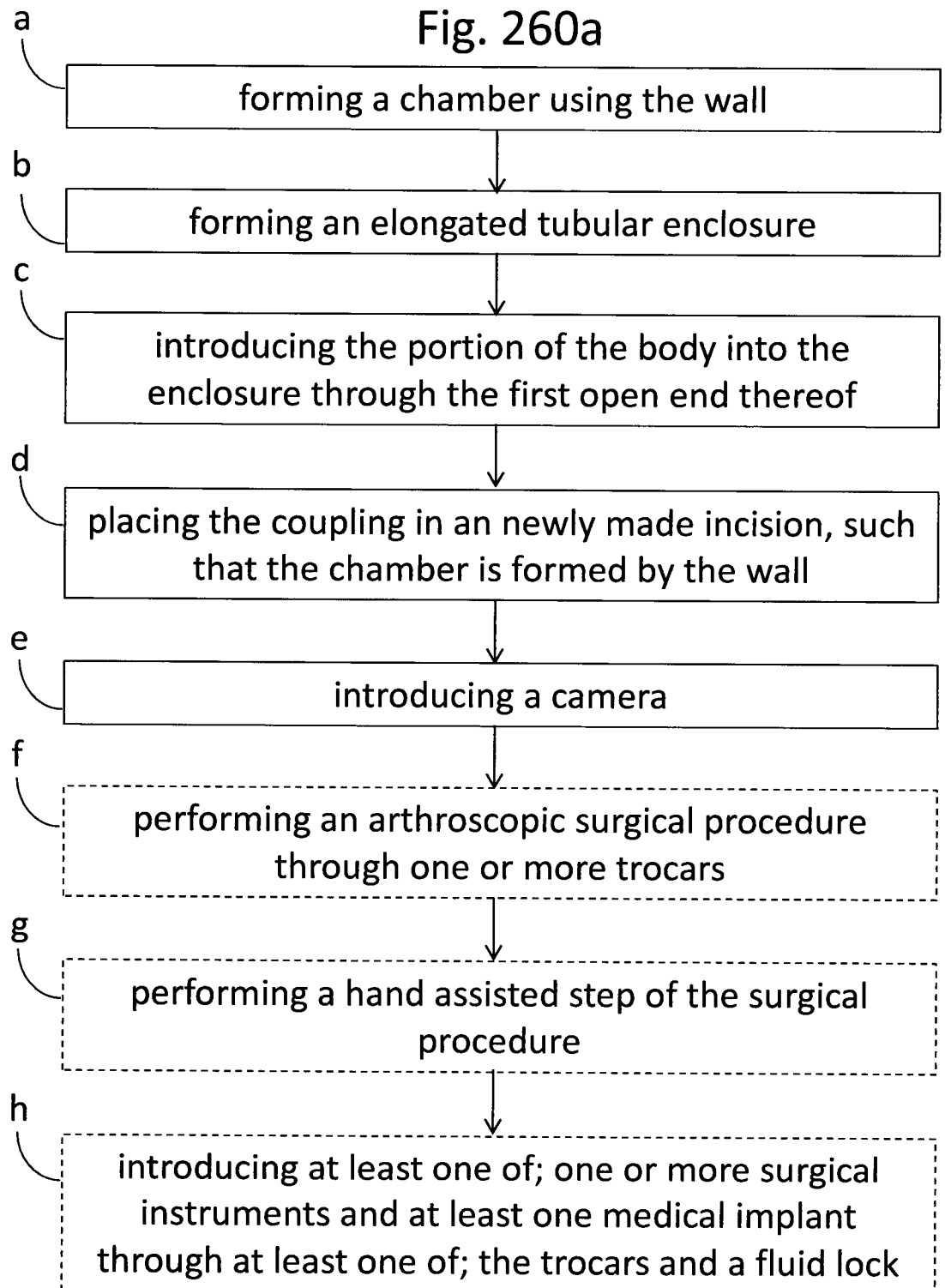
Figure 260C:
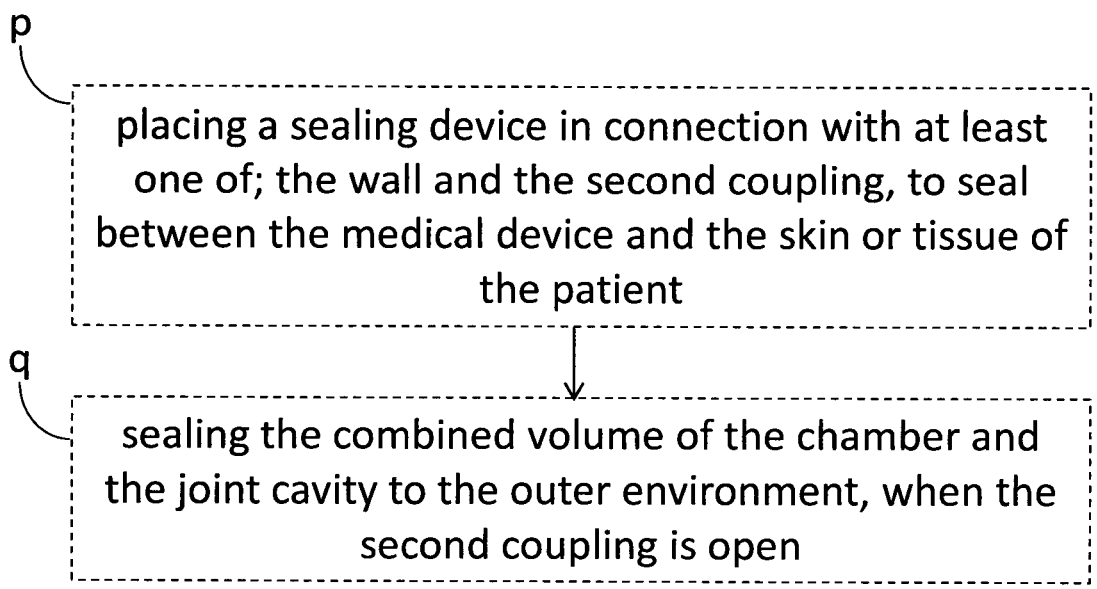

FIG. 258 is a flow chart describing a surgical method using a medical device. The medical device comprises a wall, a first inset and an interconnectable port. The interconnectable port comprises a first port, and a second coupling. The method comprises: creating an incision in the skin of the patient a, connecting to a joint cavity, placing the coupling in the incision b, such that a chamber is formed by the wall connected to the first port, first inset and second coupling, introducing a camera c through at least one of; the first port being a single or multiport including two or more individual ports, an additional port being included in the device, and a trocar introduced into the joint from outside the chamber, performing an arthroscopic surgical procedure through one or more trocars d included in the first port being a single or multiport including two or more individual ports or an additional port being included in the device, performing the arthroscopic surgical procedure with the first port being at least one of connected to the second coupling and detached from the second coupling e, using at least one glove being part of the first inset or one or more additional insets to introduce one or more hands f for assisting the surgical procedure, and performing a hand assisted step of the surgical procedure g within at least one of the joint cavity and the chamber, and: introducing the at least one glove, introducing at least one of; one or more surgical instruments and at least one medical implant through at least one of; the trocars and an fluid lock h as being part of the medical device, for performing at least one of a hand assisted or arthroscopic surgical procedure such as at least one joint surface replacement or other joint surgical procedure.

The medical device may further comprise a sealing device, and the surgical method may further comprise the steps of: placing a sealing device in connection with at least one of; the wall and the second coupling, to seal between the medical device and the skin or tissue of the patient, sealing the combined volume of the chamber and the joint cavity to the outer environment, when the second coupling is open.

The step of performing a step of the surgical procedure within the chamber may comprise: removing a specimen from the cavity in the joint of the patient, transferring the specimen through the second coupling, and placing the specimen within the chamber of the medical device.

The surgical method may further comprise: connecting the first port and second coupling such that the interconnectable port is integrated, performing a surgical step in the chamber, using the integrated first port.

FIG. 259 is a flow chart showing a method of performing hip joint surgery on a patient, using a medical device. The method comprising forming a chamber a using the wall together with or without the patient's body, placing, at least partly on the patient's body, the chamber b encompassing at least part of one step of the hip joint surgery procedure to be performed and maintaining by the chamber a sealed environment for the surgical procedure, sealing with the first sealing device connected to the wall between the wall and the skin or tissue of the patient c, the step of sealing including: sealing at least a part of the hip joint surgery operational field from at least one of: the anal orifice, the urethra orifice and at least part of the perineum region d, while still maintaining the chamber sealed, holding the medical device in place by encircling at least one leg of the patient or the prolongation thereof to be involved in the sealing of the chamber, using at least one of; a first part of the sealing device and a first holding member e, holding the medical device in place by encircling the whole body left to right on the level above the legs selected from at least one of the level of the pelvic, abdominal or thorax region of the patient to further be involved in the sealing of the chamber f, using at least one of a second part of the sealing device and a second holding member, sealing from the medial cranial part of the leg g where it is meeting the inguinal region or its prolongation, further in a cranial direction lateral of the patient's ventro-dorsal mid-sagittal plane on the side where the hip surgery is performed, using a third part of the sealing device at least partly extending in cranial direction until meeting the second part of the sealing device, using at least one of; a third part of the sealing device and a third holding member, the wall interconnecting the first, second and third part of the sealing device to seal the chamber, thus sealing the chamber and exclude from the chamber at least one of the anal orifice, the urethra orifice and at least part of the perineum region h.

The method may further comprise positioning the sealing device such that both of the urethra and the anus is excluded from the enclosed chamber forming the sealed environment.

The medical device may further comprise a second sealing device comprising a first and second sealing member. The method may include the steps of positioning the first sealing member at the inside of the patient's skin around an incision to be performed in the skin, positioning the second sealing member at the outside of the patient's skin around the incision, interconnecting sealingly the first and second sealing members, using a connecting member, sealing with the sealing device between at least one of (a) the second sealing member and the skin of the patient, and (b) the first sealing member and tissue of the patient.

The method may further comprise encircling a portion of the patient's body by at least one of the first and second holding member, by itself or together with the sealing device, and holding the medical device in the desired position.

FIGS. 260a-260d are flow charts showing a method of performing a surgical procedure on a patient using a medical device comprising a wall, a first inset and an interconnectable port. The interconnectable port comprises a first port, and a second coupling. The method comprising: applying a wall at least partially on the patient's body forming a chamber a without or together with the patient's body, maintaining a sealed environment for encompassing part of the surgical procedure to be performed on the patient, forming an elongated tubular enclosure b directly or indirectly by at least a portion of the wall, the elongated tubular enclosure having a first or more open end, the enclosure being adapted to fit at least a portion of the body of the patient, and introducing the portion of the body into the enclosure through the first open end thereof c, placing the coupling in an newly made incision, such that the chamber is formed by the wall d connected to the first port, first inset and second coupling, introducing a camera e through at least one of; the first port being a single or multiport including two or more individual ports, an additional port being included in the device, and a trocar introduced into the joint from outside the chamber, performing at least one of an arthroscopic surgical procedure f through one or more trocars included in the first port being a single or multiport including two or more individual ports or an additional port being included in the device, the first port being at least one of; connected to the second coupling and detached from the second coupling, and a hand assisted step of the surgical procedure g within at least one of the joint cavity and the chamber, introducing the at least one glove being part of the first inset or one or more additional insets to introduce one or more hands for assisting the surgical procedure, and introducing at least one of; one or more surgical instruments and at least one medical implant through at least one of; the trocars and a fluid lock as being part of the medical device h, performing at least one of: a hand assisted or arthroscopic surgical procedure such as at least one of; a joint surface replacement and other joint surgical procedure.

The method can optionally comprise the steps of; exiting the medical device such that the portion of the body is exiting through the second open end thereof.

The elongated tubular enclosure further comprises a third open end, and the method may optionally comprise fitting at least a portion of both the legs or both the arms of the patient in the same enclosure i, the medical device is arranged such that the portion of the body is; entering the enclosure through the first open end thereof j, and exiting the enclosure through both the second and the third open end thereof k.

The method may optionally comprise sealing at the first or more open ends of the tubular enclosure also by the patient's body portion I.

According to one embodiment, the chamber is formed by the wall without involving the patient's body, and the method may further comprise forming the chamber by part of the wall also forming the tubular enclosure, the wall comprises two wall sides of which one is facing the inside of the chamber and the other is facing the tubular enclosure, the method may further comprise forming by the tubular enclosure a second chamber at least partly encompassed by the tubular enclosure m and sealing at the first or more open ends using the patient's body portion n, and forming the second chamber together with the patient's body partly by the wall part facing the tubular enclosure o.

The method may further comprise placing a sealing device in connection with at least one of; the wall and the second coupling, to seal between the medical device and the skin or tissue of the patient p, and sealing the combined volume of the chamber and the joint cavity to the outer environment, when the second coupling is open q.

The surgical method may further comprise the steps of removing a specimen from the cavity in the joint of the patient r, transferring the specimen through the second coupling s, and placing the specimen within the chamber of the medical device t.

The surgical method may further comprise connecting the first port and second coupling such that the interconnectable port is integrated u, and performing a surgical step in the chamber, using the integrated first port v.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way. All examples herein should be seen as part of the general description and therefore possible to combine in any way in general terms.

NUMBERED EMBODIMENTS

In the following, exemplifying numbered embodiments are provided in groups A-AK and numbered within that group. The numbered embodiments are not to be seen as limiting the scope of the invention, which is defined by the appended claims. The reference numerals in the different numbered embodiments are to be seen only as examples of elements in the appended drawings which correspond to elements described in the numbered embodiments.

Numbered Embodiment A1-25

1. A medical device for performing a surgical procedure on a patient, the medical device comprising:
   a wall (01) adapted to be at least partially applied on the patient's body to form a chamber (C), in which a sealed environment can be maintained, the chamber being adapted to encompass part of the surgical procedure to be performed, wherein a portion of the wall directly or indirectly forms an elongated tubular enclosure (04) having a single open end (99), the elongated tubular enclosure extending in the chamber and being adapted to fit a portion of an extremity of the patient inserted into the elongated tubular enclosure through the open end thereof, such that the surgical procedure can be performed on the portion of the patient's extremity, and
   a fluid evacuation system (06;08) adapted to evacuate fluid from the interior of the elongated tubular enclosure, when the portion of the patient's extremity is placed in the enclosure.
2. The medical device according to embodiment 1, wherein the elongated tubular enclosure comprises an adhesive surface (50) adapted to contact the skin (S) of the patient when the fluid has been evacuated from the interior of the elongated tubular enclosure.
3. The medical device according to embodiment 2, wherein a first portion of the elongated tubular enclosure comprises an adhesive surface, wherein the medical device further comprises a separating layer adapted to cover the first portion and wherein the separating layer is adapted to be removed from the first portion, when the adhesive surface is placed onto the skin of the patient.
4. The medical device according to any one of embodiments 1-3, further comprising at least one sealing device (05) adapted to seal between the skin of the extremity of the patient and at least one of: the wall of the medical device and the elongated tubular enclosure.
5. The medical device according to embodiment 4, wherein the sealing device is adapted to exert an adjustable sealing force.
6. The medical device according to any one of embodiments 4 and 5, wherein the sealing device comprises an hydraulically, pneumatically, or electrically powered pressure sealing member (05").
7. The medical device according to any one of embodiments 4-6, wherein the sealing device comprises a vacuum sealing member (05') attached to at least one of; the wall and enclosure and adapted to provide a pressure less than atmospheric pressure to create a vacuum seal between the skin of the patient's extremity and at least one of the wall and elongated tubular enclosure.
8. The medical device according to any one of embodiments 6 and 7, wherein the medical device further comprises at least one of:
   a pressure creating member (67;09) connected to the at least one of; the hydraulically, pneumatically and electrically powered sealing member, and
   a vacuum creating member (08) connected to the vacuum sealing member (05').
9. The medical device according to embodiment 8, wherein the medical device further comprises a monitoring unit (98) adapted to monitor a physiological parameter of the patient, and wherein the pressure creating member (67;08) is adapted to adjust the pressure in a pressure sealing member (05") on the basis of input from the monitoring unit.
10. The medical device according to any one of the preceding embodiments, wherein the wall is at least partially collapsible.
11. The medical device according to embodiment 10, wherein the collapsible wall is adapted to be inflated by a fluid.
12. The medical device according to any one of embodiments 1-11, further comprising at least one glove integrated in the wall such that a surgeon is able to use the glove from outside the chamber to make manual manipulations inside the chamber while maintaining sterile environment in the chamber.
13. The medical device according to any one of the preceding embodiments, further comprising an instrument mount (20) adapted to retain instruments within the chamber.
14. The medical device according to any one of the preceding embodiments, further comprising a body multi-port (48) adapted to be placed inside the chamber in an incision in the skin of the patient.
15. The medical device according to embodiment 14, wherein the body multi port is fixated in the elongated tubular enclosure.
16. The medical device according to any one of the preceding embodiments, further comprising at least one port provided in the wall enabling passage of an object between the chamber and the ambient environment (A), wherein the port comprises at least one of an elastic membrane and a flexible membrane, and wherein the membrane (43) is adapted to, in a non-compressed state, seal between the chamber and the ambient environment, and in a compressed state enable a hand or object to be inserted through the membrane.
17. The medical device according to any one of the preceding embodiments, further comprising a second sealing device having a first sealing member (35) adapted to be positioned at the inside of the patient's skin around an incision cut in the patient's skin made from within the chamber, a second sealing member (37) adapted to be positioned at the outside of the patient's skin inside the chamber, around the incision in the skin of the patient and the elongated tubular enclosure, and a flexible, spring-loaded or elastic connecting member (36) sealingly interconnecting the first and second sealing members, such that the flexible, spring-loaded or elastic connecting member seals between at least one of: the second sealing member and the elongated tubular enclosure, and the first sealing member and tissue of the patient.

18. The medical device according to any one of the preceding embodiments, further comprising at least one inlet (30) provided in the wall for supplying a fluid to the chamber.

19. The medical device according to embodiment 18, further comprising:
    at least one inlet (30) provided in the wall of the medical device or in the skin of the patient for supplying a fluid into at least one of the chamber and the body cavity,
    at least one outlet (31) provided in the wall of the medical device or the skin of the patient for discharging the fluid from at least one of; the chamber and the body cavity, and
    a pump (27) adapted to circulate the fluid from the outlet member to the inlet member.

20. The medical device according to any one of the preceding embodiments,
    wherein the medical device comprises at least one of:
    a filtering unit for filtering fluid supplied to the chamber,
    a sterilization unit for directly or indirectly sterilizing fluid supplied to the chamber,
    a fluid tempering unit adapted change the temperature of fluid supplied to the chamber,
    a filtering unit for filtering fluid and a sterilization unit for directly or indirectly sterilizing fluid supplied to the chamber,
    a filtering unit for filtering fluid supplied to the chamber and a fluid tempering unit adapted change the temperature of fluid supplied to the chamber,
    a sterilization unit for directly or indirectly sterilizing fluid supplied to the chamber and a fluid tempering unit adapted change the temperature of fluid supplied to the chamber, and
    a filtering unit for filtering fluid supplied to the chamber, a sterilization unit for directly or indirectly sterilizing fluid supplied to the chamber and a fluid tempering unit adapted change the temperature of fluid supplied to the chamber.

21. The medical device according to any one of embodiments 18-20, in which the fluid is a liquid.

22. A method embodiment of forming a sterile environment using a medical device comprising a wall (01) adapted to form a chamber (C), in which a sealed environment can be maintained, wherein a portion of the wall directly or indirectly forms an elongated tubular enclosure (04) extending in the chamber, having a single open end (99), the method comprising:
    fitting the medical device on an extremity of a patient, such that the extremity of the patient is placed inside the elongated tubular enclosure,
    evacuating a fluid from the elongated tubular enclosure such that the tubular enclosure fits snuggly against the skin of the extremity.

23. The method according to embodiment 22, further comprising inflating the wall of the medical device such that an inflated chamber is formed.

24. The method according to any one of embodiments 22 and 23, further comprising inflating the elongated tubular enclosure prior to fitting the medical device on the extremity of the patient.

25. The method according to any one of embodiments 22-24, wherein the medical device further comprises a separating layer covering an adhesive surface of a first portion of the elongated tubular enclosure, wherein the method further comprises removing the separating layer from the elongated tubular enclosure prior to fitting the medical device on the extremity of the patient.

Numbered Embodiment B 1-22

1. A medical device for performing a surgical procedure on a patient, when performing an incision in the patient's body for communication with a body cavity, comprising:
    a wall (01) adapted to be applied exteriorly on the patient's body to form a chamber (C), in which a sealed environment can be maintained for encompassing part of the surgical procedure to be performed,
    a sealing device (05) adapted to seal between the medical device and the patient's body, to allow the chamber to be in fluid connection with a cavity in the patient's body, sealed from the ambient environment,
    at least one of:
        at least one first port (17) detachably fixed to the wall for enabling access to and manipulation within the chamber, and
        at least one first inset (42) detachably fixed to the wall and forming part of the chamber, and
    at least one of:
        at least one second port (17) adapted to be detachably fixed to the wall, the second port having a design different from the first port, and
        at least one second inset (42) adapted to be detachably fixed to the wall, the second inset having a design different from the first inset,
    wherein the first port is exchangeable by at least one of: the second port, the first inset and the second inset, and the first inset is exchangeable by at least one of: the first port, the second port and the second inset.

2. The medical device according to embodiment 1, wherein at least at least one of: a part of the first inset, and at least a part of the first port, is detachably fixed to the wall to a coupling (80) in the wall, and wherein both the first port and the first inset is adapted to close the coupling (80) to close the chamber.

3. The medical device according to embodiment 2, wherein the coupling further comprises a valve member (38) adapted to close the coupling when at least a part of the first inset or first port is removed.

4. The medical device according to embodiment 3, wherein the valve member (38) is adapted to remain closed until at least one of: at least a part of an inset, and at least a part of a port, is placed in the first hole in the wall.

5. The medical device according to any one of embodiments 3 and 4, wherein the medical device is further adapted to enable the change of ports or insets, or parts thereof, with all removed parts removed to the ambient environment (A) outside of the chamber.

6. The medical device according to any one of embodiments 1-5, wherein the wall is collapsible and adapted to be inflated by a fluid, and wherein the chamber is adapted to hold a fluid having a pressure exceeding atmospheric pressure.
7. The medical device according to any one of embodiments 1-6, wherein the wall comprises an outer wall and at least one partition wall dividing the chamber into at least a first compartment and a second compartment, wherein the first port or first inset is fixed to the outer wall of the first compartment and the second port or second inset is fixed to the partition wall, whereby the first port, and the first compartment and the second port function as an airlock sluice (18), such that the environment in the second compartment remains closed, also when the first port is detached from the outer wall of the first chamber.
8. The medical device according to any one of embodiments 1-7, further comprising an adhesive surface (50) adapted to provide at least one of: (a) fixation of the wall to the skin of the patient and (b) sealing between the wall and the skin of patient.
9. The medical device according to any one of embodiments 1-8, further comprising an airlock sluice (18) provided in the wall to allow passage of an object between the chamber and the ambient environment (A) while maintaining the sealed environment in the chamber.
10. The medical device according to any one of the preceding embodiments, wherein the first or second port is selected from a group consisting of: laparoscopic ports, hand access ports and multi-ports.
11. The medical device according to any one of the preceding embodiments, wherein the inset is adapted to form part of the wall forming the chamber such that the sealed environment can be maintained in the chamber, and wherein the inset is selected from a group consisting of: indentations, surgical gloves, bellows, elastic membranes and holding devices.
12. The medical device according to any one of the preceding embodiments, wherein the wall comprises a free top wall portion and a bottom wall portion adapted to contact the patient's skin surface to surface, the chamber being defined by the top and bottom wall portions, and wherein the bottom wall portion is adapted to be attached to the patient's body prior to the start of the surgical procedure, such that an incision in the patient can be performed inside the chamber through the bottom wall portion and the skin of the patient.
13. The medical device according to any one of the preceding embodiments, further comprising a body multi-port adapted to be placed inside the chamber in an incision in the skin of the patient, wherein the body multi-port comprises at least two ports adapted to enable passage of an object between the chamber and the inside of the patient's body via the incision.
14. The medical device according to any one of the preceding embodiments, wherein each port comprises at least one of an elastic membrane and a flexible membrane, and wherein the membrane (43) is adapted to, in a non-compressed state, seal between the chamber and the environment outside the chamber, and in a compressed state enable a hand or an object to be inserted through the membrane.
15. The medical device according to any one of the preceding embodiments, further comprising a second sealing device having a first sealing member (35) adapted to be positioned at the inside of the patient's skin around an incision cut in the patient's skin within the chamber, a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
16. The medical device according to any one of the preceding embodiments, wherein the medical device comprises at least one of:
    a filtering unit (26*b*) for filtering fluid supplied to the chamber,
    a sterilization unit (26*a*) for directly or indirectly sterilizing fluid supplied to the chamber,
    a fluid tempering unit (26*c*) adapted change the temperature of fluid supplied to the chamber,
    a filtering unit (26*b*) for filtering fluid and a sterilization unit (26*a*) for directly or indirectly sterilizing fluid supplied to the chamber,
    a filtering unit (26*b*) for filtering fluid supplied to the chamber and a fluid tempering unit (26*c*) adapted change the temperature of fluid supplied to the chamber,
    a sterilization unit (26*a*) for directly or indirectly sterilizing fluid supplied to the chamber and a fluid tempering unit (26*c*) adapted change the temperature of fluid supplied to the chamber, and
    a filtering unit (26*b*) for filtering fluid supplied to the chamber, a sterilization unit (26*a*) for directly or indirectly sterilizing fluid supplied to the chamber and a fluid tempering unit (26*c*) adapted change the temperature of fluid supplied to the chamber.
17. The medical device according to any one of the preceding embodiments, further comprising at least one inlet (30) provided in at least one of the wall and the skin of the patient for supplying a fluid into at least one of the chamber and the body cavity, at least one outlet (30) provided in at least one of the wall and skin of the patient for discharging the fluid from at least one of; the chamber and the body cavity, and a pump (27) adapted to circulate the fluid from the outlet to the inlet.
18. The medical device according to embodiment 17, further comprising a pump adapted to circulate the fluid from the outlet to the inlet.
19. The medical device according to any one of the preceding embodiments, further comprising a body port adapted to be placed in an incision cut in the skin of the patient within the chamber to enable passage between the chamber and the inside of the patient's body.
20. The medical device according to any one of the preceding embodiments, further comprising a retractor (35;36;37) adapted to be placed in an incision cut in the skin of the patient within the chamber and adapted to be continuously open for enabling passage between the chamber and the inside of the patient's body.
21. The medical device according to any one of embodiments 1-20, further comprising an airlock sluice (18) being at least one of; placed between the first port and the body port, and integrated in the first port, having a first valve (38*a*) and second valve (38*b*) for allowing passage of an object from the chamber through the first valve and further through the second valve out to the ambient environment, and vice versa.

22. A method of performing a surgical procedure on a patient using a medical device comprising a wall (01) adapted to be applied exteriorly on the patient's body to form a chamber (C), in which a sealed environment can be maintained for encompassing part of the surgical procedure to be performed, a sealing device (05) adapted to seal between the medical device and the patient's body, to allow the chamber to be in fluid connection with a cavity in the patient's body, sealed from the ambient environment, at least one of: at least one first port (17) detachably fixed to the wall for enabling access to and manipulation within the chamber, and at least one first inset (42) detachably fixed to the wall and forming part of the chamber, and at least one of: at least one second port (17) adapted to be detachably fixed to the wall, the second port having a design different from the first port, and at least one second inset (42) adapted to be detachably fixed to the wall, the second inset having a design different from the first inset, the method comprising the steps of:
  applying a wall (01) on the patient's body to form a chamber (C) together with the patient's body, such that the sealed environment can be maintained,
  applying a sealing device (05) against the skin (S) of the patient, such that sealing is created between the wall of the medical device and the skin of the patient, and at least one of:
    i. exchanging the first port to at least one of: the second port, the first inset and the second inset, and
    ii. exchanging the first inset to at least one of: the first port, the second port and the second inset.

Numbered Embodiment C 1-24

1. A medical device for performing a surgical procedure on a patient, comprising: a wall (01) adapted to be at least partially applied on the patient's body to form a first chamber (C) adapted to hold a first pressure exceeding atmospheric pressure, in which a sealed environment can be maintained for encompassing part of the surgical procedure to be performed, wherein a portion of the wall is adapted to contact the skin (S) of the patient to create a substantially airtight seal between the wall portion and the skin of the patient, to enable an incision to be performed through the skin of the patient in sealed environment such that a fluid connection between a cavity within the patient and the first chamber can be created, the wall being adapted to maintain the seal between the wall portion and the patient's skin substantially airtight after such an incision has been performed, and wherein the medical device is adapted to hold a pressure in the first chamber, allowing fluid connection with the cavity, exceeding atmospheric pressure, when such an incision has been performed during the surgical procedure, wherein the wall comprises:
  i. a first wall part, designed to allow the first pressure to be maintained in the first chamber, and
  ii. a second wall part, designed to allow a second pressure to be maintained in a second chamber adapted to create a sealing between the medical device and the patient's body, and
wherein the first and second pressures are different.

2. The medical device according to embodiment 1, wherein the wall comprises a top portion and a bottom portion, which is adapted to contact and press against the patient's skin, surface to surface, to seal between the bottom wall portion and the skin of the patient, and wherein the first wall part is adapted to allow a pressure in the first chamber exceeding atmospheric pressure.

3. The medical device according to embodiment 2, wherein the bottom wall portion is adapted to be cut through when the incision in the skin of the patient is to be performed in the sealed environment.

4. The medical device according to embodiments 2 or 3, wherein the bottom wall portion comprises an adhesive surface (50) for at least one of: (a) fixating the wall to the patient's skin and (b) sealing between the bottom wall portion and the patient.

5. The medical device according to any one of the preceding embodiments, further comprising at least one glove (02) integrated in the wall such that a surgeon is able to use the glove from outside the chamber to make manual manipulations inside the chamber while maintaining sealed environment in the chamber.

6. The medical device according to any one of the preceding embodiments, further comprising an airlock sluice (18) provided in the wall to allow passage of an object between the chamber and the environment outside of the chamber while maintaining sealed environment in the chamber.

7. The medical device according to any one of the preceding embodiments, wherein the bottom wall portion comprises a vacuum sealing member (05') at least one of attached to and integrated in the wall and adapted to provide a pressure less than atmospheric pressure between the vacuum sealing member and the patient's skin to create a vacuum sealing between the skin and the wall.

8. The medical device according to any one of the preceding embodiments, wherein the wall is at least partially collapsible and adapted to be inflated by a fluid.

9. The medical device according to any one of the preceding embodiments, further comprising at least one non-collapsible transparent window (21) provided in the wall for enabling viewing into the chamber.

10. The medical device according to any one of the preceding embodiments, wherein the volume of the chamber is larger than 100 000 mm3 or larger than 500 000 mm3.

11. The medical device according to any one of the preceding embodiments, further comprising a body multi-port adapted to be placed from inside the chamber in the incision in the skin of the patient, wherein the body multi-port comprises at least two body ports adapted to enable passage of an object between the chamber and the inside of the patient's body.

12. The medical device according to any one of the preceding embodiments, further comprising at least one wall port (17) placed in the wall enabling passage between the chamber and the outside of the chamber, wherein the wall port comprises at least one of an elastic membrane and a flexible membrane, and wherein the membrane (43) is adapted to, in a non-compressed state, seal between the chamber and the environment outside the chamber, and in an compressed state enable a hand or an object to be inserted through the membrane.

13. The medical device according to any one of the preceding embodiments, further comprising a sealing device having a first sealing member (35) adapted to be positioned at the inside of the patient's skin around the incision and a second sealing member (37) adapted to be positioned at outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
14. The medical device according to any one of the preceding embodiments, wherein the medical device comprises at least one of:
    a filtering unit (26b) for filtering fluid supplied to the chamber,
    a sterilization unit (26a) for directly or indirectly sterilizing fluid supplied to the chamber,
    a fluid tempering unit (26c) adapted change the temperature of fluid supplied to the chamber,
    a filtering unit (26b) for filtering fluid and a sterilization unit (26a) for directly or indirectly sterilizing fluid supplied to the chamber,
    a filtering unit (26b) for filtering fluid supplied to the chamber and a fluid tempering unit (26c) adapted change the temperature of fluid supplied to the chamber,
    a sterilization unit (26a) for directly or indirectly sterilizing fluid supplied to the chamber and a fluid tempering unit (26c) adapted change the temperature of fluid supplied to the chamber, and
    a filtering unit (26b) for filtering fluid supplied to the chamber, a sterilization unit (26a) for directly or indirectly sterilizing fluid supplied to the chamber and a fluid tempering unit (26c) adapted change the temperature of fluid supplied to the chamber.
15. The medical device according to any one of the preceding embodiments, further comprising at least one inlet (30) provided in at least one of; the wall and the skin of the patient for supplying a fluid into at least one of the chamber and the body cavity, at least one outlet (31) provided in at least one of; the wall and skin of the patient for discharging the fluid from at least one of; the chamber and the body cavity, and a pump (27) adapted to circulate the fluid from the outlet to the inlet.
16. The medical device according to embodiment 15, further comprising a pump adapted to circulate the fluid from the outlet to the inlet.
17. The medical device according to any one of embodiments 1-16, further comprising a body port (22) adapted to be placed inside the chamber in the incision (I) in the skin of the patient to enable passage between the chamber and the inside of the patient's body.
18. The medical device according to embodiment, 17, further comprising a coupling (80) adapted to detachably attach the body port to the patient's skin to enable exchange and removal of the body port
19. The medical device according to any one of embodiments 1-18, further comprising an airlock sluice (18) being at least one of; between a wall port (17) and a body port (22), and integrated in the first port, having a first valve (38a) and second valve (38b) for allowing passage of objects from the chamber through the first valve and further through the second valve out to the environment outside of the chamber, and vice versa
20. The medical device according to any one of embodiments 1-19, wherein the medical device further comprises a monitoring unit (98) for monitoring at least one of: the blood pressure of the patient, the pressure in the first chamber, and the pressure in the second chamber.
21. The medical device according to embodiment 21, wherein the medical device further comprises a pressure creating member (67) adapted to create the pressure in the second chamber.
22. The medical device according to embodiment 22, wherein the pressure creating member (67) is adapted to receive feedback from the monitoring unit and control the pressure in the second chamber based on the received feedback.
23. The medical device according to any one of embodiments 20-22, wherein the monitoring unit is adapted monitor the blood pressure of the patient and provide feedback to a pressure creating member (67) adapted to control the pressure in the second chamber.
24. A method embodiment of performing a surgical procedure in a sealed environment, the method comprising:
    a. applying a first wall part on the patient's body to form a first chamber (C) together with the patient's body, such that a sealed environment can be maintained,
    b. applying a second wall part on the patient's body to form a second chamber together with the patient's body, for providing a sealing between the ambient environment and the first chamber,
    c. inflating the first chamber with a fluid for creating a first pressure in the first chamber,
    d. inflating the second chamber with a fluid for creating a second pressure in the second chamber, the second chamber being different from the first pressure, and
    e. creating an incision in the patient's body in the sealed environment of the first chamber.

Numbered Embodiment D 1-26

1. A medical device for performing a surgical procedure on a patient comprising:
    a wall (01) adapted to be applied at least partially on the patient's body to form a chamber (C) by itself or together with the body of the patient, in which a sealed environment can be maintained for encompassing part of the surgical procedure to be performed,
    a sealing device (05) adapted to seal between a portion of the wall and the patient's body, when the wall is applied on the patient's body,
    wherein the sealing device comprises a pressurized sealing member (05") adapted to exert a pneumatic, hydraulic or mechanic pressure against the body of the patient such that the chamber is at least substantially sealed from the ambient environment (A) allowing a pressure inside the chamber higher than atmospheric pressure during the surgical procedure, thus the wall sealing device being adapted to seal the chamber, after the medical device has been applied at least partially on the patient's body, when at least one of an incision (I) has been performed in the wall of the chamber contacting the patient's body and an incision has been performed in the skin (S) of the patient forming part of the chamber for creating a fluid connection between the chamber and a cavity in the patient inside the incision, and wherein the sealing device is adapted to remain unaffected by the incision and thus sealing with unaffected force, wherein the sealing device has a closed geometrical configuration, and a holding member (96) adapted to hold the medical device in a direction substantially opposite to the direction of the pressure applied from the sealing device onto the skin of the patient, thus holding the closed geometrical configuration sealingly in contact with the skin of the patient, the medical device further comprising at least one of a pressure adjustment device (93) adapted to adjust the pressure exerted by the sealing device, and a monitoring unit (98) for monitoring at least one of:
the pressure exerted by the sealing device,
the blood flow passing the sealing device, and
the direct or indirect leakage of fluid from the chamber.

2. The medical device according to embodiment 1, wherein the sealing device has a closed geometrical configuration adapted to be applied on a surface of the skin without encircling any limb of the patient.

3. The medical device according to embodiment 1, wherein the sealing device has a closed geometrical configuration adapted to encircle a limb of the patient.

4. The medical device according to embodiment 1, further comprising at least one of;
at least one glove (02) integrated in the wall such that a surgeon is able to use the glove from outside the chamber to make manual manipulations inside the chamber while maintaining sealed environment in the chamber, at least one inset (42), and
at least one inset comprising an integrated glove such that a surgeon is able to use the glove from outside the chamber to make manual manipulations inside the chamber while maintaining sealed environment in the chamber.

5. The medical device according to any one of embodiments 1-4, further comprising an airlock sluice (18) having a first valve (38a) and second valve (38b) for allowing passage of an object from the chamber through the first valve and further through the second valve out to the ambient environment, and vice versa.

6. The medical device according to any one of embodiments 1-5, wherein the wall comprises a bottom portion adapted to contact and press against the patient's skin, to seal between the bottom wall portion and the skin of the patient, and wherein the wall is adapted to allow a pressure in the chamber exceeding atmospheric pressure.

7. The medical device according to embodiment 6, wherein the bottom wall portion is adapted to be cut through when an incision in the skin of the patient is to be performed in sealed environment.

8. The medical device according to embodiment 6 or 7, wherein the bottom wall portion comprises an adhesive surface (50) for at least one of: (a) fixating the wall to the patient's skin and (b) sealing between the bottom wall portion and the patient.

9. The medical device according to any one of the preceding embodiments, further comprising at least one wall port (17) placed in the wall enabling passage between the chamber and the outside of the chamber, wherein the wall port is detachably fixated to the wall such that the wall port can be exchanged by another wall port.

10. The medical device according to any one of the preceding embodiments, wherein the wall is at least partially collapsible.

11. The medical device according to embodiment 10, wherein the collapsible wall is adapted to be inflated by a fluid.

12. The medical device according to any one of the preceding embodiments, further comprising at least one non-collapsible transparent window (21) provided in the wall for enabling viewing into the chamber.

13. The medical device according to any one of the preceding embodiments, wherein the volume of the chamber is larger than 100 000 mm3 or larger than 500 000 mm3.

14. The medical device according to any one of the preceding embodiments, further comprising a body multi-port (48) adapted to be placed from inside the chamber in an incision to be performed in the skin of the patient.

15. The medical device according to any one of the preceding embodiments, further comprising at least one wall port placed in the wall enabling passage between the chamber and the outside of the chamber, wherein the wall port comprises at least one of an elastic membrane and a flexible membrane, and wherein the membrane (43) is adapted to, in a non-compressed state, seal between the chamber and the environment outside the chamber, and in a compressed state enable a hand or an object to be inserted through or by-passing the membrane.

16. The medical device according to any one of the preceding embodiments, further comprising a second sealing device having a first sealing member (35) adapted to be positioned at the inside of the patient's skin around an incision to be performed in the skin of the patient and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.

17. The medical device according to any one of the preceding embodiments, wherein the medical device further comprises at least one of:
a. a filtering unit (26b) for filtering the fluid,
b. a sterilization unit (26a) for directly or indirectly sterilizing the fluid,
c. a fluid tempering unit (26c) adapted change the temperature of the fluid,
d. a filtering unit for filtering the fluid and a sterilization unit for directly or indirectly sterilizing the fluid,
e. a filtering unit for filtering the fluid and a fluid tempering unit adapted change the temperature of the fluid,
f. a sterilization unit for directly or indirectly sterilizing the fluid and a fluid tempering unit adapted change the temperature of the fluid, and
g. a filtering unit for filtering the fluid, a sterilization unit for directly or indirectly sterilizing the fluid and a fluid tempering unit adapted change the temperature of the fluid.

18. The medical device according to any one of the preceding embodiments, wherein the chamber is in fluid connection with the cavity in the patient's body through an incision in the patient's body, when the medical device is applied on the patient's body for performing a surgical procedure, and wherein the medical device further comprises:
a. at least one inlet (30) provided in at least one of:
 i. the wall of the medical device, and
 ii. the skin of the patient for supplying a fluid to at least one of
  1. the chamber, and
  2. the cavity in the patient's body, and
b. at least one outlet (31) provided in at least one of:
 i. the wall of the medical device, and
 ii. the skin of the patient for discharging the fluid from at least one of:
  1. the chamber, and
  2. the body cavity.

19. The medical device according to embodiment 18, further comprising a pump (27) adapted to circulate the fluid from the outlet member to the inlet member.

20. The medical device according to any one of embodiments 1-13 and 15-19, further comprising a closable body port (22) adapted to be placed inside the chamber in an incision to be performed in the skin of the patient to enable passage between the chamber and the inside of the patient's body.

21. The medical device according to embodiment 20, further comprising a coupling (80) adapted to detachably attach the body port to the patient's skin to enable exchange and removal of the body port.

22. The medical device according to any one of embodiments 20-21, comprising a closable wall port placed in a portion of the wall, wherein at least one of
the closeable body port comprises a closeable body multi-port adapted to be placed from inside the chamber in an incision to be performed in the skin of the patient, and wherein the body multiport is adapted to be connected to at least one of
 the wall port, and
 a wall multiport, when the medical device is applied on the patient's body for performing a surgical procedure, and
the closable wall port comprises a closeable wall multiport, wherein the wall multiport is adapted to be connected to at least one of;
 the body port, and
 a body multiport placed in an incision in the patient's body,
when the medical device is applied on the patient's body for performing a surgical procedure.

23. The medical device according to embodiment 5, 14, 15 and 22, wherein the object comprises a tool, a medical device or a human body part.

24. The medical device according to any one of embodiments 1-23, further comprising a pressure adjustment device adapted to hold a pressure within the chamber exceeding atmospheric pressure.

25. The medical device according to embodiment 16-22 and 24, wherein the second sealing device is adapted to be at least one of
 sealingly connected to at least one of the wall and the closable body port, and
 an integrated part of at least one of the wall and the closable body port, the sealing device is further adapted to seal against at least one of the skin and tissue of the patient.

26. A method embodiment of performing a surgical procedure on a patient using a medical device, the method comprising:
a. applying a wall (01) on the skin (S) of the patient to form a chamber (C), in which a sealed environment can be maintained for encompassing part of the surgical procedure to be performed,
b. applying a pressure sealing device (05) adapted to seal between a portion of the wall and the patient's body,
c. applying a holding member (96) adapted to hold the medical device in a direction substantially opposite to the direction of the pressure applied from the sealing device onto the skin of the patient
d. injecting a fluid into the chamber, such that the pressure inside the chamber exceeds atmospheric pressure,
e. creating an incision (I) in the skin (S) of the patient in the sealed environment of the chamber, and
f. at least one of:
 i. adjusting the pressure exerted by the sealing device (05), and
 ii. monitoring at least one of:
  1. the pressure exerted by the sealing device,
  2. the blood flow passing the sealing device, and
  3. the direct or indirect leakage of fluid from the chamber.

Numbered Embodiment E 1-28

1. A medical device for performing a surgical procedure on a patient, the medical device comprising:
a wall (01) adapted to be at least partially applied on the patient's body and further adapted to form a chamber (C) alone or together with the patient's body, in which a sealed environment can be maintained for encompassing part of the surgical procedure to be performed, wherein a portion of the wall is adapted to be in contact with the patient's skin, and
at least one wall inset (42) or wall port (17) attached to the wall and adapted to enable manipulation within the chamber, wherein the wall inset (42) or wall port (17) is displaceable between:
 a first position, in which the inset or wall port is fixated relative to the skin or tissue of the patient, and
 a second position, more remote from the patient's skin than the first position, in which the inset or wall port is moveable relative to the skin or tissue of the patient.

2. The medical device according to embodiment 1, wherein the wall inset or wall port comprises a first coupling (80) adapted to fixate the inset or wall port directly or indirectly to the skin or tissue of the patient.

3. The medical device according to embodiment 1, wherein the wall comprises a first and second coupling (80*a*;80*b*), and wherein the first coupling is positioned at the first position, and wherein the second coupling is adapted to connect to the first coupling for locking the wall inset or wall port in the first position.

4. The medical device according to any one of the preceding embodiments, wherein the medical device further comprises a body inset or body port adapted to be mounted in another wall portion or the skin or tissue of the patient, wherein the first coupling is adapted to be positioned in connection with the body port or body inset, and wherein the wall port and the body port is adapted to form an integrated port when the first and second coupling are connected in the first position.

5. The medical device according to embodiment 4, wherein the body port comprises a second coupling adapted to connect to the first coupling.

6. The medical device according to any one of the preceding embodiments, wherein at least one of the wall port and the body port is closeable.

7. The medical device according to embodiment 6, wherein at least one of the wall port and the body port comprises at least one of an elastic membrane and a flexible membrane, and wherein the membrane (43) is adapted to, in a non-expanded state, provide a seal, and in an expanded state, enable a hand or an object to be inserted through the membrane.

8. The medical device according to any one of the preceding embodiments, wherein the wall is at least partially flexible to enable the wall to flex when the wall inset or wall port is moved between the first and second positions.

9. The medical device according to any one of embodiments 1-8, wherein the chamber assumes a first volume, when the wall inset or wall port is in the first position, and assumes a second volume larger than the first volume, when the inset or wall port is in the second position.

10. The medical device according to any one of the preceding embodiments, wherein at least one of; the wall inset and body inset, comprises at least one glove (02), such that a surgeon is able to use the glove from outside the chamber to make manual manipulations inside the chamber while maintaining the sealed environment in the chamber.

11. The medical device according to any one of the preceding embodiments, wherein at least one of the wall inset or at least part of the wall port is detachably fixed to the wall across a hole formed in the wall, and wherein the wall port comprises a valve (38) for closing the hole in the wall port to close the chamber.

12. The medical device according to any one of the preceding embodiments, wherein the wall is collapsible and adapted to be inflated by a fluid.

13. The medical device according to embodiment 12, wherein the wall is adapted to hold a fluid having a pressure exceeding atmospheric pressure.

14. The medical device according to any one of the preceding embodiments, further comprising an airlock (18) or liquid lock provided in the wall for allowing passage of an object between the chamber and the environment outside of the chamber or vice versa.

15. The medical device according to any one of the preceding embodiments, wherein the portion of the wall adapted to be applied on the patient's body when the surgical procedure is to be performed, further comprises a vacuum sealing device (05') adapted to hold a pressure less than atmospheric pressure between the wall portion and the patient's skin to seal between the wall portion and the patient's skin.

16. The medical device according to embodiment 15, wherein the vacuum sealing member is adapted to create a substantially airtight seal between the wall portion and the skin of the patient, to enable an incision to be performed through the skin of the patient in sealed environment such that a fluid connection between a cavity within the patient and the chamber can be created.

17. The medical device according to any one of the preceding embodiments, wherein the portion of the wall adapted to be applied on the patient's body when the surgical procedure is to be performed further comprises a pressure sealing member (05") adapted to hold a pressure above atmospheric pressure between the wall portion and the patient's skin to seal between the wall portion and the patient's skin.

18. The medical device according to any one of the preceding embodiments, further comprising a body multi-port adapted to be placed from inside the chamber in an incision to be performed in the skin of the patient, wherein the body multi-port is adapted to enable passage of an object between the chamber and a cavity in the patient's body.

19. The medical device according to any one of the preceding embodiments, wherein at least one of the wall port and body port comprises a further sealing device having a first sealing member adapted to be positioned at the inside of the patient's skin around an incision to be performed in the skin and a second sealing member adapted to be positioned at the outside of the patient's skin around the incision, and a spring-loaded or elastic connecting member, sealingly interconnecting the first and second sealing members, whereby the spring-loaded or elastic connecting member seals between at least one of: (a) the second sealing member and the skin of the patient, and (b) the first sealing member and tissue of the patient.

20. The medical device according to any one of the preceding embodiments, wherein the chamber is in fluid connection with the cavity in the patient's body through an incision in the patient's body, when the medical device is applied on the patient's body for performing a surgical procedure, and wherein the medical device further comprises:
   a. at least one inlet (30) provided in at least one of:
      i. the wall of the medical device, and
      ii. the skin of the patient for supplying a fluid to at least one of
         1. the chamber, and
         2. the cavity in the patient's body, and
   b. at least one outlet (30) provided in at least one of:
      i. the wall of the medical device, and
      ii. the skin of the patient for discharging the fluid from at least one of:
         1. the chamber, and
         2. the body cavity.

21. The medical device according to embodiment 20, further comprising a pump (27) adapted to circulate the fluid from the outlet to the inlet.

22. The medical device according to any one of the preceding embodiments, wherein the medical device comprises at least one of:
   a filtering unit (26*b*) for filtering fluid supplied to the chamber,
   a sterilization unit (26*a*) for directly or indirectly sterilizing fluid supplied to the chamber,
   a fluid tempering unit (26*c*) adapted change the temperature of fluid supplied to the chamber,
   a filtering unit (26*b*) for filtering fluid and a sterilization unit (26*a*) for directly or indirectly sterilizing fluid supplied to the chamber,
   a filtering unit (26*b*) for filtering fluid supplied to the chamber and a fluid tempering unit (26*c*) adapted change the temperature of fluid supplied to the chamber, a sterilization unit (26*a*) for directly or indirectly sterilizing fluid supplied to the chamber and a fluid tempering unit (26*c*) adapted change the temperature of fluid supplied to the chamber, and a filtering unit (26*b*) for filtering fluid supplied to the chamber, a sterilization unit (26*a*) for directly or indirectly sterilizing fluid supplied to the chamber and a fluid tempering unit (26*c*) adapted change the temperature of fluid supplied to the chamber.

23. A surgical method embodiment for performing a laparoscopic procedure in a sealed environment, the surgical method comprising:
    a. placing a medical device comprising a wall in connection with the patient, such that a portion of the wall of the medical device sealingly connects to the skin of the patient, such that a chamber is formed by the wall of the medical device and the skin of the patient, wherein the wall further comprises an wall inset or wall port,
    b. moving the wall inset or wall port from a first position, in which the wall inset or wall port is fixated relative to the skin or tissue of the patient to a second position, more remote from the patient's skin than the first position, in which the wall inset or wall port is moveable relative to the skin or tissue of the patient.
24. The surgical method according to embodiment 23, further comprising the step of making an incision in the skin of the patient's body creating a fluid connection between the chamber and a cavity in the patient's body.
25. The surgical method according to embodiment 24, further comprising placing a portion of the wall inset or wall port in the incision made in the skin of the patient
26. The surgical method according to any one of embodiments 23-25, further comprising sealing the wall portion to the skin of the patient by applying a negative pressure to a sealing device.
27. The surgical method according to any one of embodiments 23-26, further comprising inflating a cavity in the patient using a laparoscopic fluid, such that a cavity enabling visual inspection within the body of the patient is formed.
28. The surgical method according to any one of embodiments 23-27, further comprising exchanging the wall inset or wall port to an additional inset or port for performing an operational step in the chamber of the medical device or in the cavity in the patient.

Numbered Embodiment F 1-23

1. A medical device for performing an endoscopic surgical procedure on a patient, the medical device comprising:
    a wall (01) adapted to at least partially be applied on the patient's body to form a chamber (C) by itself or together with the patient's body, in which a sealed environment can be maintained for encompassing part of the surgical procedure to be performed, wherein a wall portion is adapted to contact the patient's skin (S) when the surgical procedure is performed, and
    a vacuum sealing member (05') adapted to hold a pressure in a second chamber between the skin and the wall, or in a second chamber between the skin and the wall, contacting the skin of the patient, the pressure being:
    different than the pressure in the chamber, and
    less than atmospheric pressure, for providing sealing between the wall portion and the patient's skin.
2. The medical device according to embodiment 1, wherein the vacuum sealing member is adapted to create a substantially airtight seal between the wall portion and the skin of the patient, to enable an incision to be performed through the skin of the patient in the sealed environment for forming a fluid connection between a cavity within the patient and the chamber.
3. The medical device according to any one of embodiments 1 and 2, wherein the medical device comprises a plurality of vacuum sealing members positioned consecutively for enhancing the sealing effect provided by the vacuum sealing.
4. The medical device according to embodiment 3, wherein the multiple vacuum sealing members comprises vacuum sealing grooves adapted to be placed consecutively.
5. The medical device according to any one of the preceding embodiments, further comprising an airlock sluice (18) provided in the wall for allowing passage of an object between the chamber and the environment outside of the chamber when the vacuum sealing member is sealing between the skin of the patient and the wall portion.
6. The medical device according to any one of the preceding embodiments, wherein the wall is at least partially collapsible.
7. The medical device according to embodiment 6, wherein the collapsible wall is adapted to be inflated by a fluid.
8. The medical device according to embodiment 7, further comprising at least one non-collapsible transparent window (21) positioned in the collapsible wall such that the window enables accurate viewing into the chamber where the surgical procedure is to be performed, when the wall is inflated.
9. The medical device according to any one of the preceding embodiments, wherein the medical device is adapted to hold a pressure within the chamber exceeding atmospheric pressure.
10. The medical device according to any one of the preceding embodiments, further comprising at least one of
    at least one glove (02) integrated in the wall such that a surgeon is able to use the glove from outside the chamber to make manual manipulations inside the chamber while maintaining sealed environment in the chamber, at least one inset (42), and
    at least one inset comprising a glove such that a surgeon is able to use the glove from outside the chamber to make manual manipulations inside the chamber while maintaining sealed environment in the chamber.
11. The medical device according to any one of the preceding embodiments, further comprising an adhesive surface (50) adapted to provide at least one of: (a) fixation of at least one of the wall and enclosure to the skin of the patient, and (b) sealing between the skin of the patient and at least one of the wall and enclosure.
12. The medical device according to any one of the preceding embodiments, further comprising at least one wall port (17) placed in the wall enabling passage between the chamber and the outside of the chamber, wherein the wall port is detachably fixated to the wall such that the wall port can be exchanged by another wall port or inset.

13. The medical device according to any one of the preceding embodiments, further comprising a body multi-port (48) adapted to be placed from inside the chamber in an incision to be performed in the skin of the patient, wherein the body multi-port is adapted to enable passage of an object between the chamber and the inside of the patient's body.
14. The medical device according to any one of the preceding embodiments, further comprising at least one wall port placed in the wall enabling passage between the chamber and the outside of the chamber, wherein the wall port comprises at least one of an elastic membrane and a flexible membrane, and wherein the membrane (43) is adapted to, in a non-compressed state, seal between the chamber and the environment outside the chamber, and in a compressed state enable a hand or an object to be inserted through the membrane.
15. The medical device according to any one of the preceding embodiments, further comprising a second sealing device having a first sealing member (35) adapted to be positioned at the inside of the patient's skin around an incision to be performed in the skin and a second sealing member (37) adapted to be positioned at outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
16. The medical device according to any one of the preceding embodiments, wherein the medical device comprises at least one of:
    a filtering unit for filtering fluid supplied to the chamber,
    a sterilization unit for directly or indirectly sterilizing fluid supplied to the chamber,
    a fluid tempering unit adapted change the temperature of fluid supplied to the chamber,
    a filtering unit for filtering fluid and a sterilization unit for directly or indirectly sterilizing fluid supplied to the chamber,
    a filtering unit for filtering fluid supplied to the chamber and a fluid tempering unit adapted change the temperature of fluid supplied to the chamber,
    a sterilization unit for directly or indirectly sterilizing fluid supplied to the chamber and a fluid tempering unit adapted change the temperature of fluid supplied to the chamber, and
    a filtering unit for filtering fluid supplied to the chamber, a sterilization unit for directly or indirectly sterilizing fluid supplied to the chamber and a fluid tempering unit adapted change the temperature of fluid supplied to the chamber.
17. The medical device according to any one of the preceding embodiments, wherein the chamber is in fluid connection with the cavity in the patient's body through an incision in the patient's body, when the medical device is applied on the patient's body for performing a surgical procedure, and wherein the medical device further comprises:
    a. at least one inlet (30) provided in at least one of:
        i. the wall of the medical device, and
        ii. the skin of the patient for supplying a fluid to at least one of
            3. the chamber, and
            4. the cavity in the patient's body, and
    b. at least one outlet (31) provided in at least one of:
        i. the wall of the medical device, and
        ii. the skin of the patient for discharging the fluid from at least one of
            5. the chamber, and
            6. the body cavity.
18. The medical device according to embodiment 17, further comprising a pump (27) adapted to circulate the fluid from the outlet member to the inlet member.
19. The medical device according to any one of the preceding embodiments, further comprising a body port (22) adapted to be placed inside the chamber in an incision to be performed in the skin of the patient to enable passage between the chamber and the inside of the patient's body.
20. The medical device according to embodiment 15-19, wherein the second sealing device is adapted to be at least one of
    sealingly connected to at least one of; the wall and the closable body port, and
    an integrated part of at least one of; the wall and the closable body port, the sealing device is further adapted to seal against at least one of the skin and tissue of the patient.
21. The medical device according to any one of the preceding embodiments, wherein at least one of;
    the closeable body port comprises a closeable body multi-port adapted to be placed from inside the chamber in an incision to be performed in the skin of the patient, and wherein the body multiport is adapted to be connected to at least one of;
        the wall port, and
        a wall multiport, when the medical device is applied on the patient's body for performing a surgical procedure, and
    the closable wall port comprises a closeable wall multiport, wherein the wall multiport is adapted to be connected to at least one of;
        the body port, and
        a body multiport placed in an incision in the patient's body, when the medical device is applied on the patient's body for performing a surgical procedure.
22. A method embodiment of performing a surgical procedure on a patient using a medical device, the method comprising:
    a. applying a wall (01) on the skin (S) of the patient to form a chamber (C), in which a sealed environment can be maintained for encompassing part of the surgical procedure to be performed,
    b. applying a vacuum sealing member (05') adapted to hold a pressure in a second chamber between the skin and the wall,
    c. evacuating fluid from the vacuum sealing member such that a negative pressure is created in the second chamber between the skin and the wall, the pressure being different than the pressure in the chamber, and less than atmospheric pressure, such that a vacuum seal is provided,
    d. creating an incision (I) in the skin of the patient, in the sealed environment of the chamber.
23. The method according to embodiment 22, further comprising injecting a fluid into the chamber, such that a pressure in the chamber exceeding atmospheric pressure is created.

Numbered Embodiment G 1-26

1. A medical device for performing a surgical procedure on a patient, comprising:
   a wall (01) adapted to be at least partially applied on the patient's body to form a chamber, in which a sealed environment can be maintained for encompassing part of the surgical procedure to be performed,
   a closeable wall port (17) placed in a portion of the wall,
   a closeable body port (22) placed in a second portion of the wall and adapted to be placed in an incision in the patient's body, and
   a sealing device (05) adapted to be at least one of
      sealingly connected to at least one of the wall and the closable body port, and
      an integrated part of at least one of; the wall and the closable body port,
   the sealing device further being adapted to seal against at least one of the skin and tissue of the patient,
   wherein the wall, wall port and body port are adapted to together form an airlock sluice (18) between a cavity in the body of the patient and the ambient environment (18), when the surgical procedure is performed.
2. The medical device according to embodiment 1, wherein the wall and body ports are positioned relative to each other such that an elongated object is longitudinally displaceable through the wall and body ports.
3. The medical device according to any one of embodiments 1-2, wherein the wall port is displaceable between a first position and a second position, wherein the second position is situated more remote from the body port.
4. The medical device according to any one of the preceding embodiments, wherein the wall port is adapted to be at least one of:
   a. connected to the body port,
   b. abutting the body port,
   c. locked to the body port,
   d. formed into an integrated port together with the body port.
5. The medical device according to any one of the preceding embodiments, wherein at least one of; the closable wall port and closable body port comprises a penetratable self sealing gel, such that an object or hand can be inserted through the wall port while maintaining the sealed environment.
6. The medical device according to any one of the preceding embodiments, further comprising at least one of an additional body port, additional body inset, additional wall port and an additional wall inset, wherein at least one of the wall port and body port is exchangeable by the additional port or additional inset.
7. The medical device according to any one of the preceding embodiments, wherein the chamber is adapted to hold a fluid having a pressure exceeding atmospheric pressure.
8. The medical device according to any one of the preceding embodiments, wherein the wall portion adapted to be applied on the patient's body, when the surgical procedure is to be performed, further comprises at least one of; a vacuum sealing member (05') adapted to hold a pressure less than atmospheric pressure between the wall portion and the patient's skin (S) to seal between the wall portion and the patient's skin, and a pressure sealing member (05") adapted to hold a pressure above atmospheric pressure between the wall and the patient's skin to seal between the wall and the patient's skin.
9. The medical device according to embodiment 8, wherein the vacuum sealing member (05') or pressure sealing member (05") is adapted to create a substantially airtight seal between the wall portion and the skin of the patient, to enable an incision to be performed through the skin of the patient in sealed environment such that a fluid connection between a cavity within the patient and the chamber can be created.
10. The medical device according to any one of the preceding embodiments, further comprising at least one of an airlock placed separate from the wall port and an airlock integrated in the wall port for allowing passage of objects between the chamber and the outside of the chamber.
11. The medical device according to any one of the preceding embodiments, wherein at least one of
    the closeable body port comprises a closeable body multi-port adapted to be placed from inside the chamber in an incision to be performed in the skin of the patient, and wherein the body multiport is adapted to be connected to at least one of;
    the wall port, and
    a wall multiport, when the medical device is applied on the patient's body for performing a surgical procedure, and
    the closable wall port comprises a closeable wall multiport, wherein the wall multiport is adapted to be connected to at least one of;
    the body port, and
    a body multiport placed in an incision in the patient's body, when the medical device is applied on the patient's body for performing a surgical procedure.
12. The medical device according to any one of the preceding embodiments, wherein at least one of; the closable wall port and closable body port, comprises at least one of an elastic membrane and a flexible membrane, and wherein the membrane (43) is adapted to, in a non-compressed state, seal between the chamber and the ambient environment, and in a compressed state enable a hand or an object to be inserted through the membrane.
13. The medical device according to any one of the preceding embodiments, wherein the sealing device comprising a first sealing member (35) adapted to be positioned at the inside of the patient's skin around an incision to be performed in the skin and a second sealing member (37) adapted to be positioned at outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
14. The medical device according to any one of the preceding embodiments, wherein the medical device comprises at least one of:
    a filtering unit (26b) for filtering fluid supplied to the chamber,
    a sterilization unit (26a) for directly or indirectly sterilizing fluid supplied to the chamber,
    a fluid tempering unit (26c) adapted change the temperature of fluid supplied to the chamber, a filtering unit (26b) for filtering fluid and a sterilization unit (26a) for directly or indirectly sterilizing fluid supplied to the chamber, a filtering unit (26b) for filtering fluid supplied to the chamber and a fluid tempering unit (26c) adapted change the temperature of fluid supplied to the chamber, a sterilization unit (26a) for directly or indirectly sterilizing fluid supplied to the chamber and a fluid tempering unit (26c) adapted change the temperature of fluid supplied to the chamber, and a filtering unit (26b) for filtering fluid supplied to the chamber, a sterilization unit (26a) for directly or indirectly sterilizing fluid supplied to the chamber and a fluid tempering unit (26c) adapted change the temperature of fluid supplied to the chamber.

15. The medical device according to any one of the preceding embodiments, wherein the chamber is in fluid connection with the cavity in the patient's body through an incision in the patient's body, when the medical device is applied on the patient's body for performing a surgical procedure, and wherein the medical device further comprises:
   a. at least one inlet (30) provided in at least one of:
      i. the wall of the medical device, and
      ii. the skin of the patient for supplying a fluid to at least one of
         1. the chamber, and
         2. the cavity in the patient's body, and
   b. at least one outlet (30) provided in at least one of:
      i. the wall of the medical device, and
      ii. the skin of the patient for discharging the fluid from at least one of:
         1. the chamber, and
         2. the body cavity.

16. The medical device according to embodiment 15, further comprising a pump 27 adapted to circulate the fluid from the outlet to the inlet.

17. The medical device according to any one of the preceding embodiments, wherein the closeable body port is adapted to be placed in an incision (I) performed in the skin of the patient to enable passage between the chamber and a cavity in the patient's body.

18. The medical device according to any one of embodiments 1-17, wherein the body port is adapted to be fitted in the patient's skin after the incision has been made, before the medical device is applied on the patient's body.

19. The medical device according to any one of embodiments 1-18, wherein the closeable wall port and the closeable body port are connected by a portion of the wall, and wherein the closeable wall and body ports can be moved in relation to each other whilst being connected by means of the wall portion.

20. A surgical method embodiment for performing a laparoscopic procedure in a sealed environment, the surgical method comprising:
   a. making an incision in the patients skin,
   b. providing a medical device comprising a wall connected both to a closable wall port and a closable body port, such that a chamber is formed by the wall and the closable wall port and the closable body port,
   c. placing the closeable body port in the incision made in the skin of the patient, such that a fluid connection is created between the chamber and a cavity in the patient,
   d. providing a sealing device being at least one of;
      i. connected to at least one of: the body port or the wall, and
      ii. integrated in at least one of the body port or the wall, to sealingly connect between,
   at least one of; the body port placed in the incision and the wall, and
   at least one of body tissue and skin of the patient.

21. A surgical method embodiment for performing a laparoscopic procedure in a sealed environment, the surgical method comprising:
   a. making an incision in the patients skin,
   b. providing a medical device comprising a wall, a closable wall port and a closable body port in connection with the patient,
   c. placing the body port in the incision,
   d. forming a chamber by the wall, the closable wall and body port, allowing communication with a cavity in the patient's body
   e. sealing the medical device to the skin or tissue of the patient, to form an sealed environment, including the chamber and the body cavity,
   f. moving the closable wall port, adapted to connect to the body port, connecting to the body port, and
   g. forming an integrated port.

22. The surgical method according to any one of embodiments 20-21, further comprising inflating the cavity in the patient using a laparoscopic fluid, such that a cavity enabling visual inspection within the body of the patient is formed.

23. The surgical method according to any one of embodiments 20-22, further comprising exchanging the closeable body port to an additional port or inset for performing an operational step in the cavity in the body of the patient.

24. The surgical method according to any one of embodiments 20-23, further comprising exchanging the closeable wall port to an additional port or inset for performing an operational step in the chamber of the medical device.

25. A method embodiment of transferring an object from the ambient environment to a cavity in a patient during a surgical procedure using a medical device according to embodiment 1, the method comprising:
   a. transferring the object through the closable wall port, placed in the wall of the medical device, into a chamber formed by the wall of the medical device and the closable wall and body port,
   b. transferring the object through the closable body port placed in the incision made in the patient's skin and into the cavity in the patient.

26. A method embodiment of forming an airlock sluice between the ambient environment and a cavity in a patient, the method comprising:
   a. providing a medical device comprising a wall connected to both a wall port and a body port
   b. making an incision in the patients skin connected to a body cavity,
   c. placing the body port in the incision,
   d. forming a chamber with the wall of the medical device, the closable body port, and the closable wall port, allowing communication with the cavity, and thus
   e. forming a an airlock sluice.

Numbered Embodiment H 1-19

1. A medical device for performing a surgical procedure on a patient, comprising:

a. a wall (01) adapted to be at least partially applied on the patient's body to form a first chamber (C), in which a sealed environment can be maintained for encompassing part of the surgical procedure to be performed, wherein a portion of the wall is adapted to be in contact with the skin (S) of the patient when the surgical procedure is performed, b. a body port (22) positioned in an incision in the skin of the patient adapted to be placed between the first chamber and a body cavity, and c. an airlock sluice (18) positioned in the wall of the medical device, the airlock sluice comprising: a first valve (38a), a second valve (38b), and a second chamber located between the valves, wherein the airlock sluice is adapted to form part of the sealed environment, wherein the medical device is adapted to allow reversible passage of objects (69) from the body cavity of the patient, through the body port into the first chamber, further through the second valve, into the second chamber of the sluice and further through the first valve out to the ambient environment (A), and vice versa, whereby the risk of contamination is reduced.

2. The medical device according to embodiment 1, wherein the medical device is adapted to hold a pressure within the first chamber exceeding atmospheric pressure.

3. The medical device according to any one of embodiments 1-2, wherein the second chamber has a volume larger than one of:
  a. 100 000 mm3,
  b. 200 000 mm3,
  c. 300 000 mm3,
  d. 400 000 mm3, and
  e. 500 000 mm3.

4. The medical device according to any one of embodiments 1-3, wherein the wall is at least partially collapsible and adapted to be inflated by a fluid.

5. The medical device according to any one of embodiments 1-4, further comprising at least one non-collapsible transparent window (21) provided in the wall for enabling viewing into the first chamber.

6. The medical device according to any one of embodiments 1-5, further comprising a wall inset (42;42').

7. The medical device according to embodiment 6, wherein the wall inset comprises at least one glove (02) integrated in the inset such that a surgeon is able to use the glove from outside the first chamber to make manual manipulations inside the first chamber while maintaining sealed environment in the first chamber.

8. The medical device according to any one of embodiments 1-7, further comprising a body inset (42;42").

9. The medical device according to embodiment 8, wherein the body inset comprises least one glove integrated in the body inset such that a surgeon is able to use the glove from outside the chamber via a wall port (17) or wall inset to make manual manipulations inside the body cavity while maintaining sealed environment in at least one of; the first chamber and the body cavity.

10. The medical device according to any one of embodiments 1-9, further comprising a device or instrument mount (20) for retaining instruments within the first chamber.

11. The medical device according to any one of embodiments 1-9, further comprising at least one of:

a. a vacuum sealing member (05') adapted to hold a pressure less than atmospheric pressure between the wall and the skin of the patient to seal between the wall and the skin of the patient, and.

b. a pressure sealing member (05") adapted to press against the skin of the patient to create a pressurized sealing between the skin of the patient and the wall, wherein the pressure sealing member is adapted to be hydraulically, pneumatically or mechanically forced against the patient's skin.

12. The medical device according to any one of embodiments 1-11, further comprising an adhesive surface (50) adapted to provide at least one of: fixation of the wall to the skin of the patient and sealing between the skin of the patient and the wall.

13. The medical device according to any one of the preceding embodiments, wherein the body port comprising a body multi-port (48;48") adapted to be placed inside the first chamber in an incision in the skin of the patient, wherein the body multi-port comprises at least two body ports adapted to enable passage of an object between the first chamber and the inside of the patient's body via the incision.

14. The medical device according to any one of the preceding embodiments, further comprising at least one wall port provided in the wall enabling passage of an object between the first chamber and the environment outside of the first chamber, wherein the wall port comprises at least one of an elastic membrane (43) and a flexible membrane, and wherein the membrane is adapted to, in a non-compressed state, seal between the first chamber and the environment outside of the first chamber, and in a compressed state enable a hand or an object to be inserted through the membrane.

15. The medical device according to any one of the preceding embodiments, further comprising a sealing device comprising:

a. a first sealing member (35) adapted to be positioned at the inside of the skin of the patient around an incision cut in the skin of the patient within the first chamber, b. a second sealing member (37) adapted to be positioned at the outside of the skin of the patient around the incision, and c. a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.

16. The medical device according to any one of the preceding embodiments, wherein the medical device is adapted to be inflated by a fluid, and wherein the medical device further comprises at least one of:
  a. a filtering unit (26b) for filtering the fluid,
  b. a sterilization unit (26a) for directly or indirectly sterilizing the fluid,
  c. a fluid tempering unit (26c) adapted change the temperature of the fluid,
  d. a filtering unit for filtering the fluid and a sterilization unit for directly or indirectly sterilizing the fluid,
  e. a filtering unit for filtering the fluid and a fluid tempering unit adapted change the temperature of the fluid, f. a sterilization unit for directly or indirectly sterilizing the fluid and a fluid tempering unit adapted change the temperature of the fluid, and g. a filtering unit for filtering the fluid, a sterilization unit for directly or indirectly sterilizing the fluid and a fluid tempering unit adapted change the temperature of the fluid.

17. The medical device according to any one of the preceding embodiments, further comprising at least one inlet (30) member provided in the wall for supplying a fluid into the first chamber, at least one outlet member (31) provided in the wall for discharging the fluid from the first chamber, and a pump (27) adapted to circulate the fluid from the outlet member to the inlet member.

18. The medical device according to any one of the preceding embodiments, further comprising a coupling (80) adapted to detachably attach the body port to the patient's skin to enable exchange and removal of the body port.

19. A method embodiment of transferring an object (69; 81) from the ambient environment (A) to a cavity in a patient, and vice versa, during a surgical procedure, using a medical device, the method comprising:

a. transferring the object through a body port (22), placed in the skin (S) of the patient, to a first chamber (C) enclosed by a wall (01) of the medical device, b. transferring the object through a second valve (38*b*) to an airlock sluice (18), and c. transferring the object through a first valve (38*a*) to the ambient environment, such that the risk of contamination is reduced.

Numbered Embodiment I 1-17

1. A medical device for performing a surgical procedure on a patient, comprising: a wall (01) adapted to be at least partially applied on the patient's body to form a chamber (C), in which a sealed environment can be maintained for encompassing part of the surgical procedure to be performed, wherein a portion of the wall is adapted to contact the skin (S) of the patient to create a substantially airtight seal between the wall portion and the skin of the patient before an incision (I) has been performed through the skin of the patient such that a fluid connection between a cavity within the patient and the chamber is created, at least one wall port (17) or wall inset (42;42') positioned in a portion of the wall, and a sealing device connected to the wall having a first sealing member (35) adapted to be positioned in the cavity inside the patient's body wall around the incision, a second sealing member (37) adapted to be positioned at the outside of the patient's skin around the incision, and a sealing connecting member (36) adapted to connect the first and second sealing members, wherein the sealing device is adapted to seal between at least one of: (a) the second sealing member and directly or indirectly the outside of the patient's skin, and (b) the first sealing member and tissue inside the cavity by exerting pressure from the inside of the cavity in the direction of the skin of the patient, wherein the sealing device, the wall, and the wall port or wall inset are connected such that they enclose a chamber in fluid connection with the body cavity.

2. The medical device according to embodiment 1, wherein the wall is at least partially collapsible and adapted to be inflated by a fluid.

3. The medical device according to any one of embodiments 1 and 2, wherein the chamber is adapted to hold a fluid having a pressure exceeding atmospheric pressure.

4. The medical device according to embodiment 1-3, further comprising at least one non-collapsible transparent window (21) provided in the collapsible wall and positioned in the wall such that the window enables accurate viewing into the chamber where the surgical procedure is to be performed, when the wall is inflated.

5. The medical device according to any one of embodiments 1-4, wherein the wall inset comprises at least one glove (02) integrated in the wall such that a surgeon is able to use the glove from outside the chamber to make manual manipulations inside the chamber while maintaining sterile environment in the chamber.

6. The medical device according to any one of embodiments 1-5, further comprising a device or instrument mount for retaining instruments within the chamber.

7. The medical device according to any one of embodiments 1-6, further comprising at least one of:

a. a vacuum sealing member (05') adapted to hold a pressure less than atmospheric pressure between the wall and the skin of the patient to seal between the wall and the skin of the patient, and.

b. a pressure sealing member (05") adapted to press against the skin of the patient to create a pressurized sealing between the skin of the patient and the wall, wherein the pressure sealing member is adapted to be hydraulically, pneumatically or mechanically forced against the patient's skin.

8. The medical device according to any one of embodiments 1-7, wherein the wall further comprising an adhesive surface (50) adapted to provide at least one of: (a) fixation of the wall to the skin of the patient and (b) sealing between the wall and the skin of patient.

9. The medical device according to any one of the preceding embodiments, further comprising a body multi-port (48) adapted to be placed inside the chamber in an incision in the skin of the patient, wherein the body multi-port comprises at least two ports adapted to enable passage of an object between the chamber and the inside of the patient's body via the incision.

10. The medical device according to any one of the preceding embodiments, wherein the at least one wall port (17) provided in the wall enabling passage of an object between the chamber and the environment outside of the chamber, wherein the wall port comprises at least one of an elastic membrane (43) and a flexible membrane (43), and wherein the membrane is adapted to, in a non-compressed state, seal between the chamber and the environment outside of the chamber, and in a compressed state enable a hand or an object to be inserted through the membrane.

11. The medical device according to any one of the preceding embodiments, wherein the sealing connecting member is spring-loaded or elastic to seal between at least one of the second sealing member and the skin of the patient, and the first sealing member and tissue of the patient.

12. The medical device according to any one of the preceding embodiments, further comprising at least one inlet (30) provided in the wall for supplying a fluid into the chamber, at least one outlet (31) provided in the wall for discharging the fluid from the chamber, and a pump (27) adapted to circulate the fluid from the outlet to the inlet.
13. The medical device according to any one of the previous embodiments, further comprising a closable body port connected to at least one of the sealing device and the wall, and adapted to be positioned in the incision in the skin of the patient inside the chamber to enable passage of an object between the chamber and the inside of the patient's body, when positioned.
14. The medical device according to embodiment 13, further comprising a coupling (80) adapted to detachably attach the body port to at least one of; the sealing device, the wall and the patient's skin to enable exchange and removal of the body port.
15. The medical device according to any one of the preceding embodiments, further comprising an airlock sluice (18) having a first valve (38*a*) and second valve (38*b*) for allowing passage of objects from the chamber through the second valve and further through the first valve out to the environment outside of the chamber, and vice versa.
16. The medical device according to any one of the preceding embodiments, wherein the medical device further comprises at least one of:
   a. a filtering unit (26*b*) for filtering the fluid,
   b. a sterilization unit (26*a*) for directly or indirectly sterilizing the fluid,
   c. a fluid tempering unit (26*c*) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.
17. A method embodiment of performing a surgical procedure on a patient using a medical device, the method comprising:
   a. applying a wall (01) on the skin (S) of the patient to form a chamber (C), in which a sealed environment can be maintained for encompassing part of the surgical procedure to be performed,
   b. creating an incision (I) through the wall of the medical device and the skin of the patient, such that a fluid connection between a cavity within the patient and the chamber is created,
   c. placing a first sealing member (35) in the cavity inside the patient's body wall around the incision,
   d. placing a second sealing member (37) on the outside of the patient's skin around the incision, and
   e. placing a sealing connecting member (36) connecting the first and second sealing members, such that at least one of:
      i. the second sealing member seals directly or indirectly against the skin of the patient, and
      ii. the first sealing member seals directly or indirectly against the tissue of the patient.

Numbered Embodiment J 1-34

1. A interconnectable port (47) adapted to be at least partially placed in an incision in a patient's body, wherein the interconnectable port comprises a first (17;22) and second (17;22) port adapted be interconnected to form the interconnectable port, wherein the second port is disconnectable from the first port, wherein the first port is connected to a first portion of a flexible wall (01), and the second port is connected to a second portion of the flexible wall, and wherein the flexible wall is adapted to form a chamber (C).
2. The interconnectable port according to embodiment 1, wherein the first port (17) forms a closable wall port when disconnected from the second port (22).
3. The interconnectable port according to any one of embodiments 1 and 2, wherein the second port (22) forms a closable body port by itself when the first port has been disconnected from the second port.
4. The interconnectable port according to any one of the preceding embodiments, wherein the chamber has a first volume when the first and second ports are interconnected and a second volume when the second port is disconnected from the first port.
5. The interconnectable port according to embodiment 4, wherein the second volume is larger than the first volume.
6. The interconnectable port according to embodiment 5, wherein the first volume is smaller than 100 000 mm3.
7. The interconnectable port according to any one of embodiments 5 and 6, wherein the second volume is larger than 500 000 mm3.
8. The interconnectable port according to any one of the preceding embodiment, wherein the flexible wall comprises a pleated portion (03) such that the flexible wall can be expanded.
9. The interconnectable port according to any one of the preceding embodiments, wherein: the medical device comprises a first (80*a*) and second (80*b*) coupling, and wherein the first port is connected to the first coupling, and the second port is connected to the second coupling.
10. The interconnectable port according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.
11. The interconnectable port according to embodiment 10, wherein the recess is a groove in at least one of the first and second coupling.
12. The interconnectable port according to any one of the preceding embodiments, wherein the chamber formed by the flexible wall is adapted to hold a pressure exceeding atmospheric pressure.
13. The interconnectable port according to any one of the preceding embodiments, wherein the interconnectable port is adapted to:
   a. in a first state, when the first and second ports are interconnected, enable a surgeon to operate through the interconnected interconnectable port, and
   b. in a second state, when the second port is disconnected from the first part enable the surgeon to perform steps of the procedure within the chamber formed by the flexible wall between the first and second ports of the interconnectable port.
14. The interconnectable port according to embodiment 12, wherein the interconnectable port is adapted to, in the second state, enable the surgeon to remove a specimen (81) from the body of the patient through the second port and into the chamber, and to perform one of: placing the specimen within the chamber, and removing the specimen from the chamber through the second port.

15. The interconnectable port according to embodiment 13, wherein the chamber further comprises a pouch for holding the specimen within the chamber.
16. The interconnectable port according to embodiment 14, wherein the pouch can be closed for creating a pouch-chamber within the chamber for isolating the removed specimen within the chamber.
17. The interconnectable port according to any one of embodiments 12-16, wherein the first and second ports are adapted to be reconnected after having been disconnected, such that the surgeon can continue operating through the interconnected port after the specimen has been removed.
18. The interconnectable port according to embodiment 9, further comprising an inset (42;42';42") detachably fixated to at least one of the first and second coupling, such that the inset could be detached and replaced by a different inset.
19. The interconnectable port according to embodiment 18, wherein the inset comprises at least one of: a surgical glove (02) and a device or instrument mount (20).
20. The interconnectable port according to any one of the preceding embodiments, wherein at least one of the first and second port comprises an elastic or flexible membrane (43) adapted to, in a non-compressed state, provide sealing, and in a compressed state enable a hand or an object to be inserted through the membrane.
21. The interconnectable port according to embodiment 20, wherein the first port comprises a first elastic or flexible membrane (43a) and the second port comprises a second elastic or flexible membrane (43b), and wherein the first and second membranes are adapted to be placed tightly together such that they act as a single elastic or flexible membrane adapted to, in a non-compressed state, provide sealing, and in a compressed state enable a hand or an object to be inserted through the membrane.
22. The interconnectable port according to embodiment 21, wherein the first and second membranes comprises a plurality of self sealing holes (44) enabling insertion of instruments through the membranes.
23. The surgical port according to any one of the preceding embodiments, wherein at least one of said first and second port comprises a penetrable self sealing gel, such that an object or hand can be inserted through the interconnectable port while maintaining a seal.
24. The interconnectable port according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.
25. The interconnectable port according to any one of the preceding embodiments, wherein the wall comprises a fluid inlet (30) for inflating the chamber with a fluid.
26. The interconnectable port according to embodiment 25, further comprising a fluid outlet (31) provided in the wall for discharging the fluid from the chamber.
27. The interconnectable port according to embodiment 26, further comprising a pump (27) adapted to circulate the fluid from the outlet member to the inlet member.
28. The interconnectable port according to any one of the preceding embodiments, wherein at least one of the first and second port comprises a non-penetrable valve (86) such that the chamber is sealed from at least one of the ambient environment and a cavity in the patient.
29. The interconnectable port according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.
30. The interconnectable port according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the port and the skin of the patient, and (b) the first sealing member and tissue of the patient.
31. The interconnectable port according to any one of the preceding embodiments, wherein the medical device further comprises at least one of:
   a. a filtering unit (26b) for filtering the fluid,
   b. a sterilization unit (26a) for directly or indirectly sterilizing the fluid,
   c. a fluid tempering unit (26c) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.
32. A surgical method embodiment to be performed on the body of a patient using an interconnectable port (47) comprising a first (17) and second (22) port, the method comprising:
   a. creating an incision (I) in the skin (S) of the patient,
   b. placing the interconnectable port in the incision,
   c. disconnecting the first port from the second port, such that a chamber (C) is formed by a wall (01) connected to the first and second port, and
   d. performing a step of the surgical procedure within the chamber.
33. The surgical method according to embodiment 32, wherein the step of performing a step of the surgical procedure within the chamber comprises:
   a. removing a specimen (81) from the cavity in the body of the patient, b. transferring the specimen through the second port, and
c. placing the specimen within the chamber of the medical device.
34. The surgical method according to any one of embodiment 32 and 33, wherein the method further comprises:
a. reconnecting the first and second ports such that the interconnectable port is formed, and
b. performing a surgical step in a cavity of the patient, through the interconnectable port.

Numbered Embodiment K 1-30

1. A medical device for performing a surgical procedure, the medical device comprising;
a wall (01) adapted to at least partially enclose a chamber (C) for encompassing part of the surgical procedure,
a wall port (17) placed in the wall,
a sealing device (05) connected to the wall and adapted to seal against the patient's body, such that the chamber is formed by the wall and the patient's body, wherein
the wall port is adapted to be detachably connected to a body port (22) at least partially placed in an incision (I) cut in a patient's body during a surgical procedure.
2. The medical device according to embodiment 1, wherein the chamber is adapted to have a first volume when the wall port is connected to a body port, and a second volume when the wall port is disconnected therefrom.
3. The medical device according to embodiment 2, wherein the second volume is larger than the first volume.
4. The medical device according to embodiment 3, wherein the first volume is smaller than 100 000 mm3.
5. The medical device according to any one of embodiments 3 and 4, wherein the second volume is larger than 500 000 mm3.
6. The medical device according to any one of the preceding embodiments, wherein the wall is adapted to hold a pressure in the chamber exceeding atmospheric pressure.
7. The medical device according to any one of the preceding embodiments, wherein the wall port comprises an elastic or flexible membrane (43) adapted to, in a non-compressed state, provide sealing, and in a compressed state enable a hand or an object to be inserted through the membrane.
8. The medical device according to embodiment 7, wherein the wall port comprises a first elastic or flexible membrane (43a), adapted to connect to a second elastic or flexible membrane (43b) in a body port, and wherein the first membrane is adapted to be placed tightly together contacting the second membrane such that the first and second membranes act as a single elastic or flexible membrane adapted to, in a non-compressed state, provide sealing, and in a compressed state enable a hand or an object to be inserted through the membrane.
9. The medical device according to embodiment 8, wherein the first membrane comprises a penetratable self sealing gel, such that an object or hand can be inserted through the port while maintaining a seal, and wherein the first membrane is adapted to be connected to a second membrane comprising a penetratable self sealing gel, such that an object or hand can be inserted through the first and second membranes acting as a single integrated seal, while maintaining a seal.
10. The medical device according to any one of the preceding embodiments, wherein the medical device further comprises a coupling (80) placed in wall, wherein the coupling is adapted to receive and fixate an inset (42).
11. The medical device according to any one of embodiments 1-10, wherein the medical device further comprises a detachable inset adapted to be fixated to the coupling.
12. The medical device according to embodiment 11 or 12, wherein the inset comprises at least one of: a surgical glove (02) and a device or instrument mount (20).
13. The medical device according to any one of embodiments 1-12, further comprising the body port.
14. The medical device according to any one of the preceding embodiments, wherein:
a. at least one of the wall and body port comprises a protruding member, and
b. at least one of the wall and body port comprises a recess, and wherein, the protruding member is adapted to engage the recess for locking the wall port to the body port.
15. The medical device according to embodiment 15, wherein the recess is a groove in at least one of the wall port and body port.
16. The medical device according to embodiment 13, wherein the wall port is adapted to be fixated to a first coupling (80a) and the body port is adapted to be fixated to a second coupling (80a), and wherein the first and second couplings are adapted to be connected for connecting the wall port and body port.
17. The medical device according to any one of the preceding embodiments, wherein:
a. at least one of the first and second coupling comprises a magnet or a first magnetic material, and
b. at least one of the first and second coupling comprises a magnet or a magnetic material, and wherein the magnet is adapted to engage a magnet or magnetic material for locking the first coupling to the second coupling.
18. The medical device according to embodiment 16, wherein:
a. at least one of the first and second coupling comprises a protruding member, and
b. at least one of the first and second coupling comprises a recess, and wherein,
the protruding member is adapted to engage the recess for locking the first coupling to the second coupling.
19. The medical device according to embodiment 18, wherein the recess is a groove in at least one of the coupling and the second coupling.
20. The medical device according to any one of the preceding embodiments, wherein the wall comprises a fluid inlet (30) for inflating the chamber with a fluid.
21. The medical device according to embodiment 20, further comprising a fluid outlet (31) provided in the wall for discharging the fluid from the chamber.
22. The medical device according to embodiment 21, further comprising a pump (27) adapted to circulate the fluid from the outlet member to the inlet member.
23. The medical device according to any one of the preceding embodiments, wherein the wall port comprises a non-penetratable valve (86) for closing the wall port such that the chamber is sealed from at least one of the ambient environment and a cavity in the patient.

24. The medical device according to any one of the preceding embodiments, wherein the medical device comprises at least one of:
   a. a vacuum seal adapted to hold a pressure less than atmospheric pressure between the patient's skin and the vacuum seal to seal the chamber by sealing towards the patient's skin, and
   b. a pressure seal adapted to hold a pressure above atmospheric pressure between the pressure seal and the patient's skin to seal the chamber by sealing towards the patient's skin.

25. The medical device according to any one of the preceding embodiments, wherein the medical device comprises a sealing device adapted to be connected to or placed in close relation to a body port placed in an incision in the skin of the patient, the sealing device comprising a first sealing member (35) adapted to be positioned at the inside of the patient's skin around an incision in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the body port and the skin of the patient, and (b) the first sealing member and tissue of the patient.

26. The medical device according to any one of the preceding embodiments, wherein the medical device further comprises at least one of:
   a. a filtering unit (26*b*) for filtering the fluid,
   b. a sterilization unit (26*a*) for directly or indirectly sterilizing the fluid,
   c. a fluid tempering unit (26*c*) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.

27. The medical device according to any one of the preceding embodiments, wherein the wall port is adapted to:
   a. in a first state, when the wall port is connected to a body port, enable a surgeon to operate inside a cavity of the patient through the wall port, and
   b. in a second state, when the wall port is disconnected from the body port, enable the surgeon to perform steps of the procedure within the chamber formed by the wall.

28. The medical device according to any one of the previous embodiments, wherein the wall of the medical device further comprises a pouch (82) for holding a specimen (81) within the chamber.

29. The medical device according to embodiment 28, wherein the pouch can be closed for creating a pouch-chamber within the chamber for isolating the removed specimen within the chamber.

30. A method embodiment of performing a surgical procedure on a patient using a medical device, the method comprising:
   applying a wall (01) on the body of a patient such that a sealed chamber (C) is formed by the wall and the body of the patient, and
   connecting a wall port (17) attached to the wall of the medical device, to a body port (22) placed in an incision in the body of the patient, such that an interconnected port is formed, and
   performing a step of the surgical procedure through the interconnected port.

Numbered Embodiment L 1-24

1. A medical device for performing a surgical procedure on a patient, comprising: a first wall (01) portion adapted to at least partially enclose a first chamber (C) for encompassing part of the surgical procedure, and a second wall portion adapted to at least partially enclose a second chamber for providing sealing between the wall and the patient, wherein
   i. the first wall portion is adapted to allow a first pressure above atmospheric pressure to be maintained in the first chamber,
   ii. the second wall portion is adapted to allow a second pressure to be maintained in the second chamber for creating a sealing between the medical device and the patient's body, wherein the second pressure is one of: above atmospheric pressure and below atmospheric pressure, for providing sealing between the medical device and the patient, and wherein
   iii. the first and second pressures are different.

2. The medical device according to embodiment 1, wherein the second chamber is adapted to hold a pressure above atmospheric pressure for exerting a pressure force on the skin and/or tissue of the patient for creating the sealing between the medical device and the patient's body.

3. The medical device according to any one of embodiments 1 and 2, wherein the second pressure is higher than the first pressure.

4. The medical device according to embodiment 1, wherein the second chamber is adapted to hold a negative pressure for exerting a suction force on the skin and/or tissue of the patient for creating the sealing between the medical device and the patient.

5. The medical device according to any one o the preceding embodiments, wherein the first chamber is adapted to be in fluid connection with a cavity of the patient via an incision (I) in the skin of the patient, and wherein the chamber and the cavity in the patient forms a joint volume having the same pressure and partially being enclosed by the medical device.

6. The medical device according to any one of the preceding embodiments, wherein the medical device is adapted to enclose the second chamber together with the skin and/or tissue of the patient.

7. The medical device according to any one of embodiments 1 and 4-6, wherein the second chamber is adapted to be in fluid connection with a vacuum creating device (08) capable of producing a negative pressure for creating a negative pressure in the second chamber.

8. The medical device according to any one of embodiments 1 and 4-7, wherein the first chamber is adapted to hold a positive pressure between 5 mmHg and 120 mmHg, and wherein the second chamber is adapted to hold a negative pressure between 5 mmHg and 120 mmHg.
9. The medical device according to any one of the preceding embodiments, wherein the second chamber is adapted to encircle an extremity of the patient and to create a sealing along the encircled portion of the extremity of the patient.
10. The medical according to embodiment 9, wherein the second wall portion is adapted to hold the second pressure exceeding the first pressure such that the second chamber exerts a pressure force on the extremity of the patient for creating a sealing between the medical device and the skin of the patient.
11. The medical device according to any one of embodiments 1-10, wherein the medical device further comprises a monitoring unit (98) for monitoring at least one of: the blood pressure of the patient, the pressure in the first chamber, and the pressure in the second chamber.
12. The medical device according to embodiment 11, wherein the medical device further comprises a pressure creating member (67) adapted to create the pressure in the second chamber.
13. The medical device according to embodiment 12, wherein the pressure creating member is adapted to receive feedback from the monitoring unit and create the pressure in the second chamber based on the received feedback.
14. The medical device according to any one of embodiments 11-13, wherein the monitoring unit is adapted monitor the blood pressure of the patient and provide feedback to the pressure creating member.
15. A system comprising:
   a. the medical device according to any one of embodiments 1, 4-9 and 11-14,
   b. a pressure creating member (67) adapted to create a pressure exceeding 5 mmHg in the first chamber of the medical device, and
   c. a vacuum creating device (08) adapted to create a negative pressure of 5 mmHg in the second chamber of the medical device for creating a sealing between the medical device and the skin and/or tissue of the patient.
16. A system comprising:
   a. the medical device according to any one of embodiments 1-3, 4-6 and 9-14,
   b. a first pressure creating member (67) adapted to create a pressure exceeding 5 mmHg in the first chamber of the medical device, and
   c. a second pressure creating member (67) adapted to create a second pressure exceeding 5 mmHg in the second chamber of the medical device for creating a sealing between the medical device and the skin of the patient.
17. The system according to embodiment 16, wherein the second pressure is higher than the first pressure.
18. A method embodiment of creating a chamber in a medical device and sealing between the medical device and the skin of a patient, the method comprising,
   a. applying a first wall portion of the medical device against the skin (S) of a patient such that a first chamber (C) is formed by the wall itself or by the wall and the skin of the patient,
   b. inflating the first chamber to a pressure exceeding atmospheric pressure,
   c. applying a second wall portion of the medical device against the skin of a patient such that a second chamber (05';05") is formed by the wall itself or by the wall and the skin of the patient, and at least one of:
      i. inflating the second chamber to a pressure exceeding atmospheric pressure, such that the second wall portion is pressed against the skin of the patient and thereby provides sealing, wherein the pressure in the second chamber is different from the pressure in the first chamber, and
      ii. evacuating fluid from the second chamber such that a pressure below atmospheric pressure is created in the second chamber, such that a vacuum sealing is created between the second wall portion and the skin of the patient.
19. The method of creating a chamber in a medical device and sealing between the medical device and the skin of a patient according to embodiment 18, wherein the step of inflating the first chamber comprises inflating the first chamber to a pressure between 5 mmHg and 120 mmHg, and wherein the step of evacuating fluid from the second chamber comprises evacuating fluid such that a negative pressure between 5 mmHg and 120 mmHg is created in the second chamber.
20. The method of creating a chamber in a medical device and sealing between the medical device and the skin of a patient according to embodiment 18, wherein the step of inflating the first chamber comprises inflating the first chamber to a pressure between 5 mmHg and 120 mmHg, and wherein the step of inflating the second chamber comprises inflating the second chamber to a pressure between 5 mmHg and 120 mmHg.
21. The method of creating a chamber in a medical device and sealing between the medical device and the skin of a patient according to any one of embodiments 18-20, further comprising the step of monitoring the pressure in as least one of the first chamber and the second chamber.
22. The method of creating a chamber in a medical device and sealing between the medical device and the skin of a patient according to any one of embodiments 18-21, further comprising the step of monitoring a physiological parameter of the patient, and inflate or evacuate at least one of the first and second chambers on the basis of the monitored physiological parameter.
23. The method of creating a chamber in a medical device and sealing between the medical device and the skin of a patient according to embodiment 22, further comprising the step of monitoring the blood pressure or blood flow of the patient, and inflate or evacuate fluid from at least one of the first and second chambers on the basis of the monitored blood pressure or blood flow.
24. The method of creating a chamber in a medical device and sealing between the medical device and the skin of a patient according to any one of embodiments 18-23, further comprising the step of creating an incision in the skin of the patient inside of the first chamber, such that a fluid connection is created between the first chamber and a cavity in the body of the patient.

Numbered Embodiment M 1-30

1. A medical device for performing a surgical procedure on a patient, the medical device comprising:
   a. a wall (01) adapted to be at least partially applied on the patient's body to form a chamber (C) together with the patient's body, in which a sealed environment can be maintained for encompassing part of the surgical procedure to be performed, b. a closeable wall port (17) placed in a portion of the wall and being adapted to be connected to a port placed in an incision in the patient's body, when the medical device is applied on the patient's body for performing the surgical procedure, c. a sealing device (05) connected to the wall and adapted to seal against the skin (S) of the patient, wherein:

d. the closable wall port is adapted to form at least a part of an airlock sluice (18) together with a closable port (22) placed in the skin, the airlock sluice between a cavity in the patient's body and the ambient environment (A), when the medical device is applied on the patient's body for performing the surgical procedure.

2. The medical device according to embodiment 1, wherein the closeable wall port is adapted to be positioned relative to an openable port (22) placed in an incision in the patient's body, such that an elongated object is longitudinally displaceable through the ports, when the medical device is applied on the patient's body for performing the surgical procedure.

3. The medical device according to any one of embodiments 1-2, wherein the closeable wall port is displaceable between a first position, in which the closeable wall port is situated relatively close to at least one of, the skin of the patient and a skin port (22) placed in a skin opening, and a second position, in which the closeable wall port is situated more remote from the skin of the patient, when the medical device is applied on the patient's body for performing the surgical procedure.

4. The medical device according to any one of embodiments 1-3, wherein the closeable wall port, when the medical device is applied on the patient's body for performing a surgical procedure, is adapted to be at least one of a. connected to a port (22) connecting to a cavity in the patient's body, and b. locked to a port connecting to a cavity in the patient's body.

5. The medical device according to any one of embodiments 1-4, wherein the closeable wall port comprises a penetratable self sealing gel (43), such that an object or hand can be inserted through the closeable wall port while maintaining the sealed environment in the chamber.

6. The medical device according to any one of embodiments 1-5, further comprising at least one of; an additional port, an inset (42), and a coupling (80) wherein the closeable wall port is adapted to be replaced by at least one of; the additional port, the inset and the coupling, when the medical device is applied on the patient's body for performing the surgical procedure.

7. The medical device according to any one of embodiments 1-6, wherein the wall is adapted to hold a fluid within the chamber having a pressure exceeding atmospheric pressure.

8. The medical device according to any one of embodiments 1-7, wherein the sealing device comprises a vacuum sealing member (05') adapted to hold a pressure less than atmospheric pressure between the wall and the patient's skin to seal between the wall and the patient's skin.

9. The medical device according to any one of embodiments 1-8, further comprising at least one of a. an airlock placed separately from the wall port, and b. an airlock integrated in the wall port, in both cases for allowing passage of objects between the chamber and the ambient environment without any substantial leakage of fluid from the chamber.

10. The medical device according to embodiment 8, wherein the vacuum seal is adapted to create a substantially airtight seal between the wall and the skin of the patient, to enable an incision to be performed through the skin of the patient in sealed environment such that a fluid connection between a cavity within the patient and the chamber can be created without any substantial fluid leakage outside of the connected chamber and cavity, when the medical device is applied on the patient's body for performing the surgical procedure.

11. The medical device according to any one of the preceding embodiments, wherein the closeable wall port is selected from a group consisting of at least one of:

a. laparoscopic ports, and b. multiports.

12. The medical device according to any one of the preceding embodiments, wherein the closeable wall port comprises a wall multiport, wherein the wall multiport is adapted to be connected to at least one of; a closable body port and a closable body multiport placed in an incision in the patient's body connecting to a body cavity, when the medical device is applied on the patient's body for performing a surgical procedure.

13. The medical device according to any one of the preceding embodiments, wherein the closeable wall port comprises at least one of an elastic membrane and a flexible membrane, and wherein the membrane is adapted to, in a non-compressed state, seal between the chamber and the environment outside the chamber, and in a compressed state enable a hand or an object to be inserted through the membrane.

14. The medical device according to any one of the preceding embodiments, wherein the closeable wall port is adapted to connect to the skin of the patient, further comprising a sealing device having a first sealing member (35) adapted to be positioned at the inside of the patient's skin around an incision to be performed in the skin and a second sealing member (37) adapted to be positioned on the outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.

15. The medical device according to any one of the preceding embodiments, wherein the medical device comprises at least one of:

a filtering unit (26*b*) for filtering fluid supplied to the chamber, a sterilization unit (26*a*) for directly or indirectly sterilizing fluid supplied to the chamber, a fluid tempering unit (26*c*) adapted change the temperature of fluid supplied to the chamber, a filtering unit (26*b*) for filtering fluid and a sterilization unit (26*a*) for directly or indirectly sterilizing fluid supplied to the chamber, a filtering unit (26*b*) for filtering fluid supplied to the chamber and a fluid tempering unit (26*a*) adapted change the temperature of fluid supplied to the chamber, a sterilization unit (26*a*) for directly or indirectly sterilizing fluid supplied to the chamber and a fluid tempering unit (26*c*) adapted change the temperature of fluid supplied to the chamber, and a filtering unit (26*b*) for filtering fluid supplied to the chamber, a sterilization unit (26*a*) for directly or indirectly sterilizing fluid supplied to the chamber and a fluid tempering device (26*c*) adapted change the temperature of fluid supplied to the chamber.

16. The medical device according to any one of the preceding embodiments, wherein the chamber is in fluid connection with the cavity in the patient's body through an incision (I) in the patient's body, when the medical device is applied on the patient's body for performing a surgical procedure, and wherein the medical device further comprises at least one of:
   a. at least one inlet (30) provided in at least one of:
      i. the wall of the medical device, and
      ii. the skin of the patient for supplying a fluid to at least one of
         1. the chamber, and
         2. the cavity in the patient's body, and
   b. at least one outlet (31) provided in at least one of:
      i. the wall of the medical device, and
      ii. the skin of the patient for discharging the fluid from at least one of:
         1. the chamber, and
         2. the body cavity.

17. The medical device according to embodiment 16, further comprising a pump (27) adapted to circulate the fluid from the outlet member to the inlet member.

18. The medical device according to any one of the preceding embodiments, further comprising a coupling (80) adapted to detachably; abut, attach, place in a defined position, lock or disconnect at least one of;
   a. the closable wall port (17) to a detach performing port (22) placed in an incision in the patient's body connecting to the body cavity, and
   b. the wall, adapted to be at least partially applied on the patient's body, to a detach performing port,
when the medical device is applied on the patient's body for performing the surgical procedure.

19. The medical device according to any one of the preceding embodiments, wherein the closeable wall port (22) is positioned in the wall portion and adapted to allow handling of an instrument for at least one of; cutting through the patient's skin via the closable wall port and cutting through the patient's skin with the instrument fully placed inside the chamber, when the wall is applied on the patient's body for performing the surgical procedure.

20. The medical device according to any one of the preceding embodiments, wherein the wall portion is adapted to allow itself to be cut through to reach and make an incision in the patient's skin, for allowing a surgical procedure when the wall is applied on the patient's body.

21. A medical device system for performing a surgical procedure, the medical device system comprising:
   a. the medical device according to any one of embodiments 1-20, and
   b. a closeable body port adapted to be placed in an incision in the patient's body connecting the chamber created by the medical device to a cavity in the patient's body, when the medical device is applied on the patient's body for performing the surgical procedure.

22. The medical device system according to embodiment 21, wherein the closeable wall port and the closeable body ports are connected by a portion of the wall, and wherein the closeable wall port and closable body port can be moved in relation to each other whilst being connected by means of the wall portion.

23. The medical device system according to embodiment 21-22, wherein the closeable body port comprises a closeable body multi-port adapted to be placed from inside the chamber in an incision to be performed in the skin of the patient, wherein the closeable body multi-port comprises at least two closeable body ports adapted to enable passage of an object between the chamber and the inside of the patient's body, wherein the closable body multiport is adapted to be connected to at least one of; a wall port and a wall multiport together placed in an incision in the patient's body connecting to a body cavity, when the medical device is applied on the patient's body for performing a surgical procedure.

24. A surgical method embodiment for performing a laparoscopic procedure in a sealed environment, the surgical method comprising:
   a. placing a medical device comprising a wall (01) and a closable wall port (17) in connection with the patient, such that a wall portion of the medical device sealingly connects to the skin (S) of the patient, such that a chamber (C) is formed by the wall of the medical device and the skin of the patient,
   b. making an incision (I) in the patient's body, inside the chamber, and
   c. placing a closeable body port (22) in the incision made in the skin of the patient, inside of the chamber, such that a fluid connection is created between the chamber and a cavity in the patient.

25. A surgical method embodiment for performing a laparoscopic procedure in a sealed environment, the surgical method comprising:
   a. placing a medical device comprising a wall (01) and a closable wall port (17) in connection with the patient, such that a wall portion of the medical device sealingly connects to the skin (S) of the patient, such that a chamber (C) is formed by the wall of the medical device and the skin of the patient,
   b. sealing the wall portion, to the skin of the patient by applying a negative pressure,
   c. making an incision in the skin of the patient's body creating a contact between the chamber and a cavity in the patient's body, and
   d. moving the closable wall port, adapted to connect directly or indirectly to the incision in the skin of the patient, towards the incision in the skin of the patient's body.

26. The surgical method according to any one of embodiments 24-25, further comprising inflating the cavity in the patient using a laparoscopic fluid, such that a cavity enabling visual inspection within the body of the patient is formed.

27. The surgical method according to any one of embodiments 24-26, further comprising exchanging the closeable body port to at least one of; an additional port, an inset (42) and a coupling (80) for performing an operational step in the cavity in the body of the patient.

28. The surgical method according to any one of embodiments 24-27, further comprising exchanging the closeable wall port to at least one of an additional port, an inset and a coupling for performing an operational step in the chamber of the medical device.

29. A method embodiment of transferring an object from the ambient environment (A) to a cavity in a patient during a surgical procedure, the method comprising:
   a. transferring the object through a first closeable wall port, placed in a wall of a medical device, into a chamber formed by the wall of the medical device and the skin of the patient, and
   b. transferring the object through a closable body port placed in an incision made in the patient's skin and into the cavity in the patient.

30. A method embodiment of forming an airlock sluice between the ambient environment and a cavity in a patient, the method comprising two in time interchangeable steps:
   a. placing a body port in an incision made in the skin of the patient, and
   b. placing a medical device comprising a closable wall port in connection with the patient, such that a wall portion of the medical device sealingly connects to the skin of the patient, and
   c. forming a chamber by the wall of the medical device, the skin of the patient, and the body port.

Numbered Embodiment N 1-23

1. A medical device for performing a surgical procedure on a patient, comprising:
   a. a wall (01) adapted to form a chamber (C) in which a sealed environment can be maintained for encompassing part of the surgical procedure to be performed,
   b. a closeable wall port (17) placed in a portion of the wall,
   c. a closeable body port (22) adapted to be placed in a portion of the wall and further placed an incision in the body of the patient, and
   d. a sealing device (05) connected to the wall and adapted to seal against the skin and/or body of the patient,
   wherein the wall port and body port together forms an airlock sluice (18) between a cavity in the body of the patient and the ambient environment (A) and at least one of; the closable wall port, closable body port and the closable wall port and closable body port together are adapted to form an airlock sluice between a cavity in the body of the patient and the ambient environment, when the medical device is applied on the patient's body for performing the surgical procedure.

2. The medical device according to embodiment 1, wherein the sealing device comprises a pressure sealing member (05") adapted to seal between the wall of the medical device and the skin (S) of the patient by pressing against the skin or tissue of the patient.

3. The medical device according to embodiment 1, wherein the sealing device comprises vacuum sealing member (05') adapted to seal against the skin or tissue of the patient by means of a pressure below atmospheric pressure.

4. The medical device according to any one of embodiments 1-3, wherein the closeable wall and body ports are positioned relative to each other such that an elongated object is longitudinally displaceable through the closeable wall and body ports.

5. The medical device according to any one of embodiments 1-4, wherein the closeable wall port is displaceable between a first position, in which the closeable wall port is situated relatively close to the closeable body port, and a second position, in which the closeable wall port is situated more remote from the closeable body port.

6. The medical device according to any one of embodiments 1-5, wherein the wall closeable port is adapted to be at least one of; attached, mounted together in a predefined position and locked to the closeable body port.

7. The medical device according to any one of embodiments 1-6, wherein at least one of the closeable wall port and closable body port comprises a penetratable self sealing gel, such that an object or hand can be inserted through the closeable wall port while maintaining the sealed environment.

8. The medical device according to any one of embodiments 1-7, further comprising an additional port or additional inset, wherein at least one of the closeable wall port and closeable body port is exchangeable by the additional port or inset.

9. The medical device according to any one of embodiments 1-8, wherein the chamber is adapted to hold a fluid having a pressure exceeding atmospheric pressure.

10. The medical device according to any one of embodiments 1-9, further comprising at least one of: an airlock sluice (18) placed separate from the wall port and an airlock sluice (18) integrated in the wall port for allowing passage of objects between the chamber and the outside of the chamber.

11. The medical device according to any one of the preceding embodiments, wherein at least one of
   a. the closeable body port comprises a closeable body multi-port adapted to be placed from inside the chamber in an incision to be performed in the skin of the patient, wherein the closeable body multi-port comprises at least two closeable body ports adapted to enable passage of an object between the chamber and the inside of the patient's body, wherein the closable body multiport is adapted to be connected to at least one of; a wall port and a wall multiport together placed in an incision in the patient's body connecting to a body cavity, when the medical device is applied on the patient's body for performing a surgical procedure, and
   b. the closable wall port comprises a wall multiport, comprising at least two closable wall ports, wherein the wall multiport is adapted to be connected to at least one of a closeable body port and a closeable body multiport placed in an incision in the patient's body connecting to a body cavity, when the medical device is applied on the patient's body for performing a surgical procedure.

12. The medical device according to any one of the preceding embodiments, wherein at least one of; the closeable wall port and closable body port comprises at least one of an elastic membrane and a flexible membrane, and wherein the membrane (43) is adapted to, in a non-compressed state, seal between the chamber and the environment outside the chamber, and in a compressed state enable a hand or an object to be inserted through the membrane.

13. The medical device according to any one of the preceding embodiments, further comprising a sealing device having a first sealing member (35) adapted to be positioned at the inside of the patient's skin around an incision to be performed in the skin and a second sealing member (37) adapted to be positioned at outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.

14. The medical device according to any one of the preceding embodiments, wherein the medical device comprises at least one of:
   a filtering unit (26b) for filtering fluid supplied to the chamber,
   a sterilization unit (26a) for directly or indirectly sterilizing fluid supplied to the chamber,
   a fluid tempering unit (26c) adapted change the temperature of fluid supplied to the chamber,
   a filtering unit (26b) for filtering fluid and a sterilization unit (26a) for directly or indirectly sterilizing fluid supplied to the chamber,
   a filtering unit (26b) for filtering fluid supplied to the chamber and a fluid tempering unit (26c) adapted change the temperature of fluid supplied to the chamber,
   a sterilization unit (26a) for directly or indirectly sterilizing fluid supplied to the chamber and a fluid tempering unit (26c) adapted change the temperature of fluid supplied to the chamber, and
   a filtering unit (26b) for filtering fluid supplied to the chamber, a sterilization unit (26a) for directly or indirectly sterilizing fluid supplied to the chamber and a fluid tempering unit (26c) adapted change the temperature of fluid supplied to the chamber.

15. The medical device according to any one of the preceding embodiments, wherein, when the medical device is applied on the patient's body for performing a surgical procedure, the medical device further comprises at least one of:
   a. at least one inlet (30) provided in at least one of:
      i. the wall of the medical device, and
      ii. the skin of the patient for supplying a fluid to at least one of
         the chamber, and
         the cavity in the patient's body, and
   b. at least one outlet (31) provided in at least one of:
      i. the wall of the medical device, and
      ii. the skin of the patient for discharging the fluid from at least one of:
         the chamber, and
         the body cavity.

16. The medical device according to embodiment 15, further comprising a pump (27) adapted to circulate the fluid from the outlet to the inlet.

17. The medical device according to any one of the preceding embodiments, wherein the closeable body port is adapted to be placed inside the chamber in an incision (I) to be performed in the skin of the patient to enable passage between the chamber and the inside of the patient's body.

18. The medical device according to embodiment 17, further comprising a coupling (80) adapted to detachably attach the closable body port to at least one of; the patient's skin and the closable wall port to enable exchange and removal of the closable body port.

19. The medical device according to any one of the preceding embodiments, wherein the closeable wall port is adapted to and positioned in the wall portion such that it allows handling of an instrument for at least one of; cutting through the patient's skin via the closable wall port and cutting through the patient's skin with the instrument fully placed inside the chamber, when the wall is applied on the patient's body.

20. The medical device according to any one of embodiments 1-19, wherein the wall portion is adapted to allow itself to be cut through to reach and make an incision in the patient's skin, for allowing a surgical procedure when the wall is applied on the patient's body.

21. The medical device according to any one of embodiments 1-20, wherein the closable body port is adapted to be at least one of;
   fitted in the patient's skin after an incision has been made in the skin, and
   fitted to the closable wall port after the closable body has been fitted in the patient's skin after an incision has been made in the skin,
   when the medical device is applied on the patient's body.

22. The medical device according to embodiment 21, wherein the closeable wall port and the closeable body port are connected by a portion of the wall, and wherein the closeable wall and body ports can be moved in relation to each other whilst being connected by means of the wall portion.

23. A method embodiment of forming an airlock sluice for use when performing a surgical procedure on a patient, the method comprising:
   a. applying a wall (01) on the patient's body to form a chamber (C) together with the patient's body, in which a sealed environment can be maintained for encompassing part of the surgical procedure to be performed, the wall comprising a closeable wall port (17) and a closeable body port (22),
   b. placing the closeable body port (22) in an incision in the body of the patient, such that an airlock sluice (18) is formed between the closeable wall port and the body port, and
   c. placing a sealing device (05) connected to the wall against the skin and/or body of the patient, for sealing between the wall of the medical device and the skin of the patient.

Numbered Embodiment O 1-35

1. A medical device for performing hip joint surgery on a patient, the medical device comprising:
   a. a wall (01) adapted to least partly be placed on the patient's body for forming a chamber (C) alone or together with the patient's body, such that a sealed surgical environment is created in the chamber, wherein the chamber is adapted to encompass at least part of one step of the hip joint surgery procedure to be performed, while maintaining the sealed surgical environment,
   b. a sealing device (05) connected to the wall and adapted to seal between the wall and the skin or tissue of the patient, wherein the sealing device forms a special loop at least partly encircling at least a portion of one or more of the following; the leg, the pelvic region, the abdominal region, the inguinal region, the gluteal region, the thoraxial region and the region of the lower back, such that the sealing device seals between the incision site of the hip joint surgery and at least one of:
  i. the anal orifice,
  ii. the urethra orifice,
  iii. the perineum region.
2. The medical device according to embodiment 1, wherein the sealing device is positioned such that both of the urethra and the anus are excluded from the enclosed chamber forming the sealed surgical environment.
3. The medical device according to any one of embodiments 1 and 2, wherein the medical device further comprises a second sealing device connected to the wall and adapted to encircle the leg of the patient for sealing between the ambient environment and the chamber.
4. The medical device according to any one of embodiments 1-3, wherein the medical device further comprises a holding member (96) adapted to encircle a portion of the patient's body, by itself or together with the medical device, for holding the medical device in the desired position.
5. The medical device according to any one of the preceding embodiments, wherein at least a portion of the wall is adapted to directly or indirectly form an elongated tubular enclosure (04) having at least one open end (99), the enclosure being adapted to fit at least a portion of a leg of the patient, and wherein the medical device is arranged such that a portion of the leg extends into the enclosure through the first open end thereof, when the surgical procedure is performed on the leg of the patient.
6. The medical device according to any one of embodiments 1-5, wherein:
  a. the wall is adapted to form the chamber without involving the patient's body,
  b. the wall portion forming the chamber also forms the tubular enclosure, and
  c. the tubular enclosure forms a second chamber together with the patient's body, and wherein the second chamber is adapted to be sealed at the first or more open ends by the patient's body.
7. The medical device according to at least one of embodiments 1-6, wherein the chamber is adapted to be in communication with an operating field during the surgical procedure, when the skin of the patient has been cut in a position inside of the chamber, and wherein the wall enclosing the chamber comprises a wall port (17) or wall inset (42;42') mounted in a wall portion for allowing at least one of; objects being moved into the chamber or operating field and/or manual manipulation being performed in the chamber or operating field.
8. The medical device according to embodiment 7, wherein medical device further comprises a body port or body inset, and wherein the wall port or wall inset is adapted to be connected to the body port or body inset for forming one of:
  a. an integrated port allowing the transfer of objects from the ambient environment to the operating field, and
  b. an integrated inset allowing manual manipulation to be performed in the operating field from the ambient environment,
and wherein the body port and wall port are adapted to be disconnected from each other such that the wall port can allow objects to be transferred into the chamber from the ambient environment, or the wall inset can allow manual manipulation to be performed in the chamber from the ambient environment, and the body port can allow objects to be transferred from the chamber into the operating field or the body inset can allow manual manipulation to be performed in the operating field in a cavity in the patient's body.
9. The medical device according to any one of embodiments 5-8, wherein the chamber is adapted to be in communication with an operating field during the surgical procedure, and wherein the part of the wall forming both the chamber and the tubular enclosure, at a portion thereof, is adapted to be opened and wherein the opening together with the hip joint surgery incision of the patient is adapted to be positioned inside of the chamber allowing such communication with the operating field, wherein a portion of the wall port encompassing only the chamber has a wall port or wall inset mounted therein for allowing, from outside the chamber at least one of;
  a. objects to be moved into at least one of the following; the chamber, and the operating field, and
  b. manual manipulation to be performed in at least one of the chamber and the operating field.
10. The medical device according to embodiment 9, comprising a port or inset including a first and second part, wherein the second part comprises the wall port or wall inset and the first part comprises a first wall port or first wall inset mounted in the opening in the portion of the part of the wall forming both the chamber and the tubular enclosure and adapted to be opened to create the communication between the chamber and the operating field to allow; objects to be moved further from the chamber into the operating field and/or manual manipulation to be performed from the chamber further into the operating field, and wherein the passage between the chamber and the operating field includes the first wall port or wall inset, and wherein the second chamber is located in between the tubular enclosure and the skin of the patient, and wherein the second chamber has a size equal to or larger than zero.
11. The medical device according to any one of embodiments 8-12, wherein the body port and wall port are adapted to be locked together in at least one fixed position.
12. The medical device according to any one of embodiments 8-11, comprising at least one of:
  a. a second exchangeable wall port, and
  b. a second exchangeable wall inset, different from the wall port and wall inset, adapted to replace at least one of the wall port or wall inset.
13. The medical device according to any one of embodiments 8-12, comprising at least one of:
  a. a second exchangeable body port, and
  b. a second exchangeable body inset different from the body port and body inset, and adapted to replace at least one of the body port and body inset.
14. The medical device according to embodiment 8, comprising a second exchangeable integrated port different from the integrated port, and adapted to replace the integrated port during the surgical procedure.
15. The medical device according to any one of embodiments 1-14, wherein the wall is at least partially collapsible.

16. The medical device according to any one of embodiments 1-15, wherein the chamber is adapted to be inflated by a fluid.
17. The medical device according to any one of embodiments 7-16, wherein the inset comprises at least one glove integrated in the wall such that a surgeon is able to use the glove from outside the chamber to make manual manipulations inside the chamber while maintaining the sterile environment in the chamber.
18. The medical device according to any one of embodiments 1-17, further comprising a device or instrument mount adapted to retain instruments within the chamber.
19. The medical device according to any one of embodiments 1-18, wherein the sealing device comprises a vacuum sealing member (05') attached to at least one of the wall and enclosure and adapted to provide a pressure less than atmospheric pressure between the vacuum sealing member and the patient's skin to create a vacuum sealing between the skin of the patient's extremity and at least one of the wall and enclosure.
20. The medical device according to any one of embodiments 1-19, wherein the sealing device comprises a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.
21. The medical device according to any one of embodiments 1-20, further comprising an adhesive adapted to provide at least one of: (a) fixation of at least one of the wall and enclosure to the skin of the patient, and (b) sealing between the skin of the patient and at least one of the wall and enclosure.
22. The medical device according to any one of embodiments 6-21, further comprising an air evacuation system adapted to evacuate air from the second chamber, when the portion of the patient's extremity is placed in the enclosure.
23. The medical device according to embodiment 19, further comprising an air evacuation system adapted to evacuate air from the vacuum sealing member.
24. The medical device according to any one of the preceding embodiments, wherein at least one of; the body port, the wall port, the second wall port and the second body port, comprising a multi-port, comprising at least two ports integrated in the multi port, and adapted to enable passage of an object to the inside of the patient's body via the cut incision in the skin, when performing the surgical procedure.
25. The medical device according to any one of the preceding embodiments, further comprising a second sealing device having a first sealing member (35) adapted to be positioned at the inside of the patient's skin around an incision cut in the patient's skin made from the chamber, a second sealing member (37) adapted to be positioned at the outside of the patient's skin around the incision in the chamber, and at least one of a flexible, spring-loaded and elastic connecting member (36) sealingly interconnecting the first and second sealing members, wherein the second sealing device is adapted to seal between at least one of the second sealing member and the skin of the patient, and the first sealing member and tissue of the patient.
26. The medical device according to any one of the preceding embodiments, wherein the medical device further comprises at least one of:
    a. a filtering unit (26b) for filtering the fluid,
    b. a sterilization unit (26a) for directly or indirectly sterilizing the fluid,
    c. a fluid tempering unit (26c) adapted change the temperature of the fluid,
    d. a filtering unit for filtering the fluid and a sterilization unit for directly or indirectly sterilizing the fluid,
    e. a filtering unit for filtering the fluid and a fluid tempering unit adapted change the temperature of the fluid,
    f. a sterilization unit for directly or indirectly sterilizing the fluid and a fluid tempering unit adapted change the temperature of the fluid, and
    g. a filtering unit for filtering the fluid, a sterilization unit for directly or indirectly sterilizing the fluid and a fluid tempering unit adapted change the temperature of the fluid.
27. The medical device according to any one of the preceding embodiments, further comprising at least one inlet member (30) provided in the wall for supplying a fluid into the chamber, at least one outlet member (31) provided in the wall for discharging the fluid from the chamber, and a circulating pump (27) adapted to circulate the fluid from the outlet member to the inlet member.
28. The medical device according to any one of the preceding embodiments, further comprising at least one of:
    a. an airlock sluice (18), and
    b. a liquid lock sluice (18),
    comprising a first valve (38a) and second valve (38b) and a sluice chamber placed in between the first and second valve, for allowing passage of objects from the chamber through the first valve and further through the second valve out to the environment outside of the chamber, and vice versa.
29. The medical device according to any one of preceding embodiments, further comprising at least one of an airlock sluice and a liquid lock sluice, comprising a first valve and second valve, wherein the first valve is mounted in at least one of the skin or tissue of the patient and the portion of the wall adapted to directly or indirectly form an elongated tubular enclosure, and wherein the second valve is mounted in the wall.
30. The medical device according to any one of the preceding embodiments, wherein the medical device comprises a slit for placing the chamber around at least a portion of the extremity of the patient radially in relation to the length axis of the extremity.
31. The medical device according to embodiment 30, wherein the slit is adapted to be at least partially closed by closing elements mounted to the wall of the medical device.
32. The medical device according to any one of embodiments 30-31, wherein the medical device comprises a first and a second portion located on a first and second side of the slit when the chamber is placed around at least a portion of the extremity, and wherein the first and second portions are adapted to be interconnected by means of at least one of: an adhesive and a mechanical connecting member.
33. The medical device according to any one of embodiments 7-32, wherein at least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

34. The medical device according to any one of embodiment 1-33, wherein the chamber being adapted to encompass at least one skin incision for the joint surgical procedure within the chamber, while maintaining a sealed environment for the surgical procedure.

35. A method embodiment of performing a portion of a hip joint surgery on a patient using a medical device, the method comprising:
   a. applying a wall (01) on the skin (S) of the patient to form a chamber (C), in which a sealed environment can be maintained for encompassing part of the surgical procedure to be performed,
   b. applying a sealing device between the wall and the skin of the patient such that the sealing device forms a special loop at least partly encircling at least a portion of one or more of the following; the leg, the pelvic region, the abdominal region, the inguinal region, the gluteal region, the thoraxial region and the region of the lower back, such that the first sealing device seals between an incision site of the hip joint surgery and at least one of:
      i. the anal orifice,
      ii. the urethra orifice,
      iii. the perineum region,
   c. creating an incision at the incision site in the sealed environment within the chamber of the medical device.

Numbered Embodiment P 1-37

1. A medical device for performing hip joint surgery on a patient, the medical device comprising:
   a wall (01) adapted to form a chamber (C) together with or without the patient's body and at least partly to be placed on the patient's body, the chamber being adapted to encompass at least part of one step of the hip joint surgery procedure to be performed, while maintaining a sealed environment for the surgical procedure, the medical device further comprising:
   a first sealing device connected to the wall and adapted to seal between the wall and the skin or tissue of the patient to seal at least a part of the hip joint surgery operational field from at least one of: the anal orifice, the urethra orifice and at least part of the perineum region, while still maintaining the chamber sealed, the first sealing device comprising at least one of:
      a first part of the sealing device, and
      a first holding member adapted to hold the medical device in place by encircling at least one leg of the patient or the prolongation thereof to be involved in the sealing of the chamber,
   wherein the first sealing device further comprising at least one of;
      a second part of the sealing device, and
      a second holding member (96) adapted to hold the medical device in place by encircling the whole body left to right on the level above the legs selected from at least one of the level of the pelvic, abdominal or thorax region of the patient to further be involved in the sealing of the chamber,
   wherein the first sealing device further comprises at least one of;
      a third part of the sealing device adapted to seal from the medial cranial part of the leg where it is meeting the inguinal region or its prolongation, further in a cranial direction lateral of the patient's ventro-dorsal mid-sagittal plane, on the side where the hip surgery is performed, and wherein the third part of the sealing device at least partly extends in cranial direction until meeting the second part of the sealing device, and wherein the wall is interconnecting to the first, second and third part of the sealing device to seal the chamber, and
      a third holding member adapted to seal the chamber and exclude from the chamber at least one of the anal orifice, the urethra orifice and at least part of the perineum region.

2. The medical device according to embodiment 1, wherein the sealing device is positioned such that both of the urethra and the anus is excluded from the enclosed chamber forming the sealed environment.

3. The medical device according to any one of embodiments 1 and 2, wherein the medical device further comprises a second sealing device comprising a first sealing member adapted to be positioned at the inside of the patient's skin around an incision to be performed in the skin and a second sealing member adapted to be positioned at outside of the patient's skin around the incision, and a connecting member sealingly interconnecting the first and second sealing members, wherein the second sealing device is adapted to seal between at least one of: (a) the second sealing member and the skin of the patient, and (b) the first sealing member and tissue of the patient.

4. The medical device according to any one of embodiments 1-3, wherein at least one of the first and second holding member is adapted to encircle a portion of the patient's body, by itself or together with the sealing device, for holding the medical device in the desired position.

5. The medical device according to any one of the preceding embodiments, wherein at least a portion of the wall is adapted to directly or indirectly form an elongated tubular enclosure (04) having at least one open end, the enclosure being adapted to fit at least a portion of the leg of the patient, and wherein the medical device is arranged such that the portion of the leg extends into the enclosure through the first open end thereof, when the surgical procedure is to be performed on the portion of the patient's body.

6. The medical device according to any one of embodiments 1-5, wherein the chamber is formed by the wall without involving the patient's body, and wherein the part of the wall forming the chamber is adapted to also form the tubular enclosure, wherein the wall comprises two wall sides of which one is facing the inside of the chamber and the other is facing the tubular enclosure, when performing the surgical procedure, and wherein the tubular enclosure forms a second chamber at least partly encompassed by the tubular enclosure and adapted to be sealed at the first or more open ends by the patient's body portion, and wherein the wall part facing the tubular enclosure is adapted to form the second chamber together with the patient's body.

7. The medical device according to at least one of embodiments 1-6, wherein the chamber is adapted to be in communication with an operating field during the surgical procedure, when the skin of the patient has been cut in a position inside of the chamber, and wherein the wall encompassing the chamber has a wall port or wall inset mounted in a wall portion of the chamber for allowing; objects to be moved into the chamber or operating field and/or manual manipulation to be performed in the chamber or operating field.

8. The medical device according to embodiment 7, further comprising a port having a first and second part, and wherein the second part comprises the wall port or wall inset and the first part comprises a body port or body inset adapted to be mounted in the cut skin of the patient to allow objects to be moved further from the chamber into the operating field and/or manual manipulation to be performed from the chamber further into the operating field.

9. The medical device according to embodiment 8, wherein the two parts of the port or inset are adapted to be mounted together, touching each other for forming an integrated port or inset and thereby allowing objects to be moved into the operating field and/or manual manipulation to be performed in the operating field directly from outside the chamber, and wherein the two parts of the port or inset are adapted to be separable from each other and be placed in to one or more positions and thereby be adapted to use the second part of the port or inset to allow objects to be moved into the chamber and/or manual manipulation to be performed in the chamber and to use the first part of the port or inset to allow objects to be moved from the chamber passing the cut skin into the operating field and/or manual manipulation to be performed from the chamber through the cut skin further into the operating field in the patient's body.

10. The medical device according to any one of embodiments 5-9, wherein the chamber is adapted to be in communication with an operating field during the surgical procedure, and wherein the part of the wall forming both the chamber and the tubular enclosure, at a portion thereof, is adapted to be opened and wherein the opening together with the hip joint surgery incision of the patient is adapted to be positioned inside of the chamber allowing such communication with the operating field, wherein a portion of the wall part encompassing only the chamber has a wall port or wall inset mounted therein for allowing, from outside the chamber, at least one of a) objects to be moved into at least one of; the chamber and the operating field, and manual manipulation to be performed in at least one of; the chamber and the operating field.

11. The medical device according to embodiment 10, comprising a port or inset including a first and second part, wherein the second part comprises the wall port or wall inset and the first part comprises a first wall port or first wall inset mounted in the opening in the portion of the part of the wall forming both the chamber and the tubular enclosure and adapted to be opened to create the communication between the chamber and the operating field to allow; objects to be moved further from the chamber into the operating field and/or manual manipulation to be performed from the chamber further into the operating field, and wherein the passage between the chamber and the operating field includes the first wall port or inset, and wherein the second chamber is located in between the tubular enclosure and the skin of the patient, and wherein the second chamber has a size equal to or larger than zero.

12. The medical device according to embodiment 11, wherein the two parts of the port or inset are adapted to be mounted together, touching each other for forming an integrated port and inset and thereby allowing; objects to be moved into the operating field and/or manual manipulation to be performed in the operating field directly from outside the chamber using the integrated port or inset, and wherein the two parts of the port or inset are adapted to be separated from each into one or more positions in which they are not touching each other and thereby; to use the wall port or inset of the second part to allow; objects to be moved into the chamber and/or manual manipulation to be performed in the chamber and further to use the first wall port or first wall inset of the first part to allow; objects to be moved from the chamber passing the cut skin into the operating field and/or manual manipulation to be performed from the chamber through the cut skin further into the operating field.

13. The medical device according to any one of embodiments 8-12, wherein the two parts of the port or inset are adapted to be locked together in at least one fixed position.

14. The medical device according to any one of embodiments 1-13, wherein the chamber encompassing the surgical procedure is adapted to reduce infection risk of the surgical procedure.

15. The medical device according to any one of embodiments 8-12, wherein both of the two parts of the port are adapted to comprise a fluid sealing valve when the two parts are separated.

16. The medical device according to any one of embodiments 8-12, wherein the second part is adapted to comprise a fluid sealing valve, when the two parts are separated.

17. The medical device according to any one of embodiments 8-16, comprising at least one of:
  a. a second exchangeable wall port, and
  b. a second exchangeable wall inset, different from the wall port and wall inset, adapted to replace at least one of the wall port or wall inset.

18. The medical device according to embodiment 17, comprising at least one of:
  c. a second exchangeable body port, and
  d. a second exchangeable body inset,
different from the body port and body inset, and adapted to replace at least one of the body port and body inset.

19. The medical device according to at least one of embodiment 9 and 12, comprising a second exchangeable integrated port different from the integrated port, and adapted to replace the integrated port during the surgical procedure.

20. The medical device according to any one of embodiments 1-19, wherein the wall is at least partially collapsible.

21. The medical device according to any one of embodiments 1-20, wherein the chamber is adapted to be inflated by a fluid.

22. The medical device according to any one of embodiments 7-21, wherein the inset comprises at least one glove (02) integrated in the wall such that a surgeon is able to use the glove from outside the chamber to make manual manipulations inside the chamber while maintaining the sterile environment in the chamber.

23. The medical device according to any one of embodiments 1-22, further comprising a device or instrument mount adapted to retain instruments within the chamber.

24. The medical device according to any one of embodiments 1-23, wherein the sealing device comprises a vacuum sealing member (05) attached to at least one of the wall and enclosure and adapted to provide a pressure less than atmospheric pressure between the vacuum sealing member (05') and the patient's skin to create a vacuum sealing between the skin of the patient's extremity and at least one of the wall and enclosure.

25. The medical device according to embodiment 24, wherein the sealing device comprises a pressure sealing member (05") attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

26. The medical device according to any one of embodiments 1-27, further comprising an adhesive surface adapted to provide at least one of: (a) fixation of at least one of the wall and enclosure to the skin of the patient, and (b) sealing between the skin of the patient and at least one of the wall and enclosure.

27. The medical device according to any one of embodiments 11-26, further comprising an air evacuation system (06;08) adapted to evacuate air from the second chamber, when the portion of the patient's extremity is placed in the enclosure.

28. The medical device according to embodiment 24, further comprising an air evacuation system adapted to evacuate air from the vacuum sealing member (05').

29. The medical device according to any one of the preceding embodiments, wherein at least one of; the body port, the wall port, the second wall port and the second body port, comprises a multi-port, comprising at least two ports integrated in the multi port, and adapted to enable passage of an object to the inside of the patient's body via the cut incision in the skin, when performing the surgical procedure.

30. The medical device according to any one of the preceding embodiments, wherein the medical device comprises at least one of:
a filtering unit (26b) for filtering fluid supplied to the chamber,
a sterilization unit (26a) for directly or indirectly sterilizing fluid supplied to the chamber,
a fluid tempering unit (26c) adapted change the temperature of fluid supplied to the chamber,
a filtering unit (26b) for filtering fluid and a sterilization unit (26a) for directly or indirectly sterilizing fluid supplied to the chamber,
a filtering unit (26b) for filtering fluid supplied to the chamber and a fluid tempering unit (26c) adapted change the temperature of fluid supplied to the chamber,
a sterilization unit (26a) for directly or indirectly sterilizing fluid supplied to the chamber and a fluid tempering unit (26c) adapted change the temperature of fluid supplied to the chamber, and
a filtering unit (26b) for filtering fluid supplied to the chamber, a sterilization unit (26a) for directly or indirectly sterilizing fluid supplied to the chamber and a fluid tempering unit (26c) adapted change the temperature of fluid supplied to the chamber.

31. The medical device according to any one of the preceding embodiments, further comprising at least one inlet (30) provided in the wall for supplying a fluid into the chamber, at least one outlet (30) provided in the wall for discharging the fluid from the chamber, and a pump (27) adapted to circulate the fluid from the outlet to the inlet.

32. The medical device according to any one of the preceding embodiments, further comprising at least one of:
e. an airlock sluice (18), and
f. a liquid lock sluice,
comprising a first valve (38a) and second valve (38b) and a sluice chamber placed in between the first and second valve, for allowing passage of objects from the chamber through the first valve and further through the second valve out to the environment outside of the chamber, and vice versa.

33. The medical device according to any one of preceding embodiments, further comprising at least one of an airlock sluice and a liquid lock sluice, comprising a first valve and second valve, wherein the first valve is mounted in at least one of the skin or tissue of the patient and the portion of the wall adapted to directly or indirectly form the elongated tubular enclosure, and wherein the second valve is mounted in the wall.

34. The medical device according to any one of the preceding embodiments, wherein the medical device comprises a slit for placing the chamber around at least a portion of the extremity of the patient radially in relation to the length axis of the extremity.

35. The medical device according to embodiment 34, wherein the slit is adapted to be at least partially closed by closing elements mounted on the wall of the medical device.

36. The medical device according to any one of embodiments 34-35, wherein the medical device comprises a first and a second portion located on a first and second side of the slit when the chamber is placed around at least a portion of the extremity, and wherein the first and second portions are adapted to be interconnected by means of at least one of: an adhesive surface and a mechanical connecting member.

37. The medical device according to any one of embodiments 7-36, wherein at least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.

38. The medical device according to any one of embodiments 1-37, wherein the chamber being adapted to encompass at least one skin incision for the joint surgical procedure within the chamber, while maintaining a sealed environment for the surgical procedure.

39. A method for performing hip joint surgery on a patient, using the medical device according to embodiment 1, the method comprising:
forming a chamber (C) using the wall (01) together with or without the patient's body placing at least partly on the patient's body, the chamber encompassing at least part of one step of the hip joint surgery procedure to be performed, maintaining by the chamber a sealed environment for the surgical procedure, sealing with the first sealing device connected to the wall between the wall and the skin or tissue of the patient, the step of sealing including:

sealing at least a part of the hip joint surgery operational field from at least one of: the anal orifice, the urethra orifice and at least part of the perineum region, while still maintaining the chamber sealed, holding the medical device in place by encircling at least one leg of the patient or the prolongation thereof to be involved in the sealing of the chamber, using at least one of; a first part of the sealing device and a first holding member, holding the medical device in place by encircling the whole body left to right on the level above the legs selected from at least one of; the level of the pelvic, abdominal or thorax region of the patient to further be involved in the sealing of the chamber, using at least one of; a second part of the sealing device and a second holding member (96), sealing from the medial cranial part of the leg where it is meeting the inguinal region or its prolongation, further in a cranial direction lateral of the patient's ventro-dorsal mid-sagittal plane on the side where the hip surgery is performed, using a third part of the sealing device at least partly extending in cranial direction until meeting the second part of the sealing device, using at least one of; a third part of the sealing device and a third holding member, the wall interconnecting the first, second and third part of the sealing device to seal the chamber, thus sealing the chamber and exclude from the chamber at least one of; the anal orifice, the urethra orifice and at least part of the perineum region.

40. The method according to embodiment 39, positioning the sealing device is such that both of the urethra and the anus is excluded from the enclosed chamber forming the sealed environment.

41. The method according to any one of embodiments 39 and 40, wherein the medical device further comprises a second sealing device comprising a first and second sealing member, the method include the steps of:

positioning the first sealing member at the inside of the patient's skin around an incision to be performed in the skin, positioning the second sealing member at the outside of the patient's skin around the incision, interconnecting sealingly the first and second sealing members, using a connecting member, sealing with the sealing device between at least one of: (a) the second sealing member and the skin of the patient, and (b) the first sealing member and tissue of the patient.

42. The method according to any one of embodiments 39-41, encircling a portion of the patient's body by at least one of the first and second holding member, by itself or together with the sealing device, and holding the medical device in the desired position.

Numbered Embodiment Q 1-19

1. A medical device for performing knee joint surgery on a patient, the medical device comprising:

a. a wall (01) adapted to form a chamber (C) at least partially encapsulating the knee joint of the patient, the chamber being adapted to encompass at least a part of the knee joint surgery to be performed while maintaining a sealed environment for the surgical procedure, and b. a closeable wall port (17) or inset (42;42') placed in a portion of the wall, wherein the closeable wall port or inset is adapted to be at least one of: abutting, attaching, and placed in a fixed position in relation to a body port (22) placed in an incision in the knee region of the patient's body, such that an arthroscopic step of the knee joint surgery can be performed.

2. The medical device according to embodiment 1, wherein the medical device further comprises a sealing device (05) connected to the wall and adapted to seal against the patient's body, such that the sealed chamber is formed by the wall and the patient's body, 3. The medical device according to any one of the preceding embodiments, further comprising a closable body port (22), wherein the closable wall port is connected to a first portion of the wall, and the closable body port is connected to a second portion of the wall, and wherein the closable wall port and the closable body port are adapted be detachably connected to form an interconnected port.

4. The medical device according to any one of the preceding embodiments, wherein the wall port and body port are positioned relative to each other such that:
    a. an object is displaceable from outside of the chamber,
    b. through the wall port,
    c. into the chamber,
    d. through the body port into the patient, when the knee joint surgery is performed.

5. The medical device according to any one of the preceding embodiments, wherein the wall port or wall inset is displaceable between:
    a. a first position relatively close to the skin of the patient, and
    b. a second position more remote from the skin of the patient than the first position.

6. The medical device according to any one of the preceding embodiments, wherein the wall port is adapted to be locked to the body port.

7. The medical device according to any one of the preceding embodiments, wherein at least one of the wall port and body port comprises at least one of:
    a. a penetratable self sealing gel, and
    b. a flexible and/or elastic membrane (43), such that an object or hand can be inserted through the port while maintaining the sealed environment in the chamber.

8. The medical device according to any one of the preceding embodiments, wherein the chamber is adapted to hold a fluid having a pressure exceeding atmospheric pressure.

9. The medical device according to any one of the preceding embodiments, wherein the medical device further comprises a vacuum sealing member adapted to hold a pressure less than atmospheric pressure between the first wall portion and the patient's skin to seal between the first wall portion and the patient's skin.

10. The medical device according to embodiment 9, wherein the vacuum sealing member is adapted to create a substantially airtight seal between the wall portion and the skin of the patient, to enable an incision to be performed through the skin of the patient in sealed environment such that a fluid connection between a cavity in the patient and the chamber can be created.

11. The medical device according to any one of the preceding embodiments, further comprising at least one of: an airlock sluice (18) placed separate from the wall port and an airlock sluice (18) integrated in the wall port for allowing passage of objects between the chamber and the outside of the chamber.

12. The medical device according to any one of the preceding embodiments, wherein at least one of the wall and body ports is selected from a group consisting of at least one:
   c. a laparoscopic port,
   d. an arthroscopic port and
   e. a multiport.

13. The medical device according to any one of the preceding embodiments, further comprising a sealing device having a first sealing member adapted to be positioned at the inside of the patient's skin around an incision to be performed in the skin and a second sealing member adapted to be positioned at outside of the patient's skin around the incision, and a spring-loaded or elastic connecting member sealingly interconnecting the first and second sealing members, whereby the spring-loaded or elastic connecting member seals between at least one of: (a) the second sealing member and the skin of the patient, and (b) the first sealing member and tissue of the patient.

14. The medical device according to any one of the preceding embodiments, wherein the medical device further comprises at least one of:
   a. a filtering unit (26*b*) for filtering the fluid,
   b. a sterilization unit (26*a*) for directly or indirectly sterilizing the fluid,
   c. a fluid tempering unit (26*c*) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.

15. The medical device according to any one of the preceding embodiments, wherein, when the medical device is applied on the patient's body for performing a surgical procedure, the medical device further comprises at least one of:
   a. at least one inlet member provided in at least one of:
      i. the wall of the medical device, and
      ii. the skin of the patient for supplying a fluid to at least one of
         the chamber, and
         the cavity in the patient's body, and
   b. at least one outlet member provided in at least one of:
      i. the wall of the medical device, and
      ii. the skin of the patient for discharging the fluid from at least one of:
         the chamber, and
         the body cavity.

16. The medical device according to embodiment 15, further comprising a pump adapted to circulate the fluid from the outlet member to the inlet member.

17. A method embodiment of performing a portion of knee joint surgery on a patient using a medical device, the method comprising:
   a. applying a wall (01) on the skin (S) of the patient to form a chamber (C), in which a sealed environment can be maintained for encompassing part of the knee joint surgery to be performed, the wall comprising a closeable wall port (17),
   b. connecting the closeable wall port to a body port (22), such that the closeable wall port is at least one of: abutting the body port and attached to the body port, such that an arthroscopic step of the knee joint surgery can be performed.

18. The method according to embodiment 17, further comprising:
   a. displacing an object (69;89) from outside of the chamber through the wall port and into the chamber,
   b. displacing the object through the body port into a cavity in the patient the patient, when the knee joint surgery is performed.

19. The method according to any one of embodiments 17 and 18, further comprising displacing the wall port from a first position relatively close to the skin of the patient to a second position more remote from the skin of the patient than the first position.

Numbered Embodiment R 1-27

1. A medical device for performing a surgical procedure on a patient, the medical device comprising:
   a. a wall (01) adapted to be at least partially applied on the patient's body to form a chamber (C) together with the patient's body, in which a sealed environment can be maintained for encompassing part of the surgical procedure to be performed,
   b. at least one of a closeable wall port (17) and inset (42) placed in a portion of the wall and being adapted to be detachably connected to a closeable body port (22) placed in an incision in the patient's body connecting to a body cavity, when the medical device is applied on the patient's body for performing the surgical procedure,
   c. at least one of; a closeable body port and an inset adapted to be placed in an incision in the patient's body and further adapted to be detachably connected to the closeable wall port, when the medical device is applied on the patient's body for performing the surgical procedure,
   d. a sealing device (05) connected to the wall and adapted to seal against the skin of the patient, when the medical device is applied on the patient's body, wherein
   at least one of the closable wall port, the closable body port and the closable wall port and the closable body port together, are adapted to form an airlock sluice (18) between a cavity in the body of the patient and the ambient environment, when the medical device is applied on the patient's body for performing the surgical procedure.

2. The medical device according to embodiment 1, wherein the closeable wall port and closeable body port are adapted to be positioned relative to each other such that an elongated object is longitudinally displaceable through the closeable wall port and closeable and body port.
3. The medical device according to any one of embodiments 1-2, wherein at least one of the closeable wall port and the inset is displaceable between a first position, in which the closeable wall port or inset is situated relatively close to at least one of the closeable body port and the inset, and a second position, in which at least one of; the closeable wall port and the inset is situated more remote from the closeable body port or the inset.
4. The medical device according to any one of embodiments 1-3, wherein the closeable wall port or inset is adapted to be at least one of; connected to the closeable body port and locked to the closeable body port, when the medical device is applied on the patient's body for performing a surgical procedure.
5. The medical device according to any one of embodiments 1-4, wherein at least one of the closable body port and the closeable wall port comprises a penetratable self sealing gel (43), such that an object or hand can be inserted through the closeable wall port while maintaining the sealed environment.
6. The medical device according to embodiment 1-5, further comprising a coupling (80) adapted to detachably attach the closable body port or inset to the closable wall port or inset.
7. The medical device according to any one of embodiments 1-6, further comprising at least one of; an additional port and an additional inset, wherein at least one of the closeable wall port or inset and the closeable body port or inset is exchangeable by the additional port.
8. The medical device according to any one of embodiments 1-7, wherein the chamber is adapted to hold a fluid having a pressure exceeding atmospheric pressure.
9. The medical device according to any one of embodiments 1-8, comprising a sealing device adapted to be positioned in the portion of the wall adapted to be applied on the patient's body when the surgical procedure is to be performed, wherein the sealing device (05) comprises a vacuum sealing member (05') adapted to hold a pressure less than atmospheric pressure between the first wall portion and the patient's skin to seal between the first wall portion and the patient's skin.
10. The medical device according to any one of embodiments 1-9, wherein the airlock sluice is least one of: placed separate from the wall port, partly using the wall port in the airlock sluice and fully integrated in the wall port for allowing passage of objects between the chamber and the outside of the chamber.
11. The medical device according to embodiment 9, wherein the vacuum sealing member is adapted to create a substantially airtight seal between the wall portion and the skin of the patient, to enable an incision to be performed through the skin of the patient in sealed environment such that a fluid connection between a cavity within the patient and the chamber can be created.
12. The medical device according to any one of the preceding embodiments, wherein any one of the at least one closeable wall port or inset and the at least one closable body port or inset is selected from a group consisting of at least one:
   a. laparoscopic port,
   b. inset,
   c. holding device integrated port,
   d. inset comprising a integrated surgical glove, and
   e. multiport.
13. The medical device according to any one of the preceding embodiments, wherein at least one of
   a. the closeable body port comprises a closeable body multi-port adapted to be placed from inside the chamber in an incision to be performed in the skin of the patient, wherein the closeable body multi-port comprises at least two closeable body ports adapted to enable passage of an object between the chamber and the inside of the patient's body, wherein the body multiport is adapted to be connected to at least one of a closable wall port and a closable wall multiport together placed in an incision in the patient's body connecting to a body cavity, when the medical device is applied on the patient's body for performing a surgical procedure, and
   b. the closable wall port comprises a wall multiport, comprising at least two closable wall ports, wherein the wall multiport is adapted to be connected to at least one of; a closable body port and a closable body multiport placed in an incision in the patient's body connecting to a body cavity, when the medical device is applied on the patient's body for performing a surgical procedure.
14. The medical device according to any one of the preceding embodiments, wherein at least one of the closeable wall port and the closable body port, comprises at least one of an elastic membrane and a flexible membrane, and wherein the membrane (43) is adapted to, in a non-compressed state, seal between the chamber and the environment outside the chamber, and in a compressed state enable a hand or an object to be inserted through the membrane.
15. The medical device according to any one of the preceding embodiments, further comprising a sealing device having a first sealing member (35) adapted to be positioned at the inside of the patient's skin around an incision to be performed in the skin and a second sealing member (37) adapted to be positioned at outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
16. The medical device according to any one of the preceding embodiments, further comprising a fluid tempering unit (26c) adapted to temper a fluid within the chamber to a temperature different from the temperature of the environment outside of the chamber.
17. The medical device according to any one of the preceding embodiments, further comprising a sterilization unit (26a) for directly or indirectly sterilizing a fluid contained in the chamber.
18. The medical device according to any one of the preceding embodiments, wherein, when the medical device is applied on the patient's body for performing a surgical procedure, the medical device further comprises at least one of:
   a. at least one inlet (30) provided in at least one of:
      i. the wall of the medical device, and
      ii. the skin of the patient for supplying a fluid to at least one of
         the chamber, and
         the cavity in the patient's body, and b. at least one outlet (31) provided in at least one of:
  i. the wall of the medical device, and
  ii. the skin of the patient for discharging the fluid from at least one of:
    the chamber, and
    the body cavity.
19. The medical device according to embodiment 17, further comprising a pump (27) adapted to circulate the fluid from the outlet to the inlet.
20. The medical device according to any one of the preceding embodiments, wherein the closeable body port is adapted to be placed inside the chamber in an incision to be performed in the skin of the patient to enable passage between the chamber and a cavity in the patient's body.
21. The medical device according to embodiment 19, further comprising a coupling (80) adapted to detachably attach the closable body port to at least one of the patient's skin and the closable wall port or inset to enable exchange and removal of the closable body port or inset.
22. The medical device according to any one of the preceding embodiments, wherein the closeable wall port is positioned in the wall portion and adapted such that it allows handling of an instrument for at least one of; cuffing through the patient's skin via the closable wall port and cutting through the patient's skin with the instrument fully placed inside the chamber, when the wall is applied on the patient's body.
23. The medical device according to any one of embodiments 1-21, wherein the wall portion is adapted to allow itself to be cut through to reach and make an incision in the patients skin for allowing a surgical procedure, when the wall is applied on the patient's body.
24. The medical device according to any one of embodiments 1-23, wherein the closable body port is adapted to be at least one of
  a. fitted in the patient's skin after an incision has been made in the skin, and
  b. fitted to the closable wall port after the closable body has been fitted in the patient's skin after an incision has been made in the skin,
when the medical device is applied on the patient's body.
25. The medical device according to anyone of embodiments 1-23, wherein the closeable wall port or inset and the closeable body port or inset are connected by a portion of the wall, and wherein the closeable wall port or inset and closable body port or inset can be moved in relation to each other whilst being connected by means of the wall portion.
26. The medical device according to anyone of embodiments 1-24, further comprising a coupling (80) adapted to be at least one of
  an integrated part of at least one of the body port or the body inset,
  an integrated part of at least one of the wall port or the wall inset,
  a body coupling (80*b*) adapted to be placed in close relation to the skin of the patient, and further adapted to be connected to the wall port or inset, and
  a wall coupling adapted to be placed in close relation to the wall of the medical device, and further adapted to be connected to the body port or inset.

27. A method embodiment of forming an airlock sluice for use when performing a surgical procedure on a patient, the method comprising:
  a. applying a wall (01) on the patient's body to form a chamber (C) together with the patient's body, in which a sealed environment can be maintained for encompassing part of the surgical procedure to be performed,
  b. applying a sealing device (05) against the skin (S) of the patient, such that sealing is created between the wall of the medical device and the skin of the patient,
  c. connecting at least one of; a closeable wall port (17) and an inset (42) placed in a portion of the wall to a closeable body port (22) placed in an incision in the patient's body.

Numbered Embodiment S 1-30

1. A medical device for performing a surgical procedure on a patient, the medical device comprising:
  a. a wall (01) adapted to at least partially be applied on the patient's body to form a chamber (C) by itself or together with the patient's body, in which a sealed environment can be maintained for encompassing part of the surgical procedure to be performed, wherein a portion of the wall is adapted to contact the patient's skin (S) when the surgical procedure is performed,
  b. a vacuum sealing device (05) comprising a vacuum sealing member (05') adapted to hold a pressure less than atmospheric pressure between the wall portion and the patient's skin to seal between the wall portion and the patient's skin, and
  c. a vacuum adjustment device (93) adapted to adjust the pressure in the vacuum sealing member.
2. The medical device according to embodiment 1, wherein the vacuum adjustment device is adapted to adjust the pressure in the vacuum sealing member as a response to at least one of:
  a. a physiological parameter of the patient, and
  b. a parameter of the medical device.
3. The medical device according to embodiment 2, wherein the parameter of the medical device is one of:
  a. the pressure in the chamber,
  b. the pressure in the vacuum sealing member,
4. The medical device according to embodiment 2, wherein the physiological parameter of the patient is one of:
  a. the blood pressure of the patient,
  b. the blood flow of the patient, and
  c. a temperature of the body of the patient.
5. The medical device according to any one of embodiments 1-4, wherein the medical device further comprises a monitoring unit (98) connected to the adjustment device, wherein the monitoring unit is adapted to monitor at least one of:
  a. the pressure in the chamber,
  b. the pressure in the vacuum sealing member,
  c. the blood pressure of the patient,
  d. the blood flow of the patient, and
  e. a temperature of the patient.
6. The medical device according to any one of embodiments 1-5, wherein the adjustment device is adapted to adjust the pressure in the vacuum sealing member such that the blood flow of the patient remains substantially unaffected.

7. The medical device according to embodiment 6, wherein the medical device comprises a first monitoring unit (98') adapted to monitor the blood flow or blood pressure of the patient and a second monitoring unit (98"), adapted to monitor the pressure in the vacuum sealing member and wherein the adjustment device is adapted to adjust the pressure in the vacuum sealing member in response to input from both the first and second monitoring unit, for mediating between keeping the chamber sealed and keeping the blood flow of the patient substantially unaffected.

8. The medical device according to any one of the preceding embodiments, wherein the adjustment device is adapted to adjust the pressure in the vacuum sealing member for keeping the pressure between at least one of:
   a. −135 mmHg and 0 mmHg,
   b. −115 mmHg and 0 mmHg,
   c. −100 mmHg and 0 mmHg,
   d. −50 mmHg and 0 mmHg,
   e. −30 mmHg and 0 mmHg,
   f. −20 mmHg and 0 mmHg,
   g. −10 mmHg and 0 mmHg, and
   h. −5 mmHg and 0 mmHg
   and thus keeping the blood flow of the patient substantially un affected.

9. The medical device according to any one of the preceding embodiments, wherein the vacuum sealing device is adapted to create a substantially airtight seal between the wall portion and the skin of the patient, to enable an incision to be performed through the skin of the patient in the sealed environment such that a fluid connection between a cavity within the patient and the chamber is formed.

10. The medical device according to any one of the preceding embodiments, wherein the medical device further comprises an airlock sluice (18) provided in the wall for allowing passage of an object between the chamber and the ambient environment when the vacuum sealing device is sealing between the skin of the patient and the wall portion.

11. The medical device according to any one of the preceding embodiments, wherein the wall is at least partially collapsible and adapted to be inflated by a fluid.

12. The medical device according to any one of the preceding embodiments, wherein the wall is adapted to hold a pressure within the chamber exceeding atmospheric pressure, and wherein the vacuum sealing device is adapted to seal between the wall of the medical device and the skin of the patient such that the pressure in the chamber, exceeding atmospheric pressure, can be maintained.

13. The medical device according to any one of the preceding embodiments, wherein the medical device comprises a first monitoring unit (98) adapted to monitor the pressure in the vacuum sealing, and a chamber pressure monitoring unit adapted to monitor the pressure inside the chamber, and wherein the adjustment device is adapted to adjust the pressure in the vacuum sealing member such that at least one of the pressure in the chamber, exceeding atmospheric pressure, can be maintained, and the pressure difference between atmospheric pressure and the pressure in the vacuum sealing exceeds the pressure difference between atmospheric pressure and the pressure in the chamber.

14. The medical device according to embodiment 13, wherein the pressure in the chamber is between 5 mmHg and 75 mmHg above atmospheric pressure, and wherein the pressure in the vacuum sealing is between 6 mmHg and 76 mmHg below atmospheric pressure.

15. The medical device according to any one of the preceding embodiments, comprising a wall inset (42; 42') integrated in the wall, wherein the inset comprises at least one of;
    a. at least one glove (02) integrated in the wall such that a surgeon is able to use the glove from outside the chamber to make manual manipulations inside the chamber while maintaining sterile environment in the chamber, and
    b. at least one device or instrument mount.

16. The medical device according to any one of the preceding embodiments, wherein the medical device further comprises at least one closeable wall port (17) placed in the wall enabling passage between the chamber and the outside of the chamber, wherein the closeable wall port is detachably fixated to the wall such that the wall port can be exchanged to another wall port or wall inset.

17. The medical device according to any one of the preceding embodiments, further comprising a second sealing device having a first sealing member (35) adapted to be positioned at the inside of the patient's skin around an incision to be performed in the skin and a second sealing member (37) adapted to be positioned at outside of the patient's skin around the incision, and a spring-loaded, elastic, or flexible connecting member (37) sealingly interconnecting the first and second sealing members, whereby the spring-loaded or elastic connecting member seals between at least one of:
    a. the second sealing member and the skin of the patient, and
    b. the first sealing member and tissue of the patient.

18. The medical device according to any one of the preceding embodiments, wherein the medical device further comprises at least one of:
    a. a filtering unit (26b) for filtering the fluid,
    b. a sterilization unit (26a) for directly or indirectly sterilizing the fluid,
    c. a fluid tempering unit (26c) adapted change the temperature of the fluid,
    d. a filtering unit for filtering the fluid and a sterilization unit for directly or indirectly sterilizing the fluid,
    e. a filtering unit for filtering the fluid and a fluid tempering unit adapted change the temperature of the fluid,
    f. a sterilization unit for directly or indirectly sterilizing the fluid and a fluid tempering unit adapted change the temperature of the fluid, and
    g. a filtering unit for filtering the fluid, a sterilization unit for directly or indirectly sterilizing the fluid and a fluid tempering unit adapted change the temperature of the fluid.

19. The medical device according to any one of the preceding embodiments, wherein, when the medical device is applied on the patient's body for performing a surgical procedure involving a body cavity, the medical device further comprises at least one of:
    a. at least one inlet member (30) provided in at least one of:
       i. the wall of the medical device, and
       ii. the skin of the patient for supplying a fluid to at least one of the chamber, and
the cavity in the patient's body, and
b. at least one outlet member (31) provided in at least one of:
   i. the wall of the medical device, and
   ii. the skin of the patient for discharging the fluid from at least one of:
       the chamber, and
       the body cavity.
20. The medical device according to embodiment 19, further comprising a circulating pump (27) adapted to circulate the fluid from the outlet member to the inlet member.
21. The medical device according to any one of the preceding embodiments, further comprising a closable body port adapted to be placed inside the chamber in an incision to be performed in the skin of the patient to enable passage between the chamber and the inside of the patient's body.
22. The medical device according to any one of the preceding embodiments, wherein a part of the wall of the medical device forms an elongated tubular enclosure (04) extending within the chamber of the medical device, contacting the skin of the patient and being adapted to separate the skin of the patient from the sealed environment of the chamber of the medical device, when implanted.
23. The medical device according to any one of the preceding embodiments, wherein the medical device further comprises an adhesive adapted to provide at least one of:
   a. fixation of the wall to the skin of the patient, and
   b. sealing between the skin of the patient and the wall.
24. The medical device according to any one of the preceding embodiments, wherein the vacuum sealing device further comprises a vacuum pump (08), and wherein the vacuum adjusting device is connected to the vacuum pump and thereby adjusts the pressure in the vacuum sealing member.
25. The medical device according to any one of the preceding embodiments, wherein the vacuum adjustment device is adapted to control the vacuum pump as a response to an input from the monitoring unit.
26. The medical device according to any one of embodiments 16-25, wherein at least one of the closeable wall port and the closable body port, comprises at least one of an elastic membrane and a flexible membrane, and wherein the membrane is adapted to, in a non-compressed state, seal between the chamber and the environment outside the chamber, and in a compressed state enable a hand or an object to be inserted through the membrane.
27. A method embodiment of providing a sealed environment using a medical device, such that a surgical procedure can be performed in the sealed environment, the method comprising:
   a. applying a wall (01) on the skin (S) of the patient to form a chamber (C), in which a sealed environment can be maintained for encompassing part of the surgical procedure to be performed,
   b. applying a vacuum sealing member (05') contacting the skin of the patient, the vacuum sealing member being connected to the wall of the medical device and adapted to seal the chamber from the ambient environment (A)
   c. adjusting the pressure in the vacuum sealing member such that sealing between the skin of the patient and the wall of the medical device is created.
28. The method according to embodiment 27, wherein the step of adjusting the pressure in the vacuum sealing member comprises adjusting the pressure in the vacuum sealing member as a response to at least one of:
   a. a monitored parameter of the medical device, and
   b. a monitored physiological parameter of the patient.
29. The method according to embodiment 28, wherein the step of adjusting the pressure in the vacuum sealing member as a response to a monitored parameter of the medical device comprises adjusting the pressure in the vacuum sealing member as a response to:
   a. the pressure in the chamber,
   b. the pressure in the vacuum sealing member,
30. The method according to embodiment 28, wherein the step of adjusting the pressure in the vacuum sealing member as a response to a monitored physiological parameter of the patient comprises adjusting the pressure in the vacuum sealing member as a response to:
   a. the blood pressure of the patient,
   b. the blood flow of the patient, and
   c. a temperature of the body of the patient.

Numbered Embodiment T 1-19

1. A medical device for performing arthroscopic surgery on a joint of a patient, the medical device comprising:
   a. a wall (01) adapted to form a chamber (C) for encapsulating at least a part of the joint of the patient for allowing the arthroscopic surgery to be performed, the chamber being adapted to encompass part of the surgery to be performed while maintaining a sealed environment,
   b. a fluid inlet (30) placed in the wall (01) and adapted for supplying a fluid to the chamber, and
   c. a fluid outlet (31) adapted to be placed in an incision performed in the joint region of the patient for evacuating the fluid from the joint region.
2. The medical device according to embodiment 1, wherein the wall is adapted to hold a liquid at least partially filling the chamber.
3. The medical device according to embodiment 2, wherein the liquid is at least one of an isotonic solution and an antibiotic liquid.
4. The medical device according to any one of the preceding embodiments, wherein the medical device is adapted for use in knee joint procedures, and wherein the medical device comprises at least one of a first opening arranged such that the leg of a patient can enter the medical device and a second opening arranged such that the leg of a patient can exit the medical device.
5. The medical device according to any one of the preceding embodiments, wherein the wall is at least partially collapsible.
6. The medical device according to any one of the preceding embodiments, further comprises a fluid system for withdrawing fluid from the fluid outlet and supplying fluid to the fluid inlet.
7. The medical device according to embodiment 6, wherein the fluid system further comprises a fluid pump (27) for circling fluid from the fluid outlet to the fluid inlet.
8. The medical device according to embodiment 6, wherein the fluid system comprises at least one of:
   a. a filtering unit (26b) for filtering the fluid, b. a sterilization unit (26*a*) for directly or indirectly sterilizing the fluid,
c. a fluid tempering unit (26*c*) adapted change the temperature of the fluid,
d. a filtering unit for filtering the fluid and a sterilization unit for directly or indirectly sterilizing the fluid,
e. a filtering unit for filtering the fluid and a fluid tempering unit adapted change the temperature of the fluid,
f. a sterilization unit for directly or indirectly sterilizing the fluid and a fluid tempering unit adapted change the temperature of the fluid, and
g. a filtering unit for filtering the fluid, a sterilization unit for directly or indirectly sterilizing the fluid and a fluid tempering unit adapted change the temperature of the fluid.

9. The medical device according to any one of the preceding embodiments, wherein a part of the wall forms an elongated tubular enclosure (04) extending within the chamber of the medical device, contacting the skin of the patient and being adapted to separate the skin of the patient from the sealed environment of the chamber of the medical device.

10. The medical device according to embodiment 9, wherein the fluid outlet is placed through the wall of the elongated tubular enclosure.

11. The medical device according to any one of the preceding embodiments, wherein the medical device comprises a sealing device (05) for sealing between the medical device and the patient.

12. The medical device according to embodiment 10, wherein the sealing device comprises a vacuum sealing member (05') adapted to hold a pressure being less than atmospheric pressure thus creating the vacuum sealing between the skin of the patient and the medical device.

13. The medical device according to embodiment 10, wherein the sealing device comprises a pressure sealing member (05") adapted to hold a pressure exceeding atmospheric pressure and thereby mechanically press against the skin of the patient to provide a sealing between the skin of the patient and the medical device.

14. The medical device according to any one of the preceding embodiments, wherein the medical device further comprises a fluid lock sluice (18) for allowing passage of objects between the sealed environment and the environment outside of the sealed environment and vice versa, when the medical device is positioned in connection with the patient, for hindering fluid leakage through the fluid lock sluice.

15. The medical device according to any one of the previous embodiments, wherein the medical device further comprises an energy transferring coupling (52; 56;58) adapted to transfer energy from outside the chamber into the sealed environment, such that a tool (16) can be energized.

16. The medical device according to any one of the previous embodiments, wherein the medical device is adapted to hold a pre-placed energy consuming tool within the sealed environment before the medical device is placed in connection with the patient.

17. The medical device according to any one of the preceding embodiments, wherein the medical device further comprises a body port (17) or body inset (42;42') adapted to be placed in an incision in the skin of the patient, wherein the body port or body inset comprises at least one of:

a. a body multi port (48) comprising at least two ports adapted to enable passage of at least one of one or more tools, one or more devices and one or more parts of the human body, from outside of the patient's body to inside of the patient's body or the opposite direction,
b. a body port comprising one port adapted to enable passage of at least one of; one or more tools, one or more devices and one or more parts of the human body, from outside of the patient's body to inside of the patient's body or the opposite direction, and
c. a body inset (42;42') comprising at least one of: a glove (02) and a device or instrument mount (20).

18. The medical device according to any one of the preceding embodiments, comprising at least one port enabling passage of at least one of surgical tools, surgical devices and one or more parts of the human body, between the sealed environment and the ambient environment (A) or in the opposite direction, wherein the at least one port comprises an elastic membrane (43), and wherein the elastic membrane is adapted to, in a non-expanded state, seal between the sealed environment and the environment outside of the sealed environment, and in an expanded state enable a hand to be inserted through the elastic membrane.

19. A method embodiment of performing an arthroscopic surgical procedure on a patient using a medical device, the method comprising:
a. applying a wall (01) on the skin (S) of the patient to form a chamber (C), in which a sealed environment can be maintained for encompassing part of the surgical procedure to be performed,
b. creating an incision (I) in the skin of the patient, in the sealed environment, such that a fluid connection is created between the chamber and a cavity in the body of the patient,
c. positioning a fluid outlet (31') in the incision created in the skin of the patient,
d. supplying fluid to the chamber through a first fluid inlet (30) placed in the wall, and
e. discharging fluid from the incision site through the fluid outlet (31) placed in the incision.

Numbered Embodiment U 1-22

1. A medical device for performing arthroscopic surgery on a joint of a patient, the medical device comprising:
a. a wall (01) adapted to form a chamber (C) adapted to encapsulate the joint of the patient, the chamber being adapted to encompass part of the surgical procedure to be performed while maintaining a sealed environment,
b. a first fluid inlet (30) placed in the wall and adapted for supplying fluid to the chamber,
c. a first fluid outlet (31) placed in the wall and adapted for discharging fluid from the chamber,
d. a second fluid inlet (30') adapted to be placed in an incision (I) in the skin (S) of the patient, in the area of the joint, for supplying fluid to the joint, and
e. a second fluid outlet (31') adapted to be placed in an incision in the skin of the patient, in the area of the joint, for discharging fluid from the joint.

2. The medical device according to embodiment 1, wherein the medical device comprises a first fluid system (28) adapted to at least one of:

a. supply fluid to the first fluid inlet and evacuate fluid from at least one of the first and second fluid outlet, and b. circulate a fluid from at least one of the first or second fluid outlet to the first fluid inlet.

3. The medical device according to embodiment 2, wherein the medical device comprises a first fluid system (28) adapted to at least one of:

a. supply fluid to the second fluid inlet, and b. evacuate fluid from at least one of the first and second fluid outlet and circulate a fluid from at least one of the first or second fluid outlet to the second fluid inlet.

4. The medical device according to anyone of embodiment 1-3, wherein the first fluid system (28) is adapted to at least one of:

a. supply fluid to the first fluid inlet and evacuate fluid from the first fluid outlet, and b. circulate a fluid from the first fluid outlet to the first fluid inlet.

5. The medical device according to anyone of embodiment 1-4, further comprising a second fluid system (28') is adapted to at least one of:

a. supply fluid to the second fluid inlet and evacuate fluid from the second fluid outlet, and b. circulate a fluid from the second fluid outlet to the second fluid inlet.

6. The medical device according to any one of embodiments 2-5, wherein at least one of the first and second fluid systems is adapted to circulating a liquid fluid.

7. The medical device according to embodiment 6, wherein the liquid is at least one of; an isotonic solution and an antibiotic liquid.

8. The medical device according to any one of embodiments 2-7, wherein at least one of the first and second fluid systems comprises a fluid pump (09) for circulating the fluid from the first or second fluid outlet to the first or second fluid inlet.

9. The medical device according to any one of embodiments 1-8, wherein at least one of the first and second fluid systems comprises at least one of:

a. a filtering unit (26b) for filtering the fluid, b. a sterilization unit (26a) for directly or indirectly sterilizing the fluid, c. a fluid tempering unit (26c) adapted change the temperature of the fluid, d. a filtering unit for filtering the fluid and a sterilization unit for directly or indirectly sterilizing the fluid, e. a filtering unit for filtering the fluid and a fluid tempering unit adapted change the temperature of the fluid, f. a sterilization unit for directly or indirectly sterilizing the fluid and a fluid tempering unit adapted change the temperature of the fluid, and g. a filtering unit for filtering the fluid, a sterilization unit for directly or indirectly sterilizing the fluid and a fluid tempering unit adapted change the temperature of the fluid.

10. The medical device according to any one of the preceding embodiments, wherein the medical device is adapted for use in knee joint procedures, and wherein the medical device comprises at least one of a first opening arranged such that the leg of a patient can enter the medical device and a second opening arranged such that the leg of a patient can exit the medical device.

11. The medical device according to any one of the preceding embodiments, wherein the wall is at least partially collapsible.

12. The medical device according to any one of the preceding embodiments, wherein a part of the wall forms an elongated tubular enclosure (04) extending within the chamber of the medical device, contacting the skin of the patient and being adapted to separate the skin of the patient from the sterile environment of the chamber of the medical device.

13. The medical device according to embodiment 12, wherein at least one of the first fluid inlet and the first fluid outlet is positioned through the wall of the elongated tubular enclosure.

14. The medical device according to any one of the preceding embodiments, wherein the medical device comprises a sealing device (05) for sealing between the medical device and the patient.

15. The medical device according to embodiment 14, wherein the sealing device comprises a vacuum sealing member adapted to hold a pressure being less than atmospheric pressure thus creating a vacuum sealing between the skin of the patient and the medical device.

16. The medical device according to embodiment 14, wherein the sealing device comprises a pressure sealing member adapted to hold a pressure exceeding atmospheric pressure and thereby mechanically press against the skin of the patient to provide a sealing between the skin of the patient and the medical device.

17. The medical device according to any one of the preceding embodiments, wherein the medical device further comprises a fluid lock sluice (18) for allowing passage of objects between the sealed environment and the environment outside of the sealed environment and vice versa, when the medical device is positioned in connection with the patient, for hindering fluid leakage through the fluid lock sluice (18).

18. The medical device according to any one of the previous embodiments, wherein the medical device further comprises an energy transferring coupling (52; 56;58) adapted to transfer energy from outside the chamber into the sealed environment, such that a tool (16) can be energized.

19. The medical device according to any one of the previous embodiments, wherein the medical device is adapted to hold a pre-placed energy consuming tool (16) within the sealed environment before the medical device is placed in connection with the patient.

20. The medical device according to any one of the preceding embodiments, wherein the medical device further comprises a body port (22) or body inset (42;42') adapted to be placed in an incision in the skin of the patient, wherein the body port or inset comprises at least one of:

a. a body multi port (48) comprising at least two ports adapted to enable passage of at least one of; one or more tools, one or more devices and one or more parts of the human body, from outside of the patient's body to inside of the patient's body or the opposite direction, b. a body port comprising one port adapted to enable passage of at least one of; one or more tools, one or more devices and one or more parts of the human body, from outside of the patient's body to inside of the patient's body or the opposite direction, and c. a body inset (42;42') comprising at least one of: a glove and a device or instrument mount.

21. The medical device according to any one of the preceding embodiments, comprising at least one wall port (17) enabling passage of at least one of: surgical tools, surgical devices and one or more parts of the human body, between the sealed environment and the environment outside of the sealed environment or in the opposite direction, wherein the at least one port comprises an elastic membrane (43), and wherein the elastic membrane is adapted to, in a non-expanded state, seal between the sealed environment and the environment outside of the sealed environment, and in an expanded state enable a hand to be inserted through the elastic membrane.

22. A method embodiment of performing an arthroscopic surgical procedure on a patient using a medical device, the method comprising:
    a. applying a wall (01) on the skin (S) of the patient to form a chamber (C), in which a sealed environment can be maintained for encompassing part of the surgical procedure to be performed,
    b. supplying fluid to the chamber through a first fluid inlet (30) placed in the wall,
    c. discharging fluid from the chamber through a fluid outlet (31) placed in the wall,
    d. supplying fluid to a cavity in the body of the patient through a second fluid inlet (30') placed in an incision (I) in the skin (S) of the patient, and
    e. discharging fluid from the cavity in the body of the patient through a second fluid outlet (31') placed in an incision in the skin of the patient.

Numbered Embodiment V 1-31

1. A medical device for performing a surgical procedure on a patient comprising:
    a wall (01) adapted to be applied at least partially on the patient's body to form a chamber (C) by itself or together with the body of the patient, in which a sealed environment can be maintained for encompassing part of the surgical procedure to be performed,
    a pressure sealing device (05) adapted to seal between a wall portion and the patient's body, when the wall is applied on the patient's body, wherein the pressure sealing device comprises a pneumatically, hydraulically or mechanically powered pressure sealing member (05") adapted to press the wall portion against the body of the patient such that the chamber is substantially sealed from the ambient environment (A) allowing a pressure inside the chamber to be higher than the atmospheric pressure during the surgical procedure, and at least one of:
      i. a pressure adjustment device (93) adapted to adjust the pressure in the sealing member, and
      ii. a monitoring unit (98) for monitoring at least one of:
        1. a parameter of the medical device, and
        2. a physiological parameter of the patient.

2. The medical device according to embodiment 1, wherein the pressure adjustment device is adapted to adjust the pressure in the sealing member as a response to input from the monitoring unit.

3. The medical device according to any one if embodiments 1 and 2, wherein the parameter of the medical device is at least one of:
    i. the pressure in the sealing member,
    ii. the pressure in the chamber, and
    iii. the direct or indirect leakage of fluid from the chamber.

4. The medical device according to embodiment 1 and 2, wherein the physiological parameter of the patient is at least one of:
    i. the blood flow passing the sealing device,
    ii. the blood pressure of the patient
    iii. a temperature of the body of the patient, 5. The medical device according to any one of the preceding embodiments, wherein the adjusting device is adapted to adjust the pressure in the sealing device based on input from the monitoring unit, such that the sealing does not substantially hinder the flow of blood passed the sealing member.

6. The medical device according to any one of the preceding embodiments, wherein the medical device comprises a first and second monitoring unit, wherein the first monitoring unit (98') is adapted to monitor at least one of:
    i. the blood pressure of the patient
    ii. the blood flow passing the sealing,
    iii. a temperature of the body of the patient,
and wherein the second monitoring unit (98") is adapted to monitor at least one of:
    i. the pressure in the sealing,
    ii. the pressure in the chamber, and
    iii. the direct or indirect leakage of fluid from the chamber.

7. The medical device according to embodiment 6, wherein the pressure adjustment device is adapted to adjust the pressure in the sealing member based on input from the first and second monitoring unit.

8. The medical device according to any one of the preceding embodiments, wherein the pressure adjustment device is adapted to adjust the pressure in the sealing member such that the pressure in the sealing member is between one of:
    10 mmHg-160 mmHg,
    20 mmHg-140 mmHg,
    30 mmHg-120 mmHg,
    30 mmHg-100 mmHg,
    40 mmHg-100 mmHg,
    40 mmHg-80 mmHg, and
    50 mmHg-70 mmHg.

9. The medical device according to any one of the preceding embodiments, wherein the pressure adjustment device comprises at least one of:
    a fluid pump (09) for pumping a gaseous fluid to the sealing member,
    a fluid pump for pumping a liquid fluid to the sealing,
    a spring loaded device involved in causing the pressure, and
    a prefilled reservoir involved in causing the pressure.

10. The medical device according to any one of the preceding embodiments, further comprising an airlock sluice (18) provided in the wall for allowing passage of an object between the chamber and the environment outside of the chamber, when the sealing device is sealing between the skin of the patient and the wall portion.

11. The medical device according to any one of the preceding embodiments, wherein the wall is at least partially collapsible.

12. The medical device according to embodiment 11, wherein the collapsible wall is adapted to be inflated by at least one of
    1. a gaseous fluid, and
    2. a liquid fluid.

13. The medical device according to any of the preceding embodiments, comprising a closable body port (22) adapted to be placed in the patient's skin between a cavity in the patient's body and the chamber, when a surgical procedure is performed, wherein the closable body port comprises at least one of
 an elastic membrane and a flexible membrane, and wherein the membrane (43) is adapted to, in a non-compressed state, seal between the chamber and the environment outside the chamber, and in a compressed state enable a hand or an object to be inserted through the membrane,
 an adaptation to be connected to a wall port, placed in the wall,
 an adaptation to be detachable and exchanged by a different second port or a body inset.
14. The medical device according to any one of the preceding embodiments, wherein the medical device is adapted to hold a pressure within the chamber exceeding atmospheric pressure.
15. The medical device according to any one of the preceding embodiments, further comprising a wall inset, comprising at least one glove integrated in the wall such that a surgeon is able to use the glove from outside the chamber to make manual manipulations inside the chamber while maintaining the sterile environment in the chamber.
16. The medical device according to any one of the preceding embodiments, further comprising an adhesive adapted to provide at least one of: (a) fixation of at least one of the wall and enclosure to the skin of the patient, and
(b) sealing between the skin of the patient and at least one of the wall and enclosure.
17. The medical device according to any one of the preceding embodiments, wherein the medical device further comprises at least one wall port (17) adapted to enable passage between the chamber and the outside of the chamber or at least one wall inset (42;42') positioned in the wall, and wherein the wall port or wall inset is detachably fixated to the wall such that the wall port or wall inset can be exchanged to another wall port or wall inset.
18. The medical device according to any one of the preceding embodiments, further comprising at least one non-collapsible transparent window (21) provided in the wall for enabling viewing into the chamber.
19. The medical device according to embodiment 17, wherein the wall is adapted to position the non-collapsible transparent window when the collapsible wall being inflated.
20. The medical device according to any one of the preceding embodiments, further comprising a body multi-port (48) adapted to be placed from inside the chamber in an incision to be performed in the skin of the patient, wherein the body multi-port comprises at least two body ports adapted to enable passage of an object between the chamber and the inside of the patient's body.
21. The medical device according to any one of the preceding embodiments, further comprising at least one wall port placed in the wall enabling passage between the chamber and the outside of the chamber, wherein the wall port comprises at least one of an elastic membrane and a flexible membrane, and wherein the membrane (43) is adapted to, in a non-compressed state, seal between the chamber and the environment outside the chamber, and in a compressed state enable a hand or an object to be inserted through the membrane.
22. The medical device according to any one of the preceding embodiments, wherein the medical device further comprises at least one of:
 a. a filtering unit (26b) for filtering the fluid,
 b. a sterilization unit (26a) for directly or indirectly sterilizing the fluid,
 c. a fluid tempering unit (26c) adapted change the temperature of the fluid,
 d. a filtering unit for filtering the fluid and a sterilization unit for directly or indirectly sterilizing the fluid,
 e. a filtering unit for filtering the fluid and a fluid tempering unit adapted change the temperature of the fluid,
 f. a sterilization unit for directly or indirectly sterilizing the fluid and a fluid tempering unit adapted change the temperature of the fluid, and
 g. a filtering unit for filtering the fluid, a sterilization unit for directly or indirectly sterilizing the fluid and a fluid tempering unit adapted change the temperature of the fluid.
23. The medical device according to any one of the preceding embodiments, wherein, when the medical device is applied on the patient's body for performing a surgical procedure, the medical device further comprises at least one of:
 a. at least one inlet member (30) provided in at least one of:
  i. the wall of the medical device, and
  ii. the skin of the patient for supplying a fluid to at least one of
   the chamber, and
   the cavity in the patient's body, and
 b. at least one outlet member (31) provided in at least one of:
  i. the wall of the medical device, and
  ii. the skin of the patient for discharging the fluid from at least one of:
   the chamber, and
   the body cavity.
24. The medical device according to embodiment 21, further comprising a circulating pump (27) adapted to circulate the fluid from the outlet member to the inlet member.
25. The medical device according to any one of the preceding embodiments, wherein a part of the wall forms an elongated tubular enclosure (04) extending within the chamber of the medical device, contacting the skin of the patient and being adapted to separate the skin of the patient from the sealed environment of the chamber of the medical device.
26. The medical device according to any one of the preceding embodiments, wherein the monitoring unit is adapted to encircle an extremity of the patient and at least one of
 measure the blood pressure of the patient periodically, and
 monitor the blood pressure of the patient by exerting a pressure on the encircled extremity exceeding the systolic arterial pressure, such that the blood flow is momentarily stopped.
27. The medical device according to embodiment 26, wherein the monitoring unit is adapted to measure the blood pressure of the patient with an interval of one of:

1-5 minutes
5-10 minutes
10-20 minutes, and
20-30 minutes.
28. A method embodiment of providing a sealed environment using a medical device, such that a surgical procedure can be performed in the sealed environment, the method comprising:
   a. applying a wall (01) on the skin (S) of the patient to form a chamber (C), in which a sealed environment can be maintained for encompassing part of the surgical procedure to be performed,
   b. applying a pressure sealing member (05") contacting the skin of the patient, the pressure sealing member being connected to the wall of the medical device and adapted to seal the chamber from the ambient environment (A)
   c. adjusting the pressure in the pressure sealing member such that sealing between the skin of the patient and the wall of the medical device is created.
29. The method according to embodiment 28, wherein the step of adjusting the pressure in the pressure sealing member comprises adjusting the pressure in the pressure sealing member as a response to at least one of:
   a. a monitored parameter of the medical device, and
   b. a monitored physiological parameter of the patient.
30. The method according to embodiment 28, wherein the step of adjusting the pressure in the pressure sealing member as a response to a monitored parameter of the medical device comprises adjusting the pressure in the pressure sealing member as a response to:
   a. the pressure in the chamber,
   b. the pressure in the pressure sealing member,
31. The method according to embodiment 28, wherein the step of adjusting the pressure in the pressure sealing member as a response to a monitored physiological parameter of the patient comprises adjusting the pressure in the pressure sealing member as a response to:
   a. the blood pressure of the patient,
   b. the blood flow of the patient, and
   c. a temperature of the body of the patient.

Numbered Embodiment W 1-26

1. A medical device for performing a surgical procedure on a patient, the medical device comprising:
   a. a wall (01) adapted to be applied at least partially on the patient's body to form a chamber (C) by itself or together with the body of the patient, in which a sealed environment can be maintained for encompassing part of the surgical procedure to be performed,
   b. at least one wall port (17) or wall inset (42;42') placed in the wall,
   c. at least one of:
      an energy transferring member (52;56;58) for transferring energy from outside of the chamber to inside of the chamber, and
      an information transferring member (55) for transferring information from outside of the chamber to inside of the chamber,
   whilst maintaining the sealed environment.
2. The medical device according to embodiment 1, wherein the energy transferring member is adapted to transfer at least one of pneumatic, hydraulic and kinetic energy.
3. The medical device according to any one of embodiments 1 and 2, wherein the energy transferring member comprises a valve (38) such that the energy transferring member can be opened for enabling transfer of at least one of; kinetic, pneumatic and hydraulic energy through the wall of the medical device.
4. The medical device according to any one of embodiments 2 and 3, wherein the medical device comprises a tool (16) placed inside of the chamber of the medical device and connected to the energy transferring member, wherein the tool is adapted to be operated by at least one of the pneumatic, hydraulic and kinetic energy.
5. The medical device according to any one of embodiment 1-4, wherein the energy transferring member comprises a magnetic coupling comprising a first part (53a) comprising a magnetic material adapted to be positioned on the outside of the wall of the medical device, and second part (53b) comprising magnetic material positioned on the inside of the wall of the medical device, wherein the first part is adapted to receive kinetic energy and transfer the kinetic energy to the second part by magnetic coupling between the first and second part, such that kinetic energy can be transferred from the outside of the chamber to the inside of the chamber while maintaining the sealed environment in the chamber.
6. The medical device according to embodiment 5, wherein the energy transferring member is adapted to transfer rotational kinetic energy by the first part transferring rotational kinetic energy to the second part by the magnetic coupling between the first and second part.
7. The medical device according to anyone of embodiments 2-6, wherein the energy transferring member comprises a sleeve (59) fixed to the wall of the medical device, wherein the sleeve is adapted to receive a rotating shaft (52), and wherein the sleeve has a first portion adapted to be positioned on the outside of the chamber, and a second portion adapted to be positioned on the inside of the chamber, such that rotational kinetic energy can be transferred from the first portion of the sleeve to the second portion of the sleeve by the rotating shaft.
8. The medical device according to embodiment 1, wherein the energy transferring member is adapted to transfer electric energy via at least one of
   1. a wireless link (55'a;55'b), and
   2. a cable connection.
9. The medical device according to embodiment 8, wherein the energy transferring member comprises an inductive coupling for transferring electric energy by a magnetic field between a first conductor positioned on the outside of the chamber, and a second conductor positioned on the inside of the chamber.
10. The medical device according to any one of embodiments 8-9, wherein the medical device comprises a tool placed inside of the chamber of the medical device and connected to the energy transferring member, wherein the tool is adapted to be operated by electric energy.
11. The medical device according to anyone of embodiments 1-10, wherein the information transferring member is adapted to transfer data from the inside of the chamber to the outside of the chamber, through the wall of the medical device.

12. The medical device according to any one of embodiment 1 and 11, wherein the information transferring member comprises at least one of:
    an optical information transferring member (74*a*;74*b*; 75*a*;75*b*),
    a capacitive information transferring member,
    an inductive information transferring member, and
    a radio based information transferring member (55'*a*; 55'*b*),
13. The medical device according to embodiment 12, wherein the optical information transferring member is an infra red information transferring member.
14. The medical device according to any one of embodiments 1, 11-13, wherein the medical device comprises a camera (65) placed inside the chamber, and wherein the camera is connected to the information transferring member for transferring data from the camera to the outside of the chamber.
15. The medical device according to any one of embodiments 1, and 11-14, wherein the medical device comprises a data communication unit adapted to communicate with an implant implanted in the patient, and wherein the data communication unit is connected to the information transferring member such that data from the implant can be transferred to the outside of the chamber.
16. The medical device according to any one of embodiments 1 and 11-15, wherein the medical device comprises a sensing probe (73) positioned inside the chamber and connected to the information transferring member (55), wherein the sensing probe is adapted to sense at least one of:
    the blood pressure of the patient,
    the blood flow of the patient,
    a temperature of the patient,
    saturation of the blood of the patient,
    at least one ischemia marker of the patient,
    the skin tone of the patient
17. The medical device according to any one of the preceding embodiments, wherein the medical device is adapted to hold a fluid in the chamber having a pressure exceeding atmospheric pressure, a pressure exceeding atmospheric pressure by more than one of:
    10 mmHg,
    20 mmHg,
    40 mmHg,
    60 mmHg,
    80 mmHg,
    100 mmHg, and
    140 mmHg
    18. The medical device according to any one of the preceding embodiments, wherein the wall is at least partially collapsible.
19. The medical device according to any one of the preceding embodiments, comprising a sealing device (05) adapted to seal directly or indirectly between the wall of the medical device and at least one of
    the skin (S) of the patient, and
    tissue of the patient,
20. The medical device according to any one of the preceding embodiments, wherein the sealing device comprises at least one of
    a vacuum sealing member (05'), and
    a pressure sealing member (05").
21. The medical device according to embodiment 23, wherein the collapsible wall is adapted to be inflated by a fluid, comprising at least one of
    1. a liquid, and
    2. a gas.
22. A method embodiment of performing a surgical procedure on a patient using a medical device, the method comprising:
    a. applying a wall (01) on the skin (S) of the patient to form a chamber (C), in which a sealed environment can be maintained for encompassing part of the surgical procedure to be performed,
    b. creating an incision (I) through the skin of the patient in the sealed chamber, such that a fluid connection between a cavity within the patient and the chamber is created,
    c. transferring at least one of: energy and information through the wall of the medical device whilst maintaining the sealed environment.
23. The method according to embodiment 22, wherein the step of transferring energy through the wall of the medical device comprises transferring at least one of: pneumatic, hydraulic and kinetic energy through the wall of the medical device.
24. The method according to any one of embodiments 22 and 23, wherein the step of transferring energy through the wall of the medical device comprises:
    supplying energy to an energy consuming tool (16) inside the chamber of the medical device, and
    operating the energy consuming tool inside the chamber of the medical device.
25. The method according to embodiment 22, wherein the step of transferring information through the wall of the medical device comprises transferring data through the wall of the medical device.
26. The method according to embodiment 25, wherein the step of transferring data comprises transferring image data.

Numbered Embodiment X 1-27

1. A medical device for performing arthroscopic surgery on a joint of a patient, the medical device comprising:
    a wall (01) adapted to form a chamber (C) adapted to encapsulate at least a part of the joint of the patient, allowing a arthroscopic surgery to be performed when the medical device is applied on the patient, the wall forming a sealed surgical environment, wherein the wall is adapted to contain a liquid filling the chamber for creating a liquid operating environment, and
    wherein the medical device is adapted to receive the liquid through at least one liquid inlet (30) placed in at least one of; the wall of the medical device and the skin (S) of the patient for supplying the liquid to at least one of: the chamber and the joint in the patient's body.
2. The medical device according to embodiment 1, wherein the medical device is adapted to discharge the liquid through at least one liquid outlet placed in at least one of; the wall of the medical device and the skin of the patient for discharging the liquid from at least one of: the chamber and the joint in the patient's body.
3. The medical device according to any one of embodiments 1 and 2, wherein the medical device further comprises a liquid inlet for receiving liquid to the chamber.

4. The medical device according to any one of embodiments 1-3, wherein the medical device further comprises a liquid outlet for evacuating liquid from the chamber.
5. The medical device according to embodiment 4, wherein the liquid outlet is adapted to be placed in an incision (I) performed in the patient for evacuating the liquid from the joint within the patient.
6. The medical device according to any one of embodiments 2-5, wherein the medical device further comprises a liquid system for circulating the liquid from the liquid outlet to the liquid inlet.
7. The medical device according to any one of embodiments 1-6, wherein the medical device further comprising at least one inlet and at least one outlet selected from the following:
    a first liquid inlet placed in the wall and adapted for supplying liquid to the chamber,
    a first liquid outlet placed in the wall and adapted for evacuating liquid from the chamber,
    a second liquid inlet adapted to be placed in an incision in the skin of the patient, in the area of the joint, for supplying liquid to the joint, and
    a second liquid outlet adapted to be placed in an incision in the skin of the patient, in the area of the joint, for evacuating liquid from the joint.
8. The medical device according to embodiment 7, wherein the medical device comprises a first liquid system adapted to at least one of:
    supply liquid to the first liquid inlet and evacuate liquid from at least one of:
        i. the first liquid outlet, and
        ii. the second liquid outlet, and
    circulate a liquid from the first or second liquid outlet to the first liquid inlet.
9. The medical device according to embodiment 7, wherein the medical device comprises a first liquid system adapted to at least one of:
    supply liquid to the second liquid inlet and evacuate liquid from at least one of:
        i. the first liquid outlet, and
        ii. the second liquid outlet, and
    circulate a liquid from at least one of the first or second liquid outlet to the second liquid inlet.
10. The medical device according to embodiment 7, wherein the first liquid system is adapted to at least one of:
    supply liquid to the first liquid inlet and evacuate liquid from the first liquid outlet, and
    circulate liquid from the first liquid outlet to the first liquid inlet,
    wherein the medical device further comprises a second liquid system adapted to circulating a liquid from the second liquid outlet to the second liquid inlet.
11. The medical device according to anyone of embodiments 6-10, wherein the liquid is at least one of; an isotonic solution and an antibiotic liquid.
12. The medical device according to any one of embodiments 4-11, wherein the system comprises a pump (09) for pumping the liquid from the liquid outlet to the liquid inlet.
13. The medical device according to any one of the preceding embodiments, wherein the medical device comprises a sealing device (05) adapted to seal between the wall of the medical device and the patient's skin (S) for containing the liquid within the chamber.
14. The medical device according to embodiment 13, wherein sealing device comprises a pressure sealing member (05") adapted to seal against the skin of the patient by exerting a pressure on the skin of the patient.
15. The medical device according to embodiment 13, wherein the sealing device comprises a vacuum sealing member (05') adapted to hold a pressure being less than atmospheric pressure thus creating a vacuum seal between the skin of the patient and the medical device.
16. The medical device according to any one of the preceding embodiments, wherein the medical device comprises at least one of:
    a filtering unit for filtering the liquid supplied to the chamber,
    a sterilization unit for directly or indirectly sterilizing the liquid supplied to the chamber,
    a liquid tempering unit adapted change the temperature of the liquid supplied to the chamber,
    a filtering unit for filtering the liquid supplied to the chamber and a sterilization unit for directly or indirectly sterilizing the liquid supplied to the chamber,
    a filtering unit for filtering the liquid supplied to the chamber and a liquid tempering unit adapted change the temperature of the liquid supplied to the chamber,
    a sterilization unit for directly or indirectly sterilizing the liquid supplied to the chamber and a liquid tempering unit adapted change the temperature of the liquid supplied to the chamber, and
    a filtering unit for filtering the liquid supplied to the chamber, a sterilization unit for directly or indirectly sterilizing the liquid supplied to the chamber and a liquid tempering unit adapted change the temperature of the liquid supplied to the chamber.
17. The medical device according to any one of the preceding embodiments, wherein the medical device is adapted for use in knee joint procedures, wherein the medical device comprises; a first opening arranged such that the leg of a patient can enter the medical device and a second opening arranged such that the leg of a patient can exit the medical device, such that the chamber is positioned between the first and second opening.
18. The medical device according to any one of the preceding embodiments, wherein the wall is at least partially collapsible.
19. The medical device according to any one of the preceding embodiments, wherein a part of the wall forms an elongated tubular enclosure (04) extending within the chamber of the medical device, contacting the skin of the patient and being adapted to separate the skin of the patient from the sealed environment of the chamber of the medical device, such that the chamber is formed between the wall of the medical device and the elongated tubular enclosure.
20. The medical device according to embodiment 7 and 19, wherein at least one of the first liquid inlet and the first liquid outlet is positioned through the wall of the elongated tubular enclosure.
21. The medical device according to any one of embodiments 19 and 20, wherein the medical device comprises a first port positioned in the wall of the medical device, and a second port positioned in the wall of the elongated tubular enclosure, and wherein the first and second ports are adapted to be connected for forming an integrated port.

22. The medical device according to any one of the preceding embodiments, wherein the medical device comprises a wall inset (42;42'), comprising a glove (02) for enabling manual manipulation within the liquid environment of the chamber.
23. The medical device according to any one of the preceding embodiments, wherein the medical device further comprises a liquid lock (18) for allowing passage of objects between the sealed environment and the environment outside of the sealed environment and vice versa, when the medical device is positioned in connection with the patient, for hindering liquid leakage through the liquid lock.
24. A method embodiment of performing a surgical procedure on a patient using a medical device, the method comprising:
    a. applying a wall (01) of the medical device on the skin (S) of the patient to form a chamber (C), in which a sealed liquid operating environment can be maintained for encompassing part of the surgical procedure to be performed,
    b. filling the chamber with a liquid through a liquid inlet (30) for creating the liquid operating environment, and
    c. creating an incision (I) in the skin of the patient, in the liquid operating environment, such that a fluid connection between a cavity within the patient and the chamber is created.
25. The method according to embodiment 24, wherein the step of filling the chamber with a liquid through a liquid inlet comprises filling the chamber with a liquid through a liquid inlet placed in at least one of:
    the wall of the medical device, and
    the body of the patient.
26. The method according to any one of embodiments 24 and 25, further comprising discharging the liquid through a liquid outlet (31).
27. The method according to embodiment 26, wherein the step of discharging the liquid through a liquid outlet comprises discharging the liquid through a liquid outlet placed in at least one of:
    the wall of the medical device, and
    the body of the patient.

Numbered Embodiment Y 1-17

1. A medical device for performing a surgical procedure on a patient on an extremity having a reduced amount of blood, the medical device comprising a wall (2301) enclosing a compartmentalized chamber (C1; C2; C3; C4; C5) in which a sealed environment can be maintained for encompassing part of the surgical procedure to be performed, wherein the compartmentalized chamber comprises:
    a first inflatable compartment (C1) placed around a first distal portion of the extremity, the first inflatable compartment comprising a first fluid inlet (2330a),
    a second inflatable compartment (C2) placed around a second, more proximal portion of the extremity, the second inflatable compartment comprising a second fluid inlet (2330b), and
    a control system (2315) adapted to inflate the first and second compartment consecutively, such that blood pushed from the distal to the proximal portions of the extremity.
2. The medical device according to embodiment 1, wherein the medical device further comprises a monitoring unit (98) connected to the control system, wherein the monitoring unit is adapted to monitor at least one of:
    the blood pressure of the patient,
    the blood flow of the patient,
    a temperature of the patient,
    saturation of the blood of the patient,
    at least one ischemia marker of the patient, and
    the skin tone of the patient
3. The medical device according to embodiment 2, wherein the control system is adapted to inflate at least one of the first and second inflatable compartments on the basis of input from the monitoring unit.
4. The medical device according to any one of embodiments 1-3, wherein the control system is adapted to inflate at least one of the first and second inflatable compartments to a pressure exceeding the systolic blood pressure by at least one of:
    0 mmHg
    10 mmHg,
    20 mmHg,
    40 mmHg,
    60 mmHg,
    80 mmHg,
    100 mmHg,
    140 mmHg,
5. The medical device according to any one of embodiments 1-4, wherein the wall comprise at least one detachable wall inset (42;42') or integrated wall inset (42;42') comprising a glove (02') enabling manual manipulation within the chamber.
6. The medical device according to any one of embodiments 1-5, wherein the wall is adapted to be inflated by a liquid for forming a liquid operating environment.
7. The medical device according to any one of embodiments 1-6, wherein the wall is adapted to be at least partially applied on the patient's body to form a chamber together with the patient's body, in which the sealed environment can be maintained for encompassing part of the surgical procedure to be performed, the medical device comprising;
    a. a sealing device (05) connected to the wall and adapted to seal against the skin of the patient, when the medical device is applied on the patient's body,
    b. a closeable wall port (17) placed in a portion of the wall,
    c. a closeable body port (22) adapted to be placed in an incision (I) in the patient's body forming a fluid connection between the chamber and a cavity in the patient's body,
    wherein:
    the closable wall port is adapted to be connected to the closeable body port, when the medical device is applied on the patient's body for performing the surgical procedure, and
    the closable wall port and closable body port are adapted to form an airlock sluice (18) between the cavity in the body of the patient and the ambient environment (A), when the medical device is applied on the patient's body for performing the surgical procedure.
8. The medical device according to embodiment 7, wherein the closeable wall port is displaceable between a first position, in which the closeable wall port is situated relatively close to the closeable body port, and a second position, in which the closeable wall port is situated more remote from the closeable body port.

9. The medical device according to any one of embodiments 7-8, wherein the closeable wall port, when the medical device is applied on the patient's body for performing a surgical procedure, is adapted to be at least one of;
   a. connected to the previously mentioned body port,
   b. abutting the previously mentioned body port, and
   c. locked to the previously mentioned body port.
10. The medical device according to any one of embodiments 7-9, further comprising an additional port, wherein at least one of the closeable wall port and the closeable body port is exchangeable by the additional port.
11. The medical device according to any one of embodiments 7-10, wherein at least one of;
   the closeable body port comprises a closeable body multi-port (48) adapted to be placed from inside the chamber in an incision to be performed in the skin of the patient, and wherein the body multiport is adapted to be connected to at least one of
      the wall port, and
      a wall multiport, when the medical device is applied on the patient's body for performing a surgical procedure, and
   the closable wall port comprises a closeable wall multiport (48), wherein the wall multiport is adapted to be connected to at least one of;
      the body port, and
      a body multiport placed in an incision in the patient's body, when the medical device is applied on the patient's body for performing a surgical procedure.
12. The medical device according to any one of embodiments 7-11, wherein at least one of the closeable wall port and the closable body port comprises at least one of an elastic membrane and a flexible membrane, and wherein the membrane (43) is adapted to, in a non-compressed state, seal between the chamber and the ambient environment, and in a compressed state enable a hand or an object to be inserted through the membrane.
13. The medical device according to any one of the preceding embodiments, further comprising a sealing device having a first sealing member (35) adapted to be positioned at the inside of the patient's skin around an incision to be performed in the skin, and a second sealing member (37) adapted to be positioned on the outside of the patient's skin around the incision, and a spring-loaded or elastic connecting member (36) sealingly interconnecting the first and second sealing members, whereby the spring-loaded or elastic connecting member seals between at least one of: (a) the second sealing member and the skin of the patient, and (b) the first sealing member and tissue of the patient.
14. The medical device according to any one of the preceding embodiments, wherein the chamber is in fluid connection with the cavity in the patient's body through an incision in the patient's body, when the medical device is applied on the patient's body for performing a surgical procedure, and wherein the medical device further comprises:
   a. at least one inlet member (30) provided in at least one of:
      i. the wall of the medical device, and
      ii. the skin of the patient for supplying a fluid to at least one of
         1. the chamber, and
         2. the cavity in the patient's body, and
   b. at least one outlet member (31) provided in at least one of:
      i. the wall of the medical device, and
      ii. the skin of the patient for discharging the fluid from at least one of:
         3. the chamber, and
         4. the body cavity.
15. A surgical method embodiment of performing a step of a surgical procedure on a patient, on an extremity of the patient having a reduced amount of blood using a medical device comprising an inflatable wall enclosing a compartmentalized chamber in which a sealed environment can be maintained for encompassing part of the surgical procedure to be performed, the surgical method comprising:
   inflating a first compartment of the compartmentalized chamber around a first distal portion of the extremity of the patient, for reducing the amount of blood in the first distal portion of the extremity,
   inflating a second compartment of the compartmentalized chamber around a second more proximal portion of the extremity of the patient, for reducing the amount of blood in the second more proximal portion of the extremity, and
   creating an incision in sealed environment inside the chamber enclosed by the wall of the medical device.
16. The method according to embodiment 7, wherein the method further comprises the step of releasing the pressure in the first portion of the compression apparatus and maintaining the pressure in the second portion of the compression apparatus.
17. The method according to any one of embodiments 7 and 8, wherein the steps of inflating the first and second chambers comprises inflating the first and second chambers with a liquid.

Numbered Embodiment Z 1-26

1. A medical device for performing a combination of open surgery and endoscopic surgery, the medical device comprising:
   a. a wall (01) adapted to be inflated by a fluid for forming a chamber (C) in which a sealed environment can be maintained for encompassing part of the surgical procedure to be performed,
   b. at least one endoscopic trocar (92) enclosed within the chamber and being adapted to be placed through the wall of the medical device and through an incision (I) performed in the body of the patient, for passing from the chamber to a cavity within the patient, when the surgical procedure is performed.
2. The medical device according to embodiment 1, wherein the medical device further comprises at least one endoscopic instrument (89) enclosed within the chamber and adapted to be used through the trocar.
3. The medical device according to embodiment 2, wherein the endoscopic instrument is at least one of:
   an endoscopic grasper
   an endoscopic claw grasper,
   an endoscopic stone grasper, an endoscopic needle holder,
an endoscopic hook,
a camera
scissors
a knife
an ultrasound dissector
a suction instrument
an endoscopic dissector, and
an endoscopic diathermy instrument.
4. The medical device according to any one of the preceding embodiments, wherein the wall of the medical device comprises an adhesive surface (50) adapted to contact the skin of the patient for fixating the medical device to the skin of the patient.
5. The medical device according to any one of the preceding embodiments, wherein the medical device comprises at least one of; a fluid inlet (30) for supplying a fluid into the medical device and an adaptation for directly or indirectly receiving fluid from a fluid inlet placed in the patients skin, for inflating at least one of; the chamber and a cavity in the patient's body, for performing the surgical procedure.
6. The medical device according to any one of the preceding embodiments, wherein the medical device comprises a device or instrument mount (20) enclosed within the chamber of the medical device and adapted to hold a device or an instrument within the chamber.
7. The medical device according to any one of the preceding embodiments, wherein the wall of the medical device comprises a transparent layer enabling viewing into the chamber of the medical device.
8. The medical device according to any one of the preceding embodiments, comprising a wall inset (17) comprising a glove (02) enabling manual manipulation within the chamber of the medical device.
9. The medical device according to any one of the preceding embodiments, wherein the medical device further comprises a pressure source adapted to at least one of
  supply a fluid having a pressure above atmospheric pressure to the sealed chamber of the medical device, and
  be enclosed in the chamber.
10. The medical device according to any one of the preceding embodiments, wherein the medical device comprises a sealing device (05) adapted to seal between the wall of the medical device and the patient's skin, wherein the sealing device comprises at least one of:
  a pressure sealing member (05") adapted to seal against the skin of the patient by exerting a pressure on the skin of the patient, and
  a vacuum sealing member (05') adapted to hold a pressure being less than atmospheric pressure thus creating a vacuum seal between the skin of the patient and the medical device.
11. The medical device according to any one of the preceding embodiments, wherein the medical device further comprises a camera (65) enclosed within the chamber of the medical device, wherein the camera is adapted to be inserted through the trocar for enabling visual inspection within a cavity of the patient.
12. The medical device according to any one of the preceding embodiments, wherein the medical device comprises at least one of:
  a. a filtering unit (26*b*) for filtering the fluid,
  b. a sterilization unit (26*a*) for directly or indirectly sterilizing the fluid,
  c. a fluid tempering unit (26*c*) adapted change the temperature of the fluid,
  d. a filtering unit for filtering the fluid and a sterilization unit for directly or indirectly sterilizing the fluid,
  e. a filtering unit for filtering the fluid and a fluid tempering unit adapted change the temperature of the fluid,
  f. a sterilization unit for directly or indirectly sterilizing the fluid and a fluid tempering unit adapted change the temperature of the fluid, and
  g. a filtering unit for filtering the fluid, a sterilization unit for directly or indirectly sterilizing the fluid and a fluid tempering unit adapted change the temperature of the fluid.
13. The medical device according to any one of the preceding embodiments, wherein the medical device is adapted for surgery on extremities of the patient, and wherein the medical device comprises at least one of;
  a. a first opening arranged such that the leg of a patient can enter the medical device and a second opening arranged such that the leg of a patient can exit the medical device, such that the chamber is positioned between the first and second opening, and
  b. an elongated tubular enclosure (04) extending within the chamber of the medical device formed by a part of the wall, contacting the skin of the patient and being adapted to separate the skin of the patient from the sterile environment of the chamber of the medical device.
14. The medical device according to any one of the preceding embodiments, wherein the medical device further comprises at least one of:
an energy transferring member (52;56;58), and
  an information transferring member (55).
15. The medical device according to embodiment 14, wherein the energy transferring member is adapted to transfer at least one of:
  hydraulic energy,
  pneumatic energy,
  kinetic energy, and
  electric energy.
16. The medical device according to any one of embodiments 14 and 15, wherein the medical device comprises an energy consuming tool (16) placed inside of the chamber of the medical device, wherein the energy consuming tool is adapted to be connected to the energy transferring member.
17. The medical device according to any one of embodiment 14, wherein the information transferring member comprises at least one of:
  an optical information transferring member,
  a capacitive information transferring member,
  an inductive information transferring member,
  a radio based information transferring member.
18. The medical device according to any one of embodiments 1-17, wherein the medical device is adapted to having the at least one endoscopic instrument enclosed within the chamber performing a surgical procedure through the at least one trocar and allowing handling of the instrument from outside the chamber contacting the instrument indirect through the wall, wherein the medical device comprises at least one of the following;
at least one flexible portion of the wall, such that a handling portion (89') of the instrument can be manually handled through holding the handling portion (89') on the outside of the flexible portion of the wall of the medical device, and at least one glove (02) in the wall allowing the handling of the at least one instrument inside the chamber.
19. The medical device according to any one of embodiments 1-18, comprising at least one of the following;
   at least one closable wall port (17) or wall inset (42;42') placed in the wall, and
   at least one closable body port (22) or body inset (42;42") placed in an incision in the body of the patient.
20. The medical device according to embodiment 19, wherein the at least one closable wall port or wall inset placed in the wall, and the at least one closable body port or body inset placed in the incision in the skin of the patient are adapted to be detachable interconnected to form an interconnected port or inset, when the surgical procedure is performed.
21. The medical device according to embodiment 20, wherein the interconnected port is a multiport adapted to enable transfer of at least one of;
   a camera, and
   a surgical instrument
22. The medical device according to embodiment 20, wherein the interconnected inset comprises a glove (02)
23. The medical device according to any one of embodiments 19-22, wherein at least one of:
   the wall port,
   the body port,
   the wall inset, and
   the body inset
   is adapted to be at least one of
   detached and replaced by a different type of port or inset, and
   an integrated part of an fluid sluice for allowing at least one of;
      i. a medical device, replacement tissue, or a part or tissue to be used inside the cavity to be introduced into the cavity from the outside environment of the chamber, and
      ii. a part of the body or foreign part from inside the body to be to be taken out from the cavity.
24. The medical device according to any one of embodiments 1-23, wherein the at least one trocar comprise a multiport adapted to have at least one of a camera and at least one surgical instrument to be introduced in separate trocar compartments into the cavity, when the surgical procedure is performed using endoscopic instruments, wherein the at least one trocar is an integrated part of an fluid sluice for allowing at least one of;
   a medical device, replacement tissue, or a part or tissue to be used inside the cavity to be introduced into the cavity from the outside environment of the chamber, and
   a part of the body or foreign part from inside the body to be to be taken out from the cavity.
25. A method embodiment of performing a combination of open and endoscopic surgery using a medical device comprising a wall (01) adapted to be inflated by a fluid for forming a chamber (C) in which a sealed environment can be maintained for encompassing part of the surgical procedure to be performed, the method comprising:
   fixating a portion of the wall of the medical device to the skin (S) of the patient,
   making an incision (I) in the skin of the patient inside or outside the chamber,
   placing a fluid inlet (30) through the incision,
   supplying a fluid into the patient, thereby creating a cavity within the body of the patient,
   making one or more additional incision(s) in the wall of the medical device continuing through the skin of the patient,
   inserting a trocar (92) in each of the one or more additional incision(s) made in the wall of the medical device,
   inserting at least one of a camera (65) and a surgical instrument (89), through one of the one or more trocar(s),
   performing at least one step of endoscopic surgery through the trocar(s),
   making a second incision in the wall of the medical device continuing through the skin of the patient, and at least one of:
      i. placing a closable body port (22),
      ii. transferring a specimen (81) from the cavity within the body of the patient to the chamber through the second incision,
      iii. transferring an object from the chamber to the cavity within the body of the patient through the second incision.
26. The method according to embodiment 25, wherein the method further comprises the step of suturing the incisions made in the skin of the patient from within the chamber of the medical device.

Numbered Embodiment AA 1-28

1. A medical device for performing a combination of open surgery and endoscopic surgery, the medical device comprising:
   a. a wall (01) adapted to be inflated by a fluid for forming a chamber (C) in which a sealed environment can be maintained for encompassing part of the surgical procedure to be performed,
   b. at least one endoscopic trocar (92) positioned through the wall of the medical device and sealingly attached to the wall, such that a first portion (p1) of the trocar is positioned inside of the chamber, and a second portion (p2) of the trocar is positioned outside of the chamber of the medical device.
2. The medical device according to embodiment 1, wherein the medical device further comprises a removable covering sheet (77) covering the second portion of the trocar.
3. The medical device according to any one of embodiments 1 and 2, wherein the medical device further comprises at least one endoscopic instrument (89) enclosed within the chamber and adapted to be used through the trocar.
4. The medical device according to embodiment 3, wherein the endoscopic instrument (89) is at least one of:
   an endoscopic grasper
   an endoscopic claw grasper,
   an endoscopic stone grasper,
   an endoscopic needle holder,
   an endoscopic hook,
   a camera
   scissors
   a knife
   an ultrasound dissector
   a suction instrument
   an endoscopic dissector, and
   an endoscopic diathermy instrument.

5. The medical device according to any one of the preceding embodiments, wherein the wall of the medical device comprises an adhesive surface (50) adapted to contact the skin of the patient for fixating the medical device to the skin of the patient.
6. The medical device according to any one of the preceding embodiments, wherein the medical device comprises at least one of; a fluid inlet (30) for supplying a fluid into the medical device and an adaptation for directly or indirectly receiving fluid from a fluid inlet placed in the patient's skin, for inflating at least one of; the chamber and a cavity in the patient's body, for performing the surgical procedure.
7. The medical device according to any one of the preceding embodiments, wherein the medical device comprises an instrument mount (20) enclosed within the chamber of the medical device and adapted to hold instruments (89) within the chamber.
8. The medical device according to any one of the preceding embodiments, wherein the wall of the medical device comprises a transparent layer enabling viewing into the chamber of the medical device.
9. The medical device according to any one of the preceding embodiments, comprising a wall inset (42; 42'), comprising a glove (02) enabling manual manipulation within the chamber of the medical device.
10. The medical device according to any one of the preceding embodiments, wherein the medical device further comprises a pressure source adapted to at least one of;
    supply a fluid having a pressure above atmospheric pressure to the sealed chamber of the medical device, and
    be enclosed in the chamber.
11. The medical device according to any one of the preceding embodiments, wherein the medical device comprises a sealing device (05) adapted to seal between the wall of the medical device and the patient's skin, wherein the sealing device comprises at least one of:
    a pressure sealing member (05") adapted to seal against the skin of the patient by exerting a pressure on the skin of the patient, and
    a vacuum sealing member (05') adapted to hold a pressure being less than atmospheric pressure thus creating a vacuum seal between the skin of the patient and the medical device.
12. The medical device according to any one of the preceding embodiments, wherein the medical device further comprises a camera (65) enclosed within the chamber of the medical device, wherein the camera is adapted to be inserted through the trocar for enabling visual inspection within a cavity of the patient.
13. The medical device according to any one of the preceding embodiments, wherein the medical device comprises at least one of:
    a. a filtering unit (26*b*) for filtering the fluid,
    b. a sterilization unit (26*a*) for directly or indirectly sterilizing the fluid,
    c. a fluid tempering unit (26*c*) adapted change the temperature of the fluid,
    d. a filtering unit for filtering the fluid and a sterilization unit for directly or indirectly sterilizing the fluid,
    e. a filtering unit for filtering the fluid and a fluid tempering unit adapted change the temperature of the fluid,
    f. a sterilization unit for directly or indirectly sterilizing the fluid and a fluid tempering unit adapted change the temperature of the fluid, and
    g. a filtering unit for filtering the fluid, a sterilization unit for directly or indirectly sterilizing the fluid and a fluid tempering unit adapted change the temperature of the fluid.
14. The medical device according to any one of the preceding embodiments, wherein the medical device is adapted for surgery on extremities of the patient, and wherein the medical device comprises at least one of
    a. a first opening arranged such that the leg of a patient can enter the medical device and a second opening arranged such that the leg of a patient can exit the medical device, such that the chamber is positioned between the first and second opening, and
    b. an elongated tubular enclosure (04) extending within the chamber of the medical device formed by a part of the wall, contacting the skin of the patient and being adapted to separate the skin of the patient from the sterile environment of the chamber of the medical device.
15. The medical device according to any one of the preceding embodiments, wherein the medical device further comprises at least one of:
    an energy transferring member (52;56;58), and
    an information transferring member (55).
16. The medical device according to embodiment 15, wherein the energy transferring member is adapted to transfer at least one of:
    hydraulic energy,
    pneumatic energy,
    kinetic energy, and
    electric energy.
17. The medical device according to any one of embodiments 15 and 16, wherein the medical device comprises an energy consuming tool (16) placed inside of the chamber of the medical device, wherein the energy consuming tool is adapted to be connected to the energy transferring member.
18. The medical device according to any one of embodiment 15, wherein the information transferring member comprises at least one of:
    an optical information transferring member,
    a capacitive information transferring member,
    an inductive information transferring member,
    a radio based information transferring member.
19. The medical device according to any one of embodiments 1-18, wherein the medical device is adapted to having the at least one endoscopic instrument enclosed within the chamber performing a surgical procedure through the at least one trocar and allowing handling of the instrument from outside the chamber contacting the instrument indirect through the wall, wherein the medical device comprises at least one of the following;
    at least one flexible portion of the wall, such that a handling portion (89') of the instrument can be manually handled through holding the handling portion (89') on the outside of the flexible portion of the wall of the medical device, and
    at least one glove (02) in the wall allowing the handling of the at least one instrument inside the chamber.
20. The medical device according to any one of embodiments 1-19, comprising at least one of the following;
    at least one closable wall port (17) or wall inset (42;42') placed in the wall, and at least one closable body port (22) or body inset (42;42") placed in an incision in the body of the patient.
21. The medical device according to embodiment 20, wherein the at least one closable wall port or wall inset placed in the wall, and the at least one closable body port or body inset placed in the incision in the skin of the patient are adapted to be detachable interconnected to form an interconnected port or inset, when the surgical procedure is performed.
22. The medical device according to embodiment 21, wherein the interconnected port is a multiport adapted to enable transfer of at least one of;
   a camera, and
   a surgical instrument
23. The medical device according to embodiment 21, wherein the interconnected inset comprises a glove (02)
24. The medical device according to any one of embodiments 20-23, wherein at least one of:
   the wall port,
   the body port,
   the wall inset, and
   the body inset
is adapted to be at least one of;
   detached and replaced by a different type of port or inset, and
   an integrated part of an fluid sluice for allowing at least one of
      i. a medical device, replacement tissue, or a part or tissue to be used inside the cavity to be introduced into the cavity from the outside environment of the chamber, and
      ii. a part of the body or foreign part from inside the body to be to be taken out from the cavity.
25. The medical device according to any one of embodiments 1-24, wherein the at least one trocar comprise a multiport adapted to have at least one of; a camera and at least one surgical instrument to be introduced in separate trocar compartments into the cavity, when the surgical procedure is performed using endoscopic instruments, wherein the at least one trocar is an integrated part of an fluid sluice for allowing at least one of
   a medical device, replacement tissue, or a part or tissue to be used inside the cavity to be introduced into the cavity from the outside environment of the chamber, and
   a part of the body or foreign part from inside the body to be to be taken out from the cavity.
26. A method embodiment of performing endoscopic surgery using a medical device comprising:
   a wall (01) adapted to be inflated by a fluid for forming a chamber (C) in which a sealed environment can be maintained for encompassing part of the surgical procedure to be performed, and at least one endoscopic trocar (92) positioned through the wall of the medical device, such that a first portion (p1) of the trocar is positioned inside of the chamber, and a second portion of the trocar (p2) is positioned outside of the chamber, the method comprising:
      creating an incision (I) in the skin (S) of the patient,
      inserting the endoscopic trocar through the incision in the skin of the patient into the body of the patient,
      fixating a portion of the wall of the medical device to the skin of the patient,
      supplying a fluid into the patient, thereby creating a cavity within the body of the patient,
      performing at least one step of endoscopic surgery through the trocar.
27. The method according to embodiment 26, wherein the medical device comprises a closable body port (22) integrated in the wall adapted to be placed in an incision in the skin, when the surgical procedure is performed, the method comprising:
   making a second incision through the skin of the patient, and at least one of:
      i. placing the closable body port in the incision,
      ii. transferring a specimen from the cavity within the body of the patient to the chamber through the second incision,
      iii. transferring an object from the chamber to the cavity within the body of the patient through the second incision.
28. The method according to any one of embodiment 26 and 27, wherein the method further comprises the step of suturing the incisions made in the skin of the patient from within the chamber of the medical device.

Numbered Embodiment AB 1-13

1. A medical device for use in an endoscopic surgical procedure, the medical device comprising:
   a wall (01) forming a chamber (C), wherein a portion of the wall is adapted to be fixated to the skin (S) of the patient,
   an endoscopic instrument (89) enclosed within the chamber, and
   a trocar (92), wherein the trocar is at least one of:
      1. enclosed within the chamber, and
      2. positioned sealingly through the wall of the medical device.
2. The medical device according to embodiment 1, wherein the surgical instrument comprises a handle portion (89'), and wherein the handle portion is operably encapsulated by the wall such that the handle portion can be manipulated from outside the chamber.
3. The medical device according to any one of the preceding embodiments, wherein the wall is at least one of flexible and elastic.
4. The medical device according to any one of the preceding embodiments, comprising a wall inset (42; 42'), comprising a glove (02) for enabling manual manipulation within the chamber of the medical device.
5. The medical device according to any one of the preceding embodiments, wherein the portion of the wall adapted to be fixated to the skin of the patient comprises at least one of:
   a vacuum sealing member (05') adapted to seal between the wall of the medical device and the skin of the patient, and
   an adhesive surface (50) adapted to adhere to the skin of the patient.
6. The trocar according to any one of embodiments 1-5, wherein the trocar comprises a pressure sealing member (05") adapted to provide sealing by pressing on the surface of the skin of the patient.
7. The medical device according to any one of the preceding embodiments, wherein the wall is adapted to hold a pressure exceeding atmospheric pressure.

8. The medical device according to any one of the preceding embodiments, further comprising an evacuation valve (38) for evacuating a fluid from the chamber.
9. The medical device according to embodiment 8, wherein the evacuation valve is connected to a filtering unit (26*b*) for filtering the evacuated fluid.
10. The medical device according to any one of embodiments 8 and 9, wherein the medical device further comprises a control system for controlling the opening of the evacuation valve, wherein the control system is adapted to control the evacuation valve on the basis of at least one of:
    the pressure in the chamber,
    manual detection of the visibility in the chamber,
    the visibility in the chamber,
    detection of smoke in the chamber,
    the temperature in the chamber, and
    a time related variable.
11. The medical device according to any one of the preceding embodiments, wherein the endoscopic instrument (89) is at least one of:
    a. an endoscopic grasper
    b. an endoscopic claw grasper,
    c. an endoscopic stone grasper,
    d. an endoscopic needle holder,
    e. an endoscopic hook,
    f. a camera
    g. scissors
    h. a knife
    i. an ultrasound dissector
    j. a suction instrument
    k. an endoscopic dissector, and
    l. an endoscopic diathermy instrument.
12. A method embodiment of performing an endoscopic surgical procedure on a patient using a medical device comprising a wall (01) enclosing a chamber (C) in which a sealed environment can be maintained, in which an endoscopic instrument (89) is enclosed, the method comprising:
    g. creating an incision (I) in the skin (S) of the patient,
    h. placing a second portion (p2) of a trocar (92) through the incision into a cavity of the patient's body, wherein the first portion of the trocar is positioned inside the chamber of the medical device, such that a fluid connection is created between the chamber of the medical device and a cavity in the body of the patient,
    i. placing the endoscopic instrument through the trocar into the cavity of the patient,
    j. using the endoscopic instrument in a step of the endoscopic surgical procedure by manipulating a handle portion (89') of the endoscopic instrument from the outside of the wall of the medical device.
13. The method according to embodiment 12, further comprising opening an evacuation valve in the wall of the medical device for evacuating a fluid from the chamber of the medical device.

Numbered Embodiment AC 1-32

1. A trocar for performing an endoscopic procedure in a cavity in a patient's body, the trocar (92) comprising:
    a first seal (43*a*) within the trocar adapted to seal between the cavity in the body of the patient and the ambient environment, when the trocar is placed through the skin of the patient during the surgical procedure, and
    a second seal (50;05), sealingly connected around the trocar and adapted to engage the surface of the skin (S) of the patient for further sealing against the skin of the patient.
2. The trocar according to embodiment 1, wherein the second seal comprises an adhesive portion (50) adapted to be placed in contact with the skin of the patient for sealing against the skin of the patient.
3. The trocar according to any one of embodiment 1 and 2, wherein the second seal comprises a vacuum sealing member (05') adapted to hold a pressure less than atmospheric pressure such that a vacuum seal is created between the skin of the patient and the vacuum sealing member.
4. The trocar according to any one of embodiments 1-3, wherein the second seal comprises a pressure sealing member (05") adapted to provide sealing by pressing against the surface of the skin of the patient.
5. The trocar according to embodiment 4, wherein the pressure sealing member is further adapted to press against the skin or tissue of the patient from within the cavity of the patient, in a direction substantially parallel to the elongation of the trocar.
6. The trocar according to any one of embodiments 4 and 5, wherein the medical device comprises a pressure sealing device, an wherein the pressure sealing device comprises an inflatable pressure sealing member (05") adapted to be inflated by a fluid.
7. The trocar according to embodiment 6, wherein the inflatable pressure sealing member (05") is shaped such that when inflated, a first sealing chamber (05"*a*) is formed on the outside skin of the patient and a second sealing chamber (05"*b*) is formed inside the cavity of the patient, such that fluid in the first sealing chamber indirectly presses on the skin of the patient and the fluid in the second sealing chamber indirectly presses on the skin and or tissue of the patient from within the cavity of the patient.
8. The trocar according to any one of the preceding embodiments, wherein the trocar comprises a trocar connecting portion (84*a*) adapted to engage a device connecting portion (84*b*) of a medical device, wherein the medical device comprising a wall (01) enclosing a chamber (C) connected to the device connection portion, the chamber containing an endoscopic instrument (89), such that the endoscopic instrument can be inserted into the cavity of the patient through the trocar when the trocar and the medical device is connected.
9. The trocar according to embodiment 8, wherein the connecting portion comprises a recess (34) or protruding member (33) adapted to engage a corresponding recess (34) or protruding member (33) of the connecting portion of the medical device.
10. The trocar according to any one of the preceding embodiments, wherein the first seal comprises a first self sealing membrane (43*a*).
11. The trocar according to embodiment 10, wherein the first self sealing membrane is positioned at the first connecting portion (84*a*) of the trocar, such that the self sealing membrane is abutting a second self sealing membrane (43*b*) of the medical device when the medical device and the trocar are connected, such that an integrated self sealing membrane is formed enabling insertion of the endoscopic instrument, contained in the medical device, into the trocar through the integrated self sealing membrane.

12. A medical device for use in an endoscopic surgical procedure, the medical device comprising:
a flexible wall (01) enclosing a chamber (C),
a device connecting portion (84*b*) positioned in the flexible wall and adapted to connect to a trocar connecting portion (84*a*) of a trocar (92), such that a fluid connection is created between the chamber enclosed by the wall, and a cavity within the patient.

13. The medical device according to embodiment 12, further comprising a surgical instrument enclosed within the chamber and adapted to operate within the cavity of the patient through the trocar.

14. The medical device according to embodiment 13, wherein the surgical instrument comprises a handle portion (89), and wherein the handle portion is operably encapsulated by the wall such that the handle portion can be manipulated from outside the chamber.

15. The medical device according to any one of embodiments 12-14, wherein the device connecting portion comprises a penetrable second self sealing membrane (43*b*) adapted to seal between the chamber and the ambient environment (A).

16. The medical device according to embodiment 15, wherein the second self sealing membrane is positioned at the device connecting portion of the medical device, such that the self sealing membrane is abutting a first self sealing membrane of the trocar when the medical device and the trocar are connected, such that an integrated self sealing membrane is formed enabling insertion of the endoscopic instrument, contained in the medical device, into the trocar through the integrated self sealing membrane.

17. The medical device according to any one of embodiments 12-16, wherein the second connecting portion comprises a sleeve (59) adapted to connect to the first connecting portion of the trocar by one of:
engaging the trocar on the outside thereof, and
engaging the trocar on the inside thereof.

18. The medical device according to embodiment 17, wherein the sleeve, comprises a sealing member (54) for sealing between the sleeve and the trocar.

19. The medical device according to any one of embodiments 12-18, wherein the device connecting portion (84*b*) comprises a recess (34) or protruding member (33) adapted to engage a corresponding recess or protruding member of the trocar connecting portion.

20. The medical device according to any one of embodiments 12-19, wherein the flexible wall is elastic.

21. The medical device according to any one of embodiments 12-12, wherein the wall of the medical device is adapted to hold a pressure exceeding atmospheric pressure in the chamber.

22. The medical device according to any one of embodiments 12-21, further comprising an evacuation valve (38) for evacuating a fluid from the chamber.

23. The medical device according to embodiment 22, wherein the evacuation valve is connected to a filtering unit (26*b*) for filtering the evacuated fluid.

24. The medical device according to any one of embodiments 22 and 23, wherein the medical device further comprises a control system for controlling the opening of the evacuation valve, wherein the control system is adapted to control the evacuation valve on the basis of at least one of:

the pressure in the chamber,
manual visibility in the chamber,
the visibility in the chamber,
detection of smoke in the chamber,
the temperature in the chamber, and
a time related variable.

25. A medical device system for performing endoscopic surgery on a patient, the medical device system comprising:
a medical device comprising a flexible wall (01) enclosing a chamber (C), wherein the medical device comprises a device connecting portion (84*b*) positioned in the flexible wall, and
a trocar (92) adapted to be positioned though the skin (S) of the patient for establishing a fluid connection with a cavity within the patient, wherein the trocar comprises a trocar connecting portion (84*a*), wherein
the device connecting portion of the medical device is adapted to be connected to the trocar connecting portion of the trocar for establishing a fluid connection between the chamber of the medical device and the cavity in the patient.

26. The medical device system according to embodiment 25, wherein the device connecting portion comprises a sleeve (59) adapted to connect to the trocar connecting portion (84*a*) of the trocar by one of:
engaging the trocar on the outside thereof, and
engaging the trocar on the inside thereof.

27. The medical device system according to embodiment 17, wherein at least one of the sleeve and the trocar comprises a sealing member (54) for sealing between the sleeve and the trocar.

28. The medical device system according to any one of embodiments 25-27, wherein the device connecting portion comprises a recess (34) or protruding member (33), and wherein the trocar connecting portion of the trocar comprises a recess or protruding member, and wherein the protruding member is adapted to engage the recess for connecting the connecting portion of the medical device to the connecting portion of the trocar.

29. The medical device system according to any one of embodiments 25-28, wherein the device connecting portion comprises a penetrable second self sealing membrane (43*b*), and the connecting portion of the trocar comprises a penetrable first self sealing membrane (43*a*), and wherein the self sealing membrane of the medical device is abutting the self sealing membrane of the trocar when the medical device and the trocar are connected, such that an integrated self sealing membrane is formed enabling insertion of an endoscopic instrument (89) from the chamber of the medical device to the cavity in the patient's body through the integrated self sealing membrane.

30. The medical device system according to nay one of embodiments 25-29, further comprising a surgical instrument enclosed within the chamber and adapted to operate within the cavity of the patient through the trocar.

31. The medical device system according to embodiment 30, wherein the surgical instrument comprises a handle portion (89'), and wherein the handle portion is operably encapsulated by the wall, such that the handle portion can be manipulated from outside the chamber.

32. An endoscopic surgical method embodiment of performing an endoscopic procedure in a cavity in a patient's body, the method comprising:

placing a trocar (92) through the skin of a patient, the trocar having a first sealing device (43) within the trocar adapted to seal between the cavity in the body of the patient and the ambient environment (A), and placing a second sealing device (05) against the surface of the skin, the second sealing being sealingly connected to the trocar and adapted to engage the surface of the skin (S) of the patient for further sealing against the skin of the patient, and performing an endoscopic procedure in the cavity of the patient through the trocar.

Numbered Embodiment AD 1-13

1. A medical device for a surgical procedure, comprising:
   a wall (01) adapted to:
      form a chamber (C) together with or without the patient's body, and
      at least partly to be placed on the patient's skin (S), the chamber being adapted to encompass a surgical incision (I) in the skin of the patient in fluid connection with a cavity in the patient's body, while maintaining a sealed environment for the surgical procedure,
   a sealing device (05) connected to the wall and adapted to seal between the wall and the skin or tissue of the patient to seal the chamber, and
   at least one evacuation valve (38) for evacuating a fluid from the chamber, when performing a laparoscopic, open or both laparoscopic and open surgical procedure,
   at least one of
      a fluid inlet (30) adapted to injecting a fluid directly into the chamber, and
      an adaptation to indirect receive fluid from an inlet placed in the patient's skin,
   for inflating at least one of; the chamber and the cavity in the patient's body.

2. A medical device for use in an endoscopic surgical procedure, the medical device comprising a wall (01) forming a chamber (C), wherein a portion of the wall is adapted to be fixated to the skin (S) of the patient, the medical device further comprising at least three of the following:
   an endoscopic instrument (89) enclosed within the chamber,
   a trocar (92), wherein the trocar is at least one of;
      1. enclosed within the chamber, and
      2. positioned sealingly through the wall of the medical device,
   an evacuation valve (38) for evacuating a fluid from the chamber, and
   a closable wall port (17) or inset (42), and
   a closable body port (22) or inset, for performing an endoscopic, open or both endoscopic and open surgical procedure.

3. The medical device according to any one of embodiments 1 and 2, wherein the evacuation valve is connected to a filter for filtering the evacuated fluid.

4. The medical device according to any one of embodiments 1-2, wherein the medical device further comprises a control system for controlling the opening of the evacuation valve, wherein the control system is adapted to control the evacuation valve on the basis of at least one of:
   the pressure in the chamber,
   manually detected visibility in the chamber,
   the visibility in the chamber,
   detection of smoke in the chamber,
   the temperature in the chamber, and
   a time related variable.

5. The medical device according to any one of the preceding embodiments, wherein the wall is adapted to hold a pressure exceeding atmospheric pressure.

6. The medical device according to any one of the preceding embodiments, wherein the sealing device comprises at least one of:
   a pressure sealing member (05") adapted to seal against the skin of the patient by exerting a pressure on the skin of the patient, and
   a vacuum sealing member (05') adapted to hold a pressure being less than atmospheric pressure thus creating a vacuum seal between the skin of the patient and the medical device.

7. The medical device according to any one of the preceding embodiments, wherein the medical device comprises at least one of:
   a. a filtering unit (26b) for filtering the fluid,
   b. a sterilization unit (26a) for directly or indirectly sterilizing the fluid,
   c. a fluid tempering unit (26c) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.

8. The medical device according to any one of the preceding embodiments, wherein the medical device comprises an instrument mount (20) enclosed within the chamber of the medical device and adapted to hold instruments (89) within the chamber.

9. The medical device according to any one of the preceding embodiments, wherein the wall of the medical device comprises a transparent layer enabling viewing into the chamber of the medical device.

10. The medical device according to any one of the preceding embodiments, comprising a wall inset (42; 42'), comprising a glove (02) enabling manual manipulation within the chamber of the medical device.

11. The medical device according to any one of the preceding embodiments, wherein the wall further comprising an adhesive surface (50) adapted to provide at least one of: (a) fixation of the wall to the skin of the patient and (b) sealing between the wall and the skin of patient.

12. The medical device according to any one of the preceding embodiments, wherein the wall of the medical device comprises a closeable wall port (17) adapted to enable transfer of objects (69) from the chamber of the medical device to the ambient environment (A) and vice versa.

13. A method embodiment of performing a surgical procedure on a patient using a medical device, the method comprising:
   a. applying a wall (01) on the skin (S) of the patient to form a chamber (C), in which a sealed environment can be maintained for encompassing part of the surgical procedure to be performed, b. applying a sealing device against the skin of the patient for sealing between the wall and the skin of the patient, c. inflating at least one of a cavity of the patient and the chamber of the medical device with a fluid, d. creating an incision (I) in the skin of the patient, in the sealed environment, such that a fluid connection between the cavity in the patient and the chamber is created, e. performing a step of the surgical procedure in the cavity of the patient, and f. opening an evacuation valve (38) in the wall (01) of the medical device for evacuating a fluid from the chamber.

Numbered Embodiment AE 1-45

1. A medical device for assisting in performing a surgical procedure, comprising a flexible wall, and an interconnectable port (47) comprising;
   a first port (17;22),
   a second coupling adapted be interconnected with the first port to form the interconnectable port, wherein the second coupling is disconnectable from the first port, and
   wherein:
   the first port is connected to a first portion of the flexible wall (01),
   the second coupling is connected to a second portion of the flexible wall,
   the flexible wall is adapted to form a chamber (C) together with the first port and the second coupling,
   the second coupling having a closable opening,
   the chamber is adapted to allow communication through the coupling into a cavity inside the patient's body, when a surgical procedure is performed,
   the first port in a first position is adapted to connect to the second coupling in close relation to the patients skin, wherein the chamber having a first smaller volume, and
   the first port in a second position is adapted to be disconnected from the second coupling, being separated from the coupling in a more remote position in relation to the patients skin, wherein the chamber having a second larger volume, and
   the medical device further comprising a sealing device, adapted to be placed in connection with at least one of the flexible wall and the second coupling, to seal between the medical device and the skin or tissue of the patient, to seal the combined volume of the chamber and the body cavity to the outer environment, when the second coupling is open.

2. The medical device according to embodiment 1, wherein the first port (17) forms a closable wall port when disconnected from the second coupling.

3. The medical device according to any one of embodiments 1 and 2, wherein the second coupling forms a closable body port by itself when the first port has been disconnected from the second coupling.

4. The medical device according to any one of the preceding embodiments, wherein the chamber has a first volume when the first port and the second coupling are interconnected and a second volume when the second coupling is disconnected from the first port.

5. The medical device according to embodiment 4, wherein the second volume is larger than the first volume.

6. The medical device according to embodiment 5, wherein the first volume is smaller than 100 000 mm3.

7. The medical device according to any one of embodiments 5 and 6, wherein the second volume is larger than 500 000 mm3.

8. The medical device according to any one of the preceding embodiments, wherein the flexible wall comprises a pleated portion (03) such that the flexible wall can be expanded.

9. The medical device according to any one of the preceding embodiments, comprising a first coupling (80a), and wherein the first port is connected to the second coupling, and the second coupling is adapted to be connected to the first coupling.

10. The medical device according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.

11. The medical device according to embodiment 10, wherein the recess is a groove in at least one of the first and second coupling.

12. The medical device according to any one of the preceding embodiments, wherein the chamber formed by the flexible wall is adapted to hold a pressure exceeding atmospheric pressure.

13. The medical device according to any one of the preceding embodiments, wherein the interconnectable port is adapted to:
    a. in a first state, when the first port and second coupling are interconnected, enable a surgeon to operate through the interconnected interconnectable port, and
    b. in a second state, when the second coupling is disconnected from the first port enable the surgeon to perform steps of the procedure within the chamber formed by the flexible wall between the first port and second coupling of the interconnectable port.

14. The medical device according to embodiment 12, wherein the interconnectable port is adapted to, in the second state, enable the surgeon to remove a specimen (81) from the body of the patient through the second coupling and into the chamber, and to perform one of: placing the specimen within the chamber, and removing the specimen from the chamber through the first port.

15. The medical device according to embodiment 13, wherein the chamber further comprises a pouch for holding the specimen within the chamber.

16. The medical device according to embodiment 14, wherein the pouch can be closed for creating a pouch-chamber within the chamber for isolating the removed specimen within the chamber.

17. The medical device according to any one of embodiments 1-16, comprising a second port adapted to also be placed in the second coupling, wherein at least one of the first port, the second port and a first coupling are adapted to be reconnected after having been disconnected, such that the surgeon can continue operating through the interconnected port after the specimen has been removed.

18. The medical device according to anyone of embodiments 9-17, further comprising an inset (42;42';42") detachably fixated to at least one of the first and second coupling, such that the inset could be detached and replaced by a different inset.
19. The medical device according to embodiment 18, wherein the inset comprises at least one of: a surgical glove (02) and a device or instrument mount (20).
20. The medical device according to any one of the preceding embodiments, comprising a second port adapted to be placed in the second coupling, wherein at least one of the first and second port comprises an elastic or flexible membrane (43) adapted to, in a non-compressed state, provide sealing, and in a compressed state enable a hand or an object to be inserted through the membrane.
21. The medical device according to embodiment 20, wherein the first port comprises a first elastic or flexible membrane (43a) and the second port comprises a second elastic or flexible membrane (43b), and wherein the first and second membranes are adapted to be placed tightly together such that they act as a single elastic or flexible membrane adapted to, in a non-compressed state, provide sealing, and in a compressed state enable a hand or an object to be inserted through the membrane.
22. The medical device according to embodiment 21, wherein the first and second membranes comprises a plurality of self sealing holes (44) enabling insertion of instruments through the membranes.
23. The surgical port according to any one of embodiments 17-22, wherein at least one of said first port and second port comprises a penetrable self sealing gel, such that an object or hand can be inserted through the interconnectable port while maintaining a seal.
24. The medical device according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.
25. The medical device according to any one of the preceding embodiments, wherein the wall comprises a fluid inlet (30) for inflating the chamber with a fluid.
26. The medical device according to embodiment 25, further comprising a fluid outlet (31) provided in the wall for discharging the fluid from the chamber.
27. The medical device according to embodiment 26, further comprising a pump (27) adapted to circulate the fluid from the outlet member to the inlet member.
28. The medical device according to any one of the preceding embodiments, wherein at least one of the first port and second coupling comprises a non-penetrable valve (86) such that the chamber is sealed from at least one of the ambient environment and a cavity in the patient.
29. The medical device according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.
30. The medical device according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the port and the skin of the patient, and (b) the first sealing member and tissue of the patient.
31. The medical device according to any one of the preceding embodiments, wherein the medical device further comprises at least one of:
 a. a filtering unit (26b) for filtering the fluid,
 b. a sterilization unit (26a) for directly or indirectly sterilizing the fluid,
 c. a fluid tempering unit (26c) adapted change the temperature of the fluid,
 d. a filtering unit for filtering the fluid and a sterilization unit for directly or indirectly sterilizing the fluid,
 e. a filtering unit for filtering the fluid and a fluid tempering unit adapted change the temperature of the fluid,
 f. a sterilization unit for directly or indirectly sterilizing the fluid and a fluid tempering unit adapted change the temperature of the fluid, and
 g. a filtering unit for filtering the fluid, a sterilization unit for directly or indirectly sterilizing the fluid and a fluid tempering unit adapted change the temperature of the fluid.
32. The medical device according to anyone of embodiments 1-31, wherein the second coupling is adapted to allow passage of a hand into the body cavity.
33. The medical device according to any one of embodiments 1-32, wherein the second coupling forms an opening, when the first port has been disconnected from the second coupling.
34. The medical device according to anyone of embodiments 1-33, wherein the second coupling comprises a detachable second inset.
35. The medical device according to anyone of embodiments 1-34, wherein the first port comprises a detachable third inset.
36. The medical device according to any one of embodiments 1-35, wherein the second coupling forms an opening, when the first port has been disconnected from the second coupling.
37. The medical device according to embodiment 34, wherein the second inset is adapted to close between the body cavity and the chamber.
38. The medical device according to anyone of embodiments 1-37, comprising a third port comprising a detachable third inset.
39. The medical device according to any one of embodiments 1-38, wherein the second coupling comprising a body port being a detachable part of the second coupling.
40. The medical device according to any one of embodiments 1-39, wherein the first port being a multiport comprising two or more individual ports, wherein the coupling being adapted to connect to the multiport to together form an integrated multiport placed in close relation to the skin.
41. The medical device according to anyone of embodiments 39-40, wherein the body port being a multiport comprising two or more individual ports, wherein the body port being adapted to connect to the first port being a multiport, to together form an integrated multiport placed in close relation to the skin.
42. A surgical method to be performed on the body of a patient using an interconnectable port (47) comprising a first port (17) and a second coupling, the method comprising:
   a. creating an incision (I) in the skin (S) of the patient, connecting to a body cavity,
   b. placing the interconnectable port in the incision,
   c. disconnecting the first port from the second coupling, such that a chamber (C) is formed by a wall (01) connected to the first port and second coupling, and
   d. performing a step of the surgical procedure within at least one of the body cavity and the chamber.
43. The surgical method according to embodiment 42, wherein the medical device further comprising a sealing device, a further step of performing the surgical procedure comprises:
   placing a sealing device in connection with at least one of; the flexible wall and the second coupling, to seal between the medical device and the skin or tissue of the patient,
   sealing the combined volume of the chamber and the body cavity to the outer environment, when the second coupling is open.
44. The surgical method according to anyone of embodiments 42-43, wherein the step of performing a step of the surgical procedure within the chamber comprises:
   a. removing a specimen (81) from the cavity in the body of the patient,
   b. transferring the specimen through the second coupling, and
   c. placing the specimen within the chamber of the medical device.
45. The surgical method according to any one of embodiments 42-44, wherein the method further comprises:
   a. reconnecting the first port and second coupling such that the interconnectable port is formed,
   b. performing a surgical step in a cavity of the patient, through the interconnectable port.

Numbered Embodiment AF 1-43

1. A medical device for assisting in performing a surgical procedure, comprising
   a first flexible wall, and
   an interconnectable port (47) comprising;
      a first port (17;22), and
      a second coupling adapted be interconnected with the first port to form the interconnectable port, wherein the second coupling is disconnectable from the first port,
   wherein:
   the first port is connected to a first portion of the first flexible wall (01),
   the second coupling is connected to a second portion of the first flexible wall,
      the first flexible wall is adapted to form a chamber (C) together with the first port and the second coupling,
      the second coupling having a closable opening,
         the chamber is adapted to allow communication through the second coupling into a cavity inside the patient's body, when an incision has been performed in the patient's skin and a surgical procedure is performed,
      the first port in a first position is adapted to connect to the second coupling in close relation to the patients skin, wherein the chamber having a first smaller volume, and
      the first port in a second position is adapted to be disconnected from the second coupling, being separated from the coupling in a more remote position in relation to the patients skin, wherein the chamber having a second larger volume, and
      the medical device further comprising a sealing device, comprising
      a flexible connecting member,
      a first sealing member (35), adapted to be positioned at the inside of the patient's skin around an incision to be performed in the skin and being sealingly connected to the flexible connecting member, and
   a second sealing member (37) sealingly connected to at least one of; the first flexible wall, the flexible connecting member, and the second coupling or being an integrated part of the second coupling, adapted to be positioned at the outside of the patient's skin around the incision, wherein
   the flexible connecting member (36) is sealingly interconnecting the first and second sealing members, whereby the first and second sealing members are adapted to be larger than the incision to seal between at least one of: the second sealing member and the skin or tissue of the patient, and the first sealing member and tissue of the patient, and wherein
   the flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.
2. The medical device according to embodiment 1, wherein the first port (17) forms a closable wall port when disconnected from the second coupling (22).
3. The medical device according to any one of embodiments 1 and 2, wherein the second coupling (22) forms a closable body port by itself when the first port has been disconnected from the second coupling.
4. The medical device according to any one of the preceding embodiments, wherein the chamber has a first volume when the first port and second coupling are interconnected and a second volume when the second coupling is disconnected from the first port.
5. The medical device according to embodiment 4, wherein the second volume is larger than the first volume.
6. The medical device according to embodiment 5, wherein the first volume is smaller than 100 000 mm3.
7. The medical device according to any one of embodiments 5 and 6, wherein the second volume is larger than 500 000 mm3.

8. The medical device according to any one of the preceding embodiment, wherein the flexible wall comprises a pleated portion (03) such that the flexible wall can be expanded.
9. The medical device according to any one of the preceding embodiments, comprising a first coupling (80*a*), and wherein the first port is connected to the first coupling, and the first coupling is adapted to be connected to the second coupling.
10. The medical device according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.
11. The medical device according to embodiment 10, wherein the recess is a groove in at least one of the first and second coupling.
12. The medical device according to any one of the preceding embodiments, wherein the chamber formed by the flexible wall is adapted to hold a pressure exceeding atmospheric pressure.
13. The medical device according to any one of the preceding embodiments, wherein the interconnectable port is adapted to:
    a. in a first state, when the first port and second coupling are interconnected, enable a surgeon to operate through the interconnected interconnectable port, and
    b. in a second state, when the second coupling is disconnected from the first port enable the surgeon to perform steps of the procedure within the chamber formed by the flexible wall between the first port and second coupling of the interconnectable port.
14. The medical device according to embodiment 13, wherein the interconnectable port is adapted to, in the second state, enable the surgeon to remove a specimen (81) from the body of the patient through the second coupling and into the chamber, and to perform one of: placing the specimen within the chamber, and removing the specimen from the chamber through the first port.
15. The medical device according to embodiment 13, wherein the chamber further comprises a pouch for holding the specimen within the chamber.
16. The medical device according to embodiment 15, wherein the pouch can be closed for creating a pouch-chamber within the chamber for isolating the removed specimen within the chamber.
17. The medical device according to any one of embodiments 1-16, comprising a second port adapted to also be placed in the second coupling, wherein at least one of the first port, the second port and a first coupling are adapted to be reconnected after having been disconnected, such that the surgeon can continue operating through the interconnected port after the specimen has been removed.
18. The medical device according to anyone of embodiments 9-17, further comprising an inset (42;42';42") detachably fixated to at least one of the first and second coupling, such that the inset could be detached and replaced by a different inset.
19. The medical device according to embodiment 18, wherein the inset comprises at least one of: a surgical glove (02) and a device or instrument mount (20).
20. The medical device according to any one of the preceding embodiments, comprising a second port adapted to be placed in the first coupling, wherein at least one of the first and second port comprises an elastic or flexible membrane (43) adapted to, in a non-compressed state, provide sealing, and in a compressed state enable a hand or an object to be inserted through the membrane.
21. The medical device according to embodiment 20, wherein the first port comprises a first elastic or flexible membrane (43*a*) and the second port comprises a second elastic or flexible membrane (43*b*), and wherein the first and second membranes are adapted to be placed tightly together such that they act as a single elastic or flexible membrane adapted to, in a non-compressed state, provide sealing, and in a compressed state enable a hand or an object to be inserted through the membrane.
22. The medical device according to embodiment 21, wherein the first and second membranes comprises a plurality of self sealing holes (44) enabling insertion of instruments through the membranes.
23. The surgical port according to any one of embodiments 17-22, wherein at least one of said first port and second port comprises a penetrable self sealing gel, such that an object or hand can be inserted through the interconnectable port while maintaining a seal.
24. The medical device according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.
25. The medical device according to any one of the preceding embodiments, wherein the wall comprises a fluid inlet (30) for inflating the chamber with a fluid.
26. The medical device according to embodiment 25, further comprising a fluid outlet (31) provided in the wall for discharging the fluid from the chamber.
27. The medical device according to embodiment 26, further comprising a pump (27) adapted to circulate the fluid from the outlet member to the inlet member.
28. The medical device according to any one of the preceding embodiments, wherein at least one of the first port and second coupling comprises a non-penetrable valve (86) such that the chamber is sealed from at least one of the ambient environment and a cavity in the patient.
29. The medical device according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.
30. The medical device according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the port and the skin of the patient, and (b) the first sealing member and tissue of the patient.

31. The medical device according to any one of the preceding embodiments, wherein the medical device further comprises at least one of:
    a. a filtering unit (26*b*) for filtering the fluid,
    b. a sterilization unit (26*a*) for directly or indirectly sterilizing the fluid,
    c. a fluid tempering unit (26*c*) adapted change the temperature of the fluid,
    d. a filtering unit for filtering the fluid and a sterilization unit for directly or indirectly sterilizing the fluid,
    e. a filtering unit for filtering the fluid and a fluid tempering unit adapted change the temperature of the fluid,
    f. a sterilization unit for directly or indirectly sterilizing the fluid and a fluid tempering unit adapted change the temperature of the fluid, and
    g. a filtering unit for filtering the fluid, a sterilization unit for directly or indirectly sterilizing the fluid and a fluid tempering unit adapted change the temperature of the fluid.
32. The medical device according to anyone of embodiments 1-31, wherein the second coupling is adapted to allow passage of a hand into the body cavity.
33. The medical device according to any one of embodiments 1-32, wherein the second coupling forms an opening, when the first port has been disconnected from the second coupling.
34. The medical device according to anyone of embodiments 1-33, wherein the second coupling comprises a detachable second inset.
35. The medical device according to anyone of embodiments 1-34, wherein the first port comprises a detachable third inset.
36. The medical device according to embodiment 35, wherein the second inset is adapted to close between the body cavity and the chamber.
37. The medical device according to anyone of embodiments 1-36, comprising a third port comprising a detachable third inset.
38. The medical device according to any one of embodiments 1-37, wherein the second coupling comprising a body port being a detachable part of the second coupling.
39. The medical device according to any one of embodiments 1-38, wherein the first port being a multiport comprising two or more individual ports, wherein the coupling being adapted to connect to the multiport to together form an integrated multiport placed in close relation to the skin.
40. The medical device according to anyone of embodiments 38-39, wherein the body port being a multiport comprising two or more individual ports, wherein the body port being adapted to connect to the first port being a multiport, to together form an integrated multiport placed in close relation to the skin.
41. A surgical method to be performed on the body of a patient placing a medical device according to embodiment 1, including the sealing device according to embodiment 1 and an interconnectable port (47) having a first port (17) and a second coupling, the sealing device includes a flexible connecting member and a first and second sealing member, the method comprising:
    a. creating an incision (I) in the skin (S) of the patient, connecting to a body cavity,
    b. placing the sealing device with its flexible connecting member through the incision,
    c. positioning the first sealing member (35), at the inside of the patient's skin around the incision being sealingly connected to the flexible connecting member,
    d. positioning the second sealing member (37) at the outside of the patient's skin around the incision,
    e. placing the interconnectable port in the incision,
    f. disconnecting the first port from the second port, such that a chamber (C) is formed by a wall (01) connected to the first and second port,
    g. sealing by the second sealing member towards the skin or tissue of the patient,
    h. sealing by the first sealing member towards tissue of the patient, and
    i. performing a step of the surgical procedure within at least one of; the chamber and the body cavity.
42. The surgical method according to embodiment 40, wherein the step of performing a step of the surgical procedure within the chamber comprises:
    a. removing a specimen (81) from the cavity in the body of the patient,
    b. transferring the specimen through the first port, and
    c. placing the specimen within the chamber of the medical device.
43. The surgical method according to any one of embodiment 40 and 41, wherein the method further comprises:
    a. reconnecting the first port and second coupling such that the interconnectable port is formed,
    b. performing a surgical step in a cavity of the patient, through the interconnectable port.

Numbered Embodiment AG 1-44

1. A medical device for assisting in performing a surgical procedure, comprising
   a first flexible wall (01), and
   an interconnectable port (47) comprising;
     a first port (17;22), and
     a second coupling (80*b*) adapted be interconnected with the first port to form the interconnectable port, wherein the second coupling is disconnectable from the first port,
   wherein:
   the first port is connected to a first portion of the first flexible wall,
   the second coupling is connected to a second portion of the first flexible wall,
     the first flexible wall is adapted to form a chamber (C) together with the first port and the second coupling,
   the second coupling having a closable opening,
     the chamber is adapted to allow communication through the second coupling into a cavity inside the patients body, when an incision has been performed in the patients skin and a surgical procedure is performed, the first port in a first position is adapted to connect to the second coupling in close relation to the patient's skin, wherein the chamber having a first smaller volume, and the first port in a second position is adapted to be disconnected from the second coupling, being separated from the second coupling in a more remote position in relation to the patients skin, wherein the chamber having a second larger volume, and the medical device further comprising a retracting system, comprising a flexible connecting member (36), a inside retracting member (35), adapted to be positioned at the inside of the patient's skin around an incision to be performed in the skin and be connected to the flexible connecting member, and a outside retracting member (37) connected to at least one of; the first flexible wall, the flexible connecting member, and the second coupling or being an integrated part of the second coupling, adapted to be positioned at the outside of the patient's skin around the incision, wherein the flexible connecting member is interconnecting the inside and outside retracting members, whereby the inside and outside retracting members are adapted to be larger than the incision allowing the flexible connecting member to retract the skin and tissue in the incision opening substantially parallel to the skin, and wherein the flexible connecting member is adapted to be placed in connection with at least one of; the first flexible wall and the second coupling or is an integrated part of the first flexible wall, adapted to be placed through the incision into the body cavity and adapted to together with inside and outside retracting members retract, substantially parallel to the skin, the skin and tissue in close relation to the incision, to enlarge the incision passage from the chamber into the body cavity, during the surgical procedure.

2. The medical device according to embodiment 1, wherein the first port (17) forms a closable wall port when disconnected from the second coupling.

3. The medical device according to any one of embodiments 1 and 2, wherein the second coupling forms a closable body port (22) by itself when the first port has been disconnected from the second coupling.

4. The medical device according to any one of the preceding embodiments, wherein the chamber has a first volume when the first port and second coupling are interconnected and a second volume when the second coupling is disconnected from the first port.

5. The medical device according to embodiment 4, wherein the second volume is larger than the first volume.

6. The medical device according to embodiment 5, wherein the first volume is smaller than 100 000 mm3.

7. The medical device according to any one of embodiments 5 and 6, wherein the second volume is larger than 500 000 mm3.

8. The medical device according to any one of the preceding embodiments, wherein the flexible wall comprises a pleated portion (03) such that the flexible wall can be expanded.

9. The medical device according to any one of the preceding embodiments, comprising a first coupling (80a), and wherein the first port is connected to the second coupling, and the second coupling (80b) is adapted to be connected to the first coupling.

10. The medical device according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.

11. The medical device according to embodiment 10, wherein the recess is a groove in at least one of the first and second coupling.

12. The medical device according to any one of the preceding embodiments, wherein the chamber formed by the flexible wall is adapted to hold a pressure exceeding atmospheric pressure.

13. The medical device according to any one of the preceding embodiments, wherein the interconnectable port is adapted to:
   a. in a first state, when the first port and second coupling are interconnected, enable a surgeon to operate through the interconnected interconnectable port, and
   b. in a second state, when the second coupling is disconnected from the first port enable the surgeon to perform steps of the procedure within the chamber formed by the flexible wall between the first port and second coupling of the interconnectable port.

14. The medical device according to embodiment 13, wherein the interconnectable port is adapted to, in the second state, enable the surgeon to remove a specimen (81) from the body of the patient through the second coupling and into the chamber, and to perform one of: placing the specimen within the chamber, and removing the specimen from the chamber through the first port.

15. The medical device according to embodiment 14, wherein the chamber further comprises a pouch for holding the specimen within the chamber.

16. The medical device according to embodiment 15, wherein the pouch can be closed for creating a pouch-chamber within the chamber for isolating the removed specimen within the chamber.

17. The medical device according to any one of embodiments 1-16, comprising a second port adapted to also be placed in the second coupling, wherein at least one of the first port, the second port and a first coupling are adapted to be reconnected after having been disconnected, such that the surgeon can continue operating through the interconnected port after the specimen has been removed.

18. The medical device according to anyone of embodiments 9-17, further comprising an inset (42;42';42") detachably fixated to at least one of the first and second coupling, such that the inset could be detached and replaced by a different inset.

19. The medical device according to embodiment 18, wherein the inset comprises at least one of: a surgical glove (02) and a device or instrument mount (20).

20. The medical device according to any one of the preceding embodiments, comprising a second port adapted to be placed in the second coupling, wherein at least one of the first and second port comprises an elastic or flexible membrane (43) adapted to, in a non-compressed state, provide sealing, and in a compressed state enable a hand or an object to be inserted through the membrane.

21. The medical device according to embodiment 20, wherein the first port comprises a first elastic or flexible membrane (43a) and the second port comprises a second elastic or flexible membrane (43b), and wherein the first and second membranes are adapted to be placed tightly together such that they act as a single elastic or flexible membrane adapted to, in a non-compressed state, provide sealing, and in a compressed state enable a hand or an object to be inserted through the membrane.

22. The medical device according to embodiment 21, wherein the first and second membranes comprises a plurality of self sealing holes (44) enabling insertion of instruments through the membranes.

23. The medical device according to any one of the embodiments 17-22, wherein at least one of said first port and second port comprises a penetrable self sealing gel, such that an object or hand can be inserted through the medical device while maintaining a seal.

24. The medical device according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.

25. The medical device according to any one of the preceding embodiments, wherein the wall comprises a fluid inlet (30) for inflating the chamber with a fluid.

26. The medical device according to embodiment 25, further comprising a fluid outlet (31) provided in the wall for discharging the fluid from the chamber.

27. The medical device according to embodiment 26, further comprising a pump (27) adapted to circulate the fluid from the outlet member to the inlet member.

28. The medical device according to any one of the preceding embodiments, wherein at least one of the first port and second coupling comprises a non-penetrable valve (86) such that the chamber is sealed from at least one of the ambient environment and a cavity in the patient.

29. The medical device according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

30. The medical device according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the port and the skin of the patient, and (b) the first sealing member and tissue of the patient.

31. The medical device according to any one of the preceding embodiments, wherein the medical device further comprises at least one of:
   a. a filtering unit (26b) for filtering the fluid,
   b. a sterilization unit (26a) for directly or indirectly sterilizing the fluid,
   c. a fluid tempering unit (26c) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.

32. The medical device according to anyone of embodiments 1-31, wherein the coupling is adapted to allow passage of a hand into the body cavity.

33. The medical device according to any one of embodiments 1-32, wherein the coupling forms an opening, when the first port has been disconnected from the coupling.

34. The medical device according to any one of embodiments 1-33, wherein the inside retracting member (35), is sealingly connected to the flexible connecting member, wherein the outside retracting member (37) is sealingly connected to at least one of the first flexible wall, the flexible connecting member, and the second coupling or being an integrated part of the second coupling, wherein
the flexible connecting member (36) is sealingly direct or indirect interconnecting the inside and outside retracting members, adapted to be placed sealingly in connection with at least one of; the first flexible wall and the second coupling or being an integrated part of the first flexible wall.

35. The medical device according to any one of embodiments 1-34, wherein the second coupling comprising a body port being a detachable part of the second coupling.

36. The medical device according to any one of embodiments 1-35, wherein the first port being a multiport comprising two or more individual ports, wherein the coupling being adapted to connect to the multiport to together form an integrated multiport placed in close relation to the skin.

37. The medical device according to anyone of embodiments 35-36, wherein the body port is a multiport comprising two or more individual ports, and wherein the body port is adapted to connect to the first port being a multiport, to together form an integrated multiport placed in close relation to the skin.

38. The medical device according to anyone of embodiments 1-37, wherein the second coupling comprises a detachable second inset.

39. The medical device according to anyone of embodiments 1-38, wherein the first port comprises a detachable third inset.

40. The medical device according to embodiment 38, wherein the second inset is adapted to close between the body cavity and the chamber.

41. The medical device according to anyone of embodiments 1-40, comprising a third port comprising a detachable third inset.
42. A surgical method to be performed on the body of a patient placing a medical device according to embodiment 1, including a retracting system and an interconnectable port (47) having a first port (17) and a second coupling, the retracting system includes a flexible connecting member and a inside and outside retracting member, the method comprising:
   a. creating an incision (I) in the skin (S) of the patient, connecting to a body cavity,
   b. placing the retracting system with its flexible connecting member through the incision,
   c. positioning the inside retracting member (35), at the inside of the patient's skin around the incision being sealingly connected to the flexible connecting member,
   d. positioning the outside retracting member (37) at the outside of the patient's skin around the incision,
   e. placing the interconnectable port in the incision,
   f. disconnecting the first port from the second port, such that a chamber (C) is formed by a wall (01) connected to the first and second port,
   g. retracting the incision and enlarging the opening by the flexible connecting member placed onto the inside and outside retracting members,
   h. retracting substantially parallel to the skin, the skin and tissue in close relation to the incision, to enlarge the incision passage from the chamber into the body cavity, during the surgical procedure, and
   i. performing a step of the surgical procedure within at least one of the chamber and the body cavity.
43. The surgical method according to embodiment 42, wherein the step of performing a step of the surgical procedure within the chamber comprises:
   a. removing a specimen (81) from the cavity in the body of the patient,
   b. transferring the specimen through the second port, and
   c. placing the specimen within the chamber of the medical device.
44. The surgical method according to any one of embodiment 42 and 43, wherein the method further comprises:
   a. reconnecting the first port and second coupling such that the interconnectable port is formed,
   b. performing a surgical step in a cavity of the patient, through the interconnectable port.

Numbered Embodiment AH 1-50

1. A medical device for assisting in performing a surgical procedure, comprising a flexible wall, a first inset (42;42';42"), and an interconnectable port (47), the interconnectable port comprising;
   a first port (17;22),
   a second coupling adapted be interconnected with at least one of; the first port to form the interconnectable port, and the first inset, wherein the second coupling is disconnectable from the first port or first inset, and
wherein:
   the first port is connected to a first portion of the flexible wall (01),
   the first inset is connected to a third portion of the flexible wall (01),
   the second coupling is connected to a second portion of the flexible wall,
      the flexible wall is adapted to form a chamber (C) together with the first port, first inset and the second coupling,
   the second coupling having a closable opening,
      the chamber is adapted to allow communication through the coupling into a cavity inside the patient's body, after an incision has been made in the skin of the patient, when a surgical procedure is performed,
      at least one of; the first port and first inset in a first position is adapted to connect to the second coupling in close relation to the patients skin, wherein the chamber having a first smaller volume, and
      at least one of; the first port and first inset in a second position is adapted to be disconnected from the second coupling, being separated from the coupling in a more remote position in relation to the patients skin, wherein the chamber having a second larger volume.
2. The medical device according to embodiment 1, wherein the first port (17) forms a closable wall port when disconnected from the second coupling.
3. The medical device according to any one of embodiments 1 and 2, wherein the second coupling forms a closable body port by itself when the first port has been disconnected from the second coupling.
4. The medical device according to any one of the preceding embodiments, wherein the first port comprises a multiport, comprising two or more individual ports.
5. The medical device according to anyone of embodiments 1-4, wherein the first inset (42;42';42") comprises at least one of: a surgical glove (02) and a device or instrument mount (20), for assisting with in the surgical procedure.
6. The medical device according to anyone of embodiments 1-5, wherein the first volume is smaller than 100 000 mm3.
7. The medical device according to any one of embodiments 1-6, wherein the second volume is larger than 500 000 mm3.
8. The medical device according to any one of the preceding embodiment, wherein the flexible wall comprises a pleated portion (03) such that the flexible wall can be expanded.
9. The medical device according to any one of the preceding embodiments, comprising a first coupling (80*a*), and wherein the first port is connected to the second coupling, and the second coupling is adapted to be connected to the first coupling.
10. The medical device according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.
11. The medical device according to embodiment 10, wherein the recess is a groove in at least one of the first and second coupling.
12. The medical device according to any one of the preceding embodiments, wherein the chamber formed by the flexible wall is adapted to hold a pressure exceeding atmospheric pressure.

13. The medical device according to any one of the preceding embodiments, wherein the interconnectable port is adapted to:
   a. in a first state, when the first port and second coupling are interconnected, enable a surgeon to operate through the interconnected interconnectable port, and
   b. in a second state, when the second coupling is disconnected from the first port enable the surgeon to perform steps of the procedure within the chamber formed by the flexible wall between the first port and second coupling of the interconnectable port.
14. The medical device according to embodiment 12, wherein the interconnectable port is adapted to, in the second state, enable the surgeon to remove a specimen (81) from the body of the patient through the second coupling and into the chamber, and to perform one of: placing the specimen within the chamber, and removing the specimen from the chamber through the first port.
15. The medical device according to embodiment 13, wherein the chamber further comprises a pouch for holding the specimen within the chamber.
16. The medical device according to embodiment 14, wherein the pouch can be closed for creating a pouch-chamber within the chamber for isolating the removed specimen within the chamber.
17. The medical device according to any one of embodiments 1-16, comprising a second port adapted to also be placed in the second coupling, wherein at least one of the first port, the second port and a first coupling are adapted to be reconnected after having been disconnected, such that the surgeon can continue operating through the interconnected port after the specimen has been removed.
18. The medical device according to anyone of embodiments 9-17, wherein the inset inset (42;42';42") is detachably fixated to at least one of the first and second coupling, such that the inset could be detached and replaced by a different inset.
19. The medical device according to anyone of embodiments 1-18, further comprising a sealing device, comprising
   a flexible connecting member,
   a first sealing member (35), adapted to be positioned at the inside of the patient's skin around an incision to be performed in the skin and being sealingly connected to the flexible connecting member, and
   a second sealing member (37) sealingly connected to at least one of the first flexible wall, the flexible connecting member, and the second coupling or being an integrated part of the second coupling, adapted to be positioned at the outside of the patient's skin around the incision, wherein
   the flexible connecting member (36) is sealingly interconnecting the first and second sealing members, whereby the first and second sealing members is adapted to be larger than the incision to seal between at least one of: the second sealing member and the skin or tissue of the patient, and the first sealing member and tissue of the patient, and wherein
   the flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.
20. The medical device according to any one of the preceding embodiments, comprising a second port adapted to be placed in the second coupling, wherein at least one of the first and second port comprises an elastic or flexible membrane (43) adapted to, in a non-compressed state, provide sealing, and in a compressed state enable a hand or an object to be inserted through the membrane.
21. The medical device according to embodiment 20, wherein the first port comprises a first elastic or flexible membrane (43a) and the second port comprises a second elastic or flexible membrane (43b), and wherein the first and second membranes are adapted to be placed tightly together such that they act as a single elastic or flexible membrane adapted to, in a non-compressed state, provide sealing, and in a compressed state enable a hand or an object to be inserted through the membrane.
22. The medical device according to embodiment 21, wherein the first and second membranes comprises a plurality of self sealing holes (44) enabling insertion of instruments through the membranes.
23. The medical device according to any one of embodiments 17-22, wherein at least one of said first port and second port comprises a penetrable self sealing gel, such that an object or hand can be inserted through the interconnectable port while maintaining a seal.
24. The medical device according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.
25. The medical device according to any one of the preceding embodiments, wherein the wall comprises a fluid inlet (30) for inflating the chamber with a fluid.
26. The medical device according to embodiment 25, further comprising a fluid outlet (31) provided in the wall for discharging the fluid from the chamber.
27. The medical device according to embodiment 26, further comprising a pump (27) adapted to circulate the fluid from the outlet member to the inlet member.
28. The medical device according to any one of the preceding embodiments, wherein at least one of the first port and second coupling comprises a non-penetrable valve (86) such that the chamber is sealed from at least one of the ambient environment and a cavity in the patient.
29. The medical device according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.
30. The medical device according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of: (a) the port and the skin of the patient, and (b) the first sealing member and tissue of the patient.
31. The medical device according to any one of the preceding embodiments, wherein the medical device further comprises at least one of:
  a. a filtering unit (26*b*) for filtering the fluid,
  b. a sterilization unit (26*a*) for directly or indirectly sterilizing the fluid,
  c. a fluid tempering unit (26*c*) adapted change the temperature of the fluid,
  d. a filtering unit for filtering the fluid and a sterilization unit for directly or indirectly sterilizing the fluid,
  e. a filtering unit for filtering the fluid and a fluid tempering unit adapted change the temperature of the fluid,
  f. a sterilization unit for directly or indirectly sterilizing the fluid and a fluid tempering unit adapted change the temperature of the fluid, and
  g. a filtering unit for filtering the fluid, a sterilization unit for directly or indirectly sterilizing the fluid and a fluid tempering unit adapted change the temperature of the fluid.
32. The medical device according to anyone of embodiments 1-31, wherein the second coupling is adapted to allow passage of a hand into the body cavity.
33. The medical device according to any one of embodiments 1-32, wherein the second coupling forms an opening, when the first port has been disconnected from the second coupling.
34. The medical device according to any one of embodiments 1-33, further comprising a retracting system, comprising
  a flexible connecting member,
  an inside retracting member (35), adapted to be positioned at the inside of the patient's skin around an incision to be performed in the skin and being connected to the flexible connecting member, and
  an outside retracting member (37) connected to at least one of the first flexible wall, the flexible connecting member, and the second coupling or being an integrated part of the second coupling, adapted to be positioned at the outside of the patient's skin around the incision, wherein
  the flexible connecting member (36) is interconnecting the inside and outside retracting members, whereby the inside and outside retracting members are adapted to be larger than the incision thus allowing the flexible connecting member to retract the skin and tissue in the incision opening substantially parallel to the skin, wherein
  the flexible connecting member is adapted to be placed in connection with at least one of; the first flexible wall and the second coupling or be an integrated part of the first flexible wall, adapted to be placed through the incision into the body cavity, adapted to together with inside and outside retracting members retracting substantially parallel to the skin, the skin and tissue in close relation to the incision, to enlarge the incision passage from the chamber into the body cavity, during the surgical procedure.
35. The medical device according to any one of embodiments 1-34, wherein the inside retracting member (35), is sealingly connected to the flexible connecting member, wherein the outside retracting member (37) is sealingly connected to at least one of; the first flexible wall, the flexible connecting member, and the second coupling or being an integrated part of the second coupling, wherein the flexible connecting member (36) is sealingly direct or indirect interconnecting the inside and outside retracting members, adapted to be placed sealingly in connection with at least one of; the first flexible wall and the second coupling or being an integrated part of the first flexible wall.
36. The medical device according to anyone of embodiments 1-35, wherein the coupling is adapted to allow passage of a hand into the body cavity.
37. The medical device according to any one of embodiments 1-36, wherein the coupling forms an opening, when the first port has been disconnected from the coupling.
38. The medical device according to any one of embodiments 1-37, the medical device further comprising a sealing device, comprising
  a flexible connecting member,
  a first sealing member (35), adapted to be positioned at the inside of the patient's skin around an incision to be performed in the skin and being sealingly connected to the flexible connecting member, and
  a second sealing member (37) sealingly connected to at least one of; the first flexible wall, the flexible connecting member, and the second coupling or being an integrated part of the second coupling, adapted to be positioned at the outside of the patient's skin around the incision, wherein
  the flexible connecting member (36) is sealingly interconnecting the first and second sealing members, whereby the first and second sealing members is adapted to be larger than the incision to seal between at least one of: the second sealing member and the skin or tissue of the patient, and the first sealing member and tissue of the patient, and wherein
  the flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.
39. The medical device according to any one of embodiments 1-38, wherein the second coupling comprising a body port being a detachable part of the second coupling.
40. The medical device according to any one of embodiments 1-39, wherein the first port being a multiport comprising two or more individual ports, wherein the coupling being adapted to connect to the multiport to together form an integrated multiport placed in close relation to the skin.
41. The medical device according to anyone of embodiments 39-40, wherein the body port being a multiport comprising two or more individual ports, wherein the body port being adapted to connect to the first port being a multiport, to together form an integrated multiport placed in close relation to the skin.

42. The medical device according to anyone of embodiments 1-41, wherein the second coupling comprises a detachable second inset.
43. The medical device according to anyone of embodiments 1-42, wherein the first port comprises a detachable third inset.
44. The medical device according to embodiment 42, wherein the second inset is adapted to close between the body cavity and the chamber.
45. The medical device according to anyone of embodiments 1-44, comprising a third port comprising a detachable third inset.
46. The medical device according to any one of embodiments 1-45, comprising a sealing device, adapted to be placed in connection with at least one of; the flexible wall and the second coupling, to seal between the medical device and the skin or tissue of the patient, to seal the combined volume of the chamber and the body cavity to the outer environment, when the second coupling is open.
47. A surgical method to be performed on the body of a patient using a medical device according to embodiment 1, as described in embodiment 1 comprising a flexible wall, a first inset and an interconnectable port (47), comprising a first port (17) being a multiport, and a second coupling, the method comprising:
    a. creating an incision (I) in the skin (S) of the patient, connecting to a body cavity,
    b. placing the coupling in the incision, such that a chamber (C) is formed by the flexible wall (01) connected to the first port, first inset and second coupling
    c. connecting the first port to the second coupling,
    d. performing the surgical procedure through two or more trocars included in the first port being a multiport,
    e. introducing a camera through one trocar,
    f. detaching the first port from the second coupling,
    g. connecting the first inset to the second coupling, and
    h. performing a hand assisted step of the surgical procedure within at least one of the body cavity and the chamber, introducing a glove being part of the first inset.
48. The surgical method according to embodiment 47, wherein the medical device further comprising a sealing device, a further step of performing the surgical procedure comprises:
    placing a sealing device in connection with at least one of; the flexible wall and the second coupling, to seal between the medical device and the skin or tissue of the patient,
    sealing the combined volume of the chamber and the body cavity to the outer environment, when the second coupling is open.
49. The surgical method according to embodiment 47, wherein the step of performing a step of the surgical procedure within the chamber comprises:
    a. removing a specimen (81) from the cavity in the body of the patient,
    b. transferring the specimen through the second coupling, and
    c. placing the specimen within the chamber of the medical device.
50. The surgical method according to any one of embodiment 47-49, wherein the method further comprises:
    a. disconnecting the first port or and second coupling such that the interconnectable port is separated,
    b. performing a surgical step in the chamber, using the first port or first inset.

Numbered Embodiment AI 1-139

1. A medical device for performing joint surgery on a patient, the medical device comprising:
    a wall (01) adapted to least partly be placed on the patient's body for forming a chamber (C) alone or together with the patient's body, such that a sealed surgical environment is created in the chamber, wherein the chamber is adapted to encompass at least part of one step of the joint surgery procedure to be performed, while maintaining the sealed surgical environment,
    a first inset (42;42';42"), and
    an interconnectable port (47) comprising;
        a first port (17;22),
        a second coupling adapted be interconnected with at least one of the first port to form the interconnectable port, and the first inset, wherein the second coupling is disconnectable from the first port or first inset, and
    wherein:
        the first port is connected to a first portion of the wall (01),
        the first inset is connected to a third portion of the wall (01),
        the second coupling is connected to a second portion of the wall,
        the wall is adapted to form a chamber (C) together with the first port, first inset and the second coupling,
        the second coupling having a closable opening,
        the chamber is adapted to allow communication through the coupling into the hip joint inside the patients body, after an incision has been made in the skin of the patient, when a surgical procedure is performed,
        at least one of; the first port and first inset in a first position is adapted to connect to the second coupling in close relation to the patients skin, wherein the chamber having a first smaller volume, and
        at least one of the first port and first inset in a second position is adapted to be disconnected from the second coupling, being separated from the coupling in a more remote position in relation to the patients skin, wherein the chamber having a second larger volume.
2. The medical device according to embodiment 1, wherein the first port (17) forms a closable wall port when disconnected from the second coupling.
3. The medical device according to any one of embodiments 1 and 2, wherein the second coupling forms a closable body port by itself when the first port has been disconnected from the second coupling.
4. The medical device according to any one of the preceding embodiments, wherein the first port comprises a multiport, comprising two or more individual ports.
5. The medical device according to anyone of embodiments 1-4, wherein the first inset (42;42';42") comprises at least one of: a surgical glove (02) and a device or instrument mount (20), for assisting with in the surgical procedure.
6. The medical device according to anyone of embodiments 1-5, wherein the first volume is smaller than 100 000 mm3.
7. The medical device according to any one of embodiments 1-6, wherein the second volume is larger than 500 000 mm3.
8. The medical device according to any one of the preceding embodiment, wherein the flexible wall comprises a pleated portion (03) such that the flexible wall can be expanded.
9. The medical device according to any one of the preceding embodiments, comprising a first coupling (80*a*), and wherein the first port is connected to the second coupling, and the second coupling is adapted to be connected to the first coupling.
10. The medical device according to embodiment 9, wherein: at least one of the first and second coupling comprises a protruding member (33), and at least one of the first and second coupling comprises a recess (34), and wherein, the protruding member is adapted to engage the recess for locking the first coupling to the second coupling.
11. The medical device according to embodiment 10, wherein the recess is a groove in at least one of the first and second coupling.
12. The medical device according to any one of the preceding embodiments, wherein the chamber formed by the flexible wall is adapted to hold a pressure exceeding atmospheric pressure.
13. The medical device according to any one of the preceding embodiments, wherein the interconnectable port is adapted to:
   a. in a first state, when the first port and second coupling are interconnected, enable a surgeon to operate through the interconnected interconnectable port, and
   b. in a second state, when the second coupling is disconnected from the first port enable the surgeon to perform steps of the procedure within the chamber formed by the flexible wall between the first port and second coupling of the interconnectable port.
14. The medical device according to embodiment 12, wherein the interconnectable port is adapted to, in the second state, enable the surgeon to remove a specimen (81) from the body of the patient through the second coupling and into the chamber, and to perform one of: placing the specimen within the chamber, and removing the specimen from the chamber through the first port.
15. The medical device according to embodiment 13, wherein the chamber further comprises a pouch for holding the specimen within the chamber.
16. The medical device according to embodiment 14, wherein the pouch can be closed for creating a pouch-chamber within the chamber for isolating the removed specimen within the chamber.
17. The medical device according to any one of embodiments 1-16, comprising a second port adapted to also be placed in the second coupling, wherein at least one of the first port, the second port and a first coupling are adapted to be reconnected after having been disconnected, such that the surgeon can continue operating through the interconnected port after the specimen has been removed.
18. The medical device according to anyone of embodiments 9-17, wherein the inset inset (42;42';42") is detachably fixated to at least one of the first and second coupling, such that the inset could be detached and replaced by a different inset.
19. The medical device according to anyone of embodiments 1-18, further comprising a sealing device, comprising
   a flexible connecting member,
   a first sealing member (35), adapted to be positioned at the inside of the patient's skin around an incision to be performed in the skin and being sealingly connected to the flexible connecting member, and
   a second sealing member (37) sealingly connected to at least one of the first flexible wall, the flexible connecting member, and the second coupling or being an integrated part of the second coupling, adapted to be positioned at the outside of the patient's skin around the incision, wherein
   the flexible connecting member (36) is sealingly interconnecting the first and second sealing members, whereby the first and second sealing members is adapted to be larger than the incision to seal between at least one of: the second sealing member and the skin or tissue of the patient, and the first sealing member and tissue of the patient, and wherein
   the flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.
20. The medical device according to any one of the preceding embodiments, comprising a second port adapted to be placed in the second coupling, wherein at least one of the first and second port comprises an elastic or flexible membrane (43) adapted to, in a non-compressed state, provide sealing, and in a compressed state enable a hand or an object to be inserted through the membrane.
21. The medical device according to embodiment 20, wherein the first port comprises a first elastic or flexible membrane (43*a*) and the second port comprises a second elastic or flexible membrane (43*b*), and wherein the first and second membranes are adapted to be placed tightly together such that they act as a single elastic or flexible membrane adapted to, in a non-compressed state, provide sealing, and in a compressed state enable a hand or an object to be inserted through the membrane.
22. The medical device according to embodiment 21, wherein the first and second membranes comprises a plurality of self sealing holes (44) enabling insertion of instruments through the membranes.
23. The medical device according to any one of embodiments 17-22, wherein at least one of said first port and second port comprises a penetrable self sealing gel, such that an object or hand can be inserted through the interconnectable port while maintaining a seal.
24. The medical device according to embodiment 23, wherein the first port comprises a first penetrable self sealing gel and the second port comprises a second penetrable self sealing gel, and wherein the first and second penetrable self sealing gels are adapted to be placed tightly together such that they act as a single penetrable self sealing gel adapted to, in a non-compressed state, provide sealing, and in a compressed state enable a hand or an object to be inserted through the self sealing gel while maintaining the seal.
25. The medical device according to any one of the preceding embodiments, wherein the wall comprises a fluid inlet (30) for inflating the chamber with a fluid.
26. The medical device according to embodiment 25, further comprising a fluid outlet (31) provided in the wall for discharging the fluid from the chamber.
27. The medical device according to embodiment 26, further comprising a pump (27) adapted to circulate the fluid from the outlet member to the inlet member.
28. The medical device according to any one of the preceding embodiments, wherein at least one of the first port and second coupling comprises a non-penetrable valve (86) such that the chamber is sealed from at least one of the ambient environment and a cavity in the patient.
29. The medical device according to any one of the preceding embodiments, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.
30. The medical device according to any one of the preceding embodiments, wherein the port further comprises a sealing device having a first sealing member (35) adapted to be positioned at the inside of the patient's skin around an incision to be performed in the skin and a second sealing member (37) adapted to be positioned at the outside of the patient's skin around the incision, and a spring-loaded or elastic connecting member (36) sealingly interconnecting the first and second sealing members, whereby the spring-loaded or elastic connecting member seals between at least one of (a) the port and the skin of the patient, and (b) the first sealing member and tissue of the patient.
31. The medical device according to any one of the preceding embodiments, wherein the medical device further comprises at least one of:
    a. a filtering unit (26b) for filtering the fluid,
    b. a sterilization unit (26a) for directly or indirectly sterilizing the fluid,
    c. a fluid tempering unit (26c) adapted change the temperature of the fluid,
    d. a filtering unit for filtering the fluid and a sterilization unit for directly or indirectly sterilizing the fluid,
    e. a filtering unit for filtering the fluid and a fluid tempering unit adapted change the temperature of the fluid,
    f. a sterilization unit for directly or indirectly sterilizing the fluid and a fluid tempering unit adapted change the temperature of the fluid, and
    g. a filtering unit for filtering the fluid, a sterilization unit for directly or indirectly sterilizing the fluid and a fluid tempering unit adapted change the temperature of the fluid.
32. The medical device according to anyone of embodiments 1-31, wherein the second coupling is adapted to allow passage of a hand into the body cavity.
33. The medical device according to any one of embodiments 1-32, wherein the second coupling forms an opening, when the first port has been disconnected from the second coupling.
34. The medical device according to any one of embodiments 1-33, further comprising a retracting system, comprising
    a flexible connecting member,
    a inside retracting member (35), adapted to be positioned at the inside of the patient's skin around an incision to be performed in the skin and being connected to the flexible connecting member, and
    a outside retracting member (37) connected to at least one of; the first flexible wall, the flexible connecting member, and the second coupling or being an integrated part of the second coupling, adapted to be positioned at the outside of the patient's skin around the incision, wherein
    the flexible connecting member (36) is interconnecting the inside and outside retracting members, whereby the inside and outside retracting members is adapted to be larger than the incision allowing the flexible connecting member to retract the skin and tissue in the incision opening substantially parallel to the skin, and wherein
    the flexible connecting member is adapted to be placed in connection with at least one of; the first flexible wall and the second coupling or being an integrated part of the first flexible wall, adapted to be placed through the incision into the body cavity, adapted to together with inside and outside retracting members retracting substantially parallel to the skin, the skin and tissue in close relation to the incision, to enlarge the incision passage from the chamber into the body cavity, during the surgical procedure.
35. The medical device according to any one of embodiments 1-34, wherein the inside retracting member (35), is sealingly connected to the flexible connecting member, wherein the outside retracting member (37) is sealingly connected to at least one of the first flexible wall, the flexible connecting member, and the second coupling or being an integrated part of the second coupling, wherein the flexible connecting member (36) is sealingly direct or indirect interconnecting the inside and outside retracting members, adapted to be placed sealingly in connection with at least one of the first flexible wall and the second coupling or being an integrated part of the first flexible wall.
36. The medical device according to anyone of embodiments 1-35, wherein the coupling is adapted to allow passage of a hand into the body cavity.
37. The medical device according to any one of embodiments 1-36, wherein the coupling forms an opening, when the first port has been disconnected from the coupling.
38. The medical device according to any one of embodiments 1-37, the medical device further comprising a second sealing device, comprising
    a flexible connecting member,
    a first sealing member (35), adapted to be positioned at the inside of the patient's skin around an incision to be performed in the skin and being sealingly connected to the flexible connecting member, and
    a second sealing member (37) sealingly connected to at least one of; the first flexible wall, the flexible connecting member, and the second coupling or being an integrated part of the second coupling, adapted to be positioned at the outside of the patient's skin around the incision, wherein
the flexible connecting member (36) is sealingly interconnecting the first and second sealing members, whereby the first and second sealing members is adapted to be larger than the incision to seal between at least one of: the second sealing member and the skin or tissue of the patient, and the first sealing member and tissue of the patient, and wherein
the flexible connecting member is adapted to be placed sealingly in connection with at least one of; the first flexible wall and the coupling or being an integrated part of the first flexible wall, adapted to be placed through the incision into the body cavity, to together with first and second sealing members being involved in sealing the combined volume of the chamber and the body cavity to the outer environment, when the second coupling is open, during the surgical procedure.

39. The medical device according to any one of embodiments 1-38, wherein the second coupling comprising a body port being a detachable part of the second coupling.
40. The medical device according to any one of embodiments 1-39, wherein the first port being a multiport comprising two or more individual ports, wherein the coupling being adapted to connect to the multiport to together form an integrated multiport placed in close relation to the skin.
41. The medical device according to anyone of embodiments 39-40, wherein the body port being a multiport comprising two or more individual ports, wherein the body port being adapted to connect to the first port being a multiport, to together form an integrated multiport placed in close relation to the skin.
42. The medical device according to anyone of embodiments 1-41, wherein the second coupling comprises a detachable second inset.
43. The medical device according to anyone of embodiments 1-42, wherein the first port comprises a detachable third inset.
44. The medical device according to embodiment 42, wherein the second inset is adapted to close between the body cavity and the chamber.
45. The medical device according to anyone of embodiments 1-44, comprising a third port comprising a detachable third inset.
46. The medical device according to any one of embodiments 1-37, comprising a second sealing device, adapted to be placed in connection with at least one of; the flexible wall and the second coupling, to seal between the medical device and the skin or tissue of the patient, to seal the combined volume of the chamber and the body cavity to the outer environment, when the second coupling is open.
47. The medical device according to any one of embodiments 1-37, comprising a special sealing device (05) connected to the wall and adapted to seal between the wall and the skin or tissue of the patient, wherein the sealing device forms a special loop at least partly encircling at least a portion of one or more of the following; the leg, the pelvic region, the abdominal region, the inguinal region, the gluteal region, the thoraxial region and the region of the lower back, such that the sealing device seals between the incision site of the hip joint surgery and at least one of:
    i. the anal orifice,
    ii. the urethra orifice,
    iii. the perineum region.
48. The medical device according to embodiment 47, wherein the special sealing device is connected to the wall and adapted to seal between the wall and the skin or tissue of the patient to seal at least a part of the hip joint surgery operational field from at least one of: the anal orifice, the urethra orifice and at least part of the perineum region, while still maintaining the chamber sealed, the first sealing device comprising at least one of:
    a first part of the sealing device, and
    a first holding member adapted to hold the medical device in place by encircling at least one leg of the patient or the prolongation thereof to be involved in the sealing of the chamber,
wherein the first sealing device further comprising at least one of;
    a second part of the sealing device, and
    a second holding member (96) adapted to hold the medical device in place by encircling the whole body left to right on the level above the legs selected from at least one of; the level of the pelvic, abdominal or thorax region of the patient to further be involved in the sealing of the chamber,
wherein the first sealing device further comprises at least one of;
    a third part of the sealing device adapted to seal from the medial cranial part of the leg where it is meeting the inguinal region or its prolongation, further in a cranial direction lateral of the patient's ventro-dorsal mid-sagittal plane, on the side where the hip surgery is performed, and wherein the third part of the sealing device at least partly extends in cranial direction until meeting the second part of the sealing device, and wherein the wall is interconnecting to the first, second and third part of the sealing device to seal the chamber, and
    a third holding member adapted to seal the chamber and exclude from the chamber at least one of; the anal orifice, the urethra orifice and at least part of the perineum region.
49. The medical device according to anyone of embodiments 47-48, wherein the sealing device is positioned such that both of the urethra and the anus are excluded from the enclosed chamber forming the sealed surgical environment.
50. The medical device according to any one of the preceding embodiments, wherein the medical device further comprises a holding member (96) adapted to encircle a portion of the patient's body, by itself or together with the medical device, for holding the medical device in the desired position.
51. The medical device according to any one of the preceding embodiments, wherein at least a portion of the wall is adapted to directly or indirectly form an elongated tubular enclosure (04) having at least one open end (99), the enclosure being adapted to fit at least a portion of a leg of the patient, and wherein the medical device is arranged such that a portion of the leg extends into the enclosure through the first open end thereof, when the surgical procedure is performed on the leg of the patient.
52. The medical device according to embodiment 50, wherein:
    a. the wall is adapted to form the chamber without involving the patient's body, b. the wall portion forming the chamber also forms the tubular enclosure, and
c. the tubular enclosure forms a second chamber together with the patient's body, and wherein the second chamber is adapted to be sealed at the first or more open ends by the patient's body.

53. The medical device according to any one of preceding embodiments, comprising at least one of:
a. one further exchangeable port, and
b. one further exchangeable inset.

54. The medical device according to any one of preceding embodiments, wherein the inset comprises at least one glove integrated in the wall such that a surgeon is able to use the glove from outside the chamber to make manual manipulations inside the chamber while maintaining the sterile environment in the chamber.

55. The medical device according to any one of the preceding embodiments, further comprising a device or instrument mount adapted to retain instruments within the chamber.

56. The medical device according to any one of embodiments 47-55, wherein the sealing device comprises a vacuum sealing member (05') attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

57. The medical device according to any one of embodiments 47-56, wherein the sealing device comprises a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

58. The medical device according to any one of the preceding embodiments, further comprising at least one of:
a. an airlock sluice (18), and
b. a liquid lock sluice (18),
comprising a first valve (38a) and second valve (38b) and a sluice chamber placed in between the first and second valve, for allowing passage of objects from the chamber through the first valve and further through the second valve out to the environment outside of the chamber, and vice versa.

59. The medical device according to any one of preceding embodiments, further comprising at least one of an airlock sluice and a liquid lock sluice, comprising a first valve and second valve, wherein the first valve is mounted in at least one of the skin or tissue of the patient and the portion of the wall adapted to directly or indirectly form an elongated tubular enclosure, and wherein the second valve is mounted in the wall.

60. The medical device according to any one of the preceding embodiments, wherein the wall is adapted to contain a liquid filling the chamber for creating a liquid operating environment, and
wherein the medical device is adapted to receive the liquid through at least one liquid inlet (30) placed in at least one of the wall of the medical device and the skin (S) of the patient for supplying the liquid to at least one of: the chamber and the joint in the patient's body.

61. The medical device according to embodiment 60, wherein the medical device further comprising at least one inlet and at least one outlet selected from the following:
a. a first liquid inlet placed in the wall and adapted for supplying liquid to the chamber,
b. a first liquid outlet placed in the wall and adapted for evacuating liquid from the chamber,
c. a second liquid inlet adapted to be placed in an incision in the skin of the patient, in the area of the joint, for supplying liquid to the joint, and
d. a second liquid outlet adapted to be placed in an incision in the skin of the patient, in the area of the joint, for evacuating liquid from the joint.

62. The medical device according to anyone of embodiments 60-61, wherein the liquid is at least one of an isotonic solution and an antibiotic liquid.

63. The medical device according to any one of embodiments 60-62, wherein the system comprises a pump (09) for pumping the liquid from the liquid outlet to the liquid inlet.

64. The medical device according to anyone of embodiments 1-59, wherein the medical device further comprising at least one inlet and at least one outlet selected from the following:
a. a first fluid inlet placed in the wall and adapted for supplying gas to the chamber,
b. a first fluid outlet placed in the wall and adapted for evacuating gas from the chamber,
c. a second fluid inlet adapted to be placed in an incision in the skin of the patient, in the area of the joint, for supplying gas to the joint, and
d. a second fluid outlet adapted to be placed in an incision in the skin of the patient, in the area of the joint, for evacuating gas from the joint.

65. The medical device according to anyone of embodiment 60-64, further comprising a second fluid system (28') is adapted to at least one of:
a. supply fluid to the second fluid inlet and evacuate fluid from the second fluid outlet, and
b. circulate a fluid from the second fluid outlet to the second fluid inlet.

66. The medical device according to embodiment 65, wherein at least one of the first and second fluid systems is adapted to circulating a liquid fluid.

67. The medical device according to any one of the previous embodiments, wherein the medical device further comprises an energy transferring coupling (52; 56;58) adapted to transfer energy from outside the chamber into the sealed environment, such that a tool (16) can be energized.

68. The medical device according to any one of preceding embodiments, comprising one or more further inset, wherein the insets comprising one glove integrated in the wall in both the first inset and at least one further inset, such that a surgeon is able to use the gloves from outside the chamber to make manual manipulations inside at least one of the chamber and joint cavity, while maintaining the sterile environment in the chamber.

69. The medical device according to any one of preceding embodiments, comprising a fluid sluice adapted to allow introduction of at least one of at least one surgical instrument and at least one artificial joint surface for performing at least a joint surface replacement, when using said gloves when performing the surgical procedure.

70. The medical device according to any one of preceding embodiments, wherein at least the first port comprising at least one trocar for allowing introduction of at least one arthroscopic surgical instrument into at least one of; the chamber and joint cavity, wherein the at least first port is adapted to allow a arthroscopic surgical procedure to be combined with manual manipulations inside at least one of the chamber and joint cavity, while maintaining the sterile environment in the chamber.
71. The medical device according to any one of preceding embodiments, comprising at least one of; one or more further ports and the first port comprising a multiport, comprising two or more trocars adapted to allow the introduction of at least one of; a surgical instrument, two or more surgical instruments, and a camera, to allow a arthroscopic surgical procedure to be combined with manual manipulations inside at least one of the chamber and joint cavity, while maintaining the sterile environment in the chamber.
72. A medical device according to any one of the preceding embodiments, wherein the wall is adapted to form the chamber without or together with the patients body, wherein at least a portion of the wall is adapted to directly or indirectly form an elongated tubular enclosure having a first or more open end, the enclosure being adapted to fit at least a portion of the body of the patient, and wherein the medical device is arranged such that the portion of the body is going into the enclosure through the first open end thereof, when the surgical procedure is to be performed on the portion of the patient's body.
73. A medical device according to any of embodiments 72, wherein the elongated tubular enclosure comprising the first and at least a second open end, wherein the medical device is arranged such that the portion of the body goes into the enclosure through the first open end thereof, and will exit the enclosure through at least the second open end thereof, when the surgical procedure is to be performed on the portion of the patient's body.
74. A medical device according to any of embodiments 73, wherein the elongated tubular enclosure further comprising a third open end, the enclosure being adapted to fit at least a portion of both the legs or both the arms of the patient in the same enclosure, and wherein the medical device is arranged such that the portion of the body that goes into the enclosure through the first open end thereof will exit the enclosure through both the second and the third open end thereof, preferable the two legs or arms exiting through the second and third opening, when the surgical procedure is performed on at least a part of the portion of the patient's body.
75. The medical device according to anyone of embodiments 72-74, when the chamber is adapted to be formed together by the wall and the patient's body, the tubular enclosure is adapted to encompass the chamber, and wherein the chamber is adapted to be sealed at the first or more open ends by the patient's body portion.
76. The medical device according to any one of embodiment 72-74, when the chamber is formed by the wall without involving the patients body, part of the wall forming the chamber is adapted to also form the tubular enclosure, the wall having two sides whereof one facing the inside of the chamber and the other side of the wall is facing the tubular enclosure, when performing the surgical procedure, wherein the tubular enclosure form a second chamber, the second chamber at least partly encompassed by the tubular enclosure and adapted to be sealed at the first or more open ends by the patient's body portion, and wherein the wall part facing the tubular enclosure is adapted to form the second chamber together with the patients body.
77. The medical device according to at least one of embodiment 72-75, wherein the chamber is adapted to be in communication with an operating field during the surgical procedure, when the skin of the patient has been cut in a position inside of the chamber, wherein the wall encompassing the chamber has a wall port being at least one of; the first port and a comprised additional port, and wall inset being at least one of; the first inset and a comprised additional inset, mounted in a wall portion of the chamber for allowing; objects including instruments to be moved into the chamber or operating field and/or manual manipulation to be performed in the chamber or operating field, wherein the wall encompassing the chamber comprises a wall port mounted in a wall portion of the medical device, the wall port being at least one of the first port and a comprised additional port, and wall inset being at least one of the first inset and a comprised additional inset, wherein
the wall port or wall inset includes a first and second part, the second part comprising the wall port or wall inset and the first part comprising at least one of the second coupling and a body port or body inset comprised in the second coupling.
78. The medical device according to embodiment 77, comprising a port or inset including two parts, a first and second part, wherein the second part comprising the wall port or wall inset and the first part comprising at least one of the second coupling and a body port or body inset comprised in the second coupling, adapted to be mounted in the cut skin of the patient to allow objects including instruments to be moved further from the chamber into the operating field and/or manual manipulation to be performed from the chamber further into the operating field.
79. The medical device according to embodiment 78, wherein the two parts of the port or inset are adapted to be mounted together, touching each other forming an integrated port or inset and thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each other to one or more positions not touching each other and thereby; to use the second part of the port or inset to allow objects including instruments to be moved into the chamber and/or manual manipulation to be performed in the chamber and further to use the first part of the port or inset to allow objects including instruments to be moved from the chamber passing the cut skin into the operating field and/or manual manipulation to be performed from the chamber through the cut skin further into the (body) operating field.
80. The medical device according to at least one of embodiment 72-74 and 76, wherein the chamber is adapted to be in communication with an operating field during the surgical procedure, when the part of the wall forming both the chamber and the tubular enclosure, at a portion thereof, is adapted to be opened, having an opening, and together with the cut skin of the patient positioned inside of the chamber allowing such communication with the operating field, wherein a portion of the wall part encompassing only the chamber has a wall port or wall inset mounted therein, wherein the wall encompassing the chamber has mounted in a wall portion of the chamber a wall port being at least one of; the first port and a comprised additional port, and wall inset being at least one of; the first inset and a comprised additional inset, for allowing, from outside the chamber; objects including instruments to be moved into the chamber or operating field and/or manual manipulation to be performed in the chamber or operating field.

81. The medical device according to embodiment 80, wherein the wall port or wall inset are including two parts, a first and second part, wherein the second part comprising the wall port or wall inset and the first part comprising at least one of the second coupling, a body port or body inset comprised in the second coupling, and a first wall port or first wall inset mounted in the opening in the portion of the part of the wall forming both the chamber and the tubular enclosure adapted to be opened to create the communication between the chamber and the operating field to allow; objects including instruments to be moved further from the chamber into the operating field and/or manual manipulation to be performed from the chamber further into the operating field, wherein the passage between the chamber and the operating field includes the first wall port or inset, the second chamber located in between the tubular enclosure and the skin of the patient and the skin of the patient, wherein the second chamber having a size equal to or larger than zero.

82. The medical device according to embodiment 81, wherein the two parts of the port or inset are adapted to be mounted together touching each other forming an integrated port and inset thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each into one or more positions when they are not touching each other and thereby; to use the wall port or inset of the second part to allow; objects including instruments to be moved into the chamber and/or manual manipulation to be performed in the chamber and further to use the first wall port or first wall inset of the first part to allow; objects including instruments to be moved from the chamber passing the cut skin into the operating field and/or manual manipulation to be performed from the chamber through the cut skin further into the operating field.

83. The medical device according to at least one of embodiment 78-82, wherein the two parts of the port or inset is adapted to be locked together in at least one fixed position.

84. The medical device according to any one of embodiments 72-83, wherein the medical device is adapted to allow the surgical procedure with its operating field to be performed on the patient on at least one of; a extremity, the prolongation of the extremity, abdomen, chest, and any joint including the hip and knee joints and the joints of the upper extremity.

85. The medical device according to any one of embodiments 72-83, wherein the chamber encompassing the surgical procedure is adapted to reduce infection risk of the surgical procedure most important for joint surgery.

86. The medical device according to embodiment 83, wherein both of the two parts of the port is adapted to comprise a fluid sealed valve when the two parts being separated.

87. The medical device according to embodiment 83, wherein only the second part of the two parts of the port is adapted to comprise a fluid sealed valve, when the two parts being separated.

88. The medical device according to at least one of embodiment 77-87, comprising at least one of a third exchangeable wall port and wall inset different from the wall port and wall inset, adapted to replace at least one of the wall port or wall inset.

89. The medical device according to at least one of embodiment 78, comprising at least one of a third exchangeable body port and body inset different from the body port and body inset, and adapted to replace at least one of the body port or body inset.

90. The medical device according to at least one of embodiment 79 and 82, comprising a second exchangeable integrated port different from the integrated port, and adapted to replace the integrated port during the surgical procedure.

91. The medical device according to any one of embodiments 72-90, wherein the wall is at least partially collapsible.

92. The medical device according to any one of embodiments 72-91, wherein the chamber is adapted to be inflated by a fluid.

93. The medical device according to any one of embodiments 72-92, further comprising a non-collapsible transparent window provided in the wall to enable viewing into the sterile environment.

94. The medical device according to any one of embodiments 77-87, wherein the inset comprising at least one glove integrated in the wall such that a surgeon is able to use the glove from outside the chamber to make manual manipulations inside the chamber while maintaining the sterile environment in the chamber.

95. The medical device according to any one of embodiments 72-94, further comprising an instrument holder adapted to retain instruments within the chamber.

96. The medical device according to any one of embodiments 72-95, further comprising at least one sealing device for the enclosure adapted to seal between the skin of the body portion of the patient and at least one of the wall and enclosure.

97. The medical device according to embodiment 96, wherein the sealing device of the enclosure comprises a vacuum sealing member attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

98. The medical device according to embodiment 96, wherein the sealing device of the enclosure comprises a pressure sealing member attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.
99. The medical device according to any one of embodiments 72-98, further comprising an adhesive adapted to provide at least one of: (a) fixation of at least one of the wall and enclosure to the skin of the patient, and (b) sealing between the skin of the patient and at least one of the wall and enclosure.
100. The medical device according to any one of embodiments 76 and 80-99, further comprising an air evacuation system adapted to evacuate air from the second chamber, when the portion of the patient's extremity is placed in the enclosure.
101. The medical device according to embodiment 100, further comprising an air evacuation system adapted to evacuate air from the vacuum sealing member.
102. The medical device according to any one of the preceding embodiments, further comprising a multi-port being the first port or an additional port, which comprises at least two ports integrated in the multi port, and adapted to enable passage of an object to the inside of the patient's body via the cut incision in the skin, when performing the surgical procedure.
103. The medical device according to any one of embodiments 76-99, wherein the wall port comprises a multi-port, which comprises at least two ports integrated in the multi port, and adapted to enable passage of an object into the chamber and further into the inside of the patient's body via the cut incision in the skin, when performing the surgical procedure.
104. The medical device according to any one of embodiments 78-79 and 83-99, the coupling comprise a body port, wherein the body port comprises a multi-port, which comprises at least two ports integrated in the multi port, and adapted to enable passage of an object from the chamber and further into the inside of the patient's body via the cut incision in the skin, when performing the surgical procedure.
105. The medical device according to any one of embodiments 82-87 and 91-99, wherein the first wall port comprises a multi-port, which comprises at least two ports integrated in the multi port, and adapted to enable passage of an object from the chamber and further into the inside of the patient's body via the cut incision in the skin, when performing the surgical procedure.
106. The medical device according to any one of the preceding embodiments, further comprising at least one further wall port provided in the wall enabling passage of an object between the chamber and the environment outside of the chamber, wherein the wall port comprises at least one of an elastic membrane and a flexible membrane, and wherein the membrane is adapted to, in a non-pushed state, seal between the chamber and the environment outside of the chamber, and in an pushed state enable a hand or an object to be inserted through the membrane.
107. The medical device according to any one of the preceding embodiments, further comprising a further sealing device having a first sealing member adapted to be positioned at the inside of the patient's skin around an incision cut in the patient's skin made from the chamber, a second sealing member adapted to be positioned at the outside of the patient's skin around the incision in the chamber, and at least one of a flexible, spring-loaded and elastic connecting member sealingly interconnecting the first and second sealing members, whereby the at least one of the flexible, spring-loaded and elastic connecting member seals between at least one of the second sealing member and the skin of the patient, and the first sealing member and tissue of the patient.
108. The medical device according to any one of the preceding embodiments, further comprising a fluid tempering unit adapted to temper a fluid to be used within the chamber to a temperature different from the temperature outside of the chamber.
109. The medical device according to any one of the preceding embodiments, further comprising a sterilization unit for directly or indirectly sterilizing a fluid contained in the chamber.
110. The medical device according to any one of the preceding embodiments, further comprising at least one inlet member provided in the wall for supplying a fluid into the chamber, at least one outlet member provided in the wall for discharging the fluid from the chamber, and a pump adapted to circulate the fluid from the outlet member to the inlet member.
111. The medical device according to embodiment 110, further comprising a sterilization unit adapted to sterilize the circulating fluid to reduce infection risk.
112. The medical device according to embodiment 110, further comprising a cleaning device adapted to clean the circulating fluid, especially from blood and operating matters to improve visibility.
113. The medical device according to embodiment 84 or 85, wherein the object comprises at least one of: a tool, a camera, a medical device or a part of a human body.
114. The medical device according to any one of the preceding embodiments, further comprising at least one of an airlock sluice and a liquid lock sluice, comprising a first valve and second valve and a sluice chamber placed in between the first and second valve, for allowing passage of objects from the chamber through the first valve and further through the second valve out to the environment outside of the chamber, and vice versa.
115. The medical device according to anyone of embodiments 72-113, further comprising at least one of an airlock sluice and a liquid lock sluice, comprising a first valve and second valve, wherein the first valve is mounted in at least one of the skin or tissue of the patient and the portion of the wall adapted to directly or indirectly form the elongated tubular enclosure, and wherein the second valve is mounted in the wall.
116. The medical device according to any of the preceding embodiments, wherein the chamber and operating field comprising a circulating liquid fluid during the surgical procedure.
117. The medical device according to any of the preceding embodiments, comprising an additional sealing subdevice comprising a wall and a sealing device adapted to be placed between the chamber and the skin of the patient and to be formed to close the anus or opening of urethra being in contact with the chamber to avoid connection between the anus or opening of the urethra and the chamber, when the surgical procedure is intended to be performed in relation thereto.
118. The medical device according to any one of the preceding embodiments, wherein the elongated tubular enclosure is formed by placing the wall forming the chamber around at least a portion of the extremity of the patient.
119. The medical device according to embodiment 118, wherein the elongated tubular enclosure comprises a slit for placing the chamber around at least a portion of the extremity of the patient radially in relation to the length axis of the extremity.
120. The medical device according to any one of embodiment 118 and 119, wherein the slit is adapted to be at least partially closed by closing elements mounted on the wall of the medical device.
121. The medical device according to embodiment 120, wherein the closing elements are elastic or adjustable for fixating the medical device to the extremity of the patient.
122. The medical device according to any one of embodiments 119-121, wherein the medical device comprises a first and a second portion located on a first and second side of the slit when the chamber is placed around at least a portion of the extremity, and wherein the first and second portions are adapted to be interconnected by means of at least one of: an adhesive and a mechanical connecting member.
123. The medical device according to any one of embodiments 77-122, wherein at least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.
124. The medical device according to any one of embodiments 72-123, wherein the wall forming the chamber comprises a first and second interconnecting member, and wherein the first interconnecting member is placed at the first position, and wherein the second interconnecting member is positioned in the second position, and wherein the second interconnecting member is adapted to connect to the first interconnecting member for locking the inset or wall port in the first position.
125. The medical device according to embodiment 124, wherein a port or inset placed in the wall is defined as the wall port or wall inset, the medical device further comprising a body port or body inset adapted to be mounted in another wall portion or the skin or tissue of the patient, wherein the first interconnecting member is adapted to be positioned in connection with a body port or body inset, and wherein the wall port and the body port is adapted to form a integrated port when the first and second interconnecting members are connected in the first position.
126. The medical device according to embodiment 125, wherein the wall port and the body port comprises at least one of an elastic membrane and a flexible membrane, and wherein the membrane is adapted to, in a non-pushed state, provide a seal, and in a pushed state, enable a hand or an object to be inserted through the membrane.
127. The medical device according to any one of embodiments 77-126, wherein at least one of said first and second part comprises a penetratable self sealing gel, such that an object or hand can be inserted through the port while maintaining a seal.
128. The medical device according to embodiment 127, wherein the first part comprises a first penetratable self sealing gel and the second part comprises a second penetratable self sealing gel, and wherein the first and second penetratable self sealing gels are adapted to be placed tightly together such that they act as a single penetratable self sealing gel adapted to, in a non-pushed state, provide sealing, and in a pushed state enable a hand or an object to be inserted through the self sealing gel while maintaining the seal.
129. The medical device according to embodiment 127, wherein the first and
    second part are adapted be interconnected to form a integrated port, wherein the
    second part is adapted to be disconnected from the first part by
a surgeon during a surgical procedure, wherein the first part is connected to a first portion of the wall, and the second part is connected to a second portion of the wall, and wherein the wall is a flexible wall.
130. The medical device according to embodiment 129, wherein the chamber has a first volume when the first and second parts are interconnected and a second volume when the second part is disconnected from the first part.
131. The medical device according to anyone of embodiment 129-130, wherein the integrated port is adapted to:
    a. in a first state, when the first and second parts are interconnected, enable a surgeon to operate through the surgical port, and
    b. in a second state, when the second part is disconnected from the first part enable the surgeon to perform steps of the procedure within the chamber formed by the flexible wall between the first and second parts of the port.
132. The medical device according to embodiment 131, wherein the integrated port is adapted to, in the second state, enable the surgeon to remove a specimen from the body of the patient through the first part and into the chamber, and to perform one of: placing the specimen within the chamber, and removing the specimen from the chamber through the second part.
133. The medical device according to embodiment 132, wherein the chamber further comprises a pouch for holding the specimen within the chamber.
134. The medical device according to embodiment 133, wherein the pouch can be closed for creating a pouch-chamber within the chamber for isolating the removed specimen within the chamber.
135. The medical device according to embodiment 132-134, wherein the first and second parts are adapted to be reconnected after being disconnected such that the surgeon can continue operating through the interconnected port after the specimen has been removed.
136. A surgical method to be performed in a joint of a patient using a medical device according to anyone of embodiment 1-71, comprising a wall, a first inset and an interconnectable port (47), comprising a first port (17), and a second coupling, the method comprising:
    a. creating an incision (I) in the skin (S) of the patient, connecting to a joint cavity,
    b. placing the coupling in the incision, such that a chamber (C) is formed by the wall (01) connected to the first port, first inset and second coupling,
    c. introducing a camera through at least one of; the first port being a single or multiport including two or more individual ports, an additional port being included in the device, and a trocar introduced into the joint from outside the chamber,
    d. performing an arthroscopic surgical procedure through one or more trocars included in the first port being a single or multiport including two or more individual ports or an additional port being included in the device, e. performing the arthroscopic surgical procedure with the first port being at least one of; connected to the second coupling and detached from the second coupling, f. using at least one glove being part of the first inset or one or more additional insets to introduce one or more hands for assisting the surgical procedure, and g. performing a hand assisted step of the surgical procedure within at least one of the joint cavity and the chamber, introducing the at least one glove, h. introducing at least one of; one or more surgical instruments and at least one medical implant through at least one of; the trocars and an fluid lock as being part of the medical device, for performing at least one of a hand assisted or arthroscopic surgical procedure such as at least one joint surface replacement or other joint surgical procedure.

137. The surgical method according to embodiment 136, wherein the medical device further comprising a sealing device, a further step of performing the surgical procedure comprises:

placing a sealing device in connection with at least one of; the wall and the second coupling, to seal between the medical device and the skin or tissue of the patient, sealing the combined volume of the chamber and the joint cavity to the outer environment, when the second coupling is open.

138. The surgical method according to any one of the embodiments 136-137, wherein the step of performing a step of the surgical procedure within the chamber comprises:

a. removing a specimen (81) from the cavity in the joint of the patient, b. transferring the specimen through the second coupling, and c. placing the specimen within the chamber of the medical device.

139. The surgical method according to any one of embodiment 136-138, wherein the method further comprises:

a. connecting the first port and second coupling such that the interconnectable port is integrated, b. performing a surgical step in the chamber, using the integrated first port.

Numbered Embodiment AJ 1-61

1. A medical device for performing a surgical procedure on a patient, comprising a wall (01) adapted to be at least partially applied on the patient's body and further adapted to form a chamber (C) without or together with the patient's body, in which a sealed environment can be maintained for encompassing part of the surgical procedure to be performed on the patient, wherein at least a portion of the wall is adapted to directly or indirectly form an elongated tubular enclosure (04) having a first or more open end (99), the enclosure being adapted to fit at least a portion of the body of the patient, and wherein the medical device is arranged such that the portion of the body is going into the enclosure through the first open end thereof, when the surgical procedure is to be performed on the portion of the patient's body.

2. A medical device according to any of embodiments 1, wherein the elongated tubular enclosure comprising the first and at least a second open end, wherein the medical device is arranged such that the portion of the body goes into the enclosure through the first open end thereof, and will exit the enclosure through at least the second open end thereof, when the surgical procedure is to be performed on the portion of the patient's body.

3. A medical device according to any of embodiments 2, wherein the elongated tubular enclosure further comprising a third open end, the enclosure being adapted to fit at least a portion of both the legs or both the arms of the patient in the same enclosure, and wherein the medical device is arranged such that the portion of the body that goes into the enclosure through the first open end thereof will exit the enclosure through both the second and the third open end thereof, preferable the two legs or arms exiting through the second and third opening, when the surgical procedure is performed on at least a part of the portion of the patient's body.

4. The medical device according to any one of embodiments 1-3, when the chamber is adapted to be formed together by the wall and the patient's body, the tubular enclosure is adapted to encompass the chamber, and wherein the chamber is adapted to be sealed at the first or more open ends by the patient's body portion.

5. The medical device according to any one of embodiments 1-3, when the chamber is formed by the wall without involving the patients body, part of the wall forming the chamber is adapted to also form the tubular enclosure, the wall having two sides whereof one facing the inside of the chamber and the other side of the wall is facing the tubular enclosure, when performing the surgical procedure, wherein the tubular enclosure form a second chamber, the second chamber at least partly encompassed by the tubular enclosure and adapted to be sealed at the first or more open ends by the patient's body portion, and wherein the wall part facing the tubular enclosure is adapted to form the second chamber together with the patient's body.

6. The medical device according to any one of embodiments 1-4, wherein the chamber is adapted to be in communication with an operating field during the surgical procedure, when the skin (S) of the patient has been cut in a position inside of the chamber, wherein the wall encompassing the chamber has a wall port or wall inset mounted in a wall portion of the chamber for allowing; objects including instruments (89) to be moved into the chamber or operating field and/or manual manipulation to be performed in the chamber or operating field.

7. The medical device according to embodiment 6, comprising a port or inset including two parts, a first and second part, wherein the second part comprising the wall port (17) or wall inset (42,42') and the first part comprising a body port (22) or body inset (42") adapted to be mounted in the cut skin of the patient to allow objects including instruments to be moved further from the chamber into the operating field and/or manual manipulation to be performed from the chamber further into the operating field.

8. The medical device according to embodiment 7, wherein the two parts of the port or inset are adapted to be mounted together, touching each other forming an integrated port or inset and thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each other to one or more positions not touching each other and thereby; to use the second part of the port or inset to allow objects including instruments to be moved into the chamber and/or manual manipulation to be performed in the chamber and further to use the first part of the port or inset to allow objects including instruments to be moved from the chamber passing the cut skin into the operating field and/or manual manipulation to be performed from the chamber through the cut skin further into the (body) operating field.

9. The medical device according to any one of embodiment 1-3 and 5, wherein the chamber is adapted to be in communication with an operating field during the surgical procedure, when the part of the wall forming both the chamber and the tubular enclosure, at a portion thereof, is adapted to be opened, having an opening, and together with the cut skin of the patient positioned inside of the chamber allowing such communication with the operating field, wherein a portion of the wall part encompassing only the chamber has a wall port or wall inset mounted therein for allowing, from outside the chamber; objects including instruments to be moved into the chamber or operating field and/or manual manipulation to be performed in the chamber or operating field.

10. The medical device according to embodiment 9, comprising a port or inset including a first and second part, wherein the second part comprising the wall port or wall inset and the first part comprising a first wall port or first wall inset mounted in the opening in the portion of the part of the wall forming both the chamber and the tubular enclosure adapted to be opened to create the communication between the chamber and the operating field to allow; objects including instruments to be moved further from the chamber into the operating field and/or manual manipulation to be performed from the chamber further into the operating field, wherein the passage between the chamber and the operating field includes the first wall port or inset, the second chamber located in between the tubular enclosure and the skin of the patient and the skin of the patient, wherein the second chamber having a size equal to or larger than zero.

11. The medical device according to embodiment 10, wherein the two parts of the port or inset are adapted to be mounted together touching each other forming an integrated port and inset thereby allowing from outside the chamber; objects including instruments to be moved into the operating field and/or manual manipulation to be performed in the operating field directly from outside the chamber using the integrated port or inset, and wherein furthermore the two parts of the port or inset are adapted to be separated from each into one or more positions when they are not touching each other and thereby; to use the wall port or inset of the second part to allow; objects including instruments to be moved into the chamber and/or manual manipulation to be performed in the chamber and further to use the first wall port or first wall inset of the first part to allow; objects including instruments to be moved from the chamber passing the cut skin into the operating field and/or manual manipulation to be performed from the chamber through the cut skin further into the operating field.

12. The medical device according to any one of embodiment 8, 9, 10 and 11, wherein the two parts of the port or inset is adapted to be locked together in at least one fixed position.

13. The medical device according to any one of embodiment 1-12, wherein the medical device is adapted to allow the surgical procedure with its operating field to be performed on the patient on at least one of; a extremity, the prolongation of the extremity, abdomen, chest, and any joint including the hip and knee joints and the joints of the upper extremity.

14. The medical device according to any one of embodiment 1-12, wherein the chamber encompassing the surgical procedure is adapted to reduce infection risk of the surgical procedure most important for joint surgery.

15. The medical device according to embodiment 12, wherein both of the two parts of the port are adapted to comprise a fluid sealing valve (86) when the two parts are separated.

16. The medical device according to embodiment 12, wherein only the second part of the two parts of the port is adapted to comprise a fluid sealing valve (86), when the two parts are separated.

17. The medical device according to any one of embodiment 6-16, comprising at least one of a third exchangeable wall port and wall inset different from the wall port and wall inset, adapted to replace at least one of the wall port or wall inset.

18. The medical device according to embodiment 7, comprising at least one of a third exchangeable body port and body inset different from the body port and body inset, and adapted to replace at least one of the body port or body inset.

19. The medical device according to any one of embodiments 8 and 11, comprising a second exchangeable integrated port different from the integrated port, and adapted to replace the integrated port during the surgical procedure.

20. The medical device according to any one of embodiments 1-19, wherein the wall is at least partially collapsible.

21. The medical device according to any one of embodiments 1-20, wherein the chamber is adapted to be inflated by a fluid.

22. The medical device according to any one of embodiments 1-21, further comprising a non-collapsible transparent window provided in the wall to enable viewing into the sterile environment.

23. The medical device according to any one of embodiments 6-16, wherein the inset comprising at least one glove (02) integrated in the wall such that a surgeon is able to use the glove from outside the chamber to make manual manipulations inside the chamber while maintaining the sterile environment in the chamber.

24. The medical device according to any one of embodiments 1-23, further comprising a device or instrument mount (20) adapted to retain instruments (89) or devices within the chamber.

25. The medical device according to any one of embodiments 1-24, further comprising at least one sealing device (05) adapted to seal between the skin of the body portion of the patient and at least one of the wall and enclosure.

26. The medical device according to embodiment 25, wherein the sealing device comprises a vacuum sealing member (05') attached to at least one of the wall and enclosure and adapted to provide a pressure less than atmospheric pressure between the vacuum sealing member and the patient's skin to create a vacuum sealing between the skin of the patient's extremity and at least one of the wall and enclosure.

27. The medical device according to embodiment 25, wherein the sealing device comprises a pressure sealing member (05") attached to at least one of the wall and enclosure and adapted to press against the patient's skin to create a pressurized sealing between the skin of the patient's extremity and at least one of the wall and enclosure, and wherein the pressure sealing member is adapted to be hydraulically, pneumatically or mechanically forced against the patient's skin.

28. The medical device according to any one of embodiments 1-27, further comprising an adhesive adapted to provide at least one of: (a) fixation of at least one of the wall and enclosure to the skin of the patient, and (b) sealing between the skin of the patient and at least one of the wall and enclosure.

29. The medical device according to any one of embodiments 5 and 9-28, further comprising an air evacuation system adapted to evacuate air from the second chamber, when the portion of the patient's extremity is placed in the enclosure.

30. The medical device according to embodiment 29, further comprising an air evacuation system adapted to evacuate air from the vacuum sealing member.

31. The medical device according to any one of the preceding embodiments, further comprising a multiport, which comprises at least two ports integrated in the multi port, and adapted to enable passage of an object to the inside of the patient's body via the cut incision in the skin, when performing the surgical procedure.

32. The medical device according to any one of embodiments 6-28, wherein the wall port comprises a multiport, which comprises at least two ports integrated in the multi port, and adapted to enable passage of an object into the chamber and further into the inside of the patient's body via the cut incision in the skin, when performing the surgical procedure.

33. The medical device according to any one of embodiments 7-8 and 12-28, wherein the body port comprises a multi-port, which comprises at least two ports integrated in the multi port, and adapted to enable passage of an object from the chamber and further into the inside of the patient's body via the cut incision in the skin, when performing the surgical procedure.

34. The medical device according to any one of embodiments 11-17 and 20-28, wherein the first wall port comprises a multi-port, which comprises at least two ports integrated in the multi port, and adapted to enable passage of an object from the chamber and further into the inside of the patient's body via the cut incision in the skin, when performing the surgical procedure.

35. The medical device according to any one of the preceding embodiments, further comprising at least one further wall port provided in the wall enabling passage of an object between the chamber and the environment outside of the chamber, wherein the wall port comprises at least one of an elastic membrane and a flexible membrane, and wherein the membrane is adapted to, in a non-pushed state, seal between the chamber and the environment outside of the chamber, and in an pushed state enable a hand or an object to be inserted through the membrane.

36. The medical device according to any one of the preceding embodiments, further comprising a further sealing device having a first sealing member (35) adapted to be positioned at the inside of the patient's skin around an incision cut in the patient's skin made from the chamber, a second sealing member (37) adapted to be positioned at the outside of the patient's skin around the incision in the chamber, and at least one of a flexible, spring-loaded and elastic connecting member (36) sealingly interconnecting the first and second sealing members, whereby the at least one of the flexible, spring-loaded and elastic connecting member seals between at least one of the second sealing member and the skin of the patient, and the first sealing member and tissue of the patient.

37. The medical device according to any one of the preceding embodiments, wherein the medical device further comprises at least one of:
   a. a filtering unit (26b) for filtering the fluid,
   b. a sterilization unit (26a) for directly or indirectly sterilizing the fluid,
   c. a fluid tempering unit (26c) adapted change the temperature of the fluid,
   d. a filtering unit for filtering the fluid and a sterilization unit for directly or indirectly sterilizing the fluid,
   e. a filtering unit for filtering the fluid and a fluid tempering unit adapted change the temperature of the fluid,
   f. a sterilization unit for directly or indirectly sterilizing the fluid and a fluid tempering unit adapted change the temperature of the fluid, and
   g. a filtering unit for filtering the fluid, a sterilization unit for directly or indirectly sterilizing the fluid and a fluid tempering unit adapted change the temperature of the fluid.

38. The medical device according to any one of the preceding embodiments, further comprising at least one inlet (30) provided in the wall for supplying a fluid into the chamber, at least one outlet (31) provided in the wall for discharging the fluid from the chamber, and a pump (09) adapted to circulate the fluid from the outlet member to the inlet member.

39. The medical device according to any one of embodiments 13 and 14, wherein the object comprises at least one of: a tool, a camera, a medical device or a part of a human body.

40. The medical device according to any one of the preceding embodiments, further comprising at least one of an airlock sluice (18) and a liquid lock sluice (18), comprising a first valve (38a) and second valve (38b) and a sluice chamber placed in between the first and second valve, for allowing passage of objects from the chamber through the first valve and further through the second valve out to the environment outside of the chamber, and vice versa.

41. The medical device according to anyone of embodiments 1-40, further comprising at least one of an airlock sluice and a liquid lock sluice, comprising a first valve and second valve, wherein the first valve is mounted in at least one of the skin or tissue of the patient and the portion of the wall adapted to directly or indirectly form the elongated tubular enclosure, and wherein the second valve is mounted in the wall.

42. The medical device according to any of the preceding embodiments, wherein the chamber and operating field comprising a circulating liquid fluid during the surgical procedure.
43. The medical device according to any of the preceding embodiments, comprising an additional sealing subdevice comprising a wall and a sealing device adapted to be placed between the chamber and the skin of the patient and to be formed to close the anus or opening of urethra being in contact with the chamber to avoid connection between the anus or opening of the urethra and the chamber, when the surgical procedure is intended to be performed in relation thereto.
44. The medical device according to any one of the preceding embodiments, wherein the elongated tubular enclosure is formed by placing the wall forming the chamber around at least a portion of the extremity of the patient.
45. The medical device according to embodiment 44, wherein the elongated tubular enclosure comprises a slit for placing the chamber around at least a portion of the extremity of the patient radially in relation to the length axis of the extremity.
46. The medical device according to any one of embodiment 44 and 45, wherein the slit is adapted to be at least partially closed by closing elements mounted on the wall of the medical device.
47. The medical device according to embodiment 46, wherein the closing elements are elastic or adjustable for fixating the medical device to the extremity of the patient.
48. The medical device according to any one of embodiments 45-47, wherein the medical device comprises a first and a second portion located on a first and second side of the slit when the chamber is placed around at least a portion of the extremity, and wherein the first and second portions are adapted to be interconnected by means of at least one of: an adhesive and a mechanical connecting member.
49. The medical device according to any one of embodiments 6-48, wherein at least one inset or port attached to the wall is adapted to be displaceable between a first position, in which the inset or port is situated relatively close to the patient's skin or tissue of the patient and directly or indirectly is connecting to the skin or tissue of the patient, and a second position, in which the inset or wall port is situated more remote from the patient's skin than in the first position, when the wall at least partly is applied on the patient's body.
50. The medical device according to embodiment 1-49, wherein the wall forming the chamber comprises a first and second interconnecting member, and wherein the first interconnecting member is placed at the first position, and wherein the second interconnecting member is positioned in the second position, and wherein the second interconnecting member is adapted to connect to the first interconnecting member for locking the inset or wall port in the first position.
51. The medical device according to embodiment 50, wherein a port or inset placed in the wall is defined as the wall port or wall inset, the medical device further comprising a body port or body inset adapted to be mounted in another wall portion or the skin or tissue of the patient, wherein the first interconnecting member is adapted to be positioned in connection with a body port or body inset, and wherein the wall port and the body port is adapted to form a integrated port when the first and second interconnecting members are connected in the first position.
52. The medical device according to embodiment 51, wherein the wall port and the body port comprises at least one of an elastic membrane and a flexible membrane, and wherein the membrane is adapted to, in a non-pushed state, provide a seal, and in a pushed state, enable a hand or an object to be inserted through the membrane.
53. The medical device according to any one of embodiments 6-52, wherein at least one of said first and second part comprises a penetratable self sealing gel, such that an object or hand can be inserted through the port while maintaining a seal.
54. The medical device according to embodiment 53, wherein the first part comprises a first penetratable self sealing gel and the second part comprises a second penetratable self sealing gel, and wherein the first and second penetratable self sealing gels are adapted to be placed tightly together such that they act as a single penetratable self sealing gel adapted to, in a non-pushed state, provide sealing, and in a pushed state enable a hand or an object to be inserted through the self sealing gel while maintaining the seal.
55. The medical device according to embodiment 53, wherein the first and second part are adapted be interconnected to form a surgical port, wherein the second part is adapted to be disconnected from the first part by a surgeon during a surgical procedure, wherein the first part is connected to a first portion of the wall, and the second part is connected to a second portion of the wall, and wherein the wall is a flexible wall.
56. The medical device according to embodiment 55, wherein the chamber has a first volume when the first and second parts are interconnected and a second volume when the second part is disconnected from the first part.
57. The medical device according to anyone of embodiment 55-56, wherein the medical device is adapted to:
in a first state, when the first and second parts are interconnected, enable a surgeon to operate through the surgical port, and
in a second state, when the second part is disconnected from the first part enable the surgeon to perform steps of the procedure within the chamber formed by the flexible wall between the first and second parts of the port.
58. The medical device according to embodiment 57, wherein the surgical port is adapted to, in the second state, enable the surgeon to remove a specimen from the body of the patient through the first part and into the chamber, and to perform one of: placing the specimen within the chamber, and removing the specimen from the chamber through the second part.
59. The medical device according to embodiment 58, wherein the chamber further comprises a pouch for holding the specimen within the chamber.
60. The medical device according to embodiment 59, wherein the pouch can be closed for creating a pouch-chamber within the chamber for isolating the removed specimen within the chamber.
61. The medical device according to embodiment 58-60, wherein the first and second parts are adapted to be reconnected after being disconnected such that the surgeon can continue operating through the interconnected port after the specimen has been removed.

Numbered Embodiment AK 1-27

1. A method of performing a surgical procedure on a patient using a medical device comprising a wall, a first inset and an interconnectable port (47), the interconnectable port comprising a first port (17), and a second coupling, the method steps comprising:
applying a wall at least partially on the patient's body forming a chamber without or together with the patient's body,
maintaining a sealed environment for encompassing part of the surgical procedure to be performed on the patient,
forming an elongated tubular enclosure directly or indirectly by at least a portion of the wall, the elongated tubular enclosure having a first or more open end, the enclosure being adapted to fit at least a portion of the body of the patient, and
introducing the portion of the body into the enclosure through the first open end thereof,
placing the coupling in an newly made incision, such that the chamber (C) is formed by the wall (01) connected to the first port, first inset and second coupling, introducing a camera through at least one of the first port being a single or multiport
including two or more individual ports, an additional port being included in the device, and a trocar introduced into the joint from outside the chamber,
performing at least one of;
an arthroscopic surgical procedure through one or more trocars included in the first port being a single or multiport including two or more individual ports or an additional port being included in the device, the first port being at least one of; connected to the second coupling and detached from the second coupling, and
a hand assisted step of the surgical procedure within at least one of the joint cavity and the chamber, introducing the at least one glove being part of the first inset or one or more additional insets to introduce one or more hands for assisting the surgical procedure, and
introducing at least one of one or more surgical instruments and at least one medical implant through at least one of; the trocars and a fluid lock as being part of the medical device,
performing at least one of: a hand assisted or arthroscopic surgical procedure such as at least one of; a joint surface replacement and other joint surgical procedure.
2. The method according to embodiment 1, wherein the elongated tubular enclosure further comprises a second open end, whereby the step of;
exiting the medical device such that the portion of the body is exiting through the second open end thereof.
3. The method according to any of embodiments 1-2, wherein the elongated tubular enclosure further comprising a third open end, allowing
fitting at least a portion of both the legs or both the arms of the patient in the same enclosure, the medical device is arranged such that the portion of the body is;
entering the enclosure through the first open end thereof, and
exiting the enclosure through both the second and the third open end thereof
4. The method according to any one of embodiments 1-3, wherein the chamber is adapted to be formed by the wall and the patient's body and the tubular enclosure is adapted to encompass the chamber, the method comprising:
sealing at the first or more open ends of the tubular enclosure also by the patient's body portion.
5. The method according to any one of embodiments 1-3, wherein the chamber is formed by the wall without involving the patient's body,
forming the chamber by part of the wall also forming the tubular enclosure, the wall comprises two wall sides of which one is facing the inside of the chamber and the other is facing the tubular enclosure,
forming by the tubular enclosure a second chamber at least partly encompassed by the tubular enclosure and
sealing at the first or more open ends using the patient's body portion, and
forming the second chamber together with the patient's body partly by the wall part facing the tubular enclosure.
6. The method according to at least one of embodiments 1-4, further comprising:
cutting the skin of the patient in a position inside of the chamber,
communicating from the chamber with an operating field during the surgical procedure, wherein the wall encompassing the chamber has a wall port or wall inset mounted in a wall portion of the chamber for allowing at least one of;
moving objects into the chamber or operating field and
manipulating manually in the chamber or operating field.
7. The method according to embodiment 6, the medical device comprising a port having a first and second part, and wherein the second part comprises the wall port or wall inset and the first part comprises a body port or body inset, the method comprising the steps of;
mounting a body port in the cut skin of the patient allowing at least one of;
moving objects from the chamber into the operating field and manipulating manually from the chamber into the operating field.
8. The method according to embodiment 7, further comprising:
mounting the two parts of the port or inset together, touching each other,
forming an integrated port or inset and thereby allowing,
moving objects into the operating field,
manipulating manually in the operating field directly from outside the chamber,
separating the two parts of the port or inset from each other and
placing the port or inset in one or more positions inside the chamber.
9. The method according to any one of embodiments 1-3 and 5, wherein the part of the wall forming both the chamber and the tubular enclosure, at a portion thereof, the method comprising:
opening by cutting the skin of the patient inside of the chamber allowing communication with the operating field, and
allowing, from outside the chamber, at least one of moving objects into the chamber or operating field and manually manipulating in the chamber or operating field.
10. The method according to embodiment 9, wherein a port or inset includes a first and second part, wherein the second part comprises the wall port or wall inset and the first part comprises a first wall port or first wall inset mounted in the opening in the portion of the part of the wall forming both the chamber and the tubular enclosure for performing the method steps of;

communicating between the chamber and the operating field, wherein the second chamber is located in between the tubular enclosure and the skin of the patient, and wherein the second chamber has a size equal to or larger than zero.

11. The method according to embodiment 10, further comprising
mounting the two parts of the port or inset touching each other, forming an integrated port and inset,
dismounting the two parts of the port or inset.

12. The method according to any one of embodiments 8, 9, 10 and 11, further comprising locking together in at least one fixed position the two parts of the port or inset.

13. The method according to any one of embodiments 1-12, wherein the method further comprises performing the surgical procedure on the patient on at least one of a extremity, the prolongation of the extremity, abdomen, chest, and any joint including the hip and knee joints and the joints of the upper extremity.

14. The method may be adapted for reducing the infection risk of the surgical procedure by using the chamber encompassing the surgical procedure.

15. The method according to embodiment, further comprising using a fluid sealed valve included in both of the two parts of the port when the two parts being separated.

16. The method according to embodiment 12, further comprising using a fluid sealed valve included in the second part, when the two parts are separated.

17. The method according to any one of embodiments 6-16, further comprising introducing at least one of a third exchangeable wall port and wall inset different from the wall port and wall inset, and replacing at least one of the wall port or wall inset.

18. The method according to embodiment 7, further comprising:
introducing at least one of a third exchangeable body port and body inset different from the body port and body inset, and
replacing at least one of the body port or body inset.

19. The method according to at least one of embodiment 8 and 11, further comprising introducing a second exchangeable integrated port different from the integrated port, and
replacing the integrated port during the surgical procedure.

20. The method according to any one of embodiments 6-16, wherein the inset comprises at least one glove integrated in the wall such that a surgeon is able to
use the glove from outside the chamber, and
manipulate manually inside the chamber while maintaining the sealed environment in the chamber.

21. The method according to any one of embodiments 1-20, further comprising a device or instrument mount for retaining an instrument within the chamber.

22. The method according to any one of embodiments 1-21, further comprising introducing at least one sealing device, sealing between the skin of the body portion of the patient and at least one of the wall and enclosure.

23. The method according to any one of embodiments 1-22, wherein the medical device is arranged such that the portion of the extremity may be inserted into the enclosure through the first open end thereof and exit the enclosure through a second open end thereof.

24. The method according to embodiment 23, when the chamber is formed by the wall without involving the patient's body, the method comprising:
forming the chamber by the part of the wall is also forming the tubular enclosure, the wall having two sides whereof one facing the inside of the chamber and the other side of the wall is facing the tubular enclosure,
forming a second chamber using at least partly the tubular enclosure, the second chamber at least partly encompassed by the tubular enclosure,
sealing at the first or more open ends by the patient's body portion, and
forming the second chamber together with the patient's body using the wall part facing the tubular enclosure.

25. The method according to embodiment 1, wherein the medical device further comprising a sealing device, a further step of performing the surgical procedure comprising:
 a. placing a sealing device in connection with at least one of the wall and the second coupling, to seal between the medical device and the skin or tissue of the patient,
 b. sealing the combined volume of the chamber and the joint cavity to the outer environment, when the second coupling is open.

26. The surgical method according to any one of the embodiments 1 and 25, wherein the step of performing a step of the surgical procedure within the chamber comprises:
 c. removing a specimen (81) from the cavity in the joint of the patient,
 d. transferring the specimen through the second coupling, and
 e. placing the specimen within the chamber of the medical device.

27. The surgical method according to any one of embodiment 1 and 25-26, wherein the method further comprises:
connecting the first port and second coupling such that the interconnectable port is integrated,
performing a surgical step in the chamber, using the integrated first port.

The different aspects or any part of an aspect of the different numbered embodiments or any part of an embodiment may all be combined in any possible way. Any method embodiment or any step of any method embodiment may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description.

The invention claimed is:
1. An interconnectable port adapted to be at least partially placed in an incision in a patient's body, wherein the interconnectable port comprises:
 a first closeable port,
 a first wall connector for sealingly connecting the first closeable port to a first portion of
 an expandable flexible wall,
 a second port,
 a second wall connector for sealingly connecting the second closeable port to a second
 portion of the expandable flexible wall, and
 a port connector for reversibly connecting the first closeable port to the second closeable port for forming the interconnectable port, wherein:

the expandable flexible wall is adapted to form a chamber between the first and second closeable ports, the first closeable port comprises a first port closer capable of reversibly closing the first closeable port when the first closeable port has been disconnected from the second closeable port, the second closeable port comprises a second port closer capable of reversibly closing the second closeable port, when the first closeable port has been disconnected from the second port, and the expandable flexible wall is configured to expand when the first closeable port is disconnected from the second closeable port such that the chamber has a first enclosed volume when the first and second closeable ports are interconnected and a second enclosed volume when the first closeable port is disconnected from the second closeable port, and wherein the second enclosed volume is larger than the first enclosed volume.

2. The interconnectable port according to claim 1, wherein the first volume is smaller than 100 000 mm3.

3. The interconnectable port according to claim 1, wherein the second volume is larger than 500 000 mm3.

4. The interconnectable port according to claim 1, wherein the expandable flexible wall comprises a pleated portion such that the expandable flexible wall can be expanded.

5. The interconnectable port according to claim 1, wherein: the interconnectable port comprises a first and second coupling, and wherein the first closeable port is connected to the first coupling, and the second closeable port is connected to the second coupling.

6. The interconnectable port according to claim 5, wherein: at least one of the first and second coupling comprises a protruding member, and at least one of the first and second coupling comprises a recess, and wherein, the protruding member is adapted to engage the recess for locking the first coupling to the second coupling.

7. The interconnectable port according to claim 6, wherein the recess is a groove in at least one of the first and second coupling.

8. The interconnectable port according to claim 5, further comprising an inset detachably fixated to at least one of the first and second coupling, such that the inset could be detached and replaced by a different inset.

9. The interconnectable port according to claim 8, wherein the inset comprises at least one of: a surgical glove and a device or instrument mount.

10. The interconnectable port according to claim 1, wherein the chamber formed by the expandable flexible wall is adapted to hold a pressure exceeding atmospheric pressure.

11. The interconnectable port according to claim 10, wherein the interconnectable port is adapted to, in the second state, enable the surgeon to remove a specimen from the body of the patient through the second closeable port and into the chamber, and to perform one of: placing the specimen within the chamber, and removing the specimen from the chamber through the second closeable port.

12. The interconnectable port according to claim 10, wherein the first and second closeable ports are adapted to be reconnected after having been disconnected, such that the surgeon can continue operating through the interconnected port after the specimen has been removed.

13. The interconnectable port according to claim 1, wherein the interconnectable port is adapted to:

a. in a first state, when the first and second closeable ports are interconnected, enable a surgeon to operate through the interconnected interconnectable port, and b. in a second state, when the second closeable port is disconnected from the first closeable port enable the surgeon to perform steps of the procedure within the chamber formed by the expandable flexible wall between the first and second closeable ports of the interconnectable port.

14. The interconnectable port according to claim 13, wherein the chamber further comprises a pouch for holding a specimen within the chamber.

15. The interconnectable port according to claim 14, wherein the pouch can be closed for creating a pouch-chamber within the chamber for isolating the removed specimen within the chamber.

16. The interconnectable port according to claim 1, wherein at least one of the first and second closeable port comprises an elastic or flexible membrane adapted to, in a non-compressed state, provide sealing, and in a compressed state enable a hand or an object to be inserted through the membrane.

17. The interconnectable port according to claim 16, wherein the first closeable port comprises a first elastic or flexible membrane and the second closeable port comprises a second elastic or flexible membrane, and wherein the first and second membranes are adapted to be placed tightly together such that they act as a single elastic or flexible membrane adapted to, in a non-compressed state, provide sealing, and in a compressed state enable a hand or an object to be inserted through the membrane.

18. The interconnectable port according to claim 17, wherein the first and second membranes comprises a plurality of self-sealing holes enabling insertion of instruments through the membranes.

19. The surgical port according to claim 1, wherein at least one of said first and second closeable port comprises a penetrable self-sealing gel, such that an object or hand can be inserted through the interconnectable port while maintaining a seal.

20. The interconnectable port according to claim 19, wherein the first closeable port comprises a first penetrable self-sealing gel and the second closeable port comprises a second penetrable self-sealing gel, and wherein the first and second penetrable self-sealing gels are adapted to be placed tightly together such that they act as a single penetrable self-sealing gel adapted to, in a non-compressed state, provide sealing, and in a compressed state enable a hand or an object to be inserted through the self-sealing gel while maintaining the seal.

21. The interconnectable port according to claim 1, wherein the expandable flexible wall comprises a fluid inlet for inflating the chamber with a fluid.

22. The interconnectable port according to claim 21, further comprising a fluid outlet provided in the wall for discharging the fluid from the chamber.

23. The interconnectable port according to claim 22, further comprising a pump adapted to circulate the fluid from the outlet member to the inlet member.

24. The interconnectable port according to claim 21, wherein the interconnectable port further comprises at least one of:

a. a filtering unit for filtering the fluid, b. a sterilization unit for directly or indirectly sterilizing the fluid, c. a fluid tempering unit adapted change the temperature of the fluid,
d. a filtering unit for filtering the fluid and a sterilization unit for directly or indirectly sterilizing the fluid,
e. a filtering unit for filtering the fluid and a fluid tempering unit adapted change the temperature of the fluid,
f. a sterilization unit for directly or indirectly sterilizing the fluid and a fluid tempering unit adapted change the temperature of the fluid, and
g. a filtering unit for filtering the fluid, a sterilization unit for directly or indirectly sterilizing the fluid and a fluid tempering unit adapted change the temperature of the fluid.

25. The interconnectable port according to claim 1, wherein at least one of the first and second closeable port comprises a non-penetrable valve such that the chamber is sealed from at least one of the ambient environment and a cavity in the patient.

26. The interconnectable port according to claim 1, further comprising at least one of: a vacuum seal adapted to hold a pressure less than atmospheric pressure between the interconnectable port and the patient's skin to seal between the interconnectable port and the patient's skin, and a pressure seal adapted to hold a pressure above atmospheric pressure between the interconnectable port and the patient's skin to seal between the interconnectable port and the patient's skin.

27. The interconnectable port according to claim 1, wherein the interconnectable port further comprises a sealing device having a first sealing member adapted to be positioned at the inside of the patient's skin around an incision to be performed in the skin and a second sealing member adapted to be positioned at the outside of the patient's skin around the incision, and a spring-loaded or elastic connecting member sealingly interconnecting the first and second sealing members, whereby the spring-loaded or elastic connecting member seals between at least one of: (a) the interconnectable port and the skin of the patient, and (b) the first sealing member and tissue of the patient.

28. A surgical method to be performed on the body of a patient using an interconnectable port comprising:
a first closeable port,
a first wall connector for sealingly connecting the first closeable port to a first portion of an expandable flexible wall,
a second closeable port,
a second wall connector for sealingly connecting the second closeable port to a second portion of the expandable flexible wall, and
a port connector for reversibly connecting the first closeable port to the second closeable port for forming the interconnectable port, wherein:
  the expandable flexible wall is adapted to form a chamber between the first and second closeable ports,
  the first closeable port comprises a first port closer capable of reversibly closing the first closeable port when the first closeable port has been disconnected from the second closeable port,
  the second closeable port comprises a second port closer capable of reversibly closing the second closeable port, when the first closeable port has been disconnected from the second closeable port, and
  the expandable flexible wall is configured to expand when the first closeable port is disconnected from the second closeable port such that the chamber has a first enclosed volume when the first and second closeable ports are interconnected and a second enclosed volume when the first closeable port is disconnected from the second closeable port, and wherein the second enlcosed volume is larger than the first enclosed volume, the method comprising:
a. creating an incision in the skin of the patient,
b. placing the interconnectable port in the incision,
c. disconnecting the first closeable port from the second closeable port, such that the chamber is formed by the expandable flexible wall connected to the first and second closeable port, and
d. performing a step of the surgical procedure within the chamber.

29. The surgical method according to claim 28, wherein the step of performing a step of the surgical procedure within the chamber comprises:
a. removing a specimen from the cavity in the body of the patient,
b. transferring the specimen through the second port, and
c. placing the specimen within the chamber of the interconnectable port.

30. The surgical method according to claim 28, wherein the method further comprises:
a. reconnecting the first and second ports such that the interconnectable port is formed,
b. performing a surgical step in a cavity of the patient, through the interconnectable port.

* * * * *